US012799104B2

(12) United States Patent
Lee et al.

(10) Patent No.: US 12,799,104 B2
(45) Date of Patent: Nov. 17, 2026

(54) COMPOUNDS AS HISTONE DEACETYLASE 6 INHIBITOR, AND PHARMACEUTICAL COMPOSITION COMPRISING THE SAME

(71) Applicant: CHONG KUN DANG PHARMACEUTICAL CORP., Seoul (KR)

(72) Inventors: Jae Kwang Lee, Gyeonggi-do (KR); Jaeki Min, Gyeonggi-do (KR); Jin Kyung In, Gyeonggi-do (KR); Yi Hyun Kim, Gyeonggi-do (KR); Bomi Jeon, Gyeonggi-do (KR); Younghue Han, Gyeonggi-do (KR); Hong Ju Yoon, Gyeonggi-do (KR); Hyunjin Michael Kim, Gyeonggi-do (KR)

(73) Assignee: Chong Kun Dang Pharmaceutical Corp. (KR)

( * ) Notice: Subject to any disclaimer, the term of this patent is extended or adjusted under 35 U.S.C. 154(b) by 823 days.

(21) Appl. No.: 18/015,809

(22) PCT Filed: Jul. 13, 2021

(86) PCT No.: PCT/IB2021/056282
§ 371 (c)(1),
(2) Date: Jan. 12, 2023

(87) PCT Pub. No.: WO2022/013728
PCT Pub. Date: Jan. 20, 2022

(65) Prior Publication Data

US 2023/0257372 A1 Aug. 17, 2023

(30) Foreign Application Priority Data

Jul. 14, 2020 (KR) ........................ 10-2020-0087126

(51) Int. Cl.

| | |
|---|---|
| ***C07D 413/10*** | (2006.01) |
| ***C07D 413/14*** | (2006.01) |
| ***C07D 417/14*** | (2006.01) |
| ***C07D 471/04*** | (2006.01) |
| ***C07D 487/08*** | (2006.01) |
| ***C07D 491/107*** | (2006.01) |
| ***C07D 495/04*** | (2006.01) |

(52) U.S. Cl.
CPC ......... *C07D 413/10* (2013.01); *C07D 413/14* (2013.01); *C07D 417/14* (2013.01); *C07D 471/04* (2013.01); *C07D 487/08* (2013.01); *C07D 491/107* (2013.01); *C07D 495/04* (2013.01)

(58) Field of Classification Search
None
See application file for complete search history.

(56) References Cited

U.S. PATENT DOCUMENTS

| | | | |
|---|---|---|---|
| 2009/0192171 | A1 | 7/2009 | Hutchinson et al. |
| 2017/0145012 | A1 | 5/2017 | Buckmelter et al. |
| 2023/0295142 | A1 | 9/2023 | Lee et al. |

FOREIGN PATENT DOCUMENTS

| | | | |
|---|---|---|---|
| CA | 3137054 | A1 | 10/2020 |
| CN | 107980040 | A | 5/2018 |
| CN | 114269739 | A | 4/2022 |
| EP | 2411009 | B1 | 3/2013 |
| JP | 2012-521974 | A | 9/2012 |
| JP | 2018-521092 | | 8/2018 |
| JP | 2018-523663 | A | 8/2018 |
| JP | 2019-504821 | A | 2/2019 |
| JP | 2019-528975 | | 10/2019 |
| JP | 2022-529695 | | 6/2022 |
| KR | 1020170013186 | | 2/2017 |
| KR | 1020170013187 | | 2/2017 |
| KR | 1020220012243 | | 2/2022 |
| RU | 2695227 | | 7/2019 |
| RU | 2709207 | | 12/2019 |
| RU | 2018121499 | A | 12/2019 |
| WO | WO 2007012661 | A1 | 2/2007 |
| WO | WO 2009/119880 | | 10/2009 |
| WO | WO 2010089303 | A1 | 8/2010 |
| WO | WO 2010109148 | A1 | 9/2010 |
| WO | WO 2011/011186 | | 1/2011 |
| WO | WO 2011/091213 | | 7/2011 |

(Continued)

OTHER PUBLICATIONS

Bolden et al., "Anticancer activities of histone deacetylase inhibitors," Nature Reviews Drug Discovery, 2006, 5(9):769-784.
Chen et al., "Computational exploration of zinc binding groups for HDAC inhibition," Manuscript, The Journal of Organic Chemistry, 2013, 78(10):5051-5055.
Hassig et al., "Nuclear histone acetylases and deacetylases and transcriptional regulation: HATs off to HDACs," Current Opinion in Chemical Biology, 1997, 1(3):300-308.

(Continued)

*Primary Examiner* — Adam C Milligan
*Assistant Examiner* — Jason M. Nolan
(74) *Attorney, Agent, or Firm* — Fish & Richardson P.C.

(57) ABSTRACT

Compounds having histone deacetylase 6 (HDAC6) inhibitory activity, stereoisomers thereof, pharmaceutically acceptable salts thereof, use thereof in preparation of a medicament, a pharmaceutical composition including the same, methods of treatment, and methods for preparing 1,3,4-oxadiazole triazole derivatives. Compounds having selective HDAC6 inhibitory activity are represented by following formula I:

[Formula I]

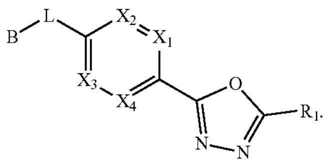

5 Claims, No Drawings

(56) References Cited

FOREIGN PATENT DOCUMENTS

| | | | |
|---|---|---|---|
| WO | WO 2013/008162 | | 1/2013 |
| WO | WO 2013/041407 | | 3/2013 |
| WO | WO 2013/052110 | | 4/2013 |
| WO | WO 2013/066833 | | 5/2013 |
| WO | WO 2013/066835 | | 5/2013 |
| WO | WO 2013/066838 | | 5/2013 |
| WO | WO 2013/066839 | | 5/2013 |
| WO | WO 2013/080120 | | 6/2013 |
| WO | WO 2013/134467 | | 9/2013 |
| WO | WO 2017/018804 | | 2/2017 |
| WO | WO 2017/018805 | | 2/2017 |
| WO | WO2017018805 | A1 | 2/2017 |
| WO | WO 2017023133 | A2 | 2/2017 |
| WO | WO 2017087837 | A1 | 5/2017 |
| WO | WO 2017/222951 | | 12/2017 |
| WO | WO 2017222950 | A1 | 12/2017 |
| WO | WO 2017222952 | A1 | 12/2017 |
| WO | WO 2018/065254 | | 4/2018 |
| WO | WO 2019/011928 | | 1/2019 |
| WO | WO 2019110663 | A1 | 6/2019 |
| WO | WO 2020/127974 | | 6/2020 |
| WO | WO 2020/212479 | | 10/2020 |
| WO | WO2020212479 | A1 | 10/2020 |
| WO | WO 2020240492 | A1 | 12/2020 |
| WO | WO 2022/029041 | A1 | 2/2022 |

OTHER PUBLICATIONS

Kovacs et al., "HDAC6 regulates Hsp90 acetylation and chaperone-dependent activation of glucocorticoid receptor," Molecular Cell, 2005, 18:601-607.

KR Office Action in Korean Appln. No. 10-2021-0091902, dated Oct. 4, 2022, 10 pages (with Machine Translation).

Li et al., "Discovery of a new class of histone deacetylase inhibitors with a novel zinc binding group," Med. Chem. Commun., 2015, 6 pages.

Li et al., "HDAC6 α-tubulin deacetylase: a potential therapeutic target in neurodegenerative diseases," Journal of the Neurological Sciences, 2011, 304:1-8.

Methot et al., "Exploration of the internal cavity of histone deacetylase (HDAC) with selective HDAC1/HDAC2 inhibitors (SHI-1:2)," Bioorganic & Medicinal Chemistry Letters, 2008, 18:973-978.

PCT International Search Report and Written Opinion in International Appln. No. PCT/IB2021/056282, dated Oct. 26, 2021, 12 pages.

Santo et al., "Preclinical activity, pharmacodynamic, and pharmacokinetic properties of a selective HDAC6 inhibitor, ACY-1215, in combination with bortezomib in multiple myeloma," Blood, 2012, 119(11):2579-2589.

Subramanian et al., "Clinical toxicities of histone deacetylase inhibitors," Pharmaceuticals, 2010, 3:2751-2767.

TW Office Action in Taiwanese Appln. No. 110125754, dated May 4, 2022, 7 pages (with English Translation).

Vishwakarma et al., "Tubastatin, a selective histone deacetylase 6 inhibitor shows anti-inflammatory and anti-rheumatic effects," International Immunopharmacology, 2013, 16:72-78.

Warrell, Jr. et al., "Therapeutic targeting of transcription in acute promyelocytic leukemia by use of an inhibitor of histone deacetylase," Journal of the National Cancer Institute, 1998, 90(21):1621-1625.

Witt et al., "HDAC family: What are the cancer relevant targets?," Cancer Letters, 2009, 277:8-21.

Zhang et al., "Mice lacking histone deacetylase 6 have hyperacetylated tubulin but are viable and develop normally," Molecular and Cellular Biology, 2008, 28(5):1688-1701.

Bonacorso et al., "Synthesis, Structure Elucidation, Antioxidant and Antimicrobial Activity of Novel 2-(5-Trifluoromethyl-1H-pyrazol-1-yl)-5-(5-trihalomethyl-1H-pyrazol-1-yl-1-carbonyl) pyridines," Journal of the Brazilian Chemical Society, 2015 26:2346-2361.

Office Action in Australian Appln. No. 2021308344, mailed on Aug. 30, 2023, 9 pages.

Office Action in India Appln. No. 202337009277, mailed on Sep. 26, 2023, 6 pages (with English translation).

Office Action in Japanese Appln. No. 2023-501800, mailed on Mar. 11, 2024, 5 pages (with English translation).

Office Action in Russia Appln. No. 2023103092, mailed on Aug. 31, 2023, 24 pages (with English translation).

Alexeev, "Optical isomerism and pharmacologic activity of drugs," Soros Educational Journal, 1998, pp. 49-55, (with English translation, 19 pages in total).

Belikov, "Pharmaceutical Chemistry", 2027, Textbook, Moscow, "MEDpress-Inform", pp. 27-29 (with English translation, 14 pages in total).

Extended European Search Report in European Appln. No. 21841400.1, mailed on Jun. 20, 2024, 7 pages.

Kümmererer, "Pharmaceuticals in the environment," Annual Review of Environment and Resources, 2010, 35:57-75 (see abstract, p. 60).

Office Action in Canadian Appln. No. 3185923, mailed on May 2, 2024, 5 pages.

Office Action in Chinese Appln. No. 202180061215.2, mailed on Oct. 8, 2024, 19 pages (with English translation).

Dyson et al., "Chemistry of Synthetic Medicinal Substances," Mir, Moscow, 1964, pp. 12-19 (with English Translation).

Extended European Search Report in European Appln. No. 21863810.4, mailed on Sep. 19, 2024, 8 pages.

International Search Report and Written Opinion in International Application No. PCT/IB2021/057975, dated Dec. 7, 2021, 10 pages.

Office Action in Australian Application No. 2021337217, dated Aug. 10, 2023, 9 pages.

Office Action in Canadian Appln.No. 3191319, mailed on Apr. 29, 2024, 4 pages.

Office Action in Chinese Application No. 202180053894.9, dated Aug. 31, 2023, 13 pages (with English Translation).

Office Action in Indian Application No. 202337023623, dated Dec. 27, 2023, 5 pages (with English Translation).

Office Action in Japanese Appln. No. 2023-514400, mailed on Mar. 7, 2024, 4 pages (with English translation).

Office Action in Russian Application No. 2023107900, dated Aug. 22, 2023, 17 pages (with English Translation).

Office Action in Taiwanese Application No. 110132427, dated Apr. 28, 2022, 8 pages (with English Translation).

Vasilenko, "Optical isomers in pharmacy," Development and registration of medicines, 2015, (1)92-97 (with English Translation).

COMPOUNDS AS HISTONE DEACETYLASE 6 INHIBITOR, AND PHARMACEUTICAL COMPOSITION COMPRISING THE SAME

TECHNICAL FIELD

The present invention relates to a novel compound having a histone deacetylase 6 (HDAC6) inhibitory activity, stereoisomers thereof, pharmaceutically acceptable salts thereof, a use thereof in preparation of a medicament, a pharmaceutical composition including the same, a preventive or therapeutic method thereof, and a method for preparing the same.

BACKGROUND

In cells, a post-translational modification such as acetylation serves as a very important regulatory module at the hub of biological processes, and is also strictly controlled by a number of enzymes. As a core protein constituting chromatin, histone functions as an axis, around which DNA winds, and thus helps a DNA condensation. Also, a balance between acetylation and deacetylation of histone plays a very important role in gene expression.

As an enzyme for removing an acetyl group from lysine residue of histone protein, which constitutes chromatin, histone deacetylase (HDAC) is known to be associated with gene silencing and induce a cell cycle arrest, angiogenic inhibition, immunoregulation, apoptosis, etc. (Hassig et al., Curr. Opin. Chem. Biol. 1997, 1, 300-308). Also, it is reported that the inhibition of HDAC enzyme functions induces cancer cells into committing apoptosis for themselves by lowering an activity of cancer cell survival-related factors and activating cancer cell death-related factors in the body (Warrell et al., J. Natl. Cancer Inst. 1998, 90, 1621-1625).

For humans, 18 HDACs are known and classified into four classes according to homology with yeast HDAC. In this case, eleven HDACs using zinc as a cofactor may be divided into three groups: Class I (HDAC1, 2, 3, 8), Class II (IIa: HDAC4, 5, 7, 9; IIb: HDAC6, 10) and Class IV (HDAC11). Further, seven HDACs of Class III (SIRT 1-7) use NAD+as a cofactor instead of zinc (Bolden et al., Nat. Rev. Drug Discov. 2006, 5(9), 769-784).

Various HDAC inhibitors are now in a preclinical or clinical development stage, but only non-selective HDAC inhibitors have been known as an anti-cancer agent so far. Vorinostat (SAHA) and romidepsin (FK228) have obtained an approval as a therapeutic agent for cutaneous T-cell lymphoma, while panobinostat (LBH-589) has won an approval as a therapeutic agent for multiple myeloma. However, it is known that the non-selective HDAC inhibitors generally bring about side effects such as fatigue, nausea and the like at high doses (Piekarz et al., Pharmaceuticals 2010, 3, 2751-2767). It is reported that the side effects are caused by the inhibition of class I HDACs. Due to the side effects, etc., the non-selective HDAC inhibitors have been subject to restriction on drug development in other fields than an anticancer agent (Witt et al., Cancer Letters 277, (2009), 8-21).

Meanwhile, it is reported that the selective inhibition of class II HDACs would not show toxicity, which have occurred in the inhibition of class I HDACs. In case of developing the selective HDAC inhibitors, it would be likely to solve side effects such as toxicity, etc., caused by the non-selective inhibition of HDACs. Accordingly, there is a chance that the selective HDAC inhibitors may be developed as an effective therapeutic agent for various diseases (Matthias et al., Mol. Cell. Biol. 2008, 28, 1688-1701).

HDAC6, one of the class IIb HDACs, is known to be mainly present in cytoplasma and contain a tubulin protein, thus being involved in the deacetylation of a number of non-histone substrates (HSP90, cortactin, etc.) (Yao et al., Mol. Cell 2005, 18, 601-607). HDAC6 has two catalytic domains, in which a zinc finger domain of C-terminal may bind to an ubiquitinated protein. HDAC6 is known to have a number of non-histone proteins as a substrate, and thus play an important role in various diseases such as cancer, inflammatory diseases, autoimmune diseases, neurological diseases, neurodegenerative disorders and the like (Santo et al., Blood 2012 119, 2579-2589; Vishwakarma et al., International Immunopharmacology 2013, 16, 72-78; Hu et al., J. Neurol. Sci. 2011, 304, 1-8).

A structural feature that various HDAC inhibitors have in common is comprised of a cap group, a linker group and a zinc binding group (ZBG) as shown in a following structure of vorinostat. Many researchers have conducted a study on the inhibitory activity and selectivity with regard to enzymes through a structural modification of the cap group and the linker group. Out of the groups, it is known that the zinc binding group plays a more important role in the enzyme inhibitory activity and selectivity (Wiest et al., J. Org. Chem. 2013 78: 5051-5055; Methot et al., Bioorg. Med. Chem. Lett. 2008, 18, 973-978).

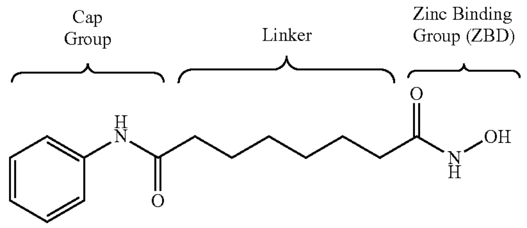 [SMILES: O=C(CCCCCCC(=O)Nc1ccccc1)NO]

Most of said zinc binding group is comprised of hydroxamic acid or benzamide, out of which hydroxamic acid derivatives show a strong HDAC inhibitory effect, but have a problem with low bioavailability and serious off-target activity. Benzamide contains aniline, and thus has a problem in that it may produce toxic metabolites in vivo (Woster et al., Med. Chem. Commun. 2015, online publication).

Accordingly, there is a need to develop a selective HDAC6 inhibitor in order to treat cancers, inflammatory diseases, autoimmune diseases, neurological diseases, neurodegenerative disorders and the like, which has a zinc binding group with improved bioavailability, while causing no side effects unlike the non-selective inhibitors having side effects.

RELATED ART REFERENCES

Patent Documents

International Patent Publication No. WO 2011/091213 (publicized on Jul. 28, 2011): ACY-1215

International Patent Publication No. WO 2011/011186 (publicized on Jan. 27, 2011): Tubastatin International Patent Publication No. WO 2013/052110 (publicized on Apr. 11, 2013): Sloan-K International Patent Publication No. WO 2013/041407 (publicized on Mar. 28, 2013): Cellzome International Patent Publication No. WO 2013/134467 (publicized on Sep. 12, 2013): Kozi International Patent Publication No. WO 2013/008162 (publicized on Jan. 17, 2013): Novartis International Patent Publication No. WO 2013/080120 (publicized on Jun. 6, 2013): Novartis International Patent Publication No. WO 2013/066835 (publicized on May 10, 2013): Tempero International Patent Publication No. WO 2013/066838 (publicized on May 10, 2013): Tempero International Patent Publication No. WO 2013/066833 (publicized on May 10, 2013): Tempero International Patent Publication No. WO 2013/066839 (publicized on May 10, 2013): Tempero

DETAILED DESCRIPTION OF THE INVENTION

Technical Problem

An object of the present invention is to provide a compound having a selective HDAC6 inhibitory activity, stereoisomers thereof or pharmaceutically acceptable salts thereof.

Another object of the present invention is to provide a pharmaceutical composition including a compound having a selective HDAC6 inhibitory activity, stereoisomers thereof or pharmaceutically acceptable salts thereof.

Still another object of the present invention is to provide a method for preparing the same.

Still another object of the present invention is to provide a pharmaceutical composition for preventing or treating HDAC6 activity-related diseases.

Still another object of the present invention is to provide a use thereof in preparation of a medicament for preventing or treating HDAC6 activity-related diseases.

Still another object of the present invention is to provide a method for preventing or treating HDAC6 activity-related diseases, including administering a therapeutically effective amount of the compounds.

Still another object of the present invention is to provide a use thereof for preventing or treating HDAC6 activity-related diseases.

Technical Solution

The present inventors have found an oxadiazole derivative compound having a histone deacetylase 6 (HDAC6) inhibitory activity and have used the same in inhibiting or treating HDAC6 activity-related diseases, thereby completing the present invention.

Hereinafter, the present invention will be described in more detail. In other words, all the combinations of various elements disclosed in the present invention fall within the scope of the present invention. In addition, it cannot be seen that the scope of the present invention is limited to the specific description below.

Compound Represented by Formula I

The present invention may provide a compound represented by formula I below, stereoisomers thereof or pharmaceutically acceptable salts thereof:

[Formula I]

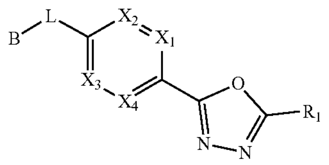

wherein $X_1$ to $X_4$ are each independently C-A or N;

A is H or halogen;

L is C1-C2 alkylene;

$R_1$ is $CF_2H$ or $CF_3$;

B is

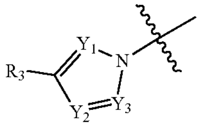

(here, $Y_1$ is $CR_2$ or N, $Y_2$ and $Y_3$ are each independently CR' or N, and R' is H or C1-C5 alkyl), or

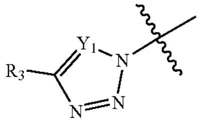

here, $Y_1$ is O or $NR_2$);

$R_2$ is H or C1-C5 alkyl, in which at least one H of C1-C5 alkyl may be substituted with OH or N(C1-C5 alkyl)$_2$;

$R_3$ is halogen; C1-C5 alkyl; C1-C5 haloalkyl;

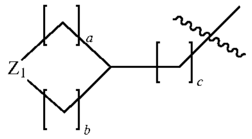

(here, a, b and c are independently 0, 1, 2 or 3, in which a and b cannot be 0 at the same time, and $Z_1$ is $CH_2$, NH or O); C4-C6 cycloalkenyl; C6-C12 aryl; 5- to 9-membered heteroaryl including at least one heteroatom selected from N, O and S;

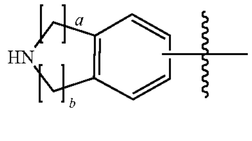

(here, a and b are each independently an integer of 1 or 2);

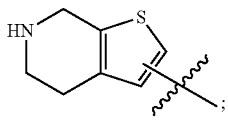;
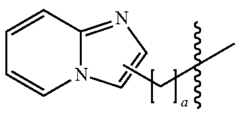

(here, a is an integer of 0, 1 or 2);

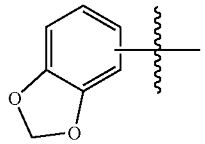

or pyridinone;

at least one H of the $R_3$ may be each independently substituted with halogen or —$(CH_2)_n$-Q1-Q2-Ra (here, n is 0 or 1);

Q1 is a single bond, —$SO_2$—, —NH—, —N(C1-C5 alkyl)-, —NHC(═O)—, —N(C1-C5 alkyl)C(═O)— or —C(═O)—;

Q2 is a single bond, C1-C5 alkylene, —NH—, —(C1-C5 alkylene)-NH—C(═O)— or —N(C1-C5 alkyl)-;

Ra is OH; C1-C5 alkyl; C1-C5 haloalkyl; —$NR_4R_5$ (here, $R_4$ and $R_5$ are each independently H or C1-C5 alkyl); C1-C5 alkoxy;

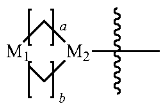

(here, a and b are each independently 1 or 2, $M_1$ is $CH_2$, O, NH or $SO_2$, and $M_2$ is CH or N);

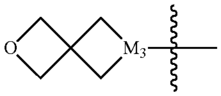

(here, $M_3$ is CH or N); diazabicycloheptane; or 5- or 6-membered heteroaryl including 1 to 3 of N; and at least one H of Ra may be each independently substituted with OH; halogen; C1-C5 alkyl;

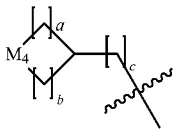

(here, a and b are each independently 0 or 1, but cannot be 0 at the same time, c is 0 or 1, $M_4$ is $CH_2$, NH, or O, and at least one H of $M_4$ may be substituted with halogen, C1-C5 alkyl, C3-C6 cycloalkyl or —C(═O)—O(C1-C5 alkyl)); C1-C6 haloalkyl; —$NR_6R_7$ (here, $R_6$ and $R_7$ are each independently H or C1-C5 alkyl); —C(═O)—(C1-C5 alkyl); C(═O)—O(C1-C5 alkyl); or —NH—C(═O)—O(C1-C5 alkyl).

In one embodiment, the compound represented by above formula I may include the compound represented by formula II below:

[Formuala II]

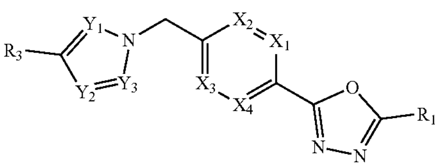

wherein $X_1$ to $X_4$, L, $R_1$, $R_3$, and $Y_1$ to $Y_3$ of formula I are the same as defined in formula I.

In one embodiment, in above formula II, $X_1$ to $X_4$ are each independently C-A or N;

A is H or halogen;

L is C1-C2 alkylene;

$R_1$ is $CF_2H$ or $CF_3$;

$Y_1$ is CH or N;

$R_3$ is phenyl; 6- or 9-membered heteroaryl including at least one heteroatom selected from N and O; or pyridinone;

at least one H of the $R_3$ may be each independently substituted with halogen or —$(CH_2)_n$-Q1-Q2-Ra (here, n is 0 or 1);

Q1 is a single bond, —NH—, —NHC(═O)— or —C(═O)—;

Q2 is a single bond, or —N(C1-C5 alkyl)-;

Ra is C1-C5 alkyl; C1-C5 haloalkyl; —$NR_4R_5$ (here, $R_4$ and $R_5$ are each independently H or C1-C5 alkyl); C1-C5 alkoxy;

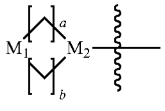

(here, a and b are each independently 1 or 2, $M_1$ is $CH_2$, O, NH or $SO_2$, and $M_2$ is CH or N); or

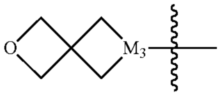

(here, $M_3$ is CH or N); and at least one H of Ra may be each independently substituted with C1-C5 alkyl;

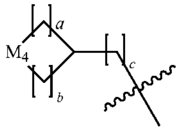

(here, a and b are each independently 0 or 1, but cannot be 0 at the same time, c is 0 or 1, $M_4$ is $CH_2$, NH, or O, and at least one H of $M_4$ may be substituted with halogen or C1-C5 alkyl); —$NR_6R_7$ (here, $R_6$ and $R_7$ are each independently H or C1-C5 alkyl); or —NH—C(═O)—O(C1-C5 alkyl).

In one embodiment, in above formula II, $X_1$ to $X_4$ are each independently C-A or N;

A is H or halogen;

L is C1-C2 alkylene;

$R_1$ is $CF_2H$;

$Y_1$ is CH;

$R_3$ is phenyl; or 9-membered heteroaryl including at least one N;

at least one H of the $R_3$ may be each independently substituted with $-(CH_2)_n$-Q1-Ra (here, n is 0 or 1);

Q1 is a single bond, NH or —NHC(=O)—;

Ra is

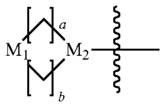

(here, a and b are each independently 1 or 2, $M_1$ is $CH_2$, O, or NH, and $M_2$ is N) or C1-C5 haloalkyl; and at least one H of Ra may be each independently substituted with C1-C5 alkyl.

In the present invention, "Cx-Cy" (here, x and y are an integer of 1 or more) refers to the number of carbons. For example, C1-C5 alkyl refers to alkyl having 1 or more and 5 or less carbon atoms, and C6-C12 aryl refers to aryl having 6 or more and 12 or less carbon atoms.

In the present invention, "halogen" refers to F, Cl, Br or I.

In the present invention, "alkyl" means a linear or branched saturated hydrocarbon group, and includes methyl, ethyl, n-propyl, isopropyl, n-butyl, sec-butyl, isobutyl, tert-butyl, n-pentyl, n-hexyl, n-heptyl, etc.

In the present invention, "alkylene" means a divalent functional group which is induced from the alkyl (including both linear and branched) as defined above.

In the present invention, "haloalkyl" means a functional group, in which at least one H of the alkyl as defined above (including both linear and branched) is substituted with halogen.

For example, haloalkyl may include $-CF_3$, $-CF_2H$ or $-CFH_2$.

In the present invention, "cycloalkyl" may be monocyclic cycloalkyl or polycyclic cycloalkyl. The carbon number of cycloalkyl may be 3 or more and 9 or less.

In the present invention, "heterocycloalkyl" may be monocyclic heterocycloalkyl or polycyclic heterocycloalkyl, and heterocycloalkyl may be a 3- to 9-membered ring.

In the present invention, cycloalkyl or heterocycloalkyl may be represented by a general formula of

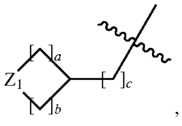

,

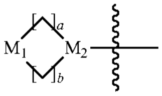

or

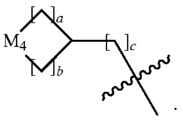

.

An example of cycloalkyl may include cyclopropyl, cyclobutyl, cyclopentyl or cyclohexyl. An example of heterocycloalkyl may include oxidized propylene, oxetane, tetrahydrofuran, tetrahydropyran, azetidine, piperidine, pyrrolidine, etc., but is not limited thereto.

In the present invention, "aryl" refers to a monocyclic aromatic or a polycyclic aromatic functional group formed of carbon and hydrogen only, and the carbon number of aryl may be 6 or more and 12 or less. An example of aryl may include phenyl, naphthyl, etc., but is not limited thereto.

In the present invention, "heteroaryl" refers to a monocyclic or polycyclic hetero ring in which at least one carbon of a monocyclic or polycyclic aromatic functional group is substituted with a heteroatom, and may be monocyclic or polycyclic. An example of the heteroatom may include nitrogen (N), oxygen (O), sulfur (S), etc. Heteroaryl may be a 5- to 10-membered or 5- to 9-membered ring. When heteroaryl includes at least two heteroatoms, the two heteroatoms or more may be the same or different from each other. An example of heteroaryl may include thiophene, benzothiophene, indazole, furan, benzofuran, indole, pyrazole, pyridine, imidazopyridine, pyrimidine, pyrrolopyridine, imidazole, benzoimidazole, thiazole, oxazole, oxadiazole, triazole, pyrizine, bipyridine, triazine, pyridazine, pyrazine, quinoline, quinazoline, or isoquinoline, but is not limited thereto.

In the present invention,

" 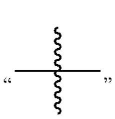 "

represents a connected part.

In the present invention, pharmaceutically acceptable salts may refer to the salts conventionally used in a pharmaceutical industry, for example, inorganic ion salts prepared from calcium, potassium, sodium, magnesium or the like; inorganic acid salts prepared from hydrochloric acid, nitric acid, phosphoric acid, bromic acid, iodic acid, perchloric acid, sulfuric acid or the like; organic acid salts prepared from acetic acid, trifluoroacetic acid, citric acid, maleic acid, succinic acid, oxalic acid, benzoic acid, tartaric acid, fumaric acid, mandelic acid, propionic acid, lactic acid, glycolic acid, gluconic acid, galacturonic acid, glutamic acid, glutaric acid, glucuronic acid, aspartic acid, ascorbric acid, carbonic acid, vanillic acid, hydroiodic acid, etc.; sulfonic acid salts prepared from methanesulfonic acid, ethanesulfonic acid, benzenesulfonic acid, p-toluenesulfonic acid, naphthalenesulfonic acid or the like; amino acid salts prepared from glycine, arginine, lysine, etc.; amine salts prepared from trimethylamine, triethylamine, ammonia, pyridine, picoline, etc.; and the like, but types of salts meant in the present invention are not limited to those listed salts.

In the present invention, preferable salts may include hydrochloric acid, trifluoroacetic acid, citric acid, bromic acid, maleic acid, phosphoric acid, sulfuric acid, tartaric acid, etc.

As one example, the pharmaceutically acceptable salt of the present invention may be a salt of compound 3867 of the present specification.

A compound represented by formula I of the present invention may contain at least one asymmetric carbon, and thus may be present as a racemate, racemic mixture, single enantiomer, mixture of diastereomers and respective diastereomers thereof. Such isomers of the compound represented by formula I may be separated by splitting itself according to the related art, for example, with a column chromatography, HPLC or the like. Alternatively, respective stereoisomers of the compound represented by formula I may be stereospecifically synthesized with a known array of optically pure starting materials and/or reagents.

In the present invention, "stereoisomer" includes a diastereomer and an optical isomer (enantiomer), in which the optical isomer includes not only an enantiomer, but also a mixture of the enantiomer and even a racemate.

The compound represented by formula I of the present invention may be any one selected from the compounds shown in table 1 below.
TABLE 1
| Example | Compound | Structure |
|---|---|---|
| 1 | 3657 | 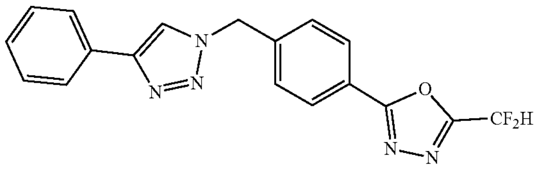 [SMILES: FC(F)c1nnc(-c2ccc(Cn3cc(-c4ccccc4)nn3)cc2)o1] |
| 2 | 3658 | 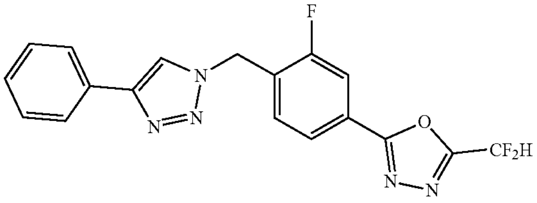 [SMILES: Fc1cc(-c2nnc(C(F)F)o2)ccc1Cn1cc(-c2ccccc2)nn1] |
| 3 | 3659 | 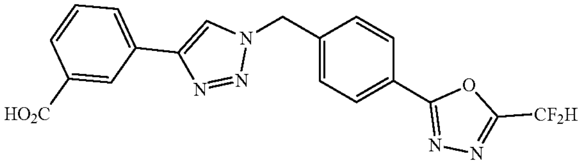 |
| 4 | 3660 | 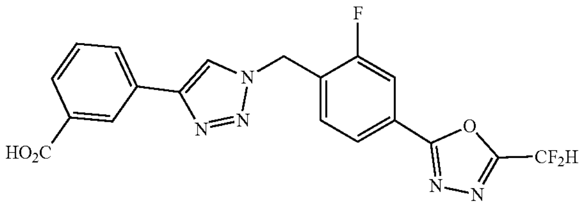 [SMILES: O=C(O)c1cccc(-c2cn(Cc3ccc(-c4nnc(C(F)F)o4)cc3F)nn2)c1] |
| 5 | 3661 | 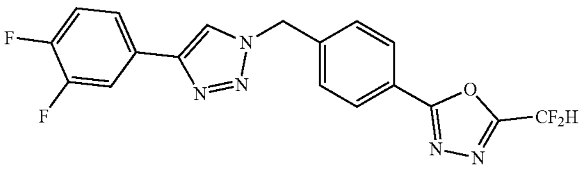 [SMILES: Fc1ccc(-c2cn(Cc3ccc(-c4nnc(C(F)F)o4)cc3)nn2)cc1F] |
| 6 | 3662 | 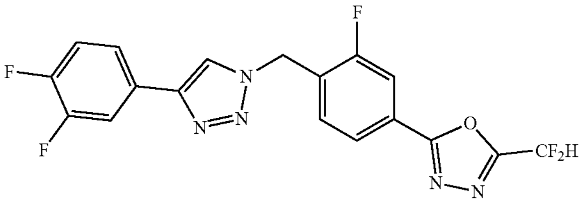 [SMILES: Fc1ccc(-c2cn(Cc3ccc(-c4nnc(C(F)F)o4)cc3F)nn2)cc1F] |
| 7 | 3695 | 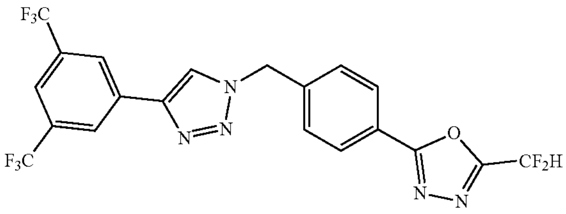 [SMILES: FC(F)c1nnc(-c2ccc(Cn3cc(-c4cc(C(F)(F)F)cc(C(F)(F)F)c4)nn3)cc2)o1] |

TABLE 1-continued
| Example | Compound | Structure |
|---|---|---|
| 8 | 3696 | 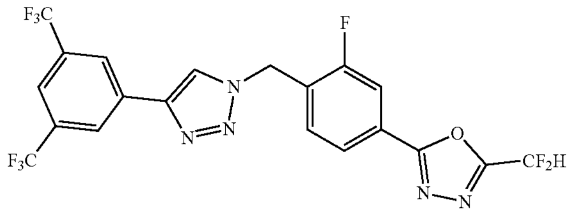 [SMILES: Fc1cc(-c2nnc(C(F)F)o2)ccc1Cn1cc(-c2cc(C(F)(F)F)cc(C(F)(F)F)c2)nn1] |
| 9 | 3697 | 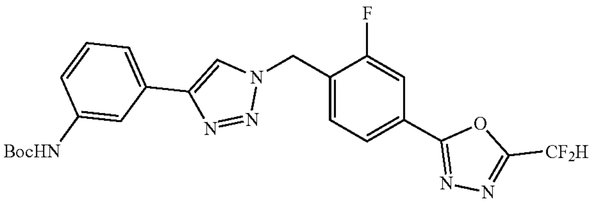 [SMILES: CC(C)(C)OC(=O)Nc1cccc(-c2cn(Cc3ccc(-c4nnc(C(F)F)o4)cc3F)nn2)c1] |
| 10 | 3698 | 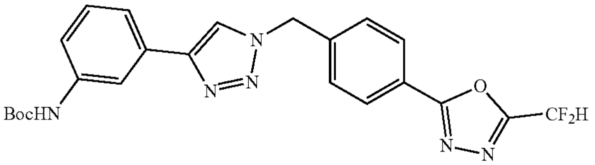 [SMILES: CC(C)(C)OC(=O)Nc1cccc(-c2cn(Cc3ccc(-c4nnc(C(F)F)o4)cc3)nn2)c1] |
| 11 | 3731 | 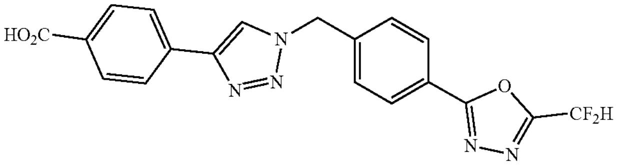 [SMILES: O=C(O)c1ccc(-c2cn(Cc3ccc(-c4nnc(C(F)F)o4)cc3)nn2)cc1] |
| 12 | 3732 | 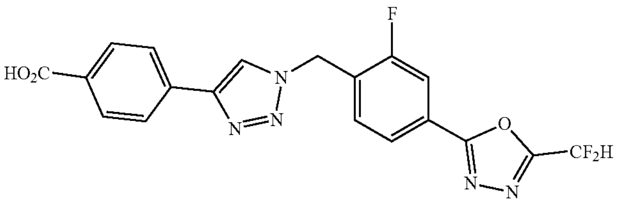 [SMILES: O=C(O)c1ccc(-c2cn(Cc3ccc(-c4nnc(C(F)F)o4)cc3F)nn2)cc1] |
| 13 | 3733 | 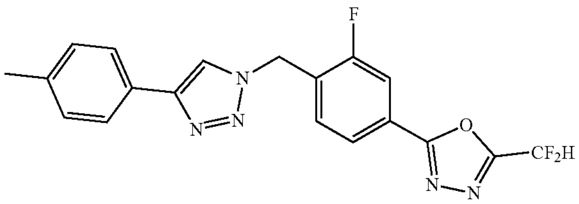 [SMILES: Cc1ccc(-c2cn(Cc3ccc(-c4nnc(C(F)F)o4)cc3F)nn2)cc1] |
| 14 | 3734 | 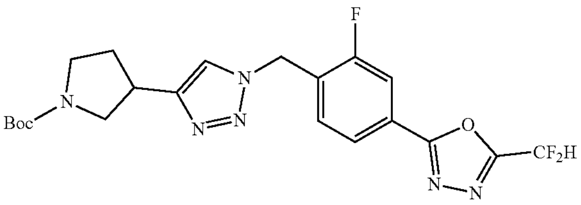 [SMILES: CC(C)(C)OC(=O)N1CCC(c2cn(Cc3ccc(-c4nnc(C(F)F)o4)cc3F)nn2)C1] |

TABLE 1-continued
| Example | Compound | Structure |
|---|---|---|
| 15 | 3735 | 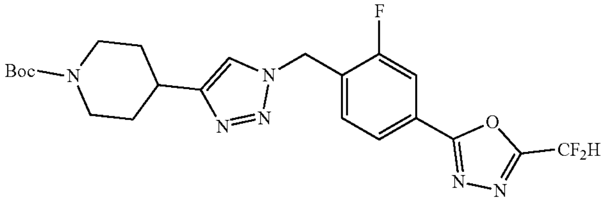 [SMILES: CC(C)(C)OC(=O)N1CCC(c2cn(Cc3ccc(-c4nnc(C(F)F)o4)cc3F)nn2)CC1] |
| 16 | 3736 | 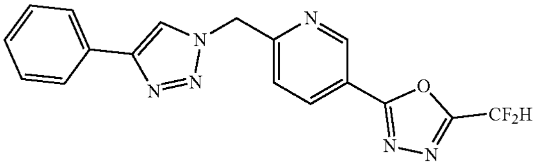 [SMILES: FC(F)c1nnc(-c2ccc(Cn3cc(-c4ccccc4)nn3)nc2)o1] |
| 17 | 3737 | 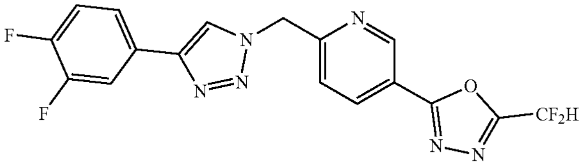 [SMILES: Fc1ccc(-c2cn(Cc3ccc(-c4nnc(C(F)F)o4)cn3)nn2)cc1F] |
| 18 | 3738 | 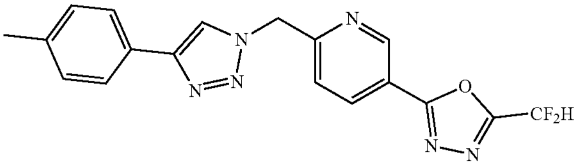 [SMILES: Cc1ccc(-c2cn(Cc3ccc(-c4nnc(C(F)F)o4)cn3)nn2)cc1] |
| 19 | 3739 | 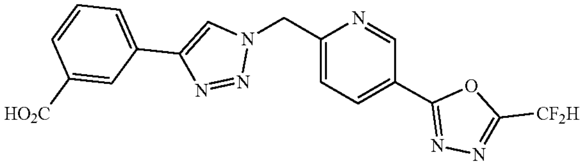 [SMILES: O=C(O)c1cccc(-c2cn(Cc3ccc(-c4nnc(C(F)F)o4)cn3)nn2)c1] |
| 20 | 3741 | 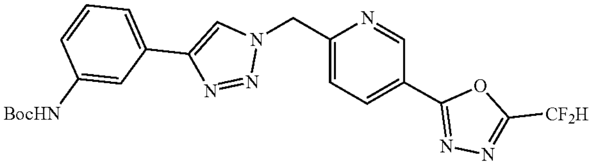 [SMILES: CC(C)(C)OC(=O)Nc1cccc(-c2cn(Cc3ccc(-c4nnc(C(F)F)o4)cn3)nn2)c1] |
| 21 | 3774 | 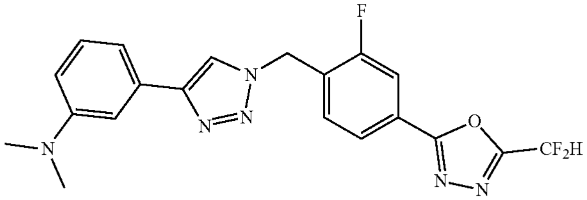 [SMILES: CN(C)c1cccc(-c2cn(Cc3ccc(-c4nnc(C(F)F)o4)cc3F)nn2)c1] |
| 22 | 3775 | 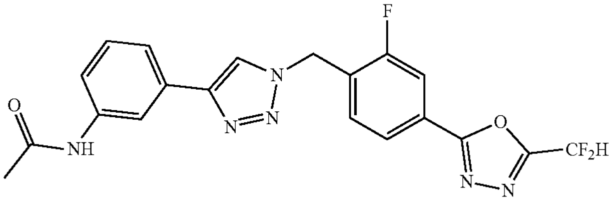 [SMILES: CC(=O)Nc1cccc(-c2cn(Cc3ccc(-c4nnc(C(F)F)o4)cc3F)nn2)c1] |

TABLE 1-continued
| Example | Compound | Structure |
|---|---|---|
| 23 | 3776 | 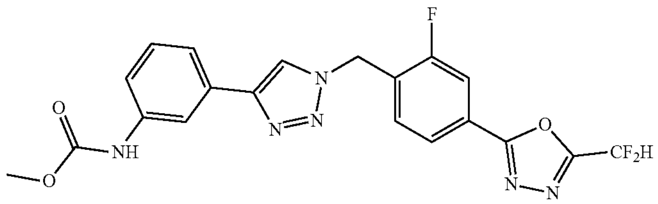 [SMILES: COC(=O)Nc1cccc(-c2cn(Cc3ccc(-c4nnc(C(F)F)o4)cc3F)nn2)c1] |
| 24 | 3777 | 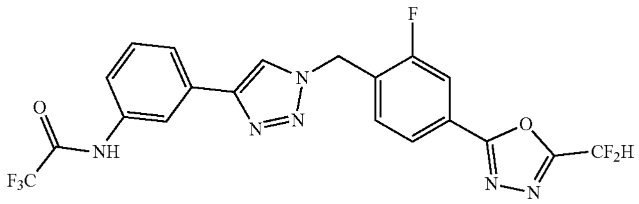 [SMILES: O=C(Nc1cccc(-c2cn(Cc3ccc(-c4nnc(C(F)F)o4)cc3F)nn2)c1)C(F)(F)F] |
| 25 | 3805 | 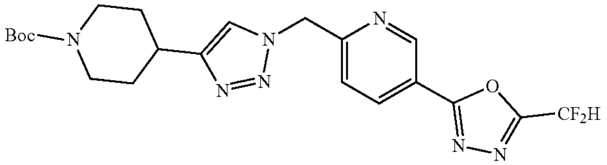 [SMILES: CC(C)(C)OC(=O)N1CCC(c2cn(Cc3ccc(-c4nnc(C(F)F)o4)cn3)nn2)CC1] |
| 26 | 3806 | 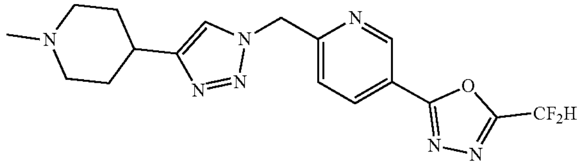 [SMILES: CN1CCC(c2cn(Cc3ccc(-c4nnc(C(F)F)o4)cn3)nn2)CC1] |
| 27 | 3807 | 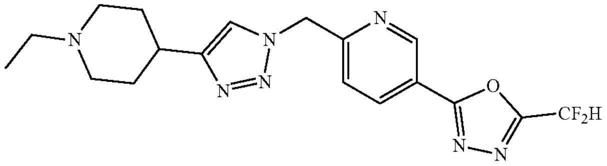 [SMILES: CCN1CCC(c2cn(Cc3ccc(-c4nnc(C(F)F)o4)cn3)nn2)CC1] |
| 28 | 3808 | 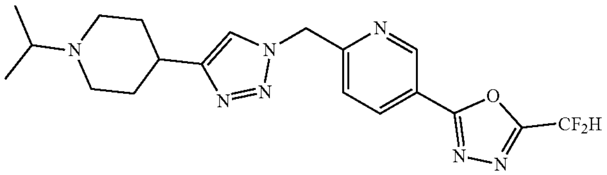 [SMILES: CC(C)N1CCC(c2cn(Cc3ccc(-c4nnc(C(F)F)o4)cn3)nn2)CC1] |
| 29 | 3809 | 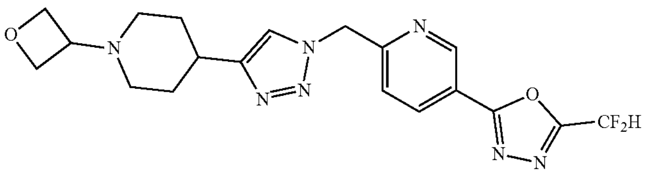 [SMILES: FC(F)c1nnc(-c2ccc(Cn3cc(C4CCN(C5COC5)CC4)nn3)nc2)o1] |
| 30 | 3810 | 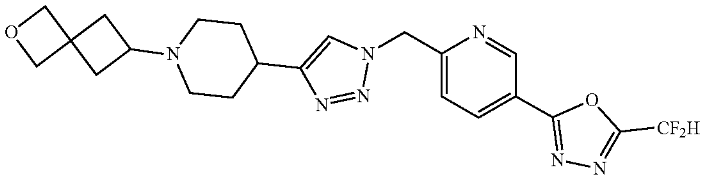 [SMILES: FC(F)c1nnc(-c2ccc(Cn3cc(C4CCN(C5CC6(COC6)C5)CC4)nn3)nc2)o1] |

TABLE 1-continued
| Example | Compound | Structure |
| --- | --- | --- |
| 31 | 3811 | 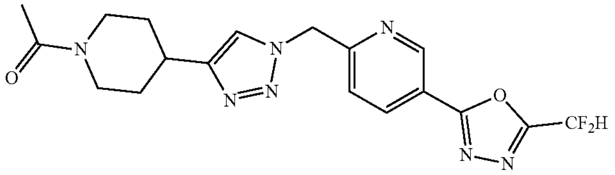 [SMILES: CC(=O)N1CCC(c2cn(Cc3ccc(-c4nnc(C(F)F)o4)cn3)nn2)CC1] |
| 32 | 3812 | 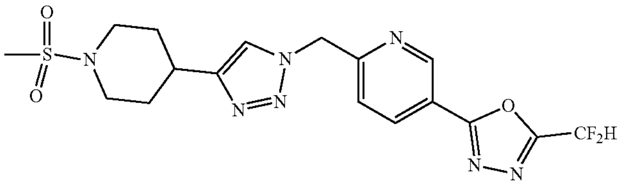 [SMILES: CS(=O)(=O)N1CCC(c2cn(Cc3ccc(-c4nnc(C(F)F)o4)cn3)nn2)CC1] |
| 33 | 3813 | 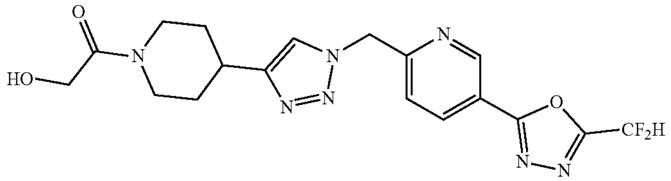 [SMILES: O=C(CO)N1CCC(c2cn(Cc3ccc(-c4nnc(C(F)F)o4)cn3)nn2)CC1] |
| 34 | 3820 | 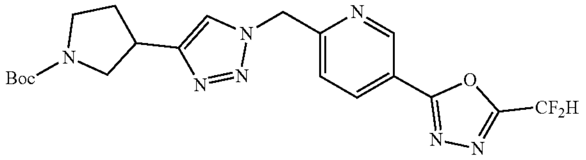 [SMILES: CC(C)(C)OC(=O)N1CCC(c2cn(Cc3ccc(-c4nnc(C(F)F)o4)cn3)nn2)C1] |
| 35 | 3822 | 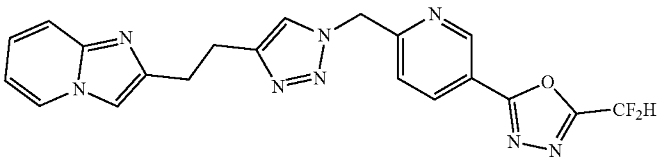 [SMILES: FC(F)c1nnc(-c2ccc(Cn3cc(CCc4cn5ccccc5n4)nn3)nc2)o1] |
| 36 | 3824 | 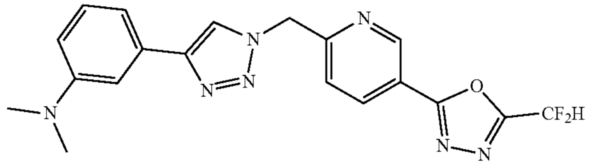 [SMILES: CN(C)c1cccc(-c2cn(Cc3ccc(-c4nnc(C(F)F)o4)cn3)nn2)c1] |
| 37 | 3825 | 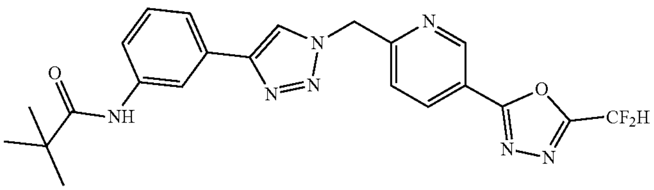 [SMILES: CC(C)(C)C(=O)Nc1cccc(-c2cn(Cc3ccc(-c4nnc(C(F)F)o4)cn3)nn2)c1] |
| 38 | 3826 | 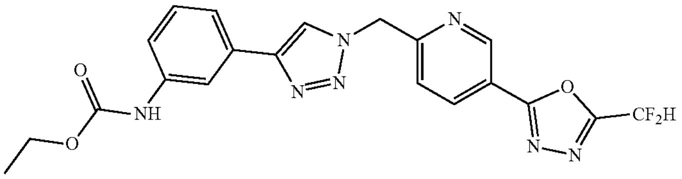 [SMILES: CCOC(=O)Nc1cccc(-c2cn(Cc3ccc(-c4nnc(C(F)F)o4)cn3)nn2)c1] |

TABLE 1-continued
| Example | Compound | Structure |
|---|---|---|
| 39 | 3827 | 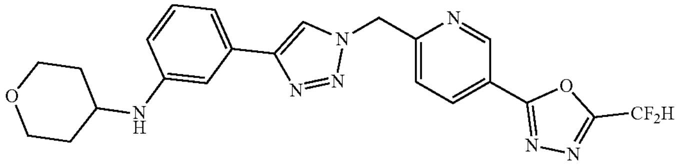 [SMILES: FC(F)c1nnc(-c2ccc(Cn3cc(-c4cccc(NC5CCOCC5)c4)nn3)nc2)o1] |
| 40 | 3828 | 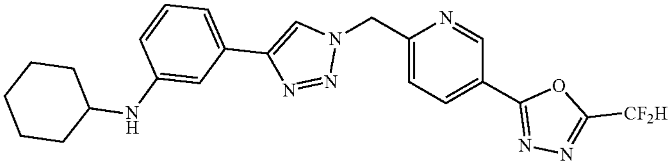 [SMILES: FC(F)c1nnc(-c2ccc(Cn3cc(-c4cccc(NC5CCCCC5)c4)nn3)nc2)o1] |
| 41 | 3829 | 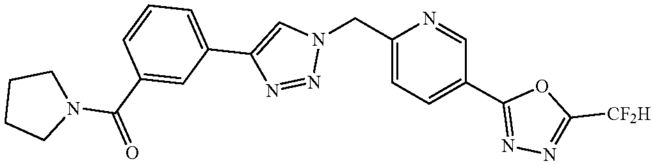 [SMILES: O=C(c1cccc(-c2cn(Cc3ccc(-c4nnc(C(F)F)o4)cn3)nn2)c1)N1CCCC1] |
| 42 | 3830 | 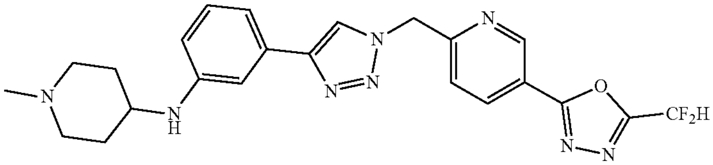 [SMILES: CN1CCC(Nc2cccc(-c3cn(Cc4ccc(-c5nnc(C(F)F)o5)cn4)nn3)c2)CC1] |
| 43 | 3831 | 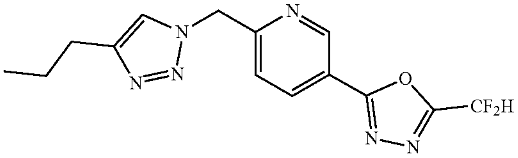 [SMILES: CCCc1cn(Cc2ccc(-c3nnc(C(F)F)o3)cn2)nn1] |
| 44 | 3832 | 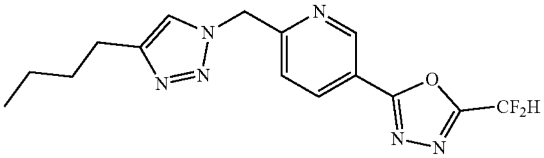 [SMILES: CCCCc1cn(Cc2ccc(-c3nnc(C(F)F)o3)cn2)nn1] |
| 45 | 3833 | 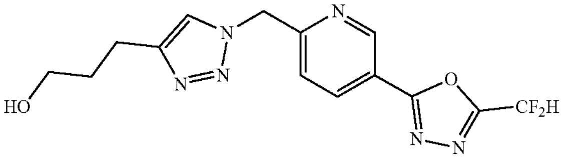 [SMILES: OCCCc1cn(Cc2ccc(-c3nnc(C(F)F)o3)cn2)nn1] |
| 46 | 3834 | 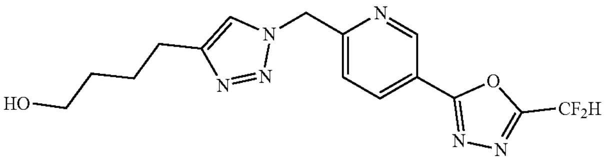 [SMILES: OCCCCc1cn(Cc2ccc(-c3nnc(C(F)F)o3)cn2)nn1] |
| 47 | 3835 | 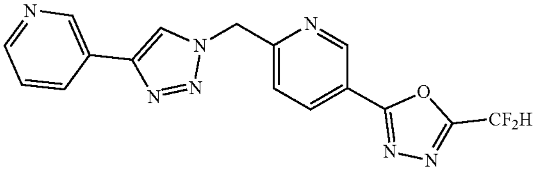 [SMILES: FC(F)c1nnc(-c2ccc(Cn3cc(-c4cccnc4)nn3)nc2)o1] |

TABLE 1-continued
| Example | Compound | Structure |
|---|---|---|
| 48 | 3837 | 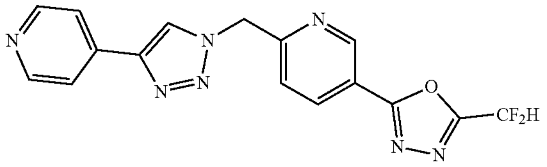 [SMILES: FC(F)c1nnc(-c2ccc(Cn3cc(-c4ccncc4)nn3)nc2)o1] |
| 49 | 3838 | 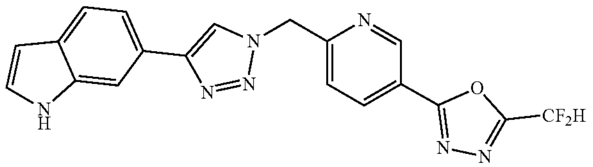 [SMILES: FC(F)c1nnc(-c2ccc(Cn3cc(-c4ccc5cc[nH]c5c4)nn3)nc2)o1] |
| 50 | 3839 | 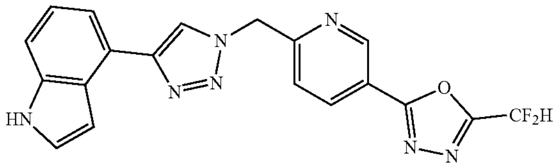 |
| 51 | 3840 | 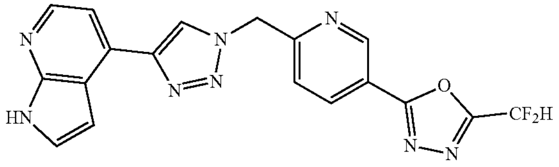 [SMILES: FC(F)c1nnc(-c2ccc(Cn3cc(-c4ccnc5[nH]ccc45)nn3)nc2)o1] |
| 52 | 3841 | 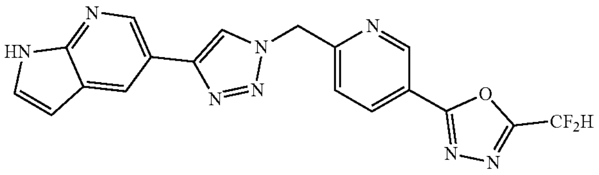 [SMILES: FC(F)c1nnc(-c2ccc(Cn3cc(-c4cnc5[nH]ccc5c4)nn3)nc2)o1] |
| 53 | 3842 | 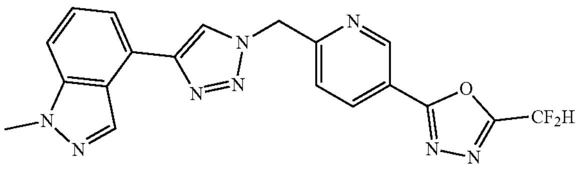 [SMILES: Cn1ncc2c(-c3cn(Cc4ccc(-c5nnc(C(F)F)o5)cn4)nn3)cccc21] |
| 54 | 3843 | 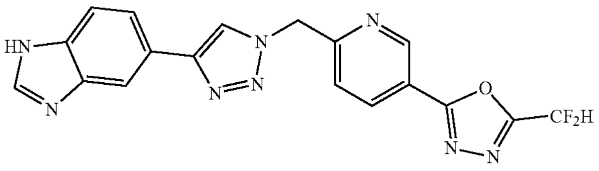 [SMILES: FC(F)c1nnc(-c2ccc(Cn3cc(-c4ccc5[nH]cnc5c4)nn3)nc2)o1] |
| 55 | 3844 | 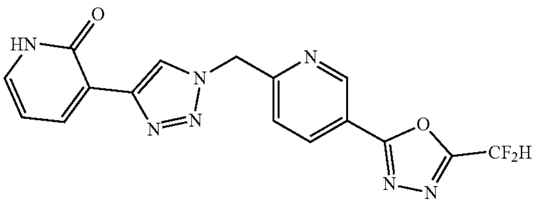 [SMILES: O=c1[nH]cccc1-c1cn(Cc2ccc(-c3nnc(C(F)F)o3)cn2)nn1] |

TABLE 1-continued
| Example | Compound | Structure |
| --- | --- | --- |
| 56 | 3845 | 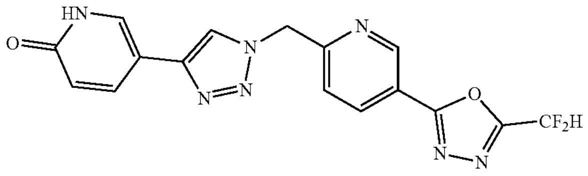 [SMILES: O=c1ccc(-c2cn(Cc3ccc(-c4nnc(C(F)F)o4)cn3)nn2)c[nH]1] |
| 57 | 3846 | 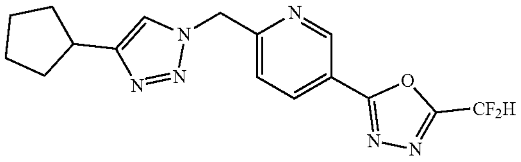 [SMILES: FC(F)c1nnc(-c2ccc(Cn3cc(C4CCCC4)nn3)nc2)o1] |
| 58 | 3853 | 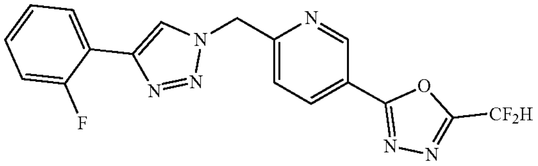 [SMILES: Fc1ccccc1-c1cn(Cc2ccc(-c3nnc(C(F)F)o3)cn2)nn1] |
| 59 | 3854 | 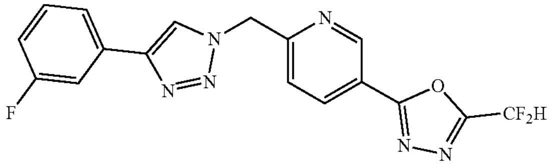 |
| 60 | 3855 | 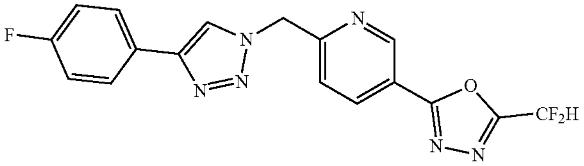 [SMILES: Fc1ccc(-c2cn(Cc3ccc(-c4nnc(C(F)F)o4)cn3)nn2)cc1] |
| 61 | 3856 | 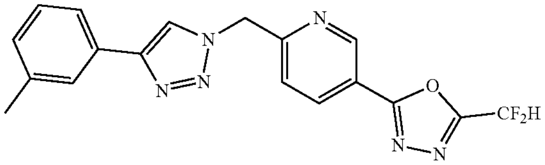 [SMILES: Cc1cccc(-c2cn(Cc3ccc(-c4nnc(C(F)F)o4)cn3)nn2)c1] |
| 62 | 3860 | 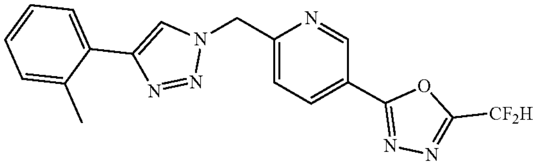 |
| 63 | 3861 | 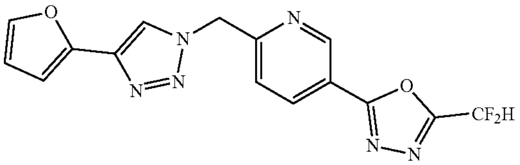 |

TABLE 1-continued
| Example | Compound | Structure |
| --- | --- | --- |
| 64 | 3866 | 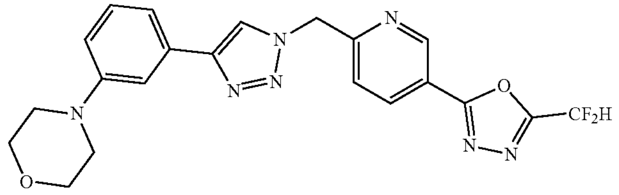 [SMILES: FC(F)c1nnc(-c2ccc(Cn3cc(-c4cccc(N5CCOCC5)c4)nn3)nc2)o1] |
| 65 | 3867 | 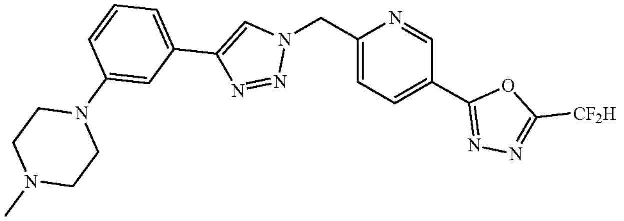 [SMILES: CN1CCN(c2cccc(-c3cn(Cc4ccc(-c5nnc(C(F)F)o5)cn4)nn3)c2)CC1] |
| 66 | 3879 | 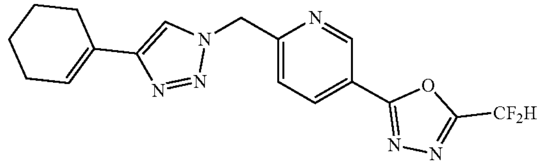 [SMILES: FC(F)c1nnc(-c2ccc(Cn3cc(C4=CCCCC4)nn3)nc2)o1] |
| 67 | 3880 | 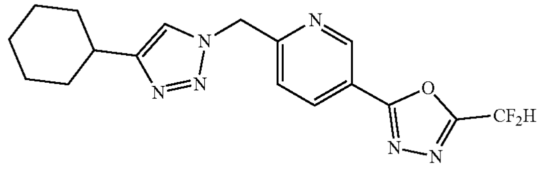 [SMILES: FC(F)c1nnc(-c2ccc(Cn3cc(C4CCCCC4)nn3)nc2)o1] |
| 68 | 3881 | 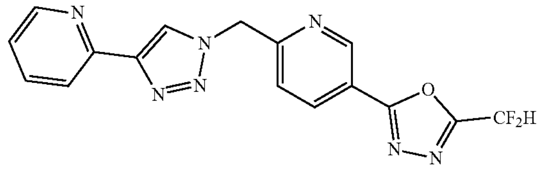 [SMILES: FC(F)c1nnc(-c2ccc(Cn3cc(-c4ccccn4)nn3)nc2)o1] |
| 69 | 3882 | 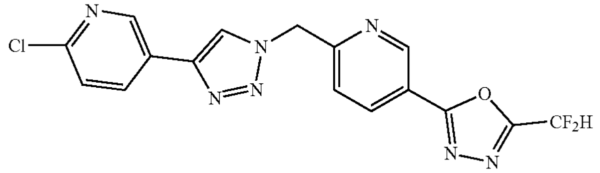 [SMILES: FC(F)c1nnc(-c2ccc(Cn3cc(-c4ccc(Cl)nc4)nn3)nc2)o1] |
| 70 | 3883 | 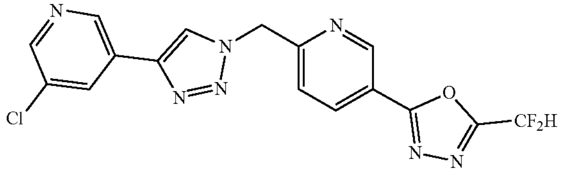 [SMILES: FC(F)c1nnc(-c2ccc(Cn3cc(-c4cncc(Cl)c4)nn3)nc2)o1] |
| 71 | 3884 | 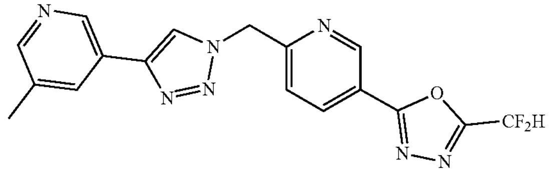 [SMILES: Cc1cncc(-c2cn(Cc3ccc(-c4nnc(C(F)F)o4)cn3)nn2)c1] |

TABLE 1-continued
| Example | Compound | Structure |
|---|---|---|
| 72 | 3885 | 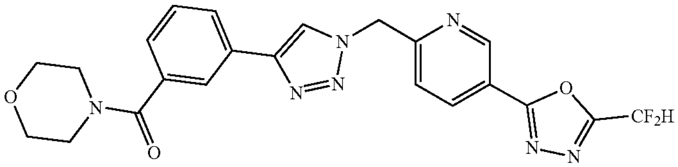 [SMILES: O=C(c1cccc(-c2cn(Cc3ccc(-c4nnc(C(F)F)o4)cn3)nn2)c1)N1CCOCC1] |
| 73 | 3886 | 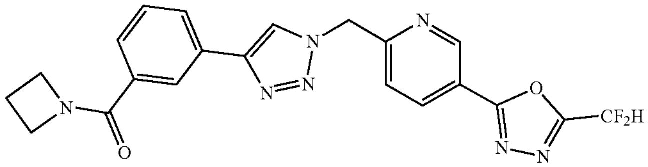 [SMILES: O=C(c1cccc(-c2cn(Cc3ccc(-c4nnc(C(F)F)o4)cn3)nn2)c1)N1CCC1] |
| 74 | 3887 | 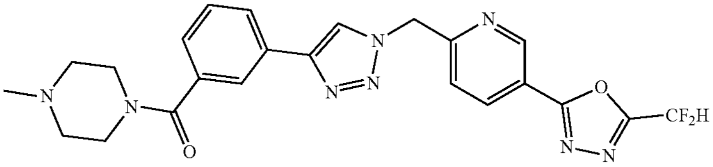 [SMILES: CN1CCN(C(=O)c2cccc(-c3cn(Cc4ccc(-c5nnc(C(F)F)o5)cn4)nn3)c2)CC1] |
| 75 | 3889 | 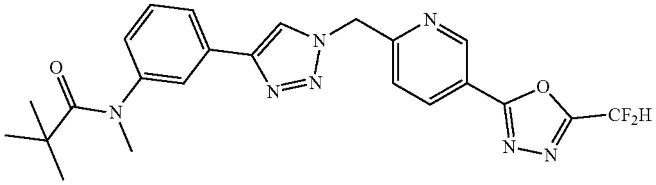 [SMILES: CN(C(=O)C(C)(C)C)c1cccc(-c2cn(Cc3ccc(-c4nnc(C(F)F)o4)cn3)nn2)c1] |
| 76 | 3890 | 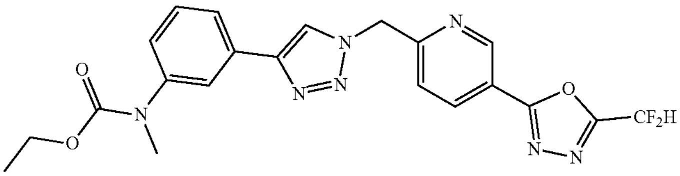 [SMILES: CCOC(=O)N(C)c1cccc(-c2cn(Cc3ccc(-c4nnc(C(F)F)o4)cn3)nn2)c1] |
| 77 | 3891 | 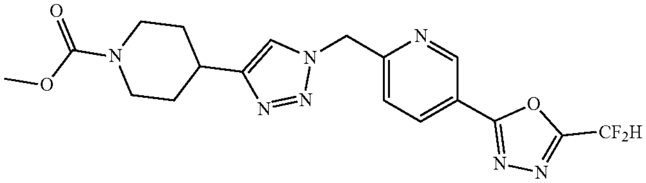 [SMILES: COC(=O)N1CCC(c2cn(Cc3ccc(-c4nnc(C(F)F)o4)cn3)nn2)CC1] |
| 78 | 3892 | 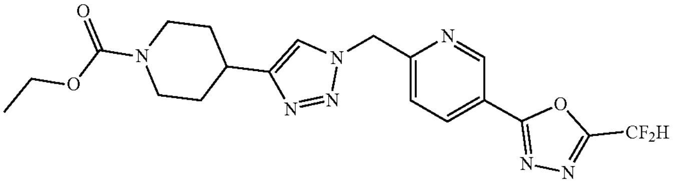 [SMILES: CCOC(=O)N1CCC(c2cn(Cc3ccc(-c4nnc(C(F)F)o4)cn3)nn2)CC1] |
| 79 | 3893 | 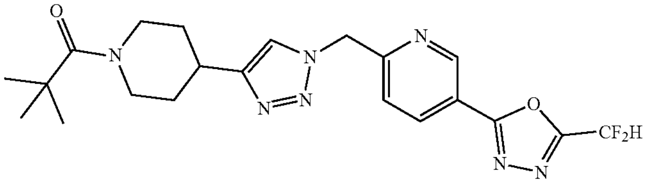 [SMILES: CC(C)(C)C(=O)N1CCC(c2cn(Cc3ccc(-c4nnc(C(F)F)o4)cn3)nn2)CC1] |

TABLE 1-continued
| Example | Compound | Structure |
| --- | --- | --- |
| 80 | 3894 | 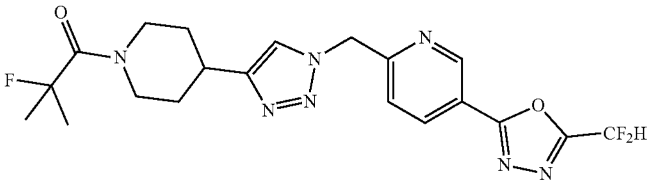 [SMILES: CC(C)(F)C(=O)N1CCC(c2cn(Cc3ccc(-c4nnc(C(F)F)o4)cn3)nn2)CC1] |
| 81 | 3895 | 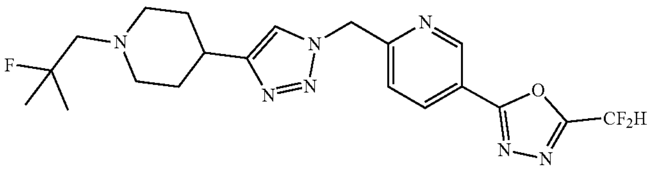 [SMILES: CC(C)(F)CN1CCC(c2cn(Cc3ccc(-c4nnc(C(F)F)o4)cn3)nn2)CC1] |
| 82 | 3896 | 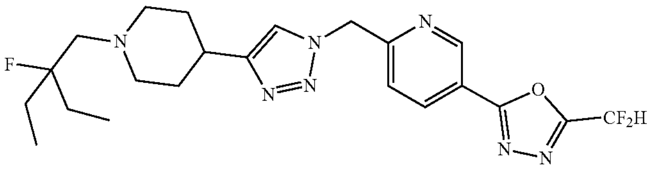 [SMILES: CCC(F)(CC)CN1CCC(c2cn(Cc3ccc(-c4nnc(C(F)F)o4)cn3)nn2)CC1] |
| 83 | 3902 | 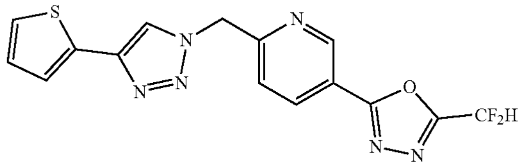 [SMILES: FC(F)c1nnc(-c2ccc(Cn3cc(-c4cccs4)nn3)nc2)o1] |
| 84 | 3914 | 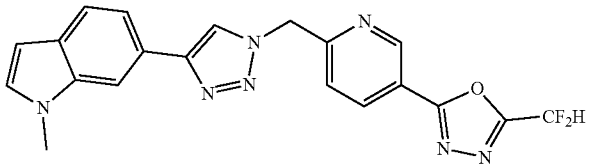 [SMILES: Cn1ccc2ccc(-c3cn(Cc4ccc(-c5nnc(C(F)F)o5)cn4)nn3)cc21] |
| 85 | 3915 | 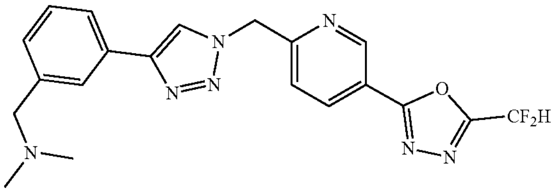 [SMILES: CN(C)Cc1cccc(-c2cn(Cc3ccc(-c4nnc(C(F)F)o4)cn3)nn2)c1] |
| 86 | 3916 | 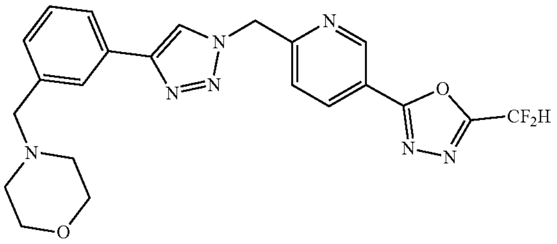 [SMILES: FC(F)c1nnc(-c2ccc(Cn3cc(-c4cccc(CN5CCOCC5)c4)nn3)nc2)o1] |

TABLE 1-continued
| Example | Compound | Structure |
|---|---|---|
| 87 | 3917 | 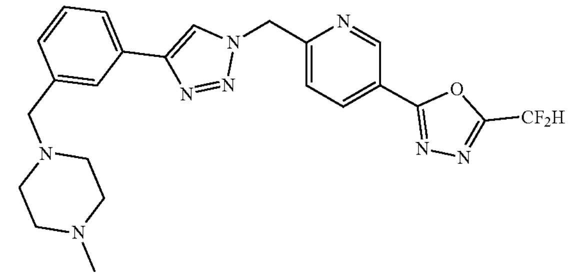 [SMILES: CN1CCN(Cc2cccc(-c3cn(Cc4ccc(-c5nnc(C(F)F)o5)cn4)nn3)c2)CC1] |
| 88 | 3918 | 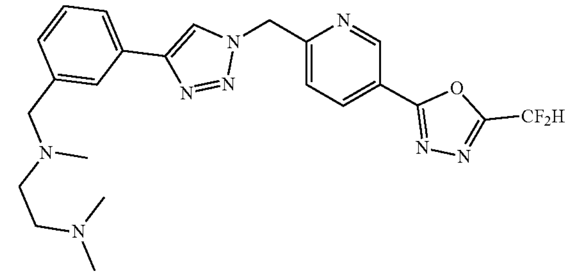 [SMILES: CN(C)CCN(C)Cc1cccc(-c2cn(Cc3ccc(-c4nnc(C(F)F)o4)cn3)nn2)c1] |
| 89 | 3919 | 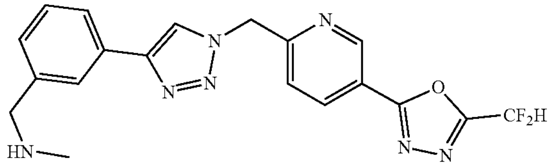 [SMILES: CNCc1cccc(-c2cn(Cc3ccc(-c4nnc(C(F)F)o4)cn3)nn2)c1] |
| 90 | 3925 | 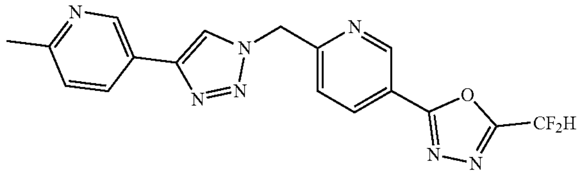 [SMILES: Cc1ccc(-c2cn(Cc3ccc(-c4nnc(C(F)F)o4)cn3)nn2)cn1] |
| 91 | 3926 | 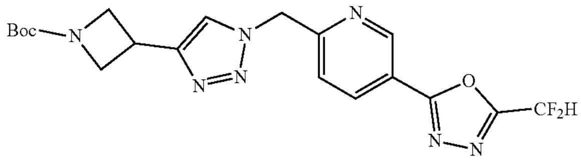 [SMILES: CC(C)(C)OC(=O)N1CC(c2cn(Cc3ccc(-c4nnc(C(F)F)o4)cn3)nn2)C1] |
| 92 | 3944 | 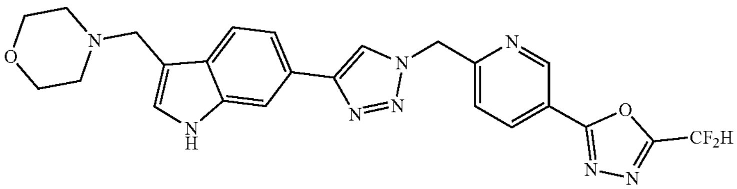 [SMILES: FC(F)c1nnc(-c2ccc(Cn3cc(-c4ccc5c(CN6CCOCC6)c[nH]c5c4)nn3)nc2)o1] |
| 93 | 3945 | 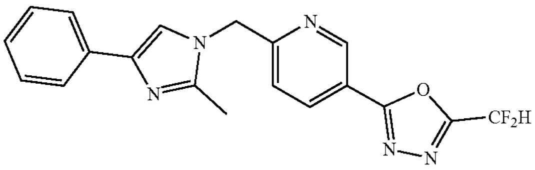 [SMILES: Cc1nc(-c2ccccc2)cn1Cc1ccc(-c2nnc(C(F)F)o2)cn1] |

TABLE 1-continued
| Example | Compound | Structure |
| --- | --- | --- |
| 94 | 3949 | 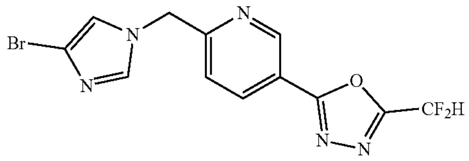 |
| 95 | 3950 | 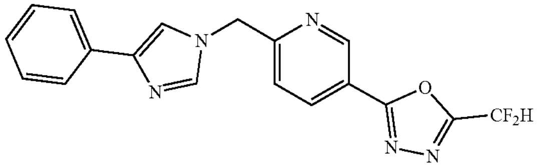 [SMILES: FC(F)c1nnc(-c2ccc(Cn3cnc(-c4ccccc4)c3)nc2)o1] |
| 96 | 3951 | 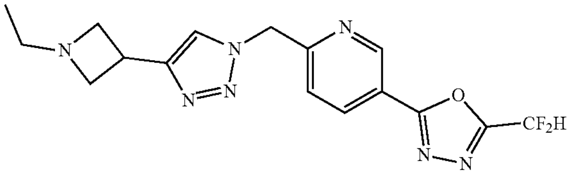 [SMILES: CCN1CC(c2cn(Cc3ccc(-c4nnc(C(F)F)o4)cn3)nn2)C1] |
| 97 | 3952 | 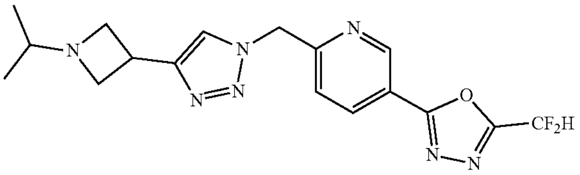 [SMILES: CC(C)N1CC(c2cn(Cc3ccc(-c4nnc(C(F)F)o4)cn3)nn2)C1] |
| 98 | 3953 | 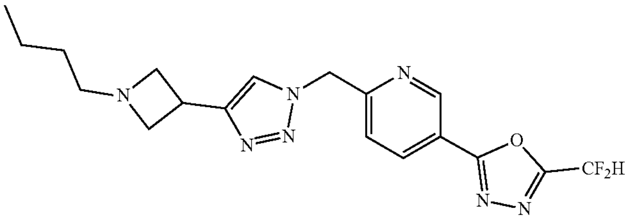 [SMILES: CCCCN1CC(c2cn(Cc3ccc(-c4nnc(C(F)F)o4)cn3)nn2)C1] |
| 99 | 3954 | 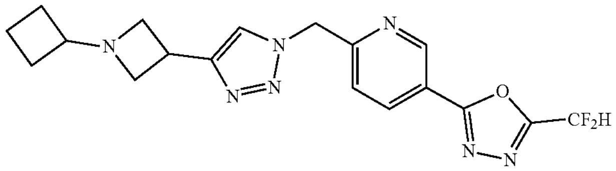 [SMILES: FC(F)c1nnc(-c2ccc(Cn3cc(C4CN(C5CCC5)C4)nn3)nc2)o1] |
| 100 | 3955 | 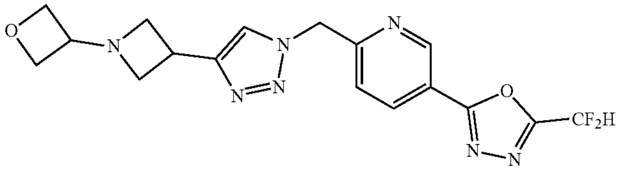 [SMILES: FC(F)c1nnc(-c2ccc(Cn3cc(C4CN(C5COC5)C4)nn3)nc2)o1] |
| 101 | 3956 | 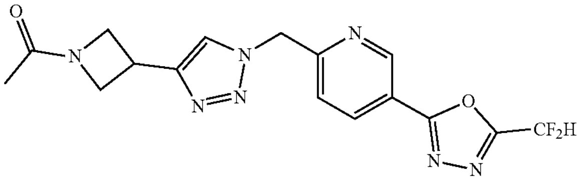 [SMILES: CC(=O)N1CC(c2cn(Cc3ccc(-c4nnc(C(F)F)o4)cn3)nn2)C1] |

TABLE 1-continued
| Example | Compound | Structure |
|---|---|---|
| 102 | 3957 | 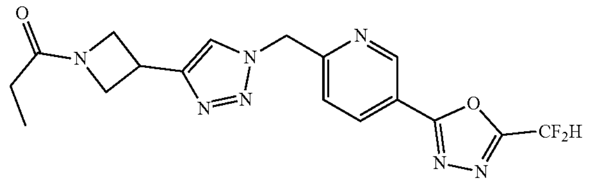 [SMILES: CCC(=O)N1CC(c2cn(Cc3ccc(-c4nnc(C(F)F)o4)cn3)nn2)C1] |
| 103 | 3958 | 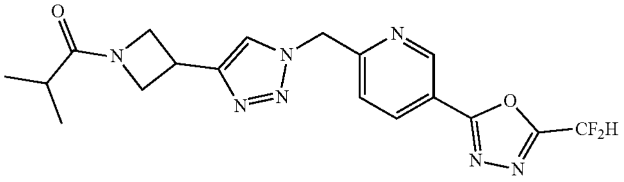 [SMILES: CC(C)C(=O)N1CC(c2cn(Cc3ccc(-c4nnc(C(F)F)o4)cn3)nn2)C1] |
| 104 | 3959 | 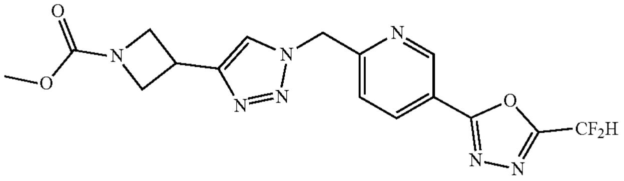 [SMILES: COC(=O)N1CC(c2cn(Cc3ccc(-c4nnc(C(F)F)o4)cn3)nn2)C1] |
| 105 | 3960 | 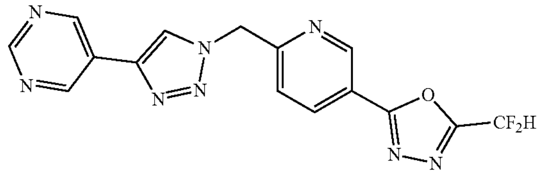 [SMILES: FC(F)c1nnc(-c2ccc(Cn3cc(-c4cncnc4)nn3)nc2)o1] |
| 106 | 3961 | 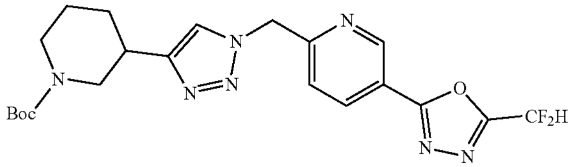 [SMILES: CC(C)(C)OC(=O)N1CCCC(c2cn(Cc3ccc(-c4nnc(C(F)F)o4)cn3)nn2)C1] |
| 107 | 3962 | 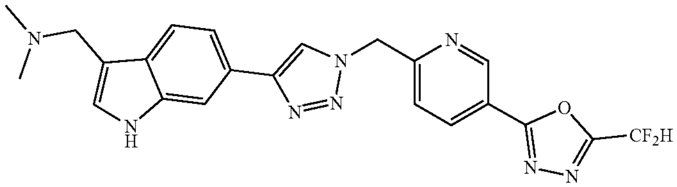 [SMILES: CN(C)Cc1c[nH]c2cc(-c3cn(Cc4ccc(-c5nnc(C(F)F)o5)cn4)nn3)ccc12] |
| 108 | 3963 | 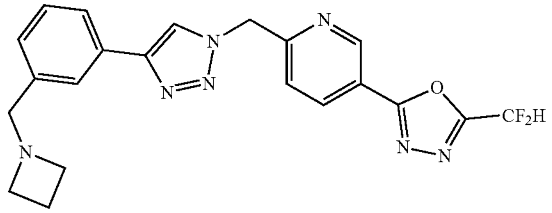 [SMILES: FC(F)c1nnc(-c2ccc(Cn3cc(-c4cccc(CN5CCC5)c4)nn3)nc2)o1] |

TABLE 1-continued
| Example | Compound | Structure |
| --- | --- | --- |
| 109 | 3964 | 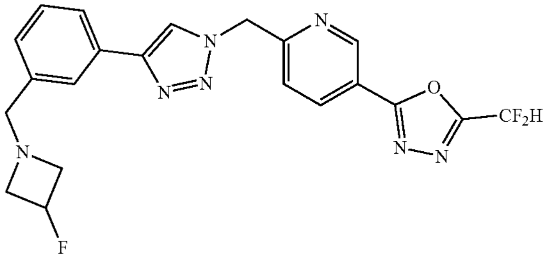 [SMILES: FC1CN(Cc2cccc(-c3cn(Cc4ccc(-c5nnc(C(F)F)o5)cn4)nn3)c2)C1] |
| 110 | 3965 | 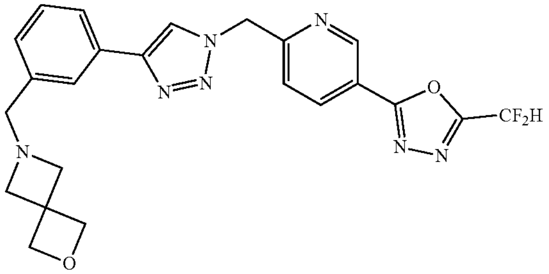 [SMILES: FC(F)c1nnc(-c2ccc(Cn3cc(-c4cccc(CN5CC6(COC6)C5)c4)nn3)nc2)o1] |
| 111 | 3966 | 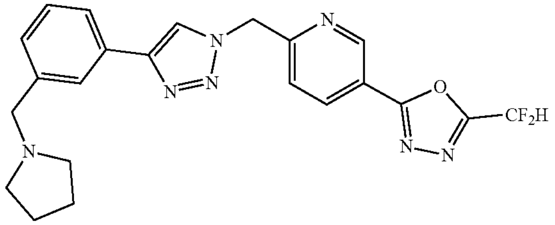 [SMILES: FC(F)c1nnc(-c2ccc(Cn3cc(-c4cccc(CN5CCCC5)c4)nn3)nc2)o1] |
| 112 | 3980 | 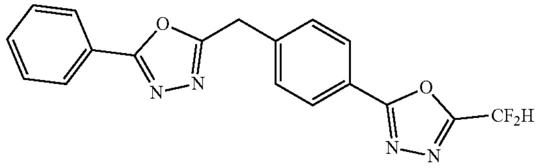 [SMILES: FC(F)c1nnc(-c2ccc(Cc3nnc(-c4ccccc4)o3)cc2)o1] |
| 113 | 3981 | 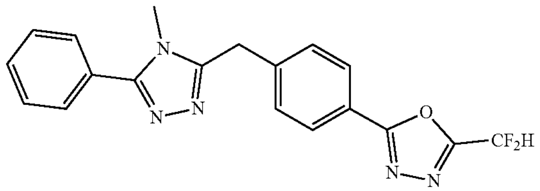 [SMILES: Cn1c(Cc2ccc(-c3nnc(C(F)F)o3)cc2)nnc1-c1ccccc1] |
| 114 | 3985 | 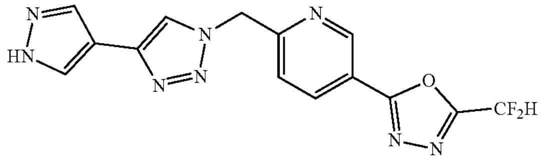 [SMILES: FC(F)c1nnc(-c2ccc(Cn3cc(-c4cn[nH]c4)nn3)nc2)o1] |
| 115 | 3986 | 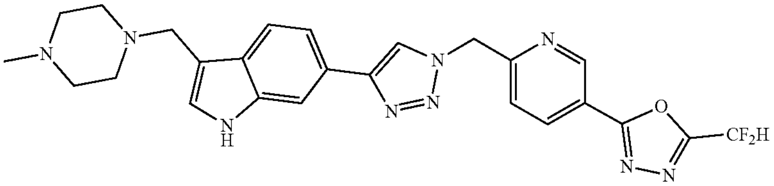 [SMILES: CN1CCN(Cc2c[nH]c3cc(-c4cn(Cc5ccc(-c6nnc(C(F)F)o6)cn5)nn4)ccc23)CC1] |

TABLE 1-continued
| Example | Compound | Structure |
| --- | --- | --- |
| 116 | 3987 | 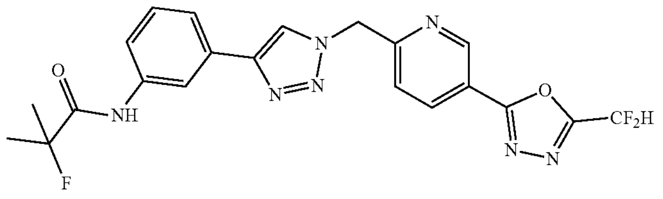 [SMILES: CC(C)(F)C(=O)Nc1cccc(-c2cn(Cc3ccc(-c4nnc(C(F)F)o4)cn3)nn2)c1] |
| 117 | 3988 | 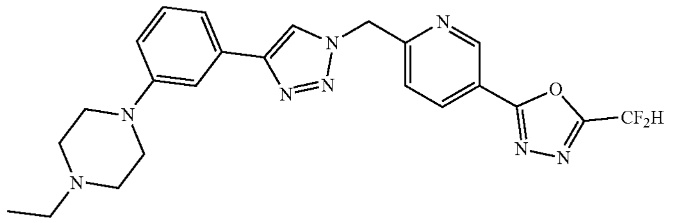 [SMILES: CCN1CCN(c2cccc(-c3cn(Cc4ccc(-c5nnc(C(F)F)o5)cn4)nn3)c2)CC1] |
| 118 | 3989 | 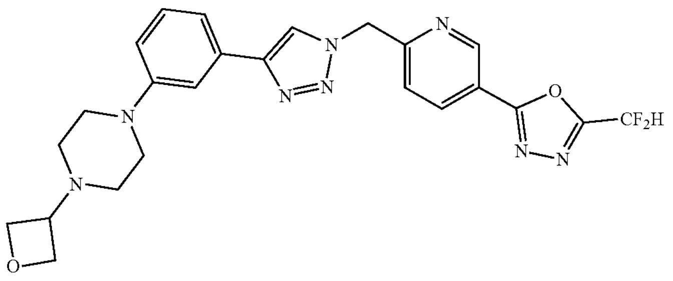 [SMILES: FC(F)c1nnc(-c2ccc(Cn3cc(-c4cccc(N5CCN(C6COC6)CC5)c4)nn3)nc2)o1] |
| 119 | 3990 | 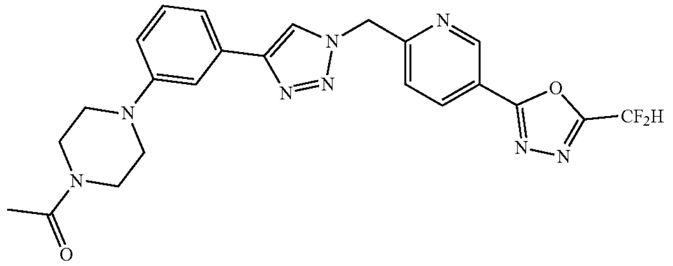 [SMILES: CC(=O)N1CCN(c2cccc(-c3cn(Cc4ccc(-c5nnc(C(F)F)o5)cn4)nn3)c2)CC1] |
| 120 | 3991 | 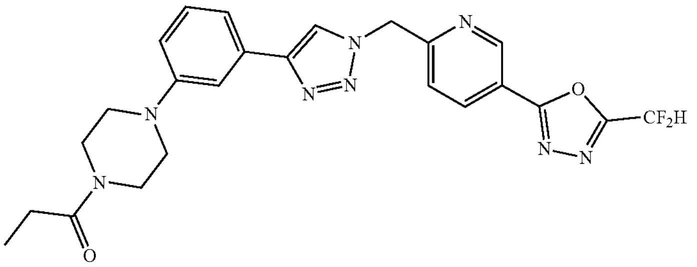 [SMILES: CCC(=O)N1CCN(c2cccc(-c3cn(Cc4ccc(-c5nnc(C(F)F)o5)cn4)nn3)c2)CC1] |
| 121 | 3999 | 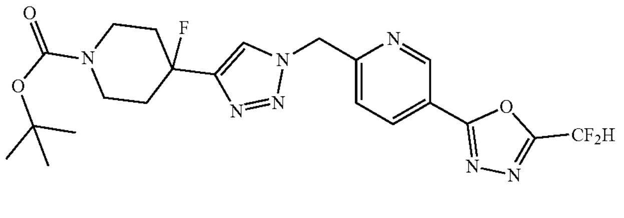 [SMILES: CC(C)(C)OC(=O)N1CCC(F)(c2cn(Cc3ccc(-c4nnc(C(F)F)o4)cn3)nn2)CC1] |

TABLE 1-continued
| Example | Compound | Structure |
| --- | --- | --- |
| 122 | 4000 | 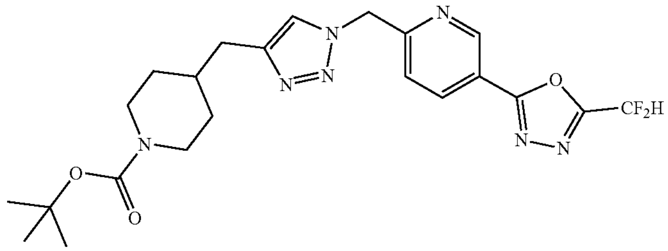 [SMILES: CC(C)(C)OC(=O)N1CCC(Cc2cn(Cc3ccc(-c4nnc(C(F)F)o4)cn3)nn2)CC1] |
| 123 | 4001 | 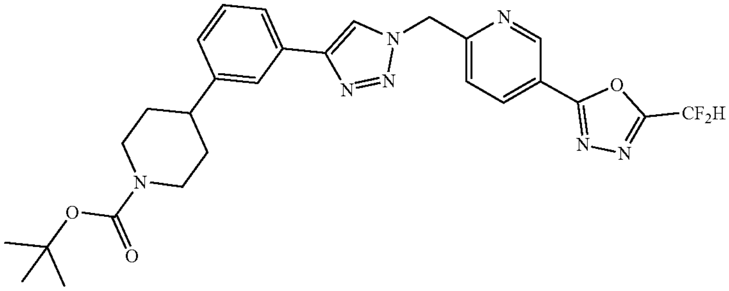 [SMILES: CC(C)(C)OC(=O)N1CCC(c2cccc(-c3cn(Cc4ccc(-c5nnc(C(F)F)o5)cn4)nn3)c2)CC1] |
| 124 | 4002 | 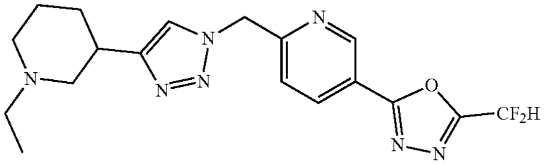 [SMILES: CCN1CCCC(c2cn(Cc3ccc(-c4nnc(C(F)F)o4)cn3)nn2)C1] |
| 125 | 4003 | 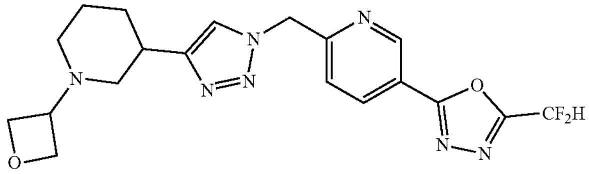 [SMILES: FC(F)c1nnc(-c2ccc(Cn3cc(C4CCCN(C5COC5)C4)nn3)nc2)o1] |
| 126 | 4004 | 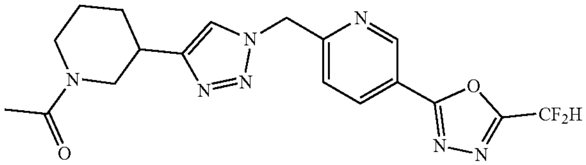 [SMILES: CC(=O)N1CCCC(c2cn(Cc3ccc(-c4nnc(C(F)F)o4)cn3)nn2)C1] |
| 127 | 4005 | 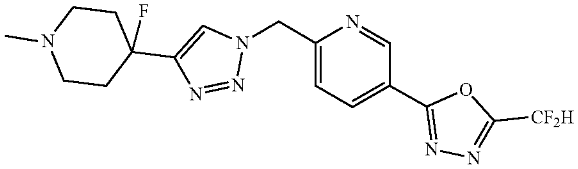 [SMILES: CN1CCC(F)(c2cn(Cc3ccc(-c4nnc(C(F)F)o4)cn3)nn2)CC1] |
| 128 | 4006 | 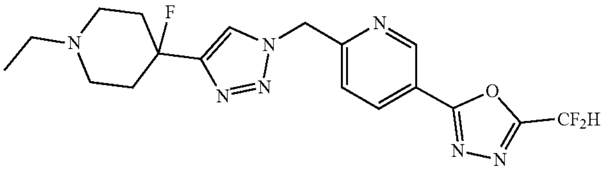 [SMILES: CCN1CCC(F)(c2cn(Cc3ccc(-c4nnc(C(F)F)o4)cn3)nn2)CC1] |

TABLE 1-continued
| Example | Compound | Structure |
|---|---|---|
| 129 | 4007 | 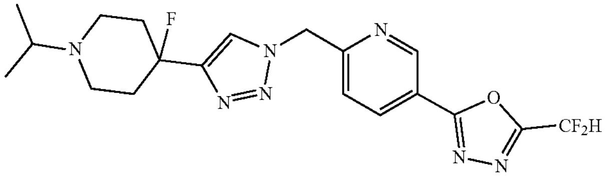 [SMILES: CC(C)N1CCC(F)(c2cn(Cc3ccc(-c4nnc(C(F)F)o4)cn3)nn2)CC1] |
| 130 | 4008 | 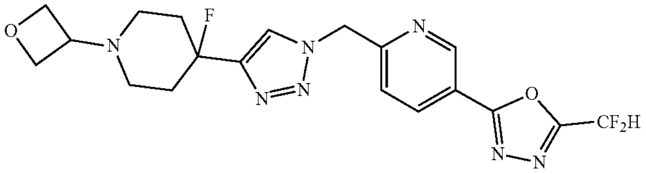 [SMILES: FC(F)c1nnc(-c2ccc(Cn3cc(C4(F)CCN(C5COC5)CC4)nn3)nc2)o1] |
| 131 | 4009 | 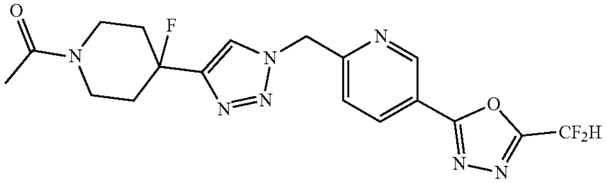 [SMILES: CC(=O)N1CCC(F)(c2cn(Cc3ccc(-c4nnc(C(F)F)o4)cn3)nn2)CC1] |
| 132 | 4010 | 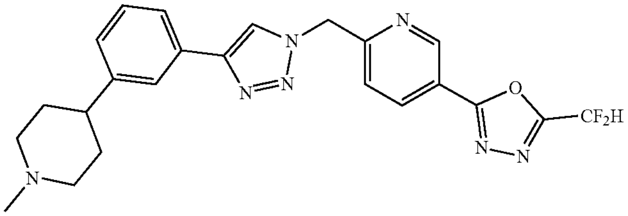 [SMILES: CN1CCC(c2cccc(-c3cn(Cc4ccc(-c5nnc(C(F)F)o5)cn4)nn3)c2)CC1] |
| 133 | 4011 | 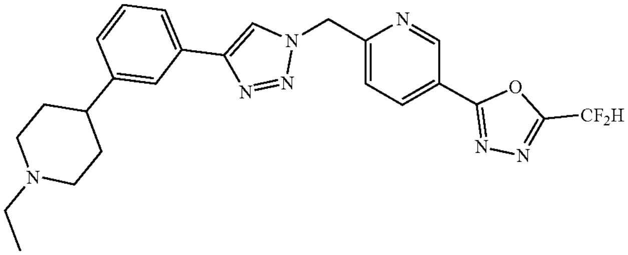 [SMILES: CCN1CCC(c2cccc(-c3cn(Cc4ccc(-c5nnc(C(F)F)o5)cn4)nn3)c2)CC1] |
| 134 | 4012 | 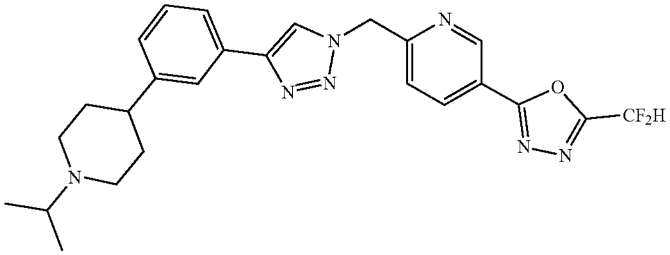 [SMILES: CC(C)N1CCC(c2cccc(-c3cn(Cc4ccc(-c5nnc(C(F)F)o5)cn4)nn3)c2)CC1] |
| 135 | 4013 | 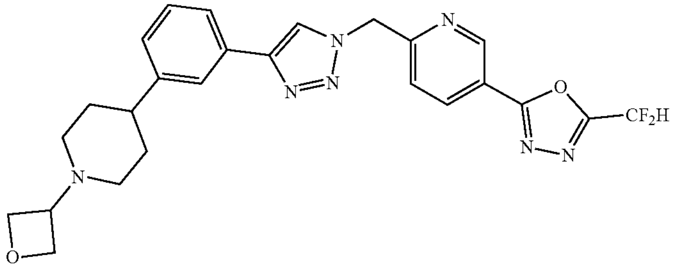 [SMILES: FC(F)c1nnc(-c2ccc(Cn3cc(-c4cccc(C5CCN(C6COC6)CC5)c4)nn3)nc2)o1] |

TABLE 1-continued
| Example | Compound | Structure |
|---|---|---|
| 136 | 4014 | 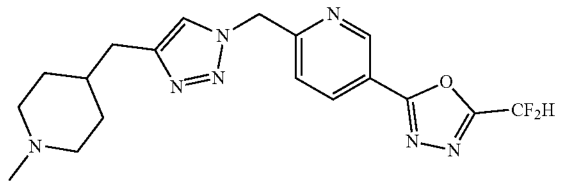 [SMILES: CN1CCC(Cc2cn(Cc3ccc(-c4nnc(C(F)F)o4)cn3)nn2)CC1] |
| 137 | 4015 | 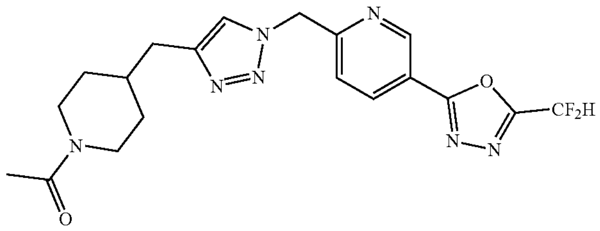 [SMILES: CC(=O)N1CCC(Cc2cn(Cc3ccc(-c4nnc(C(F)F)o4)cn3)nn2)CC1] |
| 138 | 4023 | 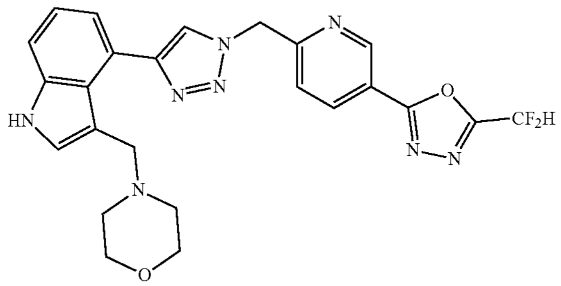 [SMILES: FC(F)c1nnc(-c2ccc(Cn3cc(-c4cccc5[nH]cc(CN6CCOCC6)c45)nn3)nc2)o1] |
| 139 | 4026 | 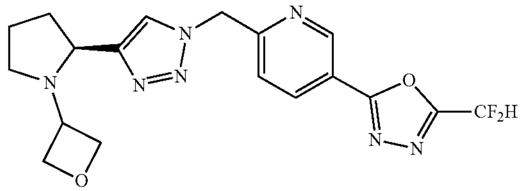 [SMILES: FC(F)c1nnc(-c2ccc(Cn3cc([C@@H]4CCCN4C4COC4)nn3)nc2)o1] |
| 140 | 4027 | 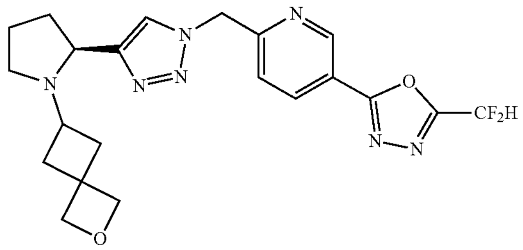 [SMILES: FC(F)c1nnc(-c2ccc(Cn3cc([C@@H]4CCCN4C4CC5(COC5)C4)nn3)nc2)o1] |
| 141 | 4028 | 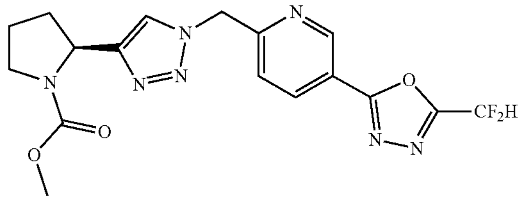 [SMILES: COC(=O)N1CCC[C@H]1c1cn(Cc2ccc(-c3nnc(C(F)F)o3)cn2)nn1] |
| 142 | 4029 | 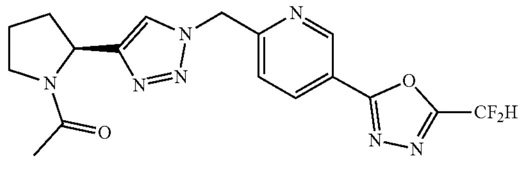 [SMILES: CC(=O)N1CCC[C@H]1c1cn(Cc2ccc(-c3nnc(C(F)F)o3)cn2)nn1] |

TABLE 1-continued
| Example | Compound | Structure |
| --- | --- | --- |
| 143 | 4051 | 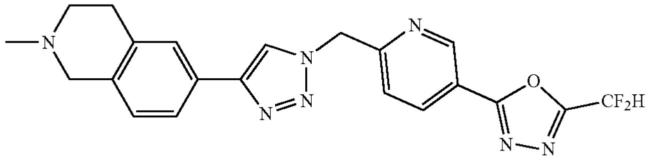 [SMILES: CN1CCc2cc(-c3cn(Cc4ccc(-c5nnc(C(F)F)o5)cn4)nn3)ccc2C1] |
| 144 | 4052 | 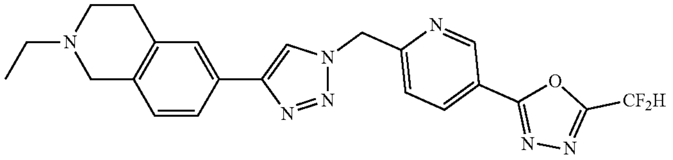 [SMILES: CCN1CCc2cc(-c3cn(Cc4ccc(-c5nnc(C(F)F)o5)cn4)nn3)ccc2C1] |
| 145 | 4053 | 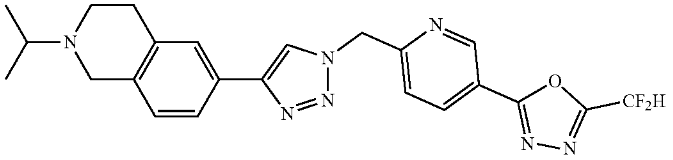 [SMILES: CC(C)N1CCc2cc(-c3cn(Cc4ccc(-c5nnc(C(F)F)o5)cn4)nn3)ccc2C1] |
| 146 | 4054 | 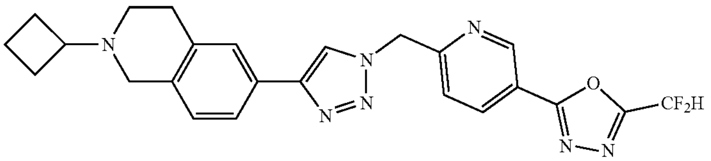 [SMILES: FC(F)c1nnc(-c2ccc(Cn3cc(-c4ccc5c(c4)CCN(C4CCC4)C5)nn3)nc2)o1] |
| 147 | 4055 | 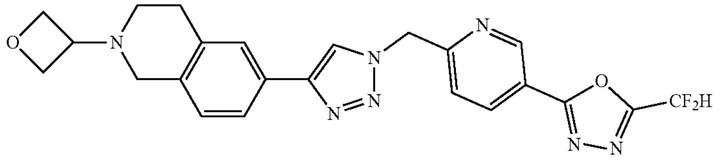 [SMILES: FC(F)c1nnc(-c2ccc(Cn3cc(-c4ccc5c(c4)CCN(C4COC4)C5)nn3)nc2)o1] |
| 148 | 4070 | 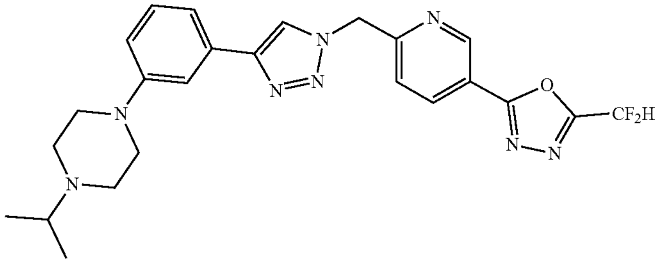 [SMILES: CC(C)N1CCN(c2cccc(-c3cn(Cc4ccc(-c5nnc(C(F)F)o5)cn4)nn3)c2)CC1] |
| 149 | 4071 | 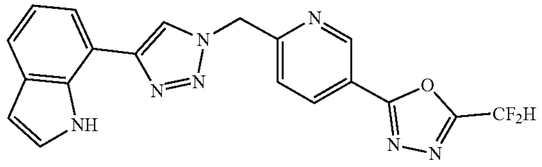 [SMILES: FC(F)c1nnc(-c2ccc(Cn3cc(-c4cccc5cc[nH]c45)nn3)nc2)o1] |
| 150 | 4072 | 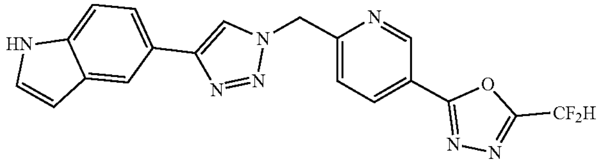 [SMILES: FC(F)c1nnc(-c2ccc(Cn3cc(-c4ccc5[nH]ccc5c4)nn3)nc2)o1] |

TABLE 1-continued
| Example | Compound | Structure |
| --- | --- | --- |
| 151 | 4073 | 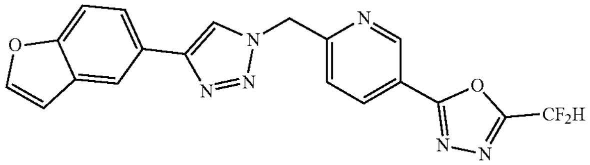 |
| 152 | 4074 | 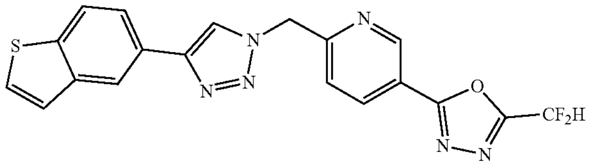 |
| 153 | 4075 | 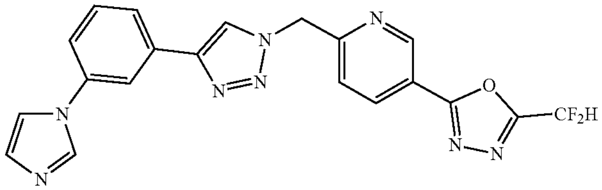 [SMILES: FC(F)c1nnc(-c2ccc(Cn3cc(-c4cccc(-n5ccnc5)c4)nn3)nc2)o1] |
| 154 | 4076 | 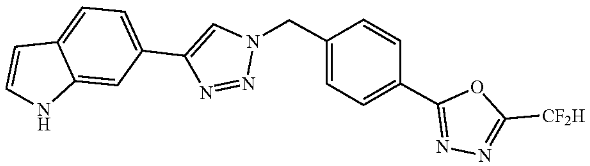 [SMILES: FC(F)c1nnc(-c2ccc(Cn3cc(-c4ccc5cc[nH]c5c4)nn3)cc2)o1] |
| 155 | 4077 | 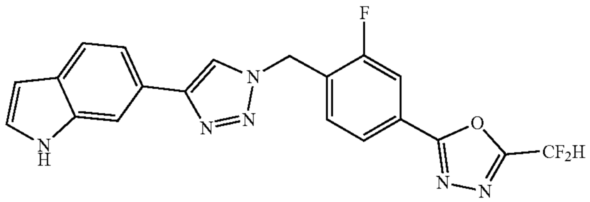 [SMILES: Fc1cc(-c2nnc(C(F)F)o2)ccc1Cn1cc(-c2ccc3cc[nH]c3c2)nn1] |
| 156 | 4078 | 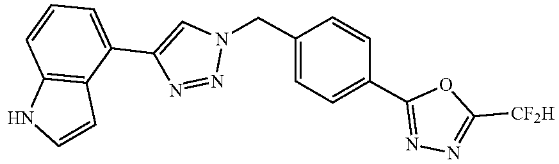 [SMILES: FC(F)c1nnc(-c2ccc(Cn3cc(-c4cccc5[nH]ccc45)nn3)cc2)o1] |
| 157 | 4079 | 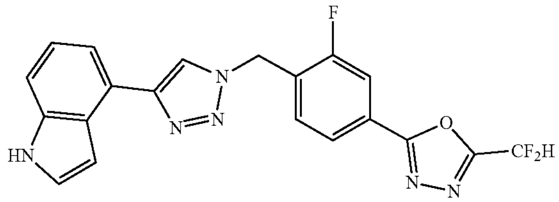 [SMILES: Fc1cc(-c2nnc(C(F)F)o2)ccc1Cn1cc(-c2cccc3[nH]ccc23)nn1] |
| 158 | 4080 | 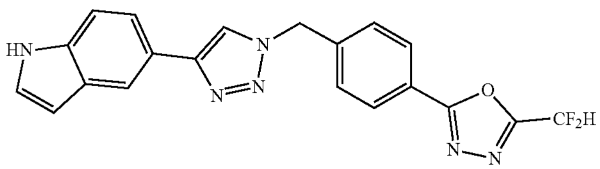 |

TABLE 1-continued
| Example | Compound | Structure |
|---|---|---|
| 159 | 4081 | 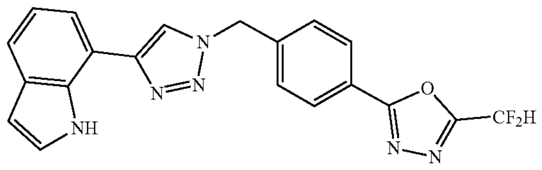 [SMILES: FC(F)c1nnc(-c2ccc(Cn3cc(-c4cccc5cc[nH]c45)nn3)cc2)o1] |
| 160 | 4082 | 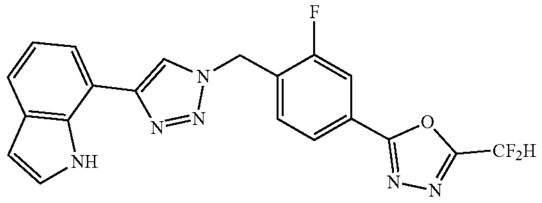 [SMILES: Fc1cc(-c2nnc(C(F)F)o2)ccc1Cn1cc(-c2cccc3cc[nH]c23)nn1] |
| 161 | 4104 | 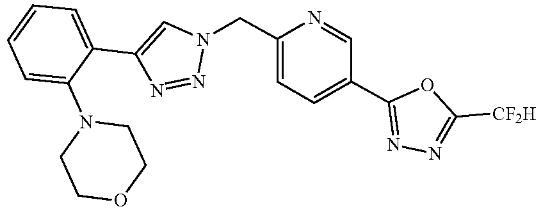 [SMILES: FC(F)c1nnc(-c2ccc(Cn3cc(-c4ccccc4N4CCOCC4)nn3)nc2)o1] |
| 162 | 4105 | 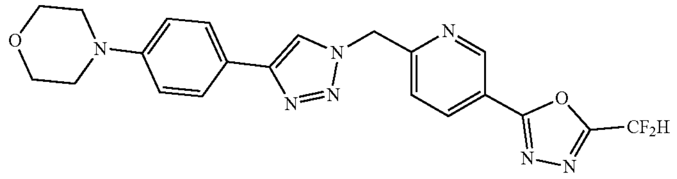 [SMILES: FC(F)c1nnc(-c2ccc(Cn3cc(-c4ccc(N5CCOCC5)cc4)nn3)nc2)o1] |
| 163 | 4106 | 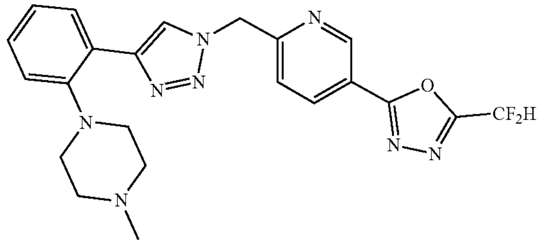 [SMILES: CN1CCN(c2ccccc2-c2cn(Cc3ccc(-c4nnc(C(F)F)o4)cn3)nn2)CC1] |
| 164 | 4107 | 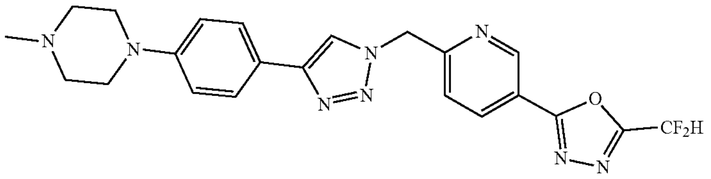 [SMILES: CN1CCN(c2ccc(-c3cn(Cc4ccc(-c5nnc(C(F)F)o5)cn4)nn3)cc2)CC1] |
| 165 | 4108 | 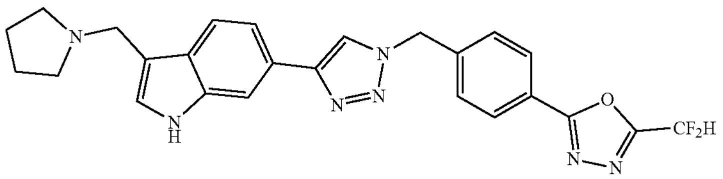 |

TABLE 1-continued
| Example | Compound | Structure |
| --- | --- | --- |
| 166 | 4109 | 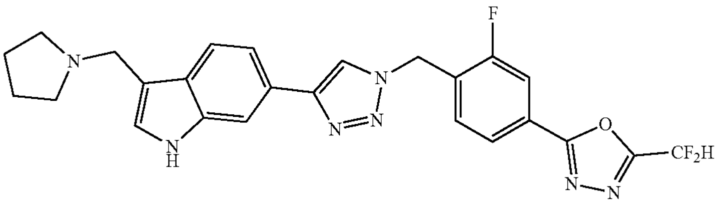 [SMILES: Fc1cc(-c2nnc(C(F)F)o2)ccc1Cn1cc(-c2ccc3c(CN4CCCC4)c[nH]c3c2)nn1] |
| 167 | 4110 | 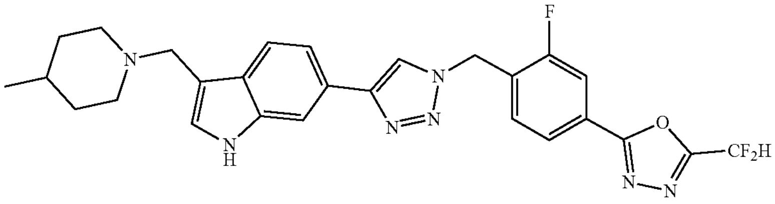 [SMILES: CC1CCN(Cc2c[nH]c3cc(-c4cn(Cc5ccc(-c6nnc(C(F)F)o6)cc5F)nn4)ccc23)CC1] |
| 168 | 4111 | 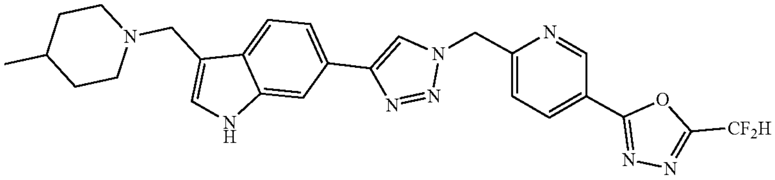 [SMILES: CC1CCN(Cc2c[nH]c3cc(-c4cn(Cc5ccc(-c6nnc(C(F)F)o6)cn5)nn4)ccc23)CC1] |
| 169 | 4112 | 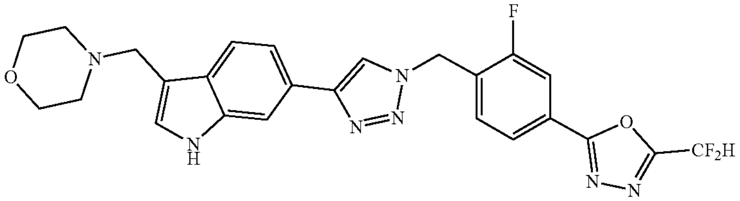 [SMILES: Fc1cc(-c2nnc(C(F)F)o2)ccc1Cn1cc(-c2ccc3c(CN4CCOCC4)c[nH]c3c2)nn1] |
| 170 | 4133 | 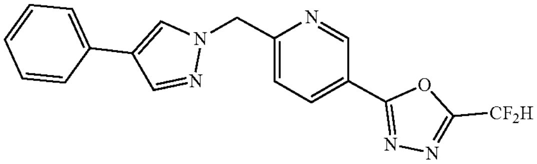 [SMILES: FC(F)c1nnc(-c2ccc(Cn3cc(-c4ccccc4)cn3)nc2)o1] |
| 171 | 4134 | 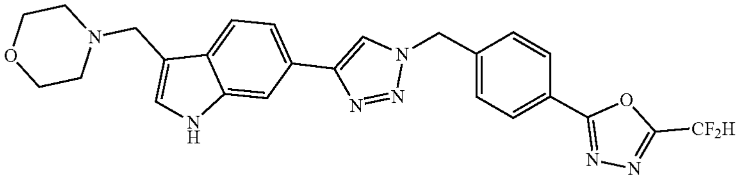 [SMILES: FC(F)c1nnc(-c2ccc(Cn3cc(-c4ccc5c(CN6CCOCC6)c[nH]c5c4)nn3)cc2)o1] |
| 172 | 4135 | 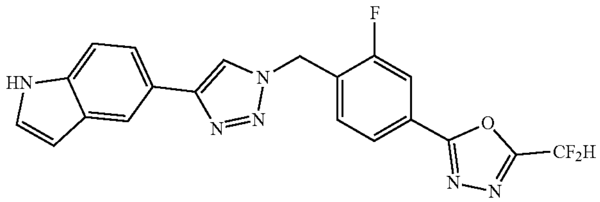 [SMILES: Fc1cc(-c2nnc(C(F)F)o2)ccc1Cn1cc(-c2ccc3[nH]ccc3c2)nn1] |
| 173 | 4136 | 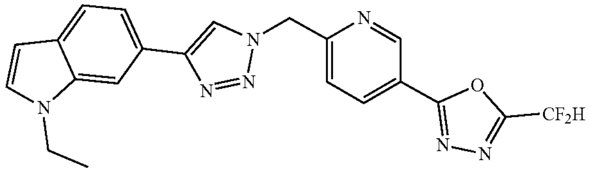 [SMILES: CCn1ccc2ccc(-c3cn(Cc4ccc(-c5nnc(C(F)F)o5)cn4)nn3)cc21] |

TABLE 1-continued
| Example | Compound | Structure |
|---|---|---|
| 174 | 4178 | 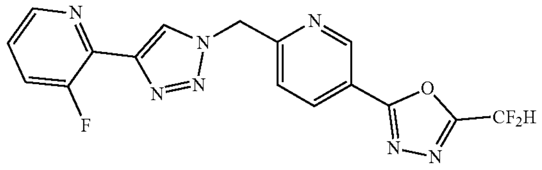 [SMILES: Fc1cccnc1-c1cn(Cc2ccc(-c3nnc(C(F)F)o3)cn2)nn1] |
| 175 | 4179 | 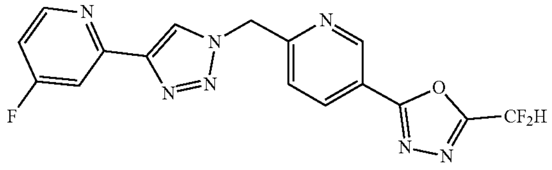 [SMILES: Fc1ccnc(-c2cn(Cc3ccc(-c4nnc(C(F)F)o4)cn3)nn2)c1] |
| 176 | 4180 | 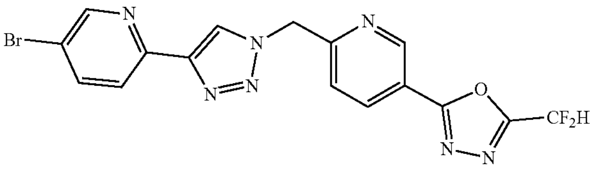 [SMILES: FC(F)c1nnc(-c2ccc(Cn3cc(-c4ccc(Br)cn4)nn3)nc2)o1] |
| 177 | 4181 | 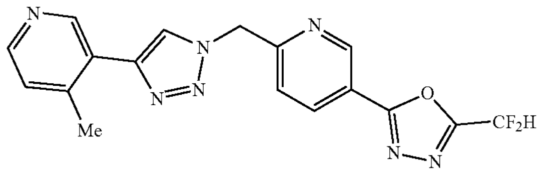 [SMILES: Cc1ccncc1-c1cn(Cc2ccc(-c3nnc(C(F)F)o3)cn2)nn1] |
| 178 | 4182 | 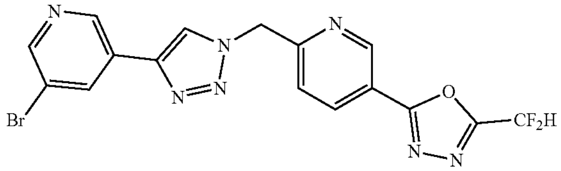 [SMILES: FC(F)c1nnc(-c2ccc(Cn3cc(-c4cncc(Br)c4)nn3)nc2)o1] |
| 179 | 4183 | 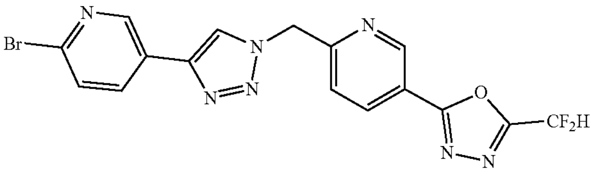 [SMILES: FC(F)c1nnc(-c2ccc(Cn3cc(-c4ccc(Br)nc4)nn3)nc2)o1] |
| 180 | 4184 | 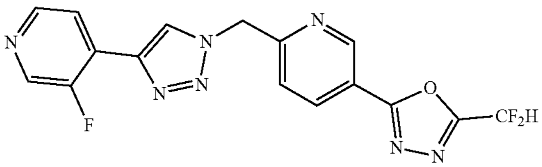 [SMILES: Fc1cnccc1-c1cn(Cc2ccc(-c3nnc(C(F)F)o3)cn2)nn1] |
| 181 | 4185 | 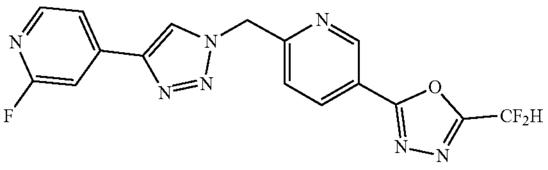 [SMILES: Fc1cc(-c2cn(Cc3ccc(-c4nnc(C(F)F)o4)cn3)nn2)ccn1] |

TABLE 1-continued
| Example | Compound | Structure |
|---|---|---|
| 182 | 4186 | 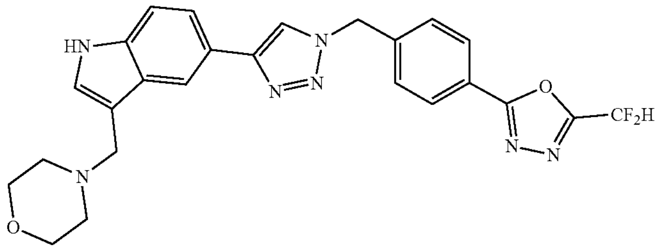 [SMILES: FC(F)c1nnc(-c2ccc(Cn3cc(-c4ccc5[nH]cc(CN6CCOCC6)c5c4)nn3)cc2)o1] |
| 183 | 4187 | 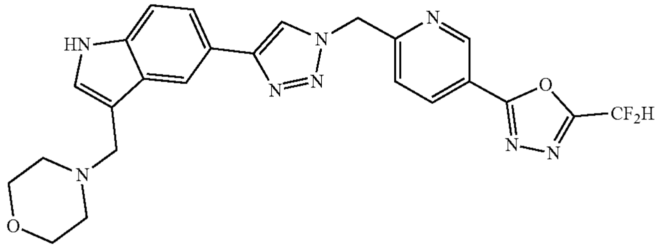 [SMILES: FC(F)c1nnc(-c2ccc(Cn3cc(-c4ccc5[nH]cc(CN6CCOCC6)c5c4)nn3)nc2)o1] |
| 184 | 4208 | 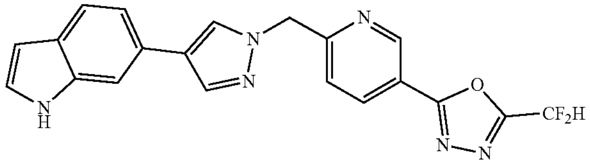 [SMILES: FC(F)c1nnc(-c2ccc(Cn3cc(-c4ccc5cc[nH]c5c4)cn3)nc2)o1] |
| 185 | 4209 | 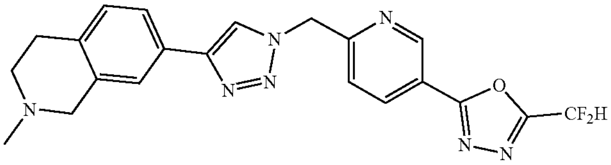 [SMILES: CN1CCc2ccc(-c3cn(Cc4ccc(-c5nnc(C(F)F)o5)cn4)nn3)cc2C1] |
| 186 | 4210 | 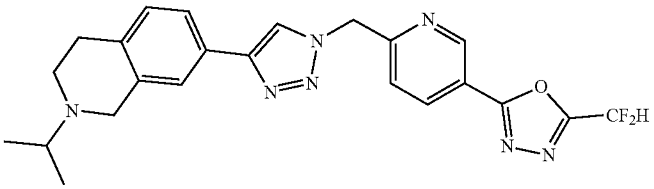 [SMILES: CC(C)N1CCc2ccc(-c3cn(Cc4ccc(-c5nnc(C(F)F)o5)cn4)nn3)cc2C1] |
| 187 | 4211 | 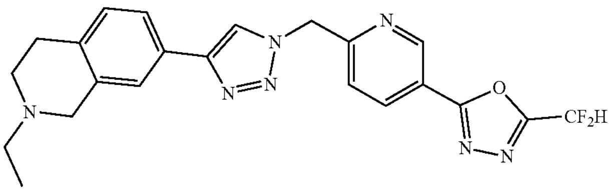 [SMILES: CCN1CCc2ccc(-c3cn(Cc4ccc(-c5nnc(C(F)F)o5)cn4)nn3)cc2C1] |
| 188 | 4212 | 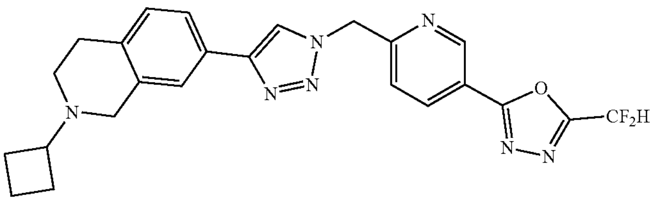 [SMILES: FC(F)c1nnc(-c2ccc(Cn3cc(-c4ccc5c(c4)CN(C4CCC4)CC5)nn3)nc2)o1] |

TABLE 1-continued
| Example | Compound | Structure |
|---|---|---|
| 189 | 4213 | 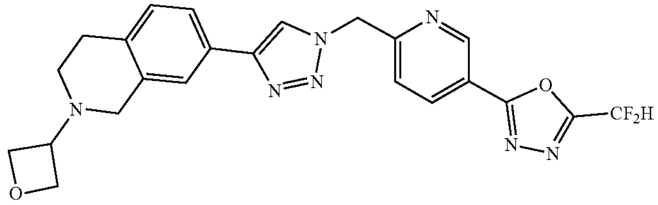 [SMILES: FC(F)c1nnc(-c2ccc(Cn3cc(-c4ccc5c(c4)CN(C4COC4)CC5)nn3)nc2)o1] |
| 190 | 4229 | 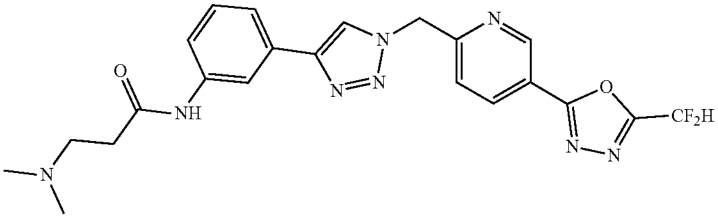 [SMILES: CN(C)CCC(=O)Nc1cccc(-c2cn(Cc3ccc(-c4nnc(C(F)F)o4)cn3)nn2)c1] |
| 191 | 4230 | 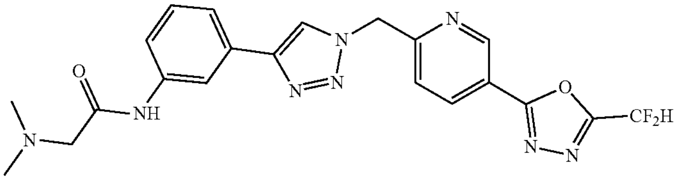 [SMILES: CN(C)CC(=O)Nc1cccc(-c2cn(Cc3ccc(-c4nnc(C(F)F)o4)cn3)nn2)c1] |
| 192 | 4231 | 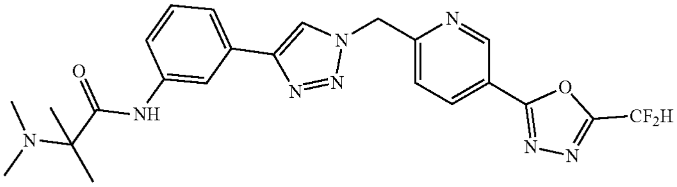 [SMILES: CN(C)C(C)(C)C(=O)Nc1cccc(-c2cn(Cc3ccc(-c4nnc(C(F)F)o4)cn3)nn2)c1] |
| 193 | 4232 | 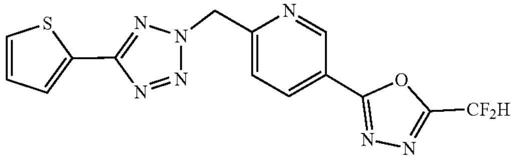 [SMILES: FC(F)c1nnc(-c2ccc(Cn3nnc(-c4cccs4)n3)nc2)o1] |
| 194 | 4233 | 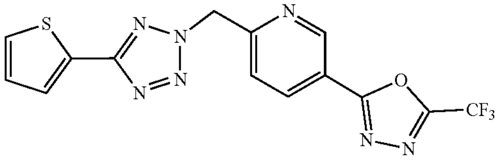 [SMILES: FC(F)(F)c1nnc(-c2ccc(Cn3nnc(-c4cccs4)n3)nc2)o1] |
| 195 | 4234 | 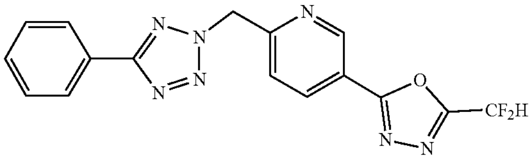 [SMILES: FC(F)c1nnc(-c2ccc(Cn3nnc(-c4ccccc4)n3)nc2)o1] |
| 196 | 4235 | 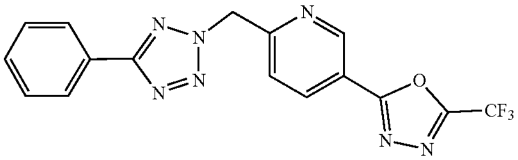 [SMILES: FC(F)(F)c1nnc(-c2ccc(Cn3nnc(-c4ccccc4)n3)nc2)o1] |

TABLE 1-continued
| Example | Compound | Structure |
|---|---|---|
| 197 | 4276 | 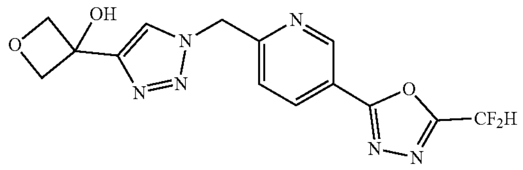 [SMILES: OC1(c2cn(Cc3ccc(-c4nnc(C(F)F)o4)cn3)nn2)COC1] |
| 198 | 4277 | 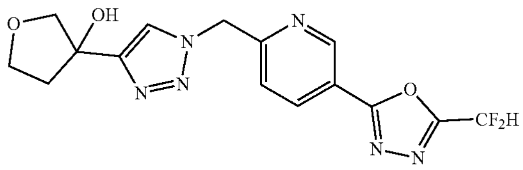 [SMILES: OC1(c2cn(Cc3ccc(-c4nnc(C(F)F)o4)cn3)nn2)CCOC1] |
| 199 | 4278 | 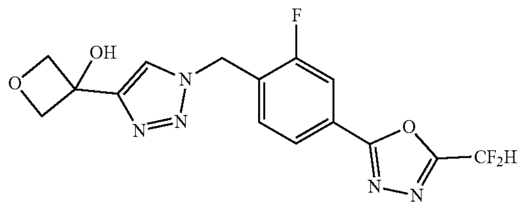 [SMILES: OC1(c2cn(Cc3ccc(-c4nnc(C(F)F)o4)cc3F)nn2)COC1] |
| 200 | 4279 | 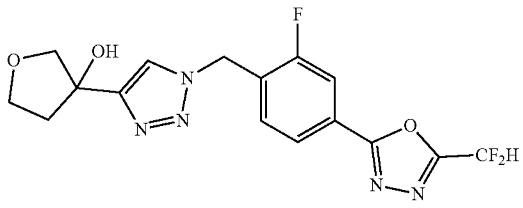 [SMILES: OC1(c2cn(Cc3ccc(-c4nnc(C(F)F)o4)cc3F)nn2)CCOC1] |
| 201 | 4280 | 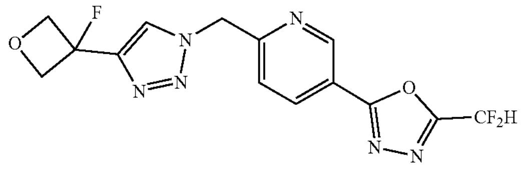 [SMILES: FC(F)c1nnc(-c2ccc(Cn3cc(C4(F)COC4)nn3)nc2)o1] |
| 202 | 4281 | 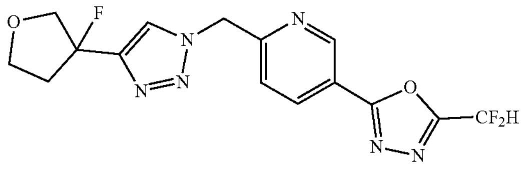 [SMILES: FC(F)c1nnc(-c2ccc(Cn3cc(C4(F)CCOC4)nn3)nc2)o1] |
| 203 | 4282 | 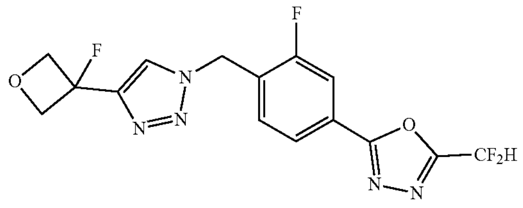 [SMILES: Fc1cc(-c2nnc(C(F)F)o2)ccc1Cn1cc(C2(F)COC2)nn1] |
| 204 | 4283 | 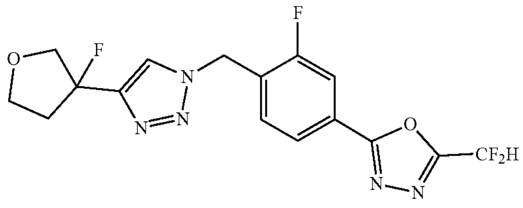 [SMILES: Fc1cc(-c2nnc(C(F)F)o2)ccc1Cn1cc(C2(F)CCOC2)nn1] |

TABLE 1-continued
| Example | Compound | Structure |
| --- | --- | --- |
| 205 | 4284 | 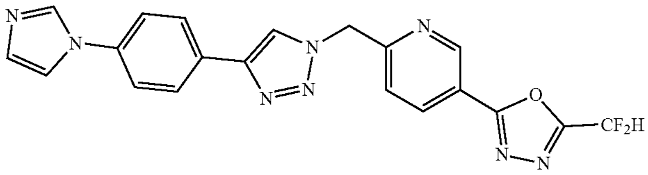 [SMILES: FC(F)c1nnc(-c2ccc(Cn3cc(-c4ccc(-n5ccnc5)cc4)nn3)nc2)o1] |
| 206 | 4285 | 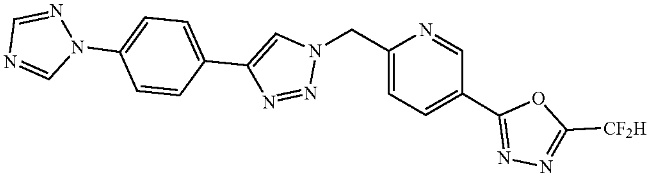 [SMILES: FC(F)c1nnc(-c2ccc(Cn3cc(-c4ccc(-n5cncn5)cc4)nn3)nc2)o1] |
| 207 | 4286 | 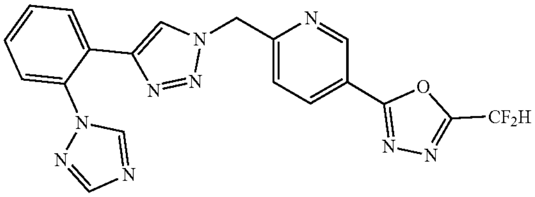 [SMILES: FC(F)c1nnc(-c2ccc(Cn3cc(-c4ccccc4-n4cncn4)nn3)nc2)o1] |
| 208 | 4287 | 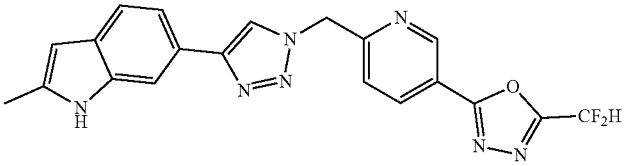 [SMILES: Cc1cc2ccc(-c3cn(Cc4ccc(-c5nnc(C(F)F)o5)cn4)nn3)cc2[nH]1] |
| 209 | 4288 | 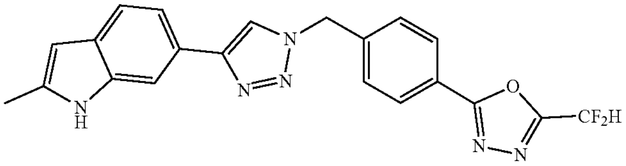 [SMILES: Cc1cc2ccc(-c3cn(Cc4ccc(-c5nnc(C(F)F)o5)cc4)nn3)cc2[nH]1] |
| 210 | 4289 | 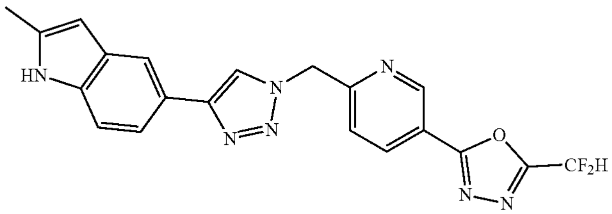 [SMILES: Cc1cc2cc(-c3cn(Cc4ccc(-c5nnc(C(F)F)o5)cn4)nn3)ccc2[nH]1] |
| 211 | 4290 | 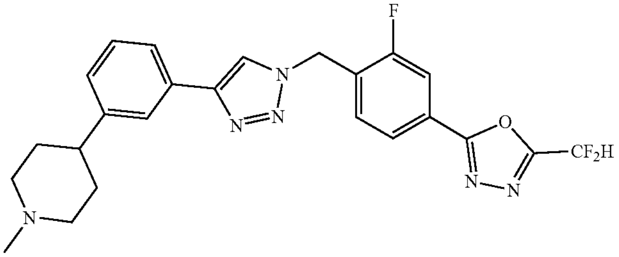 [SMILES: CN1CCC(c2cccc(-c3cn(Cc4ccc(-c5nnc(C(F)F)o5)cc4F)nn3)c2)CC1] |

TABLE 1-continued
| Example | Compound | Structure |
| --- | --- | --- |
| 212 | 4291 | 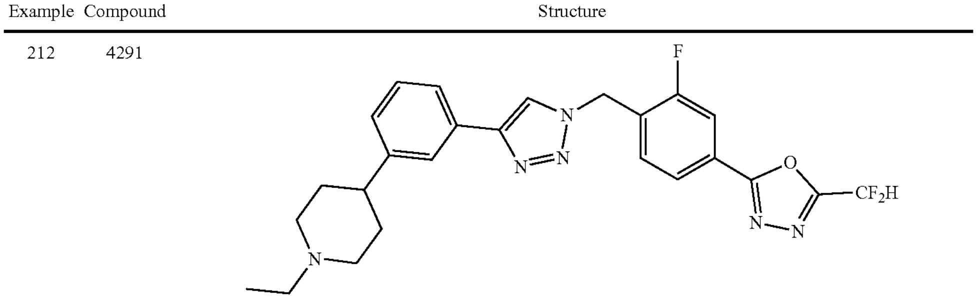 |
| 213 | 4292 | 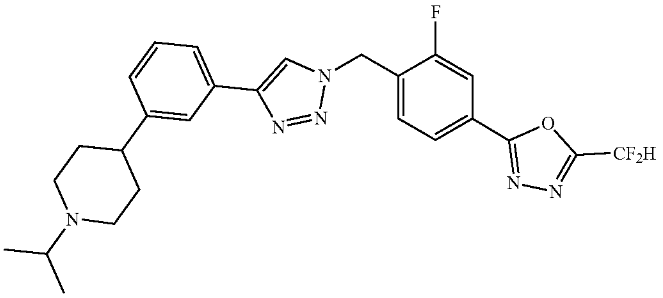 [SMILES: CC(C)N1CCC(c2cccc(-c3cn(Cc4ccc(-c5nnc(C(F)F)o5)cc4F)nn3)c2)CC1] |
| 214 | 4293 | 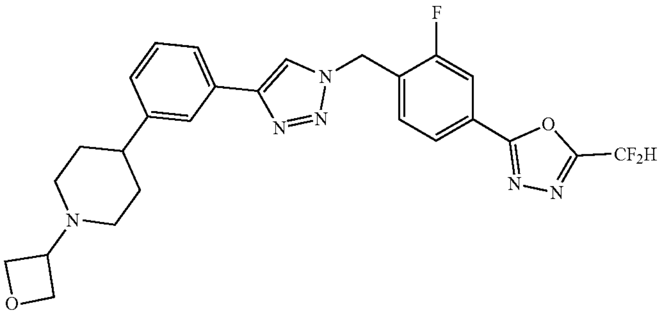 [SMILES: Fc1cc(-c2nnc(C(F)F)o2)ccc1Cn1cc(-c2cccc(C3CCN(C4COC4)CC3)c2)nn1] |
| 215 | 4294 | 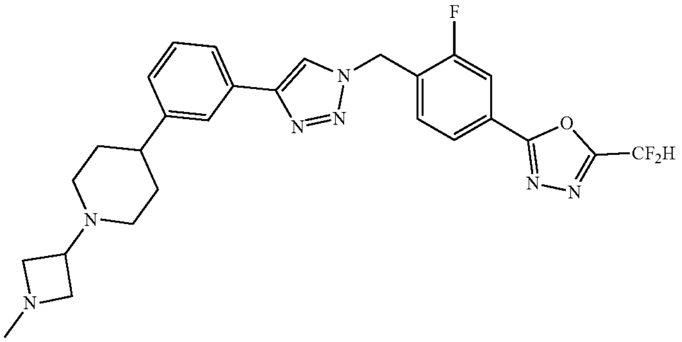 [SMILES: CN1CC(N2CCC(c3cccc(-c4cn(Cc5ccc(-c6nnc(C(F)F)o6)cc5F)nn4)c3)CC2)C1] |
| 216 | 4295 | 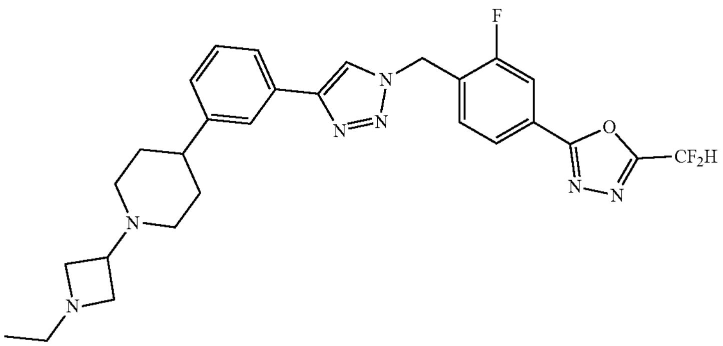 [SMILES: CCN1CC(N2CCC(c3cccc(-c4cn(Cc5ccc(-c6nnc(C(F)F)o6)cc5F)nn4)c3)CC2)C1] |

TABLE 1-continued
| Example | Compound | Structure |
| --- | --- | --- |
| 217 | 4296 | 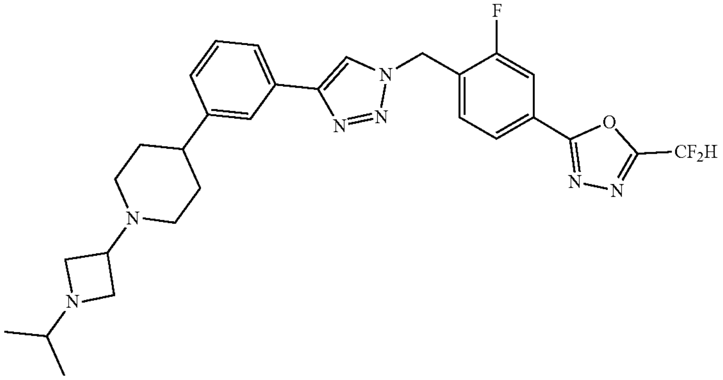 [SMILES: CC(C)N1CC(N2CCC(c3cccc(-c4cn(Cc5ccc(-c6nnc(C(F)F)o6)cc5F)nn4)c3)CC2)C1] |
| 218 | 4316 | 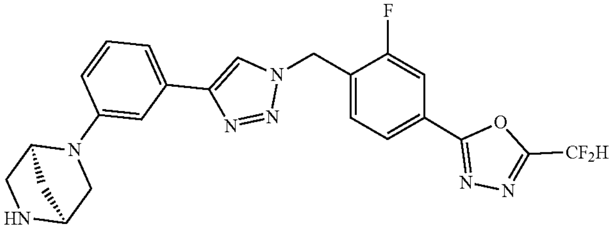 [SMILES: Fc1cc(-c2nnc(C(F)F)o2)ccc1Cn1cc(-c2cccc(N3C[C@@H]4C[C@H]3CN4)c2)nn1] |
| 219 | 4317 | 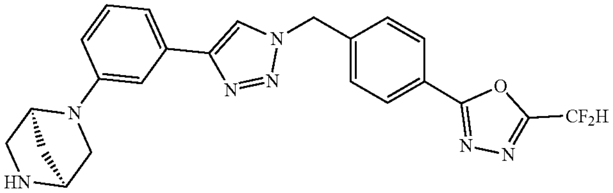 [SMILES: FC(F)c1nnc(-c2ccc(Cn3cc(-c4cccc(N5C[C@@H]6C[C@H]5CN6)c4)nn3)cc2)o1] |
| 220 | 4318 | 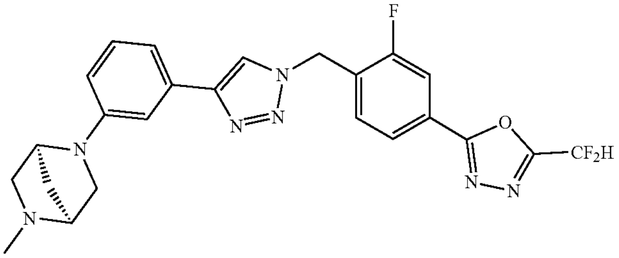 [SMILES: CN1C[C@@H]2C[C@H]1CN2c1cccc(-c2cn(Cc3ccc(-c4nnc(C(F)F)o4)cc3F)nn2)c1] |
| 221 | 4319 | 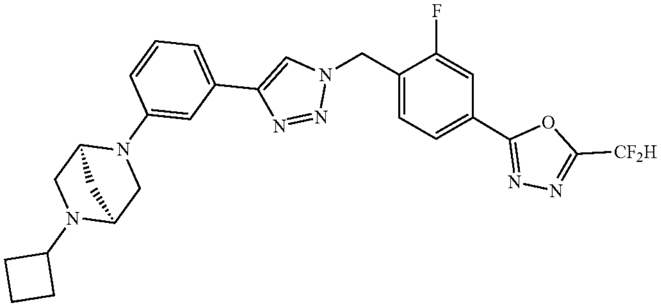 [SMILES: Fc1cc(-c2nnc(C(F)F)o2)ccc1Cn1cc(-c2cccc(N3C[C@@H]4C[C@H]3CN4C3CCC3)c2)nn1] |

TABLE 1-continued
| Example | Compound | Structure |
|---|---|---|
| 222 | 4320 | 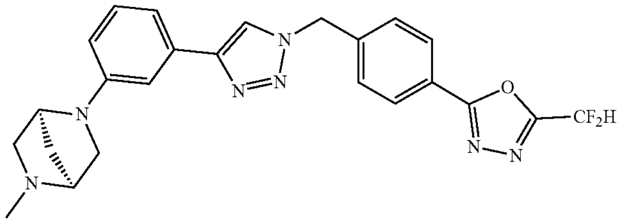 [SMILES: CN1C[C@@H]2C[C@H]1CN2c1cccc(-c2cn(Cc3ccc(-c4nnc(C(F)F)o4)cc3)nn2)c1] |
| 223 | 4321 | 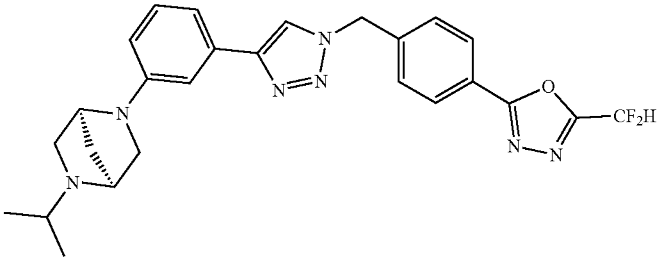 [SMILES: CC(C)N1C[C@@H]2C[C@H]1CN2c1cccc(-c2cn(Cc3ccc(-c4nnc(C(F)F)o4)cc3)nn2)c1] |
| 224 | 4322 | 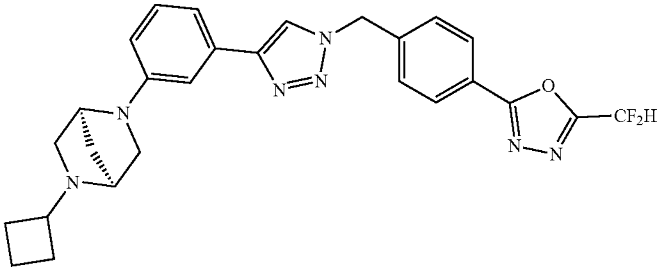 [SMILES: FC(F)c1nnc(-c2ccc(Cn3cc(-c4cccc(N5C[C@@H]6C[C@H]5CN6C5CCC5)c4)nn3)cc2)o1] |
| 225 | 4323 | 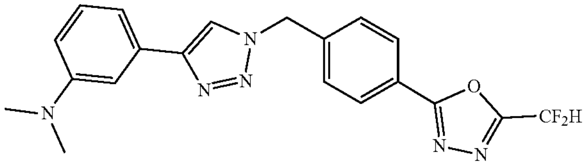 [SMILES: CN(C)c1cccc(-c2cn(Cc3ccc(-c4nnc(C(F)F)o4)cc3)nn2)c1] |
| 226 | 4324 | 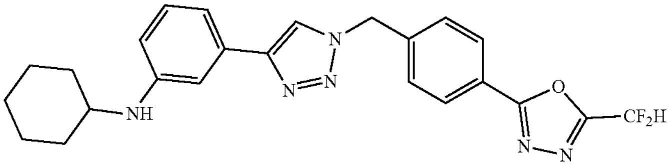 [SMILES: FC(F)c1nnc(-c2ccc(Cn3cc(-c4cccc(NC5CCCCC5)c4)nn3)cc2)o1] |
| 227 | 4325 | 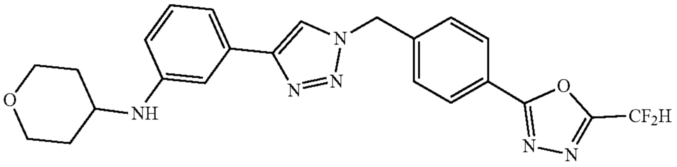 [SMILES: FC(F)c1nnc(-c2ccc(Cn3cc(-c4cccc(NC5CCOCC5)c4)nn3)cc2)o1] |
| 228 | 4326 | 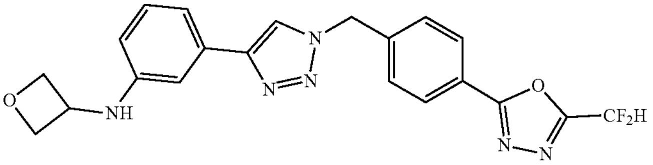 [SMILES: FC(F)c1nnc(-c2ccc(Cn3cc(-c4cccc(NC5COC5)c4)nn3)cc2)o1] |

TABLE 1-continued
| Example | Compound | Structure |
|---|---|---|
| 229 | 4327 | 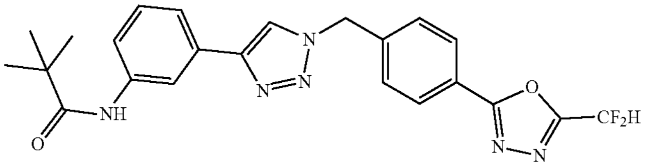 [SMILES: CC(C)(C)C(=O)Nc1cccc(-c2cn(Cc3ccc(-c4nnc(C(F)F)o4)cc3)nn2)c1] |
| 230 | 4328 | 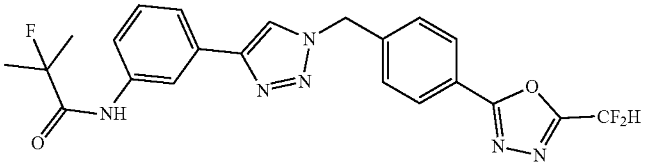 [SMILES: CC(C)(F)C(=O)Nc1cccc(-c2cn(Cc3ccc(-c4nnc(C(F)F)o4)cc3)nn2)c1] |
| 231 | 4329 | 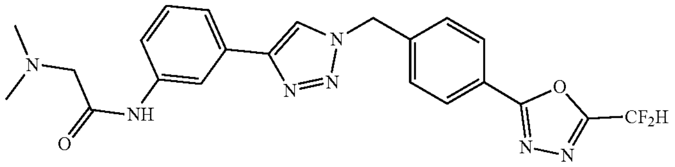 [SMILES: CN(C)CC(=O)Nc1cccc(-c2cn(Cc3ccc(-c4nnc(C(F)F)o4)cc3)nn2)c1] |
| 232 | 4330 | 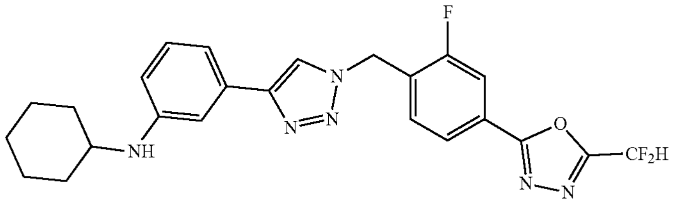 [SMILES: Fc1cc(-c2nnc(C(F)F)o2)ccc1Cn1cc(-c2cccc(NC3CCCCC3)c2)nn1] |
| 233 | 4331 | 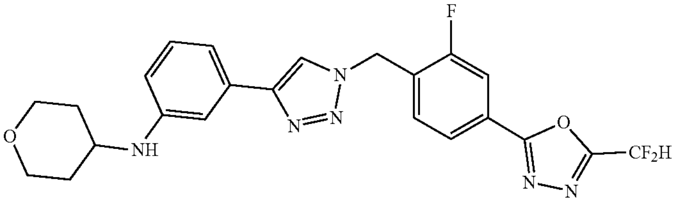 [SMILES: Fc1cc(-c2nnc(C(F)F)o2)ccc1Cn1cc(-c2cccc(NC3CCOCC3)c2)nn1] |
| 234 | 4332 | 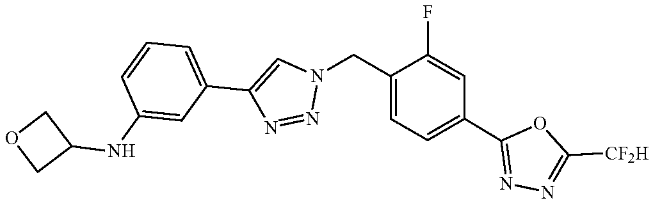 [SMILES: Fc1cc(-c2nnc(C(F)F)o2)ccc1Cn1cc(-c2cccc(NC3COC3)c2)nn1] |
| 235 | 4333 | 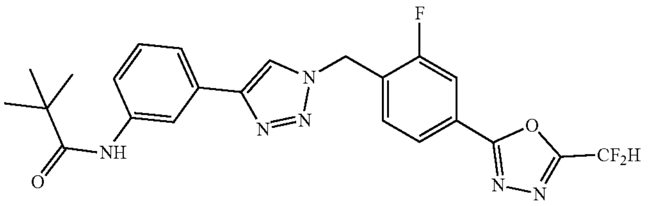 [SMILES: CC(C)(C)C(=O)Nc1cccc(-c2cn(Cc3ccc(-c4nnc(C(F)F)o4)cc3F)nn2)c1] |
| 236 | 4334 | 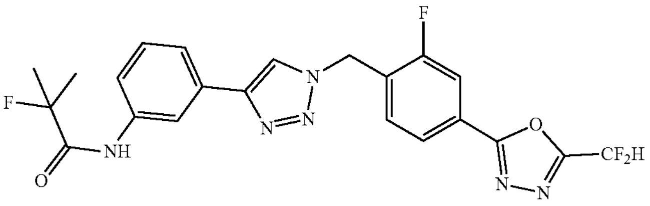 [SMILES: CC(C)(F)C(=O)Nc1cccc(-c2cn(Cc3ccc(-c4nnc(C(F)F)o4)cc3F)nn2)c1] |

TABLE 1-continued
| Example | Compound | Structure |
| --- | --- | --- |
| 237 | 4335 | 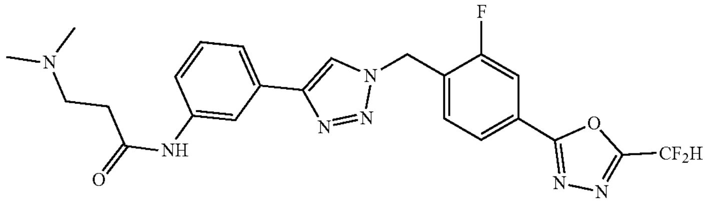 [SMILES: CN(C)CCC(=O)Nc1cccc(-c2cn(Cc3ccc(-c4nnc(C(F)F)o4)cc3F)nn2)c1] |
| 238 | 4336 | 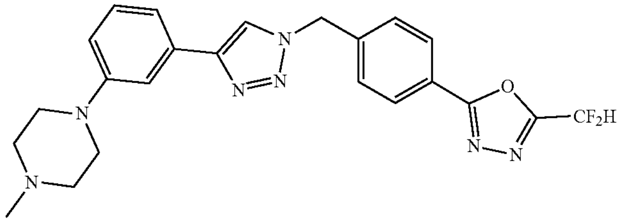 [SMILES: CN1CCN(c2cccc(-c3cn(Cc4ccc(-c5nnc(C(F)F)o5)cc4)nn3)c2)CC1] |
| 239 | 4337 | 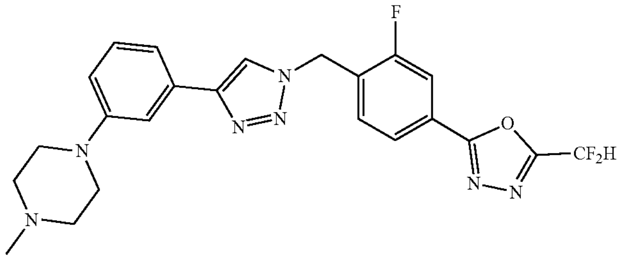 [SMILES: CN1CCN(c2cccc(-c3cn(Cc4ccc(-c5nnc(C(F)F)o5)cc4F)nn3)c2)CC1] |
| 240 | 4338 | 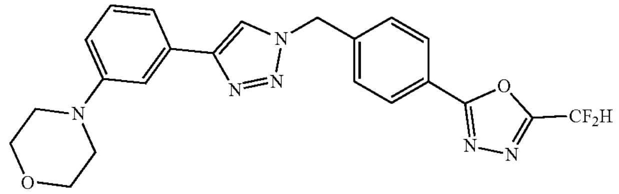 [SMILES: FC(F)c1nnc(-c2ccc(Cn3cc(-c4cccc(N5CCOCC5)c4)nn3)cc2)o1] |
| 241 | 4339 | 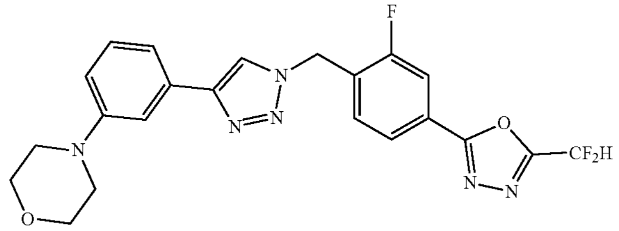 [SMILES: Fc1cc(-c2nnc(C(F)F)o2)ccc1Cn1cc(-c2cccc(N3CCOCC3)c2)nn1] |
| 242 | 4340 | 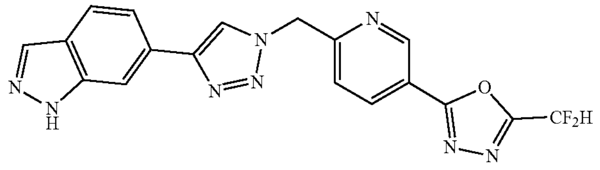 [SMILES: FC(F)c1nnc(-c2ccc(Cn3cc(-c4ccc5cn[nH]c5c4)nn3)nc2)o1] |
| 243 | 4341 | 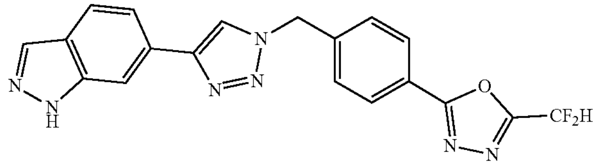 [SMILES: FC(F)c1nnc(-c2ccc(Cn3cc(-c4ccc5cn[nH]c5c4)nn3)cc2)o1] |

TABLE 1-continued
| Example | Compound | Structure |
| --- | --- | --- |
| 244 | 4342 | 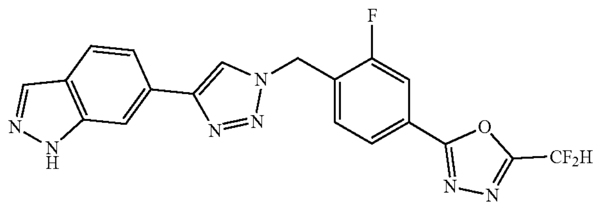 [SMILES: Fc1cc(-c2nnc(C(F)F)o2)ccc1Cn1cc(-c2ccc3cn[nH]c3c2)nn1] |
| 245 | 4343 | 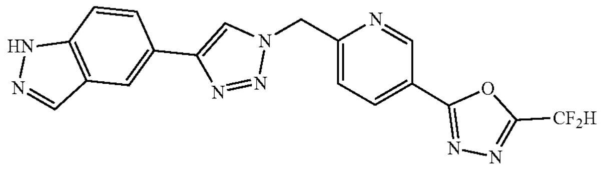 [SMILES: FC(F)c1nnc(-c2ccc(Cn3cc(-c4ccc5[nH]ncc5c4)nn3)nc2)o1] |
| 246 | 4344 | 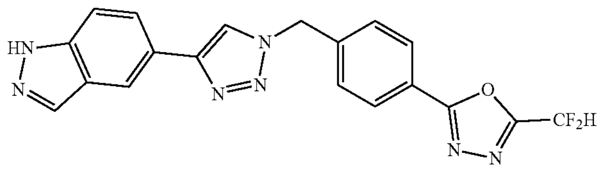 [SMILES: FC(F)c1nnc(-c2ccc(Cn3cc(-c4ccc5[nH]ncc5c4)nn3)cc2)o1] |
| 247 | 4345 | 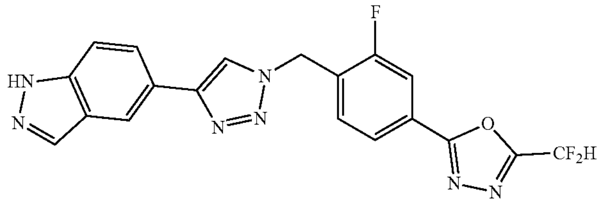 [SMILES: Fc1cc(-c2nnc(C(F)F)o2)ccc1Cn1cc(-c2ccc3[nH]ncc3c2)nn1] |
| 248 | 4346 | 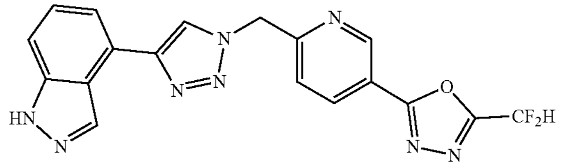 [SMILES: FC(F)c1nnc(-c2ccc(Cn3cc(-c4cccc5[nH]ncc45)nn3)nc2)o1] |
| 249 | 4347 | 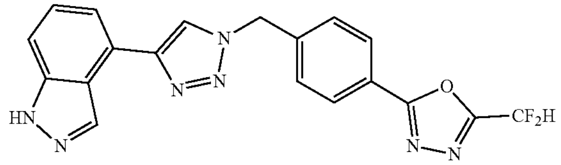 [SMILES: FC(F)c1nnc(-c2ccc(Cn3cc(-c4cccc5[nH]ncc45)nn3)cc2)o1] |
| 250 | 4348 | 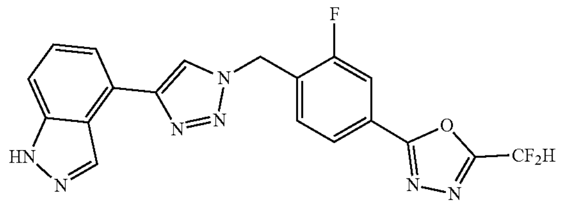 [SMILES: Fc1cc(-c2nnc(C(F)F)o2)ccc1Cn1cc(-c2cccc3[nH]ncc23)nn1] |

TABLE 1-continued
| Example | Compound | Structure |
|---|---|---|
| 251 | 4349 | 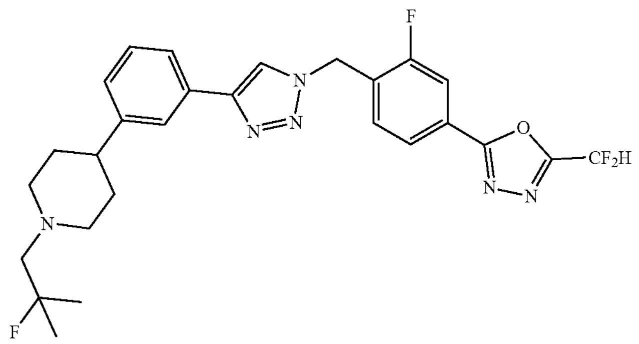 [SMILES: CC(C)(F)CN1CCC(c2cccc(-c3cn(Cc4ccc(-c5nnc(C(F)F)o5)cc4F)nn3)c2)CC1] |
| 252 | 4350 | 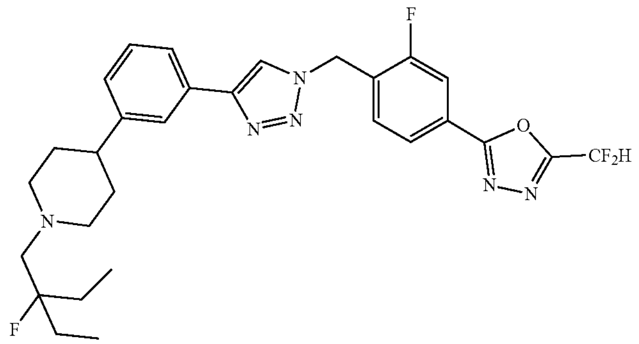 [SMILES: CCC(F)(CC)CN1CCC(c2cccc(-c3cn(Cc4ccc(-c5nnc(C(F)F)o5)cc4F)nn3)c2)CC1] |
| 253 | 4351 | 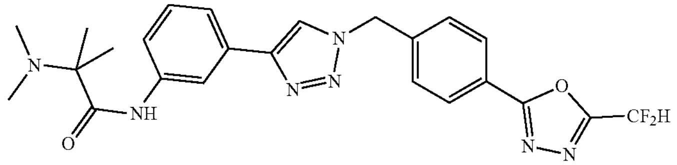 [SMILES: CN(C)C(C)(C)C(=O)Nc1cccc(-c2cn(Cc3ccc(-c4nnc(C(F)F)o4)cc3)nn2)c1] |
| 254 | 4352 | 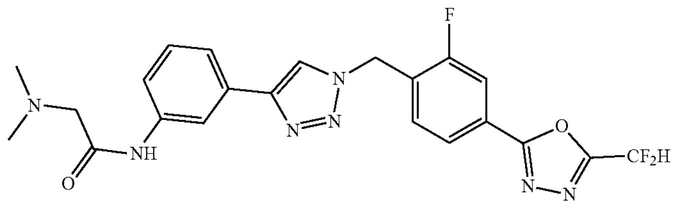 [SMILES: CN(C)CC(=O)Nc1cccc(-c2cn(Cc3ccc(-c4nnc(C(F)F)o4)cc3F)nn2)c1] |
| 255 | 4353 | 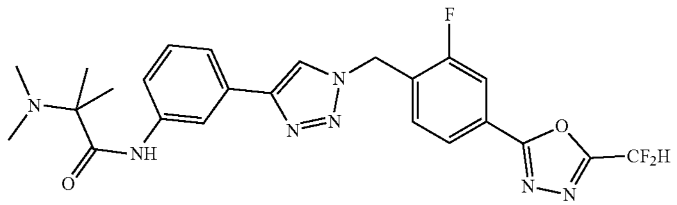 [SMILES: CN(C)C(C)(C)C(=O)Nc1cccc(-c2cn(Cc3ccc(-c4nnc(C(F)F)o4)cc3F)nn2)c1] |
| 256 | 4358 | 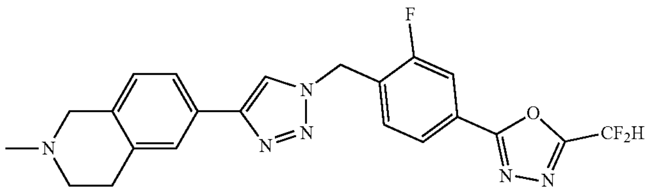 [SMILES: CN1CCc2cc(-c3cn(Cc4ccc(-c5nnc(C(F)F)o5)cc4F)nn3)ccc2C1] |

TABLE 1-continued
| Example | Compound | Structure |
|---|---|---|
| 257 | 4359 | 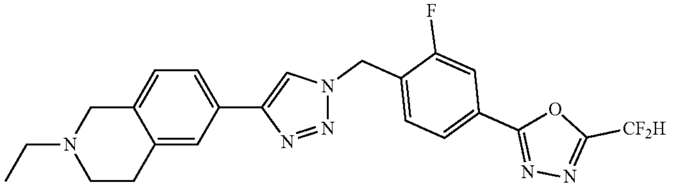 [SMILES: CCN1CCc2cc(-c3cn(Cc4ccc(-c5nnc(C(F)F)o5)cc4F)nn3)ccc2C1] |
| 258 | 4360 | 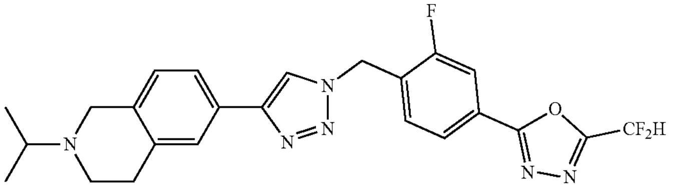 [SMILES: CC(C)N1CCc2cc(-c3cn(Cc4ccc(-c5nnc(C(F)F)o5)cc4F)nn3)ccc2C1] |
| 259 | 4361 | 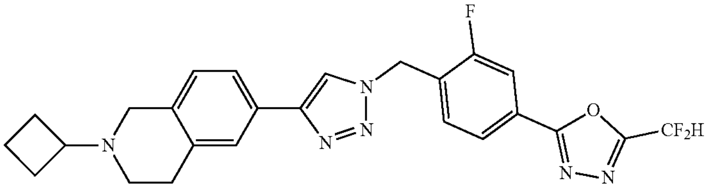 [SMILES: Fc1cc(-c2nnc(C(F)F)o2)ccc1Cn1cc(-c2ccc3c(c2)CCN(C2CCC2)C3)nn1] |
| 260 | 4362 | 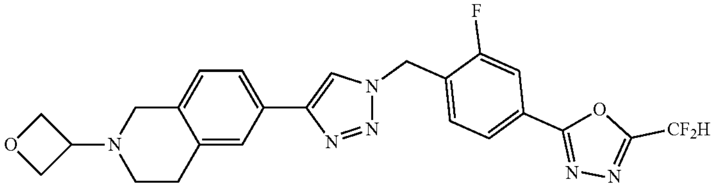 [SMILES: Fc1cc(-c2nnc(C(F)F)o2)ccc1Cn1cc(-c2ccc3c(c2)CCN(C2COC2)C3)nn1] |
| 261 | 4363 | 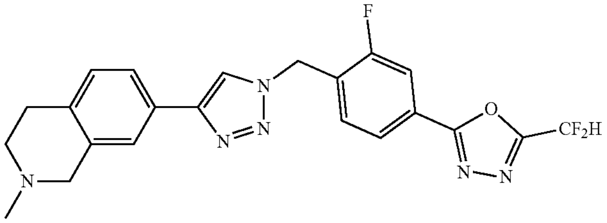 [SMILES: CN1CCc2ccc(-c3cn(Cc4ccc(-c5nnc(C(F)F)o5)cc4F)nn3)cc2C1] |
| 262 | 4364 | 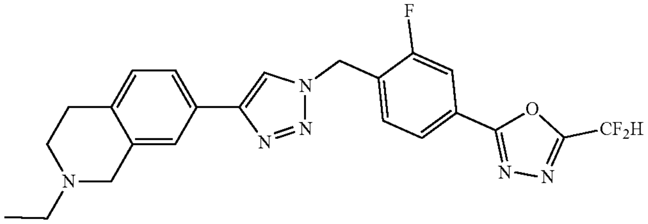 [SMILES: CCN1CCc2ccc(-c3cn(Cc4ccc(-c5nnc(C(F)F)o5)cc4F)nn3)cc2C1] |
| 263 | 4365 | 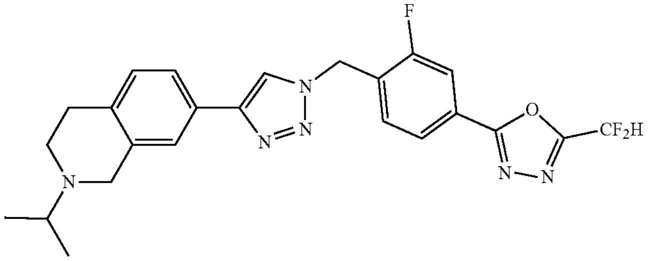 [SMILES: CC(C)N1CCc2ccc(-c3cn(Cc4ccc(-c5nnc(C(F)F)o5)cc4F)nn3)cc2C1] |

TABLE 1-continued
| Example | Compound | Structure |
| --- | --- | --- |
| 264 | 4366 | 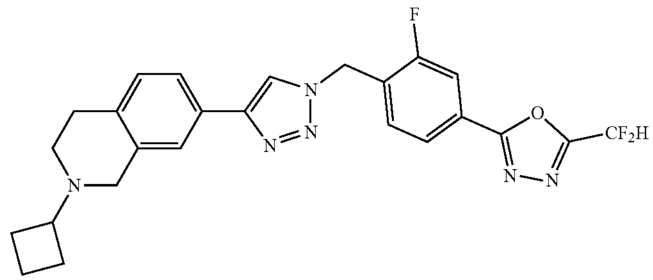 [SMILES: Fc1cc(-c2nnc(C(F)F)o2)ccc1Cn1cc(-c2ccc3c(c2)CN(C2CCC2)CC3)nn1] |
| 265 | 4367 | 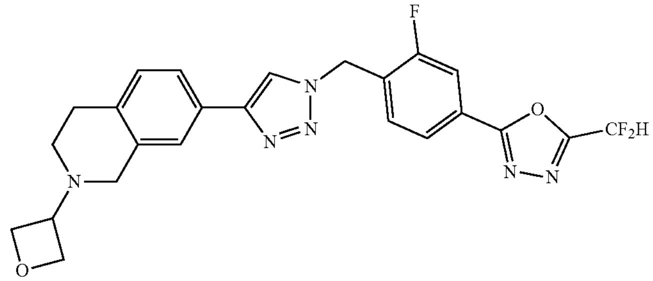 [SMILES: Fc1cc(-c2nnc(C(F)F)o2)ccc1Cn1cc(-c2ccc3c(c2)CN(C2COC2)CC3)nn1] |
| 266 | 4368 | 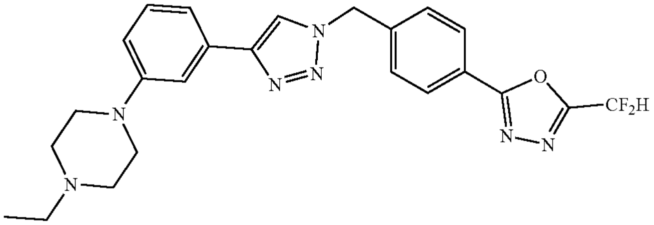 [SMILES: CCN1CCN(c2cccc(-c3cn(Cc4ccc(-c5nnc(C(F)F)o5)cc4)nn3)c2)CC1] |
| 267 | 4369 | 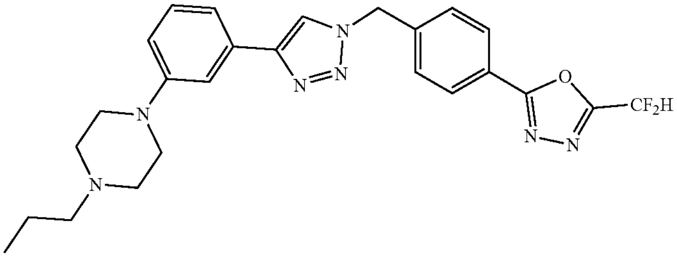 [SMILES: CCCN1CCN(c2cccc(-c3cn(Cc4ccc(-c5nnc(C(F)F)o5)cc4)nn3)c2)CC1] |
| 268 | 4370 | 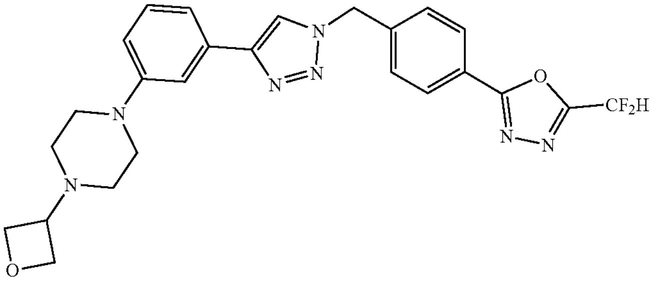 [SMILES: FC(F)c1nnc(-c2ccc(Cn3cc(-c4cccc(N5CCN(C6COC6)CC5)c4)nn3)cc2)o1] |

TABLE 1-continued
| Example | Compound | Structure |
|---|---|---|
| 269 | 4371 | 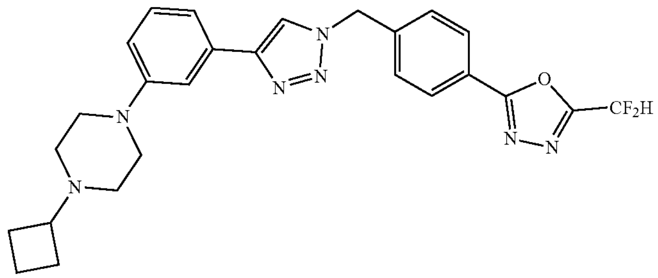 [SMILES: FC(F)c1nnc(-c2ccc(Cn3cc(-c4cccc(N5CCN(C6CCC6)CC5)c4)nn3)cc2)o1] |
| 270 | 4372 | 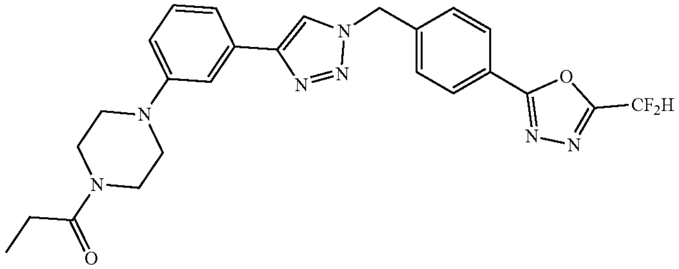 [SMILES: CCC(=O)N1CCN(c2cccc(-c3cn(Cc4ccc(-c5nnc(C(F)F)o5)cc4)nn3)c2)CC1] |
| 271 | 4373 | 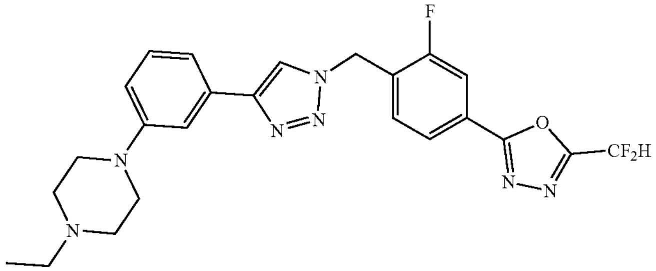 [SMILES: CCN1CCN(c2cccc(-c3cn(Cc4ccc(-c5nnc(C(F)F)o5)cc4F)nn3)c2)CC1] |
| 272 | 4374 | 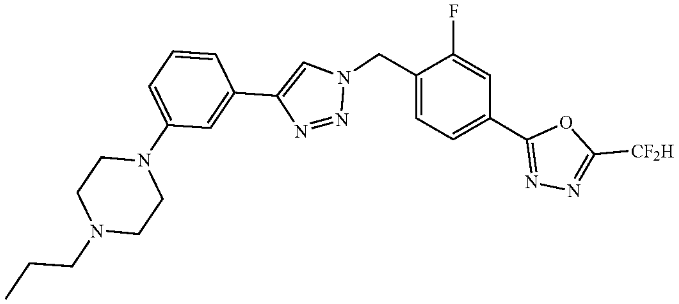 [SMILES: CCCN1CCN(c2cccc(-c3cn(Cc4ccc(-c5nnc(C(F)F)o5)cc4F)nn3)c2)CC1] |
| 273 | 4375 | 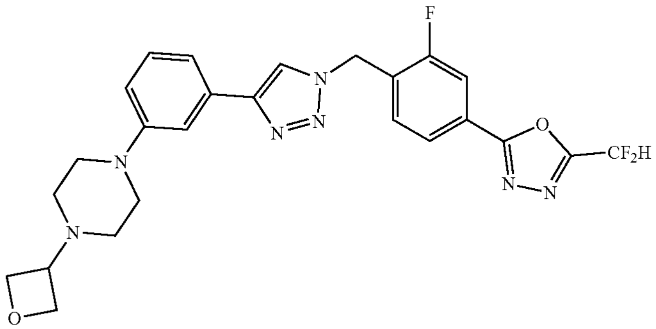 [SMILES: Fc1cc(-c2nnc(C(F)F)o2)ccc1Cn1cc(-c2cccc(N3CCN(C4COC4)CC3)c2)nn1] |

TABLE 1-continued
| Example | Compound | Structure |
| --- | --- | --- |
| 274 | 4376 | 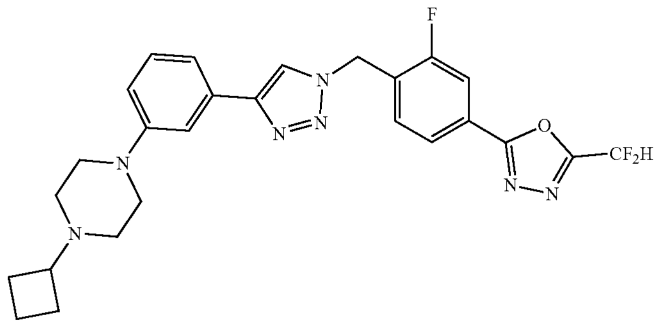 [SMILES: Fc1cc(-c2nnc(C(F)F)o2)ccc1Cn1cc(-c2cccc(N3CCN(C4CCC4)CC3)c2)nn1] |
| 275 | 4377 | 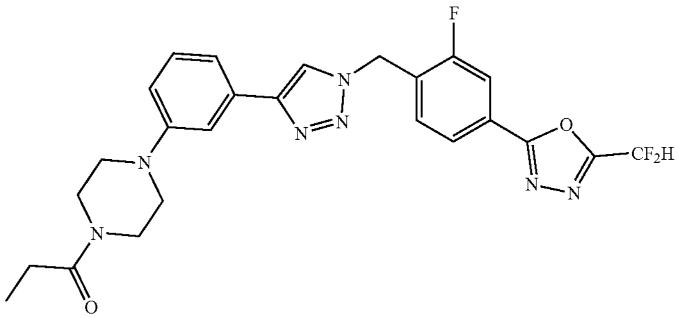 [SMILES: CCC(=O)N1CCN(c2cccc(-c3cn(Cc4ccc(-c5nnc(C(F)F)o5)cc4F)nn3)c2)CC1] |
| 276 | 4392 | 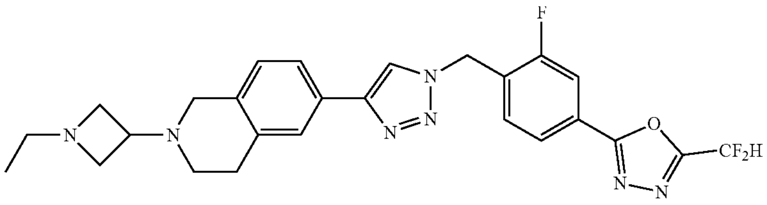 [SMILES: CCN1CC(N2CCc3cc(-c4cn(Cc5ccc(-c6nnc(C(F)F)o6)cc5F)nn4)ccc3C2)C1] |
| 277 | 4393 | 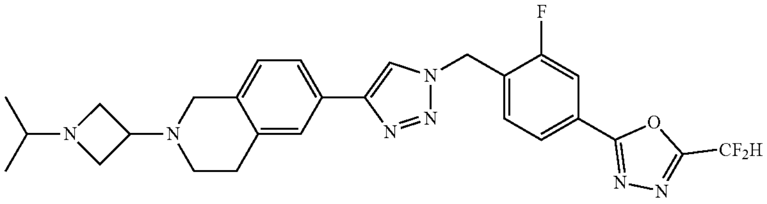 [SMILES: CC(C)N1CC(N2CCc3cc(-c4cn(Cc5ccc(-c6nnc(C(F)F)o6)cc5F)nn4)ccc3C2)C1] |
| 278 | 4394 | 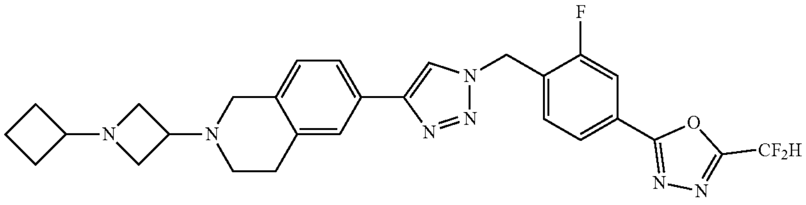 [SMILES: Fc1cc(-c2nnc(C(F)F)o2)ccc1Cn1cc(-c2ccc3c(c2)CCN(C2CN(C4CCC4)C2)C3)nn1] |
| 279 | 4395 | 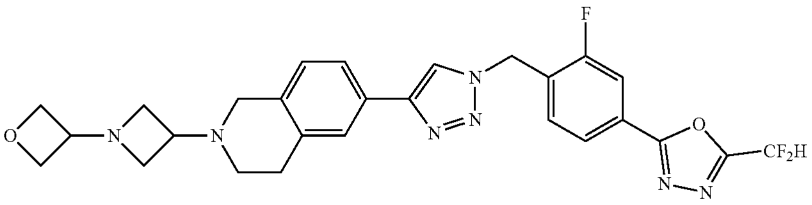 [SMILES: Fc1cc(-c2nnc(C(F)F)o2)ccc1Cn1cc(-c2ccc3c(c2)CCN(C2CN(C4COC4)C2)C3)nn1] |

TABLE 1-continued
| Example | Compound | Structure |
| --- | --- | --- |
| 280 | 4396 | 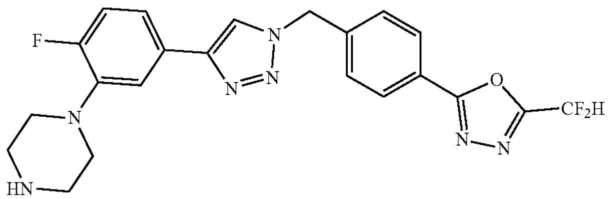 [SMILES: Fc1ccc(-c2cn(Cc3ccc(-c4nnc(C(F)F)o4)cc3)nn2)cc1N1CCNCC1] |
| 281 | 4397 | 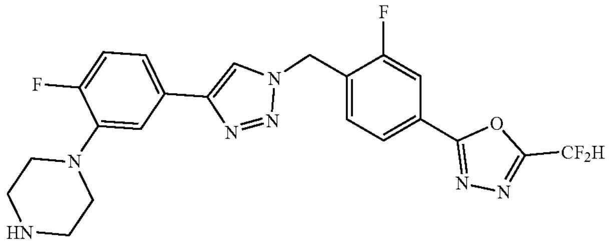 [SMILES: Fc1cc(-c2nnc(C(F)F)o2)ccc1Cn1cc(-c2ccc(F)c(N3CCNCC3)c2)nn1] |
| 282 | 4398 | 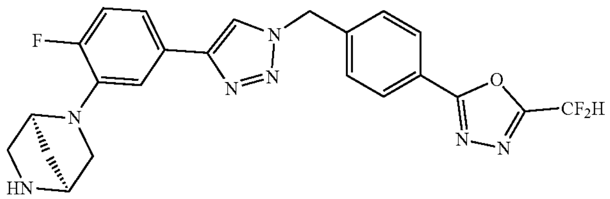 [SMILES: Fc1ccc(-c2cn(Cc3ccc(-c4nnc(C(F)F)o4)cc3)nn2)cc1N1C[C@@H]2C[C@H]1CN2] |
| 283 | 4399 | 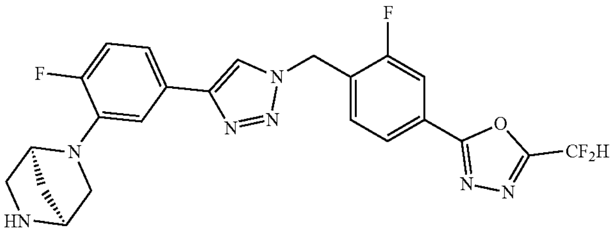 [SMILES: Fc1cc(-c2nnc(C(F)F)o2)ccc1Cn1cc(-c2ccc(F)c(N3C[C@@H]4C[C@H]3CN4)c2)nn1] |
| 284 | 4400 | 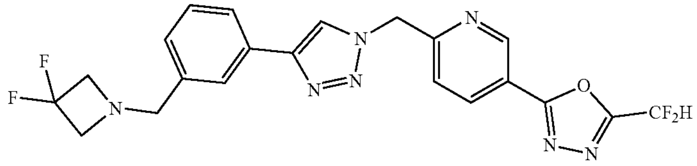 [SMILES: FC(F)c1nnc(-c2ccc(Cn3cc(-c4cccc(CN5CC(F)(F)C5)c4)nn3)nc2)o1] |
| 285 | 4401 | 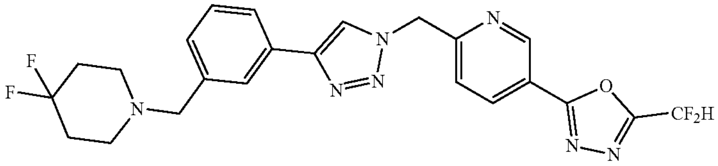 [SMILES: FC(F)c1nnc(-c2ccc(Cn3cc(-c4cccc(CN5CCC(F)(F)CC5)c4)nn3)nc2)o1] |
| 286 | 4402 | 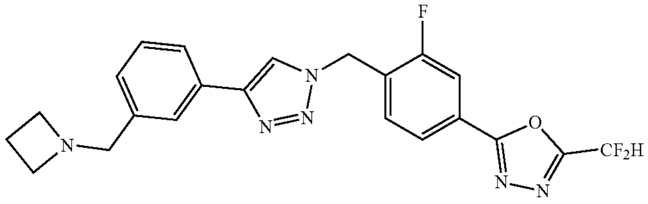 [SMILES: Fc1cc(-c2nnc(C(F)F)o2)ccc1Cn1cc(-c2cccc(CN3CCC3)c2)nn1] |

TABLE 1-continued
| Example | Compound | Structure |
|---|---|---|
| 287 | 4403 | 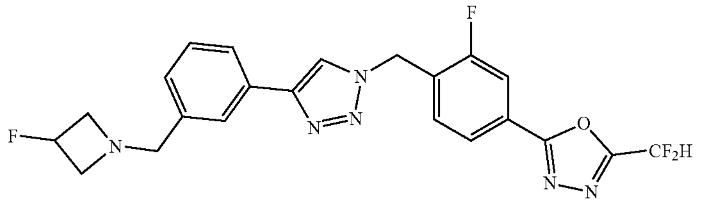 [SMILES: Fc1cc(-c2nnc(C(F)F)o2)ccc1Cn1cc(-c2cccc(CN3CC(F)C3)c2)nn1] |
| 288 | 4404 | 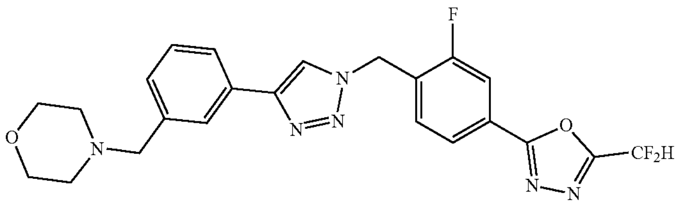 [SMILES: Fc1cc(-c2nnc(C(F)F)o2)ccc1Cn1cc(-c2cccc(CN3CCOCC3)c2)nn1] |
| 289 | 4405 | 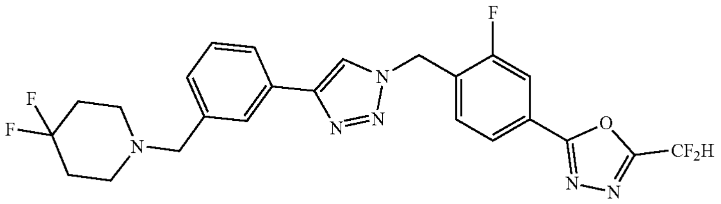 [SMILES: Fc1cc(-c2nnc(C(F)F)o2)ccc1Cn1cc(-c2cccc(CN3CCC(F)(F)CC3)c2)nn1] |
| 290 | 4406 | 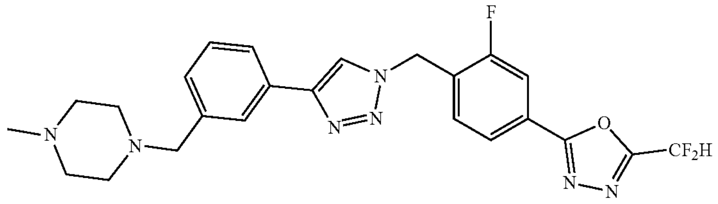 [SMILES: CN1CCN(Cc2cccc(-c3cn(Cc4ccc(-c5nnc(C(F)F)o5)cc4F)nn3)c2)CC1] |
| 291 | 4407 | 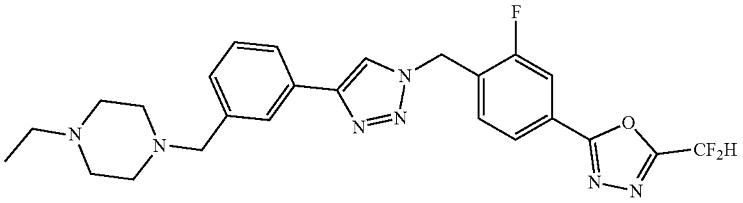 [SMILES: CCN1CCN(Cc2cccc(-c3cn(Cc4ccc(-c5nnc(C(F)F)o5)cc4F)nn3)c2)CC1] |
| 292 | 4408 | 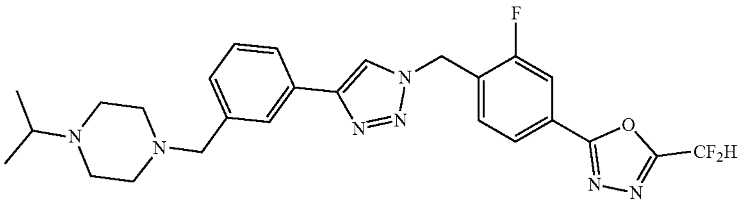 [SMILES: CC(C)N1CCN(Cc2cccc(-c3cn(Cc4ccc(-c5nnc(C(F)F)o5)cc4F)nn3)c2)CC1] |
| 293 | 4409 | 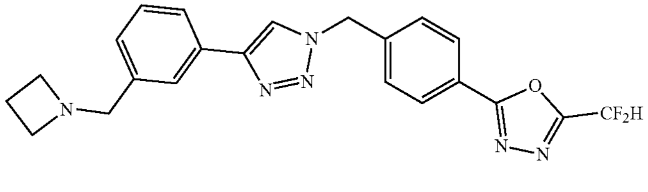 [SMILES: FC(F)c1nnc(-c2ccc(Cn3cc(-c4cccc(CN5CCC5)c4)nn3)cc2)o1] |

TABLE 1-continued
| Example | Compound | Structure |
|---|---|---|
| 294 | 4410 | 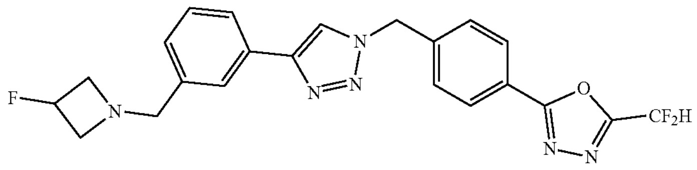 [SMILES: FC1CN(Cc2cccc(-c3cn(Cc4ccc(-c5nnc(C(F)F)o5)cc4)nn3)c2)C1] |
| 295 | 4411 | 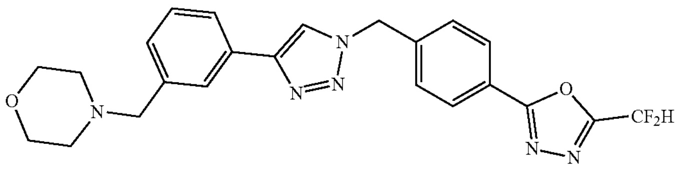 [SMILES: FC(F)c1nnc(-c2ccc(Cn3cc(-c4cccc(CN5CCOCC5)c4)nn3)cc2)o1] |
| 296 | 4412 | 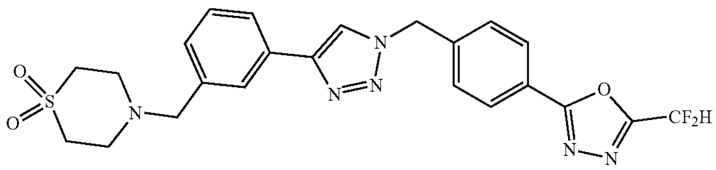 [SMILES: O=S1(=O)CCN(Cc2cccc(-c3cn(Cc4ccc(-c5nnc(C(F)F)o5)cc4)nn3)c2)CC1] |
| 297 | 4413 | 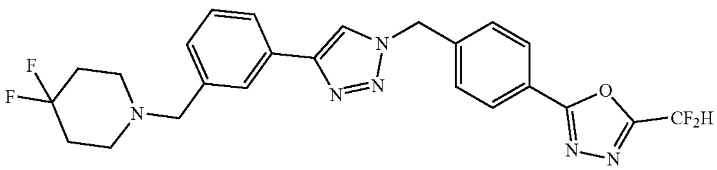 [SMILES: FC(F)c1nnc(-c2ccc(Cn3cc(-c4cccc(CN5CCC(F)(F)CC5)c4)nn3)cc2)o1] |
| 298 | 4414 | 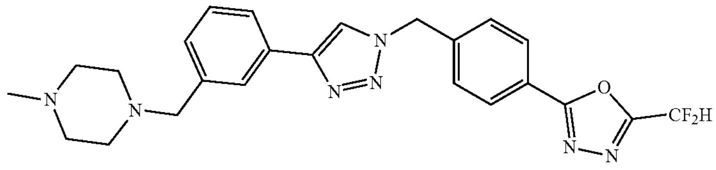 [SMILES: CN1CCN(Cc2cccc(-c3cn(Cc4ccc(-c5nnc(C(F)F)o5)cc4)nn3)c2)CC1] |
| 299 | 4415 | 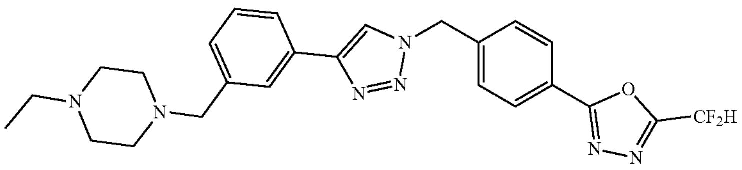 [SMILES: CCN1CCN(Cc2cccc(-c3cn(Cc4ccc(-c5nnc(C(F)F)o5)cc4)nn3)c2)CC1] |
| 300 | 4416 | 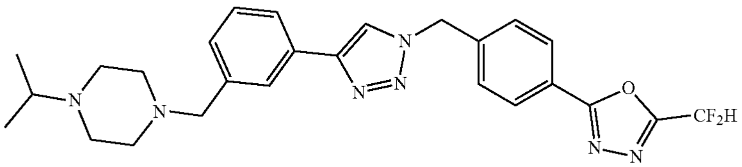 [SMILES: CC(C)N1CCN(Cc2cccc(-c3cn(Cc4ccc(-c5nnc(C(F)F)o5)cc4)nn3)c2)CC1] |
| 301 | 4417 | 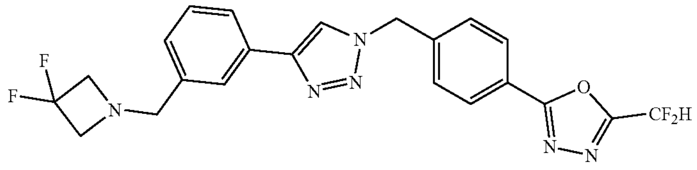 [SMILES: FC(F)c1nnc(-c2ccc(Cn3cc(-c4cccc(CN5CC(F)(F)C5)c4)nn3)cc2)o1] |

TABLE 1-continued
| Example | Compound | Structure |
|---|---|---|
| 302 | 4418 | 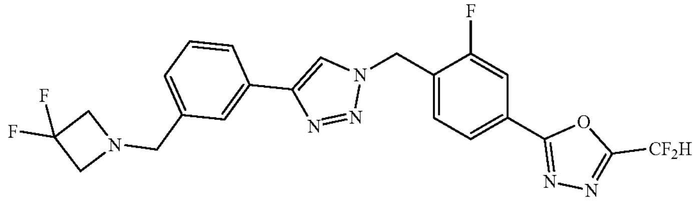 [SMILES: Fc1cc(-c2nnc(C(F)F)o2)ccc1Cn1cc(-c2cccc(CN3CC(F)(F)C3)c2)nn1] |
| 303 | 4419 | 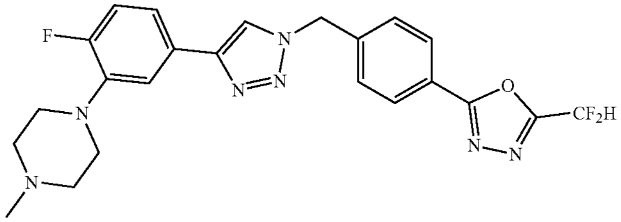 [SMILES: CN1CCN(c2cc(-c3cn(Cc4ccc(-c5nnc(C(F)F)o5)cc4)nn3)ccc2F)CC1] |
| 304 | 4420 | 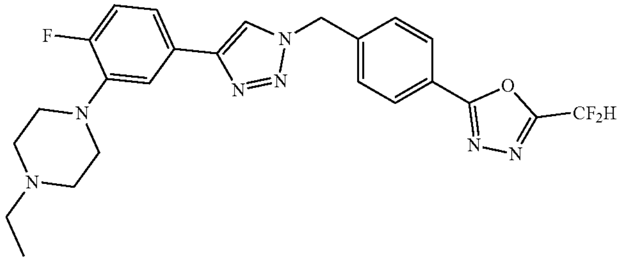 [SMILES: CCN1CCN(c2cc(-c3cn(Cc4ccc(-c5nnc(C(F)F)o5)cc4)nn3)ccc2F)CC1] |
| 305 | 4421 | 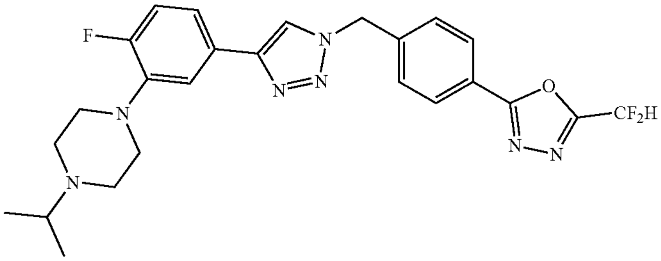 [SMILES: CC(C)N1CCN(c2cc(-c3cn(Cc4ccc(-c5nnc(C(F)F)o5)cc4)nn3)ccc2F)CC1] |
| 306 | 4422 | 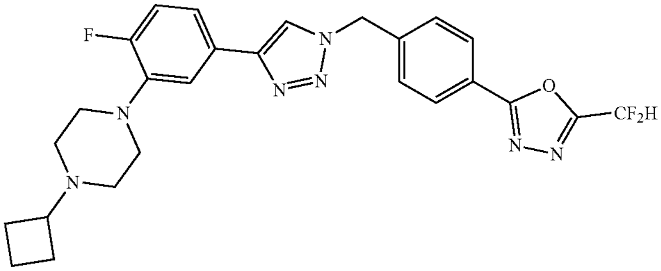 [SMILES: Fc1ccc(-c2cn(Cc3ccc(-c4nnc(C(F)F)o4)cc3)nn2)cc1N1CCN(C2CCC2)CC1] |
| 307 | 4424 | 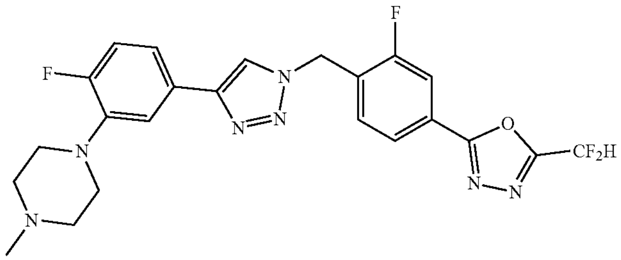 [SMILES: CN1CCN(c2cc(-c3cn(Cc4ccc(-c5nnc(C(F)F)o5)cc4F)nn3)ccc2F)CC1] |

TABLE 1-continued
| Example | Compound | Structure |
|---|---|---|
| 308 | 4425 | 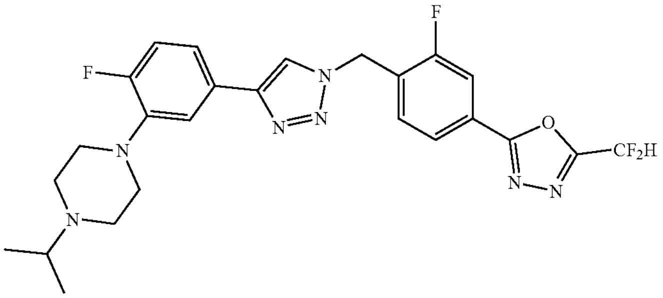 [SMILES: CC(C)N1CCN(c2cc(-c3cn(Cc4ccc(-c5nnc(C(F)F)o5)cc4F)nn3)ccc2F)CC1] |
| 309 | 4426 | 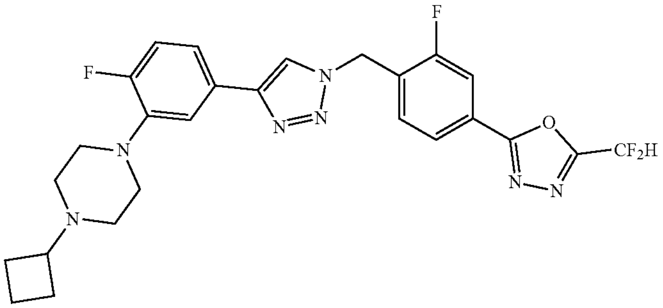 [SMILES: Fc1cc(-c2nnc(C(F)F)o2)ccc1Cn1cc(-c2ccc(F)c(N3CCN(C4CCC4)CC3)c2)nn1] |
| 310 | 4427 | 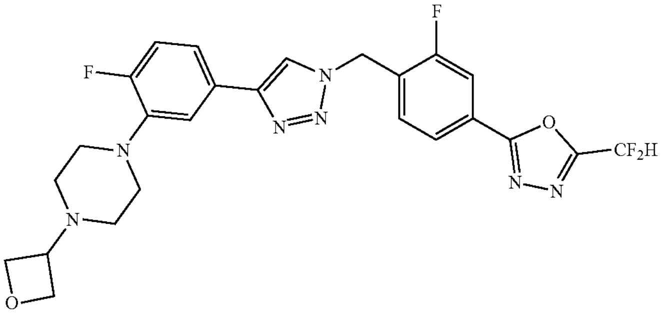 [SMILES: Fc1cc(-c2nnc(C(F)F)o2)ccc1Cn1cc(-c2ccc(F)c(N3CCN(C4COC4)CC3)c2)nn1] |
| 311 | 4429 | 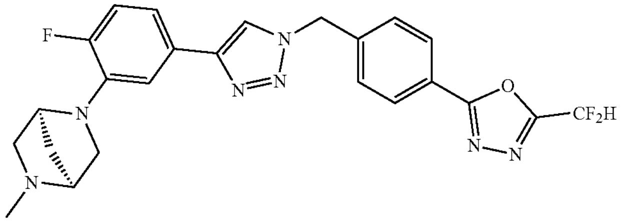 [SMILES: CN1C[C@@H]2C[C@H]1CN2c1cc(-c2cn(Cc3ccc(-c4nnc(C(F)F)o4)cc3)nn2)ccc1F] |
| 312 | 4430 | 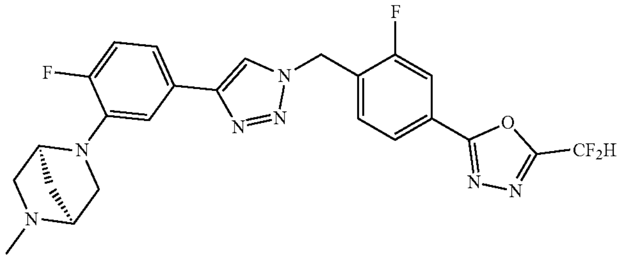 [SMILES: CN1C[C@@H]2C[C@H]1CN2c1cc(-c2cn(Cc3ccc(-c4nnc(C(F)F)o4)cc3F)nn2)ccc1F] |

TABLE 1-continued
| Example | Compound | Structure |
|---|---|---|
| 313 | 4431 | 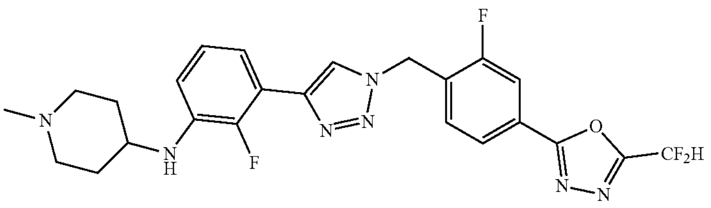 [SMILES: CN1CCC(Nc2cccc(-c3cn(Cc4ccc(-c5nnc(C(F)F)o5)cc4F)nn3)c2F)CC1] |
| 314 | 4432 | 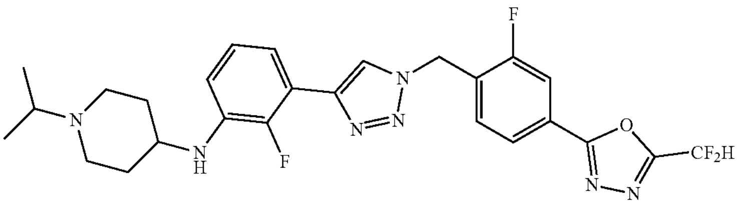 [SMILES: CC(C)N1CCC(Nc2cccc(-c3cn(Cc4ccc(-c5nnc(C(F)F)o5)cc4F)nn3)c2F)CC1] |
| 315 | 4433 | 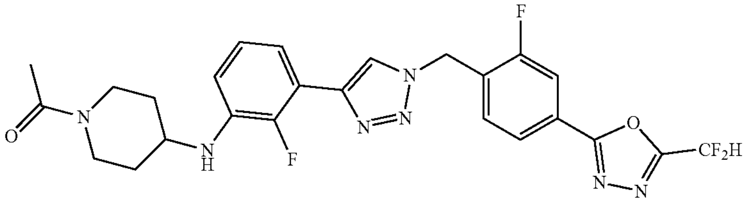 [SMILES: CC(=O)N1CCC(Nc2cccc(-c3cn(Cc4ccc(-c5nnc(C(F)F)o5)cc4F)nn3)c2F)CC1] |
| 316 | 4434 | 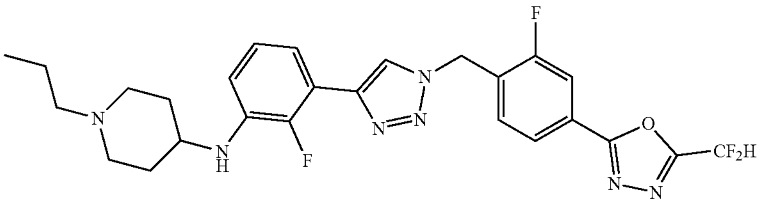 [SMILES: CCCN1CCC(Nc2cccc(-c3cn(Cc4ccc(-c5nnc(C(F)F)o5)cc4F)nn3)c2F)CC1] |
| 317 | 4435 | 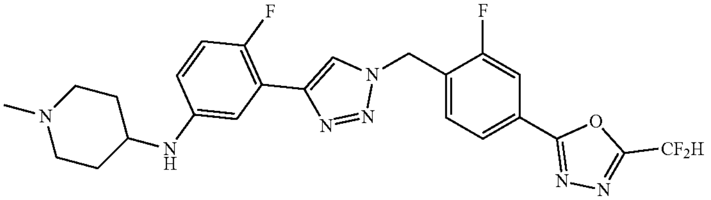 [SMILES: CN1CCC(Nc2ccc(F)c(-c3cn(Cc4ccc(-c5nnc(C(F)F)o5)cc4F)nn3)c2)CC1] |
| 318 | 4436 | 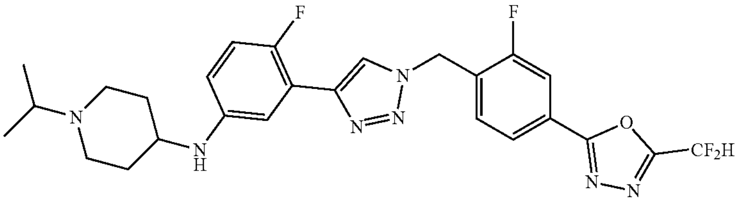 [SMILES: CC(C)N1CCC(Nc2ccc(F)c(-c3cn(Cc4ccc(-c5nnc(C(F)F)o5)cc4F)nn3)c2)CC1] |
| 319 | 4437 | 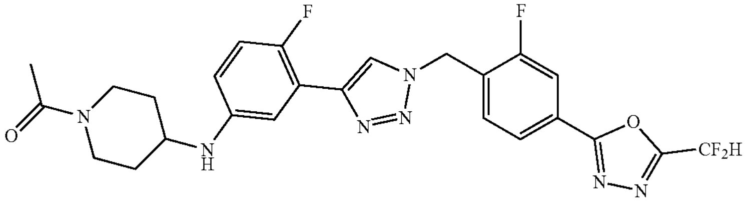 [SMILES: CC(=O)N1CCC(Nc2ccc(F)c(-c3cn(Cc4ccc(-c5nnc(C(F)F)o5)cc4F)nn3)c2)CC1] |

TABLE 1-continued
| Example | Compound | Structure |
| --- | --- | --- |
| 320 | 4438 | 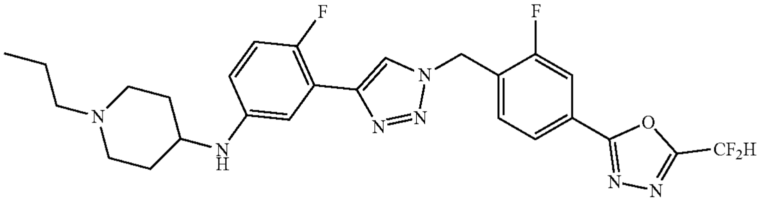 [SMILES: CCCN1CCC(Nc2ccc(F)c(-c3cn(Cc4ccc(-c5nnc(C(F)F)o5)cc4F)nn3)c2)CC1] |
| 321 | 4439 | 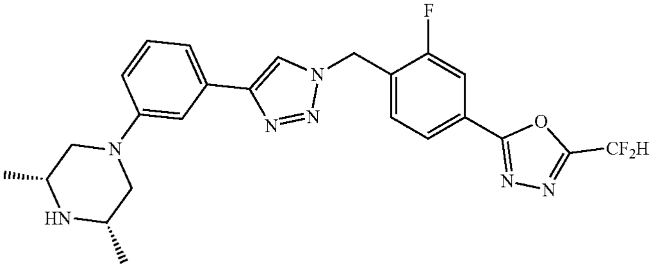 [SMILES: C[C@@H]1CN(c2cccc(-c3cn(Cc4ccc(-c5nnc(C(F)F)o5)cc4F)nn3)c2)C[C@H](C)N1] |
| 322 | 4440 | 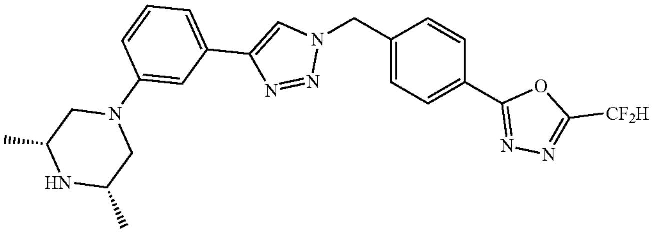 [SMILES: C[C@@H]1CN(c2cccc(-c3cn(Cc4ccc(-c5nnc(C(F)F)o5)cc4)nn3)c2)C[C@H](C)N1] |
| 323 | 4441 | 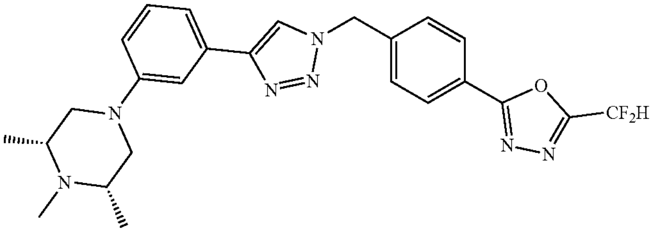 [SMILES: C[C@@H]1CN(c2cccc(-c3cn(Cc4ccc(-c5nnc(C(F)F)o5)cc4)nn3)c2)C[C@H](C)N1C] |
| 324 | 4442 | 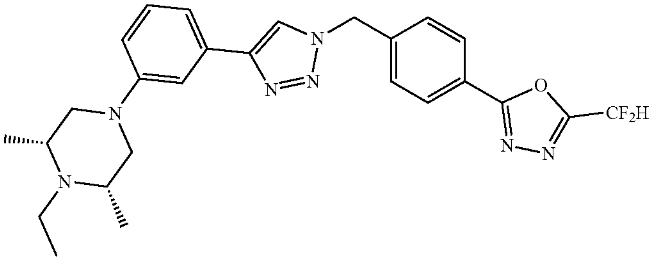 [SMILES: CCN1[C@H](C)CN(c2cccc(-c3cn(Cc4ccc(-c5nnc(C(F)F)o5)cc4)nn3)c2)C[C@@H]1C] |
| 325 | 4443 | 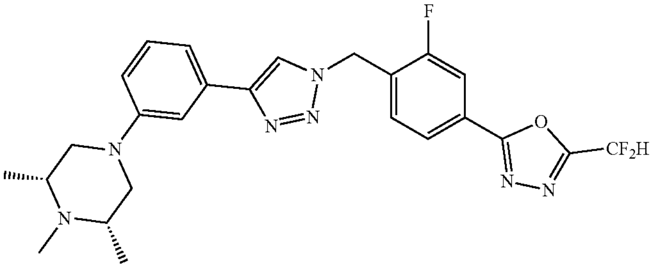 [SMILES: C[C@@H]1CN(c2cccc(-c3cn(Cc4ccc(-c5nnc(C(F)F)o5)cc4F)nn3)c2)C[C@H](C)N1C] |

TABLE 1-continued
| Example | Compound | Structure |
|---|---|---|
| 326 | 4444 | 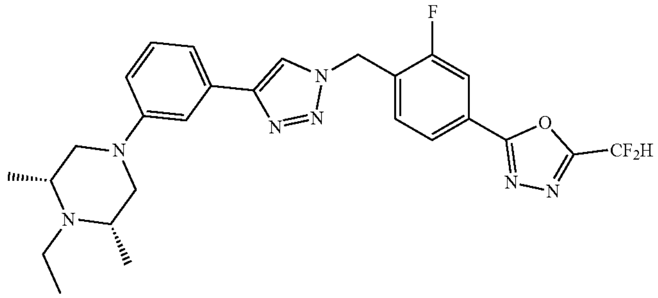 [SMILES: CCN1[C@H](C)CN(c2cccc(-c3cn(Cc4ccc(-c5nnc(C(F)F)o5)cc4F)nn3)c2)C[C@@H]1C] |
| 327 | 4448 | 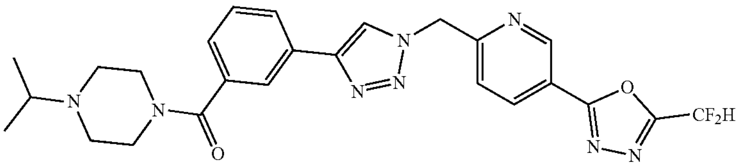 [SMILES: CC(C)N1CCN(C(=O)c2cccc(-c3cn(Cc4ccc(-c5nnc(C(F)F)o5)cn4)nn3)c2)CC1] |
| 328 | 4449 | 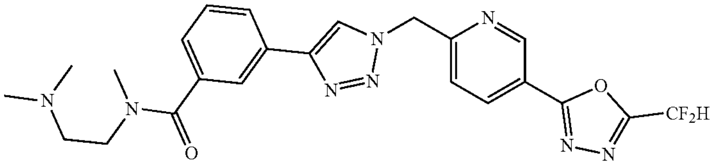 [SMILES: CN(C)CCN(C)C(=O)c1cccc(-c2cn(Cc3ccc(-c4nnc(C(F)F)o4)cn3)nn2)c1] |
| 329 | 4450 | 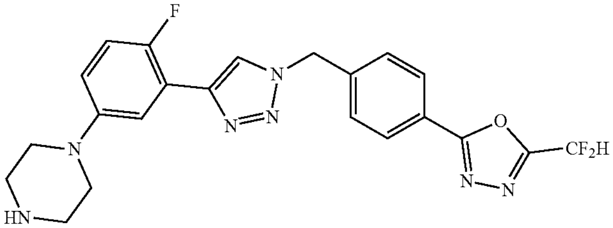 [SMILES: Fc1ccc(N2CCNCC2)cc1-c1cn(Cc2ccc(-c3nnc(C(F)F)o3)cc2)nn1] |
| 330 | 4451 | 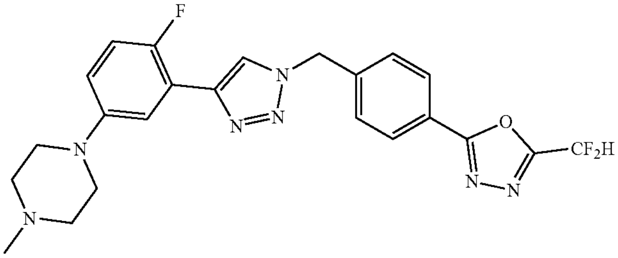 [SMILES: CN1CCN(c2ccc(F)c(-c3cn(Cc4ccc(-c5nnc(C(F)F)o5)cc4)nn3)c2)CC1] |
| 331 | 4452 | 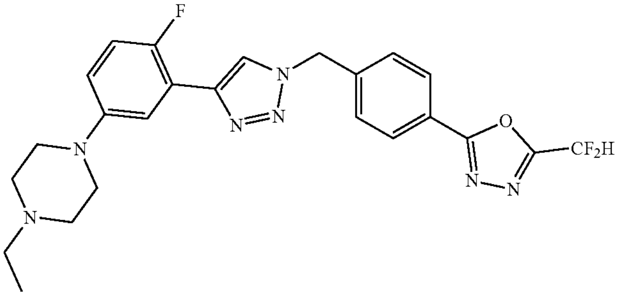 [SMILES: CCN1CCN(c2ccc(F)c(-c3cn(Cc4ccc(-c5nnc(C(F)F)o5)cc4)nn3)c2)CC1] |

TABLE 1-continued
| Example | Compound | Structure |
|---|---|---|
| 332 | 4453 | 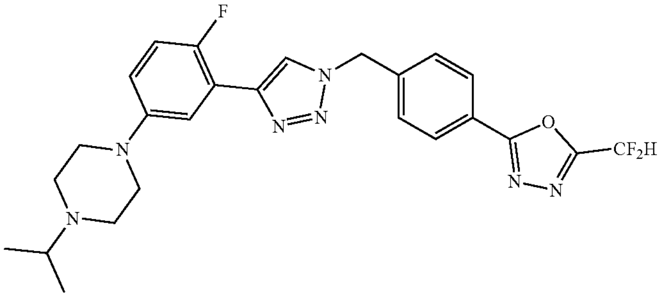 [SMILES: CC(C)N1CCN(c2ccc(F)c(-c3cn(Cc4ccc(-c5nnc(C(F)F)o5)cc4)nn3)c2)CC1] |
| 333 | 4454 | 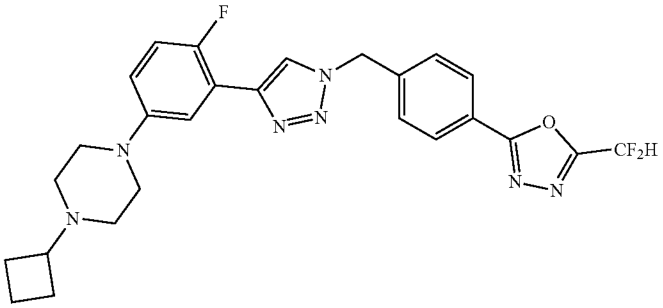 [SMILES: Fc1ccc(N2CCN(C3CCC3)CC2)cc1-c1cn(Cc2ccc(-c3nnc(C(F)F)o3)cc2)nn1] |
| 334 | 4455 | 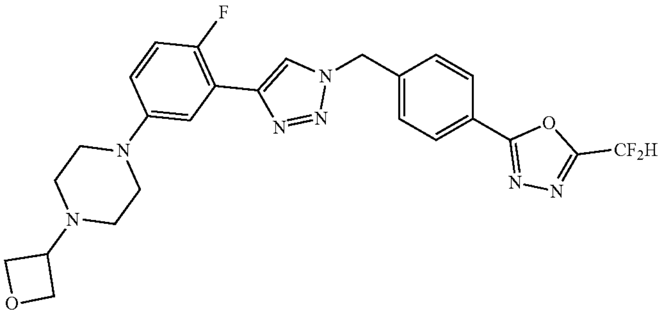 [SMILES: Fc1ccc(N2CCN(C3COC3)CC2)cc1-c1cn(Cc2ccc(-c3nnc(C(F)F)o3)cc2)nn1] |
| 335 | 4460 | 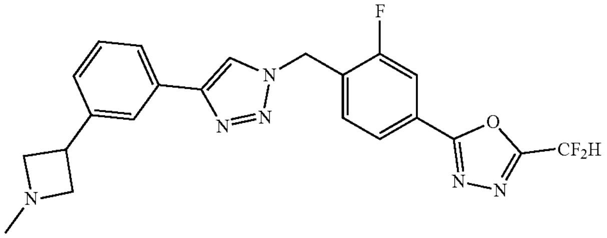 [SMILES: CN1CC(c2cccc(-c3cn(Cc4ccc(-c5nnc(C(F)F)o5)cc4F)nn3)c2)C1] |
| 336 | 4461 | 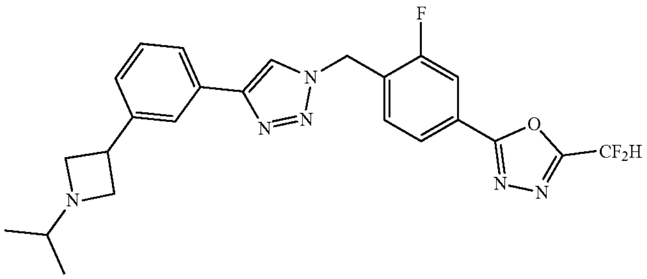 [SMILES: CC(C)N1CC(c2cccc(-c3cn(Cc4ccc(-c5nnc(C(F)F)o5)cc4F)nn3)c2)C1] |

TABLE 1-continued
| Example | Compound | Structure |
| --- | --- | --- |
| 337 | 4462 | 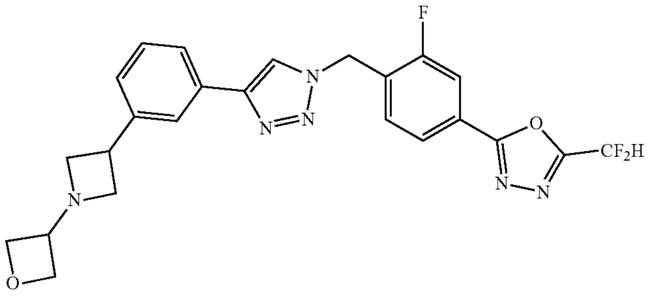 [SMILES: Fc1cc(-c2nnc(C(F)F)o2)ccc1Cn1cc(-c2cccc(C3CN(C4COC4)C3)c2)nn1] |
| 338 | 4463 | 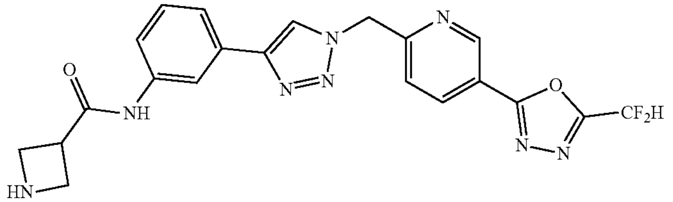 [SMILES: O=C(Nc1cccc(-c2cn(Cc3ccc(-c4nnc(C(F)F)o4)cn3)nn2)c1)C1CNC1] |
| 339 | 4464 | 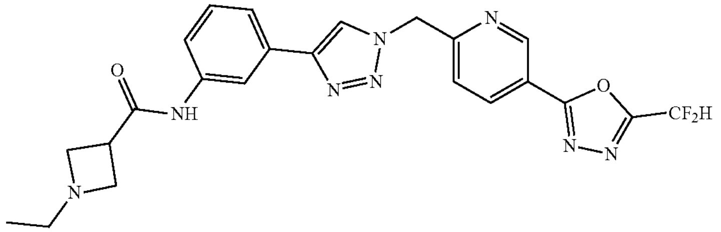 [SMILES: CCN1CC(C(=O)Nc2cccc(-c3cn(Cc4ccc(-c5nnc(C(F)F)o5)cn4)nn3)c2)C1] |
| 340 | 4465 | 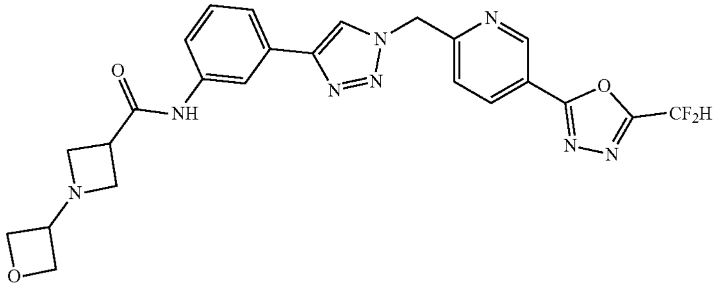 [SMILES: O=C(Nc1cccc(-c2cn(Cc3ccc(-c4nnc(C(F)F)o4)cn3)nn2)c1)C1CN(C2COC2)C1] |
| 341 | 4466 | 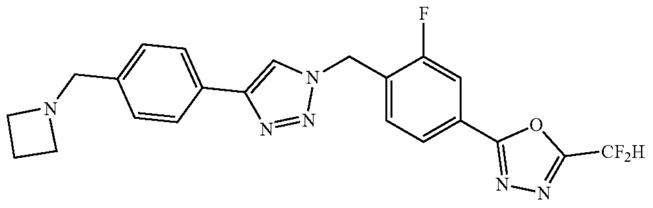 |
| 342 | 4467 | 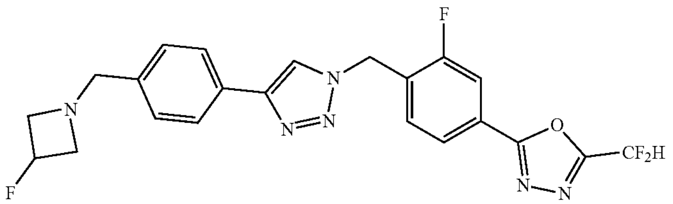 [SMILES: Fc1cc(-c2nnc(C(F)F)o2)ccc1Cn1cc(-c2ccc(CN3CC(F)C3)cc2)nn1] |

TABLE 1-continued
| Example | Compound | Structure |
|---|---|---|
| 343 | 4468 | 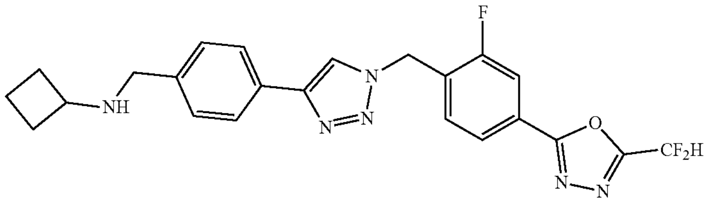 [SMILES: Fc1cc(-c2nnc(C(F)F)o2)ccc1Cn1cc(-c2ccc(CNC3CCC3)cc2)nn1] |
| 344 | 4469 | 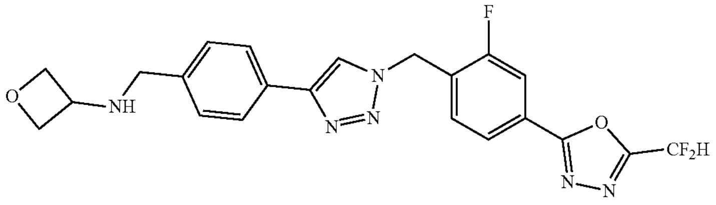 [SMILES: Fc1cc(-c2nnc(C(F)F)o2)ccc1Cn1cc(-c2ccc(CNC3COC3)cc2)nn1] |
| 345 | 4470 | 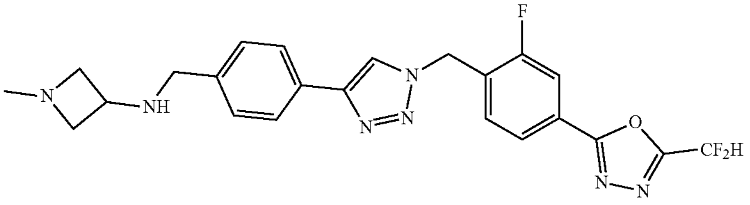 [SMILES: CN1CC(NCc2ccc(-c3cn(Cc4ccc(-c5nnc(C(F)F)o5)cc4F)nn3)cc2)C1] |
| 346 | 4471 | 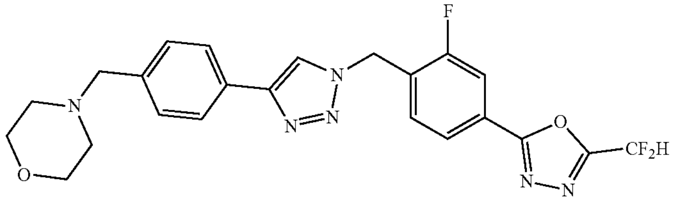 |
| 347 | 4472 | 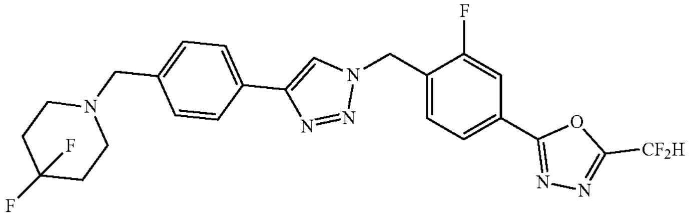 |
| 348 | 4473 | 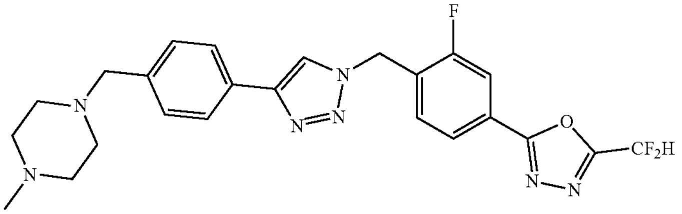 [SMILES: CN1CCN(Cc2ccc(-c3cn(Cc4ccc(-c5nnc(C(F)F)o5)cc4F)nn3)cc2)CC1] |
| 349 | 4474 | 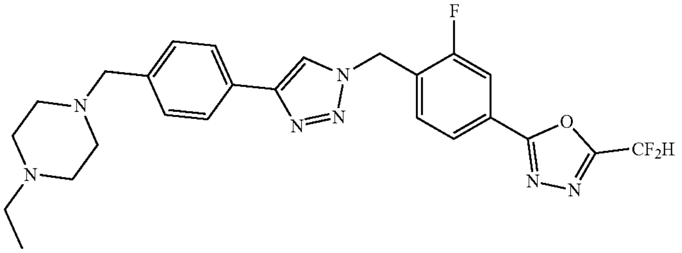 [SMILES: CCN1CCN(Cc2ccc(-c3cn(Cc4ccc(-c5nnc(C(F)F)o5)cc4F)nn3)cc2)CC1] |

TABLE 1-continued
| Example | Compound | Structure |
|---|---|---|
| 350 | 4475 | 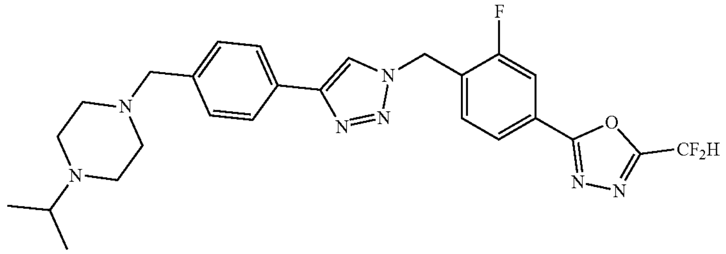 [SMILES: CC(C)N1CCN(Cc2ccc(-c3cn(Cc4ccc(-c5nnc(C(F)F)o5)cc4F)nn3)cc2)CC1] |
| 351 | 4476 | 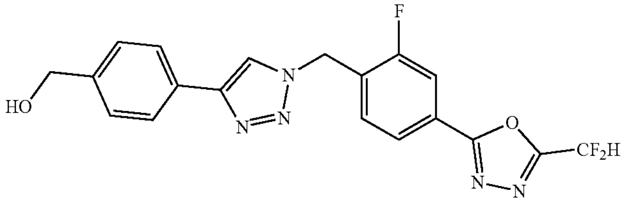 [SMILES: OCc1ccc(-c2cn(Cc3ccc(-c4nnc(C(F)F)o4)cc3F)nn2)cc1] |
| 352 | 4477 | 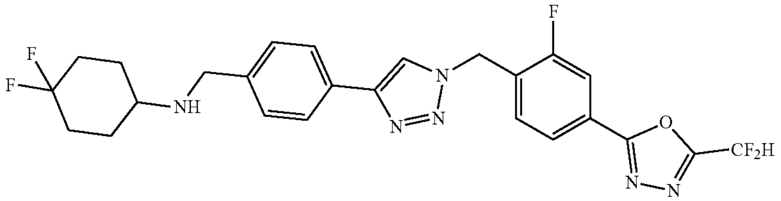 [SMILES: Fc1cc(-c2nnc(C(F)F)o2)ccc1Cn1cc(-c2ccc(CNC3CCC(F)(F)CC3)cc2)nn1] |
| 353 | 4478 | 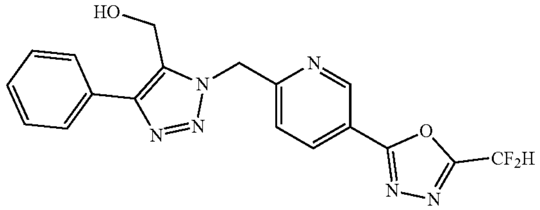 [SMILES: OCc1c(-c2ccccc2)nnn1Cc1ccc(-c2nnc(C(F)F)o2)cn1] |
| 354 | 4479 | 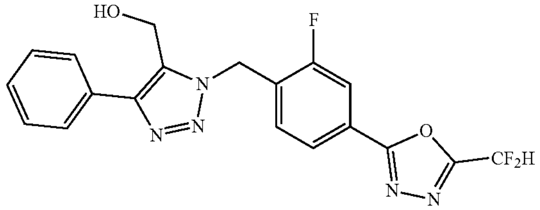 [SMILES: OCc1c(-c2ccccc2)nnn1Cc1ccc(-c2nnc(C(F)F)o2)cc1F] |
| 355 | 4480 | 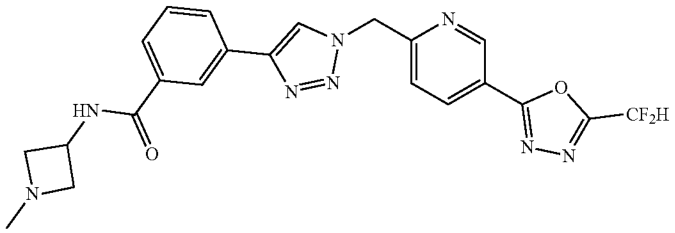 [SMILES: CN1CC(NC(=O)c2cccc(-c3cn(Cc4ccc(-c5nnc(C(F)F)o5)cn4)nn3)c2)C1] |
| 356 | 4482 | 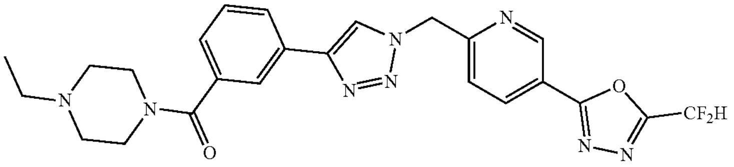 [SMILES: CCN1CCN(C(=O)c2cccc(-c3cn(Cc4ccc(-c5nnc(C(F)F)o5)cn4)nn3)c2)CC1] |

TABLE 1-continued
| Example | Compound | Structure |
|---|---|---|
| 357 | 4483 | 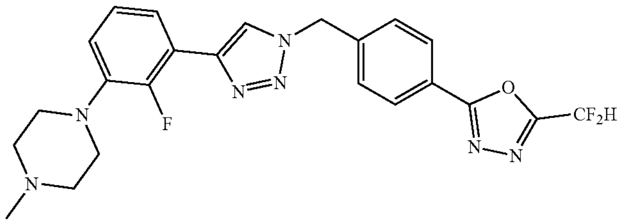 [SMILES: CN1CCN(c2cccc(-c3cn(Cc4ccc(-c5nnc(C(F)F)o5)cc4)nn3)c2F)CC1] |
| 358 | 4484 | 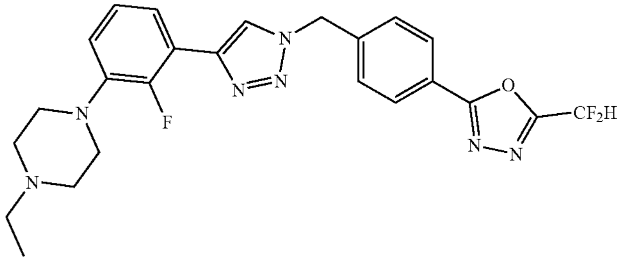 [SMILES: CCN1CCN(c2cccc(-c3cn(Cc4ccc(-c5nnc(C(F)F)o5)cc4)nn3)c2F)CC1] |
| 359 | 4485 | 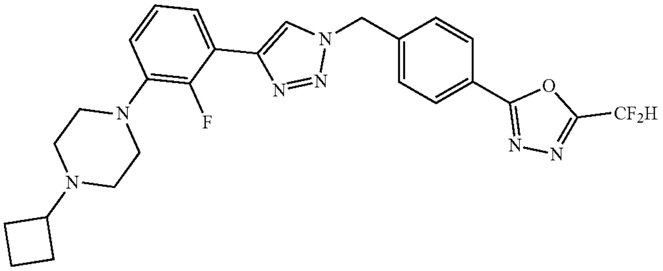 [SMILES: Fc1c(-c2cn(Cc3ccc(-c4nnc(C(F)F)o4)cc3)nn2)cccc1N1CCN(C2CCC2)CC1] |
| 360 | 4486 | 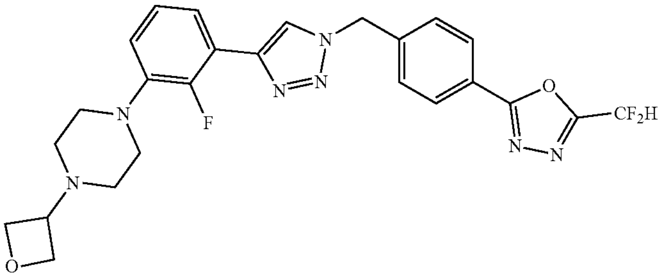 [SMILES: Fc1c(-c2cn(Cc3ccc(-c4nnc(C(F)F)o4)cc3)nn2)cccc1N1CCN(C2COC2)CC1] |
| 361 | 4487 | 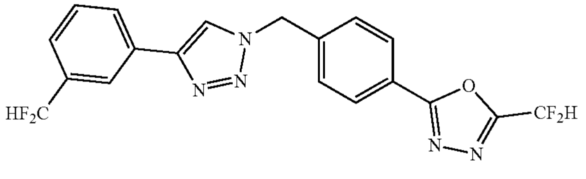 |
| 362 | 4488 | 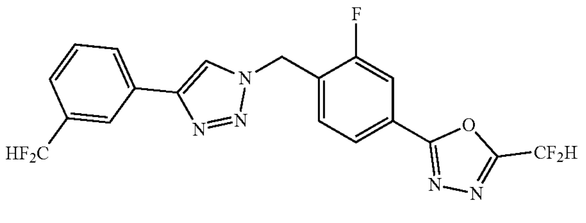 |

TABLE 1-continued
| Example | Compound | Structure |
|---|---|---|
| 363 | 4489 | 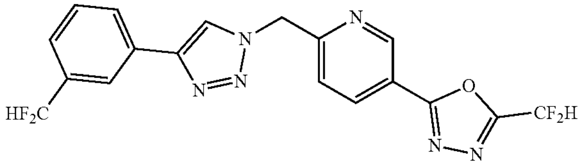 |
| 364 | 4490 | 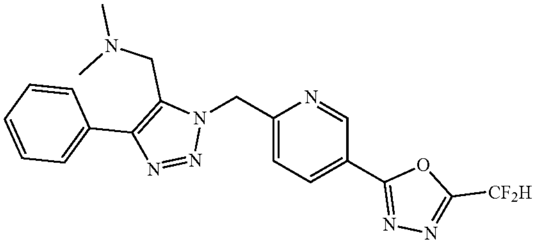 [SMILES: CN(C)Cc1c(-c2ccccc2)nnn1Cc1ccc(-c2nnc(C(F)F)o2)cn1] |
| 365 | 4491 | 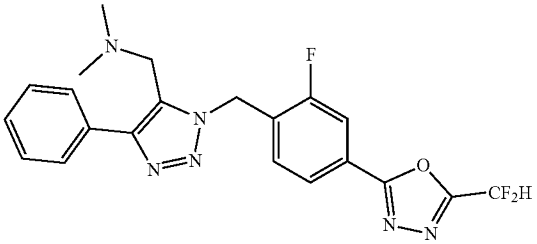 [SMILES: CN(C)Cc1c(-c2ccccc2)nnn1Cc1ccc(-c2nnc(C(F)F)o2)cc1F] |
| 366 | 4492 | 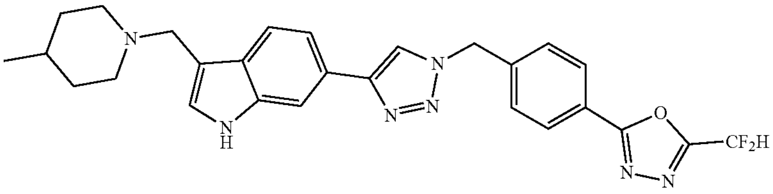 [SMILES: CC1CCN(Cc2c[nH]c3cc(-c4cn(Cc5ccc(-c6nnc(C(F)F)o6)cc5)nn4)ccc23)CC1] |
| 367 | 4493 | 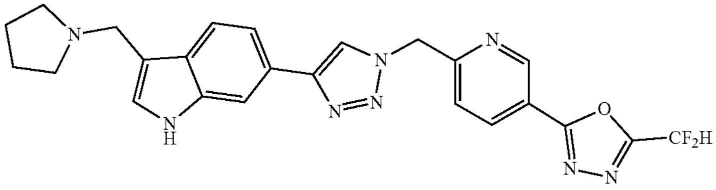 [SMILES: FC(F)c1nnc(-c2ccc(Cn3cc(-c4ccc5c(CN6CCCC6)c[nH]c5c4)nn3)nc2)o1] |
| 368 | 4494 | 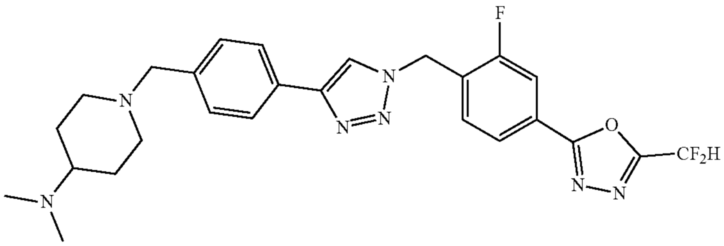 [SMILES: CN(C)C1CCN(Cc2ccc(-c3cn(Cc4ccc(-c5nnc(C(F)F)o5)cc4F)nn3)cc2)CC1] |
| 369 | 4495 | 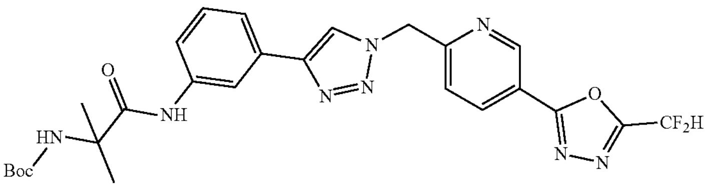 [SMILES: CC(C)(C)OC(=O)NC(C)(C)C(=O)Nc1cccc(-c2cn(Cc3ccc(-c4nnc(C(F)F)o4)cn3)nn2)c1] |

TABLE 1-continued
| Example | Compound | Structure |
|---|---|---|
| 370 | 4496 | 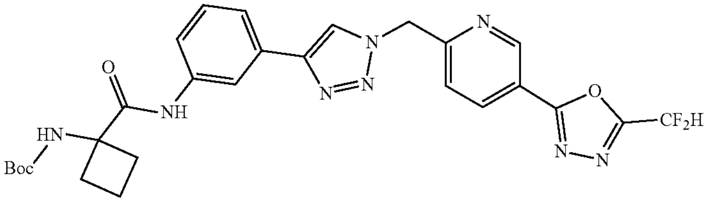 [SMILES: CC(C)(C)OC(=O)NC1(C(=O)Nc2cccc(-c3cn(Cc4ccc(-c5nnc(C(F)F)o5)cn4)nn3)c2)CCC1] |
| 371 | 4497 | 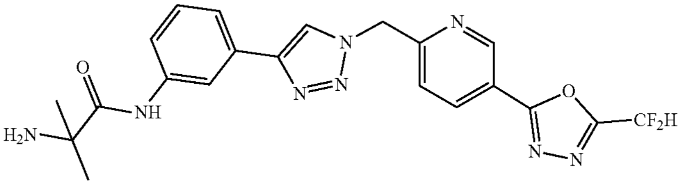 [SMILES: CC(C)(N)C(=O)Nc1cccc(-c2cn(Cc3ccc(-c4nnc(C(F)F)o4)cn3)nn2)c1] |
| 372 | 4498 | 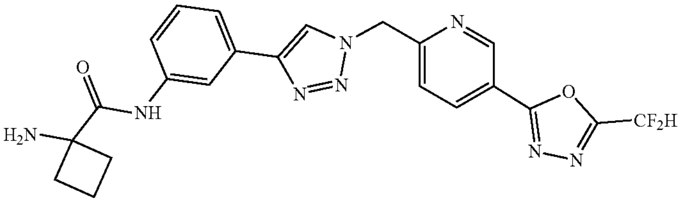 [SMILES: NC1(C(=O)Nc2cccc(-c3cn(Cc4ccc(-c5nnc(C(F)F)o5)cn4)nn3)c2)CCC1] |
| 373 | 4499 | 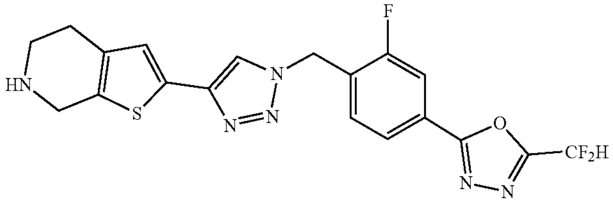 [SMILES: Fc1cc(-c2nnc(C(F)F)o2)ccc1Cn1cc(-c2cc3c(s2)CNCC3)nn1] |
| 374 | 4500 | 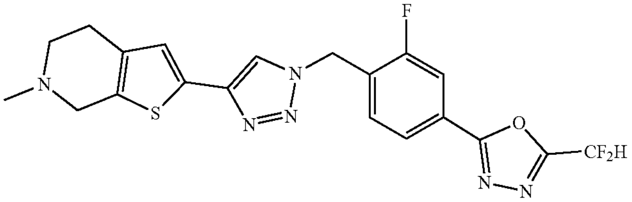 [SMILES: CN1CCc2cc(-c3cn(Cc4ccc(-c5nnc(C(F)F)o5)cc4F)nn3)sc2C1] |
| 375 | 4501 | 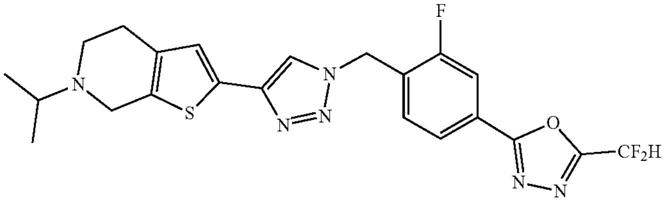 [SMILES: CC(C)N1CCc2cc(-c3cn(Cc4ccc(-c5nnc(C(F)F)o5)cc4F)nn3)sc2C1] |
| 376 | 4502 | 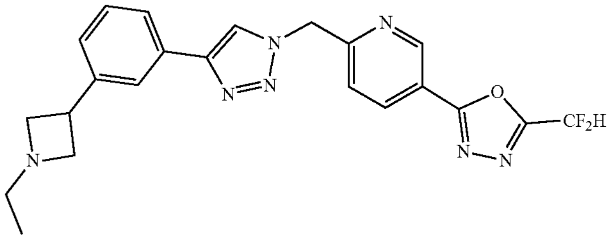 [SMILES: CCN1CC(c2cccc(-c3cn(Cc4ccc(-c5nnc(C(F)F)o5)cn4)nn3)c2)C1] |

TABLE 1-continued
| Example | Compound | Structure |
| --- | --- | --- |
| 377 | 4503 | 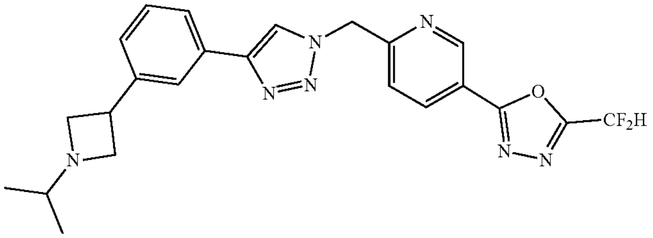 [SMILES: CC(C)N1CC(c2cccc(-c3cn(Cc4ccc(-c5nnc(C(F)F)o5)cn4)nn3)c2)C1] |
| 378 | 4504 | 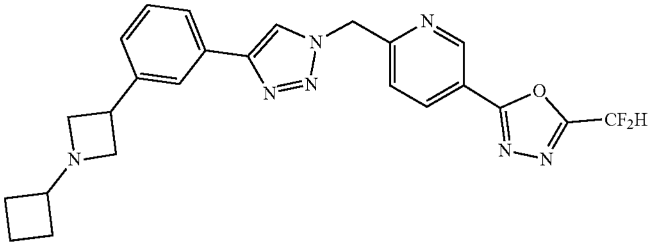 [SMILES: FC(F)c1nnc(-c2ccc(Cn3cc(-c4cccc(C5CN(C6CCC6)C5)c4)nn3)nc2)o1] |
| 379 | 4505 | 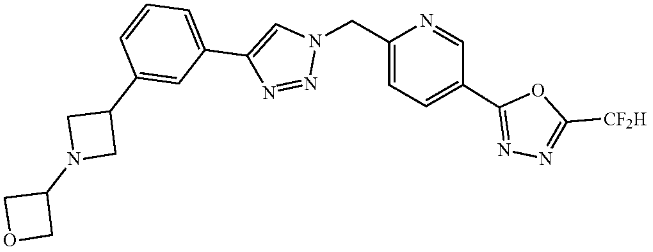 [SMILES: FC(F)c1nnc(-c2ccc(Cn3cc(-c4cccc(C5CN(C6COC6)C5)c4)nn3)nc2)o1] |
| 380 | 4506 | 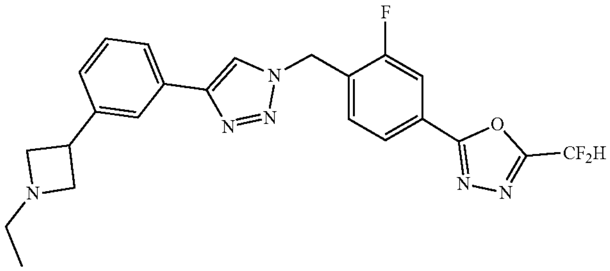 [SMILES: CCN1CC(c2cccc(-c3cn(Cc4ccc(-c5nnc(C(F)F)o5)cc4F)nn3)c2)C1] |
| 381 | 4507 | 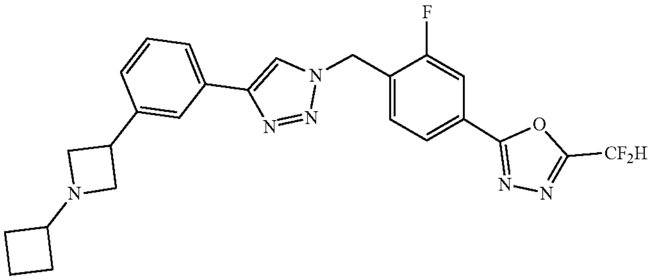 [SMILES: Fc1cc(-c2nnc(C(F)F)o2)ccc1Cn1cc(-c2cccc(C3CN(C4CCC4)C3)c2)nn1] |
| 382 | 4508 | 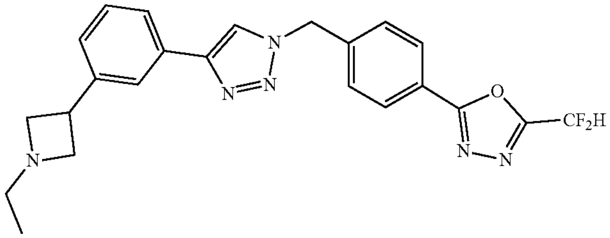 [SMILES: CCN1CC(c2cccc(-c3cn(Cc4ccc(-c5nnc(C(F)F)o5)cc4)nn3)c2)C1] |

TABLE 1-continued
| Example | Compound | Structure |
| --- | --- | --- |
| 383 | 4509 | 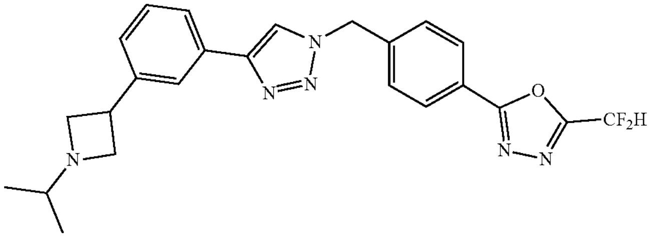 [SMILES: CC(C)N1CC(c2cccc(-c3cn(Cc4ccc(-c5nnc(C(F)F)o5)cc4)nn3)c2)C1] |
| 384 | 4510 | 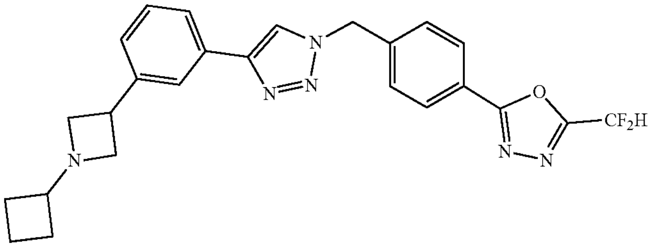 [SMILES: FC(F)c1nnc(-c2ccc(Cn3cc(-c4cccc(C5CN(C6CCC6)C5)c4)nn3)cc2)o1] |
| 385 | 4511 | 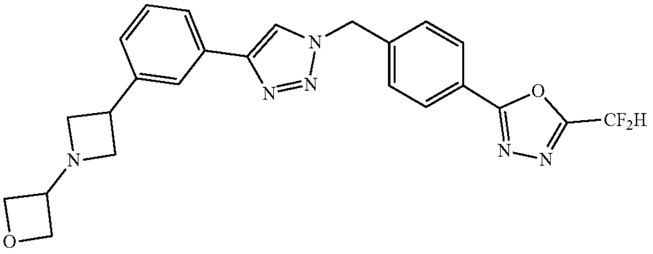 [SMILES: FC(F)c1nnc(-c2ccc(Cn3cc(-c4cccc(C5CN(C6COC6)C5)c4)nn3)cc2)o1] |
| 386 | 4513 | 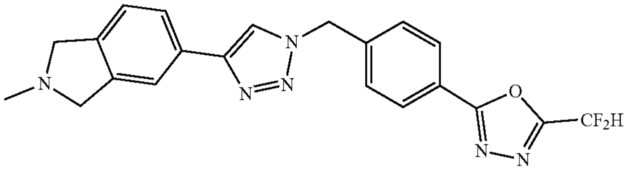 [SMILES: CN1Cc2ccc(-c3cn(Cc4ccc(-c5nnc(C(F)F)o5)cc4)nn3)cc2C1] |
| 387 | 4515 | 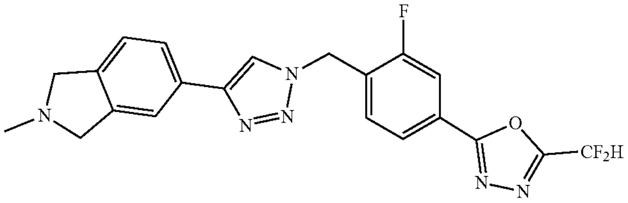 [SMILES: CN1Cc2ccc(-c3cn(Cc4ccc(-c5nnc(C(F)F)o5)cc4F)nn3)cc2C1] |
| 388 | 4516 | 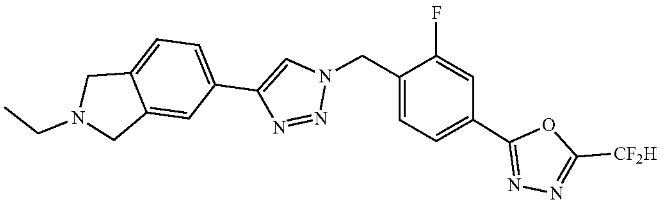 [SMILES: CCN1Cc2ccc(-c3cn(Cc4ccc(-c5nnc(C(F)F)o5)cc4F)nn3)cc2C1] |
| 389 | 4517 | 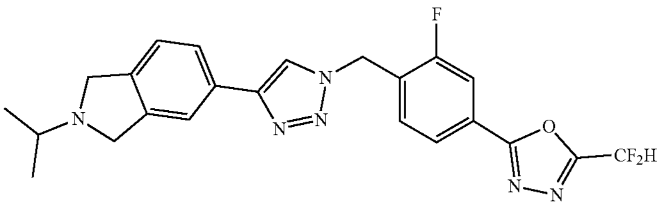 [SMILES: CC(C)N1Cc2ccc(-c3cn(Cc4ccc(-c5nnc(C(F)F)o5)cc4F)nn3)cc2C1] |

TABLE 1-continued
| Example | Compound | Structure |
| --- | --- | --- |
| 390 | 4518 | 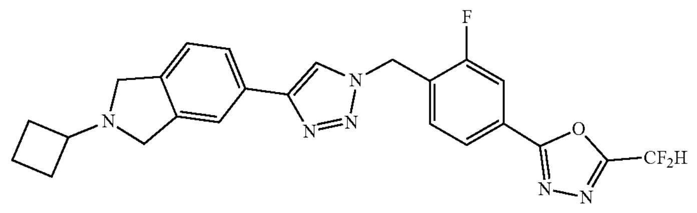 [SMILES: Fc1cc(-c2nnc(C(F)F)o2)ccc1Cn1cc(-c2ccc3c(c2)CN(C2CCC2)C3)nn1] |
| 391 | 4519 | 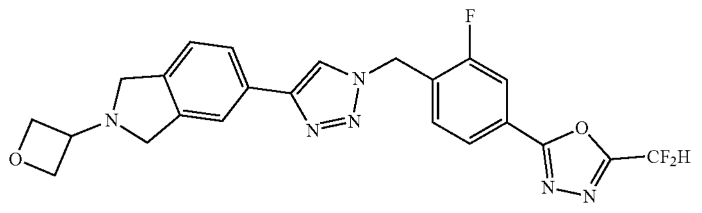 [SMILES: Fc1cc(-c2nnc(C(F)F)o2)ccc1Cn1cc(-c2ccc3c(c2)CN(C2COC2)C3)nn1] |
| 392 | 4521 | 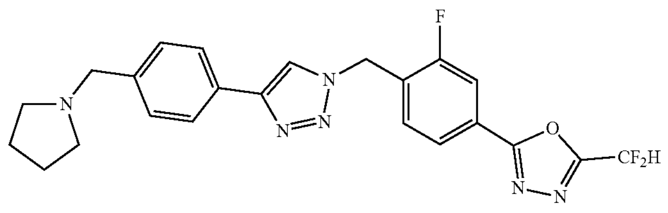 [SMILES: Fc1cc(-c2nnc(C(F)F)o2)ccc1Cn1cc(-c2ccc(CN3CCCC3)cc2)nn1] |
| 393 | 4522 | 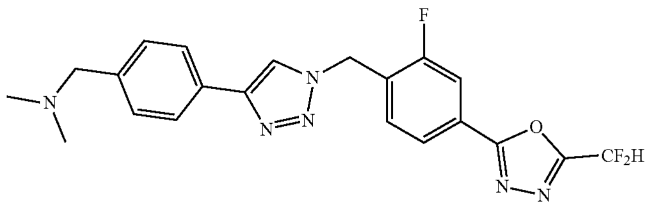 [SMILES: CN(C)Cc1ccc(-c2cn(Cc3ccc(-c4nnc(C(F)F)o4)cc3F)nn2)cc1] |
| 394 | 4523 | 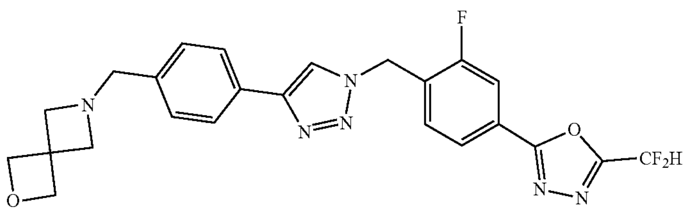 [SMILES: Fc1cc(-c2nnc(C(F)F)o2)ccc1Cn1cc(-c2ccc(CN3CC4(COC4)C3)cc2)nn1] |
| 395 | 4524 | 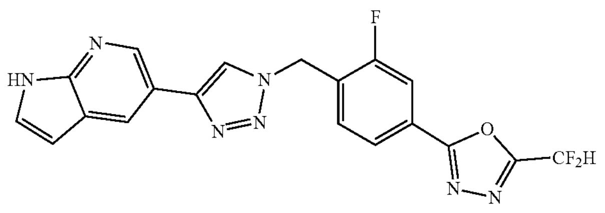 [SMILES: Fc1cc(-c2nnc(C(F)F)o2)ccc1Cn1cc(-c2cnc3[nH]ccc3c2)nn1] |
| 396 | 4525 | 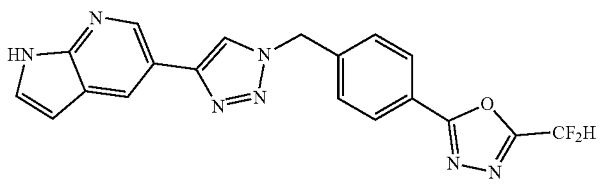 [SMILES: FC(F)c1nnc(-c2ccc(Cn3cc(-c4cnc5[nH]ccc5c4)nn3)cc2)o1] |

TABLE 1-continued
| Example | Compound | Structure |
|---|---|---|
| 397 | 4526 | 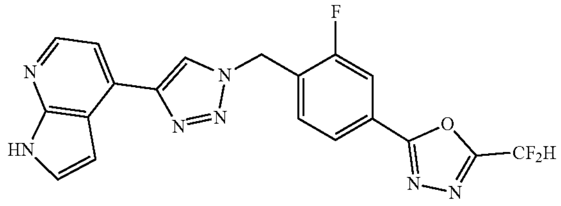 |
| 398 | 4527 | 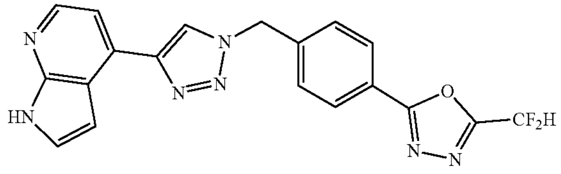 [SMILES: FC(F)c1nnc(-c2ccc(Cn3cc(-c4ccnc5[nH]ccc45)nn3)cc2)o1] |
| 399 | 4528 | 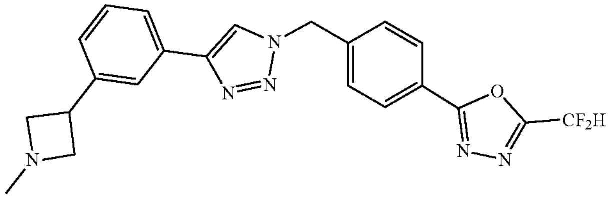 [SMILES: CN1CC(c2cccc(-c3cn(Cc4ccc(-c5nnc(C(F)F)o5)cc4)nn3)c2)C1] |
| 400 | 4529 | 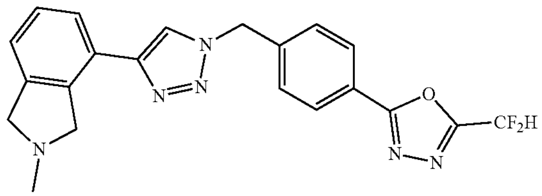 [SMILES: CN1Cc2cccc(-c3cn(Cc4ccc(-c5nnc(C(F)F)o5)cc4)nn3)c2C1] |
| 401 | 4530 | 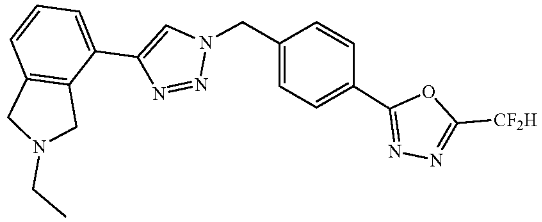 [SMILES: CCN1Cc2cccc(-c3cn(Cc4ccc(-c5nnc(C(F)F)o5)cc4)nn3)c2C1] |
| 402 | 4531 | 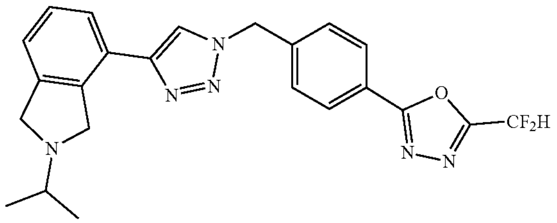 [SMILES: CC(C)N1Cc2cccc(-c3cn(Cc4ccc(-c5nnc(C(F)F)o5)cc4)nn3)c2C1] |
| 403 | 4532 | 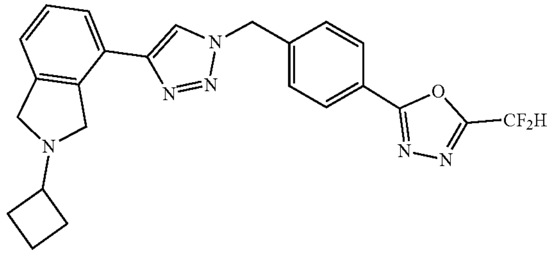 [SMILES: FC(F)c1nnc(-c2ccc(Cn3cc(-c4cccc5c4CN(C4CCC4)C5)nn3)cc2)o1] |

TABLE 1-continued
| Example | Compound | Structure |
|---|---|---|
| 404 | 4533 | 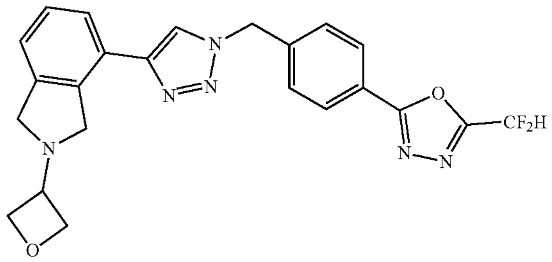 |
| 405 | 4534 | 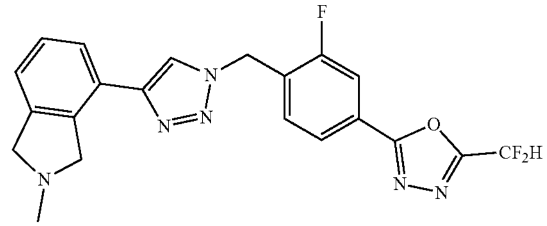 [SMILES: CN1Cc2cccc(-c3cn(Cc4ccc(-c5nnc(C(F)F)o5)cc4F)nn3)c2C1] |
| 406 | 4535 | 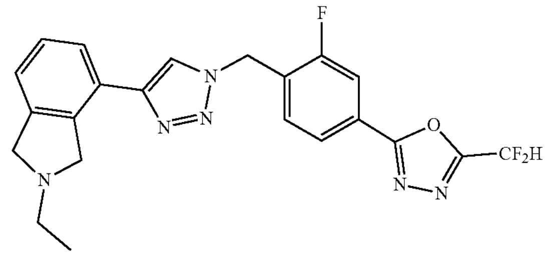 [SMILES: CCN1Cc2cccc(-c3cn(Cc4ccc(-c5nnc(C(F)F)o5)cc4F)nn3)c2C1] |
| 407 | 4536 | 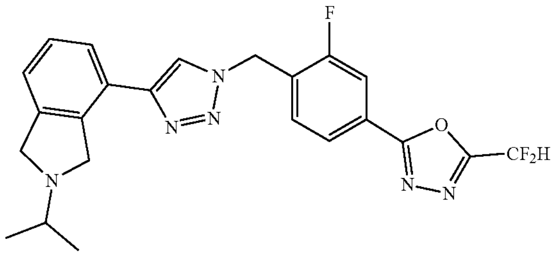 [SMILES: CC(C)N1Cc2cccc(-c3cn(Cc4ccc(-c5nnc(C(F)F)o5)cc4F)nn3)c2C1] |
| 408 | 4537 | 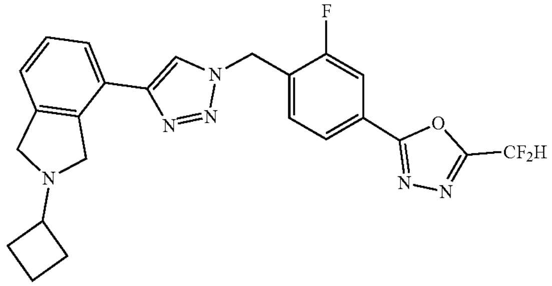 [SMILES: Fc1cc(-c2nnc(C(F)F)o2)ccc1Cn1cc(-c2cccc3c2CN(C2CCC2)C3)nn1] |
| 409 | 4538 | 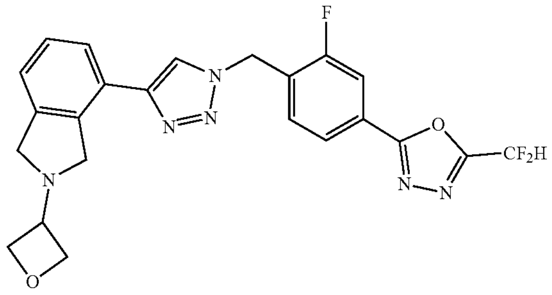 [SMILES: Fc1cc(-c2nnc(C(F)F)o2)ccc1Cn1cc(-c2cccc3c2CN(C2COC2)C3)nn1] |

TABLE 1-continued
| Example | Compound | Structure |
|---|---|---|
| 410 | 4539 | 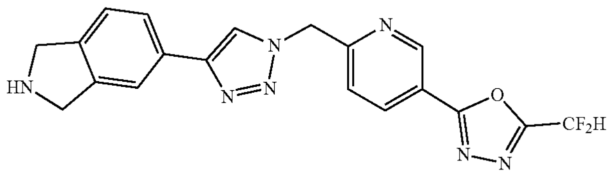 [SMILES: FC(F)c1nnc(-c2ccc(Cn3cc(-c4ccc5c(c4)CNC5)nn3)nc2)o1] |
| 411 | 4540 | 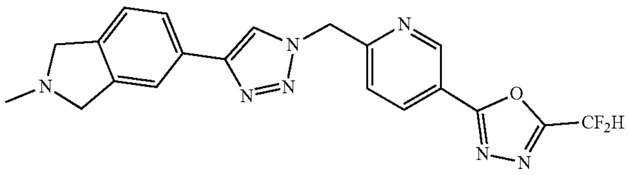 [SMILES: CN1Cc2ccc(-c3cn(Cc4ccc(-c5nnc(C(F)F)o5)cn4)nn3)cc2C1] |
| 412 | 4541 | 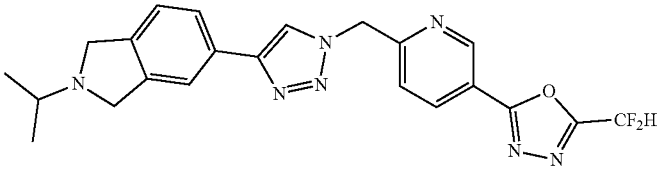 [SMILES: CC(C)N1Cc2ccc(-c3cn(Cc4ccc(-c5nnc(C(F)F)o5)cn4)nn3)cc2C1] |
| 413 | 4542 | 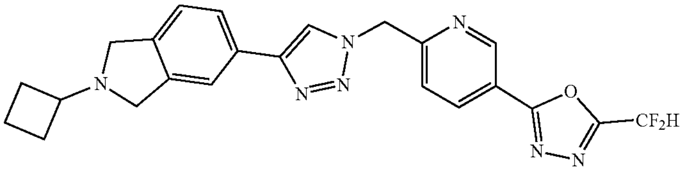 [SMILES: FC(F)c1nnc(-c2ccc(Cn3cc(-c4ccc5c(c4)CN(C4CCC4)C5)nn3)nc2)o1] |
| 414 | 4543 | 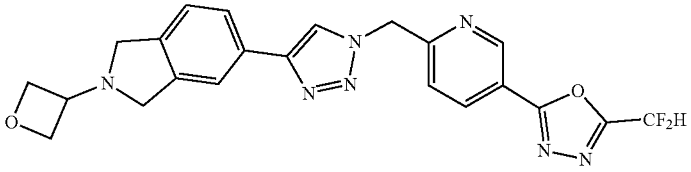 [SMILES: FC(F)c1nnc(-c2ccc(Cn3cc(-c4ccc5c(c4)CN(C4COC4)C5)nn3)nc2)o1] |
| 415 | 4548 | 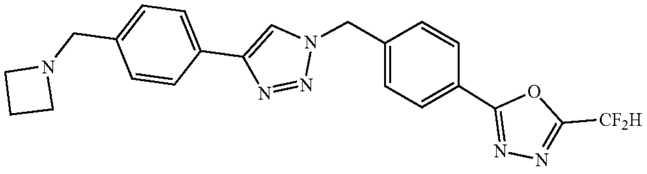 [SMILES: FC(F)c1nnc(-c2ccc(Cn3cc(-c4ccc(CN5CCC5)cc4)nn3)cc2)o1] |
| 416 | 4549 | 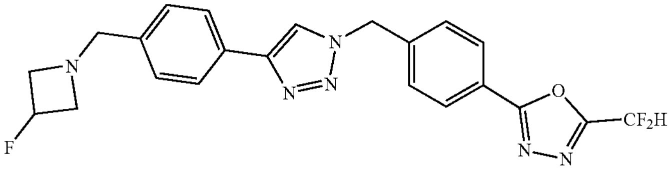 [SMILES: FC1CN(Cc2ccc(-c3cn(Cc4ccc(-c5nnc(C(F)F)o5)cc4)nn3)cc2)C1] |
| 417 | 4550 | 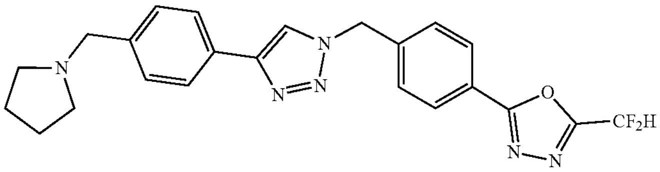 [SMILES: FC(F)c1nnc(-c2ccc(Cn3cc(-c4ccc(CN5CCCC5)cc4)nn3)cc2)o1] |

TABLE 1-continued
| Example | Compound | Structure |
| --- | --- | --- |
| 418 | 4551 | 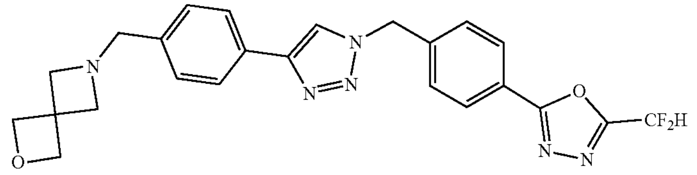 [SMILES: FC(F)c1nnc(-c2ccc(Cn3cc(-c4ccc(CN5CC6(COC6)C5)cc4)nn3)cc2)o1] |
| 419 | 4552 | 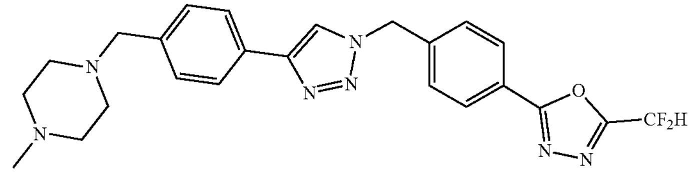 [SMILES: CN1CCN(Cc2ccc(-c3cn(Cc4ccc(-c5nnc(C(F)F)o5)cc4)nn3)cc2)CC1] |
| 420 | 4553 | 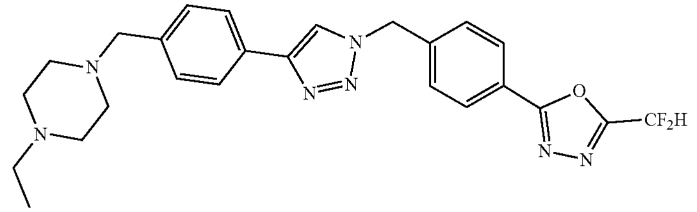 [SMILES: CCN1CCN(Cc2ccc(-c3cn(Cc4ccc(-c5nnc(C(F)F)o5)cc4)nn3)cc2)CC1] |
| 421 | 4554 | 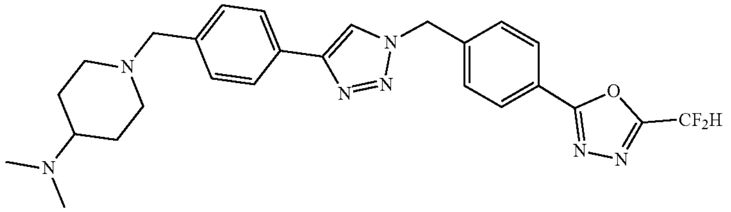 [SMILES: CN(C)C1CCN(Cc2ccc(-c3cn(Cc4ccc(-c5nnc(C(F)F)o5)cc4)nn3)cc2)CC1] |
| 422 | 4555 | 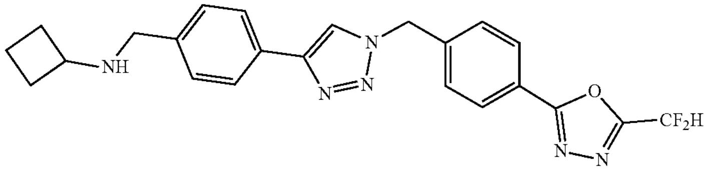 [SMILES: FC(F)c1nnc(-c2ccc(Cn3cc(-c4ccc(CNC5CCC5)cc4)nn3)cc2)o1] |
| 423 | 4556 | 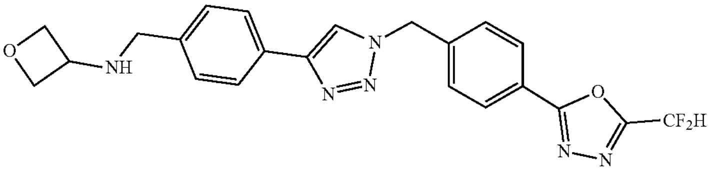 [SMILES: FC(F)c1nnc(-c2ccc(Cn3cc(-c4ccc(CNC5COC5)cc4)nn3)cc2)o1] |
| 424 | 4557 | 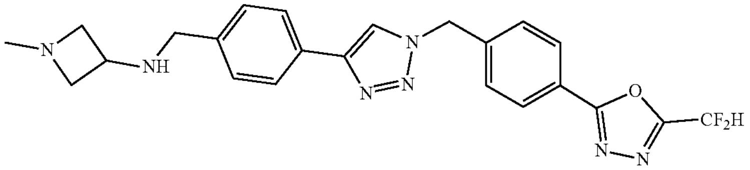 [SMILES: CN1CC(NCc2ccc(-c3cn(Cc4ccc(-c5nnc(C(F)F)o5)cc4)nn3)cc2)C1] |
| 425 | 4558 | 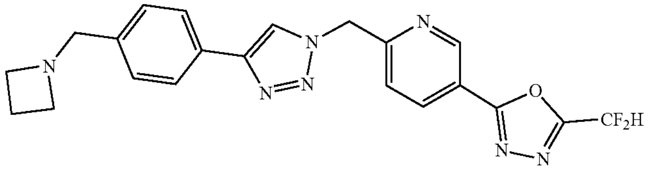 [SMILES: FC(F)c1nnc(-c2ccc(Cn3cc(-c4ccc(CN5CCC5)cc4)nn3)nc2)o1] |

TABLE 1-continued
| Example | Compound | Structure |
|---|---|---|
| 426 | 4559 | 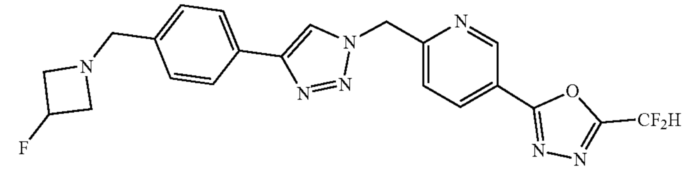 [SMILES: FC1CN(Cc2ccc(-c3cn(Cc4ccc(-c5nnc(C(F)F)o5)cn4)nn3)cc2)C1] |
| 427 | 4560 | 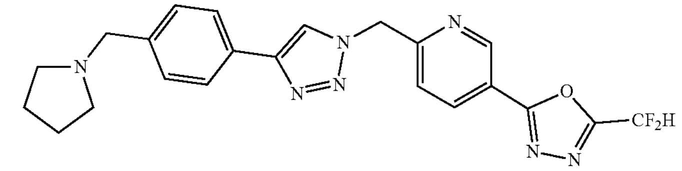 [SMILES: FC(F)c1nnc(-c2ccc(Cn3cc(-c4ccc(CN5CCCC5)cc4)nn3)nc2)o1] |
| 428 | 4561 | 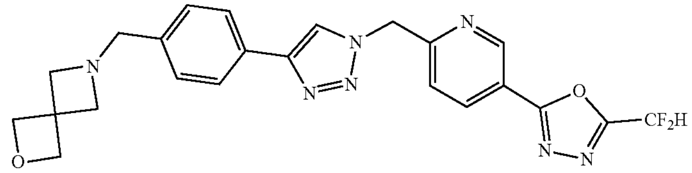 [SMILES: FC(F)c1nnc(-c2ccc(Cn3cc(-c4ccc(CN5CC6(COC6)C5)cc4)nn3)nc2)o1] |
| 429 | 4562 | 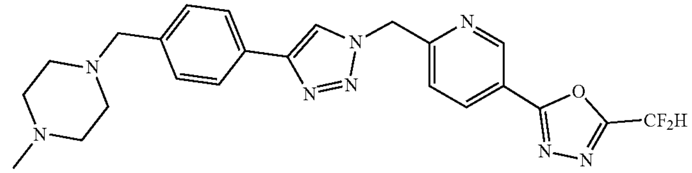 [SMILES: CN1CCN(Cc2ccc(-c3cn(Cc4ccc(-c5nnc(C(F)F)o5)cn4)nn3)cc2)CC1] |
| 430 | 4563 | 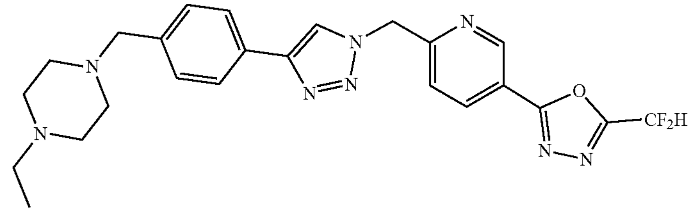 [SMILES: CCN1CCN(Cc2ccc(-c3cn(Cc4ccc(-c5nnc(C(F)F)o5)cn4)nn3)cc2)CC1] |
| 431 | 4564 | 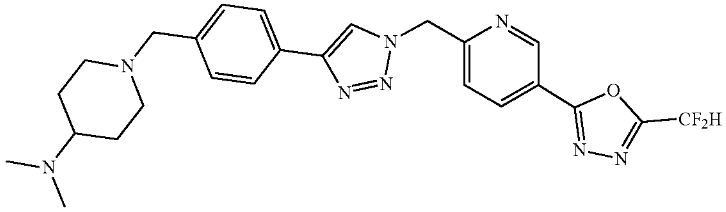 [SMILES: CN(C)C1CCN(Cc2ccc(-c3cn(Cc4ccc(-c5nnc(C(F)F)o5)cn4)nn3)cc2)CC1] |
| 432 | 4565 | 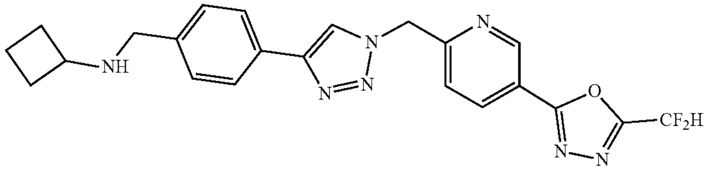 [SMILES: FC(F)c1nnc(-c2ccc(Cn3cc(-c4ccc(CNC5CCC5)cc4)nn3)nc2)o1] |
| 433 | 4566 | 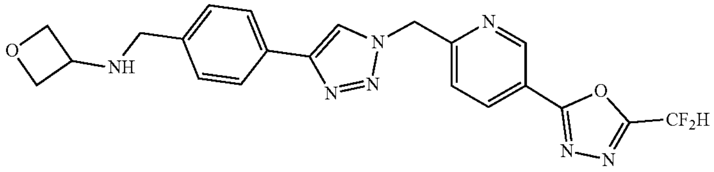 [SMILES: FC(F)c1nnc(-c2ccc(Cn3cc(-c4ccc(CNC5COC5)cc4)nn3)nc2)o1] |

TABLE 1-continued
| Example | Compound | Structure |
| --- | --- | --- |
| 434 | 4567 | 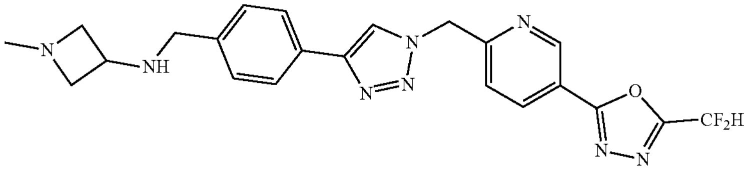 [SMILES: CN1CC(NCc2ccc(-c3cn(Cc4ccc(-c5nnc(C(F)F)o5)cn4)nn3)cc2)C1] |
| 435 | 4569 | 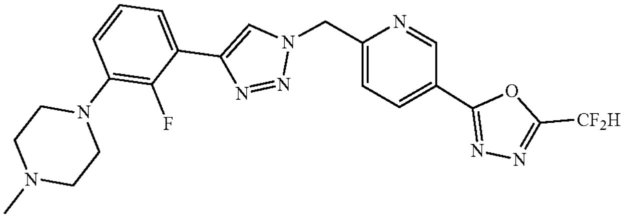 [SMILES: CN1CCN(c2cccc(-c3cn(Cc4ccc(-c5nnc(C(F)F)o5)cn4)nn3)c2F)CC1] |
| 436 | 4570 | 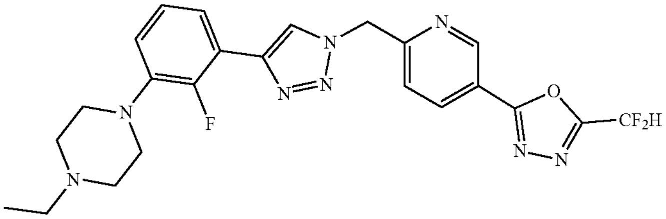 [SMILES: CCN1CCN(c2cccc(-c3cn(Cc4ccc(-c5nnc(C(F)F)o5)cn4)nn3)c2F)CC1] |
| 437 | 4571 | 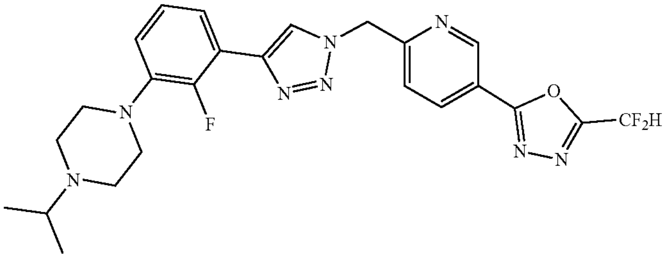 [SMILES: CC(C)N1CCN(c2cccc(-c3cn(Cc4ccc(-c5nnc(C(F)F)o5)cn4)nn3)c2F)CC1] |
| 438 | 4572 | 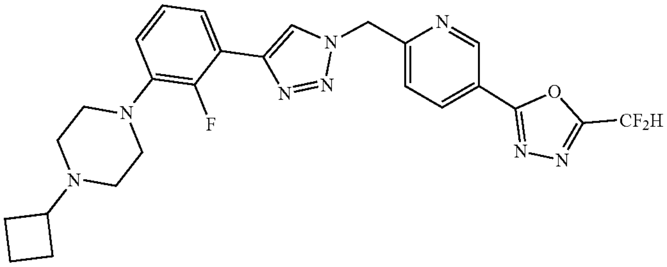 [SMILES: Fc1c(-c2cn(Cc3ccc(-c4nnc(C(F)F)o4)cn3)nn2)cccc1N1CCN(C2CCC2)CC1] |
| 439 | 4573 | 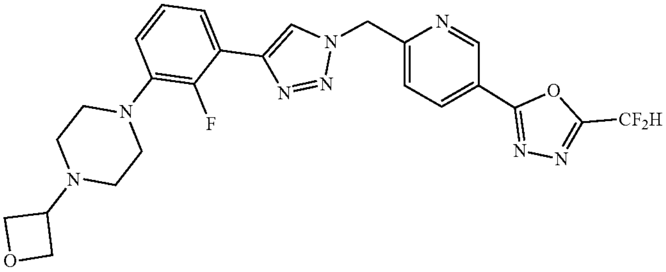 [SMILES: Fc1c(-c2cn(Cc3ccc(-c4nnc(C(F)F)o4)cn3)nn2)cccc1N1CCN(C2COC2)CC1] |

TABLE 1-continued
| Example | Compound | Structure |
| --- | --- | --- |
| 440 | 4576 | 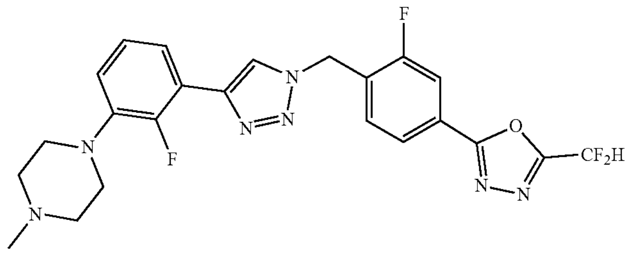 [SMILES: CN1CCN(c2cccc(-c3cn(Cc4ccc(-c5nnc(C(F)F)o5)cc4F)nn3)c2F)CC1] |
| 441 | 4577 | 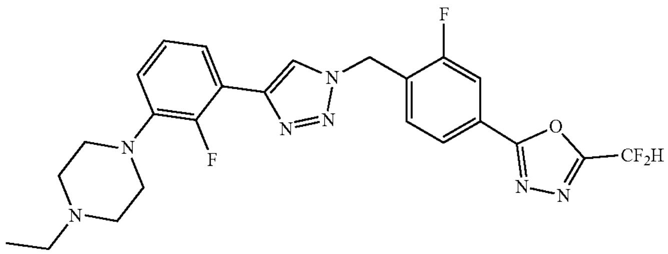 [SMILES: CCN1CCN(c2cccc(-c3cn(Cc4ccc(-c5nnc(C(F)F)o5)cc4F)nn3)c2F)CC1] |
| 442 | 4578 | 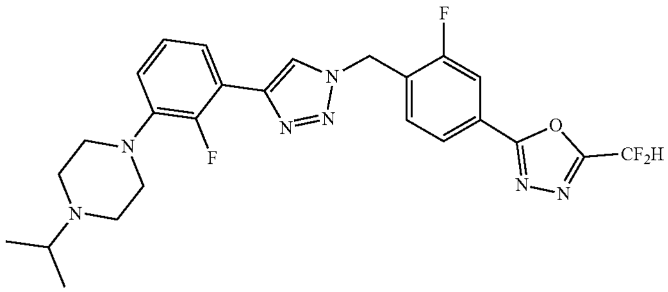 [SMILES: CC(C)N1CCN(c2cccc(-c3cn(Cc4ccc(-c5nnc(C(F)F)o5)cc4F)nn3)c2F)CC1] |
| 443 | 4579 | 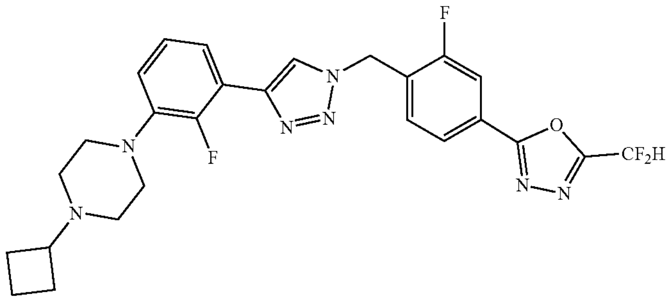 [SMILES: Fc1cc(-c2nnc(C(F)F)o2)ccc1Cn1cc(-c2cccc(N3CCN(C4CCC4)CC3)c2F)nn1] |
| 444 | 4580 | 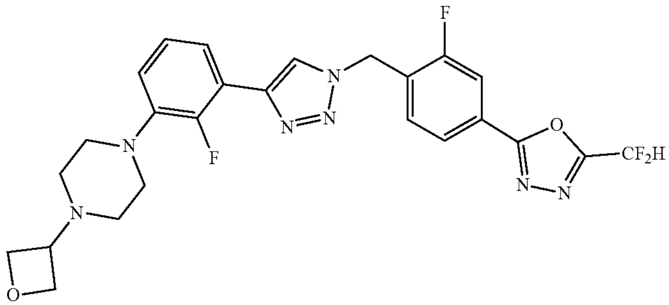 [SMILES: Fc1cc(-c2nnc(C(F)F)o2)ccc1Cn1cc(-c2cccc(N3CCN(C4COC4)CC3)c2F)nn1] |

TABLE 1-continued
| Example | Compound | Structure |
| --- | --- | --- |
| 445 | 4582 | 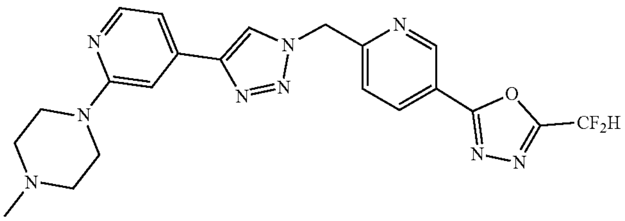 [SMILES: CN1CCN(c2cc(-c3cn(Cc4ccc(-c5nnc(C(F)F)o5)cn4)nn3)ccn2)CC1] |
| 446 | 4583 | 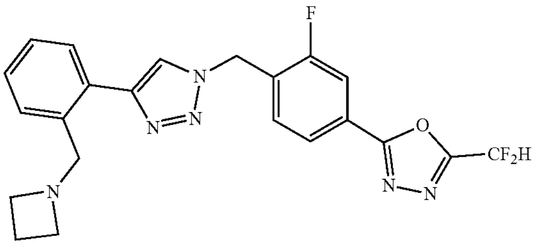 [SMILES: Fc1cc(-c2nnc(C(F)F)o2)ccc1Cn1cc(-c2ccccc2CN2CCC2)nn1] |
| 447 | 4585 | 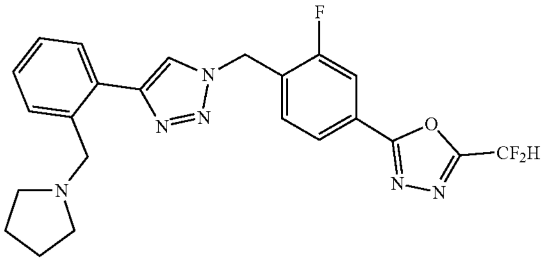 [SMILES: Fc1cc(-c2nnc(C(F)F)o2)ccc1Cn1cc(-c2ccccc2CN2CCCC2)nn1] |
| 448 | 4586 | 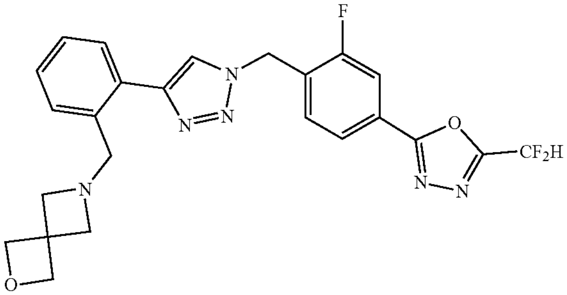 [SMILES: Fc1cc(-c2nnc(C(F)F)o2)ccc1Cn1cc(-c2ccccc2CN2CC3(COC3)C2)nn1] |
| 449 | 4587 | 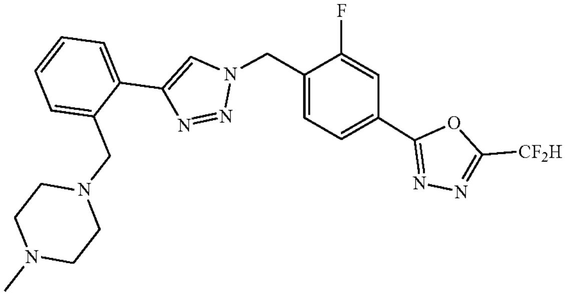 [SMILES: CN1CCN(Cc2ccccc2-c2cn(Cc3ccc(-c4nnc(C(F)F)o4)cc3F)nn2)CC1] |

TABLE 1-continued
| Example | Compound | Structure |
| --- | --- | --- |
| 450 | 4588 | 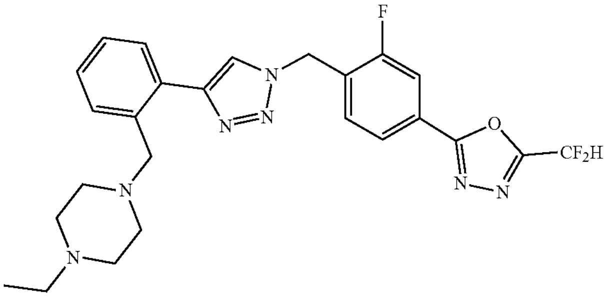 [SMILES: CCN1CCN(Cc2ccccc2-c2cn(Cc3ccc(-c4nnc(C(F)F)o4)cc3F)nn2)CC1] |
| 451 | 4589 | 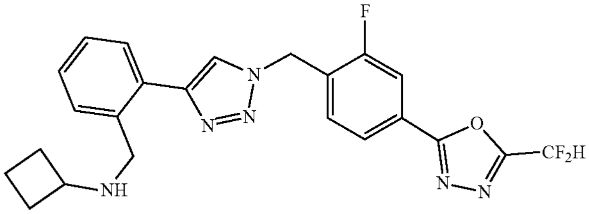 [SMILES: Fc1cc(-c2nnc(C(F)F)o2)ccc1Cn1cc(-c2ccccc2CNC2CCC2)nn1] |
| 452 | 4590 | 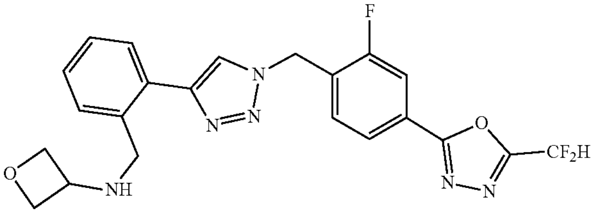 [SMILES: Fc1cc(-c2nnc(C(F)F)o2)ccc1Cn1cc(-c2ccccc2CNC2COC2)nn1] |
| 453 | 4591 | 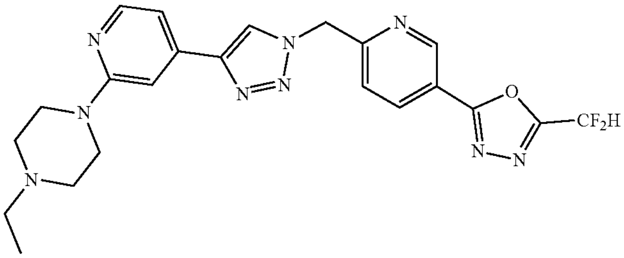 [SMILES: CCN1CCN(c2cc(-c3cn(Cc4ccc(-c5nnc(C(F)F)o5)cn4)nn3)ccn2)CC1] |
| 454 | 4592 | 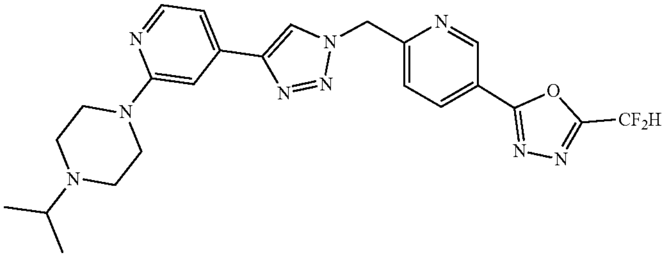 [SMILES: CC(C)N1CCN(c2cc(-c3cn(Cc4ccc(-c5nnc(C(F)F)o5)cn4)nn3)ccn2)CC1] |
| 455 | 4593 | 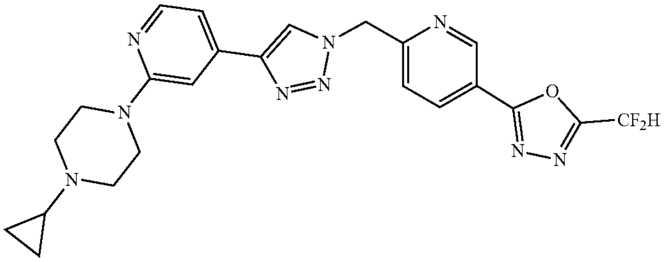 [SMILES: FC(F)c1nnc(-c2ccc(Cn3cc(-c4ccnc(N5CCN(C6CC6)CC5)c4)nn3)nc2)o1] |

TABLE 1-continued
| Example | Compound | Structure |
|---|---|---|
| 456 | 4594 | 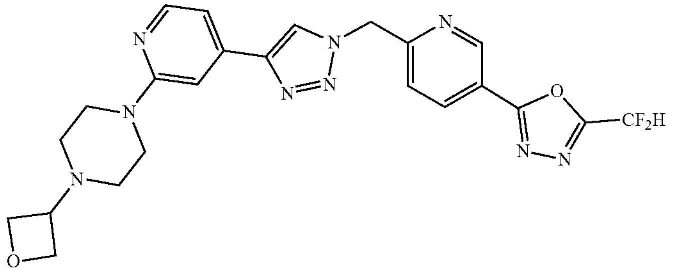 [SMILES: FC(F)c1nnc(-c2ccc(Cn3cc(-c4ccnc(N5CCN(C6COC6)CC5)c4)nn3)nc2)o1] |
| 457 | 4595 | 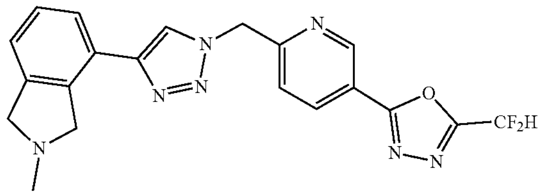 [SMILES: CN1Cc2cccc(-c3cn(Cc4ccc(-c5nnc(C(F)F)o5)cn4)nn3)c2C1] |
| 458 | 4596 | 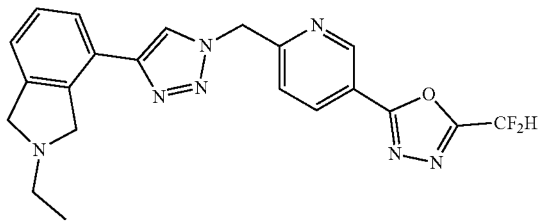 [SMILES: CCN1Cc2cccc(-c3cn(Cc4ccc(-c5nnc(C(F)F)o5)cn4)nn3)c2C1] |
| 459 | 4597 | 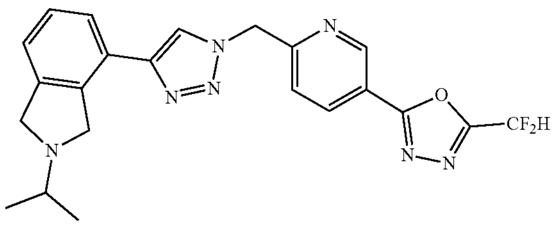 [SMILES: CC(C)N1Cc2cccc(-c3cn(Cc4ccc(-c5nnc(C(F)F)o5)cn4)nn3)c2C1] |
| 460 | 4598 | 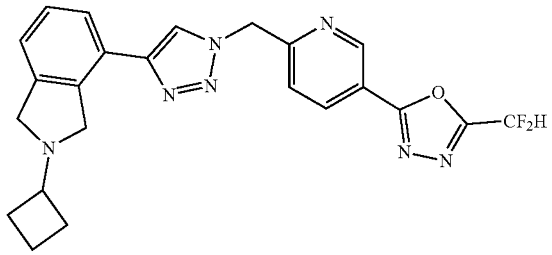 [SMILES: FC(F)c1nnc(-c2ccc(Cn3cc(-c4cccc5c4CN(C4CCC4)C5)nn3)nc2)o1] |
| 461 | 4599 | 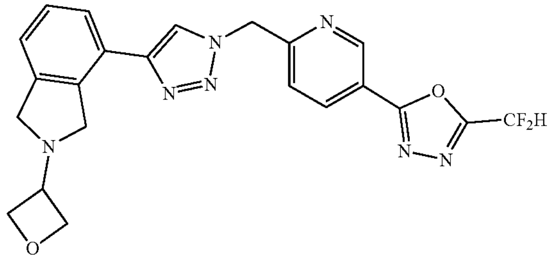 [SMILES: FC(F)c1nnc(-c2ccc(Cn3cc(-c4cccc5c4CN(C4COC4)C5)nn3)nc2)o1] |

TABLE 1-continued
| Example | Compound | Structure |
|---|---|---|
| 462 | 4600 | 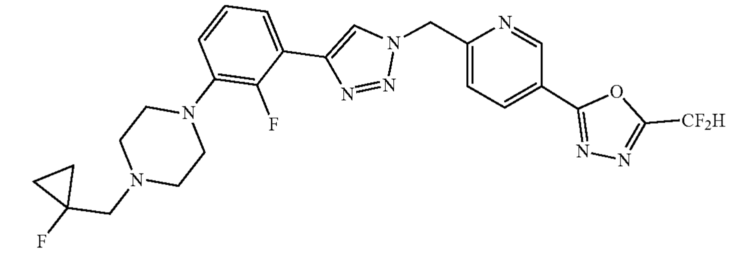 [SMILES: Fc1c(-c2cn(Cc3ccc(-c4nnc(C(F)F)o4)cn3)nn2)cccc1N1CCN(CC2(F)CC2)CC1] |
| 463 | 4601 | 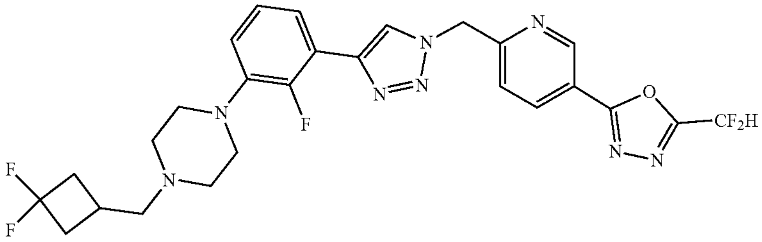 [SMILES: Fc1c(-c2cn(Cc3ccc(-c4nnc(C(F)F)o4)cn3)nn2)cccc1N1CCN(CC2CC(F)(F)C2)CC1] |
| 464 | 4602 | 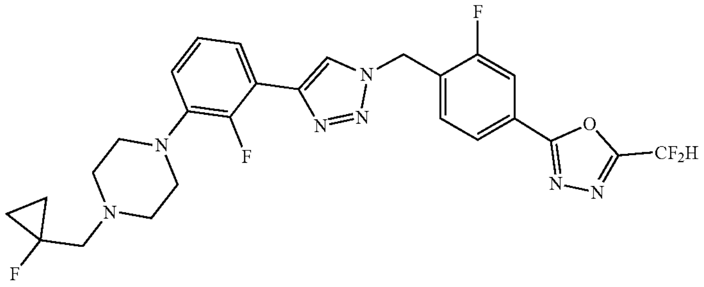 [SMILES: Fc1cc(-c2nnc(C(F)F)o2)ccc1Cn1cc(-c2cccc(N3CCN(CC4(F)CC4)CC3)c2F)nn1] |
| 465 | 4603 | 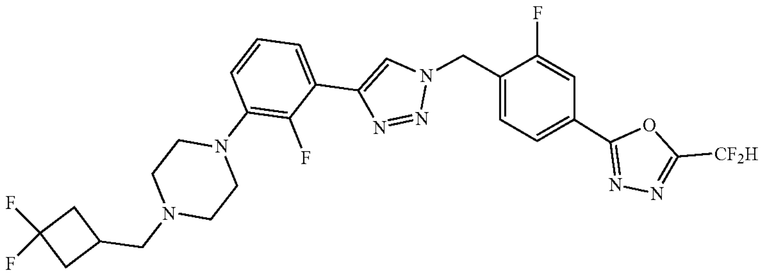 [SMILES: Fc1cc(-c2nnc(C(F)F)o2)ccc1Cn1cc(-c2cccc(N3CCN(CC4CC(F)(F)C4)CC3)c2F)nn1] |
| 466 | 4604 | 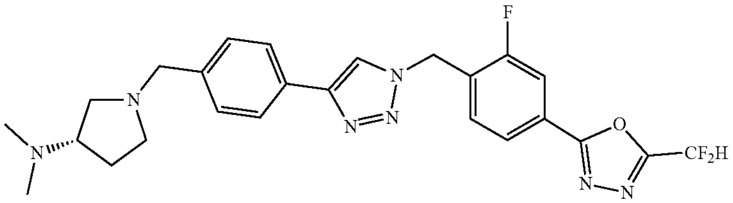 [SMILES: CN(C)[C@H]1CCN(Cc2ccc(-c3cn(Cc4ccc(-c5nnc(C(F)F)o5)cc4F)nn3)cc2)C1] |
| 467 | 4605 | 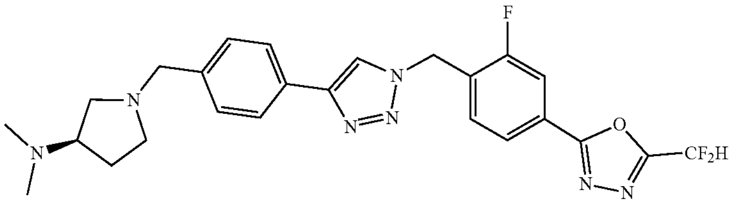 [SMILES: CN(C)[C@@H]1CCN(Cc2ccc(-c3cn(Cc4ccc(-c5nnc(C(F)F)o5)cc4F)nn3)cc2)C1] |

TABLE 1-continued
| Example | Compound | Structure |
|---|---|---|
| 468 | 4606 | 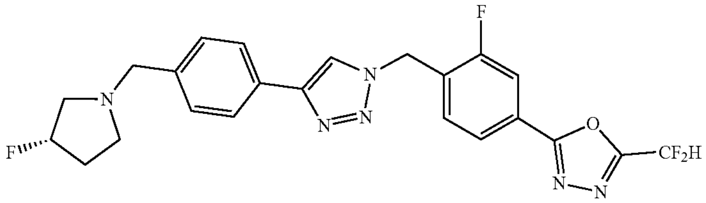 [SMILES: Fc1cc(-c2nnc(C(F)F)o2)ccc1Cn1cc(-c2ccc(CN3CC[C@H](F)C3)cc2)nn1] |
| 469 | 4607 | 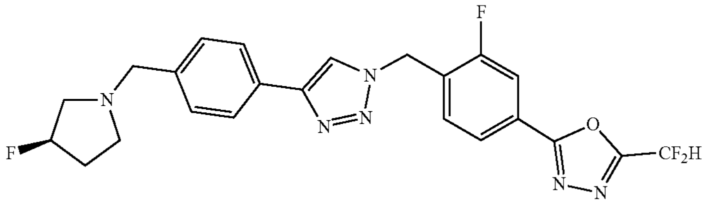 [SMILES: Fc1cc(-c2nnc(C(F)F)o2)ccc1Cn1cc(-c2ccc(CN3CC[C@@H](F)C3)cc2)nn1] |
| 470 | 4608 | 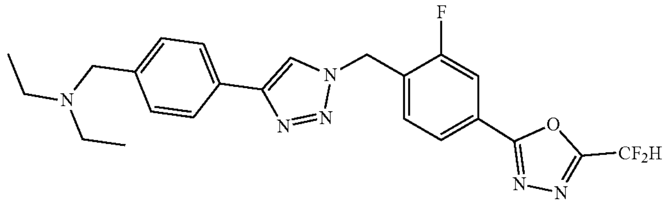 [SMILES: CCN(CC)Cc1ccc(-c2cn(Cc3ccc(-c4nnc(C(F)F)o4)cc3F)nn2)cc1] |
| 471 | 4609 | 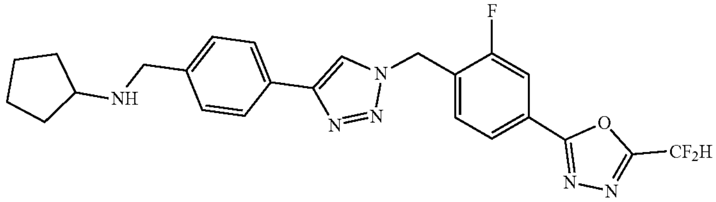 [SMILES: Fc1cc(-c2nnc(C(F)F)o2)ccc1Cn1cc(-c2ccc(CNC3CCCC3)cc2)nn1] |
| 472 | 4610 | 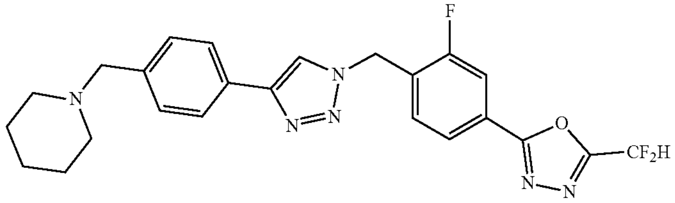 [SMILES: Fc1cc(-c2nnc(C(F)F)o2)ccc1Cn1cc(-c2ccc(CN3CCCCC3)cc2)nn1] |
| 473 | 4611 | 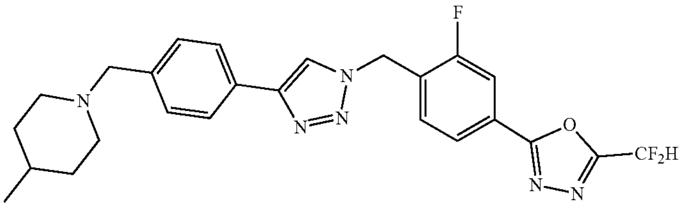 [SMILES: CC1CCN(Cc2ccc(-c3cn(Cc4ccc(-c5nnc(C(F)F)o5)cc4F)nn3)cc2)CC1] |
| 474 | 4633 | 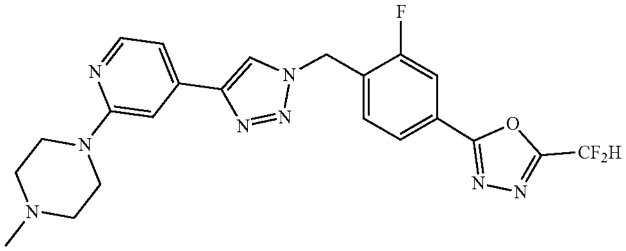 [SMILES: CN1CCN(c2cc(-c3cn(Cc4ccc(-c5nnc(C(F)F)o5)cc4F)nn3)ccn2)CC1] |

TABLE 1-continued
| Example | Compound | Structure |
| --- | --- | --- |
| 475 | 4634 | 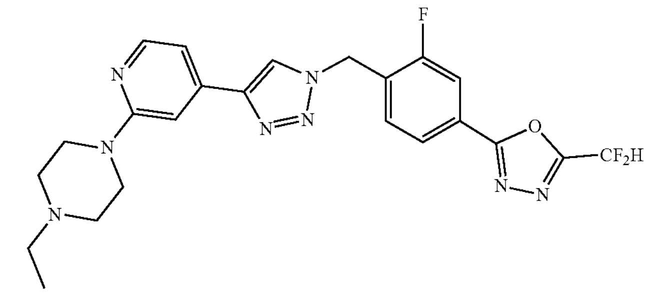 [SMILES: CCN1CCN(c2cc(-c3cn(Cc4ccc(-c5nnc(C(F)F)o5)cc4F)nn3)ccn2)CC1] |
| 476 | 4635 | 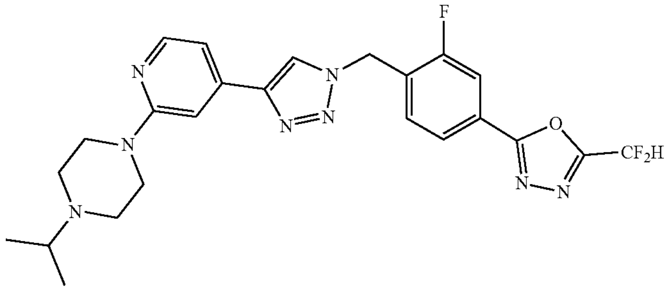 [SMILES: CC(C)N1CCN(c2cc(-c3cn(Cc4ccc(-c5nnc(C(F)F)o5)cc4F)nn3)ccn2)CC1] |
| 477 | 4636 | 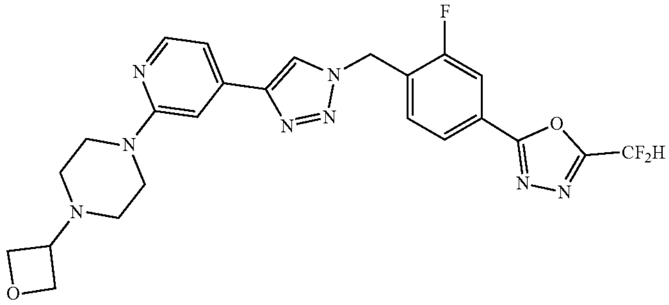 [SMILES: Fc1cc(-c2nnc(C(F)F)o2)ccc1Cn1cc(-c2ccnc(N3CCN(C4COC4)CC3)c2)nn1] |
| 478 | 4640 | 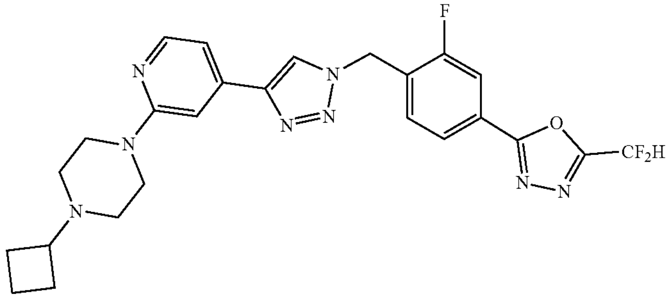 [SMILES: Fc1cc(-c2nnc(C(F)F)o2)ccc1Cn1cc(-c2ccnc(N3CCN(C4CCC4)CC3)c2)nn1] |
| 479 | 16781 | 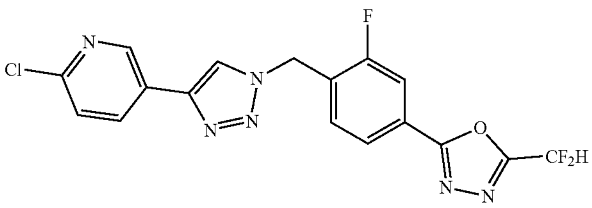 [SMILES: Fc1cc(-c2nnc(C(F)F)o2)ccc1Cn1cc(-c2ccc(Cl)nc2)nn1] |

TABLE 1-continued
| Example | Compound | Structure |
| --- | --- | --- |
| 480 | 16789 | 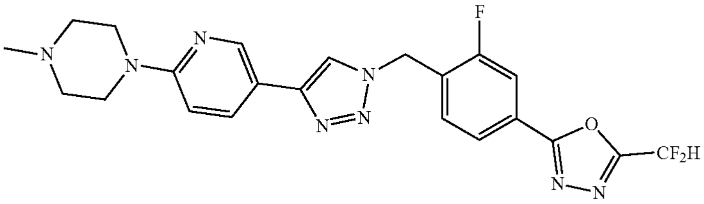 [SMILES: CN1CCN(c2ccc(-c3cn(Cc4ccc(-c5nnc(C(F)F)o5)cc4F)nn3)cn2)CC1] |
| 481 | 16797 | 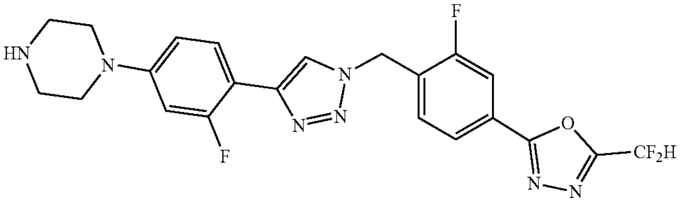 [SMILES: Fc1cc(-c2nnc(C(F)F)o2)ccc1Cn1cc(-c2ccc(N3CCNCC3)cc2F)nn1] |
| 482 | 16928 | 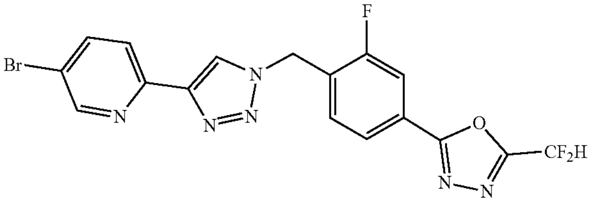 |
| 483 | 16930 | 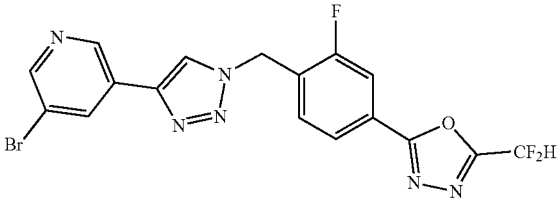 [SMILES: Fc1cc(-c2nnc(C(F)F)o2)ccc1Cn1cc(-c2cncc(Br)c2)nn1] |
| 484 | 17058 | 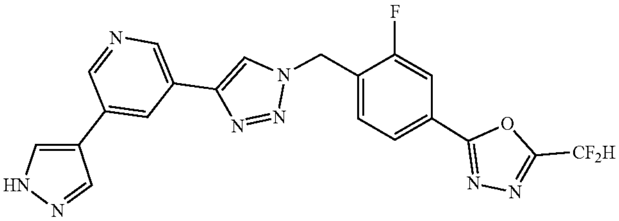 [SMILES: Fc1cc(-c2nnc(C(F)F)o2)ccc1Cn1cc(-c2cncc(-c3cn[nH]c3)c2)nn1] |
| 485 | 17198 | 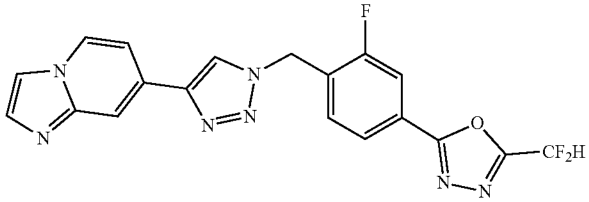 [SMILES: Fc1cc(-c2nnc(C(F)F)o2)ccc1Cn1cc(-c2ccn3ccnc3c2)nn1] |
| 486 | 17201 | 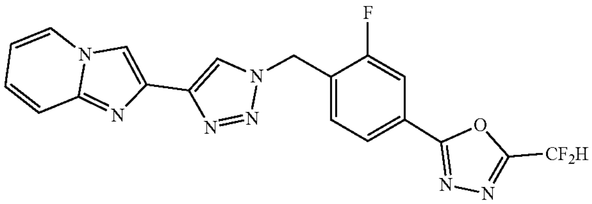 [SMILES: Fc1cc(-c2nnc(C(F)F)o2)ccc1Cn1cc(-c2cn3ccccc3n2)nn1] |

TABLE 1-continued
| Example | Compound | Structure |
|---|---|---|
| 487 | 17255 | 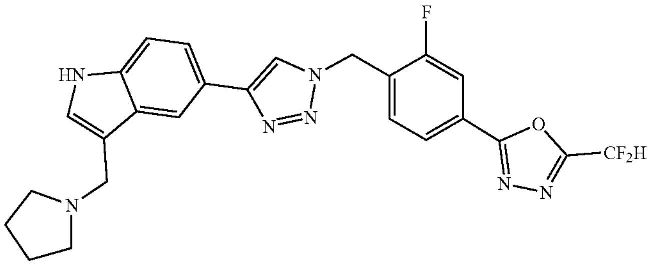 [SMILES: Fc1cc(-c2nnc(C(F)F)o2)ccc1Cn1cc(-c2ccc3[nH]cc(CN4CCCC4)c3c2)nn1] |
| 488 | 17261 | 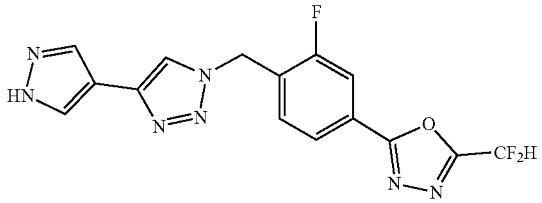 [SMILES: Fc1cc(-c2nnc(C(F)F)o2)ccc1Cn1cc(-c2cn[nH]c2)nn1] |
| 489 | 17263 | 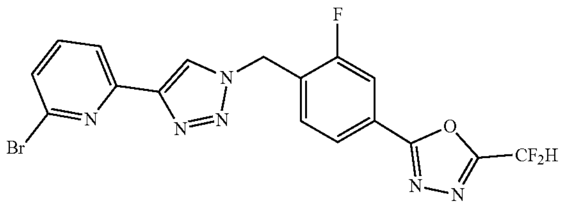 [SMILES: Fc1cc(-c2nnc(C(F)F)o2)ccc1Cn1cc(-c2cccc(Br)n2)nn1] |
| 490 | 17347 | 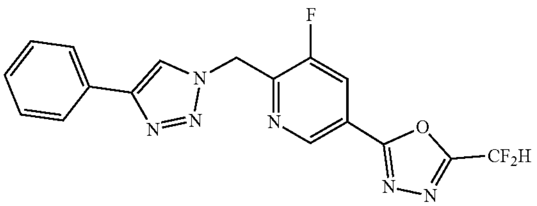 [SMILES: Fc1cc(-c2nnc(C(F)F)o2)cnc1Cn1cc(-c2ccccc2)nn1] |
| 491 | 17362 | 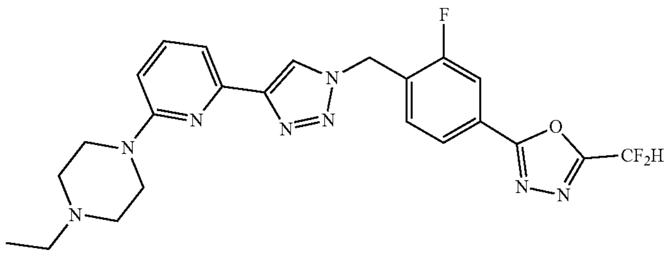 [SMILES: CCN1CCN(c2cccc(-c3cn(Cc4ccc(-c5nnc(C(F)F)o5)cc4F)nn3)n2)CC1] |
| 492 | 17363 | 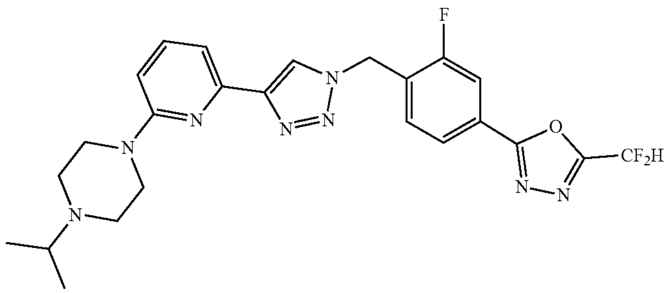 [SMILES: CC(C)N1CCN(c2cccc(-c3cn(Cc4ccc(-c5nnc(C(F)F)o5)cc4F)nn3)n2)CC1] |

TABLE 1-continued
| Example | Compound | Structure |
|---|---|---|
| 493 | 17364 | 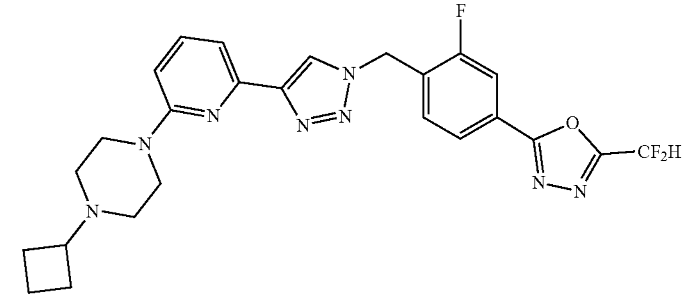 [SMILES: Fc1cc(-c2nnc(C(F)F)o2)ccc1Cn1cc(-c2cccc(N3CCN(C4CCC4)CC3)n2)nn1] |
| 494 | 17365 | 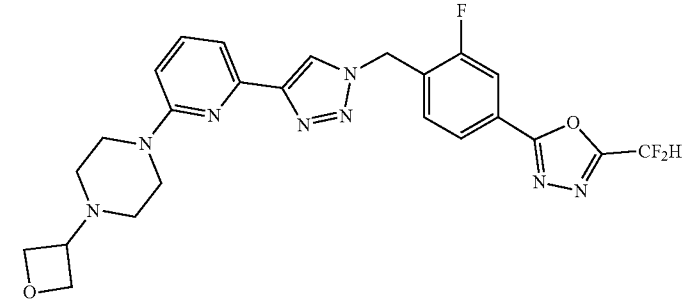 [SMILES: Fc1cc(-c2nnc(C(F)F)o2)ccc1Cn1cc(-c2cccc(N3CCN(C4COC4)CC3)n2)nn1] |
| 495 | 17458 | 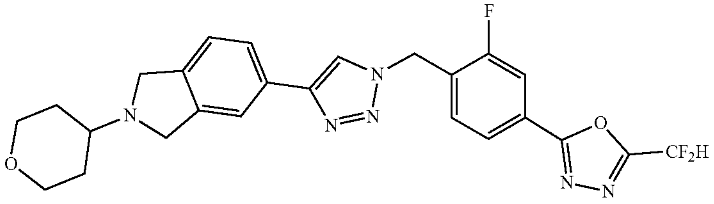 [SMILES: Fc1cc(-c2nnc(C(F)F)o2)ccc1Cn1cc(-c2ccc3c(c2)CN(C2CCOCC2)C3)nn1] |
| 496 | 17460 | 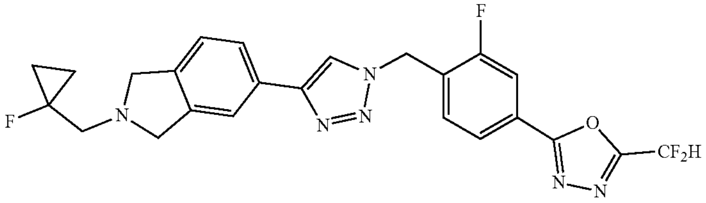 [SMILES: Fc1cc(-c2nnc(C(F)F)o2)ccc1Cn1cc(-c2ccc3c(c2)CN(CC2(F)CC2)C3)nn1] |
| 497 | 17532 | 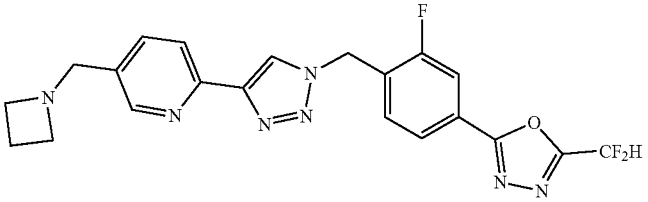 |
| 498 | 17533 | 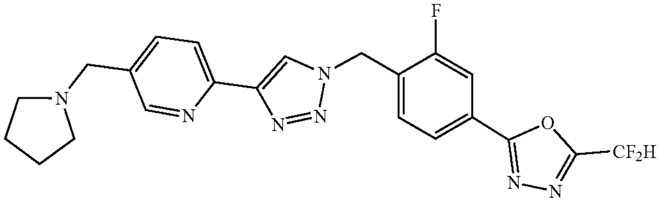 |

TABLE 1-continued
| Example | Compound | Structure |
|---|---|---|
| 499 | 17534 | 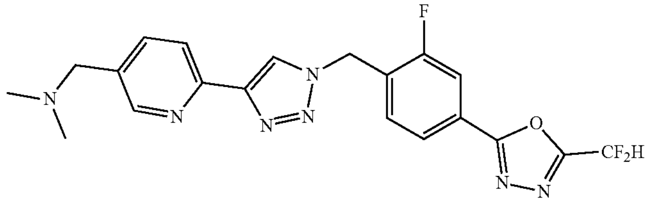 |
| 500 | 17535 | 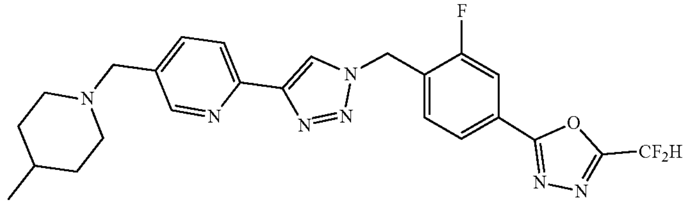 [SMILES: CC1CCN(Cc2ccc(-c3cn(Cc4ccc(-c5nnc(C(F)F)o5)cc4F)nn3)nc2)CC1] |
| 501 | 17545 | 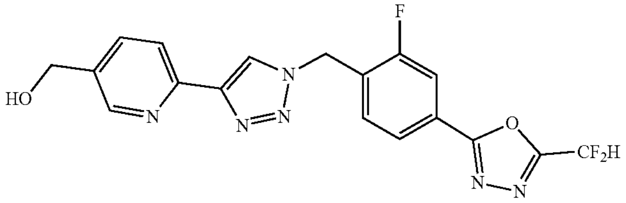 [SMILES: OCc1ccc(-c2cn(Cc3ccc(-c4nnc(C(F)F)o4)cc3F)nn2)nc1] |
| 502 | 17698 | 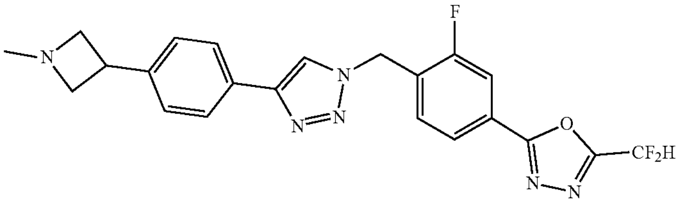 [SMILES: CN1CC(c2ccc(-c3cn(Cc4ccc(-c5nnc(C(F)F)o5)cc4F)nn3)cc2)C1] |
| 503 | 17699 | 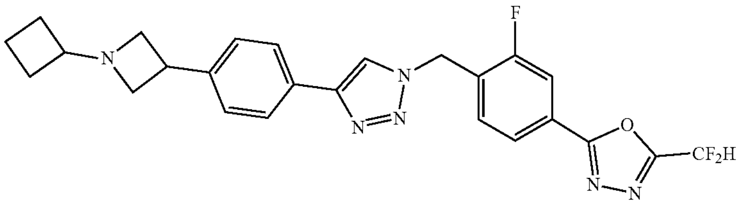 [SMILES: Fc1cc(-c2nnc(C(F)F)o2)ccc1Cn1cc(-c2ccc(C3CN(C4CCC4)C3)cc2)nn1] |
| 504 | 17700 | 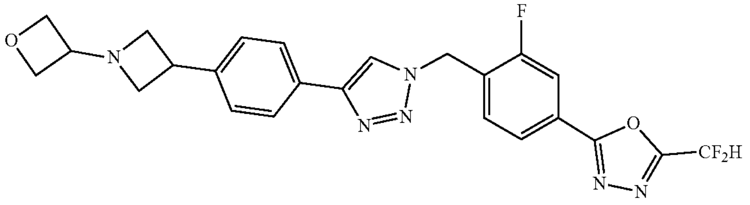 [SMILES: Fc1cc(-c2nnc(C(F)F)o2)ccc1Cn1cc(-c2ccc(C3CN(C4COC4)C3)cc2)nn1] |
| 505 | 17773 | 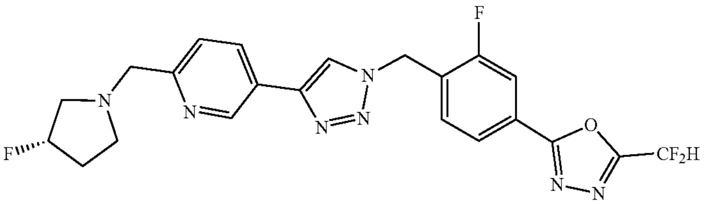 |

TABLE 1-continued
| Example | Compound | Structure |
|---|---|---|
| 506 | 17774 | 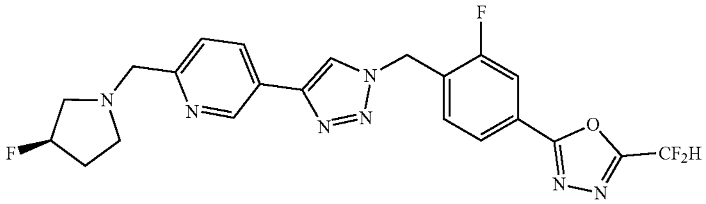 |
| 507 | 17775 | 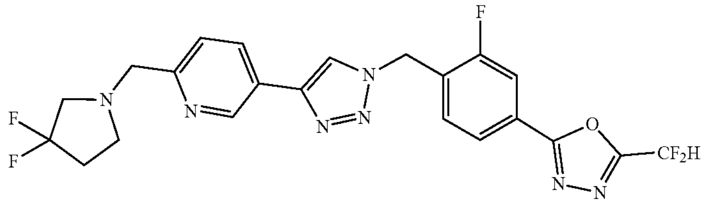 [SMILES: Fc1cc(-c2nnc(C(F)F)o2)ccc1Cn1cc(-c2ccc(CN3CCC(F)(F)C3)nc2)nn1] |
| 508 | 17777 | 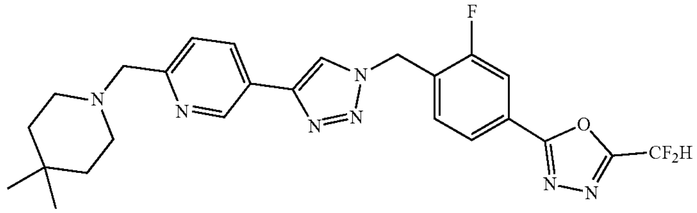 [SMILES: CC1(C)CCN(Cc2ccc(-c3cn(Cc4ccc(-c5nnc(C(F)F)o5)cc4F)nn3)cn2)CC1] |
| 509 | 17778 | 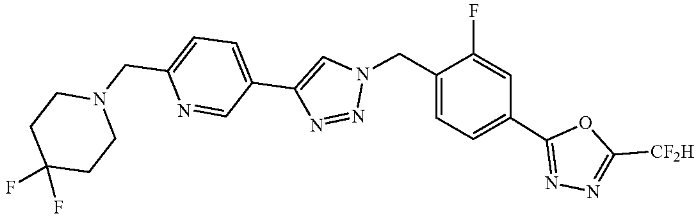 [SMILES: Fc1cc(-c2nnc(C(F)F)o2)ccc1Cn1cc(-c2ccc(CN3CCC(F)(F)CC3)nc2)nn1] |
| 510 | 17848 | 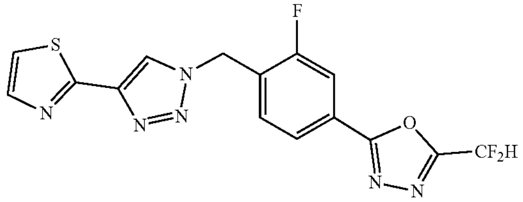 [SMILES: Fc1cc(-c2nnc(C(F)F)o2)ccc1Cn1cc(-c2nccs2)nn1] |
| 511 | 17851 | 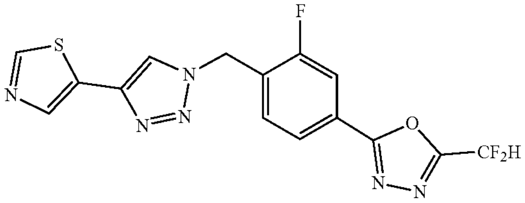 [SMILES: Fc1cc(-c2nnc(C(F)F)o2)ccc1Cn1cc(-c2cncs2)nn1] |
| 512 | 17854 | 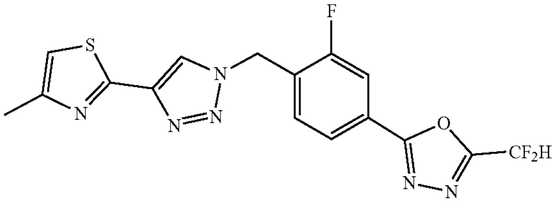 [SMILES: Cc1csc(-c2cn(Cc3ccc(-c4nnc(C(F)F)o4)cc3F)nn2)n1] |

TABLE 1-continued
| Example | Compound | Structure |
|---|---|---|
| 513 | 17857 | 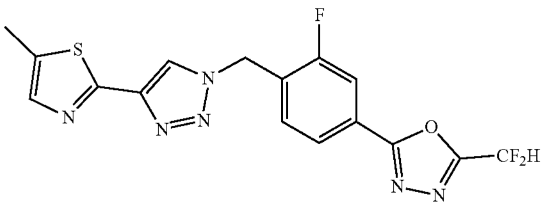 [SMILES: Cc1cnc(-c2cn(Cc3ccc(-c4nnc(C(F)F)o4)cc3F)nn2)s1] |
| 514 | 17912 | 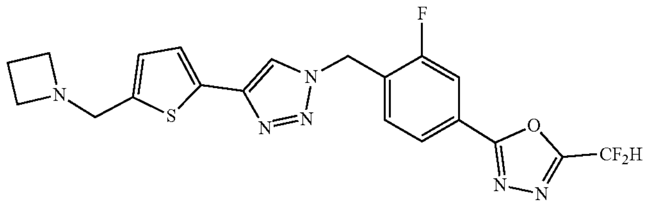 [SMILES: Fc1cc(-c2nnc(C(F)F)o2)ccc1Cn1cc(-c2ccc(CN3CCC3)s2)nn1] |
| 515 | 17913 | 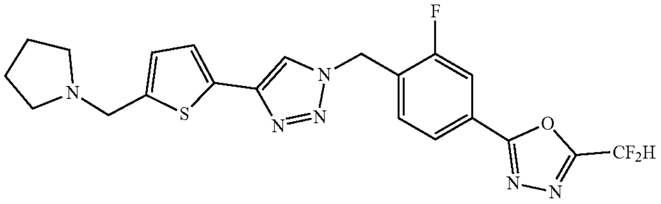 [SMILES: Fc1cc(-c2nnc(C(F)F)o2)ccc1Cn1cc(-c2ccc(CN3CCCC3)s2)nn1] |
| 516 | 17914 | 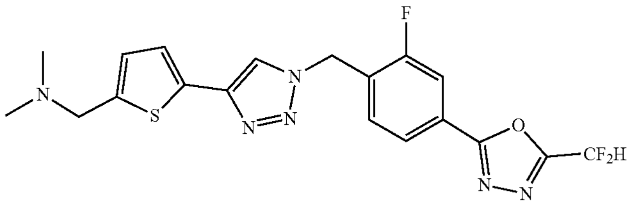 [SMILES: CN(C)Cc1ccc(-c2cn(Cc3ccc(-c4nnc(C(F)F)o4)cc3F)nn2)s1] |
| 517 | 17915 | 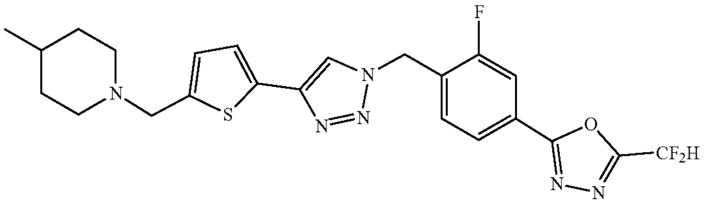 [SMILES: CC1CCN(Cc2ccc(-c3cn(Cc4ccc(-c5nnc(C(F)F)o5)cc4F)nn3)s2)CC1] |
| 518 | 17916 | 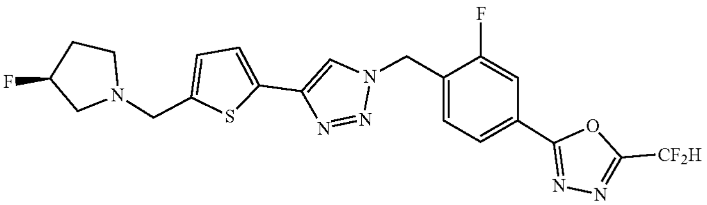 [SMILES: Fc1cc(-c2nnc(C(F)F)o2)ccc1Cn1cc(-c2ccc(CN3CC[C@H](F)C3)s2)nn1] |
| 519 | 17917 | 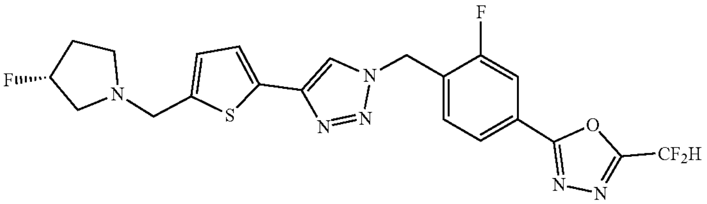 [SMILES: Fc1cc(-c2nnc(C(F)F)o2)ccc1Cn1cc(-c2ccc(CN3CC[C@@H](F)C3)s2)nn1] |

TABLE 1-continued
| Example | Compound | Structure |
|---|---|---|
| 520 | 17922 | 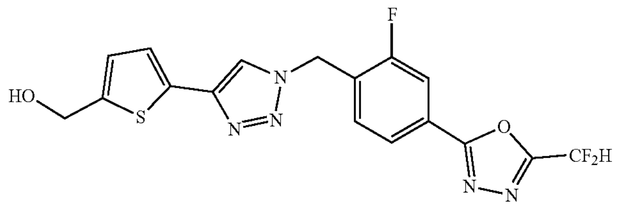 [SMILES: OCc1ccc(-c2cn(Cc3ccc(-c4nnc(C(F)F)o4)cc3F)nn2)s1] |
| 521 | 17983 | 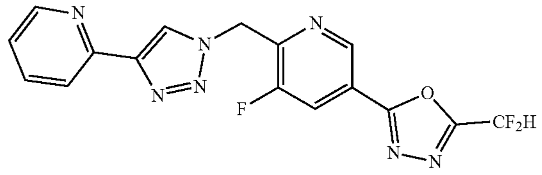 [SMILES: Fc1cc(-c2nnc(C(F)F)o2)cnc1Cn1cc(-c2ccccn2)nn1] |
| 522 | 17984 | 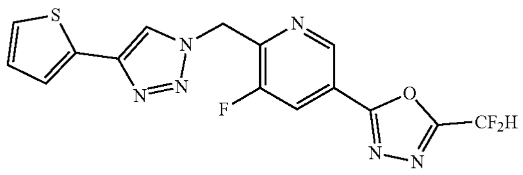 [SMILES: Fc1cc(-c2nnc(C(F)F)o2)cnc1Cn1cc(-c2cccs2)nn1] |
| 523 | 18058 | 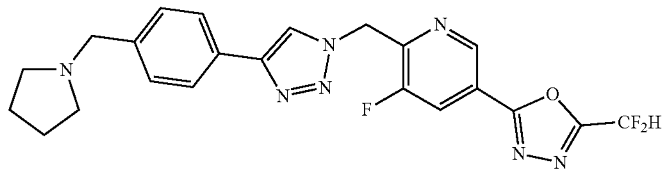 [SMILES: Fc1cc(-c2nnc(C(F)F)o2)cnc1Cn1cc(-c2ccc(CN3CCCC3)cc2)nn1] |
| 524 | 18059 | 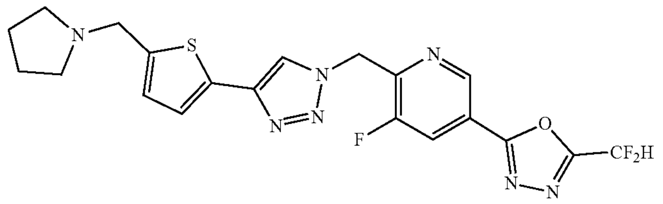 [SMILES: Fc1cc(-c2nnc(C(F)F)o2)cnc1Cn1cc(-c2ccc(CN3CCCC3)s2)nn1] |
| 525 | 18174 | 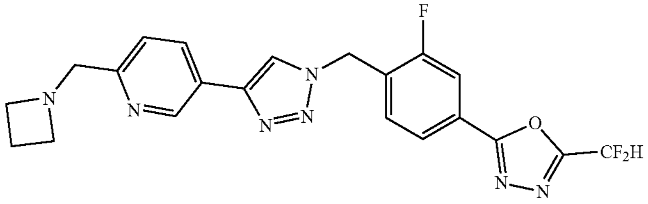 [SMILES: Fc1cc(-c2nnc(C(F)F)o2)ccc1Cn1cc(-c2ccc(CN3CCC3)nc2)nn1] |
| 526 | 18175 | 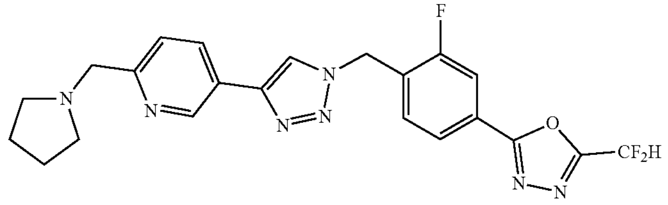 |
| 527 | 18176 | 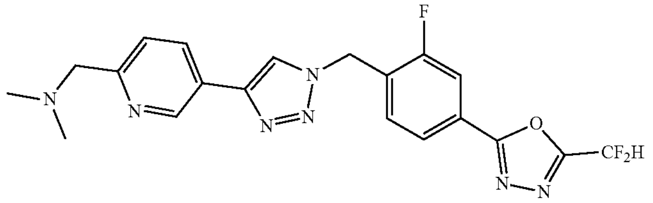 [SMILES: CN(C)Cc1ccc(-c2cn(Cc3ccc(-c4nnc(C(F)F)o4)cc3F)nn2)cn1] |

TABLE 1-continued
| Example | Compound | Structure |
|---|---|---|
| 528 | 18177 | 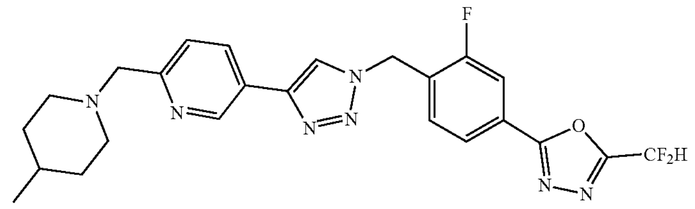 [SMILES: CC1CCN(Cc2ccc(-c3cn(Cc4ccc(-c5nnc(C(F)F)o5)cc4F)nn3)cn2)CC1] |
| 529 | 18178 | 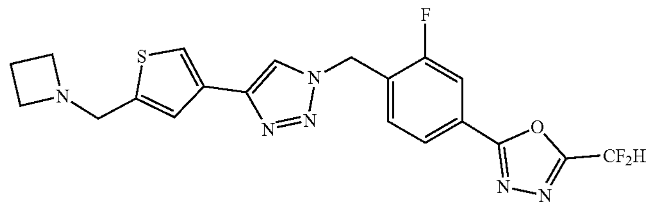 [SMILES: Fc1cc(-c2nnc(C(F)F)o2)ccc1Cn1cc(-c2csc(CN3CCC3)c2)nn1] |
| 530 | 18180 | 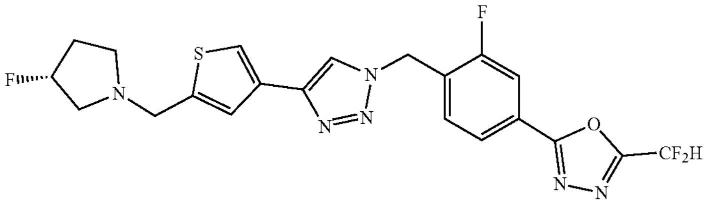 [SMILES: Fc1cc(-c2nnc(C(F)F)o2)ccc1Cn1cc(-c2csc(CN3CC[C@@H](F)C3)c2)nn1] |
| 531 | 18185 | 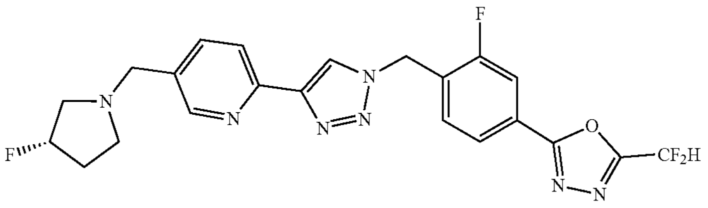 [SMILES: Fc1cc(-c2nnc(C(F)F)o2)ccc1Cn1cc(-c2ccc(CN3CC[C@H](F)C3)cn2)nn1] |
| 532 | 18187 | 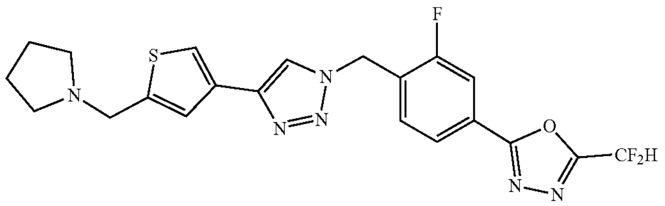 [SMILES: Fc1cc(-c2nnc(C(F)F)o2)ccc1Cn1cc(-c2csc(CN3CCCC3)c2)nn1] |
| 533 | 18188 | 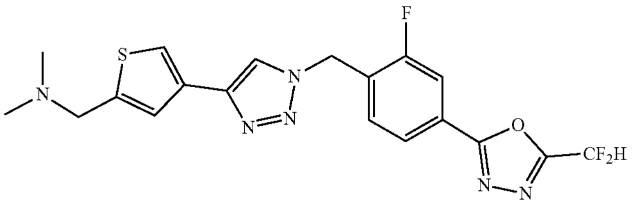 [SMILES: CN(C)Cc1cc(-c2cn(Cc3ccc(-c4nnc(C(F)F)o4)cc3F)nn2)cs1] |
| 534 | 18256 | 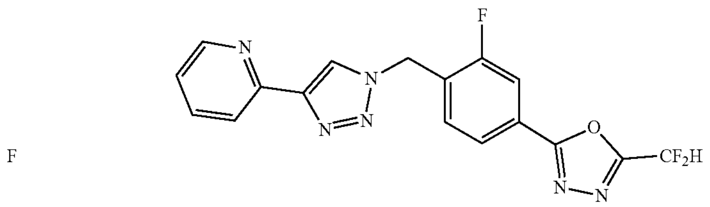 |

TABLE 1-continued
| Example | Compound | Structure |
| --- | --- | --- |
| 535 | 18258 | 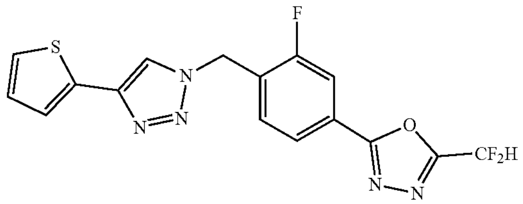 [SMILES: Fc1cc(-c2nnc(C(F)F)o2)ccc1Cn1cc(-c2cccs2)nn1] |
| 536 | 18260 | 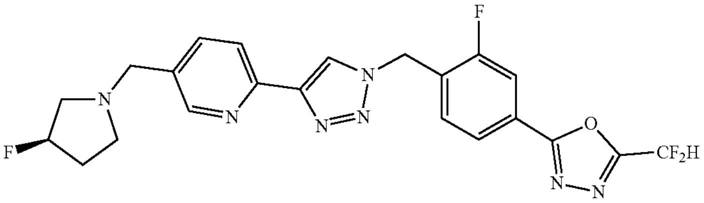 [SMILES: Fc1cc(-c2nnc(C(F)F)o2)ccc1Cn1cc(-c2ccc(CN3CC[C@@H](F)C3)cn2)nn1] |
| 537 | 18305 | 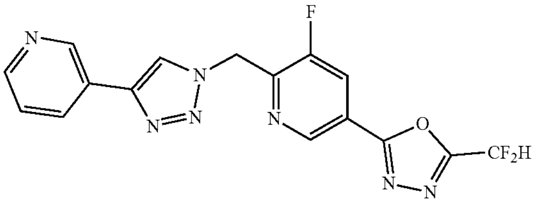 [SMILES: Fc1cc(-c2nnc(C(F)F)o2)cnc1Cn1cc(-c2cccnc2)nn1] |
| 538 | 18306 | 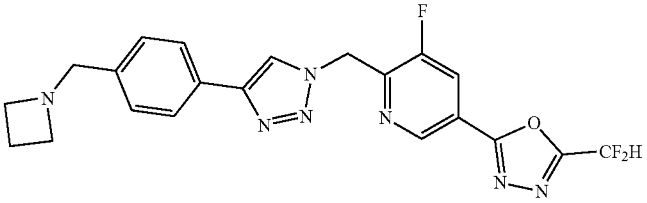 [SMILES: Fc1cc(-c2nnc(C(F)F)o2)cnc1Cn1cc(-c2ccc(CN3CCC3)cc2)nn1] |
| 539 | 18307 | 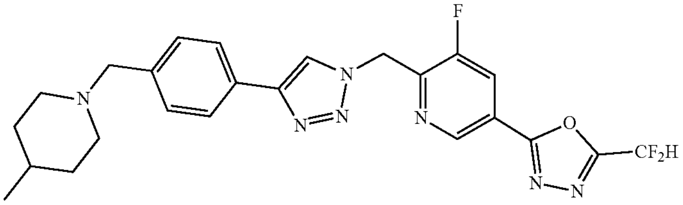 |
| 540 | 18308 | 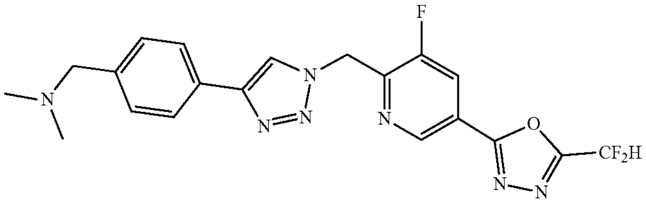 [SMILES: CN(C)Cc1ccc(-c2cn(Cc3ncc(-c4nnc(C(F)F)o4)cc3F)nn2)cc1] |
| 541 | 18309 | 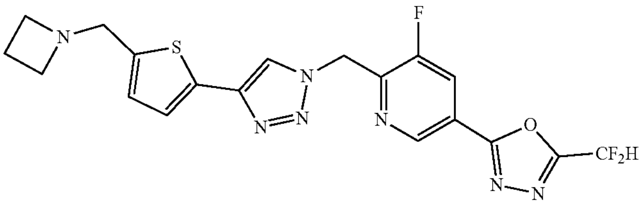 [SMILES: Fc1cc(-c2nnc(C(F)F)o2)cnc1Cn1cc(-c2ccc(CN3CCC3)s2)nn1] |

TABLE 1-continued
| Example | Compound | Structure |
| --- | --- | --- |
| 542 | 18310 | 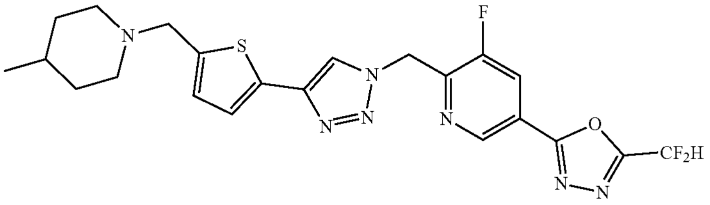 [SMILES: CC1CCN(Cc2ccc(-c3cn(Cc4ncc(-c5nnc(C(F)F)o5)cc4F)nn3)s2)CC1] |
| 543 | 18311 | 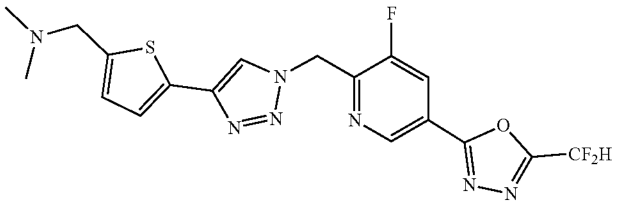 [SMILES: CN(C)Cc1ccc(-c2cn(Cc3ncc(-c4nnc(C(F)F)o4)cc3F)nn2)s1] |
| 544 | 18327 | 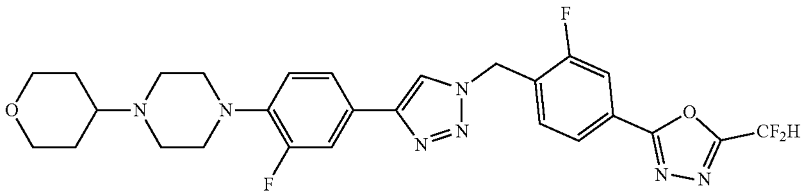 [SMILES: Fc1cc(-c2nnc(C(F)F)o2)ccc1Cn1cc(-c2ccc(N3CCN(C4CCOCC4)CC3)c(F)c2)nn1] |
| 545 | 18457 | 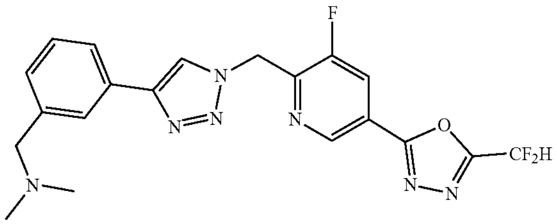 [SMILES: CN(C)Cc1cccc(-c2cn(Cc3ncc(-c4nnc(C(F)F)o4)cc3F)nn2)c1] |
| 546 | 18459 | 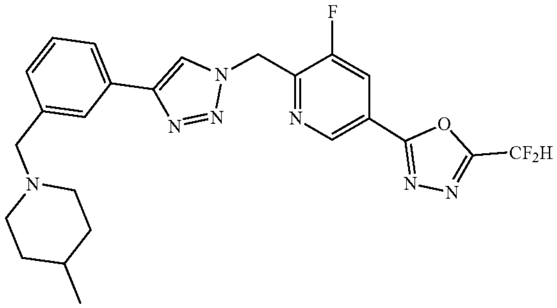 [SMILES: CC1CCN(Cc2cccc(-c3cn(Cc4ncc(-c5nnc(C(F)F)o5)cc4F)nn3)c2)CC1] |
| 547 | 18470 | 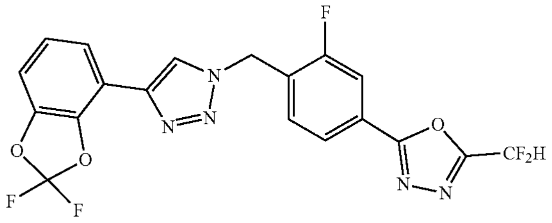 [SMILES: Fc1cc(-c2nnc(C(F)F)o2)ccc1Cn1cc(-c2cccc3c2OC(F)(F)O3)nn1] |

TABLE 1-continued
| Example | Compound | Structure |
|---|---|---|
| 548 | 18483 | 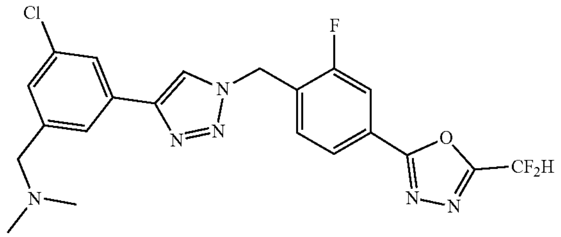 [SMILES: CN(C)Cc1cc(Cl)cc(-c2cn(Cc3ccc(-c4nnc(C(F)F)o4)cc3F)nn2)c1] |
| 549 | 18554 | 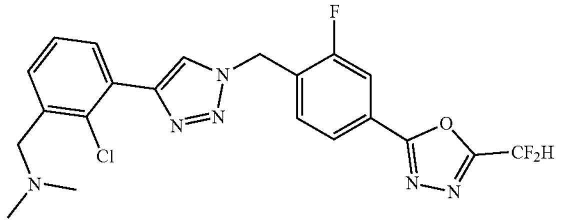 [SMILES: CN(C)Cc1cccc(-c2cn(Cc3ccc(-c4nnc(C(F)F)o4)cc3F)nn2)c1Cl] |
| 550 | 18622 | 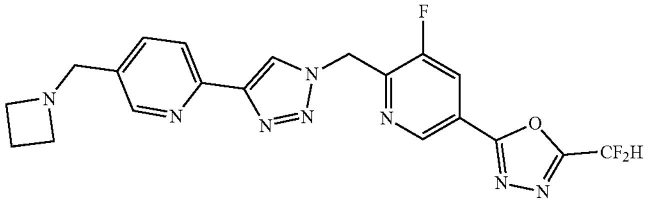 [SMILES: Fc1cc(-c2nnc(C(F)F)o2)cnc1Cn1cc(-c2ccc(CN3CCC3)cn2)nn1] |
| 551 | 18711 | 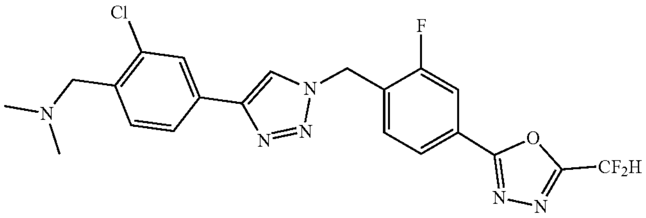 [SMILES: CN(C)Cc1ccc(-c2cn(Cc3ccc(-c4nnc(C(F)F)o4)cc3F)nn2)cc1Cl] |
| 552 | 18712 | 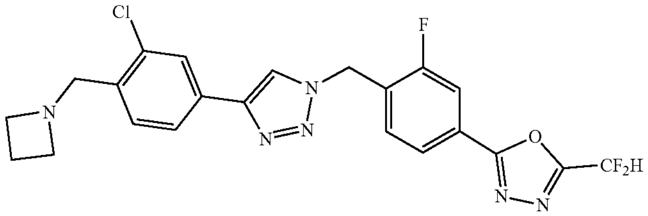 [SMILES: Fc1cc(-c2nnc(C(F)F)o2)ccc1Cn1cc(-c2ccc(CN3CCC3)c(Cl)c2)nn1] |
| 553 | 18713 | 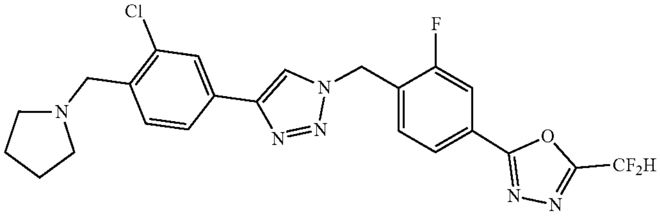 [SMILES: Fc1cc(-c2nnc(C(F)F)o2)ccc1Cn1cc(-c2ccc(CN3CCCC3)c(Cl)c2)nn1] |
| 554 | 18736 | 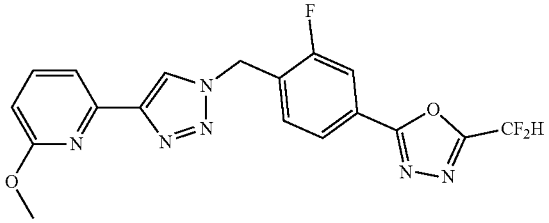 [SMILES: COc1cccc(-c2cn(Cc3ccc(-c4nnc(C(F)F)o4)cc3F)nn2)n1] |

TABLE 1-continued
| Example | Compound | Structure |
| --- | --- | --- |
| 555 | 18822 | 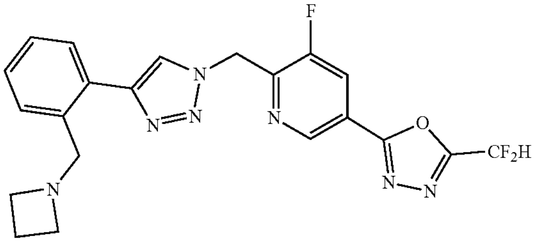 [SMILES: Fc1cc(-c2nnc(C(F)F)o2)cnc1Cn1cc(-c2ccccc2CN2CCC2)nn1] |
| 556 | 18823 | 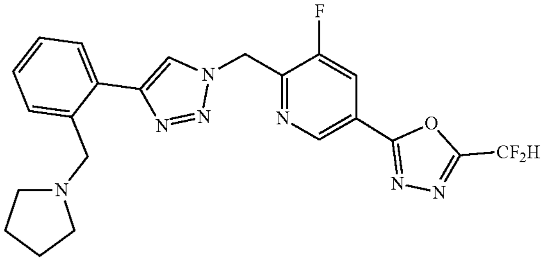 [SMILES: Fc1cc(-c2nnc(C(F)F)o2)cnc1Cn1cc(-c2ccccc2CN2CCCC2)nn1] |
| 557 | 18868 | 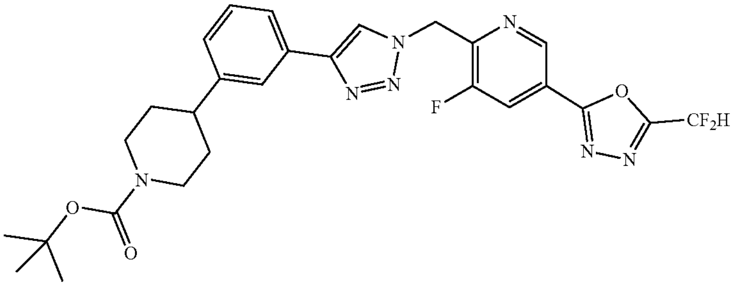 [SMILES: CC(C)(C)OC(=O)N1CCC(c2cccc(-c3cn(Cc4ncc(-c5nnc(C(F)F)o5)cc4F)nn3)c2)CC1] |
| 558 | 18869 | 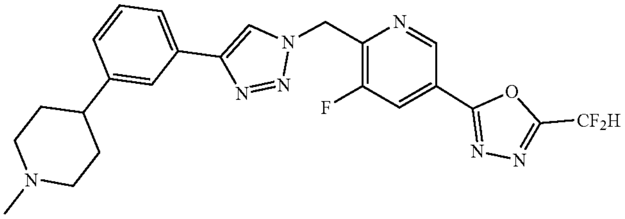 [SMILES: CN1CCC(c2cccc(-c3cn(Cc4ncc(-c5nnc(C(F)F)o5)cc4F)nn3)c2)CC1] |
| 559 | 18870 | 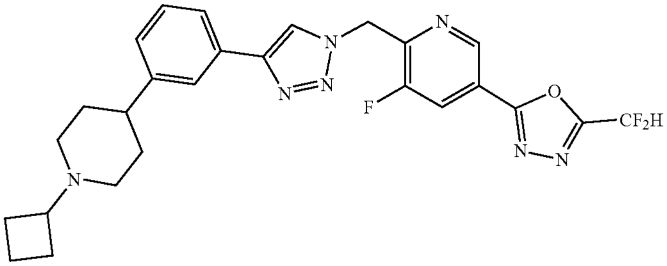 [SMILES: Fc1cc(-c2nnc(C(F)F)o2)cnc1Cn1cc(-c2cccc(C3CCN(C4CCC4)CC3)c2)nn1] |
| 560 | 18871 | 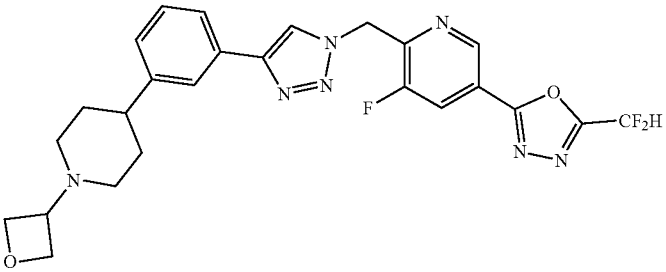 [SMILES: Fc1cc(-c2nnc(C(F)F)o2)cnc1Cn1cc(-c2cccc(C3CCN(C4COC4)CC3)c2)nn1] |

TABLE 1-continued
| Example | Compound | Structure |
|---|---|---|
| 561 | 18872 | 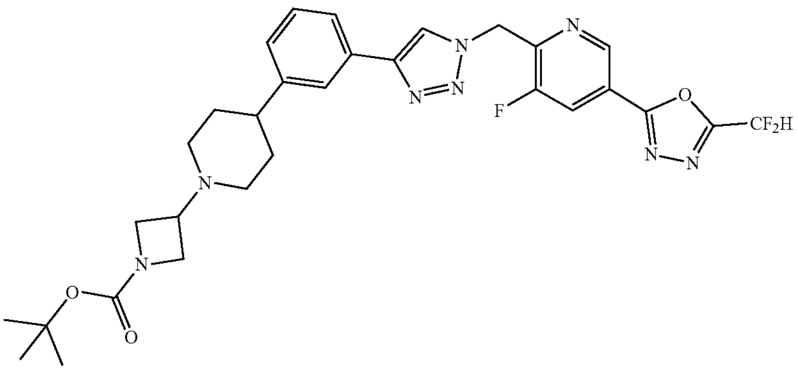 [SMILES: CC(C)(C)OC(=O)N1CC(N2CCC(c3cccc(-c4cn(Cc5ncc(-c6nnc(C(F)F)o6)cc5F)nn4)c3)CC2)C1] |
| 562 | 18877 | 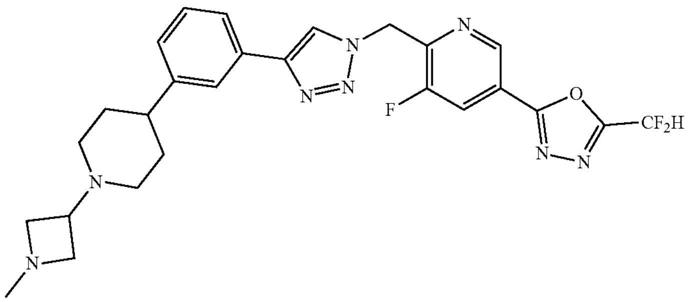 [SMILES: CN1CC(N2CCC(c3cccc(-c4cn(Cc5ncc(-c6nnc(C(F)F)o6)cc5F)nn4)c3)CC2)C1] |
| 563 | 18878 | 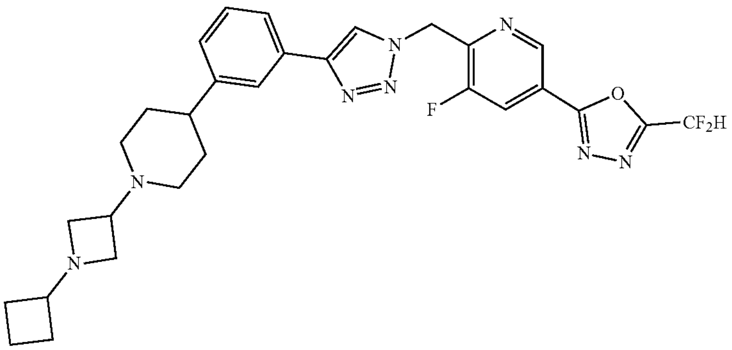 [SMILES: Fc1cc(-c2nnc(C(F)F)o2)cnc1Cn1cc(-c2cccc(C3CCN(C4CN(C5CCC5)C4)CC3)c2)nn1] |
| 564 | 18882 | 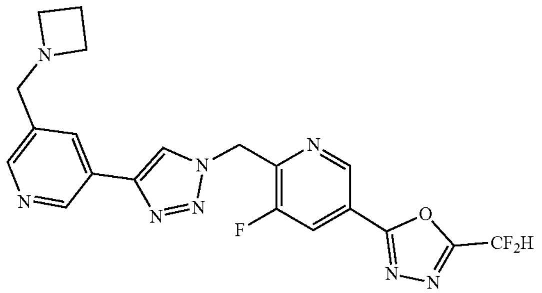 [SMILES: Fc1cc(-c2nnc(C(F)F)o2)cnc1Cn1cc(-c2cncc(CN3CCC3)c2)nn1] |
| 565 | 18893 | 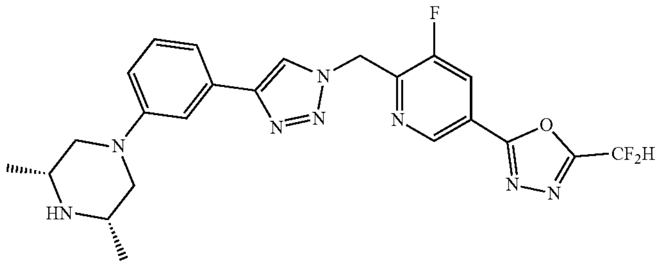 [SMILES: C[C@@H]1CN(c2cccc(-c3cn(Cc4ncc(-c5nnc(C(F)F)o5)cc4F)nn3)c2)C[C@H](C)N1] |

TABLE 1-continued
| Example | Compound | Structure |
|---|---|---|
| 566 | 18918 | 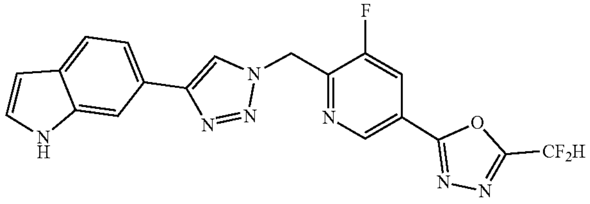 [SMILES: Fc1cc(-c2nnc(C(F)F)o2)cnc1Cn1cc(-c2ccc3cc[nH]c3c2)nn1] |
| 567 | 18919 | 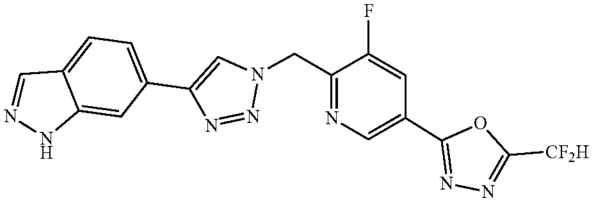 [SMILES: Fc1cc(-c2nnc(C(F)F)o2)cnc1Cn1cc(-c2ccc3cn[nH]c3c2)nn1] |
| 568 | 18920 | 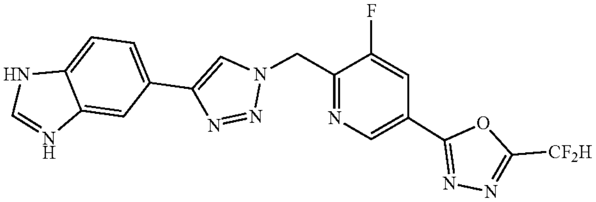 [SMILES: Fc1cc(-c2nnc(C(F)F)o2)cnc1Cn1cc(-c2ccc3[nH]cnc3c2)nn1] |
| 569 | 18921 | 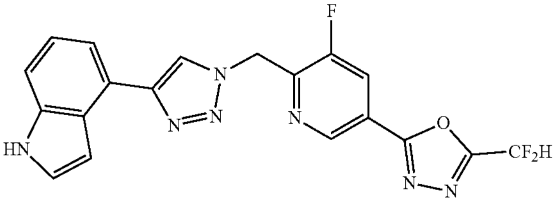 [SMILES: Fc1cc(-c2nnc(C(F)F)o2)cnc1Cn1cc(-c2cccc3[nH]ccc23)nn1] |
| 570 | 18924 | 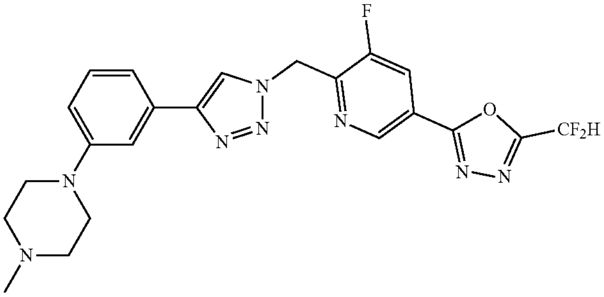 [SMILES: CN1CCN(c2cccc(-c3cn(Cc4ncc(-c5nnc(C(F)F)o5)cc4F)nn3)c2)CC1] |
| 571 | 18926 | 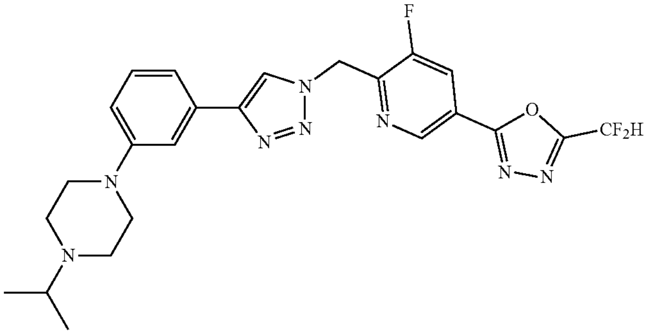 [SMILES: CC(C)N1CCN(c2cccc(-c3cn(Cc4ncc(-c5nnc(C(F)F)o5)cc4F)nn3)c2)CC1] |

TABLE 1-continued
| Example | Compound | Structure |
| --- | --- | --- |
| 572 | 18947 | 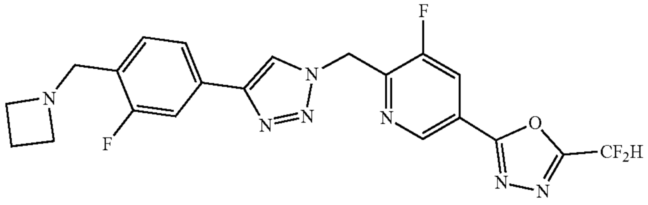 [SMILES: Fc1cc(-c2cn(Cc3ncc(-c4nnc(C(F)F)o4)cc3F)nn2)ccc1CN1CCC1] |
| 573 | 18948 | 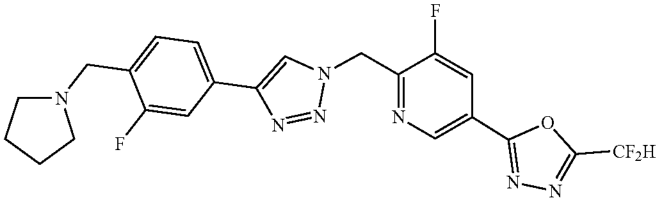 [SMILES: Fc1cc(-c2cn(Cc3ncc(-c4nnc(C(F)F)o4)cc3F)nn2)ccc1CN1CCCC1] |
| 574 | 18949 | 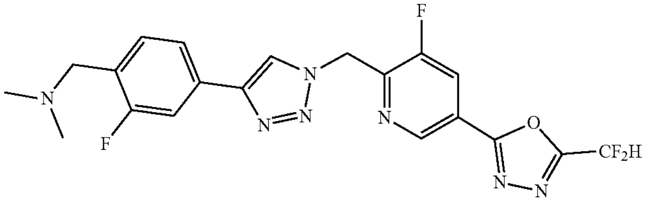 [SMILES: CN(C)Cc1ccc(-c2cn(Cc3ncc(-c4nnc(C(F)F)o4)cc3F)nn2)cc1F] |
| 575 | 18950 | 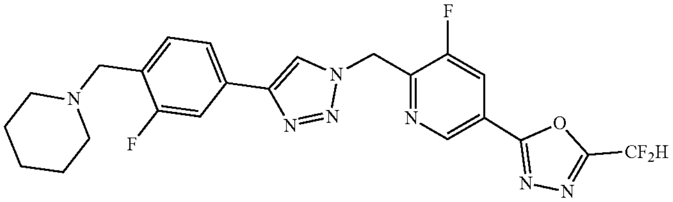 [SMILES: Fc1cc(-c2cn(Cc3ncc(-c4nnc(C(F)F)o4)cc3F)nn2)ccc1CN1CCCCC1] |
| 576 | 18961 | 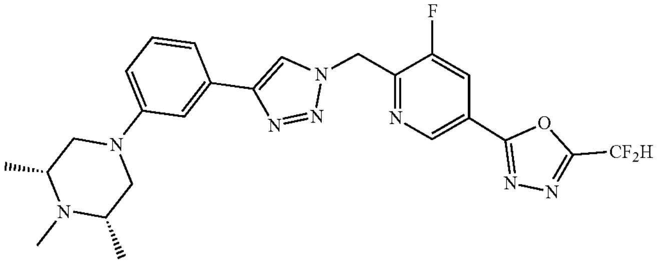 [SMILES: C[C@@H]1CN(c2cccc(-c3cn(Cc4ncc(-c5nnc(C(F)F)o5)cc4F)nn3)c2)C[C@H](C)N1C] |
| 577 | 19002 | 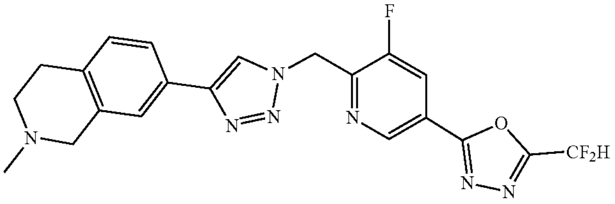 [SMILES: CN1CCc2ccc(-c3cn(Cc4ncc(-c5nnc(C(F)F)o5)cc4F)nn3)cc2C1] |
| 578 | 19004 | 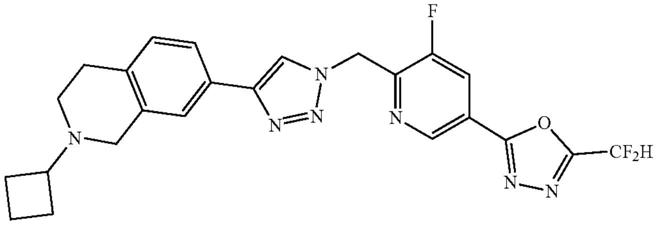 [SMILES: Fc1cc(-c2nnc(C(F)F)o2)cnc1Cn1cc(-c2ccc3c(c2)CN(C2CCC2)CC3)nn1] |

TABLE 1-continued
| Example | Compound | Structure |
| --- | --- | --- |
| 579 | 19058 | 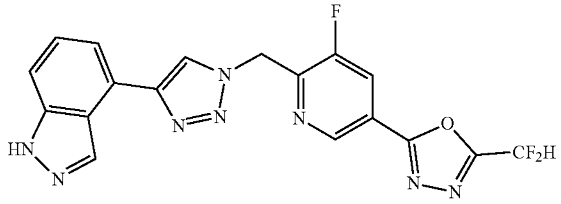 [SMILES: Fc1cc(-c2nnc(C(F)F)o2)cnc1Cn1cc(-c2cccc3[nH]ncc23)nn1] |
| 580 | 19087 | 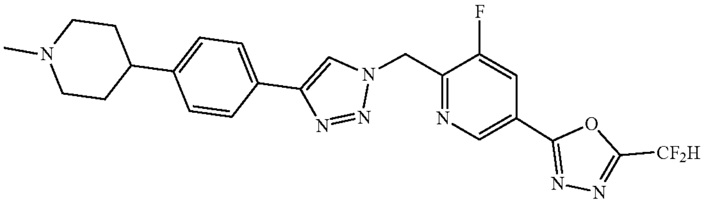 [SMILES: CN1CCC(c2ccc(-c3cn(Cc4ncc(-c5nnc(C(F)F)o5)cc4F)nn3)cc2)CC1] |
| 581 | 19088 | 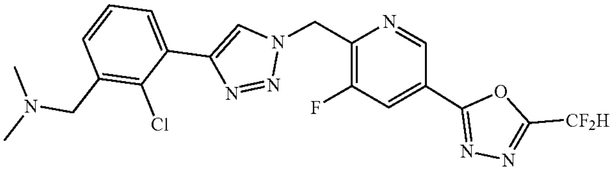 [SMILES: CN(C)Cc1cccc(-c2cn(Cc3ncc(-c4nnc(C(F)F)o4)cc3F)nn2)c1Cl] |
| 582 | 19089 | 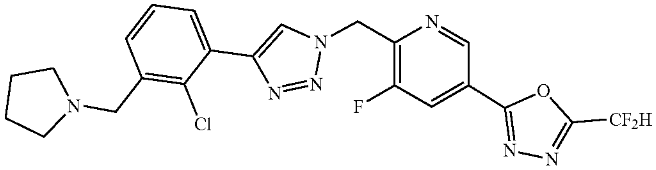 [SMILES: Fc1cc(-c2nnc(C(F)F)o2)cnc1Cn1cc(-c2cccc(CN3CCCC3)c2Cl)nn1] |
| 583 | 19090 | 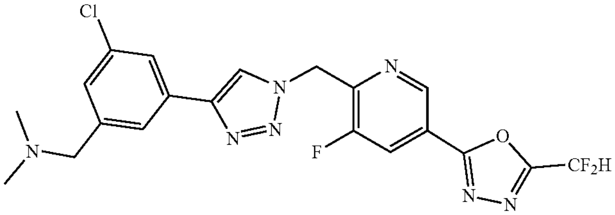 [SMILES: CN(C)Cc1cc(Cl)cc(-c2cn(Cc3ncc(-c4nnc(C(F)F)o4)cc3F)nn2)c1] |
| 584 | 19091 | 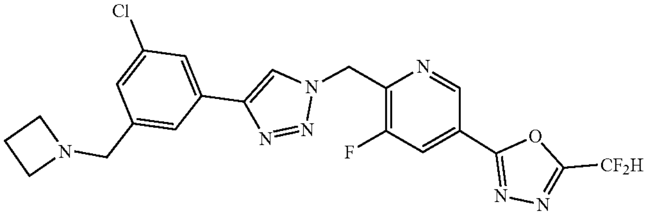 [SMILES: Fc1cc(-c2nnc(C(F)F)o2)cnc1Cn1cc(-c2cc(Cl)cc(CN3CCC3)c2)nn1] |
| 585 | 19092 | 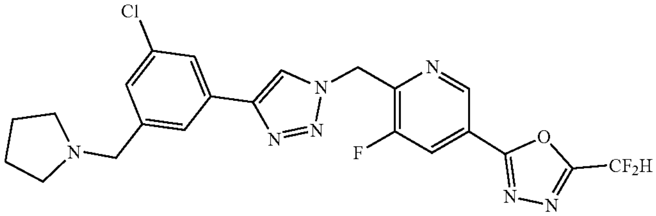 [SMILES: Fc1cc(-c2nnc(C(F)F)o2)cnc1Cn1cc(-c2cc(Cl)cc(CN3CCCC3)c2)nn1] |

TABLE 1-continued
| Example | Compound | Structure |
| --- | --- | --- |
| 586 | 19093 | 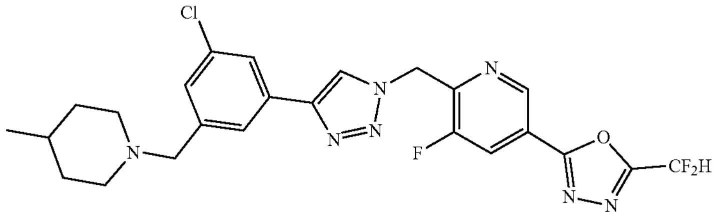 [SMILES: CC1CCN(Cc2cc(Cl)cc(-c3cn(Cc4ncc(-c5nnc(C(F)F)o5)cc4F)nn3)c2)CC1] |
| 587 | 19094 | 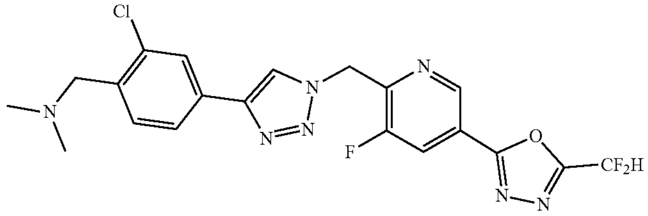 [SMILES: CN(C)Cc1ccc(-c2cn(Cc3ncc(-c4nnc(C(F)F)o4)cc3F)nn2)cc1Cl] |
| 588 | 19096 | 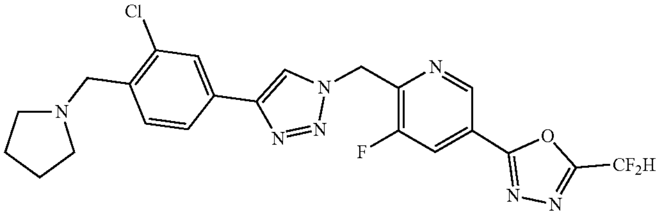 [SMILES: Fc1cc(-c2nnc(C(F)F)o2)cnc1Cn1cc(-c2ccc(CN3CCCC3)c(Cl)c2)nn1] |
| 589 | 19098 | 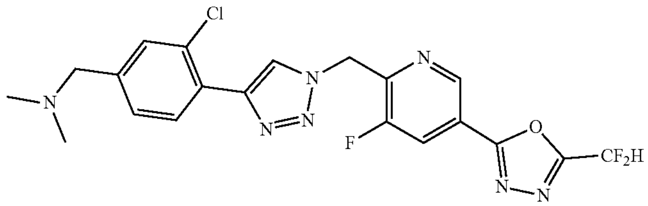 [SMILES: CN(C)Cc1ccc(-c2cn(Cc3ncc(-c4nnc(C(F)F)o4)cc3F)nn2)c(Cl)c1] |
| 590 | 19099 | 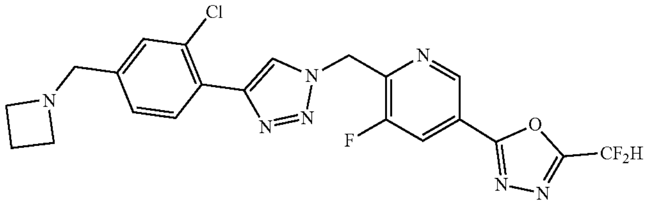 [SMILES: Fc1cc(-c2nnc(C(F)F)o2)cnc1Cn1cc(-c2ccc(CN3CCC3)cc2Cl)nn1] |
| 591 | 19100 | 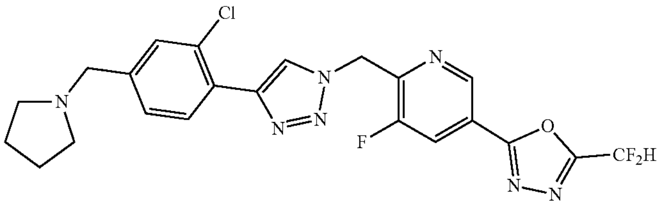 [SMILES: Fc1cc(-c2nnc(C(F)F)o2)cnc1Cn1cc(-c2ccc(CN3CCCC3)cc2Cl)nn1] |

In the present invention, the compound represented by above formula I, stereoisomers thereof or pharmaceutically acceptable salts thereof may be selected from the group consisting of compounds 3825, 3826, 3838, 3839, 3840, 3841, 3843, 3845, 3944, 3962, 3986, 3987, 3988, 4072, 4075, 4108, 4109, 4110, 4111, 4112, 4134, 4186, 4187, 4233, 4340, 4343, 4344, 4345, 4346, 4347, 4348, 4449, 4453, 4466, 4484, 4489, 4492, 4493, 4496, 4497, 4502, 4503, 4504, 4521, 4523, 4524, 4525, 4526, 4527, 4548, 4551, 4558, 4560, 4565, 4569, 4591, 4592, 4609, 4610 and 17255.

In the present invention, the compound represented by above formula I, stereoisomers thereof or pharmaceutically acceptable salts thereof may be selected from the group consisting of compounds 3838, 3839, 3840, 3841, 3843, 3944, 3986, 3987, 4108, 4187, 4340, 4343, 4346, 4347, 4348, 4466, 4493, 4524, 4525, 4558, 4565 and 17255.

Method for Preparing Compound of Formula I

A preferable method for preparing the compound represented by above formula I, stereoisomers thereof or pharmaceutically acceptable salts thereof is the same as shown in reaction formulas 1 to 19, and even a preparation method modified at a level apparent to those skilled in the art is also included therein.

Hereinafter, in the reaction formulas, the same symbols as those of the formula (I) and not specifically described are the same as those defined in the formula (I), and the overlapping description is omitted. In addition, in the reaction formulas, PG may represent an amine protecting group, and may be, for example, tert-Butyloxycarbonyl (Boc).

Furthermore, in the reaction formulas, Xa to Xc each independently represent H, halogen, C1-C5 alkyl group or C1-C5 haloalkyl group.

[Reaction Formula 1]

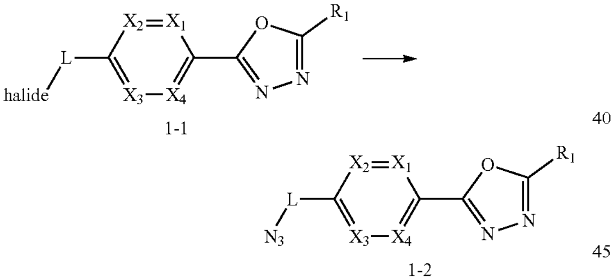

1-1

1-2

According to above reaction formula 1, compound 1-2 may be synthesized by substituting a halide portion of compound 1-1 with an azide.

Compound 1-2 may be used in the synthesis of all compounds having a triazole scaffold.

[Reaction Formula 1-1]

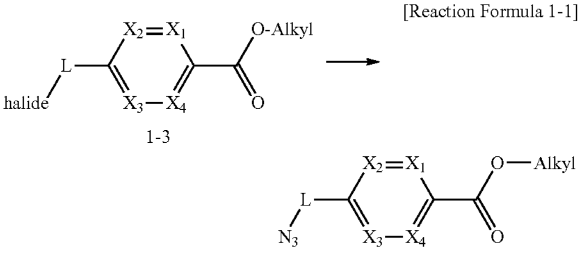

1-3

1-4

According to above reaction formula 1-1, compound 1-4 may be prepared by substituting a halide portion of compound 1-3 with an azide. Compound 1-4 may be used in the synthesis of all compounds having a triazole scaffold. In above reaction formula 1-1, alkyl may be C1-C5 alkyl.

[Reaction Formula 2]

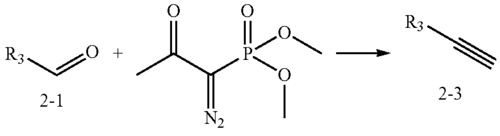

2-1

2-2

2-3

Above reaction formula 2 may be a reaction for synthesizing compound 2-3 having a triple bond, a precursor of a compound having a triazole structure, and may synthesize compound 2-3 having a triple bond by reacting aldehyde of compound 2-1 with compound 2-2 as a phosphonate reagent.

Compound 2-3 may be used in the synthesis of all compounds having a triazole scaffold.

[Reaction Formula 2-1]

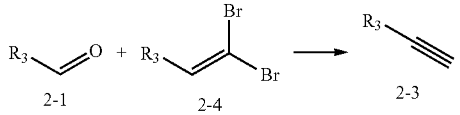

2-1

2-4

2-3

Like reaction formula 2, above reaction formula 2-1 may be a reaction for synthesizing compound 2-3 including a triple bond, which is a precursor of a compound having a triazole structure. According to above reaction formula 2-1, compound 2-3 having a triple bond may be synthesized by using the aldehyde of compound 2-1 through Corey-Fuchs reaction. Compound 2-3 may be used in the synthesis of all compounds having a triazole scaffold.

[Reaction Formula 3]

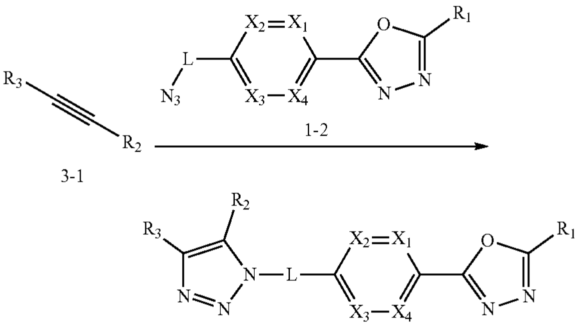

1-2

3-1

3-2

Above reaction formula 3 may be a method for synthesizing a compound having a triazole structure. According to above reaction formula 3, compound 3-2 may be prepared by a click reaction between formula 3-1 and compound 1-2.

The compound prepared by above reaction formula 3 may be compounds 3657, 3658, 3661, 3662, 3695, 3696, 3697, 3698, 3733, 3734, 3735, 3736, 3737, 3738, 3820, 3822, 3831, 3832, 3833, 3834, 3835, 3837, 3838, 3839, 3840, 3841, 3842, 3843, 3844, 3845, 3846, 3853, 3854, 3855, 3856, 3860, 3861, 3879, 3880, 3881, 3882, 3883, 3884, 3902, 3925, 3960, 3985, 4071, 4072, 4073, 4074, 4075, 4076, 4077, 4078, 4079, 4080, 4081, 4082, 4135, 4178, 4179, 4180, 4181, 4182, 4183, 4184, 4185, 4284, 4285, 4286, 4289, 4340, 4341, 4342, 4343, 4344, 4345, 4346, 4347, 4348, 4487, 4488, 4489, 4524, 4525, 4526, 4527, 16781, 16928, 16930, 17261, 17263, 17347, 17983, 17984, 18256, 18258, 18305, 18470, 18736, 17198, 17201, 17848, 17851, 17854, 17857, 18918, 18919, 18920, 18921, 19058, etc.

[Reaction Formula 3-1]

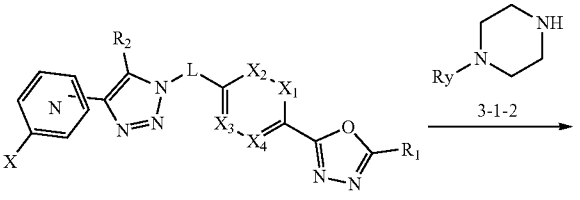

3-1-1

3-1-2

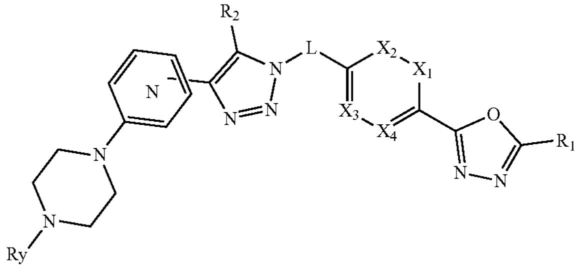

3-1-3

Above reaction formula 3-1 may represent a reaction for preparing compound 3-1-3 through an amine substitution reaction between compound 3-1-1 and compound 3-1-2 prepared through substantially the same method as described in above reaction formula 3. At this time, in above reaction formula 3-1, X may be F, Cl, etc., as a leaving group, and Ry may be OH; halogen; C1-C5 alkyl;

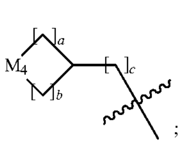

;

C1-C6 haloalkyl; —$NR_6R_7$; —C(═O)—(C1-C5 alkyl); C(═O)—O(C1-C5 alkyl); or —NH—C(═O)—O(C1-C5 alkyl).

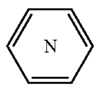

may refer to heteroaryl including N, for example, pyridinyl.

The compound prepared by above reaction formula 3-1 may be 4582, 4591, 4592, 4593, 4594, 4633, 4634, 4635, 4636, 16789, etc.

[Reaction Formula 3-2]

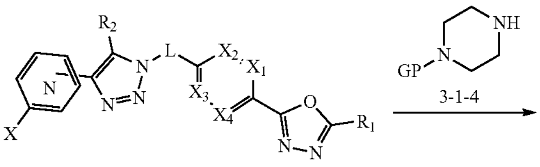

3-1-4

3-1-1

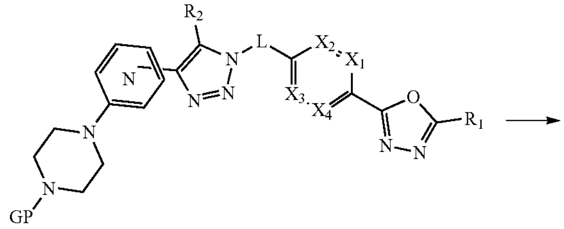

3-1-5

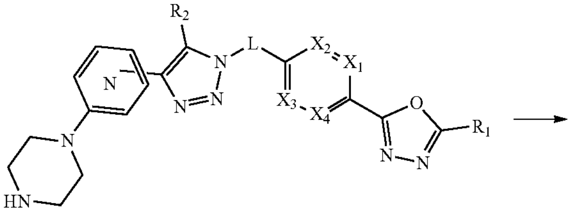

3-1-6

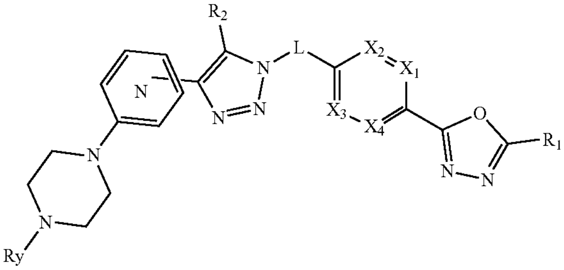

3-1-3

In above reaction formula 3-3, compound 3-1-5 may be prepared through an amine substitution reaction between compound 3-1-1 and compound 3-1-4 prepared through substantially the same method as described in above reaction formula 3. After removing an amine protecting group, compound 3-1-3 subjected to reductive amination reaction was prepared by using an Ry-H compound. In this case, in above reaction formula 3-2, X, Ry and

may be the same as defined in above reaction formula 3-1.

As compound 3-2-1 prepared by above reaction formula 3-2, there may be compounds 4640, 17362, 17363, 17364, 17635, etc.

[Reaction Formula 3-3]

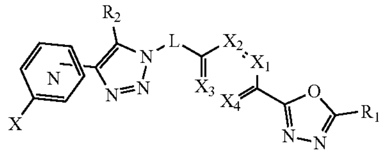

3-1-1

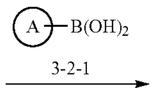

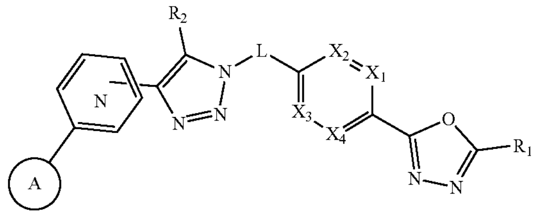

3-2-2

According to above reaction formula 3-3, compound 3-1-6 may be prepared by a Suzuki reaction between compound 3-1-1 and boronic compound 3-2-1. In above reaction formula 3-3, A ring may be

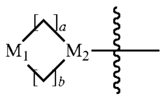

(here, a and b are each independently 1 or 2, $M_1$ is $CH_2$, O, NH or $SO_2$, and $M_2$ is CH or N);

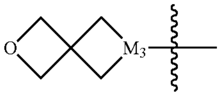

(here, $M_3$ is CH or N); diazabicycloheptane; or 5- or 6-membered heteroaryl including 1 to 3 of N.

The compound prepared according to above reaction formula 3-2 may be compound 17058, etc.

[Reaction Formula 4]

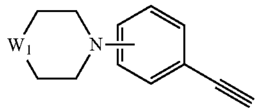

4-1

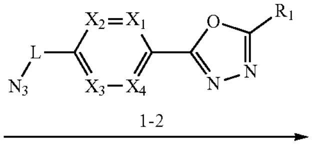

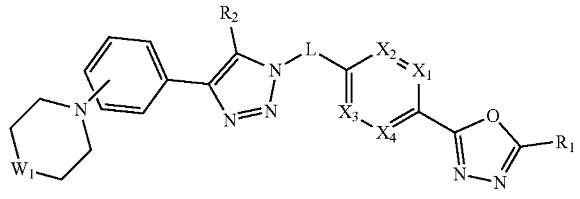

4-2

According to above reaction formula 4, compound 4-2 may be prepared by a click reaction between compound 4-1 having a triple bond and compound 1-2. In above reaction formula 4, $W_1$ represents N—(C1-C5 alkyl) or 0.

The compound prepared by above reaction formula 4 may be compounds 3866, 3867, 4104, 4105, 4106, 4107, 4336, 4337, 4338, 4339, etc.

[Reaction Formula 5]

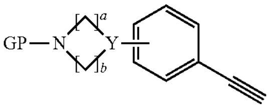

5-1

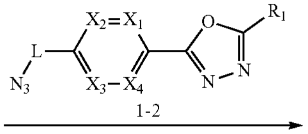

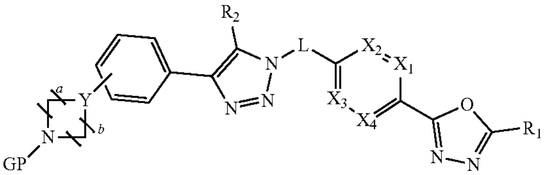

5-2

-continued

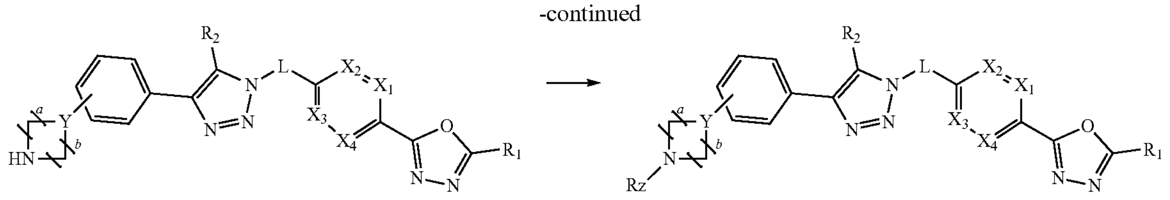

5-3

5-4

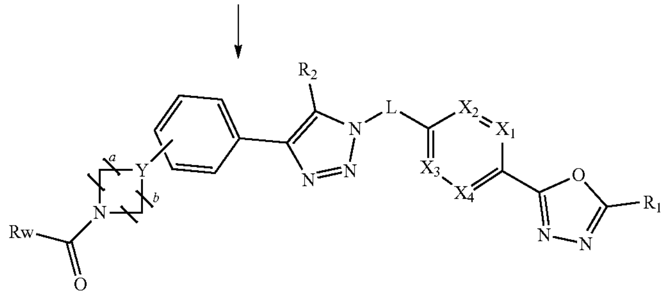

5-5

In above reaction formula 5, a and b may each independently represent 1 or 2, Y may represent N or CH, and PG may be C(═O)—O(C1-C5 alkyl), for example, Boc. Rz may be OH; halogen; C1-C5 alkyl;

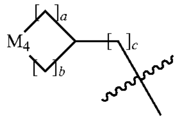

(here, a and b are each independently 0 or 1, but cannot be 0 at the same time, c is 0 or 1, $M_4$ is $CH_2$, NH, or O, and at least one H of $M_4$ may be substituted with halogen or C1-C5 alkyl); C1-C6 haloalkyl; —$NR_6R_7$ (here, $R_4$ and $R_5$ are each independently H or C1-C5 alkyl); —C(═O)—(C1-C5 alkyl); C(═O)—O(C1-C5 alkyl); or —NH—C(═O)—O (C1-C5 alkyl). Rw may be C1-C5 alkyl.

According to above reaction formula 5, compound 18868 may be prepared as compound 5-2 having a triazol structure through a click reaction between compound 5-1 including a triple bond obtained from reaction formula 2 or reaction formula 2-1, and compound 1-2.

After that, an amine protecting group may be removed from compound 5-2 and subjected to a reductive amination reaction (preparation of compound 5-3), so as to prepare compounds 3988, 3989, 3990, 3991, 4070, 4368, 4369, 4370, 4371, 4373, 4374, 4375, 4376, 4460, 4461, 4462, 4502, 4503, 4504, 4505, 4506, 4507, 4508, 4509, 4510, 4511, 4528, 17698, 17699, 17700, 18869, 18870, 18871, 18924, 18926, etc. as compound 5-4.

Alternatively, according to above reaction formula 5, compounds 4372 and 4377 may be prepared as compound 5-5 through an acylation reaction of compound 5-3.

[Reaction Formula 5-1]

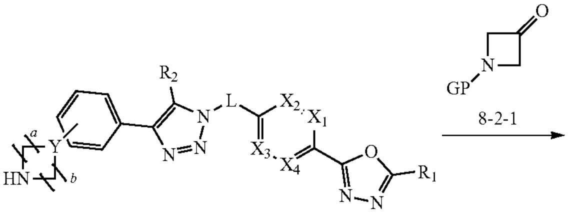

5-3

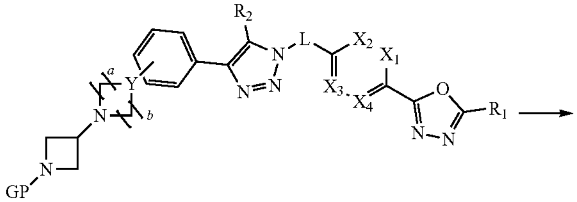

5-3-1

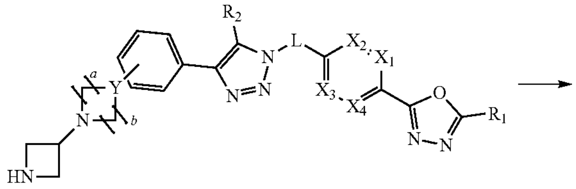

5-3-2

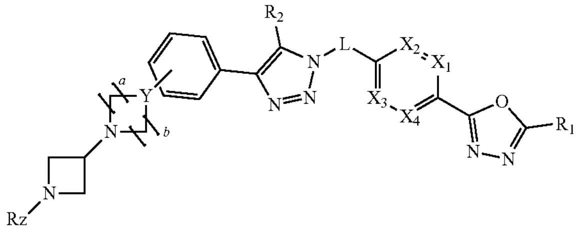

5-3-3

In above reaction formula 5-1, a and b may each independently represent 1 or 2, Y may represent N or CH, and PG may be C(=O)—O(C1-C5 alkyl), for example, Boc. In above reaction formula 5-1, Rz may represent halogen, C1-C5 alkyl, or C3-C6 cycloalkyl.

According to above reaction formula 5-1, compound 18872 may be prepared as compound 5-3-1 through a reductive amination reaction between compound 5-3 prepared in reaction formula 5 and compound 8-2-1 having an amine protecting group.

After that, an amine protecting group may be removed from compound 5-3-1 to prepare compound 5-3-2 and prepare compounds 18877 and 18878 as compound 5-3-3 through a reductive amination reaction.

[Reaction Formula 6]

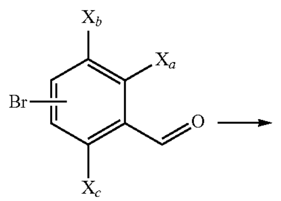

6-1

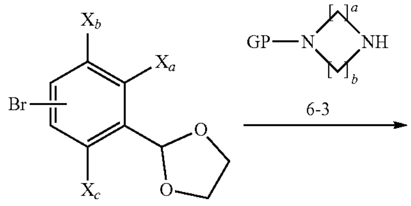

6-2

6-3

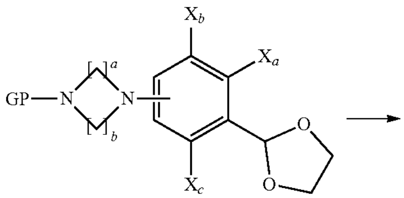

6-4

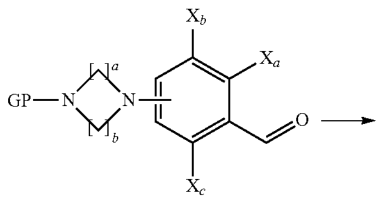

6-5

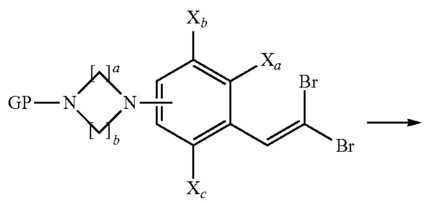

6-6

-continued

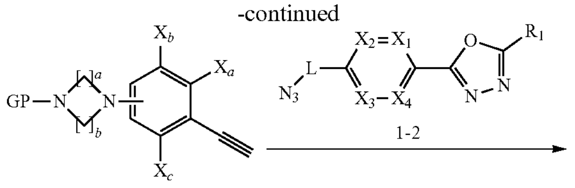

6-7

1-2

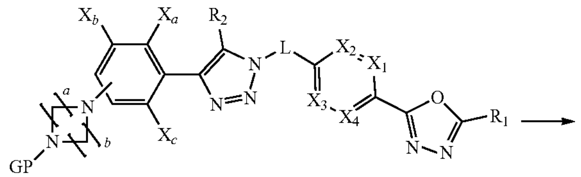

6-8

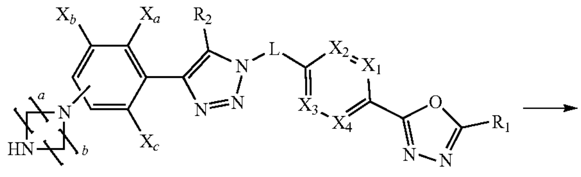

6-9

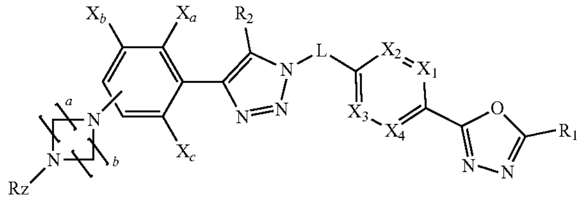

6-10

In above reaction formula 6, a and b may each independently represent 1 or 2, and Rz may be the same as described in reaction formula 5 or reaction formula 5-1.

According to above reaction formula 6, compound 6-2 in which an aldehyde group of compound 6-1 is protected with an acetal group may be prepared, and compound 6-4 may be prepared through C—N coupling (Buchwald reaction) with compound 6-3. After that, compound 6-5 having an aldehyde structure may be prepared by removing the acetal protecting group, and compound 6-7 having a triple bond may be prepared by performing a Corey-Fuchs reaction, and then compound 6-8 having a triazole structure may be prepared through a click reaction with compound 1-2. An amine protecting group (PG) of compound 6-8 may be removed to synthesize compounds 4316, 4317, 4396, 4397, 4398, 4399, 4439, 4440, 4450, 16797 and 18893 corresponding to compound 6-9. A reductive amination reaction may be performed with compound 6-9 so as to prepare compound 6-10.

Compounds 6-10 prepared by above reaction formula 6 may be compounds 4318, 4319, 4320, 4321, 4322, 4419, 4420, 4421, 4422, 4424, 4425, 4426, 4427, 4429, 4430, 4441, 4442, 4443, 4444, 4451, 4452, 4453, 4454, 4455, 4483, 4484, 4485, 4486, 4569, 4570, 4571, 4572, 4573, 4576, 4577, 4578, 4579, 4580, 4600, 4601, 4602, 4603, 18327, 18961, etc.

[Reaction Formula 7]

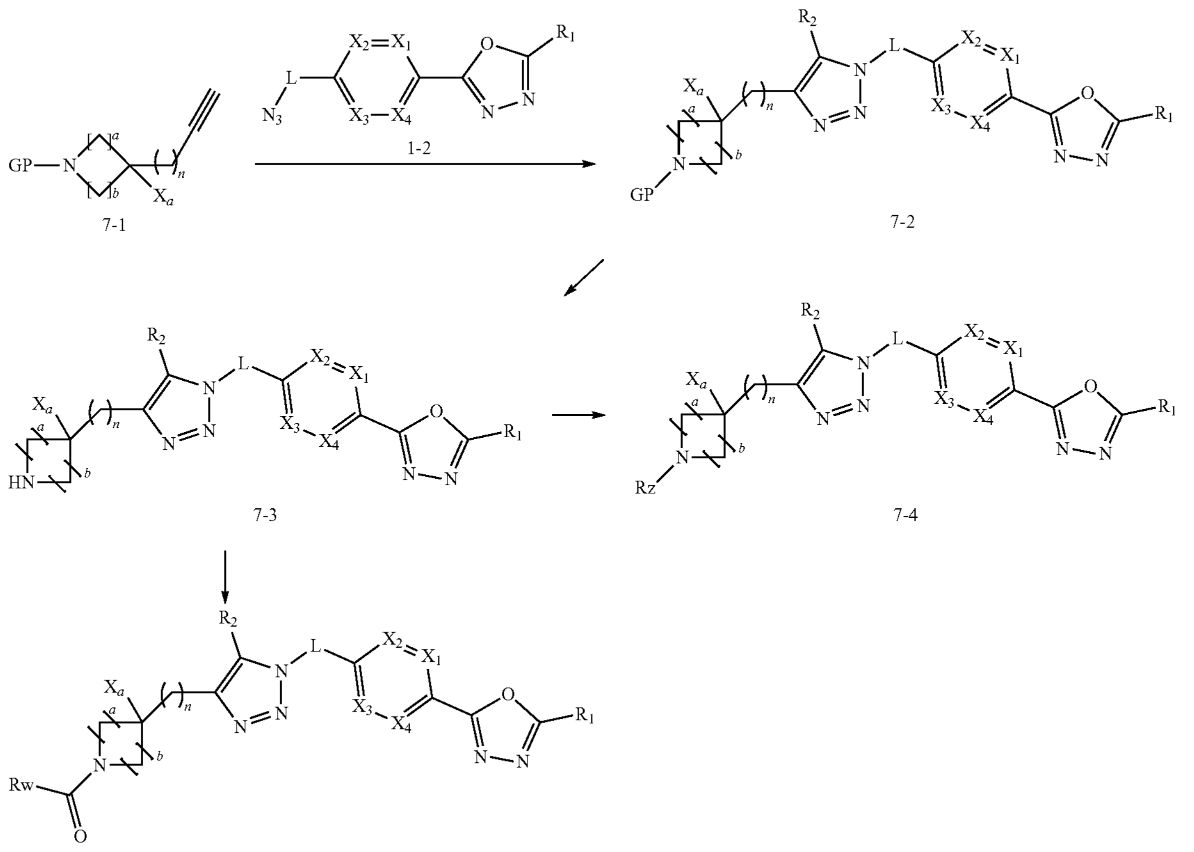

7-1 1-2 7-2 7-3 7-4 7-5

In above reaction formula 7, a and b may each independently represent 1 or 2, n may represent an integer of 0 to 5, and Rz and Rw may be the same as described in reaction formula 5.

According to above reaction formula 7, compounds 3805, 3926, 3961, 3999, 4000, etc., may be prepared as compound 7-2 having a triazole structure through a click reaction between compound 7-1 having a triple bond and compound 1-2. In addition, an amine protecting group may be removed from compound 7-2 to prepare compound 7-3 and then prepare compound 7-4 through a reductive amination reaction.

Compounds 7-4 prepared by above reaction formula 7 may be compounds 3806, 3807, 3808, 3809, 3810, 3951, 3952, 3953, 3954, 3955, 4002, 4003, 4005, 4006, 4007, 4008, 4014, 4026, 4027, etc.

In addition, compound 7-3 may be subjected to an acylation reaction or an amide reaction to prepare amide compound 7-5, for example, compounds 3811, 3812, 3813, 3891, 3892, 3893, 3894, 3956, 3957, 3958, 3959, 4004, 4009, 4015, 4028, 4029, etc.

[Reaction Formula 7-1]

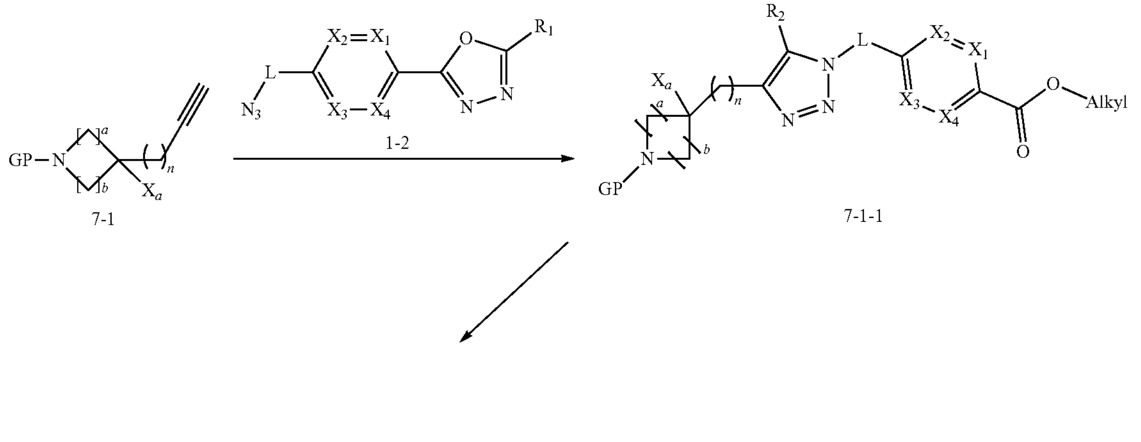

7-1 1-2 7-1-1

-continued

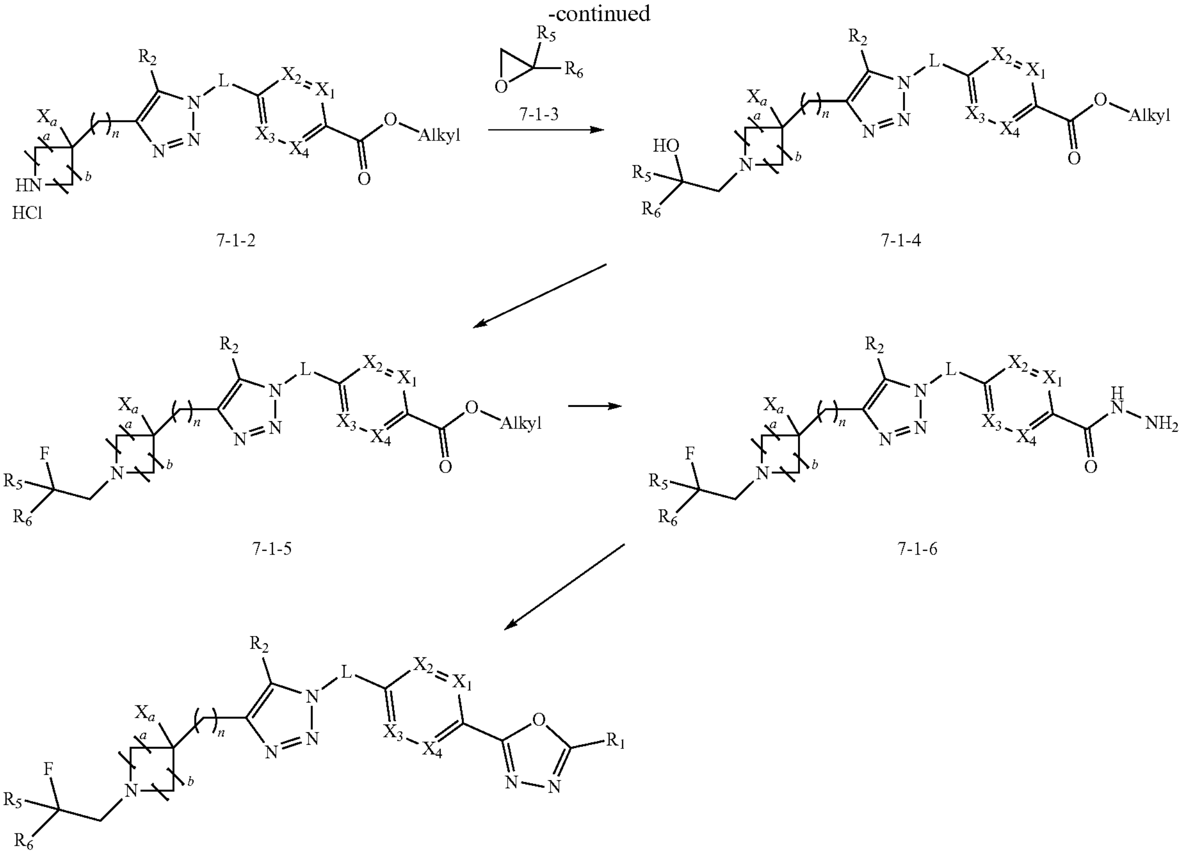

7-1-2

7-1-3

7-1-4

7-1-5

7-1-6

7-1-7

In above reaction formula 7-1, a and b may each independently represent 1 or 2, n may represent an integer of 0 to 5, alkyl may be C1-C5 alkyl, and $R_5$ and $R_6$ may each independently represent H, halogen or C1-C5 alkyl group.

According to above reaction formula 7-1, compound 7-1-1 having a triazol structure may be prepared through a click reaction between compound 7-1 and compound 1-4, after which an amine protecting group may be removed with acid to prepare compound 7-1-2. After that, compound 7-1-4 may be prepared by reacting with compound 7-1-3, which is an oxirane compound, and compound 7-1-5 may be prepared by substituting a hydroxy group with fluoride, and then compound 7-1-6 may be prepared by using hydrazine. After that, compound 7-1-7 may be prepared in reaction with trifluoroacetic anhydride or difluoroacetic anhydride.

The compound prepared by reaction formula 7-1 may be compounds 3895, 3896, etc.

[Reaction Formula 8]

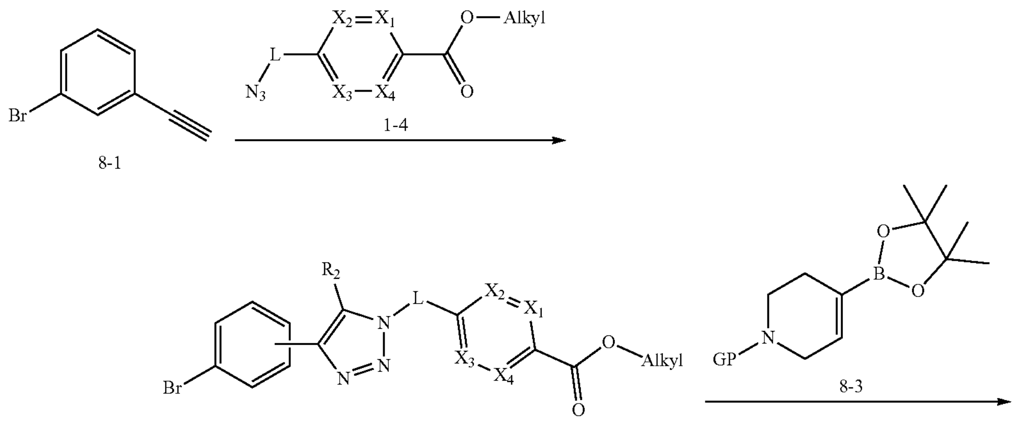

8-1

1-4

8-2

8-3

-continued

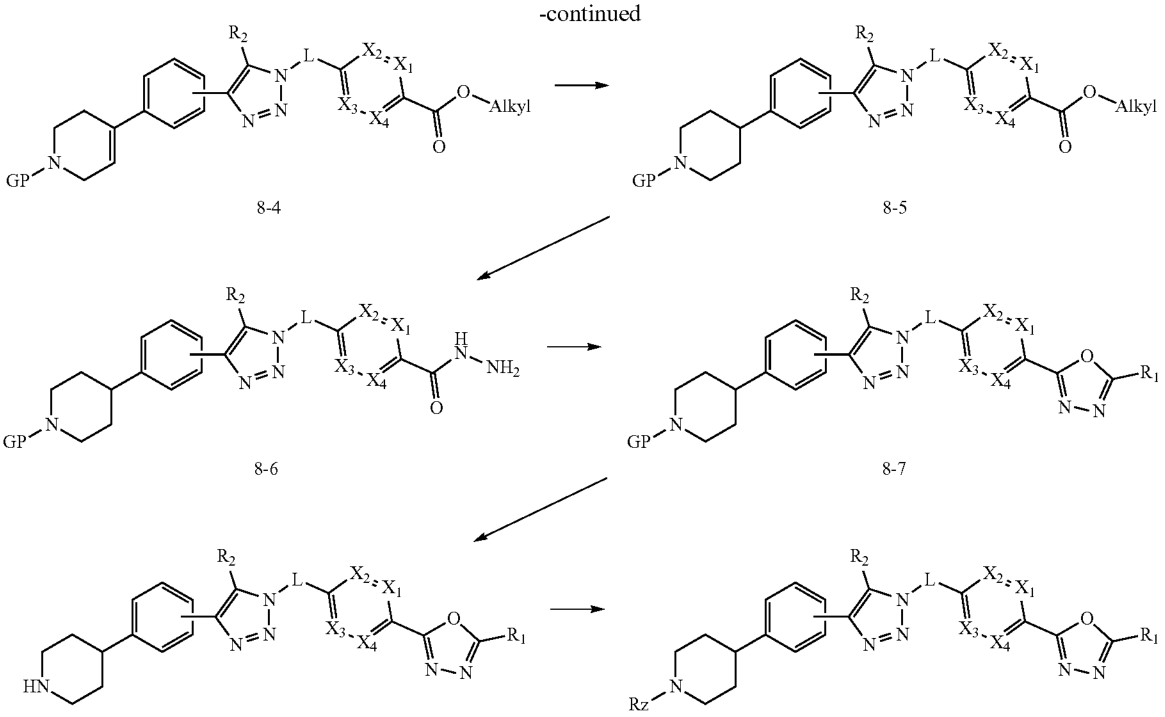

8-4 8-5 8-6 8-7 8-8 8-9

In above reaction formula 8, a and b may each independently represent 1 or 2, alkyl may be C1-C5 alkyl, and Rz may be the same as described in reaction formula 5.

According to above reaction formula 8, compound 8-2 having a triazol structure may be prepared through a click reaction between compound 8-1 having a triple bond and compound 1-4, after which compound 8-4 may be prepared through C—C coupling (Suzuki reaction) with compound 8-3 having a protecting group. After that, compound 8-5 may be prepared through a reduction reaction, and compound 8-6 may be prepared by using hydrazine, and then reacted with trifluoroacetic anhydride or difluoroacetic anhydride to prepare compound 4001 as compound 8-7. After preparing compound 8-8 by removing an amine protecting group of compound 8-7, compound 8-9 may be prepared through a reductive amination reaction, and there may be compounds 4010, 4011, 4012, 4013, 4290, 4291, 4292, 4293, 19087, etc., as compound 8-9.

[Reaction Formula 8-1]

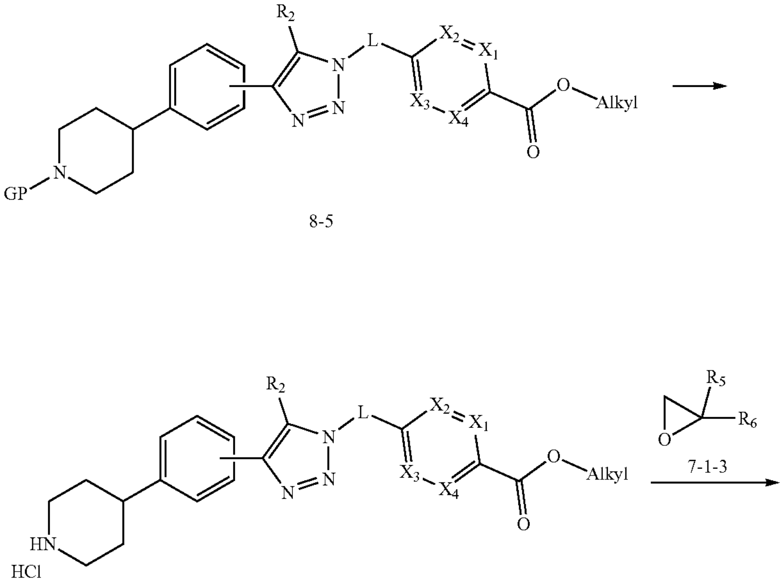

8-5

8-1-1

-continued

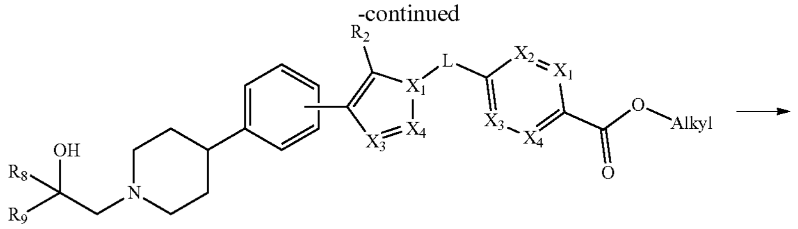

8-1-2

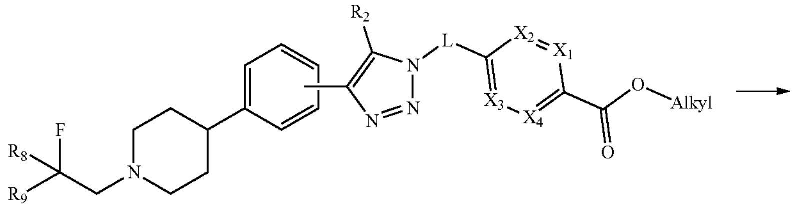

8-1-3

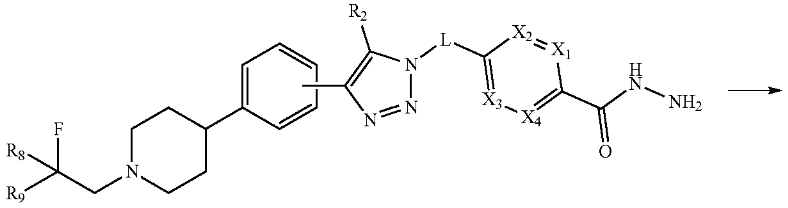

8-1-4

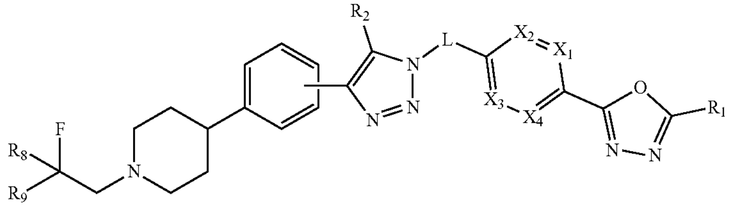

8-1-5

In above reaction formula 8-1, alkyl may be C1-C5 alkyl, and $R_8$ and $R_9$ may each independently represent H, halogen or C1-C5 alkyl group.

According to above reaction formula 8-1, compound 8-1-1 may be prepared by removing an amine protecting group of compound 8-5 prepared in reaction formula 8 with an acid, and then reacted with compound 7-1-3, which is an oxirane compound, to prepare compound 8-1-2. After preparing compound 8-1-3 by substituting a hydroxyl group of compound 8-1-2 with fluoride, compound 8-1-4 may be prepared by using hydrazine, and then reacted with trifluoroacetic anhydride or difluoroacetic anhydride to prepare compound 8-1-5.

The compound prepared by reaction formula 8-1 may be compounds 4349, 4350, etc.

[Reaction Formula 8-2]

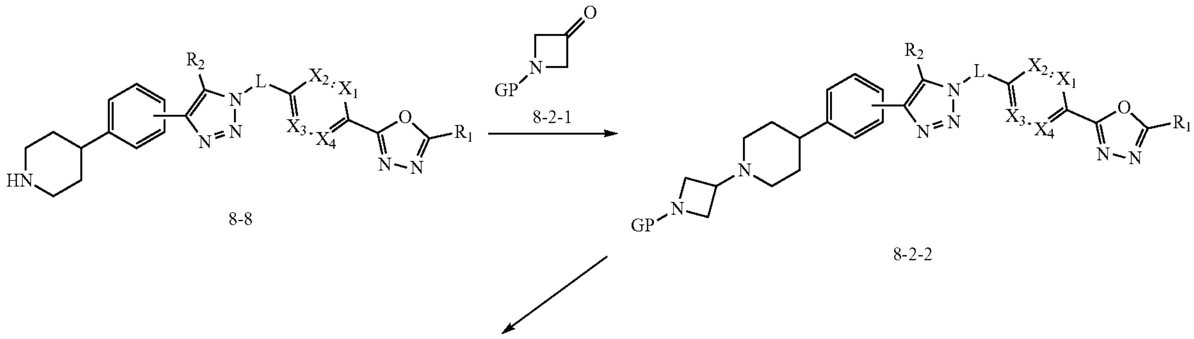

8-8

8-2-1

8-2-2

-continued

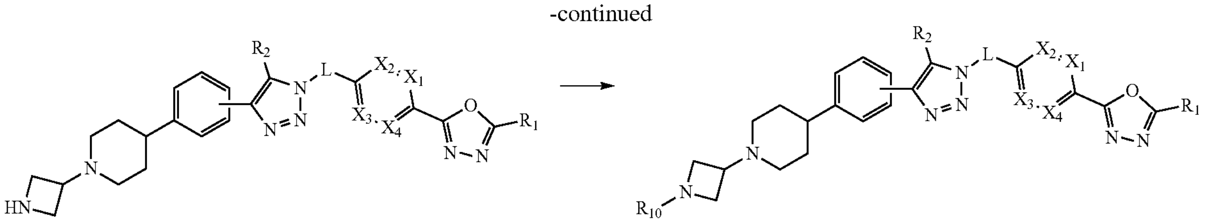

8-2-3 8-2-4

In above reaction formula 8-2, $R_{10}$ may represent H, halogen or C1-C5 alkyl.

According to above reaction formula 8-2, compound 8-2-2 may be prepared through a reductive amination reaction between compound 8-8 prepared in reaction formula 8 and compound 8-2-1 having an amine protecting group, and the amine protecting group may be removed to prepare compound 8-2-3 and then prepare compound 8-2-4 through a reductive amination reaction.

The compound prepared by reaction formula 8-2 may be compounds 4294, 4295, 4296, etc.

[Reaction Formula 9]

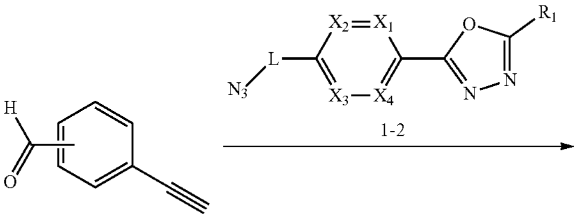

1-2

9-1

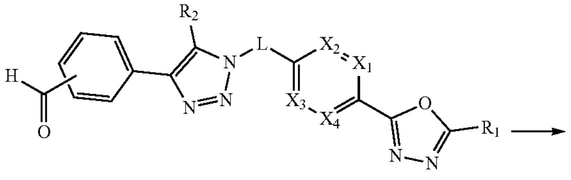

9-2

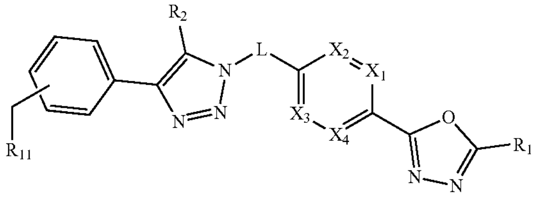

9-3

In above reaction formula 9, $R_1$ may be

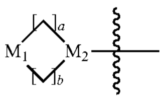

or

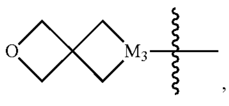

, in which H of the functional group may be each independently substituted with OH; halogen; C1-C5 alkyl; C1-C6 haloalkyl, etc.

According to above reaction formula 9, compound 9-2 having a triazol structure may be prepared through a click reaction between compound 9-1 and compound 1-2, after which compound 9-3 may be prepared through a reductive amination reaction.

The compound prepared by above reaction formula 9 may be compounds 3915, 3916, 3917, 3918, 3919, 3963, 3964, 3965, 3966, 4400, 4401, 4402, 4403, 4404, 4405, 4406, 4407, 4408, 4409, 4410, 4411, 4412, 4413, 4414, 4415, 4416, 4417, 4418, 4466, 4467, 4468, 4469, 4470, 4471, 4472, 4473, 4474, 4475, 4476, 4477, 4494, 4521, 4522, 4523, 4548, 4549, 4550, 4551, 4552, 4553, 4554, 4555, 4556, 4557, 4558, 4559, 4560, 4561, 4562, 4563, 4564, 4565, 4566, 4567, 4583, 4585, 4586, 4587, 4588, 4589, 4590, 18058, 18306, 18307, 18308, 18457, 18459, 18822, 18823, 18882, 4604, 4605, 4606, 4607, 4608, 4609, 4610, 4611, etc.

[Reaction Formula 9-1]

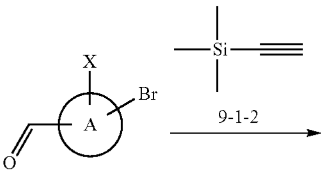

9-1-2

9-1-1

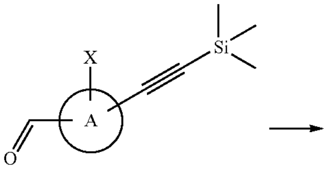

9-1-3

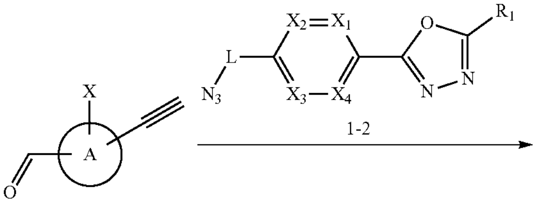

1-2

9-1-4

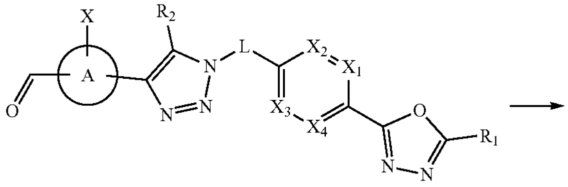

9-1-5

-continued

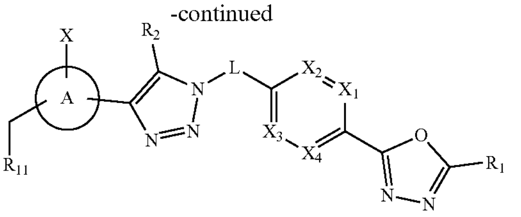

9-1-6

In above reaction formula 9-1, A ring may be C4-C6 cycloalkenyl; C6-C12 aryl; 5- to 9-membered heteroaryl including at least one heteroatom selected from N, O and S;

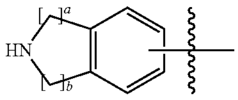

(here, a or b is each independently an integer of 1 or 2);

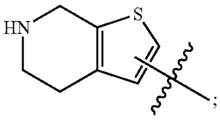

;

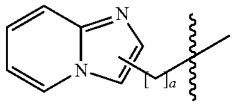

(here, a is an integer of 0, 1 or 2); or pyridinone. In this case, Ru may be halogen or -Q1-Q2-Ra. In addition, X linked to the A ring may represent F, Cl or Br.

According to above reaction formula 9-1, compound 9-1-3 having a trimethyl silane protecting group may be prepared through a C—C coupling (Sonogashira) between halide compound 9-1-1 and compound 9-1-2 having a triple bond, after which compound 9-1-4 having an aldehyde structure may be prepared by removing a trimethyl silane protecting group.

Compound 9-1-5 having a triazol structure may be prepared through a click reaction between compound 9-1-4 and compound 1-2, after which compound 9-1-6 may be prepared through a reductive amination reaction.

The compound prepared by above reaction formula 9-1 may be compounds 18059, 18309, 18310, 18311, 18483, 18554, 18622, 18711, 18712, 18713, 19088, 19089, 19090, 19091, 19092, 19093, 19094, 19096, 19098, 19099, 19100, 17532, 17533, 17534, 17535, 17545, 17773, 17774, 17775, 17777, 17778, 17912, 17913, 17914, 17915, 17916, 17917, 17922, 18174, 18175, 18176, 18177, 18178, 18180, 18185, 18187, 18188, 18260, 18947, 18948, 18949, and 18950.

[Reaction Formula 10]

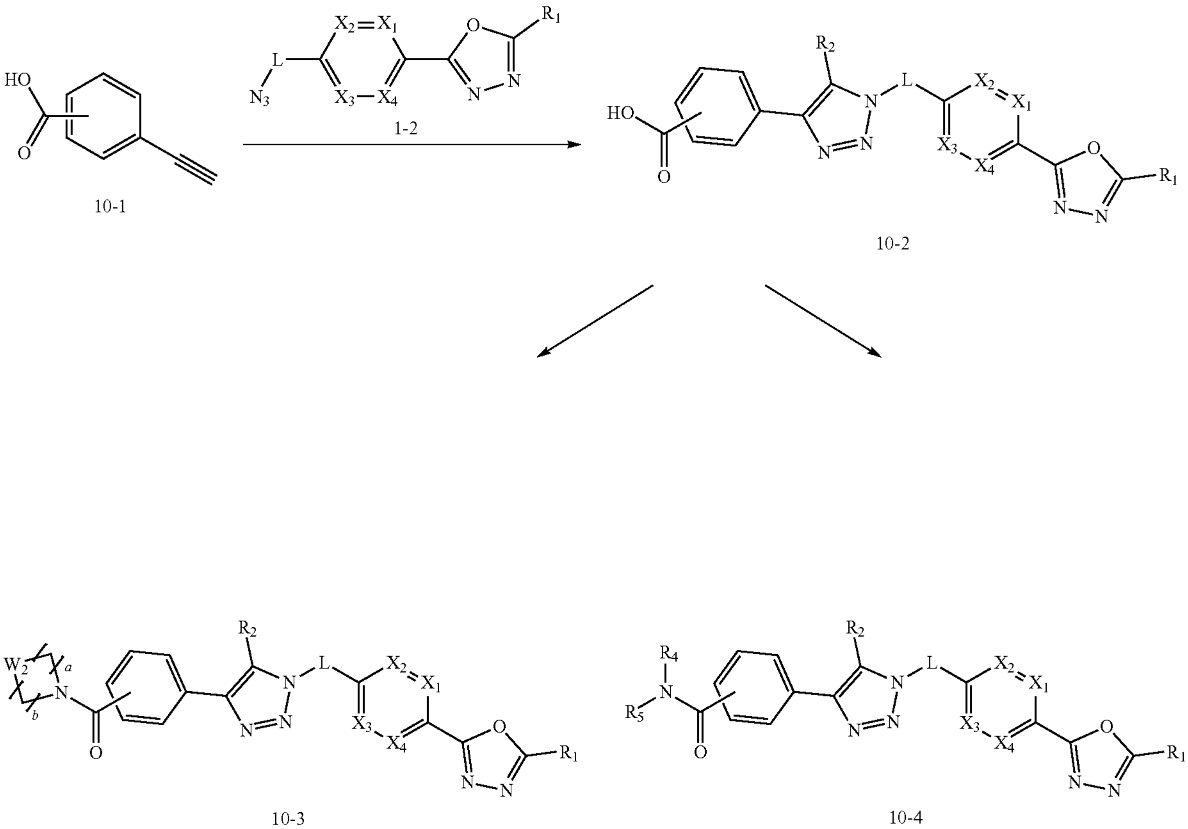

In above reaction formula 10, a and b may be each independently 1 or 2, and $W_2$ may be O, $CH_2$, CH(C1-C5 alkyl), NH or N—(C1-C5)alkyl.

In above reaction formula 10, $R_4$ and $R_5$ may be each independently H or C1-C5 alkyl, and at least one H may be each independently

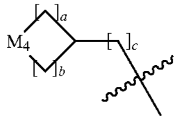

(here, a and b are each independently 0 or 1, but cannot be 0 at the same time, c is 0 or 1, $M_4$ is $CH_2$, NH, or O, and at least one H of $M_4$ may be substituted with halogen, C1-C5 alkyl, C3-C6 cycloalkyl or —C(═O)—O(C1-C5 alkyl), or —$NR_6R_7$ (here, $R_6$ and $R_7$ are each independently H or C1-C5 alkyl).

According to above reaction formula 10, compounds 3659, 3660, 3731, 3732 and 3739 may be prepared as compound 10-2 having a triazole structure through a click reaction between compound 10-1 and compound 1-2.

Through an amide bond with compound 10-2, compounds 3829, 3885, 3886, 3887, 4448, 4482, etc., may be prepared as amid compound 10-3, and compounds 4449 and 4480 may be prepared as compound 10-4.

In above reaction formula 11, $R_4$ and $R_5$ may be each independently H or C1-C5 alkyl, and at least one H may be each independently substituted with OH; halogen;

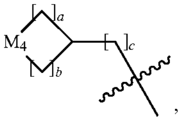

, etc.

According to above reaction formula 11, compound 11-2 having a triazole structure may be prepared through a click reaction between compound 11-1 and compound 1-2, after which compounds 3774, 3824, 3827, 3828, 3830, 4323, 4324, 4325, 4326, 4330, 4331, 4332, 4431, 4432, 4433, 4434, 4435, 4436, 4437 and 4438 may be prepared as compound 11-3 through a reductive amination reaction.

Compound 11-2 may be subjected to an acylation reaction and an amide reaction to prepare compounds 3775, 3776, 3777, 3825, 3826, 3987, 4229, 4230, 4231, 4327, 4328, 4329, 4333, 4334, 4335, 4351, 4352, 4353, etc., as compound 11-4.

[Reaction Formula 11]

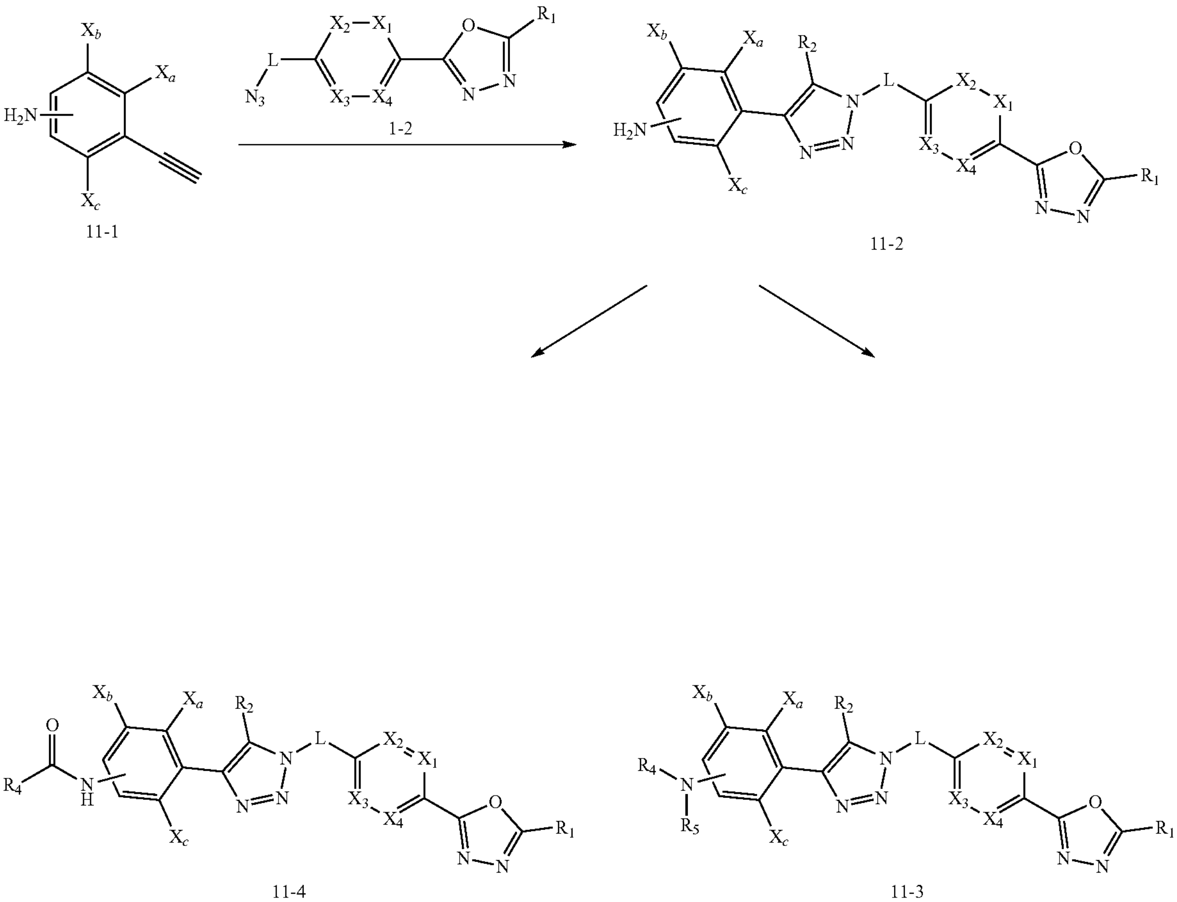

11-1 1-2 11-2 11-4 11-3

[Reaction Formula 11-1]

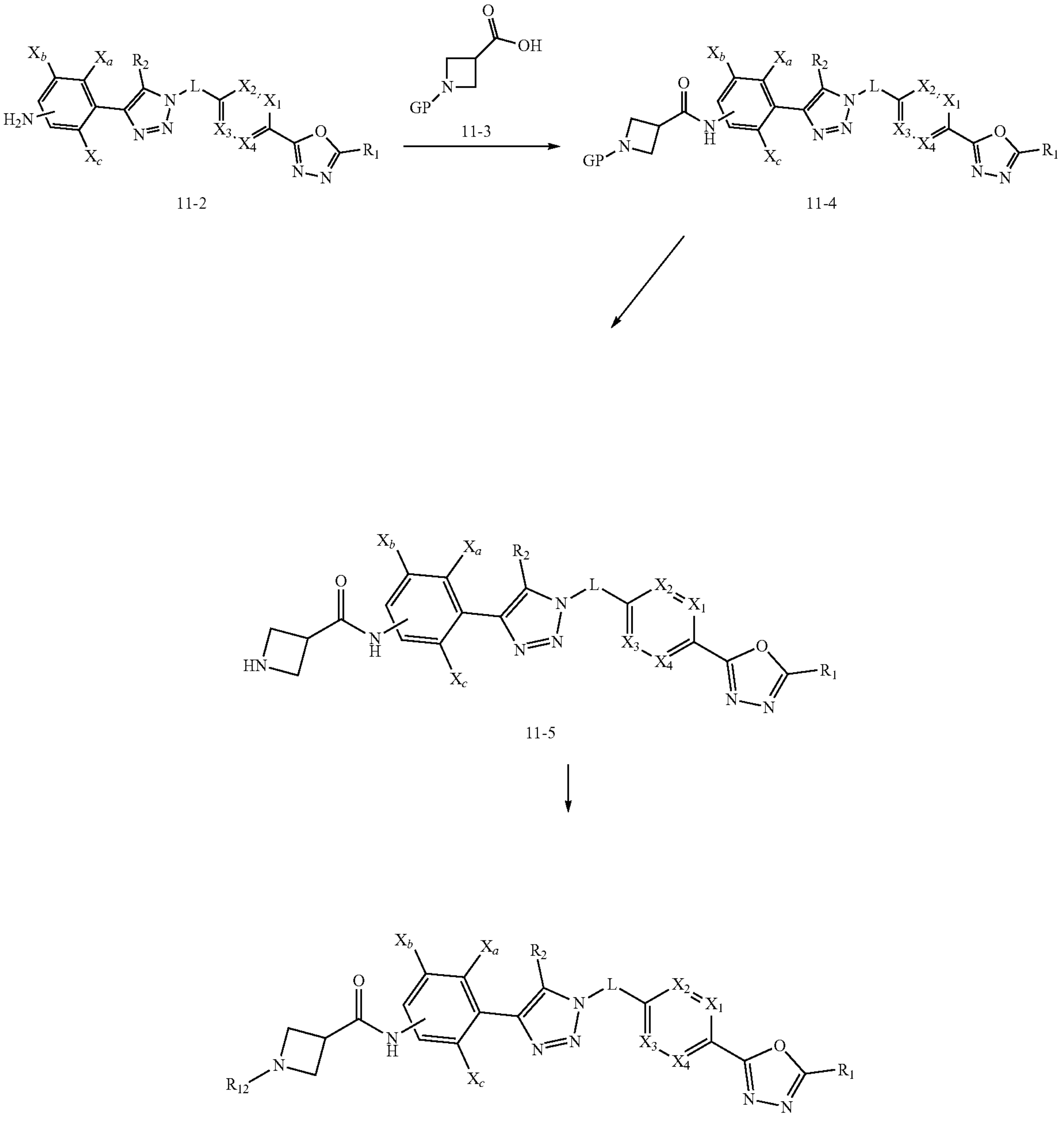

11-2 11-4 11-5

11-6

In above reaction formula 11-1, $R_{12}$ may be OH; halogen; C1-C5 alkyl;

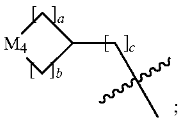
;

C1-C6 haloalkyl; —$NR_6R_7$ (here, $R_6$ and $R_7$ may be each independently H or C1-C5 alkyl); —C(═O)—(C1-C5 alkyl); C(═O)—O(C1-C5 alkyl); or —NH—C(═O)—O (C1-C5 alkyl).

According to reaction formula 11-1, after preparing compound 11-4 that forms an amide bond between compound 11-2 prepared in reaction formula 11 and compound 11-3 having an amine protecting group, compound 4463 may be prepared as compound 11-5 by removing an amine protecting group.

Compound 11-5 may be subjected to a reductive amination reaction to prepare compounds 4464 and 4465 as compound 11-6.

[Reaction Formula 11-2]

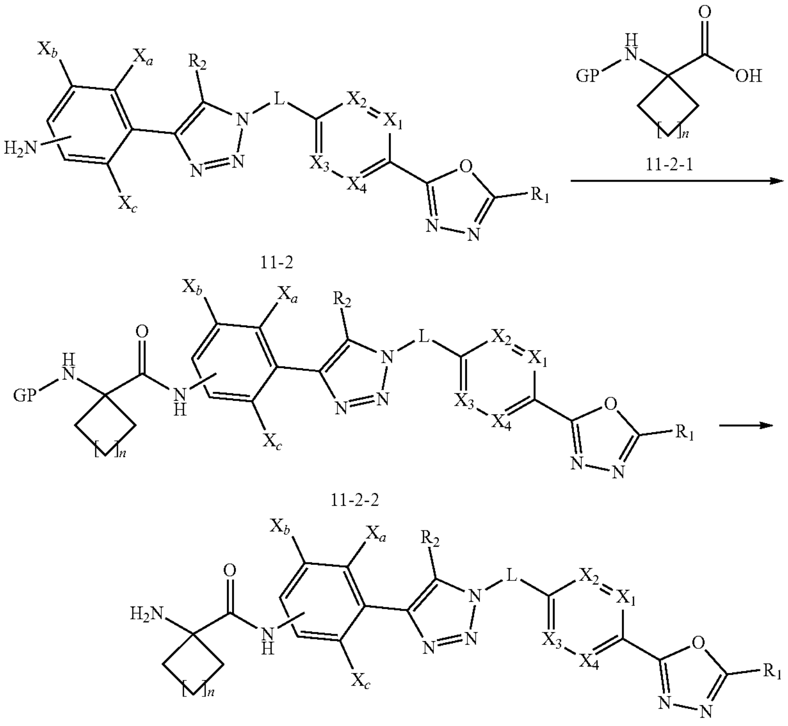

11-2

11-2-1

11-2-2

11-2-3

In above reaction formula 11-2, n may be 1 or 2.

According to above reaction formula 11-2, compounds 4495 and 4496 may be prepared as compound 11-2-2 that forms an amide bond between compound 11-2 prepared in reaction formula 11 and compound 11-2-1 having an amine protecting group. After that, the amine protecting group may be removed to prepare compounds 4497 and 4498 as compound 11-2-3.

-continued

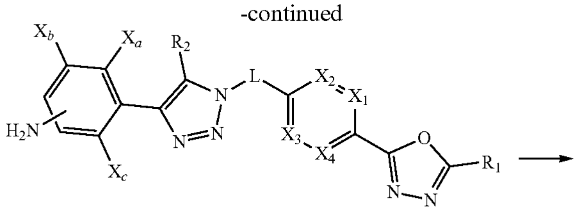

11-2

[Reaction Formula 11-3]

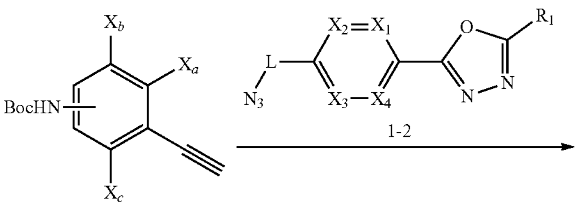

11-3-1

1-2

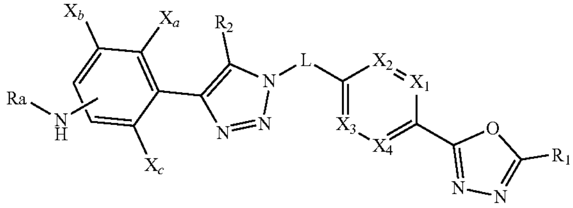

11-3-3

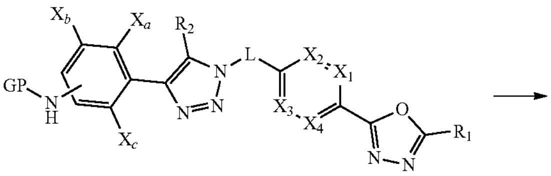

11-3-2

According to above reaction formula 11-3, compound 3741 having a structure of compound 11-3-2 having a triazole structure may be prepared through a click reaction between compound 11-3-1 having an amine protecting group and compound 1-2. After that, the amine protecting group may be removed to prepare compound 11-2, and then compound 11-3-3 is prepared through a reductive amination reaction.

[Reaction Formula 11-4]

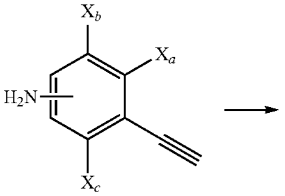

11-1

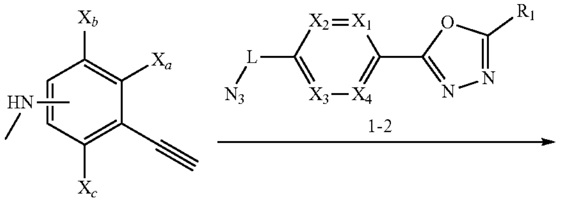

11-4-1

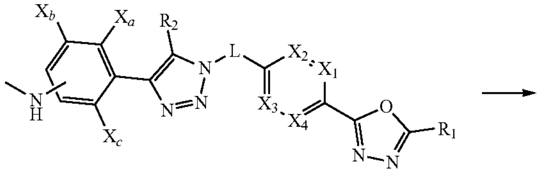

11-4-2

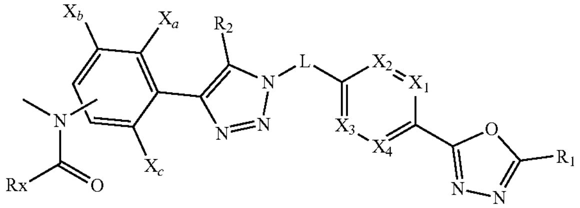

11-4-3

In above reaction formula 11-4, Rx may be C1-C5 alkyl or C1-C5 alkoxy.

According to above reaction formula 11-4, compound 11-1 having a triple bond may be subjected to a reductive amination reaction to prepare compound 11-4-1, and prepare compound 11-4-2 having a triazole structure through a click reaction with compound 1-2. After that, compounds 3889 and 3890 may be prepared as compound 11-4-3 through an acylation reaction.

[Reaction Formula 12]

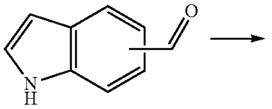

12-1

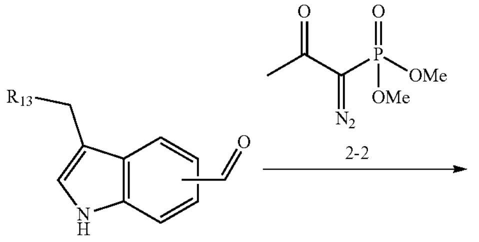

12-2

-continued

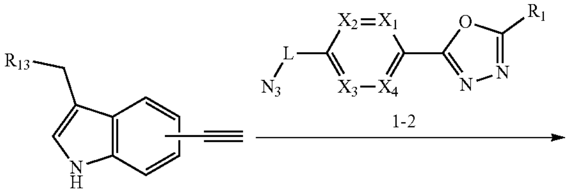

12-3

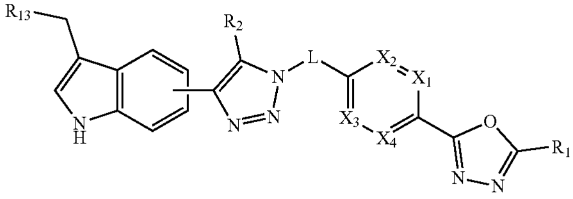

12-4

In above reaction formula 12, $R_{13}$ may be -Q1-Q2-Ra.

According to above reaction formula 12, compound 12-1 having an aldehyde structure may be subjected to a Mannich reaction to prepare compound 12-2, after which compound 12-3 having a triple bond structure may be synthesized with compound 2-2, which is a phosphonate reagent. After that, compounds 3944, 3962, 3986, 4108, 4109, 4110, 4111, 4112, 4134, 4492, 4493 and 17255 may be prepared as compound 12-4 having a triazole structure through a click reaction with compound 1-2.

[Reaction Formula 12-1]

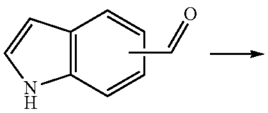

12-1

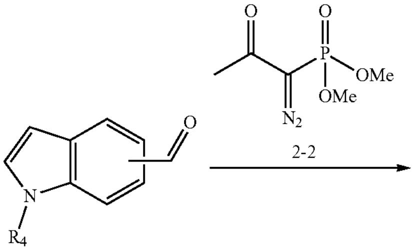

12-1-1

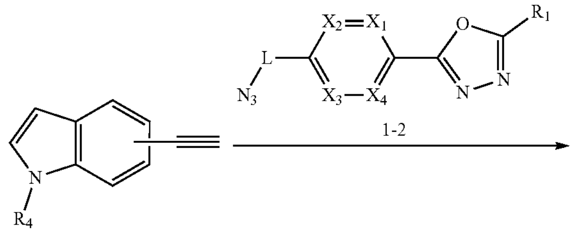

12-1-2

-continued

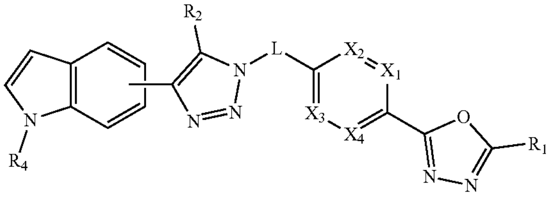

12-1-3

In above reaction formula 12-1, $R_{13}$ may be $-(CH_2)_n$-Q1-Q2-Ra (here, n is 0 or 1).

According to above reaction formula 12-1, compound 12-1 having an aldehyde structure may be subjected to a reductive amination reaction to prepare compound 12-1-1, after which compound 12-1-2 having a triple bond structure may be synthesized with compound 2-2, which is a phosphonate reagent. After that, compounds 3914 and 4136 may be prepared as compound 12-1-3 having a triazole structure through a click reaction with compound 1-2.

[Reaction Formula 12-2]

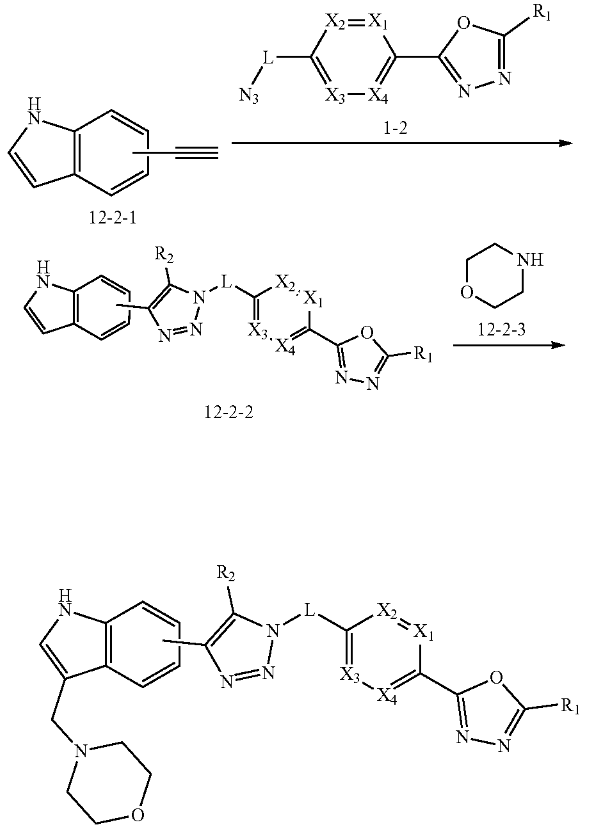

1-2

12-2-1

12-2-3

12-2-2

12-2-4

According to above reaction formula 12-2, compound 12-2-2 having a triazole structure may be prepared through a click reaction between compound 12-2-1 obtained through reaction formula 2 and compound 1-2, after which compounds 4023, 4186 and 4187 may be prepared as compound 12-2-4 through a Mannich reaction with compound 12-2-3.

[Reaction Formula 12-3]

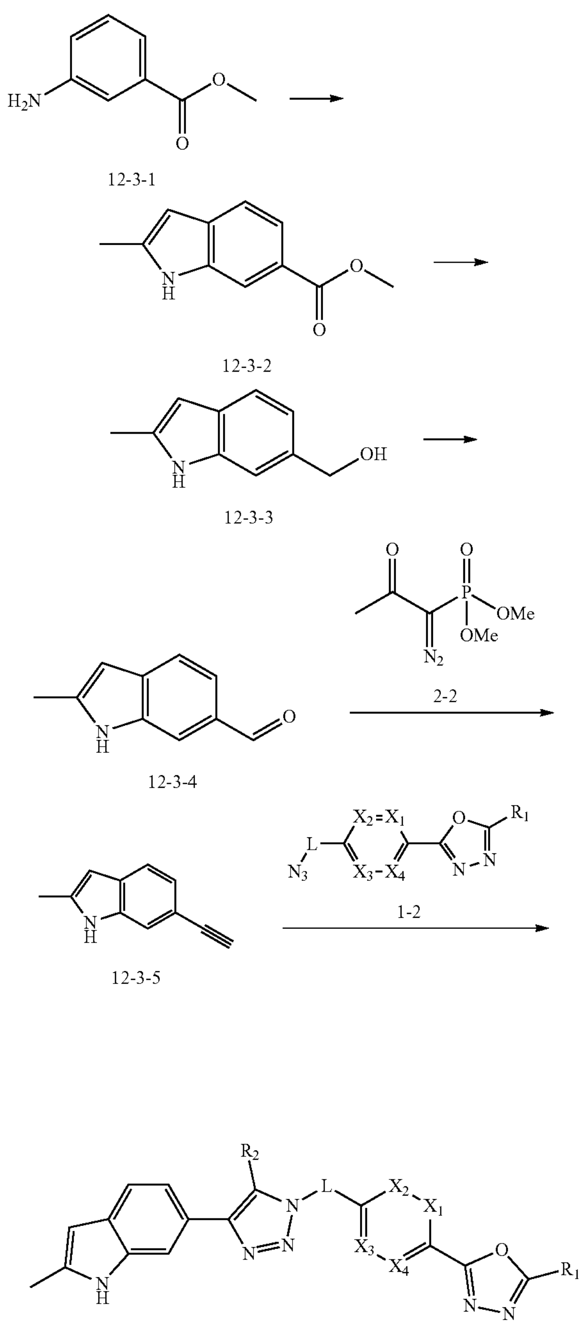

12-3-1

12-3-2

12-3-3

2-2

12-3-4

1-2

12-3-5

12-3-6

According to above reaction formula 12-3, compound 12-3-1 may be subjected to Pd(II)-catalyzed indole synthesis to prepare compound 12-3-2, and prepare compound 12-3-3 having an alcohol structure through a reduction reaction. Then, compound 12-3-4 having an aldehyde structure may be prepared through an oxidation reaction, and compound 12-3-5 having a triple bond structure may be prepared with compound 2-2, which is a phosphonate reagent. After that, compounds 4287 and 4288 may be prepared as compound 12-3-6 having a triazole structure through a click reaction with compounds 1-2, which is 1,3,4-oxadiazol.

[Reaction Formula 13]

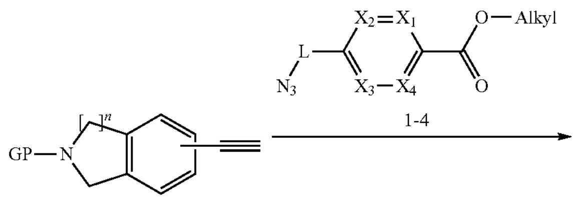

1-4

13-1

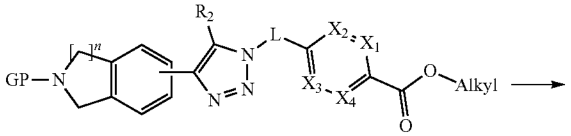

13-2

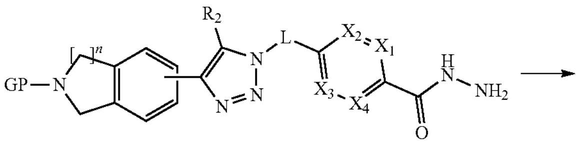

13-3

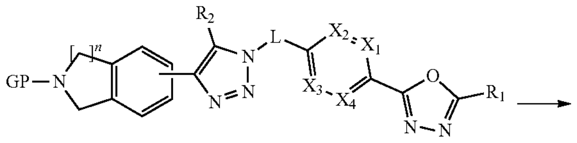

13-4

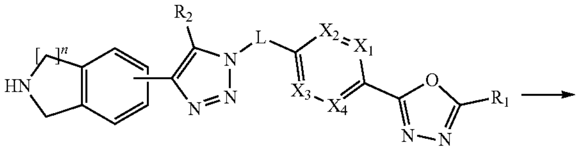

13-5

-continued

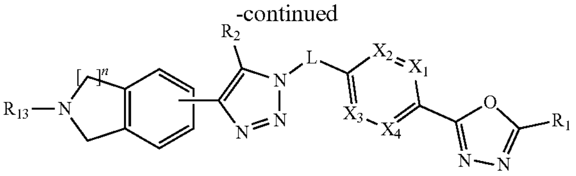

13-6

In above reaction formula 13, n may be 1 or 2, alkyl may be C1-C5 alkyl, and $R_{13}$ may be —$(CH_2)_n$-Q1-Q2-Ra (here, n is 0 or 1).

According to above reaction formula 13, compound 13-2 having a triazol structure may be prepared through a click reaction between compound 13-1 obtained through reaction formula 2 and compound 1-4, after which compound 13-3 may be prepared by using hydrazine, and then reacted with trifluoroacetic anhydride or difluoroacetic anhydride to prepare compound 13-4. After that, an amine protecting group may be removed to prepare compound 4539 as compound 13-5, and then compound 13-6 is prepared through a reductive amination reaction.

The compound prepared by above reaction formula 13 may be compounds 4051, 4052, 4053, 4054, 4055, 4209, 4210, 4211, 4212, 4213, 4358, 4359, 4360, 4361, 4362, 4363, 4364, 4365, 4366, 4367, 4513, 4515, 4516, 4517, 4518, 4519, 4529, 4530, 4531, 4532, 4533, 4534, 4535, 4536, 4537, 4538, 4540, 4541, 4542, 4543, 4595, 4596, 4597, 4598, 4599, 17458, 17460, 19002, 19004, etc.

[Reaction Formula 13-1]

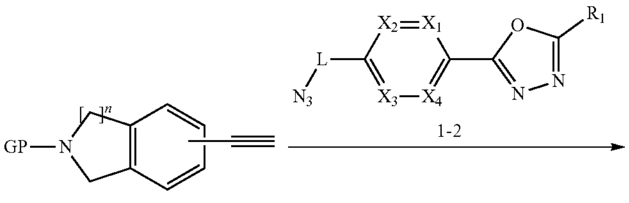

1-2

13-1

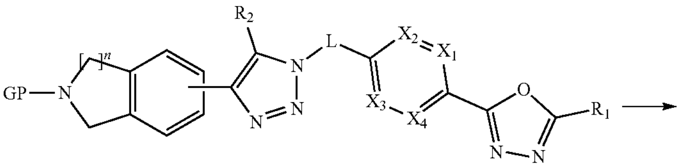

13-4

-continued

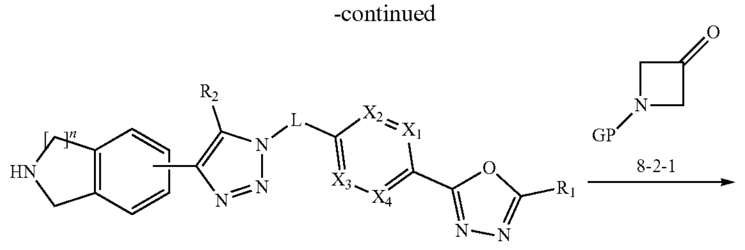

13-5

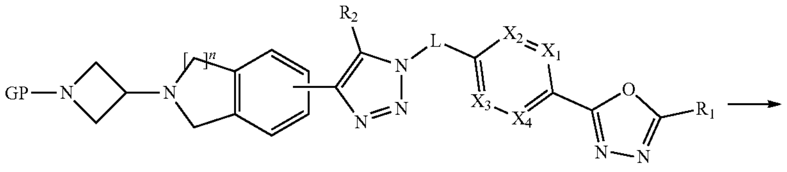

13-1-1

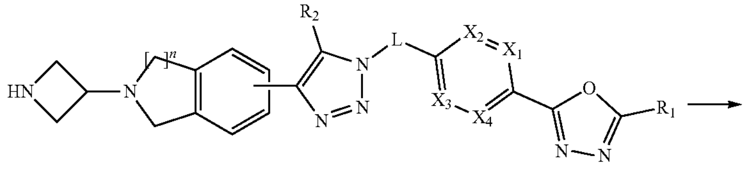

13-1-2

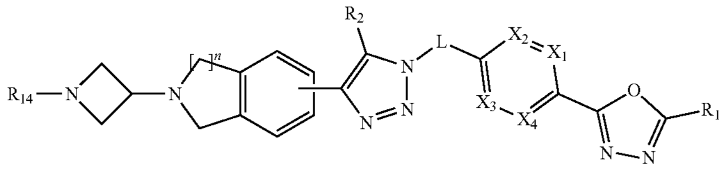

13-1-3

In above reaction formula 13-1, $R_{14}$ may be OH; halogen; C1-C5 alkyl;

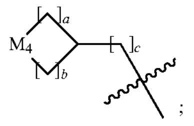

;

C1-C6 haloalkyl; —$NR_6R_7$; —C(═O)—(C1-C5 alkyl); C(═O)—O(C1-C5 alkyl); or —NH—C(═O)—O(C1-C5 alkyl).

According to above reaction formula 13-1, compound 13-4 having a triazol structure may be prepared through a click reaction between compound 13-1 obtained through reaction formula 2 and compound 1-2, after which an amine protecting group may be removed to prepare compound 13-5. After that, compound 13-1-1 may be prepared through a reductive amination reaction with compound 8-2-1 having an amine protecting group, and an amine protecting group may be removed to prepare compound 13-1-2 and then prepare compound 13-1-3 through a reductive amination reaction.

The compound prepared by above reaction formula 13-1 may be compounds 4392, 4393, 4394, 4395, etc.

[Reaction Formula 14]

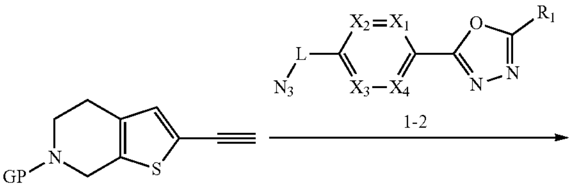

14-1

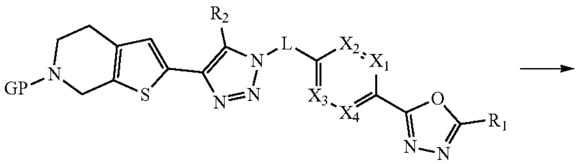

14-2

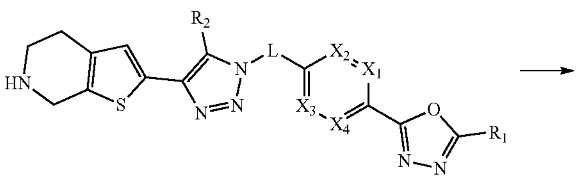

14-3

-continued

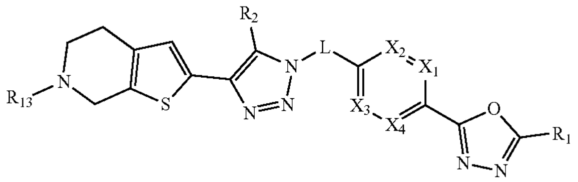

14-4

In above reaction formula 14, $R_{13}$ may be $—(CH_2)_n$-Q1-Q2-Ra (here, n is 0 or 1).

According to above reaction formula 14, compound 14-2 having a triazol structure may be prepared through a click reaction between compound 14-1 having an amine protecting group obtained through reaction formula 2-1 and compound 1-2, after which the amine protecting group may be removed to prepare compound 4499 as compound 14-3. After that, compounds 4500, 4501, etc., may be prepared as compound 14-4 through a reductive amination reaction.

[Reaction Formula 15]

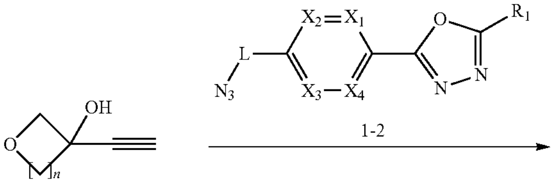

1-2

15-1

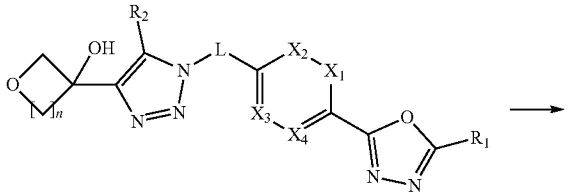

15-2

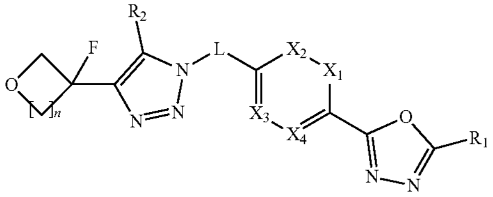

15-3

According to above reaction formula 15, compound 15-2 having a triazol structure may be prepared through a click reaction between compound 15-1 having a triple bond and compound 1-2. Compounds prepared by the above reaction formula may be 4276, 4277, 4278 and 4279. After that, the hydroxyl group of compound 15-2 may be substituted with fluoride to prepare compounds 4280, 4281, 4282, and 4283 having a structure of compound 15-3.

[Reaction Formula 16]

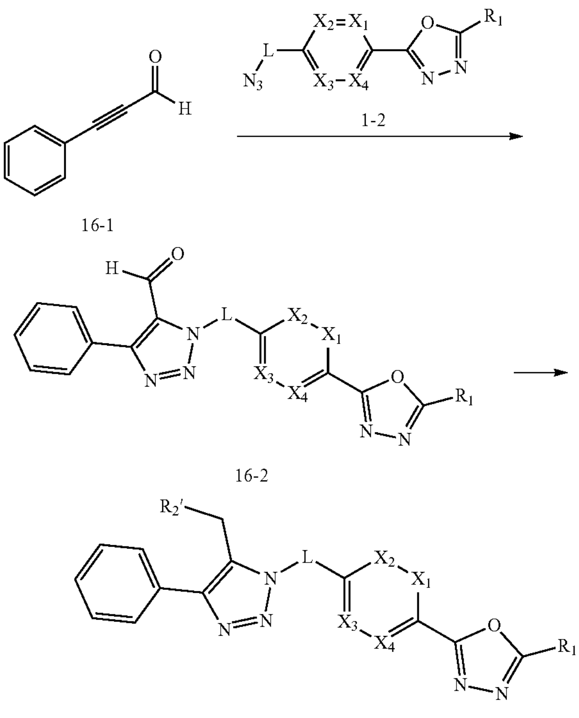

1-2

16-1

16-2

16-3

In above reaction formula 16, $R_2$' may be H, C1-C5 alkyl, OH or N(C1-C5 alkyl)$_2$.

According to above reaction formula 16, compound 16-2 having a triazol structure may be prepared through a click reaction between aldehyde compound 16-1 having a triple bond and compound 1-2, after which compound 16-3 may be prepared through a reduction reaction and a reductive amination reaction.

The compound prepared by above reaction formula 16 may be compounds 4478, 4479, 4490 and 4491.

[Reaction Formula 17]

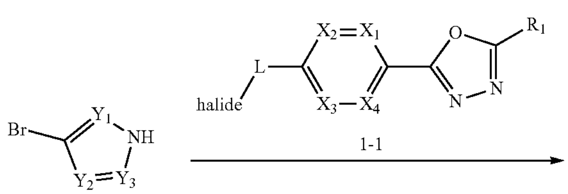

1-1

17-1

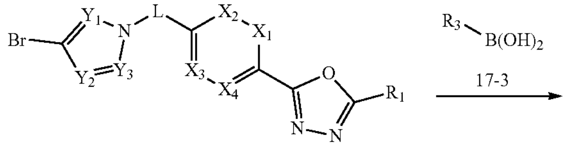

17-3

17-2

-continued

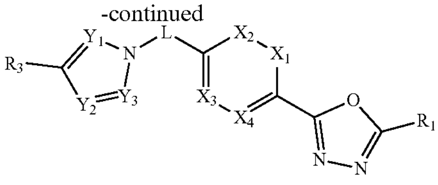

17-4

According to above reaction formula 17, compound 3949 may be prepared as compound 17-2 through a substitution reaction between compound 17-1 and compound 1-1. After that, compound 17-4 may be prepared through C—C coupling (Suzuki reaction) with compound 17-3.

The compound prepared by above reaction formula 17 may be compounds 3945, 3950, 4133, 4208, etc.

[Reaction Formula 18]

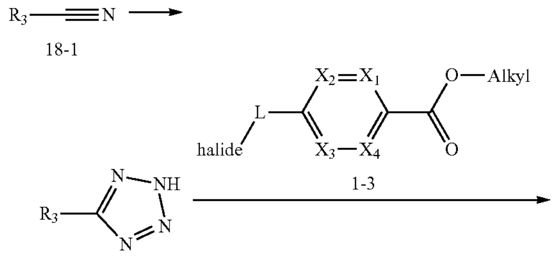

18-1

1-3

18-2

-continued

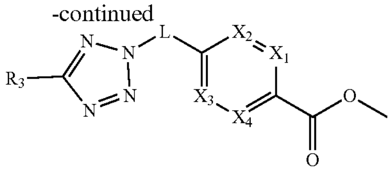

18-3

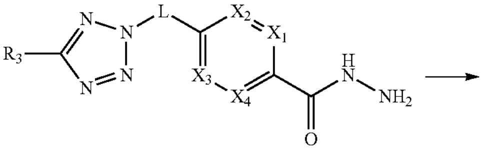

18-4

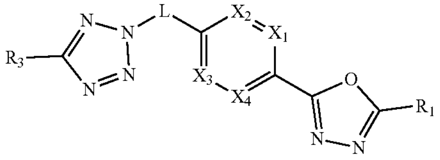

18-5

In above reaction formula 18, alkyl may be C1-C5 alkyl.

According to above reaction formula 18, compound 18-1 may be used to prepare compound 18-2 as tetrazole, and compound 18-3 may be prepared by a substitution reaction with compound 1-3 under basic conditions. After that, compound 18-4 may be prepared by using hydrazine, and then reacted with trifluoroacetic anhydride or difluoroacetic anhydride to prepare compound 18-5.

The compound prepared by above reaction formula 18 may be compounds 4232, 4233, 4234, 4235, etc.

[Reaction Formula 19]

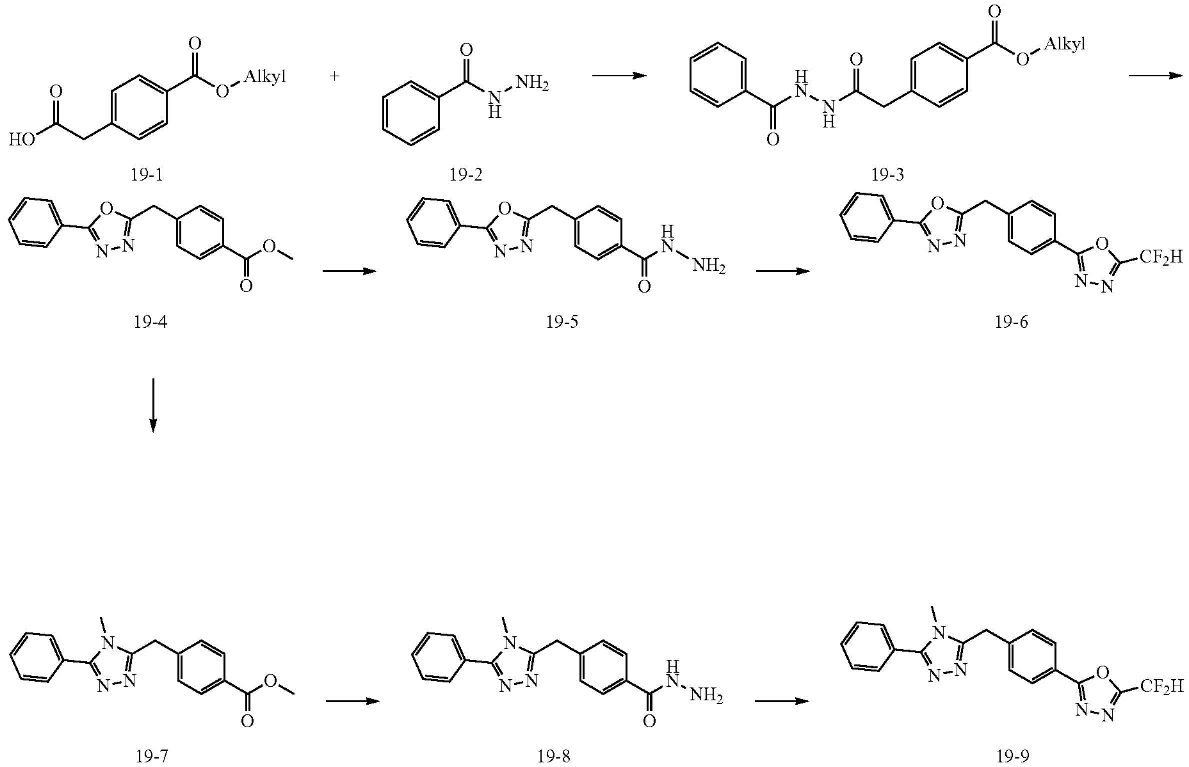

19-1 19-2 19-3

19-4 19-5 19-6

19-7 19-8 19-9

In above reaction formula 19, alkyl may be C1-C5 alkyl.

According to above reaction formula 19, compound 19-3 may be prepared through an amide bond reaction between compound 19-1 and compound 19-2, and then reacted with 1-methoxy-N-triethylammoniosulfonyl-methanimidate (Burgess reagent) to prepare compound 19-4 having an oxadiazole structure. After that, compound 19-5 may be prepared by using hydrazine, and then reacted with trifluoroacetic anhydride or difluoroacetic anhydride to prepare compound 3980 as compound 19-6.

In addition, compound 19-4 may be subjected to methylamine (2.0 M in THF) to prepare compound 19-7, after which compound 19-8 may prepared by using hydrazine, and then reacted with trifluoroacetic anhydride or difluoroacetic anhydride to prepare compound 3981 as compound 19-9.

Composition Including Compound Represented by Formula I, Use Thereof and Therapeutic Method Using the Same The present invention may provide a pharmaceutical composition including a compound represented by above formula I, stereoisomers thereof or pharmaceutically acceptable salts thereof as an effective ingredient.

In addition, the present invention may provide a pharmaceutical composition for preventing or treating histone deacetylase 6 activity-related diseases, including a compound represented by above formula I, stereoisomers thereof or pharmaceutically acceptable salts thereof as an effective ingredient.

The pharmaceutical composition of the present invention may selectively inhibit histone deacetylase 6, thereby showing a remarkable effect on preventing or treating histone deacetylase 6 activity-related diseases.

Histone deacetylase 6 activity-related diseases may include cancer, inflammatory disease, autoimmune disease, neurological or degenerative neurological disease, specifically, lung cancer, colon cancer, breast cancer, prostate cancer, liver cancer, brain cancer, ovarian cancer, gastric cancer, skin cancer, pancreatic cancer, glioma, glioblastoma carcinoma, leukemia, lymphoma, multiple myeloma, solid cancer, Wilson's disease, spinal cerebellar ataxia, prion disease, Parkinson's disease, Huntington's disease, amyotrophic lateral sclerosis, amyloidosis, Alzheimer's disease, alcoholic liver disease, spinal muscular atrophy, rheumatoid arthritis or osteoarthritis, in addition to symptoms or diseases related to abnormal functions of histone deacetylase.

An example of histone deacetylase-mediated diseases may include infectious diseases, neoplasm, endocrinopathy, nutritional and metabolic diseases, mental and behavioral disorders, neurological diseases, eye and ocular adnexal diseases, circulatory diseases, respiratory diseases, digestive troubles, skin and subcutaneous tissue diseases, musculoskeletal system and connective tissue diseases, or teratosis, deformities and chromosomal aberration.

The endocrinopathy, nutritional and metabolic disease may be Wilson's disease, amyloidosis or diabetes, the mental and behavioral disorder may be depression or Rett syndrome, and the neurological disease may be central nervous system atrophy, neurodegenerative disease, movement disorder, neuropathy, motor neuron disease or central nervous system demyelinating disease, the eye and ocular adnexal disease may be uveitis, the skin and subcutaneous tissue disease may be psoriasis, the musculoskeletal system and connective tissue disease may be rheumatoid arthritis, osteoarthritis or systemic lupus erythematosus, the teratosis, deformities and chromosomal aberration may be autosomal dominant polycystic kidney disease, the infectious disease may be prion disease, the neoplasm may be benign tumor or malignant tumor, the circulatory disease may be atrial fibrillation or stroke, the respiratory disease may be asthma, and the digestive disease may be alcoholic liver disease, inflammatory bowel disease, Crohn's disease or ulcerative bowel disease.

Said pharmaceutically acceptable salts are the same as described in the pharmaceutically acceptable salts of the compound represented by the formula I of the present invention.

For its administration, the pharmaceutical composition of the present invention may further contain at least one type of a pharmaceutically acceptable carrier, in addition to the compound represented by above formula I, stereoisomers thereof or pharmaceutically acceptable salts thereof. In this case, the pharmaceutically acceptable carrier to be used may include saline solution, sterilized water, Ringer's solution, buffered saline, dextrose solution, maltodextrin solution, glycerol, ethanol and a mixture of at least one ingredient thereof, and with the addition of other conventional additives such as antioxidants, buffer solutions, bacteriostatic agents, etc., if needed. Also, diluents, dispersing agents, surfactants, binders and lubricants may be added to be formulated into injectable dosage forms such as aqueous solutions, suspensions, emulsions, etc., pills, capsules, granules or tablets. Thus, the composition of the present invention may be patches, liquid medicines, pills, capsules, granules, tablets, suppositories, etc. The preparations may be prepared according to a conventional method used for formulation in the art or a method disclosed in Remington's Pharmaceutical Science (latest edition), Merck Publishing Company, Easton PA, and the composition may be formulated into various preparations depending on each disease or component.

The composition of the present invention may be orally or parenterally administered (for example, applied intravenously, hypodermically, intraperitoneally or locally) according to a targeted method, in which a dosage thereof varies in a range thereof depending on a patient's weight, age, gender, health condition and diet, an administration time, an administration method, an excretion rate, a severity of a disease and the like. A daily dosage of the compound represented by the formula I of the present invention may be about 1 to 1000 mg/kg, preferably 5 to 100 mg/kg, and may be administered at one time a day or several times a day by dividing the daily dosage of the compound.

Said pharmaceutical composition of the present invention may further contain at least one effective component, which shows the same or similar medicinal effect, in addition to the compound represented by above formula I, stereoisomers thereof or pharmaceutically acceptable salts thereof.

The present invention may provide a method for preventing or treating histone deacetylase 6 activity-related diseases, including a step of administering a therapeutically effective amount of the compound represented by above formula I, stereoisomers thereof or pharmaceutically acceptable salts thereof.

As used herein, the term "therapeutically effective amount" may refer to an amount of the compound represented by above formula I, which is effective in preventing or treating histone deacetylase 6 activity-related diseases.

In addition, the present invention may provide a method for selectively inhibiting HDAC6 by administering the compound represented by above formula I, stereoisomers thereof or pharmaceutically acceptable salts thereof into mammals including humans.

The method for preventing or treating histone deacetylase 6 activity-related diseases according to the present invention may include not only dealing with the diseases themselves before expression of their symptoms, but also inhibiting or avoiding such symptoms by administering the compound represented by above formula I. In managing the disease, a preventive or therapeutic dose of a certain active component may vary depending on a nature and severity of the disease or condition and a route of administering the active component. A dose and a frequency thereof may vary depending on an individual patient's age, weight and reactions. A suitable dose and usage may be easily selected by those skilled in the art, naturally considering such factors. In addition, the method for preventing or treating histone deacetylase 6 activity-related diseases of the present invention may further include administering a therapeutically effective amount of an additional active agent, which is helpful in treating the diseases, along with the compound represented by above formula I, in which the additional active agent may show a synergy effect or an adjuvant effect together with the compound of above formula I.

The present invention may be also intended to provide a use of the compound represented by above formula I, stereoisomers thereof or pharmaceutically acceptable salts thereof in preparing a drug for treating histone deacetylase 6 activity-related diseases. The compound represented by above formula I for preparing a drug may be combined with an acceptable adjuvant, diluent, carrier, etc., and may be prepared into a complex agent together with other active agents, thus having a synergy action of active components.

Matters mentioned in the use, composition and therapeutic method of the present invention are equally applied, if not contradictory to each other.

Advantageous Effects

According to the present invention, the compound represented by above formula I, stereoisomers thereof or pharmaceutically acceptable salts thereof may selectively inhibit HDAC6, thus having a remarkably excellent effect of preventing or treating histone deacetylase 6 activity-related diseases.

MODE FOR INVENTION

Hereinafter, the present invention will be described in detail through preferred Examples for better understanding of the present invention. However, the following Examples are provided only for the purpose of illustrating the present invention, and thus the present invention is not limited thereto.

The reagents and solvents mentioned below were purchased from Sigma-Aldrich, TCI, unless otherwise specified, and Waters e2695 was used for HPLC, and Merck (230-400 mesh) was used for silica gel for column chromatography. $^{1}H$ NMR data was measured by using Bruker 400 MHz, and Mass Spectrum was Agilent 1100 series.

Example 1: Synthesis of compound 3657, 2-(difluoromethyl)-5-(4-((4-phenyl-1H-1,2,3-triazol-1-yl)methyl)phenyl)-1,3,4-oxadiazole

[Step 1] Synthesis of 2-(4-(azidomethyl)phenyl)-5-(difluoromethyl)-1,3,4-oxadiazole

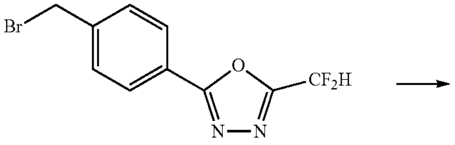

-continued

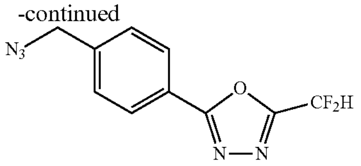

2-(4-(Bromomethyl)phenyl)-5-(difluoromethyl)-1,3,4-oxadiazole (1.500 g, 5.189 mmol) and sodium azide (0.405 g, 6.227 mmol) were dissolved in N,N-dimethylformamide (15 mL) at room temperature, after which the resulting solution was stirred at 40 °C for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(4-(azidomethyl)phenyl)-5-(difluoromethyl)-1,3,4-oxadiazole (0.950 g, 72.9%) in a colorless oil form.

[Step 2] Synthesis of Compound 3657

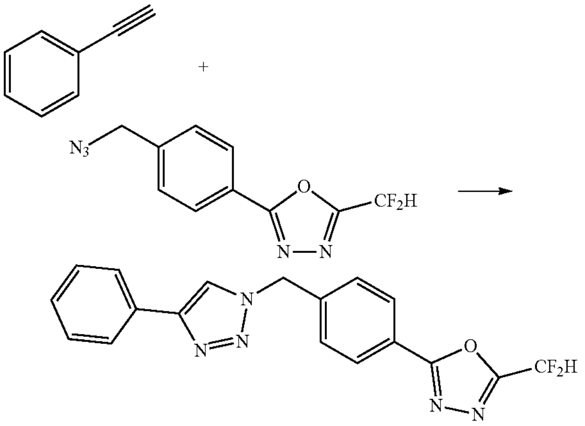

The 2-(4-(azidomethyl)phenyl)-5-(difluoromethyl)-1,3,4-oxadiazole (0.080 g, 0.318 mmol) prepared in step 1 was dissolved in tert-butanol (1 mL)/water (1 mL) at room temperature, after which ethynylbenzene (0.035 mL, 0.318 mmol) was added to the resulting solution and stirred at the same temperature. Sodium ascorbate (1.00 M solution, 0.032 mL, 0.032 mmol) and copper(II) sulfate pentahydrate (0.001 g, 0.003 mmol) were added to the reaction mixture and further stirred at the same temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=10 to 50%) and concentrated to obtain 2-(difluoromethyl)-5-(4-((4-phenyl-1H-1,2,3-triazol-1-yl)methyl)phenyl)-1,3,4-oxadiazole (0.070 g, 62.2%) in a white solid form.

$^{1}H$ NMR (700 MHz, $CD_3OD$) δ 8.44 (s, 1H), 8.19-8.15 (m, 2H), 7.86-7.82 (m, 2H), 7.64-7.60 (m, 2H), 7.48-7.42 (m, 2H), 7.39-7.34 (m, 1H), 7.23 (t, J=51.6 Hz, 1H), 5.80 (s, 2H); LRMS (ES) m/z 354.2 ($M^{+}$+1).

Example 2: Synthesis of compound 3658, 2-(difluoromethyl)-5-(3-fluoro-4-((4-phenyl-1H-1,2,3-triazol-1-yl)methyl)phenyl)-1,3,4-oxadiazole

[Step 1] Synthesis of 2-(4-(azidomethyl)fluorophenyl)-5-(difluoromethyl)-1,3,4-oxadiazole

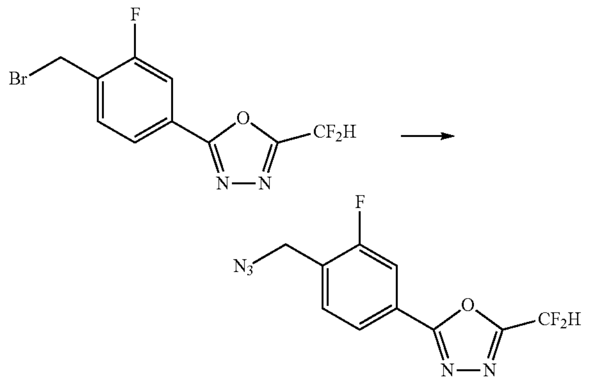

2-(4-(bromomethyl)-3-fluorophenyl)-5-(difluoromethyl)-1,3,4-oxadiazole (1.500 g, 4.885 mmol) and sodium azide (0.381 g, 5.862 mmol) were dissolved in N,N-dimethylformamide (15 mL) at room temperature, after which the resulting solution was stirred at 40 °C for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(4-(azidomethyl)-3-fluorophenyl)-5-(difluoromethyl)-1,3,4-oxadiazole (0.930 g, 70.7%) in a colorless oil form.

[Step 2] Synthesis of Compound 3658

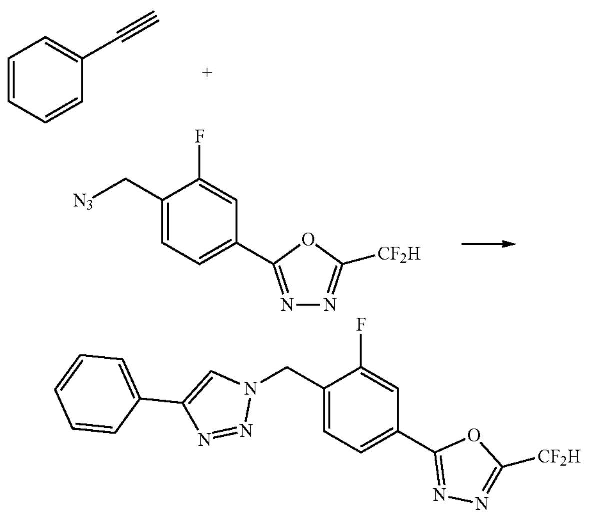

The 2-(4-(azidomethyl)-3-fluorophenyl)-5-(difluoromethyl)-1,3,4-oxadiazole (0.080 g, 0.297 mmol) prepared in step 1 was dissolved in tert-butanol (1 mL)/water (1 mL) at room temperature, after which ethynylbenzene (0.033 mL, 0.297 mmol) was added to the resulting solution and stirred at the same temperature. Sodium ascorbate (1.00 M solution, 0.030 mL, 0.030 mmol) and copper(II) sulfate pentahydrate (0.001 g, 0.003 mmol) were added to the reaction mixture and further stirred at the same temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=10 to 50%) and concentrated to obtain 2-(difluoromethyl)-5-(3-fluoro-4-((4-phenyl-1H-1,2,3-triazol-1-yl)methyl)phenyl)-1,3,4-oxadiazole (0.065 g, 58.9%) in a white solid form.

$^1H$ NMR (700 MHz, $CD_3OD$) δ 8.45 (s, 1H), 8.00 (dd, J=8.0, 1.7 Hz, 1H), 7.97 (dd, J=10.1, 1.7 Hz, 1H), 7.88-7.82 (m, 2H), 7.61 (t, J=7.7 Hz, 1H), 7.48-7.43 (m, 2H), 7.37 (ddt, J=7.9, 6.9, 1.3 Hz, 2H), 7.24 (t, J=51.6 Hz, 1H), 5.86 (s, 2H); LRMS (ES) m/z 372.3 ($M^+$+1).

Example 16: Synthesis of compound 3736, 2-(difluoromethyl)-5-(6-((4-phenyl-1H-1,2,3-triazol-1-yl)methyl)pyridin-3-yl)-1,3,4-oxadiazole

[Step 1] Synthesis of 2-(6-(azidomethyl)pyridin-3-yl)-5-(difluoromethyl)-1,3,4-oxadiazole

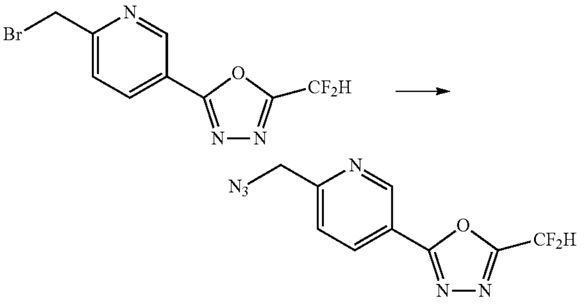

2-(6-(bromomethyl)pyridin-3-yl)-5-(difluoromethyl)-1,3,4-oxadiazole (1.000 g, 3.447 mmol) was dissolved in N,N-dimethylformamide (10 mL) at room temperature, after which sodium azide (0.224 g, 3.447 mmol) was added to the resulting solution and stirred at 40 °C for 2 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 50%) and concentrated to obtain 2-(6-(azidomethyl)pyridin-3-yl)-5-(difluoromethyl)-1,3,4-oxadiazole (0.800 g, 92.0%) in a yellow solid form.

[Step 2] Synthesis of Compound 3736

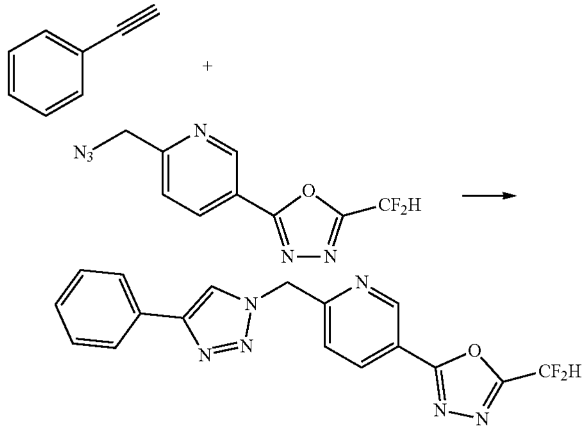

The 2-(6-(azidomethyl)pyridin-3-yl)-5-(difluoromethyl)-1,3,4-oxadiazole (0.050 g, 0.198 mmol) prepared in step 1 was dissolved in tert-butanol (1 mL)/water (1 mL) at room temperature, after which ethynylbenzene (0.022 mL, 0.198 mmol) was added to the resulting solution and stirred at the same temperature. Sodium ascorbate (1.00 M solution, 0.020 mL, 0.020 mmol) and copper(II) sulfate pentahydrate (0.50 M solution, 0.004 mL, 0.002 mmol) were added to the reaction mixture and further stirred at the same temperature for 18 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(6-((4-phenyl-1H-1,2,3-triazol-1-yl)methyl)pyridin-3-yl)-1,3,4-oxadiazole (0.035 g, 49.8%) in a white solid form.

$^1H$ NMR (400 MHz, $CDCl_3$) δ 9.31 (d, J=1.8 Hz, 1H), 8.41 (dt, J=8.1, 1.8 Hz, 1H), 8.03 (d, J=1.4 Hz, 1H), 7.81 (dt, J=8.1, 1.3 Hz, 2H), 7.48-7.35 (m, 4H), 7.33 (d, J=8.2 Hz, 1H), 6.95 (t, J=51.6, 1.4 Hz, 1H), 5.81 (d, J=1.5 Hz, 2H); LRMS (ES) m/z 356.1 ($M^+$+1).

Example 21: Synthesis of compound 3774, 3-(1-(4-(5-(difluoromethyl)-1,3,4-oxadiazol-2-yl)-2-fluorobenzyl)-1H-1,2,3-triazol-4-yl)-N,N-dimethylaniline

[Step 1] Synthesis of 3-(1-(4-(5-(difluoromethyl)-1,3,4-oxadiazol-2-yl)-2-fluorobenzyl)-1H-1,2,3-triazol-4-yl)aniline

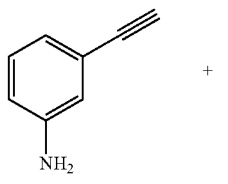

-continued

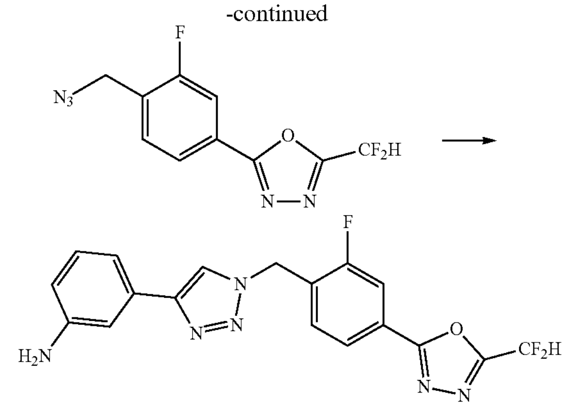

The 2-(4-(azidomethyl)-3-fluorophenyl)-5-(difluoromethyl)-1,3,4-oxadiazole (0.200 g, 0.743 mmol) prepared in step 1 of example 2 was dissolved in tert-butanol (1 mL)/water (1 mL) at room temperature, after which 3-ethynylaniline (0.087 g, 0.743 mmol) was added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 40%) and concentrated to obtain 3-(1-(4-(5-(difluoromethyl)-1,3,4-oxadiazol-2-yl)-2-fluorobenzyl)-1H-1,2,3-triazol-4-yl)aniline (0.198 g, 69.0%) in a beige solid form.

[Step 2] Synthesis of Compound 3774

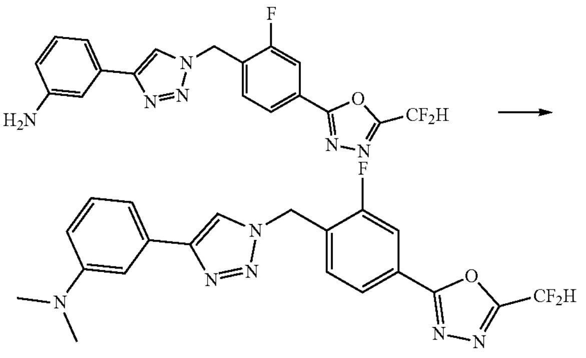

The 3-(1-(4-(5-(difluoromethyl)-1,3,4-oxadiazol-2-yl)-2-fluorobenzyl)-1H-1,2,3-triazol-4-yl)aniline (0.030 g, 0.078 mmol) prepared in step 1 and formaldehyde (37.00%, 0.063 g, 0.777 mmol) were dissolved in acetonitrile (1 mL)/acetic acid (0.01 mL), after which the resulting solution was stirred at room temperature for 0.5 hours, and then sodium cyanoborohydride (0.015 g, 0.233 mmol) was added thereto and further stirred at the same temperature for 1 hour. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 3-(1-(4-(5-(difluoromethyl)-1,3,4-oxadiazol-2-yl)-2-fluorobenzyl)-1H-1,2,3-triazol-4-yl)-N,N-dimethylaniline (0.020 g, 62.2%) in a light yellow oil form.

$^1$H NMR (400 MHz, $CD_3OD$) δ 8.40 (s, 1H), 8.02-7.92 (m, 2H), 7.59 (t, J=7.7 Hz, 1H), 7.30-7.24 (m, 2H), 7.24 (t, J=51.6 Hz, 1H), 7.13 (dt, J=7.6, 1.2 Hz, 1H), 6.79 (ddd, J=8.4, 2.7, 0.9 Hz, 1H), 5.84 (s, 2H), 3.00 (s, 6H); LRMS (ES) m/z 415.3 ($M^+$+1).

The compounds of table 3 were synthesized according to substantially the same process as described above in the synthesis of compound 3774 with an exception of using 3-(1-(4-(5-(difluoromethyl)-1,3,4-oxadiazol-2-yl)-2-fluorobenzyl)-1H-1,2,3-triazol-4-yl)aniline and the reactant of table 2.

TABLE 2

| Example | Compound No. | Reactant | Yield (%) |
|---|---|---|---|
| 232 | 4330 | Cyclohexanone | 69 |
| 233 | 4331 | Tetrahydro-4H-pyran-4-one | 67 |
| 234 | 4332 | Oxetan-3-one | 52 |

TABLE 3

| Example | Compound No. | Compound Name, $^1$H-NMR, MS (ESI) |
|---|---|---|
| 232 | 4330 | N-cyclohexyl-3-(1-(4-(5-(difluoromethyl)-1,3,4-oxadiazol-2-yl)-2-fluorobenzyl)-1H-1,2,3-triazol-4-yl)aniline $^1$H NMR (400 MHZ, $CD_3OD$) δ 8.34 (s, 1H), 8.02-7.92 (m, 2H), 7.58 (t, J = 7.7 Hz, 1H), 7.38-7.09 (m, 3H), 7.03 (dt, J = 7.7, 1.2 Hz, 1H), 6.64 (ddd, J = 8.2, 2.5, 1.0 Hz, 1H), 5.83 (s, 2H), 2.07 (d, J = 12.6 Hz, 2H), 1.81 (dt, J = 13.3, 3.7 Hz, 2H), 1.74-1.64 (m, 1H), 1.51-1.36 (m, 2H), 1.34-1.14 (m, 4H); LRMS (ESI) m/z 469.5 ($M^+$ + H). |
| 233 | 4331 | N-(3-(1-(4-(5-(difluoromethyl)-1,3,4-oxadiazol-2-yl)-2-fluorobenzyl)-1H-1,2,3-triazol-4-yl)phenyl)tetrahydro-2H-pyran-4-amine $^1$H NMR (400 MHZ, $CD_3OD$) δ 8.36 (s, 1H), 8.02-7.92 (m, 2H), 7.58 (t, J = 7.7 Hz, 1H), 7.24 (t, J = 51.6 Hz, 1H), 7.20-7.14 (m, 2H), 7.05 (dt, J = 7.8,1.1 Hz, 1H), 6.68 (ddd, J = 8.3, 2.4, 1.0 Hz, 1H), 5.84 (s, 2H), 3.99 (dt, J = 11.9, 3.5 Hz, 2H), 3.64-3.52 (m, 3H), 2.07-1.99 (m, 2H), 1.58-1.43 (m, 2H); LRMS (ESI) m/z 471.5 ($M^+$ + H). |
| 234 | 4332 | N-(3-(1-(4-(5-(difluoromethyl)-1,3,4-oxadiazol-2-yl)-2-fluorobenzyl)-1H-1,2,3-triazol-4-yl)phenyl)oxetan-3-amine $^1$H NMR (400 MHZ, $CD_3OD$) δ 8.37 (s, 1H), 8.02-7.92 (m, 2H), 7.59 (t, J = 7.6 Hz, 1H), 7.37-7.10 (m, 3H), 7.01 (t, J = 2.0 Hz, 1H), 6.56 (ddd, J = 8.1, 2.4, 1.0 Hz, 1H), 5.84 (s, 2H), 5.03 (t, J = 6.6 Hz, 2H), 4.70 (p, J = 6.5 Hz, 1H), 4.58 (t, J = 6.1 Hz, 2H); LRMS (ESI) m/z 443.5 ($M^+$ + H). |

Example 22: Synthesis of compound 3775, N-(3-(1-(4-(5-(difluoromethyl)-1,3,4-oxadiazol-2-yl)-2-fluorobenzyl)-1H-1,2,3-triazol-4-yl)phenyl)acetamide

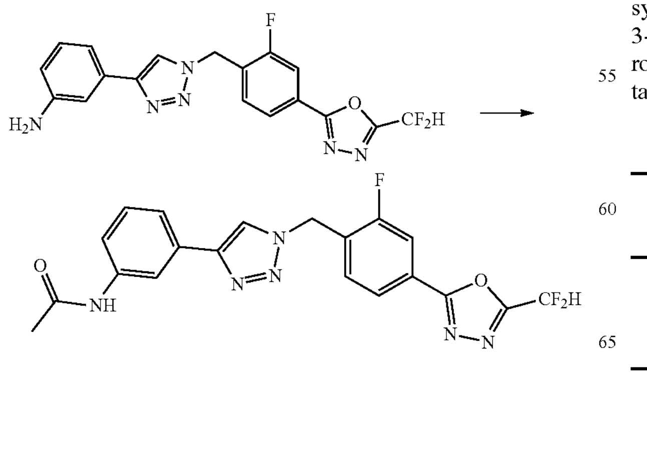

The 3-(1-(4-(5-(difluoromethyl)-1,3,4-oxadiazol-2-yl)-2-fluorobenzyl)-1H-1,2,3-triazol-4-yl)aniline (0.030 g, 0.078 mmol) prepared in step 1 of example 21 and triethylamine (0.013 mL, 0.093 mmol) were dissolved in dichloromethane (1 mL) at room temperature, after which acetyl chloride (0.006 mL, 0.078 mmol) was added into the resulting solution and stirred at the same temperature for 1 hour. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain N-(3-(1-(4-(5-(difluoromethyl)-1,3,4-oxadiazol-2-yl)-2-fluorobenzyl)-1H-1,2,3-triazol-4-yl)phenyl)acetamide (0.022 g, 66.1%) in a white solid form.

$^1$H NMR (400 MHz, $CD_3OD$) δ 8.42 (s, 1H), 8.05 (s, 1H), 8.02-7.93 (m, 2H), 7.58 (dt, J=17.6, 8.6 Hz, 3H), 7.40 (t, J=7.9 Hz, 1H), 7.24 (t, J=51.6 Hz, 1H), 5.88-5.84 (m, 2H), 2.16 (s, 3H); LRMS (ES) m/z 429.2 ($M^+$+1).

The compounds of table 5 were synthesized according to substantially the same process as described above in the synthesis of compound 3775 with an exception of using 3-(1-(4-(5-(difluoromethyl)-1,3,4-oxadiazol-2-yl)-2-fluorobenzyl)-1H-1,2,3-triazol-4-yl)aniline and the reactant of table 4.

TABLE 4

| Example | Compound No. | Reactant | Yield (%) |
|---|---|---|---|
| 23 | 3776 | Methylchloroformate | 66 |
| 24 | 3777 | Trifluoroacetic anhydride | 72 |
| 235 | 4333 | Trimethylacetyl chloride | 82 |

TABLE 5

| Example | Compound No. | Compound Name, $^{1}$H-NMR, MS (ESI) |
|---|---|---|
| 23 | 3776 | Methyl (3-(1-(4-(5-(difluoromethyl)-1,3,4-oxadiazol-2-yl)-2-fluorobenzyl)-1H-1,2,3-triazol-4-yl)phenyl)carbamate $^{1}$H NMR (400 MHZ, $CD_3OD$) δ 8.41 (s, 1H), 7.98 (ddd, J = 11.7, 9.0, 1.7 Hz, 2H), 7.91 (d, J = 2.0 Hz, 1H), 7.60 (t, J = 7.7 Hz, 1H), 7.51 (dt, J = 7.6,1.4 Hz,1H), 7.45 (d, J = 8.3 Hz, 1H), 7.39-7.36 (m, 1H), 7.36-7.09 (m, 1H), 5.86 (s, 2H), 3.77 (s, 3H); LRMS (ES) m/z 445,2 ($M^+$ + 1). |
| 24 | 3777 | N-(3-(1-(4-(5-(difluoromethyl)-1,3,4-oxadiazol-2-yl)-2-fluorobenzyl)-1H-1,2,3-triazol-4-yl)phenyl)-2,2,2-trifluoroacetamide $^{1}$H NMR (400 MHZ, $CD_3OD$) δ 8.47 (s, 1H), 8.14 (t, J = 1.9 Hz, 1H), 8.03-7.93 (m, 2H), 7.74-7.63 (m, 2H), 7.61 (t, J = 7.6 Hz, 1H), 7.49 (t, J = 7.9 Hz, 1H), 7.24 (t, J = 51.6 Hz, 1H), 5.87 (s, 2H); LRMS (ES) m/z 483.2 ($M^+$ + 1). |
| 235 | 4333 | N-(4-(1-(4-(5-(difluoromethyl)-1,3,4-oxadiazol-2-yl)-2-fluorobenzyl)-1H-1,2,3-triazol-4-yl)phenyl)pivalamide $^{1}$H NMR (400 MHZ, $CD_3OD$) δ 8.37 (s, 1H), 8.41 (s, 1H), 8.04-7.92 (m, 3H), 7.65-7.58 (m, 2H), 7.54 (ddd, J = 8.1, 2.1, 1.1 Hz, 1H), 7.44-7.11 (m, 2H), 5.85 (s, 2H), 1.33 (s, 9H); LRMS (ESI) m/z 471.5 ($M^+$ + H). |

Example 25: Synthesis of compound 3805, tert-butyl 4-(1-((5-(5-(difluoromethyl)-1,3,4-oxadiazol-2-yl)pyridin-2-yl)methyl)-1H-1,2,3-triazol-4-yl)piperidin-1-carboxylate

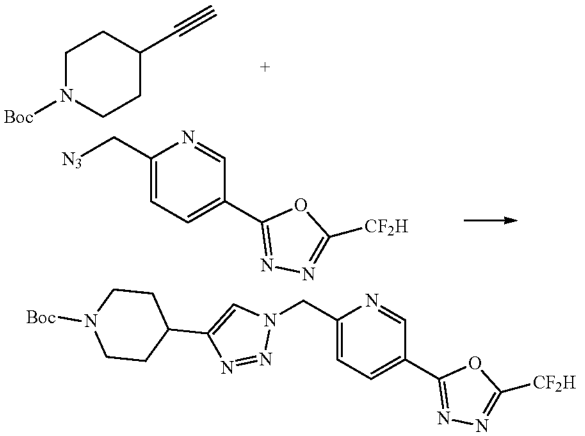

The 2-(6-(azidomethyl)pyridin-3-yl)-5-(difluoromethyl)-1,3,4-oxadiazole (0.800 g, 3.172 mmol) prepared in step 1 of example 16, tert-butyl 4-ethynylpiperidin-1-carboxylate (0.730 g, 3.490 mmol), sodium ascorbate (1.00 M solution in $H_2O$, 0.317 mL, 0.317 mmol), and copper(II) sulfate pentahydrate (0.50 M solution in $H_2O$, 0.063 mL, 0.032 mmol) were dissolved in tert-butanol (10 mL)/water (10 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 70%) and concentrated to obtain tert-butyl 4-(1-((5-(5-(difluoromethyl)-1,3,4-oxadiazol-2-yl)pyridin-2-yl)methyl)-1H-1,2,3-triazol-4-yl)piperidin-1-carboxylate (1.100 g, 75.1%) in a white solid form.

$^{1}$H NMR (400 MHz, $CDCl_3$) δ 9.33 (dd, J=2.2, 0.8 Hz, 1H), 8.41 (dd, J=8.2, 2.2 Hz, 1H), 7.49 (d, J=0.4 Hz, 1H), 7.37 (dd, J=8.2, 0.6 Hz, 1H), 7.09 (s, 0.2H), 6.96 (s, 0.5H), 6.83 (s, 0.3H), 5.75 (s, 2H), 4.16 (s, 2H), 3.09-2.75 (m, 3H), 2.05 (dd, J=12.9, 2.3 Hz, 2H), 1.73-1.54 (m, 2H), 1.48 (s, 9H); LRMS (ES) m/z 462.22 ($M^+$+1).

Example 26: Synthesis of compound 3806, 2-(difluoromethyl)-5-(6-((4-(1-methylpiperidin-4-yl)-1H-1,2,3-triazol-1-yl)methyl)pyridin-3-yl)-1,3,4-oxadiazole

[Step 1] Synthesis of 2-(difluoromethyl)-5-(6-((4-(piperidin-4-yl)-1H-1,2,3-triazol-1-yl)methyl)pyridin-3-yl)-1,3,4-oxadiazole

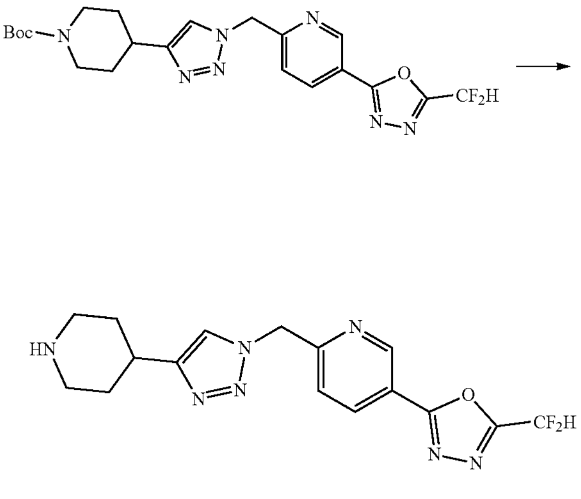 [SMILES: CC(C)(C)OC(=O)N1CCC(c2cn(Cc3ccc(-c4nnc(C(F)F)o4)cn3)nn2)CC1 ; FC(F)c1nnc(-c2ccc(Cn3cc(C4CCNCC4)nn3)nc2)o1]

The tert-butyl 4-(1-((5-(5-(difluoromethyl)-1,3,4-oxadiazol-2-yl)pyridin-2-yl)methyl)-1H-1,2,3-triazol-4-yl)piperidin-1-carboxylate (1.100 g, 2.384 mmol) prepared in example 25 and trifluoroacetic acid (0.548 mL, 7.151 mmol) were dissolved in dichloromethane (80 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(6-((4-(piperidin-4-yl)-1H-1,2,3-triazol-1-yl)methyl)pyridin-3-yl)-1,3,4-oxadiazole (0.700 g, 81.3%, yellow oil).

[Step 2] Synthesis of Compound 3806

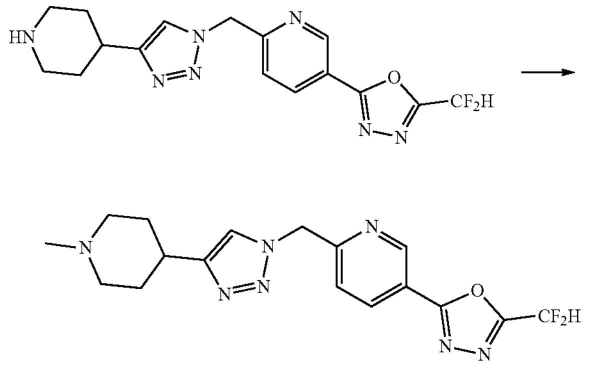

The 2-(difluoromethyl)-5-(6-((4-(piperidin-4-yl)-1H-1,2,3-triazol-1-yl)methyl)pyridin-3-yl)-1,3,4-oxadiazole (0.050 g, 0.138 mmol) prepared in step 1, N,N-diisopropylethylamine (0.048 mL, 0.277 mmol) and formaldehyde (0.008 g, 0.277 mmol) were dissolved in dichloromethane (20 mL), after which the resulting solution was stirred at room temperature for 30 minutes, and then sodium triacetoxyborohydride (0.059 g, 0.277 mmol) was added thereto and further stirred at the same temperature for 12 hours. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(6-((4-(1-methylpiperidin-4-yl)-1H-1,2,3-triazol-1-yl)methyl)pyridin-3-yl)-1,3,4-oxadiazole (0.029 g, 55.8%) in a white solid form.

$^1$H NMR (400 MHz, $CDCl_3$) δ 9.33 (d, J=1.5 Hz, 1H), 8.40 (dd, J=8.2, 2.2 Hz, 1H), 7.50 (s, 1H), 7.35 (d, J=8.2 Hz, 1H), 7.09 (s, 0.2H), 6.96 (s, 0.5H), 6.83 (s, 0.3H), 5.75 (s, 2H), 3.02 (d, J=11.6 Hz, 2H), 2.85 (t, J=11.5 Hz, 1H), 2.39 (s, 3H), 2.29-2.01 (m, 4H), 1.95-1.65 (m, 2H); LRMS (ES) m/z 376.2 ($M^+$+1).

The compounds of table 7 were synthesized according to substantially the same process as described above in the synthesis of compound 3806 with an exception of using 2-(difluoromethyl)-5-(6-((4-(piperidin-4-yl)-1H-1,2,3-triazol-1-yl)methyl)pyridin-3-yl)-1,3,4-oxadiazole and the reactant of table 6.

TABLE 6

| Example | Compound No. | Reactant | Yield (%) |
|---|---|---|---|
| 27 | 3807 | Acetaldehyde | 55 |
| 28 | 3808 | Propan-2-one | 66 |
| 29 | 3809 | Oxetan-3-one | 58 |
| 30 | 3810 | 2-oxaspiro[3.3]heptan-6-one | 61 |

TABLE 7

| Example | Compound No. | Compound Name, $^1$H-NMR, MS (ESI) |
|---|---|---|
| 27 | 3807 | 2-(difluoromethyl)-5-(6-((4-(1-ethylpiperidin-4-yl)-1H-1,2,3-triazol-1-yl)methyl)pyridin-3-yl)-1,3,4-oxadiazole<br>$^1$H NMR (400 MHZ, $CDCl_3$) δ 9.33 (d, J = 1.5 Hz, 1H), 8.40 (dd, J = 8.2, 2.2 Hz, 1H), 7.60-7.45 (m, 1H), 7.35 (d, J = 8.1 Hz, 1H), 7.09 (s, 0.2H), 6.96 (s, 0.5H), 6.83 (s, 0.3H), 5.75 (s, 2H), 3.14 (d, J = 11.4 Hz, 2H), 2.91 (s, 1H), 2.57 (s, 2H), 2.16 (d, J = 12.4 Hz, 4H), 1.87 (d, J = 11.7 Hz, 2H), 1.20 (t, J = 7.1 Hz, 3H); LRMS (ES) m/z 390.4 ($M^+$ + 1). |
| 8 | 3808 | 2-(difluoromethyl)-5-(6-((4-(1-isopropylpiperidin-4-yl)-1H-1,2,3-triazol-1-yl)methyl)pyridin-3-yl)-1,3,4-oxadiazole<br>$^1$H NMR (400 MHZ, $CDCl_3$) δ 9.33 (d, J = 1.5 Hz, 1H), 8.40 (dd, J = 8.2, 2.2 Hz, 1H), 7.51 (s, 1H), 7.34 (d, J = 8.1 Hz, 1H), 7.09 (s, 0.2H), 6.96 (s, 0.5H), 6.83 (s, 0.3H), 5.75 (s, 2H), 3.09 (s, 2H), 2.90 (s, 2H), 2.42 (s, 2H), 2.15 (s, 2H), 1.90 (s, 2H), 1.17 (s, 6H); LRMS (ES) m/z 404.4 ($M^+$ + 1). |
| 29 | 3809 | 2-(difluoromethyl)-5-(6-((4-(1-(oxetan-3-yl)piperidin-4-yl)-1H-1,2,3-triazol-1-yl)methyl)pyridin-3-yl)-1,3,4-oxadiazole<br>$^1$H NMR (400 MHZ, $CDCl_3$) δ 9.31 (d, J = 1.7 Hz, 1H), 8.39 (dd, J = 8.2, 2.2 Hz, 1H), 7.49 (s, 1H), 7.34 (d, J = 8.2 Hz, 1H), 7.09 (s, 0.2H), 6.96 (s, 0.5H), 6.83(s, 0.3H), 5.74 (s, 2H), 4.77-4.52 (m, 4H), 3.54 (dd, J = 12.9, 6.5 Hz, 1H), 2.86 (dd, J = 11.2, 8.5 Hz, 3H), 2.22-1.88 (m, 4H), 1.78 (qd, J = 12.4, 3.3 Hz, 2H); LRMS (ES) m/z 418.0 ($M^+$ + 1). |
| 30 | 3810 | 2-(6-((4-(1-(2-oxaspiro[3.3]heptan-6-yl)piperidin-4-yl)-1H-1,2,3-triazol-1-yl)methyl)pyridin-3-yl)-5-(difluoromethyl)-1,3,4-oxadiazole<br>$^1$H NMR (400 MHZ, $CDCl_3$) δ 9.35-9.21 (m, 1H), 8.37 (dd, J = 8.2, 2.2 Hz, 1H), 7.47 (s, 1H), 7.32 (d, J = 8.2 Hz, 1H), 7.08 (s, 0.2H), 6.95 (s, 0.5H),6.82 (s, 0.3H), 5.72 (s, 2H), 4.70 (s, 2H), 4.58 (s, 2H), 2.98 (d, J = 9.6 Hz, 2H), 2.84 (s, 1H), 2.61 (s, 1H), 2.50-2.32 (m, 2H), 2.08 (t, J = 15.7 Hz, 4H), 1.97 (d, J = 10.4 Hz, 2H), 1.73 (d, J = 11.2 Hz, 2H); LRMS (ES) m/z 458.3 ($M^+$ + 1). |

Example 31: Synthesis of compound 3811, 1-(4-(1-((5-(5-(difluoromethyl)-1,3,4-oxadiazol-2-yl)pyridin-2-yl)methyl)-1H-1,2,3-triazol-4-yl)piperidin-1-yl)ethan-1-one

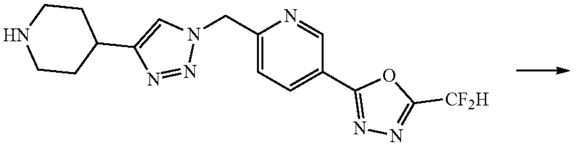

-continued

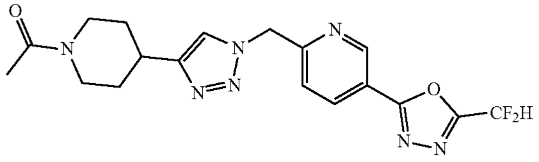

The 2-(difluoromethyl)-5-(6-((4-(piperidin-4-yl)-1H-1,2,3-triazol-1-yl)methyl)pyridin-3-yl)-1,3,4-oxadiazole (0.050 g, 0.138 mmol) prepared in step 1 of example 26, triethylamine (0.023 mL, 0.166 mmol) and acetic anhydride (0.026 mL, 0.277 mmol) were dissolved in dichloromethane (10 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 1-(4-(1-((5-(5-(difluoromethyl)-1,3,4-oxadiazol-2-yl)pyridin-2-yl)methyl)-1H-1,2,3-triazol-4-yl)piperidin-1-yl)ethan-1-one (0.041 g, 73.5%) in a white solid form.

$^1$H NMR (400 MHz, $CDCl_3$) δ 9.31 (d, J=1.8 Hz, 1H), 8.40 (dd, J=8.2, 2.2 Hz, 1H), 7.51 (s, 1H), 7.38 (d, J=8.2 Hz, 1H), 7.09 (s, 0.2H), 6.96 (s, 0.5H), 6.83 (s, 0.3H), 5.74 (s, 2H), 4.64 (d, J=13.0 Hz, 1H), 3.89 (d, J=13.0 Hz, 1H), 3.22 (t, J=12.3 Hz, 1H), 3.05 (tt, J=11.4, 3.8 Hz, 1H), 2.76 (t, J=11.9 Hz, 1H), 2.27-1.97 (m, 5H), 1.66 (dd, J=25.7, 12.8 Hz, 2H); LRMS (ES) m/z 403.9 ($M^+$+1).

The compounds of table 9 were synthesized according to substantially the same process as described above in the synthesis of compound 3811 with an exception of using 2-(difluoromethyl)-5-(6-((4-(piperidin-4-yl)-1H-1,2,3-triazol-1-yl)methyl)pyridin-3-yl)-1,3,4-oxadiazole and the reactant of table 8.

TABLE 8

| Example | Compound No. | Reactant | Yield (%) |
|---|---|---|---|
| 32 | 3812 | Methanesulfonyl chloride | 34 |
| 77 | 3891 | Methyl chloroformate | 56 |
| 78 | 3892 | Ethyl carbonochloridate | 46 |
| 79 | 3893 | Trimethylacetyl chloride | 45 |

TABLE 9

| Example | Compound No. | Compound Name, $^1$H-NMR, MS (ESI) |
|---|---|---|
| 32 | 3812 | 2-(difluoromethyl)-5-(6-((4-(1-(methylsulfony])piperidin-4-yl)-1H-1,2,3-triazol-1-yl)methyl)pyridin-3-yl)-1,3,4-oxadiazole<br>$^1$H NMR (400 MHZ, $CDCl_3$) δ 9.34 (d, J = 1.9 Hz, 1H), 8.43 (dd, J = 8.2, 2.2 Hz, 1H), 7.55 (s, 1H), 7.42 (d, J = 8.4 Hz, 1H), 7.09 (s, 0.2H), 6.99 (s, 0.5H), 6.84 (s, 0.3H), 5.76 (s, 2H), 3.89 (d, J = 12.4 Hz, 2H), 3.03-2.93 (m, 1H), 2.88 (td, J = 12.0, 2.6 Hz, 2H), 2.83 (s, 3H), 2.21 (d, J = 10.7 Hz, 2H), 1.84 (ddd, J = 25.0, 11.7,3.9 Hz, 2H); LRMS (ES) m/z 440.1 ($M^+$ + 1). |
| 77 | 3891 | Methyl4-(1-((5-(5-(difluoromethyl)-1,3,4-oxadiazol-2-yl)pyridin-2-yl)methyl)-1H-1,2,3-triazol-4-yl)piperidin-1-carboxylate<br>$^1$H NMR (400 MHZ, $CDCl_3$) δ 9.32 (d, J = 1.6 Hz, 1H), 8.41 (dd, J = 8.2, 2.2 Hz, 1H), 7.49 (s, 1H), 7.38 (d, J = 8.2 Hz, 1H), 7.09 (s, 0.2H), 6.96 (s, 0.5H), 6.83 (s, 0.3H), 5.74 (s, 2H), 4.20 (s, 2H), 3.71 (s, 3H), 3.02-2.92 (m, 3H), 2.08-2.04 (m, 2H), 1.68-1.58 (m, 2H); LRMS (ES) m/z 420.2 ($M^+$ + 1). |
| 78 | 3892 | Ethyl4-(1-((5-(5-(difluoromethyl)-1,3,4-oxadiazol-2-yl)pyridin-2-yl)methyl)-1H-1,2,3-triazol-4-yl)piperidin-1-carboxylate<br>$^1$H NMR (400 MHZ, $CDCl_3$) δ 9.33 (dd, J = 2.2, 0.7 Hz, 1H), 8.41 (dd, J = 8.2, 2.2 Hz, 1H), 7.52-7.48 (m, 1H), 7.41-7.34 (m, 1H), 7.10 (s, 0.2H), 6.97 (s, 0.5H), 6.83 (s, 0.3H), 5.75 (s, 2H), 4.30-4.06 (m, 4H), 2.98 (ddt, J = 27.3, 19.7, 5.4 Hz, 3H), 2.14-1.99 (m, 2H), 1.64 (ddd, J = 25.1, 12.2, 4.2 Hz, 2H), 1.27 (q, J = 6.8 Hz, 3H); LRMS (ES) m/z 434.3 ($M^+$ + 1). |
| 79 | 3893 | 1-(4-(1-((5-(5-(difluoromethyl)-1,3,4-oxadiazol-2-yl)pyridin-2-yl)methyl)-1H-1,2,3-triazol-4-yl)piperidin-1-yl)-2,2-dimethylpropan-1-one<br>$^1$H NMR (400 MHZ, $CD_3OD$) δ 9.25 (s, 1H), 8.50 (dd, J = 8.2, 2.1 Hz, 1H), 7.97 (s, 1H), 7.52 (d, J = 8.2 Hz, 1H), 7.38 (s, 0.2H), 7.25 (s, 0.5H), 7.12 (s, 0.3H), 5.83 (s, 2H), 4.49 (d, J = 13.2 Hz, 2H), 3.10-3.03 (m, 3H), 2.09 (d, J = 13.2 Hz, 2H), 1.70-1.61 (m, 2H), 1.31 (s, 9H); LRMS (ES) m/z 446.4 ($M^+$ + 1). |

Example 33: Synthesis of compound 3813, 1-(4-(1-((5-(5-(difluoromethyl)-1,3,4-oxadiazol-2-yl)pyridin-2-yl)methyl)-1H-1,2,3-triazol-4-yl)piperidin-1-yl)-2-hydroxyethan-1-one

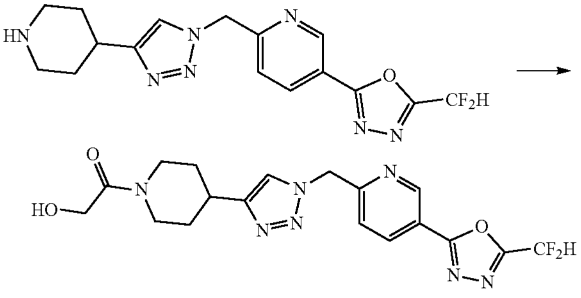

The 2-(difluoromethyl)-5-(6-((4-(piperidin-4-yl)-1H-1,2,3-triazol-1-yl)methyl)pyridin-3-yl)-1,3,4-oxadiazole (0.050 g, 0.138 mmol) prepared in step 1 of example 26, 2-hydroxyacetic acid (0.013 g, 0.166 mmol), 1-ethyl-3-(3-dimethylaminopropyl)carbodiimide (0.043 g, 0.277 mmol) and 1H-benzo[d][1,2,3]triazol-1-ol (0.037 g, 0.277 mmol) were dissolved in dichloromethane (10 mL) at room temperature, after which N,N-diisopropylethylamine (0.048 mL, 0.277 mmol) was added to the resulting solution and stirred at the same temperature for 30 minutes. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 1-(4-(1-((5-(5-(difluoromethyl)-1,3,4-oxadiazol-2-yl)pyridin-2-yl)methyl)-1H-1,2,3-triazol-4-yl)piperidin-1-yl)-2-hydroxyethan-1-one (0.021 g, 36.2%) in a white solid form.

$^1$H NMR (400 MHz, $CDCl_3$) δ 9.32 (d, J=1.7 Hz, 1H), 8.41 (dd, J=8.2, 2.2 Hz, 1H), 7.60-7.47 (m, 2H), 7.41 (d, J=8.1 Hz, 1H), 7.09 (s, 0.2H), 6.96 (s, 0.5H), 6.83 (s, 0.3H), 5.75 (s, 2H), 4.61 (d, J=13.6 Hz, 1H), 4.19 (s, 2H), 3.59 (d, J=13.9 Hz, 1H), 3.24-2.99 (m, 2H), 2.99-2.81 (m, 1H), 2.24-2.07 (m, 2H), 1.77-1.54 (m, 2H); LRMS (ES) m/z 420.3 ($M^+$+1).

The compound of table 11 was synthesized according to substantially the same process as described above in the synthesis of compound 3813 with an exception of using 2-(difluoromethyl)-5-(6-((4-(piperidin-4-yl)-1H-1,2,3-triazol-1-yl)methyl)pyridin-3-yl)-1,3,4-oxadiazole and the reactant of table 10.

TABLE 10

| Example | Compound No. | Reactant | Yield (%) |
|---|---|---|---|
| 80 | 3894 | 2-fluoro-2-methylpropanoic acid | 47 |

TABLE 11

| Example | Compound No. | Compound Name, $^1$H-NMR, MS (ESI) |
|---|---|---|
| 80 | 3894 | 1-(4-(1-((5-(5-(difluoromethyl)-1,3,4-oxadiazol-2-yl)pyridin-2-yl)methyl)-1H-1,2,3-triazol-4-yl)piperidin-1-yl)-2-fluoro-2-methylpropan-1-one<br>$^1$H NMR (400 MHz, $CDCl_3$) δ 9.34 (d, J = 1.7 Hz, 1H), 8.44 (dd, J = 8.2, 2.2 Hz, 1H), 7.59 (s, 1H), 7.44 (d, J = 8.0 Hz, 1H), 7.10 (s, 0.2H), 6.97 (s, 0.5H), 6.84 (s, 0.3H), 5.78 (s, 2H), 4.58 (d, J = 26.7 Hz, 2H), 3.30-3.06 (m, 2H), 2.83 (s, 1H), 2.16 (s, 2H), 1.68 (s, 2H), 1.67 (s, 3H), 1.61 (s, 3H); LRMS (ES) m/z 450.2 ($M^+$ + 1). |

Example 36: Synthesis of compound 3824, 3-(1-((5-(5-(difluoromethyl)-1,3,4-oxadiazol-2-yl)pyridin-2-yl)methyl)-1H-1,2,3-triazol-4-yl)-N,N-dimethylaniline

[Step 1] Synthesis of 3-(1-((5-(5-(difluoromethyl)-1,3,4-oxadiazol-2-yl)pyridin-2-yl)methyl)-1H-1,2,3-triazol-4-yl)aniline

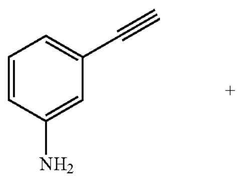

-continued

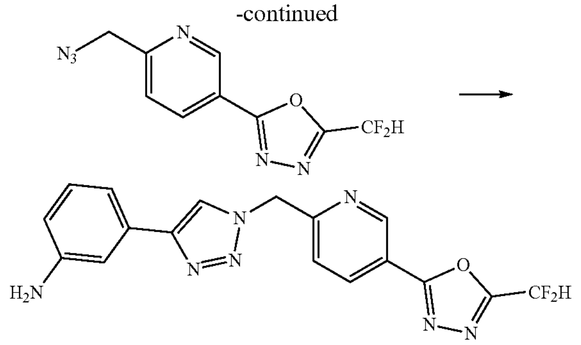

The 2-(6-(azidomethyl)pyridin-3-yl)-5-(difluoromethyl)-1,3,4-oxadiazole (0.500 g, 1.983 mmol) prepared in step 1 of example 16 was dissolved in tert-butanol (4 mL)/water (4 mL) at room temperature, after which 3-ethynylaniline (0.223 mL, 1.983 mmol) was added to the resulting solution and stirred at the same temperature. Sodium ascorbate (1.00 M solution, 0.198 mL, 0.198 mmol) and copper(II) sulfate pentahydrate (0.50 M solution, 0.040 mL, 0.020 mmol) were added to the reaction mixture and further stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 40%) and concentrated to obtain 3-(1-((5-(5-(difluoromethyl)-1,3,4-oxadiazol-2-yl)pyridin-2-yl)methyl)-1H-1,2,3-triazol-4-yl)aniline (0.650 g, 88.8%) in a beige solid form.

[Step 2] Synthesis of Compound 3824

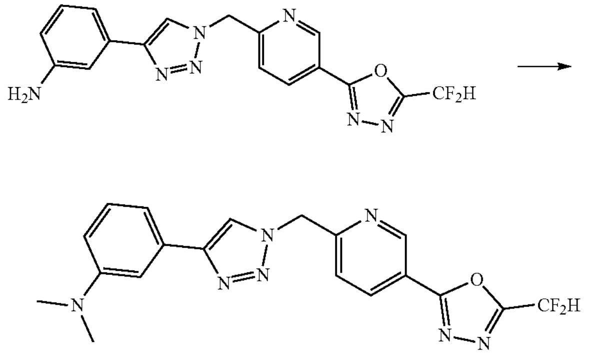

The 3-(1-((5-(5-(difluoromethyl)-1,3,4-oxadiazol-2-yl)pyridin-2-yl)methyl)-1H-1,2,3-triazol-4-yl)aniline (0.030 g, 0.078 mmol) prepared in step 1 and formaldehyde (37.00%, 0.063 g, 0.777 mmol) were dissolved in acetonitrile (1 mL)/acetic acid (0.01 mL), after which the resulting solution was stirred at room temperature for 0.5 hours, and then sodium cyanoborohydride (0.015 g, 0.233 mmol) was added thereto and further stirred at the same temperature for 1 hour. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 3-(1-((5-(5-(difluoromethyl)-1,3,4-oxadiazol-2-yl)pyridin-2-yl)methyl)-1H-1,2,3-triazol-4-yl)-N,N-dimethylaniline (0.012 g, 37.3%) in a light yellow oil form.

$^1H$ NMR (400 MHz, DMSO-$d_6$) δ 9.20 (d, J=2.2 Hz, 1H), 8.69 (s, 1H), 8.49 (dd, J=8.2, 2.3 Hz, 1H), 7.73-7.44 (m, 3H), 7.28-7.20 (m, 2H), 6.75-6.68 (m, 1H), 5.92 (s, 2H), 2.95 (s, 6H); LRMS (ES) m/z 398.2 ($M^+$+1).

The compounds of table 13 were synthesized according to substantially the same process as described above in the synthesis of compound 3824 with an exception of using 3-(1-((5-(5-(difluoromethyl)-1,3,4-oxadiazol-2-yl)pyridin-2-yl)methyl)-1H-1,2,3-triazol-4-yl)aniline and the reactant of table 12.

TABLE 12

| Example | Compound No. | Reactant | Yield (%) |
|---|---|---|---|
| 39 | 3827 | Tetrahydro-4H-pyran-4-one | 45 |
| 40 | 3828 | Cyclohexanone | 52 |
| 42 | 3830 | 1-methylpiperidin-4-one | 33 |

Example 37: Synthesis of compound 3825, N-(3-(1-((5-(5-(difluoromethyl)-1,3,4-oxadiazol-2-yl)pyridin-2-yl)methyl)-1H-1,2,3-triazol-4-yl)phenyl)pivalamide

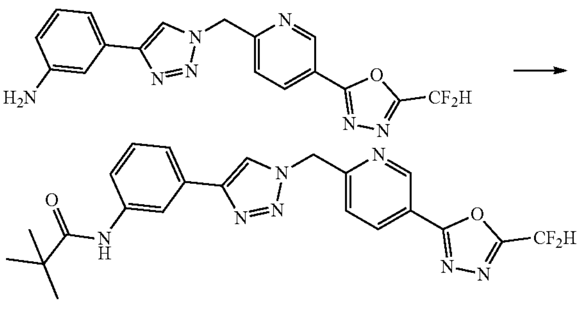

The 3-(1-((5-(5-(difluoromethyl)-1,3,4-oxadiazol-2-yl)pyridin-2-yl)methyl)-1H-1,2,3-triazol-4-yl)aniline (0.050 g, 0.135 mmol) prepared in step 1 of example 36 and triethylamine (0.028 mL, 0.203 mmol) were dissolved in dichloromethane (1 mL) at room temperature, after which trimethylacetyl chloride (0.020 mL, 0.162 mmol) was added into the resulting solution and stirred at the same temperature for 1 hour. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain N-(3-(1-((5-(5-(difluoromethyl)-1,3,4-oxadiazol-2-yl)pyridin-2-yl)methyl)-1H-1,2,3-triazol-4-yl)phenyl)pivalamide (0.023 g, 37.5%) in a white solid form.

$^1H$ NMR (400 MHz, DMSO-$d_6$) δ 9.32 (s, 1H), 9.21 (dd, J=2.3, 0.9 Hz, 1H), 8.67 (s, 1H), 8.50 (dd, J=8.2, 2.3 Hz, 1H), 8.21 (t, J=1.9 Hz, 1H), 7.65 (ddd, J=8.1, 2.1, 1.0 Hz, 1H), 7.72-7.45 (m, 2H), 7.52 (dt, J=7.7, 1.3 Hz, 1H), 7.37 (t, J=7.9 Hz, 1H), 5.93 (s, 2H), 1.25 (s, 9H); LRMS (ES) m/z 454.3 ($M^+$+1).

TABLE 13

| Example | Compound No. | Compound Name, $^1H$-NMR, MS (ESI) |
|---|---|---|
| 39 | 3827 | N-(3-(1-((5-(5-(difluoromethyl)-1,3,4-oxadiazol-2-yl)pyridin-2-yl)methyl)-1H-1,2,3-triazol-4-yl)phenyl)tetrahydro-2H-pyran-4-amine<br>$^1H$ NMR (400 MHz, DMSO-$d_6$) δ 9.23-9.17 (m, 1H), 8.60 (s, 1H), 8.49 (dd, J = 8.2, 2.3 Hz, 1H), 7.58 (t, J = 51.3 Hz, 1H), 7.54 (d, J = 8.2 Hz, 1H), 7.17-7.09 (m, 2H), 7.00 (dd, J = 7.6, 1.4 Hz, 1H), 6.62-6.55 (m, 1H), 5.91 (s, 2H), 3.93-3.84 (m, 2H), 3.58-3.48 (m, 1H), 3.44 (td, J = 11.5, 2.2 Hz, 2H), 1.90 (d, J = 12.9 Hz, 2H), 1.47-1.32 (m, 2H); LRMS (ES) m/z 454.2 ($M^+$ + 1). |
| 40 | 3828 | N-cyclohexyl-3-(1-((5-(5-(difluoromethyl)-1,3,4-oxadiazol-2-yl)pyridin-2-yl)methyl)-1H-1,2,3-triazol-4-yl)aniline<br>$^1H$ NMR (400 MHz, DMSO-$d_6$) δ 9.20 (dd, J = 2.2, 0.8 Hz, 1H), 8.58 (s, 1H), 8.49 (dd, J = 8.2, 2.3 Hz, 1H), 7.58 (t, J = 51.3 Hz, 1H), 7.54 (d, J = 8.2 Hz, 1H), 7.15-7.07 (m, 2H), 6.96 (d, J = 7.6 Hz, 1H), 6.58-6.51 (m, 1H), 5.91 (s, 2H), 3.24 (s, 1H), 2.02-1.91 (m, 2H), 1.73 (d, J = 13.1 Hz, 2H), 1.61 (d, J = 12.7 Hz, 1H), 1.34 (t, J = 12.5 Hz, 2H), 1.23-1.13 (m, 3H); LRMS (ES) m/z 451.9 ($M^+$ + 1). |
| 42 | 3830 | N-(3-(1-((5-(5-(difluoromethyl)-1,3,4-oxadiazol-2-yl)pyridin-2-yl)methyl)-1H-1,2,3-triazol-4-yl)phenyl)-1-methylpiperidin-4-amine<br>$^1H$ NMR (400 MHz, DMSO) δ 9.23-9.17 (m, 1H), 8.59 (s, 1H), 8.49 (dd, J = 8.2, 2.3 Hz, 1H), 7.58 (t, J = 51.3 Hz, 1H), 7.54 (d, J = 8.1 Hz, 1H), 7.16-7.08 (m, 2H), 6.98 (d, J = 7.7 Hz, 1H), 6.56 (d, J = 7.1 Hz, 1H), 5.91 (s, 2H), 3.23 (s, 1H), 2.73 (d, J = 11.7 Hz, 2H), 2.17 (s, 3H), 2.07-1.97 (m, 2H), 1.90 (d, J = 12.6 Hz, 2H), 1.41 (q, J = 9.9 Hz, 2H); LRMS (ES) m/z 467.3 ($M^+$ + 1). |

The compound of table 15 was synthesized according to substantially the same process as described above in the synthesis of compound 3825 with an exception of using 3-(1-((5-(5-(difluoromethyl)-1,3,4-oxadiazol-2-yl)pyridin-2-yl)methyl)-1H-1,2,3-triazol-4-yl)aniline and the reactant of table 14.

TABLE 14

| Example | Compound No. | Reactant | Yield (%) |
|---|---|---|---|
| 38 | 3826 | Ethylchloroformate | 50 |

TABLE 15

| Example | Compound No. | Compound Name, $^1$H-NMR, MS (ESI) |
|---|---|---|
| 38 | 3826 | Ethyl(3-(1-((5-(5-(difluoromethyl)-1,3,4-oxadiazol-2-yl)pyridin-2-yl)methyl)-1H-1,2,3-triazol-4-yl)phenyl)carbamate $^1$H NMR (400 MHz, DMSO-d$_6$) δ 9.72 (s, 1H), 9.20 (dd, J = 2.3, 0.8 Hz, 1H), 8.65 (s, 1H), 8.49 (dd, J = 8.3, 2.3 Hz, 1H), 8.07 (s, 1H), 7.72-7.53 (m, 1H), 7.49-7.40 (m, 2H), 7.38-7.32 (m, 1H), 5.93 (s, 2H), 4.15 (q, J = 7.1 Hz, 2H), 1.26 (t, J = 7.1 Hz, 3H); LRMS (ES) m/z 442.2 (M$^+$ + 1). |

Example 41: Synthesis of compound 3829, (3-(1-((5-(5-(difluoromethyl)-1,3,4-oxadiazol-2-yl)pyridin-2-yl)methyl)-1H-1,2,3-triazol-4-yl)phenyl)(pyrrolidin-1-yl)methanone

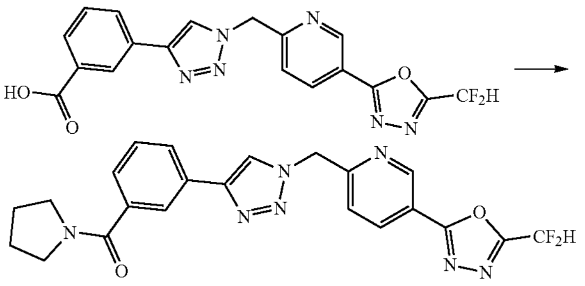

The 3-(1-((5-(5-(difluoromethyl)-1,3,4-oxadiazol-2-yl)pyridin-2-yl)methyl)-1H-1,2,3-triazol-4-yl)benzoic acid (0.050 g, 0.126 mmol) prepared in example 19, pyrrolidine (0.012 g, 0.163 mmol) and 1-[bis(dimethylamino)methylene]-1H-1,2,3-triazolo[4,5-b]pyridinium 3-oxide hexafluorophosphate (0.095 g, 0.251 mmol) were dissolved in dichloromethane (5 mL) at room temperature, after which diisopropylethylamine (0.032 g, 0.251 mmol) was added into the resulting solution and stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain (3-(1-((5-(5-(difluoromethyl)-1,3,4-oxadiazol-2-yl)pyridin-2-yl)methyl)-1H-1,2,3-triazol-4-yl)phenyl)(pyrrolidin-1-yl)methanone (0.032 g, 56.5%) in a light yellow gum form.

$^1$H NMR (400 MHz, $CD_3OD$) δ 9.28 (dd, J=2.3, 0.9 Hz, 1H), 8.58 (s, 1H), 8.53 (dd, J=8.2, 2.2 Hz, 1H), 8.02 (t, J=1.6 Hz, 1H), 7.98 (dt, J=7.5, 1.6 Hz, 1H), 7.61 (dd, J=8.2, 0.8 Hz, 1H), 7.59-7.54 (m, 1H), 7.52 (dt, J=7.7, 1.5 Hz, 1H), 7.26 (t, J=51.6 Hz, 1H), 5.93 (s, 2H), 3.64 (t, J=7.0 Hz, 2H), 3.52 (t, J=6.6 Hz, 2H), 2.02 (dt, J=7.7, 5.8 Hz, 2H), 1.99-1.89 (m, 2H); LRMS (ES) m/z 452.2 (M$^+$+1).

The compounds of table 17 were synthesized according to substantially the same process as described above in the synthesis of compound 3829 with an exception of using 3-(1-((5-(5-(difluoromethyl)-1,3,4-oxadiazol-2-yl)pyridin-2-yl)methyl)-1H-1,2,3-triazol-4-yl)benzoic acid and the reactant of table 16.

TABLE 16

| Example | Compound No. | Reactant | Yield (%) |
|---|---|---|---|
| 72 | 3885 | Morpholine | 42 |
| 73 | 3886 | Azetidine | 56 |
| 74 | 3887 | 1-methylpiperazine | 47 |
| 327 | 4448 | 1-isopropylpiperazine | 51 |
| 328 | 4449 | N1,N1,N2-trimethylethane-1,2-diamine | 49 |
| 355 | 4480 | 1-methylazetidin-3-amine | 54 |
| 356 | 4482 | 1-ethylpiperazine | 46 |

TABLE 17

| Example | Compound No. | Compound Name, $^1$H-NMR, MS (ESI) |
|---|---|---|
| 72 | 3885 | (3-(1-((5-(5-(difluoromethyl)-1,3,4-oxadiazol-2-yl)pyridin-2-yl)methyl)-1H-1,2,3-triazol-4-yl)phenyl)(morpholino)methanone $^1$H NMR (400 MHz, DMSO-d$_6$) δ 9.20 (dd, J = 2.3, 0.9 Hz, 1H), 8.81 (s, 1H), 8.50 (dd, J = 8.2, 2.3 Hz, 1H), 7.98 (dt, J = 7.8, 1.4 Hz, 1H), 7.90 (t, J = 1.7 Hz, 1H), 7.72-7.44 (m, 4H), 7.38 (dt, J = 7.6, 1.4 Hz, 1H), 5.94 (s, 2H), 3.63 (dd, J = 10.5, 6.3 Hz, 4H), 3.21-3.10 (m, 4H); LRMS (ES) m/z 468.3 (M$^+$ + 1). |

TABLE 17-continued

| Example | Compound No. | Compound Name, ¹H-NMR, MS (ESI) |
|---|---|---|
| 73 | 3886 | Azetidin-1-yl(3-(1-((5-(5-(difluoromethyl)-1,3,4-oxadiazol-2-yl)pyridin-2-yl)methyl)-1H-1,2,3-triazol-4-yl)phenyl)methanone<br>$^1$H NMR (400 MHz, DMSO-$d_6$) δ 9.20 (dd, J = 2.3, 0.8 Hz, 1H), 8.84 (s, 1H), 8.50 (dd, J = 8.2, 2.3 Hz, 1H), 8.10 (s, 1H), 8.01 (dt, J = 7.1, 1.8 Hz, 1H), 7.73-7.44 (m, 4H), 5.94 (s, 2H), 4.33 (t, J = 7.6 Hz, 2H), 4.11-4.05 (m, 2H), 2.28 (p, J = 7.7 Hz, 2H); LRMS (ES) m/z 438.3 ($M^+$ + 1). |
| 74 | 3887 | (3-(1-((5-(5-(difluoromethyl)-1,3,4-oxadiazol-2-yl)pyridin-2-yl)methyl)-1H-1,2,3-triazol-4-yl)phenyl)(4-methylpiperazin-1-yl)methanone<br>$^1$H NMR (400 MHz, $CD_3OD$) δ 9.27 (dd, J = 2.2, 0.9 Hz, 1H), 8.59 (s, 1H), 8.53 (dd, J = 8.2, 2.2 Hz, 1H), 7.98 (dt, J = 7.9, 1.5 Hz, 1H), 7.93 (t, J = 1.8 Hz, 1H), 7.65-7.53 (m, 2H), 7.42 (dt, J = 7.7, 1.4 Hz, 1H), 7.26 (t, J = 51.6 Hz, 1H), 5.93 (s, 2H), 3.83 (br s, 2H), 3.53 (br s, 2H), 2.58 (br s, 2H), 2.48 (br s, 2H), 2.36 (s, 3H); LRMS (ES) m/z 481.3 ($M^+$ + 1). |
| 327 | 4448 | (3-(1-((5-(5-(difluoromethyl)-1,3,4-oxadiazol-2-yl)pyridin-2-yl)methyl)-1H-1,2,3-triazol-4-yl)phenyl)(4-isopropylpiperazin-1-yl)methanone<br>$^1$H NMR (400 MHz, $CD_3OD$) δ 9.27-8.29 (m, 1H), 8.57 (d, J = 8.48 Hz, 1H), 8.53 (dd, J = 8.20, 2.20 Hz, 1H), 8.36 (t, J = 1.71 Hz, 1H), 8.08-7.86(m, 2H), 7.62 (dd, J = 8.20, 1.28 Hz, 1H), 7.57 (t, J = 7.71 Hz, 1H), 7.26 (t, J = 51.6 Hz, 1H), 5.94 (s, 2H), 3.82-3.50 (m, 4H), 2.80-2.59 (m, 5H), 1.12 (d, J = 6.56 Hz, 6H); LRMS (ES) m/z 509.5 ($M^+$ + 1). |
| 328 | 4449 | 3-(1-((5-(5-(difluoromethyl)-1,3,4-oxadiazol-2-yl)pyridin-2-yl)methyl)-1H-1,2,3-triazol-4-yl)-N-(2-(dimethylamino)ethyl)-N-methylbenzamide<br>$^1$H NMR (400 MHz, $CD_3OD$) δ 9.29 (dd, J = 2.3, 0.9 Hz, 1H), 8.57 (s, 1H), 8.54 (dd, J = 8.2, 2.2 Hz, 1H), 8.37 (t, J = 1.7 Hz, 1H), 8.07 (dt, J = 7.8, 1.3 Hz, 1H), 7.91-7.84 (m, 1H), 7.62 (d, J = 8.3 Hz, 1H), 7.58 (t, J = 7.7 Hz, 1H), 7.26 (t, J = 51.6 Hz, 1H), 5.95 (s, 2H), 3.11-2.93 (m, 10H), 2.22 (s, 3H); LRMS (ES) m/z 483.5 ($M^+$ + 1). |
| 355 | 4480 | 3-(1-((5-(5-(difluoromethyl)-1,3,4-oxadiazol-2-yl)pyridin-2-yl)methyl)-1H-1,2,3-triazol-4-yl)-N-(1-methylazetidin-3-yl)benzamide<br>$^1$H NMR (400 MHz, $CD_3OD$) δ 9.28 (dd, J = 2.3, 0.9 Hz, 1H), 8.61 (s, 1H), 8.53 (dd, J = 8.2, 2.2 Hz, 1H), 8.43 (t, J = 1.8 Hz, 1H), 8.10-8.03 (m, 1H), 7.89 (ddd, J = 7.8, 1.9, 1.1 Hz, 1H), 7.67-7.56 (m, 2H), 7.26 (t, J = 51.6 Hz, 1H), 5.95 (s, 2H), 4.84-4.76 (m, 1H), 4.65-4.35 (m, 4H), 3.06 (s, 3H); LRMS (ES) m/z 467.5 ($M^+$ + 1). |
| 356 | 4482 | (3-(1-((5-(5-(difluoromethyl)-1,3,4-oxadiazol-2-yl)pyridin-2-yl)methyl)-1H-1,2,3-triazol-4-yl)phenyl)(4-ethylpiperazin-1-yl)methanone<br>$^1$H NMR (400 MHz, $CD_3OD$) δ 9.26 (dd, J = 2.2, 0.9 Hz, 1H), 8.58 (s, 1H), 8.52 (dd, J = 8.2, 2.2 Hz, 1H), 8.02-7.95 (m, 1H), 7.94 (d, J = 1.7 Hz, 1H), 7.65-7.54 (m, 2H), 7.44 (dt, J = 7.7, 1.3 Hz, 1H), 7.26 (t, J = 51.6 Hz, 1H), 5.93 (s, 2H), 3.95-3.54 (m, 4H), 2.91-2.60 (m, 6H), 1.20 (t, J = 7.3 Hz, 3H); LRMS (ES) m/z 495.5 ($M^+$ + 1). |

Example 47: Synthesis of compound 3835, 2-(difluoromethyl)-5-(6-((4-(pyridin-3-yl)-1H-1,2,3-triazol-1-yl)methyl)pyridin-3-yl)-1,3,4-oxadiazole

[Step 1] Synthesis of 3-ethynylpyridine

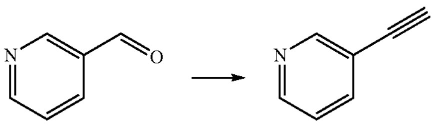

Dimethyl (1-diazo-2-oxopropyl)phosphonate (0.771 mL, 5.135 mmol) and potassium carbonate (1.290 g, 9.336 mmol) were dissolved in methanol (20 mL) at room temperature, after which nicotinealdehyde (0.439 mL, 4.668 mmol) was added into the resulting solution and stirred at the same temperature for 4 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%) and concentrated to obtain 3-ethynylpyridine (0.204 g, 42.4%) in a white solid form.

[Step 2] Synthesis of Compound 3835

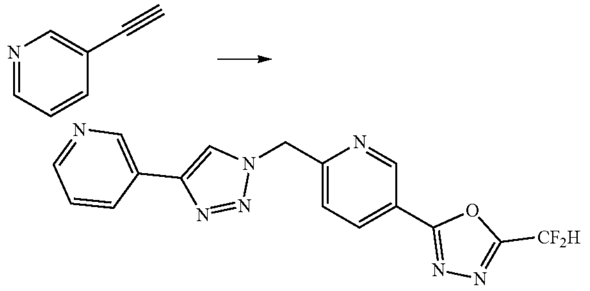

The 3-ethynylpyridine (0.100 g, 0.970 mmol) prepared in step 1, 2-(6-(azidomethyl)pyridin-3-yl)-5-(difluoromethyl)-1,3,4-oxadiazole (0.245 g, 0.970 mmol) prepared in step 1 of example 16, sodium ascorbate (0.019 g, 0.097 mmol) and copper(II) sulfate pentahydrate (0.002 g, 0.010 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. Hexane (20 mL) and dichloromethane (10 mL) were added to the resulting concentrate and stirred to filter out a precipitated solid, washed with hexane, and dried to obtain 2-(difluoromethyl)-5-(6-((4-(pyridin-3-yl)-1H-1,2,3-triazol-1-yl)methyl)pyridin-3-yl)-1,3,4-oxadiazole (0.270 g, 78.4%) in a white solid form.

$^1$H NMR (400 MHz, $CD_3OD$) δ 9.27 (dd, J=2.2, 0.9 Hz, 1H), 9.08 (s, 1H), 8.67 (s, 1H), 8.54 (d, J=2.2 Hz, 1H), 8.52 (d, J=2.2 Hz, 1H), 8.36-8.29 (m, 1H), 7.63 (dd, J=8.2, 0.9 Hz, 1H), 7.56 (t, J=6.5 Hz, 1H), 7.26 (t, J=51.6 Hz, 1H), 5.96 (s, 2H); LRMS (ES) m/z 356.2 ($M^+$+1).

Example 75: Synthesis of compound 3889, (N-(3-(1-((5-(5-(difluoromethyl)-1,3,4-oxadiazol-2-yl)pyridin-2-yl)methyl)-1H-1,2,3-triazol-4-yl)phenyl)-N-methylpivalamide

[Step 1] Synthesis of 3-ethynyl-N-methylaniline

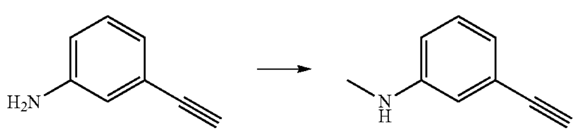

3-ethynylaniline (0.800 g, 6.829 mmol), potassium carbonate (3.775 g, 27.315 mmol) and iodomethane (1.063 mL, 17.072 mmol) were dissolved in dimethyl sulfoxide (8 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 3-ethynyl-N-methylaniline (0.100 g, 11.2%) in a colorless oil form.

[Step 2] Synthesis of 3-(1-((5-(5-(difluoromethyl)-1,3,4-oxadiazol-2-yl)pyridin-2-yl)methyl)-1H-1,2,3-triazol-4-yl)-N-methylaniline

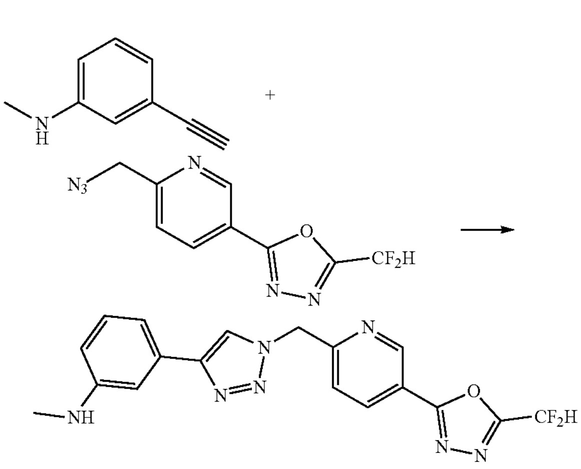

The 2-(6-(azidomethyl)pyridin-3-yl)-5-(difluoromethyl)-1,3,4-oxadiazole (0.050 g, 0.198 mmol) prepared in step 1 of example 16 and the 3-ethynyl-N-methylaniline (0.026 g, 0.198 mmol) prepared in step 1 were dissolved in tert-butanol (0.5 mL)/water (0.5 mL) at room temperature, after which sodium ascorbate (1.00 M solution, 0.020 mL, 0.020 mmol) and copper(II) sulfate pentahydrate (0.50 M solution, 0.004 mL, 0.002 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 40%) and concentrated to obtain 3-(1-((5-(5-(difluoromethyl)-1,3,4-oxadiazol-2-yl)pyridin-2-yl)methyl)-1H-1,2,3-triazol-4-yl)-N-methylaniline (0.040 g, 52.6%) in a light yellow solid form.

[Step 3] Synthesis of Compound 3889

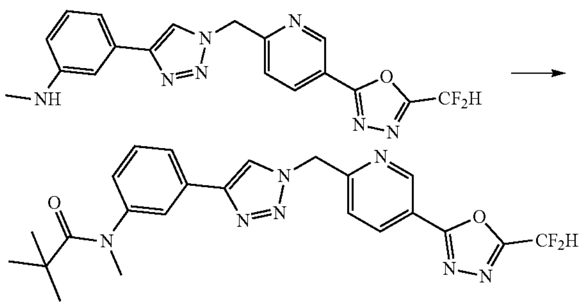

The 3-(1-((5-(5-(difluoromethyl)-1,3,4-oxadiazol-2-yl)pyridin-2-yl)methyl)-1H-1,2,3-triazol-4-yl)-N-methylaniline (0.010 g, 0.026 mmol) prepared in step 2, triethylamine (0.005 mL, 0.039 mmol) and pivaloyl chloride (0.004 mL, 0.031 mmol) were dissolved in dichloromethane (0.5 mL) at room temperature, after which the resulting solution was stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 40%) and concentrated to obtain N-(3-(1-((5-(5-(difluoromethyl)-1,3,4-oxadiazol-2-yl)pyridin-2-yl)methyl)-1H-1,2,3-triazol-4-yl)phenyl)-N-methylpivalamide (0.005 g, 41.0%) in a white solid form.

$^1$H NMR (400 MHz, $CDCl_3$) δ 9.37 (s, 1H), 8.54-8.45 (m, 1H), 8.08 (s, 1H), 7.87-7.76 (m, 2H), 7.58-7.44 (m, 2H), 7.25-7.20 (m, 1H), 6.97 (t, J=51.6 Hz, 1H), 5.88 (s, 2H), 3.28 (d, J=1.6 Hz, 3H), 1.10 (s, 9H); LRMS (ES) m/z 468.3 ($M^+$+1).

The compound of table 19 was synthesized according to substantially the same process as the synthesis of compound 3889 described above with an exception of using 3-(1-((5-(5-(difluoromethyl)-1,3,4-oxadiazol-2-yl)pyridin-2-yl)methyl)-1H-1,2,3-triazol-4-yl)-N-methylaniline and the reactant of table 18.

TABLE 18

| Example | Compound No. | Reactant | Yield (%) |
|---|---|---|---|
| 76 | 3890 | Ethylchloroformate | 50 |

TABLE 19

| Example | Compound No. | Compound Name, $^1$H-NMR, MS (ESI) |
|---|---|---|
| 76 | 3890 | Ethyl(3-(1-((5-(5-(difluoromethyl)-1,3,4-oxadiazol-2-yl)pyridin-2-yl)methyl)-1H-1,2,3-triazol-4-yl)phenyl)(methyl)carbamate (0.006 g, 50.5%) was obtained in a white solid form. $^1$H NMR (400 MHz, $CDCl_3$) δ 9.37 (s, 1H), 8.50-8.43 (m, 1H), 8.06 (s, 1H), 7.81 (s, 1H), 7.70 (d, J = 7.8 Hz, 1H), 7.50 (d, J = 8.2 Hz, 1H), 7.44 (t, J = 7.9 Hz, 2H), 6.97 (t, J = 51.6 Hz, 1H), 5.87 (s, 2H), 4.21 (q, J = 7.1 Hz, 2H), 3.37 (s, 3H), 1.27 (t, J = 7.2 Hz, 3H); LRMS (ES) m/z 456.3 ($M^+$ + 1). |

Example 81: Synthesis of compound 3895, 2-(difluoromethyl)-5-(6-((4-(1-(2-fluoro-2-methylpropyl)piperidin-4-yl)-1H-1,2,3-triazol-1-yl)methyl)pyridin-3-yl)-1,3,4-oxadiazole

[Step 1] Synthesis of methyl 6-(azidomethyl)nicotinate

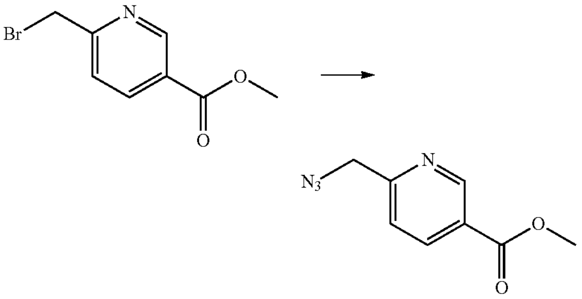

Methyl 6-(bromomethyl)nicotinate (5.000 g, 21.733 mmol) and sodium azide (1.695 g, 26.080 mmol) were dissolved in N,N-dimethylformamide (120 mL) at 50 °C, after which the resulting solution was stirred at the same temperature for 12 hours, and then a reaction was finished by lowering a temperature to room temperature. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 30%), and concentrated to obtain methyl 6-(azidomethyl)nicotinate (4.000 g, 95.8%) in a yellow solid form.

[Step 2] Synthesis of methyl 6-((4-(1-(tert-butoxycarbonyl)piperidin-4-yl)-1H-1,2,3-triazol-1-yl)methyl)nicotinate

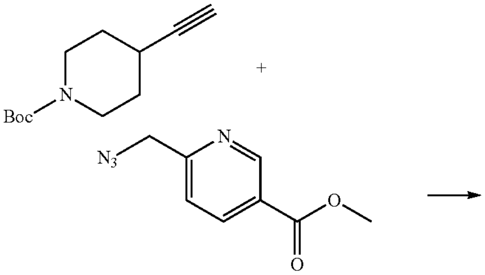

-continued

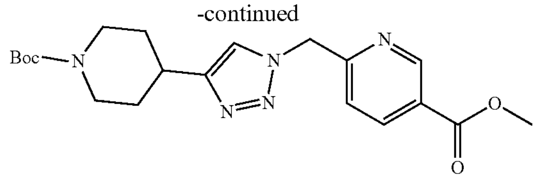

The methyl 6-(azidomethyl)nicotinate (1.500 g, 7.805 mmol) prepared in step 1, tert-butyl 4-ethynylpiperidin-1-carboxylate (1.797 g, 8.586 mmol), sodium ascorbate (1.00 M solution in $H_2O$, 0.781 mL, 0.781 mmol), and copper(II) sulfate pentahydrate (0.50 M solution in $H_2O$, 0.156 mL, 0.078 mmol) were dissolved in tert-butanol (10 mL)/water (10 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 70%) and concentrated to obtain methyl 6-((4-(1-(tert-butoxycarbonyl)piperidin-4-yl)-1H-1,2,3-triazol-1-yl)methyl)nicotinate (1.800 g, 57.4%) in a yellow solid form.

[Step 3] Synthesis of methyl 6-((4-(piperidin-4-yl)-1H-1,2,3-triazol-1-yl)methyl)nicotinate hydrochloride

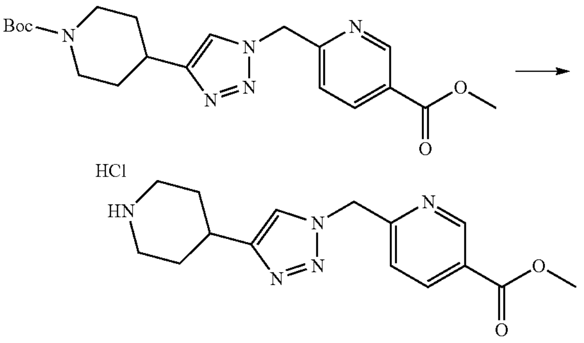

The methyl 6-((4-(1-(tert-butoxycarbonyl)piperidin-4-yl)-1H-1,2,3-triazol-1-yl)methyl)nicotinate (1.000 g, 2.491 mmol) prepared in step 1 and hydrogen chloride (4.00 M solution in 1,4-dioxane, 1.868 mL, 7.473 mmol) were dissolved in dichloromethane (30 mL) at room temperature, after which the resulting solution was stirred at the same temperature for 12 hours. Solvent was removed from the reaction mixture under reduced pressure, after which a precipitated solid was filtered out, washed with dichloromethane, and dried to obtain methyl 6-((4-(piperidin-4-yl)-1H-1,2,3-triazol-1-yl)methyl)nicotinate hydrochloride (0.800 g, 95.1%) in a yellow solid form.

[Step 4] Synthesis of methyl 6-((4-(1-(2-hydroxy-2-methylpropyl)piperidin-4-yl)-1H-1,2,3-triazol-1-yl)methyl)nicotinate

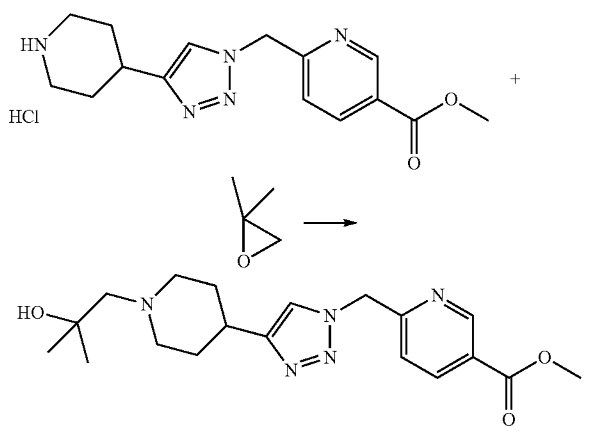

The methyl 6-((4-(piperidin-4-yl)-1H-1,2,3-triazol-1-yl)methyl)nicotinate hydrochloride (0.200 g, 0.592 mmol) prepared in step 2, potassium carbonate (0.164 g, 1.184 mmol) and 2,2-dimethyloxylane (0.213 g, 2.960 mmol) were mixed in ethanol (12 mL)/water (3 mL), heated at 110 °C for 15 minutes by irradiation with microwaves, and a reaction was finished by lowering a temperature to room temperature. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. Then, the obtained product was used without an additional purification process (methyl 6-((4-(1-(2-hydroxy-2-methylpropyl)piperidin-4-yl)-1H-1,2,3-triazol-1-yl)methyl)nicotinate, 0.160 g, 72.4%, yellow oil).

[Step 5] Synthesis of methyl 6-((4-(1-(2-fluoro-2-methylpropyl)piperidin-4-yl)-1H-1,2,3-triazol-1-yl)methyl)nicotinate

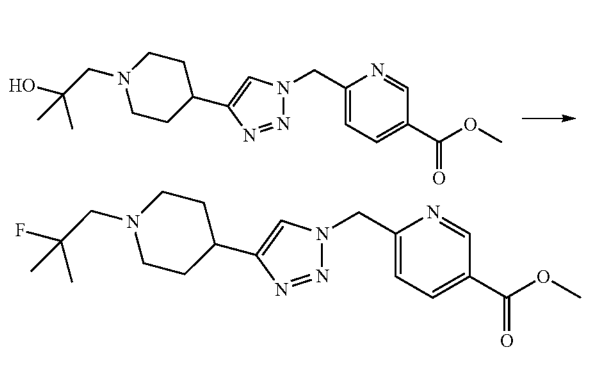

The methyl 6-((4-(1-(2-hydroxy-2-methylpropyl)piperidin-4-yl)-1H-1,2,3-triazol-1-yl)methyl)nicotinate (0.100 g, 0.268 mmol) prepared in step 3 and diethylaminosulfur trifluoride (0.042 mL, 0.321 mmol) were dissolved in dichloromethane (10 mL) at room temperature, after which the resulting solution was stirred at the same temperature for 3 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (methyl 6-((4-(1-(2-fluoro-2-methylpropyl)piperidin-4-yl)-1H-1,2,3-triazol-1-yl)methyl)nicotinate, 0.076 g, 75.6%, yellow solid).

[Step 6] Synthesis of 6-((4-(1-(2-fluoro-2-methylpropyl)piperidin-4-yl)-1H-1,2,3-triazol-1-yl)methyl)nicotinohydrazide

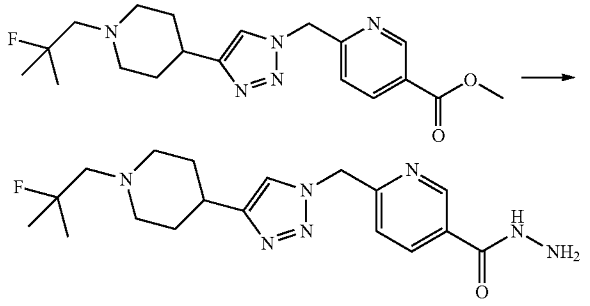

The methyl 6-((4-(1-(2-fluoro-2-methylpropyl)piperidin-4-yl)-1H-1,2,3-triazol-1-yl)methyl)nicotinate (0.076 g, 0.202 mmol) prepared in step 4 and hydrazine monohydrate (0.098 mL, 2.024 mmol) were dissolved in ethanol (30 mL) at 90 °C, after which the resulting solution was stirred at the same temperature for 12 hours, and then a reaction was finished by lowering a temperature to room temperature. Solvent was removed from the reaction mixture under reduced pressure, after which the obtained product was used without an additional purification process (6-((4-(1-(2-fluoro-2-methylpropyl)piperidin-4-yl)-1H-1,2,3-triazol-1-yl)methyl)nicotinohydrazide, 0.070 g, 92.1%, white solid).

[Step 7] Synthesis of Compound 3895

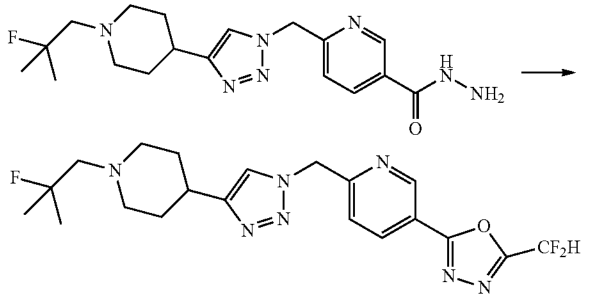

The 6-((4-(1-(2-fluoro-2-methylpropyl)piperidin-4-yl)-1H-1,2,3-triazol-1-yl)methyl)nicotinohydrazide (0.070 g, 0.186 mmol) prepared in step 5, imidazole (0.038 g, 0.559 mmol) and 2,2-difluoroacetic anhydride (0.070 mL, 0.559 mmol) were mixed in dichloromethane (30 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 3%) and concentrated to obtain 2-(difluoromethyl)-5-(6-((4-(1-(2-fluoro-2-methylpropyl)piperidin-4-yl)-1H-1,2,3-triazol-1-yl)methyl)pyridin-3-yl)-1,3,4-oxadiazole (0.039 g, 48.0%) in a white solid form.

$^1H$ NMR (400 MHz, $CDCl_3$) δ 9.33 (d, J=1.5 Hz, 1H), 8.40 (dd, J=8.2, 2.2 Hz, 1H), 7.49 (s, 1H), 7.34 (d, J=8.2 Hz, 1H), 7.09 (s, 0.2H), 6.96 (s, 0.5H), 6.84 (s, 0.3H), 5.75 (s, 2H), 3.05 (s, 2H), 2.80 (s, 1H), 2.51 (d, J=23.0 Hz, 2H), 2.32 (s, 2H), 2.02 (s, 2H), 1.80 (s, 2H), 1.42 (t, J=21.6 Hz, 6H); LRMS (ES) m/z 436.3 ($M^+$+1).

Example 82: Synthesis of compound 3896, 2-(difluoromethyl)-5-(6-((4-(1-(2-ethyl-2-fluorobutyl)piperidin-4-yl)-1H-1,2,3-triazol-1-yl)methyl)pyridin-3-yl)-1,3,4-oxadiazole

[Step 1] Synthesis of methyl 6-((4-(1-(2-ethyl-2-hydroxybutyl)piperidin-4-yl)-1H-1,2,3-triazol-1-yl)methyl)nicotinate

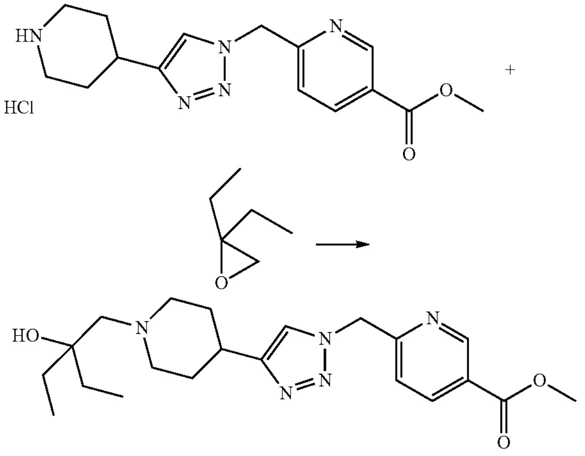

The methyl 6-((4-(piperidin-4-yl)-1H-1,2,3-triazol-1-yl)methyl)nicotinate hydrochloride (0.200 g, 0.592 mmol) prepared in step 2 of example 81, potassium carbonate (0.164 g, 1.184 mmol) and 2,2-dimethyloxylane (0.296 g, 2.960 mmol) were mixed in ethanol (12 mL)/water (3 mL), heated at 110 °C for 15 minutes by irradiation with microwaves, and a reaction was finished by lowering a temperature to room temperature. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. Then, the obtained product was used without an additional purification process (methyl 6-((4-(1-(2-ethyl-2-hydroxybutyl)piperidin-4-yl)-1H-1,2,3-triazol-1-yl)methyl)nicotinate, 0.140 g, 58.9%, yellow oil).

[Step 2] Synthesis of methyl 6-((4-(1-(2-fluoro-2-methylpropyl)piperidin-4-yl)-1H-1,2,3-triazol-1-yl)methyl)nicotinate

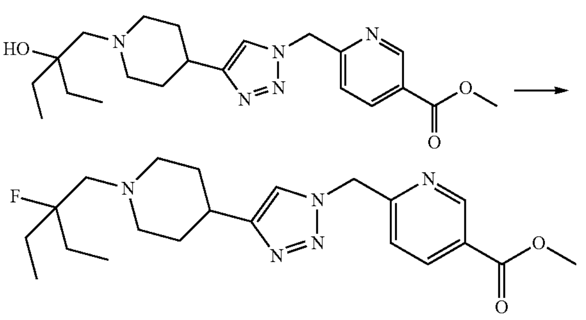

The methyl 6-((4-(1-(2-ethyl-2-hydroxybutyl)piperidin-4-yl)-1H-1,2,3-triazol-1-yl)methyl)nicotinate(0.100 g, 0.249 mmol) prepared in step 1 and diethylaminosulfur trifluoride (0.039 mL, 0.299 mmol) were dissolved in dichloromethane (10 mL) at room temperature, after which the resulting solution was stirred at the same temperature for 3 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (methyl 6-((4-(1-(2-fluoro-2-methylpropyl)piperidin-4-yl)-1H-1,2,3-triazol-1-yl)methyl)nicotinate, 0.066 g, 70.6%, yellow solid).

[Step 3] Synthesis of 6-((4-(1-(2-ethyl-2-fluorobutyl)piperidin-4-yl)-1H-1,2,3-triazol-1-yl)methyl)nicotinohydrazide

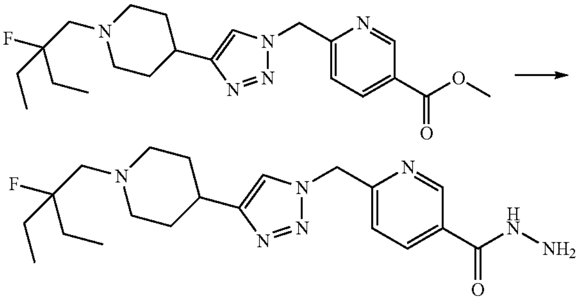

The methyl 6-((4-(1-(2-ethyl-2-fluorobutyl)piperidin-4-yl)-1H-1,2,3-triazol-1-yl)methyl)nicotinate (0.066 g, 0.164 mmol) prepared in step 2 and hydrazine monohydrate (0.079 mL, 1.636 mmol) were dissolved in ethanol (30 mL) at 90 °C, after which the resulting solution was stirred at the same temperature for 12 hours, and then a reaction was finished by lowering a temperature to room temperature. Solvent was removed from the reaction mixture under reduced pressure, after which the obtained product was used without an additional purification process (6-((4-(1-(2-ethyl-2-fluorobutyl)piperidin-4-yl)-1H-1,2,3-triazol-1-yl)methyl)nicotinohydrazide, 0.060 g, 90.9%, white solid).

[Step 4] Synthesis of Compound 3896

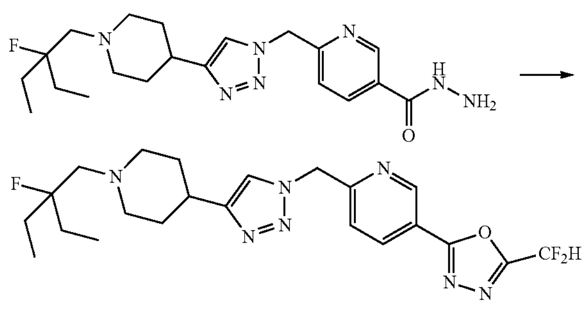

The 6-((4-(1-(2-ethyl-2-fluorobutyl)piperidin-4-yl)-1H-1,2,3-triazol-1-yl)methyl)nicotinohydrazide (0.060 g, 0.149 mmol) prepared in step 3, imidazole (0.030 g, 0.446 mmol) and 2,2-difluoroacetic anhydride (0.055 mL, 0.446 mmol) were mixed in dichloromethane (30 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 3%) and concentrated to obtain 2-(difluoromethyl)-5-(6-((4-(1-(2-ethyl-2-fluorobutyl)piperidin-4-yl)-1H-1,2,3-triazol-1-yl)methyl)pyridin-3-yl)-1,3,4-oxadiazole (0.039 g, 56.6%) in a white solid form.

$^1H$ NMR (400 MHz, $CDCl_3$) δ 9.32 (d, J=1.4 Hz, 1H), 8.39 (dd, J=8.2, 2.2 Hz, 1H), 7.47 (d, J=13.7 Hz, 1H), 7.33 (d, J=8.2 Hz, 1H), 7.09 (s, 0.2H), 6.96 (s, 0.5H), 6.83 (s, 0.3H), 5.74 (s, 2H), 3.06 (d, J=11.3 Hz, 2H), 2.79 (t, J=11.6 Hz, 1H), 2.56 (dd, J=25.7, 15.4 Hz, 2H), 2.30 (t, J=11.2 Hz, 2H), 2.01 (s, 2H), 1.74 (tt, J=15.0, 9.6 Hz, 6H), 0.89 (t, J=7.5 Hz, 6H); LRMS (ES) m/z 464.10 ($M^+$+1).

Example 84: Synthesis of compound 3914, 2-(difluoromethyl)-5-(6-((4-(1-methyl-1H-indol-6-yl)-1H-1,2,3-triazol-1-yl)methyl)pyridin-3-yl)-1,3,4-oxadiazole

[Step 1] Synthesis of 1-methyl-1H-indol-6-carbaldehyde

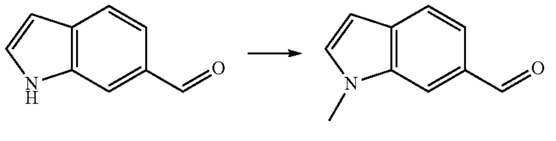

1H-indol-6-carbaldehyde (0.500 g, 3.444 mmol) and cesium carbonate (1.329 g, 6.889 mmol) were dissolved in acetonitrile (7 mL) at room temperature, after which the resulting solution was heated under reflux for 2 hours, and iodomethane (0.236 mL, 3.789 mmol) was added and heated again under reflux for 1 hour, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 1-methyl-1H-indol-6-carbaldehyde (0.200 g, 36.5%) in a colorless oil form.

[Step 2] Synthesis of 6-ethynyl-1-methyl-1H-indole

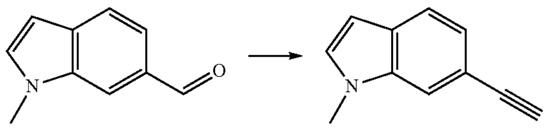

The 1-methyl-1H-indol-6-carbaldehyde (0.095 g, 0.597 mmol) prepared in step 1 and dimethyl(1-diazo-2-oxopropyl)phosphonate (0.134 mL, 0.895 mmol) were dissolved in methanol (2 mL) at room temperature, after which potassium carbonate (0.165 g, 1.194 mmol) was added to the resulting solution and stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%) and concentrated to obtain 6-ethynyl-1-methyl-1H-indole (0.080 g, 86.4%) in a light yellow solid form.

[Step 3] Synthesis of Compound 3914

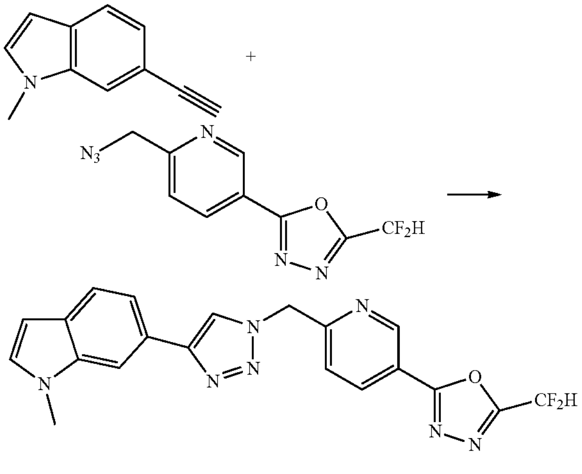

The 2-(6-(azidomethyl)pyridin-3-yl)-5-(difluoromethyl)-1,3,4-oxadiazole (0.050 g, 0.198 mmol) prepared in step 1 of example 16 and 6-ethynyl-1-methyl-1H-indole (0.031 g, 0.198 mmol) were dissolved in tert-butanol (1 mL)/water (1 mL) at room temperature, after which sodium ascorbate (1.00 M solution, 0.020 mL, 0.020 mmol) and copper(II) sulfate pentahydrate (0.50 M solution, 0.004 mL, 0.002 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure.

The resulting concentrate was purified via column chromatography ($SiO_2$, 4 g cartridge; dichloromethane/methanol=5 to 40%) and concentrated to obtain 2-(difluoromethyl)-5-(6-((4-(1-methyl-1H-indol-6-yl)-1H-1,2,3-triazol-1-yl)methyl)pyridin-3-yl)-1,3,4-oxadiazole (0.050 g, 61.9%) in a white solid form.

$^1H$ NMR (400 MHz, $CD_3OD$) δ 9.30 (s, 1H), 8.71 (s, 1H), 8.57-8.50 (m, 2H), 7.79-7.71 (m, 2H), 7.67 (d, J=8.2 Hz, 1H), 7.61 (d, J=8.4 Hz, 1H), 7.26 (t, J=51.6 Hz, 1H), 6.71 (d, J=3.7 Hz, 1H), 5.94 (s, 2H), 4.10 (s, 3H); LRMS (ES) m/z 408.3 ($M^+$+1).

Example 85: Synthesis of compound 3915, 1-(3-(1-((5-(5-(difluoromethyl)-1,3,4-oxadiazol-2-yl)pyridin-2-yl)methyl)-1H-1,2,3-triazol-4-yl)phenyl)-N,N-dimethylmethanamine

[Step 1] Synthesis of 3-(1-((5-(5-(difluoromethyl)-1,3,4-oxadiazol-2-yl)pyridin-2-yl)methyl)-1H-1,2,3-triazol-4-yl)benzaldehyde

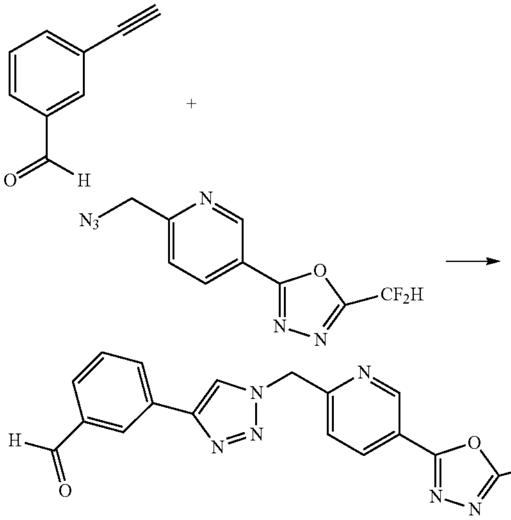

The 2-(6-(azidomethyl)pyridin-3-yl)-5-(difluoromethyl)-1,3,4-oxadiazole (0.250 g, 0.991 mmol) prepared in step 1 of example 16 and 3-ethynylbenzaldehyde (0.129 g, 0.991 mmol) were dissolved in tert-butanol (1 mL)/water (1 mL) at room temperature, after which sodium ascorbate (1.00 M solution, 0.099 mL, 0.099 mmol) and copper(II) sulfate pentahydrate (0.50 M solution, 0.020 mL, 0.010 mmol) were added to the resulting solution and stirred at the same temperature for 18 hours. Saturated ammonium aqueous solution was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=10 to 50%) and concentrated to obtain 3-(1-((5-(5-(difluoromethyl)-1,3,4-oxadiazol-2-yl)pyridin-2-yl)methyl)-1H-1,2,3-triazol-4-yl)benzaldehyde (0.300 g, 79.2%) in a light yellow solid form.

[Step 2] Synthesis of Compound 3915

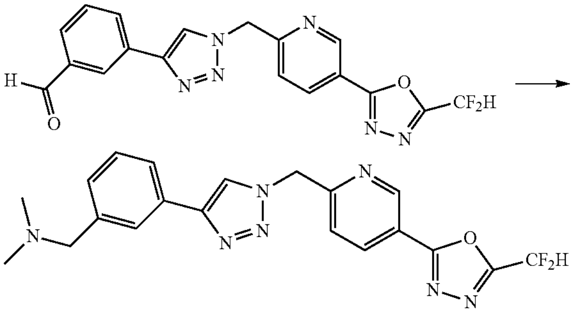

The 3-(1-((5-(5-(difluoromethyl)-1,3,4-oxadiazol-2-yl)pyridin-2-yl)methyl)-1H-1,2,3-triazol-4-yl)benzaldehyde (0.030 g, 0.078 mmol) prepared in step 1 and dimethylamine (2.00 M solution, 0.039 mL, 0.078 mmol) were dissolved in dichloromethane (0.7 mL) at room temperature, after which sodium triacetoxyborohydride (0.050 mL, 0.235 mmol) was added into the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 1-(3-(1-((5-(5-(difluoromethyl)-1,3,4-oxadiazol-2-yl)pyridin-2-yl)methyl)-1H-1,2,3-triazol-4-yl)phenyl)-N,N-dimethylmethanamine (0.015 g, 46.5%) in a colorless oil form.

$^1H$ NMR (400 MHz, $CD_3OD$) δ 9.31-9.26 (m, 1H), 8.53 (dd, J=8.2, 2.3 Hz, 1H), 8.50 (s, 1H), 7.85-7.78 (m, 2H), 7.60 (d, J=8.2 Hz, 1H), 7.46 (t, J=7.6 Hz, 1H), 7.38-7.33 (m, 1H), 7.26 (t, J=51.6 Hz, 1H), 5.93 (s, 2H), 3.59 (s, 2H), 2.31 (s, 6H); LRMS (ES) m/z 412.3 ($M^+$+1).

The compounds of table 21 were synthesized according to substantially the same process as described above in the synthesis of compound 3915 with an exception of using 3-(1-((5-(5-(difluoromethyl)-1,3,4-oxadiazol-2-yl)pyridin-2-yl)methyl)-1H-1,2,3-triazol-4-yl)benzaldehyde and the reactant of table 20.

TABLE 20

| Example | Compound No. | Reactant | Yield (%) |
|---|---|---|---|
| 86 | 3916 | Morpholine | 61 |
| 87 | 3917 | 1-methylpiperazine | 51 |
| 88 | 3918 | N1,N1,N2-trimethylethane-1,2-diamine | 49 |
| 89 | 3919 | Methylamine | 48 |
| 108 | 3963 | Azetidine hydrochloride | 60 |
| 109 | 3964 | 3-fluoro azetidine hydrochloride | 60 |
| 110 | 3965 | 2-oxa-6-azaspiro[3.3]heptane oxalic acid | 49 |
| 111 | 3966 | Pyrrolidine | 64 |
| 284 | 4400 | 3,3-difluoroazetidine | 49 |
| 285 | 4401 | 4,4-difluoropiperidine | 55 |

TABLE 21

| Example | Compound No. | Compound Name, 1H-NMR, MS (ESI) |
|---|---|---|
| 86 | 3916 | 4-(3-(1-((5-(5-(difluoromethyl)-1,3,4-oxadiazol-2-yl)pyridin-2-yl)methyl)-1H-1,2,3-triazol-4-yl)benzyl)morpholine $^1$H NMR (400 MHz, $CD_3OD$) δ 8.00 (dd, J = 2.2, 0.9 Hz, 1H), 7.25 (dd, J = 8.2, 2.3 Hz, 1H), 7.23 (s, 1H), 6.58 (t, J = 1.8 Hz, 1H), 6.50 (dt, J = 7.7, 1.5 Hz, 1H), 6.32 (dd, J = 8.3, 0.9 Hz, 1H), 6.16 (t, J = 7.6 Hz, 1H), 6.12-5.84 (m, 2H), 4.65 (s, 2H), 2.47-2.40 (m, 4H), 2.32 (s, 2H), 1.23 (t, J = 4.7 Hz, 4H); LRMS (ES) m/z 454.3 ($M^+$ + 1). |
| 87 | 3917 | 2-(difluoromethyl)-5-(6-((4-(3-((4-methylpiperazin-1-yl)methyl)phenyl)-1H-1,2,3-triazol-1-yl)methyl)pyridin-3-yl)-1,3,4-oxadiazole $^1$H NMR (400 MHz, $CD_3OD$) δ 7.60 (d, J =2.2 Hz, 1H), 6.85 (dd, J =8.2, 2.3 Hz, 1H), 6.82 (s, 1H), 6.17 (d, J = 1.8 Hz, 1H), 6.10 (dt, J = 7.6, 1.6 Hz, 1H), 5.92 (d, J = 8.2 Hz, 1H), 5.76 (t, J = 7.6 Hz, 1H), 5.70-5.66 (m, 1H), 5.58 (t, J = 51.6 Hz, 1H), 4.25 (s, 2H), 1.95 (s, 2H), 0.90 (s, 8H), 0.66 (s, 3H); LRMS (ES) m/z 467.3 ($M^+$ + 1). |
| 88 | 3918 | N1-(3-(1-((5-(5-(difluoromethyl)-1,3,4-oxadiazol-2-yl)pyridin-2-yl)methyl)-1H-1,2,3-triazol-4-yl)benzyl)-N1,N2,N2-trimethylethane-1,2-diamine $^1$H NMR (400 MHz, $CD_3OD$) δ 9.28 (d, J = 2.2 Hz, 1H), 8.53 (dd, J = 8.2, 2.2 Hz, 1H), 8.50 (s, 1H), 7.86 (s, 1H), 7.78 (d, J = 8.0 Hz, 1H), 7.61 (d, J = 8.3 Hz, 1H), 7.44 (t, J = 7.7 Hz, 1H), 7.37 (d, J = 7.8 Hz, 1H), 7.26 (t, J = 51.6 Hz, 1H), 5.93 (s, 2H), 3.63 (s, 2H), 3.37 (s, 4H), 2.60 (s, 3H), 2.29 (s, 6H); LRMS (ES) m/z 369.3 ($M^+$ + 1). |
| 89 | 3919 | 1-(3-(1-((5-(5-(difluoromethyl)-1,3,4-oxadiazol-2-yl)pyridin-2-yl)methyl)-1H-1,2,3-triazol-4-yl)phenyl)-N-methylmethanamine $^1$H NMR (400 MHz, $CD_3OD$) δ 9.28 (d, J = 2.2 Hz, 1H), 8.53 (dd, J = 8.2, 2.3 Hz, 1H), 8.50 (s, 1H), 7.85 (s, 1H), 7.80 (d, J = 7.7 Hz, 1H), 7.61 (d, J = 8.1 Hz, 1H), 7.46 (t, J = 7.7 Hz, 1H), 7.40-7.12 (m, 2H), 5.93 (s, 2H), 3.83 (s, 2H), 2.45 (s, 3H); LRMS (ES) m/z 398.3 ($M^+$ + 1). |
| 108 | 3963 | 2-(6-((4-(3-(azetidin-1-ylmethyl)phenyl)-1H-1,2,3-triazol-1-yl)methyl)pyridin-3-yl)-5-(difluoromethyl)-1,3,4-oxadiazole $^1$H NMR (400 MHz, $CD_3OD$) δ 9.31-9.25 (m, 1H), 8.53 (dd, J = 8.2, 2.2 Hz, 1H), 8.51 (s, 1H), 7.84-7.77 (m, 2H), 7.61 (d, J = 8.2 Hz, 1H), 7.45 (t, J = 7.6 Hz, 1H), 7.34 (d, J = 8.0 Hz, 1H), 7.26 (t, J = 51.6 Hz, 1H), 5.93 (s, 2H), 3.80 (s, 2H), 3.48 (t, J = 7.3 Hz, 4H), 2.21 (p, J = 7.3 Hz, 2H); LRMS (ES) m/z 424.3 ($M^+$ + 1). |
| 109 | 3964 | 2-(difluoromethyl)-5-(6-((4-(3-((3-fluoroazetidin-1-yl)methyl)phenyl)-1H-1,2,3-triazol-1-yl)methyl)pyridin-3-yl)-1,3,4-oxadiazole $^1$H NMR (400 MHz, $CD_3OD$) δ 9.28 (d, J = 2.2 Hz, 1H), 8.53 (dd, J = 8.2, 2.3 Hz, 1H), 8.50 (d, J = 1.8 Hz, 1H), 7.88-7.75 (m, 2H), 7.60 (d, J = 8.2 Hz, 1H), 7.44 (td, J = 7.6, 2.8 Hz, 1H), 7.33 (d, J = 7.7 Hz, 1H), 7.26 (t, J = 51.6 Hz, 1H),5.93 (s, 2H), 5.26-5.04 (m, 1H), 3.77 (s, 2H), 3.74-3.61 (m, 2H), 3.41-3.33 (m, 7H); LRMS (ES) m/z 442.3 ($M^+$ + 1). |
| 110 | 3965 | 6-(3-(1-((5-(5-(difluoromethyl)-1,3,4-oxadiazol-2-yl)pyridin-2-yl)methyl)-1H-1,2,3-triazol-4-yl)benzyl)-2-oxa-6-azaspiro[3.3]heptane $^1$H NMR (400 MHz, $CD_3OD$) δ 7.78-7.73 (m, 1H), 7.00 (dd, J = 8.2, 2.3 Hz, 1H), 6.97 (s, 1H), 6.25 (dd, J = 7.4, 1.4 Hz, 2H), 6.08 (d, J = 8.2 Hz, 1H), 5.90 (td, J = 7.4, 1.0 Hz, 1H), 5.77 (dt, J = 7.6, 1.5 Hz, 1H), 5.73 (t, J = 51.6 Hz, 1H), 4.40 (s, 2H), 3.22 (s, 4H), 2.13 (s, 2H), 1.96 (s, 4H); LRMS (ES) m/z 466.4 ($M^+$ + 1). |
| 111 | 3966 | 2-(difluoromethyl)-5-(6-((4-(3-(pyrrolidin-1-ylmethyl)phenyl)-1H-1,2,3-triazol-1-yl)methyl)pyridin-3-yl)-1,3,4-oxadiazole $^1$H NMR (400 MHz, $CD_3OD$) δ 9.31-9.25 (m, 1H), 8.53 (dd, J = 8.2, 2.2 Hz, 1H), 8.50 (s, 1H), 7.86 (d, J = 1.8 Hz, 1H), 7.80 (dt, J = 7.7, 1.5 Hz, 1H), 7.60 (d, J = 8.2 Hz, 1H), 7.45 (t, J = 7.7 Hz, 1H), 7.40-7.36 (m, 1H), 7.26 (d, J = 51.6 Hz, 1H), 5.93 (s, 2H), 3.77 (s, 2H), 2.71-2.63 (m, 4H), 1.86 (p, J = 3.2 Hz, 4H); LRMS (ES) m/z 438.3 ($M^+$ + 1). |
| 284 | 4400 | 2-(6-((4-(3-((3,3-difluoroazetidin-1-yl)methyl)phenyl)-1H-1,2,3-triazol-1-yl)methyl)pyridin-3-yl)-5-(difluoromethyl)-1,3,4-oxadiazole $^1$H NMR (400 MHz, $CD_3OD$) δ 9.28 (dd, J = 2.3, 0.8 Hz, 1H), 8.56-8.48 (m, 2H), 7.83 (d, J = 1.9 Hz, 1H), 7.79 (dt, J = 7.7, 1.5 Hz, 1H),7.60 (dd, J = 8.2, 0.9 Hz, 1H), 7.44 (t, J = 7.6 Hz, 1H), 7.35 (dt, J = 7.9, 1.4 Hz, 1H), 7.26 (t, J = 51.6 Hz, 1H), 5.93 (s, 2H), 3.84 (d, J = 1.9 Hz, 2H), 3.68 (t, J = 12.1 Hz, 4H); LRMS (ES) m/z 460.3 ($M^+$ + 1). |
| 285 | 4401 | 2-(difluoromethyl)-5-(6-((4-(3-((4,4-difluoropiperidin-1-yl)methyl)phenyl)-1H-1,2,3-triazol-1-yl)methyl)pyridin-3-yl)-1,3,4-oxadiazole $^1$H NMR (400 MHz, $CD_3OD$) δ 9.28 (d, J = 2.3 Hz, 1H), 8.52 (d, J = 11.6 Hz, 2H), 7.86 (d, J = 2.1 Hz, 1H), 7.77 (d, J = 7.7 Hz, 1H), 7.60 (d, J = 8.2 Hz, 1H), 7.44 (t, J = 7.6 Hz, 1H), 7.37 (d, J = 7.6 Hz, 1H), 7.26 (t, J = 51.6 Hz, 1H), 5.93 (s, 2H), 3.65 (s, 2H), 2.62 (t, J = 5.8 Hz, 4H), 2.01 (ddt, J = 19.4, 12.6, 5.6 Hz, 4H); LRMS (ES) m/z 488.5 ($M^+$ + 1). |

Example 92: Synthesis of compound 3944, 4-((6-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine

[Step 1] Synthesis of 3-(morpholinomethyl)-1H-indol-6-carbaldehyde

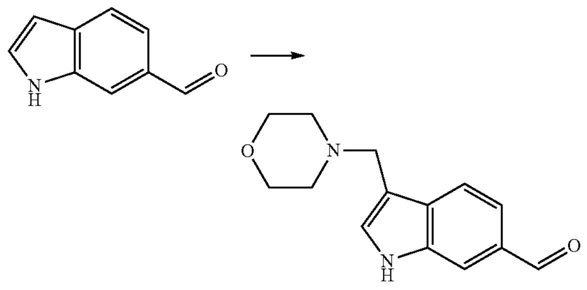

Morpholine (0.238 mL, 2.755 mmol) and formaldehyde (37.00%, 0.224 g, 2.755 mmol) were dissolved in acetic acid (3 mL), after which the resulting solution was stirred at 0 °C for 0.4 hours, and then 1H-indol-6-carbaldehyde (0.260 g, 1.791 mmol) was added and further stirred at room temperature for 18 hours. TN-sodium hydroxide aqueous solution was poured into the resulting reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 60%) and concentrated to obtain 3-(morpholinomethyl)-1H-indol-6-carbaldehyde (0.180 g, 26.7%) in a light yellow oil form.

[Step 2] Synthesis of 4-((6-ethynyl-1H-indol-3-yl)methyl)morpholine

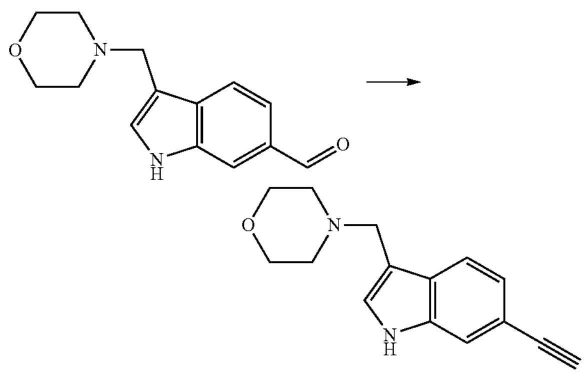

The 3-(morpholinomethyl)-1H-indol-6-carbaldehyde (0.100 g, 0.409 mmol) prepared in step 1, dimethyl(1-diazo-2-oxopropyl)phosphonate (0.094 g, 0.491 mmol) and potassium carbonate (0.113 g, 0.819 mmol) were dissolved in methanol (3 mL) at room temperature, after which the resulting solution was stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=90 to 40%) and concentrated to obtain 4-((6-ethynyl-1H-indol-3-yl)methyl)morpholine (0.050 g, 50.8%) in a white solid form.

[Step 3] Synthesis of Compound 3944

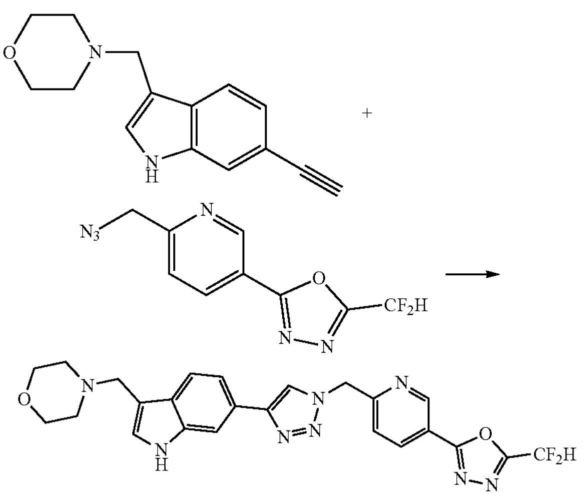

The 2-(6-(azidomethyl)pyridin-3-yl)-5-(difluoromethyl)-1,3,4-oxadiazole (0.030 g, 0.119 mmol) prepared in step 1 of example 16 and the 4-((6-ethynyl-1H-indol-3-yl)methyl) morpholine (0.026 g, 0.107 mmol) prepared in step 2 were dissolved in tert-butanol (1 mL)/water (1 mL) at room temperature, after which sodium ascorbate (1.00 M solution, 0.012 mL, 0.012 mmol) and copper(II) sulfate pentahydrate (0.50 M solution, 0.002 mL, 0.001 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 4-((6-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine (0.025 g, 42.7%) in a white solid form.

$^1H$ NMR (400 MHz, $CD_3OD$) δ 9.30 (dd, J=2.2, 0.9 Hz, 1H), 8.54 (dd, J=8.2, 2.3 Hz, 1H), 8.44 (s, 1H), 7.90 (dd, J=1.5, 0.7 Hz, 1H), 7.75 (dd, J=8.3, 0.8 Hz, 1H), 7.60 (d, J=8.0 Hz, 1H), 7.53 (dd, J=8.3, 1.5 Hz, 1H), 7.30 (s, 1H), 7.26 (t, J=51.6 Hz, 1H), 5.93 (s, 2H), 3.77 (s, 2H), 3.71 (t, J=4.7 Hz, 4H), 2.58 (s, 4H); LRMS (ES) m/z 393.3 ($M^+$+1).

The compounds of table 23 were synthesized according to substantially the same process as described above in the synthesis of compound 3944 with an exception of using 4-((6-ethynyl-1H-indol-3-yl)methyl)morpholine and the reactant of table 22.

TABLE 22

| Example | Compound No. | Reactant | Yield (%) |
|---|---|---|---|
| 169 | 4112 | 2-(4-(bromomethyl)-3-fluorophenyl)-5-(difluoromethyl)-1,3,4-oxadiazole | 36 |
| 174 | 4134 | 2-(4-(azidomethyl)pyridyl)-5-(difluoromethyl)-1,3,4-oxadiazole | 42 |

TABLE 23

| Example | Compound No. | Compound Name, $^1$H-NMR, MS (ESI) |
|---|---|---|
| 169 | 4112 | 4-((6-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine<br>$^1$H NMR (400 MHz, $CD_3OD$) δ 8.38 (s, 1H), 8.03-7.93 (m, 2H), 7.89 (dd, J = 1.5, 0.7 Hz, 1H), 7.74 (dd, J = 8.3, 0.7 Hz, 1H), 7.61 (t, J = 7.6 Hz, 1H), 7.51 (dd, J = 8.3, 1.5 Hz, 1H), 7.30 (s, 1H), 7.24 (t, J = 51.6 Hz, 1H), 5.86 (s, 2H), 3.77 (s, 2H), 3.71 (t, J = 4.7 Hz, 4H), 2.61-2.53 (m, 4H); LRMS (ES) m/z 510.1 ($M^+$ + 1). |
| 171 | 4134 | 4-((6-(1-(4-(5-(difluoromethyl)-1,3,4-oxadiazol-2-yl)benzyl)-1H-1,2,3-triazol-4-yl)-1H-indol-3-yl)methyl)morpholine<br>$^1$H NMR (400 MHz, $CDCl_3$) δ 8.04 (d, J = 8.0 Hz, 2H), 7.98 (s, 1H), 7.88 (s, 1H), 7.59 (d, J = 12.5 Hz, 2H), 7.43 (t, J = 7.5 Hz, 3H), 6.80 (d, J = 51.8 Hz, 1H), 5.63 (s, 2H), 4.34 (s, 2H), 3.98-3.82 (m, 4H), 3.32-3.26 (m, 2H), 2.96-2.87 (m, 2H); LRMS (ES) m/z 492.5 ($M^+$ + 1). |

Example 93: Synthesis of compound 3945, 2-(difluoromethyl)-5-(6-((2-methyl-4-phenyl-1H-imidazol-1-yl)methyl)pyridin-3-yl)-1,3,4-oxadiazole

[Step 1] Synthesis of 2-(6-((4-bromo-2-methyl-1H-imidazol-1-yl)methyl)pyridin-3-yl)-5-(difluoromethyl)-1,3,4-oxadiazole

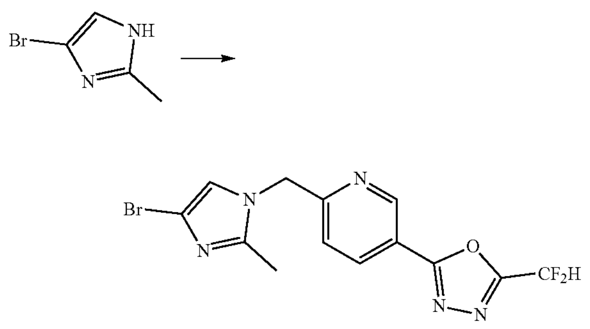

4-bromo-2-methyl-1H-imidazole (0.200 g, 1.242 mmol), 2-(6-(bromomethyl)pyridin-3-yl)-5-(difluoromethyl)-1,3,4-oxadiazole (0.360 g, 1.242 mmol) and potassium carbonate (0.343 g, 2.484 mmol) were dissolved in N,N-dimethylformamide (5 mL) at room temperature, after which the resulting solution was stirred at the same temperature for 3 hours. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(6-((4-bromo-2-methyl-1H-imidazol-1-yl)methyl)pyridin-3-yl)-5-(difluoromethyl)-1,3,4-oxadiazole (0.308 g, 67.0%) in a yellow solid form.

[Step 2] Synthesis of Compound 3945

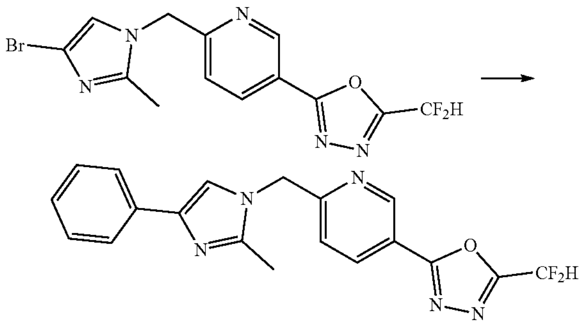

The 2-(6-((4-bromo-2-methyl-1H-imidazol-1-yl)methyl)pyridin-3-yl)-5-(difluoromethyl)-1,3,4-oxadiazole (0.100 g, 0.270 mmol) prepared in step 1, phenylboronic acid (0.033 g, 0.270 mmol), [1,1'-bis(di-tert-butylphosphino)ferrocene] palladium(II) dichloride ($Pd(dtbpf)Cl_2$, 0.018 g, 0.027 mmol) and cesium carbonate (0.156 g, 0.810 mmol) were mixed in 1,4-dioxane (3 mL)/water (1 mL) at room temperature, after which the resulting mixture was irradiated with microwaves, then heated at 100 °C for 20 minutes, and then a reaction was finished by lowering a temperature to room temperature. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(6-((2-methyl-4-phenyl-1H-imidazol-1-yl)methyl)pyridin-3-yl)-1,3,4-oxadiazole (0.032 g, 32.2%) in a brown solid form.

$^1$H NMR (400 MHz, $CD_3OD$) δ 9.28 (d, J=2.2 Hz, 1H), 8.50 (dd, J=8.2, 2.3 Hz, 1H), 7.75-7.68 (m, 2H), 7.51 (s, 1H), 7.44 (dd, J=8.3, 3.0 Hz, 1H), 7.40-7.33 (m, 2H), 7.27-7.11 (m, 2H), 5.43 (d, J=23.7 Hz, 2H), 2.41 (d, J=29.3 Hz, 3H); LRMS (ES) m/z 368.2 ($M^{+}$+1).

Example 94: Synthesis of compound 3949, 2-(6-((4-bromo-1H-imidazol-1-yl)methyl)pyridin-3-yl)-5-(difluoromethyl)-1,3,4-oxadiazole

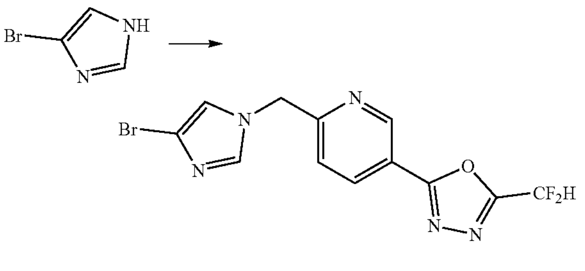

4-bromo-1H-imidazole (0.200 g, 1.361 mmol), 2-(6-(bromomethyl)pyridin-3-yl)-5-(difluoromethyl)-1,3,4-oxadiazole (0.395 g, 1.361 mmol) and potassium carbonate (0.376 g, 2.721 mmol) were dissolved in N,N-dimethylformamide (5 mL) at room temperature, after which the resulting solution was stirred at the same temperature for 3 hours. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(6-((4-bromo-1H-imidazol-1-yl)methyl)pyridin-3-yl)-5-(difluoromethyl)-1,3,4-oxadiazole (0.344 g, 71.0%) in a yellow solid form.

$^{1}$H NMR (400 MHz, $CD_3OD$) δ 9.26 (dd, J=2.3, 0.9 Hz, 1H), 8.51 (dd, J=8.2, 2.2 Hz, 1H), 7.81 (d, J=1.5 Hz, 1H), 7.51 (dd, J=8.2, 0.9 Hz, 1H), 7.30 (d, J=1.5 Hz, 1H), 7.26 (t, J=51.6 Hz, 1H), 5.47 (s, 2H); LRMS (ES) m/z 358.1 ($M^{+}$+1).

Example 95: Synthesis of compound 3950, 2-(difluoromethyl)-5-(6-((4-phenyl-1H-imidazol-1-yl)methyl)pyridin-3-yl)-1,3,4-oxadiazole

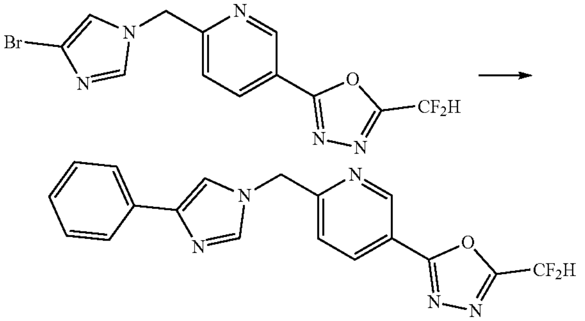

The 2-(6-((4-bromo-1H-imidazol-1-yl)methyl)pyridin-3-yl)-5-(difluoromethyl)-1,3,4-oxadiazole (0.100 g, 0.281 mmol), which is compound 3949 of example 94, phenylboronic acid (0.034 g, 0.281 mmol), [1,1'-bis(di-tert-butylphosphino)ferrocene]palladium(II) dichloride (Pd(dtbpf)$Cl_2$, 0.018 g, 0.028 mmol) and cesium carbonate (0.163 g, 0.842 mmol) were mixed in 1,4-dioxane (3 mL)/water (1 mL) at room temperature, after which the resulting mixture was irradiated with microwaves, then heated at 100 °C for 20 minutes, and then a reaction was finished by lowering a temperature to room temperature. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(6-((4-phenyl-1H-imidazol-1-yl)methyl)pyridin-3-yl)-1,3,4-oxadiazole (0.007 g, 7.1%) in a brown oil form.

$^{1}$H NMR (400 MHz, $CD_3OD$) δ 9.27 (ddd, J=7.2, 2.2, 0.8 Hz, 1H), 8.50 (dt, J=8.2, 1.9 Hz, 1H), 7.86 (dd, J=44.8, 1.4 Hz, 1H), 7.76-7.69 (m, 1H), 7.60 (d, J=1.4 Hz, 1H), 7.51 (dd, J=8.2, 3.8 Hz, 1H), 7.44-7.32 (m, 2H), 7.31-7.11 (m, 2H), 5.49 (d, J=22.3 Hz, 2H); LRMS (ES) m/z 353.3 ($M^{+}$+1).

Example 96: Synthesis of compound 3951, 2-(difluoromethyl)-5-(6-((4-(1-ethylazetidin-3-yl)-1H-1,2,3-triazol-1-yl)methyl)pyridin-3-yl)-1,3,4-oxadiazole

[Step 1] Synthesis of 2-(6-((4-(azetidin-3-yl)-1H-1,2,3-triazol-1-yl)methyl)pyridin-3-yl)-5-(difluoromethyl)-1,3,4-oxadiazole

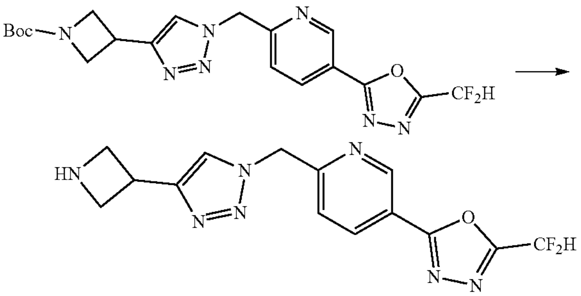

The tert-butyl 3-(1-((5-(5-(difluoromethyl)-1,3,4-oxadiazol-2-yl)pyridin-2-yl)methyl)-1H-1,2,3-triazol-4-yl)azetidin-1-carboxylate (0.625 g, 1.442 mmol) prepared in example 91 and trifluoroacetic acid (1.104 mL, 14.420 mmol) were dissolved in dichloromethane (10 mL) at room temperature, after which the resulting solution was stirred at the same temperature for 4 hours. Solvent was removed from the reaction mixture under reduced pressure, after which the obtained product was used without an additional purification process (2-(6-((4-(azetidin-3-yl)-1H-1,2,3-triazol-1-yl)methyl)pyridin-3-yl)-5-(difluoromethyl)-1,3,4-oxadiazole, 0.480 g, 99.9%, yellow oil).

[Step 2] Synthesis of Compound 3951

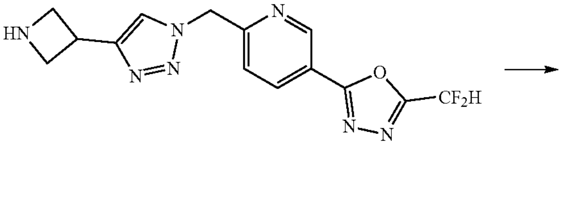

-continued

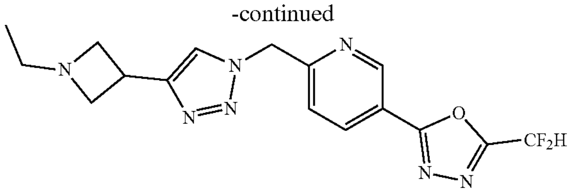

The 2-(6-((4-(azetidin-3-yl)-1H-1,2,3-triazol-1-yl)methyl)pyridin-3-yl)-5-(difluoromethyl)-1,3,4-oxadiazole (0.040 g, 0.120 mmol) prepared in step 1, and acetaldehyde (0.013 mL, 0.240 mmol) were dissolved in dichloromethane (1 mL), after which the resulting solution was stirred at room temperature for 15 minutes, and then sodium triacetoxyborohydride (0.076 g, 0.360 mmol) was added and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(6-((4-(1-ethylpiperidin-3-yl)-1H-1,2,3-triazol-1-yl)methyl)pyridin-3-yl)-1,3,4-oxadiazole (0.013 g, 30.0%) in a white solid form.

$^1$H NMR (400 MHz, $CD_3OD$) δ 9.25 (dd, J=2.2, 0.9 Hz, 1H), 8.51 (dd, J=8.2, 2.2 Hz, 1H), 8.08 (s, 1H), 7.56 (dd, J=8.2, 0.9 Hz, 1H), 7.26 (t, J=51.6 Hz, 1H), 5.86 (s, 2H), 4.03-3.91 (m, 3H), 3.60 (s, 2H), 2.82 (q, J=7.3 Hz, 2H), 1.09 (t, J=7.2 Hz, 3H); LRMS (ES) m/z 362.3 ($M^+$+1).

The compounds of table 25 were synthesized according to substantially the same process as described above in the synthesis of compound 3951 with an exception of using 2-(6-((4-(azetidin-3-yl)-1H-1,2,3-triazol-1-yl)methyl)pyridin-3-yl)-5-(difluoromethyl)-1,3,4-oxadiazole and the reactant of table 24.

TABLE 24

| Example | Compound No. | Reactant | Yield (%) |
|---|---|---|---|
| 97 | 3952 | Acetone | 76 |
| 98 | 3953 | Butyraldehyde | 77 |
| 99 | 3954 | Cyclobutanone | 60 |
| 100 | 3955 | Oxetanone | 62 |

TABLE 25

| Example | Compound No. | Compound Name, $^1$H-NMR, MS (ESI) |
|---|---|---|
| 97 | 3952 | 2-(difluoromethyl)-5-(6-((4-(1-isopropylazetidin-3-yl)-1H-1,2,3-triazol-1-yl)methyl)pyridin-3-yl)-1,3,4-oxadiazole<br>$^1$H NMR (400 MHz, $CD_3OD$) δ 9.25 (dd, J = 2.3, 0.9 Hz, 1H), 8.51 (dd, J = 8.2, 2.2 Hz, 1H), 8.09 (s, 1H), 7.57 (dd, J = 8.2, 0.8 Hz, 1H), 7.26 (t, J = 51.6 Hz, 1H), 5.86 (s, 2H), 4.07-3.99 (m, 2H), 3.99-3.87 (m, 1H), 3.67 (t, J = 7.8 Hz, 2H), 2.90 (p, J = 6.3 Hz, 1H), 1.10 (d, J = 6.3 Hz, 6H); LRMS (ESI) m/z 376.3 ($M^+$ + H). |
| 98 | 3953 | 2-(6-((4-(1-butylazetidin-3-yl)-1H-1,2,3-triazol-1-yl)methyl)pyridin-3-yl)-5-(difluoromethyl)-1,3,4-oxadiazole<br>$^1$H NMR (400 MHz, DMSO-$d_6$) δ 9.19 (dd, J = 2.3, 0.9 Hz, 1H), 8.48 (dd, J = 8.2, 2.3 Hz, 1H), 8.19 (s, 1H), 7.59 (t, J = 51.3 Hz, 1H), 7.52 (dd, J = 8.2, 0.9 Hz, 1H), 5.85 (s, 2H), 3.87 (s, 3H), 3.47 (s, 2H), 2.69 (s, 2H), 1.32 (qt, J = 5.7, 3.4 Hz, 4H), 0.92-0.84 (m, 3H); LRMS (ESI) m/z 390.3 ($M^+$ + H). |
| 99 | 3954 | 2-(6-((4-(1-cyclobutylazetidin-3-yl)-1H-1,2,3-triazol-1-yl)methyl)pyridin-3-yl)-5-(difluoromethyl)-1,3,4-oxadiazole<br>$^1$H NMR (400 MHz, DMSO-$d_6$) δ 9.19 (dd, J = 2.3, 0.8 Hz, 1H), 8.48 (dd, J = 8.2, 2.3 Hz, 1H), 8.19 (s, 1H), 7.58 (t, J = 51.2 Hz, 1H), 7.52 (dd, J = 8.2, 0.9 Hz, 1H), 5.85 (s, 2H), 3.82 (s, 3H), 3.51 (s, 3H), 2.00 (dd, J = 10.7, 5.9 Hz, 2H), 1.95-1.83 (m, 2H), 1.80-1.61 (m, 2H); LRMS (ESI) m/z 388.3 ($M^+$ + H). |
| 100 | 3955 | 2-(difluoromethyl)-5-(6-((4-(1-(oxetan-3-yl)azetidin-3-yl)-1H-1,2,3-triazol-1-yl)methyl)pyridin-3-yl)-1,3,4-oxadiazole<br>$^1$H NMR (400 MHz, $CD_3OD$) δ 9.26 (dd, J = 2.3, 0.9 Hz, 1H), 8.51 (dd, J = 8.2, 2.3 Hz, 1H), 8.09 (d, J = 0.5 Hz, 1H), 7.55 (dd, J = 8.2, 0.8 Hz, 1H), 7.26 (t, J = 51.6 Hz, 1H), 5.85 (s, 2H), 4.77 (td, J = 6.7, 0.6 Hz, 2H), 4.56 (ddd, J = 6.8, 5.0, 0.6 Hz, 2H), 3.98-3.85 (m, 2H), 3.85-3.76 (m, 2H), 3.51-3.42 (m, 2H); LRMS (ESI) m/z 390.3 ($M^+$ + H). |

Example 101: Synthesis of compound 3956, 1-(3-(1-((5-(5-(difluoromethyl)-1,3,4-oxadiazol-2-yl)pyridin-2-yl)methyl)-1H-1,2,3-triazol-4-yl)azetidin-1-yl)ethan-1-one

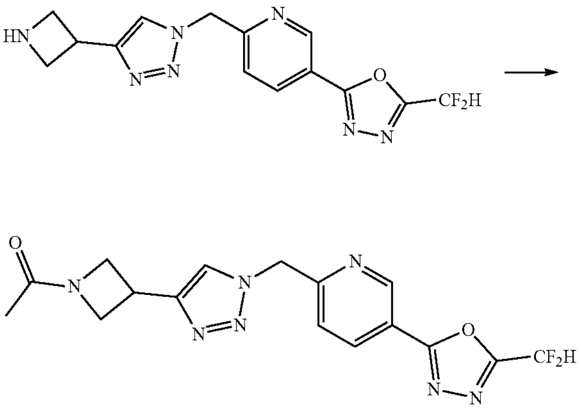

The 2-(6-((4-(azetidin-3-yl)-1H-1,2,3-triazol-1-yl)methyl)pyridin-3-yl)-5-(difluoromethyl)-1,3,4-oxadiazole (0.040 g, 0.120 mmol) prepared in step 1 of example 96, and N,N-diisopropylethylamine (0.042 mL, 0.240 mmol) were dissolved in dichloromethane (1 mL) at room temperature, after which acetyl chloride (0.010 mL, 0.144 mmol) was added to the resulting solution and stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 5%) and concentrated to obtain 1-(3-(1-((5-(5-(difluoromethyl)-1,3,4-oxadiazol-2-yl)pyridin-2-yl)methyl)-1H-1,2,3-triazol-4-yl)azetidin-1-yl)ethan-1-one (0.028 g, 62.2%) in a white solid form.

$^1H$ NMR (400 MHz, $CD_3OD$) δ 9.28-9.23 (m, 1H), 8.51 (dd, J=8.2, 2.2 Hz, 1H), 8.13 (s, 1H), 7.56 (d, J=8.0 Hz, 1H), 7.26 (t, J=51.6 Hz, 1H), 5.87 (s, 2H), 4.63 (t, J=8.5 Hz, 1H), 4.45-4.33 (m, 2H), 4.15-4.00 (m, 2H), 1.92 (s, 3H); LRMS (ES) m/z 376.2 ($M^+$+1).

The compounds of table 27 were synthesized according to substantially the same process as described above in the synthesis of compound 3956 with an exception of using 2-(6-((4-(azetidin-3-yl)-1H-1,2,3-triazol-1-yl)methyl)pyridin-3-yl)-5-(difluoromethyl)-1,3,4-oxadiazole and the reactant of table 26.

TABLE 26

| Example | Compound No. | Reactant | Yield (%) |
|---|---|---|---|
| 102 | 3957 | Propionyl chloride | 36 |
| 103 | 3958 | Isobutyryl chloride | 45 |
| 104 | 3959 | Methyl carbonochloridate | 60 |

Example 107: Synthesis of compound 3962, 1-(6-(1-((5-(5-(difluoromethyl)-1,3,4-oxadiazol-2-yl)pyridin-2-yl)methyl)-1H-1,2,3-triazol-4-yl)-1H-indol-3-yl)-N,N-dimethylmethanamine

[Step 1] Synthesis of 3-((dimethylamino)methyl)-1H-indol-6-carbaldehyde

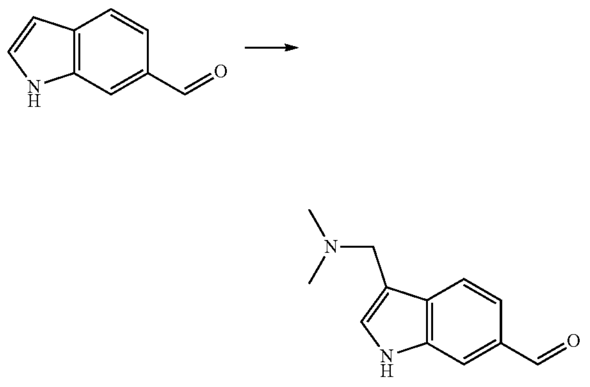

Dimethylamine (2.00 M solution in THF, 1.331 mL, 2.661 mmol) and formaldehyde (37.00%, 0.216 g, 2.661 mmol) were dissolved in acetic acid (3 mL), after which the resulting solution was stirred at 0 °C for 0.4 hours, and then 1H-indol-6-carbaldehyde (0.251 g, 1.730 mmol) was added and further stirred at room temperature for 18 hours. 1N-sodium hydroxide aqueous solution was poured into the resulting reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 60%) and concentrated to obtain 3-((dimethylamino)methyl)-1H-indol-6-carbaldehyde (0.070 g, 13.0%) in alight yellow oil form.

TABLE 27

| Example | Compound No. | Compound Name, $^1H$-NMR, MS (ESI) |
|---|---|---|
| 102 | 3957 | 1-(3-(1-((5-(5-(difluoromethyl)-1,3,4-oxadiazol-2-yl)pyridin-2-yl)methyl)-1H-1,2,3-triazol-4-yl)azetidin-1-yl)propan-1-one<br>$^1H$ NMR (400 MHz, $CD_3OD$) δ 9.26 (dd, J = 2.3, 0.9 Hz, 1H), 8.51 (dd, J = 8.2, 2.2 Hz, 1H), 8.12 (s, 1H), 7.56 (dd, J = 8.2, 0.8 Hz, 1H), 7.26 (t, J = 51.6 Hz, 1H), 5.87 (s, 2H), 4.62 (t, J = 8.4 Hz, 1H), 4.45-4.31 (m, 2H), 4.15 – 4.01 (m, 2H), 2.21 (q, J = 7.6 Hz, 2H), 1.13 (t, J = 7.6 Hz, 3H); LRMS (ESI) m/z 390.2 ($M^+$ + H). |
| 103 | 3958 | 1-(3-(1-((5-(5-(difluoromethyl)-1,3,4-oxadiazol-2-yl)pyridin-2-yl)methyl)-1H-1,2,3-triazol-4-yl)azetidin-1-yl)-2-methylpropan-1-one<br>$^1H$ NMR (400 MHz, $CD_3OD$) δ 9.26 (dd, J = 2.3, 0.9 Hz, 1H), 8.51 (dd, J = 8.2, 2.3 Hz, 1H), 8.12 (s, 1H), 7.56 (dd, J = 8.2, 0.9 Hz, 1H), 7.26 (t, J = 51.6 Hz, 1H), 5.87 (s, 2H), 4.71-4.62 (m, 1H), 4.45-4.35 (m, 2H), 4.15-4.03 (m, 2H), 2.60 (h, J = 6.8 Hz, 1H), 1.12 (dd, J = 6.8, 3.0 Hz, 6H); LRMS (ESI) m/z 404.2 ($M^+$ + H). |
| 104 | 3959 | Methyl 3-(1-((5-(5-(difluoromethyl)-1,3,4-oxadiazol-2-yl)pyridin-2-yl)methyl)-1H-1,2,3-triazol-4-yl)azetidin-1-carboxylate<br>$^1H$ NMR (400 MHz, $CD_3OD$) δ 9.25 (dd, J = 2.2, 0.9 Hz, 1H), 8.51 (dd, J = 8.2, 2.2 Hz, 1H), 8.11 (d, J = 0.5 Hz, 1H), 7.55 (dq, J = 8.2, 0.6 Hz, 1H), 7.26 (t, J = 51.6 Hz, 1H), 5.86 (s, 2H), 4.40 (t, J = 8.5 Hz, 2H), 4.14 (t, J = 7.2 Hz, 2H), 4.03 (dddd, J = 9.0, 8.4, 6.3, 5.7 Hz, 1H), 3.69 (s, 3H); LRMS (ESI) m/z 392.2 ($M^+$ + H). |

[Step 2] Synthesis of 1-(6-ethynyl-1H-indol-3-yl)-N,N-dimethylmethanamine

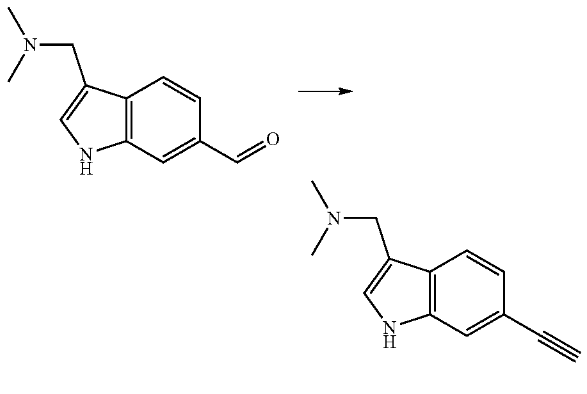

The 3-((dimethylamino)methyl)-1H-indol-6-carbaldehyde (0.100 g, 0.494 mmol) prepared in step 1, dimethyl(1-diazo-2-oxopropyl)phosphonate (0.114 g, 0.593 mmol) and potassium carbonate (0.137 g, 0.989 mmol) were dissolved in methanol (3 mL) at room temperature, after which the resulting solution was stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=90 to 40%) and concentrated to obtain 1-(6-ethynyl-1H-indol-3-yl)-N,N-dimethylmethanamine (0.020 g, 20.4%) in a colorless oil form.

[Step 3] Synthesis of Compound 3962

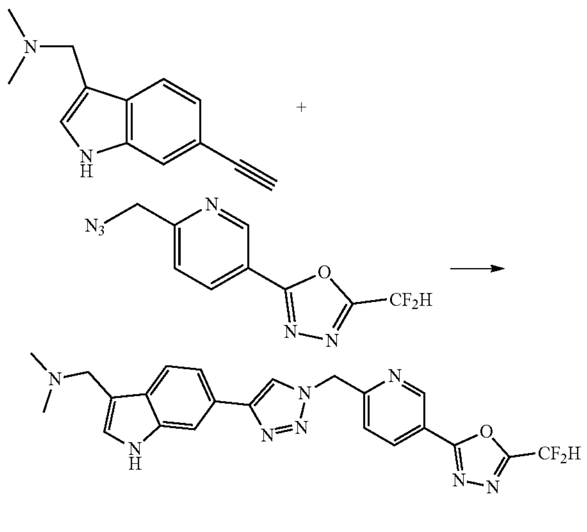

The 2-(6-(azidomethyl)pyridin-3-yl)-5-(difluoromethyl)-1,3,4-oxadiazole (0.050 g, 0.198 mmol) prepared in step 1 of example 16 and the 1-(6-ethynyl-1H-indol-3-yl)-N,N-dimethylmethanamine (0.035 g, 0.178 mmol) prepared in step 2 were dissolved in tert-butanol (1 mL)/water (1 mL) at room temperature, after which sodium ascorbate (1.00 M solution, 0.020 mL, 0.020 mmol) and copper(II) sulfate pentahydrate (0.50 M solution, 0.004 mL, 0.002 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated, after which the obtained product was purified again via column chromatography ($SiO_2$ plate, 20×20×1 mm; dichloromethane/methanol=80%) and concentrated to obtain 1-(6-(1-((5-(5-(difluoromethyl)-1,3,4-oxadiazol-2-yl)pyridin-2-yl)methyl)-1H-1,2,3-triazol-4-yl)-1H-indol-3-yl)-N,N-dimethylmethanamine (0.010 g, 11.2%)) in a light yellow gum form.

$^1H$ NMR (400 MHz, $CD_3OD$) δ 9.29 (s, 1H), 8.54 (dd, J=8.2, 2.3 Hz, 1H), 8.50 (s, 1H), 8.00 (s, 1H), 7.82 (d, J=8.3 Hz, 1H), 7.70-7.65 (m, 1H), 7.65-7.59 (m, 2H), 7.26 (t, J=51.6 Hz, 1H), 5.94 (s, 2H), 3.59 (d, J=10.8 Hz, 2H), 2.90 (s, 6H); LRMS (ES) m/z 451.2 ($M^+$+1).

Example 112: Synthesis of compound 3980, 2-(difluoromethyl)-5-(4-((5-phenyl-1,3,4-oxadiazol-2-yl)methyl)phenyl)-1,3,4-oxadiazole

[Step 1] Synthesis of methyl 4-(2-(2-benzoylhydrazineyl)-2-oxoethyl)benzoate

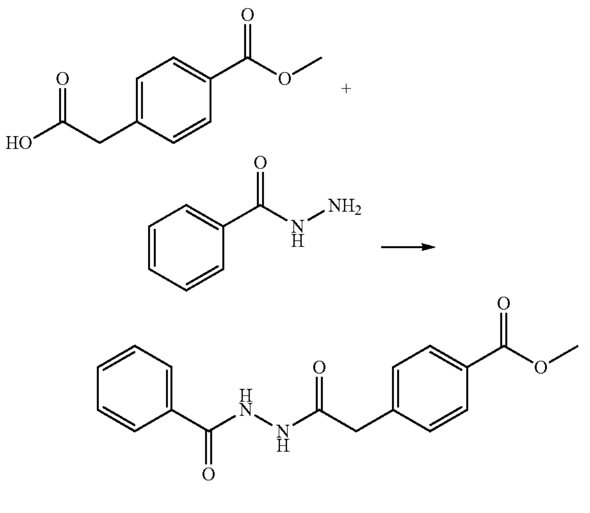

Benzohydrazide (0.500 g, 3.672 mmol), 2-(4-(methoxycarbonyl)phenyl)acetic acid (0.927 g, 4.774 mmol) and 1-[bis(dimethylamino)methylene]-1H-1,2,3-triazolo[4,5-b]pyridinium 3-oxide hexafluorophosphate (1.815 g, 4.774 mmol) were dissolved in N,N-dimethylformamide (50 mL), after which the resulting solution was stirred at room temperature for 30 hours, and then N,N-diisopropylethylamine (1.663 mL, 9.548 mmol) was added thereto and further stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The obtained product was used without an additional purification process (methyl 4-(2-(2-benzoylhydrazineyl)-2-oxoethyl)benzoate, 1.000 g, 87.2%, white solid).

[Step 2] Synthesis of methyl 4-((5-phenyl-1,3,4-oxadiazol-2-yl)methyl)benzoate

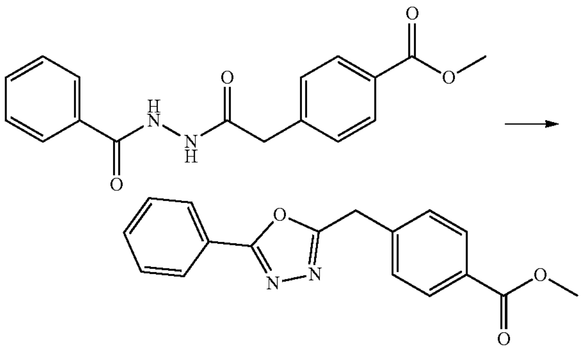

The methyl 4-(2-(2-benzoylhydrazineyl)-2-oxoethyl)benzoate (1.000 g, 3.202 mmol) prepared in step 1 and 1-methoxy-N-triethylammoniosulfonyl-methanimidate (Burgess reagent, 2.289 g, 9.605 mmol) were mixed in tetrahydrofuran (20 mL) at room temperature, after which the resulting mixture was heated under reflux for 12 hours and cooled down to room temperature. Then, water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 40%), and concentrated to obtain methyl 4-((5-phenyl-1,3,4-oxadiazol-2-yl)methyl)benzoate (0.600 g, 63.7%) in a white solid form.

[Step 3] Synthesis of methyl 4-((5-phenyl-1,3,4-oxadiazol-2-yl)methyl)benzoate

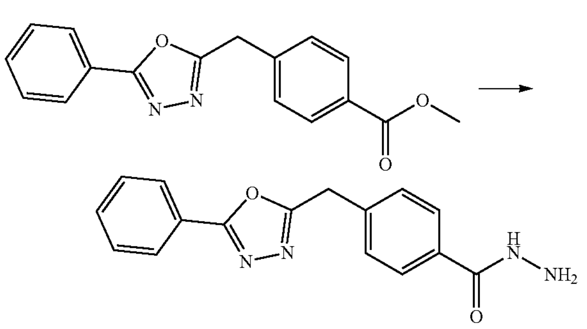

The methyl 4-((5-phenyl-1,3,4-oxadiazol-2-yl)methyl)benzoate (0.600 g, 2.039 mmol) prepared in step 2 and hydrazine monohydrate (0.991 mL, 20.387 mmol) were dissolved in ethanol (50 mL) at 90 °C, after which the resulting solution was stirred at the same temperature for 12 hours, and then a reaction was finished by lowering a temperature to room temperature.

Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (4-((5-phenyl-1,3,4-oxadiazol-2-yl)methyl)benzohydrazide, 0.380 g, 63.3%, white solid).

[Step 4] Synthesis of Compound 3980

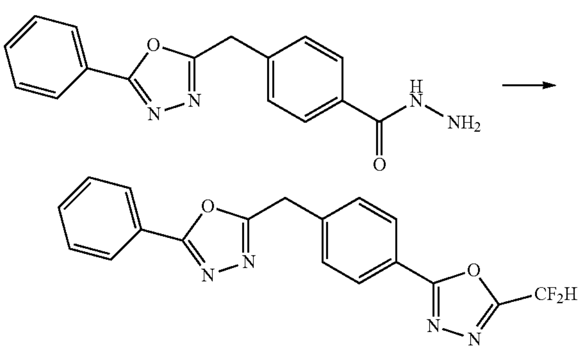

The 4-((5-phenyl-1,3,4-oxadiazol-2-yl)methyl)benzohydrazide (0.380 g, 1.291 mmol) prepared in step 3, imidazole (0.264 g, 3.873 mmol) and 2,2-difluoroacetic anhydride (0.482 mL, 3.873 mmol) were mixed in dichloromethane (20 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 60%) and concentrated to obtain 2-(difluoromethyl)-5-(4-((5-phenyl-1,3,4-oxadiazol-2-yl)methyl)phenyl)-1,3,4-oxadiazole (0.120 g, 26.2%) in a white solid form.

$^1H$ NMR (400 MHz, $CDCl_3$) δ 8.15 (d, J=8.3 Hz, 2H), 8.08-7.99 (m, 2H), 7.63-7.45 (m, 5H), 7.06 (s, 0.2H), 6.93 (s, 0.5H), 6.80 (s, 0.3H), 4.41 (s, 2H).

Example 113: Synthesis of compound 3981, 2-(difluoromethyl)-5-(4-((4-methyl-5-phenyl-4H-1,2,4-triazol-3-yl)methyl)phenyl)-1,3,4-oxadiazole

[Step 1] Synthesis of methyl 4-((4-methyl-5-phenyl-4H-1,2,4-triazol-3-yl)methyl)benzoate

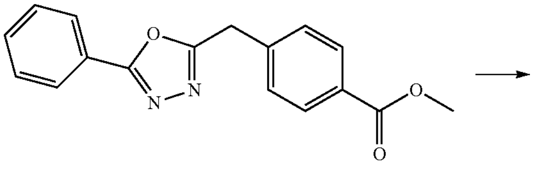

-continued

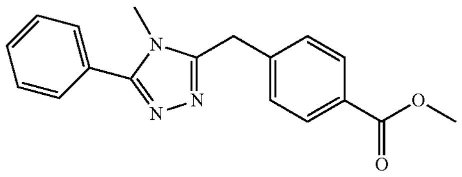

The methyl 4-((5-phenyl-1,3,4-oxadiazol-2-yl)methyl) benzoate (0.210 g, 0.714 mmol) prepared in step 2 of example 112, acetic acid (0.163 mL, 2.854 mmol) and methanamine (2.00 M solution in THF, 8.919 mL, 17.838 mmol) were mixed at 150 °C, after which the reaction mixture was stirred at the same temperature for 12 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 70%), and concentrated to obtain methyl 4-((4-methyl-5-phenyl-4H-1,2,4-triazol-3-yl)methyl)benzoate (0.100 g, 45.6%) in a white solid form.

[Step 2] Synthesis of 4-((4-methyl-5-phenyl-4H-1,2,4-triazol-3-yl)methyl)benzohydrazide

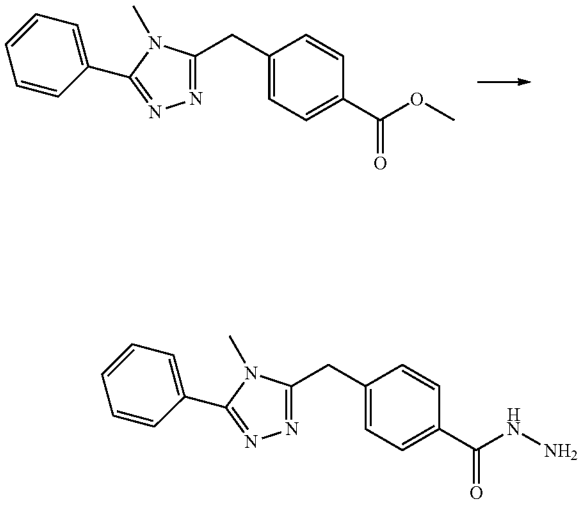

The methyl 4-((4-methyl-5-phenyl-4H-1,2,4-triazol-3-yl) methyl)benzoate (0.100 g, 0.325 mmol) prepared in step 1 and hydrazine monohydrate (0.158 mL, 3.254 mmol) were dissolved in ethanol (15 mL) at 90 °C, after which the resulting solution was stirred at the same temperature for 12 hours, and then a reaction was finished by lowering a temperature to room temperature. Solvent was removed from the reaction mixture under reduced pressure, after which the obtained product was used without an additional purification process (4-((4-methyl-5-phenyl-4H-1,2,4-triazol-3-yl)methyl)benzohydrazide, 0.081 g, 81.0%, white solid).

[Step 3] Synthesis of Compound 3981

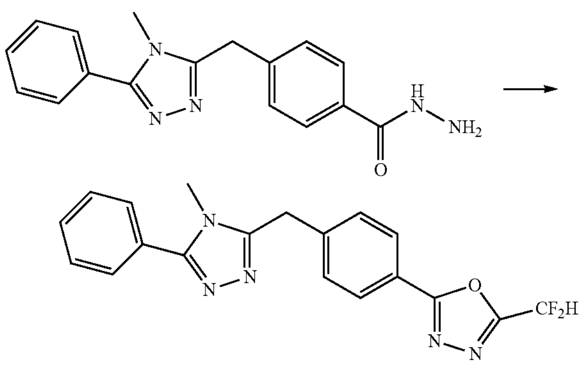

The 4-((4-methyl-5-phenyl-4H-1,2,4-triazol-3-yl)methyl) benzohydrazide (0.080 g, 0.260 mmol) prepared in step 2, imidazole (0.053 g, 0.781 mmol) and 2,2-difluoroacetic anhydride (0.097 mL, 0.781 mmol) were mixed in dichloromethane (30 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(4-((4-methyl-5-phenyl-4H-1,2,4-triazol-3-yl)methyl)phenyl)-1,3,4-oxadiazole (0.061 g, 63.8%) in a white solid form.

$^1H$ NMR (400 MHz, $CDCl_3$) δ 8.12 (d, J=8.3 Hz, 2H), 7.69-7.58 (m, 2H), 7.52 (dd, J=7.6, 4.7 Hz, 5H), 7.06 (s, 0.2H), 6.93 (s, 0.5H), 6.80 (s, 0.3H), 4.39 (s, 2H), 3.51 (s, 3H); LRMS (ES) m/z 368.4 ($M^+$+1).

Example 115: Synthesis of compound 3986, 2-(difluoromethyl)-5-(6-((4-(3-((4-methylpiperazin-1-yl) methyl)-1H-indol-6-yl)-1H-1,2,3-triazol-1-yl) methyl)pyridin-3-yl)-1,3,4-oxadiazole

[Step 1] Synthesis of 3-((4-methylpiperazin-1-yl) methyl)-1H-indol-6-carbaldehyde

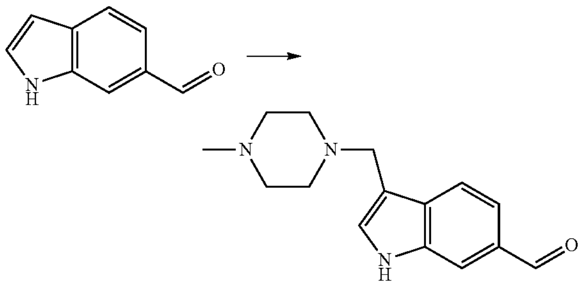

1-methylpiperazine (0.278 mL, 2.496 mmol) and formaldehyde (37.00%, 0.203 g, 2.496 mmol) were dissolved in acetic acid (3 mL), after which the resulting solution was stirred at 0 °C for 0.4 hours, and then 1H-indol-6-carbaldehyde (0.235 g, 1.622 mmol) was added and further stirred at room temperature for 18 hours. 1N-sodium hydroxide aqueous solution was poured into the resulting reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 60%) and concentrated to obtain 3-((4-methylpiperazin-1-yl)methyl)-1H-indol-6-carbaldehyde (0.100 g, 15.6%) in a light yellow oil form.

[Step 2] Synthesis of 6-ethynyl-3-((4-methylpiperazin-1-yl)methyl)-1H-indole

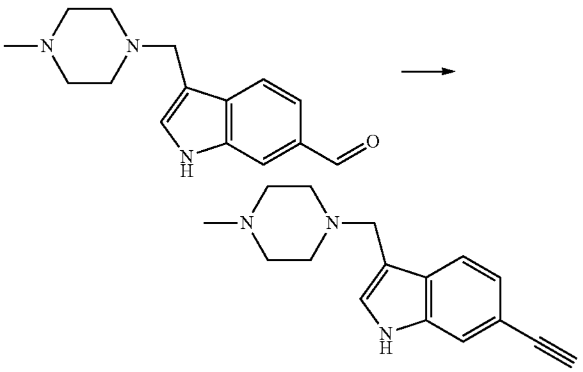

The 3-((4-methylpiperazin-1-yl)methyl)-1H-indol-6-carbaldehyde (0.100 g, 0.389 mmol) prepared in step 1, dimethyl(1-diazo-2-oxopropyl)phosphonate (0.090 g, 0.466 mmol) and potassium carbonate (0.107 g, 0.777 mmol) were dissolved in methanol (3 mL) at room temperature, after which the resulting solution was stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=90 to 40%) and concentrated to obtain 6-ethynyl-3-((4-methylpiperazin-1-yl)methyl)-1H-indole (0.030 g, 30.5%) in a white solid form.

[Step 3] Synthesis of Compound 3986

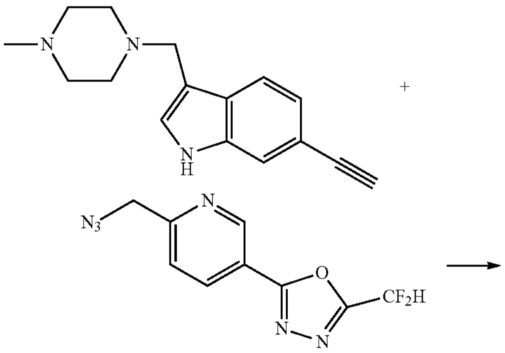

-continued

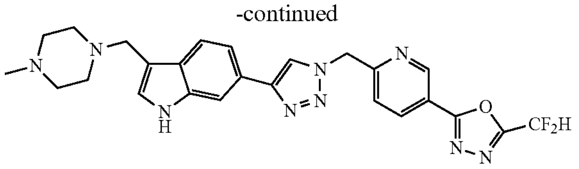

The 2-(6-(azidomethyl)pyridin-3-yl)-5-(difluoromethyl)-1,3,4-oxadiazole (0.020 g, 0.079 mmol) prepared in step 1 of example 16 and 6-ethynyl-3-((4-methylpiperazin-1-yl)methyl)-1H-indole (0.018 g, 0.071 mmol) prepared in step 2 were dissolved in tert-butanol (1 mL)/water (1 mL) at room temperature, after which sodium ascorbate (1.00 M solution, 0.008 mL, 0.008 mmol) and copper(II) sulfate pentahydrate (0.50 M solution, 0.002 mL, 0.001 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(difluoromethyl)-5-(6-((4-(3-((4-methylpiperazin-1-yl)methyl)-1H-indol-6-yl)-1H-1,2,3-triazol-1-yl)methyl)pyridin-3-yl)-1,3,4-oxadiazole (0.007 g, 17.5%) in a light yellow gum form.

$^1H$ NMR (400 MHz, $CD_3OD$) δ 9.29 (d, J=2.4 Hz, 1H), 8.54 (dd, J=8.2, 2.3 Hz, 1H), 8.47 (s, 1H), 7.94 (d, J=1.3 Hz, 1H), 7.79 (d, J=8.3 Hz, 1H), 7.61 (t, J=9.6 Hz, 2H), 7.44 (s, 1H), 7.26 (t, J=51.6 Hz, 1H), 5.93 (s, 2H), 4.17 (s, 2H), 3.27-2.78 (m, 8H), 2.62 (s, 3H); LRMS (ES) m/z 506.4 ($M^{+}$+1).

Example 116: Synthesis of compound 3987, N-(3-(1-((5-(5-(difluoromethyl)-1,3,4-oxadiazol-2-yl)pyridin-2-yl)methyl)-1H-1,2,3-triazol-4-yl)phenyl)-2-fluoro-2-methylpropanamide

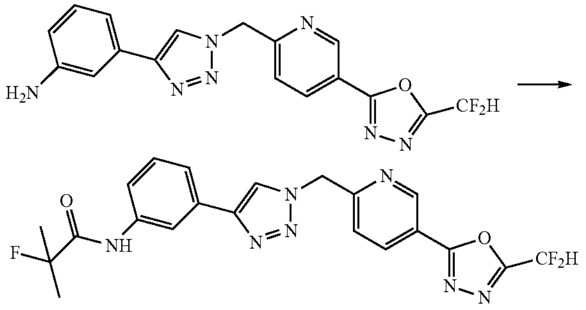

The 3-(1-((5-(5-(difluoromethyl)-1,3,4-oxadiazol-2-yl)pyridin-2-yl)methyl)-1H-1,2,3-triazol-4-yl)aniline (0.050 g, 0.135 mmol) prepared in step 1 of example 36, and 2-fluoro-2-methylpropanoic acid (0.017 g, 0.162 mmol) were dissolved in dichloromethane (2 mL) at room temperature, after which 1-[bis(dimethylamino)methylene]-1H-1,2,3-triazolo[4,5-b]pyridinium 3-oxide hexafluorophosphate (0.103 g, 0.271 mmol) and N,N-diisopropylethylamine (0.047 mL, 0.271 mmol) were added into the resulting solution and stirred at the same temperature for 18 hours. Saturated sodium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated, after which the obtained product was purified again via column chromatography ($SiO_2$, 4 g cartridge; ethyl acetate/hexane=0 to 20%) and concentrated to obtain N-(3-(1-((5-(5-(difluoromethyl)-1,3,4-oxadiazol-2-yl)pyridin-2-yl)methyl)-1H-1,2,3-triazol-4-yl)phenyl)-2-fluoro-2-methylpropanamide (0.025 g, 40.4%) in a white solid form.

$^1$H NMR (400 MHz, $CDCl_3$) δ 9.37 (s, 1H), 8.45 (dd, J=8.4, 2.3 Hz, 1H), 8.13 (s, 1H), 8.06 (s, 1H), 7.72 (d, J=7.7 Hz, 1H), 7.59 (d, J=8.6 Hz, 1H), 7.45 (t, J=8.0 Hz, 2H), 6.97 (t, J=51.7 Hz, 1H), 5.85 (s, 2H), 1.67 (s, 6H); LRMS (ES) m/z 358.3 ($M^+$+1).

The compounds of table 29 were synthesized according to substantially the same process as described above in the synthesis of compound 3987 with an exception of using 3-(1-((5-(5-(difluoromethyl)-1,3,4-oxadiazol-2-yl)pyridin-2-yl)methyl)-1H-1,2,3-triazol-4-yl)aniline and the reactant of table 28.

TABLE 28

| Example | Compound No. | Reactant | Yield (%) |
|---|---|---|---|
| 190 | 4229 | 3-(dimethylamino)propanoic acid | 39 |
| 191 | 4230 | Dimethylglycine | 46 |
| 192 | 4231 | 2-(dimethylamino)-2-methylpropanoic acid | 30 |
| 369 | 4495 | 2-((tert-butoxycarbonyl)amino)-2-methylpropanoic acid | 58 |
| 370 | 4496 | 2-((tert-butoxycarbonyl)amino)-2-methylpropanoic acid | 58 |

Example 117: Synthesis of compound 3988, 2-(difluoromethyl)-5-(6-((4-(3-(4-ethylpiperazin-1-yl)phenyl)-1H-1,2,3-triazol-1-yl)methyl)pyridin-3-yl)-1,3,4-oxadiazole

[Step 1] Synthesis of tert-butyl 4-(3-ethynylphenyl)piperazin-1-carboxylate

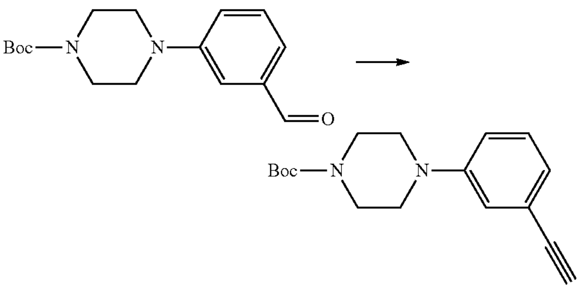

Tert-butyl 4-(3-formylphenyl)piperazin-1-carboxylate (0.500 g, 1.722 mmol) and dimethyl (1-diazo-2-oxopropyl) phosphonate (0.397 g, 2.066 mmol) were dissolved in methanol (7 mL) at room temperature, after which potassium carbonate (0.476 g, 3.444 mmol) was added to the resulting solution and stirred at the same temperature for 18 hours. Solvent was removed from the reaction mixture under reduced pressure, after which saturated ammonium chloride aqueous solution was poured into the resulting concentrate, and then an extraction was performed with ethyl acetate. An organic layer was washed with saturated aqueous solution,

TABLE 29

| Example | Compound No. | Compound Name, $^1$H-NMR, MS (ESI) |
|---|---|---|
| 190 | 4229 | N-(3-(1-((5-(5-(difluoromethyl)-1,3,4-oxadiazol-2-yl)pyridin-2-yl)methyl)-1H-1,2,3-triazol-4-yl)phenyl)-3-(dimethylamino)propanamide $^1$H NMR (400 MHz, $CD_3OD$) δ 9.26 (dd, J = 2.2, 0.8 Hz, 1H), 8.51 (dd, J = 8.2, 2.2 Hz, 1H), 8.49 (s, 1H), 8.14 (t, J = 1.9 Hz, 1H), 7.61 (dd, J = 8.2, 0.8 Hz, 1H), 7.57 (ddd, J = 8.3, 2.8, 1.2 Hz, 2H), 7.43-7.12 (m, 2H), 5.93 (s, 2H), 3.51 (t, J = 6.4 Hz, 2H), 2.98 (d, J = 6.4 Hz, 2H), 2.96 (s, 6H); LRMS (ES) m/z 469.3 ($M^+$ + 1). |
| 191 | 4230 | N-(3-(1-((5-(5-(difluoromethyl)-1,3,4-oxadiazol-2-yl)pyridin-2-yl)methyl)-1H-1,2,3-triazol-4-yl)phenyl)-2-(dimethylamino)acetamide $^1$H NMR (400 MHZ, $CD_3OD$) δ 9.26 (dd, J = 2.2, 0.9 Hz, 1H), 8.51 (dd, J = 8.2, 2.2 Hz, 1H), 8.48 (s, 1H), 8.10 (t, J = 1.9 Hz, 1H), 7.60 (dddd, J = 8.2, 5.5, 3.0, 1.2 Hz, 3H), 7.42 (t, J = 7.9 Hz, 1H), 7.25 (t, J = 51.6 Hz, 1H), 5.92 (s, 2H), 3.32 (s, 2H), 2.50 (s, 6H); LRMS (ES) m/z 455.4 ($M^+$ + 1). |
| 192 | 4231 | N-(3-(1-((5-(5-(difluoromethyl)-1,3,4-oxadiazol-2-yl)pyridin-2-yl)methyl)-1H-1,2,3-triazol-4-yl)phenyl)-2-(dimethylamino)-2-methylpropanamide $^1$H NMR (400 MHz, $CD_3OD$) δ 9.27 (dd, J = 2.2, 0.9 Hz, 1H), 8.58 (s, 1H), 8.54 (dd, J = 8.2, 2.2 Hz, 1H), 8.35 (d, J = 8.4 Hz, 1H), 7.70 (dt, J = 7.8, 1.2 Hz, 1H), 7.64 (dd, J = 8.2, 0.9 Hz, 1H), 7.61 (t, J = 1.9 Hz, 1H), 7.54 (t, J = 7.9 Hz, 1H), 7.46 (dd, J = 8.3, 4.3 Hz, 1H), 7.26 (t, J = 51.6 Hz, 1H), 7.07 (ddd, J = 8.0, 2.3, 1.0 Hz, 1H), 5.94 (s, 2H), 3.04 (s, 12H); LRMS (ES) m/z 483.3 ($M^+$ + 1). |
| 369 | 4495 | tert-butyl (1-((3-(1-((5-(5-(difluoromethyl)-1,3,4-oxadiazol-2-yl)pyridin-2-yl)methyl)-1H-1,2,3-triazol-4-yl)phenyl)carbamoyl)cyclobutyl)carbamate $^1$H NMR (400 MHz, $CD_3OD$) δ 9.28 (dd, J = 2.3, 0.9 Hz, 1H), 8.53 (dd, J = 8.2, 2.3 Hz, 1H), 8.47 (s, 1H), 8.05 (s, 1H), 7.65-7.57 (m, 2H), 7.55 (s, 1H), 7.46-7.10 (m, 2H), 5.93 (s, 2H), 1.52 (s, 6H), 1.44 (s, 9H); LRMS (ES) m/z 555.5 ($M^+$ + 1). |
| 370 | 4496 | tert-butyl (1-((3-(1-((5-(5-(difluoromethyl)-1,3,4-oxadiazol-2-yl)pyridin-2-yl)methyl)-1H-1,2,3-triazol-4-yl)phenyl)carbamoyl)cyclobutyl)carbamate $^1$H NMR (400 MHz, $CD_3OD$) δ 9.31-9.26 (m, 1H), 8.52 (dd, J = 8.2, 2.2 Hz, 1H), 8.45 (s, 1H), 8.06 (s, 1H), 7.84 (s, 1H), 7.65-7.56 (m, 2H), 7.41 (t, J = 7.9 Hz, 1H), 7.23 (t, J = 51.6 Hz, 1H), 5.92 (s, 2H), 3.73 (p, J = 6.7 Hz, 1H), 3.23 (q, J = 7.4 Hz, 1H), 2.79-2.67 (m, 2H), 2.19 (q, J = 9.0 Hz, 2H), 1.99 (dd, J = 16.3, 8.7 Hz, 2H), 1.43-1.35 (m, 10H); LRMS (ES) m/z 567.6 ($M^+$ + 1). |

dehydrated with anhydrous sodium sulfate, filtered, and concentrated under reduced pressure. The resulting concentrate was purified via column chromatography ($SiO_2$, 12 g cartridge; dichloromethane/methanol=100 to 20%), and concentrated to obtain tert-butyl 4-(3-ethynylphenyl)piperazin-1-carboxylate (0.450 g, 91.3%) in a white solid form.

[Step 2] Synthesis of tert-butyl 4-(3-(1-((5-(5-(difluoromethyl)-1,3,4-oxadiazol-2-yl)pyridin-2-yl)methyl)-1H-1,2,3-triazol-4-yl)phenyl)piperazin-1-carboxylate

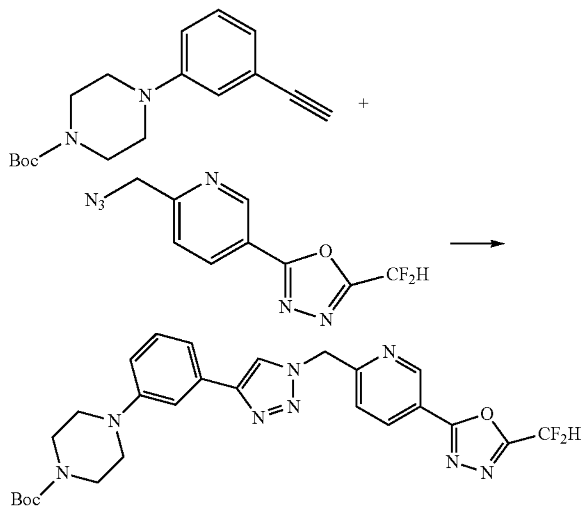

The 2-(6-(azidomethyl)pyridin-3-yl)-5-(difluoromethyl)-1,3,4-oxadiazole (0.190 g, 0.753 mmol) prepared in step 1 of example 16 and the tert-butyl 4-(3-ethynylphenyl)piperazin-1-carboxylate (0.216 g, 0.753 mmol) prepared in step 1 were dissolved in tert-butanol (1 mL)/water (1 mL) at room temperature, after which sodium ascorbate (1.00 M solution, 0.075 mL, 0.075 mmol) and copper(II) sulfate pentahydrate (0.50 M solution, 0.015 mL, 0.008 mmol) were added to the resulting solution and stirred at the same temperature for 18 hours. Saturated aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=10 to 50%) and concentrated to obtain tert-butyl 4-(3-(1-((5-(5-(difluoromethyl)-1,3,4-oxadiazol-2-yl)pyridin-2-yl)methyl)-1H-1,2,3-triazol-4-yl)phenyl)piperazin-1-carboxylate (0.300 g, 74.0%) in a white solid form.

[Step 3] Synthesis of 2-(difluoromethyl)-5-(6-((4-(3-(piperazin-1-yl)phenyl)-1H-1,2,3-triazol-1-yl)methyl)pyridin-3-yl)-1,3,4-oxadiazole

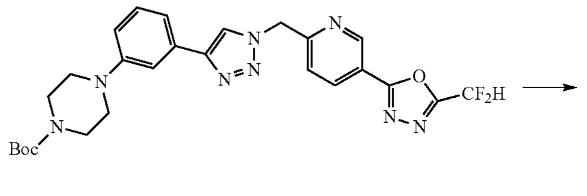

-continued

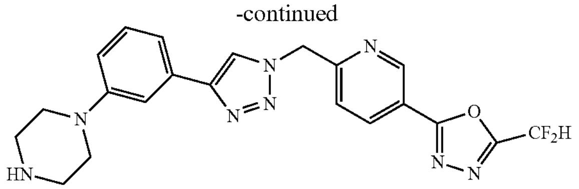

The tert-butyl 4-(3-(1-((5-(5-(difluoromethyl)-1,3,4-oxadiazol-2-yl)pyridin-2-yl)methyl)-1H-1,2,3-triazol-4-yl)phenyl)piperazin-1-carboxylate (0.200 g, 0.371 mmol) prepared in step 2 and trifluoroacetic acid (0.853 mL, 11.141 mmol) were dissolved in dichloromethane (3 mL) at room temperature, after which the resulting solution was stirred at the same temperature for 18 hours. Solvent was removed from the reaction mixture under reduced pressure, after which the obtained product was used without an additional purification process (2-(difluoromethyl)-5-(6-((4-(3-(piperazin-1-yl)phenyl)-1H-1,2,3-triazol-1-yl)methyl)pyridin-3-yl)-1,3,4-oxadiazole, 0.190 g, 116.7%, light yellow oil).

[Step 4] Synthesis of Compound 3988

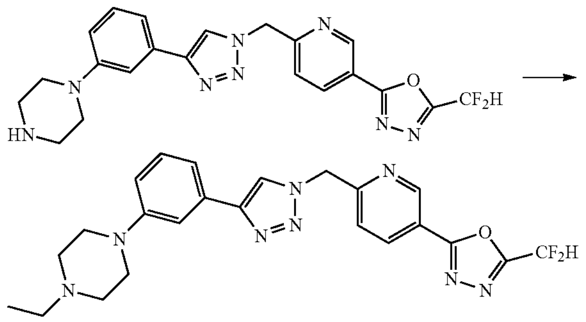

The 2-(difluoromethyl)-5-(6-((4-(3-(piperazin-1-yl)phenyl)-1H-1,2,3-triazol-1-yl)methyl)pyridin-3-yl)-1,3,4-oxadiazole (0.020 g, 0.046 mmol) prepared in step 3, and acetaldehyde (0.006 g, 0.137 mmol) were dissolved in dichloromethane (1 mL) at room temperature, after which sodium triacetoxyborohydride (0.048 g, 0.228 mmol) was added to the resulting solution and stirred at the same temperature for 18 hours. Saturated aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(6-((4-(3-(4-ethylpiperazin-1-yl)phenyl)-1H-1,2,3-triazol-1-yl)methyl)pyridin-3-yl)-1,3,4-oxadiazole (0.010 g, 47.0%) in a colorless oil form.

$^1H$ NMR (400 MHz, $CD_3OD$) δ 9.28 (dd, J=2.3, 0.9 Hz, 1H), 8.53 (dd, J=8.2, 2.3 Hz, 1H), 8.49 (s, 1H), 7.60 (dd, J=8.2, 0.9 Hz, 1H), 7.54-7.49 (m, 1H), 7.37-7.31 (m, 2H), 7.26 (t, J=51.6 Hz, 1H), 7.01 (dt, J=6.7, 2.6 Hz, 1H), 5.92 (s, 2H), 3.34 (t, 7H), 2.83 (t, J=5.1 Hz, 4H), 2.67 (q, J=7.3 Hz, 2H), 1.22 (t, J=7.3 Hz, 3H); LRMS (ES) m/z 367.3 ($M^++1$).

The compounds of table 31 were synthesized according to substantially the same process as described above in the synthesis of compound 3988 with an exception of using 2-(difluoromethyl)-5-(6-((4-(3-(piperazin-1-yl)phenyl)-1H-1,2,3-triazol-1-yl)methyl)pyridin-3-yl)-1,3,4-oxadiazole and the reactant of table 30.

TABLE 30

| Example | Compound No. | Reactant | Yield (%) |
|---|---|---|---|
| 118 | 3989 | Oxetan-3-one | 31 |
| 148 | 4070 | N,N-diisopropylethylamine | 32 |

TABLE 31

| Example | Compound No. | Compound Name, $^1$H-NMR, MS (ESI) |
|---|---|---|
| 118 | 3989 | 2-(difluoromethyl)-5-(6-((4-(3-(4-(oxetan-3-yl)piperazin-1-yl)phenyl)-1H-1,2,3-triazol-1-yl)methyl)pyridin-3-yl)-1,3,4-oxadiazole $^1$H NMR (400 MHz, $CD_3OD$) δ 9.28 (dd, J = 2.3, 0.8 Hz, 1H), 8.53 (dd, J = 8.2, 2.2 Hz, 1H), 8.48 (s, 1H), 7.60 (d, J = 8.2 Hz, 1H), 7.50 (d, J = 2.8 Hz, 1H), 7.37-7.29 (m, 2H), 7.26 (t, J = 51.6 Hz, 1H), 7.00 (dt, J = 7.0, 2.5 Hz, 1H), 5.92 (s, 2H), 4.75 (t, J = 6.7 Hz, 2H), 4.67 (t, J = 6.2 Hz, 2H), 3.58 (q, J = 6.4 Hz, 2H), 3.32-3.27 (m, 4H), 2.60-2.53 (m, 4H); LRMS (ES) m/z 495.3 ($M^+$ + 1). |
| 148 | 4070 | 2-(difluoromethyl)-5-(6-((4-(3-(4-isopropylpiperazin-1-yl)phenyl)-1H-1,2,3-triazol-1-yl)methyl)pyridin-3-yl)-1,3,4-oxadiazole $^1$H NMR (400 MHz, $CD_3OD$) δ 9.28 (dd, J = 2.3, 0.9 Hz, 1H), 8.53 (dd, J = 8.2, 2.2 Hz, 1H), 8.49 (s, 1H), 7.63-7.56 (m, 1H), 7.50 (s, 1H), 7.37-7.31 (m, 2H), 7.26 (t, J = 51.6 Hz, 1H), 7.01 (dt, J = 7.0, 2.6 Hz, 1H), 5.92 (s, 2H), 3.33-3.17 (m, 4H), 2.87-2.78 (m, 5H), 1.18 (d, J = 6.5 Hz, 6H); LRMS (ES) m/z 481.4 ($M^+$ + 1). |

Example 119: Synthesis of compound 3990, 1-(4-(3-(1-((5-(5-(difluoromethyl)-1,3,4-oxadiazol-2-yl)pyridin-2-yl)methyl)-1H-1,2,3-triazol-4-yl)phenyl)piperazin-1-yl)ethan-1-one

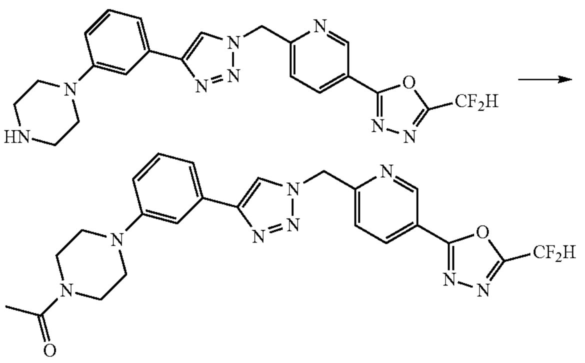

The 2-(difluoromethyl)-5-(6-((4-(3-(piperazin-1-yl)phenyl)-1H-1,2,3-triazol-1-yl)methyl)pyridin-3-yl)-1,3,4-oxadiazole (0.025 g, 0.057 mmol) prepared in step 3 of example 117, and triethylamine (0.040 mL, 0.285 mmol) were dissolved in dichloromethane (1 mL) at room temperature, after which acetyl chloride (0.013 g, 0.171 mmol) was added to the resulting solution and stirred at the same temperature for 18 hours. Saturated aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 10%) and concentrated to obtain 1-(4-(3-(1-((5-(5-(difluoromethyl)-1,3,4-oxadiazol-2-yl)pyridin-2-yl)methyl)-1H-1,2,3-triazol-4-yl)phenyl)piperazin-1-yl)ethan-1-one (0.011 g, 40.2%) in a colorless oil form.

$^1$H NMR (400 MHz, $CD_3OD$) δ 9.28 (dd, J=2.3, 0.9 Hz, 1H), 8.53 (dd, J=8.2, 2.3 Hz, 1H), 8.49 (s, 1H), 7.60 (d, J=8.2 Hz, 1H), 7.52 (t, J=1.7 Hz, 1H), 7.37-7.31 (m, 2H), 7.26 (t, J=51.6 Hz, 1H), 7.06-6.99 (m, 1H), 5.92 (s, 2H), 3.76 (dt, J=16.1, 5.3 Hz, 4H), 3.33-3.21 (m, 4H), 2.17 (s, 3H); LRMS (ES) m/z 481.3 ($M^+$+1).

The compound of table 33 was synthesized according to substantially the same process as described above in the synthesis of compound 3990 with an exception of using 2-(difluoromethyl)-5-(6-((4-(3-(piperazin-1-yl)phenyl)-1H-1,2,3-triazol-1-yl)methyl)pyridin-3-yl)-1,3,4-oxadiazole and the reactant of table 32.

TABLE 32

| Example | Compound No. | Reactant | Yield (%) |
|---|---|---|---|
| 120 | 3991 | Propionyl chloride | 35 |

TABLE 33

| Example | Compound No. | Compound Name, $^1$H-NMR, MS (ESI) |
|---|---|---|
| 120 | 3991 | 1-(4-(3-(1-((5-(5-(difluoromethyl)-1,3,4-oxadiazol-2-yl)pyridin-2-yl)methyl)-1H-1,2,3-triazol-4-yl)phenyl)piperazin-1-yl)propan-1-one $^1$H NMR (400 MHz, $CD_3OD$) δ 9.28 (dd, J = 2.3, 0.9 Hz, 1H), 8.53 (dd, J = 8.2, 2.3 Hz, 1H), 8.49 (s, 1H), 7.60 (d, J = 8.3 Hz, 1H), 7.54-7.49 (m, 1H), 7.36-7.33 (m, 2H), 7.26 (t, J = 51.6 Hz, 1H), 7.06-6.98 (m, 1H), 5.92 (s, 2H), 3.76 (dt, J = 17.3, 5.3 Hz, 4H), 3.27 (dt, J = 18.9, 5.2 Hz, 4H), 2.49 (q, J = 7.5 Hz, 2H), 1.17 (t, J = 7.5 Hz, 3H); LRMS (ES) m/z 495.4 ($M^+$ + 1). |

Example 123: Synthesis of compound 4001, tert-butyl 4-(3-(1-((5-(5-(difluoromethyl)-1,3,4-oxadiazol-2-yl)pyridin-2-yl)methyl)-1H-1,2,3-triazol-4-yl)phenyl)piperidin-1-carboxylate

[Step 1] Synthesis of methyl 6-((4-(3-bromophenyl)-1H-1,2,3-triazol-1-yl)methyl)nicotinate

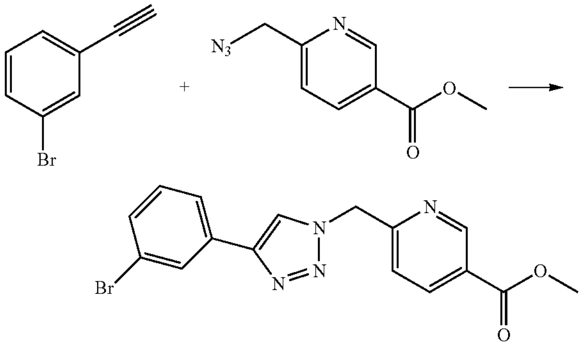

The methyl 6-(azidomethyl)nicotinate (1.000 g, 5.203 mmol) prepared in step 1 of example 81, 1-bromo-3-ethynylbenzene (1.130 g, 6.244 mmol), sodium ascorbate (1.00 M solution, 0.520 mL, 0.520 mmol), and copper(II) sulfate pentahydrate (0.50 M solution, 0.104 mL, 0.052 mmol) were dissolved in tert-butanol (20 mL)/water (20 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 70%), and concentrated to obtain methyl 6-((4-(3-bromophenyl)-1H-1,2,3-triazol-1-yl)methyl)nicotinate (1.500 g, 77.2%) in a white solid form.

[Step 2] Synthesis of methyl 6-((4-(3-(1-(tert-butoxycarbonyl)-1,2,3,6-tetrahydropyridin-4-yl)phenyl)-1H-1,2,3-triazol-1-yl)methyl)nicotinate

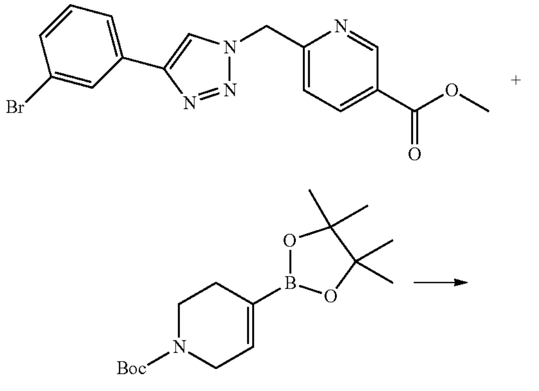

-continued

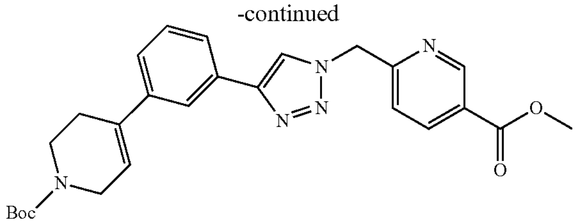

The methyl 6-((4-(3-bromophenyl)-1H-1,2,3-triazol-1-yl)methyl)nicotinate (1.000 g, 2.679 mmol) prepared in step 1, tert-butyl 4-(4,4,5,5-tetramethyl-1,3,2-dioxaborolan-2-yl)-3,6-dihydropyridin-1(2H)-carboxylate (0.911 g, 2.947 mmol), [1,1'-bis(di-tert-butylphosphino)ferrocene]palladium(II) dichloride (0.175 g, 0.268 mmol) and cesium carbonate (1.746 g, 5.359 mmol) were mixed in 1,4-dioxane (20 mL)/water (5 mL) at room temperature, after which the resulting mixture was heated under reflux for 12 hours and cooled down to room temperature. Then, water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 60%) and concentrated to obtain methyl 6-((4-(3-(1-(tert-butoxycarbonyl)-1,2,3,6-tetrahydropyridin-4-yl)phenyl)-1H-1,2,3-triazol-1-yl)methyl)nicotinate (0.450 g, 35.3%) in a white solid form.

[Step 3] Synthesis of methyl 6-((4-(3-(1-(tert-butoxycarbonyl)piperidin-4-yl)phenyl)-1H-1,2,3-triazol-1-yl)methyl)nicotinate

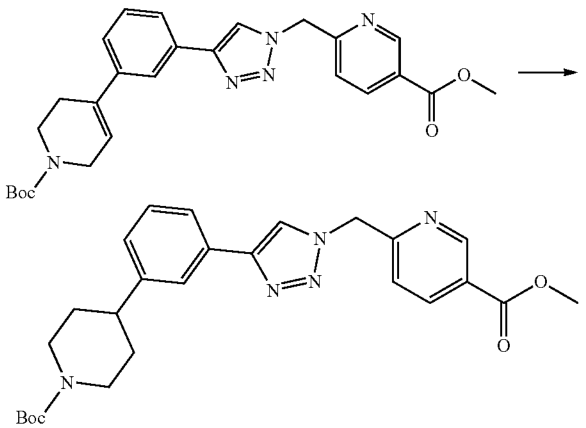

The methyl 6-((4-(3-(1-(tert-butoxycarbonyl)-1,2,3,6-tetrahydropyridin-4-yl)phenyl)-1H-1,2,3-triazol-1-yl)methyl)nicotinate (0.450 g, 0.946 mmol) prepared in step 2 was dissolved in methanol (20 mL) at room temperature, after which 10%-Pd/C (90 mg) was slowly added thereto, and stirred for 12 hours in the presence of a hydrogen balloon attached thereto at the same temperature. The reaction mixture was filtered via a celite pad to remove a solid therefrom, after which solvent was removed from the resulting filtrate under reduced pressure, and then the resulting concentrate was purified via column chromatography ($SiO_2$, 12 g cartridge; ethyl acetate/hexane=0 to 70%) and concentrated to obtain methyl 6-((4-(3-(1-(tert-butoxycarbonyl)piperidin-4-yl)phenyl)-1H-1,2,3-triazol-1-yl)methyl)nicotinate (0.420 g, 92.9%) in a yellow oil form.

[Step 4] Synthesis of tert-butyl 4-(3-(1-((5-(hydrazinecarbonyl)pyridin-2-yl)methyl)-1H-1,2,3-triazol-4-yl)phenyl)piperidin-1-carboxylate

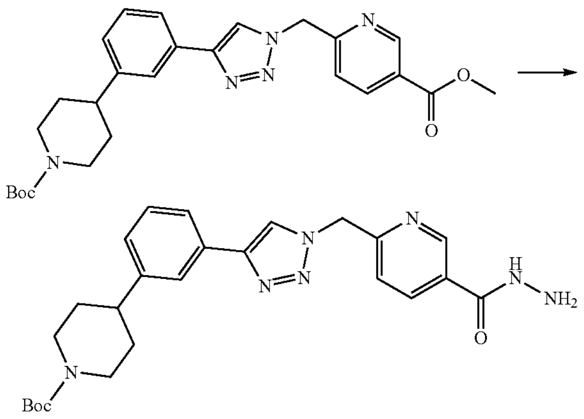

The methyl 6-((4-(3-(1-(tert-butoxycarbonyl)piperidin-4-yl)phenyl)-1H-1,2,3-triazol-1-yl)methyl)nicotinate (0.420 g, 0.879 mmol) prepared in step 3 and hydrazine monohydrate (0.427 mL, 8.795 mmol) were dissolved in ethanol (30 mL) at 90 °C, after which the resulting solution was stirred at the same temperature for 12 hours, and then a reaction was finished by lowering a temperature to room temperature. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (tert-butyl 4-(3-(1-((5-(hydrazinecarbonyl)pyridin-2-yl)methyl)-1H-1,2,3-triazol-4-yl)phenyl)piperidin-1-carboxylate, 0.350 g, 83.3%, white solid).

[Step 5] Synthesis of Compound 4001

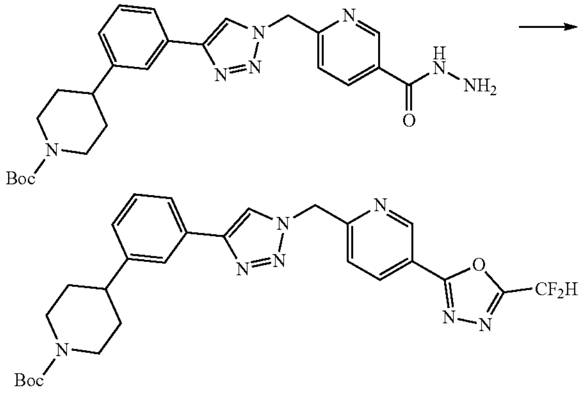

The tert-butyl 4-(3-(1-((5-(hydrazinecarbonyl)pyridin-2-yl)methyl)-1H-1,2,3-triazol-4-yl)phenyl)piperidin-1-carboxylate (0.350 g, 0.733 mmol) prepared in step 4, imidazole (0.150 g, 2.199 mmol) and 2,2-difluoroacetic anhydride (0.273 mL, 2.199 mmol) were mixed in dichloromethane (50 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 60%) and concentrated to obtain tert-butyl 4-(3-(1-((5-(5-(difluoromethyl)-1,3,4-oxadiazol-2-yl)pyridin-2-yl)methyl)-1H-1,2,3-triazol-4-yl)phenyl)piperidin-1-carboxylate (0.320 g, 81.2%) in a white solid form. $^1H$ NMR (400 MHz, $CDCl_3$) δ 9.35 (d, J=1.6 Hz, 1H), 8.42 (dd, J=8.2, 2.2 Hz, 1H), 8.00 (s, 1H), 7.76 (d, J=1.6 Hz, 1H), 7.70-7.61 (m, 1H), 7.47-7.35 (m, 2H), 7.21 (d, J=7.7 Hz, 1H), 7.09 (s, 0.2H), 6.96 (s, 0.5H), 6.83 (s, 0.3H), 5.84 (s, 2H), 4.27 (s, 2H), 2.83 (t, J=12.3 Hz, 2H), 2.72 (ddd, J=12.2, 7.9, 3.5 Hz, 1H), 1.87 (d, J=13.6 Hz, 2H), 1.69 (qd, J=12.7, 4.4 Hz, 2H), 1.51 (d, J=4.3 Hz, 9H); LRMS (ES) m/z 538.42 ($M^+$+1).

Example 124: Synthesis of compound 4002, 2-(difluoromethyl)-5-(6-((4-(1-ethylpiperidin-3-yl)-1H-1,2,3-triazol-1-yl)methyl)pyridin-3-yl)-1,3,4-oxadiazole

[Step 1] Synthesis of 2-(difluoromethyl)-5-(6-((4-(piperidin-3-yl)-1H-1,2,3-triazol-1-yl)methyl)pyridin-3-yl)-1,3,4-oxadiazole

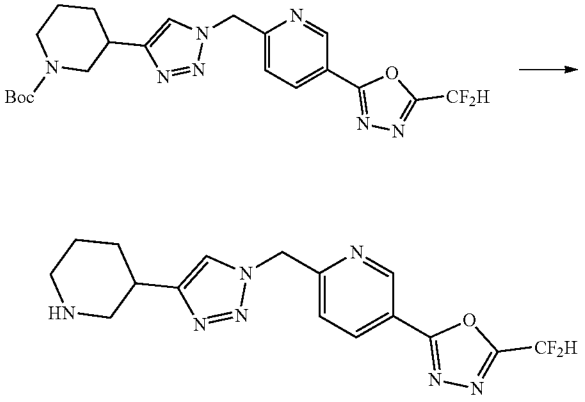

The tert-butyl 3-(1-((5-(5-(difluoromethyl)-1,3,4-oxadiazol-2-yl)pyridin-2-yl)methyl)-1H-1,2,3-triazol-4-yl)piperidin-1-carboxylate (0.446 g, 0.966 mmol) prepared in example 106 and trifluoroacetic acid (0.740 mL, 9.665 mmol) were dissolved in dichloromethane (5 mL) at room temperature, after which the resulting solution was stirred at the same temperature for 18 hours. Solvent was removed from the reaction mixture under reduced pressure, after which the obtained product was used without an additional purification process (2-(difluoromethyl)-5-(6-((4-(piperidin-3-yl)-1H-1,2,3-triazol-1-yl)methyl)pyridin-3-yl)-1,3,4-oxadiazole (0.350 g, 100.2%, orange color oil).

[Step 2] Synthesis of Compound 4002

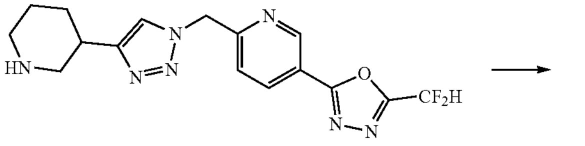

-continued

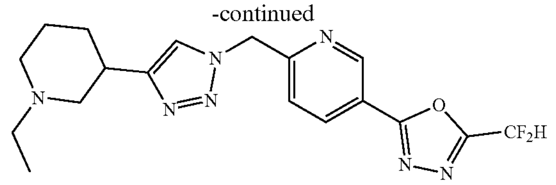

The 2-(difluoromethyl)-5-(6-((4-(piperidin-3-yl)-1H-1,2,3-triazol-1-yl)methyl)pyridin-3-yl)-1,3,4-oxadiazole (0.070 g, 0.194 mmol) prepared in step 1, and acetaldehyde (0.022 mL, 0.387 mmol) were dissolved in dichloromethane (1 mL), after which the resulting solution was stirred at room temperature for 15 minutes, and then sodium triacetoxyborohydride (0.123 g, 0.581 mmol) was added thereto and further stirred at the same temperature for 18 hours. 1N-sodium hydrogen carbonate aqueous solution was poured into the resulting reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(6-((4-(1-ethylpiperidin-3-yl)-1H-1,2,3-triazol-1-yl)methyl)pyridin-3-yl)-1,3,4-oxadiazole (0.039 g, 51.7%) in a light yellow oil form.

$^1$H NMR (400 MHz, $CD_3OD$) δ 9.25 (dd, J=2.3, 0.9 Hz, 1H), 8.51 (dd, J=8.2, 2.3 Hz, 1H), 8.03 (d, J=0.6 Hz, 1H), 7.55 (dd, J=8.2, 0.9 Hz, 1H), 7.26 (t, J=51.6 Hz, 1H), 5.85 (s, 2H), 3.44 (d, J=12.0 Hz, 1H), 3.28-3.12 (m, 2H), 2.81 (q, J=7.3 Hz, 2H), 2.49 (dt, J=36.9, 11.4 Hz, 2H), 2.15 (dd, J=13.4, 3.5 Hz, 1H), 1.97-1.91 (m, 1H), 1.89-1.77 (m, 1H), 1.64 (qd, J=12.2, 4.1 Hz, 1H), 1.25 (t, J=7.3 Hz, 3H); LRMS (ES) m/z 390.1 ($M^+$+1).

The compound of table 35 was synthesized according to substantially the same process as described above in the synthesis of compound 4002 with an exception of using 2-(difluoromethyl)-5-(6-((4-(piperidin-3-yl)-1H-1,2,3-triazol-1-yl)methyl)pyridin-3-yl)-1,3,4-oxadiazole and the reactant of table 34.

TABLE 34

| Example | Compound No. | Reactant | Yield (%) |
|---|---|---|---|
| 125 | 4003 | Oxetanone | 87 |

Example 126: Synthesis of compound 4004, 1-(3-(1-((5-(5-(difluoromethyl)-1,3,4-oxadiazol-2-yl)pyridin-2-yl)methyl)-1H-1,2,3-triazol-4-yl)piperidin-1-yl)ethan-1-one

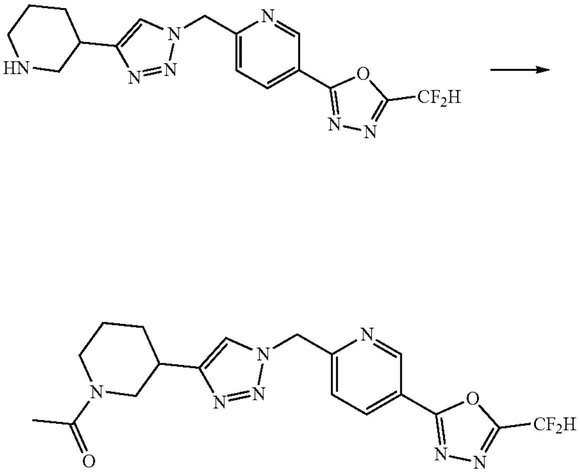

The 2-(difluoromethyl)-5-(6-((4-(piperidin-3-yl)-1H-1,2,3-triazol-1-yl)methyl)pyridin-3-yl)-1,3,4-oxadiazole (0.070 g, 0.194 mmol) prepared in step 1 of example 124, and N,N-diisopropylethylamine (0.067 mL, 0.387 mmol) were dissolved in dichloromethane (1 mL) at room temperature, after which acetyl chloride (0.017 mL, 0.232 mmol) was added to the resulting solution and stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 5%) and concentrated to obtain 1-(3-(1-((5-(5-(difluoromethyl)-1,3,4-oxadiazol-2-yl)pyridin-2-yl)methyl)-1H-1,2,3-triazol-4-yl)piperidin-1-yl)ethan-1-one (0.064 g, 81.9%) in a light yellow oil form.

$^1$H NMR (400 MHz, $CD_3OD$) δ 9.26 (dd, J=2.0, 1.0 Hz, 1H), 8.51 (dt, J=8.2, 2.2 Hz, 1H), 8.05-7.98 (m, 1H), 7.58-7.48 (m, 1H), 7.26 (td, J=51.6, 0.7 Hz, 1H), 5.85 (d, J=4.3 Hz, 2H), 4.55-3.83 (m, 2H), 3.27 (ddd, J=14.0, 10.7, 2.9 Hz, 1H), 3.10-2.86 (m, 2H), 2.23-2.14 (m, 1H), 2.14 (s, 3H), 1.93-1.76 (m, 2H), 1.75-1.54 (m, 1H); LRMS (ES) m/z 404.2 ($M^+$+1).

TABLE 35

| Example | Compound No. | Compound Name, $^1$H-NMR, MS (ESI) |
|---|---|---|
| 125 | 4003 | 2-(difluoromethyl)-5-(6-((4-(1-(oxetan-3-yl)piperidin-3-yl)-1H-1,2,3-triazol-1-yl)methyl)pyridin-3-yl)-1,3,4-oxadiazole<br>$^1$H NMR (400 MHz, $CD_3OD$) δ 9.26 (dd, J = 2.3, 0.9 Hz, 1H), 8.50 (dd, J = 8.2, 2.2 Hz, 1H), 7.99 (d, J = 0.6 Hz, 1H), 7.51 (dd, J = 8.3, 0.8 Hz, 1H), 7.26 (t, J = 51.6 Hz, 1H), 5.83 (s, 2H), 4.67 (dtd, J = 24.0, 6.4, 4.6 Hz, 4H), 3.60-3.49 (m, 1H), 3.09 (tt, J = 10.9, 3.8 Hz, 1H), 2.99 (d, J = 11.4 Hz, 1H), 2.77 (d, J = 11.2 Hz, 1H), 2.14-1.91 (m, 3H), 1.89-1.67 (m, 2H), 1.62-1.48 (m, 1H); LRMS (ESI) m/z 345.2 ($M^+$ + H). |

Example 127: Synthesis of compound 4005, 2-(difluoromethyl)-5-(6-((4-(4-fluoro-1-methylpiperidin-4-yl)-1H-1,2,3-triazol-1-yl)methyl)pyridin-3-yl)-1,3,4-oxadiazole

[Step 1] Synthesis of 2-(difluoromethyl)-5-(6-((4-(4-fluoropiperidin-4-yl)-1H-1,2,3-triazol-1-yl)methyl)pyridin-3-yl)-1,3,4-oxadiazole

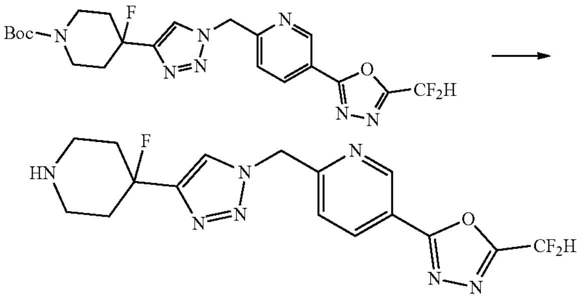

The tert-butyl 4-(1-((5-(5-(difluoromethyl)-1,3,4-oxadiazol-2-yl)pyridin-2-yl)methyl)-1H-1,2,3-triazol-4-yl)-4-fluoropiperidin-1-carboxylate (0.650 g, 1.356 mmol) prepared in example 121 and trifluoroacetic acid (0.311 mL, 4.067 mmol) were dissolved in dichloromethane (20 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(6-((4-(4-fluoropiperidin-4-yl)-1H-1,2,3-triazol-1-yl)methyl)pyridin-3-yl)-1,3,4-oxadiazole, 0.500 g, 97.2%, yellow oil)

[Step 2] Synthesis of Compound 4005

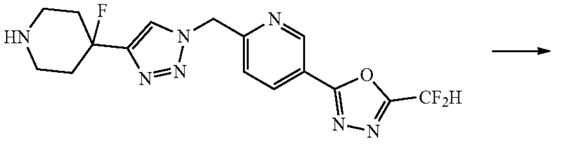

-continued

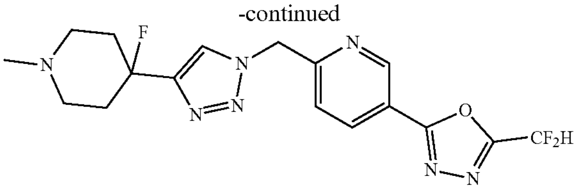

The 2-(difluoromethyl)-5-(6-((4-(4-fluoropiperidin-4-yl)-1H-1,2,3-triazol-1-yl)methyl)pyridin-3-yl)-1,3,4-oxadiazole (0.080 g, 0.211 mmol) prepared in step 1, N,N-diisopropylethylamine (0.073 mL, 0.422 mmol), formaldehyde (37.00%, 0.034 g, 0.422 mmol) and sodium triacetoxyborohydride (0.089 g, 0.422 mmol) were dissolved in dichloromethane (5 mL) at room temperature, after which the resulting solution was stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(6-((4-(4-fluoro-1-methylpiperidin-4-yl)-1H-1,2,3-triazol-1-yl)methyl)pyridin-3-yl)-1,3,4-oxadiazole (0.021 g, 25.3%) in a white solid form.

$^1$H NMR (400 MHz, $CDCl_3$) δ 9.33 (d, J=1.6 Hz, 1H), 8.47-8.37 (m, 1H), 7.78 (d, J=0.6 Hz, 1H), 7.40 (t, J=11.6 Hz, 1H), 7.09 (s, 0.2H), 6.96 (s, 0.5H), 6.83 (s, 0.3H), 5.77 (s, 2H), 2.78 (d, J=11.5 Hz, 2H), 2.50 (t, J=10.9 Hz, 2H), 2.45-2.32 (m, 4H), 2.31-2.19 (m, 3H); LRMS (ES) m/z 494.26 ($M^+$+1).

The compounds of table 37 were synthesized according to substantially the same process as described above in the synthesis of compound 4005 with an exception of using 2-(difluoromethyl)-5-(6-((4-(4-fluoropiperidin-4-yl)-1H-1,2,3-triazol-1-yl)methyl)pyridin-3-yl)-1,3,4-oxadiazole and the reactant of table 36.

TABLE 36

| Example | Compound No. | Reactant | Yield (%) |
|---|---|---|---|
| 128 | 4006 | Acetaldehyde | 14 |
| 129 | 4007 | Propan-2-one | 24 |
| 130 | 4008 | Oxetan-3-one | 33 |

TABLE 37

| Example | Compound No. | Compound Name, $^1$H-NMR, MS (ESI) |
|---|---|---|
| 128 | 4006 | 2-(difluoromethyl)-5-(6-((4-(1-ethyl-4-fluoropiperidin-4-yl)-1H-1,2,3-triazol-1-yl)methyl)pyridin-3-yl)-1,3,4-oxadiazole<br>$_1$H NMR (400 MHz, $CDCl_3$) δ 9.34 (d, J = 1.6 Hz, 1H), 8.42 (dd, J = 8.2, 2.2 Hz, 1H), 7.78 (s, 1H), 7.42 (d, J = 8.2 Hz, 1H), 7.09 (s, 0.2H), 6.96 (s, 0.5H), 6.83 (s, 0.3H), 5.78 (s, 2H), 2.94 (d, J = 10.7 Hz, 2H), 2.59 (dt, J = 18.8, 9.4 Hz, 4H), 2.42 (ddd, J = 13.1, 11.4, 4.5 Hz, 1H), 2.30 (t, J = 12.7 Hz, 3H), 1.19 (t, J = 7.2 Hz, 3H); LRMS (ES) m/z 408.29 ($M^+$ + 1). |
| 129 | 4007 | 2-(difluoromethyl)-5-(6-((4-(4-fluoro-1-isopropylpiperidin-4-yl)-1H-1,2,3-triazol-1-yl)methyl)pyridin-3-yl)-1,3,4-oxadiazole<br>$_1$H NMR (400 MHz, $CDCl_3$) δ 9.34 (d, J = 1.7 Hz, 1H), 8.44 (dd, J = 8.2, 2.2 Hz, 1H), 7.82 (s, 1H), 7.45 (d, J = 8.1 Hz, 1H), 7.09 (s, 0.2H), 6.96 (s, 0.5H), 6.83 (s, 0.3H), 5.78 (s, 2H), 3.27-3.20 (m, 3H), 3.02 (s, 2H), 2.61-2.50 (m, 4H), 1.30 (d, J = 6.6 Hz, 6H); LRMS (ES) m/z 422.03 ($M^+$ + 1). |
| 130 | 4008 | 2-(difluoromethyl)-5-(6-((4-(4-fluoro-1-(oxetan-3-yl)piperidin-4-yl)-1H-1,2,3-triazol-1-yl)methyl)pyridin-3-yl)-1,3,4-oxadiazole<br>$_1$H NMR ((400 MHz, $CDCl_3$) δ 9.34 (d, J = 1.6 Hz, 1H), 8.42 (dd, J = 8.2, 2.2 Hz, 1H), 7.79 (s, 1H), 7.41 (d, J = 10.1 Hz, 1H), 7.09 (s, 0.2H), 6.96 (s, 0.5H), 6.83 (s, 0.3H), 5.78 (s, 2H), 4.76-4.59 (m, 4H), 3.59 (p, J = 6.5 Hz, 1H), 2.72-2.59 (m, 2H), 2.44-2.17 (m, 6H); LRMS (ES) m/z 436.27 ($M^+$ + 1). |

Example 131: Synthesis of compound 4009, 1-(4-(1-((5-(5-(difluoromethyl)-1,3,4-oxadiazol-2-yl)pyridin-2-yl)methyl)-1H-1,2,3-triazol-4-yl)-4-fluoropiperidin-1-yl)ethan-1-one

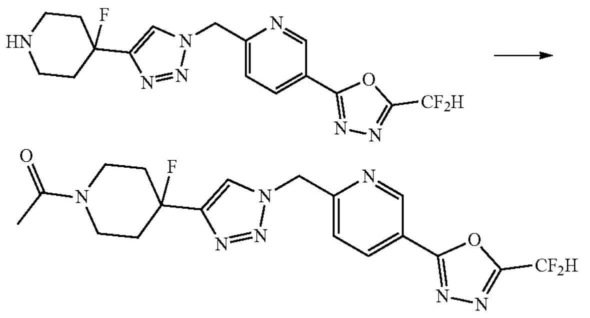

The 2-(difluoromethyl)-5-(6-((4-(4-fluoropiperidin-4-yl)-1H-1,2,3-triazol-1-yl)methyl)pyridin-3-yl)-1,3,4-oxadiazole (0.080 g, 0.211 mmol) prepared in step 1 of example 127, triethylamine (0.059 mL, 0.422 mmol) and acetic anhydride (0.060 mL, 0.633 mmol) were dissolved in dichloromethane (5 mL) at room temperature, after which the resulting solution was stirred at the same temperature for 12 hours. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 1-(4-(1-((5-(5-(difluoromethyl)-1,3,4-oxadiazol-2-yl)pyridin-2-yl)methyl)-1H-1,2,3-triazol-4-yl)-4-fluoropiperidin-1-yl)ethan-1-one (0.021 g, 23.6%) in a white solid form.

$^1H$ NMR (400 MHz, $CDCl_3$) δ 9.34 (d, J=1.7 Hz, 1H), 8.43 (dd, J=8.2, 2.2 Hz, 1H), 7.82 (s, 1H), 7.45 (d, J=8.2 Hz, 1H), 7.09 (s, 0.2H), 6.96 (s, 0.5H), 6.83 (s, 0.3H), 5.78 (s, 2H), 4.48 (d, J=13.2 Hz, 1H), 3.79 (d, J=13.6 Hz, 1H), 3.63-3.51 (m, 1H), 3.24-3.10 (m, 1H), 2.38-2.11 (m, 7H); LRMS (ES) m/z 422.24 ($M^+$+1).

Example 132: Synthesis of compound 4010, 2-(difluoromethyl)-5-(6-((4-(3-(1-methylpiperidin-4-yl)phenyl)-1H-1,2,3-triazol-1-yl)methyl)pyridin-3-yl)-1,3,4-oxadiazole

[Step 1] Synthesis of 2-(difluoromethyl)-5-(6-((4-(3-(piperidin-4-yl)phenyl)-1H-1,2,3-triazol-1-yl)methyl)pyridin-3-yl)-1,3,4-oxadiazole

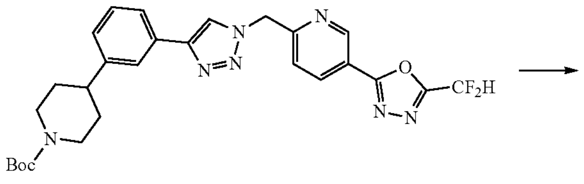

-continued

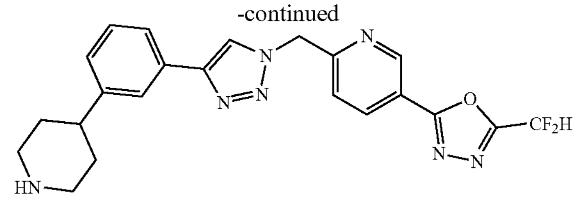

The tert-butyl 4-(3-(1-((5-(5-(difluoromethyl)-1,3,4-oxadiazol-2-yl)pyridin-2-yl)methyl)-1H-1,2,3-triazol-4-yl)phenyl)piperidin-1-carboxylate (0.320 g, 0.595 mmol) prepared in step 5 of example 123 and trifluoroacetic acid (0.137 mL, 1.786 mmol) were dissolved in dichloromethane (20 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(6-((4-(3-(piperidin-4-yl)phenyl)-1H-1,2,3-triazol-1-yl)methyl) pyridin-3-yl)-1,3,4-oxadiazole, 0.250 g, 96.0%, yellow oil).

[Step 2] Synthesis of Compound 4010

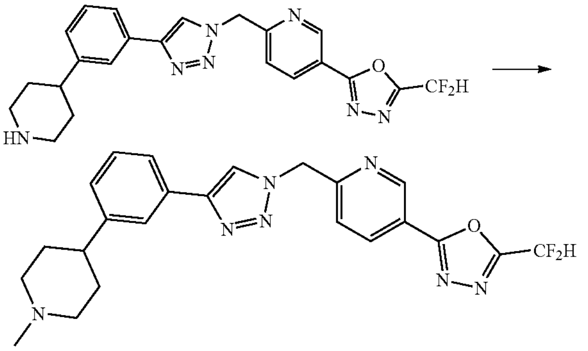

The 2-(difluoromethyl)-5-(6-((4-(3-(piperidin-4-yl)phenyl)-1H-1,2,3-triazol-1-yl)methyl)pyridin-3-yl)-1,3,4-oxadiazole (0.080 g, 0.183 mmol) prepared in step 1, N,N-diisopropylethylamine (0.064 mL, 0.366 mmol) and formaldehyde (37.00%, 0.030 g, 0.366 mmol) were dissolved in dichloromethane (5 mL), after which the resulting solution was stirred at room temperature for 30 minutes, and then sodium triacetoxyborohydride (0.078 g, 0.366 mmol) was added thereto and further stirred at the same temperature for 12 hours. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(6-((4-(3-(1-methylpiperidin-4-yl)phenyl)-1H-1,2,3-triazol-1-yl)methyl)pyridin-3-yl)-1,3,4-oxadiazole (0.032 g, 38.8%) in a white solid form.

$^1H$ NMR (400 MHz, $CDCl_3$) δ 9.35 (d, J=1.7 Hz, 1H), 8.41 (dd, J=8.2, 2.2 Hz, 1H), 7.97 (s, 1H), 7.75 (s, 1H), 7.68 (d, J=7.7 Hz, 1H), 7.44-7.33 (m, 2H), 7.24 (d, J=7.7 Hz, 1H), 7.09 (s, 0.2H), 6.96 (s, 0.5H), 6.83 (s, 0.3H), 5.83 (s, 2H), 3.04 (d, J=11.7 Hz, 2H), 2.62-2.48 (m, 1H), 2.37 (s, 3H), 2.18-2.07 (m, 2H), 1.94-1.85 (m, 4H); LRMS (ES) m/z 452.13 ($M^+$+1).

The compounds of table 39 were synthesized according to substantially the same process as described above in the synthesis of compound 4010 with an exception of using 2-(difluoromethyl)-5-(6-((4-(3-(piperidin-4-yl)phenyl)-1H-1,2,3-triazol-1-yl)methyl)pyridin-3-yl)-1,3,4-oxadiazole and the reactant of table 38.

TABLE 38

| Example | Compound No. | Reactant | Yield (%) |
|---|---|---|---|
| 133 | 4011 | Acetaldehyde | 24 |
| 134 | 4012 | Propan-2-one | 12 |
| 135 | 4013 | Oxetan-3-one | 16 |

The tert-butyl 4-((1-((5-(5-(difluoromethyl)-1,3,4-oxadiazol-2-yl)pyridin-2-yl)methyl)-1H-1,2,3-triazol-4-yl)methyl)piperidin-1-carboxylate (0.700 g, 1.472 mmol) prepared in example 122 and trifluoroacetic acid (0.338 mL, 4.416 mmol) were dissolved in dichloromethane (20 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(6-((4-(piperidin-4-ylmethyl)-1H-1,2,3-triazol-1-yl)methyl)pyridin-3-yl)-1,3,4-oxadiazole (0.550 g, 99.5%, yellow oil)

TABLE 39

| Example | Compound No. | Compound Name, $^{1}$H-NMR, MS (ESI) |
|---|---|---|
| 133 | 4011 | 2-(difluoromethyl)-5-(6-((4-(3-(1-ethylpiperidin-4-yl)phenyl)-1H-1,2,3-triazol-1-yl)methyl)pyridin-3-yl)-1,3,4-oxadiazole<br>$^{1}$H NMR (400 MHz, $CDCl_3$) δ 9.36 (dd, J = 2.2, 0.8 Hz, 1H), 8.42 (dd, J = 8.2, 2.2 Hz, 1H), 7.98 (s, 1H), 7.76 (d, J = 1.8 Hz, 1H), 7.73-7.66 (m, 1H), 7.40 (dd, J = 17.6, 7.9 Hz, 2H), 7.25 (d, J = 7.7 Hz, 1H), 7.09 (s, 0.2H), 6.96 (s, 0.5H), 6.83 (s, 0.3H), 5.84 (s, 2H), 3.22 (d, J = 11.3 Hz, 2H), 2.63-2.55 (m, 3H), 2.18 (dd, J = 14.8, 8.4 Hz, 2H), 2.02-1.87 (m, 4H), 1.20 (t, J = 7.3 Hz, 3H); LRMS (ES) m/z 466.04 ($M^+$ + 1). |
| 134 | 4012 | 2-(difluoromethyl)-5-(6-((4-(3-(1-isopropylpiperidin-4-yl)phenyl)-1H-1,2,3-triazol-1-yl)methyl)pyridin-3-yl)-1,3,4-oxadiazole<br>$^{1}$H NMR (400 MHz, $CDCl_3$) δ 9.36 (dd, J = 2.2, 0.8 Hz, 1H), 8.42 (dd, J = 8.2, 2.2 Hz, 1H), 7.96 (s, 1H), 7.76 (t, J = 1.7 Hz, 1H), 7.73-7.65 (m, 1H), 7.44-7.33 (m, 2H), 7.25 (d, J = 7.7 Hz, 1H), 7.09 (s, 0.2H), 6.96 (s, 0.5H), 6.83 (s, 0.3H), 5.83 (s, 2H), 3.06 (d, J = 11.4 Hz, 2H), 2.83 (dt, J = 13.2, 6.5 Hz, 1H), 2.57 (ddd, J = 16.0, 10.8, 5.3 Hz, 1H), 2.30 (tt, J = 15.9, 7.8 Hz, 2H), 1.97-1.88 (m, 4H), 1.12 (d, J = 6.6 Hz, 6H); LRMS (ES) m/z 480.08 ($M^+$ + 1). |
| 135 | 4013 | 2-(difluoromethyl)-5-(6-((4-(3-(1-(oxetan-3-yl)piperidin-4-yl)phenyl)-1H-1,2,3-triazol-1-yl)methyl)pyridin-3-yl)-1,3,4-oxadiazole<br>$^{1}$H NMR (400 MHz, $CDCl_3$) δ 9.36 (dd, J = 2.2, 0.8 Hz, 1H), 8.42 (dd, J = 8.2, 2.2 Hz, 1H), 7.97 (s, 1H), 7.78 (t, J = 1.7 Hz, 1H), 7.71-7.65 (m, 1H), 7.47-7.34(m, 2H), 7.24 (d, J = 7.7 Hz, 1H), 7.09 (s, 0.2H), 6.96 (s, 0.5H), 6.83 (s, 0.3H), 5.83 (s, 2H), 4.73-4.64 (m, 4H), 3.60-3.48 (m, 1H), 2.91 (d, J = 9.8 Hz, 2H), 2.66-2.54 (m, 1H), 2.03-1.83 (m, 6H); LRMS (ES) m/z 494.31 ($M^+$ + 1). |

Example 136: Synthesis of compound 4014, 2-(difluoromethyl)-5-(6-((4-((1-methylpiperidin-4-yl)methyl)-1H-1,2,3-triazol-1-yl)methyl)pyridin-3-yl)-1,3,4-oxadiazole

[Step 1] Synthesis of 2-(difluoromethyl)-5-(6-((4-(piperidin-4-ylmethyl)-1H-1,2,3-triazol-1-yl)methyl)pyridin-3-yl)-1,3,4-oxadiazole

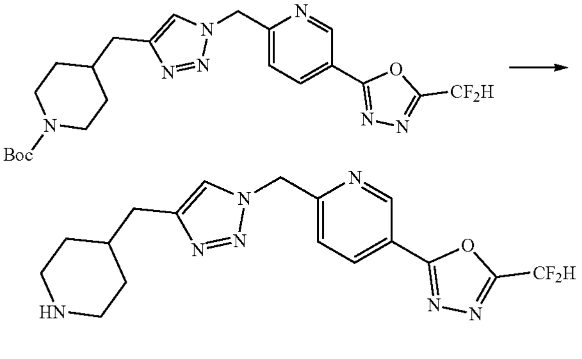

[Step 2] Synthesis of Compound 4014

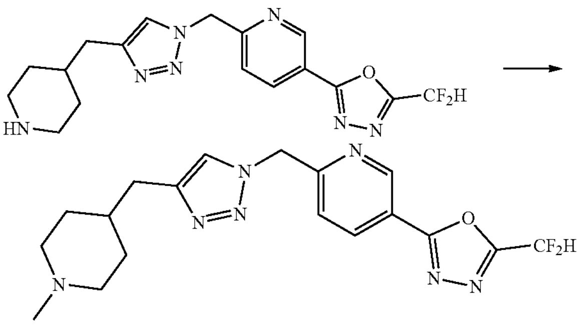

The 2-(difluoromethyl)-5-(6-((4-(piperidin-4-ylmethyl)-1H-1,2,3-triazol-1-yl)methyl)pyridin-3-yl)-1,3,4-oxadiazole (0.080 g, 0.213 mmol) prepared in step 1, N,N-diisopropylethylamine (0.074 mL, 0.426 mmol) and formaldehyde (37.00%, 0.035 g, 0.426 mmol) were dissolved in dichloromethane (5 mL), after which the resulting solution was stirred at room temperature for 30 minutes, and then sodium triacetoxyborohydride (0.090 g, 0.426 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(6-((4-((1-methylpiperidin-4-yl)methyl)-1H-1,2,3-triazol-1-yl)methyl)pyridin-3-yl)-1,3,4-oxadiazole (0.021 g, 25.3%) in a white solid form.

$^1H$ NMR (400 MHz, $CDCl_3$) δ 9.33 (d, J=1.6 Hz, 1H), 8.40 (dd, J=8.2, 2.2 Hz, 1H), 7.48 (d, J=12.2 Hz, 1H), 7.34 (d, J=8.2 Hz, 1H), 7.09 (s, 0.2H), 6.96 (s, 0.5H), 6.83 (s, 0.3H), 5.74 (s, 2H), 2.87 (d, J=11.5 Hz, 2H), 2.69 (d, J=6.4 Hz, 2H), 2.29 (s, 3H), 1.94 (t, J=11.0 Hz, 2H), 1.69 (t, J=10.1 Hz, 3H), 1.35 (dt, J=32.6, 18.4 Hz, 2H); LRMS (ES) m/z 390.5 ($M^+$+1).

Example 137: Synthesis of compound 4015, 1-(4-((1-((5-(5-(difluoromethyl)-1,3,4-oxadiazol-2-yl)pyridin-2-yl)methyl)-1H-1,2,3-triazol-4-yl)methyl)piperidin-1-yl)ethan-1-one

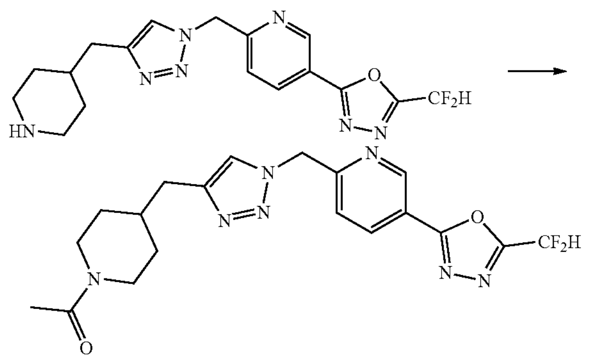

The 2-(difluoromethyl)-5-(6-((4-(piperidin-4-ylmethyl)-1H-1,2,3-triazol-1-yl)methyl)pyridin-3-yl)-1,3,4-oxadiazole (0.080 g, 0.213 mmol) prepared in step 1 of example 136, triethylamine (0.036 mL, 0.256 mmol) and acetic anhydride (0.022 mL, 0.234 mmol) were dissolved in dichloromethane (5 mL) at room temperature, after which the resulting solution was stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 1-(4-((1-((5-(5-(difluoromethyl)-1,3,4-oxadiazol-2-yl)pyridin-2-yl)methyl)-1H-1,2,3-triazol-4-yl)methyl)piperidin-1-yl)ethan-1-one (0.023 g, 25.9%) in a white solid form.

$^1H$ NMR (400 MHz, $CDCl_3$) δ 9.30 (d, J=1.7 Hz, 1H), 8.39 (dd, J=8.2, 2.2 Hz, 1H), 7.51 (s, 1H), 7.36 (d, J=8.2 Hz, 1H), 7.08 (s, 0.2H), 6.96 (s, 0.5H), 6.83 (s, 0.3H), 5.73 (s, 2H), 4.58 (d, J=13.3 Hz, 1H), 3.79 (d, J=13.6 Hz, 1H), 3.09-2.92 (m, 1H), 2.68 (d, J=6.9 Hz, 2H), 2.50 (dd, J=18.2, 7.5 Hz, 1H), 2.06 (s, 3H), 2.00-1.88 (m, 1H), 1.74 (dd, J=29.3, 13.0 Hz, 2H), 1.30-1.05 (m, 2H); LRMS (ES) m/z 418.2 ($M^+$+1).

Example 138: Synthesis of compound 4023, 4-((4-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine

[Step 1] Synthesis of 4-ethynyl-1H-indole

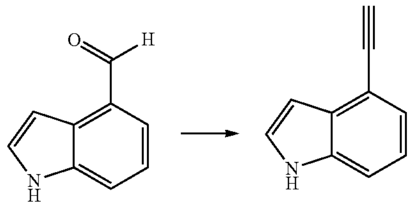

1H-indol-4-carbaldehyde (0.500 g, 3.444 mmol), dimethyl (1-diazo-2-oxopropyl)phosphonate (0.794 g, 4.133 mmol) and potassium carbonate (0.952 g, 6.889 mmol) were dissolved in methanol (5 mL) at room temperature, after which the resulting solution was stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 30%) and concentrated to obtain 4-ethynyl-1H-indole (0.300 g, 61.7%) in a yellow solid form.

[Step 2]2-(6-((4-(1H-indol-4-yl)-1H-1,2,3-triazol-1-yl)methyl)pyridin-3-yl)-5-(difluoromethyl)-1,3,4-oxadiazole

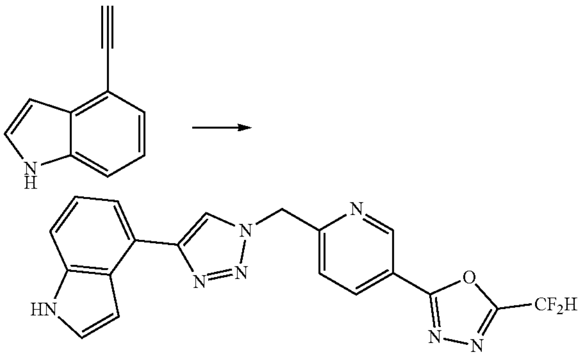

The 4-ethynyl-1H-indole (0.280 g, 1.983 mmol) prepared in step 1, 2-(6-(azidomethyl)pyridin-3-yl)-5-(difluoromethyl)-1,3,4-oxadiazole (0.500 g, 1.983 mmol) prepared in step 1 of example 16, copper(II) sulfate pentahydrate (0.005 g, 0.020 mmol) and sodium ascorbate (0.039 g, 0.198 mmol) were dissolved in tert-butanol (5 mL)/water (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 60%) and concentrated to obtain 2-(6-((4-(1H-indol-4-yl)-1H-1,2,3-triazol-1-yl)methyl)pyridin-3-yl)-5-(difluoromethyl)-1,3,4-oxadiazole (0.400 g, 51.3%) in a white solid form.

[Step 3] Synthesis of Compound 4023

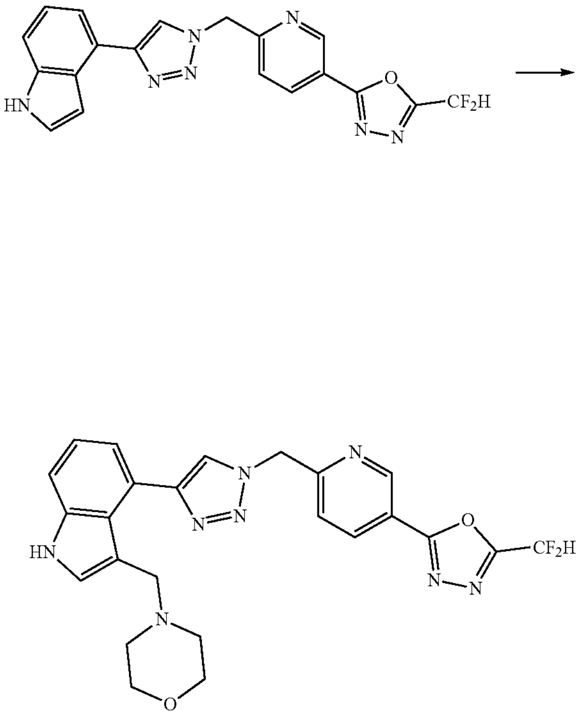

Morpholine (10.00 M solution In water, 0.023 mL, 0.230 mmol), formaldehyde (37.00%, 0.020 g, 0.253 mmol) and acetic acid (0.013 mL, 0.230 mmol) were dissolved in methanol (5 mL) at room temperature, after which 2-(6-((4-(1H-indol-4-yl)-1H-1,2,3-triazol-1-yl)methyl)pyridin-3-yl)-5-(difluoromethyl)-1,3,4-oxadiazole (1.00 M solution In MeOH, 0.230 mL, 0.230 mmol) prepared in step 3 was added to the resulting solution and stirred at the same temperature for 12 hours. 1N-sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 4-((4-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine (0.020 g, 17.7%) in a white solid form.

$^1H$ NMR (400 MHz, $CDCl_3$) δ 9.29 (d, J=2.3 Hz, 1H), 9.08 (s, 1H), 8.42 (s, 1H), 8.37 (dd, J=8.1, 2.3 Hz, 1H), 7.46 (d, J=8.2 Hz, 1H), 7.37 (d, J=8.0 Hz, 1H), 7.28-7.20 (m, 1H), 7.20-7.10 (m, 1H), 7.09-6.78 (m, 2H), 5.79 (s, 2H), 3.47 (d, J=4.1 Hz, 6H), 2.21 (t, J=4.7 Hz, 4H); LRMS (ES) m/z 493.4 ($M^+$+1).

Example 139: Synthesis of compound 4026, (S)-2-(difluoromethyl)-5-(6-((4-(1-(oxetan-3-yl)pyrrolidin-2-yl)-1H-1,2,3-triazol-1-yl)methyl)pyridin-3-yl)-1,3,4-oxadiazole

[Step 1] Synthesis of tert-butyl (S)-2-(1-((5-(5-(difluoromethyl)-1,3,4-oxadiazol-2-yl)pyridin-2-yl)methyl)-1H-1,2,3-triazol-4-yl)pyrrolidin-1-carboxylate

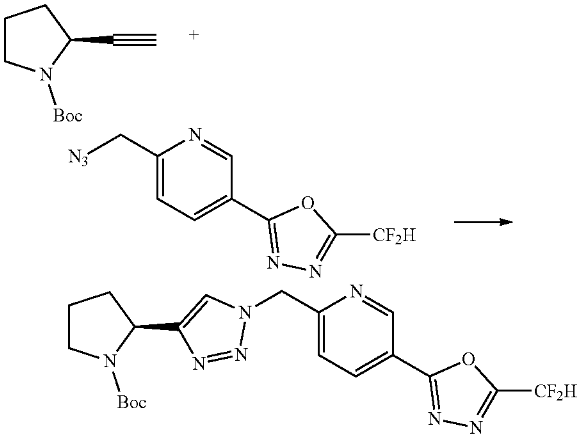

Tert-butyl (S)-2-ethynylpyrrolidin-1-carboxylate (0.400 g, 2.049 mmol), 2-(6-(azidomethyl)pyridin-3-yl)-5-(difluoromethyl)-1,3,4-oxadiazole (0.517 g, 2.049 mmol) prepared in step 1 of example 16, sodium ascorbate (0.036 g, 0.205 mmol) and copper(II) sulfate pentahydrate (0.005 g, 0.020 mmol) were dissolved in water (3 mL)/tert-butanol (3 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium hydrogen carbonate aqueous solution, dehydrated with anhydrous magnesium sulfate, filtered, and concentrated under reduced pressure. Then, the obtained product was used without an additional purification process (tert-butyl (S)-2-(1-((5-(5-(difluoromethyl)-1,3,4-oxadiazol-2-yl)pyridin-2-yl)methyl)-1H-1,2,3-triazol-4-yl)pyrrolidin-1-carboxylate, 0.850 g, 92.7%, brown solid form).

[Step 2] Synthesis of (S)-2-(difluoromethyl)-5-(6-((4-(pyrrolidin-2-yl)-1H-1,2,3-triazol-1-yl)methyl)pyridin-3-yl)-1,3,4-oxadiazole IDC-81C3

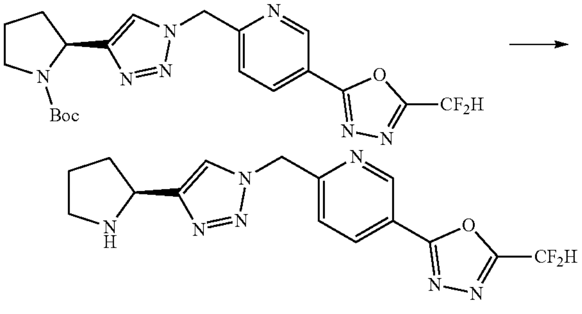

The tert-butyl (S)-2-(1-((5-(5-(difluoromethyl)-1,3,4-oxadiazol-2-yl)pyridin-2-yl)methyl)-1H-1,2,3-triazol-4-yl)pyrrolidin-1-carboxylate (0.850 g, 1.900 mmol) prepared in step 1 and trifluoroacetic acid (2.909 mL, 37.993 mmol) were dissolved in dichloromethane (10 mL) at room temperature, after which the resulting solution was stirred at the same temperature for 18 hours. Solvent was removed from the reaction mixture under reduced pressure, after which the resulting concentrate was purified via column chromatography ($SiO_2$, 40 g cartridge; methanol/dichloromethane=10%) and concentrated to obtain (S)-2-(difluoromethyl)-5-(6-((4-(pyrrolidin-2-yl)-1H-1,2,3-triazol-1-yl)methyl)pyridin-3-yl)-1,3,4-oxadiazole (0.775 g, 117.5%) in a colorless gel form.

[Step 3] Synthesis of Compound 4026

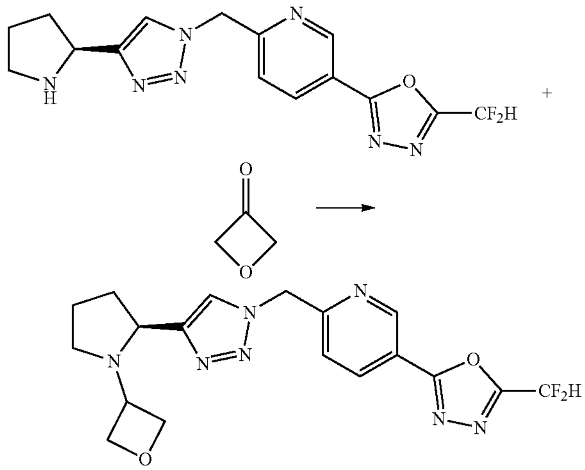

The (S)-2-(difluoromethyl)-5-(6-((4-(pyrrolidin-2-yl)-1H-1,2,3-triazol-1-yl)methyl)pyridin-3-yl)-1,3,4-oxadiazole (0.070 g, 0.202 mmol) prepared in step 2, oxetan-3-one (0.029 g, 0.403 mmol) and sodium triacetoxyborohydride (0.128 g, 0.605 mmol) were dissolved in dichloromethane (1 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via chromatography ($SiO_2$ plate, 20×20×1 mm; methanol/dichloromethane=10%) and concentrated to obtain (S)-2-(difluoromethyl)-5-(6-((4-(1-(oxetan-3-yl)pyrrolidin-2-yl)-1H-1,2,3-triazol-1-yl)methyl)pyridin-3-yl)-1,3,4-oxadiazole (0.012 g, 14.8%) in a light yellow solid form.

$^1$H NMR (400 MHz, $CDCl_3$) δ 9.32 (dd, J=2.2, 0.9 Hz, 1H), 8.40 (dd, J=8.2, 2.2 Hz, 1H), 7.59 (s, 1H), 7.37 (d, J=8.2 Hz, 1H), 6.94 (t, J=51.6 Hz, 1H), 5.73 (s, 2H), 4.71 (dd, J=12.7, 6.8 Hz, 4H), 3.84 (s, 1H), 3.71-3.60 (m, 1H), 3.16 (s, 1H), 2.88 (s, 1H), 2.76 (s, 2H), 2.07 (dt, J=13.2, 6.9 Hz, 1H); LRMS (ES) m/z 404.3 ($M^+$+1).

The compound of table 41 was synthesized according to substantially the same process as described above in the synthesis of compound 4026 with an exception of using (S)-2-(difluoromethyl)-5-(6-((4-(pyrrolidin-2-yl)-1H-1,2,3-triazol-1-yl)methyl)pyridin-3-yl)-1,3,4-oxadiazole and the reactant of table 40.

TABLE 40

| Example | Compound No. | Reactant | Yield (%) |
|---|---|---|---|
| 140 | 4027 | 2-oxaspiro[3.3]heptan-6-one | 29 |

TABLE 41

| Example | Compound No. | Compound Name, $^1$H-NMR, MS (ESI) |
|---|---|---|
| 140 | 4027 | (S)-2-(6-((4-(1-(2-oxaspiro[3.3]heptan-6-yl)pyrrolidin-2-yl)-1H-1,2,3-triazol-1-yl)methyl)pyridin-3-yl)-5-(difluoromethyl)-1,3,4-oxadiazole $_1$H NMR ((400 MHZ, $CDCl_3$) δ 9.30 (d, J = 2.1 Hz, 1H), 8.38 (dd, J = 8.2, 2.3 Hz, 1H), 7.66 (s, 1H), 7.35 (d, J = 8.2 Hz, 1H), 6.94 (t, J = 51.6 Hz, 1H), 5.73 (s, 2H), 4.61 (q, J = 5.9 Hz, 2H), 4.51 (d, J = 6.4 Hz, 1H), 4.43 (d, J = 6.5 Hz, 1H), 3.73 (s,1H), 3.04 (s, 1H), 2.87 (q, J = 8.0 Hz, 1H), 2.45-2.17 (m, 3H), 2.17-2.01 (m, 2H), 1.99-1.86 (m, 2H), 1.83 (t, J = 8.4 Hz, 1H), 1.72 (t, J = 10.2 Hz, 1H); LRMS (ES) m/z 444.3 ($M^+$ + 1). |

Example 141: Synthesis of compound 4028, methyl (S)-2-(1-((5-(5-(difluoromethyl)-1,3,4-oxadiazol-2-yl)pyridin-2-yl)methyl)-1H-1,2,3-triazol-4-yl)pyrrolidin-1-carboxylate

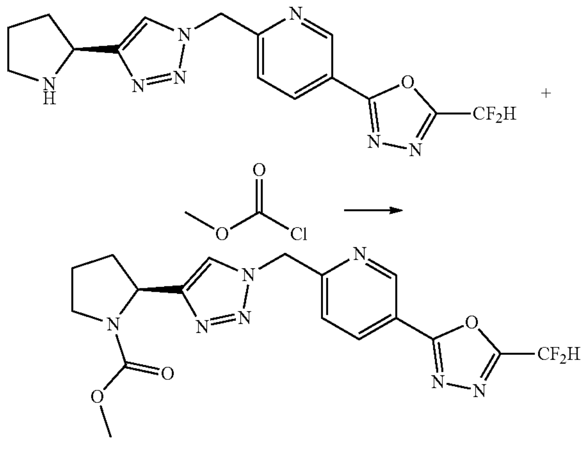

The (S)-2-(difluoromethyl)-5-(6-((4-(pyrrolidin-2-yl)-1H-1,2,3-triazol-1-yl)methyl)pyridin-3-yl)-1,3,4-oxadiazole (0.070 g, 0.202 mmol) prepared in step 2 of example 139, (chlorocarbonyl)oxy)methyl (0.023 g, 0.242 mmol) and triethylamine (0.034 mL, 0.242 mmol) were dissolved in dichloromethane (1 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium hydrogen carbonate aqueous solution, dehydrated with anhydrous magnesium sulfate, filtered, and concentrated under reduced pressure.

The resulting concentrate was purified via chromatography ($SiO_2$ plate, 20×20×1 mm; methanol/dichloromethane=10%) and concentrated to obtain methyl (S)-2-(1-((5-(5-(difluoromethyl)-1,3,4-oxadiazol-2-yl)pyridin-2-yl)methyl)-1H-1,2,3-triazol-4-yl)pyrrolidin-1-carboxylate (0.035 g, 42.8%) in a white solid form.

$^1$H NMR (400 MHz, $CDCl_3$; two rotamers in a 6:4 ratio) δ 9.31 (d, J=2.2 Hz, 1H), 8.38 (d, J=8.0 Hz, 1H), 7.71 (s, 0.6H), 7.52 (s, 0.4H), 7.31 (d, J=8.8 Hz, 1H), 6.94 (t, J=51.6 Hz, 1H), 5.72 (d, J=6.7 Hz, 2H), 5.09 (dd, J=7.5, 2.7 Hz, 1H), 3.68 (s, 2H), 3.63 (s, 1H), 3.59-3.40 (m, 2H), 2.48 (s, 0.5H), 2.38-2.08 (m, 2H), 1.98 (s, 1.5H); LRMS (ES) m/z 406.3 ($M^+$+1).

The compound of table 43 was synthesized according to substantially the same process as described above in the synthesis of compound 4028 with an exception of using (S)-2-(difluoromethyl)-5-(6-((4-(pyrrolidin-2-yl)-1H-1,2,3-triazol-1-yl)methyl)pyridin-3-yl)-1,3,4-oxadiazole and the reactant of table 42.

TABLE 42

| Example | Compound No. | Reactant | Yield (%) |
|---|---|---|---|
| 142 | 4029 | Acetic anhydride | 53 |

TABLE 43

| Example | Compound No. | Compound Name, $^1$H-NMR, MS (ESI) |
|---|---|---|
| 142 | 4029 | (S)-1-(2-(1-((5-(5-(difluoromethyl)-1,3,4-oxadiazol-2-yl)pyridin-2-yl)methyl)-1H-1,2,3-triazol-4-yl)pyrrolidin-1-yl)ethan-1-one $^1$H NMR (400 MHz, $CDCl_3$; two rotamers in a 7:3 ratio) δ 9.30 (s, 1H), 8.42 (dd, J = 8.2, 2.2 Hz, 0.3H), 8.37 (dd, J = 8.2, 2.2 Hz, 0.7H), 7.74 (s, 0.7H), 7.55 (s, 0.3H), 7.41 (d, J = 8.2 Hz, 0.3H), 7.30 (dd, J = 8.2,0.8 Hz, 0.7H), 6.94 (td, J = 51.6, 1.6 Hz, 1H), 5.78-5.71 (m, 1H), 5.67 (d, J = 15.8 Hz, 1H), 5.28 (d, J = 7.8 Hz, 1H), 5.16 (d, J = 7.4 Hz, OH), 3.73-3.61 (m, 1H), 3.61-3.46 (m, 1H), 2.57 (d, J = 10.5 Hz, 1H), 2.43-2.29 (m, 1H), 2.19 (td, J = 11.4, 5.5 Hz, 1H), 2.06 (s, 3H), 1.97 (s, 1H); LRMS (ES) m/z 390.3 ($M^+$ + 1). |

Example 143: Synthesis of compound 4051, 2-(difluoromethyl)-5-(6-((4-(2-methyl-1,2,3,4-tetrahydroisoquinolin-6-yl)-1H-1,2,3-triazol-1-yl)methyl)pyridin-3-yl)-1,3,4-oxadiazole

[Step 1] Synthesis of tert-butyl 6-ethynyl-3,4-dihydroisoquinolin-2(1H)-carboxylate

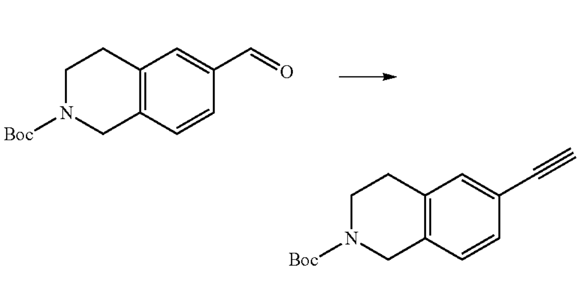

Tert-butyl 6-formyl-3,4-dihydroisoquinolin-2(1H)-carboxylate (0.500 g, 1.913 mmol), dimethyl (1-diazo-2-oxopropyl)phosphonate (0.345 mL, 2.296 mmol) and potassium carbonate (0.529 g, 3.827 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. Then, the obtained product was used without an additional purification process (tert-butyl 6-ethynyl-3,4-dihydroisoquinolin-2(1H)-carboxylate, 0.490 g, 99.5%, yellow solid).

[Step 2] Synthesis of tert-butyl 6-(1-((5-(methoxycarbonyl)pyridin-2-yl)methyl)-1H-1,2,3-triazol-4-yl)-3,4-dihydroisoquinolin-2(1H)-carboxylate

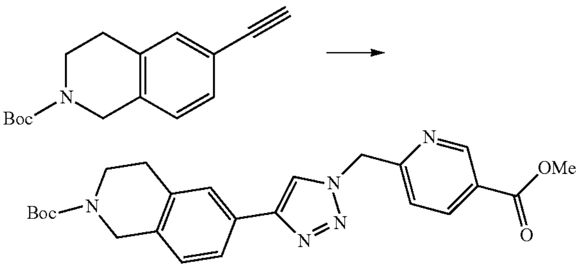

The tert-butyl 6-ethynyl-3,4-dihydroisoquinolin-2(1H)-carboxylate (0.500 g, 1.943 mmol) prepared in step 1, methyl 6-(azidomethyl)nicotinate (0.373 g, 1.943 mmol) prepared in step 1 of example 81, sodium ascorbate (0.038 g, 0.194 mmol) and copper(II) sulfate pentahydrate (0.005 g, 0.019 mmol) were dissolved in ethanol (150 mL) at room temperature, after which the resulting solution was stirred at 80 °C for 18 hours, and then a reaction was finished by lowering a temperature to room temperature. Solvent was removed from the reaction mixture under reduced pressure, after which the resulting concentrate was purified via column chromatography ($SiO_2$, 12 g cartridge; ethyl acetate/hexane=0 to 80%) and concentrated to obtain tert-butyl 6-(1-((5-(methoxycarbonyl)pyridin-2-yl)methyl)-1H-1,2,3-triazol-4-yl)-3,4-dihydroisoquinolin-2(1H)-carboxylate (0.853 g, 97.7%) in a yellow solid form.

[Step 3] Synthesis of tert-butyl 6-(1-((5-(hydrazinecarbonyl)pyridin-2-yl)methyl)-1H-1,2,3-triazol-4-yl)-3,4-dihydroisoquinolin-2(1H)-carboxylate

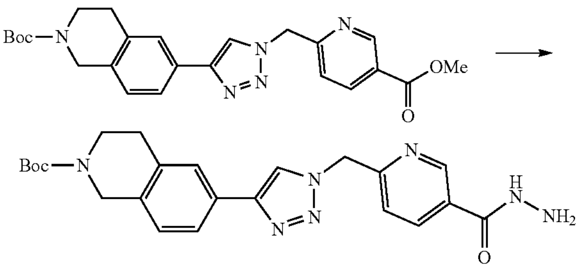

The tert-butyl 6-(1-((5-(methoxycarbonyl)pyridin-2-yl)methyl)-1H-1,2,3-triazol-4-yl)-3,4-dihydroisoquinolin-2

(1H)-carboxylate (1.100 g, 2.447 mmol) prepared in step 2 and hydrazine monohydrate (1.287 mL, 36.707 mmol) were mixed in ethanol (50 mL) at room temperature, after which the resulting mixture was heated under reflux and cooled down to room temperature. Then, solvent was removed from the reaction mixture under reduced pressure, after which the obtained product was used without an additional purification process (tert-butyl 6-(1-((5-(hydrazinecarbonyl)pyridin-2-yl)methyl)-1H-1,2,3-triazol-4-yl)-3,4-dihydroisoquinolin-2 (1H)-carboxylate, 1.100 g, 100.0%, yellow solid).

[Step 4] Synthesis of tert-butyl 6-(1-((5-(5-(difluoromethyl)-1,3,4-oxadiazol-2-yl)pyridin-2-yl) methyl)-1H-1,2,3-triazol-4-yl)-3,4-dihydroisoquinolin-2(1H)-carboxylate

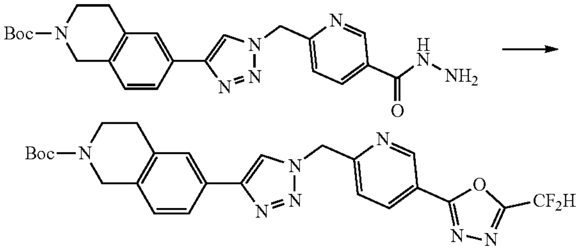

The tert-butyl 6-(1-((5-(hydrazinecarbonyl)pyridin-2-yl) methyl)-1H-1,2,3-triazol-4-yl)-3,4-dihydroisoquinolin-2 (1H)-carboxylate (0.490 g, 1.090 mmol) prepared in step 3 and triethylamine (0.456 mL, 3.270 mmol) were dissolved in tetrahydrofuran (15 mL) at room temperature, after which difluoroacetic anhydride (0.678 mL, 5.450 mmol) was added to the resulting solution and stirred at the same temperature for 5 hours. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 80%) and concentrated to obtain tert-butyl 6-(1-((5-(5-(difluoromethyl)-1,3,4-oxadiazol-2-yl)pyridin-2-yl)methyl)-1H-1,2,3-triazol-4-yl)-3,4-dihydroisoquinolin-2 (1H)-carboxylate(0.471 g, 84.8%) in a white solid form.

[Step 5] Synthesis of 2-(difluoromethyl)-5-(6-((4-(1,2,3,4-tetrahydroisoquinolin-6-yl)-1H-1,2,3-triazol-1-yl)methyl)pyridin-3-yl)-1,3,4-oxadiazole trifluoroacetic acid

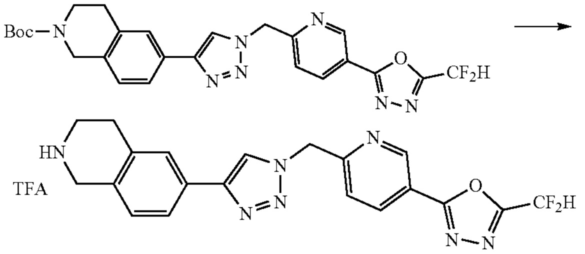

The tert-butyl 6-(1-((5-(5-(difluoromethyl)-1,3,4-oxadiazol-2-yl)pyridin-2-yl)methyl)-1H-1,2,3-triazol-4-yl)-3,4-dihydroisoquinolin-2(1H)-carboxylate (0.471 g, 0.924 mmol) prepared in step 4 was dissolved in dichloromethane (15 mL) at room temperature, after which trifluoroacetic acid (TFA, 0.212 mL, 2.773 mmol) was added to the resulting solution and stirred at the same temperature for 5 hours. Solvent was removed from the reaction mixture under reduced pressure, after which a precipitated solid was filtered out, washed with dichloromethane, and dried to obtain 2-(difluoromethyl)-5-(6-((4-(1,2,3,4-tetrahydroisoquinolin-6-yl)-1H-1,2,3-triazol-1-yl)methyl)pyridin-3-yl)-1,3,4-oxadiazole trifluoroacetic acid (0.450 g, 96.1%) in a white solid form.

[Step 6] Synthesis of Compound 4051

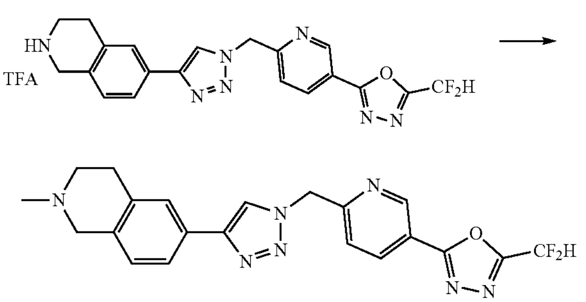

The 2-(difluoromethyl)-5-(6-((4-(1,2,3,4-tetrahydroisoquinolin-6-yl)-1H-1,2,3-triazol-1-yl)methyl)pyridin-3-yl)-1,3,4-oxadiazole trifluoroacetic acid (0.050 g, 0.099 mmol) prepared in step 5, formaldehyde(37.00% solution in $H_2O$, 0.020 mL, 0.197 mmol) and N,N-diisopropylethylamine (0.034 mL, 0.197 mmol) were dissolved in dichloromethane (5 mL) at room temperature, after which sodium triacetoxyborohydride (0.052 g, 0.246 mmol) was added to the resulting solution and stirred at the same temperature for 18 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 15%) and concentrated to obtain 2-(difluoromethyl)-5-(6-((4-(2-methyl-1,2,3,4-tetrahydroisoquinolin-6-yl)-1H-1,2,3-triazol-1-yl)methyl)pyridin-3-yl)-1,3,4-oxadiazole (0.007 g, 16.8%) in a yellow solid form.

$^1H$ NMR (400 MHz, $CDCl_3$) δ 9.32 (dd, J=2.3, 0.9 Hz, 1H), 8.38 (dd, J=8.2, 2.3 Hz, 1H), 7.93 (s, 1H), 7.63 (d, J=1.8 Hz, 1H), 7.56 (dd, J=7.9, 1.8 Hz, 1H), 7.39 (dd, J=8.2, 0.9 Hz, 1H), 7.08 (d, J=8.2 Hz, 1H), 7.06-6.94 (m, 1H), 5.80 (s, 2H), 3.62 (s, 2H), 2.98 (t, J=6.0 Hz, 2H), 2.73 (t, J=6.0 Hz, 2H), 2.48 (s, 3H); LRMS (ES) m/z 424.1 ($M^+$+1).

The compounds of table 45 were synthesized according to substantially the same process as described above in the synthesis of compound 4051 with an exception of using 2-(difluoromethyl)-5-(6-((4-(1,2,3,4-tetrahydroisoquinolin-6-yl)-1H-1,2,3-triazol-1-yl)methyl)pyridin-3-yl)-1,3,4-oxadiazole and the reactant of table 44.

TABLE 44

| Example | Compound No. | Reactant | Yield (%) |
|---|---|---|---|
| 144 | 4052 | Acetaldehyde | 16 |
| 145 | 4053 | Propan-2-one | 11 |
| 146 | 4054 | Cyclobutanone | 24 |
| 147 | 4055 | Oxetan-3-one | 21 |

TABLE 45

| Example | Compound No. | Compound Name, $^1$H-NMR, MS (ESI) |
|---|---|---|
| 144 | 4052 | 2-(difluoromethyl)-5-(6-((4-(2-ethyl-1,2,3,4-tetrahydroisoquinolin-6-yl)-1H-1,2,3-triazol-1-yl)methyl)pyridin-3-yl)-1,3,4-oxadiazole<br>$^1$H NMR (400 MHZ, $CDCl_3$) δ 9.33 (dd, J = 2.2, 0.9 Hz, 1H), 8.39 (dd, J = 8.2, 2.2 Hz, 1H), 7.93 (s, 1H), 7.65-7.53 (m, 2H), 7.39 (dt, J = 8.3, 1.5 Hz, 1H), 7.12-7.04 (m, 1H), 7.07-6.94 (m, 1H), 5.80 (s, 2H), 3.70 (s, 2H), 3.03-2.90 (m, 2H), 2.81 (t, J = 6.0 Hz, 2H), 2.65 (q, J = 7.2 Hz, 2H), 1.22 (t, J = 7.2 Hz, 3H); LRMS (ES) m/z 438.3 ($M^+$ + 1). |
| 145 | 4053 | 2-(difluoromethyl)-5-(6-((4-(2-isopropyl-1,2,3,4-tetrahydroisoquinolin-6-yl)-1H-1,2,3-triazol-1-yl)methyl)pyridin-3-yl)-1,3,4-oxadiazole<br>$^1$H NMR (400 MHZ, $CDCl_3$) δ 9.33 (dd, J = 2.2, 0.9 Hz, 1H), 8.39 (dd, J = 8.2, 2.2 Hz, 1H), 7.92 (s, 1H), 7.62 (d, J = 1.7 Hz, 1H), 7.56 (dd, J = 7.9, 1.8 Hz, 1H), 7.40 (dd, J = 8.2, 0.9 Hz, 1H), 7.09 (d, J = 7.9 Hz, 1H), 7.07-6.94 (m, 1H), 5.80 (s, 2H), 3.79 (s, 2H), 2.97 (s, 3H), 2.84 (t, J = 5.9 Hz, 2H), 1.17 (d, J = 6.5 Hz, 6H); LRMS (ES) m/z 452.4 ($M^+$ + 1). |
| 146 | 4054 | 2-(6-((4-(2-cyclobutyl-1,2,3,4-tetrahydroisoquinolin-6-yl)-1H-1,2,3-triazol-1-yl)methyl)pyridin-3-yl)-5-(difluoromethyl)-1,3,4-oxadiazole<br>$^1$H NMR (400 MHZ, $CDCl_3$) δ 9.32 (dd, J = 2.2, 0.8 Hz, 1H), 8.38 (dd, J = 8.2, 2.2 Hz, 1H), 7.92 (s, 1H), 7.62 (d, J = 1.8 Hz, 1H), 7.55 (dd, J = 7.9, 1.8 Hz, 1H), 7.39 (dd, J = 8.2, 0.9 Hz, 1H), 7.08 (d, J = 8.2 Hz, 1H), 7.06-6.94 (m, 1H), 5.79 (s, 2H), 3.54 (s, 2H), 2.94 (q, J = 9.0, 7.6 Hz, 3H), 2.64 (t, J = 6.0 Hz, 2H), 2.20-2.08 (m, 2H), 2.05-1.97 (m, 2H), 1.75 (qt, J = 10.2, 8.3 Hz, 2H); LRMS (ES) m/z 464.5 ($M^+$ + 1). |
| 147 | 4055 | 2-(difluoromethyl)-5-(6-((4-(2-(oxetan-3-yl)-1,2,3,4-tetrahydroisoquinolin-6-yl)-1H-1,2,3-triazol-1-yl)methyl)pyridin-3-yl)-1,3,4-oxadiazole<br>$^1$H NMR (400 MHZ, $CDCl_3$) δ 9.32 (dd, J = 2.2, 0.9 Hz, 1H), 8.39 (dd, J = 8.2, 2.2 Hz, 1H), 7.93 (s, 1H), 7.64 (d, J = 1.7 Hz, 1H), 7.56 (dd, J = 7.9, 1.8 Hz, 1H), 7.40 (dd, J = 8.2, 0.9 Hz, 1H), 7.10-7.03 (m, 1H), 7.07-6.94 (m, 1H), 5.80 (s, 2H), 4.74 (dd, J = 6.5, 2.9 Hz, 4H), 3.70 (p, J = 6.5 Hz, 1H), 3.53 (s, 2H), 2.97 (t, J = 6.0 Hz, 2H), 2.63 (t, J = 5.9 Hz, 2H); LRMS (ES) m/z 466.4 ($M^+$ + 1). |

Example 165: Synthesis of compound 4108, 2-(difluoromethyl)-5-(4-((4-(3-(pyrrolidin-1-ylmethyl)-1H-indol-6-yl)-1H-1,2,3-triazol-1-yl)methyl)phenyl)-1,3,4-oxadiazole

[Step 1] Synthesis of 3-(pyrrolidin-1-ylmethyl)-1H-indol-6-carbaldehyde

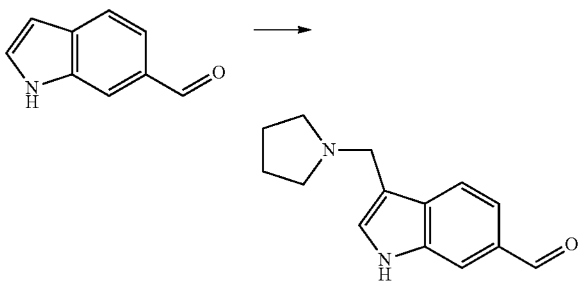

Pyrrolidine (0.300 g, 4.218 mmol) and formaldehyde (37.00%, 0.377 g, 4.640 mmol) were dissolved in acetic acid (3 mL), after which the resulting solution was stirred at 0 °C for 0.4 hours, and then 1H-indol-6-carbaldehyde (0.490 g, 3.375 mmol) was added and further stirred at room temperature for 18 hours. 2N-sodium hydroxide aqueous solution was poured into the resulting reaction mixture, and an extraction was performed with ethyl acetate. An organic layer was washed with saturated aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 5%) and concentrated to obtain 3-(pyrrolidin-1-ylmethyl)-1H-indol-6-carbaldehyde (0.300 g, 31.2%) in a yellow gum form.

[Step 2] Synthesis of 6-ethynyl-3-(pyrrolidin-1-ylmethyl)-1H-indole

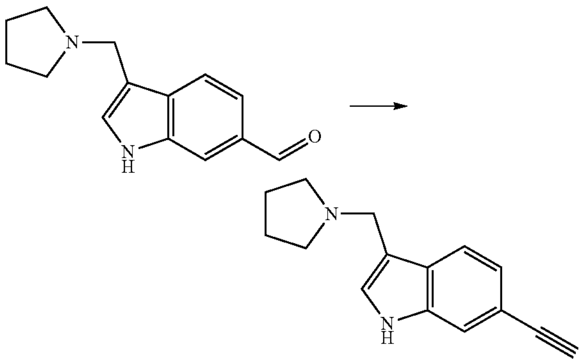

The 3-(pyrrolidin-1-ylmethyl)-1H-indol-6-carbaldehyde (0.100 g, 0.438 mmol) prepared in step 1 and dimethyl(1-diazo-2-oxopropyl)phosphonate (0.101 g, 0.526 mmol) were dissolved in methanol (2 mL) at room temperature, after which potassium carbonate (0.121 g, 0.876 mmol) was added to the resulting solution and stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 5%) and concentrated to obtain 6-ethynyl-3-(pyrrolidin-1-ylmethyl)-1H-indole (0.065 g, 66.2%) in a yellow oil form.

[Step 3] Synthesis of Compound 4108

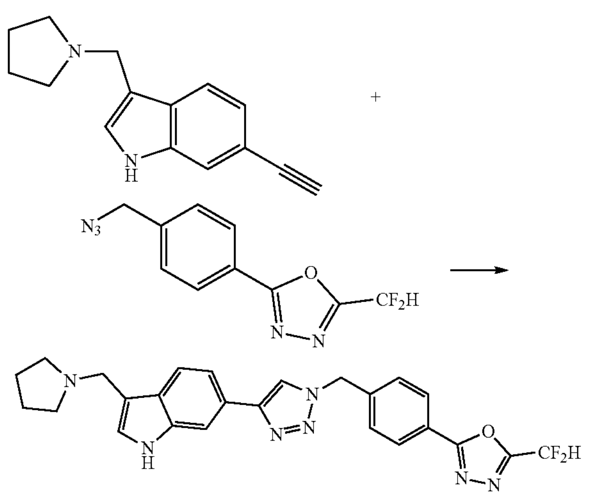

The 2-(4-(azidomethyl)phenyl)-5-(difluoromethyl)-1,3,4-oxadiazole (0.030 g, 0.104 mmol) prepared in step 1 of example 1 and 6-ethynyl-3-(pyrrolidin-1-ylmethyl)-1H-indole (0.023 g, 0.104 mmol) prepared in step 2 were dissolved in tert-butanol (1 mL)/water (1 mL) at room temperature, after which sodium ascorbate (1.00 M solution, 0.010 mL, 0.010 mmol) and copper(II) sulfate pentahydrate (0.50 M solution, 0.002 mL, 0.001 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(4-((4-(3-(pyrrolidin-1-ylmethyl)-1H-indol-6-yl)-1H-1,2,3-triazol-1-yl)methyl)phenyl)-1,3,4-oxadiazole (0.012 g, 24.3%) in a light yellow oil form.

$^1$H NMR (400 MHz, $CD_3OD$) δ 8.43 (s, 1H), 8.21-8.14 (m, 2H), 7.97 (d, J=1.6 Hz, 1H), 7.82 (d, J=8.4 Hz, 1H), 7.67-7.61 (m, 3H), 7.59 (s, 1H), 7.23 (t, J=51.6 Hz, 1H), 5.81 (s, 2H), 4.59 (d, J=7.9 Hz, 2H), 3.38 (d, J=7.1 Hz, 4H), 2.09 (s, 4H); LRMS (ES) m/z 476.3 ($M^+$+1).

The compounds of table 47 were synthesized according to substantially the same process as described above in the synthesis of compound 4108 with an exception of using 6-ethynyl-3-(pyrrolidin-1-ylmethyl)-1H-indole and the reactant of table 46.

TABLE 46

| Example | Compound No. | Reactant | Yield (%) |
|---|---|---|---|
| 166 | 4109 | 2-(4-(azidomethyl)-3-fluorophenyl)-5-(difluoromethyl)-1,3,4-oxadiazole | 27 |
| 367 | 4493 | 2-(6-(azidomethyl)pyridin-3-yl)-5-(difluoromethyl)-1,3,4-oxadiazole | 20 |

TABLE 47

| Example | Compound No. | Compound Name, $^1$H-NMR, MS (ESI) |
|---|---|---|
| 166 | 4109 | 2-(difluoromethyl)-5-(3-fluoro-4-((4-(3-(pyrrolidin-1-ylmethyl)-1H-indol-6-yl)-1H-1,2,3-triazol-1-yl)methyl)phenyl)-1,3,4-oxadiazole $^1$H NMR (400 MHZ, $CD_3OD$) δ 8.43 (s, 1H), 8.04-7.94 (m, 3H), 7.82 (d, J = 8.4 Hz, 1H), 7.69-7.58 (m, 3H), 7.24 (t, J = 51.6 Hz, 2H), 5.87 (s, 2H), 4.59 (s, 2H), 3.48-3.35 (m, 4H), 2.16-2.01 (m, 4H); LRMS (ES) m/z 494.5 ($M^+$ + 1). |
| 367 | 4493 | 2-(difluoromethyl)-5-(6-((4-(3-(pyrrolidin-1-ylmethyl)-1H-indol-6-yl)-1H-1,2,3-triazol-1-yl)methyl)pyridin-3-yl)-1,3,4-oxadiazole $^1$H NMR (400 MHZ, $CD_3OD$) δ 9.28 (dd, J = 2.3, 0.9 Hz, 1H), 8.53 (dd, J = 8.2, 2.2 Hz, 1H), 8.50 (s, 1H), 7.98 (d, J = 1.4 Hz, 1H), 7.86-7.81 (m, 1H), 7.69-7.59 (m, 3H), 7.26 (t, J = 51.6 Hz, 1H), 5.94 (s, 2H), 4.60 (s, 2H), 3.45-3.35 (m, 4H), 2.10 (p, J = 3.7 Hz, 4H); LRMS (ES) m/z 477.2 ($M^+$ + 1). |

Example 167: Synthesis of compound 4110, 2-(difluoromethyl)-5-(3-fluoro-4-((4-(3-((4-methylpiperidin-1-yl)methyl)-1H-indol-6-yl)-1H-1,2,3-triazol-1-yl)methyl)phenyl)-1,3,4-oxadiazole

[Step 1] Synthesis of 3-((4-methylpiperidin-1-yl)methyl)-1H-indol-6-carbaldehyde

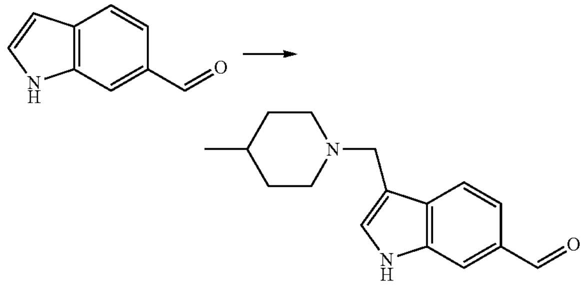

4-methylpiperidine (0.300 g, 3.025 mmol) and formaldehyde (37.00%, 0.270 g, 3.327 mmol) were dissolved in acetic acid (3 mL), after which the resulting solution was stirred at 0 °C for 0.4 hours, and then 1H-indol-6-carbaldehyde (0.351 g, 2.420 mmol) was added and further stirred at room temperature for 18 hours. 2N-sodium hydroxide aqueous solution was poured into the resulting reaction mixture, and an extraction was performed with ethyl acetate. An organic layer was washed with saturated aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 5%) and concentrated to obtain 3-((4-methylpiperidin-1-yl)methyl)-1H-indol-6-carbaldehyde (0.150 g, 19.3%) in a yellow gum form.

[Step 2] Synthesis of 6-ethynyl-3-((4-methylpiperidin-1-yl)methyl)-1H-indole

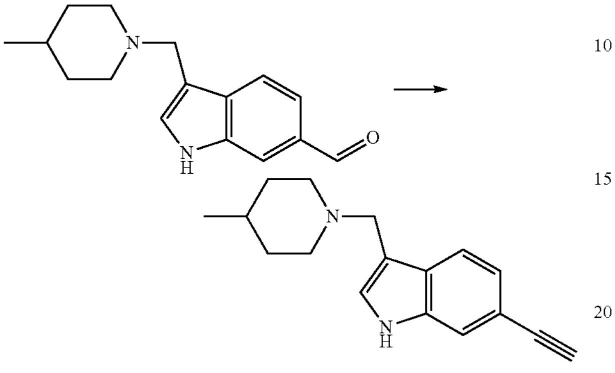

The 3-((4-methylpiperidin-1-yl)methyl)-1H-indol-6-carbaldehyde (0.100 g, 0.390 mmol) prepared in step 1 and dimethyl(1-diazo-2-oxopropyl)phosphonate (0.090 g, 0.468 mmol) were dissolved in methanol (2 mL) at room temperature, after which potassium carbonate (0.108 g, 0.780 mmol) was added to the resulting solution and stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; methanol/dichloromethane=0 to 5%) and concentrated to obtain 6-ethynyl-3-((4-methylpiperidin-1-yl)methyl)-1H-indole (0.055 g, 55.9%) in a yellow oil form.

[Step 3] Synthesis of Compound 4110

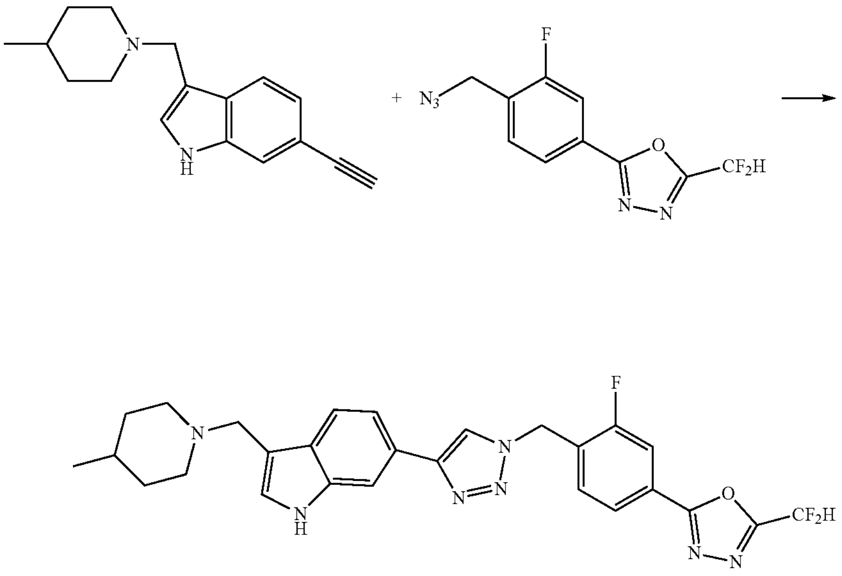 [SMILES: C#Cc1ccc2c(CN3CCC(C)CC3)c[nH]c2c1 ; [N-]=[N+]=NCc1ccc(-c2nnc(C(F)F)o2)cc1F ; CC1CCN(Cc2c[nH]c3cc(-c4cn(Cc5ccc(-c6nnc(C(F)F)o6)cc5F)nn4)ccc23)CC1]

The 2-(4-(azidomethyl)-3-fluorophenyl)-5-(difluoromethyl)-1,3,4-oxadiazole (0.030 g, 0.111 mmol) prepared in step 1 of example 2 and 6-ethynyl-3-((4-methylpiperidin-1-yl)methyl)-1H-indole (0.028 g, 0.111 mmol) prepared in step 2 were dissolved in tert-butanol (1 mL)/water (1 mL) at room temperature, after which sodium ascorbate (1.00 M solution, 0.011 mL, 0.011 mmol) and copper(II) sulfate pentahydrate (0.50 M solution, 0.002 mL, 0.001 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 50%) and concentrated to obtain 2-(difluoromethyl)-5-(3-fluoro-4-((4-(3-((4-methylpiperidin-1-yl)methyl)-1H-indol-6-yl)-1H-1,2,3-triazol-1-yl)methyl)phenyl)-1,3,4-oxadiazole (0.011 g, 18.9%) in a light yellow oil form.

$^1H$ NMR (400 MHz, $CD_3OD$) δ 8.43 (s, 1H), 8.02-7.93 (m, 3H), 7.80 (d, J=8.5 Hz, 1H), 7.68-7.60 (m, 2H), 7.59 (s, 1H), 7.24 (t, J=51.6 Hz, 1H), 5.87 (s, 2H), 4.49 (s, 2H), 3.57-3.46 (m, 2H), 3.10-2.96 (m, 2H), 1.93 (d, J=14.3 Hz, 2H), 1.75-1.64 (m, 1H), 1.51-1.34 (2, 3H), 1.02 (d, J=6.5 Hz, 3H); LRMS (ES) m/z 522.5 ($M^+$+1).

The compounds of table 49 were synthesized according to substantially the same process as described above in the synthesis of compound 4110 with an exception of using 6-ethynyl-3-((4-methylpiperidin-1-yl)methyl)-1H-indole and the reactant of table 48.

TABLE 48

| Example | Compound No. | Reactant | Yield (%) |
|---|---|---|---|
| 168 | 4111 | 2-(6-(bromomethyl)pyridin-3-yl)-5-(difluoromethyl)-1,3,4-oxadiazole | 17 |
| 366 | 4492 | 2-(4-(azidomethyl)phenyl)-5-(difluoromethyl)-1,3,4-oxadiazole | 15 |

TABLE 49

| Example | Compound No. | Compound Name, $^1$H-NMR, MS (ESI) |
|---|---|---|
| 168 | 4111 | 2-(difluoromethyl)-5-(6-((4-(3-((4-methylpiperidin-1-yl)methyl)-1H-indol-6-yl)-1H-1,2,3-triazol-1-yl)methyl)pyridin-3-yl)-1,3,4-oxadiazole<br>$^1$H NMR (400 MHZ, $CD_3OD$) δ 9.29 (d, J = 1.8 Hz, 1H), 8.54 (dd, J = 8.2, 2.2 Hz, 1H), 8.49 (s, 1H), 7.98 (d, J = 1.1 Hz, 1H), 7.80 (d, J =8.3 Hz, 1H), 7.69-7.60 (m, 2H), 7.57 (s, 1H), 7.26 (t, J = 51.6 Hz, 1H), 5.94 (s, 2H), 4.44 (s, 2H), 3.57-3.46 (m, 2H), 2.97 (s, 2H), 1.91 (d, J = 14.4 Hz, 2H), 1.73-1.59 (m, 1H), 1.56-1.25 (m, 2H), 1.01 (d, J = 6.5 Hz, 3H); LRMS (ES) m/z 505.5 ($M^+$ + 1). |
| 366 | 4492 | 2-(difluoromethyl)-5-(4-((4-(3-((4-methylpiperidin-1-yl)methyl)-1H-indol-6-yl)-1H-1,2,3-triazol-1-yl)methyl)phenyl)-1,3,4-oxadiazole<br>$^1$H NMR (400 MHZ, $CD_3OD$) δ 8.42 (s, 1H), 8.20-8.14 (m, 2H), 7.96 (d, J = 1.3 Hz, 1H), 7.82-7.75 (m, 1H), 7.63 (dd, J = 8.2, 1.3 Hz, 3H), 7.56 (s, 1H), 7.23 (t, J = 51.6 Hz, 2H), 5.81 (s, 2H), 4.42 (s, 2H), 3.48 (d, J = 12.4 Hz, 2H), 2.96 (t, J = 12.3 Hz, 2H), 1.96-1.86 (m, 2H), 1.67 (s, 1H), 1.41 (q, J = 17.2, 14.8 Hz, 2H), 1.01 (d, J = 6.5 Hz, 3H); LRMS (ES) m/z 504.3 ($M^+$ + 1). |

Example 170: Synthesis of compound 4133, 2-(difluoromethyl)-5-(6-((4-phenyl-1H-pyrazol-1-yl)methyl)pyridin-3-yl)-1,3,4-oxadiazole

[Step 1] Synthesis of 2-(6-((4-bromo-1H-pyrazol-1-yl)methyl)pyridin-3-yl)-5-(difluoromethyl)-1,3,4-oxadiazole

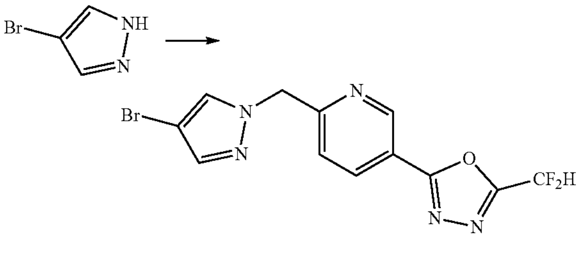

4-bromo-1H-pyrazole (0.200 g, 1.361 mmol), 2-(6-(bromomethyl)pyridin-3-yl)-5-(difluoromethyl)-1,3,4-oxadiazole (0.395 g, 1.361 mmol) and potassium carbonate (0.376 g, 2.721 mmol) were dissolved in N,N-dimethylformamide (5 mL) at room temperature, after which the resulting solution was stirred at the same temperature for 18 hours. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(6-((4-bromo-1H-pyrazol-1-yl)methyl)pyridin-3-yl)-5-(difluoromethyl)-1,3,4-oxadiazole (0.395 g, 81.5%) in a yellow oil form.

[Step 2] Synthesis of Compound 4133

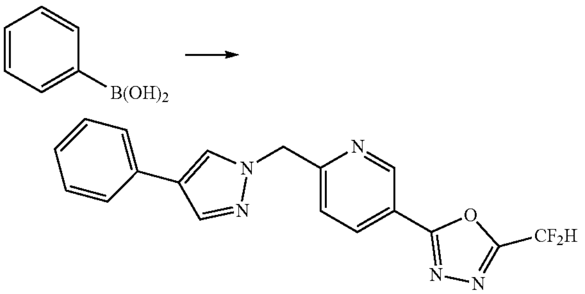

Phenylboronic acid (0.040 g, 0.328 mmol), 2-(6-((4-bromo-1H-pyrazol-1-yl)methyl)pyridin-3-yl)-5-(difluoromethyl)-1,3,4-oxadiazole (0.117 g, 0.328 mmol) prepared in step 1, [1,1'-bis(di-tert-butylphosphino)ferrocene]palladium (II) dichloride ($Pd(dtbpf)Cl_2$, 0.021 g, 0.033 mmol) and cesium carbonate (0.190 g, 0.984 mmol) were mixed in 1,4-dioxane (3 mL)/water (1 mL) at room temperature, after which the resulting mixture was irradiated with microwaves, and heated at 100 °C for 20 minutes, and then a reaction was finished by lowering a temperature to room temperature. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via chromatography ($SiO_2$, 4 g cartridge; methanol/dichloromethane=0 to 5%) and concentrated to obtain to 2-(difluoromethyl)-5-(6-((4-phenyl-1H-pyrazol-1-yl)methyl)pyridin-3-yl)-1,3,4-oxadiazole (0.014 g, 12.1%) in a brown solid form.

$^1$H NMR (400 MHz, $CDCl_3$) δ 9.33 (dd, J=2.3, 0.9 Hz, 1H), 8.38 (dd, J=8.2, 2.2 Hz, 1H), 7.92 (d, J=0.8 Hz, 1H), 7.85 (d, J=0.8 Hz, 1H), 7.56-7.48 (m, 2H), 7.45-7.37 (m, 2H), 7.28-7.23 (m, 2H), 6.96 (t, J=51.6 Hz, 1H), 5.61 (s, 2H); LRMS (ES) m/z 354.2 ($M^+$+1).

The compound of table 51 was synthesized according to substantially the same process as described above in the synthesis of compound 4133 with an exception of using 2-(6-((4-bromo-1H-pyrazol-1-yl)methyl)pyridin-3-yl)-5-(difluoromethyl)-1,3,4-oxadiazole and the reactant of table 50.

TABLE 50

| Example | Compound No. | Reactant | Yield (%) |
|---|---|---|---|
| 184 | 4208 | (1H-indol-6-yl)boronic acid | 15 |

TABLE 51

| Example | Compound No. | Compound Name, $^1$H-NMR, MS (ESI) |
|---|---|---|
| 184 | 4208 | 2-(6-((4-(1H-indol-6-yl)-1H-pyrazol-1-yl)methyl)pyridin-3-yl)-5-(difluoromethyl)-1,3,4-oxadiazole $^1$H NMR (400 MHZ, DMSO-$d_6$) δ 11.05 (s, 1H), 9.21 (dd, J = 2.3, 0.8 Hz, 1H), 8.45 (dd, J = 8.2, 2.3 Hz, 1H), 8.33 (d, J = 0.8 Hz, 1H), 7.96 (d, J = 0.9 Hz, 1H), 7.72-7.43 (m, 3H), 7.34-7.29 (m, 2H), 7.26 (dd, J = 8.2, 1.5 Hz, 1H), 6.40 (dt, J = 2.7, 1.6 Hz, 1H), 5.61 (s, 2H); LRMS (ESI) m/z 393.3 ($M^+$ + H). |

Example 173: Synthesis of compound 4136, 2-(difluoromethyl)-5-(6-((4-(1-ethyl-1H-indol-6-yl)-1H-1,2,3-triazol-1-yl)methyl)pyridin-3-yl)-1,3,4-oxadiazole

[Step 1] Synthesis of 1-ethyl-1H-indol-6-carbaldehyde

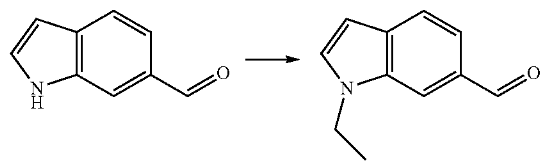

1H-indol-6-carbaldehyde (0.500 g, 3.444 mmol) and cesium carbonate (1.329 g, 6.889 mmol) were dissolved in acetonitrile (7 mL) at room temperature, after which the resulting solution was heated under reflux for 2 hours, and iodoethane (0.305 mL, 3.789 mmol) was added and heated again under reflux for 1 hour, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 1-ethyl-1H-indol-6-carbaldehyde (0.180 g, 30.2%) in a colorless oil form.

[Step 2] Synthesis of 6-ethynyl-1-methyl-1H-indole

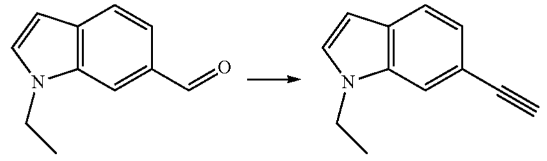

The 1-methyl-1H-indol-6-carbaldehyde (0.095 g, 0.597 mmol) prepared in step 1 and dimethyl(1-diazo-2-oxopropyl)phosphonate (0.134 mL, 0.895 mmol) were dissolved in methanol (2 mL) at room temperature, after which potassium carbonate (0.165 g, 1.194 mmol) was added to the resulting solution and stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%) and concentrated to obtain 6-ethynyl-1-methyl-1H-indole (0.080 g, 86.4%) in a light yellow solid form.

[Step 3] Synthesis of Compound 4136

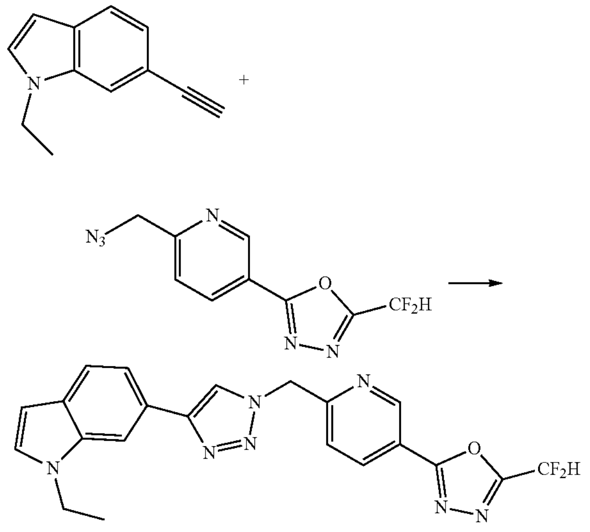

The 2-(6-(azidomethyl)pyridin-3-yl)-5-(difluoromethyl)-1,3,4-oxadiazole (0.040 g, 0.159 mmol) prepared in step 1 of example 16 and the 1-ethyl-6-ethynyl-1H-indole (0.027 g, 0.159 mmol) prepared in step 2 were dissolved in tert-butanol (1 mL)/water (1 mL) at room temperature, after which sodium ascorbate (1.00 M solution, 0.016 mL, 0.016 mmol) and copper(II) sulfate pentahydrate (0.50 M solution, 0.003 mL, 0.002 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=5 to 40%) and concentrated to obtain 2-(difluoromethyl)-5-(6-((4-(1-ethyl-1H-indol-6-yl)-1H-1,2,3-triazol-1-yl)methyl)pyridin-3-yl)-1,3,4-oxadiazole (0.050 g, 74.8%) in a light yellow solid form.

$^1$H NMR (400 MHz, $CDCl_3$) δ 9.40-9.35 (m, 1H), 8.47 (dd, J=8.2, 2.2 Hz, 1H), 8.29 (d, J=32.0 Hz, 1H), 8.14 (d, J=7.3 Hz, 1H), 7.70-7.66 (m, 1H), 7.55 (d, J=8.0 Hz, 1H), 7.43 (dd, J=8.2, 1.5 Hz, 1H), 7.23 (d, J=3.1 Hz, 1H), 6.97 (t, J=51.6 Hz, 1H), 6.53 (dd, J=3.2, 0.9 Hz, 1H), 5.89 (s, 2H), 4.30 (q, J=7.3 Hz, 2H), 1.58-1.51 (m, 3H); LRMS (ES) m/z 422.3 ($M^+$+1).

Example 182: Synthesis of compound 4186, 4-((5-(1-(4-(5-(difluoromethyl)-1,3,4-oxadiazol-2-yl)benzyl)-1H-1,2,3-triazol-4-yl)-1H-indol-3-yl)methyl)morpholine

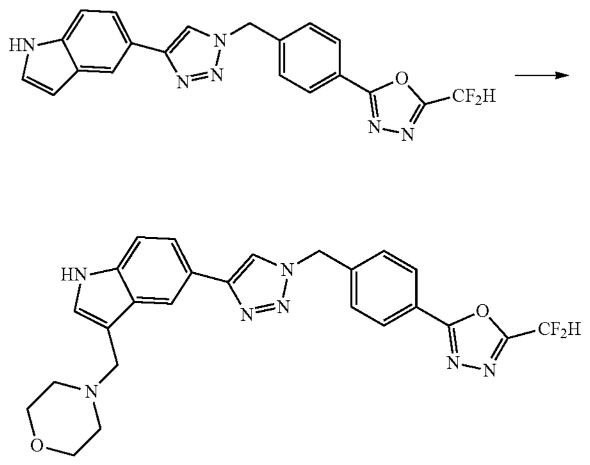

Morpholine (0.010 mL, 0.115 mmol) and formaldehyde (37.00%, 0.010 g, 0.126 mmol) were dissolved in acetic acid (0.5 mL)/methanol (0.5 mL), after which the resulting solution was stirred at 0 °C for 0.4 hours, and then 2-(4-((4-(1H-indol-5-yl)-1H-1,2,3-triazol-1-yl)methyl)phenyl)-5-(difluoromethyl)-1,3,4-oxadiazole (0.027 g, 0.069 mmol) prepared in example 158 was added thereto and further stirred at room temperature for 18 hours. 2N-sodium hydroxide aqueous solution was poured into the resulting reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 4-((5-(1-(4-(5-(difluoromethyl)-1,3,4-oxadiazol-2-yl)benzyl)-1H-1,2,3-triazol-4-yl)-1H-indol-3-yl)methyl)morpholine (0.003 g, 5.3%) in a yellow gum form.

$^1H$ NMR (400 MHz, $CD_3OD$) δ 8.41 (s, 1H), 8.27-8.20 (m, 1H), 8.21-8.15 (m, 3H), 7.70-7.61 (m, 4H), 7.54 (dd, J=8.6, 0.7 Hz, 1H), 7.24 (t, J=51.6 Hz, 1H), 5.81 (d, J=8.1 Hz, 2H), 4.61 (s, 2H), 4.12-3.97 (m, 2H), 3.80-3.60 (m, 4H), 3.54-3.40 (m, 2H); LRMS (ES) m/z 492.2 ($M^+$+1).

Example 183: Synthesis of compound 4187, 4-((5-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine

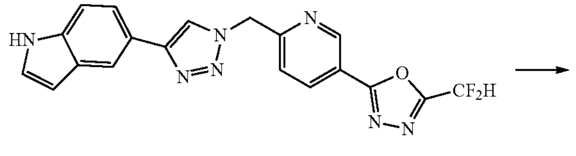

-continued

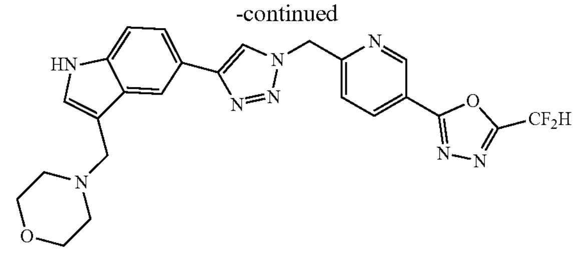

Morpholine (0.010 mL, 0.115 mmol) and formaldehyde (37.00%, 0.010 g, 0.126 mmol) were dissolved in acetic acid (0.5 mL)/methanol (0.5 mL), after which the resulting solution was stirred at 0 °C for 0.4 hours, and then 2-(6-((4-(1H-indol-5-yl)-1H-1,2,3-triazol-1-yl)methyl)pyridin-3-yl)-5-(difluoromethyl)-1,3,4-oxadiazole (0.027 g, 0.069 mmol) prepared in step 2 of example 150 was added thereto and further stirred at room temperature for 18 hours. 2N-sodium hydroxide aqueous solution was poured into the resulting reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 4-((5-(1-((5-(5-(difluoromethyl)-1,3,4-oxadiazol-2-yl)pyridin-2-yl)methyl)-1H-1,2,3-triazol-4-yl)-1H-indol-3-yl)methyl)morpholine (0.005 g, 8.8%) in a colorless oil form.

$^1H$ NMR (400 MHz, $CD_3OD$) δ 9.30 (d, J=1.7 Hz, 1H), 8.54 (dd, J=8.2, 2.2 Hz, 1H), 8.46 (d, J=8.5 Hz, 1H), 8.23 (d, J=10.5 Hz, 1H), 7.73-7.63 (m, 1H), 7.62 (d, J=7.7 Hz, 1H), 7.56-7.49 (m, 1H), 7.45 (d, J=25.6 Hz, 1H), 7.26 (t, J=51.6 Hz, 1H), 5.93 (s, 2H), 4.14-4.07 (m, 2H), 3.84-3.76 (m, 3H), 3.67-3.54 (m, 2H), 3.08 (d, J=12.0 Hz, 1H), 2.89 (s, 2H); LRMS (ES) m/z 493.5 ($M^+$+1).

Example 185: Synthesis of compound 4209, 2-(difluoromethyl)-5-(6-((4-(2-methyl-1,2,3,4-tetrahydroisoquinolin-7-yl)-1H-1,2,3-triazol-1-yl)methyl)pyridin-3-yl)-1,3,4-oxadiazole

[Step 1] Synthesis of tert-butyl 7-ethynyl-3,4-dihydroisoquinolin-2(1H)-carboxylate

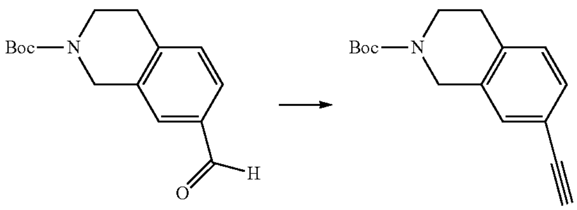 [SMILES: CC(C)(C)OC(=O)N1CCc2ccc(C=O)cc2C1 ; C#Cc1ccc2c(c1)CN(C(=O)OC(C)(C)C)CC2]

Tert-butyl 7-formyl-3,4-dihydroisoquinolin-2(1H)-carboxylate (1.000 g, 3.827 mmol), dimethyl (1-diazo-2-oxopropyl)phosphonate (0.882 g, 4.592 mmol) and potassium carbonate (1.058 g, 7.653 mmol) were dissolved in methanol (5 mL) at room temperature, after which the resulting solution was stirred at the same temperature for 12 hours. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 20%) and concentrated to obtain tert-butyl 7-ethynyl-3,4-dihydroisoquinolin-2(1H)-carboxylate (1.200 g, 87.8%) in a yellow oil form.

[Step 2] Synthesis of tert-butyl 7-(1-((5-(methoxycarbonyl)pyridin-2-yl)methyl)-1H-1,2,3-triazol-4-yl)-3,4-dihydroisoquinolin-2(1H)-carboxylate

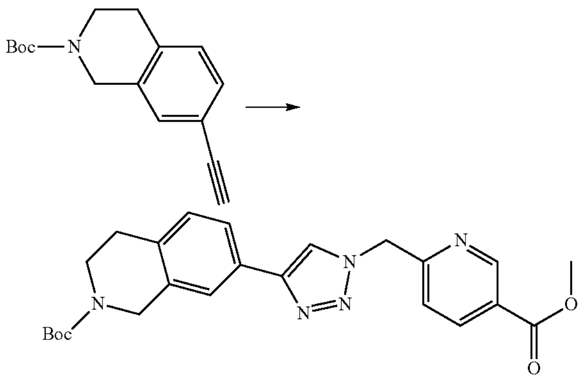

The tert-butyl 7-ethynyl-3,4-dihydroisoquinolin-2(1H)-carboxylate (1.170 g, 4.547 mmol) prepared in step 1, the methyl 6-(azidomethyl)nicotinate (0.874 g, 4.547 mmol) prepared in step 1 of example 81, copper(II) sulfate pentahydrate (0.114 g, 0.455 mmol) and sodium ascorbate (0.009 g, 0.045 mmol) were dissolved in tert-butanol (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%) and concentrated to obtain tert-butyl 7-(1-((5-(methoxycarbonyl)pyridin-2-yl)methyl)-1H-1,2,3-triazol-4-yl)-3,4-dihydroisoquinolin-2(1H)-carboxylate (2.100 g, 102.8%) in a yellow solid form.

[Step 3] Synthesis of tert-butyl 7-(1-((5-(hydrazinecarbonyl)pyridin-2-yl)methyl)-1H-1,2,3-triazol-4-yl)-3,4-dihydroisoquinolin-2(1H)-carboxylate

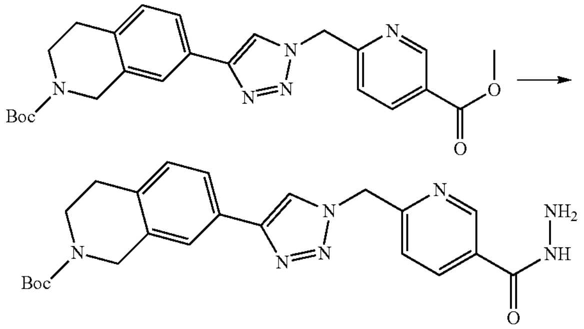

The tert-butyl 7-(1-((5-(methoxycarbonyl)pyridin-2-yl)methyl)-1H-1,2,3-triazol-4-yl)-3,4-dihydroisoquinolin-2(1H)-carboxylate (2.100 g, 4.672 mmol) prepared in step 2 and hydrazine monohydrate (2.271 mL, 46.718 mmol) were dissolved in ethanol (50 mL) at room temperature, after which the resulting solution was heated under reflux for 12 hours, and then a reaction was finished by lowering a temperature to room temperature. Solvent was removed from the reaction mixture under reduced pressure, after which the obtained product was used without an additional purification process (tert-butyl 7-(1-((5-(hydrazinecarbonyl)pyridin-2-yl)methyl)-1H-1,2,3-triazol-4-yl)-3,4-dihydroisoquinolin-2(1H)-carboxylate, 2.000 g, 95.2%, yellow solid).

[Step 4] Synthesis of tert-butyl 7-(1-((5-(5-(difluoromethyl)-1,3,4-oxadiazol-2-yl)pyridin-2-yl)methyl)-1H-1,2,3-triazol-4-yl)-3,4-dihydroisoquinolin-2(1H)-carboxylate

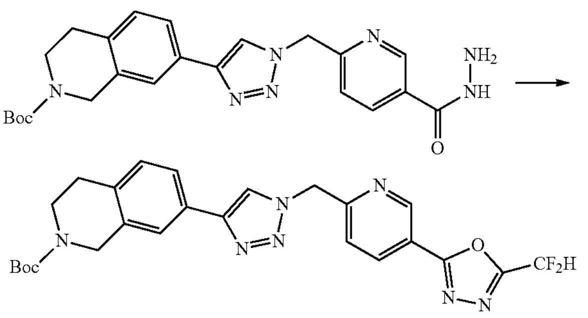

The tert-butyl 7-(1-((5-(hydrazinecarbonyl)pyridin-2-yl)methyl)-1H-1,2,3-triazol-4-yl)-3,4-dihydroisoquinolin-2(1H)-carboxylate(2.000 g, 4.449 mmol) prepared in step 3, difluoroacetic anhydride (2.323 g, 13.348 mmol) and triethylamine (1.850 mL, 13.348 mmol) were dissolved in dichloromethane (100 mL) at room temperature, after which the resulting solution was heated under reflux for 12 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 100%) and concentrated to obtain tert-butyl 7-(1-((5-(5-(difluoromethyl)-1,3,4-oxadiazol-2-yl)pyridin-2-yl)methyl)-1H-1,2,3-triazol-4-yl)-3,4-dihydroisoquinolin-2(1H)-carboxylate (1.000 g, 44.1%) in a white solid form.

[Step 5] Synthesis of 2-(difluoromethyl)-5-(6-((4-(1,2,3,4-tetrahydroisoquinolin-7-yl)-1H-1,2,3-triazol-1-yl)methyl)pyridin-3-yl)-1,3,4-oxadiazole

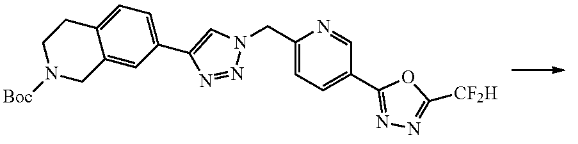

-continued

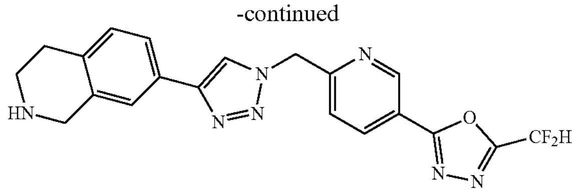

The tert-butyl 7-(1-((5-(5-(difluoromethyl)-1,3,4-oxadiazol-2-yl)pyridin-2-yl)methyl)-1H-1,2,3-triazol-4-yl)-3,4-dihydroisoquinolin-2(1H)-carboxylate (1.000 g, 1.963 mmol) prepared in step 4 and trifluoroacetic acid (1.503 mL, 19.626 mmol) were dissolved in dichloromethane (50 mL) at room temperature, after which the resulting solution was stirred at the same temperature for 3 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(6-((4-(1,2,3,4-tetrahydroisoquinolin-7-yl)-1H-1,2,3-triazol-1-yl)methyl)pyridin-3-yl)-1,3,4-oxadiazole (0.600 g, 74.7%) in a white solid form.

[Step 6] Synthesis of Compound 4209

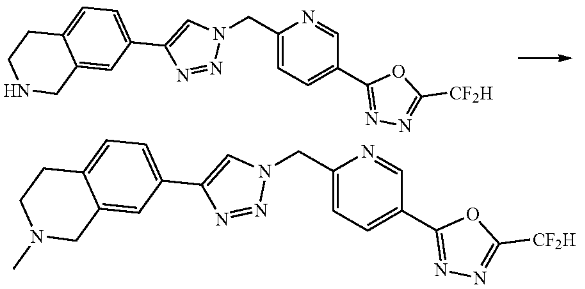

The 2-(difluoromethyl)-5-(6-((4-(1,2,3,4-tetrahydroisoquinolin-7-yl)-1H-1,2,3-triazol-1-yl)methyl)pyridin-3-yl)-1,3,4-oxadiazole (0.060 g, 0.147 mmol) prepared in step 5, formaldehyde (0.009 g, 0.293 mmol) and acetic acid (0.009 mL, 0.161 mmol) were dissolved in methanol (5 mL) at room temperature, after which sodium triacetoxyborohydride (0.062 g, 0.293 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(6-((4-(2-methyl-1,2,3,4-tetrahydroisoquinolin-7-yl)-1H-1,2,3-triazol-1-yl)methyl)pyridin-3-yl)-1,3,4-oxadiazole (0.025 g, 40.3%) in a yellow solid form.

$^1H$ NMR (400 MHz, $CDCl_3$) δ 9.32-9.26 (m, 1H), 8.36 (dd, J=8.2, 2.3 Hz, 1H), 7.93 (s, 1H), 7.60-7.50 (m, 2H), 7.38 (d, J=8.2 Hz, 1H), 7.14 (d, J=7.9 Hz, 1H), 6.93 (t, J=51.6 Hz, 1H), 5.78 (s, 2H), 3.73 (s, 2H), 2.97 (t, J=6.0 Hz, 2H), 2.84 (t, J=6.0 Hz, 2H), 2.51 (s, 3H); LRMS (ES) m/z 493.4 ($M^+$+1).

The compounds of table 53 were synthesized according to substantially the same process as described above in the synthesis of compound 4209 with an exception of using 2-(difluoromethyl)-5-(6-((4-(1,2,3,4-tetrahydroisoquinolin-7-yl)-1H-1,2,3-triazol-1-yl)methyl)pyridin-3-yl)-1,3,4-oxadiazole and the reactant of table 52.

TABLE 52

| Example | Compound No. | Reactant | Yield (%) |
|---|---|---|---|
| 186 | 4210 | Propan-2-one | 45 |
| 187 | 4211 | Acetaldehyde | 15 |
| 188 | 4212 | Cyclobutanone | 51 |
| 189 | 4213 | Oxetan-3-one | 51 |

TABLE 53

| Example | Compound No. | Compound Name, $^1H$-NMR, MS (ESI) |
|---|---|---|
| 186 | 4210 | 2-(difluoromethyl)-5-(6-((4-(2-isopropyl-1,2,3,4-tetrahydroisoquinolin-7-yl)-1H-1,2,3-triazol-1-yl)methyl)pyridin-3-yl)-1,3,4-oxadiazole<br>$^1H$ NMR (400 MHZ, $CDCl_3$) δ 9.32 (d, J = 2.3 Hz, 1H), 8.39 (dt, J = 8.2, 1.7 Hz, 1H), 7.93 (d, J = 2.4 Hz, 1H), 7.65-7.53 (m, 2H), 7.40 (dd, J = 8.3, 3.3 Hz, 1H), 7.16 (d, J = 8.0 Hz, 1H), 6.94 (s, 1H), 5.79 (s, 2H), 3.02 (d, J = 5.8 Hz, 1H), 2.96 (d, J = 6.0 Hz, 2H), 2.77 (t, J = 6.0 Hz, 2H), 2.51 (s, 2H), 1.28-1.22 (m, 6H); LRMS (ES) m/z 452.5 ($M^+$ + 1). |
| 187 | 4211 | 2-(difluoromethyl)-5-(6-((4-(2-ethyl-1,2,3,4-tetrahydroisoquinolin-7-yl)-1H-1,2,3-triazol-1-yl)methyl)pyridin-3-yl)-1,3,4-oxadiazole<br>$^1H$ NMR (400 MHZ, $CDCl_3$) δ 9.32 (s, 1H), 8.39 (d, J = 8.0 Hz, 1H), 7.93 (d, J = 9.7 Hz, 1H), 7.63-7.53 (m, 2H), 7.41 (d, J = 8.3 Hz, 1H), 7.18 (d, J = 8.1 Hz, 1H), 6.93 (t, J = 51.6 Hz, 1H), 5.79 (s, 2H), 3.93 (s, 2H), 3.05 (s, 2H), 2.67 (d, J = 28.8 Hz, 2H), 1.77 (s, 2H), 0.98 (t, J = 7.3 Hz, 3H); LRMS (ES) m/z 438.5 ($M^+$ + 1). |
| 188 | 4212 | 2-(6-((4-(2-cyclobutyl-1,2,3,4-tetrahydroisoquinolin-7-yl)-1H-1,2,3-triazol-1-yl)methyl)pyridin-3-yl)-5-(difluoromethyl)-1,3,4-oxadiazole<br>$^1H$ NMR (400 MHZ, $CDCl_3$) δ 9.28 (s, 1H), 8.35 (dd, J = 8.2, 2.3 Hz, 1H), 7.92 (s, 1H), 7.57-7.50 (m, 2H), 7.37 (d, J = 8.2 Hz, 1H), 7.12 (d, J = 7.9 Hz, 1H), 6.93 (t, J = 51.6 Hz, 1H), 5.77 (s, 2H), 3.60 (s, 2H), 2.97 (t, J = 8.0 Hz, 1H), 2.91 (t, J = 6.4 Hz, 2H), 2.69 (t, J = 6.0 Hz, 2H), 2.08 (dt, J = 20.0, 9.2 Hz, 4H), 1.73 (tt, J = 19.3, 8.7 Hz, 2H); LRMS (ES) m/z 464.50 ($M^+$ + 1). |
| 189 | 4213 | 2-(difluoromethyl)-5-(6-((4-(2-(oxetan-3-yl)-1,2,3,4-tetrahydroisoquinolin-7-yl)-1H-1,2,3-triazol-1-yl)methyl)pyridin-3-yl)-1,3,4-oxadiazole<br>$^1H$ NMR (400 MHZ, $CDCl_3$) δ 9.30 (d, J = 2.2 Hz, 1H), 8.37 (dd, J = 8.2, 2.3 Hz, 1H), 7.92 (s, 1H), 7.55 (d, J = 9.1 Hz, 2H), 7.39 (d, J = 8.2 Hz, 1H), 7.15 (d, J =7.8 Hz, 1H), 6.93 (t, J = 51.6 Hz, 1H), 5.78 (s, 2H), 4.78-4.68 (m, 4H), 3.71 (p, J = 6.5 Hz, 1H), 3.56 (s, 2H), 2.94 (t, J = 6.0 Hz, 2H), 2.64 (t, J = 6.0 Hz, 2H); LRMS (ES) m/z 466.5 ($M^+$ + 1). |

Example 193: Synthesis of compound 4232, 2-(difluoromethyl)-5-(6-((5-(thiophen-2-yl)-2H-tetrazol-2-yl)methyl)pyridin-3-yl)-1,3,4-oxadiazole

[Step 1] Synthesis of 5-(thiophen-2-yl)-2H-tetrazole

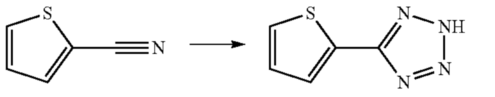

Thiophen-2-carbonitrile (0.500 g, 4.581 mmol), sodium azide (0.655 g, 10.078 mmol) and ammonium chloride (0.539 g, 10.078 mmol) were dissolved in N,N-dimethylformamide (10 mL) at room temperature, after which the resulting solution was stirred at 120 °C for 18 hours, and then a reaction was finished by lowering a temperature to room temperature. After adding 10 ml of water, 1N hydrogen chloride was added to filter out a precipitated solid, which was then washed with hexane and dried to obtain 5-(thiophen-2-yl)-2H-tetrazole (0.620 g, 88.9%) in a white solid form.

[Step 2] Synthesis of methyl 6-((5-(thiophen-2-yl)-2H-tetrazol-2-yl)methyl)nicotinate

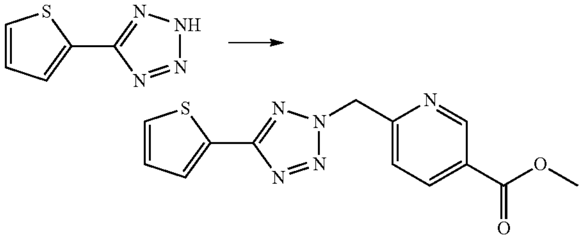

The 5-(thiophen-2-yl)-2H-tetrazole (0.200 g, 1.314 mmol) prepared in step 1 and potassium carbonate (0.182 g, 1.314 mmol) were dissolved in acetonitrile (5 mL) at room temperature, after which methyl 6-(bromomethyl)nicotinate (0.333 g, 1.446 mmol) was added to the resulting solution and stirred at 100 °C for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%), and concentrated to obtain methyl 6-((5-(thiophen-2-yl)-2H-tetrazol-2-yl)methyl)nicotinate (0.320 g, 80.8%) in a white solid form.

[Step 3]6-((5-(thiophen-2-yl)-2H-tetrazol-2-yl)methyl)nicotinohydrazide

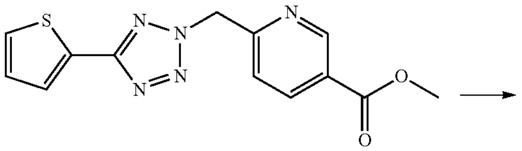

-continued

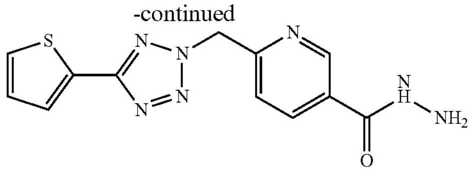

The methyl 6-((5-(thiophen-2-yl)-2H-tetrazol-2-yl)methyl)nicotinate (0.150 g, 0.499 mmol) prepared in step 2 and hydrazine monohydrate (0.485 mL, 9.989 mmol) were dissolved in ethanol (3 mL), after which the resulting solution was stirred at 80 °C for 18 hours, and further stirred at room temperature for 18 hours. Solvent was removed from the reaction mixture under reduced pressure, after which the obtained product was used without an additional purification process (6-((5-(thiophen-2-yl)-2H-tetrazol-2-yl)methyl)nicotinohydrazide, 0.150 g, 100.0%, white solid).

[Step 4] Synthesis of Compound 4232

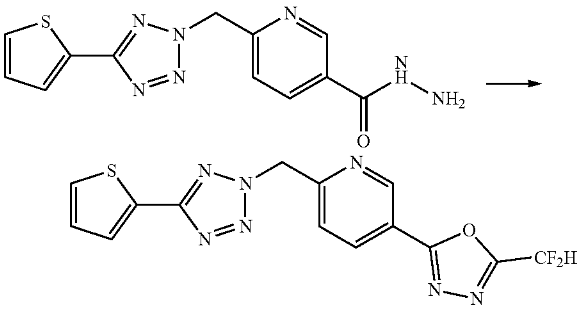

The 6-((5-(thiophen-2-yl)-2H-tetrazol-2-yl)methyl)nicotinohydrazide (0.070 g, 0.233 mmol) prepared in step 3, triethylamine (0.195 mL, 1.398 mmol) and 2,2-difluoroacetic acid anhydride (0.116 mL, 0.932 mmol) were dissolved in tetrahydrofuran (3 mL) at room temperature, after which the resulting solution was heated stirred at 80 °C for 4 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(difluoromethyl)-5-(6-((5-(thiophen-2-yl)-2H-tetrazol-2-yl)methyl)pyridin-3-yl)-1,3,4-oxadiazole(0.055 g, 65.3%) in a white solid form.

$^1H$ NMR (400 MHz, $CDCl_3$) δ 9.36 (dd, J=2.3, 0.8 Hz, 1H), 8.45 (dd, J=8.2, 2.2 Hz, 1H), 7.86 (dd, J=3.7, 1.2 Hz, 1H), 7.50 (dd, J=5.0, 1.2 Hz, 1H), 7.39 (d, J=8.2 Hz, 1H), 7.19 (dd, J=5.0, 3.7 Hz, 1H), 6.96 (t, J=51.6 Hz, 1H), 6.10 (s, 2H); LRMS (ES) m/z 362.1 ($M^+$+1).

The compound of table 55 was synthesized according to substantially the same process as described above in the synthesis of compound 4232 with an exception of using 6-((5-(thiophen-2-yl)-2H-tetrazol-2-yl)methyl)nicotinohydrazide and the reactant of table 54.

TABLE 54

| Example | Compound No. | Reactant | Yield (%) |
|---|---|---|---|
| 194 | 4233 | Trifluoroacetic anhydride | 69 |

TABLE 55

| Example | Compound No. | Compound Name, $^1$H-NMR, MS (ESI) |
|---|---|---|
| 194 | 4233 | 2-(6-((5-(thiophen-2-yl)-2H-tetrazol-2-yl)methyl)pyridin-3-yl)-5-(trifluoromethyl)-1,3,4-oxadiazole<br>$^1$H NMR (400 MHZ, $CDCl_3$) δ 9.35 (dd, J = 2.2, 0.9 Hz, 1H), 8.45 (dd, J = 8.2, 2.2 Hz, 1H), 7.86 (dd, J = 3.7, 1.2 Hz, 1H), 7.50 (dd, J = 5.0, 1.2 Hz, 1H), 7.44-7.37 (m, 1H), 7.19 (dd, J = 5.0, 3.7 Hz, 1H), 6.10 (s, 2H); LRMS (ES) m/z 380.3 ($M^+$ + 1). |

Example 195: Synthesis of compound 4234, 2-(difluoromethyl)-5-(6-((5-phenyl-2H-tetrazol-2-yl)methyl)pyridin-3-yl)-1,3,4-oxadiazole

[Step 1] Synthesis of 5-phenyl-2H-tetrazole

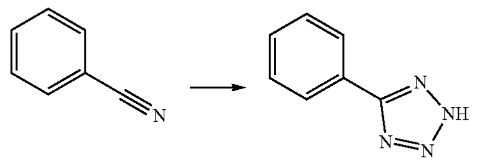 [SMILES: N#Cc1ccccc1 ; c1ccc(-c2nn[nH]n2)cc1]

Benzonitrile (0.500 g, 4.128 mmol), sodium azide (0.590 g, 9.083 mmol) and ammonium chloride (0.486 g, 9.083 mmol) were dissolved in N,N-dimethylformamide (10 mL) at room temperature, after which the resulting solution was stirred at 120 °C for 18 hours, and then a reaction was finished by lowering a temperature to room temperature. After adding 10 ml of water, 1N hydrogen chloride was added to filter out a precipitated solid, which was then washed with hexane and dried to obtain 5-phenyl-2H-tetrazole (0.600 g, 99.4%) in a white solid form.

[Step 2] Synthesis of methyl 6-((5-phenyl-2H-tetrazol-2-yl)methyl)nicotinate

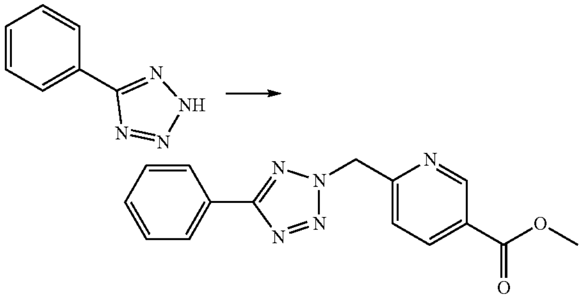

The 5-phenyl-2H-tetrazole (0.200 g, 1.368 mmol) prepared in step 1 and potassium carbonate (0.189 g, 1.368 mmol) were dissolved in acetonitrile (5 mL) at room temperature, after which methyl 6-(bromomethyl)nicotinate (0.346 g, 1.505 mmol) was added to the resulting solution and stirred at 100 °C for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%), and concentrated to obtain methyl 6-((5-phenyl-2H-tetrazol-2-yl)methyl) nicotinate (0.300 g, 74.2%) in a white solid form.

[Step 3] Synthesis of (6-((5-phenyl-2H-tetrazol-2-yl)methyl)nicotinohydrazide

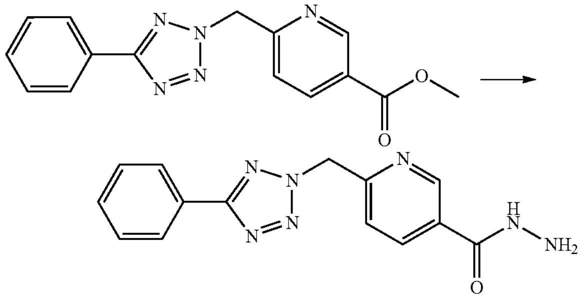

The methyl 6-((5-phenyl-2H-tetrazol-2-yl)methyl)nicotinate (0.150 g, 0.508 mmol) prepared in step 2 and hydrazine monohydrate (0.494 mL, 10.159 mmol) were dissolved in ethanol (3 mL), after which the resulting solution was stirred at 80 °C for 18 hours, and further stirred at room temperature for 18 hours. Solvent was removed from the reaction mixture under reduced pressure, after which a product obtained was used without an additional purification process (6-((5-phenyl-2H-tetrazol-2-yl)methyl)nicotinohydrazide, 0.150 g, 100.3%, white solid).

[Step 4] Synthesis of Compound 4234

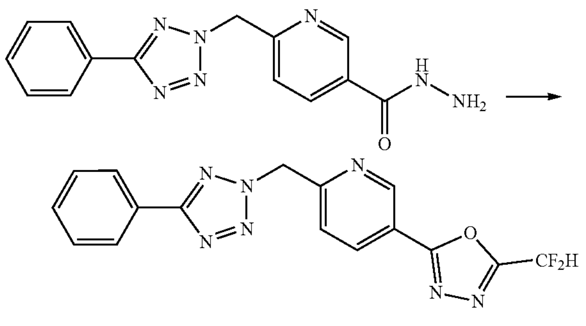

The 6-((5-phenyl-2H-tetrazol-2-yl)methyl)nicotinohydrazide (0.070 g, 0.237 mmol) prepared in step 3, triethylamine (0.198 mL, 1.422 mmol) and 2,2-difluoroacetic acid anhydride (0.118 mL, 0.948 mmol) were dissolved in tetrahydrofuran (3 mL) at room temperature, after which the resulting solution was stirred at 80 °C for 4 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(difluoromethyl)-5-(6-((5-phenyl-2H-tetrazol-2-yl)methyl)pyridin-3-yl)-1,3,4-oxadiazole (0.056 g, 66.5%) in a white solid form.

$^1$H NMR (400 MHz, $CDCl_3$) δ 9.36 (dd, J=2.1, 0.9 Hz, 1H), 8.44 (dd, J=8.2, 2.2 Hz, 1H), 8.23-8.16 (m, 2H), 7.52 (dd, J=5.1, 2.0 Hz, 3H), 7.39 (d, J=8.2 Hz, 1H), 6.96 (t, J=51.6 Hz, 1H), 6.12 (s, 2H); LRMS (ES) m/z 356.3 ($M^+$+1).

The compound of table 57 was synthesized according to substantially the same process as described above in the synthesis of compound 4234 with an exception of using 6-((5-phenyl-2H-tetrazol-2-yl)methyl)nicotinohydrazide and the reactant of table 56.

TABLE 56

| Example | Compound No | Reactant | Yield (%) |
|---|---|---|---|
| 196 | 4235 | Trifluoroacetic anhydride | 64 |

TABLE 57

| Example | Compound No. | Compound Name, $^1$H-NMR, MS (ESI) |
|---|---|---|
| 196 | 4235 | 2-(6-((5-phenyl-2H-tetrazol-2-yl)methyl)pyridin-3-yl)-5-(trifluoromethyl)-1,3,4-oxadiazole<br>$^1$H NMR (400 MHZ, $CDCl_3$) δ 9.36 (dd, J = 2.3, 0.9 Hz, 1H), 8.45 (dd, J = 8.2, 2.2 Hz, 1H), 8.22-8.17 (m, 2H), 7.56-7.48 (m, 3H), 7.43-7.37 (m, 1H), 6.13 (s, 2H); LRMS (ES) m/z 374.3 ($M^+$ + 1). |

Example 201: Synthesis of compound 4280, 2-(difluoromethyl)-5-(6-((4-(3-fluorooxetan-3-yl)-1H-1,2,3-triazol-1-yl)methyl)pyridin-3-yl)-1,3,4-oxadiazole

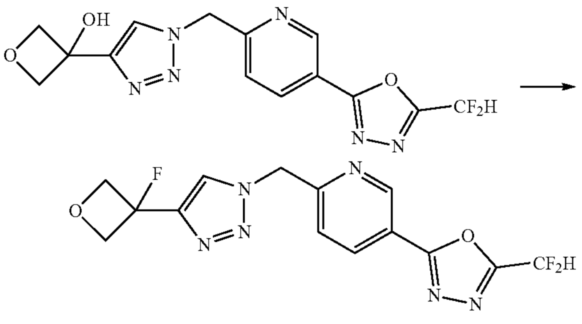

The 3-(1-((5-(5-(difluoromethyl)-1,3,4-oxadiazol-2-yl)pyridin-2-yl)methyl)-1H-1,2,3-triazol-4-yl)oxetan-3-ol (0.020 g, 0.057 mmol) prepared in example 197 and diethylaminosulfur trifluoride (0.009 mL, 0.069 mmol) were dissolved in dichloromethane (5 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(difluoromethyl)-5-(6-((4-(3-fluorooxetan-3-yl)-1H-1,2,3-triazol-1-yl)methyl)pyridin-3-yl)-1,3,4-oxadiazole (0.011 g, 54.7%) in a white solid form.

$^1$H NMR (400 MHz, $CDCl_3$) δ 9.34 (s, 1H), 8.44 (dd, J=8.2, 2.2 Hz, 1H), 7.86 (s, 1H), 7.47 (d, J=8.2 Hz, 1H), 7.09 (s, 0.2H), 6.96 (s, 0.5H), 6.84 (s, 0.3H), 5.80 (s, 2H), 5.19 (dd, J=7.9, 1.1 Hz, 1H), 5.11 (ddd, J=17.2, 8.0, 1.1 Hz, 2H), 5.04 (dd, J=7.9, 1.1 Hz, 1H); LRMS (ES) m/z 353.25 ($M^+$+1).

Example 202: Synthesis of compound 4281, 2-(difluoromethyl)-5-(6-((4-(3-fluorotetrahydrofuran-3-yl)-1H-1,2,3-triazol-1-yl)methyl)pyridin-3-yl)-1,3,4-oxadiazole

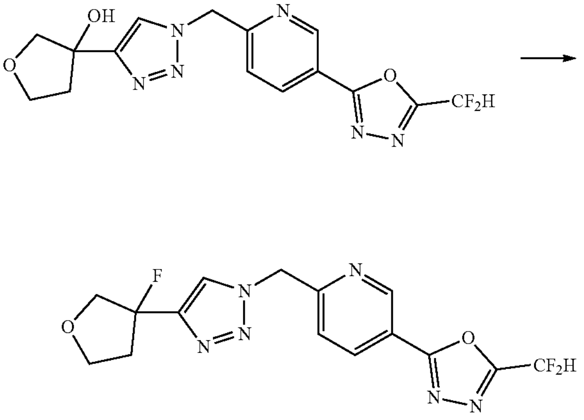

The 3-(1-((5-(5-(difluoromethyl)-1,3,4-oxadiazol-2-yl)pyridin-2-yl)methyl)-1H-1,2,3-triazol-4-yl)tetrahydrofuran-3-ol (0.020 g, 0.057 mmol) prepared in example 198 and diethylaminosulfur trifluoride (DAST, 0.009 mL, 0.069 mmol) were dissolved in dichloromethane (5 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(difluoromethyl)-5-(6-((4-(3-fluorotetrahydrofuran-3-yl)-1H-1,2,3-triazol-1-yl)methyl)pyridin-3-yl)-1,3,4-oxadiazole (0.008 g, 39.8%) in a white solid form.

$^1$H NMR (400 MHz, $CDCl_3$) δ 9.35 (d, J=1.5 Hz, 1H), 8.44 (dd, J=8.2, 2.2 Hz, 1H), 7.86 (s, 1H), 7.45 (d, J=8.2 Hz, 1H), 7.09 (s, 0.2H), 6.97 (s, 0.5H), 6.84 (s, 0.3H), 5.79 (s, 2H), 4.35-4.06 (m, 4H), 2.81-2.46 (m, 2H).

Example 203: Synthesis of compound 4282, 2-(difluoromethyl)-5-(3-fluoro-4-((4-(3-fluorooxetan-3-yl)-1H-1,2,3-triazol-1-yl)methyl)phenyl)-1,3,4-oxadiazole

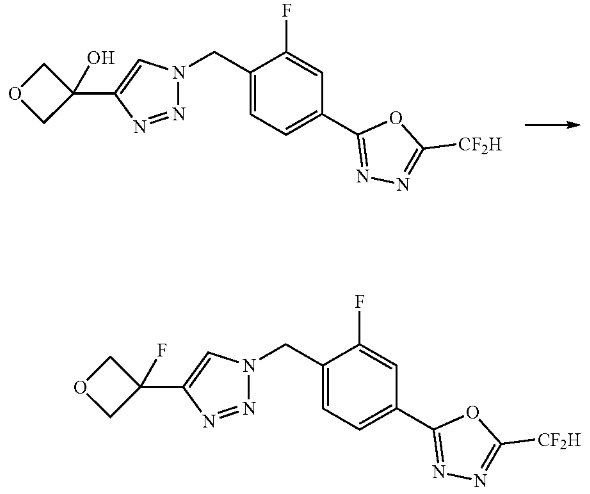

The 3-(1-(4-(5-(difluoromethyl)-1,3,4-oxadiazol-2-yl)-2-fluorobenzyl)-1H-1,2,3-triazol-4-yl)oxetan-3-ol (0.020 g, 0.054 mmol) prepared in example 199 and diethylaminosulfur trifluoride (0.009 mL, 0.065 mmol) were dissolved in dichloromethane (5 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(difluoromethyl)-5-(3-fluoro-4-((4-(3-fluorooxetan-3-yl)-1H-1,2,3-triazol-1-yl)methyl)phenyl)-1,3,4-oxadiazole (0.013 g, 64.6%) in a white solid form.

$^1$H NMR (400 MHz, $CDCl_3$) δ 7.99-7.90 (m, 2H), 7.70 (s, 1H), 7.50 (t, J=7.6 Hz, 1H), 7.07 (s, 0.2H), 6.94 (s, 0.51H), 6.82 (s, 0.3H), 5.72 (s, 2H), 5.18 (dd, J=8.0, 1.2 Hz, 1H), 5.10 (ddd, J=17.9, 8.0, 1.2 Hz, 2H), 5.02 (dd, J=8.0, 1.1 Hz, 1H); LRMS (ES) m/z 370.29 ($M^+$+1).

Example 204: Synthesis of compound 4283, 2-(difluoromethyl)-5-(3-fluoro-4-((4-(3-fluorotetrahydrofuran-3-yl)-1H-1,2,3-triazol-1-yl)methyl)phenyl)-1,3,4-oxadiazole

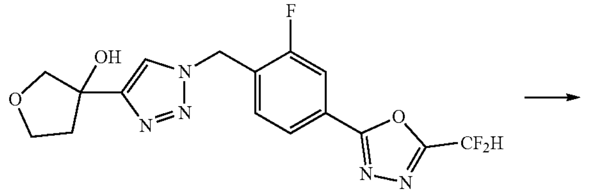

-continued

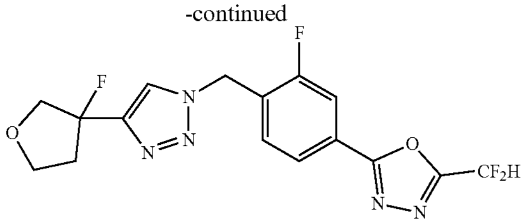

The 3-(1-(4-(5-(difluoromethyl)-1,3,4-oxadiazol-2-yl)-2-fluorobenzyl)-1H-1,2,3-triazol-4-yl)tetrahydrofuran-3-ol (0.020 g, 0.052 mmol) prepared in example 200 and diethylaminosulfur trifluoride (DAST, 0.008 mL, 0.063 mmol) were dissolved in dichloromethane (5 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain 2-(difluoromethyl)-5-(3-fluoro-4-((4-(3-fluorotetrahydrofuran-3-yl)-1H-1,2,3-triazol-1-yl)methyl)phenyl)-1,3,4-oxadiazole (0.016 g, 79.6%) in a white solid form.

$^1$H NMR (400 MHz, $CDCl_3$) δ 7.99-7.89 (m, 2H), 7.71 (s, 1H), 7.50 (t, J=7.6 Hz, 1H), 7.07 (s, 0.2H), 6.94 (s, 0.5H), 6.82 (s, 0.3H), 5.70 (s, 2H), 4.32-4.03 (m, 4H), 2.83-2.43 (m, 2H); LRMS (ES) m/z 384.33 ($M^+$+1).

Example 208: Synthesis of compound 4287, 2-(difluoromethyl)-5-(6-((4-(2-methyl-1H-indol-6-yl)-1H-1,2,3-triazol-1-yl)methyl)pyridin-3-yl)-1,3,4-oxadiazole

[Step 1] Synthesis of methyl 2-methyl-1H-indol-6-carboxylate

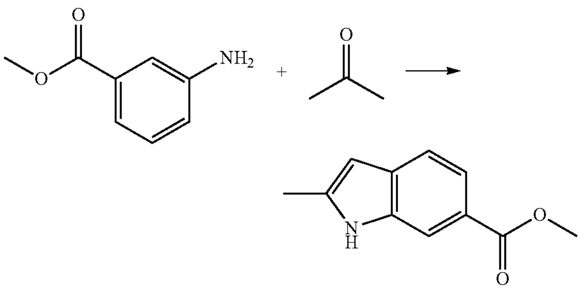

Methyl 3-aminobenzoate (3.000 g, 19.845 mmol), copper acetate monohydrate (11.886 g, 59.536 mmol), acetone (34.578 g, 595.356 mmol) and acetic acid palladium (II, 0.089 g, 0.397 mmol) were dissolved in dimethyl sulfoxide (15 mL) at room temperature, after which the resulting solution was stirred at the same temperature for 48 hours. The reaction mixture was filtered via a celite pad to remove a solid therefrom, after which solvent was removed from the resulting filtrate without the solid under reduced pressure. Then, the resulting concentrate was purified via column chromatography ($SiO_2$, 24 g cartridge; ethyl acetate/ hexane=0 to 30%), and concentrated to obtain methyl 2-methyl-1H-indol-6-carboxylate (0.150 g, 4.0%) in a light yellow solid form.

[Step 2] Synthesis of (2-methyl-1H-indol-6-yl)methanol

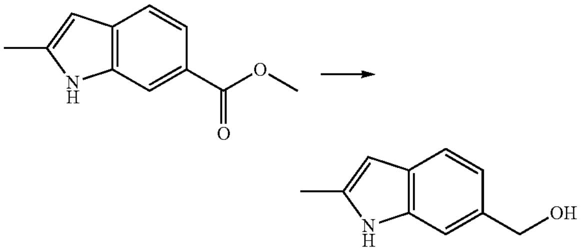

Methyl 2-methyl-1H-indol-6-carboxylate (0.130 g, 0.687 mmol) prepared in step 1 was dissolved in tetrahydrofuran (2 mL), after which the resulting solution was stirred at 0 °C for 0.1 hours, and then lithium aluminum hydride (1.00 M solution, 1.718 mL, 1.718 mmol) was added to the resulting solution and further stirred at room temperature for 2 hours. The reaction mixture was filtered via a celite pad to remove a solid therefrom, after which solvent was removed from a resulting filtrate without the solid under reduced pressure, and then a product obtained was used without an additional purification process ((2-methyl-1H-indol-6-yl)methanol, 0.113 g, 102.0%, colorless oil).

[Step 3] Synthesis of 2-methyl-1H-indol-6-carbaldehyde

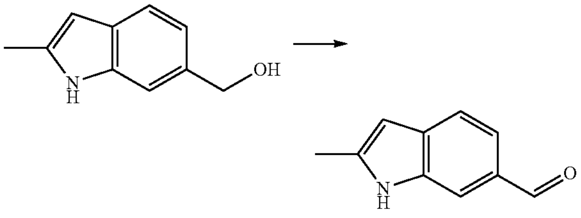

The (2-methyl-1H-indol-6-yl)methanol (0.130 g, 0.806 mmol) prepared in step 2 and MANGAS(ip) oxide (0.491 g, 5.645 mmol) were dissolved in dichloromethane (3 mL) at room temperature, after which the resulting solution was stirred at the same temperature for 18 hours. The reaction mixture was filtered via a celite pad to remove a solid therefrom, after which solvent was removed from a resulting filtrate without the solid under reduced pressure, and then a product obtained was used without an additional purification process (2-methyl-1H-indol-6-carbaldehyde, 0.110 g, 85.7%, yellow solid).

[Step 4] Synthesis of 6-ethynyl-2-methyl-1H-indole

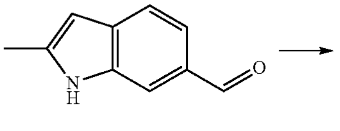

-continued

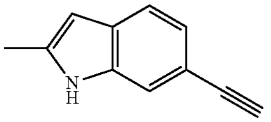

The 2-methyl-1H-indol-6-carbaldehyde (0.100 g, 0.628 mmol) prepared in step 3 and dimethyl(1-diazo-2-oxopropyl)phosphonate (0.189 mL, 1.256 mmol) were dissolved in methanol (2 mL) at room temperature, after which potassium carbonate (0.243 g, 1.759 mmol) was added to the resulting solution and stirred at the same temperature for 18 hours. Solvent was removed from the reaction mixture under reduced pressure, after which water was poured into the resulting concentrate, and then an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 40%) and concentrated to obtain 6-ethynyl-2-methyl-1H-indole (0.040 g, 41.0%) in a light yellow solid form.

[Step 5] Synthesis of Compound 4287

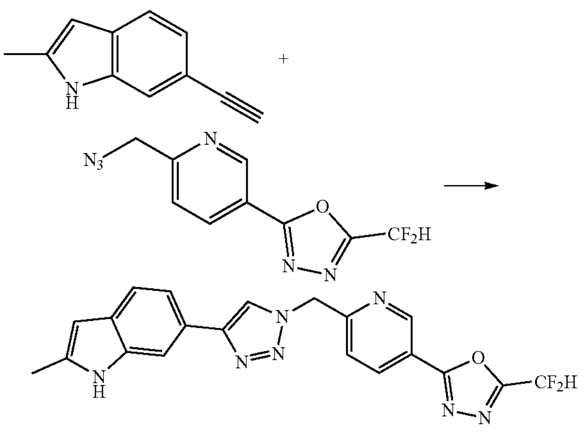

The 2-(4-(azidomethyl)phenyl)-5-(difluoromethyl)-1,3,4-oxadiazole (0.028 g, 0.111 mmol) prepared in step 1 of example 18 and 6-ethynyl-2-methyl-1H-indole (0.017 g, 0.111 mmol) prepared in step 4 were dissolved in tert-butanol (1 mL)/water (1 mL) at room temperature, after which sodium ascorbate (1.00 M solution, 0.011 mL, 0.011 mmol) and copper(II) sulfate pentahydrate (0.50 M solution, 0.002 mL, 0.001 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 80%) and concentrated to obtain 2-(difluoromethyl)-5-(6-((4-(2-methyl-1H-indol-6-yl)-1H-1,2,3-triazol-1-yl)methyl)pyridin-3-yl)-1,3,4-oxadiazole (0.032 g, 70.8%) in a light yellow solid form.

$^1$H NMR (400 MHz, DMSO-$d_6$) δ 11.02 (s, 1H), 9.21 (dd, J=2.3, 0.9 Hz, 1H), 8.61 (s, 1H), 8.49 (dd, J=8.2, 2.3 Hz, 1H), 7.79 (q, J=1.0 Hz, 1H), 7.58 (t, J=51.2 Hz, 1H), 7.55 (d, J=8.1 Hz, 1H), 7.43 (d, J=1.5 Hz, 1H), 6.16-6.11 (m, 1H), 5.91 (s, 2H), 2.40 (d, J=1.0 Hz, 3H); LRMS (ES) m/z 408.1 ($M^+$+1).

The compound of table 59 was synthesized according to substantially the same process as described above in the synthesis of compound 4287 with an exception of using 6-ethynyl-2-methyl-1H-indole and the reactant of table 58.

TABLE 58

| Example | Compound No. | Reactant | Yield (%) |
|---|---|---|---|
| 209 | 4288 | 2-(4-(azidomethyl)phenyl)-5-(difluoromethyl)-1,3,4-oxadiazole | 77 |

TABLE 59

| Example | Compound No. | Compound Name, $^1$H-NMR, MS (ESI) |
|---|---|---|
| 209 | 4288 | 2-(difluoromethyl)-5-(4-((4-(2-methyl-1H-indol-6-yl)-1H-1,2,3-triazol-1-yl)methyl)phenyl)-1,3,4-oxadiazole $^1$H NMR (400 MHZ, DMSO-$d_6$) δ 11.01 (s, 1H), 8.61 (s, 1H), 8.10 (d, J = 7.9 Hz, 2H), 7.78 (s, 1H), 7.69-7.53 (m, 3H), 7.47-7.37 (m, 2H), 6.13 (s, 1H), 5.78 (s, 2H), 2.40 (s, 3H); LRMS (ES) m/z 407.2 ($M^+$ + 1). |

Example 211: Synthesis of compound 4290, 2-(difluoromethyl)-5-(3-fluoro-4-((4-(3-(1-methylpiperidin-4-yl)phenyl)-1H-1,2,3-triazol-1-yl)methyl)phenyl)-1,3,4-oxadiazole

[Step 1] Synthesis of methyl 4-(azidomethyl)-3-fluorobenzoate

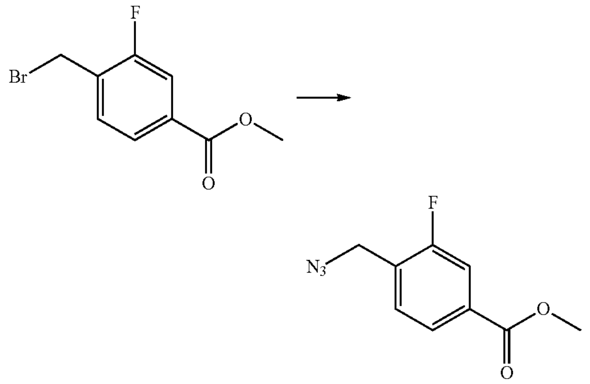

Methyl 4-(bromomethyl)-3-fluorobenzoate (2.000 g, 8.095 mmol) and sodium azide (0.632 g, 9.714 mmol) were dissolved in N,N-dimethylformamide (50 mL) at 50 °C, after which the resulting solution was stirred at the same temperature for 5 hours, and then a reaction was finished by lowering a temperature to room temperature. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 20%), and concentrated to obtain methyl 4-(azidomethyl)-3-fluorobenzoate (1.500 g, 88.6%) in a yellow oil form.

[Step 2] Synthesis of methyl 4-((4-(3-bromophenyl)-1H-1,2,3-triazol-1-yl)methyl)-3-fluorobenzoate

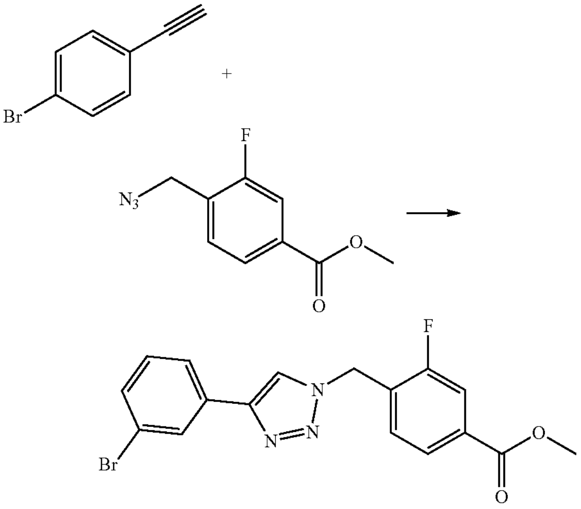

The methyl 4-(azidomethyl)-3-fluorobenzoate (0.900 g, 4.303 mmol) prepared in step 1, 1-bromo-4-ethynylbenzene (0.935 g, 5.163 mmol), sodium ascorbate (1.00 M solution in $H_2O$, 0.430 mL, 0.430 mmol), and copper(II) sulfate pentahydrate (0.50 M solution in $H_2O$, 0.086 mL, 0.043 mmol) were dissolved in tert-butanol (15 mL)/water (15 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%), and concentrated to obtain methyl 4-((4-(3-bromophenyl)-1H-1,2,3-triazol-1-yl)methyl)-3-fluorobenzoate (1.300 g, 77.4%) in a white solid form.

[Step 3] Synthesis of methyl 4-((4-(3-bromophenyl)-1H-1,2,3-triazol-1-yl)methyl)-3-fluorobenzoate

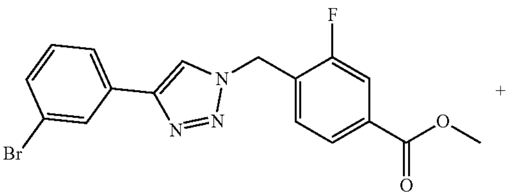

-continued

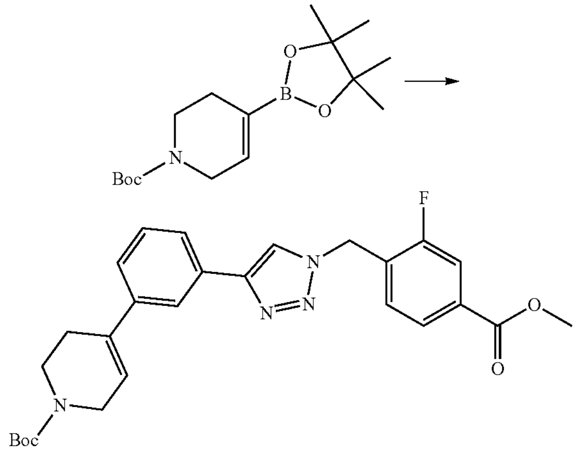

The methyl 4-((4-(3-bromophenyl)-1H-1,2,3-triazol-1-yl) methyl)-3-fluorobenzoate (1.300 g, 3.332 mmol) prepared in step 2, tert-butyl 4-(4,4,5,5-tetramethyl-1,3,2-dioxaborolan-2-yl)-3,6-dihydropyridin-1(2H)-carboxylate (1.236 g, 3.998 mmol), bis(triphenylphosphine)palladium(I) dichloride (0.117 g, 0.167 mmol) and sodium carbonate (1.059 g, 9.995 mmol) were mixed in N,N-dimethylformamide (20 mL)/water (10 mL) at 60 °C, after which the resulting mixture was stirred at the same temperature for 5 hours, and then a reaction was finished by lowering a temperature to room temperature. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 40%) and concentrated to obtain tert-butyl 4-(3-(1-(2-fluoro-4-(methoxycarbonyl)benzyl)-1H-1,2,3-triazol-4-yl)phenyl)-3,6-dihydropyridin-1(2H)-carboxylate (1.400 g, 85.3%) in a white solid form.

[Step 4] Synthesis of tert-butyl 4-(3-(1-(2-fluoro-4-(methoxycarbonyl)benzyl)-1H-1,2,3-triazol-4-yl) phenyl)piperidin-1-carboxylate

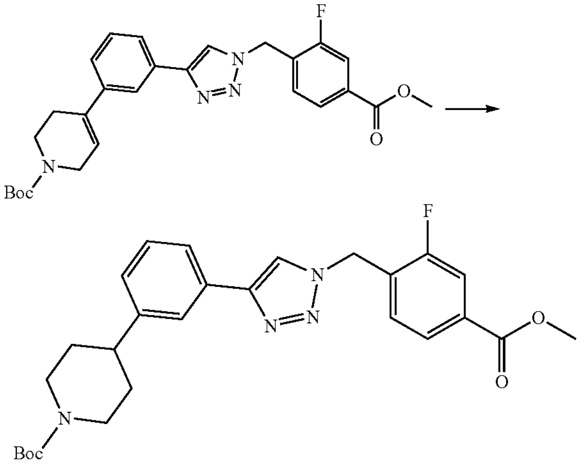

The tert-butyl 4-(3-(1-(2-fluoro-4-(methoxycarbonyl) benzyl)-1H-1,2,3-triazol-4-yl)phenyl)-3,6-dihydropyridin-1(2H)-carboxylate (1.000 g, 2.030 mmol) prepared in step 3 was dissolved in methanol (50 mL) at room temperature, after which 10%-Pd/C (150 mg) was slowly added thereto, and stirred for 12 hours in the presence of a hydrogen balloon attached thereto at the same temperature. The reaction mixture was filtered via a celite pad to remove a solid therefrom, after which solvent was removed from the resulting filtrate under reduced pressure, and then the resulting concentrate was purified via column chromatography ($SiO_2$, 24 g cartridge; ethyl acetate/hexane=0 to 30%) and concentrated to obtain tert-butyl 4-(3-(1-(2-fluoro-4-(methoxycarbonyl)benzyl)-1H-1,2,3-triazol-4-yl)phenyl)piperidin-1-carboxylate (0.900 g, 89.6%) in a yellow oil form

[Step 5] Synthesis of tert-butyl 4-(3-(1-(2-fluoro-4-(hydrazinecarbonyl)benzyl)-1H-1,2,3-triazol-4-yl) phenyl)piperidin-1-carboxylate

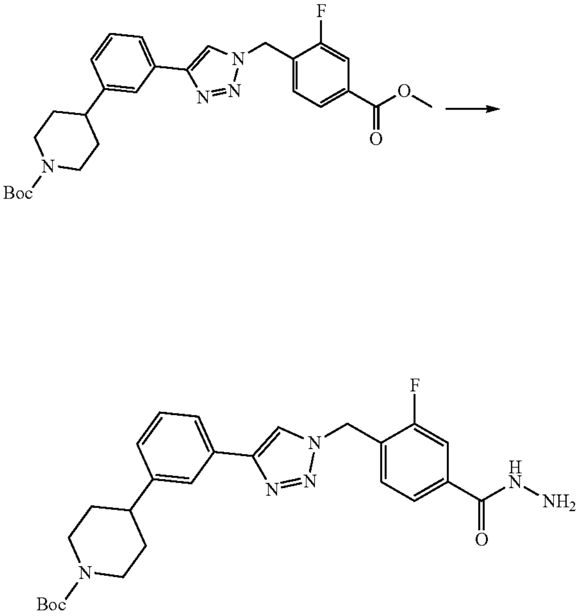

The tert-butyl 4-(3-(1-(2-fluoro-4-(methoxycarbonyl) benzyl)-1H-1,2,3-triazol-4-yl)phenyl)piperidin-1-carboxylate (0.900 g, 1.820 mmol) prepared in step 4 and hydrazine monohydrate (0.884 mL, 18.198 mmol) were dissolved in ethanol (50 mL) at 90 °C, after which the resulting solution was stirred at the same temperature for 12 hours, and then a reaction was finished by lowering a temperature to room temperature. Solvent was removed from the reaction mixture under reduced pressure, after which water was poured into the resulting concentrate, and then an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (tert-butyl 4-(3-(1-(2-fluoro-4-(hydrazinecarbonyl)benzyl)-1H-1,2,3-triazol-4-yl)phenyl)piperidin-1-carboxylate, 0.820 g, 91.1%, white solid).

[Step 6] Synthesis of tert-butyl 4-(3-(1-(4-(5-(difluoromethyl)-1,3,4-oxadiazol-2-yl)-2-fluorobenzyl)-1H-1,2,3-triazol-4-yl)phenyl)piperidin-1-carboxylate

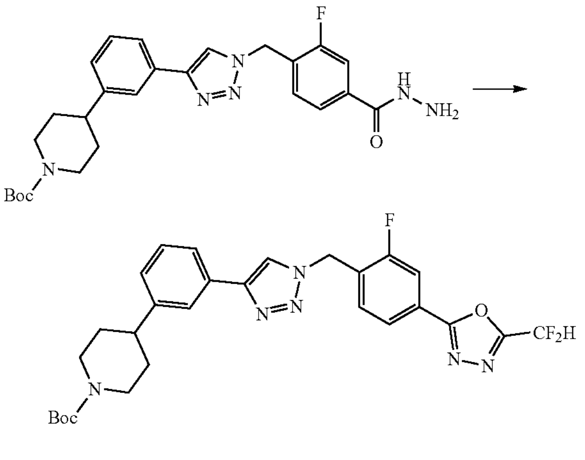

The tert-butyl 4-(3-(1-(2-fluoro-4-(hydrazinecarbonyl)benzyl)-1H-1,2,3-triazol-4-yl)phenyl)piperidin-1-carboxylate (0.820 g, 1.658 mmol) prepared in step 5, imidazole (0.339 g, 4.974 mmol) and 2,2-difluoroacetic anhydride (0.618 mL, 4.974 mmol) were mixed in dichloromethane (50 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(3-(1-(4-(5-(difluoromethyl)-1,3,4-oxadiazol-2-yl)-2-fluorobenzyl)-1H-1,2,3-triazol-4-yl)phenyl)piperidin-1-carboxylate (0.770 g, 83.7%) in a white solid form.

[Step 7] Synthesis of 2-(difluoromethyl)-5-(3-fluoro-4-((4-(3-(piperidin-4-yl)phenyl)-1H-1,2,3-triazol-1-yl)methyl)phenyl)-1,3,4-oxadiazole

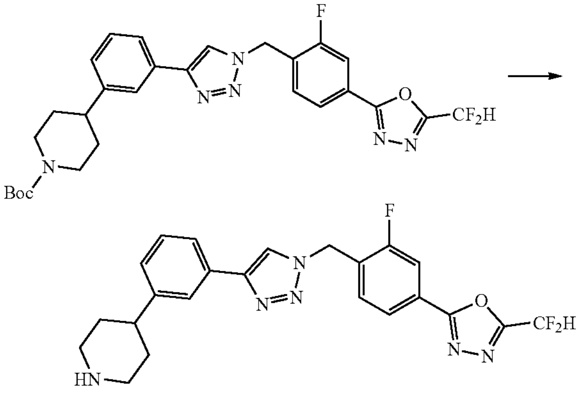

The tert-butyl 4-(3-(1-(4-(5-(difluoromethyl)-1,3,4-oxadiazol-2-yl)-2-fluorobenzyl)-1H-1,2,3-triazol-4-yl)phenyl)piperidin-1-carboxylate (0.770 g, 1.388 mmol) prepared in step 6 and trifluoroacetic acid (0.319 mL, 4.165 mmol) were dissolved in dichloromethane (20 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(3-fluoro-4-((4-(3-(piperidin-4-yl)phenyl)-1H-1,2,3-triazol-1-yl)methyl)phenyl)-1,3,4-oxadiazole, 0.510 g, 80.8%, yellow oil).

[Step 8] Synthesis of Compound 4290

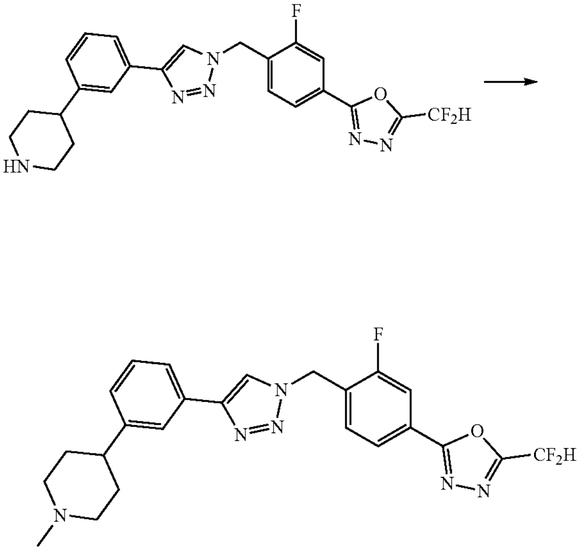

The 2-(difluoromethyl)-5-(3-fluoro-4-((4-(3-(piperidin-4-yl)phenyl)-1H-1,2,3-triazol-1-yl)methyl)phenyl)-1,3,4-oxadiazole (0.070 g, 0.154 mmol) prepared in step 7, formaldehyde (36.00%, 0.026 g, 0.308 mmol), acetic acid (0.011 mL, 0.185 mmol) and sodium triacetoxyborohydride (0.065 g, 0.308 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(3-fluoro-4-((4-(3-(1-methylpiperidin-4-yl)phenyl)-1H-1,2,3-triazol-1-yl)methyl)phenyl)-1,3,4-oxadiazole (0.029 g, 40.2%) in a white solid form.

$^1H$ NMR (400 MHz, $CDCl_3$) δ 7.97-7.91 (m, 2H), 7.89 (s, 1H), 7.73 (d, J=9.0 Hz, 2H), 7.47 (t, J=7.7 Hz, 1H), 7.40 (t, J=7.6 Hz, 1H), 7.26 (d, J=7.5 Hz, 1H), 7.07 (s, 0.2H), 6.94 (s, 0.5H), 6.81 (s, 0.3H), 5.75 (s, 2H), 3.37 (s, 2H), 2.77-2.47 (m, 5H), 2.30-2.28 (m, 3H), 2.01 (d, J=12.0 Hz, 2H); LRMS (ES) m/z 469.5 ($M^+$+1).

The compounds of table 61 were synthesized according to substantially the same process as described above in the synthesis of compound 4290 with an exception of using 2-(difluoromethyl)-5-(3-fluoro-4-((4-(3-(piperidin-4-yl) phenyl)-1H-1,2,3-triazol-1-yl)methyl)phenyl)-1,3,4-oxadiazole and the reactant of table 60.

TABLE 60

| Example | Compound No. | Reactant | Yield (%) |
|---|---|---|---|
| 212 | 4291 | Acetaldehyde | 40 |
| 213 | 4292 | Propan-2-one | 40 |
| 214 | 4293 | Oxetan-3-one | 36 |

TABLE 61

| Example | Compound No. | Compound Name, $^1$H-NMR, MS (ESI) |
|---|---|---|
| 212 | 4291 | 2-(difluoromethyl)-5-(4-((4-(3-(1-ethylpiperidin-4-yl)phenyl)-1H-1,2,3-triazol-1-yl)methyl)-3-fluorophenyl)-1,3,4-oxadiazole $^1$H NMR (400 MHZ, $CDCl_3$) δ 7.96-7.89 (m, 2H), 7.86 (s, 1H), 7.76-7.67 (m, 2H), 7.47 (t, J = 7.7 Hz, 1H), 7.37 (t, J = 7.7 Hz, 1H), 7.23 (d, J = 7.7 Hz, 1H), 7.07 (s, 0.2H), 6.94 (s, 0.5H), 6.81 (s, 0.3H), 5.74 (s, 2H), 3.29 (d, J = 11.6 Hz, 2H), 2.73-2.56 (m, 3H), 2.27 (dd, J = 12.2, 10.2 Hz, 2H), 2.12-1.85 (m, 4H), 1.22 (t, J = 7.2 Hz, 3H); LRMS (ES) m/z 483.5 ($M^+$ + 1). |
| 213 | 4292 | 2-(difluoromethyl)-5-(3-fluoro-4-((4-(3-(1-isopropylpiperidin-4-yl)phenyl)-1H-1,2,3-triazol-1-yl)methyl)phenyl)-1,3,4-oxadiazole $^1$H NMR (400 MHZ, $CDCl_3$) δ 7.93 (dd, J = 8.8, 6.5 Hz, 3H), 7.76 (d, J = 6.4 Hz, 2H), 7.46 (t, J = 7.7 Hz, 1H), 7.39 (t, J = 7.9 Hz, 1H), 7.26 (d, J = 7.5 Hz, 1H), 7.07 (s, 0.2H), 6.94 (s, 0.5H), 6.81 (s, 0.3H), 5.75 (s, 2H), 3.33 (s, 2H), 2.69-2.61 (m, 3H), 2.00 (d, J = 12.7 Hz, 2H), 1.69-1.58 (m, 3H), 1.30 (d, J = 12.9 Hz, 6H); LRMS (ES) m/z 497.5 ($M^+$ + 1). |
| 214 | 4293 | 2-(difluoromethyl)-5-(3-fluoro-4-((4-(3-(1-(oxetan-3-yl)piperidin-4-yl)phenyl)-1H-1,2,3-triazol-1-yl)methyl)phenyl)-1,3,4-oxadiazole $^1$H NMR (400 MHZ, $CDCl_3$) δ 7.94 (d, J = 8.6 Hz, 2H), 7.83 (s, 1H), 7.75 (s, 1H), 7.67 (d, J = 7.7 Hz, 1H), 7.48 (t, J = 7.6 Hz, 1H), 7.38 (t, J = 7.7 Hz, 1H), 7.24 (d, J = 7.7 Hz, 1H), 7.07 (s, 0.2H), 6.94 (s, 0.5H), 6.81 (s, 0.3H), 5.75 (s, 2H), 4.71(t, J = 8.4 Hz, 4H), 3.61-3.48 (m, 1H), 2.92 (d, J = 9.7 Hz, 2H), 2.70-2.50 (m, 1H), 1.95 (dd, J = 22.2, 7.6 Hz, 6H); LRMS (ES) m/z 511.6 ($M^+$ + 1). |

Example 215: Synthesis of compound 4294, 2-(difluoromethyl)-5-(3-fluoro-4-((4-(3-(1-(1-methylazetidin-3-yl)piperidin-4-yl)phenyl)-1H-1,2,3-triazol-1-yl)methyl)phenyl)-1,3,4-oxadiazole

[Step 1] Synthesis of tert-butyl 3-(4-(3-(1-(4-(5-(difluoromethyl)-1,3,4-oxadiazol-2-yl)-2-fluorobenzyl)-1H-1,2,3-triazol-4-yl)phenyl)piperidin-1-yl) azetidin-1-carboxylate

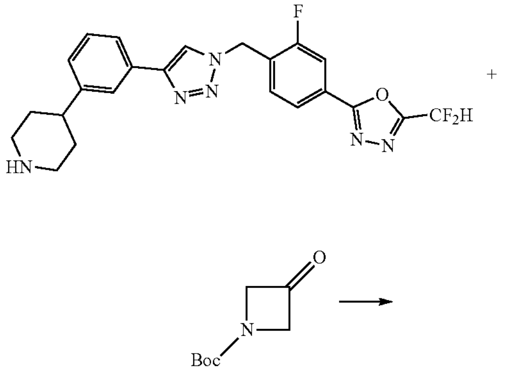

-continued

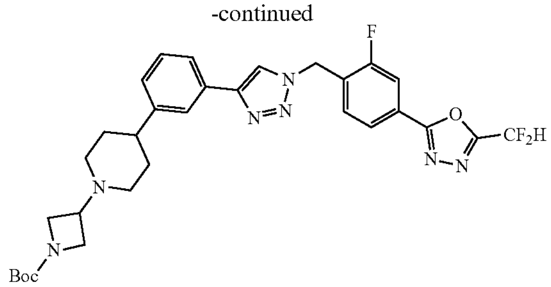

The 2-(difluoromethyl)-5-(3-fluoro-4-((4-(3-(piperidin-4-yl)phenyl)-1H-1,2,3-triazol-1-yl)methyl)phenyl)-1,3,4-oxadiazole (0.400 g, 0.880 mmol) prepared in step 7 of example 211, tert-butyl 3-oxoazetidin-1-carboxylate (0.301 g, 1.760 mmol), acetic acid (0.060 mL, 1.056 mmol) and sodium triacetoxyborohydride (0.373 g, 1.760 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain tert-butyl 3-(4-(3-(1-(4-(5-(difluoromethyl)-1,3,4-oxadiazol-2-yl)-2-fluorobenzyl)-1H-1,2,3-triazol-4-yl)phenyl)piperidin-1-yl)azetidin-1-carboxylate (0.300 g, 55.9%) in a white solid form.

[Step 2] Synthesis of 2-(4-((4-(3-(1-(azetidin-3-yl)piperidin-4-yl)phenyl)-1H-1,2,3-triazol-1-yl)methyl)-3-fluorophenyl)-5-(difluoromethyl)-1,3,4-oxadiazole

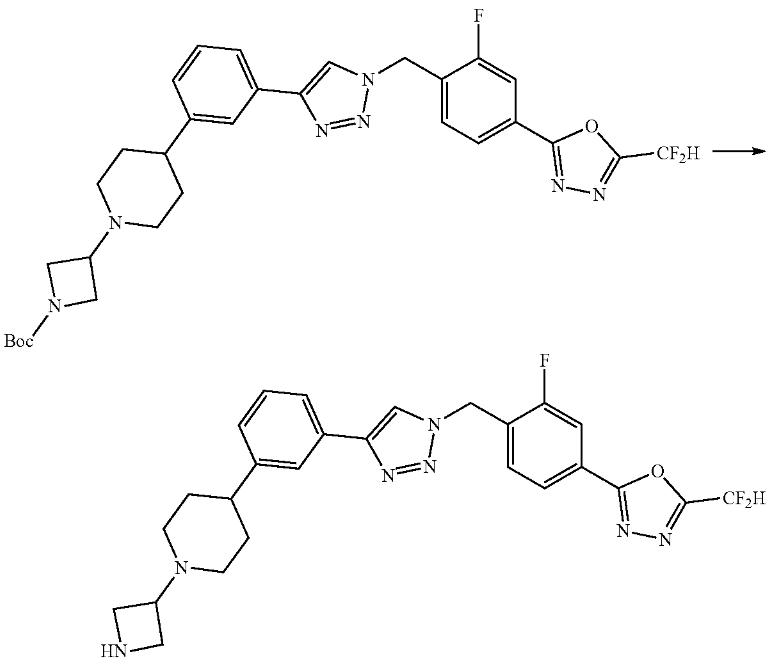

The tert-butyl 3-(4-(3-(1-(4-(5-(difluoromethyl)-1,3,4-oxadiazol-2-yl)-2-fluorobenzyl)-1H-1,2,3-triazol-4-yl)phenyl)piperidin-1-yl)azetidin-1-carboxylate (0.300 g, 0.492 mmol) prepared in step 1 and trifluoroacetic acid (0.113 mL, 1.476 mmol) were dissolved in dichloromethane (20 mL) at room temperature, after which the resulting solution was stirred at the same temperature for 3 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (2-(4-((4-(3-(1-(azetidin-3-yl)piperidin-4-yl)phenyl)-1H-1,2,3-triazol-1-yl)methyl)-3-fluorophenyl)-5-(difluoromethyl)-1,3,4-oxadiazole, 0.200 g, 79.8%, yellow oil).

[Step 3] Synthesis of Compound 4294

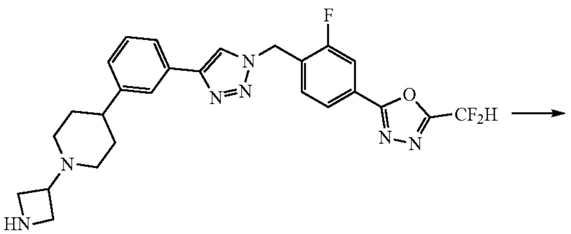

-continued

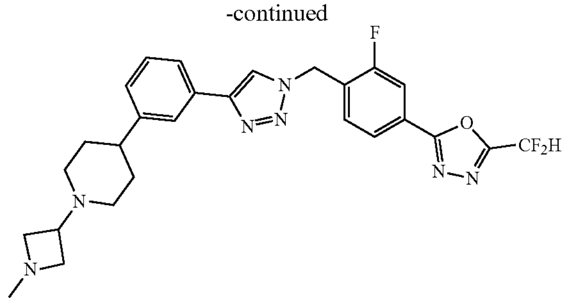

The 2-(4-((4-(3-(1-(azetidin-3-yl)piperidin-4-yl)phenyl)-1H-1,2,3-triazol-1-yl)methyl)-3-fluorophenyl)-5-(difluoromethyl)-1,3,4-oxadiazole (0.070 g, 0.137 mmol) prepared in step 2, formaldehyde (0.008 g, 0.275 mmol) and acetic acid (0.009 mL, 0.165 mmol) were dissolved in dichloromethane (5 mL), after which the resulting solution was stirred at room temperature for 30 minutes, and then sodium triacetoxyborohydride (0.058 g, 0.275 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(3-fluoro-4-((4-(3-(1-(1-methylazetidin-3-yl)piperidin-4-yl)

phenyl)-1H-1,2,3-triazol-1-yl)methyl)phenyl)-1,3,4-oxadiazole (0.036 g, 50.1%) in a white solid form.

$^1$H NMR (400 MHz, $CDCl_3$) δ 7.94 (d, J=8.8 Hz, 2H), 7.81 (s, 1H), 7.76 (d, J=9.6 Hz, 1H), 7.66 (d, J=7.6 Hz, 1H), 7.48 (t, J=7.6 Hz, 1H), 7.37 (t, J=7.7 Hz, 1H), 7.22 (d, J=7.7 Hz, 1H), 7.07 (s, 0.2H), 6.94 (s, 0.5H), 6.81 (s, 0.3H), 5.74 (s, 2H), 3.71 (s, 2H), 3.05 (s, 3H), 2.89 (d, J=11.0 Hz, 2H), 2.64-2.52 (m, 1H), 2.47 (s, 3H), 2.02-1.73 (m, 6H); LRMS (ES) m/z 524.2 ($M^+$+1).

The compounds of table 63 were synthesized according to substantially the same process as described above in the synthesis of compound 4294 with an exception of using 2-(4-((4-(3-(1-(azetidin-3-yl)piperidin-4-yl)phenyl)-1H-1,2,3-triazol-1-yl)methyl)-3-fluorophenyl)-5-(difluoromethyl)-1,3,4-oxadiazole and the reactant of table 62.

TABLE 62

| Example | Compound No. | Reactant | Yield (%) |
|---|---|---|---|
| 216 | 4295 | Acetaldehyde | 39 |
| 217 | 4296 | Propan-2-one | 40 |

TABLE 63

| Example | Compound No. | Compound Name, $^1$H-NMR, MS (ESI) |
|---|---|---|
| 216 | 4295 | 2-(difluoromethyl)-5-(4-((4-(3-(1-(1-ethylazetidin-3-yl)piperidin-4-yl)phenyl)-1H-1,2,3-triazol-1-yl)methyl)-3-fluorophenyl)-1,3,4-oxadiazole<br>$^1$H NMR (400 MHZ, $CDCl_3$) δ 7.94 (d, J = 9.1 Hz, 2H), 7.82 (s, 1H), 7.75 (s, 1H), 7.65 (d, J = 7.7 Hz, 1H), 7.47 (t, J =7.7 Hz, 1H), 7.37 (t, J = 7.7 Hz, 1H), 7.22 (d, J = 7.7 Hz, 1H), 7.07 (s, 0.2H), 6.94 (s, 0.5H), 6.81 (s, 0.3H), 5.74 (s, 2H), 3.86 (S, 2H), 3.16 (dd, J = 16.0, 6.3 Hz, 3H), 2.89 (d, J = 11.1 Hz, 2H), 2.76 (dd, J = 14.2, 7.1 Hz, 2H), 2.64-2.49 (m, 1H), 2.01-1.73 (m, 6H), 1.11 (t, J = 7.2 Hz, 3H); LRMS (ES) m/z 538.6 ($M^+$ + 1). |
| 217 | 4296 | 2-(difluoromethyl)-5-(3-fluoro-4-((4-(3-(1-(1-isopropylazetidin-3-yl)piperidin-4-<br>$^1$H NMR (400 MHZ, $CDCl_3$) δ 7.95-7.89 (m, 2H), 7.82 (s, 1H), 7.73 (s, 1H), 7.64 (d, J = 7.8 Hz, 1H), 7.46 (t, J = 7.7 Hz, 1H), 7.35 (t, J = 7.7 Hz, 1H), 7.21 (d, J = 7.8 Hz, 1H), 7.07 (s, 0.2H), 6.94 (s, 0.5H), 6.81 (s, 0.3H), 5.73 (s, 2H), 3.70 (d, J = 30.7 Hz, 2H), 3.11-2.98 (m, 3H), 2.89 (d, J = 11.2 Hz, 2H), 2.65-2.48 (m, 2H), 1.99-1.73 (m, 6H), 1.04 (d, J = 6.3 Hz, 6H); LRMS (ES) m/z 552.6 ($M^+$ + 1). |

Example 218: Synthesis of compound 4316, 2-(4-((4-(3-((1S,4S)-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole

[Step 1] Synthesis of 2-(3-bromophenyl)-1,3-dioxolane

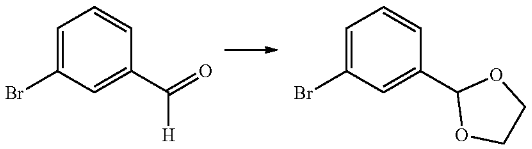 [SMILES: O=Cc1cccc(Br)c1 ; Brc1cccc(C2OCCO2)c1]

3-bromobenzaldehyde (3.145 mL, 27.024 mmol), para-toluenesulfonic acid monohydrate (0.051 g, 0.270 mmol) and ethylene glycol (1.813 mL, 32.429 mmol) were dissolved in toluene (20 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The obtained product was used without an additional purification process (2-(3-bromophenyl)-1,3-dioxolane, 5.500 g, 88.8%, brown oil).

[Step 2] Synthesis of tert-butyl (1S,4S)-5-(3-(1,3-dioxolan-2-yl)phenyl)-2,5-diazabicyclo[2.2.1]heptan-2-carboxylate

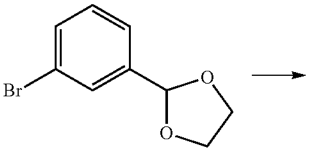

-continued

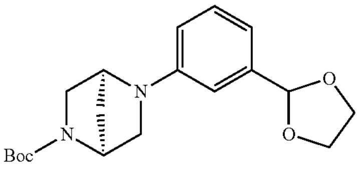

The tert-butyl (1S,4S)-5-(3-(1,3-dioxolan-2-yl)phenyl)-2,5-diazabicyclo[2.2.1]heptan-2-carboxylate (0.900 g, 2.598 mmol) prepared in step 1 and hydrochloric acid (1.00 M solution, 12.990 mL, 12.990 mmol) were dissolved in water (50 mL) at room temperature, after which the resulting solution was stirred at the same temperature for 6 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%), and concentrated to obtain tert-butyl (1S,4S)-5-(3-(1,3-dioxolan-2-yl)phenyl)-2,5-diazabicyclo[2.2.1]heptan-2-carboxylate (0.550 g, 70.0%) in a yellow solid form.

[Step 3] Synthesis of tert-butyl (1S,4S)-5-(3-formylphenyl)-2,5-diazabicyclo[2.2.1]heptan-2-carboxylate

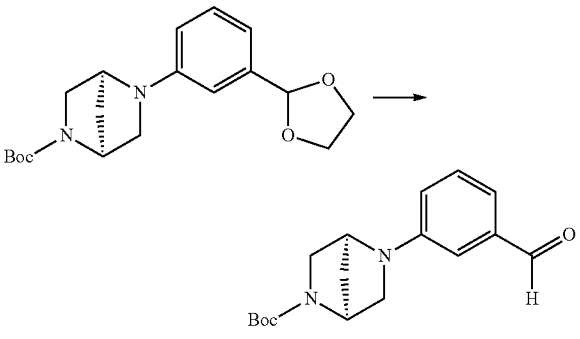

The tert-butyl (1S,4S)-5-(3-(1,3-dioxolan-2-yl)phenyl)-2,5-diazabicyclo[2.2.1]heptan-2-carboxylate (0.900 g, 2.598 mmol) prepared in step 2 and hydrochloric acid (1.00 M solution, 12.990 mL, 12.990 mmol) were dissolved in water (50 mL) at room temperature, after which the resulting solution was stirred at the same temperature for 6 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%), and concentrated to obtain tert-butyl (1S,4S)-5-(3-formylphenyl)-2,5-diazabicyclo[2.2.1]heptan-2-carboxylate (0.550 g, 70.0%) in a yellow solid form.

[Step 4] Synthesis of tert-butyl (1S,4S)-5-(3-(2,2-dibromovinyl)phenyl)-2,5-diazabicyclo[2.2.1]heptan-2-carboxylate

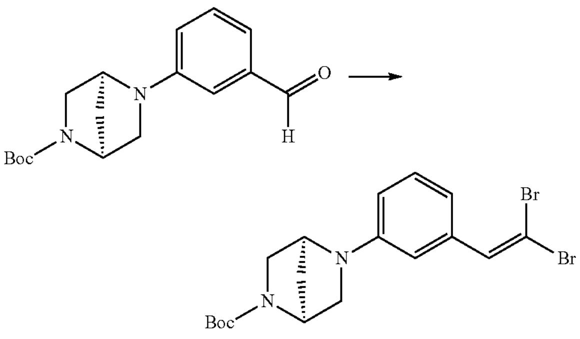

The tert-butyl (1S,4S)-5-(3-formylphenyl)-2,5-diazabicyclo[2.2.1]heptan-2-carboxylate (2.300 g, 7.607 mmol) prepared in step 3, carbon tetrabromide (5.045 g, 15.213 mmol) and triphenylphosphine triphenylphosphine (5.985 g, 22.820 mmol) were dissolved in dichloromethane (50 mL) at room temperature, after which the resulting solution was stirred at the same temperature for two hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl (1S,4S)-5-(3-(2,2-dibromovinyl)phenyl)-2,5-diazabicyclo[2.2.1]heptan-2-carboxylate (3.450 g, 99.0%) in a yellow oil form.

[Step 5] Synthesis of tert-butyl (1S,4S)-5-(3-ethynylphenyl)-2,5-diazabicyclo[2.2.1]heptan-2-carboxylate

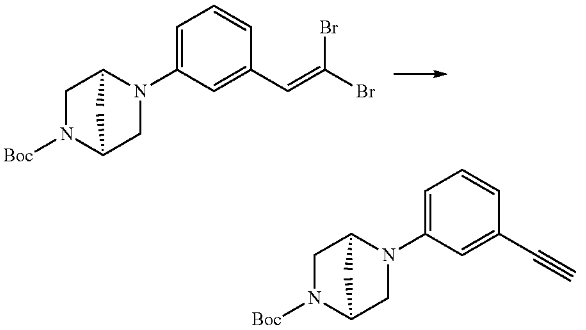

The tert-butyl (1S,4S)-5-(3-(2,2-dibromovinyl)phenyl)-2,5-diazabicyclo[2.2.1]heptan-2-carboxylate (3.450 g, 7.530 mmol) prepared in step 4 and 2,3,4,6,7,8,9,10-octahydropyrimido[1,2-a]azepine (4.504 mL, 30.119 mmol) were dissolved in acetonitrile (50 mL) at room temperature, after which the resulting solution was stirred at the same temperature for 16 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%), and concentrated to obtain tert-butyl (1S,4S)-5-(3-ethynylphenyl)-2,5-diazabicyclo[2.2.1]heptan-2-carboxylate (1.100 g, 49.0%) in a white solid form.

[Step 6] Synthesis of tert-butyl (1S,4S)-5-(3-(1-(4-(5-(difluoromethyl)-1,3,4-oxadiazol-2-yl)-2-fluorobenzyl)-1H-1,2,3-triazol-4-yl)phenyl)-2,5-diazabicyclo[2.2.1]heptan-2-carboxylate

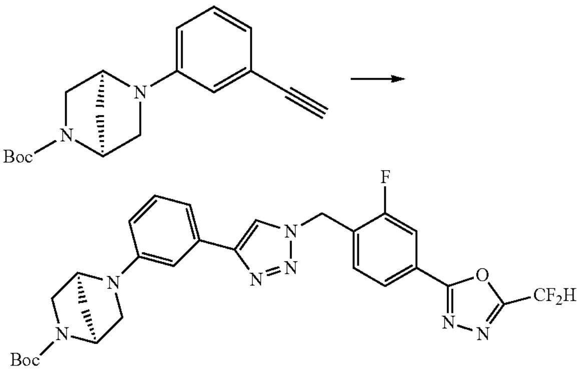

The tert-butyl (1S,4S)-5-(3-ethynylphenyl)-2,5-diazabicyclo[2.2.1]heptan-2-carboxylate (0.500 g, 1.676 mmol) prepared in step 5, the 2-(4-(azidomethyl)-3-fluorophenyl)-5-(difluoromethyl)-1,3,4-oxadiazole (0.451 g, 1.676 mmol) prepared in step 1 of example 2, copper(II) sulfate pentahydrate (0.004 g, 0.017 mmol) and sodium ascorbate (0.033 g, 0.168 mmol) were dissolved in tert-butanol (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl (1S,4S)-5-(3-(1-(4-(5-(difluoromethyl)-1,3,4-oxadiazol-2-yl)-2-fluorobenzyl)-1H-1,2,3-triazol-4-yl)phenyl)-2,5-diazabicyclo[2.2.1]heptan-2-carboxylate (0.400 g, 42.1%) in a yellow solid form.

[Step 7] Synthesis of Compound 4316

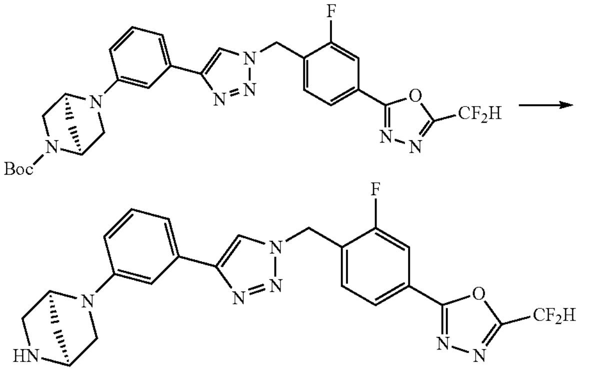

The tert-butyl (1S,4S)-5-(3-(1-(4-(5-(difluoromethyl)-1,3,4-oxadiazol-2-yl)-2-fluorobenzyl)-1H-1,2,3-triazol-4-yl)phenyl)-2,5-diazabicyclo[2.2.1]heptan-2-carboxylate (0.420 g, 0.740 mmol) prepared in step 6 and trifluoroacetic acid (0.567 mL, 7.400 mmol) were dissolved in dichloromethane (50 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(4-((4-(3-((1S,4S)-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole (0.200 g, 57.8%) in a white solid form.

$^1H$ NMR (400 MHz, $CDCl_3$) δ 7.94-7.85 (m, 2H), 7.82 (s, 1H), 7.42 (t, J=7.6 Hz, 1H), 7.22 (q, J=6.8, 5.7 Hz, 1H), 7.12 (t, J=1.9 Hz, 1H), 7.05-6.76 (m, 2H), 6.55-6.48 (m, 1H), 5.70 (s, 2H), 4.41 (s, 1H), 3.95 (s, 1H), 3.65 (dd, J=9.4, 2.2 Hz, 1H), 3.22-3.07 (m, 3H), 2.67 (s, 1H), 2.00 (d, J=10.0 Hz, 1H), 1.92 (d, J=9.9 Hz, 1H); LRMS (ES) m/z 468.2 ($M^+$+1).

Example 219: Synthesis of compound 4317, 2-(4-((4-(3-((1S,4S)-2,5-diazabicyclo[2.2.1]heptan-2-yl)phenyl)-1H-1,2,3-triazol-1-yl)methyl)phenyl)-5-(difluoromethyl)-1,3,4-oxadiazole

[Step 1] Synthesis of tert-butyl (1S,4S)-5-(3-(1-(4-(5-(difluoromethyl)-1,3,4-oxadiazol-2-yl)benzyl)-1H-1,2,3-triazol-4-yl)phenyl)-2,5-diazabicyclo[2.2.1]heptan-2-carboxylate

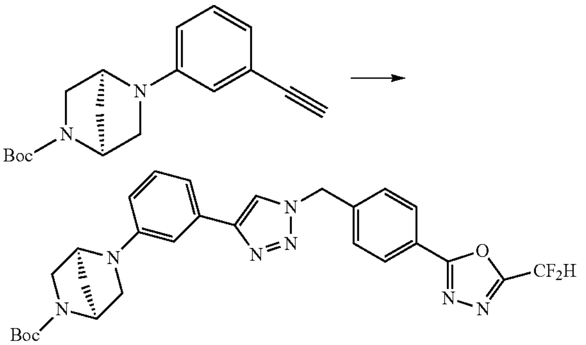

The tert-butyl (1S,4S)-5-(3-ethynylphenyl)-2,5-diazabicyclo[2.2.1]heptan-2-carboxylate (0.400 g, 1.341 mmol) prepared in step 5 of example 218, the 2-(4-(azidomethyl)phenyl)-5-(difluoromethyl)-1,3,4-oxadiazole (0.337 g, 1.341 mmol) prepared in step 1 of example 2, copper(II) sulfate pentahydrate (0.003 g, 0.013 mmol) and sodium ascorbate (0.027 g, 0.134 mmol) were dissolved in tert-butanol (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl (1S,4S)-5-(3-(1-(4-(5-(difluoromethyl)-1,3,4-oxadiazol-2-yl)benzyl)-1H-1,2,3-triazol-4-yl)phenyl)-2,5-diazabicyclo[2.2.1]heptan-2-carboxylate (0.560 g, 76.0%) in a yellow solid form.

[Step 2] Synthesis of Compound 4317

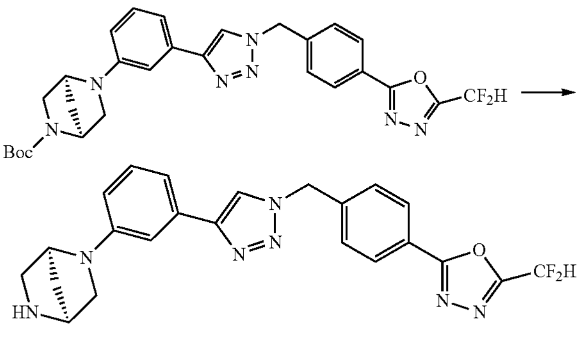

The tert-butyl (1S,4S)-5-(3-(1-(4-(5-(difluoromethyl)-1,3,4-oxadiazol-2-yl)benzyl)-1H-1,2,3-triazol-4-yl)phenyl)-2, 5-diazabicyclo[2.2.1]heptan-2-carboxylate (0.560 g, 1.019 mmol) prepared in step 1 and trifluoroacetic acid (0.780 mL, 10.190 mmol) were dissolved in dichloromethane (50 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(4-((4-(3-((1S,4S)-2,5-diazabicyclo[2.2.1]heptan-2-yl)phenyl)-1H-1,2,3-triazol-1-yl)methyl)phenyl)-5-(difluoromethyl)-1,3,4-oxadiazole (0.360 g, 78.6%) in a brown solid form.

$^1$H NMR (400 MHz, $CDCl_3$) δ 7.92 (d, J=8.0 Hz, 2H), 7.86 (s, 1H), 7.32 (d, J=8.1 Hz, 2H), 7.10 (t, J=8.0 Hz, 1H), 7.03-6.73 (m, 3H), 6.51 (s, 1H), 6.37 (d, J=8.2 Hz, 1H), 5.52 (s, 2H), 4.27 (s, 1H), 3.92 (s, 1H), 3.48 (d, J=9.0 Hz, 1H), 3.08 (dd, J=15.5, 10.0 Hz, 2H), 3.00 (d, J=10.1 Hz, 1H), 1.88 (d, J=9.6 Hz, 1H); LRMS (ES) m/z 450.9 ($M^+$+1).

Example 220: Synthesis of compound 4318, 2-(difluoromethyl)-5-(3-fluoro-4-((4-(3-((1S,4S)-5-methyl-2,5-diazabicyclo[2.2.1]heptan-2-yl)phenyl)-1H-1,2,3-triazol-1-yl)methyl)phenyl)-1,3,4-oxadiazole

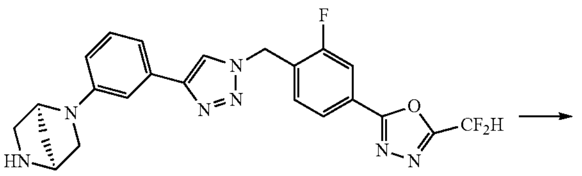

mmol) were dissolved in dichloromethane (5 mL) at room temperature, after which sodium triacetoxyborohydride (0.054 g, 0.257 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(3-((1S,4S)-5-methyl-2,5-diazabicyclo[2.2.1]heptan-2-yl)phenyl)-1H-1,2,3-triazol-1-yl)methyl)phenyl)-1,3,4-oxadiazole (0.025 g, 40.5%) in a white solid form.

$^1$H NMR (400 MHz, $CDCl_3$) δ 7.88 (dt, J=9.8, 1.7 Hz, 2H), 7.81 (s, 1H), 7.46-7.37 (m, 1H), 7.22 (t, J=7.9 Hz, 1H), 7.18-7.12 (m, 1H), 7.05-6.77 (m, 2H), 6.52 (dd, J=8.0, 2.5 Hz, 1H), 5.70 (s, 2H), 4.33 (s, 1H), 3.69 (s, 1H), 3.46 (d, J=1.5 Hz, 2H), 3.10 (dd, J=10.0, 2.0 Hz, 1H), 2.77 (dd, J=10.0, 1.6 Hz, 1H), 2.45 (s, 3H), 2.13-2.06 (m, 1H), 1.98 (d, J=9.2 Hz, 1H); LRMS (ES) m/z 482.1 ($M^+$+1).

The compound of table 65 was synthesized according to substantially the same process as described above in the synthesis of compound 4318 with an exception of using 2-(4-((4-(3-((1S,4S)-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole and the reactant of table 64.

TABLE 64

| Example | Compound No. | Reactant | Yield (%) |
|---|---|---|---|
| 221 | 4319 | Cyclobutanone | 52 |

TABLE 65

| Example | Compound No. | Compound Name, $^1$H-NMR, MS (ESI) |
|---|---|---|
| 221 | 4319 | 2-(4-((4-(3-((1S, 4S)-5-cyclobutyl-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole $^1$H NMR (400 MHZ, $CDCl_3$) δ 7.93-7.82 (m, 3H), 7.42 (t, J = 7.7 Hz, 1H), 7.23 (t, J = 7.9 Hz, 1H), 7.15 (dd, J = 2.6, 1.5 Hz, 1H), 7.06-6.76 (m, 2H), 6.55-6.48 (m, 1H), 5.70 (s, 2H), 4.33 (s, 1H), 4.08 (d, J = 3.7 Hz, 1H), 3.50 (dd, J = 10.1, 2.2 Hz, 1H), 3.47-3.38 (m, 2H), 2.79-2.62 (m, 2H), 2.25 (d, J = 10.8 Hz, 1H), 2.03 (d, J = 10.9 Hz, 1H), 1.17 (dd, J = 17.3,6.2 Hz, 6H); LRMS(ES) m/z 522.5 ($M^+$ + 1). |

-continued

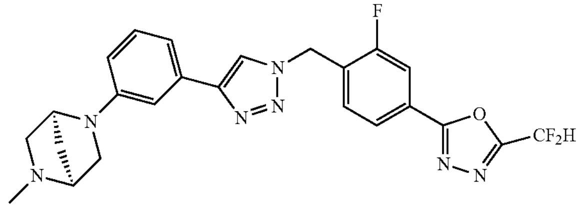

The 2-(4-((4-(3-((1S,4S)-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole (0.060 g, 0.128 mmol) prepared in step 8 of example 218, paraformaldehyde (0.008 g, 0.257 mmol) and acetic acid (0.008 mL, 0.141

Example 222: Synthesis of compound 4320, 2-(difluoromethyl)-5-(4-((4-(3-((1S,4S)-5-methyl-2,5-diazabicyclo[2.2.1]heptan-2-yl)phenyl)-1H-1,2,3-triazol-1-yl)methyl)phenyl)-1,3,4-oxadiazole

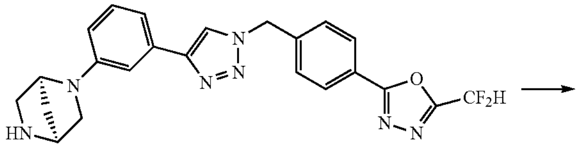

-continued

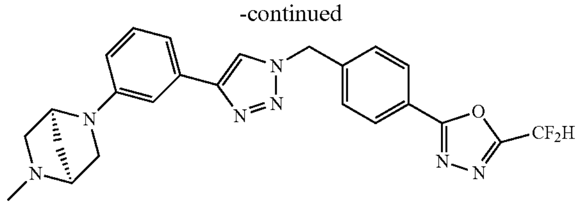

The 2-(4-((4-(3-((1S,4S)-2,5-diazabicyclo[2.2.1]heptan-2-yl)phenyl)-1H-1,2,3-triazol-1-yl)methyl)phenyl)-5-(difluoromethyl)-1,3,4-oxadiazole (0.060 g, 0.128 mmol) prepared in step 2 of example 219, cyclobutanone (0.018 g, 0.257 mmol) and acetic acid (0.008 mL, 0.141 mmol) were dissolved in dichloromethane (5 mL) at room temperature, after which sodium triacetoxyborohydride (0.054 g, 0.257 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(3-((1S,4S)-5-methyl-2,5-diazabicyclo[2.2.1]heptan-2-yl)phenyl)-1H-1,2,3-triazol-1-yl)methyl)phenyl)-1,3,4-oxadiazole (0.036 g, 53.8%) in a white solid form.

$^1$H NMR (400 MHz, $CDCl_3$) δ 8.15-8.07 (m, 2H), 7.73 (s, 1H), 7.44 (d, J=8.3 Hz, 2H), 7.23 (dd, J=16.6, 8.7 Hz, 1H), 7.17-7.12 (m, 1H), 7.06-6.76 (m, 2H), 6.52 (dd, J=8.1, 2.5 Hz, 1H), 5.65 (s, 2H), 4.32 (s, 1H), 3.69 (s, 1H), 3.45 (s, 2H), 3.10 (dd, J=9.9, 2.0 Hz, 1H), 2.75 (dd, J=9.9, 1.6 Hz, 1H), 2.44 (s, 3H), 2.08 (dt, J=10.0, 1.6 Hz, 1H), 1.96 (s, 1H); LRMS (ES) m/z 464.1 ($M^+$+1).

The compounds of table 67 were synthesized according to substantially the same process as described above in the synthesis of compound 4320 with an exception of using 2-(4-((4-(3-((1S,4S)-2,5-diazabicyclo[2.2.1]heptan-2-yl)phenyl)-1H-1,2,3-triazol-1-yl)methyl)phenyl)-5-(difluoromethyl)-1,3,4-oxadiazole and the reactant of table 66.

TABLE 66

| Example | Compound No. | Reactant | Yield (%) |
|---|---|---|---|
| 223 | 4321 | Propan-2-one | 54 |
| 224 | 4322 | Cyclobutanone | 51 |

TABLE 67

| Example | Compound No | Compound Name, $^1$H-NMR, MS (ESI) |
|---|---|---|
| 223 | 4321 | 2-(difluoromethyl)-5-(4-((4-(3-((1S, 4S)-5-isopropyl-2,5-diazabicyclo[2.2.1]heptan-2-yl)phenyl)-1H-1,2,3-triazol-1-yl)methyl)phenyl)-1,3,4-oxadiazole<br>$^1$H NMR (400 MHZ, $CDCl_3$) δ 8.11-8.03 (m, 2H), 7.82 (s, 1H), 7.46-7.37 (m, 2H), 7.21 (t, J = 7.9 Hz, 1H), 7.17-7.11 (m, 1H), 7.02 (dd, J = 2.4, 1.3 Hz, 1H), 6.83 (d, J = 51.7 Hz, 1H), 6.53-6.46 (m, 1H), 5.64 (s, 2H), 4.33 (s, 1H), 4.14 (s, 1H), 3.55-3.40 (m, 3H), 2.82-2.68 (m, 2H), 2.32-2.25 (m, 1H), 2.09-2.00 (m, 1H), 1.20 (dd, J = 15.9, 6.3 Hz, 6H); LRMS (ES) m/z 492.1 ($M^+$ + 1). |
| 224 | 4322 | 2-(4-((4-(3-((1S, 4S)-5-cyclobutyl-2,5-diazabicyclo[2.2.1]heptan-2-yl)phenyl)-1H-<br>$^1$H NMR (400 MHZ, $CDCl_3$) δ 8.12-8.04 (m, 2H), 7.80 (s, 1H), 7.46-7.39 (m, 2H), 7.20 (t, J = 7.9 Hz, 1H), 7.11 (dd, J = 2.5, 1.5 Hz, 1H), 7.05-6.75 (m, 2H), 6.48 (ddd, J = 8.3, 2.6, 1.0 Hz, 1H), 5.63 (s, 2H), 4.33 (s, 1H), 3.89 (d, J = 2.1 Hz, 1H), 3.44 (d, J = 1.4 Hz, 2H), 3.24 (p, J = 7.9 Hz, 1H), 3.15 (dd, J = 10.2, 2.0 Hz, 1H), 2.77 (dd, J = 10.4, 1.8 Hz, 1H), 2.19-1.97 (m, 6H), 1.77 (tdt, J = 11.9, 9.5, 2.5 Hz, 1H), 1.64 (tt, J = 10.6, 8.3 Hz, 1H); LRMS (ES) m/z 504.4 ($M^+$ + 1). |

Example 225: Synthesis of compound 4323, 3-(1-(4-(5-(difluoromethyl)-1,3,4-oxadiazol-2-yl)benzyl)-1H-1,2,3-triazol-4-yl)-N,N-dimethylaniline

[Step 1] Synthesis of 3-(1-(4-(5-(difluoromethyl)-1,3,4-oxadiazol-2-yl)benzyl)-1H-1,2,3-triazol-4-yl) aniline

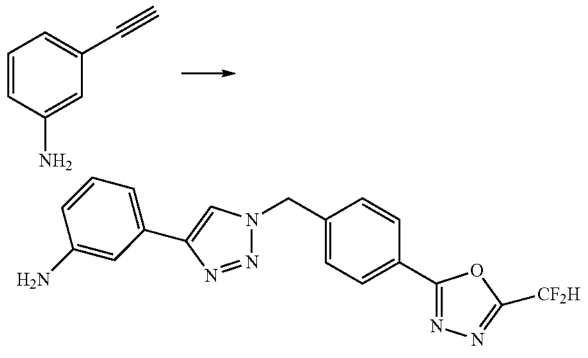

3-ethynylaniline (0.289 mL, 2.089 mmol), 2-(4-(azidomethyl)phenyl)-5-(difluoromethyl)-1,3,4-oxadiazole (0.525 g, 2.089 mmol) prepared in step 1 of example 1, sodium ascorbate (0.50 M solution in water, 0.418 mL, 0.209 mmol) and copper(II) sulfate pentahydrate (1.00 M solution in water, 0.042 mL, 0.042 mmol) were dissolved in tert-butanol (5 mL)/water (5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. A precipitated solid was filtered, washed with hexane and dried to obtain 3-(1-(4-(5-(difluoromethyl)-1,3,4-oxadiazol-2-yl)benzyl)-1H-1,2,3-triazol-4-yl)aniline (0.193 g, 25.1%) in a brown solid form.

[Step 2] Synthesis of Compound 4323

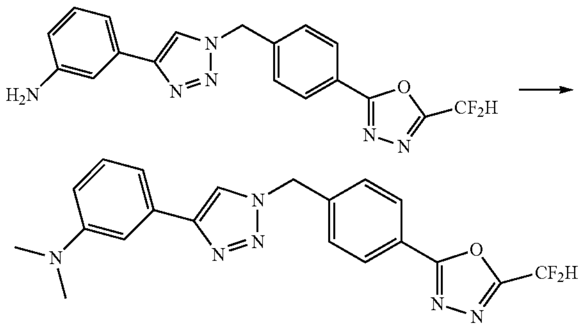

The 3-(1-(4-(5-(difluoromethyl)-1,3,4-oxadiazol-2-yl)benzyl)-1H-1,2,3-triazol-4-yl)aniline (0.040 g, 0.109 mmol) prepared in step 1 and formaldehyde (37.00% solution in water, 0.016 mL, 0.217 mmol) were dissolved in dichloromethane (1 mL), after which the resulting solution was stirred at room temperature for 15 minutes, and then sodium triacetoxyborohydride (0.069 g, 0.326 mmol) was added thereto and further stirred at the same temperature for 18 hours. 1N-sodium hydrogen carbonate aqueous solution was poured into the resulting reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 3-(1-(4-(5-(difluoromethyl)-1,3,4-oxadiazol-2-yl)benzyl)-1H-1,2,3-triazol-4-yl)-N,N-dimethylaniline(0.004 g, 9.3%) in a yellow solid form.

$^1$H NMR (400 MHz, $CD_3OD$) δ 8.40 (s, 1H), 8.18-8.14 (m, 2H), 7.61 (d, J=8.4 Hz, 2H), 7.36-7.10 (m, 4H), 6.83-6.75 (m, 1H), 5.79 (d, J=4.3 Hz, 2H), 3.00 (s, 6H); LRMS (ES) m/z 397.4 ($M^+$+1).

The compounds of table 69 were synthesized according to substantially the same process as described above in the synthesis of compound 4323 with an exception of using 3-(1-(4-(5-(difluoromethyl)-1,3,4-oxadiazol-2-yl)benzyl)-1H-1,2,3-triazol-4-yl)aniline and the reactant of table 68.

TABLE 68

| Example | Compound No. | Reactant | Yield (%) |
|---|---|---|---|
| 226 | 4324 | Cyclohexanone | 35 |
| 227 | 4325 | Tetrahydro-4H-pyran-4-one | 55 |
| 228 | 4326 | Oxetan-3-one | 61 |

TABLE 69

| Example | Compound No. | Compound Name, $^1$H-NMR, MS (ESI) |
|---|---|---|
| 226 | 4324 | N-cyclohexyl-3-(1-(4-(5-(difluoromethyl)-1,3,4-oxadiazol-2-yl)benzyl)-1H-1,2,3-triazol-4-yl)aniline<br>$^1$H NMR (400 MHZ, DMSO-$d_6$) δ 8.57 (s, 1H), 8.13-8.06 (m, 2H), 7.69-7.41 (m, 3H), 7.14-7.06 (m, 2H), 6.94 (dd, J = 7.7, 1.4 Hz, 1H), 6.58-6.50 (m, 1H), 5.78 (s, 2H), 5.51 (d, J = 8.2 Hz, 1H), 1.94 (d, J = 12.1 Hz, 2H), 1.73 (d, J = 13.4 Hz, 2H), 1.61 (d, J = 12.7 Hz, 1H), 1.33 (t, J = 12.5 Hz, 2H), 1.24-1.10 (m, 3H); LRMS (ESI) m/z 451.5 ($M^+$ + H). |
| 227 | 4325 | N-(3-(1-(4-(5-(difluoromethyl)-1,3,4-oxadiazol-2-yl)benzyl)-1H-1,2,3-triazol-4-yl)phenyl)tetrahydro-2H-pyran-4-amine<br>$^1$H NMR (400 MHZ, $CD_3OD$) δ 8.35 (s, 1H), 8.20-8.12 (m, 2H), 7.63-7.56 (m, 2H), 7.23 (t, J = 51.7 Hz, 1H), 7.21-7.15 (m, 2H), 7.05 (dt, J = 7.8, 1.2 Hz, 1H), 6.68 (ddd, J = 8.2, 2.4, 1.0 Hz, 1H), 5.78 (s, 2H), 3.99 (dt, J = 11.8, 3.6 Hz, 2H), 3.64-3.52 (m, 3H), 2.07-1.99 (m, 2H), 1.58-1.43 (m, 2H); LRMS (ESI) m/z 453.5 ($M^+$ + H). |
| 228 | 4326 | N-(3-(1-(4-(5-(difluoromethyl)-1,3,4-oxadiazol-2-yl)benzyl)-1H-1,2,3-triazol-4-yl)phenyl)oxetan-3-amine<br>$^1$H NMR (400 MHZ, $CD_3OD$) δ 8.36 (s, 1H), 8.20-8.13 (m, 2H), 7.64-7.57 (m, 2H), 7.36-7.09 (m, 3H), 7.01 (t, J = 2.0 Hz, 1H), 6.56 (ddd, J = 8.0, 2.4, 1.0 Hz, 1H), 5.79 (s, 2H), 5.03 (t, J = 6.6 Hz, 2H), 4.70 (p, J = 6.6 Hz, 1H), 4.58 (t, J = 6.1 Hz, 2H); LRMS (ESI) m/z 425.4 ($M^+$ + H). |

Example 229: Synthesis of compound 4327, N-(3-(1-(4-(5-(difluoromethyl)-1,3,4-oxadiazol-2-yl)benzyl)-1H-1,2,3-triazol-4-yl)phenyl)pivalamide

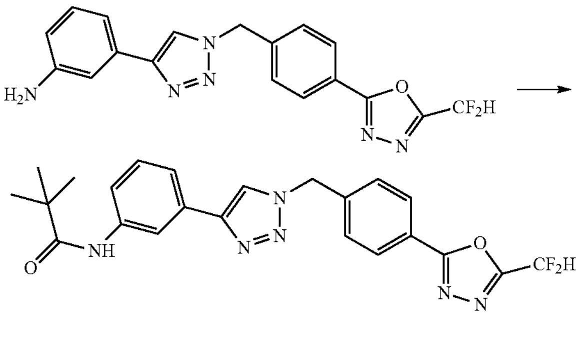

The 3-(1-(4-(5-(difluoromethyl)-1,3,4-oxadiazol-2-yl)benzyl)-1H-1,2,3-triazol-4-yl)aniline (0.040 g, 0.109 mmol) prepared in step 1 of example 225 and N,N-diisopropylethylamine (0.038 mL, 0.217 mmol) were dissolved in dichloromethane (1 mL) at room temperature, after which trimethylacetyl chloride (0.016 mL, 0.130 mmol) was added into the resulting solution and stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain N-(3-(1-(4-(5-(difluoromethyl)-1,3,4-oxadiazol-2-yl)benzyl)-1H-1,2,3-triazol-4-yl)phenyl)pivalamide (0.031 g, 63.1%) in a brown solid form.

$^1$H NMR (400 MHz, $CD_3OD$) δ 8.40 (s, 1H), 8.20-8.12 (m, 2H), 8.02 (t, J=1.9 Hz, 1H), 7.65-7.58 (m, 3H), 7.54 (ddd, J=8.1, 2.2, 1.1 Hz, 1H), 7.40 (t, J=7.9 Hz, 1H), 7.23 (t, J=51.7 Hz, 1H), 5.80 (s, 2H), 1.33 (s, 9H); LRMS (ES) m/z 453.5 ($M^+$+1).

Example 230: Synthesis of compound 4328, N-(3-(1-(4-(5-(difluoromethyl)-1,3,4-oxadiazol-2-yl)benzyl)-1H-1,2,3-triazol-4-yl)phenyl)-2-fluoro-2-methylpropanamide

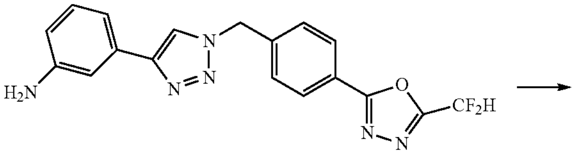

-continued

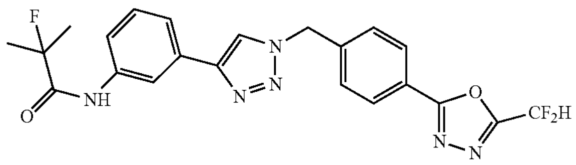

The 3-(1-(4-(5-(difluoromethyl)-1,3,4-oxadiazol-2-yl)benzyl)-1H-1,2,3-triazol-4-yl)aniline (0.040 g, 0.109 mmol) prepared in step 1 of example 225, 2-fluoro-2-methylpropanoic acid (0.014 g, 0.130 mmol), 1-[bis(dimethylamino)methylene]-1H-1,2,3-triazolo[4,5-b]pyridinium 3-oxide hexafluorophosphate (0.124 g, 0.326 mmol) and N,N-diisopropylethylamine (0.038 mL, 0.217 mmol) were dissolved in N,N-dimethylformamide (1 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain N-(3-(1-(4-(5-(difluoromethyl)-1,3,4-oxadiazol-2-yl)benzyl)-1H-1,2,3-triazol-4-yl)phenyl)-2-fluoro-2-methylpropanamide (0.022 g, 44.4%) in a brown solid form.

$^1$H NMR (400 MHz, $CD_3OD$) δ 8.42 (s, 1H), 8.20-8.13 (m, 2H), 8.08 (t, J=1.9 Hz, 1H), 7.63 (dddd, J=7.9, 6.5, 2.4, 1.2 Hz, 4H), 7.43 (t, J=8.0 Hz, 1H), 7.23 (t, J=51.7 Hz, 1H), 5.80 (s, 2H), 1.65 (d, J=21.7 Hz, 6H); LRMS (ES) m/z 457.4 ($M^+$+1).

The compounds of table 71 were synthesized according to substantially the same process as described above in the synthesis of compound 4328 with an exception of using 3-(1-(4-(5-(difluoromethyl)-1,3,4-oxadiazol-2-yl)benzyl)-1H-1,2,3-triazol-4-yl)aniline and the reactant of table 70.

TABLE 70

| Example | Compound No. | Reactant | Yield (%) |
|---|---|---|---|
| 231 | 4329 | Dimethylglycine | 24 |
| 253 | 4351 | 2-(dimethylamino)-2-methylpropanoic acid | 4 |

TABLE 71

| Example | Compound No. | Compound Name, $^1$H-NMR, MS (ESI) |
|---|---|---|
| 231 | 4329 | N-(3-(1-(4-(5-(difluoromethyl)-1,3,4-oxadiazol-2-yl)benzyl)-1H-1,2,3-triazol-4-yl)phenyl)-2-(dimethylamino)acetamide<br>1H NMR (400 MHZ, $CD_3OD$) δ 8.42 (s, 1H), 8.20-8.12 (m, 2H), 8.09 (t, J = 1.9 Hz, 1H), 7.65-7.56 (m, 4H), 7.42 (t, J = 7.9 Hz, 1H), 7.23 (t, J = 51.6 Hz, 1H), 5.80 (s, 2H), 3.20 (s, 2H), 2.42 (s, 6H); LRMS (ESI) m/z 454.4 ($M^+$ + H). |
| 253 | 4351 | N-(3-(1-(4-(5-(difluoromethyl)-1,3,4-oxadiazol-2-yl)benzyl)-1H-1,2,3-triazol-4-yl)phenyl)-2-(dimethylamino)-2-methylpropanamide<br>$^1$H NMR (400 MHZ, $CD_3OD$) δ 8.42 (s, 1H), 8.20-8.13 (m, 2H), 8.05 (t, J = 1.9 Hz, 1H), 7.65-7.55 (m, 4H), 7.41 (t, J = 7.9 Hz, 1H), 7.23 (t, J = 51.7 Hz, 1H), 5.80 (s, 2H), 2.32 (s, 6H), 1.29 (s, 6H); LRMS (ESI) m/z 482.5 ($M^+$ + H). |

Example 236: Synthesis of compound 4334, N-(4-(1-(4-(5-(difluoromethyl)-1,3,4-oxadiazol-2-yl)-2-fluorobenzyl)-1H-1,2,3-triazol-4-yl)phenyl)-2-fluoro-2-methylpropanamide

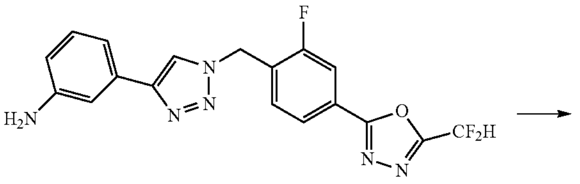

-continued

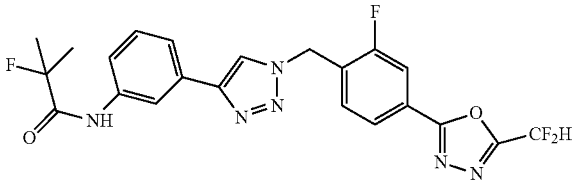

The 3-(1-(4-(5-(difluoromethyl)-1,3,4-oxadiazol-2-yl)-2-fluorobenzyl)-1H-1,2,3-triazol-4-yl)aniline (0.080 g, 0.207 mmol) prepared in step 1 of example 232, 2-fluoro-2-methylpropanoic acid (0.026 g, 0.248 mmol), 1-[bis(dimethylamino)methylene]-1H-1,2,3-triazolo[4,5-b]pyridinium 3-oxide hexafluorophosphate (0.236 g, 0.621 mmol) and N,N-diisopropylethylamine (0.072 mL, 0.414 mmol) were dissolved in N,N-dimethylformamide (1 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain N-(4-(1-(4-(5-(difluoromethyl)-1,3,4-oxadiazol-2-yl)-2-fluorobenzyl)-1H-1,2,3-triazol-4-yl)phenyl)-2-fluoro-2-methylpropanamide (0.038 g, 38.7%) in a white solid form.

$^1$H NMR (400 MHz, $CD_3OD$) δ 8.43 (s, 1H), 8.09 (t, J=1.9 Hz, 1H), 8.03-7.92 (m, 2H), 7.68-7.57 (m, 3H), 7.43 (t, J=7.9 Hz, 1H), 7.24 (t, J=51.6 Hz, 1H), 5.86 (s, 2H), 1.68 (s, 3H), 1.63 (s, 3H); LRMS (ES) m/z 475.4 ($M^+$+1).

The compound of table 73 was synthesized according to substantially the same process as described above in the synthesis of compound 4334 with an exception of using 3-(1-(4-(5-(difluoromethyl)-1,3,4-oxadiazol-2-yl)-2-fluorobenzyl)-1H-1,2,3-triazol-4-yl)aniline and the reactant of table 72.

TABLE 72

| Example | Compound No. | Reactant | Yield (%) |
|---|---|---|---|
| 237 | 4335 | 3-(dimethylamino)propanoic acid | 49 |

TABLE 73

| Example | Compound No. | Compound Name, $^1$H-NMR, MS (ESI) |
|---|---|---|
| 237 | 4335 | N-(3-(1-(4-(5-(difluoromethyl)-1,3,4-oxadiazol-2-yl)-2-fluorobenzyl)-1H-1,2,3-triazol-4-yl)phenyl)-3-(dimethylamino)propanamide<br>$^1$H NMR (400 MHZ, $CD_3OD$) δ 8.40 (d, J = 15.5 Hz, 1H), 8.16 (t, J = 1.9 Hz, 1H), 8.03-7.92 (m, 2H), 7.65-7.51 (m, 3H), 7.44-7.11 (m, 2H), 5.85 (d, J = 7.7 Hz, 2H), 3.51 (t, J = 6.2 Hz, 2H), 3.04-2.86 (m, 8H); LRMS (ESI) m/z 486.5 ($M^+$ + H). |

Example 251: Synthesis of compound 4349, 2-(difluoromethyl)-5-(3-fluoro-4-((4-(3-(1-(2-fluoro-2-methylpropyl)piperidin-4-yl)phenyl)-1H-1,2,3-triazol-1-yl)methyl)phenyl)-1,3,4-oxadiazole

[Step 1] Synthesis of methyl 3-fluoro-4-((4-(3-(piperidin-4-yl)phenyl)-1H-1,2,3-triazol-1-yl)methyl) benzoate hydrochloride

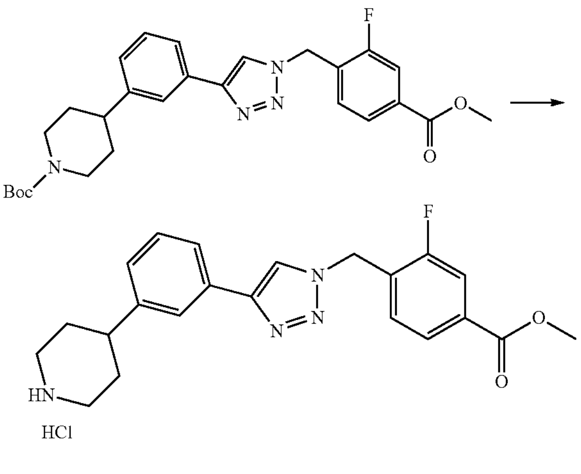

The tert-butyl 4-(3-(1-(2-fluoro-4-(methoxycarbonyl)benzyl)-1H-1,2,3-triazol-4-yl)phenyl)piperidin-1-carboxylate (0.500 g, 0.841 mmol) prepared in step 4 of example 211 and hydrogen chloride (4.00 M solution in 1,4-dioxane, 0.841 mL, 3.364 mmol) were dissolved in dichloromethane (50 mL) at room temperature, after which the resulting solution was stirred at the same temperature for 12 hours. Solvent was removed from the reaction mixture under reduced pressure, after which the obtained product was used without an additional purification process (methyl 3-fluoro- 4-((4-(3-(piperidin-4-yl)phenyl)-1H-1,2,3-triazol-1-yl) methyl)benzoate hydrochloride, 0.420 g, 94.1%, white solid).

[Step 2] Synthesis of methyl 3-fluoro-4-((4-(3-(1-(2-hydroxy-2-methylpropyl)piperidin-4-yl)phenyl)-1H-1,2,3-triazol-1-yl)methyl)benzoate

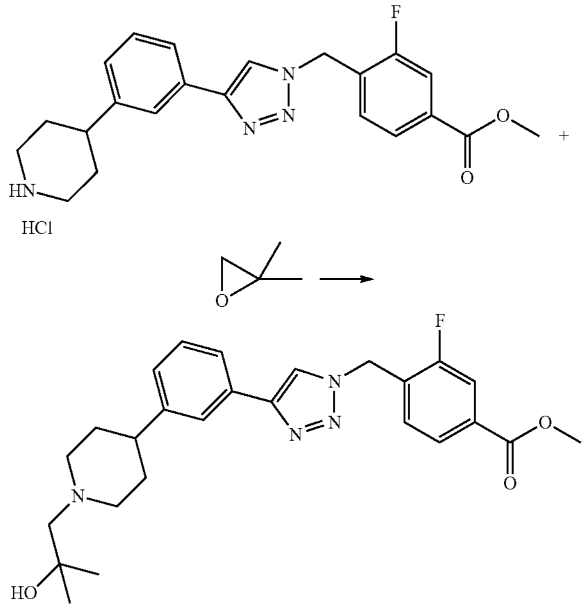

The methyl 3-fluoro-4-((4-(3-(piperidin-4-yl)phenyl)-1H-1,2,3-triazol-1-yl)methyl)benzoate hydrochloride (0.200 g, 0.464 mmol) prepared in step 1, 2,2-dimethyloxylane (0.335 g, 4.641 mmol) and potassium carbonate (0.128 g, 0.928 mmol) were mixed in ethanol (10 mL), heated at 110 °C for 20 hours by irradiation with microwaves, and a reaction was finished by lowering a temperature to room temperature. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. Then, the obtained product was used without an additional purification process (methyl 3-fluoro-4-((4-(3-(1-(2-hydroxy-2-methylpropyl) piperidin-4-yl)phenyl)-1H-1,2,3-triazol-1-yl)methyl)benzoate, 0.100 g, 46.2%, yellow oil).

[Step 3] Synthesis of methyl 3-fluoro-4-((4-(3-(1-(2-fluoro-2-methylpropyl)piperidin-4-yl)phenyl)-1H-1,2,3-triazol-1-yl)methyl)benzoate

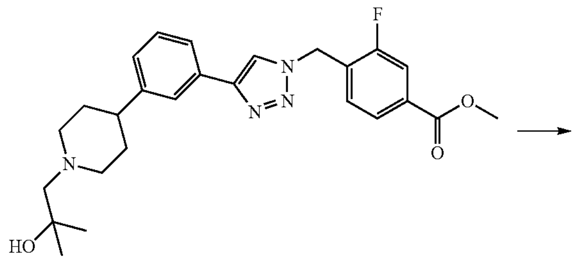

-continued

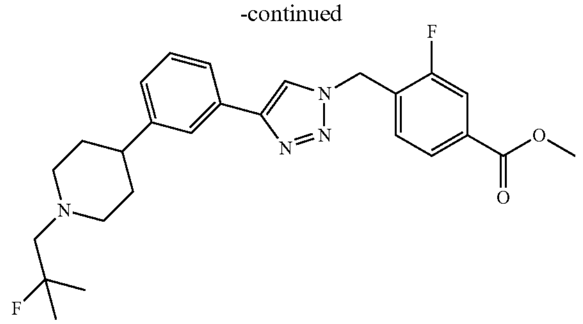

The methyl 3-fluoro-4-((4-(3-(1-(2-hydroxy-2-methylpropyl)piperidin-4-yl)phenyl)-1H-1,2,3-triazol-1-yl) methyl)benzoate (0.100 g, 0.214 mmol) prepared in step 2 and diethylaminosulfur trifluoride (0.031 mL, 0.236 mmol) were dissolved in dichloromethane (20 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain methyl 3-fluoro-4-((4-(3-(1-(2-fluoro-2-methylpropyl)piperidin-4-yl)phenyl)-1H-1,2,3-triazol-1-yl) methyl)benzoate (0.090 g, 89.6%) in a white solid form.

[Step 4] Synthesis of 3-fluoro-4-((4-(3-(1-(2-fluoro-2-methylpropyl)piperidin-4-yl)phenyl)-1H-1,2,3-triazol-1-yl)methyl)benzohydrazide

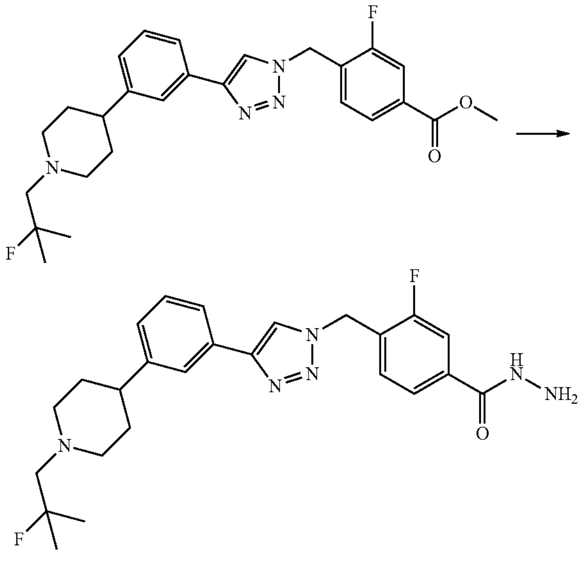

The methyl 3-fluoro-4-((4-(3-(1-(2-fluoro-2-methylpropyl)piperidin-4-yl)phenyl)-1H-1,2,3-triazol-1-yl)methyl) benzoate (0.090 g, 0.192 mmol) prepared in step 3 and hydrazine monohydrate (0.093 mL, 1.921 mmol) were dissolved in ethanol (10 mL) at 90 °C, after which the resulting solution was stirred at the same temperature for 12 hours, and then a reaction was finished by lowering a temperature to room temperature. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (3-fluoro-4-((4-(3-(1-(2-fluoro-2-methylpropyl)piperidin-4-yl)phenyl)-1H-1,2,3-triazol-1-yl)methyl)benzohydrazide, 0.081 g, 90.0%, white solid).

[Step 5] Synthesis of Compound 4349

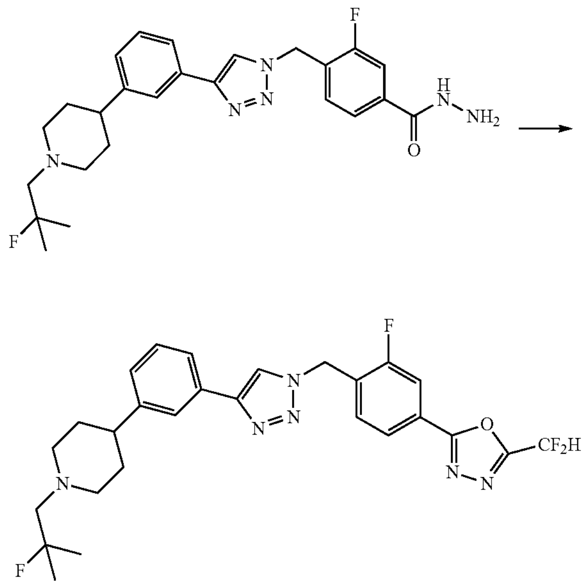

The 3-fluoro-4-((4-(3-(1-(2-fluoro-2-methylpropyl)piperidin-4-yl)phenyl)-1H-1,2,3-triazol-1-yl)methyl)benzohydrazide (0.081 g, 0.173 mmol) prepared in step 4, imidazole (0.035 g, 0.519 mmol) and 2,2-difluoroacetic anhydride (0.064 mL, 0.519 mmol) were mixed in dichloromethane (20 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 70%) and concentrated to obtain 2-(difluoromethyl)-5-(3-fluoro-4-((4-(3-(1-(2-fluoro-2-methylpropyl)piperidin-4-yl)phenyl)-1H-1,2,3-triazol-1-yl)methyl)phenyl)-1,3,4-oxadiazole (0.055 g, 60.2%) in a white solid form.

$^1$H NMR (400 MHz, $CDCl_3$) δ 7.94 (d, J=8.7 Hz, 2H), 7.85 (s, 1H), 7.76 (s, 1H), 7.66 (dd, J=4.8, 2.7 Hz, 1H), 7.47 (ddd, J=17.0, 8.1, 2.0 Hz, 1H), 7.37 (t, J=7.7 Hz, 1H), 7.24 (d, J=7.8 Hz, 1H), 7.07 (s, 0.2H), 6.94 (s, 0.5H), 6.81 (s, 0.3H), 5.75 (s, 2H), 3.11 (s, 2H), 2.56 (s, 3H), 2.33-2.30 (m, 2H), 1.84 (d, J=10.3 Hz, 4H), 1.69 (s, 3H), 1.64 (s, 3H); LRMS (ES) m/z 529.6 ($M^+$+1).

Example 252: Synthesis of compound 4350, 2-(difluoromethyl)-5-(4-((4-(3-(1-(2-ethyl-2-fluorobutyl)piperidin-4-yl)phenyl)-1H-1,2,3-triazol-1-yl)methyl)-3-fluorophenyl)-1,3,4-oxadiazole

[Step 1] Synthesis of methyl 4-((4-(3-(1-(2-ethyl-2-hydroxybutyl)piperidin-4-yl)phenyl)-1H-1,2,3-triazol-1-yl)methyl)-3-fluorobenzoate

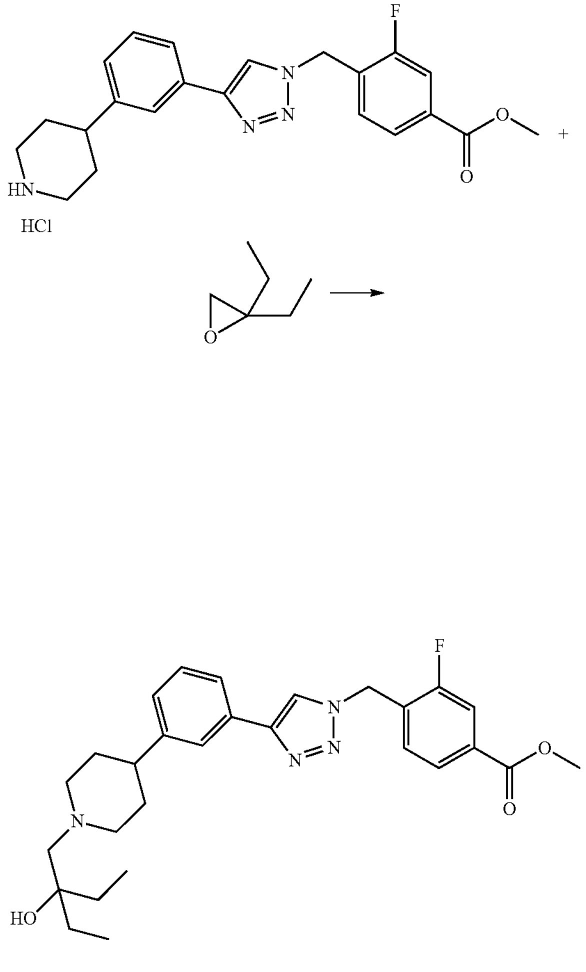

The methyl 3-fluoro-4-((4-(3-(piperidin-4-yl)phenyl)-1H-1,2,3-triazol-1-yl)methyl)benzoate hydrochloride (0.200 g, 0.464 mmol) prepared in step 1 of example 251, 2,2-diethyloxylane (0.465 g, 4.641 mmol) and potassium carbonate (0.128 g, 0.928 mmol) were mixed in ethanol (10 mL), heated at 110 °C for 20 hours by irradiation with microwaves, and a reaction was finished by lowering a temperature to room temperature. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. Then, the obtained product was used without an additional purification process (methyl 4-((4-(3-(1-(2-ethyl-2-hydroxybutyl)piperidin-4-yl)phenyl)-1H-1,2,3-triazol-1-yl)methyl)-3-fluorobenzoate, 0.110 g, 47.9%, yellow oil).

[Step 2] Synthesis of methyl 4-((4-(3-(1-(2-ethyl-2-fluorobutyl)piperidin-4-yl)phenyl)-1H-1,2,3-triazol-1-yl)methyl)-3-fluorobenzoate

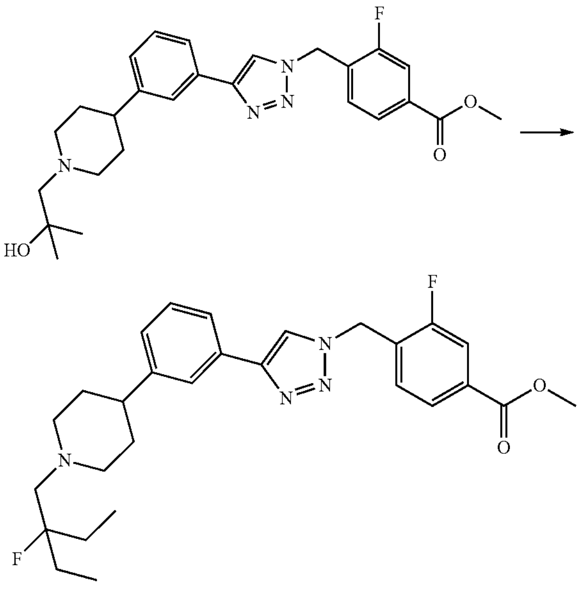

The methyl 4-((4-(3-(1-(2-ethyl-2-hydroxybutyl)piperidin-4-yl)phenyl)-1H-1,2,3-triazol-1-yl)methyl)-3-fluorobenzoate (0.110 g, 0.222 mmol) prepared in step 1 and diethylaminosulfur trifluoride (0.032 mL, 0.245 mmol) were dissolved in dichloromethane (20 mL) at room temperature, after which the resulting solution was stirred at the same temperature for 1 hour. Water was poured into the reaction mixture and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain methyl 4-((4-(3-(1-(2-ethyl-2-fluorobutyl)piperidin-4-yl)phenyl)-1H-1,2,3-triazol-1-yl)methyl)-3-fluorobenzoate (0.080 g, 72.4%) in a white solid form.

[Step 3] Synthesis of 4-((4-(3-(1-(2-ethyl-2-fluorobutyl)piperidin-4-yl)phenyl)-1H-1,2,3-triazol-1-yl)methyl)-3-fluorobenzohydrazide

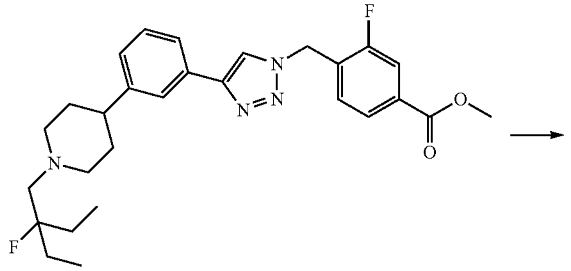

-continued

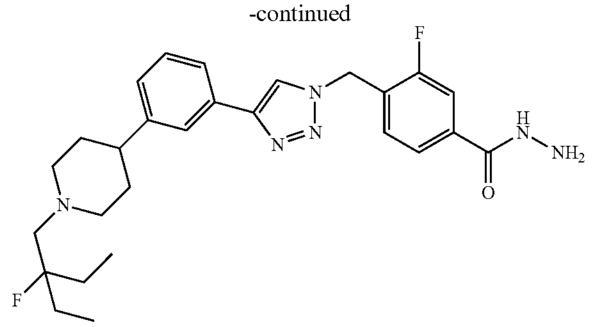

The methyl 4-((4-(3-(1-(2-ethyl-2-fluorobutyl)piperidin-4-yl)phenyl)-1H-1,2,3-triazol-1-yl)methyl)-3-fluorobenzoate (0.080 g, 0.161 mmol) prepared in step 2 and hydrazine monohydrate (0.078 mL, 1.611 mmol) were dissolved in ethanol (10 mL) at 90 °C, after which the resulting solution was stirred at the same temperature for 12 hours, and then a reaction was finished by lowering a temperature to room temperature. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (4-((4-(3-(1-(2-ethyl-2-fluorobutyl)piperidin-4-yl)phenyl)-1H-1,2,3-triazol-1-yl)methyl)-3-fluorobenzohydrazide, 0.070 g, 87.5%, white solid).

[Step 4] Synthesis of Compound 4350

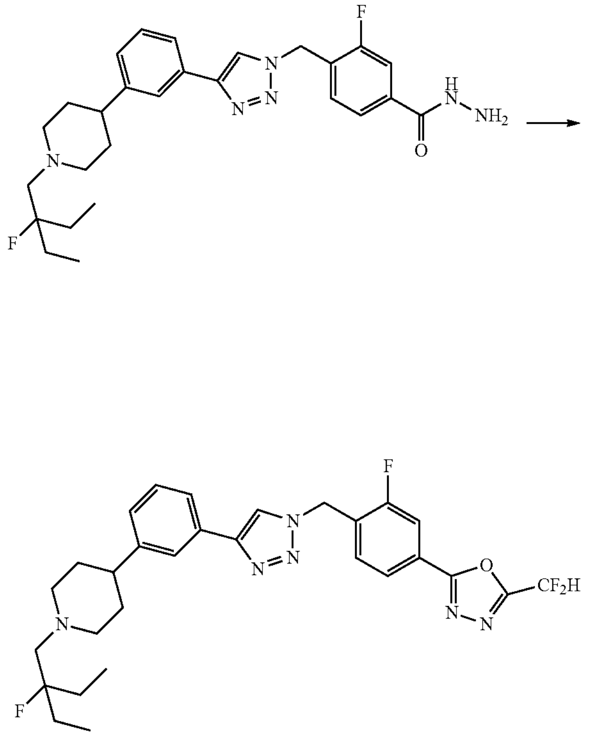

The 4-((4-(3-(1-(2-ethyl-2-fluorobutyl)piperidin-4-yl)phenyl)-1H-1,2,3-triazol-1-yl)methyl)-3-fluorobenzohydrazide (0.081 g, 0.163 mmol) prepared in step 3, imidazole (0.033 g, 0.489 mmol) and 2,2-difluoroacetic anhydride (0.061 mL, 0.489 mmol) were mixed in dichloromethane (20 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 70%) and concentrated to obtain 2-(difluoromethyl)-5-(4-((4-(3-(1-(2-ethyl-2-fluorobutyl)piperidin-4-yl)phenyl)-1H-1,2,3-triazol-1-yl)methyl)-3-fluorophenyl)-1,3,4-oxadiazole(0.060 g, 66.1%) in a white solid form.

$^1H$ NMR (400 MHz, $CDCl_3$) δ 7.94 (d, J=8.6 Hz, 2H), 7.85 (s, 1H), 7.76 (s, 1H), 7.66 (d, J=6.8 Hz, 1H), 7.46 (t, J=7.6 Hz, 1H), 7.37 (t, J=7.7 Hz, 1H), 7.24 (d, J=7.7 Hz, 1H), 7.07 (s, 0.2H), 6.94 (s, 0.5H), 6.81 (s, 0.3H), 5.75 (s, 2H), 3.08 (s, 1H), 2.50 (d, J=24.2 Hz, 2H), 2.23 (s, 1H), 1.80 (d, J=32.7 Hz, 6H), 1.60 (s, 3H), 1.28 (t, J=7.1 Hz, 2H), 0.94 (t, J=7.3 Hz, 6H); LRMS (ES) m/z 557.6 ($M^+$+1).

Example 254: Synthesis of compound 4352, N-(3-(1-(4-(5-(difluoromethyl)-1,3,4-oxadiazol-2-yl)-2-fluorobenzyl)-1H-1,2,3-triazol-4-yl)phenyl)-2-(dimethylamino)acetamide

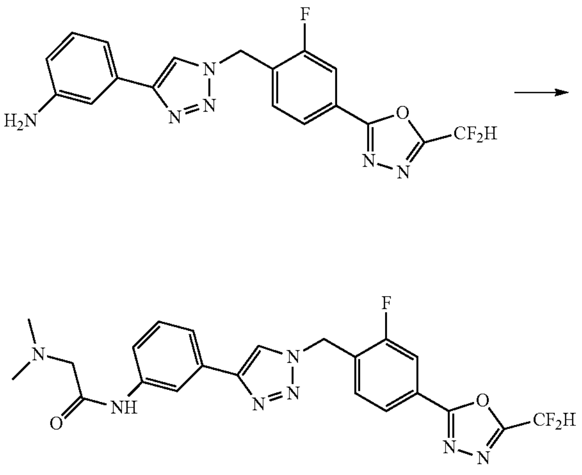

The 3-(1-(4-(5-(difluoromethyl)-1,3,4-oxadiazol-2-yl)-2-fluorobenzyl)-1H-1,2,3-triazol-4-yl)aniline (0.080 g, 0.207 mmol) prepared in step 1 of example 232, dimethylglycine (0.026 g, 0.248 mmol), 1-[bis(dimethylamino)methylene]-1H-1,2,3-triazolo[4,5-b]pyridinium 3-oxide hexafluorophosphate (0.236 g, 0.621 mmol) and N,N-diisopropylethylamine (0.072 mL, 0.414 mmol) were dissolved in N,N-dimethylformamide (1 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain N-(3-(1-(4-(5-(difluoromethyl)-1,3,4-oxadiazol-2-yl)-2-fluorobenzyl)-1H-1,2,3-triazol-4-yl)phenyl)-2-(dimethylamino)acetamide (0.015 g, 15.4%) in a yellow solid form.

$^1H$ NMR (400 MHz, $CD_3OD$) δ 8.43 (s, 1H), 8.09 (t, J=1.9 Hz, 1H), 8.02-7.92 (m, 2H), 7.61 (dddd, J=8.3, 4.5, 2.4, 1.1 Hz, 3H), 7.42 (t, J=7.9 Hz, 1H), 7.24 (t, J=51.6 Hz, 1H), 5.86 (s, 2H), 3.25 (s, 2H), 2.45 (s, 6H); LRMS (ES) m/z 472.5 ($M^+$+1).

The compound of table 75 was synthesized according to substantially the same process as described above in the synthesis of compound 4352 with an exception of using 3-(1-(4-(5-(difluoromethyl)-1,3,4-oxadiazol-2-yl)-2-fluorobenzyl)-1H-1,2,3-triazol-4-yl)aniline and the reactant of table 74.

TABLE 74

| Example | Compound No. | Reactant | Yield (%) |
|---|---|---|---|
| 255 | 4353 | 2-(dimethylamino)-2-methylpropanoic acid | 5 |

TABLE 75

| Example | Compound No. | Compound Name, $^1H$-NMR, MS (ESI) |
|---|---|---|
| 255 | 4353 | N-(4-(1-(4-(5-(difluoromethyl)-1,3,4-oxadiazol-2-yl)-2-fluorobenzyl)-1H-1,2,3-triazol-4-yl)phenyl)-2-(dimethylamino)-2-methylpropanamide<br>$^1H$ NMR (400 MHZ, $CD_3OD$) δ 8.42 (s, 1H), 8.05 (t, J = 1.9 Hz, 1H), 8.02 – 7.92 (m, 2H), 7.65 – 7.55 (m, 3H), 7.41 (t, J = 7.9 Hz, 1H), 7.24 (t, J = 51.6 Hz, 1H), 5.85 (s, 2H), 2.32 (s, 6H), 1.29 (s,6H); LRMS (ESI) m/z 500.5 ($M^+$ + H). |

Example 256: Synthesis of compound 4358, 2-(difluoromethyl)-5-(3-fluoro-4-((4-(2-methyl-1,2,3,4-tetrahydroisoquinolin-6-yl)-1H-1,2,3-triazol-1-yl)methyl)phenyl)-1,3,4-oxadiazole

[Step 1] Synthesis of tert-butyl 6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate

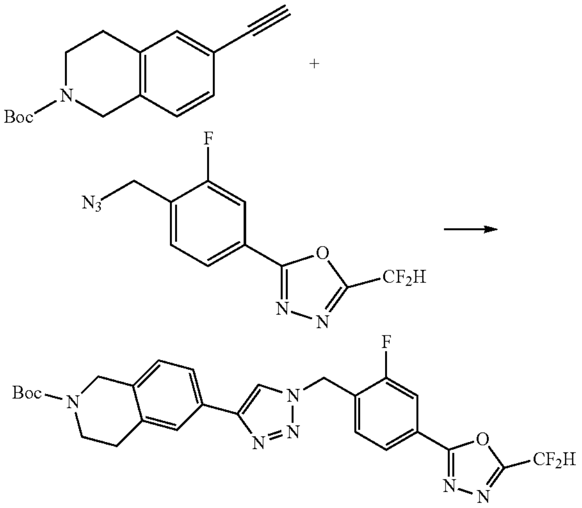

The 2-(4-(azidomethyl)-3-fluorophenyl)-5-(difluoromethyl)-1,3,4-oxadiazole (0.300 g, 1.114 mmol) prepared in step 1 of example 2, tert-butyl 6-ethynyl-3,4-dihydroisoquinolin-2(1H)-carboxylate (0.344 g, 1.337 mmol) prepared in step 1 of example 150, sodium ascorbate (1.00 M solution in $H_2O$, 0.111 mL, 0.111 mmol), and copper(II) sulfate pentahydrate (0.50 M solution in $H_2O$, 0.022 mL, 0.011 mmol) were dissolved in tert-butanol (10 mL)/water (10 mL) at room temperature, after which the resulting solution was stirred at the same temperature for 12 hours. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 70%) and concentrated to obtain tert-butyl 6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate (0.450 g, 76.7%) in a white solid form.

[Step 2] Synthesis of 2-(difluoromethyl)-5-(3-fluoro-4-((4-(1,2,3,4-tetrahydroisoquinolin-6-yl)-1H-1,2,3-triazol-1-yl)methyl)phenyl)-1,3,4-oxadiazole

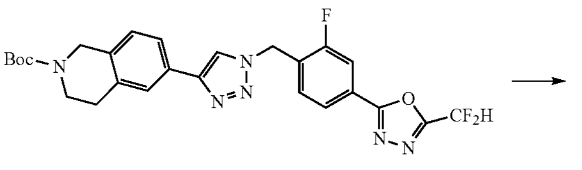

-continued

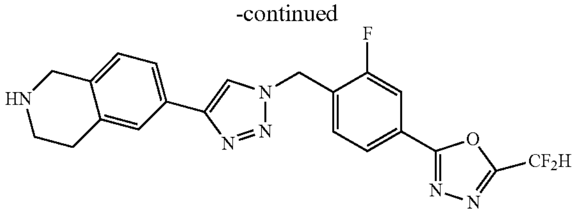

The tert-butyl 6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate (0.450 g, 0.855 mmol) prepared in step 1 and trifluoroacetic acid (0.196 mL, 2.564 mmol) were dissolved in dichloromethane (50 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(3-fluoro-4-((4-(1,2,3,4-tetrahydroisoquinolin-6-yl)-1H-1,2,3-triazol-1-yl)methyl)phenyl)-1,3,4-oxadiazole, 0.350 g, 96.0%, yellow oil).

[Step 3] Synthesis of Compound 4358

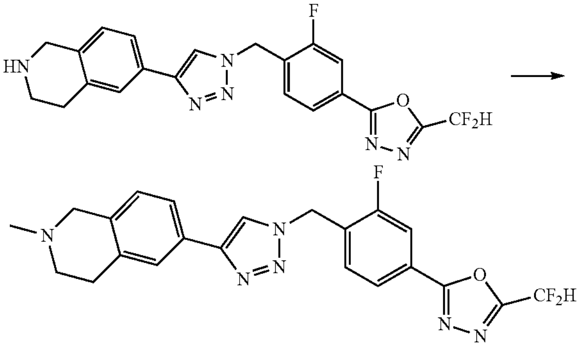

The 2-(difluoromethyl)-5-(3-fluoro-4-((4-(1,2,3,4-tetrahydroisoquinolin-6-yl)-1H-1,2,3-triazol-1-yl)methyl)phenyl)-1,3,4-oxadiazole (0.070 g, 0.164 mmol) prepared in step 2, formaldehyde (0.010 g, 0.328 mmol), acetic acid (0.010 mL, 0.181 mmol) and sodium triacetoxyborohydride (0.070 g, 0.328 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(3-fluoro-4-((4-(2-methyl-1,2,3,4-tetrahydroisoquinolin-6-yl)-1H-1,2,3-triazol-1-yl)methyl)phenyl)-1,3,4-oxadiazole (0.033 g, 45.6%) in a white solid form.

$^1$H NMR (400 MHz, $CDCl_3$) δ 7.92 (dd, J=6.2, 4.7 Hz, 2H), 7.81 (s, 1H), 7.63 (s, 1H), 7.56 (dd, J=7.9, 1.7 Hz, 1H), 7.46 (t, J=7.7 Hz, 1H), 7.09 (d, J=8.0 Hz, 1H), 7.07 (s, 0.2H), 6.94 (s, 0.5H), 6.81 (s, 0.3H), 5.73 (s, 2H), 3.65 (s, 2H), 3.00 (t, J=5.9 Hz, 2H), 2.76 (t, J=6.0 Hz, 2H), 2.51 (s, 3H); LRMS (ES) m/z 441.5 ($M^+$+1).

The compounds of table 77 were synthesized according to substantially the same process as described above in the synthesis of compound 4358 with an exception of using 2-(difluoromethyl)-5-(3-fluoro-4-((4-(1,2,3,4-tetrahydroisoquinolin-6-yl)-1H-1,2,3-triazol-1-yl)methyl)phenyl)-1,3,4-oxadiazole and the reactant of table 76.

TABLE 76

| Example | Compound No. | Reactant | Yield (%) |
|---|---|---|---|
| 257 | 4359 | Acetaldehyde | 38 |
| 258 | 4360 | Propan-2-one | 50 |
| 259 | 4361 | Cyclobutanone | 49 |
| 260 | 4362 | Oxetan-3-one | 51 |

TABLE 77

| Example | Compound No. | Compound Name, $^1$H-NMR, MS (ESI) |
|---|---|---|
| 257 | 4359 | 2-(difluoromethyl)-5-(4-((4-(2-ethyl-1,2,3,4-tetrahydroisoquinolin-6-yl)-1H-1,2,3-triazol-1-yl)methyl)-3-fluorophenyl)-1,3,4-oxadiazole<br>$^1$H NMR (400 MHZ, $CDCl_3$) δ 7.93 (dd, J = 6.4, 4.6 Hz, 2H), 7.81 (s, 1H), 7.63 (s, 1H), 7.57 (dt, J = 9.4, 4.7 Hz, 1H), 7.47 (t, J = 7.7 Hz, 1H), 7.11 (d, J = 8.0 Hz, 1H), 7.07 (s, 0.2H), 6.94 (s, 0.5H), 6.81 (s, 0.3H), 5.73 (s, 2H), 3.74 (s, 2H), 3.07-2.94 (m, 2H), 2.85 (t, J = 5.9 Hz, 2H), 2.69 (q, J = 7.2 Hz, 2H), 1.30-1.22 (m, 3H); LRMS (ES) m/z 455.5 ($M^+$ + 1). |
| 258 | 4360 | 2-(difluoromethyl)-5-(3-fluoro-4-((4-(2-isopropyl-1,2,3,4-tetrahydroisoquinolin-6-yl)-1H-1,2,3-triazol-1-yl)methyl)phenyl)-1,3,4-oxadiazole<br>$^1$H NMR (400 MHZ, $CDCl_3$) δ 7.93 (dd, J = 6.3, 4.7 Hz, 2H), 7.81 (s, 1H), 7.62 (s, 1H), 7.57 (dd, J = 7.9, 1.6 Hz, 1H), 7.47 (t, J = 7.7 Hz, 1H), 7.11 (d, J = 8.0 Hz, 1H), 7.07 (s, 0.2H), 6.94 (s, 0.5H), 6.81 (s, 0.3H), 5.73 (s, 2H), 3.80 (s, 2H), 3.00 (dd, J = 12.6, 6.4 Hz, 3H), 2.91-2.79 (m, 2H), 1.20 (d, J = 6.5 Hz, 6H); LRMS (ES) m/z 469.3 ($M^+$ + 1). |
| 259 | 4361 | 2-(4-((4-(2-cyclobutyl-1,2,3,4-tetrahydroisoquinolin-6-yl)-1H-1,2,3-triazol-1-yl)methyl)-3-fluorophenyl)-5-(difluoromethyl)-1,3,4-oxadiazole<br>$^1$H NMR (400 MHZ, $CDCl_3$) δ 7.92 (dd, J = 6.5, 4.6 Hz, 2H), 7.80 (s, 1H), 7.62 (s, 1H), 7.56 (dd, J = 7.9, 1.7 Hz, 1H), 7.47 (t, J = 7.7 Hz, 1H), 7.09 (d, J = 8.0 Hz, 1H), 7.07 (s, 0.2H), 6.94 (s, 0.5H), 6.81 (s, 0.3H), 5.73 (s, 2H), 3.56 (s, 2H), 3.01-2.88 (m, 3H), 2.66 (t, J = 6.0 Hz, 2H), 2.23-2.11 (m, 2H), 2.10-1.97 (m, 2H), 1.87-1.66 (m, 2H); LRMS (ES) m/z 481.6 ($M^+$ + 1). |
| 260 | 4362 | 2-(difluoromethyl)-5-(3-fluoro-4-((4-(2-(oxetan-3-yl)-1,2,3,4-tetrahydroisoquinolin-6-yl)-1H-1,2,3-triazol-1-yl)methyl)phenyl)-1,3,4-oxadiazole<br>$^1$H NMR (400 MHZ, $CDCl_3$) δ 7.98-7.90 (m, 2H), 7.82 (s, 1H), 7.65 (s, 1H), 7.58 (d, J = 7.9 Hz, 1H), 7.51-7.45 (m, 1H), 7.09 (d, J = 8.0 Hz,1H), 7.07 (s, 0.2H), 6.94 (s, 0.5H), 6.81 (s, 0.3H), 5.75 (s, 2H), 4.78 (d, J = 6.5 Hz, 4H), 3.80-3.70 (m, 1H), 3.59 (s, 2H), 3.01 (t, J = 5.6 Hz, 2H), 2.69 (s, 2H); LRMS (ES) m/z 483.15 ($M^+$ + 1). |

Example 261: Synthesis of compound 4363, 2-(difluoromethyl)-5-(3-fluoro-4-((4-(2-methyl-1,2,3,4-tetrahydroisoquinolin-7-yl)-1H-1,2,3-triazol-1-yl)methyl)phenyl)-1,3,4-oxadiazole

[Step 1] Synthesis of tert-butyl 7-ethynyl-3,4-dihydroisoquinolin-2(1H)-carboxylate

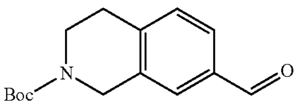

+

-continued

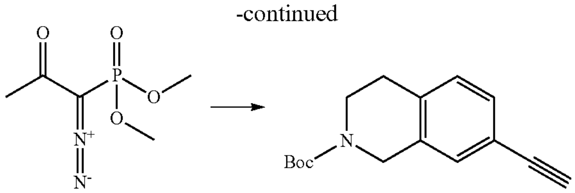

Tert-butyl 7-formyl-3,4-dihydroisoquinolin-2(1H)-carboxylate (0.500 g, 1.913 mmol), dimethyl (1-diazo-2-oxopropyl)phosphonate (0.441 g, 2.296 mmol) and potassium carbonate (0.529 g, 3.827 mmol) were dissolved in methanol (20 mL) at room temperature, after which the resulting solution was stirred at the same temperature for 12 hours. Water was poured into the reaction mixture and an extraction was performed with dichloromethane. An organic layer was washed with saturated ammonium chloride aqueous solution, dehydrated with anhydrous sodium sulfate, filtered, and concentrated under reduced pressure. Then, the obtained product was used without an additional purification process (tert-butyl 7-ethynyl-3,4-dihydroisoquinolin-2(1H)-carboxylate, 0.450 g, 91.4%, white solid).

[Step 2] Synthesis of tert-butyl 7-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate

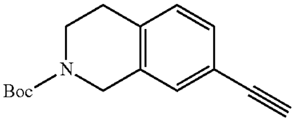

+

-continued

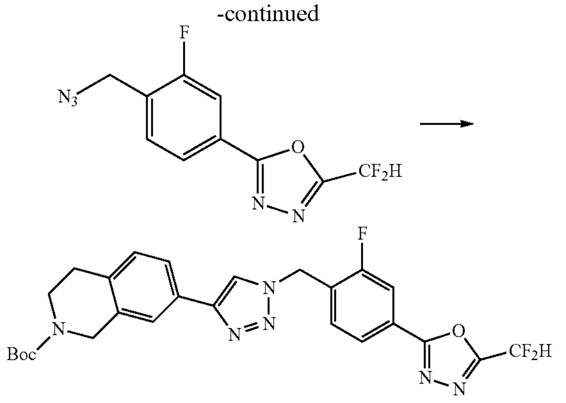

The 2-(4-(azidomethyl)-3-fluorophenyl)-5-(difluoromethyl)-1,3,4-oxadiazole (0.500 g, 1.857 mmol) prepared in step 1 of example 2, tert-butyl 7-ethynyl-3,4-dihydroisoquinolin-2(1H)-carboxylate (0.574 g, 2.229 mmol) prepared in step 1, sodium ascorbate (1.00 M solution in $H_2O$, 0.186 mL, 0.186 mmol), and copper(II) sulfate pentahydrate (0.50 M solution in $H_2O$, 0.037 mL, 0.019 mmol) were dissolved in tert-butanol (10 mL)/water (10 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 60%) and concentrated to obtain tert-butyl 7-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate (0.580 g, 59.3%) in a white solid form.

[Step 3] Synthesis of 2-(difluoromethyl)-5-(3-fluoro-4-((4-(1,2,3,4-tetrahydroisoquinolin-7-yl)-1H-1,2,3-triazol-1-yl)methyl)phenyl)-1,3,4-oxadiazole

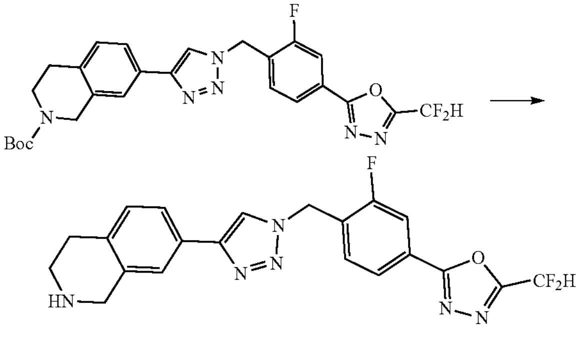

The tert-butyl 7-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-carboxylate (0.400 g, 0.760 mmol) prepared in step 2 and trifluoroacetic acid (0.175 mL, 2.279 mmol) were dissolved in dichloromethane (30 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(3-fluoro-4-((4-(1,2,3,4-tetrahydroisoquinolin-7-yl)-1H-1,2,3-triazol-1-yl)methyl)phenyl)-1,3,4-oxadiazole, 0.320 g, 98.8%, yellow oil).

[Step 4] Synthesis of Compound 4363

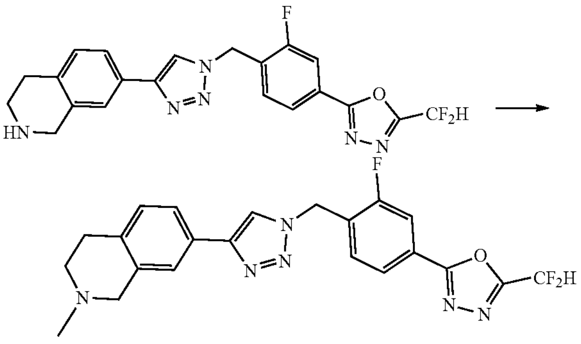

The 2-(difluoromethyl)-5-(3-fluoro-4-((4-(1,2,3,4-tetrahydroisoquinolin-7-yl)-1H-1,2,3-triazol-1-yl)methyl)phenyl)-1,3,4-oxadiazole (0.070 g, 0.164 mmol) prepared in step 3, formaldehyde (0.006 g, 0.197 mmol), acetic acid (0.010 mL, 0.181 mmol) and sodium triacetoxyborohydride (0.070 g, 0.328 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(3-fluoro-4-((4-(2-methyl-1,2,3,4-tetrahydroisoquinolin-7-yl)-1H-1,2,3-triazol-1-yl)methyl)phenyl)-1,3,4-oxadiazole (0.026 g, 36.0%) in a white solid form.

$^1H$ NMR (400 MHz, $CDCl_3$) δ 7.91 (dd, J=6.6, 4.6 Hz, 2H), 7.81 (d, J=2.4 Hz, 1H), 7.55 (d, J=6.4 Hz, 2H), 7.45 (t, J=7.7 Hz, 1H), 7.17 (d, J=8.5 Hz, 1H), 7.07 (s, 0.2H), 6.94 (s, 0.5H), 6.81 (s, 0.3H), 5.72 (s, 2H), 3.63 (d, J=6.2 Hz, 2H), 2.96 (t, J=5.8 Hz, 2H), 2.74 (t, J=6.0 Hz, 2H), 2.49 (s, 3H); LRMS (ES) m/z 441.5 ($M^+$+1).

The compounds of table 79 were synthesized according to substantially the same process as described above in the synthesis of compound 4363 with an exception of using 2-(difluoromethyl)-5-(3-fluoro-4-((4-(1,2,3,4-tetrahydroisoquinolin-7-yl)-1H-1,2,3-triazol-1-yl)methyl)phenyl)-1,3,4-oxadiazole and the reactant of table 78.

TABLE 78

| Example | Compound No. | Reactant | Yield (%) |
|---|---|---|---|
| 262 | 4364 | Acetaldehyde | 50 |
| 263 | 4365 | Propan-2-one | 50 |
| 264 | 4366 | Cyclobutanone | 52 |
| 265 | 4367 | Oxetan-3-one | 61 |

TABLE 79

| Example | Compound No. | Compound Name, $^1$H-NMR, MS (ESI) |
|---|---|---|
| 262 | 4364 | 2-(difluoromethyl)-5-(4-((4-(2-ethyl-1,2,3,4-tetrahydroisoquinolin-7-yl)-1H-1,2,3-triazol-1-yl)methyl)-3-fluorophenyl)-1,3,4-oxadiazole $^1$H NMR (400 MHZ, $CDCl_3$) δ 7.95-7.88 (m, 2H), 7.81 (d, J = 2.9 Hz, 1H), 7.56 (d, J = 6.8 Hz, 2H), 7.47 (dd, J = 13.8, 6.0 Hz, 1H), 7.16 (d, J = 8.5 Hz, 1H),7.07 (s, 0.2H), 6.94 (s, 0.5H), 6.81 (s, 0.3H), 5.72 (s, 2H), 3.79-3.64 (m, 2H), 2.98 (dd, J = 13.8, 7.9 Hz, 2H), 2.84 (t, J = 6.0 Hz, 2H), 2.68 (q, J = 7.2 Hz, 2H), 1.23 (t, J = 7.2 Hz, 3H); LRMS (ES) m/z 455.3 ($M^+$ + 1). |
| 263 | 4365 | 2-(difluoromethyl)-5-(3-fluoro-4-((4-(2-isopropyl-1,2,3,4-tetrahydroisoquinolin-7-yl)-1H-1,2,3-triazol-1-yl)methyl)phenyl)-1,3,4-oxadiazole $^1$H NMR (400 MHZ, $CDCl_3$) δ 7.94-7.88 (m, 2H), 7.80 (s, 1H), 7.54 (dd, J = 10.8, 3.0 Hz, 2H), 7.46 (t, J = 7.8 Hz, 1H), 7.15 (d, J = 7.9 Hz, 1H), 7.07 (s,0.2H),6.94 (s, 0.5H), 6.81 (s, 0.3H), 5.72 (s, 2H), 3.77 (d, J = 7.1 Hz, 2H), 3.00-2.89 (m, 3H), 2.80 (dd, J = 14.4, 8.4 Hz, 2H), 1.16 (d, J = 6.5 Hz, 6H); LRMS (ES) m/z 469.5 ($M^+$ + 1). |
| 264 | 4366 | 2-(4-((4-(2-cyclobutyl-1,2,3,4-tetrahydroisoquinolin-7-yl)-1H-1,2,3-triazol-1-yl)methyl)-3-fluorophenyl)-5-(difluoromethyl)-1,3,4-oxadiazole $^1$H NMR (400 MHZ, $CDCl_3$) δ 7.91 (dt, J = 3.8, 1.6 Hz, 2H), 7.80 (d, J = 4.4 Hz, 1H), 7.55 (d, J = 6.4 Hz, 2H), 7.46 (t, J = 7.7 Hz, 1H), 7.15 (d, J = 8.5 Hz,1H), 7.07 (s, 0.2H), 6.94 (s, 0.5H), 6.81 (s, 0.3H), 5.72 (s, 2H), 3.55 (d, J = 7.5 Hz, 2H), 2.98-2.85 (m, 3H), 2.65 (t, J = 6.0 Hz, 2H), 2.22-2.10 (m, 2H), 2.08-1.94 (m, 2H), 1.87-1.67 (m, 2H); LRMS (ES) m/z 481.6 ($M^+$ + 1). |
| 265 | 4367 | 2-(difluoromethyl)-5-(3-fluoro-4-((4-(2-(oxetan-3-yl)-1,2,3,4-tetrahydroisoquinolin-7-yl)-1H-1,2,3-triazol-1-yl)methyl)phenyl)-1,3,4-oxadiazole $^1$H NMR (400 MHZ, $CDCl_3$) δ 7.95-7.88 (m, 2H), 7.80 (s, 1H), 7.60-7.53 (m, 2H), 7.50-7.43 (m, 1H), 7.18 (d, J = 8.3 Hz, 1H), 7.07 (s, 0.2H), 6.94 (s,0.5H), 6.81 (s, 0.3H), 5.72 (s, 2H), 4.82-4.71 (m, 4H), 3.73 (p, J = 6.5 Hz, 1H), 3.58 (s, 2H), 2.97 (dd, J = 13.7, 7.8 Hz, 2H), 2.66 (t, J = 5.9 Hz, 2H); LRMS (ES) m/z 483.4 ($M^+$ + 1). |

Example 266: Synthesis of compound 4368, 2-(difluoromethyl)-5-(4-((4-(3-(4-ethylpiperazin-1-yl)phenyl)-1H-1,2,3-triazol-1-yl)methyl)phenyl)-1,3,4-oxadiazole

[Step 1] Synthesis of tert-butyl 4-(3-(1-(4-(5-(difluoromethyl)-1,3,4-oxadiazol-2-yl)benzyl)-1H-1,2,3-triazol-4-yl)phenyl)piperazin-1-carboxylate

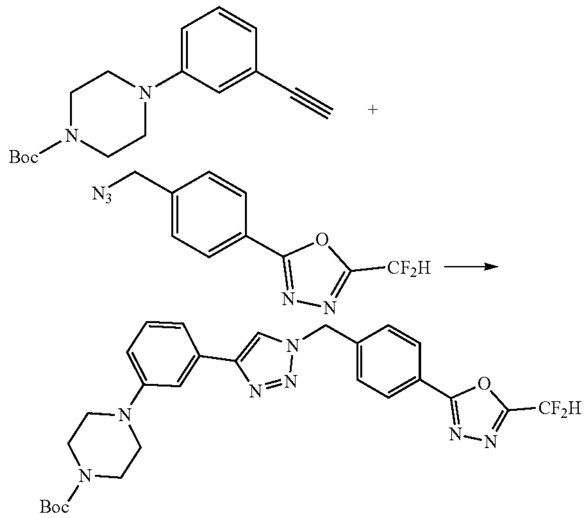

The 2-(4-(azidomethyl)phenyl)-5-(difluoromethyl)-1,3,4-oxadiazole (0.300 g, 1.194 mmol) prepared in step 1 of example 1 and the tert-butyl 4-(3-ethynylphenyl)piperazin-1-carboxylate (0.342 g, 1.194 mmol) prepared in step 1 of example 117 were dissolved in tert-butanol (1 mL)/water (1 mL) at room temperature, after which sodium ascorbate (1.00 M solution, 0.119 mL, 0.119 mmol) and copper(II) sulfate pentahydrate (0.50 M solution, 0.024 mL, 0.012 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 70%) and concentrated to obtain tert-butyl 4-(3-(1-(4-(5-(difluoromethyl)-1,3,4-oxadiazol-2-yl)benzyl)-1H-1,2,3-triazol-4-yl)phenyl)piperazin-1-carboxylate (0.430 g, 67.0%) in a white solid form.

[Step 2] Synthesis of (2-(difluoromethyl)-5-(4-((4-(3-(piperazin-1-yl)phenyl)-1H-1,2,3-triazol-1-yl)methyl)phenyl)-1,3,4-oxadiazole

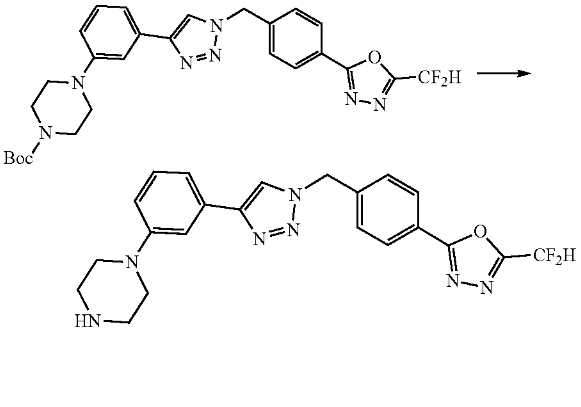

The tert-butyl 4-(3-(1-(4-(5-(difluoromethyl)-1,3,4-oxadiazol-2-yl)benzyl)-1H-1,2,3-triazol-4-yl)phenyl)piperazin-1-carboxylate (0.300 g, 0.558 mmol) prepared in step 1 and trifluoroacetic acid (1.282 mL, 16.742 mmol) were dissolved in dichloromethane (3.5 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(4-((4-(3-(piperazin-1-yl) phenyl)-1H-1,2,3-triazol-1-yl)methyl)phenyl)-1,3,4-oxadiazole, 0.310 g, 100.7%, light yellow oil).

[Step 3] Synthesis of Compound 4368

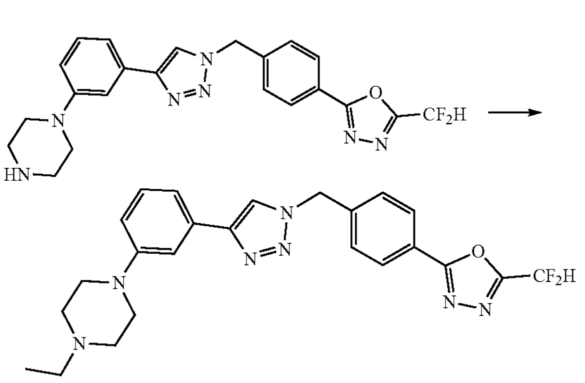

The 2-(difluoromethyl)-5-(4-((4-(3-(piperazin-1-yl)phenyl)-1H-1,2,3-triazol-1-yl)methyl)phenyl)-1,3,4-oxadiazole (0.050 g, 0.114 mmol) prepared in step 2, and acetaldehyde (0.015 g, 0.342 mmol) were dissolved in dichloromethane (1 mL) at room temperature, after which sodium triacetoxyborohydride (0.121 g, 0.570 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(difluoromethyl)-5-(4-((4-(3-(4-ethylpiperazin-1-yl)phenyl)-1H-1,2,3-triazol-1-yl)methyl)phenyl)-1,3,4-oxadiazole (0.035 g, 65.9%) in a light yellow oil form.

$^1$H NMR (400 MHz, $CD_3OD$) δ 8.42 (s, 1H), 8.20-8.13 (m, 2H), 7.62 (d, J=8.4 Hz, 2H), 7.48 (d, J=2.1 Hz, 1H), 7.35-7.28 (m, 2H), 7.23 (t, J=51.6 Hz, 1H), 6.99 (dt, J=7.5, 2.2 Hz, 1H), 5.79 (s, 2H), 3.30 (d, J=5.4 Hz, 4H), 2.73-2.66 (m, 4H), 2.54 (q, J=7.3 Hz, 2H), 1.18 (t, J=7.2 Hz, 3H); LRMS (ES) m/z 466.3 ($M^+$+1).

The compounds of table 81 were synthesized according to substantially the same process as described above in the synthesis of compound 4368 with an exception of using 2-(difluoromethyl)-5-(4-((4-(3-(piperazin-1-yl)phenyl)-1H-1,2,3-triazol-1-yl)methyl)phenyl)-1,3,4-oxadiazole and the reactant of table 80.

TABLE 80

| Example | Compound No. | Reactant | Yield (%) |
|---|---|---|---|
| 267 | 4369 | Propionaldehyde | 67 |
| 268 | 4370 | Oxetan-3-one | 67 |
| 269 | 4371 | Cyclobutanone | 69 |

TABLE 81

| Example | Compound No | Compound Name, $^1$H-NMR, MS (ESI) |
|---|---|---|
| 267 | 4369 | 2-(difluoromethyl)-5-(4-((4-(3-(4-propylpiperazin-1-yl)phenyl)-1H-1,2,3-triazol-1-yl)methyl)phenyl)-1,3,4-oxadiazole<br>$^1$H NMR (400 MHZ, $CD_3OD$) δ 8.42 (s, 1H), 8.20-8.13 (m, 2H), 7.65-7.58 (m, 2H), 7.51-7.45 (m, 1H), 7.35-7.26 (m, 2H), 7.23 (t, J = 51.7 Hz, 1H), 6.99 (dt, J = 7.5, 2.1 Hz, 1H), 5.79 (s, 2H), 3.32-3.27 (m, 4H), 2.75-2.68 (m, 4H), 2.49-2.41 (m, 2H), 1.69-1.55 (m, 2H), 0.98 (t, J = 7.4 Hz,3H); LRMS (ES) m/z 480.3 ($M^+$ + 1). |
| 268 | 4370 | 2-(difluoromethyl)-5-(4-((4-(3-(4-(oxetan-3-yl)piperazin-1-yl)phenyl)-1H-1,2,3-triazol-1-yl)methyl)phenyl)-1,3,4-oxadiazole<br>$^1$H NMR (400 MHZ, $CD_3OD$) δ 8.42 (s, 1H), 8.20-8.13 (m, 2H), 7.61 (d, J = 8.3 Hz, 2H), 7.48 (t, J = 2.0 Hz, 1H), 7.35-7.26 (m, 2H), 7.23 (t, J = 51.7 Hz, 1H), 6.99 (dt, J = 7.5, 2.0 Hz, 1H), 5.79 (s, 2H), 4.75 (t, J = 6.7 Hz, 2H), 4.67 (t, J = 6.2 Hz, 2H), 3.58 (p, J = 6.3 Hz, 1H), 3.30 (d, J = 4.9 Hz, 4H), 2.59-2.52 (m, 4H); LRMS (ES) m/z 494.3 ($M^+$ + 1). |
| 269 | 4371 | 2-(4-((4-(3-(4-cyclobutylpiperazin-1-yl)phenyl)-1H-1,2,3-triazol-1-yl)methyl)phenyl)-5-(difluoromethyl)-1,3,4-oxadiazole<br>$^1$H NMR (400 MHZ, $CD_3OD$) δ 8.42 (s, 1H), 8.17 (d, J = 8.4 Hz, 2H), 7.61 (d, J = 8.3 Hz, 2H), 7.47 (s, 1H), 7.31 (q, J = 7.9 Hz, 2H), 7.23 (t, J = 51.7 Hz, 1H), 7.02-6.96 (m, 1H), 5.79 (s, 2H), 3.29 (t, J = 5.1 Hz, 5H), 2.87 (t, J = 8.1 Hz, 1H), 2.60-2.53 (m, 4H), 2.12 (s, 2H), 1.98 (t, J = 10.5 Hz, 2H), 1.80 (dd, J = 9.6, 5.3 Hz, 2H); LRMS (ES) m/z 492.2 ($M^+$ + 1). |

Example 270: Synthesis of compound 4372, 1-(4-(3-(1-(4-(5-(difluoromethyl)-1,3,4-oxadiazol-2-yl)benzyl)-1H-1,2,3-triazol-4-yl)phenyl)piperazin-1-yl)propan-1-one

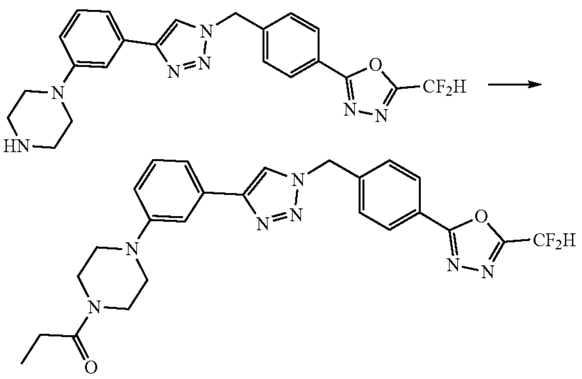

The 2-(difluoromethyl)-5-(4-((4-(3-(piperazin-1-yl)phenyl)-1H-1,2,3-triazol-1-yl)methyl)phenyl)-1,3,4-oxadiazole (0.050 g, 0.114 mmol) prepared in step 2 of example 266, and propionyl chloride (0.032 g, 0.342 mmol) were dissolved in dichloromethane (1 mL) at room temperature, after which triethylamine (0.079 mL, 0.570 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 1-(4-(3-(1-(4-(5-(difluoromethyl)-1,3,4-oxadiazol-2-yl)benzyl)-1H-1,2,3-triazol-4-yl)phenyl)piperazin-1-yl)propan-1-one (0.034 g, 60.4%) in a light yellow oil form.

$^1H$ NMR (400 MHz, $CD_3OD$) δ 8.43 (s, 1H), 8.20-8.13 (m, 2H), 7.65-7.58 (m, 2H), 7.52-7.47 (m, 1H), 7.35-7.29 (m, 2H), 7.23 (t, J=51.6 Hz, 1H), 7.01 (dt, J=6.9, 2.6 Hz, 1H), 5.80 (s, 2H), 3.75 (dt, J=17.5, 5.3 Hz, 4H), 3.30-3.20 (m, 4H), 2.49 (q, J=7.5 Hz, 2H), 1.16 (t, J=7.5 Hz, 3H); LRMS (ES) m/z 494.3 ($M^+$+1).

Example 271: Synthesis of compound 4373, 2-(difluoromethyl)-5-(4-((4-(3-(4-ethylpiperazin-1-yl)phenyl)-1H-1,2,3-triazol-1-yl)methyl)-3-fluorophenyl)-1,3,4-oxadiazole

[Step 1] Synthesis of tert-butyl 4-(3-(1-(4-(5-(difluoromethyl)-1,3,4-oxadiazol-2-yl)-2-fluorobenzyl)-1H-1,2,3-triazol-4-yl)phenyl)piperazin-1-carboxylate

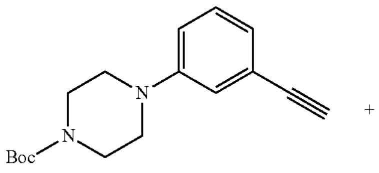

-continued

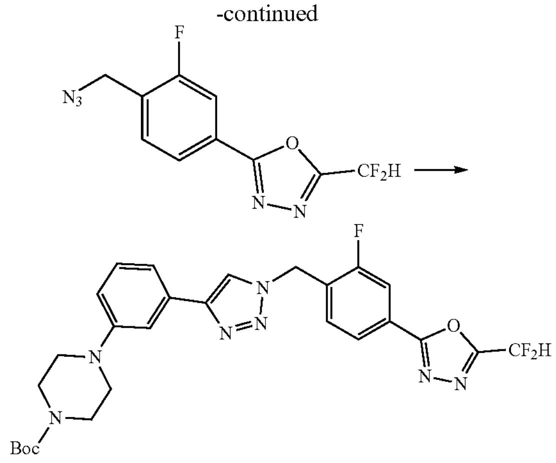

The 2-(4-(azidomethyl)-3-fluorophenyl)-5-(difluoromethyl)-1,3,4-oxadiazole (0.300 g, 1.114 mmol) prepared in step 1 of example 2 and the tert-butyl 4-(3-ethynylphenyl)piperazin-1-carboxylate (0.319 g, 1.114 mmol) prepared in step 1 of example 117 were dissolved in tert-butanol (1 mL)/water (1 mL) at room temperature, after which sodium ascorbate (1.00 M solution, 0.111 mL, 0.111 mmol) and copper(II) sulfate pentahydrate (0.50 M solution, 0.022 mL, 0.011 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 70%) and concentrated to obtain tert-butyl 4-(3-(1-(4-(5-(difluoromethyl)-1,3,4-oxadiazol-2-yl)-2-fluorobenzyl)-1H-1,2,3-triazol-4-yl)phenyl)piperazin-1-carboxylate (0.470 g, 75.9%) in a white solid form.

[Step 2] Synthesis of (2-(difluoromethyl)-5-(3-fluoro-4-((4-(3-(piperazin-1-yl)phenyl)-1H-1,2,3-triazol-1-yl)methyl)phenyl)-1,3,4-oxadiazole

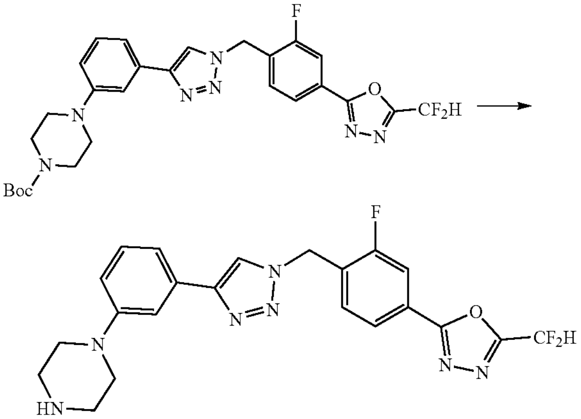

The tert-butyl 4-(3-(1-(4-(5-(difluoromethyl)-1,3,4-oxadiazol-2-yl)-2-fluorobenzyl)-1H-1,2,3-triazol-4-yl)phenyl)piperazin-1-carboxylate (0.300 g, 0.540 mmol) prepared in step 1 and trifluoroacetic acid (1.241 mL, 16.200 mmol) were dissolved in dichloromethane (3.5 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(3-fluoro-4-((4-(3-(piperazin-1-yl)phenyl)-1H-1,2,3-triazol-1-yl)methyl)phenyl)-1,3,4-oxadiazole, 0.310 g, 100.8%, light yellow oil).

[Step 3] Synthesis of Compound 4373

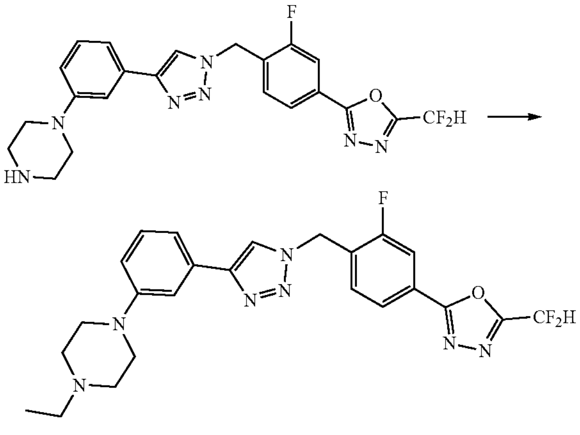

The 2-(difluoromethyl)-5-(3-fluoro-4-((4-(3-(piperazin-1-yl)phenyl)-1H-1,2,3-triazol-1-yl)methyl)phenyl)-1,3,4-oxadiazole (0.050 g, 0.110 mmol) prepared in step 2, and acetaldehyde (0.015 g, 0.329 mmol) were dissolved in dichloromethane (1 mL) at room temperature, after which sodium triacetoxyborohydride (0.116 g, 0.549 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(difluoromethyl)-5-(4-((4-(3-(4-ethylpiperazin-1-yl)phenyl)-1H-1,2,3-triazol-1-yl)methyl)-3-fluorophenyl)-1,3,4-oxadiazole (0.036 g, 67.8%) in a light yellow oil form.

$^1$H NMR (400 MHz, $CD_3OD$) δ 8.43 (s, 1H), 8.03-7.93 (m, 2H), 7.61 (t, J=7.7 Hz, 1H), 7.50 (d, J=2.8 Hz, 1H), 7.37-7.28 (m, 2H), 7.24 (t, J=51.6 Hz, 1H), 7.00 (dt, J=7.3, 2.4 Hz, 1H), 5.85 (s, 2H), 3.35 (d, J=3.8 Hz, 4H), 2.81 (t, J=5.1 Hz, 4H), 2.66 (q, J=7.3 Hz, 2H), 1.22 (t, J=7.3 Hz, 3H); LRMS (ES) m/z 484.3 ($M^+$+1).

The compounds of table 83 were synthesized according to substantially the same process as described above in the synthesis of compound 4373 with an exception of using 2-(difluoromethyl)-5-(3-fluoro-4-((4-(3-(piperazin-1-yl)phenyl)-1H-1,2,3-triazol-1-yl)methyl)phenyl)-1,3,4-oxadiazole and the reactant of table 82.

TABLE 82

| Example | Compound No. | Reactant | Yield (%) |
|---|---|---|---|
| 272 | 4374 | Propionaldehyde | 75 |
| 273 | 4375 | Oxetan-3-one | 76 |
| 274 | 4376 | Cyclobutanone | 66 |

TABLE 83

| Example | Compound No. | Compound Name, $^1$H-NMR, MS (ESI) |
|---|---|---|
| 272 | 4374 | 2-(difluoromethyl)-5-(3-fluoro-4-((4-(3-(4-propylpiperazin-1-yl)phenyl)-1H-1,2,3-triazol-1-yl)methyl)phenyl)-1,3,4-oxadiazole<br>$^1$H NMR (400 MHZ, $CD_3OD$) δ 8.43 (s, 1H), 8.03-7.92 (m, 2H), 7.60 (t, J = 7.6 Hz, 1H), 7.51-7.46 (m, 1H), 7.36-7.27 (m, 2H), 7.24 (t, J = 51.6 Hz, 1H), 6.99 (dt, J = 7.3, 2.3 Hz, 1H), 5.85 (s, 2H), 3.30 (d, J = 4.8 Hz, 4H), 2.78-2.71 (m, 4H), 2.52 -2.44 (m, 2H), 1.63 (dq, J = 15.0, 7.4 Hz, 2H), 0.98 (t, J = 7.4 Hz, 3H); LRMS (ES) m/z 498.3 ($M^+$ + 1). |
| 273 | 4375 | 2-(difluoromethyl)-5-(3-fluoro-4-((4-(3-(4-(oxetan-3-yl)piperazin-1-yl)phenyl)-1H-1,2,3-triazol-1-yl)methyl)phenyl)-1,3,4-oxadiazole<br>$^1$H NMR (400 MHZ, $CD_3OD$) δ 8.43 (s, 1H), 8.03-7.92 (m, 2H), 7.60 (t, J = 7.6 Hz, 1H), 7.48 (s, 1H), 7.36-7.27 (m, 2H), 7.24 (t, J = 51.6 Hz, 1H), 6.99 (dt, J = 7.5, 2.2 Hz, 1H), 5.85 (s, 2H), 4.75 (t, J = 6.7 Hz, 2H), 4.71-4.63 (m, 2H), 3.59 (p, J = 6.3 Hz, 1H), 3.30 (s, 4H), 2.60-2.53 (m, 4H); LRMS (ES) m/z 512.1 ($M^+$ + 1). |
| 274 | 4376 | 2-(4-((4-(3-(4-cyclobutylpiperazin-1-yl)phenyl)-1H-1,2,3-triazol-1-yl)methyl)-3-fluorophenyl)-5-(difluoromethyl)-1,3,4-oxadiazole<br>$^1$H NMR (400 MHZ, $CD_3OD$) δ 8.43 (s, 1H), 8.03-7.92 (m, 2H), 7.60 (t, J = 7.7 Hz, 1H), 7.47 (s, 1H), 7.36-7.26 (m, 2H), 7.24 (t, J = 51.6 Hz, 1H), 6.99 (dt, J = 7.3, 2.2 Hz, 1H), 5.85 (s, 2H), 3.31-3.25 (m, 4H), 2.87 (p, J = 7.9 Hz, 1H), 2.60-2.53 (m, 4H), 2.13 (dt, J = 8.5, 5.4 Hz, 2H), 2.01-1.89 (m, 2H), 1.84-1.71 (m, 2H); LRMS (ES) m/z 510.3 ($M^+$ + 1). |

Example 275: Synthesis of compound 4377, 1-(4-(3-(1-(4-(5-(difluoromethyl)-1,3,4-oxadiazol-2-yl)-2-fluorobenzyl)-1H-1,2,3-triazol-4-yl)phenyl)piperazin-1-yl)propan-1-one

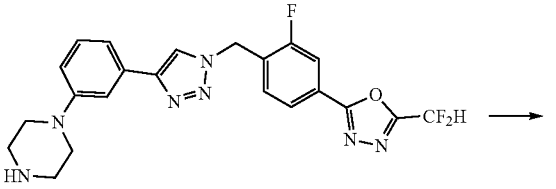

$^1$H NMR (400 MHz, $CD_3OD$) δ 8.43 (s, 1H), 8.03-7.93 (m, 2H), 7.61 (t, J=7.7 Hz, 1H), 7.52-7.47 (m, 1H), 7.37-7.29 (m, 2H), 7.24 (t, J=51.6 Hz, 1H), 7.05-6.98 (m, 1H), 5.85 (s, 2H), 3.75 (dt, J=17.5, 5.3 Hz, 4H), 3.26 (dt, J=18.6, 5.4 Hz, 4H), 2.49 (q, J=7.5 Hz, 2H), 1.16 (t, J=7.5 Hz, 3H); LRMS (ES) m/z 512.3 ($M^+$+1).

Example 276: Synthesis of compound 4392, 2-(difluoromethyl)-5-(4-((4-(2-(1-ethylazetidin-3-yl)-1,2,3,4-tetrahydroisoquinolin-6-yl)-1H-1,2,3-triazol-1-yl)methyl)-3-fluorophenyl)-1,3,4-oxadiazole

[Step 1] Synthesis of tert-butyl 3-(6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-yl)azetidin-1-carboxylate

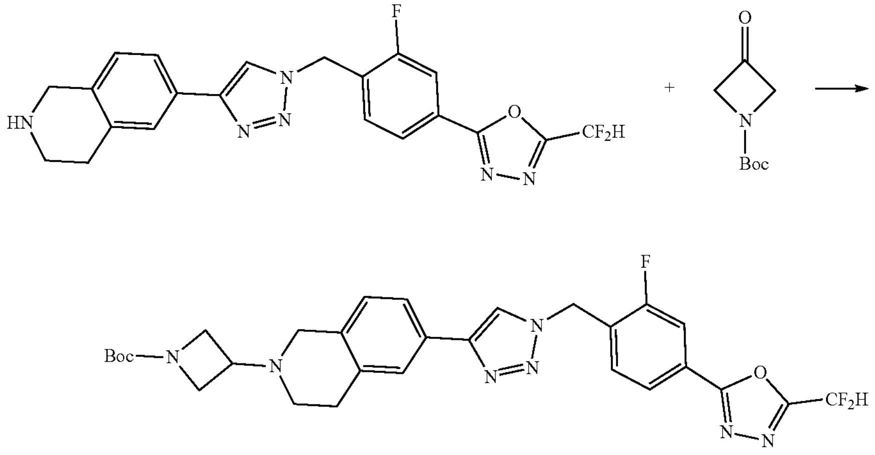 [SMILES: Fc1cc(-c2nnc(C(F)F)o2)ccc1Cn1cc(-c2ccc3c(c2)CCNC3)nn1 ; CC(C)(C)OC(=O)N1CC(=O)C1 ; CC(C)(C)OC(=O)N1CC(N2CCc3cc(-c4cn(Cc5ccc(-c6nnc(C(F)F)o6)cc5F)nn4)ccc3C2)C1]

-continued

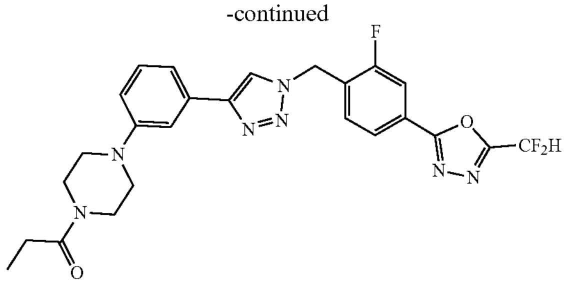

The 2-(difluoromethyl)-5-(3-fluoro-4-((4-(3-(piperazin-1-yl)phenyl)-1H-1,2,3-triazol-1-yl)methyl)phenyl)-1,3,4-oxadiazole (0.050 g, 0.110 mmol) prepared in step 2 of example 271, and propionyl chloride (0.030 g, 0.329 mmol) were dissolved in dichloromethane (1 mL) at room temperature, after which triethylamine (0.077 mL, 0.549 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 1-(4-(3-(1-(4-(5-(difluoromethyl)-1,3,4-oxadiazol-2-yl)-2-fluorobenzyl)-1H-1,2,3-triazol-4-yl)phenyl)piperazin-1-yl)propan-1-one (0.032 g, 57.0%) in a light yellow oil form.

The 2-(difluoromethyl)-5-(3-fluoro-4-((4-(1,2,3,4-tetrahydroisoquinolin-6-yl)-1H-1,2,3-triazol-1-yl)methyl)phenyl)-1,3,4-oxadiazole (0.200 g, 0.469 mmol) prepared in step 2 of example 256, tert-butyl 3-oxoazetidin-1-carboxylate (0.096 g, 0.563 mmol), acetic acid (0.030 mL, 0.516 mmol) and sodium triacetoxyborohydride (0.199 g, 0.938 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain tert-butyl 3-(6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-yl)azetidin-1-carboxylate (0.150 g, 55.0%) in a white solid form.

[Step 2] Synthesis of 2-(4-((4-(2-(azetidin-3-yl)-1,2,3,4-tetrahydroisoquinolin-6-yl)-1H-1,2,3-triazol-1-yl)methyl)-3-fluorophenyl)-5-(difluoromethyl)-1,3,4-oxadiazole

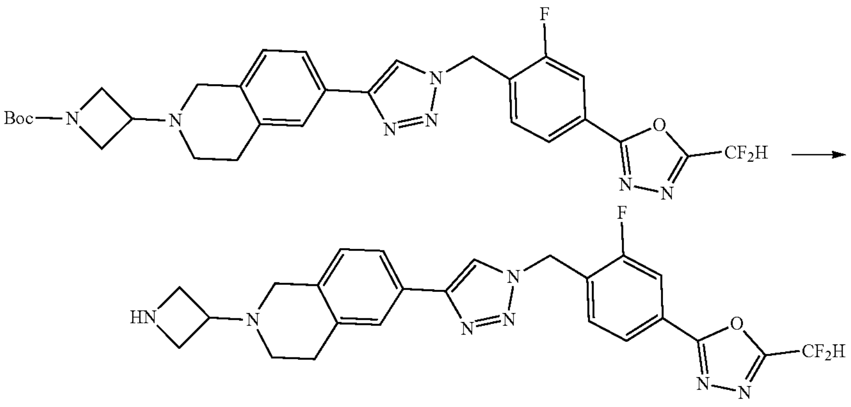

The tert-butyl 3-(6-(1-(4-(5-(difluoromethyl)-1,3,4-oxadiazol-2-yl)-2-fluorobenzyl)-1H-1,2,3-triazol-4-yl)-3,4-dihydroisoquinolin-2(1H)-yl)azetidin-1-carboxylate (0.150 g, 0.258 mmol) prepared in step 1 and trifluoroacetic acid (0.059 mL, 0.774 mmol) were dissolved in dichloromethane (30 mL) at room temperature, after which the resulting solution was stirred at the same temperature for 3 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. Then, the obtained product was used without an additional purification process (2-(4-((4-(2-(azetidin-3-yl)-1,2,3,4-tetrahydroisoquinolin-6-yl)-1H-1,2,3-triazol-1-yl)methyl)-3-fluorophenyl)-5-(difluoromethyl)-1,3,4-oxadiazole, 0.120 g, 96.6%, yellow oil).

[Step 3] Synthesis of Compound 4392

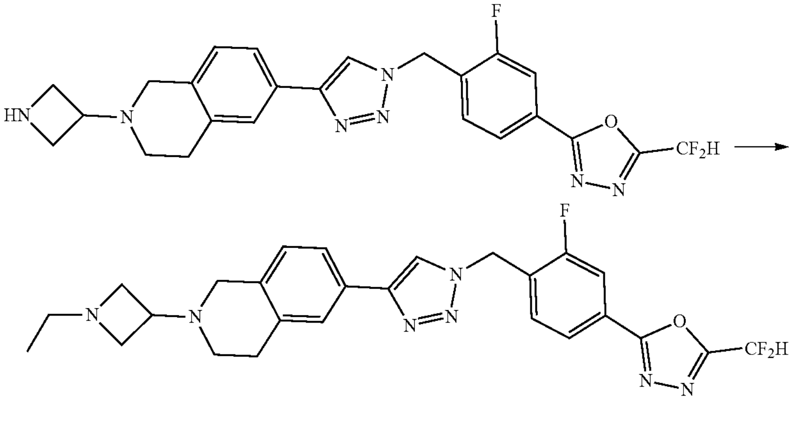

The 2-(4-((4-(2-(azetidin-3-yl)-1,2,3,4-tetrahydroisoquinolin-6-yl)-1H-1,2,3-triazol-1-yl)methyl)-3-fluorophenyl)-5-(difluoromethyl)-1,3,4-oxadiazole (0.050 g, 0.104 mmol) prepared in step 2, acetaldehyde (0.006 g, 0.208 mmol) and acetic acid (0.007 mL, 0.114 mmol) were dissolved in dichloromethane (5 mL), after which the resulting solution was stirred at room temperature for 30 minutes, and then sodium triacetoxyborohydride (0.044 g, 0.208 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(4-((4-(2-(1-ethylazetidin-3-yl)-1,2,3,4-tetrahydroisoquinolin-6-yl)-1H-1,2,3-triazol-1-yl)methyl)-3-fluorophenyl)-1,3,4-oxadiazole (0.031 g, 58.6%) in a white solid form.

$^1$H NMR (400 MHz, $CDCl_3$) δ 7.92 (dd, J=7.8, 2.5 Hz, 2H), 7.81 (s, 1H), 7.63 (s, 1H), 7.59-7.52 (m, 1H), 7.48 (t, J=7.7 Hz, 1H), 7.10-7.04 (m, 1.2H), 6.94 (s, 0.5H), 6.81 (s, 0.3H), 5.74 (d, J=10.4 Hz, 2H), 4.00 (t, J=7.1 Hz, 2H), 3.53 (s, 2H), 3.38 (dt, J=13.2, 6.5 Hz, 1H), 3.27 (t, J=7.5 Hz, 2H), 2.96 (t, J=5.9 Hz, 2H), 2.82 (q, J=7.2 Hz, 2H), 2.63 (t, J=5.9 Hz, 2H), 1.19-1.06 (m, 3H); LRMS (ES) m/z 510.6 ($M^+$+1).

The compounds of table 85 were synthesized according to substantially the same process as described above in the synthesis of compound 4392 with an exception of using 2-(4-((4-(2-(azetidin-3-yl)-1,2,3,4-tetrahydroisoquinolin-6-yl)-1H-1,2,3-triazol-1-yl)methyl)-3-fluorophenyl)-5-(difluoromethyl)-1,3,4-oxadiazole and the reactant of table 84.

TABLE 84

| Example | Compound No. | Reactant | Yield (%) |
|---|---|---|---|
| 277 | 4393 | Propan-2-one | 53 |
| 278 | 4394 | Cyclobutanone | 37 |
| 279 | 4395 | Oxetan-3-one | 55 |

TABLE 85

| Example | Compound No. | Compound Name, $^1$H-NMR, MS (ESI) |
|---|---|---|
| 277 | 4393 | 2-(difluoromethyl)-5-(3-fluoro-4-((4-(2-(1-isopropylazetidin-3-yl)-1,2,3,4-tetrahydroisoquinolin-6-yl)-1H-1,2,3-triazol-1-yl)methyl)phenyl)-1,3,4-oxadiazole<br>$^1$H NMR (400 MHZ, $CDCl_3$) δ 7.92 (dt, J = 3.8, 1.5 Hz, 2H), 7.81 (s, 1H), 7.62 (s, 1H), 7.55 (dd, J = 7.9, 1.6 Hz, 1H), 7.47 (t, J = 7.7 Hz, 1H), 7.10-7.04 (m, 1.2H), 6.94 (s, 0.5H), 6.81 (s, 0.3H), 5.73 (s, 2H), 3.74 (t, J = 6.8 Hz, 2H), 3.52 (s, 2H), 3.25-3.13 (m, 1H), 3.05 (t, J = 7.3 Hz, 2H), 3.00-2.88 (m, 2H), 2.62 (t, J = 6.0 Hz, 2H), 2.50 (dt, J = 12.3, 6.1 Hz, 1H), 1.03 (d, J = 6.2 Hz, 6H); LRMS (ES) m/z 524.6 ($M^+$ + 1). |
| 278 | 4394 | 2-(4-((4-(2-(1-cyclobutylazetidin-3-yl)-1,2,3,4-tetrahydroisoquinolin-6-yl)-1H-1,2,3-triazol-1-yl)methyl)-3-fluorophenyl)-5-(difluoromethyl)-1,3,4-oxadiazole<br>$^1$H NMR (400 MHZ, $CDCl_3$) δ 7.95-7.88 (m, 2H), 7.81 (s, 1H), 7.62 (s, 1H), 7.58-7.53 (m, 1H), 7.47 (t, J = 7.7 Hz, 1H), 7.09-7.04 (m, 1.2H), 6.94 (s, 0.5H), 6.81 (s, 0.3H), 5.74 (s, 2H), 3.71 (t, J = 6.8 Hz, 2H), 3.51 (s, 2H), 3.36-3.22 (m, 2H), 3.16 (t, J = 7.3 Hz, 2H), 3.00-2.87 (m, 2H), 2.61 (t, J = 5.9 Hz, 2H), 2.10-1.90 (m, 4H), 1.87-1.62 (m, 2H); LRMS (ES) m/z 536.5 ($M^+$ + 1). |
| 279 | 4395 | 2-(difluoromethyl)-5-(3-fluoro-4-((4-(2-(1-(oxetan-3-yl)azetidin-3-yl)-1,2,3,4-tetrahydroisoquinolin-6-yl)-1H-1,2,3-triazol-1-yl)methyl)phenyl)-1,3,4-oxadiazole<br>$^1$H NMR (400 MHZ, $CDCl_3$) δ 7.95-7.89 (m, 2H), 7.81 (s, 1H), 7.63 (s, 1H), 7.56 (d, J = 7.9 Hz, 1H), 7.47 (t, J = 7.7 Hz, 1H), 7.08 (d, J = 7.8 Hz, 1.2H), 6.94 (s, 0.5H), 6.81 (s, 0.3H), 5.73 (s, 2H), 4.71 (t, J = 6.7 Hz, 2H), 4.62-4.53 (m, 2H), 3.90-3.79 (m, 1H), 3.65 (t, J = 6.4 Hz, 2H), 3.54 (s, 2H), 3.29-3.22 (m, 1H), 3.18 (t, J = 6.8 Hz, 2H), 2.96 (t, J = 5.8 Hz, 2H), 2.64 (t, J = 5.9 Hz, 2H); LRMS (ES) m/z 538.4 ($M^+$ + 1). |

Example 280: Synthesis of compound 4396, 2-(difluoromethyl)-5-(4-((4-(4-fluoro-3-(piperazin-1-yl)phenyl)-1H-1,2,3-triazol-1-yl)methyl)phenyl)-1,3,4-oxadiazole

[Step 1] Synthesis of 2-(3-bromo-4-fluorophenyl)-1,3-dioxolane

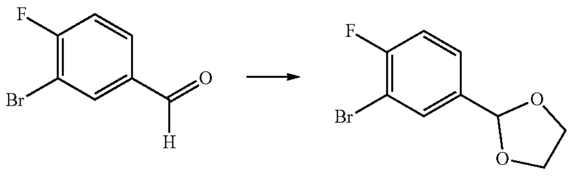 [SMILES: O=Cc1ccc(F)c(Br)c1 ; Fc1ccc(C2OCCO2)cc1Br]

3-bromo-4-fluorobenzaldehyde (10.500 g, 51.722 mmol), PTSA (0.098 g, 0.517 mmol) and ethylene glycol (3.471 mL, 62.066 mmol) were dissolved in toluene (50 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 20%) and concentrated to obtain 2-(3-bromo-4-fluorophenyl)-1,3-dioxolane (10.420 g, 81.5%) in a yellow oil form.

[Step 2] Synthesis of tert-butyl 4-(5-(1,3-dioxolan-2-yl)-2-fluorophenyl)piperazin-1-carboxylate

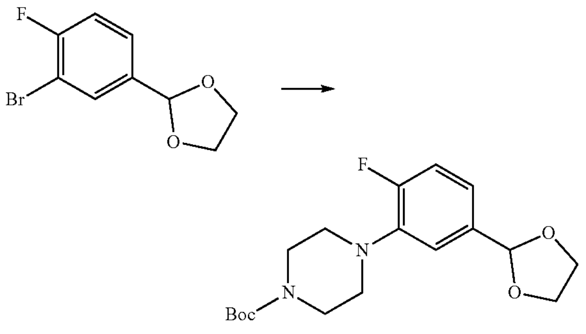

The 2-(3-bromo-4-fluorophenyl)-1,3-dioxolane (5.000 g, 20.238 mmol) prepared in step 1, tert-butyl piperazin-1-carboxylate (4.146 g, 22.262 mmol), tris(dibenzylidene acetone)dipalladium ($Pd_2(dba)_3$, 0.185 g, 0.202 mmol), rac-BINAP (0.252 g, 0.405 mmol) and NaOBut (3.890 g, 40.476 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(5-(1,3-dioxolan-2-yl)-2-fluorophenyl) piperazin-1-carboxylate (3.450 g, 48.4%) in a yellow oil form.

[Step 3] Synthesis of tert-butyl 4-(2-fluoro-5-formylphenyl)piperazin-1-carboxylate

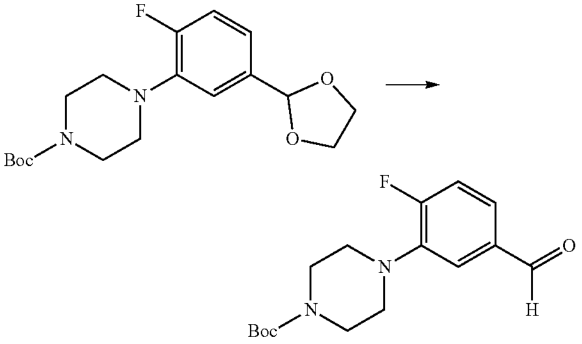

The tert-butyl 4-(5-(1,3-dioxolan-2-yl)-2-fluorophenyl) piperazin-1-carboxylate (3.450 g, 9.790 mmol) prepared in step 2 and hydrochloric acid (1.00 M solution, 29.369 mL, 29.369 mmol) were dissolved in methanol (10 mL) at room temperature, after which the resulting solution was stirred at the same temperature for 4 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(2-fluoro-5-formylphenyl)piperazin-1-carboxylate (2.600 g, 86.1%) in a yellow oil form.

[Step 4] Synthesis of tert-butyl 4-(5-(2,2-dibromovinyl)-2-fluorophenyl)piperazin-1-carboxylate

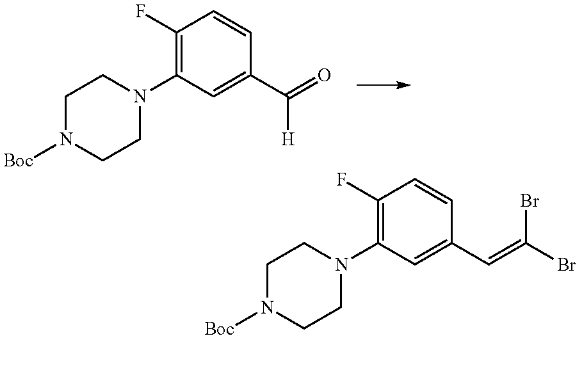

The tert-butyl 4-(2-fluoro-5-formylphenyl)piperazin-1-carboxylate (2.600 g, 8.432 mmol) prepared in step 3, carbon tetrabromide (5.593 g, 16.864 mmol) and triphenylphosphine triphenylphosphine (8.846 g, 33.728 mmol) were dissolved in dichloromethane (100 mL) at room temperature, after which the resulting solution was stirred at the same temperature for two hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(5-(2,2-dibromovinyl)-2-fluorophenyl)piperazin-1-carboxylate (3.300 g, 84.3%) in a yellow oil form.

[Step 5] Synthesis of tert-butyl 4-(5-ethynyl-2-fluorophenyl)piperazin-1-carboxylate

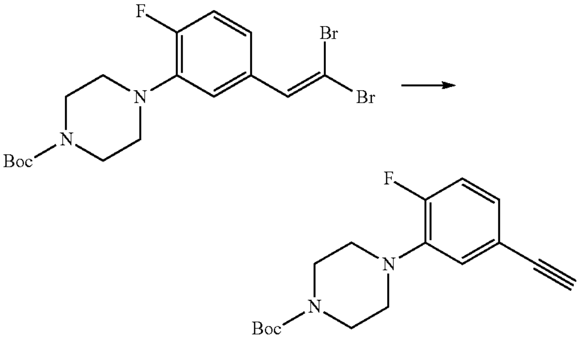

The tert-butyl 4-(5-(2,2-dibromovinyl)-2-fluorophenyl) piperazin-1-carboxylate (3.300 g, 7.109 mmol) prepared in step 4 and 2,3,4,6,7,8,9,10-octahydropyrimido[1,2-a] azepine (4.253 mL, 28.438 mmol) were dissolved in acetonitrile (50 mL) at room temperature, after which the resulting solution was stirred at the same temperature for 16 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(5-ethynyl-2-fluorophenyl)piperazin-1-carboxylate (0.550 g, 25.4%) in a colorless oil form.

[Step 6] Synthesis of tert-butyl 4-(5-(1-(4-(5-(difluoromethyl)-1,3,4-oxadiazol-2-yl)benzyl)-1H-1,2,3-triazol-4-yl)-2-fluorophenyl)piperazin-1-carboxylate

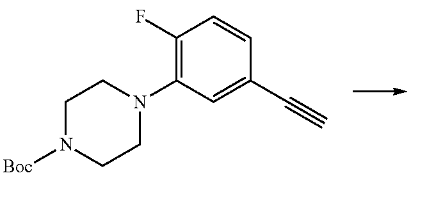

-continued

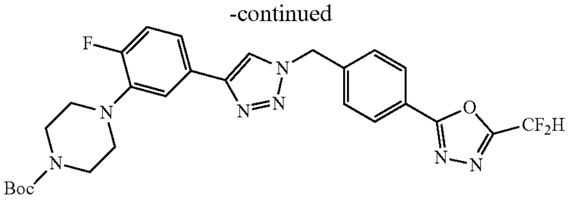

The tert-butyl 4-(5-ethynyl-2-fluorophenyl)piperazin-1-carboxylate (0.275 g, 0.904 mmol) prepared in step 5, 2-(4-(azidomethyl)phenyl)-5-(difluoromethyl)-1,3,4-oxadiazole (0.272 g, 1.084 mmol) prepared in step 1 of example 1, copper(II) sulfate pentahydrate (0.002 g, 0.009 mmol) and sodium ascorbate (0.018 g, 0.090 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(5-(1-(4-(5-(difluoromethyl)-1,3,4-oxadiazol-2-yl)benzyl)-1H-1,2,3-triazol-4-yl)-2-fluorophenyl)piperazin-1-carboxylate (0.480 g, 95.6%) in a white solid form.

[Step 7] Synthesis of Compound 4396

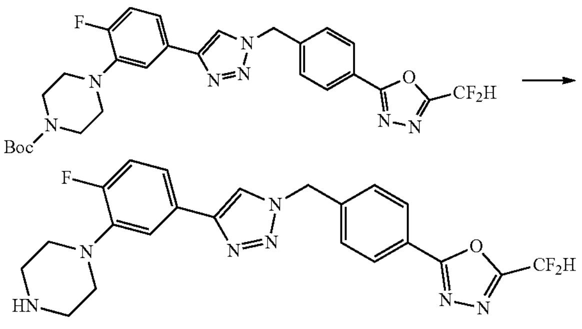

The tert-butyl 4-(5-(1-(4-(5-(difluoromethyl)-1,3,4-oxadiazol-2-yl)benzyl)-1H-1,2,3-triazol-4-yl)-2-fluorophenyl) piperazin-1-carboxylate (0.480 g, 0.864 mmol) prepared in step 6 and trifluoroacetic acid (0.662 mL, 8.640 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(4-fluoro-3-(piperazin-1-yl)phenyl)-1H-1,2,3-triazol-1-yl)methyl)phenyl)-1,3,4-oxadiazole (0.330 g, 83.9%) in a yellow solid form.

$^1H$ NMR (400 MHz, $CDCl_3$) δ 7.90 (p, J=9.4 Hz, 4H), 7.34 (d, J=8.1 Hz, 2H), 7.27-7.22 (m, 1H), 7.05-6.70 (m, 2H), 5.56 (s, 2H), 3.17 (s, 8H); LRMS (ES) m/z 456.3 ($M^+$+1).

Example 281: Synthesis of compound 4397, 2-(difluoromethyl)-5-(3-fluoro-4-((4-(4-fluoro-3-(piperazin-1-yl)phenyl)-1H-1,2,3-triazol-1-yl)methyl)phenyl)-1,3,4-oxadiazole

[Step 1] Synthesis of tert-butyl 4-(5-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate

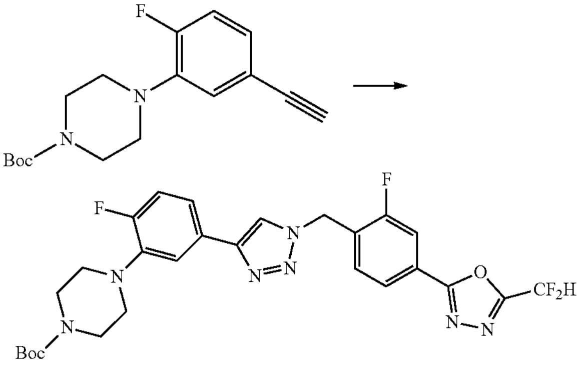

The tert-butyl 4-(5-ethynyl-2-fluorophenyl)piperazin-1-carboxylate (0.275 g, 0.904 mmol) prepared in step 5 of example 280, 2-(4-(azidomethyl)-3-fluorophenyl)-5-(difluoromethyl)-1,3,4-oxadiazole (0.292 g, 1.084 mmol) prepared in step 1 of example 2, copper(II) sulfate pentahydrate (0.002 g, 0.009 mmol) and sodium ascorbate (0.018 g, 0.090 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(5-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.480 g, 92.6%) in a white solid form.

[Step 2] Synthesis of Compound 4397

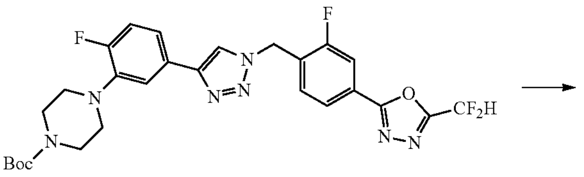

-continued

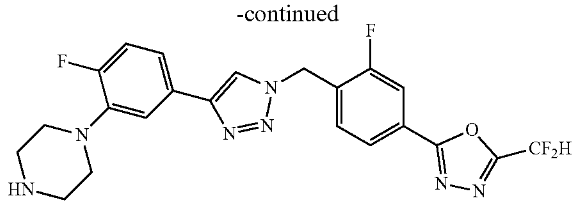

The tert-butyl 4-(5-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.480 g, 0.837 mmol) prepared in step 1 and trifluoroacetic acid (0.641 mL, 8.369 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(4-fluoro-3-(piperazin-1-yl)phenyl)-1H-1,2,3-triazol-1-yl)methyl)phenyl)-1,3,4-oxadiazole (0.350 g, 88.3%) in a yellow solid form.

$^1H$ NMR (400 MHz, $CDCl_3$) δ 7.86-7.73 (m, 3H), 7.47-7.34 (m, 2H), 7.22 (ddd, J=8.6, 4.1, 2.0 Hz, 1H), 7.07-6.68 (m, 2H), 5.64 (s, 2H), 3.17-2.90 (m, 8H); LRMS (ES) m/z 474.4 ($M^+$+1).

Example 282: Synthesis of compound 4398, 2-(4-((4-(3-((1S,4S)-2,5-diazabicyclo[2.2.1]heptan-2-yl)-4-fluorophenyl)-1H-1,2,3-triazol-1-yl)methyl)phenyl)-5-(difluoromethyl)-1,3,4-oxadiazole

[Step 1] Synthesis of tert-butyl (1S,4S)-5-(5-(1,3-dioxolan-2-yl)-2-fluorophenyl)-2,5-diazabicyclo[2.2.1]heptan-2-carboxylate

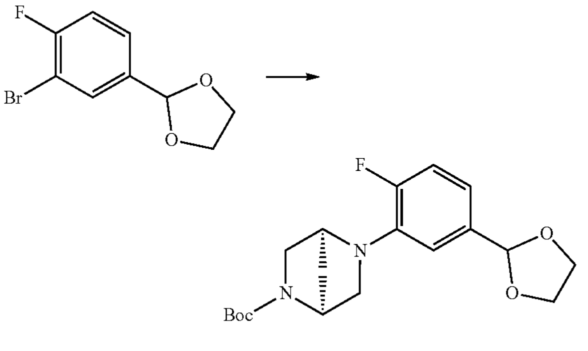

The 2-(3-bromo-4-fluorophenyl)-1,3-dioxolane (5.000 g, 20.238 mmol) prepared in step 1 of example 280, tert-butyl (1S,4S)-2,5-diazabicyclo[2.2.1]heptan-2-carboxylate (4.414 g, 22.262 mmol), tris(dibenzylidene acetone)dipalladium ($Pd_2(dba)_3$, 0.185 g, 0.202 mmol), rac-BINAP (0.252 g, 0.405 mmol) and NaOBut (3.890 g, 40.476 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl (1S,4S)-5-(5-(1,3-dioxolan-2-yl)-2-fluorophenyl)-2,5-diazabicyclo[2.2.1]heptan-2-carboxylate (3.740 g, 50.7%) in a yellow oil form.

[Step 2] Synthesis of tert-butyl (1S,4S)-5-(2-fluoro-5-formylphenyl)-2,5-diazabicyclo[2.2.1]heptan-2-carboxylate

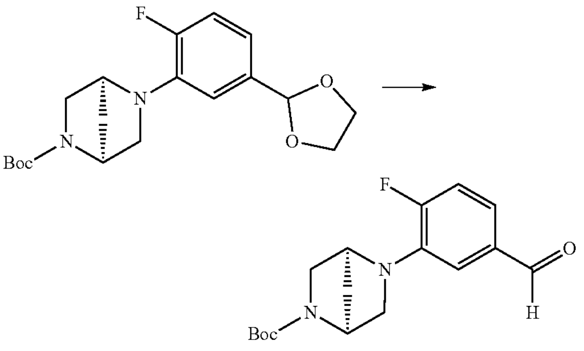

The tert-butyl (1S,4S)-5-(5-(1,3-dioxolan-2-yl)-2-fluorophenyl)-2,5-diazabicyclo[2.2.1]heptan-2-carboxylate (5.450 g, 14.955 mmol) prepared in step 1 and hydrochloric acid (1.00 M solution, 44.866 mL, 44.866 mmol) were dissolved in methanol (10 mL) at room temperature, after which the resulting solution was stirred at the same temperature for 4 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%), and concentrated to obtain tert-butyl (1S,4S)-5-(2-fluoro-5-formylphenyl)-2,5-diazabicyclo[2.2.1]heptan-2-carboxylate (4.200 g, 87.7%) in a yellow oil form.

[Step 3] Synthesis of tert-butyl (1S,4S)-5-(5-(2,2-dibromovinyl)-2-fluorophenyl)-2,5-diazabicyclo[2.2.1]heptan-2-carboxylate

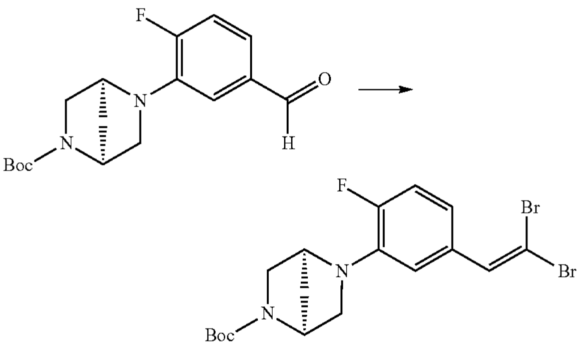

The tert-butyl (1S,4S)-5-(2-fluoro-5-formylphenyl)-2,5-diazabicyclo[2.2.1]heptan-2-carboxylate (4.300 g, 13.422 mmol) prepared in step 2, carbon tetrabromide (8.903 g, 26.845 mmol) and triphenylphosphine triphenylphosphine (14.082 g, 53.690 mmol) were dissolved in dichloromethane (100 mL) at room temperature, after which the resulting solution was stirred at the same temperature for two hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl (1S,4S)-5-(5-(2,2-dibromovinyl)-2-fluorophenyl)-2,5-diazabicyclo[2.2.1]heptan-2-carboxylate (2.500 g, 39.1%) in a white solid form.

[Step 4] Synthesis of tert-butyl (1S,4S)-5-(5-ethynyl-2-fluorophenyl)-2,5-diazabicyclo[2.2.1]heptan-2-carboxylate

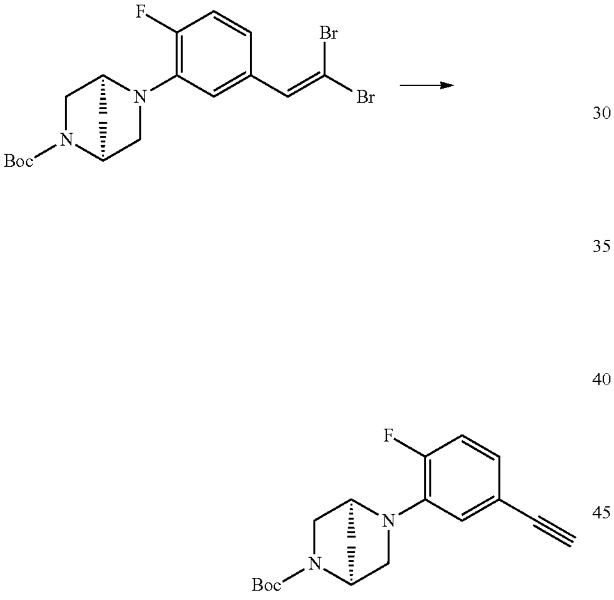

The tert-butyl (1S,4S)-5-(5-(2,2-dibromovinyl)-2-fluorophenyl)-2,5-diazabicyclo[2.2.1]heptan-2-carboxylate (2.500 g, 5.250 mmol) prepared in step 3 and 2,3,4,6,7,8,9,10-octahydropyrimido[1,2-a]azepine (3.141 mL, 21.000 mmol) were dissolved in acetonitrile (50 mL) at room temperature, after which the resulting solution was stirred at the same temperature for 16 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl (1S,4S)-5-(5-ethynyl-2-fluorophenyl)-2,5-diazabicyclo[2.2.1]heptan-2-carboxylate (0.450 g, 27.1%) in a white solid form.

[Step 5] Synthesis of tert-butyl (1S,4S)-5-(5-(1-(4-(5-(difluoromethyl)-1,3,4-oxadiazol-2-yl)benzyl)-1H-1,2,3-triazol-4-yl)-2-fluorophenyl)-2,5-diazabicyclo[2.2.1]heptan-2-carboxylate

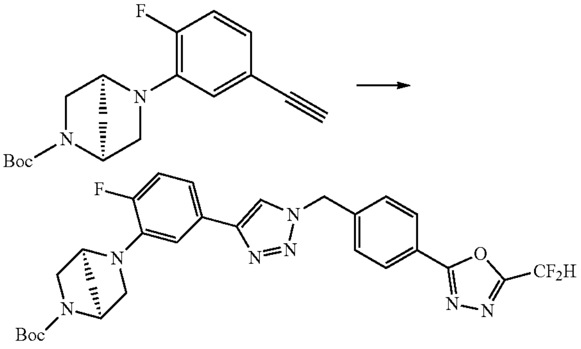

The tert-butyl (1S,4S)-5-(5-ethynyl-2-fluorophenyl)-2,5-diazabicyclo[2.2.1]heptan-2-carboxylate (0.220 g, 0.695 mmol) prepared in step 4, 2-(4-(azidomethyl)phenyl)-5-(difluoromethyl)-1,3,4-oxadiazole (0.210 g, 0.834 mmol) prepared in step 1 of example 1, copper(II) sulfate pentahydrate (0.002 g, 0.007 mmol) and sodium ascorbate (0.014 g, 0.070 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl (1S,4S)-5-(5-(1-(4-(5-(difluoromethyl)-1,3,4-oxadiazol-2-yl)benzyl)-1H-1,2,3-triazol-4-yl)-2-fluorophenyl)-2,5-diazabicyclo[2.2.1]heptan-2-carboxylate (0.200 g, 50.7%) in a white solid form.

[Step 6] Synthesis of Compound 4398

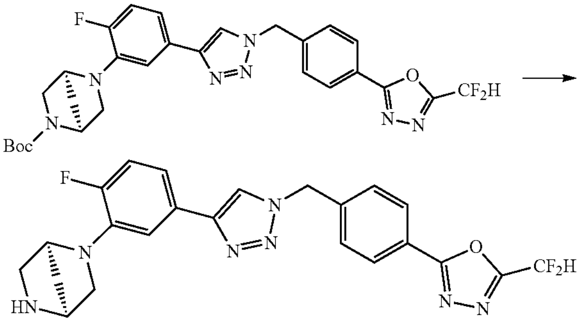

The tert-butyl (1S,4S)-5-(5-(1-(4-(5-(difluoromethyl)-1,3,4-oxadiazol-2-yl)benzyl)-1H-1,2,3-triazol-4-yl)-2-fluorophenyl)-2,5-diazabicyclo[2.2.1]heptan-2-carboxylate (0.200 g, 0.352 mmol) prepared in step 5 and trifluoroacetic acid (0.270 mL, 3.524 mmol) were dissolved in dichloromethane (25 mL) at room temperature, after which the resulting solution was stirred at the same temperature for 12 hours.

Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 10%) and concentrated to obtain 2-(4-((4-(3-((1S,4S)-2,5-diazabicyclo[2.2.1]heptan-2-yl)-4-fluorophenyl)-1H-1,2,3-triazol-1-yl)methyl)phenyl)-5-(difluoromethyl)-1,3,4-oxadiazole (0.055 g, 33.4%) in a yellow solid form.

$^1H$ NMR (400 MHz, $CDCl_3$) δ 7.88-7.77 (m, 3H), 7.38 (t, J=7.7 Hz, 1H), 7.13-7.07 (m, 1H), 7.07-6.75 (m, 3H), 5.64 (s, 2H), 4.49 (s, 1H), 4.08 (s, 1H), 3.68 (d, J=10.2 Hz, 1H), 3.51-3.23 (m, 2H), 3.16 (d, J=10.5 Hz, 1H), 2.08-1.83 (m, 2H); LRMS (ES) m/z 468.5 ($M^+$+1).

Example 283: Synthesis of compound 4399, 2-(4-((4-(3-((1S,4S)-2,5-diazabicyclo[2.2.1]heptan-2-yl)-4-fluorophenyl)-1H-1,2,3-triazol-1-yl)methyl)-3-fluorophenyl)-5-(difluoromethyl)-1,3,4-oxadiazole

[Step 1] Synthesis of tert-butyl (1S,4S)-5-(5-(1-(4-(5-(difluoromethyl)-1,3,4-oxadiazol-2-yl)-2-fluorobenzyl)-1H-1,2,3-triazol-4-yl)-2-fluorophenyl)-2,5-diazabicyclo[2.2.1]heptan-2-carboxylate

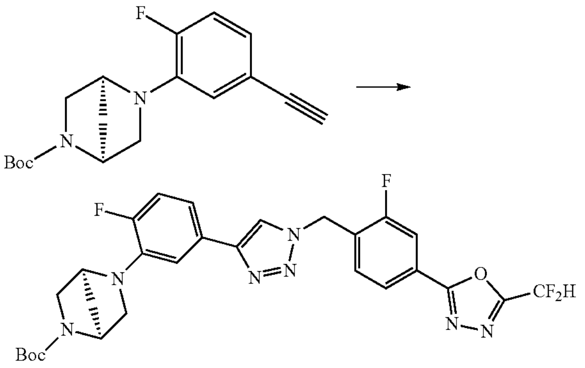

The tert-butyl (1S,4S)-5-(5-ethynyl-2-fluorophenyl)-2,5-diazabicyclo[2.2.1]heptan-2-carboxylate (0.220 g, 0.695 mmol) prepared in step 4 of example 281, 2-(4-(azidomethyl)-3-fluorophenyl)-5-(difluoromethyl)-1,3,4-oxadiazole (0.225 g, 0.834 mmol) prepared in step 1 of example 2, copper(II) sulfate pentahydrate (0.002 g, 0.007 mmol) and sodium ascorbate (0.014 g, 0.070 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl (1S,4S)-5-(5-(1-(4-(5-(difluoromethyl)-1,3,4-oxadiazol-2-yl)-2-fluorobenzyl)-1H-1,2,3-triazol-4-yl)-2-fluorophenyl)-2,5-diazabicyclo[2.2.1]heptan-2-carboxylate (0.200 g, 49.1%) in a white solid form.

[Step 2] Synthesis of Compound 4399

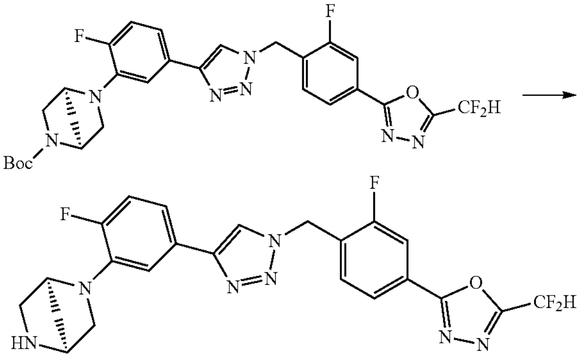

The tert-butyl (1S,4S)-5-(5-(1-(4-(5-(difluoromethyl)-1,3,4-oxadiazol-2-yl)-2-fluorobenzyl)-1H-1,2,3-triazol-4-yl)-2-fluorophenyl)-2,5-diazabicyclo[2.2.1]heptan-2-carboxylate (0.200 g, 0.342 mmol prepared in step 1 and trifluoroacetic acid (0.262 mL, 3.416 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=0 to 10%) and concentrated to obtain 2-(4-((4-(3-((1S,4S)-2,5-diazabicyclo[2.2.1]heptan-2-yl)-4-fluorophenyl)-1H-1,2,3-triazol-1-yl)methyl)-3-fluorophenyl)-5-(difluoromethyl)-1,3,4-oxadiazole (0.060 g, 36.2%) in a yellow solid form.

$^1H$ NMR (400 MHz, $CDCl_3$) δ 8.09-8.03 (m, 2H), 7.79 (s, 1H), 7.44-7.39 (m, 2H), 7.04-6.76 (m, 3H), 5.60 (s, 2H), 4.56 (s, 1H), 4.25 (s, 1H), 3.69 (d, J=10.9 Hz, 1H), 3.52 (d, J=10.8 Hz, 1H), 3.41 (d, J=11.0 Hz, 1H), 3.26 (d, J=10.8 Hz, 1H), 2.15-2.01 (m, 2H); LRMS (ES) m/z 486.5 ($M^+$+1).

Example 286: Synthesis of compound 4402, 2-(4-((4-(3-(azetidin-1-ylmethyl)phenyl)-1H-1,2,3-triazol-1-yl)methyl)-3-fluorophenyl)-5-(difluoromethyl)-1,3,4-oxadiazole

[Step 1] Synthesis of 3-(1-(4-(5-(difluoromethyl)-1,3,4-oxadiazol-2-yl)-2-fluorobenzyl)-1H-1,2,3-triazol-4-yl)benzaldehyde

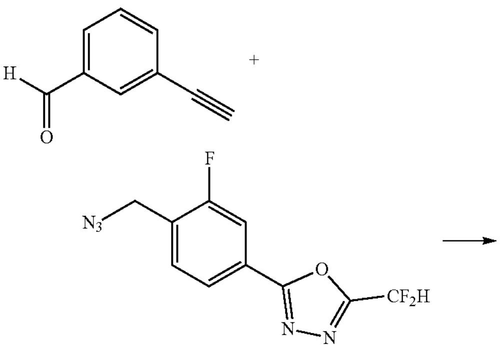

-continued

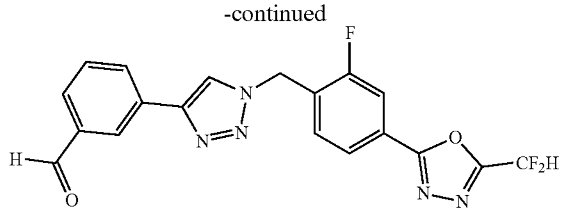

The 2-(4-(azidomethyl)-3-fluorophenyl)-5-(difluoromethyl)-1,3,4-oxadiazole (0.500 g, 1.857 mmol) prepared in step 1 of example 2 and 3-ethynylbenzaldehyde (0.242 g, 1.857 mmol) were dissolved in tert-butanol (3 mL)/water (3 mL) at room temperature, after which sodium ascorbate (1.00 M solution, 0.186 mL, 0.186 mmol) and copper(II) sulfate pentahydrate (0.50 M solution, 0.037 mL, 0.019 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 30%) and concentrated to obtain 3-(1-(4-(5-(difluoromethyl)-1,3,4-oxadiazol-2-yl)-2-fluorobenzyl)-1H-1,2,3-triazol-4-yl) benzaldehyde (0.620 g, 83.6%) in a white solid form.

[Step 2] Synthesis of Compound 4402

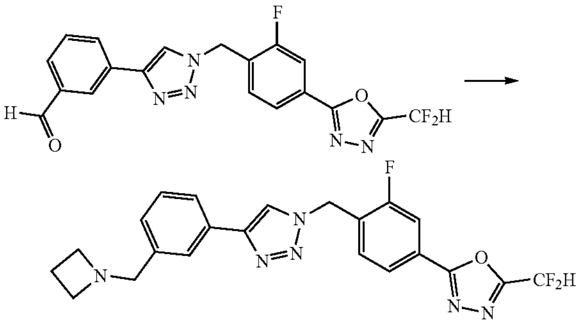

The 3-(1-(4-(5-(difluoromethyl)-1,3,4-oxadiazol-2-yl)-2-fluorobenzyl)-1H-1,2,3-triazol-4-yl)benzaldehyde (0.040 g, 0.100 mmol) prepared in step 1 and azetidine (0.028 g, 0.301 mmol) were dissolved in dichloromethane (1 mL) at room temperature, after which sodium triacetoxyborohydride (0.106 g, 0.501 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(4-((4-(3-(azetidin-1-ylmethyl)phenyl)-1H-1,2,3-triazol-1-yl) methyl)-3-fluorophenyl)-5-(difluoromethyl)-1,3,4-oxadiazole (0.034 g, 77.1%) in a white solid form.

$^1$H NMR (400 MHz, $CD_3OD$) δ 8.44 (s, 1H), 8.03-7.93 (m, 2H), 7.80-7.74 (m, 2H), 7.61 (t, J=7.7 Hz, 1H), 7.43 (t, J=8.0 Hz, 1H), 7.31 (d, J=7.7 Hz, 1H), 7.24 (t, J=51.6 Hz, 1H), 5.86 (s, 2H), 3.71 (s, 2H), 3.41-3.35 (m, 4H), 2.16 (p, J=7.2 Hz, 2H); LRMS (ES) m/z 441.5 ($M^+$+1).

The compounds of table 87 were synthesized according to substantially the same process as described above in the synthesis of compound 4402 with an exception of using 3-(1-(4-(5-(difluoromethyl)-1,3,4-oxadiazol-2-yl)-2-fluorobenzyl)-1H-1,2,3-triazol-4-yl)benzaldehyde and the reactant of table 86.

TABLE 86

| Example | Compound No. | Reactant | Yield (%) |
|---|---|---|---|
| 287 | 4403 | 3-fluoroazetidin | 58 |
| 288 | 4404 | Morpholine | 83 |
| 289 | 4405 | 4,4-difluoropiperidine | 61 |
| 290 | 4406 | 1-methylpiperazine | 70 |
| 291 | 4407 | 1-ethylpiperazine | 64 |
| 292 | 4408 | 1-isopropylpiperazine | 56 |
| 302 | 4418 | 3,3-difluoroazetidine | 60 |

TABLE 87

| Example | Compound No. | Compound Name, $^1$H-NMR, MS (ESI) |
|---|---|---|
| 287 | 4403 | 2-(difluoromethyl)-5-(3-fluoro-4-((4-(3-((3-fluoroazetidin-1-yl)methyl)phenyl)-1H-1,2,3-triazol-1-yl)methyl)phenyl)-1,3,4-oxadiazole $^1$H NMR (400 MHZ, $CD_3OD$) δ 8.45 (d, J = 1.1 Hz, 1H), 8.03-7.93 (m, 2H), 7.81-7.72 (m, 2H), 7.61 (t, J = 7.7 Hz, 1H), 7.46-7.38 (m, 1H), 7.35-7.29 (m, 1H), 7.24 (t, J = 51.6 Hz, 1H), 5.86 (s, 2H), 5.26-5.19 (m, 0.5H), 5.08 (s, 0.5H), 3.76 (s, 2H), 3.73-3.60 (m, 2H), 3.37 (s, 2H), 3.33-3.26 (m, 2H); LRMS (ES) m/z 459.5 ($M^+$ + 1). |
| 288 | 4404 | 4-(3-(1-(4-(5-(difluoromethyl)-1,3,4-oxadiazol-2-yl)-2-fluorobenzyl)-1H-1,2,3-triazol-4-yl)benzyl)morpholine<br>$^1$H NMR (400 MHZ, $CD_3OD$) δ 8.45 (s, 1H), 8.03-7.93 (m, 2H), 7.87-7.82 (m, 1H), 7.76 (dt, J = 7.6, 1.5 Hz, 1H), 7.61 (t, J = 7.7 Hz, 1H), 7.43 (t, J = 7.6 Hz, 1H), 7.39-7.10 (m, 2H), 5.86 (s, 2H), 3.74-3.68 (m, 4H), 3.59 (s, 2H), 2.50 (t, J = 4.7 Hz, 4H); LRMS (ES) m/z 471.5 ($M^+$ + 1). |
| 289 | 4405 | 2-(difluoromethyl)-5-(4-((4-(3-((4,4-difluoropiperidin-1-yl)methyl)phenyl)-1H-1,2,3-triazol-1-yl)methyl)-3-fluorophenyl)-1,3,4-oxadiazole<br>$^1$H NMR (400 MHZ, $CD_3OD$) δ 8.45 (s, 1H), 8.03-7.93 (m, 2H), 7.85 (d, J = 1.9 Hz, 1H), 7.76 (dt, J = 7.7, 1.6 Hz, 1H), 7.61 (t, J = 7.7 Hz, 1H), 7.43 (t, J = 7.6 Hz, 1H), 7.38-7.10 (m, 2H), 5.86 (s, 2H), 3.64 (s, 2H), 2.61 (t, J = 5.6 Hz, 4H), 2.01 (ddd, J = 19.5, 12.9, 5.7 Hz, 4H); LRMS (ES) m/z 505.5 ($M^+$ + 1). |

TABLE 87-continued

| Example | Compound No. | Compound Name, $^1$H-NMR, MS (ESI) |
|---|---|---|
| 290 | 4406 | 2-(difluoromethyl)-5-(3-fluoro-4-((4-(3-((4-methylpiperazin-1-yl)methyl)phenyl)-1H-1,2,3-triazol-1-yl)methyl)phenyl)-1,3,4-oxadiazole $^1$H NMR (400 MHZ, $CD_3OD$) δ 8.44 (s, 1H), 8.03-7.92 (m, 2H), 7.83 (t, J = 1.8 Hz, 1H), 7.76 (dt, J = 7.8, 1.5 Hz, 1H), 7.61 (t, J = 7.6 Hz, 1H), 7.43 (t, J = 7.6 Hz, 1H), 7.35 (dt, J = 7.8, 1.4 Hz, 1H), 7.24 (t, J = 51.6 Hz, 1H), 5.86 (s, 2H), 3.61 (s, 2H), 2.55 (s, 8H), 2.31 (s, 3H); LRMS (ES) m/z 484.6 ($M^+$ + 1). |
| 291 | 4407 | 2-(difluoromethyl)-5-(4-((4-(3-((4-ethylpiperazin-1-yl)methyl)phenyl)-1H-1,2,3-triazol-1-yl)methyl)-3-fluorophenyl)-1,3,4-oxadiazole $^1$H NMR (400 MHZ, $CD_3OD$) δ 8.44 (s, 1H), 8.03-7.93 (m, 2H), 7.83 (d, J = 1.8 Hz, 1H), 7.77 (dt, J = 7.7, 1.5 Hz, 1H), 7.61 (t, J = 7.7 Hz, 1H), 7.43 (t, J = 7.7 Hz, 1H), 7.37-7.34 (m, 1H), 7.24 (t, J = 51.6 Hz, 1H), 5.86 (s, 2H), 3.61 (s, 2H), 2.82-2.36 (m, 10H), 1.11 (t, J = 7.3 Hz, 3H); LRMS (ES) m/z 498.5 ($M^+$ + 1). |
| 292 | 4408 | 2-(difluoromethyl)-5-(3-fluoro-4-((4-(3-((4-isopropylpiperazin-1- $^1$H NMR (400 MHZ, $CD_3OD$) δ 8.44 (s, 1H), 8.03-7.93 (m, 2H), 7.83 (s, 1H), 7.80-7.73 (m, 1H), 7.61 (t, J = 7.7 Hz, 1H), 7.43 (t, J = 7.7 Hz, 1H), 7.38-7.11 (m, 2H), 5.86 (s, 2H), 3.61 (s, 2H), 2.63 (s, 9H), 1.10 (d, J = 6.6 Hz, 6H); LRMS (ES) m/z 512.6 ($M^+$ + 1). |
| 302 | 4418 | 2-(4-((4-(3-((3,3-difluoroazetidin-1-yl)methyl)phenyl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.46 (s, 1H), 8.03-7.93 (m, 2H), 7.82 (s, 1H), 7.78 (d, J = 7.9 Hz, 1H), 7.61 (t, J = 7.7 Hz, 1H), 7.44 (t, J = 7.6 Hz, 1H), 7.35 (d, J = 7.7 Hz, 1H), 7.24 (t, J = 51.6 Hz, 1H), 5.86 (s, 2H), 3.83 (s, 2H), 3.67 (t, J = 12.1 Hz, 4H); LRMS (ES) m/z 477.4 ($M^+$ + 1). |

Example 293: Synthesis of compound 4409, 2-(4-((4-(3-(azetidin-1-ylmethyl)phenyl)-1H-1,2,3-triazol-1-yl)methyl)phenyl)-5-(difluoromethyl)-1,3,4-oxadiazole

[Step 1] Synthesis of 3-(1-(4-(5-(difluoromethyl)-1,3,4-oxadiazol-2-yl)benzyl)-1H-1,2,3-triazol-4-yl)benzaldehyde

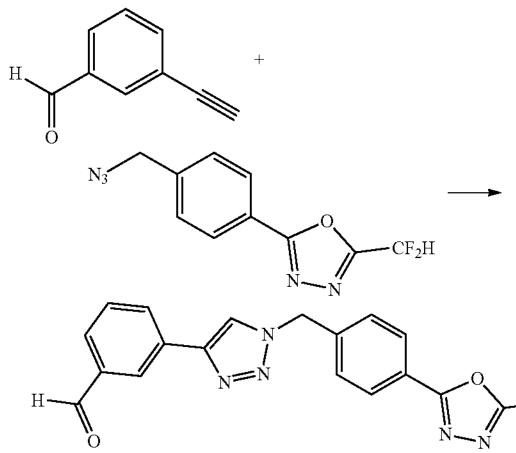

The 2-(4-(azidomethyl)phenyl)-5-(difluoromethyl)-1,3,4-oxadiazole (0.500 g, 1.990 mmol) prepared in step 1 of example 1 and 3-ethynylbenzaldehyde (0.259 g, 1.990 mmol) were dissolved in tert-butanol (3 mL)/water (3 mL) at room temperature, after which sodium ascorbate (1.00 M solution, 0.199 mL, 0.199 mmol) and copper(II) sulfate pentahydrate (0.50 M solution, 0.040 mL, 0.020 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 30%) and concentrated to obtain 3-(1-(4-(5-(difluoromethyl)-1,3,4-oxadiazol-2-yl)benzyl)-1H-1,2,3-triazol-4-yl)benzaldehyde (0.640 g, 84.3%) in a white solid form.

[Step 2] Synthesis of Compound 4409

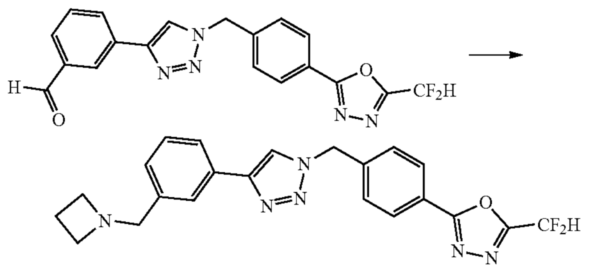

The 3-(1-(4-(5-(difluoromethyl)-1,3,4-oxadiazol-2-yl)benzyl)-1H-1,2,3-triazol-4-yl)benzaldehyde (0.050 g, 0.131 mmol) prepared in step 1 and azetidine (0.037 g, 0.393 mmol) were dissolved in dichloromethane (1 mL) at room temperature, after which sodium triacetoxyborohydride (0.139 g, 0.656 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(4-

((4-(3-(azetidin-1-ylmethyl)phenyl)-1H-1,2,3-triazol-1-yl)methyl)phenyl)-5-(difluoromethyl)-1,3,4-oxadiazole (0.037 g, 66.8%) in a white solid form.

$^1$H NMR (400 MHz, $CD_3OD$) δ 8.43 (s, 1H), 8.21-8.13 (m, 2H), 7.76 (dd, J=6.4, 1.4 Hz, 2H), 7.65-7.58 (m, 2H), 7.46-7.39 (m, 1H), 7.31 (dt, J=7.7, 1.5 Hz, 1H), 7.23 (t, J=51.6 Hz, 1H), 5.81 (s, 2H), 3.69 (s, 2H), 3.36 (d, J=7.2 Hz, 4H), 2.15 (p, J=7.2 Hz, 2H); LRMS (ES) m/z 423.4 ($M^+$+1).

The compounds of table 89 were synthesized according to substantially the same process as described above in the synthesis of compound 4409 with an exception of using 3-(1-(4-(5-(difluoromethyl)-1,3,4-oxadiazol-2-yl)benzyl)-1H-1,2,3-triazol-4-yl)benzaldehyde and the reactant of table 88.

TABLE 88

| Example | Compound No. | Reactant | Yield (%) |
|---|---|---|---|
| 294 | 4410 | 3-fluoroazetidin | 60 |
| 295 | 4411 | Morpholine | 64 |
| 296 | 4412 | Thiomorpholine 1,1-dioxide | 38 |
| 297 | 4413 | 4,4-difluoropiperidine | 54 |
| 298 | 4414 | 1-methylpiperazine | 70 |
| 299 | 4415 | 1-ethylpiperazine | 50 |
| 300 | 4416 | 1-isopropylpiperazine | 44 |
| 301 | 4417 | 3,3-difluoroazetidine | 53 |

TABLE 89

| Example | Compound No | Compound Name, $^1$H-NMR, MS (ESI) |
|---|---|---|
| 294 | 4410 | 2-(difluoromethyl)-5-(4-((4-(3-((3-fluoroazetidin-1-yl)methyl)phenyl)-1H-1,2,3-triazol-1-yl)methyl)phenyl)-1,3,4-oxadiazole<br>$^1$H NMR (400 MHZ, $CD_3OD$) δ 8.44 (s, 1H), 8.21-8.13 (m, 2H), 7.81-7.74 (m, 2H), 7.65-7.58 (m, 2H), 7.46-7.39 (m, 1H), 7.34-7.30 (m, 1H), 7.23 (t, J = 51.7 Hz, 1H), 5.81 (s, 2H), 5.25-5.18 (m, 0.5H), 5.11-5.04 (m, 0.5H), 3.76 (s, 2H), 3.73-3.60 (m, 2H), 3.37 (d, J = 4.3 Hz, 1H), 3.31-3.26 (m, 1H); LRMS (ES) m/z 441.5 ($M^+$ + 1). |
| 295 | 4411 | 4-(3-(1-(4-(5-(difluoromethyl)-1,3,4-oxadiazol-2-yl)benzyl)-1H-1,2,3-triazol-4-yl)benzyl)morpholine<br>$^1$H NMR (400 MHZ, $CD_3OD$) δ 8.44 (s, 1H), 8.21-8.13 (m, 2H), 7.84 (s, 1H), 7.76 (dt, J = 7.6, 1.6 Hz, 1H), 7.65 -7.59 (m, 2H), 7.43 (t, J = 7.6 Hz, 1H), 7.39-7.35 (m, 1H), 7.25-7.10 (m, 1H), 5.80 (s, 2H), 3.74-3.67 (m, 4H), 3.59 (s, 2H), 2.50 (t, J = 4.7 Hz, 4H); LRMS (ES) m/z 453.5 ($M^+$ + 1). |
| 296 | 4412 | 4-(3-(1-(4-(5-(difluoromethyl)-1,3,4-oxadiazol-2-yl)benzyl)-1H-1,2,3-triazol-4-yl)benzyl)thiomorpholine 1,1-dioxide<br>$^1$H NMR (400 MHZ, $CD_3OD$) δ 8.46 (s, 1H), 8.19-8.14 (m, 2H), 7.88 (s, 1H), 7.75 (d, J = 7.7 Hz, 1H), 7.62 (d, J = 8.3 Hz, 2H), 7.44 (t, J = 7.6 Hz, 1H), 7.41-7.09 (m, 2H), 5.81 (s, 2H), 3.76 (s, 2H), 3.17-3.11 (m, 4H), 3.02 (dd, J = 7.1, 3.5 Hz, 4H); LRMS (ES) m/z 501.3 ($M^+$ + 1). |
| 297 | 4413 | 2-(difluoromethyl)-5-(4-((4-(3-((4,4-difluoropiperidin-1-yl)methyl)phenyl)-1H-1,2,3-triazol-1-yl)methyl)phenyl)-1,3,4-oxadiazole<br>$^1$H NMR (400 MHZ, $CD_3OD$) δ 8.44 (s, 1H), 8.21-8.14 (m, 2H), 7.84 (s, 1H), 7.76 (d, J = 7.6 Hz, 1H), 7.62 (d, J =8.3 Hz, 2H), 7.43 (t, J = 7.6 Hz, 1H), 7.39-7.33 (m, 1H), 7.25-7.08 (m, 1H), 5.80 (s, 2H), 3.64 (s, 2H), 2.65-2.56 (m, 4H), 2.00 (tt, J = 13.1, 5.8 Hz, 4H); LRMS (ES) m/z 487.3 ($M^+$ + 1). |
| 298 | 4414 | 2-(difluoromethyl)-5-(4-((4-(3-((4-methylpiperazin-1-yl)methyl)phenyl)-1H-<br>$^1$H NMR (400 MHZ, $CD_3OD$) δ 8.44 (s, 1H), 8.21-8.13 (m, 2H), 7.83 (s, 1H), 7.76 (dt, J = 7.8, 1.5 Hz, 1H), 7.62 (d, J = 8.4 Hz, 2H), 7.43 (t, J = 7.7 Hz, 1H), 7.37-7.33 (m, 1H), 7.25-7.09 (m, 1H), 5.80 (s, 2H), 3.61 (s, 2H), 2.57 (br s, 8H), 2.32 (s, 3H); LRMS (ES) m/z 466.3 ($M^+$ + 1). |
| 299 | 4415 | 2-(difluoromethyl)-5-(4-((4-(3-((4-ethylpiperazin-1-yl)methyl)phenyl)-1H-1,2,3-triazol-1-yl)methyl)phenyl)-1,3,4-oxadiazole<br>$^1$H NMR (400 MHZ, $CD_3OD$) δ 8.44 (s, 1H), 8.17 (d, J = 8.4 Hz, 2H), 7.83 (s, 1H), 7.80-7.73 (m, 1H), 7.62 (d, J = 8.3 Hz, 2H), 7.43 (t, J = 7.6 Hz, 1H), 7.38-7.33 (m, 1H), 7.25-7.09 (m, 1H), 5.80 (s, 2H), 3.61 (s, 2H), 2.71-2.38 (m, 10H), 1.11 (t, J = 7.2 Hz, 3H); LRMS (ES) m/z 480.5 ($M^+$ + 1). |
| 300 | 4416 | 2-(difluoromethyl)-5-(4-((4-(3-((4-isopropylpiperazin-1-yl)methyl)phenyl)-1H-1,2,3-triazol-1-yl)methyl)phenyl)-1,3,4-oxadiazole<br>$^1$H NMR (400 MHZ, $CD_3OD$) δ 8.44 (s, 1H), 8.21-8.14 (m, 2H), 7.83 (d, J = 1.8 Hz, 1H), 7.80-7.73 (m, 1H), 7.62 (d, J = 8.4 Hz, 2H), 7.43 (t, J = 7.6 Hz, 1H), 7.39-7.32 (m, 1H), 7.25-7.09 (m, 1H), 5.80 (s, 2H), 3.61 (s, 2H), 2.73-2.48 (m, 9H), 1.09 (d, J = 6.6 Hz, 6H); LRMS (ES) m/z 494.6 ($M^+$ + 1). |
| 301 | 4417 | 2-(4-((4-(3-((3,3-difluoroazetidin-1-yl)methyl)phenyl)-1H-1,2,3-triazol-1-yl)methyl)phenyl)-5-(difluoromethyl)-1,3,4-oxadiazole<br>$^1$H NMR (400 MHZ, $CD_3OD$) δ 8.45 (s, 1H), 8.21-8.13 (m, 2H), 7.81 (d, J = 1.9 Hz, 1H), 7.77 (dt, J = 7.7, 1.5 Hz, 1H), 7.62 (d, J = 8.4 Hz, 2H), 7.44 (t, J = 7.7 Hz, 1H), 7.36-7.32 (m, 1H), 7.23 (t, J = 51.6 Hz, 1H), 5.81 (s, 2H), 3.83 (s, 2H), 3.67 (t, J = 12.1 Hz, 4H); LRMS (ES) m/z 459.4($M^+$ + 1). |

Example 303: Synthesis of compound 4419, 2-(difluoromethyl)-5-(4-((4-(4-fluoro-3-(4-methylpiperazin-1-yl)phenyl)-1H-1,2,3-triazol-1-yl)methyl)phenyl)-1,3,4-oxadiazole

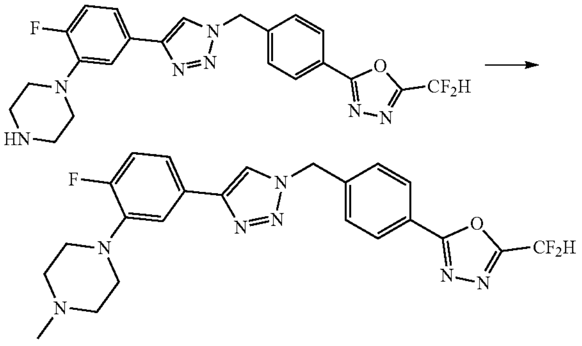

The 2-(difluoromethyl)-5-(4-((4-(4-fluoro-3-(piperazin-1-yl)phenyl)-1H-1,2,3-triazol-1-yl)methyl)phenyl)-1,3,4-oxadiazole (0.060 g, 0.132 mmol) prepared in step 7 of example 280, formaldehyde (0.008 g, 0.263 mmol) and acetic acid (0.008 mL, 0.145 mmol) were dissolved in dichloromethane (5 mL) at room temperature, after which sodium triacetoxyborohydride (0.056 g, 0.263 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(4-fluoro-3-(4-methylpiperazin-1-yl)phenyl)-1H-1,2,3-triazol-1-yl)methyl)phenyl)-1,3,4-oxadiazole (0.035 g, 56.6%) in a white solid form.

$^1H$ NMR (400 MHz, $CDCl_3$) δ 8.10 (d, J=7.9 Hz, 2H), 7.70 (s, 1H), 7.45 (t, J=9.3 Hz, 3H), 7.30-7.22 (m, 1H), 7.02 (dd, J=9.3, 3.1 Hz, 1H), 7.00-6.75 (m, 1H), 5.65 (s, 2H), 3.16 (t, J=4.8 Hz, 4H), 2.60 (t, J=4.8 Hz, 4H), 2.34 (s, 3H); LRMS (ES) m/z 470.0 ($M^+$+1).

The compounds of table 91 were synthesized according to substantially the same process as described above in the synthesis of compound 4419 with an exception of using 2-(difluoromethyl)-5-(4-((4-(4-fluoro-3-(piperazin-1-yl)phenyl)-1H-1,2,3-triazol-1-yl)methyl)phenyl)-1,3,4-oxadiazole and the reactant of table 90.

TABLE 90

| Example | Compound No. | Reactant | Yield (%) |
|---|---|---|---|
| 304 | 4420 | Acetaldehyde | 53 |
| 305 | 4421 | Propan-2-one | 55 |
| 306 | 4422 | Cyclobutanone | 55 |

TABLE 91

| Example | Compound No. | Compound Name, $^1H$-NMR, MS (ESI) |
|---|---|---|
| 304 | 4420 | 2-(difluoromethyl)-5-(4-((4-(3-(4-ethylpiperazin-1-yl)-4-fluorophenyl)-1H-1,2,3-triazol-1-yl)methyl)phenyl)-1,3,4-oxadiazole $^1H$ NMR (400 MHZ, $CDCl_3$) δ 8.08 (d, J = 7.9 Hz, 2H), 7.71 (s, 1H), 7.42 (d, J = 7.9 Hz, 3H), 7.25 (dd, J = 8.0, 3.9 Hz, 1H), 7.01 (dd, J = 11.3, 3.2 Hz, 1H), 6.98-6.75 (m, 1H), 5.63 (s, 2H), 3.15 (t, J = 5.9 Hz, 4H), 2.67-2.60 (m, 4H), 2.48 (q, J = 7.1 Hz, 2H), 1.17-1.06 (m, 3H); LRMS (ES) m/z 484.6 ($M^+$ + 1). |
| 305 | 4421 | 2-(difluoromethyl)-5-(4-((4-(4-fluoro-3-(4-isopropylpiperazin-1-yl)phenyl)-1H-1,2,3-triazol-1-yl)methyl)phenyl)-1,3,4-oxadiazole $^1H$ NMR (400 MHZ, $CDCl_3$) δ 8.17-8.10 (m, 2H), 7.68 (s, 1H), 7.51-7.42 (m, 3H), 7.31 (ddd, J=8.3, 4.3, 2.1 Hz, 1H), 7.09-7.03 (m, 1H), 7.03-6.76 (m, 1H), 5.67 (s, 2H), 3.23 (t, J = 4.9 Hz, 4H), 2.82 (dt, J = 17.7, 5.7 Hz, 5H), 1.14 (d, J = 6.5 Hz, 6H); LRMS (ES) m/z 498.55 ($M^+$ + 1). |
| 306 | 4422 | 2-(4-((4-(3-(4-cyclobutylpiperazin-1-yl)-4-fluorophenyl)-1H-1,2,3-triazol-1-yl)methyl)phenyl)-5-(difluoromethyl)-1,3,4-oxadiazol $^1H$ NMR (400 MHZ, $CDCl_3$) δ 8.11 (d, J = 8.0 Hz, 2H), 7.69 (s, 1H), 7.45 (td, J = 5.6, 2.6 Hz, 3H), 7.30-7.22 (m, 1H), 7.03 (dd, J = 9.0, 3.3 Hz, 1H), 7.00-6.76 (m, 1H), 5.65 (s, 2H), 3.17 (t, J = 4.9 Hz, 4H), 2.82 (p, J = 8.1 Hz, 1H), 2.53 (t, J = 4.9 Hz, 4H), 2.05 (qd, J = 9.6, 8.5, 2.7 Hz, 2H), 2.00-1.86 (m, 2H), 1.79-1.62 (m, 2H); LRMS (ES) m/z 510.2 ($M^+$ + 1). |

Example 307: Synthesis of compound 4424, 2-(difluoromethyl)-5-(3-fluoro-4-((4-(4-fluoro-3-(4-methylpiperazin-1-yl)phenyl)-1H-1,2,3-triazol-1-yl)methyl)phenyl)-1,3,4-oxadiazol

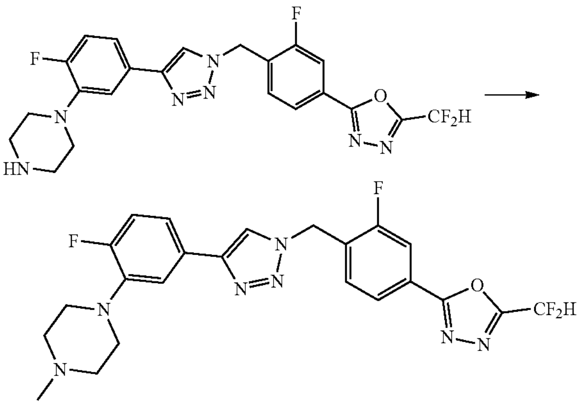

The 2-(difluoromethyl)-5-(3-fluoro-4-((4-(4-fluoro-3-(piperazin-1-yl)phenyl)-1H-1,2,3-triazol-1-yl)methyl)phenyl)-1,3,4-oxadiazole (0.060 g, 0.127 mmol) prepared in step 2 of example 281, formaldehyde (0.008 g, 0.253 mmol) and acetic acid (0.008 mL, 0.139 mmol) were dissolved in dichloromethane (5 mL) at room temperature, after which sodium triacetoxyborohydride (0.054 g, 0.253 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(4-fluoro-3-(4-methylpiperazin-1-yl)phenyl)-1H-1,2,3-triazol-1-yl)methyl)phenyl)-1,3,4-oxadiazole (0.043 g, 69.6%) in a white solid form.

$^1$H NMR (400 MHz, $CDCl_3$) δ 7.86 (dd, J=8.6, 4.9 Hz, 2H), 7.78 (s, 1H), 7.43 (q, J=8.2, 7.5 Hz, 2H), 7.25 (d, J=5.6 Hz, 1H), 7.06-7.00 (m, 1H), 6.99-6.75 (m, 1H), 5.68 (s, 2H), 3.16 (t, J=4.9 Hz, 4H), 2.61 (t, J=4.9 Hz, 4H), 2.34 (s, 3H); LRMS (ES) m/z 488.3 ($M^+$+1).

The compounds of table 93 were synthesized according to substantially the same process as described above in the synthesis of compound 4424 with an exception of using 2-(difluoromethyl)-5-(3-fluoro-4-((4-(4-fluoro-3-(piperazin-1-yl)phenyl)-1H-1,2,3-triazol-1-yl)methyl)phenyl)-1,3,4-oxadiazole and the reactant of table 92.

TABLE 92

| Example | Compound No. | Reactant | Yield (%) |
|---|---|---|---|
| 308 | 4425 | Propan-2-one | 69 |
| 309 | 4426 | Cyclobutanone | 67 |
| 310 | 4427 | Oxetan-3-one | 66 |

Example 311: Synthesis of compound 4429, 2-(difluoromethyl)-5-(4-((4-(4-fluoro-3-((1S,4S)-5-methyl-2,5-diazabicyclo[2.2.1]heptan-2-yl)phenyl)-1H-1,2,3-triazol-1-yl)methyl)phenyl)-1,3,4-oxadiazole

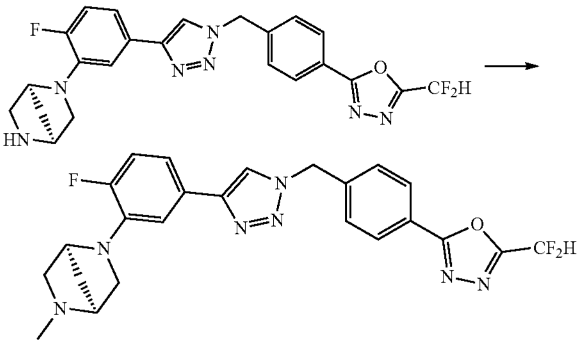

The 2-(4-((4-(3-((1S,4S)-2,5-diazabicyclo[2.2.1]heptan-2-yl)-4-fluorophenyl)-1H-1,2,3-triazol-1-yl)methyl)phenyl)-5-(difluoromethyl)-1,3,4-oxadiazole (0.050 g, 0.107 mmol) prepared in step 6 of example 282, formaldehyde (0.006 g, 0.214 mmol) and acetic acid (0.007 mL, 0.118 mmol) were dissolved in dichloromethane (5 mL) at room temperature, after which sodium triacetoxyborohydride (0.045 g, 0.214 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(4-fluoro-3-((1S,4S)-5-methyl-2,5-diazabicyclo[2.2.1]heptan-2-yl)phenyl)-1H-1,2,3-triazol-1-yl)methyl)phenyl)-1,3,4-oxadiazole(0.033 g, 64.1%) in a white solid form.

$^1$H NMR (400 MHz, $CDCl_3$) δ 8.16-8.05 (m, 2H), 7.73 (s, 1H), 7.49-7.41 (m, 2H), 7.26-7.18 (m, 1H), 7.06-6.76 (m,

TABLE 93

| Example | Compound No. | Compound Name, $^1$H-NMR, MS (ESI) |
|---|---|---|
| 308 | 4425 | 2-(difluoromethyl)-5-(3-fluoro-4-((4-(4-fluoro-3-(4-isopropylpiperazin-1- $^1$H NMR (400 MHZ, $CDCl_3$) δ 7.93-7.84 (m, 2H), 7.77 (s, 1H), 7.49-7.39 (m, 2H), 7.28 (dq, J = 6.4, 2.2 Hz, 1H), 7.04 (dd, J = 7.7, 4.6 Hz, 1H), 7.01-6.77 (m, 1H), 5.69 (s, 2H), 3.18 (t, J = 4.8 Hz, 4H), 2.74 (dt, J = 9.7, 5.6 Hz, 5H), 1.09 (d, J = 6.5 Hz, 6H); LRMS (ES) m/z 516.1 ($M^+$ + 1). |
| 309 | 4426 | 2-(4-((4-(3-(4-cyclobutylpiperazin-1-yl)-4-fluorophenyl)-1H-1,2,3-triazol-1-yl)methyl)-3-fluorophenyl)-5-(difluoromethyl)-1,3,4-oxadiazole $^1$H NMR (400 MHZ, $CDCl_3$) δ 7.90-7.82 (m, 2H), 7.77 (s, 1H), 7.47-7.37 (m, 2H), 7.30-7.22 (m, 1H), 7.02 (dd, J = 11.3, 3.0 Hz, 1H), 6.99-6.76 (m, 1H), 5.68 (s, 2H), 3.16 (t, J = 4.8 Hz, 4H), 2.81 (p, J = 7.9, 7.2 Hz, 1H), 2.52 (t, J = 4.8 Hz, 4H), 2.10-2.00 (m, 2H), 1.98-1.85 (m, 2H), 1.78-1.55 (m, 2H); LRMS (ES) m/z 528.1 ($M^+$ + 1). |
| 310 | 4427 | 2-(difluoromethyl)-5-(3-fluoro-4-((4-(4-fluoro-3-(4-(oxetan-3-yl)piperazin-1-yl)phenyl)-1H-1,2,3-triazol-1-yl)methyl)phenyl)-1,3,4-oxadiazole $^1$H NMR (400 MHZ, $CDCl_3$) δ 7.91-7.83 (m, 2H), 7.78 (s, 1H), 7.50-7.38 (m, 2H), 7.30-7.22 (m, 1H), 7.07-7.01 (m, 1H), 7.00-6.77 (m, 1H), 5.69 (s, 2H), 4.65 (dt, J = 14.7, 6.4 Hz, 4H), 3.56 (p, J = 6.4 Hz, 1H), 3.18 (t, J = 4.8 Hz, 4H), 2.51 (t, J = 4.8 Hz, 4H); LRMS (ES) m/z 530.4 ($M^+$ + 1). |

3H), 5.65 (s, 2H), 4.45 (s, 1H), 3.73 (s, 1H), 3.61 (dd, J=3.0, 1.6 Hz, 2H), 3.11 (dd, J=10.4, 2.2 Hz, 1H), 2.98 (dd, J=10.5, 1.7 Hz, 1H), 2.52 (s, 3H), 2.10 (dt, J=10.2, 1.7 Hz, 1H), 2.06-1.97 (m, 1H); LRMS (ES) m/z 482.1 ($M^{+}$+1).

Example 312: Synthesis of compound 4430, 2-(difluoromethyl)-5-(3-fluoro-4-((4-(4-fluoro-3-((1S,4S)-5-methyl-2,5-diazabicyclo[2.2.1]heptan-2-yl)phenyl)-1H-1,2,3-triazol-1-yl)methyl)phenyl)-1,3,4-oxadiazole

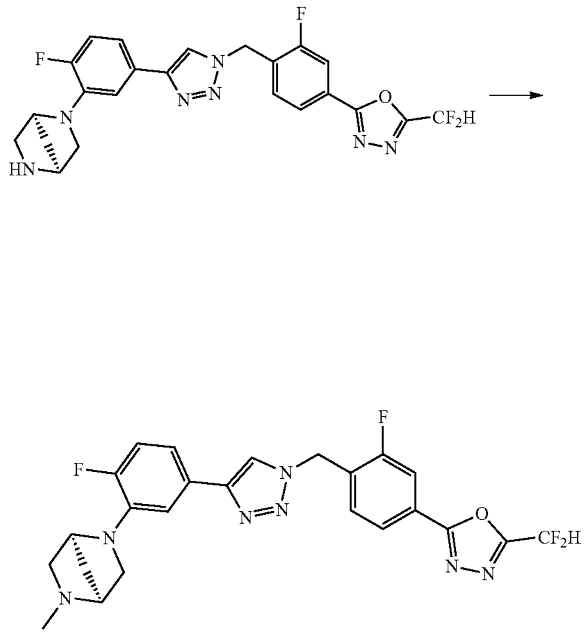

The 2-(4-((4-(3-((1S,4S)-2,5-diazabicyclo[2.2.1]heptan-2-yl)phenyl)-1H-1,2,3-triazol-1-yl)methyl)-3-fluorophenyl)-5-(difluoromethyl)-1,3,4-oxadiazole (0.060 g, 0.128 mmol) prepared in step 2 of example 283, paraformaldehyde (0.008 g, 0.257 mmol) and acetic acid (0.008 mL, 0.141 mmol) were dissolved in dichloromethane (5 mL) at room temperature, after which sodium triacetoxyborohydride (0.054 g, 0.257 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(3-((1S,4S)-5-methyl-2,5-diazabicyclo[2.2.1]heptan-2-yl)phenyl)-1H-1,2,3-triazol-1-yl)methyl)phenyl)-1,3,4-oxadiazole (0.025 g, 40.5%) in a white solid form.

$^{1}$H NMR (400 MHz, $CDCl_3$) δ 7.89-7.78 (m, 3H), 7.40 (dd, J=8.2, 7.2 Hz, 1H), 7.20-7.13 (m, 1H), 7.05-6.76 (m, 3H), 5.67 (s, 2H), 4.40 (s, 1H), 3.65 (d, J=2.3 Hz, 1H), 3.62-3.49 (m, 2H), 3.05 (dd, J=10.3, 2.2 Hz, 1H), 2.92 (dd, J=10.3, 1.6 Hz, 1H), 2.47 (s, 3H), 2.08-2.00 (m, 1H), 1.96 (q, J=1.9, 1.5 Hz, 1H); LRMS (ES) m/z 500.4 ($M^{+}$+1).

Example 313: Synthesis of compound 4431, N-(3-(1-(4-(5-(difluoromethyl)-1,3,4-oxadiazol-2-yl)-2-fluorobenzyl)-1H-1,2,3-triazol-4-yl)-2-fluorophenyl)-1-methylpiperidin-4-amine

[Step 1] Synthesis of 3-(1-(4-(5-(difluoromethyl)-1,3,4-oxadiazol-2-yl)-2-fluorobenzyl)-1H-1,2,3-triazol-4-yl)-2-fluoroaniline

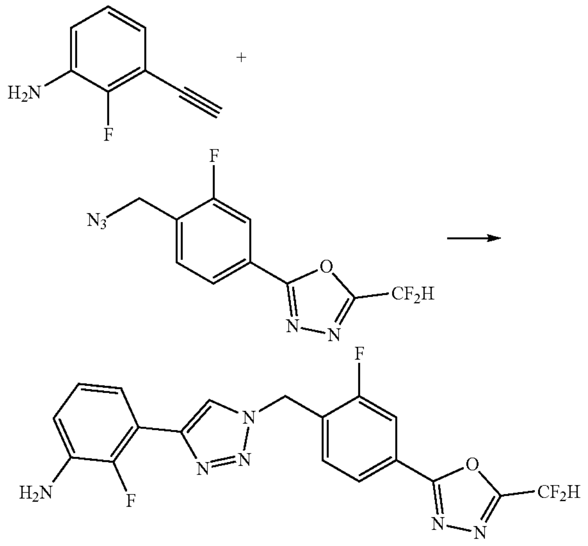

The 2-(4-(azidomethyl)-3-fluorophenyl)-5-(difluoromethyl)-1,3,4-oxadiazole (0.300 g, 1.114 mmol) prepared in step 1 of example 2, 3-ethynyl-2-fluoroaniline (0.181 g, 1.337 mmol), sodium ascorbate (1.00 M solution, 0.111 mL, 0.111 mmol), and copper(II) sulfate pentahydrate (0.50 M solution, 0.022 mL, 0.011 mmol) were dissolved in tert-butanol (10 mL)/water (10 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 40%) and concentrated to obtain 3-(1-(4-(5-(difluoromethyl)-1,3,4-oxadiazol-2-yl)-2-fluorobenzyl)-1H-1,2,3-triazol-4-yl)-2-fluoroaniline (0.410 g, 91.0%) in a white solid form.

[Step 2] Synthesis of Compound 4431

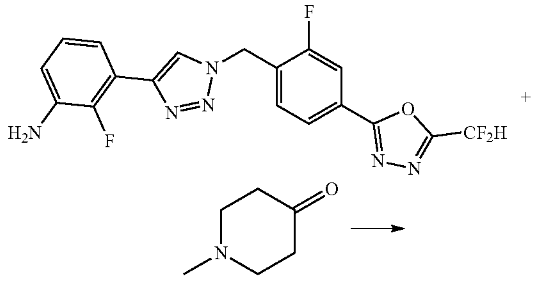

-continued

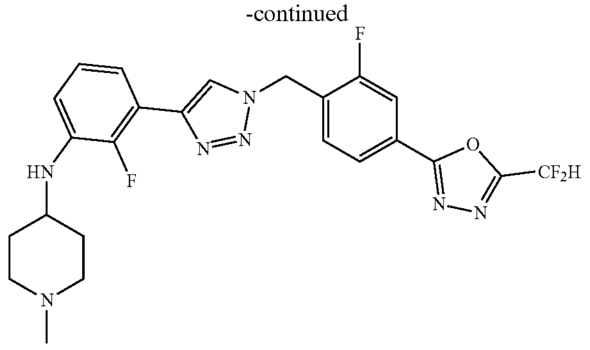

The 3-(1-(4-(5-(difluoromethyl)-1,3,4-oxadiazol-2-yl)-2-fluorobenzyl)-1H-1,2,3-triazol-4-yl)-2-fluoroaniline (0.070 g, 0.173 mmol) prepared in step 1, 1-methylpiperidin-4-one (0.039 g, 0.346 mmol) and sodium triacetoxyborohydride (0.073 g, 0.346 mmol) were dissolved in dichloromethane (5 mL), after which the resulting solution was stirred at room temperature for 30 minutes, and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 10%) and concentrated to obtain N-(3-(1-(4-(5-(difluoromethyl)-1,3,4-oxadiazol-2-yl)-2-fluorobenzyl)-1H-1,2,3-triazol-4-yl)-2-fluorophenyl)-1-methylpiperidin-4-amine (0.039 g, 44.9%) in a white solid form.

$^1$H NMR (400 MHz, $CDCl_3$) δ 7.99 (d, J=3.6 Hz, 1H), 7.92 (d, J=9.0 Hz, 2H), 7.57 (t, J=6.7 Hz, 1H), 7.44 (t, J=7.7 Hz, 1H), 7.09 (dd, J=14.2, 6.2 Hz, 1.2H), 6.94 (s, 0.5H), 6.81 (s, 0.3H), 6.70 (t, J=7.8 Hz, 1H), 5.76 (s, 2H), 3.86 (s, 1H), 3.39 (s, 1H), 2.94 (t, J=12.6 Hz, 2H), 2.41 (s, 3H), 2.31 (t, J=10.5 Hz, 2H), 2.14 (d, J=11.5 Hz, 2H), 1.68 (dd, J=20.5, 10.0 Hz, 2H); LRMS (ES) m/z 502.6 ($M^+$+1).

The compounds of table 95 were synthesized according to substantially the same process as described above in the synthesis of compound 4431 with an exception of using 3-(1-(4-(5-(difluoromethyl)-1,3,4-oxadiazol-2-yl)-2-fluorobenzyl)-1H-1,2,3-triazol-4-yl)-2-fluoroaniline and the reactant of table 94.

TABLE 94

| Example | Compound No. | Reactant | Yield (%) |
|---|---|---|---|
| 314 | 4432 | 1-isopropylpiperidin-4-one | 28 |
| 315 | 4433 | 1-acetylpiperidin-4-one | 33 |
| 316 | 4434 | 1-propylpiperidin-4-one | 39 |

TABLE 95

| Example | Compound No. | Compound Name, $^1$H-NMR, MS (ESI) |
|---|---|---|
| 314 | 4432 | N-(3-(1-(4-(5-(difluoromethyl)-1,3,4-oxadiazol-2-yl)-2-fluorobenzyl)-1H-1,2,3-triazol-4-yl)-2-fluorophenyl)-1-isopropylpiperidin-4-amine<br>$^1$H NMR (400 MHZ, $CDCl_3$) δ 8.00 (d, J = 3.5 Hz, 1H), 7.93 (d, J = 9.0 Hz, 2H), 7.60 (t, J = 6.8 Hz, 1H), 7.44 (t, J = 7.7 Hz, 1H), 7.09 (dd, J = 14.6, 6.6 Hz, 1.2H), 6.94 (s, 0.5H), 6.81 (s, 0.3H), 6.70 (t, J = 8.0 Hz, 1H), 5.77 (s, 2H), 3.92 (s, 1H), 3.46 (s, 1H), 3.13 (s, 3H), 2.61 (s, 2H), 2.25 (s, 2H), 1.91 (s, 2H), 1.27 (d, J = 6.4 Hz, 6H); LRMS (ES) m/z 530.46 ($M^+$ + 1). |
| 315 | 4433 | 1-(4-((3-(1-(4-(5-(difluoromethyl)-1,3,4-oxadiazol-2-yl)-2-fluorobenzyl)-1H-1,2,3-triazol-4-yl)-2-fluorophenyl)amino)piperidin-1-yl)ethan-1-one<br>$^1$H NMR (400 MHZ, $CDCl_3$) δ 7.99 (d, J = 3.6 Hz, 1H), 7.95-7.88 (m, 2H), 7.62 (t, J = 6.9 Hz, 1H), 7.44 (t, J = 7.7 Hz, 1H), 7.12 (t, J = 7.9 Hz, 1H), 7.07 (s, 0.2H), 6.94 (s, 0.5H), 6.81 (s, 0.3H), 6.76 (t, J = 7.7 Hz, 1H), 5.76 (s, 2H), 4.51 (d, J = 13.4 Hz, 1H), 3.84 (ddd, J = 26.6, 12.6, 6.3 Hz, 3H), 3.64-3.47 (m, 1H), 3.22 (dd, J = 18.2, 6.9 Hz, 1H), 2.88 (dd, J = 14.9, 7.8 Hz, 1H), 2.50 (dt, J = 9.8, 6.4 Hz, 1H), 2.11 (d, J = 11.0 Hz, 3H), 1.51-1.35 (m,2H); LRMS (ES) m/z 530.34 ($M^+$ + 1). |
| 316 | 4434 | N-(3-(1-(4-(5-(difluoromethyl)-1,3,4-oxadiazol-2-yl)-2-fluorobenzyl)-1H-1,2,3-triazol-4-yl)-2-fluorophenyl)-1-propylpiperidin-4-amine<br>$^1$H NMR (400 MHZ, $CDCl_3$) δ 8.00 (d, J = 3.6 Hz, 1H), 7.93 (d, J = 9.0 Hz, 2H), 7.59 (t, J = 6.7 Hz, 1H), 7.44 (t, J = 7.7 Hz, 1H), 7.10 (dd, J = 15.2, 7.3 Hz, 1.2H), 6.94 (s, 0.5H), 6.81 (s, 0.3H), 6.70 (t, J = 7.6 Hz, 1H), 5.77 (s, 2H), 3.90 (s, 1H), 3.46 (s, 1H), 3.14 (s, 2H), 2.49 (d, J = 52.9 Hz, 4H), 2.19 (s, 2H), 1.76 (d, J = 54.1 Hz, 4H), 0.97 (t, J = 7.3 Hz, 3H); LRMS (ES) m/z 530.6 ($M^+$ + 1). |

Example 317: Synthesis of compound 4435, N-(3-(1-(4-(5-(difluoromethyl)-1,3,4-oxadiazol-2-yl)-2-fluorobenzyl)-1H-1,2,3-triazol-4-yl)-4-fluorophenyl)-1-methylpiperidin-4-amine

[Step 1] Synthesis of 3-(1-(4-(5-(difluoromethyl)-1,3,4-oxadiazol-2-yl)-2-fluorobenzyl)-1H-1,2,3-triazol-4-yl)-4-fluoroaniline

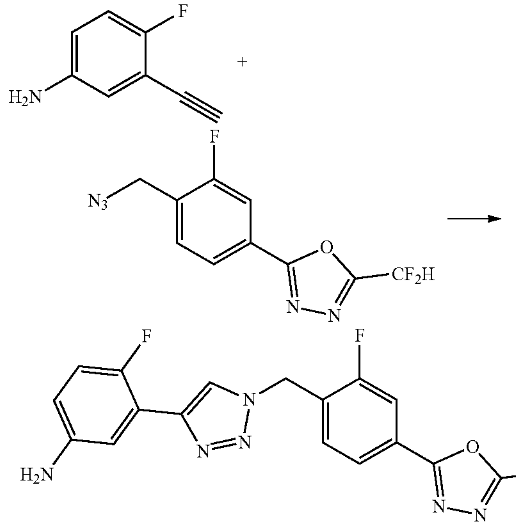

The 2-(4-(azidomethyl)-3-fluorophenyl)-5-(difluoromethyl)-1,3,4-oxadiazole (0.300 g, 1.114 mmol) prepared in step 1 of example 2, 3-ethynyl-4-fluoroaniline (0.181 g, 1.337 mmol), sodium ascorbate (1.00 M solution, 0.111 mL, 0.111 mmol), and copper(II) sulfate pentahydrate (0.50 M solution, 0.022 mL, 0.011 mmol) were dissolved in tert-butanol (10 mL)/water (10 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 40%) and concentrated to obtain 3-(1-(4-(5-(difluoromethyl)-1,3,4-oxadiazol-2-yl)-2-fluorobenzyl)-1H-1,2,3-triazol-4-yl)-4-fluoroaniline (0.410 g, 91.0%) in a white solid form.

[Step 2] Synthesis of Compound 4435

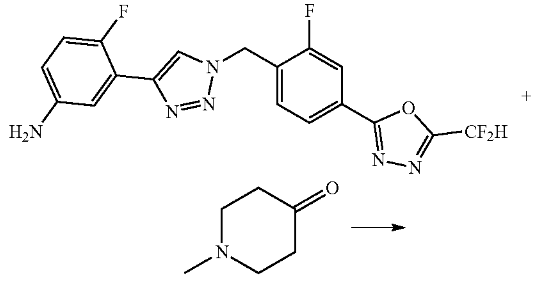

-continued

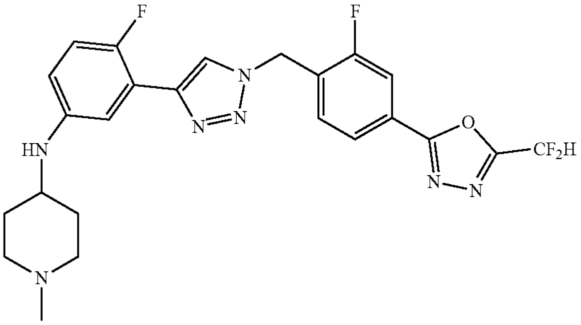

The 3-(1-(4-(5-(difluoromethyl)-1,3,4-oxadiazol-2-yl)-2-fluorobenzyl)-1H-1,2,3-triazol-4-yl)-4-fluoroaniline (0.050 g, 0.124 mmol) prepared in step 1 was dissolved in dichloromethane (5 mL), after which the resulting solution was stirred at room temperature for 30 minutes, and then 1-methylpiperidin-4-one (0.017 g, 0.148 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain N-(3-(1-(4-(5-(difluoromethyl)-1,3,4-oxadiazol-2-yl)-2-fluorobenzyl)-1H-1,2,3-triazol-4-yl)-4-fluorophenyl)-1-methylpiperidin-4-amine (0.029 g, 46.8%) in a white solid form.

$^1H$ NMR (400 MHz, $CDCl_3$) δ 8.00 (d, J=3.5 Hz, 1H), 7.92 (dt, J=4.3, 1.7 Hz, 2H), 7.53 (dd, J=6.0, 3.0 Hz, 1H), 7.43 (t, J=7.7 Hz, 1H), 7.07 (s, 0.2H), 7.00-6.95 (m, 1H), 6.94 (s, 0.5H), 6.81 (s, 0.3H), 6.54 (ddd, J=8.8, 4.0, 3.1 Hz, 1H), 5.75 (s, 2H), 3.41 (s, 1H), 2.93 (d, J=11.5 Hz, 2H), 2.3 8 (d, J=11.5 Hz, 3H), 2.28 (t, J=11.0 Hz, 2H), 2.15 (t, J=13.9 Hz, 2H), 1.61 (dd, J=20.4, 10.3 Hz, 2H); LRMS (ES) m/z 502.45 ($M^+$+1).

The compounds of table 97 were synthesized according to substantially the same process as described above in the synthesis of compound 4435 with an exception of using 3-(1-(4-(5-(difluoromethyl)-1,3,4-oxadiazol-2-yl)-2-fluorobenzyl)-1H-1,2,3-triazol-4-yl)-4-fluoroaniline and the reactant of table 96.

TABLE 96

| Example | Compound No. | Reactant | Yield (%) |
|---|---|---|---|
| 318 | 4436 | 1-isopropylpiperidin-4-one | 59 |
| 319 | 4437 | 1-acetylpiperidin-4-one | 47 |
| 320 | 4438 | 1-propylpiperidin-4-one | 58 |

TABLE 97

| Example | Compound No. | Compound Name, $^1$H-NMR, MS (ESI) |
|---|---|---|
| 318 | 4436 | N-(3-(1-(4-(5-(difluoromethyl)-1,3,4-oxadiazol-2-yl)-2-fluorobenzyl)-1H-1,2,3-triazol-4-yl)-4-fluorophenyl)-1-isopropylpiperidin-4-amine $^1$H NMR (400 MHZ, $CDCl_3$) δ 8.00 (d, J = 3.5 Hz, 1H), 7.92 (dt, J = 4.4, 1.7 Hz, 2H), 7.52 (dd, J = 6.0, 3.0 Hz, 1H), 7.43 (t. J = 7.7 Hz, 1H), 7.07 (s, 0.2H), 6.99-6.91 (m, 1.5H), 6.81 (s, 0.3H), 6.54 (ddd, J = 8.8, 4.0, 3.1 Hz, 1H), 5.75 (s, 2H), 3.41 (td, J = 10.2, 5.2 Hz, 1H), 3.04-2.85 (m, 3H), 2.44 (t, J = 10.5 Hz, 2H), 2.14 (t, J = 14.4 Hz, 3H), 1.63 (dd, J = 20.7, 10.0 Hz, 2H), 1.14 (d, J = 6.6 Hz, 6H); LRMS (ES) m/z 530.40 ($M^+$ + 1). |
| 319 | 4437 | 1-(4-((3-(1-(4-(5-(difluoromethyl)-1,3,4-oxadiazol-2-yl)-2-fluorobenzyl)-1H-1,2,3-triazol-4-yl)-4-fluorophenyl)amino)piperidin-1-yl)ethan-1-one $^1$H NMR (400 MHZ, $CDCl_3$) δ 8.02 (d, J = 3.5 Hz, 1H), 7.96-7.89 (m, 2H), 7.60 (dd, J = 5.8, 2.9 Hz, 1H), 7.45 (dd, J = 10.1, 5.3 Hz, 1H), 7.07 (s, 0.2H), 7.03-6.95 (m, 1H), 6.94 (s, 0.5H), 6.81 (s, 0.3H), 6.66-6.57 (m, 1H), 5.76 (s, 2H), 4.52 (dd, J = 13.6, 1.7 Hz, 1H), 3.94-3.73 (m, 2H), 3.66-3.50 (m, 1H), 3.23 (ddd, J = 14.0, 11.6, 2.8 Hz, 1H), 2.92-2.79 (m, 1H), 2.51 (dt, J = 9.6, 6.4 Hz, 1H), 2.18 (d, J = 6.4 Hz, 1H), 2.13 (d, J = 3.9 Hz, 4H); LRMS (ES) m/z 530.09 ($M^+$ + 1). |
| 320 | 4438 | N-(3-(1-(4-(5-(difluoromethyl)-1,3,4-oxadiazol-2-yl)-2-fluorobenzyl)-1H-1,2,3-triazol-4-yl)-4-fluorophenyl)-1-propylpiperidin-4-amine $^1$H NMR (400 MHZ, $CDCl_3$) δ 8.00 (d, J = 3.5 Hz, 1H), 7.96-7.88 (m, 2H), 7.53 (dd, J = 6.0, 3.0 Hz, 1H), 7.43 (t, J = 7.7 Hz, 1H), 7.07 (s, 0.2H), 7.00-6.90 (m, 1.5H), 6.81 (s, 0.3H), 6.58-6.51 (m, 1H), 5.75 (s, 2H), 3.42 (d, J = 10.0 Hz, 1H), 2.98 (d, J = 10.3 Hz, 2H), 2.47-2.33 (m, 2H), 2.23 (d, J = 11.2 Hz, 2H), 2.13 (d, J = 12.1 Hz, 2H), 1.59 (td, J = 14.9, 7.4 Hz, 4H), 0.98-0.90 (m, 3H); LRMS (ES) m/z 530.40 ($M^+$ + 1). |

Example 321: Synthesis of compound 4439, 2-(difluoromethyl)-5-(4-((4-(3-((3R,5S)-3,5-dimethylpiperazin-1-yl)phenyl)-1H-1,2,3-triazol-1-yl)methyl)-3-fluorophenyl)-1,3,4-oxadiazole

[Step 1] Synthesis of (3R,5S)-1-(3-(1,3-dioxolan-2-yl)phenyl)-3,5-dimethylpiperazine

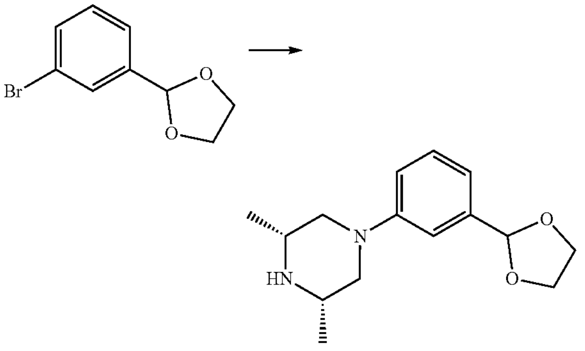

The 2-(3-bromophenyl)-1,3-dioxolane (1.500 g, 6.548 mmol) prepared in step 2 of example 218, (2R,6S)-2,6-dimethylpiperazine (0.748 g, 6.548 mmol), tris(dibenzylidene acetone)dipalladium ($Pd_2(dba)_3$, 0.060 g, 0.065 mmol), rac-BINAP (0.082 g, 0.131 mmol) and NaOBut (1.259 g, 13.096 mmol) were dissolved in toluene (25 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain (3R,5S)-1-(3-(1,3-dioxolan-2-yl)phenyl)-3,5-dimethylpiperazine (1.260 g, 73.3%) in a yellow oil form.

[Step 2] Synthesis of tert-butyl (2R,6S)-4-(3-(1,3-dioxolan-2-yl)phenyl)-2,6-dimethylpiperazin-1-carboxylate

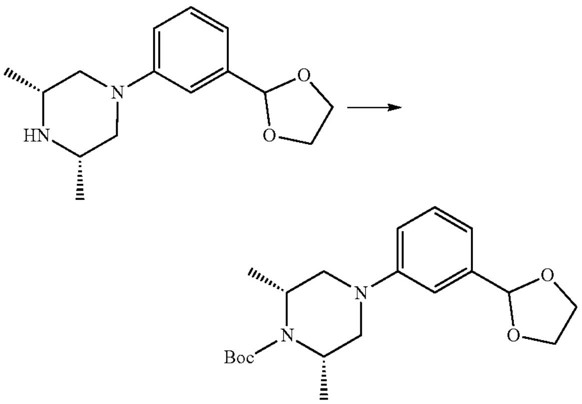

The (3R,5S)-1-(3-(1,3-dioxolan-2-yl)phenyl)-3,5-dimethylpiperazine (2.440 g, 9.301 mmol) prepared in step 1, di-tert-butyl dicarbonate (2.564 mL, 11.161 mmol) and N,N-diisopropylethylamine (1.944 mL, 11.161 mmol) were dissolved in dichloromethane (50 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl (2R,6S)-4-(3-(1,3-dioxolan-2-yl)phenyl)-2,6-dimethylpiperazin-1-carboxylate (3.550 g, 105.3%) in a brown oil form.

[Step 3] Synthesis of tert-butyl (2R,6S)-4-(3-(1,3-dioxolan-2-yl)phenyl)-2,6-dimethylpiperazin-1-carboxylate

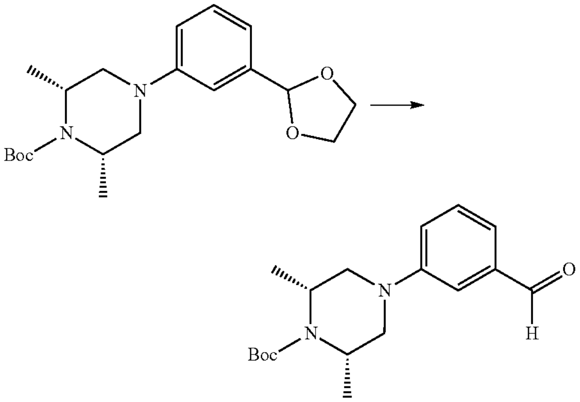

The tert-butyl (2R,6S)-4-(3-(1,3-dioxolan-2-yl)phenyl)-2,6-dimethylpiperazin-1-carboxylate (3.550 g, 9.794 mmol) prepared in step 2 and hydrochloric acid (1.00 M solution, 29.382 mL, 29.382 mmol) were dissolved in methanol (5 mL) at room temperature, after which the resulting solution was stirred at the same temperature for 4 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl (2R,6S)-4-(3-formylphenyl)-2,6-dimethylpiperazin-1-carboxylate (2.160 g, 69.3%) in a yellow oil form.

[Step 4] Synthesis of tert-butyl (2R,6S)-4-(3-(2,2-dibromovinyl)phenyl)-2,6-dimethylpiperazin-1-carboxylate

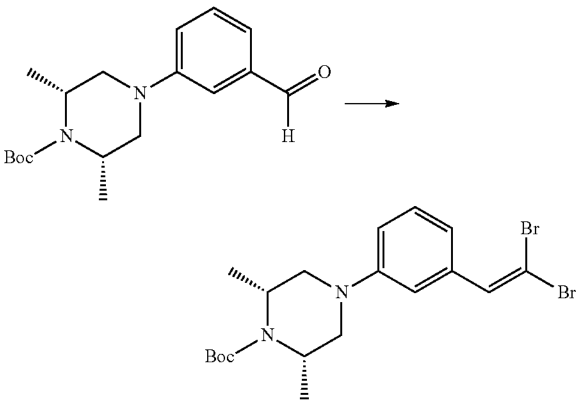

The tert-butyl (2R,6S)-4-(3-formylphenyl)-2,6-dimethylpiperazin-1-carboxylate (2.160 g, 6.783 mmol) prepared in step 3, carbon tetrabromide (4.499 g, 13.567 mmol) and triphenylphosphine triphenylphosphine (7.117 g, 27.134 mmol) were dissolved in dichloromethane (50 mL) at room temperature, after which the resulting solution was stirred at the same temperature for two hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%) and concentrated to obtain tert-butyl (2R,6S)-4-(3-(2,2-dibromovinyl)phenyl)-2,6-dimethylpiperazin-1-carboxylate(2.541 g, 79.0%) in a yellow oil form.

[Step 5] Synthesis of tert-butyl (2R,6S)-4-(3-ethynylphenyl)-2,6-dimethylpiperazin-1-carboxylate

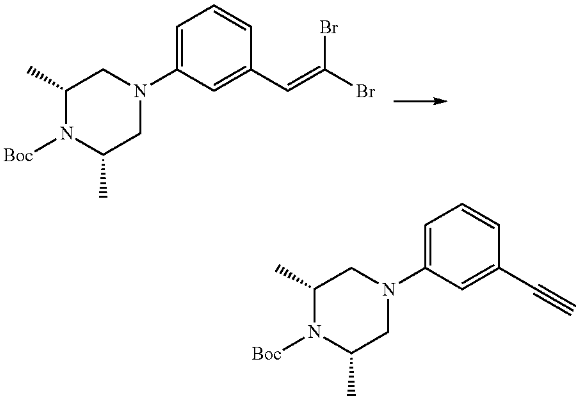

The tert-butyl (2R,6S)-4-(3-(2,2-dibromovinyl)phenyl)-2,6-dimethylpiperazin-1-carboxylate (2.541 g, 5.358 mmol) prepared in step 4 and 2,3,4,6,7,8,9,10-octahydropyrimido[1,2-a]azepine (3.205 mL, 21.432 mmol) were dissolved in acetonitrile (50 mL) at room temperature, after which the resulting solution was stirred at the same temperature for 16 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 10%) and concentrated to obtain tert-butyl (2R,6S)-4-(3-ethynylphenyl)-2,6-dimethylpiperazin-1-carboxylate (0.475 g, 28.2%) in a yellow oil form.

[Step 6] Synthesis of tert-butyl (2R,6S)-4-(3-(1-(4-(5-(difluoromethyl)-1,3,4-oxadiazol-2-yl)-2-fluorobenzyl)-1H-1,2,3-triazol-4-yl)phenyl)-2,6-dimethylpiperazin-1-carboxylate

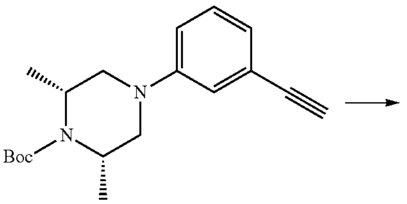

-continued

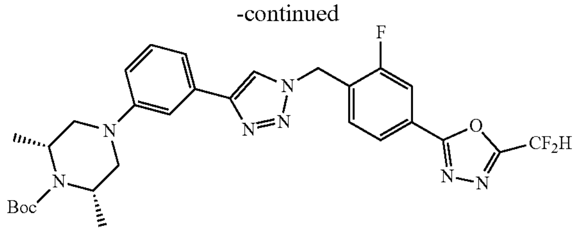

The tert-butyl (2R,6S)-4-(3-ethynylphenyl)-2,6-dimethylpiperazin-1-carboxylate (0.250 g, 0.795 mmol) prepared in step 5, the 2-(4-(azidomethyl)-3-fluorophenyl)-5-(difluoromethyl)-1,3,4-oxadiazole (0.257 g, 0.954 mmol) prepared in step 1 of example 2, copper(II) sulfate pentahydrate (0.002 g, 0.008 mmol) and sodium ascorbate (0.016 g, 0.080 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl (2R,6S)-4-(3-(1-(4-(5-(difluoromethyl)-1,3,4-oxadiazol-2-yl)-2-fluorobenzyl)-1H-1,2,3-triazol-4-yl)phenyl)-2,6-dimethylpiperazin-1-carboxylate (0.300 g, 64.7%) in a colorless oil form.

[Step 7] Synthesis of Compound 4439 ethylpiperazin-1-yl)phenyl)-1H-1,2,3-triazol-1-yl)methyl)-3-fluorophenyl)-1,3,4-oxadiazole (0.180 g, 72.4%) in a white solid form.

$^1$H NMR (400 MHz, $CDCl_3$) δ 7.87-7.78 (m, 3H), 7.38 (t, J=7.7 Hz, 1H), 7.24 (t, J=7.6 Hz, 1H), 7.17 (d, J=7.6 Hz, 1H), 7.06-6.74 (m, 3H), 5.66 (s, 2H), 4.92 (s, 1H), 3.64-3.56 (m, 2H), 3.26-3.14 (m, 2H), 2.61 (t, J=11.6 Hz, 2H), 1.22 (d, J=6.4 Hz, 7H); LRMS (ES) m/z 484.5 ($M^+$+1).

Example 322: Synthesis of compound 4440, 2-(difluoromethyl)-5-(4-((4-(3-((3R,5S)-3,5-dimethylpiperazin-1-yl)phenyl)-1H-1,2,3-triazol-1-yl)methyl)phenyl)-1,3,4-oxadiazole

[Step 1] Synthesis of tert-butyl (2R,6S)-4-(3-(1-(4-(5-(difluoromethyl)-1,3,4-oxadiazol-2-yl)benzyl)-1H-1,2,3-triazol-4-yl)phenyl)-2,6-dimethylpiperazin-1-carboxylate

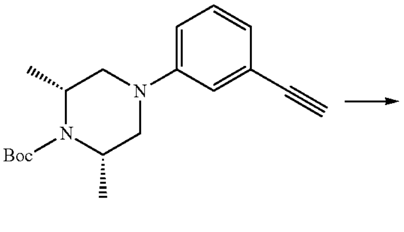

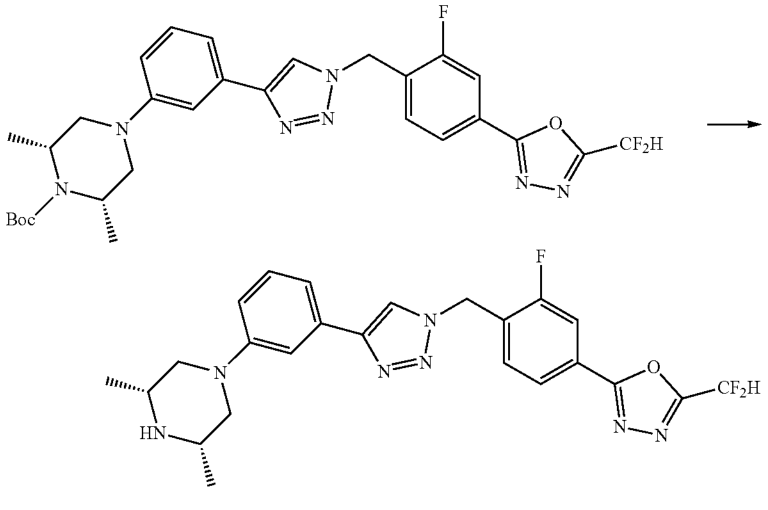

The tert-butyl (2R,6S)-4-(3-(1-(4-(5-(difluoromethyl)-1,3,4-oxadiazol-2-yl)-2-fluorobenzyl)-1H-1,2,3-triazol-4-yl)phenyl)-2,6-dimethylpiperazin-1-carboxylate (0.300 g, 0.514 mmol) prepared in step 5 and trifluoroacetic acid (0.394 mL, 5.140 mmol) were dissolved in dichloromethane (50 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(difluoromethyl)-5-(4-((4-(3-((3R,5S)-3,5-dim- -continued

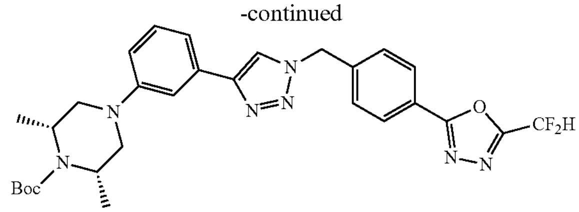

The tert-butyl (2R,6S)-4-(3-ethynylphenyl)-2,6-dimethylpiperazin-1-carboxylate (0.250 g, 0.795 mmol) prepared in step 5 of example 321, the 2-(4-(azidomethyl)phenyl)-5-(difluoromethyl)-1,3,4-oxadiazole (0.240 g, 0.954 mmol) prepared in synthesis step 1 of compound 1, copper(II) sulfate pentahydrate (0.002 g, 0.008 mmol) and sodium ascorbate (0.016 g, 0.080 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl (2R,6S)-4-(3-(1-(4-(5-(difluoromethyl)-1,3,4-oxadiazol-2-yl)benzyl)-1H-1,2,3-triazol-4-yl)phenyl)-2,6-dimethylpiperazin-1-carboxylate (0.290 g, 64.5%) in a white solid form.

[Step 2] Synthesis of Compound 4440

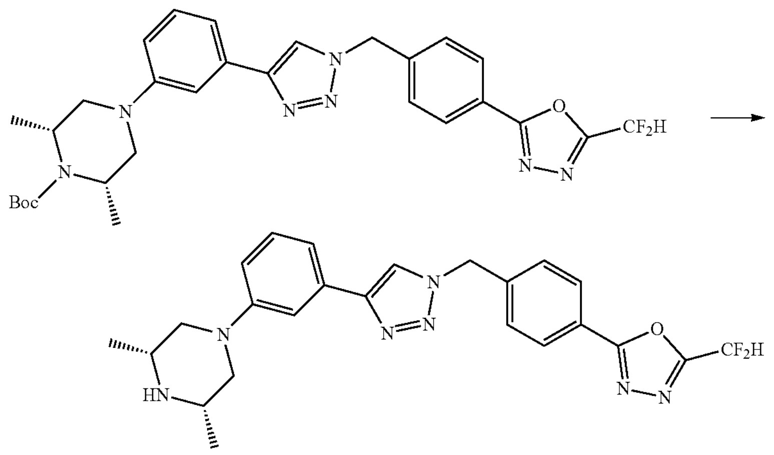

The tert-butyl (2R,6S)-4-(3-(1-(4-(5-(difluoromethyl)-1,3,4-oxadiazol-2-yl)benzyl)-1H-1,2,3-triazol-4-yl)phenyl)-2,6-dimethylpiperazin-1-carboxylate (0.300 g, 0.530 mmol) prepared in step 1 and trifluoroacetic acid (0.406 mL, 5.304 mmol) were dissolved in dichloromethane (50 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(4-((4-(3-((3R,5S)-3,5-dimethylpiperazin-1-yl)phenyl)-1H-1,2,3-triazol-1-yl)methyl)phenyl)-1,3,4-oxadiazole (0.165 g, 66.8%) in a white solid form.

$^1$H NMR (400 MHz, $CDCl_3$) δ 8.02 (s, 3H), 7.78 (s, 1H), 7.38 (s, 3H), 7.13-6.76 (m, 3H), 5.59 (s, 2H), 3.54 (d, J=11.6 Hz, 2H), 3.17 (s, 2H), 3.04 (s, 2H), 1.12 (s, 6H); LRMS (ES) m/z 466.6 ($M^+$+1).

Example 323: Synthesis of compound 4441, 2-(difluoromethyl)-5-(4-((4-(3-((3R,5S)-3,4,5-trimethylpiperazin-1-yl)phenyl)-1H-1,2,3-triazol-1-yl)methyl)phenyl)-1,3,4-oxadiazole

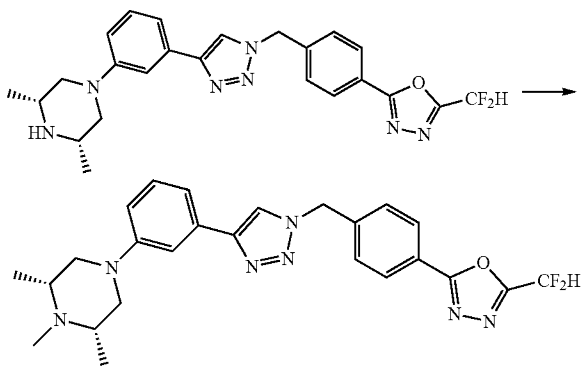

The 2-(difluoromethyl)-5-(4-((4-(3-((3R,5S)-3,5-dimethylpiperazin-1-yl)phenyl)-1H-1,2,3-triazol-1-yl)methyl)phenyl)-1,3,4-oxadiazole (0.080 g, 0.172 mmol) prepared in step 2 of example 322, formaldehyde (0.010 g, 0.344 mmol) and acetic acid (0.011 mL, 0.189 mmol) were dissolved in dichloromethane (5 mL) at room temperature, after which sodium triacetoxyborohydride (0.073 g, 0.344 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(3-((3R,5S)-3,4,5-trimethylpiperazin-1-yl) phenyl)-1H-1,2,3-triazol-1-yl)methyl)phenyl)-1,3,4-oxadiazole (0.043 g, 52.2%) in a white solid form.

$^1$H NMR (400 MHz, $CDCl_3$) δ 8.12-8.06 (m, 2H), 7.75 (s, 1H), 7.51-7.41 (m, 3H), 7.29-7.21 (m, 1H), 7.14 (d, J=7.5 Hz, 1H), 7.05-6.75 (m, 2H), 5.64 (s, 2H), 3.57-3.48 (m, 2H), 2.67 (t, J=11.3 Hz, 2H), 2.51-2.39 (m, 2H), 2.34 (s, 3H), 1.19 (d, J=6.2 Hz, 6H); LRMS (ES) m/z 480.6 ($M^+$+1).

The compound of table 99 was synthesized according to substantially the same process as described above in the synthesis of compound 4441 with an exception of using 2-(difluoromethyl)-5-(4-((4-(3-((3R,5S)-3,5-dimethylpiperazin-1-yl)phenyl)-1H-1,2,3-triazol-1-yl)methyl)phenyl)-1,3,4-oxadiazole and the reactant of table 98.

TABLE 98

| Example | Compound No. | Reactant | Yield (%) |
|---|---|---|---|
| 324 | 4442 | Acetaldehyde | 48 |

TABLE 99

| Example | Compound No. | Compound Name, $^1$H-NMR, MS (ESI) |
|---|---|---|
| 324 | 4442 | 2-(difluoromethyl)-5-(4-((4-(3-((3R,5S)-4-ethyl-3,5-dimethylpiperazin-1-<br>$^1$H NMR (400 MHZ, $CDCl_3$) δ 8.14-8.06 (m, 2H), 7.74 (s, 1H), 7.50-7.42 (m, 3H), 7.29-7.21 (m, 1H), 7.14 (d, J = 7.5 Hz, 1H), 7.05-6.76 (m, 2H), 5.65(s, 2H), 3.58-3.49 (m, 2H), 3.02 (q, J = 7.2 Hz, 2H), 2.85 (qd, J = 6.5, 3.5 Hz, 2H), 2.66 (t, J = 11.2 Hz, 2H), 1.18 (d, J = 6.2 Hz, 6H), 0.95 (t, J = 7.1 Hz, 3H); LRMS (ES) m/z 494.1 ($M^+$ + 1). |

Example 325: Synthesis of compound 4443, 2-(difluoromethyl)-5-(3-fluoro-4-((4-(3-((3R,5S)-3,4,5-trimethylpiperazin-1-yl)phenyl)-1H-1,2,3-triazol-1-yl)methyl)phenyl)-1,3,4-oxadiazole

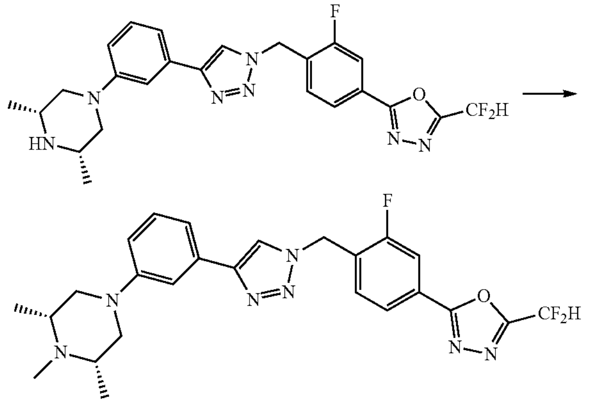

The 2-(difluoromethyl)-5-(4-((4-(3-((3R,5S)-3,5-dimethylpiperazin-1-yl)phenyl)-1H-1,2,3-triazol-1-yl)methyl)-3-fluorophenyl)-1,3,4-oxadiazole (0.080 g, 0.165 mmol) prepared in step 7 of example 321, formaldehyde (0.010 g, 0.331 mmol) and acetic acid (0.010 mL, 0.182 mmol) were dissolved in dichloromethane (5 mL) at room temperature, after which sodium triacetoxyborohydride (0.070 g, 0.331 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(3-((3R,5S)-3,4,5-trimethylpiperazin-1-yl)phenyl)-1H-1,2,3-triazol-1-yl)methyl)phenyl)-1,3,4-oxadiazole (0.025 g, 30.4%) in a yellow solid form.

$^1$H NMR (400 MHz, $CDCl_3$) δ 7.93-7.85 (m, 2H), 7.82 (s, 1H), 7.52-7.38 (m, 2H), 7.32-7.23 (m, 1H), 7.16 (s, 1H), 7.07-6.75 (m, 2H), 5.71 (s, 2H), 3.59-3.51 (m, 2H), 2.73 (t, J=11.4 Hz, 2H), 2.59-2.46 (m, 2H), 2.38 (s, 3H), 1.23 (d, J=6.2 Hz, 6H); LRMS (ES) m/z 498.1 ($M^+$+1).

The compound of table 101 was synthesized according to substantially the same process as described above in the synthesis of compound 4443 with an exception of using 2-(difluoromethyl)-5-(4-((4-(3-((3R,5S)-3,5-dimethylpiperazin-1-yl)phenyl)-1H-1,2,3-triazol-1-yl)methyl)-3-fluorophenyl)-1,3,4-oxadiazole and the reactant of table 100.

TABLE 100

| Example | Compound No. | Reactant | Yield (%) |
|---|---|---|---|
| 326 | 4444 | Acetaldehyde | 30 |

TABLE 101

| Example | Compound No. | Compound Name, $^1$H-NMR, MS (ESI) |
|---|---|---|
| 326 | 4444 | 2-(difluoromethyl)-5-(4-((4-(3-((3R,5S)-4-ethyl-3,5-dimethylpiperazin-1-yl)phenyl)-1H-1,2,3-triazol-1-yl)methyl)-3-flourophenyl)-1,3,4-oxadiazole $^1$H NMR (400 MHz, $CDCl_3$) δ 7.90 (d, J = 8.8 Hz, 2H), 7.82 (s, 1H), 7.49 (t, J = 2.1 Hz, 1H), 7.42 (t, J = 7.6 Hz, 1H), 7.32-7.24 (m, 1H), 7.18 (s, 1H), 7.06-6.78 (m, 2H), 5.72 (s, 2H), 3.57 (d, J = 11.5 Hz, 2H), 3.02 (q, J = 7.2 Hz, 2H), 2.85 (ddd, J = 15.6, 7.3, 4.1 Hz, 2H), 2.65 (t, J = 11.1 Hz, 2H), 1.20 (d, J = 6.2 Hz, 6H), 0.96 (t, J = 7.1 Hz, 3H); LRMS (ES) m/z 512.2 ($M^+$ + 1). |

Example 329: Synthesis of compound 4450, 2-(difluoromethyl)-5-(4-((4-(2-fluoro-5-(piperazin-1-yl)phenyl)-1H-1,2,3-triazol-1-yl)methyl)phenyl)-1,3,4-oxadiazole

[Step 1] Synthesis of 2-(5-bromo-2-fluorophenyl)-1,3-dioxolane

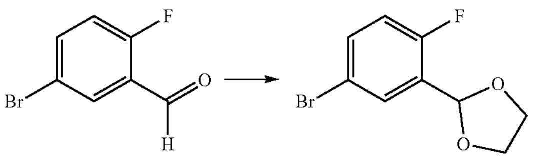 [SMILES: O=Cc1cc(Br)ccc1F ; Fc1ccc(Br)cc1C1OCCO1]

5-bromo-2-fluorobenzaldehyde (5.000 g, 24.629 mmol), p-toluenesulfonic acid (0.047 g, 0.246 mmol) and ethylene glycol (7.302 g, 29.555 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%) and concentrated to obtain 2-(5-bromo-2-fluorophenyl)-1,3-dioxolane (6.000 g, 98.6%) in a yellow oil form.

[Step 2] Synthesis of tert-butyl 4-(3-(1,3-dioxolan-2-yl)-4-fluorophenyl)piperazin-1-carboxylate

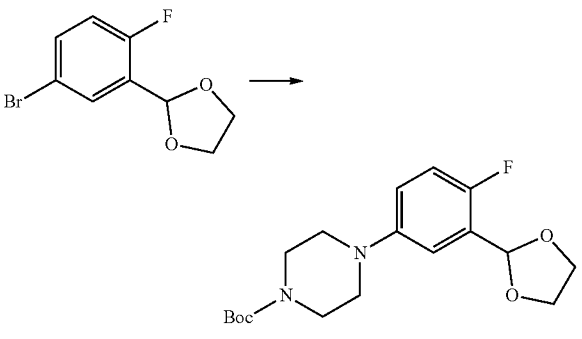

The 2-(5-bromo-2-fluorophenyl)-1,3-dioxolane (5.000 g, 20.238 mmol) prepared in step 1, tert-butyl piperazin-1-carboxylate (3.770 g, 20.238 mmol), tris(dibenzylidene acetone)dipalladium ($Pd_2(dba)_3$, 0.185 g, 0.202 mmol), rac-BINAP (0.252 g, 0.405 mmol) and NaOBut (3.890 g, 40.476 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(3-(1,3-dioxolan-2-yl)-4-fluorophenyl)piperazin-1-carboxylate (6.950 g, 97.4%) in a brown oil form.

[Step 3] Synthesis of tert-butyl 4-(4-fluoro-3-formylphenyl)piperazin-1-carboxylate

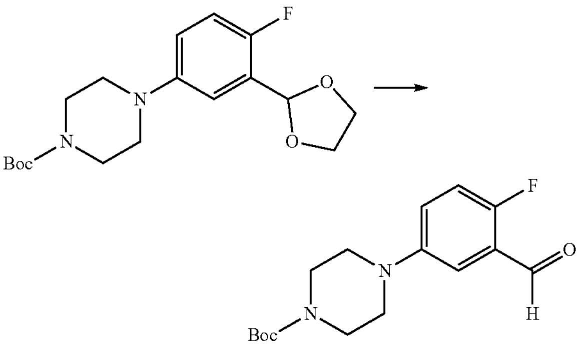

The tert-butyl 4-(3-(1,3-dioxolan-2-yl)-4-fluorophenyl)piperazin-1-carboxylate (6.950 g, 19.721 mmol) prepared in step 2 and hydrochloric acid (1.00 M solution, 59.164 mL, 59.164 mmol) were dissolved in methanol (5 mL) at room temperature, after which the resulting solution was stirred at the same temperature for 3 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(4-fluoro-3-formylphenyl)piperazin-1-carboxylate (2.400 g, 39.5%) in a brown oil form.

[Step 4] Synthesis of tert-butyl 4-(3-(2,2-dibromovinyl)-4-fluorophenyl)piperazin-1-carboxylate

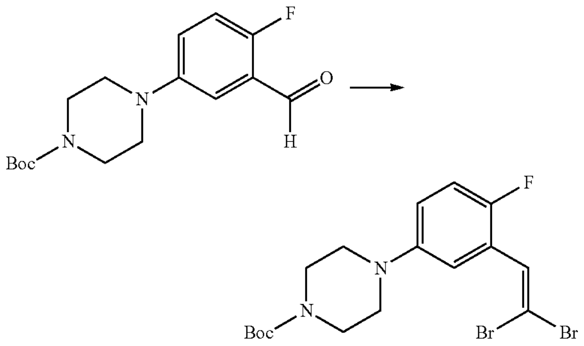

The tert-butyl 4-(4-fluoro-3-formylphenyl)piperazin-1-carboxylate (2.400 g, 7.783 mmol) prepared in step 3, carbon tetrabromide (5.162 g, 15.567 mmol) and triphenylphosphine triphenylphosphine (8.166 g, 31.133 mmol) were dissolved in dichloromethane (50 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 30%) and concentrated to obtain tert-butyl 4-(3-(2,2-dibromovinyl)-4-fluorophenyl)piperazin-1-carboxylate (3.340 g, 92.4%) in a brown oil form.

[Step 5] Synthesis of tert-butyl 4-(3-ethynyl-4-fluorophenyl)piperazin-1-carboxylate

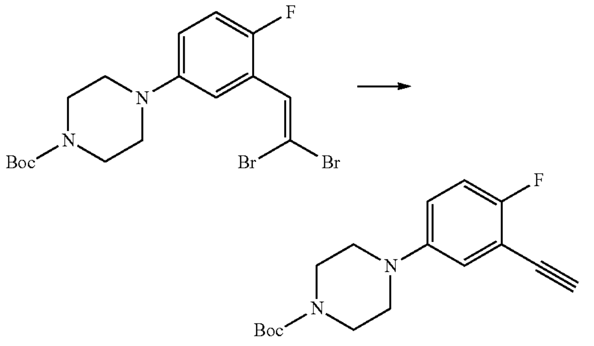

The tert-butyl 4-(3-(2,2-dibromovinyl)-4-fluorophenyl) piperazin-1-carboxylate (3.340 g, 7.196 mmol) prepared in step 4 and 2,3,4,6,7,8,9,10-octahydropyrimido[1,2-a]azepine (4.304 mL, 28.783 mmol) were dissolved in acetonitrile (50 mL) at room temperature, after which the resulting solution was stirred at the same temperature for 16 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(3-ethynyl-4-fluorophenyl)piperazin-1-carboxylate (0.500 g, 22.8%) in a brown solid form.

[Step 6] Synthesis of tert-butyl 4-(3-(1-(4-(5-(difluoromethyl)-1,3,4-oxadiazol-2-yl)-2-fluorobenzyl)-1H-1,2,3-triazol-4-yl)-4-fluorophenyl)piperazin-1-carboxylate

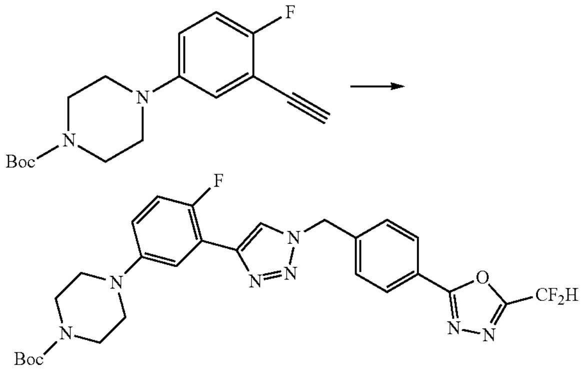

The tert-butyl 4-(3-ethynyl-4-fluorophenyl)piperazin-1-carboxylate (0.500 g, 1.643 mmol) prepared in step 5, 2-(4-(azidomethyl)phenyl)-5-(difluoromethyl)-1,3,4-oxadiazole (0.495 g, 1.971 mmol) prepared in step 1 of example 2, copper(II) sulfate pentahydrate (0.004 g, 0.016 mmol) and sodium ascorbate (0.033 g, 0.164 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(3-(1-(4-(5-(difluoromethyl)-1,3,4-oxadiazol-2-yl)-2-benzyl)-1H-1,2,3-triazol-4-yl)-4-fluorophenyl)piperazin-1-carboxylate (0.650 g, 69.0%) in a white solid form.

[Step 7] Synthesis of Compound 4450

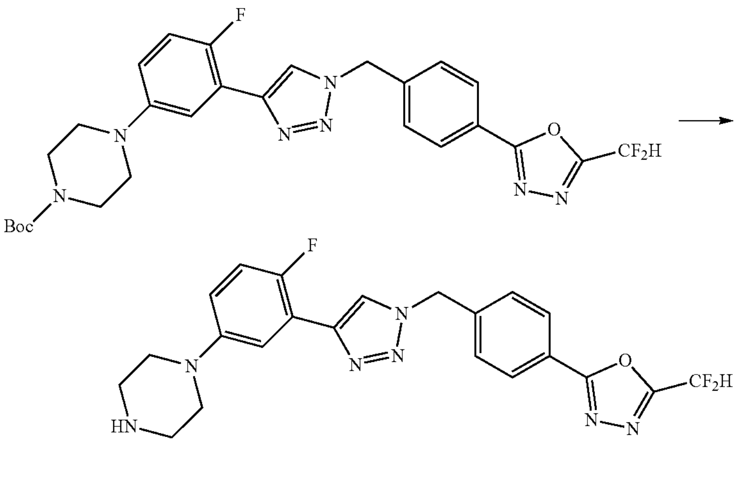

The tert-butyl 4-(3-(1-(4-(5-(difluoromethyl)-1,3,4-oxadiazol-2-yl)-2-benzyl)-1H-1,2,3-triazol-4-yl)-4-fluorophenyl)piperazin-1-carboxylate (0.650 g, 1.133 mmol) prepared in step 6 and trifluoroacetic acid (0.868 mL, 11.333 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(4-((4-(2-fluoro-5-(piperazin-1-yl)phenyl)-1H-1,2,3-triazol-1-yl)methyl)phenyl)-1,3,4-oxadiazole (0.530 g, 98.8%) in a yellow solid form.

$^1$H NMR (400 MHz, $CDCl_3$) δ 8.12 (d, J=8.0 Hz, 2H), 7.92 (d, J=3.6 Hz, 1H), 7.86 (dd, J=6.2, 3.1 Hz, 1H), 7.45 (d, J=8.0 Hz, 2H), 7.07-6.76 (m, 3H), 5.69 (s, 2H), 3.21 (t, J=4.9 Hz, 4H), 3.09 (dd, J=6.6, 3.5 Hz, 4H); LRMS (ES) m/z 456.5 ($M^+$+1).

Example 330: Synthesis of compound 4451, 2-(difluoromethyl)-5-(4-((4-(2-fluoro-5-(4-methylpiperazin-1-yl)phenyl)-1H-1,2,3-triazol-1-yl)methyl)phenyl)-1,3,4-oxadiazole

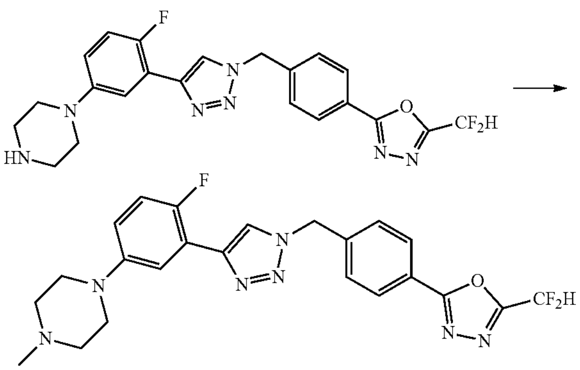

The 2-(difluoromethyl)-5-(4-((4-(2-fluoro-5-(piperazin-1-yl)phenyl)-1H-1,2,3-triazol-1-yl)methyl)phenyl)-1,3,4-oxadiazole (0.060 g, 0.132 mmol) prepared in step 7 of example 329, formaldehyde (0.008 g, 0.263 mmol) and acetic acid (0.008 mL, 0.145 mmol) were dissolved in dichloromethane (5 mL) at room temperature, after which sodium triacetoxyborohydride (0.056 g, 0.263 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(2-fluoro-5-(4-methylpiperazin-1-yl)phenyl)-1H-1,2,3-triazol-1-yl)methyl)phenyl)-1,3,4-oxadiazole(0.030 g, 48.5%) in a yellow solid form.

$^1$H NMR (400 MHz, $CDCl_3$) δ 8.10 (d, J=8.0 Hz, 2H), 7.91 (d, J=3.6 Hz, 1H), 7.84 (dd, J=6.2, 3.1 Hz, 1H), 7.43 (d, J=7.9 Hz, 2H), 7.05-6.74 (m, 3H), 5.67 (s, 2H), 3.23 (t, J=5.1 Hz, 4H), 2.61 (t, J=4.9 Hz, 4H), 2.36 (s, 3H); LRMS (ES) m/z 470.5 ($M^+$+1).

The compounds of table 103 were synthesized according to substantially the same process as described above in the synthesis of compound 4451 with an exception of using 2-(difluoromethyl)-5-(4-((4-(2-fluoro-5-(piperazin-1-yl)phenyl)-1H-1,2,3-triazol-1-yl)methyl)phenyl)-1,3,4-oxadiazole and the reactant of table 102.

TABLE 102

| Example | Compound No. | Reactant | Yield (%) |
|---|---|---|---|
| 331 | 4452 | Acetaldehyde | 47 |
| 332 | 4453 | Propan-2-one | 49 |
| 333 | 4454 | Cyclobutanone | 52 |
| 334 | 4455 | Oxetan-3-one | 45 |

TABLE 103

| Exampe | Compound No. | Compound Name, $^1$H-NMR, MS (ESI) |
|---|---|---|
| 331 | 4452 | 2-(difluoromethyl)-5-(4-((4-(5-(4-ethylpiperazin-1-yl)-2-fluorophenyl)-1H-1,2,3-triazol-1-yl)methyl)phenyl)-1,3,4-oxadiazole $^1$H NMR (400 MHz, $CDCl_3$) δ 8.12-8.05 (m, 2H), 7.91 (d, J = 3.5 Hz, 1H), 7.83 (dd, J = 6.2, 3.1 Hz, 1H), 7.46-7.39 (m, 2H), 7.05-6.74 (m, 3H), 5.66 (s, 2H), 3.30-3.23 (m, 4H), 2.71 (t, J = 5.0 Hz, 4H), 2.55 (q, J = 7.2 Hz, 2H), 1.14 (t, J = 7.2 Hz, 3H); LRMS (ES) m/z 484.6 ($M^+$ + 1). |
| 332 | 4453 | 2-(difluoromethyl)-5-(4-((4-(2-fluoro-5-(4-isopropylpiperazin-1-yl)phenyl)-1H-1,2,3-triazol-1-yl)methyl)phenyl)-1,3,4-oxadiazole $^1$H NMR (400 MHz, $CDCl_3$) δ 8.12-8.05 (m, 2H), 7.91 (d, J = 3.5 Hz, 1H), 7.83 (dd, J = 6.2, 3.1 Hz, 1H), 7.46-7.39 (m, 2H), 7.05-6.74 (m, 3H), 5.66 (s, 2H), 3.32-3.23 (m, 4H), 2.90 (p, J = 6.5 Hz, 1H), 2.81 (t. J = 5.0 Hz, 4H), 1.14 (d, J = 6.5 Hz, 6H); LRMS (ES) m/z 498.6 ($M^+$ + 1). |
| 333 | 4454 | 2-(4-((4-(5-(4-cyclobutylpiperazin-1-yl)-2-fluorophenyl)-1H-1,2,3-triazol-1-yl)methyl)phenyl)-5-(difluoromethyl)-1,3,4-oxadiazol $^1$H NMR (400 MHz, $CDCl_3$) δ 8.08 (d, J = 8.0 Hz, 2H), 7.91 (d, J = 3.5 Hz, 1H), 7.83 (dd, J = 6.2, 3.1 Hz, 1H), 7.42 (d, J = 8.0 Hz, 2H), 7.05-6.73 (m, 3H), 5.66 (s, 2H), 3.23 (t, J = 5.0 Hz, 4H), 2.81 (p, J = 8.0 Hz, 1H), 2.52 (t, J = 5.0 Hz, 4H), 2.08-1.92 (m, 4H), 1.80-1.61 (m, 2H); LRMS (ES) m/z 510.6 ($M^+$ + 1). |
| 334 | 4455 | 2-(difluoromethyl)-5-(4-((4-(2-fluoro-5-(4-(oxetan-3-yl)piperazin-1-yl)phenyl)-1H-1,2,3-triazol-1-yl)methyl)phenyl)-1,3,4-oxadiazole $^1$H NMR (400 MHz, $CDCl_3$) δ 8.09 (d, J = 8.1 Hz, 2H), 7.92 (d, J = 3.6 Hz, 1H), 7.84 (dd, J = 6.2, 3.1 Hz, 1H), 7.43 (d, J = 8.0 Hz, 2H), 7.05-6.75 (m, 3H), 5.67 (s, 2H), 4.66 (dt, J = 14.7, 6.3 Hz, 4H), 3.54 (p, J = 6.4 Hz, 1H), 3.24 (t, J = 4.9 Hz, 4H), 2.50 (t, J = 4.9 Hz, 4H); LRMS (ES) m/z 512.6 ($M^+$ + 1). |

Example 335: Synthesis of compound 4460, 2-(difluoromethyl)-5-(3-fluoro-4-((4-(3-(1-methylazetidin-3-yl)phenyl)-1H-1,2,3-triazol-1-yl)methyl)phenyl)-1,3,4-oxadiazole

[Step 1] Synthesis of tert-butyl 3-(3-(1-(4-(5-(difluoromethyl)-1,3,4-oxadiazol-2-yl)-2-fluorobenzyl)-1H-1,2,3-triazol-4-yl)phenyl)azetidin-1-carboxylate

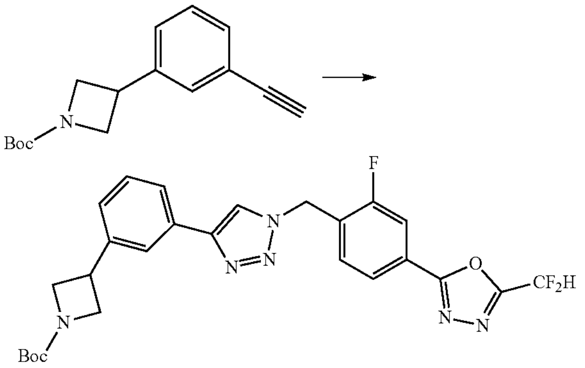

Tert-butyl 3-(3-ethynylphenyl)azetidin-1-carboxylate (0.130 g, 0.505 mmol), 2-(4-(azidomethyl)-3-fluorophenyl)-5-(difluoromethyl)-1,3,4-oxadiazole (0.136 g, 0.505 mmol) prepared in step 1 of example 2, sodium ascorbate (0.50 M solution in water, 0.101 mL, 0.051 mmol) and copper sulfate pentahydrate (1.00 M solution in water, 0.010 mL, 0.010 mmol) were dissolved in tert-butanol (1.5 mL)/water (1.5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain tert-butyl 3-(3-(1-(4-(5-(difluoromethyl)-1,3,4-oxadiazol-2-yl)-2-fluorobenzyl)-1H-1,2,3-triazol-4-yl)phenyl) azetidin-1-carboxylate (0.221 g, 83.1%) in a white solid form.

[Step 2] Synthesis of 2-(4-((4-(3-(azetidin-3-yl) phenyl)-1H-1,2,3-triazol-1-yl)methyl)-3-fluorophenyl)-5-(difluoromethyl)-1,3,4-oxadiazole

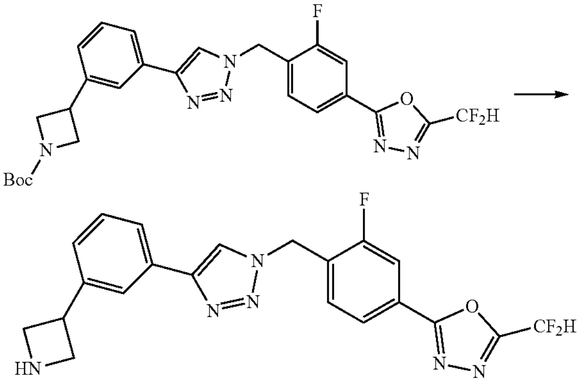

The tert-butyl 3-(3-(1-(4-(5-(difluoromethyl)-1,3,4-oxadiazol-2-yl)-2-fluorobenzyl)-1H-1,2,3-triazol-4-yl)phenyl) azetidin-1-carboxylate (0.221 g, 0.420 mmol) prepared in step 1 and trifluoroacetic acid (0.321 mL, 4.197 mmol) were dissolved in dichloromethane (2 mL) at room temperature, after which the resulting solution was stirred at the same temperature for 18 hours. 1N-sodium chloride aqueous solution was poured into the resulting reaction mixture, and an extraction was performed with dichloromethane. An organic layer was washed with saturated sodium chloride aqueous solution, dehydrated with anhydrous magnesium sulfate, filtered, and concentrated under reduced pressure. Then, the obtained product was used without an additional purification process (2-(4-((4-(3-(azetidin-3-yl)phenyl)-1H-1,2,3-triazol-1-yl)methyl)-3-fluorophenyl)-5-(difluoromethyl)-1,3,4-oxadiazole, 0.180 g, 100.6%, yellow oil).

[Step 3] Synthesis of Compound 4460

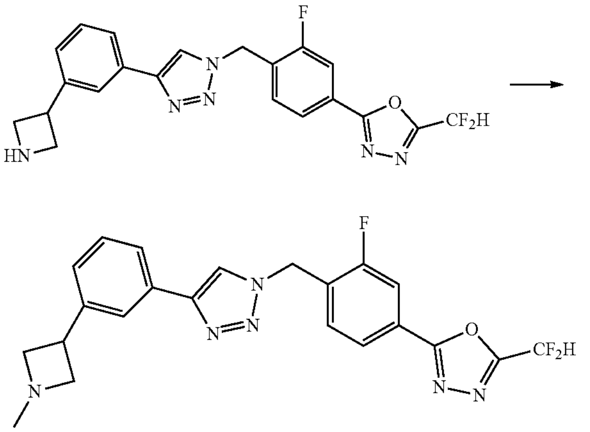

$^1H$ NMR (400 MHz, $CD_3OD$) δ 8.48 (s, 1H), 8.03-7.92 (m, 2H), 7.84 (d, J=1.9 Hz, 1H), 7.73 (dt, J=7.8, 1.4 Hz, 1H), 7.62 (t, J=7.7 Hz, 1H), 7.44 (t, J=7.7 Hz, 1H), 7.36-7.30 (m, 1H), 7.24 (t, J=51.6 Hz, 1H), 5.86 (s, 2H), 4.05 (td, J=7.8, 7.4, 1.9 Hz, 2H), 3.94 (p, J=7.9 Hz, 1H), 3.63 (t, J=8.2 Hz, 2H), 2.61 (s, 3H); LRMS (ES) m/z 441.5 ($M^+$+1).

The compounds of table 105 were synthesized according to substantially the same process as described above in the synthesis of compound 4460 with an exception of using 2-(4-((4-(3-(azetidin-3-yl)phenyl)-1H-1,2,3-triazol-1-yl)methyl)-3-fluorophenyl)-5-(difluoromethyl)-1,3,4-oxadiazole and the reactant of table 104.

TABLE 104

| Example | Compound No. | Reactant | Yield (%) |
|---|---|---|---|
| 336 | 4461 | Acetone | 73 |
| 337 | 4462 | Oxetanone | 66 |

TABLE 105

| Example | Compound No. | Compound Name, $^1H$-NMR, MS (ESI) |
|---|---|---|
| 336 | 4461 | 2-(difluoromethyl)-5-(3-fluoro-4-((4-(3-(1-isopropylazetidin-3-yl)phenyl)-1H-1,2,3-triazol-1-yl)methyl)phenyl)-1,3,4-oxadiazole $^1H$ NMR (400 MHz, $CD_3OD$) δ 8.48 (s, 1H), 8.01-7.89 (m, 2H), 7.83 (t, J = 1.9 Hz, 1H), 7.72 (dt, J = 7.7, 1.4 Hz, 1H), 7.61 (t, J = 7.6 Hz, 1H), 7.43 (t, J = 7.7 Hz, 1H), 7.34-7.28 (m, 1H), 7.24 (t, J = 51.6 Hz, 1H), 5.85 (s, 2H), 4.02 (ddd, J = 8.8, 7.2, 1.9 Hz, 2H), 3.87 (p, J = 8.3 Hz, 1H), 3.54 (td, J = 7.7, 6.8, 1.8 Hz, 2H), 2.81 (dq, J = 12.7, 6.4 Hz, 1H), 1.09 (d, J = 6.4 Hz, 6H); LRMS (ESI) m/z 469.5 ($M^+$ + H). |
| 337 | 4462 | 2-(difluoromethyl)-5-(3-fluoro-4-((4-(3-(1-(oxetan-3-yl)azetidin-3-yl)phenyl)-1H-1,2,3-triazol-1-yl)methyl)phenyl)-1,3,4-oxadiazole $^1H$ NMR (400 MHz, $CD_3OD$) δ 8.47 (s, 1H), 8.00-7.90 (m, 2H), 7.82 (t, J = 1.8 Hz, 1H), 7.70 (dt, J = 7.7, 1.4 Hz, 1H), 7.60 (t, J = 7.7 Hz, 1H), 7.41 (t, J = 7.7 Hz, 1H), 7.32 (dt, J = 7.7, 1.5 Hz, 1H), 7.24 (t, J = 51.6 Hz, 1H), 5.84 (s, 2H), 4.77 (t, J = 6.7 Hz, 2H), 4.55 (dd, J = 6.8, 5.0 Hz, 2H), 3.94-3.77 (m, 4H), 3.44-3.34 (m, 2H); LRMS (ESI) m/z 483.5 ($M^+$ + H). |

The 2-(4-((4-(3-(azetidin-3-yl)phenyl)-1H-1,2,3-triazol-1-yl)methyl)-3-fluorophenyl)-5-(difluoromethyl)-1,3,4-oxadiazole (0.060 g, 0.141 mmol) prepared in step 2 and formaldehyde (37.00% solution in water, 0.021 mL, 0.281 mmol) were dissolved in dichloromethane (1 mL), after which the resulting solution was stirred at room temperature for 15 minutes, and then sodium triacetoxyborohydride (0.089 g, 0.422 mmol) was added thereto and further stirred at the same temperature for 18 hours. Saturated sodium chloride aqueous solution was poured into the reaction mixture, and an extraction was performed with dichloromethane. An organic layer was washed with saturated aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain to 2-(difluoromethyl)-5-(3-fluoro-4-((4-(3-(1-methylazetidin-3-yl)phenyl)-1H-1,2,3-triazol-1-yl)methyl)phenyl)-1,3,4-oxadiazole (0.009 g, 14.5%) in a colorless oil form.

Example 338: Synthesis of compound 4463, N-(3-(1-((5-(5-(difluoromethyl)-1,3,4-oxadiazol-2-yl)pyridin-2-yl)methyl)-1H-1,2,3-triazol-4-yl)phenyl)azetidin-3-carboxamide

[Step 1] Synthesis of tert-butyl 3-((3-(1-((5-(5-(difluoromethyl)-1,3,4-oxadiazol-2-yl)pyridin-2-yl)methyl)-1H-1,2,3-triazol-4-yl)phenyl)carbamoyl)azetidin-1-carboxylate

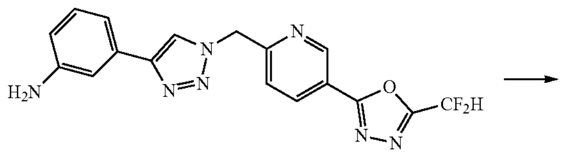

-continued

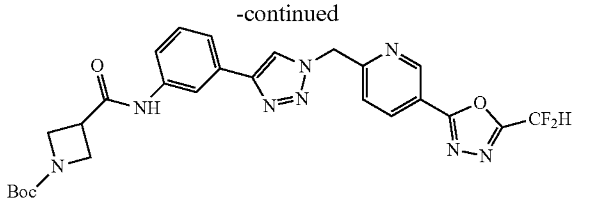

The 3-(1-((5-(5-(difluoromethyl)-1,3,4-oxadiazol-2-yl)pyridin-2-yl)methyl)-1H-1,2,3-triazol-4-yl)aniline (0.245 g, 0.663 mmol) prepared in step 1 of example 36, 1-(tert-butoxycarbonyl)azetidin-3-carboxylic acid (0.147 g, 0.730 mmol), 1-[bis(dimethylamino)methylene]-1H-1,2,3-triazolo[4,5-b]pyridinium 3-oxide hexafluorophosphate (0.504 g, 1.327 mmol) and N,N-diisopropylethylamine (0.231 mL, 1.327 mmol) were dissolved in dichloromethane (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 80%) and concentrated to obtain tert-butyl 3-((3-(1-((5-(5-(difluoromethyl)-1,3,4-oxadiazol-2-yl)pyridin-2-yl)methyl)-1H-1,2,3-triazol-4-yl)phenyl)carbamoyl)azetidin-1-carboxylate (0.270 g, 73.7%) in a light yellow solid form.

[Step 2] Synthesis of Compound 4463

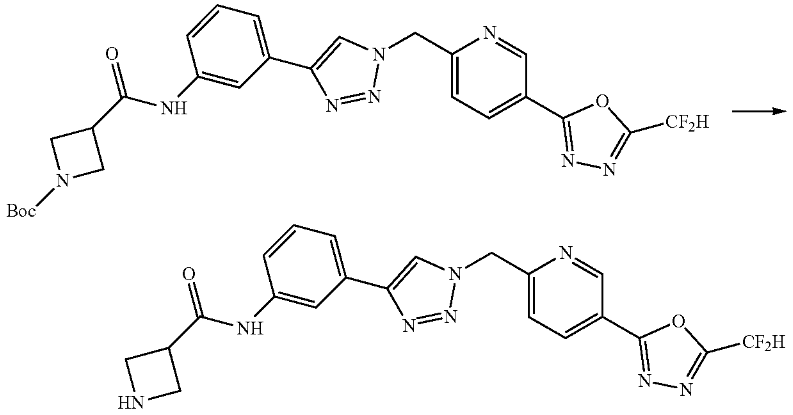

The tert-butyl 3-((3-(1-((5-(5-(difluoromethyl)-1,3,4-oxadiazol-2-yl)pyridin-2-yl)methyl)-1H-1,2,3-triazol-4-yl)phenyl)carbamoyl)azetidin-1-carboxylate (0.150 g, 0.271 mmol) prepared in step 1 was dissolved in dichloromethane (2 mL) at room temperature, after which trifluoroacetic acid (0.624 mL, 8.144 mmol) was added to the resulting solution and stirred at the same temperature for 3 hours. Solvent was removed from the reaction mixture under reduced pressure, after which the resulting concentrate was purified via column chromatography ($SiO_2$, 12 g cartridge; dichloromethane/methanol=100 to 70%) and concentrated to obtain N-(3-(1-((5-(5-(difluoromethyl)-1,3,4-oxadiazol-2-yl)pyridin-2-yl)methyl)-1H-1,2,3-triazol-4-yl)phenyl)azetidin-3-carboxamide (0.115 g, 93.6%) in a yellow oil form.

$^1H$ NMR (400 MHz, $CD_3OD$) δ 9.28 (dd, J=2.2, 0.9 Hz, 1H), 8.54 (dd, J=8.2, 2.2 Hz, 1H), 8.50 (d, J=0.9 Hz, 1H), 8.16 (t, J=1.9 Hz, 1H), 7.66-7.57 (m, 3H), 7.43 (t, J=7.9 Hz, 1H), 7.26 (t, J=51.6 Hz, 1H), 5.93 (s, 2H), 4.39-4.25 (m, 4H), 3.86 (td, J=8.8, 7.1 Hz, 1H); LRMS (ES) m/z 453.5 ($M^+$+1).

Example 339: Synthesis of compound 4464, N-(3-(1-((5-(5-(difluoromethyl)-1,3,4-oxadiazol-2-yl)pyridin-2-yl)methyl)-1H-1,2,3-triazol-4-yl)phenyl)-1-ethylazetidin-3-carboxamide

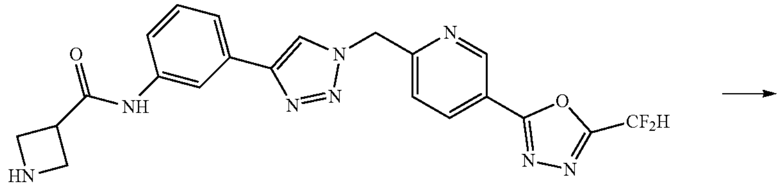

-continued

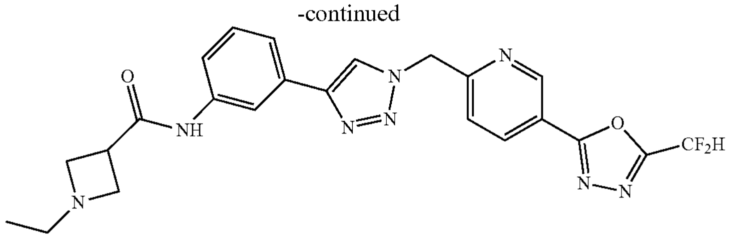

The N-(3-(1-((5-(5-(difluoromethyl)-1,3,4-oxadiazol-2-yl)pyridin-2-yl)methyl)-1H-1,2,3-triazol-4-yl)phenyl)azetidin-3-carboxamide (0.050 g, 0.111 mmol) prepared in step 2 of example 338 and acetaldehyde (0.010 g, 0.221 mmol) were dissolved in dichloromethane (1.5 mL) at room temperature, after which sodium triacetoxyborohydride (0.117 g, 0.553 mmol) was added to the resulting solution and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain N-(3-(1-((5-(5-(difluoromethyl)-1,3,4-oxadiazol-2-yl)pyridin-2-yl)methyl)-1H-1,2,3-triazol-4-yl)phenyl)-1-ethylazetidin-3-carboxamide (0.020 g, 37.7%) in a colorless oil form.

$^1H$ NMR (400 MHz, $CD_3OD$) δ 9.28 (dd, J=2.2, 0.9 Hz, 1H), 8.52 (dd, J=8.2, 2.3 Hz, 1H), 8.48 (s, 1H), 8.11 (t, J=1.9 Hz, 1H), 7.65-7.56 (m, 3H), 7.41 (t, J=7.9 Hz, 1H), 7.26 (t, J=51.6 Hz, 1H), 5.93 (s, 2H), 3.92-3.85 (m, 2H), 3.72 (dd, J=8.8, 7.1 Hz, 2H), 3.66-3.55 (m, 1H), 2.84 (q, J=7.2 Hz, 2H), 1.09 (t, J=7.2 Hz, 3H); LRMS (ES) m/z 481.6 ($M^+$+1).

The compound of table 107 was synthesized according to substantially the same process as described above in the synthesis of compound 4464 with an exception of using 2-(4-((4-(3-(azetidin-3-yl)phenyl)-1H-1,2,3-triazol-1-yl)methyl)-3-fluorophenyl)-5-(difluoromethyl)-1,3,4-oxadiazole and the reactant of table 106.

TABLE 106

| Example | Compound No. | Reactant | Yield (%) |
| --- | --- | --- | --- |
| 340 | 4465 | Oxetan-3-one | 40 |

Example 341: Synthesis of compound 4466, 2-(4-((4-(4-(azetidin-1-ylmethyl)phenyl)-1H-1,2,3-triazol-1-yl)methyl)-3-fluorophenyl)-5-(difluoromethyl)-1,3,4-oxadiazole

[Step 1] Synthesis of 4-(1-(4-(5-(difluoromethyl)-1,3,4-oxadiazol-2-yl)-2-fluorobenzyl)-1H-1,2,3-triazol-4-yl)benzaldehyde

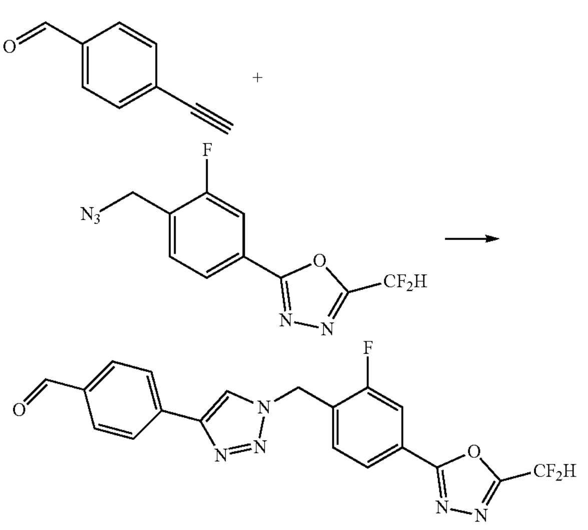

2-(4-(azidomethyl)-3-fluorophenyl)-5-(difluoromethyl)-1,3,4-oxadiazole (1.000 g, 3.715 mmol) prepared in step 1 of example 2 and 4-ethynylbenzaldehyde (0.484 g, 3.715 mmol) were dissolved in tert-butanol (5 mL)/water (5 mL) at room temperature, after which sodium ascorbate (1.00 M solution, 0.371 mL, 0.371 mmol) and copper(II) sulfate pentahydrate (0.50 M solution, 0.074 mL, 0.037 mmol) were added to the resulting solution and stirred at the same temperature for 18 hours. Saturated ammonium chloride aqueous solution was poured into the reaction mixture, and an extraction was performed with ethyl acetate. An organic

TABLE 107

| Example | Compound No. | Compound Name, $^1H$-NMR, MS (ESI) |
| --- | --- | --- |
| 340 | 4465 | N-(3-(1-((5-(5-(difluoromethyl)-1,3,4-oxadiazol-2-yl)pyridin-2-yl)methyl)-1H-1,2,3-triazol-4-yl)phenyl)-1-(oxetan-3-yl)azetidin-3-carboxamide $^1H$ NMR (400 MHz, $CD_3OD$) δ 9.28 (dd, J = 2.3, 0.8 Hz, 1H), 8.53 (dd, J = 8.2, 2.2 Hz, 1H), 8.48 (s, 1H), 8.10 (t, J = 1.9 Hz, 1H), 7.63-7.55 (m, 3H), 7.41 (t, J = 7.9 Hz, 1H), 7.26 (t, J = 51.6 Hz, 1H), 5.93 (s, 2H), 4.77 (t, J = 6.8 Hz, 2H), 4.57 (dd, J = 6.9, 5.0 Hz, 2H), 3.88 (tt, J = 6.7, 5.0 Hz, 1H), 3.73-3.65 (m, 2H), 3.61-3.53 (m, 3H); LRMS (ES) m/z 509.5 ($M^+$ + 1). |

layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; dichloromathane/methanol=100 to 90%) and concentrated to obtain 4-(1-(4-(5-(difluoromethyl)-1,3,4-oxadiazol-2-yl)-2-fluorobenzyl)-1H-1,2,3-triazol-4-yl)benzaldehyde (1.200 g, 80.9%) in a white solid form.

[Step 2] Synthesis of Compound 4466

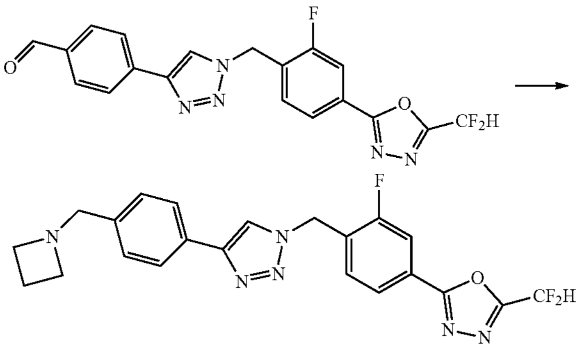

The 4-(1-(4-(5-(difluoromethyl)-1,3,4-oxadiazol-2-yl)-2-fluorobenzyl)-1H-1,2,3-triazol-4-yl)benzaldehyde (0.040 g, 0.100 mmol) prepared in step 1 and azetidine hydrochloride (0.019 g, 0.200 mmol) were dissolved in dichloromethane (1.5 mL) at room temperature, after which sodium triacetoxyborohydride (0.106 g, 0.501 mmol) was added to the resulting solution and stirred at the same temperature. Sodium triacetoxy borohydride (0.106 g, 0.501 mmol) was poured into the reaction mixture, and further stirred at room temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-(4-((4-(4-(azetidin-1-ylmethyl)phenyl)-1H-1,2,3-triazol-1-yl)methyl)-3-fluorophenyl)-5-(difluoromethyl)-1,3,4-oxadiazole (0.030 g, 68.0%) in a white solid form.

$^1$H NMR (400 MHz, $CD_3OD$) δ 8.44 (s, 1H), 8.02-7.93 (m, 2H), 7.82 (d, J=8.1 Hz, 2H), 7.60 (t, J=7.7 Hz, 1H), 7.39 (d, J=7.9 Hz, 2H), 7.24 (t, J=51.6 Hz, 1H), 5.85 (s, 2H), 3.69 (s, 2H), 3.41-3.34 (m, 4H), 2.17 (q, J=7.3 Hz, 2H); LRMS (ES) m/z 441.2 ($M^+$+1).

The compounds of table 109 were synthesized according to substantially the same process as described above in the synthesis of compound 4466 with an exception of using 4-(1-(4-(5-(difluoromethyl)-1,3,4-oxadiazol-2-yl)-2-fluorobenzyl)-1H-1,2,3-triazol-4-yl)benzaldehyde and the reactant of table 108.

TABLE 108

| Example | Compound No. | Reactant | Yield (%) |
|---|---|---|---|
| 342 | 4467 | 3-fluoroazetidin | 47 |
| 343 | 4468 | 3-fluoroazetidine hydrogen chloride | 46 |
| 344 | 4469 | Oxetan-3-amine | 41 |
| 345 | 4470 | 1-methylazetidin-3-amine | 42 |
| 346 | 4471 | Morpholine | 48 |
| 347 | 4472 | 3-fluoroazetidine hydrogen chloride | 41 |
| 348 | 4473 | 1-methylpiperazine | 51 |
| 349 | 4474 | 1-ethylpiperazine | 52 |
| 350 | 4475 | 1-isopropylpiperazine | 41 |
| 351 | 4476 | — | 39 |
| 352 | 4477 | 4,4-difluorocyclohexan-1-amine | 28 |
| 368 | 4494 | N,N-dimethylpiperidin-4-amine | 48 |
| 392 | 4521 | Pyrrolidine | 50 |
| 393 | 4522 | Dimethylamine | 55 |
| 394 | 4523 | 2-oxa-6-azaspiro[3.3]heptane | 64 |
| 466 | 4604 | (S)-N,N-dimethylpyrrolidin-3-amine | 56 |
| 467 | 4605 | (R)N,N-dimethylpyrrolidin-3-amine | 72 |
| 468 | 4606 | (S)-3-fluoropyrrolidine | 65 |
| 469 | 4607 | (R)-3-fluoropyrrolidine | 71 |
| 470 | 4608 | -diethylamine | 56 |
| 471 | 4609 | Cyclopentanamine | 66 |
| 472 | 4610 | Piperidine | 69 |
| 473 | 4611 | 4-methylpiperidine | 65 |

TABLE 109

| Exampe | Compound No. | Compound Name, $^1$H-NMR, MS (ESI) |
|---|---|---|
| 342 | 4467 | 2-(difluoromethyl)-5-(3-fluoro-4-((4-(4-((3-fluoroazetidin-1-yl)methyl)phenyl)-1H-1,2,3-triazol-1-yl)methyl)phenyl)-1,3,4-oxadiazole $^1$H NMR (400 MHz, $CD_3OD$) δ 8.44 (d, J = 2.5 Hz, 1H), 8.03-7.92 (m, 2H), 7.86-7.79 (m, 2H), 7.60 (t, J = 7.7 Hz, 1H), 7.43 (dd, J = 20.4, 8.1 Hz, 2H), 7.24 (t, J = 51.6 Hz, 1H), 5.85 (s, 2H), 5.23 (t, J = 4.6 Hz, 0.5H), 5.09 (s, 0.5H), 3.74 (s, 2H), 3.71-3.59 (m, 2H), 3.38-3.25 (m, 2H); LRMS (ES) m/z 459.2 ($M^+$ + 1). |
| 343 | 4468 | N-(4-(1-(4-(5-(difluoromethyl)-1,3,4-oxadiazol-2-yl)-2-fluorobenzyl)-1H-1,2,3-triazol-4-yl)benzyl)cyclobutanamine $^1$H NMR (400 MHz, $CD_3OD$) δ 8.44 (s, 1H), 8.02-7.93 (m, 2H), 7.82 (d, J = 8.2 Hz, 2H), 7.60 (t, J = 7.6 Hz, 1H), 7.44 (d, J = 8.2 Hz, 2H), 7.24 (t, J = 51.6 Hz, 1H), 5.86 (s, 2H), 3.74 (s, 2H), 3.32-3.27 (m, 1H), 2.25-2.15 (m, 2H), 1.94-1.64 (m, 4H); LRMS (ES) m/z 455.2 ($M^+$ + 1). |
| 344 | 4469 | N-(4-(1-(4-(5-(difluoromethyl)-1,3,4-oxadiazol-2-yl)-2-fluorobenzyl)-1H-1,2,3-triazol-4-yl)benzyl)oxetan-3-amine $^1$H NMR (400 MHz, $CD_3OD$) δ 8.44 (s, 1H), 8.02-7.93 (m, 2H), 7.82 (d, J = 8.2 Hz, 2H), 7.60 (t, J = 7.7 Hz, 1H), 7.43 (d, J = 8.1 Hz, 2H), 7.24 (t, J = 51.6 Hz, 1H), 5.86 (s, 2H), 4.72 (t, J = 6.8 Hz, 2H), 4.45 (t, J = 6.4 Hz, 2H), 4.03 (p, J = 6.7 Hz, 1H), 3.74 (s, 2H); LRMS (ES) m/z 457.3 ($M^+$ + 1). |
| 345 | 4470 | N-(4-(1-(4-(5-(difluoromethyl)-1,3,4-oxadiazol-2-yl)-2-fluorobenzyl)-1H-1,2,3-triazol-4-yl)benzyl)-1-methylazetidin-3-amine $^1$H NMR (400 MHz, $CD_3OD$) δ 8.45 (s, 1H), 8.03-7.93 (m, 2H), 7.87-7.81 (m, |

TABLE 109-continued

| Exampe | Compound No. | Compound Name, $^1$H-NMR, MS (ESI) |
|---|---|---|
| | | 2H), 7.61 (t, J = 7.7 Hz, 1H), 7.45 (d, J = 8.2 Hz, 2H), 7.38-7.09 (m, 1H), 5.86 (s, 2H), 4.19 (s, 2H), 3.87-3.66 (m, 5H), 2.88 (s, 3H); LRMS (ES) m/z 470.5 ($M^+$ + 1). |
| 346 | 4471 | 4-(4-(1-(4-(5-(difluoromethyl)-1,3,4-oxadiazol-2-yl)-2-fluorobenzyl)-1H-1,2,3-triazol-4-yl)benzyl)morpholine $^1$H NMR (400 MHz, $CD_3OD$) δ 8.44 (s, 1H), 8.02-7.93 (m, 2H), 7.82 (d, J = 8.2 Hz, 2H), 7.60 (t, J = 7.7 Hz, 1H), 7.44 (d, J = 8.1 Hz, 2H), 7.24 (t, J = 51.6 Hz, 1H), 5.85 (s, 2H), 3.75-3.68 (m, 4H), 3.57 (s, 2H), 2.49 (t, J = 4.7 Hz, 4H); LRMS (ES) m/z 471.2 ($M^+$ + 1). |
| 347 | 4472 | 2-(difluoromethyl)-5-(4-((4-(4-((4,4-difluoropiperidin-1-yl)methyl)phenyl)-1H-1,2,3-triazol-1-yl)methyl)-3-fluorophenyl)-1,3,4-oxadiazole $^1$H NMR (400 MHz, $CD_3OD$) δ 8.44 (s, 1H), 8.02-7.93 (m, 2H), 7.82 (d, J = 8.2 Hz, 2H), 7.61 (t, J = 7.6 Hz, 1H), 7.44 (d, J = 8.1 Hz, 2H), 7.24 (t, J = 51.6 Hz, 1H), 5.86 (s, 2H), 3.62 (s, 2H), 2.60 (d, J = 5.9 Hz, 4H), 2.05-1.93 (m, 4H); LRMS (ES) m/z 505.2 ($M^+$ + 1). |
| 348 | 4473 | 2-(difluoromethyl)-5-(3-fluoro-4-((4-(4-((4-methylpiperazin-1-yl)methyl)phenyl)-1H-1,2,3-triazol-1-yl)methyl)phenyl)-1,3,4-oxadiazole $^1$H NMR (400 MHz, $CD_3OD$) δ 8.44 (s, 1H), 8.02-7.93 (m, 2H), 7.82 (d, J = 8.3 Hz, 2H), 7.60 (t, J = 7.6 Hz, 1H), 7.43 (d, J = 8.2 Hz, 2H), 7.24 (t, J = 51.6 Hz, 1H), 5.85 (s, 2H), 3.59 (s, 2H), 2.61 (d, J = 53.9 Hz, 8H), 2.31 (s, 3H); LRMS (ES) m/z 484.1 ($M^+$ + 1). |
| 349 | 4474 | 2-(difluoromethyl)-5-(4-((4-(4-((4-ethylpiperazin-1-yl)methyl)phenyl)-1H-1,2,3-triazol-1-yl)methyl)-3-fluorophenyl)-1,3,4-oxadiazole $^1$H NMR (400 MHz, $CD_3OD$) δ 8.44 (s, 1H), 8.03-7.93 (m, 2H), 7.82 (d, J = 8.2 Hz, 2H), 7.60 (t, J = 7.6 Hz, 1H), 7.44 (d, J = 8.1 Hz, 2H), 7.24 (t, J = 51.6 Hz, 1H), 5.86 (s, 2H), 3.59 (s, 2H), 2.75-2.37 (m, 10H), 1.12 (t, J = 7.2 Hz, 3H); LRMS (ES) m/z 498.3 ($M^+$ + 1). |
| 350 | 4475 | 2-(difluoromethyl)-5-(3-fluoro-4-((4-(4-((4-isopropylpiperazin-1-yl)methyl)phenyl)-1H-1,2,3-triazol-1-yl)methyl)phenyl)-1,3,4-oxadiazole $^1$H NMR (400 MHz, $CD_3OD$) δ 8.44 (s, 1H), 8.03-7.92 (m, 2H), 7.85-7.79 (m, 2H), 7.61 (t, J = 7.6 Hz, 1H), 7.44 (d, J = 8.2 Hz, 2H), 7.24 (t, J = 51.6 Hz, 1H), 5.85 (s, 2H), 3.59 (s, 2H), 2.78-2.47 (m, 9H), 1.12 (d, J = 6.5 Hz, 6H); LRMS (ES) m/z 512.1 ($M^+$ + 1). |
| 351 | 4476 | (4-(1-(4-(5-(difluoromethyl)-1,3,4-oxadiazol-2-yl)-2-fluorobenzyl)-1H-1,2,3-triazol-4-yl)phenyl)methanol $^1$H NMR (400 MHz, $CD_3OD$) δ 8.43 (s, 1H), 8.03-7.93 (m, 2H), 7.86-7.80 (m, 2H), 7.60 (t, J = 7.6 Hz, 1H), 7.45 (d, J = 8.1 Hz, 2H), 7.24 (t, J = 51.6 Hz, 1H), 5.86 (s, 2H), 4.65 (s, 2H); LRMS (ES) m/z 402.4 ($M^+$ + 1). |
| 352 | 4477 | N-(4-(1-(4-(5-(difluoromethyl)-1,3,4-oxadiazol-2-yl)-2-fluorobenzyl)-1H-1,2,3-triazol-4-yl)benzyl)-4,4-difluorocyclohexan-1-amine $^1$H NMR (400 MHz, $CD_3OD$) δ 8.43 (s, 1H), 8.00-7.94 (m, 2H), 7.82 (d, = 8.32 Hz, 2H), 7.60 (t, J = 7.48 Hz, 1H), 7.46 (d, J = 8.28 Hz, 2H), 7.24 (t, J = 51.6 Hz, 1H), 5.85 (s, 2H), 3.84 (s, 2H), 2.65-2.69 (m, 1H), 2.17-1.99 (m, 4H), 1.95-1.95 (m, 2H), 1.61-1.52 (m, 2H) ; LRMS (ES) m/z 519.5 ($M^+$ + 1). |
| 368 | 4494 | 1-(4-(1-(4-(5-(difluoromethyl)-1,3,4-oxadiazol-2-yl)-2-fluorobenzyl)-1H-1,2,3-triazol-4-yl)benzyl)-N,N-dimethylpiperidin-4-amine $^1$H NMR (400 MHz, $CD_3OD$) δ 8.44 (s, 1H), 8.03-7.92 (m, 2H), 7.85-7.78 (m, 2H), 7.60 (t, J = 7.7 Hz, 1H), 7.46-7.39 (m, 2H), 7.24 (t, J = 51.6 Hz, 1H), 5.85 (s, 2H), 3.56 (s, 2H), 3.00 (d, J = 11.7 Hz, 2H), 2.31 (s, 6H), 2.28-2.19 (m, 1H), 2.06 (t, J = 11.3 Hz, 2H), 1.93-1.84 (m, 2H), 1.56 (qd, J = 12.3, 3.8 Hz, 2H); LRMS (ES) m/z 512.3 ($M^+$ + 1). |
| 392 | 4521 | 2-(difluoromethyl)-5-(3-fluoro-4-((4-(4-(pyrrolidin-1-ylmethyl)phenyl)-1H-1,2,3-triazol-1-yl)methyl)phenyl)-1,3,4-oxadiazole $^1$H NMR (400 MHz, $CD_3OD$) δ 8.44 (s, 1H), 8.03-7.93 (m, 2H), 7.83 (d, J = 8.0 Hz, 2H), 7.60 (t, J = 7.7 Hz, 1H), 7.45 (d, J = 8.0 Hz, 2H), 7.24 (t, J = 51.6 Hz, 1H), 5.86 (s, 2H), 3.71 (s, 2H), 2.67-2.56 (m, 4H), 1.90-1.79 (m, 4H); LRMS (ES) m/z 455.3 ($M^+$ + 1). |
| 393 | 4522 | 1-(4-(1-(4-(5-(difluoromethyl)-1,3,4-oxadiazol-2-yl)-2-fluorobenzyl)-1H-1,2,3-triazol-4-yl)phenyl)-N,N-dimethylmethanamine $^1$H NMR (400 MHz, $CD_3OD$) δ 8.45 (s, 1H), 8.02-7.93 (m, 2H), 7.84 (d, J = 7.9 Hz, 2H), 7.60 (t, J = 7.6 Hz, 1H), 7.42 (d, J = 8.0 Hz, 2H), 7.24 (t, J = 51.6 Hz, 2H), 5.86 (s, 2H), 3.55 (s, 2H), 2.29 (s, 6H); LRMS (ES) m/z 429.4 ($M^+$ + 1). |
| 394 | 4523 | 6-(4-(1-(4-(5-(difluoromethyl)-1,3,4-oxadiazol-2-yl)-2-fluorobenzyl)-1H-1,2,3-triazol-4-yl)benzyl)-2-oxa-6-azaspiro[3.3]heptane $^1$H NMR (400 MHz, $CD_3OD$) δ 8.44 (s, 1H), 8.03-7.93 (m, 2H), 7.81 (d, J = 8.0 Hz, 2H), 7.60 (t, J = 7.6 Hz, 1H), 7.41-7.09 (m, 3H), 5.85 (s, 2H), 4.75 (s, 4H), 3.62 (s, 2H), 3.47 (s, 4H); LRMS (ES) m/z 483.5 ($M^+$ + 1). |
| 466 | 4604 | (S)-1-(4-(1-(4-(5-(difluoromethyl)-1,3,4-oxadiazol-2-yl)-2-fluorobenzyl)-1H-1,2,3-triazol-4-yl)benzyl)-N,N-dimethylpyrrolidin-3-amine $^1$H NMR (400 MHz, $CD_3OD$) δ 8.44 (s, 3H), 8.02-7.93 (m, 6H), 7.82 (d, J = 8.2 Hz, 6H), 7.60 (t, J = 7.7 Hz, 3H), 7.44 (d, J = 8.2 Hz, 6H), 7.24 (t, J = 51.6 Hz, 1H), 5.85 (s, 6H), 3.68 (dd, J = 32.5, 12.9 Hz, 7H), 3.33 (dt, J = 3.3, 1.6 Hz, 75H), 2.96-2.83 (m, 1H), 2.82-2.72 (m, 1H), 2.58 (dd, J = 15.7, 9.0 Hz, 1H), 2.44-2.29 (m, 1H), 2.25 (s, 2H), 2.13-1.96 (m, 1H), 2.10-1.77 (m, 7H), 1.85-1.69 (m, 1H); LRMS (ES) m/z 498.34 ($M^+$ + 1). |
| 467 | 4605 | (R)-1-(4-(1-(4-(5-(difluoromethyl)-1,3,4-oxadiazol-2-yl)-2-fluorobenzyl)-1H-1,2,3-triazol-4-yl)benzyl)-N,N-dimethylpyrrolidin-3-amine $^1$H NMR (400 MHz, $CD_3OD$) δ 8.44 (s, 1H), 7.98 (dd, J = 10.7, 9.0 Hz, 1H), 7.82 |

TABLE 109-continued

| Exampe | Compound No. | Compound Name, $^1$H-NMR, MS (ESI) |
|---|---|---|
| | | (d, J = 8.2 Hz, 1H), 7.60 (t, J = 7.6 Hz, 1H), 7.44 (d, J = 8.2 Hz, 1H), 7.44 (d, J = 8.2 Hz, 1H), 7.24 (t, J = 51.6 Hz, 1H), 5.85 (s, 1H), 4.87 (s, 74H), 4.60 (s, 1H), 3.77-3.48 (m, 2H), 2.96-2.83 (m, 1H), 2.78 (dd, J = 14.0, 8.7 Hz, 1H), 2.58 (dd, J = 16.0, 9.1 Hz, 1H), 2.34 (d, J = 23.4 Hz, 1H), 2.25 (s, 3H), 2.03 (d, J = 6.7 Hz, 1H), 1.76 (s, 1H); LRMS (ES) m/z 498.34 ($M^+$ + 1). |
| 468 | 4606 | (S)-2-(difluoromethyl)-5-(3-fluoro-4-((4-(4-((3-fluoropyrrolidin-1-yl)methyl)phenyl)-1H-1,2,3-triazol-1-yl)methyl)phenyl)-1,3,4-oxadiazole $^1$H NMR (400 MHz, $CD_3OD$) δ 8.44 (s, J = 3.4 Hz, 1H), 8.03-7.92 (m, 2H), 7.82 (d, J = 8.2 Hz, 2H), 7.60 (t, J = 7.7 Hz, 1H), 7.45 (d, J = 8.1 Hz, 2H), 7.24 (t, J = 51.6 Hz, 1H), 5.86 (s, 2H), 5.31-5.08 (m, J = 55.7 Hz, 1H), 3.71 (dd, J = 29.6, 12.8 Hz, 2H), 2.99-2.82 (m, 2H), 2.72 (ddd, J = 30.7, 11.8, 5.1 Hz, 1H), 2.48 (dd, J = 15.1, 8.2 Hz, 1H), 2.34-2.13 (m, 1H), 2.01 (dd, J = 26.1, 20.1 Hz, 1H); LRMS (ES) m/z 473.32 ($M^+$ + 1). |
| 469 | 4607 | (R)-2-(difluoromethyl)-5-(3-fluoro-4-((4-(4-((3-fluoropyrrolidin-1-yl)methyl)phenyl)-1H-1,2,3-triazol-1-yl)methyl)phenyl)-1,3,4-oxadiazole $^1$H NMR (400 MHz, $CD_3OD$) δ 8.44 (s, J = 3.4 Hz, 1H), 8.03-7.92 (m, 2H), 7.82 (d, J = 8.2 Hz, 2H), 7.60 (t, J = 7.6 Hz, 1H), 7.45 (d, J = 8.2 Hz, 2H), 7.24 (t, J = 51.6 Hz, 1H), 5.86 (s, 2H), 5.29-5.08 (m, J = 55.7 Hz, 1H), 3.71 (dd, J = 29.6, 12.8 Hz, 2H), 2.99-2.82 (m, 2H), 2.72 (ddd, J = 30.4, 11.6, 4.9 Hz, 1H), 2.48 (dd, J = 16.0, 8.1 Hz, 1H), 2.31-2.14 (m, 1H), 2.10-1.96 (m, 1H); LRMS (ES) m/z 473.32 ($M^+$ + 1). |
| 470 | 4608 | N-(4-(1-(4-(5-(difluoromethyl)-1,3,4-oxadiazol-2-yl)-2-fluorobenzyl)-1H-1,2,3-triazol-4-yl)benzyl)-N-ethylethanamine $^1$H NMR (400 MHz, $CD_3OD$) δ 8.44 (s, 1H), 7.98 (dd, J = 10.7, 9.1 Hz, 2H), 7.82 (d, J = 8.2 Hz, 2H), 7.60 (t, J = 7.7 Hz, 1H), 7.44 (d, J = 8.1 Hz, 2H), 7.24 (t, J = 51.6 Hz, 1H), 5.86 (s, 2H), 3.68 (s, 2H), 2.61 (dd, J = 14.6, 7.5 Hz, 4H), 1.12 (t, J = 7.2 Hz, 6H); LRMS (ES) m/z 457.30 ($M^+$ + 1). |
| 471 | 4609 | N-(4-(1-(4-(5-(difluoromethyl)-1,3,4-oxadiazol-2-yl)-2-fluorobenzyl)-1H-1,2,3-triazol-4-yl)benzyl)cyclopentanamine $^1$H NMR (400 MHz, $CD_3OD$) δ 8.44 (s, 1H), 8.02-7.92 (m, 2H), 7.83 (d, J = 8.2 Hz, 2H), 7.60 (t, J = 7.7 Hz, 2H), 7.46 (d, J = 8.2 Hz, 2H), 7.24 (t, J = 51.6 Hz, 1H), 5.85 (s, 2H), 3.82 (s, 2H), 3.20-3.08 (m, 1H), 1.95 (dt, J = 10.6, 6.3 Hz, 2H), 1.82-1.67 (m, 2H), 1.65-1.51 (m, 2H), 1.50-1.37 (m, 2H); LRMS (ES) m/z 469.35 ($M^+$ + 1). |
| 472 | 4610 | 2-(difluoromethyl)-5-(3-fluoro-4-((4-(4-(piperidin-1-ylmethyl)phenyl)-1H-1,2,3-triazol-1-yl)methyl)phenyl)-1,3,4-oxadiazole $^1$H NMR (400 MHz, $CD_3OD$) δ 8.44 (s, 2H), 8.02-7.92 (m, 2H), 7.82 (d, J = 8.2 Hz, 2H), 7.60 (t, J = 7.7 Hz, 1H), 7.43 (d, J = 8.2 Hz, 2H), 7.24 (t, J = 51.6 Hz, 1H), 5.86 (s, 2H), 3.57 (s, J = 29.2 Hz, 2H), 2.59-2.40 (m, 3H), 1.70-1.56 (m, 5H), 1.49 (s, 2H); LRMS (ES) m/z 469.35 ($M^+$ + 1). |
| 473 | 4611 | 2-(difluoromethyl)-5-(3-fluoro-4-((4-(4-((4-methylpiperidin-1-yl)methyl)phenyl)-1H-1,2,3-triazol-1-yl)methyl)phenyl)-1,3,4-oxadiazole $^1$H NMR (400 MHz, $CD_3OD$) δ 8.44 (s, 1H), 7.98 (dd, J = 10.8, 9.1 Hz, 2H), 7.82 (d, J = 8.2 Hz, 2H), 7.60 (t, J = 7.6 Hz, 1H), 7.43 (d, J = 8.2 Hz, 2H), 7.24 (t, J = 51.6 Hz, 1H), 5.86 (s, 2H), 3.59 (s, 2H), 2.94 (d, J = 12.2 Hz, 2H), 2.20-2.01 (m, 2H), 1.67 (d, J = 13.0 Hz, 2H), 1.49-1.36 (m, 1H), 1.36-1.20 (m, 2H), 0.95 (d, J = 6.4 Hz, 3H); LRMS (ES) m/z 483.38 ($M^+$ + 1). |

Examples 353 and 364: Synthesis of compounds 4478 and 4490, (1-((5-(5-(difluoromethyl)-1,3,4-oxadiazol-2-yl)pyridin-2-yl)methyl)-4-phenyl-1H-1,2,3-triazol-5-yl)methanol (4478), 1-(1-((5-(5-(difluoromethyl)-1,3,4-oxadiazol-2-yl)pyridin-2-yl)methyl)-4-phenyl-1H-1,2,3-triazol-5-yl)-N,N-dimethylmethanamine (4490)

[Step 1] Synthesis of 1-((5-(5-(difluoromethyl)-1,3,4-oxadiazol-2-yl)pyridin-2-yl)methyl)-4-phenyl-1H-1,2,3-triazol-5-carbaldehyde

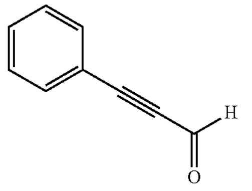

+

-continued

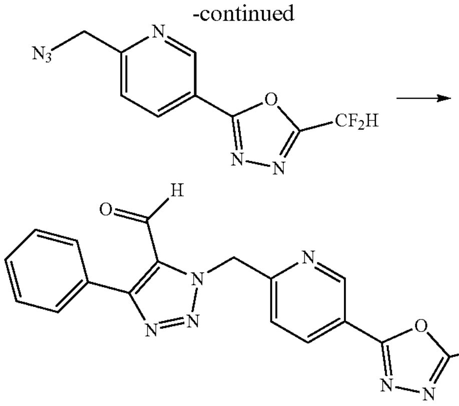

3-phenylpropiolaldehyde (0.050 g, 0.384 mmol) and 2-(6-(azidomethyl)pyridin-3-yl)-5-(difluoromethyl)-1,3,4-oxadiazole (0.097 g, 0.384 mmol) prepared in step 1 of example 16 were dissolved in toluene (2 mL) at room temperature, after which the resulting solution was stirred at 80 °C for 18 hours, and then a reaction was finished by lowering a temperature to room temperature. Solvent was removed from the reaction mixture under reduced pressure, after which the resulting concentrate was purified via column chromatography ($SiO_2$, 4 g cartridge; ethyl acetate/hexane=0 to 50%) and concentrated to obtain 1-((5-(5-(difluoromethyl)-1,3,4-oxadiazol-2-yl)pyridin-2-yl)methyl)-4-phenyl-1H-1,2,3-triazol-5-carbaldehyde (0.035 g, 23.8%) in a brown oil form.

[Step 2] Synthesis of Compounds 4478 and 4490

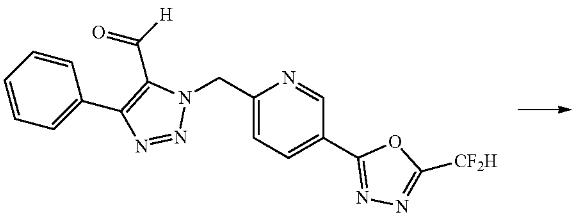

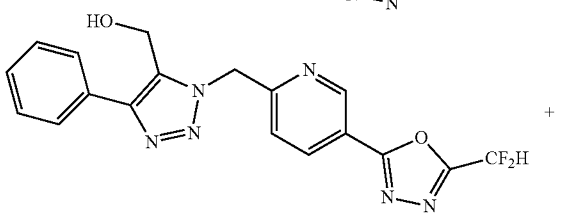

4478

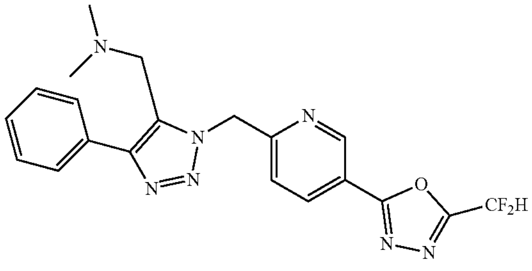

4490

The 1-((5-(5-(difluoromethyl)-1,3,4-oxadiazol-2-yl)pyridin-2-yl)methyl)-4-phenyl-1H-1,2,3-triazol-5-carbaldehyde (0.090 g, 0.235 mmol) prepared in step 1 and dimethylamine (2.00 M solution, 0.235 mL, 0.471 mmol) were dissolved in dichloromethane (2 mL) at room temperature, after which sodium triacetoxy borohydride (0.249 g, 1.177 mmol) was added to the resulting solution and stirred at the same temperature. Sodium triacetoxy borohydride (0.249 g, 1.177 mmol) was poured into the reaction mixture, and further stirred at room temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain (1-((5-(5-(difluoromethyl)-1,3,4-oxadiazol-2-yl)pyridin-2-yl)methyl)-4-phenyl-1H-1,2,3-triazol-5-yl)methanol (0.010 g, 11.1%) and 1-(1-((5-(5-(difluoromethyl)-1,3,4-oxadiazol-2-yl)pyridin-2-yl)methyl)-4-phenyl-1H-1,2,3-triazol-5-yl)-N,N-dimethylmethanamine (0.012 g, 12.4%) in a colorless oil form.

4478: $^1H$ NMR (400 MHz, $CD_3OD$) δ 9.16 (dd, J=2.3, 0.9 Hz, 1H), 8.42 (dd, J=8.2, 2.3 Hz, 1H), 7.50 (s, 5H), 7.40-7.36 (m, 1H), 7.36-7.11 (m, 1H), 5.81 (s, 2H), 4.63 (s, 2H); LRMS (ES) m/z 435.3 ($M^+$+1).

4490: $^1H$ NMR (400 MHz, $CD_3OD$) δ 9.15 (dd, J=2.2, 0.9 Hz, 1H), 8.41 (dd, J=8.2, 2.3 Hz, 1H), 7.53-7.42 (m, 5H), 7.34 (dd, J=8.2, 0.9 Hz, 1H), 7.25 (t, J=51.6 Hz, 1H), 5.79 (s, 2H), 3.61 (s, 2H), 2.24 (s, 6H); LRMS (ES) m/z 412.5 ($M^+$+1).

Examples 354 and 365: Synthesis of compounds 4479 and 4491, (1-(4-(5-(difluoromethyl)-1,3,4-oxadiazol-2-yl)-2-fluorobenzyl)-4-phenyl-1H-1,2,3-triazol-5-yl)methanol (4479), 1-(1-(4-(5-(difluoromethyl)-1,3,4-oxadiazol-2-yl)-2-fluorobenzyl)-4-phenyl-1H-1,2,3-triazol-5-yl)-N,N-dimethylmethanamine (4491)

[Step 1] Synthesis of 1-(4-(5-(difluoromethyl)-1,3,4-oxadiazol-2-yl)-2-fluorobenzyl)-4-phenyl-1H-1,2,3-triazol-5-carbaldehyde

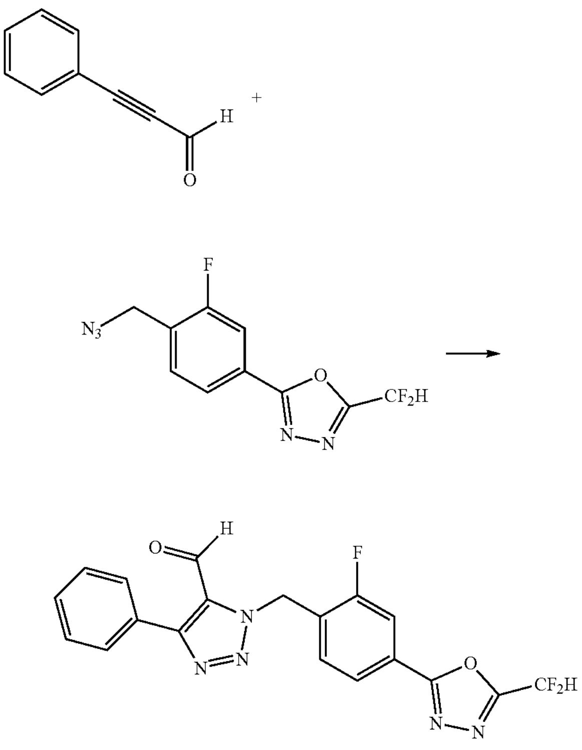

3-phenylpropiolaldehyde (0.050 g, 0.384 mmol) and 2-(4-(azidomethyl)-3-fluorophenyl)-5-(difluoromethyl)-1,3,4-oxadiazole (0.103 g, 0.384 mmol) prepared in step 1 of example 2 were dissolved in toluene (2 mL) at room temperature, after which the resulting solution was stirred at 80 °C for 18 hours, and then a reaction was finished by lowering a temperature to room temperature. Solvent was removed from the reaction mixture under reduced pressure, after which the resulting concentrate was purified via column chromatography ($SiO_2$, 4 g cartridge; ethyl acetate/hexane=0 to 50%) and concentrated to obtain 1-(4-(5-(difluoromethyl)-1,3,4-oxadiazol-2-yl)-2-fluorobenzyl)-4-phenyl-1H-1,2,3-triazol-5-carbaldehyde (0.040 g, 26.1%) in a light yellow solid form.

[Step 2] Synthesis of Compounds 4479 and 4491

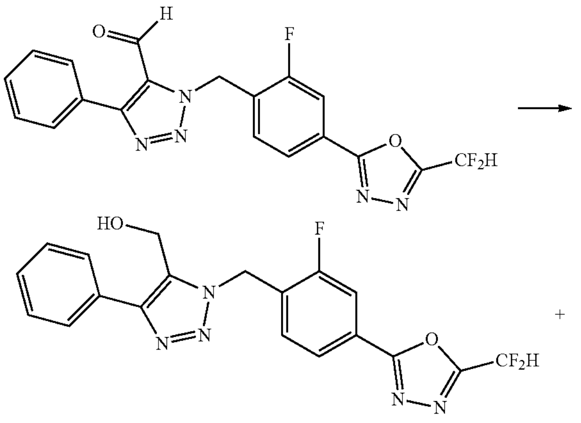

4479

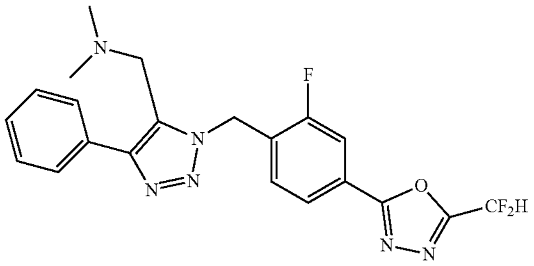

4491

The 4-(1-(4-(5-(difluoromethyl)-1,3,4-oxadiazol-2-yl)-2-fluorobenzyl)-1H-1,2,3-triazol-4-yl)benzaldehyde (0.030 g, 0.075 mmol) prepared in step 1 and dimethylamine (2.00 M solution, 0.075 mL, 0.150 mmol) were dissolved in dichloromethane (1 mL) at room temperature, after which sodium triacetoxyborohydride (0.080 g, 0.376 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain (1-(4-(5-(difluoromethyl)-1,3,4-oxadiazol-2-yl)-2-fluorobenzyl)-4-phenyl-1H-1,2,3-triazol-5-yl)methanol (0.008 g, 26.5%) and 1-(1-(4-(5-(difluoromethyl)-1,3,4-oxadiazol-2-yl)-2-fluorobenzyl)-4-phenyl-1H-1,2,3-triazol-5-yl)-N,N-dimethylmethanamine (0.009 g, 28.0%) in a white solid form.

4479: $^1$H NMR (400 MHz, $CD_3OD$) δ 7.85 (dd, J=8.0, 1.7 Hz, 1H), 7.80 (dd, J=10.2, 1.7 Hz, 1H), 7.53 (dd, J=5.0, 2.0 Hz, 3H), 7.47-7.41 (m, 2H), 7.36-7.08 (m, 2H), 5.75 (s, 2H), 4.60 (s, 2H); LRMS (ES) m/z 402.4 ($M^+$+1).

4491: $^1$H NMR (400 MHz, $CD_3OD$) δ 7.84 (dd, J=8.0, 1.7 Hz, 1H), 7.79 (dd, J=10.2, 1.7 Hz, 1H), 7.58-7.47 (m, 3H), 7.44-7.37 (m, 2H), 7.37-7.08 (m, 2H), 5.72 (s, 2H), 3.57 (s, 2H), 2.22 (s, 6H); LRMS (ES) m/z 429.4 ($M^+$+1).

Example 357: Synthesis of compound 4483, 2-(difluoromethyl)-5-(4-((4-(2-fluoro-3-(4-methylpiperazin-1-yl)phenyl)-1H-1,2,3-triazol-1-yl)methyl)phenyl)-1,3,4-oxadiazole

[Step 1] Synthesis of 2-(3-bromo-2-fluorophenyl)-1,3-dioxolane

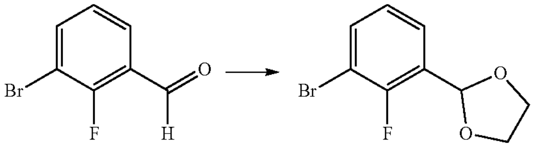 [SMILES: O=Cc1cccc(Br)c1F ; Fc1c(Br)cccc1C1OCCO1]

3-bromo-2-fluorobenzaldehyde (5.000 g, 24.629 mmol), p-toluenesulfonic acid (0.047 g, 0.246 mmol) and ethylene glycol (7.302 g, 29.555 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%) and concentrated to obtain 2-(3-bromo-2-fluorophenyl)-1,3-dioxolane (6.000 g, 98.6%) in a yellow oil form.

[Step 2] Synthesis of tert-butyl 4-(3-(1,3-dioxolan-2-yl)-2-fluorophenyl)piperazin-1-carboxylate

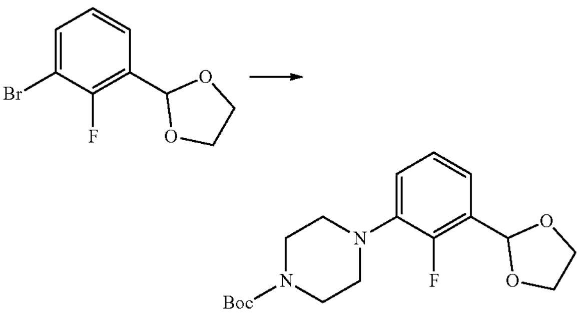

The 2-(3-bromo-2-fluorophenyl)-1,3-dioxolane (5.000 g, 20.238 mmol) prepared in step 1, tert-butyl piperazin-1-carboxylate (3.769 g, 20.238 mmol), tris(dibenzylidene acetone)dipalladium ($Pd_2(dba)_3$, 0.185 g, 0.202 mmol), rac-BINAP (0.252 g, 0.405 mmol) and sodium tert-butoxide (3.890 g, 40.476 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(3-(1,3-dioxolan-2-yl)-2-fluorophenyl) piperazin-1-carboxylate (3.950 g, 53.6%) in a brown oil form.

[Step 3] Synthesis of tert-butyl 4-(2-fluoro-3-formylphenyl)piperazin-1-carboxylate

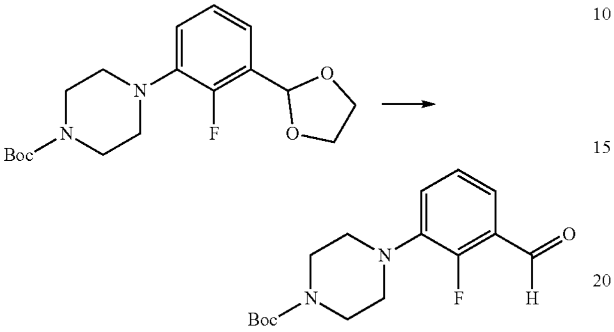

The tert-butyl 4-(3-(1,3-dioxolan-2-yl)-2-fluorophenyl) piperazin-1-carboxylate (3.950 g, 11.209 mmol) prepared in step 2 and hydrochloric acid (1.00 M solution, 33.626 mL, 33.626 mmol) were dissolved in methanol (5 mL) at room temperature, after which the resulting solution was stirred at the same temperature for 3 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(2-fluoro-3-formylphenyl)piperazin-1-carboxylate (2.900 g, 83.9%) in a brown oil form.

[Step 4] Synthesis of tert-butyl 4-(3-(2,2-dibromovinyl)-2-fluorophenyl)piperazin-1-carboxylate

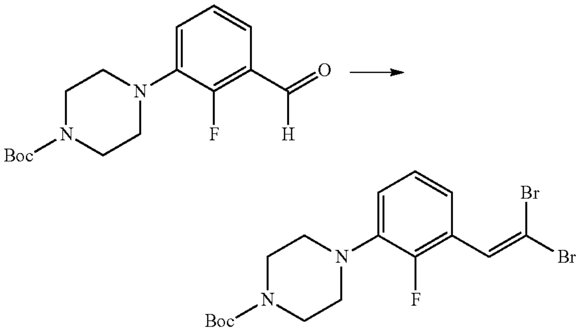

The tert-butyl 4-(2-fluoro-3-formylphenyl)piperazin-1-carboxylate (2.900 g, 9.405 mmol) prepared in step 3, carbon tetrabromide (6.238 g, 18.810 mmol) and triphenylphosphine triphenylphosphine (9.867 g, 37.620 mmol) were dissolved in dichloromethane (50 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 30%) and concentrated to obtain tert-butyl 4-(3-(2,2-dibromovinyl)-2-fluorophenyl)piperazin-1-carboxylate (2.100 g, 48.1%) in a brown oil form.

[Step 5] Synthesis of tert-butyl 4-(3-ethynyl-2-fluorophenyl)piperazin-1-carboxylate

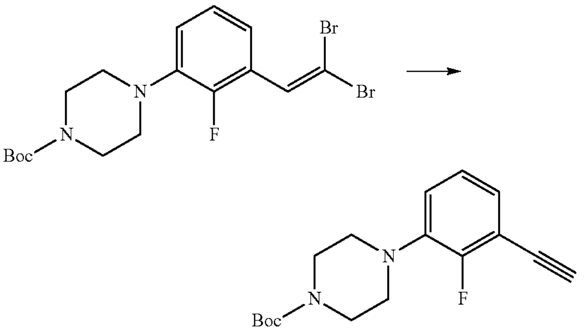

The tert-butyl 4-(3-(2,2-dibromovinyl)-2-fluorophenyl) piperazin-1-carboxylate (2.100 g, 4.524 mmol) prepared in step 4 and 2,3,4,6,7,8,9,10-octahydropyrimido[1,2-a] azepine (2.706 mL, 18.097 mmol) were dissolved in acetonitrile (50 mL) at room temperature, after which the resulting solution was stirred at the same temperature for 16 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(3-ethynyl-2-fluorophenyl)piperazin-1-carboxylate (0.570 g, 41.4%) in a yellow oil form.

[Step 6] Synthesis of tert-butyl 4-(3-(1-(4-(5-(difluoromethyl)-1,3,4-oxadiazol-2-yl)benzyl)-1H-1,2,3-triazol-4-yl)-2-fluorophenyl)piperazin-1-carboxylate

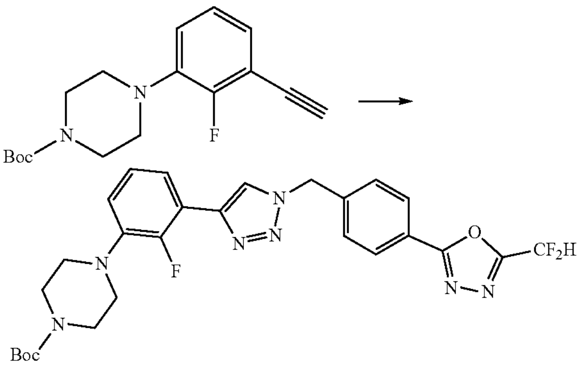

The tert-butyl 4-(3-ethynyl-2-fluorophenyl)piperazin-1-carboxylate (0.570 g, 1.873 mmol) prepared in step 5, 2-(4-(azidomethyl)phenyl)-5-(difluoromethyl)-1,3,4-oxadiazole (0.565 g, 2.247 mmol) prepared in step 1 of example 16, copper(II) sulfate pentahydrate (0.005 g, 0.019 mmol) and sodium ascorbate (0.037 g, 0.187 mmol) were dissolved in tert-butanol (10 mL) at room temperature, after which the resulting solution was stirred at the same temperature for 2 hours. Saturated sodium hydrogen carbonate aqueous solution was poured into the reaction mixture, and an extraction was performed with dichloromethane. An organic layer was washed with saturated aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(3-(1-(4-(5-(difluoromethyl)-1,3,4-oxadiazol-2-yl)benzyl)-1H-1,2,3-triazol-4-yl)-2-fluorophenyl)piperazin-1-carboxylate (0.450 g, 43.3%) in a yellow oil form.

[Step 7] Synthesis of 2-(difluoromethyl)-5-(4-((4-(2-fluoro-3-(piperazin-1-yl)phenyl)-1H-1,2,3-triazol-1-yl)methyl)phenyl)-1,3,4-oxadiazole

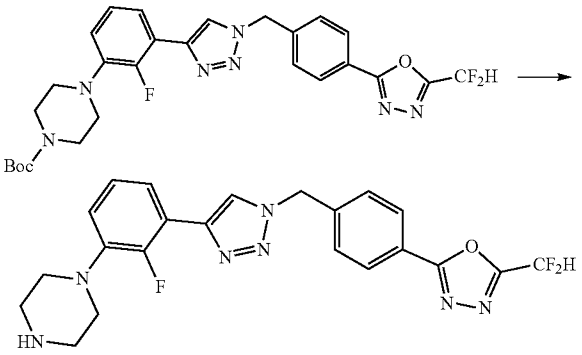

The tert-butyl 4-(3-(1-(4-(5-(difluoromethyl)-1,3,4-oxadiazol-2-yl)benzyl)-1H-1,2,3-triazol-4-yl)-2-fluorophenyl)piperazin-1-carboxylate (0.450 g, 0.810 mmol) prepared in step 6 and trifluoroacetic acid (0.924 g, 8.100 mmol) were dissolved in dichloromethane (25 mL) at room temperature, after which the resulting solution was stirred at the same temperature for 12 hours. Saturated sodium chloride aqueous solution was poured into the reaction mixture, and an extraction was performed with dichloromethane. An organic layer was washed with saturated aqueous solution, then dehydrated with anhydrous sodium sulfate, filtered, and concentrated under reduced pressure. The resulting concentrate was purified via column chromatography ($SiO_2$, 12 g cartridge; methanol/dichloromethane=0 to 5%) and concentrated to obtain 2-(difluoromethyl)-5-(4-((4-(2-fluoro-3-(piperazin-1-yl)phenyl)-1H-1,2,3-triazol-1-yl)methyl)phenyl)-1,3,4-oxadiazole (0.260 g, 70.5%) in a white solid form.

[Step 8] Synthesis of Compound 4483

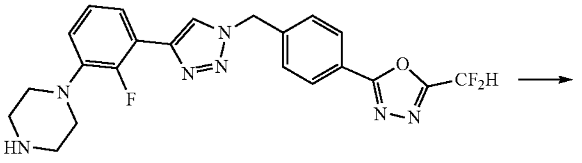

-continued

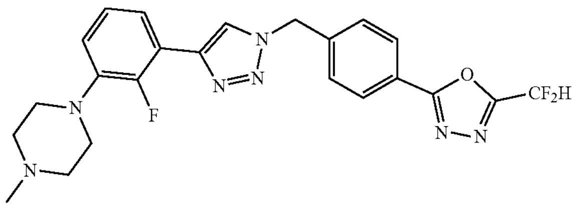

The 2-(difluoromethyl)-5-(4-((4-(2-fluoro-3-(piperazin-1-yl)phenyl)-1H-1,2,3-triazol-1-yl)methyl)phenyl)-1,3,4-oxadiazole (0.060 g, 0.132 mmol) prepared in step 7, formaldehyde (0.008 g, 0.263 mmol) and acetic acid (0.008 mL, 0.145 mmol) were dissolved in dichloromethane (5 mL) at room temperature, after which sodium triacetoxyborohydride (0.056 g, 0.263 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(2-fluoro-3-(4-methylpiperazin-1-yl)phenyl)-1H-1,2,3-triazol-1-yl)methyl)phenyl)-1,3,4-oxadiazole (0.030 g, 48.5%) in a yellow solid form.

$^1H$ NMR (400 MHz, $CDCl_3$) δ 8.13 (d, J=7.9 Hz, 2H), 7.92 (q, J=5.5, 3.7 Hz, 2H), 7.46 (d, J=7.9 Hz, 2H), 7.17 (t, J=7.9 Hz, 1H), 7.06-6.77 (m, 2H), 5.69 (s, 2H), 3.17 (t, J=4.7 Hz, 4H), 2.70 (s, 4H), 2.41 (s, 3H); LRMS (ES) m/z 470.5 ($M^+$+1).

The compounds of table 111 were synthesized according to substantially the same process as described above in the synthesis of compound 4483 with an exception of using 2-(difluoromethyl)-5-(4-((4-(2-fluoro-3-(piperazin-1-yl)phenyl)-1H-1,2,3-triazol-1-yl)methyl)phenyl)-1,3,4-oxadiazole and the reactant of table 110.

TABLE 110

| Example | Compound No. | Reactant | Yield (%) |
|---|---|---|---|
| 358 | 4484 | Acetaldehyde | 47 |
| 359 | 4485 | Cyclobutanone | 52 |
| 360 | 4486 | Oxetan-3-one | 45 |

TABLE 111

| Example | Compound No. | Compound Name, $^1$H-NMR, MS (ESI) |
|---|---|---|
| 358 | 4484 | 2-(difluoromethyl)-5-(4-((4-(5-(4-ethylpiperazin-1-yl)-2-fluorophenyl)-1H-1,2,3-triazol-1-yl)methyl)phenyl)-1,3,4-oxadiazole $^1$H NMR (400 MHz, $CDCl_3$) δ 8.11 (d, J = 7.9 Hz, 2H), 7.90 (t, J = 5.8 Hz, 2H), 7.44 (d, J = 7.9 Hz, 2H), 7.15 (t, J = 7.9 Hz, 1H), 7.05-6.76 (m, 2H), 5.68 (s, 2H), 3.14 (t, J = 5.0 Hz, 4H), 2.65 (s, 4H), 2.50 (q, J = 8.1, 7.3 Hz, 2H), 1.12 (t, J = 7.2 Hz, 3H); LRMS (ES) m/z 484.5 ($M^+$ + 1). |
| 359 | 4485 | 2-(4-((4-(5-(4-cyclobutylpiperazin-1-yl)-2-fluorophenyl)-1H-1,2,3-triazol-1-yl)methyl)phenyl)-5-(difluoromethyl)-1,3,4-oxadiazol $^1$H NMR (400 MHz, $CDCl_3$) δ 8.11 (d, J = 7.9 Hz, 2H), 7.91 (q, J = 5.7, 4.4 Hz, 2H), 7.45 (d, J = 7.9 Hz, 2H), 7.16 (t, J = 7.9 Hz, 1H), 7.04-6.77 (m, 2H), 5.68 (s, 2H), 3.13 (t, J = 4.9 Hz, 4H), 2.82 (p, J = 7.6 Hz, 1H), 2.53 (s, 4H), 2.06 (q, J = 8.4 Hz, 2H), 1.93 (q, J = 10.0 Hz, 2H), 1.70 (dt, J = 19.3, 9.5 Hz, 2H); LRMS (ES) m/z 510.6 ($M^+$ + 1). |
| 360 | 4486 | 2-(difluoromethyl)-5-(4-((4-(2-fluoro-5-(4-(oxetan-3-yl)piperazin-1-yl)phenyl)-1H-1,2,3-triazol-1-yl)methyl)phenyl)-1,3,4-oxadiazole $^1$H NMR (400 MHz, $CDCl_3$) δ 8.13 (d, J = 8.0 Hz, 2H), 7.98-7.88 (m, 2H), 7.46 (d, J = 8.0 Hz, 2H), 7.18 (t, J = 7.9 Hz, 1H), 7.05-6.77 (m, 2H), 5.69 (s, 2H), 4.73-4.66 (m, 4H), 3.64-3.56 (m, 1H), 3.17 (t, J = 4.9 Hz, 4H), 2.55 (s, 4H), 1.25 (s, 1H); LRMS (ES) m/z 512.5 ($M^+$ + 1). |

Example 361: Synthesis of compound 4487, 2-(difluoromethyl)-5-(4-((4-(3-(difluoromethyl)phenyl)-1H-1,2,3-triazol-1-yl)methyl)phenyl)-1,3,4-oxadiazole

[Step 1] Synthesis of 1-(difluoromethyl)-3-ethynylbenzene

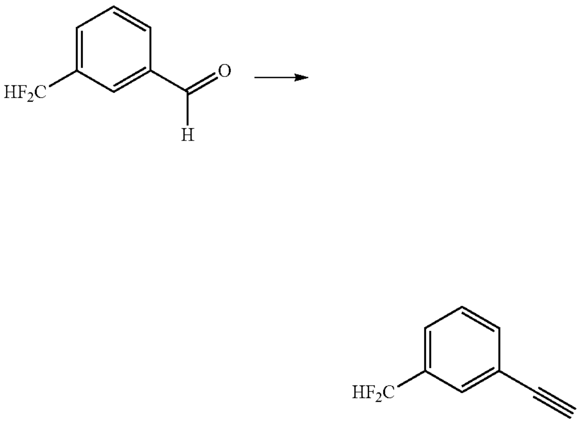

3-(difluoromethyl)benzaldehyde (0.500 g, 3.202 mmol), dimethyl (1-diazo-2-oxopropyl)phosphonate (0.577 mL, 3.843 mmol) and potassium carbonate (0.885 g, 6.405 mmol) were dissolved in methanol (25 mL) at room temperature, after which the resulting solution was stirred at the same temperature for 12 hours. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%), and concentrated to obtain 1-(difluoromethyl)-3-ethynylbenzene (0.300 g, 61.6%) in a yellow oil form.

[Step 2] Synthesis of Compound 4487

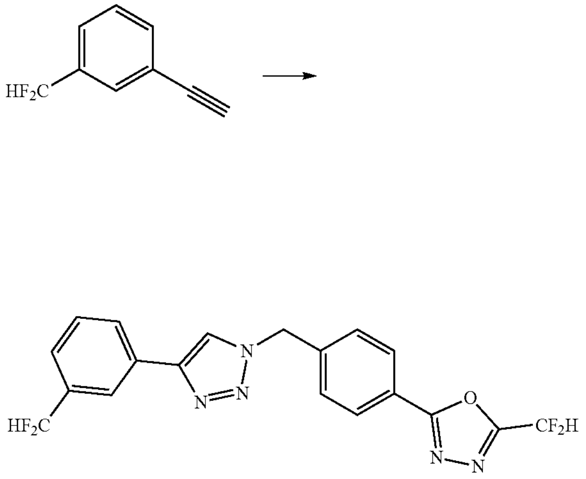

The 1-(difluoromethyl)-3-ethynylbenzene (0.100 g, 0.657 mmol) prepared in step 1, 2-(4-(azidomethyl)phenyl)-5-(difluoromethyl)-1,3,4-oxadiazole (0.165 g, 0.657 mmol) prepared in step 1 of example 1, copper(II) sulfate pentahydrate (0.002 g, 0.007 mmol) and sodium ascorbate (0.013 g, 0.066 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 30%) and concentrated to obtain 2-(difluoromethyl)-5-(4-((4-(3-(difluoromethyl)phenyl)-1H-1,2,3-triazol-1-yl)methyl)phenyl)-1,3,4-oxadiazole (0.260 g, 98.1%) in a white solid form.

$^1$H NMR (400 MHz, $CDCl_3$) δ 8.10 (d, J=7.9 Hz, 2H), 7.92 (d, J=7.7 Hz, 2H), 7.84 (s, 1H), 7.46 (t, J=7.0 Hz, 4H), 7.07-6.47 (m, 2H), 5.67 (s, 2H); LRMS (ES) m/z ($M^+$+1).

Example 362: Synthesis of compound 4488, 2-(difluoromethyl)-5-(4-((4-(3-(difluoromethyl)phenyl)-1H-1,2,3-triazol-1-yl)methyl)-3-fluorophenyl)-1,3,4-oxadiazole

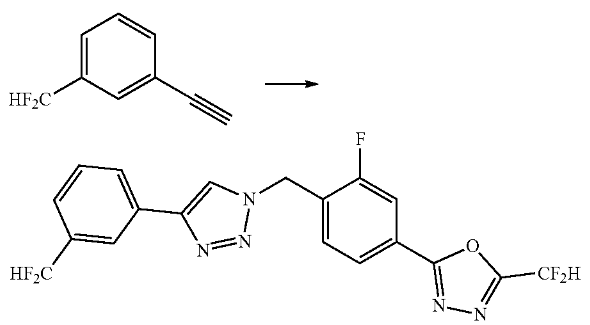

The 1-(difluoromethyl)-3-ethynylbenzene (0.100 g, 0.657 mmol) prepared in step 1 of example 361, 2-(4-(azidomethyl)-3-fluorophenyl)-5-(difluoromethyl)-1,3,4-oxadiazole (0.177 g, 0.657 mmol) prepared in step 1 of example 2, copper(II) sulfate pentahydrate (0.002 g, 0.007 mmol) and sodium ascorbate (0.013 g, 0.066 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 30%) and concentrated to obtain 2-(difluoromethyl)-5-(4-((4-(3-(difluoromethyl)phenyl)-1H-1,2,3-triazol-1-yl)methyl)-3-fluorophenyl)-1,3,4-oxadiazole (0.250 g, 90.3%) in a white solid form.

$^1H$ NMR (400 MHz, $CDCl_3$) δ 7.98-7.83 (m, 5H), 7.54-7.41 (m, 3H), 7.08-6.79 (m, 1H), 6.79-6.49 (m, 1H), 5.73 (d, J=1.1 Hz, 2H); LRMS (ES) m/z ($M^+$+1).

Example 371: Synthesis of compound 4497, 2-amino-N-(3-(1-((5-(5-(difluoromethyl)-1,3,4-oxadiazol-2-yl)pyridin-2-yl)methyl)-1H-1,2,3-triazol-4-yl)phenyl)-2-methylpropanamide

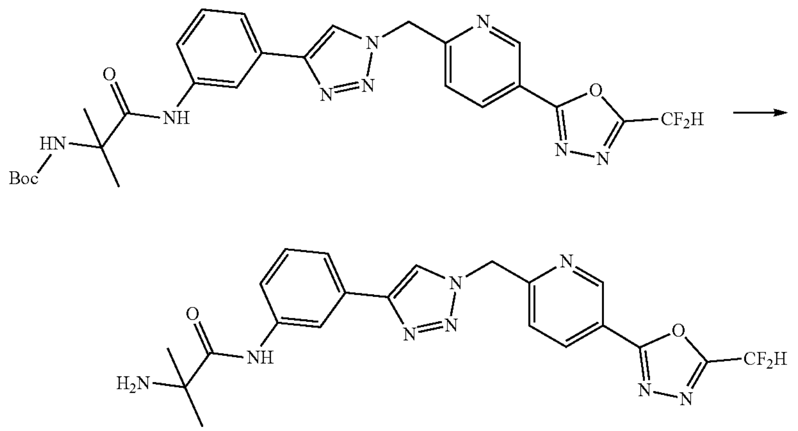

The tert-butyl (1-((3-(1-((5-(5-(difluoromethyl)-1,3,4-oxadiazol-2-yl)pyridin-2-yl)methyl)-1H-1,2,3-triazol-4-yl)phenyl)amino)-2-methyl-1-oxopropan-2-yl)carbamate (0.030 g, 0.054 mmol) prepared in example 369 was dissolved in dichloromethane (0.5 mL) at room temperature, after which trifluoroacetic acid (0.124 mL, 1.623 mmol) was added to the resulting solution and stirred at the same temperature for 18 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 2-amino-N-(3-(1-((5-(5-(difluoromethyl)-1,3,4-oxadiazol-2-yl)pyridin-2-yl)methyl)-1H-1,2,3-triazol-4-yl)phenyl)-2-methylpropanamide (0.017 g, 69.2%) in a colorless oil form.

$^1H$ NMR (400 MHz, $CD_3OD$) δ 9.28 (dd, J=2.2, 0.9 Hz, 1H), 8.53 (dd, J=8.2, 2.2 Hz, 1H), 8.49 (s, 1H), 8.10 (t, J=1.9 Hz, 1H), 7.66-7.55 (m, 3H), 7.43 (t, J=7.9 Hz, 1H), 7.26 (t, J=51.6 Hz, 1H), 5.93 (s, 2H), 1.45 (s, 6H); LRMS (ES) m/z 455.3 ($M^+$+1).

Example 372: Synthesis of compound 4498, 1-amino-N-(3-(1-((5-(5-(difluoromethyl)-1,3,4-oxadiazol-2-yl)pyridin-2-yl)methyl)-1H-1,2,3-triazol-4-yl)phenyl)cyclobutan-1-carboxamide

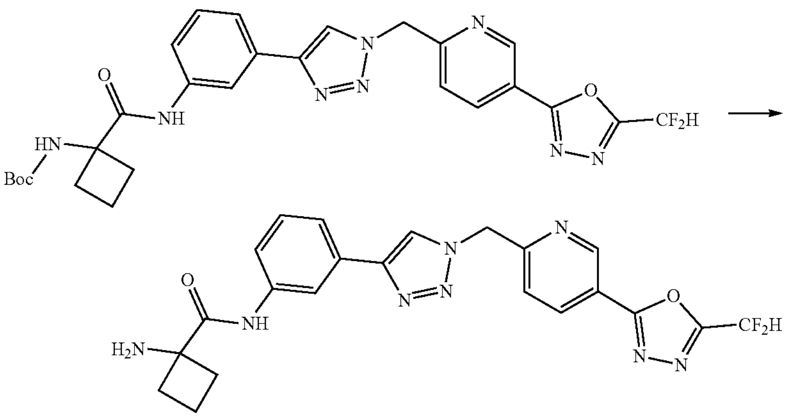

The tert-butyl (1-((3-(1-((5-(5-(difluoromethyl)-1,3,4-oxadiazol-2-yl)pyridin-2-yl)methyl)-1H-1,2,3-triazol-4-yl) phenyl)carbamoyl)cyclobutyl)carbamate (0.030 g, 0.053 mmol) prepared in example 370 was dissolved in dichloromethane (0.5 mL) at room temperature, after which trifluoroacetic acid (0.122 mL, 1.589 mmol) was added to the resulting solution and stirred at the same temperature for 18 hours. Solvent was removed from the reaction mixture under reduced pressure, after which saturated sodium hydrogen carbonate aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 70%) and concentrated to obtain 1-amino-N-(3-(1-((5-(5-(difluoromethyl)-1,3,4-oxadiazol-2-yl)pyridin-2-yl)methyl)-1H-1,2,3-triazol-4-yl)phenyl)cyclobutan-1-carboxamide (0.018 g, 72.9%) in a colorless oil form.

$^1$H NMR (400 MHz, $CD_3OD$) δ 9.28 (dt, J=2.8, 1.4 Hz, 1H), 8.53 (dd, J=8.2, 2.2 Hz, 1H), 8.49 (s, 1H), 8.11 (t, J=1.9 Hz, 1H), 7.66-7.54 (m, 3H), 7.47-7.12 (m, 2H), 5.93 (s, 2H), 2.76-2.64 (m, 2H), 2.59 (ddd, J=13.2, 9.1, 4.7 Hz, 1H), 2.33 (ddd, J=12.6, 10.1, 8.1 Hz, 1H), 2.12-1.91 (m, 2H); LRMS (ES) m/z 467.3 ($M^+$+1).

Example 373: Synthesis of compound 4499, 2-(difluoromethyl)-5-(3-fluoro-4-((4-(4,5,6,7-tetrahydrothieno[2,3-c]pyridin-2-yl)-1H-1,2,3-triazol-1-yl) methyl)phenyl)-1,3,4-oxadiazole

[Step 1] Synthesis of tert-butyl 2-(2,2-dibromovinyl)-4,7-dihydrothieno[2,3-c]pyridin-6(5H)-carboxylate

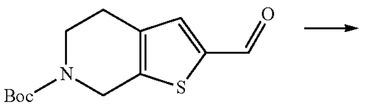

-continued

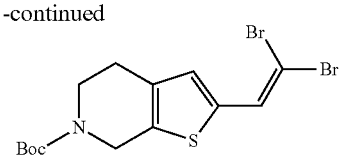

Tert-butyl 2-formyl-4,7-dihydrothieno[2,3-c]pyridin-6 (5H)-carboxylate (1.000 g, 3.741 mmol), carbon tetrabromide (2.481 g, 7.481 mmol) and triphenylphosphine triphenylphosphine (3.924 g, 14.962 mmol) were dissolved in dichloromethane (100 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 30%) and concentrated to obtain tert-butyl 2-(2,2-dibromovinyl)-4,7-dihydrothieno[2,3-c]pyridin-6(5H)-carboxylate (1.100 g, 69.5%) in a yellow solid form.

[Step 2] Synthesis of tert-butyl 2-ethynyl-4,7-dihydrothieno[2,3-c]pyridin-6(5H)-carboxylate

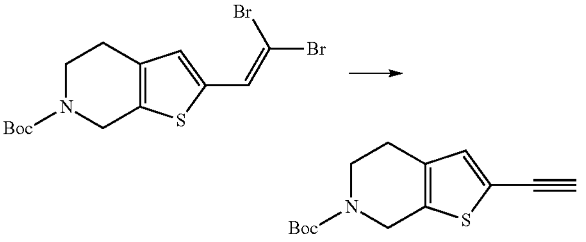

The tert-butyl 2-(2,2-dibromovinyl)-4,7-dihydrothieno[2,3-c]pyridin-6(5H)-carboxylate (1.100 g, 2.599 mmol) prepared in step 1 and 2,3,4,6,7,8,9,10-octahydropyrimido[1,2-a]azepine (1.555 mL, 10.398 mmol) were dissolved in acetonitrile (25 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 2-ethynyl-4,7-dihydrothieno[2,3-c]pyridin-6(5H)-carboxylate (0.180 g, 26.3%) in a colorless oil form.

[Step 3] Synthesis of tert-butyl 2-(1-(4-(5-(difluoromethyl)-1,3,4-oxadiazol-2-yl)-2-fluorobenzyl)-1H-1,2,3-triazol-4-yl)-4,7-dihydrothieno[2,3-c]pyridin-6(5H)-carboxylate

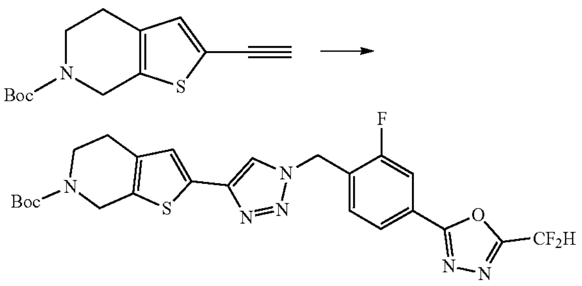

The tert-butyl 2-ethynyl-4,7-dihydrothieno[2,3-c]pyridin-6(5H)-carboxylate (0.180 g, 0.684 mmol) prepared in step 2, 2-(4-(azidomethyl)-3-fluorophenyl)-5-(difluoromethyl)-1,3,4-oxadiazole (0.184 g, 0.684 mmol) prepared in step 1 of example 2, copper(II) sulfate pentahydrate (0.002 g, 0.007 mmol) and sodium ascorbate (0.014 g, 0.068 mmol) were dissolved in tert-butanol (10 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 30%) and concentrated to obtain tert-butyl 2-(1-(4-(5-(difluoromethyl)-1,3,4-oxadiazol-2-yl)-2-fluorobenzyl)-1H-1,2,3-triazol-4-yl)-4,7-dihydrothieno[2,3-c]pyridin-6(5H)-carboxylate (0.310 g, 85.2%) in a yellow solid form.

[Step 4] Synthesis of Compound 4499

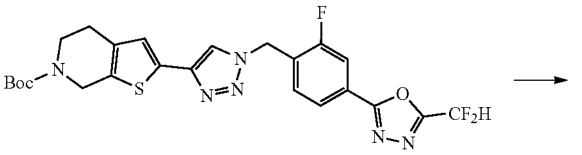

-continued

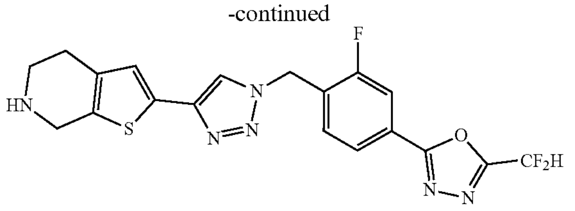

The tert-butyl 2-(1-(4-(5-(difluoromethyl)-1,3,4-oxadiazol-2-yl)-2-fluorobenzyl)-1H-1,2,3-triazol-4-yl)-4,7-dihydrothieno[2,3-c]pyridin-6(5H)-carboxylate (0.310 g, 0.582 mmol) prepared in step 3 and trifluoroacetic acid (0.446 mL, 5.821 mmol) were dissolved in dichloromethane (50 mL) at room temperature, after which the resulting solution was stirred at the same temperature for 6 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(3-fluoro-4-((4-(4,5,6,7-tetrahydrothieno[2,3-c]pyridin-2-yl)-1H-1,2,3-triazol-1-yl)methyl)phenyl)-1,3,4-oxadiazole (0.070 g, 27.8%) in a white solid form.

$^1H$ NMR (400 MHz, $CDCl_3$) δ 7.86 (dd, J=8.6, 5.7 Hz, 2H), 7.68 (s, 1H), 7.41 (t, J=7.7 Hz, 1H), 7.07-6.76 (m, 2H), 5.66 (s, 2H), 3.99 (s, 2H), 3.09 (t, J=5.8 Hz, 2H), 2.61 (t, J=6.0 Hz, 2H), 2.07 (s, 1H); LRMS (ES) m/z ($M^+$+1).

Example 374: Synthesis of compound 4500, 2-(difluoromethyl)-5-(3-fluoro-4-((4-(6-methyl-4,5,6,7-tetrahydrothieno[2,3-c]pyridin-2-yl)-1H-1,2,3-triazol-1-yl)methyl)phenyl)-1,3,4-oxadiazole

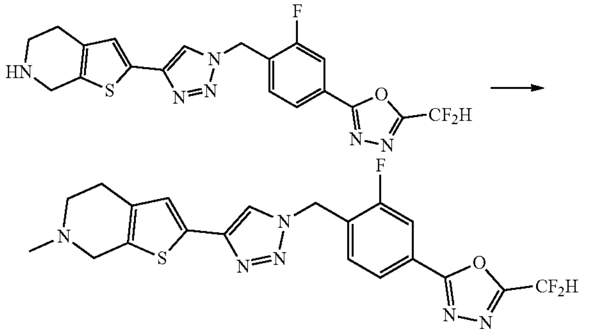

The 2-(difluoromethyl)-5-(3-fluoro-4-((4-(4,5,6,7-tetrahydrothieno[2,3-c]pyridin-2-yl)-1H-1,2,3-triazol-1-yl)methyl)phenyl)-1,3,4-oxadiazole (0.040 g, 0.093 mmol) prepared in step 4 of example 373, formaldehyde (0.006 g, 0.185 mmol) and acetic acid (0.006 mL, 0.102 mmol) were dissolved in dichloromethane (5 mL) at room temperature, after which sodium triacetoxyborohydride (0.039 g, 0.185 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(6-methyl-4,5,6,7-tetrahydrothieno[2,3-c]pyridin-2-yl)-1H-1,2,3-triazol-1-yl)methyl)phenyl)-1,3,4-oxadiazole (0.010 g, 24.2%) in a white solid form.

$^1$H NMR (400 MHz, $CDCl_3$) δ 7.93-7.84 (m, 2H), 7.67 (s, 1H), 7.44 (t, J=7.7 Hz, 1H), 7.07 (s, 1H), 6.92 (t, J=51.7 Hz, 1H), 5.68 (s, 2H), 3.68 (s, 2H), 2.78 (s, 4H), 2.52 (s, 3H); LRMS (ES) m/z 447.4 ($M^+$+1).

The compound of table 113 was synthesized according to substantially the same process as described above in the synthesis of compound 4500 with an exception of using 2-(difluoromethyl)-5-(3-fluoro-4-((4-(4,5,6,7-tetrahydrothieno[2,3-c]pyridin-2-yl)-1H-1,2,3-triazol-1-yl)methyl)phenyl)-1,3,4-oxadiazole and the reactant of table 112.

TABLE 112

| Example | Compound No. | Reactant | Yield (%) |
|---|---|---|---|
| 375 | 4501 | Propan-2-one | 23 |

TABLE 113

| Example | Compound No. | Compound Name, $^1$H-NMR, MS (ESI) |
|---|---|---|
| 375 | 4501 | 2-(difluoromethyl)-5-(3-fluoro-4-((4-(6-isopropyl-4,5,6,7-tetrahydrothieno[2,3-c]pyridin-2-yl)-1H-1,2,3-triazol-1-yl)methyl)phenyl)-1,3,4-oxadiazole $^1$H NMR (400 MHz, $CDCl_3$) δ 7.94-7.88 (m, 2H), 7.67 (s, 1H), 7.45 (t, J = 7.7 Hz, 1H), 7.07-6.78 (m, 2H), 5.68 (s, 2H), 3.96 (s, 2H), 3.19 (s, 1H), 2.95 (d, J = 47.4 Hz, 4H), 1.30-1.25 (m, 6H); LRMS (ES) m/z 475.4 ($M^+$ + 1). |

Example 376: Synthesis of compound 4502, 2-(difluoromethyl)-5-(6-((4-(3-(1-ethylazetidin-3-yl)phenyl)-1H-1,2,3-triazol-1-yl)methyl)pyridin-3-yl)-1,3,4-oxadiazole

[Step 1] Synthesis of tert-butyl 3-(3-(1-((5-(5-(difluoromethyl)-1,3,4-oxadiazol-2-yl)pyridin-2-yl)methyl)-1H-1,2,3-triazol-4-yl)phenyl)azetidin-1-carboxylate

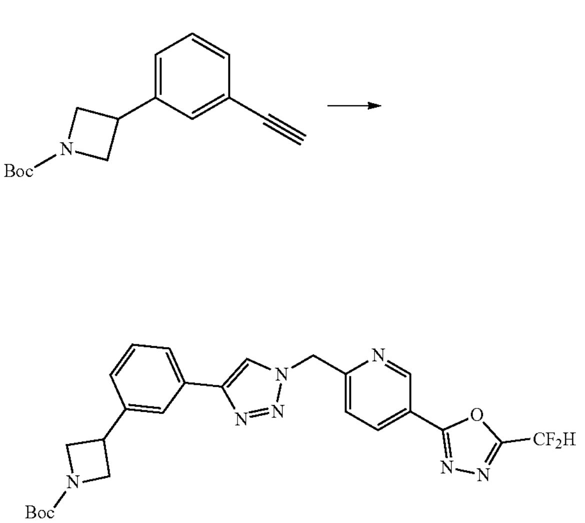

Tert-butyl 3-(3-ethynylphenyl)azetidin-1-carboxylate (0.300 g, 1.166 mmol), 2-(6-(azidomethyl)pyridin-3-yl)-5-(difluoromethyl)-1,3,4-oxadiazole (0.294 g, 1.166 mmol) prepared in step 1 of example 16, sodium ascorbate (0.50 M solution in water, 0.233 mL, 0.117 mmol) and copper(II) sulfate pentahydrate (1.00 M solution in water, 0.023 mL, 0.023 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain tert-butyl 3-(3-(1-((5-(5-(difluoromethyl)-1,3,4-oxadiazol-2-yl)pyridin-2-yl)methyl)-1H-1,2,3-triazol-4-yl)phenyl)azetidin-1-carboxylate (0.500 g, 84.2%) in a yellow solid form.

[Step 2] Synthesis of 2-(6-((4-(3-(azetidin-3-yl)phenyl)-1H-1,2,3-triazol-1-yl)methyl)pyridin-3-yl)-5-(difluoromethyl)-1,3,4-oxadiazole

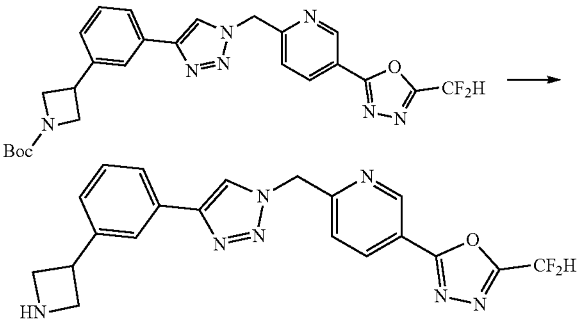

The tert-butyl 3-(3-(1-((5-(5-(difluoromethyl)-1,3,4-oxadiazol-2-yl)pyridin-2-yl)methyl)-1H-1,2,3-triazol-4-yl)phenyl)azetidin-1-carboxylate (0.500 g, 0.981 mmol) prepared in step 1 and trifluoroacetic acid (0.751 mL, 9.813 mmol) were dissolved in dichloromethane (2 mL) at room temperature, after which the resulting solution was stirred at the same temperature for 18 hours. Saturated sodium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Then, the obtained product was used without an additional purification process (2-(6-((4-(3-(azetidin-3-yl)phenyl)-1H-

1,2,3-triazol-1-yl)methyl)pyridin-3-yl)-5-(difluoromethyl)-1,3,4-oxadiazole, 0.400 g, 99.6%, yellow oil).

[Step 3] Synthesis of Compound 4502

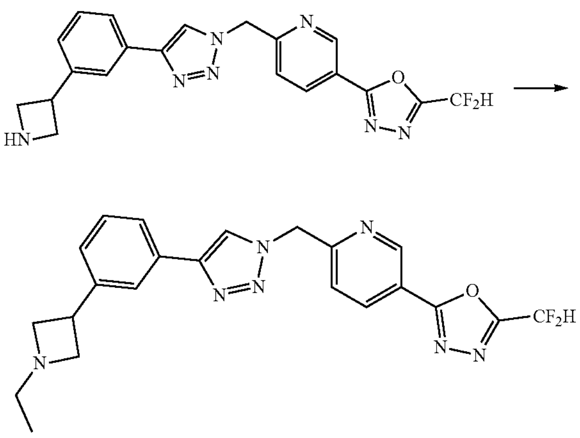

The 2-(6-((4-(3-(azetidin-3-yl)phenyl)-1H-1,2,3-triazol-1-yl)methyl)pyridin-3-yl)-5-(difluoromethyl)-1,3,4-oxadiazole (0.080 g, 0.195 mmol) prepared in step 2 and acetaldehyde (0.022 mL, 0.391 mmol) were dissolved in dichloromethane (1 mL), after which the resulting solution was stirred at room temperature for 15 minutes, and then sodium triacetoxyborohydride (0.124 g, 0.586 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(6-((4-(3-(1-ethylazetidin-3-yl)phenyl)-1H-1,2,3-triazol-1-yl)methyl)pyridin-3-yl)-1,3,4-oxadiazole (0.051 g, 59.7%) in an orange color solid form.

$^1$H NMR (400 MHz, $CD_3OD$) δ 9.28 (dd, J=2.3, 0.9 Hz, 1H), 8.54 (d, J=5.7 Hz, 2H), 7.88 (d, J=1.8 Hz, 1H), 7.79-7.73 (m, 1H), 7.63 (d, J=8.1 Hz, 1H), 7.47 (t, J=7.7 Hz, 1H), 7.35 (d, J=7.8 Hz, 1H), 7.26 (t, J=51.6 Hz, 1H), 5.93 (s, 2H), 4.16 (t, J=8.5 Hz, 2H), 4.04 (p, J=8.2 Hz, 1H), 3.75 (d, J=8.7 Hz, 2H), 2.96 (q, J=7.2 Hz, 2H), 1.15 (t, J=7.2 Hz, 3H); LRMS (ES) m/z 438.0 ($M^+$+1).

The compounds of table 115 were synthesized according to substantially the same process as described above in the synthesis of compound 4502 with an exception of using 2-(6-((4-(3-(azetidin-3-yl)phenyl)-1H-1,2,3-triazol-1-yl)methyl)pyridin-3-yl)-5-(difluoromethyl)-1,3,4-oxadiazole and the reactant of table 114.

TABLE 114

| Example | Compound No. | Reactant | Yield (%) |
|---|---|---|---|
| 377 | 4503 | Acetone | 19 |
| 378 | 4504 | Cyclobutanone | 36 |
| 379 | 4505 | Oxetanone | 25 |

TABLE 115

| Example | Compound No. | Compound Name, $^1$H-NMR, MS (ESI) |
|---|---|---|
| 377 | 4503 | 2-(difluoromethyl)-5-(6-((4-(3-(1-isopropylazetidin-3-yl)phenyl)-1H-1,2,3-triazol-1-yl)methyl)pyridin-3-yl)-1,3,4-oxadiazole<br>$^1$H NMR (400 MHZ, $CD_3OD$) δ 9.28 (dd, J = 2.3, 0.9 Hz, 1H), 8.57-8.48 (m, 2H), 7.84 (t, J = 1.8 Hz, 1H), 7.74 (dt, J = 7.6, 1.4 Hz, 1H), 7.61 (d, J = 8.2 Hz, 1H), 7.44 (t, J = 7.7 Hz, 1H), 7.33 (d, J = 7.7 Hz, 1H), 7.26 (t, J = 51.6 Hz, 1H), 5.93 (s, 2H), 3.97 (t, J = 8.0 Hz, 2H), 3.85 (p, J = 8.2 Hz, 1H), 3.47 (t, J = 8.1 Hz, 2H), 2.78-2.71 (m, 1H), 1.08 (d, J = 6.3 Hz, 6H); LRMS (ESI) m/z 452.1 ($M^+$ + H). |
| 378 | 4504 | 2-(6-((4-(3-(1-cyclobutylazetidin-3-yl)phenyl)-1H-1,2,3-triazol-1-yl)methyl)pyridin-3-yl)-5-(difluoromethyl)-1,3,4-oxadiazole<br>$^1$H NMR (400 MHZ, $CD_3OD$) δ 9.28 (dd, J = 2.2, 0.9 Hz, 1H), 8.57-8.50 (m, 2H), 7.85 (t, J = 1.8 Hz, 1H), 7.75 (dt, J = 7.7, 1.4 Hz, 1H), 7.65-7.59 (m, 1H), 7.46 (t, J = 7.7 Hz, 1H), 7.33 (dt, J = 7.7, 1.4 Hz, 1H), 7.26 (t, J = 51.6 Hz, 1H), 5.93 (s, 2H), 3.95 (d, J = 5.5 Hz, 3H), 3.60 (s, 2H), 3.53 (d, J = 7.6 Hz, 1H), 2.23-2.11 (m, 2H), 2.08-1.94 (m, 2H), 1.91-1.77 (m, 2H); LRMS (ESI) m/z 464.2 ($M^+$ + H). |
| 379 | 4505 | 2-(difluoromethyl)-5-(6-((4-(3-(1-(oxetan-3-yl)azetidin-3-yl)phenyl)-1H-1,2,3-triazol-1-yl)methyl)pyridin-3-yl)-1,3,4-oxadiazole<br>$^1$H NMR (400 MHZ, $CD_3OD$) δ 9.31-9.26 (m, 1H), 8.57-8.50 (m, 2H), 7.85 (d, J = 1.8 Hz, 1H), 7.73 (dt, J = 7.8, 1.4 Hz, 1H), 7.61 (d, J = 8.6 Hz, 1H), 7.44 (t, J = 7.7 Hz, 1H), 7.37-7.31 (m, 1H), 7.26 (t, J = 51.6 Hz, 1H), 5.93 (s, 2H), 4.79 (t, J = 6.8 Hz, 2H), 4.56 (dd, J = 6.8, 5.0 Hz, 2H), 3.94-3.82 (m, 4H), 3.41 (td, J = 5.7, 2.4 Hz, 2H); LRMS (ESI) m/z 466.0 ($M^+$ + H). |

Example 380: Synthesis of compound 4506, 2-(difluoromethyl)-5-(4-((4-(3-(1-ethylazetidin-3-yl)phenyl)-1H-1,2,3-triazol-1-yl)methyl)-3-fluorophenyl)-1,3,4-oxadiazole

[Step 1] Synthesis of tert-butyl 3-(3-(1-(4-(5-(difluoromethyl)-1,3,4-oxadiazol-2-yl)-2-fluorobenzyl)-1H-1,2,3-triazol-4-yl)phenyl)azetidin-1-carboxylate

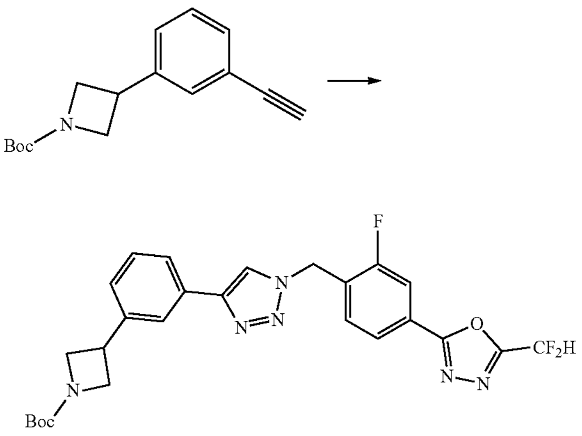

Tert-butyl 3-(3-ethynylphenyl)azetidin-1-carboxylate (0.150 g, 0.583 mmol), 2-(4-(azidomethyl)-3-fluorophenyl)-5-(difluoromethyl)-1,3,4-oxadiazole (0.157 g, 0.583 mmol) prepared in step 1 of example 2, sodium ascorbate (0.50 M solution in water, 0.117 mL, 0.058 mmol) and copper(II) sulfate pentahydrate (1.00 M solution in water, 0.012 mL, 0.012 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl 3-(3-(1-(4-(5-(difluoromethyl)-1,3,4-oxadiazol-2-yl)-2-fluorobenzyl)-1H-1,2,3-triazol-4-yl)phenyl)azetidin-1-carboxylate (0.287 g, 93.5%) in a white solid form.

[Step 2] Synthesis of 2-(4-((4-(3-(azetidin-3-yl)phenyl)-1H-1,2,3-triazol-1-yl)methyl)-3-fluorophenyl)-5-(difluoromethyl)-1,3,4-oxadiazole

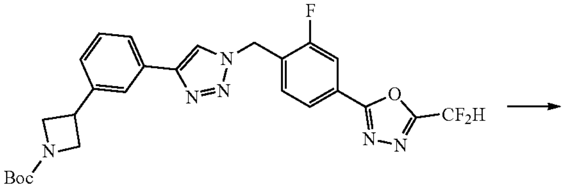

-continued

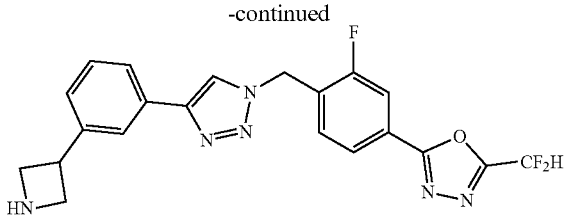

The tert-butyl 3-(3-(1-(4-(5-(difluoromethyl)-1,3,4-oxadiazol-2-yl)-2-fluorobenzyl)-1H-1,2,3-triazol-4-yl)phenyl)azetidin-1-carboxylate (0.287 g, 0.545 mmol) prepared in step 1 and trifluoroacetic acid (0.417 mL, 5.451 mmol) were dissolved in dichloromethane (2 mL) at room temperature, after which the resulting solution was stirred at the same temperature for 3 hours. Saturated sodium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Then, the obtained product was used without an additional purification process (2-(4-((4-(3-(azetidin-3-yl)phenyl)-1H-1,2,3-triazol-1-yl)methyl)-3-fluorophenyl)-5-(difluoromethyl)-1,3,4-oxadiazole, 0.230 g, 99.0%, yellow oil).

[Step 3] Synthesis of Compound 4506

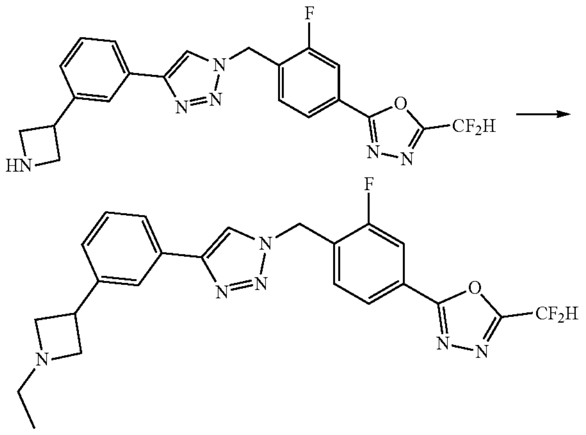

The 2-(4-((4-(3-(azetidin-3-yl)phenyl)-1H-1,2,3-triazol-1-yl)methyl)-3-fluorophenyl)-5-(difluoromethyl)-1,3,4-oxadiazole (0.075 g, 0.176 mmol) prepared in step 2, acetaldehyde (0.020 mL, 0.352 mmol) and acetic acid (0.010 mL, 0.176 mmol) were dissolved in dichloromethane (1 mL), after which the resulting solution was stirred at room temperature for 15 minutes, and then sodium triacetoxyborohydride (0.112 g, 0.528 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(4-((4-(3-(1-ethylazetidin-3-yl)phenyl)-1H-1,2,3-triazol-1-yl)methyl)-3-fluorophenyl)-1,3,4-oxadiazole (0.056 g, 70.1%) in a yellow oil form.

$^1$H NMR (400 MHz, $CD_3OD$) δ 8.47 (s, 1H), 8.02-7.92 (m, 2H), 7.81 (t, J=1.7 Hz, 1H), 7.71 (dt, J=7.8, 1.4 Hz, 1H), 7.61 (t, J=7.7 Hz, 1H), 7.42 (t, J=7.7 Hz, 1H), 7.31 (dt, J=7.6, 1.5 Hz, 1H), 7.24 (t, J=51.6 Hz, 1H), 5.86 (s, 2H), 3.90-3.78 (m, 3H), 3.30 (q, J=3.3 Hz, 2H), 2.64 (q, J=7.2 Hz, 2H), 1.05 (t, J=7.2 Hz, 3H); LRMS (ES) m/z 455.5 ($M^+$+1).

The compound of table 117 was synthesized according to substantially the same process as described above in the synthesis of compound 4506 with an exception of using 2-(4-((4-(3-(azetidin-3-yl)phenyl)-1H-1,2,3-triazol-1-yl)methyl)-3-fluorophenyl)-5-(difluoromethyl)-1,3,4-oxadiazole and the reactant of table 116.

TABLE 116

| Example | Compound No. | Reactant | Yield (%) |
|---|---|---|---|
| 381 | 4507 | Cyclobutanone | 65 |

TABLE 117

| Example | Compound No | Compound Name, $^1$H-NMR, MS (ESI) |
|---|---|---|
| 381 | 4507 | 2-(4-((4-(3-(1-cyclobutylazetidin-3-yl)phenyl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.47 (s, 1H), 8.02-7.92 (m, 2H), 7.82-7.77 (m, 1H), 7.71 (dt, J = 7.7, 1.4 Hz, 1H), 7.61 (t, J = 7.7 Hz, 1H), 7.41 (t, J = 7.7 Hz, 1H), 7.30 (dt, J = 7.6, 1.7 Hz, 1H), 7.24 (t, J = 51.6 Hz, 1H), 5.86 (s, 2H), 3.88-3.71 (m, 3H), 3.34 (s, 1H), 3.32-3.23 (m, 2H), 2.14-2.01 (m, 2H), 2.00-1.88 (m, 2H), 1.88-1.67 (m, 2H); LRMS (ESI) m/z 481.6 ($M^+$ + H). |

Example 382: Synthesis of compound 4508, 2-(difluoromethyl)-5-(4-((4-(3-(1-ethylazetidin-3-yl)phenyl)-1H-1,2,3-triazol-1-yl)methyl)phenyl)-1,3,4-oxadiazole

[Step 1] Synthesis of tert-butyl 3-(3-(1-(4-(5-(difluoromethyl)-1,3,4-oxadiazol-2-yl)benzyl)-1H-1,2,3-triazol-4-yl)phenyl)azetidin-1-carboxylate

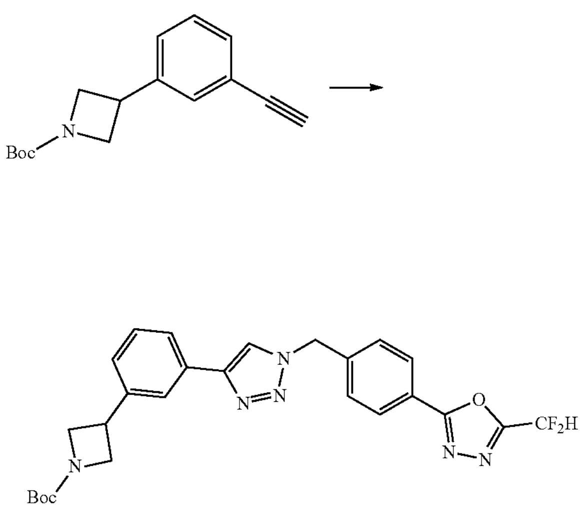

Tert-butyl 3-(3-ethynylphenyl)azetidin-1-carboxylate (0.300 g, 1.166 mmol), 2-(4-(azidomethyl)phenyl)-5-(difluoromethyl)-1,3,4-oxadiazole (0.293 g, 1.166 mmol) prepared in step 1 of example 1, sodium ascorbate (0.50 M solution in water, 0.233 mL, 0.117 mmol) and copper(II) sulfate pentahydrate (1.00 M solution in water, 0.023 mL, 0.023 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl 3-(3-(1-(4-(5-(difluoromethyl)-1,3,4-oxadiazol-2-yl)benzyl)-1H-1,2,3-triazol-4-yl)phenyl)azetidin-1-carboxylate (0.583 g, 98.3%) in a white solid form.

[Step 2] Synthesis of 2-(4-((4-(3-(azetidin-3-yl)phenyl)-1H-1,2,3-triazol-1-yl)methyl)phenyl)-5-(difluoromethyl)-1,3,4-oxadiazole

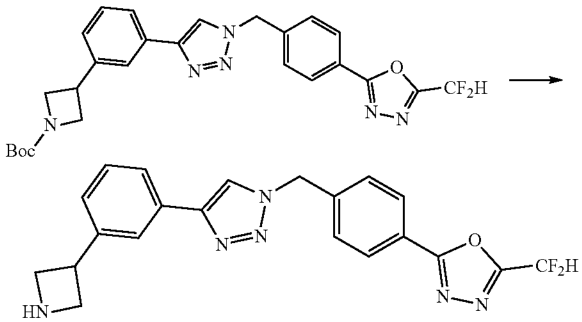

The tert-butyl 3-(3-(1-(4-(5-(difluoromethyl)-1,3,4-oxadiazol-2-yl)benzyl)-1H-1,2,3-triazol-4-yl)phenyl)azetidin-1-carboxylate (0.583 g, 1.146 mmol) prepared in step 1 and trifluoroacetic acid (0.878 mL, 11.464 mmol) were dissolved in dichloromethane (4 mL) at room temperature, after which the resulting solution was stirred at the same temperature for 3 hours. Saturated sodium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Then, the obtained product was used without an additional purification process (2-(4-((4-(3-(azetidin-3-yl)phenyl)-1H-1,2,3-triazol-1-yl)methyl)phenyl)-5-(difluoromethyl)-1,3,4-oxadiazole, 0.460 g, 98.2%, yellow oil).

[Step 3] Synthesis of Compound 4508

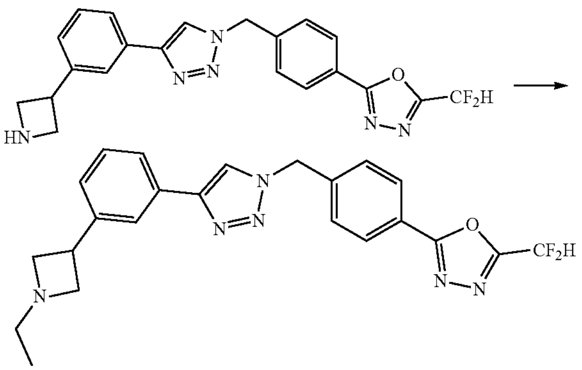

The 2-(4-((4-(3-(azetidin-3-yl)phenyl)-1H-1,2,3-triazol-1-yl)methyl)phenyl)-5-(difluoromethyl)-1,3,4-oxadiazole (0.090 g, 0.220 mmol) prepared in step 2, acetaldehyde (0.025 mL, 0.441 mmol) and acetic acid (0.013 mL, 0.220 mmol) were dissolved in dichloromethane (1 mL), after which the resulting solution was stirred at room temperature for minutes, and then sodium triacetoxyborohydride (0.140 g, 0.661 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(4-((4-(3-(1-ethylazetidin-3-yl)phenyl)-1H-1,2,3-triazol-1-yl)methyl)phenyl)-1,3,4-oxadiazole (0.038 g, 39.5%) in a yellow oil form.

$^1H$ NMR (400 MHz, $CD_3OD$) δ 8.46 (s, 1H), 8.20-8.12 (m, 2H), 7.80 (d, J=1.8 Hz, 1H), 7.70 (dt, J=7.7, 1.4 Hz, 1H), 7.65-7.58 (m, 2H), 7.41 (t, J=7.7 Hz, 1H), 7.30 (dt, J=7.7, 1.5 Hz, 1H), 7.23 (t, J=51.6 Hz, 1H), 5.80 (s, 2H), 3.87-3.75 (m, 3H), 3.31-3.20 (m, 2H), 2.61 (q, J=7.2 Hz, 2H), 1.04 (t, J=7.2 Hz, 3H); LRMS (ES) m/z 437.5 ($M^+$+1).

The compounds of table 119 were synthesized according to substantially the same process as described above in the synthesis of compound 4508 with an exception of using 2-(4-((4-(3-(azetidin-3-yl)phenyl)-1H-1,2,3-triazol-1-yl)methyl)phenyl)-5-(difluoromethyl)-1,3,4-oxadiazole and the reactant of table 118.

TABLE 118

| Example | Compound No. | Reactant | Yield (%) |
|---|---|---|---|
| 383 | 4509 | Acetone | 36 |
| 384 | 4510 | Cyclobutanone | 17 |
| 385 | 4511 | Oxetanone | 19 |
| 399 | 4528 | Formaldehyde | 5 |

TABLE 119

| Example | Compound No. | Compound Name, $^1H$-NMR, MS (ESI) |
|---|---|---|
| 383 | 4509 | 2-(difluoromethyl)-5-(4-((4-(3-(1-isopropylazetidin-3-yl)phenyl)-1H-1,2,3-triazol-1-yl)methyl)phenyl)-1,3,4-oxadiazole<br>$^1H$ NMR (400 MHZ, $CD_3OD$) δ 8.47 (s, 1H), 8.20-8.10 (m, 2H), 7.80 (t, J = 1.8 Hz, 1H), 7.70 (dt, J = 7.8, 1.4 Hz, 1H), 7.65-7.58 (m, 2H), 7.47-7.37 (m, 1H), 7.33-7.26 (m, 1H), 7.23 (t, J = 51.7 Hz, 1H), 5.80 (s, 2H), 3.88-3.71 (m, 3H), 3.31-3.24 (m, 2H), 2.56 (hept, J = 6.1 Hz, 1H), 1.02 (d, J = 6.3 Hz, 6H); LRMS (ESI) m/z 451.5 ($M^+$ + H). |
| 384 | 4510 | 2-(4-((4-(3-(1-cyclobutylazetidin-3-yl)phenyl)-1H-1,2,3-triazol-1-yl)methyl)phenyl)-5-(difluoromethyl)-1,3,4-oxadiazole<br>$^1H$ NMR (400 MHZ, $CD_3OD$) δ 8.46 (s, 1H), 8.20-8.12 (m, 2H), 7.79 (t, J = 1.8 Hz, 1H), 7.70 (dt, J = 7.7, 1.4 Hz, 1H), 7.65-7.58 (m, 2H), 7.41 (t, J = 7.7 Hz, 1H), 7.33-7.26 (m, 1H), 7.23 (t, J = 51.7 Hz, 1H), 5.80 (s, 2H), 3.88-3.72 (m, 3H), 3.35 (d, J = 1.3 Hz, 1H), 3.32-3.23 (m, 2H), 2.14-2.01 (m,2H), 2.01-1.87 (m, 2H), 1.87-1.70 (m, 2H); LRMS (ESI) m/z 463.6 ($M^+$ + H). |
| 385 | 4511 | 2-(difluoromethyl)-5-(4-((4-(3-(1-(oxetan-3-yl)azetidin-3-yl)phenyl)-1H-1,2,3-triazol-1-yl)methyl)phenyl)-1,3,4-oxadiazole<br>$^1H$ NMR (400 MHZ, $CD_3OD$) δ 8.46 (s, 1H), 8.20-8.10 (m, 2H), 7.86-7.80 (m, 1H), 7.71 (dt, J = 7.7, 1.4 Hz, 1H), 7.65-7.58 (m, 2H), 7.42 (t, J = 7.7 Hz, 1H), 7.33 (dt, J = 7.7, 1.5 Hz, 1H), 7.23 (t, J = 51.6 Hz, 1H), 5.80 (s, 2H), 4.78 (t, J = 6.7 Hz, 2H), 4.55 (dd, J = 6.8, 5.0 Hz, 2H), 3.95-3.80 (m, 4H), 3.46-3.36 (m, 2H); LRMS (ESI) m/z 465.5 ($M^+$ + H). |
| 399 | 4528 | 2-(difluoromethyl)-5-(4-((4-(3-(1-methylazetidin-3-yl)phenyl)-1H-1,2,3-triazol-1-yl)methyl)phenyl)-1,3,4-oxadiazole<br>$^1H$ NMR (400 MHZ, $CD_3OD$) δ 8.48 (s, 1H), 8.20-8.11 (m, 2H), 7.86 (t, J = 1.8 Hz, 1H), 7.74 (dt, J = 7.8, 1.5 Hz, 1H), 7.62 (d, J = 8.3 Hz, 2H), 7.45 (t, J = 7.7 Hz, 1H), 7.34 (d, J = 7.8 Hz, 1H), 7.23 (t, J = 51.7 Hz, 1H), 5.81 (s, 2H), 4.17-4.08 (m, 2H), 4.06-3.94 (m, 1H), 3.75 (t, J = 8.5 Hz, 2H), 2.68 (s, 3H); LRMS (ESI) m/z 423.4 ($M^+$ + H). |

Example 386: Synthesis of compound 4513, 2-(difluoromethyl)-5-(4-((4-(2-methylisoindolin-5-yl)-1H-1,2,3-triazol-1-yl)methyl)phenyl)-1,3,4-oxadiazole

[Step 1] Synthesis of tert-butyl 5-ethynylisoindolin-2-carboxylate

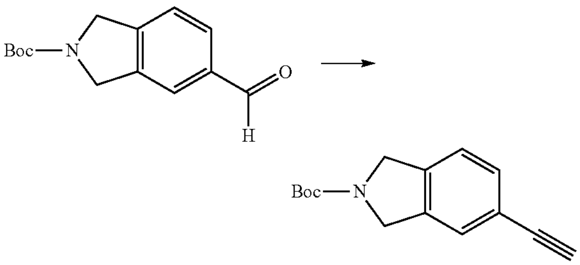

Tert-butyl 5-formylisoindolin-2-carboxylate (2.500 g, 10.110 mmol), dimethyl (1-diazo-2-oxopropyl)phosphonate (1.821 mL, 12.132 mmol) and potassium carbonate (2.794 g, 20.219 mmol) were dissolved in methanol (10 mL) at room temperature, after which the resulting solution was stirred at the same temperature for 12 hours. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 5-ethynylisoindolin-2-carboxylate (1.460 g, 59.4%) in a yellow oil form.

[Step 2] Synthesis of tert-butyl 5-(1-(4-(5-(difluoromethyl)-1,3,4-oxadiazol-2-yl)benzyl)-1H-1,2,3-triazol-4-yl)isoindolin-2-carboxylate

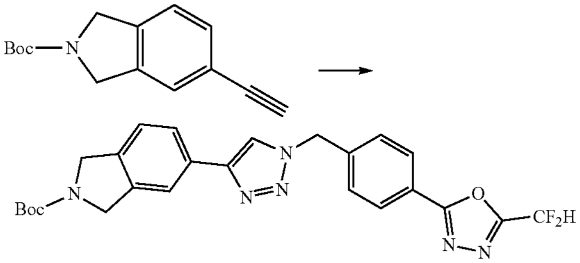

The tert-butyl 5-ethynylisoindolin-2-carboxylate (0.550 g, 2.260 mmol) prepared in step 1, 2-(4-(azidomethyl) phenyl)-5-(difluoromethyl)-1,3,4-oxadiazole (0.625 g, 2.487 mmol) prepared in step 1 of example 1, copper(II) sulfate pentahydrate (0.006 g, 0.023 mmol) and sodium ascorbate (0.045 g, 0.226 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%) and concentrated to obtain tert-butyl 5-(1-(4-(5-(difluoromethyl)-1,3,4-oxadiazol-2-yl)benzyl)-1H-1,2,3-triazol-4-yl)isoindolin-2-carboxylate (0.370 g, 33.1%) in a white solid form.

[Step 3] Synthesis of 2-(difluoromethyl)-5-(4-((4-(isoindolin-5-yl)-1H-1,2,3-triazol-1-yl)methyl)phenyl)-1,3,4-oxadiazole

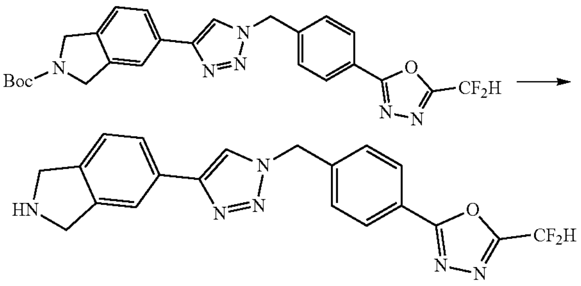

The tert-butyl 5-(1-(4-(5-(difluoromethyl)-1,3,4-oxadiazol-2-yl)benzyl)-1H-1,2,3-triazol-4-yl)isoindolin-2-carboxylate (0.370 g, 0.748 mmol) prepared in step 2 and trifluoroacetic acid (0.573 mL, 7.482 mmol) were dissolved in dichloromethane (50 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(4-((4-(isoindolin-5-yl)-1H-1,2,3-triazol-1-yl)methyl)phenyl)-1,3,4-oxadiazole (0.070 g, 23.7%) in a white solid form.

[Step 4] Synthesis of Compound 4513

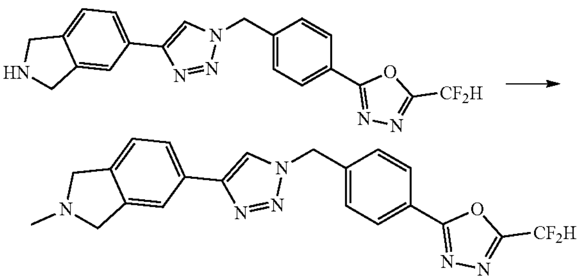

The 2-(difluoromethyl)-5-(4-((4-(isoindolin-5-yl)-1H-1,2,3-triazol-1-yl)methyl)phenyl)-1,3,4-oxadiazole (0.070 g, 0.177 mmol) prepared in step 3, formaldehyde (0.011 g, 0.355 mmol) and acetic acid (0.011 mL, 0.195 mmol) were dissolved in dichloromethane (5 mL) at room temperature, after which sodium triacetoxyborohydride (0.075 g, 0.355 mmol) was added to the resulting solution and stirred at the same temperature for 12 hours. 1N-sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(4-((4-(2-methylisoindolin-5-yl)-1H-1,2,3-triazol-1-yl)methyl)phenyl)-1,3,4-oxadiazole (0.025 g, 34.5%) in a brown solid form.

$^1$H NMR (400 MHz, $CDCl_3$) δ 8.10 (d, J=8.1 Hz, 2H), 7.73 (s, 1H), 7.66 (s, 1H), 7.64-7.57 (m, 1H), 7.44 (d, J=8.0 Hz, 2H), 7.21 (d, J=7.8 Hz, 1H), 6.91 (t, J=51.7 Hz, 1H), 5.64 (s, 2H), 3.97 (s, 3H), 2.61 (s, 3H); LRMS (ES) m/z 409.1 ($M^+$+1).

Example 387: Synthesis of compound 4515, 2-(difluoromethyl)-5-(3-fluoro-4-((4-(2-methylisoindolin-5-yl)-1H-1,2,3-triazol-1-yl)methyl)phenyl)-1,3,4-oxadiazole

[Step 1] Synthesis of tert-butyl 5-(1-(4-(5-(difluoromethyl)-1,3,4-oxadiazol-2-yl)-2-fluorobenzyl)-1H-1,2,3-triazol-4-yl)isoindolin-2-carboxylate

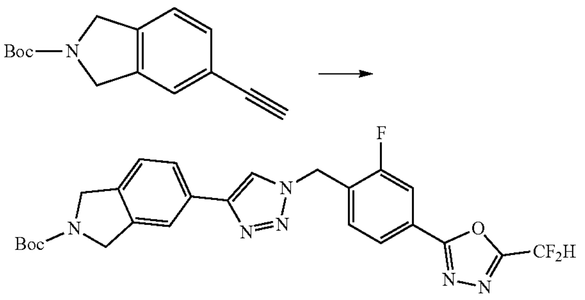

The tert-butyl 5-ethynylisoindolin-2-carboxylate (0.550 g, 2.260 mmol) prepared in step 1 of example 386, 2-(4-(azidomethyl)-3-fluorophenyl)-5-(difluoromethyl)-1,3,4-oxadiazole (0.669 g, 2.487 mmol) prepared in step 1 of example 2, copper(II) sulfate pentahydrate (0.006 g, 0.023 mmol) and sodium ascorbate (0.045 g, 0.226 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 80%) and concentrated to obtain tert-butyl 5-(1-(4-(5-(difluoromethyl)-1,3,4-oxadiazol-2-yl)-2-fluorobenzyl)-1H-1,2,3-triazol-4-yl)isoindolin-2-carboxylate (0.960 g, 82.9%) in a white solid form.

[Step 2] Synthesis of 2-(difluoromethyl)-5-(3-fluoro-4-((4-(isoindolin-5-yl)-1H-1,2,3-triazol-1-yl)methyl)phenyl)-1,3,4-oxadiazole

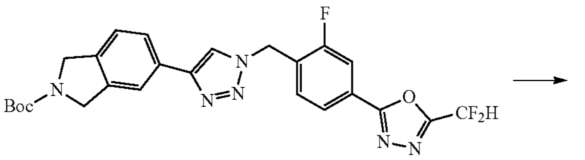

-continued

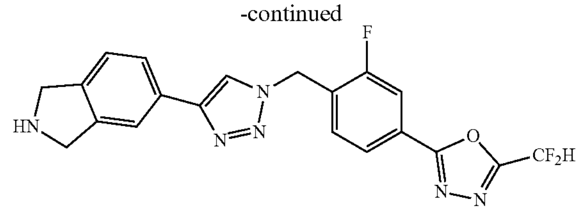

The tert-butyl 5-(1-(4-(5-(difluoromethyl)-1,3,4-oxadiazol-2-yl)-2-fluorobenzyl)-1H-1,2,3-triazol-4-yl)isoindolin-2-carboxylate (0.960 g, 1.873 mmol) prepared in step 1 and trifluoroacetic acid (1.434 mL, 18.732 mmol) were dissolved in dichloromethane (50 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(3-fluoro-4-((4-(isoindolin-5-yl)-1H-1,2,3-triazol-1-yl)methyl)phenyl)-1,3,4-oxadiazole (0.590 g, 76.4%) in a white solid form.

[Step 3] Synthesis of Compound 4515

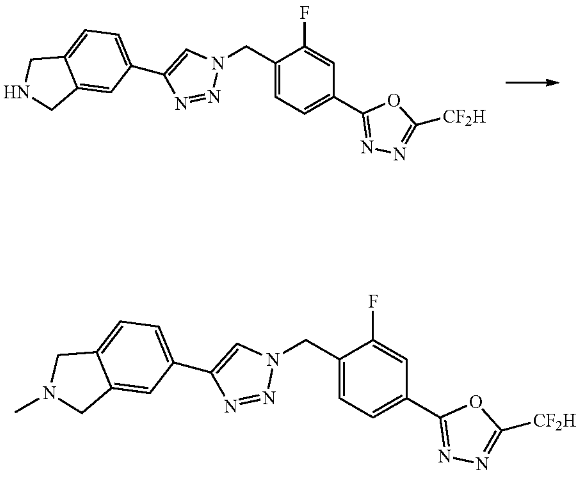

The 2-(difluoromethyl)-5-(3-fluoro-4-((4-(isoindolin-5-yl)-1H-1,2,3-triazol-1-yl)methyl)phenyl)-1,3,4-oxadiazole (0.080 g, 0.194 mmol) prepared in step 2, formaldehyde (0.012 g, 0.388 mmol) and acetic acid (0.012 mL, 0.213 mmol) were dissolved in dichloromethane (5 mL) at room temperature, after which sodium triacetoxyborohydride (0.082 g, 0.388 mmol) was added to the resulting solution and stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(2-methylisoindolin-5-yl)-1H-1,2,3-triazol-1-yl)methyl)phenyl)-1,3,4-oxadiazole (0.030 g, 36.3%) in a brown solid form.

$^1$H NMR (400 MHz, $CDCl_3$) δ 7.87 (dd, J=8.3, 4.2 Hz, 2H), 7.81 (s, 1H), 7.67 (s, 1H), 7.63 (d, J=7.8 Hz, 1H), 7.42 (t, J=7.7 Hz, 1H), 7.22 (d, J=7.8 Hz, 1H), 6.91 (t, J=51.7 Hz, 1H), 5.69 (s, 2H), 4.01 (s, 4H), 2.63 (s, 3H); LRMS (ES) m/z 427.1 ($M^+$+1).

The compounds of table 121 were synthesized according to substantially the same process as described above in the synthesis of compound 4515 with an exception of using 2-(difluoromethyl)-5-(3-fluoro-4-((4-(isoindolin-5-yl)-1H-1,2,3-triazol-1-yl)methyl)phenyl)-1,3,4-oxadiazole and the reactant of table 120.

TABLE 120

| Example | Compound No. | Reactant | Yield (%) |
|---|---|---|---|
| 388 | 4516 | Acetaldehyde | 35 |
| 389 | 4517 | Propan-2-one | 37 |
| 390 | 4518 | Cyclobutanone | 39 |
| 391 | 4519 | Oxetan-3-one | 44 |
| 495 | 17458 | Tetrahydro-4H-pyran-4-one | 47 |
| 496 | 17460 | 1-fluorocyclopropan-1-carbaldehyde | 43 |

TABLE 121

| Example | Compound No. | Compound Name, $^1$H-NMR, MS (ESI) |
|---|---|---|
| 388 | 4516 | 2-(difluoromethyl)-5-(4-((4-(2-ethylisoindolin-5-yl)-1H-1,2,3-triazol-1-yl)methyl)-3-fluorophenyl)-1,3,4-oxadiazole $^1$H NMR (400 MHZ, $CDCl_3$) δ 7.94-7.86 (m, 2H), 7.84 (s, 1H), 7.75-7.61 (m, 2H), 7.46 (t, J = 7.7 Hz, 1H), 7.28 (s, 1H), 6.92 (t, J = 51.7 Hz, 1H), 5.71 (s, 2H), 4.24 (s, 4H), 3.03 (q, J = 7.2 Hz, 2H), 1.42-1.21 (m, 3H); LRMS (ES) m/z 441.5 ($M^+$ + 1). |
| 389 | 4517 | 2-(difluoromethyl)-5-(3-fluoro-4-((4-(2-isopropylisoindolin-5-yl)-1H-1,2,3-triazol-1-yl)methyl)phenyl)-1,3,4-oxadiazole $^1$H NMR (400 MHZ, $CDCl_3$) δ 7.86-7.79 (m, 3H), 7.64 (s, 1H), 7.59 (d, J = 7.9 Hz, 1H), 7.39 (t, J = 7.7 Hz, 1H), 7.19 (d, J = 7.8 Hz, 1H), 6.90 (t, J = 51.7 Hz, 1H), 5.65 (s, 2H), 4.07 (s, 4H), 2.91 (hept, J = 6.3 Hz, 1H), 1.20 (d, J = 6.3 Hz, 6H); LRMS (ES) m/z 455.1 ($M^+$ + 1). |
| 390 | 4518 | 2-(4-((4-(2-cyclobutylisoindolin-5-yl)-1H-1,2,3-triazol-1-yl)methyl)-3-fluorophenyl)-5-(difluoromethyl)-1,3,4-oxadiazole $^1$H NMR (400 MHZ, $CDCl_3$) δ 7.88-7.80 (m, 3H), 7.66 (s, 1H), 7.64-7.58 (m, 1H), 7.41 (t, J = 7.7 Hz, 1H), 7.21 (d, J = 7.8 Hz, 1H), 6.91 (t, J = 51.7 Hz, 1H), 5.67 (s, 2H), 4.03 (s, 4H), 3.38 (p, J = 7.8 Hz, 1H), 2.22-2.04 (m, 4H), 1.87-1.70 (m, 2H); LRMS (ES) m/z 467.2 ($M^+$ + 1). |
| 391 | 4519 | 2-(difluoromethyl)-5-(3-fluoro-4-((4-(2-(oxetan-3-yl)isoindolin-5-yl)-1H-1,2,3-triazol-1-yl)methyl)phenyl)-1,3,4-oxadiazole $^1$H NMR (400 MHZ, $CDCl_3$) δ 7.90-7.84 (m, 2H), 7.82 (s, 1H), 7.70 (d, J = 1.6 Hz, 1H), 7.63 (dd, J = 7.8, 1.6 Hz, 1H), 7.43 (t, J = 7.7 Hz, 1H), 7.23 (d, J = 7.8 Hz, 1H), 6.91 (t, J = 51.6 Hz, 1H), 5.69 (s, 2H), 4.75 (dt, J = 16.4, 6.4 Hz, 4H), 4.05 (p, J = 6.3 Hz, 1H), 3.98 (s, 4H); LRMS (ES) m/z 469.5 ($M^+$ + 1). |
| 495 | 17458 | 2-(difluoromethyl)-5-(3-fluoro-4-((4-(2-(tetrahydro-2H-pyran-4-yl)isoindolin-5-yl)-1H-1,2,3-triazol-1-yl)methyl)phenyl)-1,3,4-oxadiazole $^1$H NMR (400 MHZ, $CDCl_3$) δ d 7.84-7.81 (m, 3H), 7.65 (s, 1H), 7.58 (d, J = 7.7 Hz, 1H), 7.39 (t, J = 7.7 Hz, 1H), 7.19 (d, J = 7.8 Hz, 1H), 6.90 (t, J = 51.7 Hz, 1H), 1.65-1.61 (m, 2H); LRMS (ES) m/z 497.2 ($M^+$ + 1). |
| 496 | 17460 | 2-(difluoromethyl)-5-(3-fluoro-4-((4-(2-((1-fluorocyclopropyl)methyl)isoindolin-5-yl)-1H-1,2,3-triazol-1-yl)methyl)phenyl)-1,3,4-oxadiazole $^1$H NMR (400 MHZ, $CDCl_3$) δ d 7.86-7.83 (m, 2H), 7.80 (s, 1H), 7.66 (s, 1H), 7.60 (d, J = 7.7 Hz, 1H), 7.48 (t, J = 40.4 Hz, 1H), 7.21 (d, J = 7.8 Hz, 1H), 6.91 (t, J = 51.7 Hz, 1H), 5.67 (s, 2H), 4.07 (s, 4H), 3.07 (d, J = 22.0 Hz, 2H), 1.13-1.08 (m, 2H), 0.69-0.67 (m, 2H); LRMS (ES) m/z 485.3($M^+$ + 1). |

Example 400: Synthesis of compound 4529, 2-(difluoromethyl)-5-(4-((4-(2-methylisoindolin-4-yl)-1H-1,2,3-triazol-1-yl)methyl)phenyl)-1,3,4-oxadiazole

[Step 1] Synthesis of tert-butyl 4-ethynylisoindolin-2-carboxylate

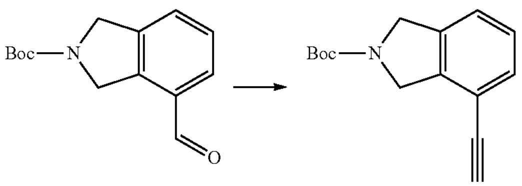 [SMILES: CC(C)(C)OC(=O)N1Cc2cccc(C=O)c2C1 ; C#Cc1cccc2c1CN(C(=O)OC(C)(C)C)C2]

Tert-butyl 4-formylisoindolin-2-carboxylate (0.500 g, 2.022 mmol), dimethyl (1-diazo-2-oxopropyl)phosphonate (0.334 mL, 2.224 mmol) and potassium carbonate (0.559 g, 4.044 mmol) were dissolved in methanol (10 mL) at room temperature, after which the resulting solution was stirred at the same temperature for 4 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 30%) and concentrated to obtain tert-butyl 4-ethynylisoindolin-2-carboxylate (0.429 g, 87.2%) in a white solid form.

[Step 2] Synthesis of tert-butyl 4-(1-(4-(5-(difluoromethyl)-1,3,4-oxadiazol-2-yl)benzyl)-1H-1,2,3-triazol-4-yl)isoindolin-2-carboxylate

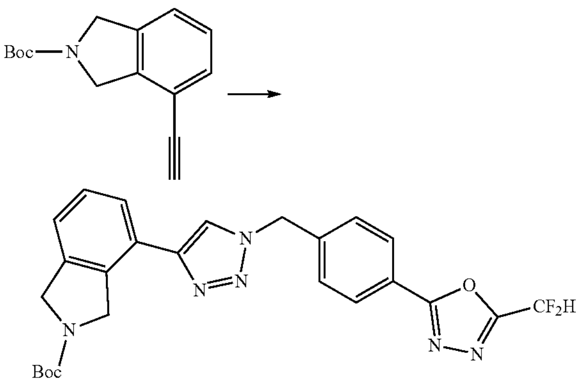

Tert-butyl 4-ethynylisoindolin-2-carboxylate (0.210 g, 0.863 mmol) prepared in step 1, 2-(4-(azidomethyl)phenyl)-5-(difluoromethyl)-1,3,4-oxadiazole (0.217 g, 0.863 mmol) prepared in step 1 of example 1, sodium ascorbate (0.50 M solution in water, 0.173 mL, 0.086 mmol) and copper(II) sulfate pentahydrate (1.00 M solution in water, 0.017 mL, 0.017 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl 4-(1-(4-(5-(difluoromethyl)-1,3,4-oxadiazol-2-yl)benzyl)-1H-1,2,3-triazol-4-yl)isoindolin-2-carboxylate (0.415 g, 97.2%) in a white solid form.

[Step 3] Synthesis of 2-(difluoromethyl)-5-(4-((4-(isoindolin-4-yl)-1H-1,2,3-triazol-1-yl)methyl)phenyl)-1,3,4-oxadiazole

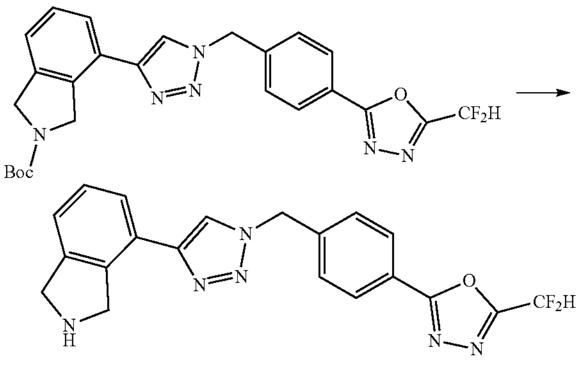

The tert-butyl 4-(1-(4-(5-(difluoromethyl)-1,3,4-oxadiazol-2-yl)benzyl)-1H-1,2,3-triazol-4-yl)isoindolin-2-carboxylate (0.415 g, 0.839 mmol) prepared in step 2 and trifluoroacetic acid (0.643 mL, 8.392 mmol) were dissolved in dichloromethane (4 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(4-((4-(isoindolin-4-yl)-1H-1,2,3-triazol-1-yl)methyl)phenyl)-1,3,4-oxadiazole, 0.330 g, 99.7%, brown oil).

[Step 4] Synthesis of Compound 4529

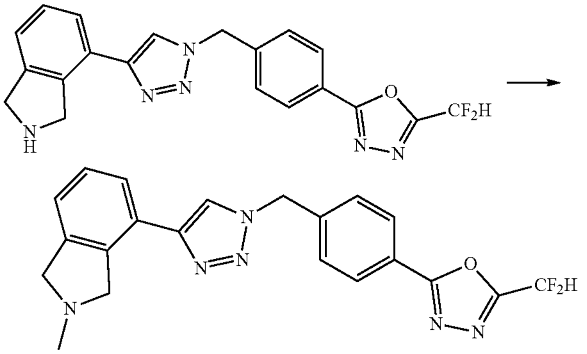

The 2-(difluoromethyl)-5-(4-((4-(isoindolin-4-yl)-1H-1,2,3-triazol-1-yl)methyl)phenyl)-1,3,4-oxadiazole (0.065 g, 0.165 mmol) prepared in step 3 and formaldehyde (37.00% solution in water, 0.025 mL, 0.330 mmol) were dissolved in dichloromethane (1 mL), after which the resulting solution was stirred at room temperature for 15 minutes, and then sodium triacetoxyborohydride (0.105 g, 0.494 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(4-((4-(2-methylisoindolin-4-yl)-1H-1,2,3-triazol-1-yl)methyl)phenyl)-1,3,4-oxadiazole (0.055 g, 81.7%) in a brown solid form.

$^1H$ NMR (400 MHz, $CD_3OD$) δ 8.48 (s, 1H), 8.20-8.13 (m, 2H), 7.77-7.70 (m, 1H), 7.65-7.54 (m, 2H), 7.42 (t, J=7.6 Hz, 1H), 7.34 (d, J=7.5 Hz, 1H), 7.23 (t, J=51.6 Hz, 1H), 5.82 (s, 2H), 4.66 (s, 2H), 4.37 (s, 2H), 2.91 (s, 3H); LRMS (ES) m/z 409.4 ($M^+$+1).

The compounds of table 123 were synthesized according to substantially the same process as described above in the synthesis of compound 4529 with an exception of using 2-(difluoromethyl)-5-(4-((4-(isoindolin-4-yl)-1H-1,2,3-triazol-1-yl)methyl)phenyl)-1,3,4-oxadiazole and the reactant of table 122.

TABLE 122

| Example | Compound No. | Reactant | Yield (%) |
|---|---|---|---|
| 401 | 4530 | Acetaldehyde | 78 |
| 402 | 4531 | Acetone | 74 |
| 403 | 4532 | Cyclobutanone | 81 |
| 404 | 4533 | Oxetanone | 81 |

TABLE 123

| Example | Compound No. | Compound Name, $^1$H-NMR, MS (ESI) |
|---|---|---|
| 401 | 4530 | 2-(difluoromethyl)-5-(4-((4-(2-ethylisoindolin-4-yl)-1H-1,2,3-triazol-1-yl)methyl)phenyl)-1,3,4-oxadiazole $^1$H NMR (400 MHZ, $CD_3OD$) δ 8.47 (s, 1H), 8.20-8.12 (m, 2H), 7.73 (d, J = 7.7 Hz, 1H), 7.67-7.59 (m, 2H), 7.41 (t, J = 7.6 Hz, 1H), 7.34 (d, J = 7.6 Hz, 1H), 7.23 (t, J = 51.6 Hz, 1H), 5.82 (s, 2H), 4.60 (s, 2H), 4.33 (s, 2H), 3.16 (q, J = 7.3 Hz, 2H), 1.35 (t, J = 7.3 Hz, 3H); LRMS (ESI) m/z 423.4 ($M^+$ + H). |
| 402 | 4531 | 2-(difluoromethyl)-5-(4-((4-(2-isopropylisoindolin-4-yl)-1H-1,2,3-triazol-1-yl)methyl)phenyl)-1,3,4-oxadiazole $^1$H NMR (400 MHZ, $CD_3OD$) δ 8.51 (d, J = 7.9 Hz, 1H), 8.20-8.13 (m, 2H), 7.75 (dd, J = 7.7, 1.1 Hz, 1H), 7.66-7.59 (m, 2H), 7.45 (t, J = 7.7 Hz, 1H), 7.39-7.10 (m, 2H), 5.83 (s, 2H), 4.76 (d, J = 16.0 Hz, 2H), 4.49 (s, 2H), 3.44 (s, 1H), 1.41 (d, J =6.5 Hz, 6H); LRMS (ESI) m/z 437.4 ($M^+$ + H). |
| 403 | 4532 | 2-(4-((4-(2-cyclobutylisoindolin-4-yl)-1H-1,2,3-triazol-1-yl)methyl)phenyl)-5-(difluoromethyl)-1,3,4-oxadiazole $^1$H NMR (400 MHZ, $CD_3OD$) δ 8.50 (s, 1H), 8.20-8.13 (m, 2H), 7.77-7.71 (m, 1H), 7.65-7.59 (m, 2H), 7.44 (t, J = 7.6 Hz, 1H), 7.39-7.10 (m, 2H), 5.82 (s, 2H), 4.63 (s, 2H), 4.35 (s, 2H), 3.82-3.73 (m, 1H), 2.35 (q, J = 9.0, 7.8 Hz, 2H), 2.21 (dd, J = 20.0, 10.0 Hz, 2H), 1.91 (dt, J = 18.5, 8.8 Hz, 2H); LRMS (ESI) m/z 449.5 ($M^+$ + H). |
| 404 | 4533 | 2-(difluoromethyl)-5-(4-((4-(2-(oxetan-3-yl)isoindolin-4-yl)-1H-1,2,3-triazol-1-yl)methyl)phenyl)-1,3,4-oxadiazole $^1$H NMR (400 MHZ, $CD_3OD$) δ 8.40 (s, 1H), 8.20-8.13 (m, 2H), 7.71 (d, J = 7.6 Hz, 1H), 7.61 (d, J = 8.2 Hz, 2H), 7.38-7.32 (m, 1H), 7.31-7.09 (m, 2H), 5.81 (s, 2H), 4.84 (d, J = 6.7 Hz, 2H), 4.79-4.71 (m, 2H), 4.26 (s, 2H), 4.12 (p, J = 6.3 Hz, 1H), 4.04 (s, 2H); LRMS (ESI) m/z 451.4 ($M^+$ + H). |

Example 405: Synthesis of compound 4534, 2-(difluoromethyl)-5-(3-fluoro-4-((4-(2-methylisoindolin-4-yl)-1H-1,2,3-triazol-1-yl)methyl)phenyl)-1,3,4-oxadiazole

[Step 1] Synthesis of tert-butyl 4-(1-(4-(5-(difluoromethyl)-1,3,4-oxadiazol-2-yl)-2-fluorobenzyl)-1H-1,2,3-triazol-4-yl)isoindolin-2-carboxylate

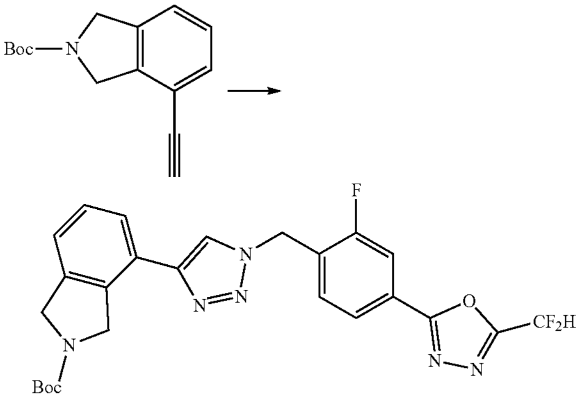

The tert-butyl 4-ethynylisoindolin-2-carboxylate (0.210 g, 0.863 mmol) prepared in step 1 of example 400, 2-(4-(azidomethyl)-3-fluorophenyl)-5-(difluoromethyl)-1,3,4-oxadiazole (0.232 g, 0.863 mmol) prepared in step 1 of example 2, sodium ascorbate (0.50 M solution in water, 0.173 mL, 0.086 mmol) and copper(II) sulfate pentahydrate (1.00 M solution in water, 0.017 mL, 0.017 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl 4-(1-(4-(5-(difluoromethyl)-1,3,4-oxadiazol-2-yl)-2-fluorobenzyl)-1H-1,2,3-triazol-4-yl)isoindolin-2-carboxylate (0.380 g, 85.9%) in a white solid form.

[Step 2] Synthesis of 2-(difluoromethyl)-5-(3-fluoro-4-((4-(isoindolin-4-yl)-1H-1,2,3-triazol-1-yl)methyl)phenyl)-1,3,4-oxadiazole

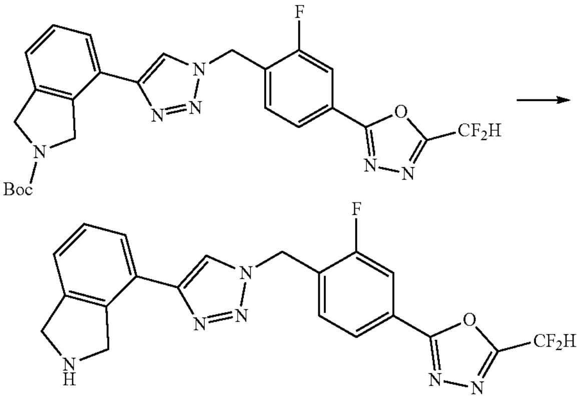

The tert-butyl 4-(1-(4-(5-(difluoromethyl)-1,3,4-oxadiazol-2-yl)-2-fluorobenzyl)-1H-1,2,3-triazol-4-yl)isoindolin-2-carboxylate (0.380 g, 0.741 mmol) prepared in step 1 and trifluoroacetic acid (0.568 mL, 7.415 mmol) were dissolved in dichloromethane (3 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(3-fluoro-4-((4-(isoindolin-4-yl)-1H-1,2,3-triazol-1-yl)methyl)phenyl)-1,3,4-oxadiazole, 0.300 g, 98.1%, brown oil).

[Step 3] Synthesis of Compound 4534

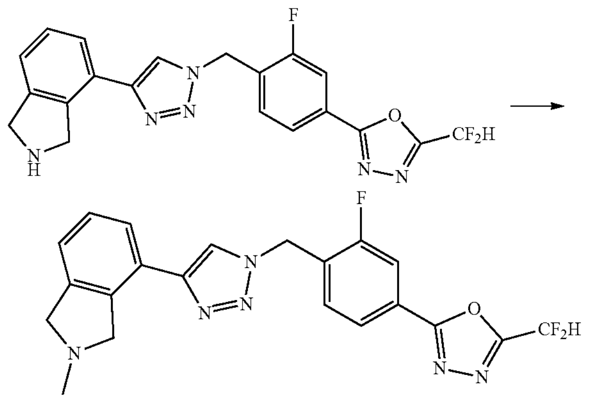

The 2-(difluoromethyl)-5-(3-fluoro-4-((4-(isoindolin-4-yl)-1H-1,2,3-triazol-1-yl)methyl)phenyl)-1,3,4-oxadiazole (0.060 g, 0.145 mmol) prepared in step 2 and formaldehyde (37.00% solution in water, 0.022 mL, 0.291 mmol) were dissolved in dichloromethane (1 mL), after which the resulting solution was stirred at room temperature for 15 minutes, and then sodium triacetoxyborohydride (0.093 g, 0.436 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(3-fluoro-4-((4-(2-methylisoindolin-4-yl)-1H-1,2,3-triazol-1-yl)methyl)phenyl)-1,3,4-oxadiazole (0.044 g, 70.9%) in a brown solid form.

$^1$H NMR (400 MHz, $CD_3OD$) δ 8.39 (s, 1H), 7.97 (ddd, J=11.7, 9.0, 1.7 Hz, 2H), 7.69 (d, J=7.7 Hz, 1H), 7.59 (t, J=7.7 Hz, 1H), 7.39-7.31 (m, 1H), 7.29-7.11 (m, 2H), 5.87 (s, 2H), 4.27 (s, 2H), 4.04 (s, 2H), 2.68 (s, 3H); LRMS (ES) m/z 427.4 ($M^+$+1).

The compounds of table 125 were synthesized according to substantially the same process as described above in the synthesis of compound 4534 with an exception of using 2-(difluoromethyl)-5-(3-fluoro-4-((4-(isoindolin-4-yl)-1H-1,2,3-triazol-1-yl)methyl)phenyl)-1,3,4-oxadiazole and the reactant of table 124.

TABLE 124

| Example | Compound No. | Reactant | Yield (%) |
|---|---|---|---|
| 406 | 4535 | Acetaldehyde | 72 |
| 407 | 4536 | Acetone | 45 |
| 408 | 4537 | Cyclobutanone | 87 |
| 409 | 4538 | Oxetanone | 78 |

TABLE 125

| Example | Compound No | Compound Name, $^1$H-NMR, MS (ESI) |
|---|---|---|
| 406 | 4535 | 2-(difluoromethyl)-5-(4-((4-(2-ethylisoindolin-4-yl)-1H-1,2,3-triazol-1-yl)methyl)-3-fluorophenyl)-1,3,4-oxadiazole $^1$H NMR (400 MHZ, $CD_3OD$) δ 8.48 (s, 1H), 8.03-7.92 (m, 2H), 7.76-7.70 (m, 1H), 7.61 (t, J = 7.7 Hz, 1H), 7.41 (t, J = 7.6 Hz, 1H), 7.38-7.11 (m, 2H), 5.88 (s, 2H), 4.59 (s, 2H), 4.31 (s, 2H), 3.15 (q, J = 7.3 Hz, 2H), 1.35 (t, J = 7.3 Hz, 3H); LRMS (ESI) m/z 441.4 ($M^+$ + H). |
| 407 | 4536 | 2-(difluoromethyl)-5-(3-fluoro-4-((4-(2-isopropylisoindolin-4-yl)-1H-1,2,3-triazol-1-yl)methyl)phenyl)-1,3,4-oxadiazole $^1$H NMR (400 MHZ, $CD_3OD$) δ 8.51 (d, J = 8.0 Hz, 1H), 8.03-7.92 (m, 2H), 7.74 (d, J = 7.7 Hz, 1H), 7.62 (t, J = 7.7 Hz, 1H), 7.44 (t, J = 7.6 Hz, 1H), 7.40-7.11 (m, 2H), 5.88 (s, 2H), 4.69 (d, J = 16.7 Hz, 2H), 4.44 (s, 2H), 3.38 (q, J = 6.4 Hz, 1H), 1.39 (d, J = 6.4 Hz, 6H); LRMS (ESI) m/z 455.5 ($M^+$ + H). |
| 408 | 4537 | 2-(4-((4-(2-cyclobutylisoindolin-4-yl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.45 (s, 1H), 8.02-7.90 (m, 2H), 7.71 (d, J = 7.7 Hz, 1H), 7.60 (t, J = 7.7 Hz, 1H), 7.43-7.11 (m, 3H), 5.87 (s, 2H), 4.40 (s, 2H), 4.15 (s, 2H), 3.65-3.49 (m, 1H), 2.26 (qd, J = 8.4, 7.2, 3.5 Hz, 2H), 2.21-2.09 (m, 2H), 1.96-1.80 (m, 2H); LRMS (ESI) m/z 467.5 ($M^+$ + H). |
| 409 | 4538 | 2-(difluoromethyl)-5-(3-fluoro-4-((4-(2-(oxetan-3-yl)isoindolin-4-yl)-1H-1,2,3-triazol-1-yl)methyl)phenyl)-1,3,4-oxadiazole $^1$H NMR (400 MHZ, $CD_3OD$) δ 8.45 (s, 1H), 8.02-7.90 (m, 2H), 7.71 (d, J = 7.7 Hz, 1H), 7.60 (t, J = 7.7 Hz, 1H), 7.43-7.11 (m, 3H), 5.87 (s, 2H), 4.40 (s, 2H), 4.15 (s, 2H), 3.65-3.49 (m, 1H), 2.26 (qd, J = 8.4, 7.2, 3.5 Hz, 2H), 2.21-2.09 (m, 2H), 1.96-1.80 (m, 2H); LRMS (ESI) m/z 469.4 ($M^+$ + H). |

Example 410: Synthesis of compound 4539, 2-(difluoromethyl)-5-(6-((4-(isoindolin-5-yl)-1H-1,2,3-triazol-1-yl)methyl)pyridin-3-yl)-1,3,4-oxadiazole

[Step 1] Synthesis of tert-butyl 5-(1-((5-(5-(difluoromethyl)-1,3,4-oxadiazol-2-yl)pyridin-2-yl)methyl)-1H-1,2,3-triazol-4-yl)isoindolin-2-carboxylate

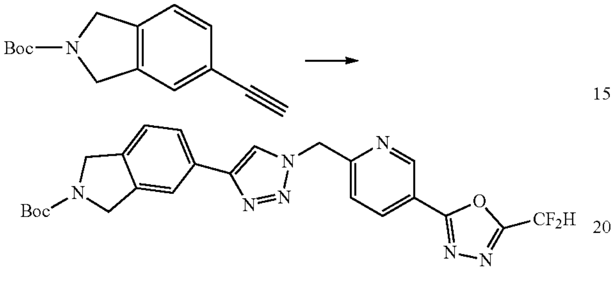

The tert-butyl 5-ethynylisoindolin-2-carboxylate (0.750 g, 3.082 mmol) prepared in step 1 of example 387, 2-(6-(azidomethyl)pyridin-3-yl)-5-(difluoromethyl)-1,3,4-oxadiazole (0.855 g, 3.391 mmol) prepared in step 1 of example 16, copper(II) sulfate pentahydrate (0.008 g, 0.031 mmol) and sodium ascorbate (0.061 g, 0.308 mmol) were dissolved in tert-butanol (5 mL)/water (5 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 5-(1-((5-(5-(difluoromethyl)-1,3,4-oxadiazol-2-yl)pyridin-2-yl)methyl)-1H-1,2,3-triazol-4-yl)isoindolin-2-carboxylate (1.300 g, 85.1%) in a brown solid form.

[Step 2] Synthesis of Compound 4539

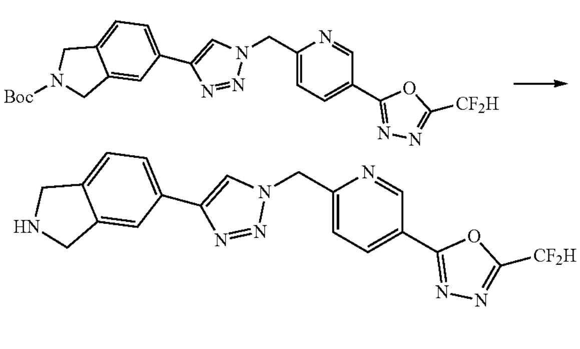

The tert-butyl 5-(1-((5-(5-(difluoromethyl)-1,3,4-oxadiazol-2-yl)pyridin-2-yl)methyl)-1H-1,2,3-triazol-4-yl)isoindolin-2-carboxylate (1.300 g, 2.624 mmol) prepared in step 1 and trifluoroacetic acid (2.009 mL, 26.237 mmol) were dissolved in dichloromethane (50 mL) at room temperature, after which the resulting solution was stirred at the same temperature for 12 hours. 1N-sodium hydrogen carbonate aqueous solution was poured into the resulting reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(6-((4-(isoindolin-5-yl)-1H-1,2,3-triazol-1-yl)methyl)pyridin-3-yl)-1,3,4-oxadiazole (0.460 g, 44.3%) in a brown solid form.

$^1$H NMR (400 MHz, $CDCl_3$) δ 9.14 (dd, J=2.2, 0.9 Hz, 1H), 8.48 (s, 1H), 8.40 (dd, J=8.2, 2.3 Hz, 1H), 7.85-7.76 (m, 2H), 7.52 (dd, J=8.2, 0.9 Hz, 1H), 7.42 (d, J=8.0 Hz, 1H), 7.20 (t, J=51.6 Hz, 1H), 5.85 (s, 2H), 4.64 (d, J=7.7 Hz, 4H); LRMS (ES) m/z 396.3 ($M^+$+1).

Example 411: Synthesis of compound 4540, 2-(difluoromethyl)-5-(6-((4-(2-methylisoindolin-5-yl)-1H-1,2,3-triazol-1-yl)methyl)pyridin-3-yl)-1,3,4-oxadiazole

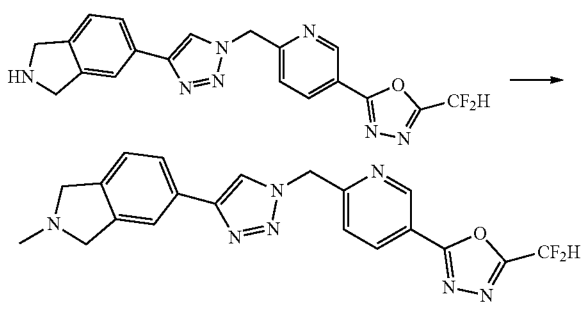

The 2-(difluoromethyl)-5-(6-((4-(isoindolin-5-yl)-1H-1,2,3-triazol-1-yl)methyl)pyridin-3-yl)-1,3,4-oxadiazole (0.070 g, 0.177 mmol) prepared in step 2 of example 410, formaldehyde (0.011 g, 0.354 mmol) and acetic acid (0.011 mL, 0.195 mmol) were dissolved in dichloromethane (5 mL) at room temperature, after which sodium triacetoxyborohydride (0.075 g, 0.354 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(6-((4-(2-methylisoindolin-5-yl)-1H-1,2,3-triazol-1-yl)methyl)pyridin-3-yl)-1,3,4-oxadiazole (0.010 g, 13.8%) in a brown solid form.

$^1$H NMR (400 MHz, $CDCl_3$) δ 9.32 (d, J=2.3 Hz, 1H), 8.40 (dd, J=8.1, 2.2 Hz, 1H), 7.97 (s, 1H), 7.77-7.68 (m, 2H), 7.43 (d, J=8.1 Hz, 1H), 7.28 (d, J=7.8 Hz, 1H), 6.94 (t, J=51.6 Hz, 1H), 5.80 (s, 2H), 4.24 (d, J=4.9 Hz, 4H), 2.01 (s, 3H); LRMS (ES) m/z 410.4 ($M^+$+1).

The compounds of table 127 were synthesized according to substantially the same process as described above in the synthesis of compound 4540 with an exception of using 2-(difluoromethyl)-5-(6-((4-(isoindolin-5-yl)-1H-1,2,3-triazol-1-yl)methyl)pyridin-3-yl)-1,3,4-oxadiazole and the reactant of table 126.

TABLE 126

| Example | Compound No. | Reactant | Yield (%) |
|---|---|---|---|
| 412 | 4541 | Propan-2-one | 32 |
| 413 | 4542 | Cyclobutanone | 38 |
| 414 | 4543 | Oxetan-3-one | 44 |

added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$,

TABLE 127

| Example | Compound No. | Compound Name, $^1$H-NMR, MS (ESI) |
|---|---|---|
| 412 | 4541 | 2-(difluoromethyl)-5-(6-((4-(2-isopropylisoindolin-5-yl)-1H-1,2,3-triazol-1-yl)methyl)pyridin-3-yl)-1,3,4-oxadiazole<br>$^1$H NMR (400 MHZ, $CDCl_3$) δ 9.27 (d, J = 2.1 Hz, 1H), 8.34 (dd, J = 8.2, 2.3 Hz, 1H), 7.94 (s, 1H), 7.67 (s, 1H), 7.62 (dd, J = 7.8, 1.6 Hz, 1H), 7.37 (d, J = 8.2 Hz, 1H), 7.21 (d, J = 7.8 Hz, 1H), 6.93 (s, 1H), 5.76 (s, 2H), 4.07 (s, 4H), 2.90 (hept, J = 6.3 Hz, 1H), 1.21 (d, J = 6.3 Hz, 6H); LRMS (ES) m/z 438.5 ($M^+$ + 1). |
| 413 | 4542 | 2-(6-((4-(2-cyclobutylisoindolin-5-yl)-1H-1,2,3-triazol-1-yl)methyl)pyridin-3-yl)-5-(difluoromethyl)-1,3,4-oxadiazole<br>$^1$H NMR (400 MHZ, $CDCl_3$) δ 9.28 (d, J = 2.2 Hz, 1H), 8.35 (dd, J = 8.2, 2.2 Hz, 1H), 7.94 (s, 1H), 7.68 (s, 1H), 7.62 (dd, J = 7.7, 1.5 Hz, 1H), 7.37 (d, J = 8.2 Hz, 1H), 7.21 (d, J = 7.8 Hz, 1H), 6.93 (t, J = 51.6 Hz, 1H), 5.77 (s, 2H), 3.96 (s, 4H), 3.33 (p, J = 7.8 Hz, 1H), 2.09 (q, J = 7.7, 7.1 Hz, 4H), 1.85-1.64 (m, 2H); LRMS (ES) m/z 450.5 ($M^+$ + 1). |
| 414 | 4543 | 2-(difluoromethyl)-5-(6-((4-(2-(oxetan-3-yl)isoindolin-5-yl)-1H-1,2,3-triazol-1-yl)methyl)pyridin-3-yl)-1,3,4-oxadiazole<br>$^1$H NMR (400 MHZ, $CDCl_3$) δ 9.31 (d, J = 2.2 Hz, 1H), 8.39 (dd, J = 8.2, 2.3 Hz, 1H), 7.96 (s, 1H), 7.73 (s, 1H), 7.66 (dd, J = 7.8, 1.6 Hz, 1H), 7.41 (d, J = 8.2 Hz, 1H), 7.26 (d, J = 7.8 Hz, 1H), 6.94 (t, J = 51.6 Hz, 1H), 5.80 (s, 2H), 4.85-4.67 (m, 4H), 4.08 (p, J = 6.3 Hz, 1H), 4.01 (s, 4H); LRMS (ES) m/z 452.5 ($M^+$ + 1). |

Example 415: Synthesis of compound 4548, 2-(4-((4-(4-(azetidin-1-ylmethyl)phenyl)-1H-1,2,3-triazol-1-yl)methyl)phenyl)-5-(difluoromethyl)-1,3,4-oxadiazole

[Step 1] Synthesis of 4-(1-(4-(5-(difluoromethyl)-1,3,4-oxadiazol-2-yl)benzyl)-1H-1,2,3-triazol-4-yl)benzaldehyde

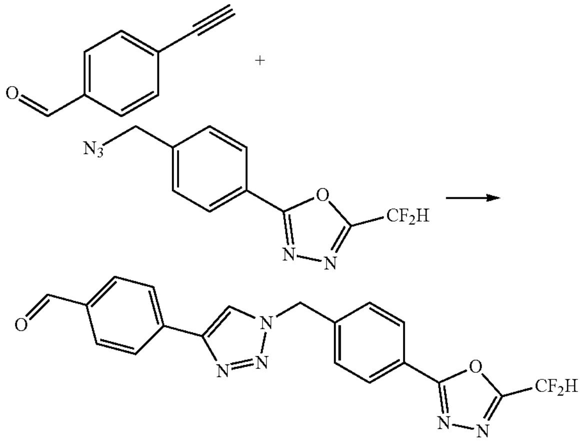

The 2-(4-(azidomethyl)phenyl)-5-(difluoromethyl)-1,3,4-oxadiazole (0.800 g, 3.185 mmol) prepared in step 1 of example 1 and 4-ethynylbenzaldehyde (0.414 g, 3.185 mmol) were dissolved in tert-butanol (2 mL)/water (2 mL) at room temperature, after which sodium ascorbate (1.00 M solution, 0.318 mL, 0.318 mmol) and copper(II) sulfate pentahydrate (0.50 M solution, 0.064 mL, 0.032 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; hexane/ethyl acetate=100 to 40%) and concentrated to obtain 4-(1-(4-(5-(difluoromethyl)-1,3,4-oxadiazol-2-yl)benzyl)-1H-1,2,3-triazol-4-yl)benzaldehyde (0.850 g, 70.0%) in a beige solid form.

[Step 2] Synthesis of Compound 4548

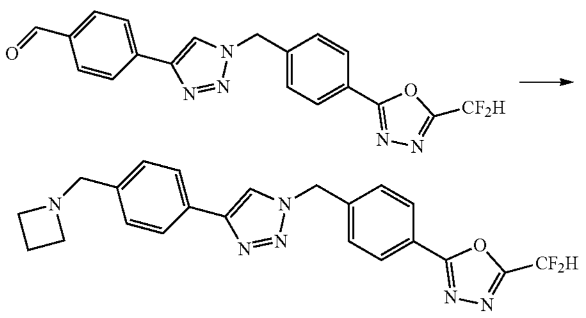

The 4-(1-(4-(5-(difluoromethyl)-1,3,4-oxadiazol-2-yl)benzyl)-1H-1,2,3-triazol-4-yl)benzaldehyde (0.050 g, 0.131 mmol) prepared in step 1 and azetidine hydrogen chloride (0.025 g, 0.262 mmol) were dissolved in dichloromethane (1 mL) at room temperature, after which sodium triacetoxyborohydride (0.139 g, 0.656 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 60%) and concentrated to obtain 2-(4-((4-(4-(azetidin-1-ylmethyl)phenyl)-1H-1,2,3-triazol-1-yl)methyl)phenyl)-5-(difluoromethyl)-1,3,4-oxadiazole (0.032 g, 57.8%) in a white solid form.

$^1$H NMR (400 MHz, $CD_3OD$) δ 8.43 (s, 1H), 8.20-8.13 (m, 2H), 7.85-7.78 (m, 2H), 7.61 (d, J=8.3 Hz, 2H), 7.39 (d, J=8.1 Hz, 2H), 7.23 (t, J=51.6 Hz, 1H), 5.80 (s, 2H), 3.68 (s, 2H), 3.40-3.34 (m, 4H), 2.16 (p, J=7.2 Hz, 2H); LRMS (ES) m/z 423.4 ($M^+$+1).

The compounds of table 129 were synthesized according to substantially the same process as described above in the synthesis of compound 4548 with an exception of using 4-(1-(4-(5-(difluoromethyl)-1,3,4-oxadiazol-2-yl)benzyl)-1H-1,2,3-triazol-4-yl)benzaldehyde and the reactant of table 128.

TABLE 128

| Example | Compound No. | Reactant | Yield (%) |
|---|---|---|---|
| 416 | 4549 | 3-fluoroazetidine hydrogen chloride | 43 |
| 417 | 4550 | Pyrrolidine | 41 |
| 418 | 4551 | 2-oxa-6-azaspiro[3.3]heptane | 50 |
| 419 | 4552 | 1-methylpiperazine | 44 |
| 420 | 4553 | 1-ethylpiperazine | 47 |
| 421 | 4554 | N,N-dimethylpiperidin-4-amine | 17 |
| 422 | 4555 | Cyclobutanamine | 57 |
| 423 | 4556 | Oxetan-3-amine | 45 |
| 424 | 4557 | 1-methylazetidin-3-amine | 30 |

TABLE 129

| Example | Compound No. | Compound Name, $^1$H-NMR, MS (ESI) |
|---|---|---|
| 416 | 4549 | 2-(difluoromethyl)-5-(4-((4-(4-((3-fluoroazetidin-1-yl)methyl)phenyl)-1H-1,2,3-triazol-1-yl)methyl)phenyl)-1,3,4-oxadiazole $^1$H NMR (400 MHZ, $CD_3OD$) δ 8.43 (d, J = 2.3 Hz, 1H), 8.20-8.13 (m, 2H), 7.85-7.78 (m, 2H), 7.61 (d, J = 8.2 Hz, 2H), 7.40 (d, J = 8.1 Hz, 2H), 7.23 (t, J = 51.7 Hz, 1H), 5.80 (s, 2H), 5.23 (p, J = 5.2 Hz, 1H), 5.08 (t, J = 5.2 Hz, 1H), 3.73 (s, 2H), 3.70-3.58 (m, 2H), 3.38-3.25 (m, 2H); LRMS (ES) m/z 441.4 ($M^+$ + 1). |
| 417 | 4550 | 2-(difluoromethyl)-5-(4-((4-(4-(pyrrolidin-1-ylmethyl)phenyl)-1H-1,2,3-triazol-1-yl)methyl)phenyl)-1,3,4-oxadiazole $^1$H NMR (400 MHZ, $CD_3OD$) δ 8.44 (s, 1H), 8.20-8.13 (m, 2H), 7.86-7.79 (m, 2H), 7.61 (d, J = 8.3 Hz, 2H), 7.45 (d, J = 8.2 Hz, 2H), 7.23 (t, J = 51.6 Hz, 1H), 5.80 (s, 2H), 3.71 (s, 2H), 2.62 (s, 4H), 1.85 (p, J = 3.2 Hz, 4H); LRMS (ES) m/z 437.3 ($M^+$ + 1). |
| 418 | 4551 | 6-(4-(1-(4-(5-(difluoromethyl)-1,3,4-oxadiazol-2-yl)benzyl)-1H-1,2,3-triazol-4-yl)benzyl)-2-oxa-6-azaspiro[3.3]heptane $^1$H NMR (400 MHZ, CD3OD) δ 8.43 (s, 1H), 8.20-8.12 (m, 2H), 7.85-7.77 (m, 2H), 7.64-7.58 (m, 2H), 7.39-7.09 (m, 3H), 5.80 (s, 2H), 4.75 (s, 4H), 3.62 (s, 2H), 3.46 (s, 4H); LRMS (ES) m/z 465.5 ($M^+$ + 1). |
| 419 | 4552 | 2-(difluoromethyl)-5-(4-((4-(4-((4-methylpiperazin-1-yl)methyl)phenyl)-1H-1,2,3-triazol-1-yl)methyl)phenyl)-1,3,4-oxadiazole $^1$H NMR (400 MHZ, $CD_3OD$) δ 8.43 (s, 1H), 8.20-8.13 (m, 2H), 7.87-7.78 (m, 2H), 7.62 (d, J = 8.4 Hz, 2H), 7.43 (d, J = 8.1 Hz, 2H), 7.23 (t, J = 51.7 Hz, 2H), 5.80 (s, 2H), 3.58 (s, 2H), 2.53 (s, 8H), 2.30 (s, 3H); LRMS (ES) m/z 466.5 ($M^+$ + 1). |
| 420 | 4553 | 2-(difluoromethyl)-5-(4-((4-(4-((4-ethylpiperazin-1-yl)methyl)phenyl)-1H-1,2,3-triazol-1-yl)methyl)phenyl)-1,3,4-oxadiazole $^1$H NMR (400 MHZ, $CD_3OD$) δ 8.43 (s, 1H), 8.20-8.13 (m, 2H), 7.85-7.78 (m, 2H), 7.62 (d, J = 8.4 Hz, 2H), 7.43 (d, J = 8.2 Hz, 2H), 7.23 (t, J = 51.6 Hz, 2H), 5.80 (s, 2H), 3.59 (s, 2H), 2.75-2.38 (m, 10H), 1.11 (t, J = 7.2 Hz, 3H); LRMS (ES) m/z 480.5 ($M^+$ + 1). |
| 421 | 4554 | 1-(4-(1-(4-(5-(difluoromethyl)-1,3,4-oxadiazol-2-yl)benzyl)-1H-1,2,3-triazol-4-yl)benzyl)-N,N-dimethylpiperidin-4-amine $^1$H NMR (400 MHZ, $CD_3OD$) δ 8.43 (s, 1H), 8.20-8.13 (m, 2H), 7.81 (d, J = 8.2 Hz, 2H), 7.62 (d, J = 8.3 Hz, 2H), 7.43 (d, J = 8.1 Hz, 2H), 7.23 (t, J = 51.7 Hz, 1H), 5.80 (s, 2H), 3.56 (s, 2H), 3.00 (d, J = 11.8 Hz, 2H), 2.32 (s, 6H), 2.29-2.20 (m, 1H), 2.06 (t, J = 11.5 Hz, 2H), 1.94-1.85 (m, 2H), 1.64-1.50 (m, 2H); LRMS (ES) m/z 494.5 ($M^+$ + 1). |
| 422 | 4555 | N-(4-(1-(4-(5-(difluoromethyl)-1,3,4-oxadiazol-2-yl)benzyl)-1H-1,2,3-triazol-4-yl)benzyl)cyclobutanamine $^1$H NMR (400 MHZ, $CD_3OD$) δ 8.42 (s, 1H), 8.20-8.13 (m, 2H), 7.84-7.77 (m, 2H), 7.61 (d, J = 8.4 Hz, 2H), 7.47-7.40 (m, 2H), 7.23 (t, J = 51.6 Hz, 1H), 5.80 (s, 2H), 3.71 (s, 2H), 3.33-3.25 (m, 1H), 2.26-2.15 (m, 2H), 1.89-1.63 (m, 4H); LRMS (ES) m/z 437.4 ($M^+$ + 1). |
| 423 | 4556 | N-(4-(1-(4-(5-(difluoromethyl)-1,3,4-oxadiazol-2-yl)benzyl)-1H-1,2,3-triazol-4-yl)benzyl)oxetan-3-amine $^1$H NMR (400 MHZ, $CD_3OD$) δ 8.43 (s, 1H), 8.20-8.12 (m, 2H), 7.85-7.78 (m, 2H), 7.61 (d, J = 8.3 Hz, 2H), 7.43 (d, J = 8.2 Hz, 2H), 7.23 (t, J = 51.7 Hz, 1H), 5.80 (s, 2H), 4.72 (t, J = 6.8 Hz, 2H), 4.45 (t, J = 6.4 Hz, 2H), 4.03 (p, J = 6.7 Hz, 1H), 3.74 (s, 2H); LRMS (ES) m/z 439.4 ($M^+$ + 1). |
| 424 | 4557 | N-(4-(1-(4-(5-(difluoromethyl)-1,3,4-oxadiazol-2-yl)benzyl)-1H-1,2,3-triazol-4-yl)benzyl)-1-methylazetidin-3-amine $^1$H NMR (400 MHZ, $CD_3OD$) δ 8.45 (s, 1H), 8.20-8.13 (m, 2H), 7.86 (d, J = 8.3 Hz, 2H), 7.62 (d, J = 8.3 Hz, 2H), 7.45 (d, J = 8.1 Hz, 2H), 7.23 (t, J = 51.7 Hz, 2H), 5.80 (s, 2H), 4.67 (d, J = 15.5 Hz, 1H), 4.47-4.33 (m, 2H), 4.24 (dd, J = 8.8, 6.2 Hz, 1H), 3.90-3.79 (m, 1H), 2.80-2.66 (m, 2H), 2.32 (s, 3H); LRMS (ES) m/z 452.4 ($M^+$ + 1). |

Example 425: Synthesis of compound 4558, 2-(6-((4-(4-(azetidin-1-ylmethyl)phenyl)-1H-1,2,3-triazol-1-yl)methyl)pyridin-3-yl)-5-(difluoromethyl)-1,3,4-oxadiazole

[Step 1] Synthesis of 4-(1-((5-(5-(difluoromethyl)-1,3,4-oxadiazol-2-yl)pyridin-2-yl)methyl)-1H-1,2,3-triazol-4-yl)benzaldehyde

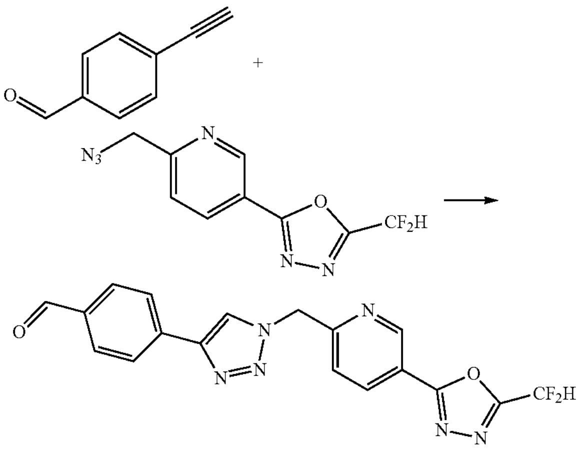

The 2-(6-(azidomethyl)pyridin-3-yl)-5-(difluoromethyl)-1,3,4-oxadiazole (0.400 g, 1.586 mmol) prepared in step 1 of example 16 and 4-ethynylbenzaldehyde (0.206 g, 1.586 mmol) were dissolved in tert-butanol (2 mL)/water (2 mL) at room temperature, after which sodium ascorbate (1.00 M solution, 0.159 mL, 0.159 mmol) and copper(II) sulfate pentahydrate (0.50 M solution, 0.032 mL, 0.016 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; hexane/ethyl acetate=100 to 40%) and concentrated to obtain 4-(1-((5-(5-(difluoromethyl)-1,3,4-oxadiazol-2-yl)pyridin-2-yl)methyl)-1H-1,2,3-triazol-4-yl)benzaldehyde(0.530 g, 87.4%) in a beige solid form.

[Step 2] Synthesis of Compound 4558

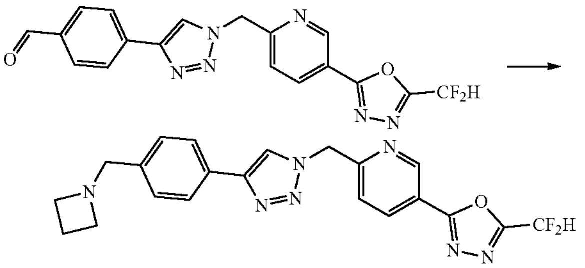

The 4-(1-((5-(5-(difluoromethyl)-1,3,4-oxadiazol-2-yl)pyridin-2-yl)methyl)-1H-1,2,3-triazol-4-yl)benzaldehyde (0.050 g, 0.131 mmol) prepared in step 1 and azetidine hydrogen chloride (0.024 g, 0.262 mmol) were dissolved in dichloromethane (1 mL) at room temperature, after which sodium triacetoxyborohydride (0.139 g, 0.654 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 60%) and concentrated to obtain 2-(6-((4-(4-(azetidin-1-ylmethyl)phenyl)-1H-1,2,3-triazol-1-yl)methyl)pyridin-3-yl)-5-(difluoromethyl)-1,3,4-oxadiazole (0.032 g, 57.8%) in a white solid form.

$^1H$ NMR (400 MHz, $CD_3OD$) δ 9.28 (d, J=2.2 Hz, 1H), 8.57-8.48 (m, 2H), 7.84 (d, J=8.1 Hz, 2H), 7.60 (d, J=8.2 Hz, 1H), 7.41 (d, J=8.1 Hz, 2H), 7.26 (t, J=51.6 Hz, 1H), 5.92 (s, 2H), 3.73 (s, 2H), 3.48-3.38 (m, 4H), 2.22-2.14 (m, 2H); LRMS (ES) m/z 424.4 ($M^+$+1).

The compounds of table 131 were synthesized according to substantially the same process as described above in the synthesis of compound 4558 with an exception of using 4-(1-((5-(5-(difluoromethyl)-1,3,4-oxadiazol-2-yl)pyridin-2-yl)methyl)-1H-1,2,3-triazol-4-yl)benzaldehyde and the reactant of table 130.

TABLE 130

| Example | Compound No. | Reactant | Yield (%) |
|---|---|---|---|
| 426 | 4559 | 3-fluoroazetidine hydrogen chloride | 43 |
| 427 | 4560 | Pyrrolidine | 54 |
| 428 | 4561 | 2-oxa-6-azaspiro[3.3]heptane | 27 |
| 429 | 4562 | 1-methylpiperazine | 34 |
| 430 | 4563 | 1-ethylpiperazine | 43 |
| 431 | 4564 | N,N-dimethylpiperidin-4-amine | 29 |
| 432 | 4565 | Cyclobutanamine | 36 |
| 433 | 4566 | Oxetan-3-amine | 43 |
| 434 | 4567 | 1-methylazetidin-3-amine | 32 |

TABLE 131

| Example | Compound No. | Compound Name, $^1H$-NMR, MS (ESI) |
|---|---|---|
| 426 | 4559 | 2-(difluoromethyl)-5-(6-((4-(4-((3-fluoroazetidin-1-yl)methyl)phenyl)-1H-1,2,3-triazol-1-yl)methyl)pyridin-3-yl)-1,3,4-oxadiazole $^1H$ NMR (400 MHz, $CD_3OD$) δ 9.28 (d, J = 2.1 Hz, 1H), 8.53 (dd, J = 8.2, 2.3 Hz, 1H), 8.49 (d, J = 2.2 Hz, 1H), 7.84 (d, J = 8.2 Hz, 2H), 7.60 (d, J = 8.3 Hz, 1H), 7.41 (d, J = 8.1 Hz, 2H), 7.26 (t, J = 51.6 Hz, 1H), 5.92 (s, 2H), 5.23 (t, J = 5.3 Hz, 0.5H), 5.10 (d, J = 4.9 Hz, 0.5H), 3.74 (s, 2H), 3.72-3.60 (m, 2H), 3.33 (dd, J = 33.2, 4.6 Hz, 2H); LRMS (ES) m/z 442.4 ($M^+$ + 1). |
| 427 | 4560 | 2-(difluoromethyl)-5-(6-((4-(4-(pyrrolidin-1-ylmethyl)phenyl)-1H-1,2,3-triazol-1-yl)methyl)pyridin-3-yl)-1,3,4-oxadiazole $^1H$ NMR (400 MHz, $CD_3OD$) δ 9.28 (dd, J = 2.2, 0.9 Hz, 1H), 8.53 (dd, J = 8.2, 2.2 Hz, 1H), 8.50 (s, 1H), 7.88-7.81 (m, 2H), 7.60 (d, J = 8.1 Hz, 1H), 7.46 (d, J = 8.2 Hz, 2H), 7.26 (t, J = 51.6 Hz, 2H), 5.93 (s, 2H), 3.73 (s, 2H), 2.63 (s, 4H), 1.86 (p, J = 3.2 Hz, 4H); LRMS (ES) m/z 438.5 ($M^+$ + 1). |

TABLE 131-continued

| Example | Compound No. | Compound Name, $^1$H-NMR, MS (ESI) |
|---|---|---|
| 428 | 4561 | 6-(4-(1-((5-(5-(difluoromethyl)-1,3,4-oxadiazol-2-yl)pyridin-2-yl)methyl)-1H-1,2,3-triazol-4-yl)benzyl)-2-oxa-6-azaspiro[3.3]heptane $^1$H NMR (400 MHz, $CD_3OD$) δ 9.28 (d, J = 2.1 Hz, 1H), 8.53 (dd, J = 8.2, 2.3 Hz, 1H), 8.50 (s, 1H), 7.87-7.80 (m, 2H), 7.60 (d, J = 8.2 Hz, 1H), 7.42-7.11 (m, 3H), 5.92 (s, 2H), 4.75 (s, 4H), 3.64 (s, 2H), 3.49 (s, 4H); LRMS (ES) m/z 466.5 ($M^+$ + 1). |
| 429 | 4562 | 2-(difluoromethyl)-5-(6-((4-(4-((4-methylpiperazin-1-yl)methyl)phenyl)-1H-1,2,3-triazol-1-yl)methyl)pyridin-3-yl)-1,3,4-oxadiazole $^1$H NMR (400 MHz, $CD_3OD$) δ 9.28 (d, J = 2.1 Hz, 1H), 8.53 (dd, J = 8.2, 2.2 Hz, 1H), 8.49 (s, 1H), 7.83 (d, J = 8.2 Hz, 2H), 7.60 (d, J = 8.2 Hz, 1H), 7.44 (d, J = 8.1 Hz, 2H), 7.26 (t, J = 51.6 Hz, 1H), 5.92 (s, 2H), 3.59 (s, 2H), 2.69-2.36 (m, 8H), 2.30 (s, 3H); LRMS (ES) m/z 467.5 ($M^+$ + 1). |
| 430 | 4563 | 2-(difluoromethyl)-5-(6-((4-(4-((4-ethylpiperazin-1-yl)methyl)phenyl)-1H-1,2,3-triazol-1-yl)methyl)pyridin-3-yl)-1,3,4-oxadiazole $^1$H NMR (400 MHz, $CD_3OD$) δ 9.30-9.26 (m, 1H), 8.53 (dd, J = 8.2, 2.2 Hz, 1H), 8.49 (s, 1H), 7.84 (d, J = 8.3 Hz, 2H), 7.60 (d, J = 8.4 Hz, 1H), 7.45 (d, J = 8.1 Hz, 2H), 7.26 (t, J = 51.6 Hz, 1H), 5.92 (s, 2H), 3.60 (s, 2H), 2.79-2.42 (m, 10H), 1.12 (t, J = 7.2 Hz, 3H); LRMS (ES) m/z 481.5 ($M^+$ + 1). |
| 431 | 4564 | 1-(4-(1-((5-(5-(difluoromethyl)-1,3,4-oxadiazol-2-yl)pyridin-2-yl)methyl)-1H-1,2,3-triazol-4-yl)benzyl)-N,N-dimethylpiperidin-4-amine $^1$H NMR (400 MHz, $CD_3OD$) δ 9.31-9.26 (m, 1H), 8.53 (dd, J = 8.2, 2.2 Hz, 1H), 8.50 (s, 1H), 7.83 (d, J = 8.2 Hz, 2H), 7.60 (d, J = 8.1 Hz, 1H), 7.44 (d, J = 8.2 Hz, 2H), 7.26 (t, J = 51.6 Hz, 2H), 5.92 (s, 2H), 3.57 (s, 2H), 3.01 (d, J = 11.6 Hz, 2H), 2.32 (s, 6H), 2.24 (d, J = 9.1 Hz, 1H), 2.07 (t, J = 11.7 Hz, 2H), 1.89 (d, J = 14.9 Hz, 2H), 1.63-1.50 (m, 2H); LRMS (ES) m/z 495.6 ($M^+$ + 1). |
| 432 | 4565 | N-(4-(1-((5-(5-(difluoromethyl)-1,3,4-oxadiazol-2-yl)pyridin-2-yl)methyl)-1H-1,2,3-triazol-4-yl)benzyl)cyclobutanamine $^1$H NMR (400 MHz, $CD_3OD$) δ 9.28 (dd, J = 2.2, 0.9 Hz, 1H), 8.53 (dd, J = 8.2, 2.2 Hz, 1H), 8.49 (s, 1H), 7.87-7.80 (m, 2H), 7.60 (d, J = 8.2 Hz, 1H), 7.44 (d, J = 8.2 Hz, 2H), 7.26 (t, J = 51.6 Hz, 1H), 5.92 (s, 2H), 3.72 (s, 2H), 3.30 (s, 1H), 2.27-2.15 (m, 2H), 1.91-1.79 (m, 2H), 1.79-1.64 (m, 2H); LRMS (ES) m/z 438.5 ($M^+$ + 1). |
| 433 | 4566 | N-(4-(1-((5-(5-(difluoromethyl)-1,3,4-oxadiazol-2-yl)pyridin-2-yl)methyl)-1H-1,2,3-triazol-4-yl)benzyl)oxetan-3-amine $^1$H NMR (400 MHz, $CD_3OD$) δ 9.28 (dd, J = 2.3, 0.9 Hz, 1H), 8.53 (dd, J = 8.2, 2.3 Hz, 1H), 8.49 (s, 1H), 7.87-7.80 (m, 2H), 7.59 (d, J = 8.2 Hz, 1H), 7.44 (d, J = 8.2 Hz, 2H), 7.26 (t, J = 51.6 Hz, 1H), 5.92 (s, 2H), 4.72 (t, J = 6.8 Hz, 2H), 4.45 (t, J = 6.4 Hz, 2H), 4.03 (p, J = 6.6 Hz, 1H), 3.75 (s, 2H); LRMS (ES) m/z 440.5 ($M^+$ + 1). |
| 434 | 4567 | N-(4-(1-((5-(5-(difluoromethyl)-1,3,4-oxadiazol-2-yl)pyridin-2-yl)methyl)-1H-1,2,3-triazol-4-yl)benzyl)-1-methylazetidin-3-amine $^1$H NMR (400 MHz, $CD_3OD$) δ 9.30-9.26 (m, 1H), 8.57-8.50 (m, 2H), 7.89 (d, J = 8.2 Hz, 2H), 7.61 (d, J = 8.1 Hz, 1H), 7.46 (d, J = 8.2 Hz, 2H), 7.40-7.11 (m, 1H), 5.93 (s, 2H), 4.68 (d, J = 15.5 Hz, 1H), 4.48-4.35 (m, 2H), 4.25 (dd, J = 8.9, 6.1 Hz, 1H), 3.90-3.82 (m, 1H), 2.82-2.71 (m, 2H), 2.35 (s, 3H); LRMS (ES) m/z 453.5 ($M^+$ + 1). |

Example 435: Synthesis of compound 4569, 2-(difluoromethyl)-5-(6-((4-(2-fluoro-3-(4-methylpiperazin-1-yl)phenyl)-1H-1,2,3-triazol-1-yl)methyl)pyridin-3-yl)-1,3,4-oxadiazole

[Step 1] Synthesis of tert-butyl 4-(3-(1-((5-(5-(difluoromethyl)-1,3,4-oxadiazol-2-yl)pyridin-2-yl)methyl)-1H-1,2,3-triazol-4-yl)-2-fluorophenyl)piperazin-1-carboxylate

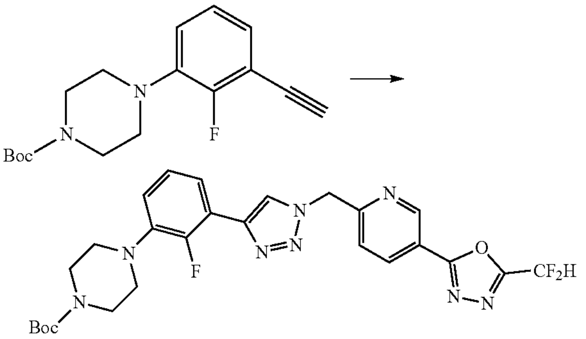

The tert-butyl 4-(3-ethynyl-2-fluorophenyl)piperazin-1-carboxylate (0.860 g, 2.826 mmol) prepared in step 5 of example 357, 2-(6-(azidomethyl)pyridin-3-yl)-5-(difluoromethyl)-1,3,4-oxadiazole (0.784 g, 3.108 mmol) prepared in step 1 of example 16, copper(II) sulfate pentahydrate (0.007 g, 0.028 mmol) and sodium ascorbate (0.056 g, 0.283 mmol) were dissolved in tert-butanol (5 mL)/water (5 mL) at room temperature, after which the resulting solution was stirred at the same temperature for 4 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(3-(1-((5-(5-(difluoromethyl)-1,3,4-oxadiazol-2-yl)pyridin-2-yl)methyl)-1H-1,2,3-triazol-4-yl)-2-fluorophenyl)piperazin-1-carboxylate (0.610 g, 38.8%) in a white solid form.

[Step 2] Synthesis of 2-(difluoromethyl)-5-(6-((4-(2-fluoro-3-(piperazin-1-yl)phenyl)-1H-1,2,3-triazol-1-yl)methyl)pyridin-3-yl)-1,3,4-oxadiazole

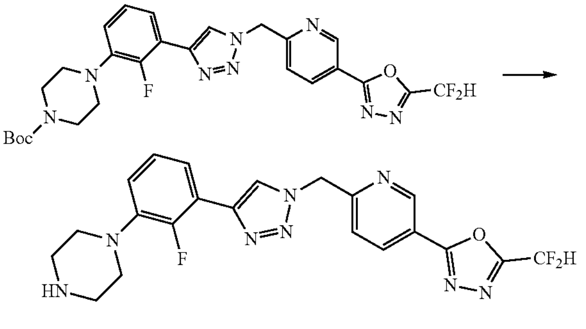

The tert-butyl 4-(3-(1-((5-(5-(difluoromethyl)-1,3,4-oxadiazol-2-yl)pyridin-2-yl)methyl)-1H-1,2,3-triazol-4-yl)-2-fluorophenyl)piperazin-1-carboxylate (0.610 g, 1.096 mmol) prepared in step 1 and trifluoroacetic acid (0.839 mL, 10.960 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(6-((4-(2-fluoro-3-(piperazin-1-yl)phenyl)-1H-1,2,3-triazol-1-yl)methyl)pyridin-3-yl)-1,3,4-oxadiazole (0.440 g, 88.0%) in a yellow oil form.

[Step 3] Synthesis of Compound 4569

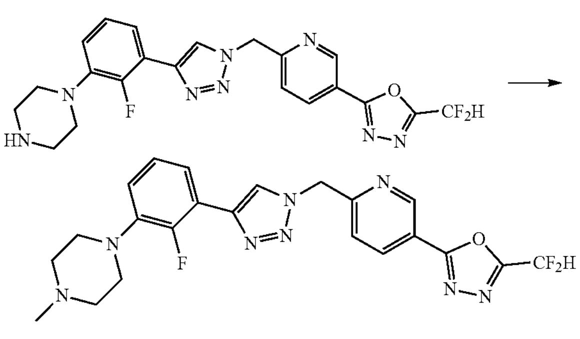

The 2-(difluoromethyl)-5-(6-((4-(2-fluoro-3-(piperazin-1-yl)phenyl)-1H-1,2,3-triazol-1-yl)methyl)pyridin-3-yl)-1,3,4-oxadiazole (0.060 g, 0.131 mmol) prepared in step 2, formaldehyde (0.008 g, 0.263 mmol) and acetic acid (0.008 mL, 0.145 mmol) were dissolved in dichloromethane (5 mL) at room temperature, after which sodium triacetoxyborohydride (0.056 g, 0.263 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(6-((4-(2-fluoro-3-(4-methylpiperazin-1-yl)phenyl)-1H-1,2,3-triazol-1-yl)methyl)pyridin-3-yl)-1,3,4-oxadiazole (0.020 g, 32.3%) in a white solid form.

$^1$H NMR (400 MHz, $CDCl_3$) δ 9.31 (d, J=2.2 Hz, 1H), 8.37 (dd, J=8.2, 2.2 Hz, 1H), 8.11 (d, J=3.9 Hz, 1H), 7.91 (ddd, J=8.0, 6.4, 1.6 Hz, 1H), 7.36 (d, J=8.2 Hz, 1H), 7.16 (t, J=7.9 Hz, 1H), 7.09-6.73 (m, 2H), 5.82 (s, 2H), 3.16 (t, J=4.9 Hz, 4H), 2.72 (t, J=4.8 Hz, 4H), 2.40 (s, 3H); LRMS (ES) m/z 471.5 ($M^+$+1).

The compounds of table 133 were synthesized according to substantially the same process as described above in the synthesis of compound 4569 with an exception of using 2-(difluoromethyl)-5-(6-((4-(2-fluoro-3-(piperazin-1-yl)phenyl)-1H-1,2,3-triazol-1-yl)methyl)pyridin-3-yl)-1,3,4-oxadiazole and the reactant of table 132.

TABLE 132

| Example | Compound No. | Reactant | Yield (%) |
|---|---|---|---|
| 436 | 4570 | Acetaldehyde | 31 |
| 437 | 4571 | Propan-2-one | 38 |
| 438 | 4572 | Cyclobutanone | 45 |
| 439 | 4573 | Oxetan-3-one | 45 |
| 462 | 4600 | 1-fluorocyclopropan-1-carbaldehyde | 29 |
| 463 | 4601 | 3,3-difluorocyclobutan-1-carbaldehyde | 27 |

TABLE 133

| Example | Compound No. | Compound Name, $^1$H-NMR, MS (ESI) |
|---|---|---|
| 436 | 4570 | 2-(difluoromethyl)-5-(6-((4-(3-(4-ethylpiperazin-1-yl)-2-fluorophenyl)-1H-1,2,3-triazol-1-yl)methyl)pyridin-3-yl)-1,3,4-oxadiazole $^1$H NMR (400 MHz, $CDCl_3$) δ 9.30 (d, J = 2.2 Hz, 1H), 8.37 (dd, J = 8.2, 2.3 Hz, 1H), 8.11 (d, J = 3.8 Hz, 1H), 7.95-7.87 (m, 1H), 7.36 (d, J = 8.2 Hz, 1H), 7.16 (t, J = 7.9 Hz, 1H), 7.09-6.74 (m, 2H), 5.82 (s, 2H), 3.20 (t, J = 4.9 Hz, 4H), 2.81 (t, J = 4.8 Hz, 4H), 2.64 (q, J = 7.3 Hz, 2H), 1.17 (t, J = 7.2 Hz, 3H); LRMS (ES) m/z 485.6 ($M^+$ + 1). |
| 437 | 4571 | 2-(difluoromethyl)-5-(6-((4-(2-fluoro-3-(4-isopropylpiperazin-1-yl)phenyl)-1H-1,2,3-triazol-1-yl)methyl)pyridin-3-yl)-1,3,4-oxadiazole $^1$H NMR (400 MHz, $CDCl_3$) δ 9.30 (d, J = 2.2 Hz, 1H), 8.37 (dd, J = 8.2, 2.3 Hz, 1H), 8.10 (d, J = 3.8 Hz, 1H), 7.91 (td, J = 7.2, 6.4, 1.6 Hz, 1H), 7.37 (d, J = 8.2 Hz, 1H), 7.15 (t, J = 7.9 Hz, 1H), 7.09-6.74 (m, 2H), 5.82 (s, 2H), 3.24 (t, J = 4.9 Hz, 4H), 3.06 (p, J = 6.6 Hz, 1H), 2.94 (t, J = 4.8 Hz, 4H), 1.19 (d, J = 6.6 Hz, 6H); LRMS (ES) m/z 499.6 ($M^+$ + 1). |
| 438 | 4572 | 2-(6-((4-(3-(4-cyclobutylpiperazin-1-yl)-2-fluorophenyl)-1H-1,2,3-triazol-1-yl)methyl)pyridin-3-yl)-5-(difluoromethyl)-1,3,4-oxadiazole $^1$H NMR (400 MHz, $CDCl_3$) δ 9.30 (d, J = 2.2 Hz, 1H), 8.37 (dd, J = 8.2, 2.3 Hz, 1H), 8.11 (d, J = 3.8 Hz, 1H), 7.90 (ddd, J = 8.0, 6.4, 1.6 Hz, 1H), 7.36 (d, J = 8.2 Hz, 1H), 7.15 (t, J = 7.9 Hz, 1H), 7.08-6.78 (m, 2H), 5.81 (s, 2H), 3.17 (t, J = 4.9 Hz, 4H), 2.91 (p, J = 8.2 Hz, 1H), 2.64 (t, J = 4.8 Hz, 4H), 2.06 (td, J = 8.4, 5.6 Hz, 4H), 1.80-1.62 (m, 2H); LRMS (ES) m/z 511.1 ($M^+$ + 1). |
| 439 | 4573 | 2-(difluoromethyl)-5-(6-((4-(2-fluoro-3-(4-(oxetan-3-yl)piperazin-1-yl)phenyl)-1H-1,2,3-triazol-1-yl)methyl)pyridin-3-yl)-1,3,4-oxadiazole $^1$H NMR (400 MHz, $CDCl_3$) δ 9.31 (d, J = 2.2 Hz, 1H), 8.37 (dd, J = 8.2, 2.2 Hz, 1H), 8.12 (d, J = 3.9 Hz, 1H), 7.92 (ddd, J = 8.0, 6.4, 1.7 Hz, 1H), 7.36 (d, J = 8.2 Hz, 1H), 7.17 (t, J = 7.9 Hz, 1H), 7.10-6.78 (m, 2H), 5.82 (s, 2H), 4.68 (p, J = 6.4 Hz, 4H), 3.59 (p, J = 6.5 Hz, 1H), 3.16 (t, J = 4.8 Hz, 4H), 2.54 (t, J = 4.7 Hz, 4H); LRMS (ES) m/z 513.5 ($M^+$ + 1). |
| 462 | 4600 | 2-(difluoromethyl)-5-(6-((4-(2-fluoro-3-(4-((1-fluorocyclopropyl)methyl)piperazin-1-yl)phenyl)-1H-1,2,3-triazol-1-yl)methyl)pyridin-3-yl)-1,3,4-oxadiazole $^1$H NMR (400 MHz, $CDCl_3$) δ 9.32 (d, J = 2.2 Hz, 1H), 8.38 (dd, J = 8.2, 2.3 Hz, 1H), 8.12 (d, J = 3.9 Hz, 1H), 7.92 (ddd, J = 7.9, 6.4, 1.6 Hz, 1H), 7.36 (d, J = 8.2 Hz, 1H), 7.17 (t, J = 7.9 Hz, 1H), 7.09-6.78 (m, 2H), 5.83 (s, 2H), 3.19 (t, J = 4.9 Hz, 4H), 2.84 (td, J = 11.8, 11.2, 6.4 Hz, 6H), 1.09 (dd, J = 18.9, 6.8 Hz, 2H), 0.65 (t, J = 8.0 Hz, 2H); LRMS (ES) m/z 529.4 ($M^+$ + 1). |

TABLE 133-continued

| Example | Compound No. | Compound Name, $^1$H-NMR, MS (ESI) |
|---|---|---|
| 463 | 4601 | 2-(6-((4-(3-(4-((3,3-difluorocyclobutyl)methyl)piperazin-1-yl)-2-fluorophenyl)-1H-1,2,3-triazol-1-yl)methyl)pyridin-3-yl)-5-(difluoromethyl)-1,3,4-oxadiazole $^1$H NMR (400 MHz, $CDCl_3$) δ 9.30 (d, J = 2.2 Hz, 1H), 8.37 (dd, J = 8.2, 2.3 Hz, 1H), 8.11 (d, J = 3.9 Hz, 1H), 7.91 (ddd, J = 8.0, 6.4, 1.6 Hz, 1H), 7.36 (d, J = 8.2 Hz, 1H), 7.15 (t, J = 7.9 Hz, 1H), 7.07-6.78 (m, 2H), 5.82 (s, 2H), 3.11 (t, J = 4.9 Hz, 4H), 2.94 (s, 2H), 2.86 (s, 2H), 2.74-2.67 (m, 1H), 2.67-2.61 (m, 4H), 2.55 (d, J = 7.3 Hz, 2H); LRMS (ES) m/z 561.4 ($M^+$ + 1). |

Example 440: Synthesis of compound 4576, 2-(difluoromethyl)-5-(3-fluoro-4-((4-(2-fluoro-3-(4-methylpiperazin-1-yl)phenyl)-1H-1,2,3-triazol-1-yl)methyl)phenyl)-1,3,4-oxadiazol

[Step 1] Synthesis of tert-butyl 4-(3-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate

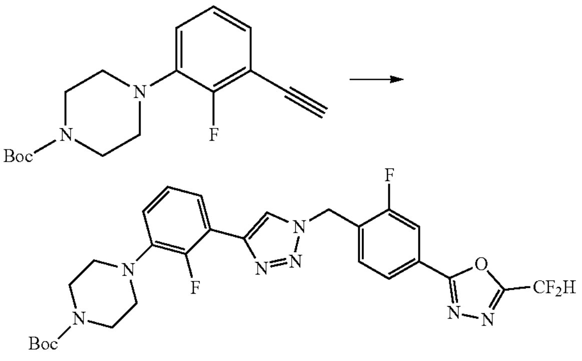

The tert-butyl 4-(3-ethynyl-2-fluorophenyl)piperazin-1-carboxylate (0.860 g, 2.826 mmol) prepared in step 5 of example 357, 2-(4-(azidomethyl)-3-fluorophenyl)-5-(difluoromethyl)-1,3,4-oxadiazole (0.837 g, 3.108 mmol) prepared in synthesis step 1 of example 2, copper(II) sulfate pentahydrate (0.007 g, 0.028 mmol) and sodium ascorbate (0.056 g, 0.283 mmol) were dissolved in tert-butanol (5 mL)/water (5 mL) at room temperature, after which the resulting solution was stirred at the same temperature for 4 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(3-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.700 g, 43.2%) in a white solid form.

[Step 2] Synthesis of 2-(difluoromethyl)-5-(3-fluoro-4-((4-(2-fluoro-3-(piperazin-1-yl)phenyl)-1H-1,2,3-triazol-1-yl)methyl)phenyl)-1,3,4-oxadiazole

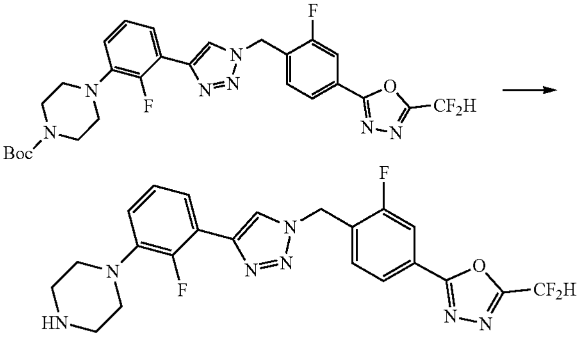

The tert-butyl 4-(3-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.700 g, 1.220 mmol) prepared in step 1 and trifluoroacetic acid (0.935 mL, 12.205 mmol) were dissolved in dichloromethane (25 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(3-fluoro-4-((4-(2-fluoro-3-(piperazin-1-yl)phenyl)-1H-1,2,3-triazol-1-yl)methyl)phenyl)-1,3,4-oxadiazole (0.630 g, 109.0%) in a yellow oil form.

[Step 3] Synthesis of Compound 4576

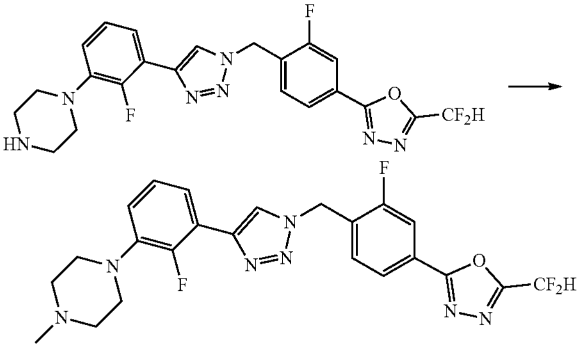

The 2-(difluoromethyl)-5-(3-fluoro-4-((4-(2-fluoro-3-(piperazin-1-yl)phenyl)-1H-1,2,3-triazol-1-yl)methyl)phenyl)-1,3,4-oxadiazole (0.060 g, 0.127 mmol) prepared in step 2, formaldehyde (0.008 g, 0.253 mmol) and acetic acid (0.008 mL, 0.139 mmol) were dissolved in dichloromethane (5 mL) at room temperature, after which sodium triacetoxyborohydride (0.054 g, 0.253 mmol) was added to the resulting solution and stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(2-fluoro-3-(4-methylpiperazin-1-yl)phenyl)-1H-1,2,3-triazol-1-yl)methyl)phenyl)-1,3,4-oxadiazole (0.015 g, 24.3%) in a colorless oil form.

$^1H$ NMR (400 MHz, $CDCl_3$) δ 7.98 (d, J=3.8 Hz, 1H), 7.93-7.82 (m, 3H), 7.41 (t, J=7.7 Hz, 1H), 7.15 (t, J=7.9 Hz, 1H), 7.07-6.75 (m, 2H), 5.72 (s, 2H), 3.15 (t, J=4.9 Hz, 4H), 2.71 (d, J=4.9 Hz, 4H), 2.39 (s, 3H); LRMS (ES) m/z 488.5 ($M^+$+1).

The compounds of table 135 were synthesized according to substantially the same process as described above in the synthesis of compound 4576 with an exception of using 2-(difluoromethyl)-5-(3-fluoro-4-((4-(2-fluoro-3-(piperazin-1-yl)phenyl)-1H-1,2,3-triazol-1-yl)methyl)phenyl)-1,3,4-oxadiazole and the reactant of table 134.

TABLE 134

| Example | Compound No. | Reactant | Yield (%) |
|---|---|---|---|
| 441 | 4577 | Acetaldehyde | 32 |
| 442 | 4578 | Propan-2-one | 46 |
| 443 | 4579 | Cyclobutanone | 45 |
| 444 | 4580 | Oxetan-3-one | 45 |
| 464 | 4602 | 1-fluorocyclopropan-1-carbaldehyde | 33 |
| 465 | 4603 | 3,3-difluorocyclobutan-1-carbaldehyde | 34 |

TABLE 135

| Example | Compound No. | Compound Name, $^1H$-NMR, MS (ESI) |
|---|---|---|
| 441 | 4577 | 2-(difluoromethyl)-5-(4-((4-(3-(4-ethylpiperazin-1-yl)-2-fluorophenyl)-1H-1,2,3-triazol-1-yl)methyl)-3-fluorophenyl)-1,3,4-oxadiazole $^1H$ NMR (400 MHz, $CDCl_3$) δ 7.98 (d, J = 3.9 Hz, 1H), 7.92-7.84 (m, 3H), 7.41 (t, J = 7.7 Hz, 1H), 7.14 (t, J = 7.9 Hz, 1H), 7.06-6.74 (m, 2H), 5.72 (s, 2H), 3.17 (t, J = 4.9 Hz, 4H), 2.73 (t, J = 4.8 Hz, 4H), 2.57 (q, J = 7.2 Hz, 2H), 1.14 (t, J = 7.2 Hz, 3H); LRMS (ES) m/z 502.5 ($M^+$ + 1). |
| 442 | 4578 | 2-(difluoromethyl)-5-(3-fluoro-4-((4-(2-fluoro-3-(4-isopropylpiperazin-1-yl-phenyl)-1H-1,2,3-triazol-1-yl)methyl)phenyl)-1,3,4-oxidiazole $^1H$ NMR (400 MHz, $CDCl_3$) δ 7.97 (d, J = 3.8 Hz, 1H), 7.94-7.81 (m, 3H), 7.42 (t, J = 7.7 Hz, 1H), 7.14 (t, J = 7.9 Hz, 1H), 7.07-6.76 (m, 2H), 5.72 (s, 2H), 3.30 (t, J = 4.9 Hz, 4H), 3.10 (hept, J = 6.5 Hz, 1H), 2.98 (t, J = 4.9 Hz, 4H), 1.24 (d, J = 6.6 Hz, 6H); LRMS (ES) m/z 516.5 ($M^+$ + 1). |
| 443 | 4579 | 2-(4-((4-(3-(4-cyclobutylpiperazin-1-yl)-2-fluorophenyl)-1H-1,2,3-triazol-1-yl)methyl)-3-fluorophenyl)-5-(difluoromethyl)-1,3,4-oxadiazole $^1H$ NMR (400 MHz, $CDCl_3$) δ 7.98 (d, J = 3.9 Hz, 1H), 7.93-7.84 (m, 3H), 7.41 (t, J = 7.7 Hz, 1H), 7.14 (t, J = 7.9 Hz, 1H), 7.06-6.73 (m, 2H), 5.72 (s, 2H), 3.14 (t, J = 4.9 Hz, 4H), 2.85 (p, J = 7.9 Hz, 1H), 2.63-2.49 (m,4H), 2.01 (ddd, J = 27.5, 14.8, 5.3 Hz, 4H), 1.80-1.62 (m, 2H); LRMS (ES) m/z 528.4 ($M^+$ + 1). |
| 444 | 4580 | 2-(difluoromethyl)-5-(3-fluoro-4-((4-(2-fluoro-3-(4-(oxetan-3-yl)piperazin-1-yl-phenyl)-1H-1,2,3-triazol-1-yl)methyl)phenyl)-1,3,4-oxidiazole $^1H$ NMR (400 MHz, $CDCl_3$) δ 7.98 (d, J = 3.8 Hz, 1H), 7.93-7.82 (m, 3H), 7.41 (t, J = 7.7 Hz, 1H), 7.15 (t, J = 7.9 Hz, 1H), 7.06-6.77 (m, 2H), 5.72 (s, 2H), 4.67 (dt, J = 14.3, 6.3 Hz, 4H), 3.57 (p, J = 6.4 Hz, 1H), 3.14 (t, J = 4.7 Hz, 4H), 2.52 (t, J = 4.7 Hz, 4H); LRMS (ES) m/z 530.4 ($M^+$ + 1). |
| 464 | 4602 | 2-(difluoromethyl)-5-(3-fluoro-4-((4-(2-fluoro-3-(4-((1-fluorocyclopropyl)methyl)piperazin-1-yl)phenyl)-1H-1,2,3-triazol-1-yl)methyl)phenyl)-1,3,4-oxadiazole $^1H$ NMR (400 MHz, $CDCl_3$) δ 7.99 (d, J = 3.9 Hz, 1H), 7.93-7.85 (m, 3H), 7.42 (t, J = 7.7 Hz, 1H), 7.16 (t, J = 7.9 Hz, 1H), 7.04-6.79 (m, 2H),5.73(s, 2H), 3.16 (q, J = 5.7, 5.2 Hz, 4H), 2.85-2.76 (m, 6H), 1.08 (dd, J = 18.9, 6.8 Hz, 2H), 0.70-0.58 (m, 2H); LRMS (ES) m/z 546.3 ($M^+$ + 1). |
| 465 | 4603 | 2-(4-((4-(3-(4-((3,3-difluorocyclobutyl)methyl)piperazin-1-yl)-2-fluorophenyl)-1H-1,2,3-triazol-1-yl)methyl)-3-fluorophenyl)-5-(difluoromethyl)-1,3,4-oxadiazole $^1H$ NMR (400 MHz, $CDCl_3$) δ 7.99 (d, J = 4.0 Hz, 1H), 7.92-7.83 (m, 3H), 7.42 (t, J = 7.8 Hz, 1H), 7.15 (t, J = 7.9 Hz, 1H), 7.03-6.78 (m, 2H),5.72 (s, 2H), 3.10 (q, J = 8.2, 6.4 Hz, 4H), 2.68-2.54 (m, 9H), 2.23 (ddd, J = 21.2, 10.3, 4.7 Hz, 2H); LRMS (ES) m/z 578.4 ($M^+$ + 1). |

Example 445: Synthesis of compound 4582, 2-(difluoromethyl)-5-(6-((4-(2-(4-methylpiperazin-1-yl)pyridin-4-yl)-1H-1,2,3-triazol-1-yl)methyl)pyridin-3-yl)-1,3,4-oxadiazole

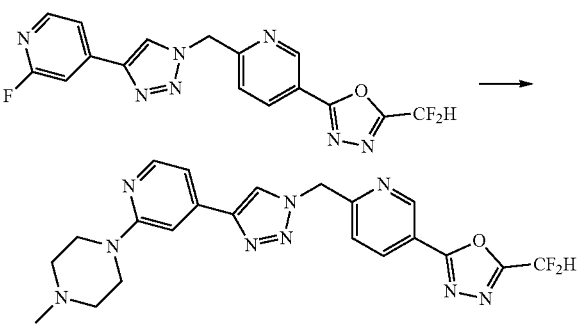

The 2-(difluoromethyl)-5-(6-((4-(2-fluoropyridin-4-yl)-1H-1,2,3-triazol-1-yl)methyl)pyridin-3-yl)-1,3,4-oxadiazole (0.050 g, 0.134 mmol) prepared in example 181, 1-methylpiperazine (0.018 mL, 0.161 mmol) and N,N-diisopropylethylamine (0.028 mL, 0.161 mmol) were dissolved in dimethyl sulfoxide (1 mL), after which the resulting solution was stirred at 100 °C for 18 hours and further stirred at 130 °C for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(6-((4-(2-(4-methylpiperazin-1-yl)pyridin-4-yl)-1H-1,2,3-triazol-1-yl)methyl)pyridin-3-yl)-1,3,4-oxadiazole (0.019 g, 31.3%) in a brown solid form.

$^1$H NMR (400 MHz, $CD_3OD$) δ 9.27 (d, J=2.2 Hz, 1H), 8.67 (s, 1H), 8.53 (dd, J=8.2, 2.2 Hz, 1H), 8.17 (d, J=5.3 Hz, 1H), 7.62 (d, J=8.2 Hz, 1H), 7.39-7.13 (m, 3H), 5.94 (s, 2H), 3.64 (t, J=5.1 Hz, 4H), 2.61 (t, J=5.1 Hz, 4H), 2.38 (s, 3H); LRMS (ES) m/z 454.4 ($M^+$+1).

The compounds of table 137 were synthesized according to substantially the same process as described above in the synthesis of compound 4582 with an exception of using 2-(difluoromethyl)-5-(6-((4-(2-fluoropyridin-4-yl)-1H-1,2,3-triazol-1-yl)methyl)pyridin-3-yl)-1,3,4-oxadiazole and the reactant of table 136.

TABLE 136

| Example | Compound No. | Reactant | Yield (%) |
|---|---|---|---|
| 453 | 4591 | 1-ethylpiperazine | 59 |
| 454 | 4592 | 1-isopropylpiperazine | 50 |
| 455 | 4593 | 1-cyclopropylpiperazine | 39 |
| 456 | 4594 | 1-(oxetan-3-yl)piperazine | 48 |

TABLE 137

| Example | Compound No. | Compound Name, $^1$H-NMR, MS (ESI) |
|---|---|---|
| 453 | 4591 | 2-(difluoromethyl)-5-(6-((4-(2-(4-ethylpiperazin-1-yl)pyridin-4-yl)-1H-1,2,3-triazol-1-yl)methyl)pyridin-3-yl)-1,3,4-oxadiazole $^1$H NMR (400 MHz, $CD_3OD$) δ 9.27 (dd, J = 2.3, 0.9 Hz, 1H), 8.68 (s, 1H), 8.53 (dd, J = 8.2, 2.2 Hz, 1H), 8.17 (d, J = 5.3 Hz, 1H), 7.62 (d, J = 8.3 Hz, 1H), 7.40-7.13 (m, 3H), 5.94 (s, 2H), 3.67-3.60 (m, 4H), 2.64 (t, J = 5.2 Hz, 4H), 2.53 (q, J = 7.3 Hz, 2H), 1.18 (t, J = 7.2 Hz, 3H); LRMS (ESI) m/z 468.4 ($M^+$ + H). |
| 454 | 4592 | 2-(difluoromethyl)-5-(6-((4-(2-(4-isopropylpiperazin-1-yl)pyridin-4-yl)-1H-1,2,3-triazol-1-yl)methyl)pyridin-3-yl)-1,3,4-oxadiazole $^1$H NMR (400 MHz, $CD_3OD$) δ 9.27 (d, J = 2.2 Hz, 1H), 8.68 (s, 1H), 8.53 (dd, J = 8.2, 2.2 Hz, 1H), 8.16 (d, J = 5.3 Hz, 1H), 7.62 (d, J = 8.2 Hz, 1H), 7.40-7.13 (m, 3H), 5.94 (s, 2H), 3.66-3.59 (m, 4H), 2.78-2.69 (m, 5H), 1.15 (d, J = 6.5 Hz, 6H); LRMS (ESI) m/z 482.4 ($M^+$ + H). |
| 455 | 4593 | 2-(6-((4-(2-(4-cyclopropylpiperazin-1-yl)pyridin-4-yl)-1H-1,2,3-triazol-1-yl)methyl)pyridin-3-yl)-5-(difluoromethyl)-1,3,4-oxadiazole $^1$H NMR (400 MHz, $CD_3OD$) δ 9.30-9.25 (m, 1H), 8.68 (s, 1H), 8.53 (dd, J = 8.2, 2.2 Hz, 1H), 8.16 (d, J = 5.3 Hz, 1H), 7.63 (d, J = 8.2 Hz, 1H), 7.40-7.13 (m, 3H), 5.94 (s, 2H), 3.59 (t, J = 5.1 Hz, 4H), 2.79 (t, J = 5.2 Hz, 4H), 1.75 (tt, J = 6.7, 3.8 Hz, 1H), 0.61-0.46 (m, 4H); LRMS (ESI) m/z 480.4 ($M^+$ + H). |
| 456 | 4594 | 2-(difluoromethyl)-5-(6-((4-(2-(4-(oxetan-3-yl)piperazin-1-yl)pyridin-4-yl)-1H-1,2,3-triazol-1-yl)methyl)pyridin-3-yl)-1,3,4-oxadiazole $^1$H NMR (400 MHz, $CD_3OD$) δ 9.30-9.25 (m, 1H), 8.68 (s, 1H), 8.54 (dd, J = 8.2, 2.2 Hz, 1H), 8.17 (d, J = 5.3 Hz, 1H), 7.63 (d, J = 8.1 Hz, 1H), 7.34 (s, 1H), 7.26 (t, J = 51.6 Hz, 1H), 7.15 (dd, J = 5.3, 1.3 Hz, 1H), 5.94 (s, 2H), 4.76-4.66 (m, 4H), 3.69-3.62 (m, 4H), 3.57 (t, J = 6.3 Hz, 1H), 2.51 (t, J = 5.1 Hz, 4H); LRMS (ESI) m/z 496.4 ($M^+$ + H). |

Example 446: Synthesis of compound 4583, 2-(4-((4-(2-(azetidin-1-ylmethyl)phenyl)-1H-1,2,3-triazol-1-yl)methyl)-3-fluorophenyl)-5-(difluoromethyl)-1,3,4-oxadiazole

[Step 1] Synthesis of 2-(1-(4-(5-(difluoromethyl)-1,3,4-oxadiazol-2-yl)-2-fluorobenzyl)-1H-1,2,3-triazol-4-yl)benzaldehyde

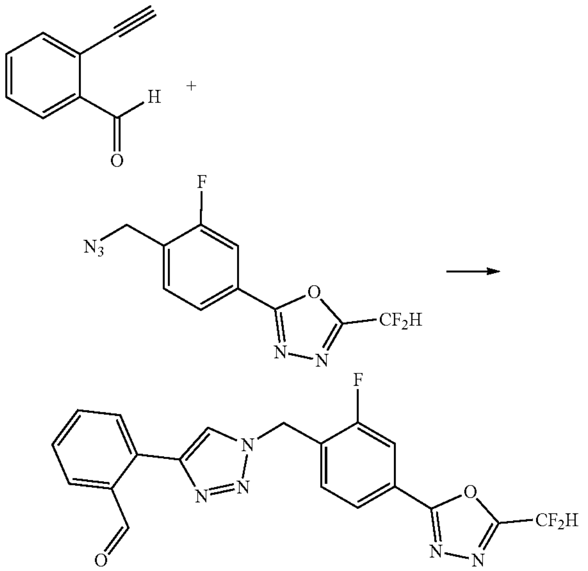

The 2-(4-(azidomethyl)-3-fluorophenyl)-5-(difluoromethyl)-1,3,4-oxadiazole (0.700 g, 2.776 mmol) prepared in step 1 of example 2 and 2-ethynylbenzaldehyde (0.361 g, 2.776 mmol) were dissolved in tert-butanol (5 mL)/water (5 mL) at room temperature, after which sodium ascorbate (1.00 M solution, 0.278 mL, 0.278 mmol) and copper(II) sulfate pentahydrate (0.50 M solution, 0.056 mL, 0.028 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; hexane/ethyl acetate=100 to 70%) and concentrated to obtain 2-(1-(4-(5-(difluoromethyl)-1,3,4-oxadiazol-2-yl)-2-fluorobenzyl)-1H-1,2,3-triazol-4-yl)benzaldehyde (0.850 g, 76.7%) in a beige solid form.

[Step 2] Synthesis of Compound 4583

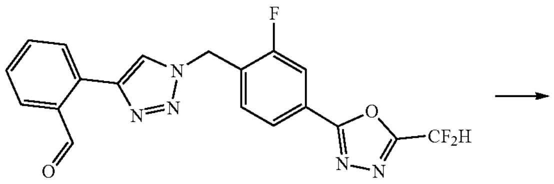

-continued

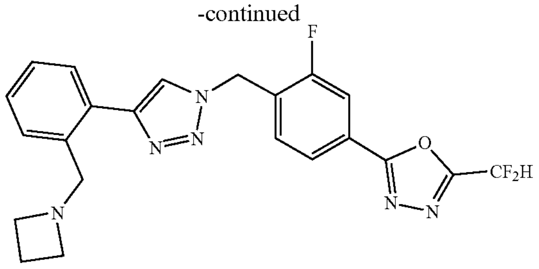

The 2-(1-(4-(5-(difluoromethyl)-1,3,4-oxadiazol-2-yl)-2-fluorobenzyl)-1H-1,2,3-triazol-4-yl)benzaldehyde (0.050 g, 0.125 mmol) prepared in step 1, azetidine hydrogen chloride (0.023 g, 0.250 mmol) and sodium triacetoxy borohydride (0.133 g, 0.626 mmol) were dissolved in dichloromethane (1 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 60%) and concentrated to obtain 2-(4-((4-(2-(azetidin-1-ylmethyl)phenyl)-1H-1,2,3-triazol-1-yl)methyl)-3-fluorophenyl)-5-(difluoromethyl)-1,3,4-oxadiazole (0.032 g, 58.0%) in a light yellow oil form.

$^1H$ NMR (400 MHz, $CD_3OD$) δ 8.44 (s, 1H), 8.05-7.94 (m, 2H), 7.68 (q, J=7.7, 7.2 Hz, 2H), 7.50 (d, J=7.3 Hz, 1H), 7.46-7.40 (m, 2H), 7.25 (t, J=51.6 Hz, 1H), 5.90 (s, 2H), 3.97 (s, 2H), 3.71-3.36 (m, 4H), 2.20 (d, J=14.5 Hz, 2H); LRMS (ES) m/z 441.1 ($M^+$+1).

The compounds of table 139 were synthesized according to substantially the same process as described above in the synthesis of compound 4583 with an exception of using 2-(1-(4-(5-(difluoromethyl)-1,3,4-oxadiazol-2-yl)-2-fluorobenzyl)-1H-1,2,3-triazol-4-yl)benzaldehyde and the reactant of table 138.

TABLE 138

| Example | Compound No | Reactant | Yield (%) |
| --- | --- | --- | --- |
| 447 | 4585 | Pyrrolidine | 56 |
| 448 | 4586 | 2-oxa-6-azaspiro[3.3]heptane | 43 |
| 449 | 4587 | 1-methylpiperazine | 64 |
| 450 | 4588 | 1-ethylpiperazine | 57 |
| 451 | 4589 | Cyclobutanamine | 38 |
| 452 | 4590 | Oxetan-3-amine | 56 |

TABLE 139

| Example | Compound No. | Compound Name, $^1H$-NMR, MS (ESI) |
| --- | --- | --- |
| 447 | 4585 | 2-(difluoromethyl)-5-(3-fluoro-4-((4-(2-(pyrrolidin-1-ylmethyl)phenyl)-1H-1,2,3-triazol-1-yl)methyl)phenyl)-1,3,4-oxadiazole $^1H$ NMR (400 MHz, $CD_3OD$) δ 8.57 (s, 1H), 8.05-7.94 (m, 2H), 7.78 (d, J = 7.6 (Hz, 1H), 7.70 (t, J = 7.7 Hz, 1H), 7.60 (d, J = 7.6 Hz, 1H), 7.55 (t, J = 7.5 Hz, 1H), 7.48 (t, J = 7.4 Hz, 1H), 7.26 (t, J = 51.6 Hz, 1H), 5.91 (s, 2H), 4.28 (s, 2H), 3.15 (s, 4H), 2.09-1.95 (m, 4H); LRMS (ES) m/z 455.4 ($M^+$ + H). |
| 448 | 4586 | 6-(2-(1-(4-(5-(difluoromethyl)-1,3,4-oxadiazol-2-yl)-2-fluorobenzyl)-1H-1,2,3-triazol-4-yl)benzyl)-2-oxa-6-azaspiro[3.3]heptane $^1H$ NMR (400 MHz, $CD_3OD$) δ 8.37 (s, 1H), 8.06-7.95 (m, 2H), 7.71-7.63 (m, 2H), 7.45-7.11 (m, 4H), 5.89 (s, 2H), 4.70 (s, 4H), 3.71 (s, 2H), 3.39 (s, 4H); LRMS (ES) m/z 483.4 ($M^+$ + H). |
| 449 | 4587 | 2-(difluoromethyl)-5-(3-fluoro-4-((4-(2-((4-methylpiperazin-1-yl)methyl)phenyl)-1H-1,2,3-triazol-1-yl)methyl)phenyl)-1,3,4-oxadiazole $^1H$ NMR (400 MHz, $CD_3OD$) δ 8.42 (s, 1H), 8.02 (dd, J = 15.1, 8.9 Hz, 2H), 7.73 (t, J = 7.9 Hz, 2H), 7.45-7.38 (m, 2H), 7.37-7.12 (m, 2H), 5.89 (s, 2H), 3.49 (s, 2H), 2.68-2.26 (m, 8H), 2.22 (s, 3H); LRMS (ES) m/z 484.5 ($M^+$ + H). |
| 450 | 4588 | 2-(difluoromethyl)-5-(4-((4-(2-((4-ethylpiperazin-1-yl)methyl)phenyl)-1H-1,2,3-triazol-1-yl)methyl)-3-fluorophenyl)-1,3,4-oxadiazole $^1H$ NMR (400 MHz, $CD_3OD$) δ 8.41 (s, 1H), 8.07-7.96 (m, 2H), 7.74 (t, J = 7.3 Hz, 2H), 7.44-7.13 (m, 4H), 5.89 (s, 2H), 3.49 (s, 2H), 2.65-2.24 (m, 10H), 1.05 (t, J = 7.2 Hz, 3H); LRMS (ES) m/z 498.5 ($M^+$ + H). |
| 451 | 4589 | N-(2-(1-(4-(5-(difluoromethyl)-1,3,4-oxadiazol-2-yl)-2-fluorobenzyl)-1H-1,2,3-triazol-4-yl)benzyl)cyclobutanamine $^1H$ NMR (400 MHz, $CD_3OD$) δ 8.39 (s, 1H), 8.05-7.94 (m, 2H), 7.66 (t, J = 7.7 Hz, 1H), 7.62-7.55 (m, 1H), 7.51 (dd, J = 5.6, 3.5 Hz, 1H), 7.42 (dd, J = 5.7, 3.4 Hz, 2H), 7.25 (t, J = 51.6 Hz, 1H), 5.90 (s, 2H), 3.84 (s, 2H), 3.39-3.35 (m, 1H), 2.14 (d, J = 9.1 Hz, 2H), 1.93-1.79 (m, 2H), 1.75-1.63 (m, 2H); LRMS (ES) m/z 455.4 ($M^+$ + H). |
| 452 | 4590 | N-(2-(1-(4-(5-(difluoromethyl)-1,3,4-oxadiazol-2-yl)-2-fluorobenzyl)-1H-1,2,3-triazol-4-yl)benzyl)oxetan-3-amine $^1H$ NMR (400 MHz, $CD_3OD$) δ 8.40 (s, 1H), 8.05-7.94 (m, 2H), 7.65 (t, J = 7.6 Hz, 1H), 7.62-7.54 (m, 1H), 7.51-7.44 (m, 1H), 7.43-7.38 (m, 2H), 7.25 (t, J = 51.6 Hz, 1H), 5.90 (s, 2H), 4.64 (t. J = 6.8 Hz, 2H), 4.36 (t, J = 6.4 Hz, 2H), 4.01 (p, J = 6.7 Hz, 1H), 3.82 (s, 2H); LRMS (ES) m/z 457.5 ($M^+$ + H). |

Example 457: Synthesis of compound 4595, 2-(difluoromethyl)-5-(6-((4-(2-methylisoindolin-4-yl)-1H-1,2,3-triazol-1-yl)methyl)pyridin-3-yl)-1,3,4-oxadiazole

[Step 1] Synthesis of tert-butyl 4-(1-((5-(5-(difluoromethyl)-1,3,4-oxadiazol-2-yl)pyridin-2-yl)methyl)-1H-1,2,3-triazol-4-yl)isoindolin-2-carboxylate

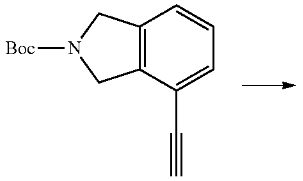

-continued

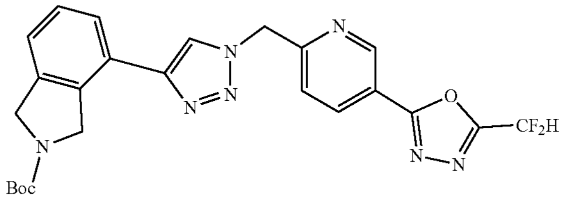

The tert-butyl 4-ethynylisoindolin-2-carboxylate (0.210 g, 0.863 mmol) prepared in step 1 of example 400, 2-(6-(azidomethyl)pyridin-3-yl)-5-(difluoromethyl)-1,3,4-oxadiazole (0.218 g, 0.863 mmol) prepared in step 1 of example 16, sodium ascorbate (0.50 M solution in water, 0.173 mL, 0.086 mmol) and copper(II) sulfate pentahydrate (1.00 M solution in water, 0.017 mL, 0.017 mmol) were dissolved in tert-butanol (2 mL)/water (2 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain tert-butyl 4-(1-((5-(5-(difluoromethyl)-1,3,4-oxadiazol-2-yl)pyridin-2-yl)methyl)-1H-1,2,3-triazol-4-yl)isoindolin-2-carboxylate (0.351 g, 82.1%) in a white solid form.

[Step 2] Synthesis of 2-(difluoromethyl)-5-(6-((4-(isoindolin-4-yl)-1H-1,2,3-triazol-1-yl)methyl)pyridin-3-yl)-1,3,4-oxadiazole

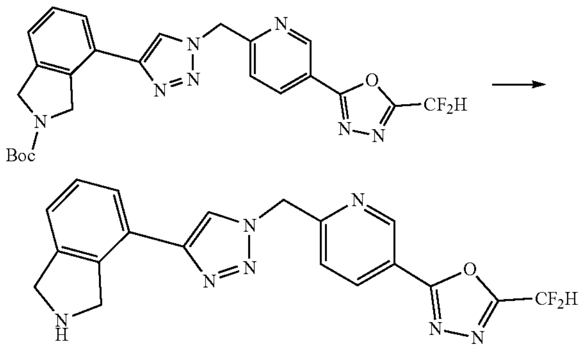

The tert-butyl 4-(1-((5-(5-(difluoromethyl)-1,3,4-oxadiazol-2-yl)pyridin-2-yl)methyl)-1H-1,2,3-triazol-4-yl)isoindolin-2-carboxylate (0.351 g, 0.708 mmol) prepared in step 1 and trifluoroacetic acid (0.542 mL, 7.084 mmol) were dissolved in dichloromethane (3 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(6-((4-(isoindolin-4-yl)-1H-1,2,3-triazol-1-yl)methyl)pyridin-3-yl)-1,3,4-oxadiazole, 0.280 g, 100.0%, brown oil).

[Step 3] Synthesis of Compound 4595

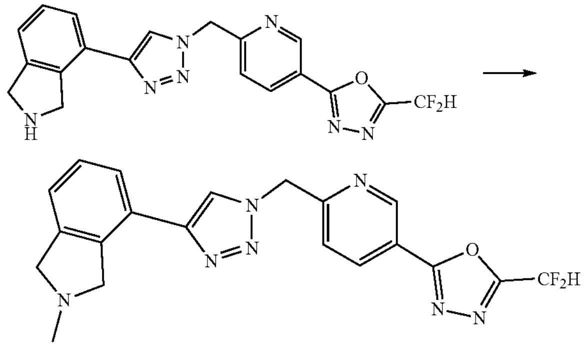

The 2-(difluoromethyl)-5-(6-((4-(isoindolin-4-yl)-1H-1,2,3-triazol-1-yl)methyl)pyridin-3-yl)-1,3,4-oxadiazole (0.056 g, 0.142 mmol) prepared in step 2 and formaldehyde (37.00% solution in water, 0.021 mL, 0.283 mmol) were dissolved in dichloromethane (1 mL), after which the resulting solution was stirred at room temperature for 15 minutes, and then sodium triacetoxyborohydride (0.090 g, 0.425 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated, after which the obtained product was purified again via column chromatography ($SiO_2$, 4 g cartridge; methanol/dichloromethane=0 to 10%) and concentrated to obtain 2-(difluoromethyl)-5-(6-((4-(2-methylisoindolin-4-yl)-1H-1,2,3-triazol-1-yl)methyl)pyridin-3-yl)-1,3,4-oxadiazole (0.011 g, 19.0%) in a yellow solid form.

$^1H$ NMR (400 MHz, $CD_3OD$) δ 9.28 (d, J=2.2 Hz, 1H), 8.53 (dd, J=8.2, 2.2 Hz, 1H), 8.45 (s, 1H), 7.72 (d, J=7.6 Hz, 1H), 7.60 (d, J=8.2 Hz, 1H), 7.36 (dd, J=14.2, 6.7 Hz, 1H), 7.30-7.12 (m, 2H), 5.94 (s, 2H), 4.28 (s, 2H), 4.04 (s, 2H), 2.68 (s, 3H); LRMS (ES) m/z 410.3 ($M^+$+1).

The compounds of table 141 were synthesized according to substantially the same process as described above in the synthesis of compound 4595 with an exception of using 2-(difluoromethyl)-5-(6-((4-(isoindolin-4-yl)-1H-1,2,3-triazol-1-yl)methyl)pyridin-3-yl)-1,3,4-oxadiazole and the reactant of table 140.

TABLE 140

| Example | Compound No. | Reactant | Yield (%) |
|---|---|---|---|
| 458 | 4596 | Acetaldehyde | 65 |
| 459 | 4597 | Acetone | 86 |
| 460 | 4598 | Cyclobutanone | 49 |
| 461 | 4599 | Oxetanone | 72 |

TABLE 141

| Example | Compound No. | Compound Name, $^1$H-NMR, MS (ESI) |
|---|---|---|
| 458 | 4596 | 2-(difluoromethyl)-5-(6-((4-(2-ethylisoindolin-4-yl)-1H-1,2,3-triazol-1-yl)methyl)pyridin-3-yl)-1,3,4-oxadiazole $^1$H NMR (400 MHz, $CD_3OD$) δ 9.27 (d, J = 2.2 Hz, 1H), 8.60-8.48 (m, 2H), 7.74 (d, J = 7.7 Hz, 1H), 7.61 (d, J = 8.2 Hz, 1H), 7.46-7.36 (m, 1H), 7.35-7.11 (m, 2H), 5.94 (s, 2H), 4.48 (s, 2H), 4.22 (s, 2H), 3.06 (q, J = 7.2 Hz, 2H), 1.32 (t, J = 7.2 Hz, 3H); LRMS (ESI) m/z 424.3 ($M^+$ + H). |
| 459 | 4597 | 2-(difluoromethyl)-5-(6-((4-(2-isopropylisoindolin-4-yl)-1H-1,2,3-triazol-1-yl)methyl)pyridin-3-yl)-1,3,4-oxadiazole $^1$H NMR (400 MHz, $CD_3OD$) δ 9.27 (d, J = 2.2 Hz, 1H), 8.53 (dd, J = 8.2, 2.3 Hz, 1H), 8.47 (s, 1H), 7.72 (d, J = 7.5 Hz, 1H), 7.60 (d, J = 8.3 Hz, 1H), 7.40-7.11 (m, 3H), 5.94 (s, 2H), 4.32 (s, 2H), 4.09 (s, 2H), 2.92 (p, J = 6.4 Hz, 1H), 1.28 (d, J = 6.3 Hz, 6H); LRMS (ESI) m/z 438.3 ($M^+$ + H). |
| 460 | 4598 | 2-(6-((4-(2-cyclobutylisoindolin-4-yl)-1H-1,2,3-triazol-1-yl)methyl)pyridin-3-yl)-5-(difluoromethyl)-1,3,4-oxadiazole $^1$H NMR (400 MHz, $CD_3OD$) δ 9.30-9.25 (m, 1H), 8.53 (dd, J = 8.2, 2.3 Hz, 1H), 8.45 (s, 1H), 7.72 (d, J = 7.6 Hz, 1H), 7.59 (d, J = 8.2 Hz, 1H), 7.40-7.12 (m, 3H), 5.94 (s, 2H), 4.22 (s, 2H), 3.99 (s, 2H), 3.44 (p, J = 7.8 Hz, 1H), 2.20 (dq, J = 7.6, 4.0 Hz, 2H), 2.15-2.01 (m, 2H), 1.94-1.78 (m, 2H); LRMS (ESI) m/z 450.4 ($M^+$ + H). |
| 461 | 4599 | 2-(difluoromethyl)-5-(6-((4-(2-(oxetan-3-yl)isoindolin-4-yl)-1H-1,2,3-triazol-1-yl)methyl)pyridin-3-yl)-1,3,4-oxadiazole $^1$H NMR (400 MHz, $CD_3OD$) δ 9.27 (d, J = 2.2 Hz, 1H), 8.52 (dd, J = 8.2, 2.3 Hz, 1H), 8.45 (s, 1H), 7.73 (d, J = 7.6 Hz, 1H), 7.59 (d, J = 8.2 Hz, 1H), 7.41-7.11 (m, 3H), 5.93 (s, 2H), 4.84 (d, J = 6.7 Hz, 2H), 4.79-4.72 (m, 2H), 4.28 (d, J = 1.9 Hz, 2H), 4.12 (ddd, J = 12.3, 6.7, 5.5 Hz, 1H), 4.05 (s, 2H); LRMS (ESI) m/z 452.3 ($M^+$ + H). |

Example 474: Synthesis of compound 4633, 2-(difluoromethyl)-5-(3-fluoro-4-((4-(2-(4-methylpiperazin-1-yl)pyridin-4-yl)-1H-1,2,3-triazol-1-yl)methyl)phenyl)-1,3,4-oxadiazole

[Step 1] Synthesis of 2-(difluoromethyl)-5-(3-fluoro-4-((4-(2-fluoropyridin-4-yl)-1H-1,2,3-triazol-1-yl)methyl)phenyl)-1,3,4-oxadiazole

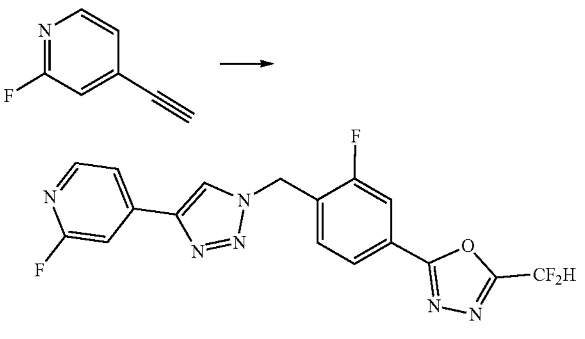

The 4-ethynyl-2-fluoropyridine (0.490 g, 4.046 mmol) prepared in step 1 of example 181, 2-(4-(azidomethyl)-3-fluorophenyl)-5-(difluoromethyl)-1,3,4-oxadiazole (1.089 g, 4.046 mmol) prepared in step 1 of example 2, sodium ascorbate (0.50 M solution in water, 0.809 mL, 0.405 mmol) and copper(II) sulfate pentahydrate (1.00 M solution in water, 0.040 mL, 0.040 mmol) were dissolved in tert-butanol (7 mL)/water (7 mL) at room temperature, after which the resulting solution was stirred at the same temperature for 18 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (20 mL) and hexane (500 mL) were added to the resulting concentrate and stirred to filter out a precipitated solid, washed with hexane, and dried to obtain 2-(difluoromethyl)-5-(3-fluoro-4-((4-(2-fluoropyridin-4-yl)-1H-1,2,3-triazol-1-yl)methyl)phenyl)-1,3,4-oxadiazole (1.100 g, 69.7%) in a light yellow solid form.

[Step 2] Synthesis of Compound 4633

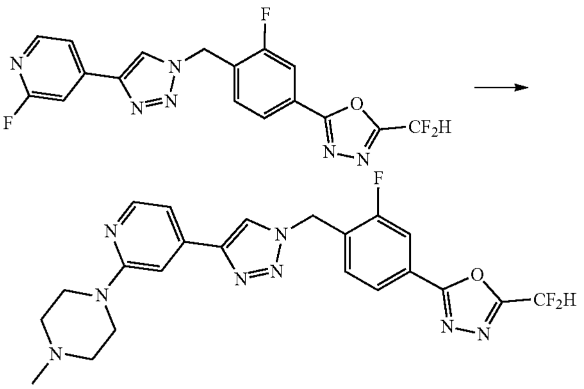

The 2-(difluoromethyl)-5-(3-fluoro-4-((4-(2-fluoropyridin-4-yl)-1H-1,2,3-triazol-1-yl)methyl)phenyl)-1,3,4-oxadiazole (0.060 g, 0.154 mmol) prepared in step 1, 1-methylpiperazine (0.026 mL, 0.231 mmol) and N,N-diisopropylethylamine (0.040 mL, 0.231 mmol) were dissolved in dimethyl sulfoxide (1 mL) at 130 °C, after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(2-(4-methylpiperazin-1-yl)pyridin-4-yl)-1H-1,2,3-triazol-1-yl)methyl)phenyl)-1,3,4-oxadiazole (0.041 g, 56.7%) in a brown solid form.

$^1$H NMR (400 MHz, $CD_3OD$) δ 8.61 (s, 1H), 8.16 (d, J=5.3 Hz, 1H), 8.00-7.94 (m, 2H), 7.62 (t, J=7.7 Hz, 1H), 7.37-7.11 (m, 3H), 5.87 (s, 2H), 3.63 (t, J=5.0 Hz, 4H), 2.59 (t, J=5.1 Hz, 4H), 2.37 (s, 3H); LRMS (ES) m/z 471.3 ($M^+$+1).

The compounds of table 143 were synthesized according to substantially the same process as described above in the synthesis of compound 4633 with an exception of using 2-(difluoromethyl)-5-(3-fluoro-4-((4-(2-fluoropyridin-4-yl)-1H-1,2,3-triazol-1-yl)methyl)phenyl)-1,3,4-oxadiazole and the reactant of table 142.

TABLE 142

| Example | Compound No. | Reactant | Yield (%) |
|---|---|---|---|
| 475 | 4634 | 1-ethylpiperazine | 59 |
| 476 | 4635 | 1-isopropylpiperazine | 74 |
| 477 | 4636 | 1-(oxetan-3-yl)piperazine | 46 |

TABLE 143

| Example | Compound No. | Compound Name, $^1$H-NMR, MS (ESI) |
|---|---|---|
| 475 | 4634 | 2-(difluoromethyl)-5-(4-((4-(2-(4-ethylpiperazin-1-yl)pyridin-4-yl)-1H-1,2,3-triazol-1-yl)methyl)-3-fluorophenyl)-1,3,4-oxadiazole $^1$H NMR (400 MHz, $CD_3OD$) δ 8.61 (s, 1H), 8.15 (d, J = 5.3 Hz, 1H), 8.00-7.94 (m, 2H), 7.62 (t, J = 7.7 Hz, 1H), 7.37-7.11 (m, 3H), 5.86 (s, 2H), 3.63 (t, J = 5.1 Hz, 4H), 2.63 (t, J = 5.1 Hz, 4H), 2.52 (q, J = 7.2 Hz, 2H), 1.18 (t, J = 7.2 Hz, 3H); LRMS (ESI) m/z 485.2 ($M^+$ + H). |
| 476 | 4635 | 2-(difluoromethyl)-5-(3-fluoro-4-((4-(2-(4-isopropylpiperazin-1-yl)pyridin-4-yl)-1H-1,2,3-triazol-1-yl)methyl)phenyl)-1,3,4-oxadiazole $^1$H NMR (400 MHz, $CD_3OD$) δ 8.61 (s, 1H), 8.15 (d, J = 5.3 Hz, 1H), 8.00-7.94 (m, 2H), 7.62 (t, J = 7.7 Hz, 1H), 7.37-7.11 (m, 3H), 5.87 (s, 2H), 3.62 (t, J = 5.1 Hz, 4H), 2.79-2.70 (m, 5H), 1.15 (d, J = 6.5 Hz, 6H); LRMS (ESI) m/z 499.3 ($M^+$ + H). |
| 477 | 4636 | 2-(difluoromethyl)-5-(3-fluoro-4-((4-(2-(4-(oxetan-3-yl)piperazin-1-yl)pyridin-4-(yl)-1H-1,2,3-triazol-1-yl)methyl)phenyl)-1,3,4-oxadiazole $^1$H NMR (400 MHz, $CD_3OD$) δ 8.61 (s, 1H), 8.16 (d, J = 5.3 Hz, 1H), 8.01-7.95 (m, 2H), 7.62 (t, J = 7.7 Hz, 1H), 7.37-7.11 (m, 3H), 5.87 (s, 2H), 4.71 (dt, J = 28.6, 6.4 Hz, 4H), 3.65 (t, J = 5.1 Hz, 4H), 3.59-3.53 (m, 1H), 2.50 (t, J = 5.0 Hz, 4H); LRMS (ESI) m/z 513.3 ($M^+$ + H). |

Example 478: Synthesis of compound 4640, 2-(4-((4-(2-(4-cyclobutylpiperazin-1-yl)pyridin-4-yl)-1H-1,2,3-triazol-1-yl)methyl)-3-fluorophenyl)-5-(difluoromethyl)-1,3,4-oxadiazole

[Step 1] Synthesis of tert-butyl 4-(4-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate

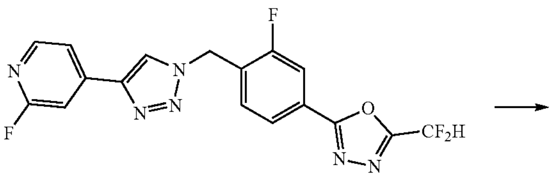

-continued

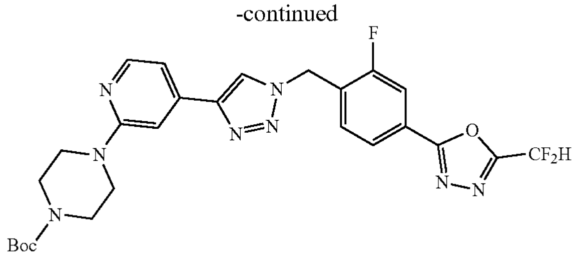

The 2-(difluoromethyl)-5-(3-fluoro-4-((4-(2-fluoropyridin-4-yl)-1H-1,2,3-triazol-1-yl)methyl)phenyl)-1,3,4-oxadiazole (0.200 g, 0.512 mmol) prepared in step 1 of example 474, tert-butyl piperazin-1-carboxylate (0.143 g, 0.769 mmol) and N,N-diisopropylethylamine (0.134 mL, 0.769 mmol) were dissolved in dimethyl sulfoxide (2 mL) at 130 °C, after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain tert-butyl 4-(4-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate (0.220 g, 77.1%) in a yellow solid form.

[Step 2] Synthesis of 2-(difluoromethyl)-5-(3-fluoro-4-((4-(2-(piperazin-1-yl)pyridin-4-yl)-1H-1,2,3-triazol-1-yl)methyl)phenyl)-1,3,4-oxadiazole

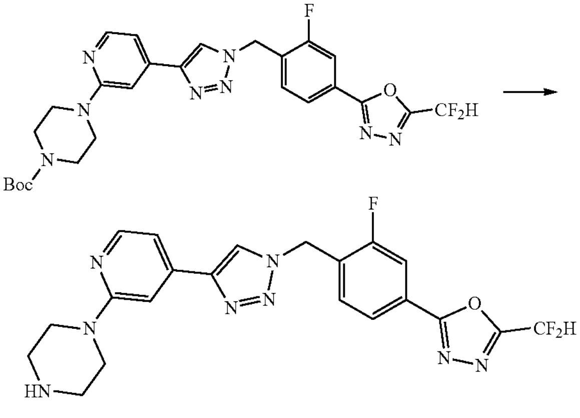

The tert-butyl 4-(4-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate (0.178 g, 0.320 mmol) prepared in step 1 and trifluoroacetic acid (0.245 mL, 3.198 mmol) were dissolved in dichloromethane (2 mL) at room temperature, after which the resulting solution was stirred at the same temperature for 18 hours. Solvent was removed from the reaction mixture under reduced pressure, after which the obtained product was used without an additional purification process (2-(difluoromethyl)-5-(3-fluoro-4-((4-

(2-(piperazin-1-yl)pyridin-4-yl)-1H-1,2,3-triazol-1-yl)methyl)phenyl)-1,3,4-oxadiazole, 0.140 g, 95.9%, brown oil).

[Step 3] Synthesis of Compound 4640

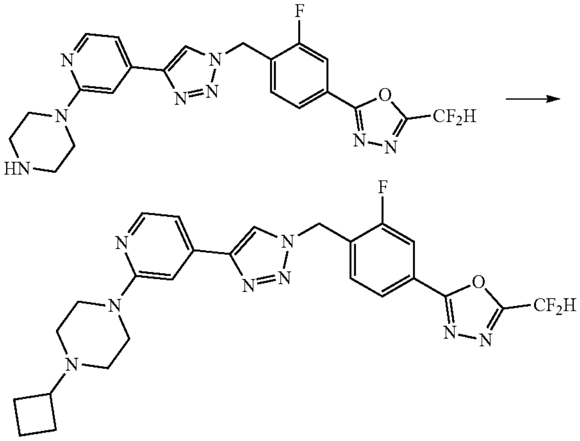

The 2-(difluoromethyl)-5-(3-fluoro-4-((4-(2-(piperazin-1-yl)pyridin-4-yl)-1H-1,2,3-triazol-1-yl)methyl)phenyl)-1,3,4-oxadiazole (0.070 g, 0.153 mmol) prepared in step 2 and cyclobutanone (0.023 mL, 0.307 mmol) were dissolved in dichloromethane (1 mL), after which the resulting solution was stirred at room temperature for 15 minutes, and then sodium triacetoxyborohydride (0.098 g, 0.460 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(4-((4-(2-(4-cyclobutylpiperazin-1-yl)pyridin-4-yl)-1H-1,2,3-triazol-1-yl)methyl)-3-fluorophenyl)-5-(difluoromethyl)-1,3,4-oxadiazole (0.046 g, 58.8%) in a white solid form.

$^1$H NMR (400 MHz, $CD_3OD$) δ 8.61 (s, 1H), 8.15 (d, J=5.3 Hz, 1H), 8.01-7.94 (m, 2H), 7.62 (t, J=7.7 Hz, 1H), 7.37-7.11 (m, 3H), 5.87 (s, 2H), 3.62 (t, J=5.1 Hz, 4H), 2.90-2.82 (m, 1H), 2.52 (t, J=5.1 Hz, 4H), 2.16-2.09 (m, 2H), 2.01-1.93 (m, 2H), 1.82-1.75 (m, 2H); LRMS (ES) m/z 511.4 ($M^+$+1).

Example 480: Synthesis of compound 16789, 2-(difluoromethyl)-5-(3-fluoro-4-((4-(6-(4-methylpiperazin-1-yl)pyridin-3-yl)-1H-1,2,3-triazol-1-yl)methyl)phenyl)-1,3,4-oxadiazole

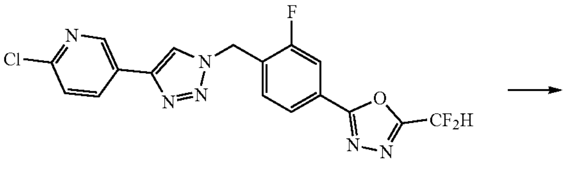

-continued

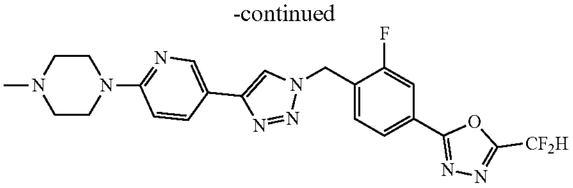

The 2-(4-((4-(6-chloropyridin-3-yl)-1H-1,2,3-triazol-1-yl)methyl)-3-fluorophenyl)-5-(difluoromethyl)-1,3,4-oxadiazole (0.100 g, 0.246 mmol) of compound 479, 1-methylpiperazine (0.041 mL, 0.369 mmol) and N,N-diisopropylethylamine (0.064 mL, 0.369 mmol) were dissolved in dimethyl sulfoxide (1 mL) at 130 °C, after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(3-fluoro-4-((4-(6-(4-methylpiperazin-1-yl)pyridin-3-yl)-1H-1,2,3-triazol-1-yl)methyl)phenyl)-1,3,4-oxadiazole (0.016 g, 13.8%) in a brown solid form.

$^1$H NMR (400 MHz, $CD_3OD$) δ 8.57 (d, J=2.0 Hz, 1H), 8.36 (s, 1H), 8.03-7.95 (m, 3H), 7.60 (t, J=7.7 Hz, 1H), 7.24 (t, J=51.6 Hz, 1H), 6.92 (d, J=9.0 Hz, 1H), 5.84 (s, 2H), 3.63 (t, J=5.0 Hz, 4H), 2.58 (t, J=5.0 Hz, 4H), 2.37 (s, 3H); LRMS (ES) m/z 471.3 ($M^+$+1).

Example 481: Synthesis of compound 16797, 2-(difluoromethyl)-5-(3-fluoro-4-((4-(2-fluoro-4-(piperazin-1-yl)phenyl)-1H-1,2,3-triazol-1-yl)methyl)phenyl)-1,3,4-oxadiazole

[Step 1] Synthesis of 2-(4-bromo-2-fluorophenyl)-1,3-dioxolane

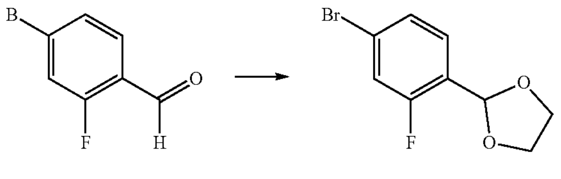

4-bromo-2-fluorobenzaldehyde (10.000 g, 49.259 mmol), p-toluenesulfonic acid (0.094 g, 0.493 mmol) and ethylene glycol (3.305 mL, 59.110 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%)

and concentrated to obtain 2-(4-bromo-2-fluorophenyl)-1,3-dioxolane (11.600 g, 95.3%) in a colorless oil form.

[Step 2] Synthesis of tert-butyl 4-(4-(1,3-dioxolan-2-yl)-3-fluorophenyl)piperazin-1-carboxylate

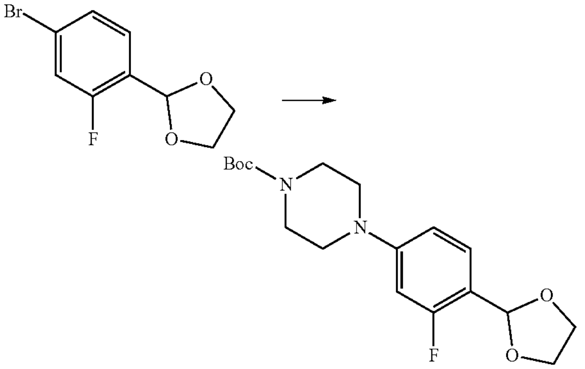

The 2-(4-bromo-2-fluorophenyl)-1,3-dioxolane (6.000 g, 24.286 mmol) prepared in step 1, tert-butyl piperazin-1-carboxylate (4.523 g, 24.286 mmol), tris(dibenzylidene acetone)dipalladium (Pd2(dba)3, 0.222 g, 0.243 mmol), rac-BINAP (0.302 g, 0.486 mmol) and sodium tert-butoxide (4.668 g, 48.571 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain tert-butyl 4-(4-(1,3-dioxolan-2-yl)-3-fluorophenyl)piperazin-1-carboxylate (6.400 g, 74.8%) in a brown solid form.

[Step 3] Synthesis of tert-butyl 4-(3-fluoro-4-formylphenyl)piperazin-1-carboxylate

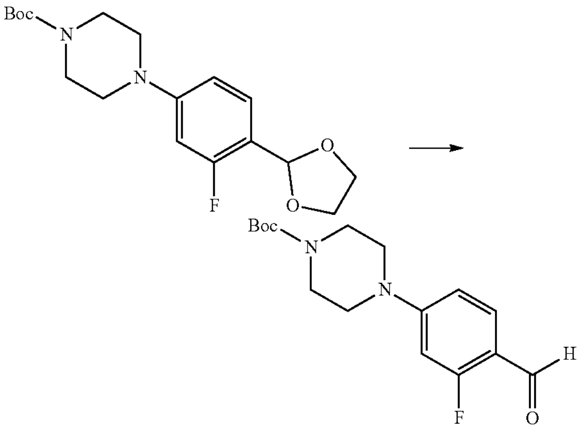

The tert-butyl 4-(4-(1,3-dioxolan-2-yl)-3-fluorophenyl)piperazin-1-carboxylate (6.400 g, 18.161 mmol) prepared in step 2 and hydrochloric acid (1.00 M solution, 54.482 mL, 54.482 mmol) were dissolved in methanol (25 mL) at room temperature, after which the resulting solution was stirred at the same temperature for 6 hours. Solvent was removed from the reaction mixture under reduced pressure, after which the obtained product was used without an additional purification process (tert-butyl 4-(3-fluoro-4-formylphenyl)piperazin-1-carboxylate, 4.200 g, 75.0%, brown solid).

[Step 4] Synthesis of tert-butyl 4-(4-(2,2-dibromovinyl)-3-fluorophenyl)piperazin-1-carboxylate

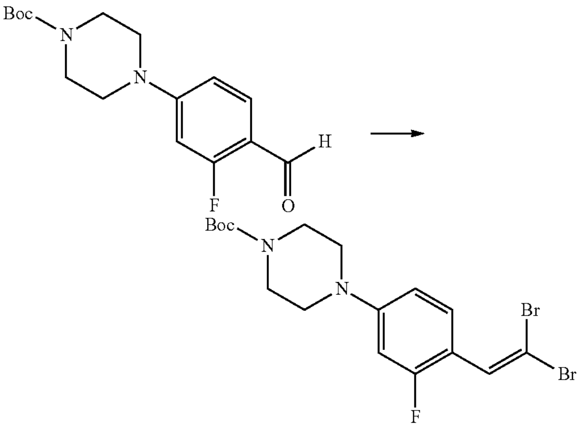

The tert-butyl 4-(3-fluoro-4-formylphenyl)piperazin-1-carboxylate (4.300 g, 13.945 mmol) prepared in step 3, carbon tetrabromide (9.249 g, 27.890 mmol) and triphenylphosphine triphenylphosphine (10.973 g, 41.836 mmol) were dissolved in dichloromethane (100 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 20%) and concentrated to obtain tert-butyl 4-(4-(2,2-dibromovinyl)-3-fluorophenyl)piperazin-1-carboxylate (4.300 g, 66.4%) in a yellow solid form.

[Step 5] Synthesis of tert-butyl 4-(4-ethynyl-3-fluorophenyl)piperazin-1-carboxylate

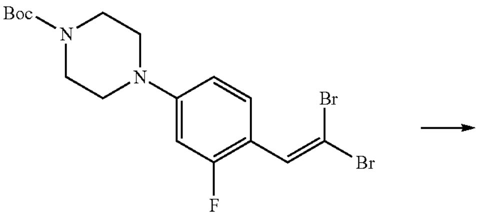

-continued

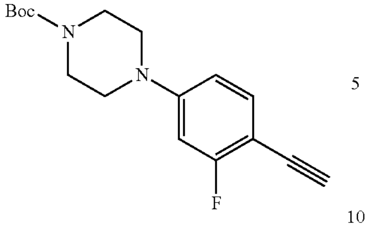

The tert-butyl 4-(4-(2,2-dibromovinyl)-3-fluorophenyl) piperazin-1-carboxylate (4.200 g, 9.048 mmol) prepared in step 4 and 2,3,4,6,7,8,9,10-octahydropyrimido[1,2-a] azepine (DBU, 4.060 mL, 27.145 mmol) were dissolved in acetonitrile (100 mL) at room temperature, after which the resulting solution was stirred at the same temperature for 12 hours. Solvent was removed from the reaction mixture under reduced pressure, after which saturated ammonium chloride aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 20%) and concentrated to obtain tert-butyl 4-(4-ethynyl-3-fluorophenyl)piperazin-1-carboxylate (1.400 g, 50.8%) in a yellow solid form.

[Step 6] Synthesis of tert-butyl 4-(4-(1-(4-(5-(difluoromethyl)-1,3,4-oxadiazol-2-yl)-2-fluorobenzyl)-1H-1,2,3-triazol-4-yl)-3-fluorophenyl)piperazin-1-carboxylate

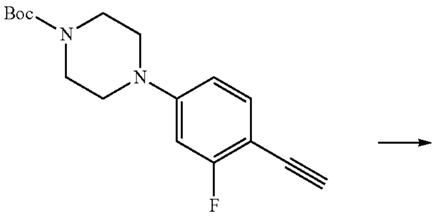

-continued

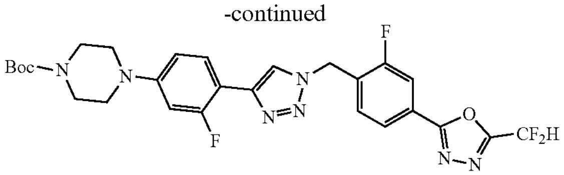

The tert-butyl 4-(4-ethynyl-3-fluorophenyl)piperazin-1-carboxylate (0.710 g, 2.333 mmol) prepared in step 5, 2-(4-(azidomethyl)phenyl)-5-(difluoromethyl)-1,3,4-oxadiazole (0.645 g, 2.566 mmol) prepared in step 1 of example 2, copper(II) sulfate pentahydrate (0.006 g, 0.023 mmol) and sodium ascorbate (0.046 g, 0.233 mmol) were dissolved in tert-butanol (10 mL)/water (10 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(4-(1-(4-(5-(difluoromethyl)-1,3,4-oxadiazol-2-yl)-2-fluorobenzyl)-1H-1,2,3-triazol-4-yl)-3-fluorophenyl)piperazin-1-carboxylate (0.300 g, 23.1%) in a yellow solid form.

[Step 7] Synthesis of Compound 16797

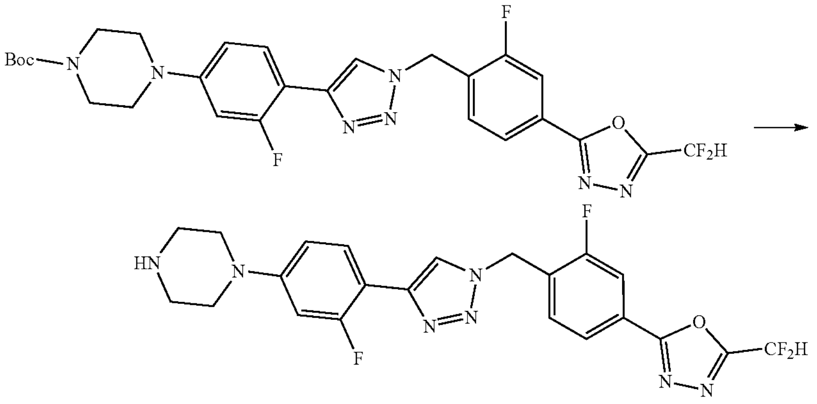

The tert-butyl 4-(4-(1-(4-(5-(difluoromethyl)-1,3,4-oxadiazol-2-yl)-2-fluorobenzyl)-1H-1,2,3-triazol-4-yl)-3-fluorophenyl)piperazin-1-carboxylate (1.000 g, 1.744 mmol) prepared in step 6 and trifluoroacetic acid (1.335 mL, 17.435 mmol) were dissolved in dichloromethane (100 mL) at room temperature, after which the resulting solution was stirred at the same temperature for 12 hours. Saturated ammonium chloride aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. Then, the obtained product was used without an additional purification process (2-(difluoromethyl)-5-(3-fluoro-4-((4-(2-fluoro-4-(piperazin-1-yl)phenyl)-1H-1,2,3-triazol-1-yl)methyl)phenyl)-1,3,4-oxadiazole, 0.660 g, 80.0%, yellow solid).

$^1H$ NMR (400 MHz, $CDCl_3$) δ 8.10 (t, J=8.8 Hz, 1H), 7.88-7.86 (m, 3H), 7.38 (t, J=7.7 Hz, 1H), 7.04-6.75 (m,

2H), 6.60 (d, J=16.4 Hz, 1H), 5.70 (s, 2H), 3.25 (t, J=4.9 Hz, 4H), 2.57 (t, J=4.8 Hz, 4H); LRMS (ES) m/z 473.4 ($M^{+}$+1).

Example 484: Synthesis of compound 17058, 2-(4-((4-(5-(1H-pyrazol-4-yl)pyridin-3-yl)-1H-1,2,3-triazol-1-yl)methyl)-3-fluorophenyl)-5-(difluoromethyl)-1,3,4-oxadiazole

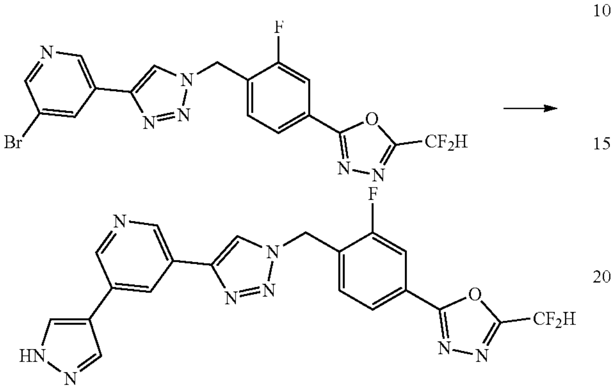

The 2-(4-((4-(5-(1H-pyrazol-4-yl)pyridin-3-yl)-1H-1,2,3-triazol-1-yl)methyl)-3-fluorophenyl)-5-(difluoromethyl)-1,3,4-oxadiazole (0.080 g, 0.177 mmol) of compound 183, (1H-pyrazol-4-yl)boronic acid (0.040 g, 0.355 mmol), [1,1'-bis(di-tert-butylphosphino)ferrocene]palladium(II) dichloride(Pd(dtbpf)$Cl_2$, 0.012 g, 0.018 mmol) and cesium carbonate (0.103 g, 0.532 mmol) were mixed in 1,4-dioxane (3 mL)/water (1 mL) at room temperature, after which the resulting mixture was irradiated with microwaves, then heated at 100 °C for 10 minutes, and then a reaction was finished by lowering a temperature to room temperature. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(4-((4-(5-(1H-pyrazol-4-yl)pyridin-3-yl)-1H-1,2,3-triazol-1-yl)methyl)-3-fluorophenyl)-5-(difluoromethyl)-1,3,4-oxadiazole (0.009 g, 11.6%) in a brown solid form.

$^{1}$H NMR (400 MHz, $CD_3OD$) δ 8.88 (d, J=2.0 Hz, 1H), 8.80 (d, J=2.0 Hz, 1H), 8.66 (s, 1H), 8.50 (t, J=2.0 Hz, 1H), 8.22-8.13 (m, 2H), 8.02-7.96 (m, 2H), 7.65 (t, J=7.7 Hz, 1H), 7.24 (t, J=51.6 Hz, 1H), 5.90 (s, 2H); LRMS (ES) m/z 439.1 ($M^{+}$+1).

Example 487: Synthesis of compound 17255, 4-((5-(1-(4-(5-(difluoromethyl)-1,3,4-oxadiazol-2-yl)benzyl)-1H-1,2,3-triazol-4-yl)-1H-indol-3-yl)methyl) morpholine

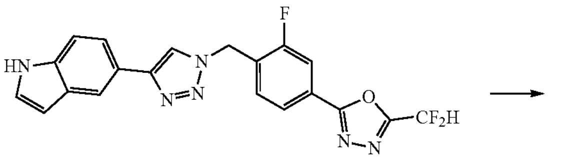

-continued

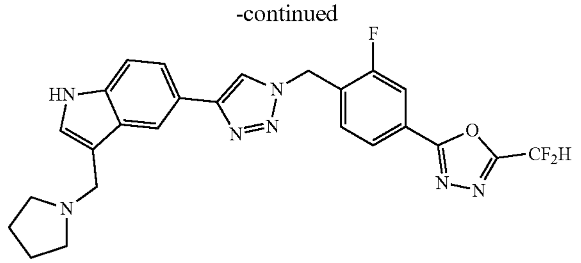

Pyrrolidine (0.020 g, 0.281 mmol) and formaldehyde (37.00%, 0.025 g, 0.309 mmol) were dissolved in acetic acid (0.5 mL)/methanol (0.5 mL), after which the resulting solution was stirred at 0 °C for 0.4 hours, and then 2-(4-((4-(1H-indol-5-yl)-1H-1,2,3-triazol-1-yl)methyl)-3-fluorophenyl)-5-(difluoromethyl)-1,3,4-oxadiazole (0.069 g, 0.169 mmol) prepared in example 172 was added thereto and further stirred at room temperature for 18 hours. 2N-potassium hydroxide aqueous solution was poured into the resulting reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 50%) and concentrated to obtain 2-(difluoromethyl)-5-(3-fluoro-4-((4-(3-(pyrrolidin-1-ylmethyl)-1H-indol-5-yl)-1H-1,2,3-triazol-1-yl)methyl)phenyl)-1,3,4-oxadiazole (0.035 g, 25.2%) in a light brown solid form.

$^{1}$H NMR (400 MHz, $CD_3OD$) δ 8.41 (s, 1H), 8.27-8.20 (m, 1H), 8.21-8.15 (m, 3H), 7.70-7.61 (m, 4H), 7.54 (dd, J=8.6, 0.7 Hz, 1H), 7.24 (t, J=51.6 Hz, 1H), 5.81 (d, J=8.1 Hz, 2H), 4.61 (s, 2H), 4.12-3.97 (m, 2H), 3.80-3.60 (m, 4H), 3.54-3.40 (m, 2H); LRMS (ES) m/z 492.2 ($M^{+}$+1).

Example 490: Synthesis of compound 17347, 2-(difluoromethyl)-5-(5-fluoro-6-((4-phenyl-1H-1,2,3-triazol-1-yl)methyl)pyridin-3-yl)-1,3,4-oxadiazole

[Step 1] Synthesis of 2-(6-(azidomethyl)-5-fluoropyridin-3-yl)-5-(difluoromethyl)-1,3,4-oxadiazole

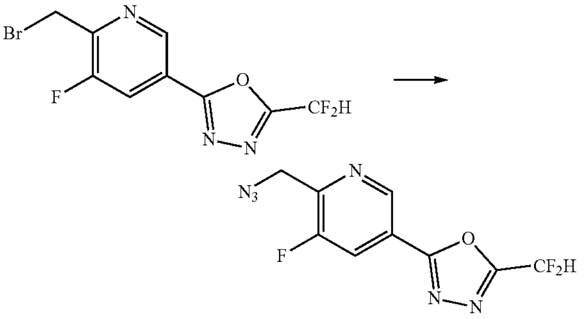

2-(6-(bromomethyl)-5-fluoropyridin-3-yl)-5-(difluoromethyl)-1,3,4-oxadiazole (0.200 g, 0.649 mmol) was dissolved in acetone (4 mL)/water (2 mL) at 0 °C, after which sodium azide (0.042 g, 0.649 mmol) was added to the resulting solution and stirred at room temperature for 3 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 30%) and concentrated to obtain 2-(6-(azidomethyl)-5-fluoropyridin-3-yl)-5-(difluoromethyl)-1,3,4-oxadiazole (0.040 g, 22.8%) in a white solid form.

[Step 2] Synthesis of Compound 17347

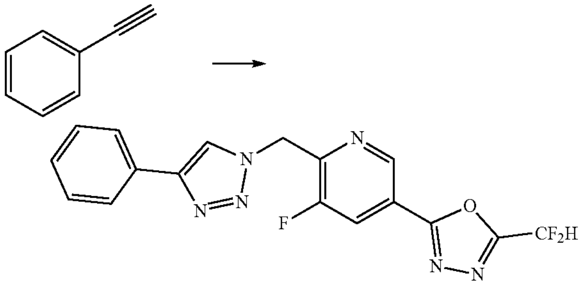

Ethynylbenzene (0.016 mL, 0.147 mmol), 2-(6-(azidomethyl)-5-fluoropyridin-3-yl)-5-(difluoromethyl)-1,3,4-oxadiazole (0.040 g, 0.147 mmol) prepared in step 1, sodium ascorbate (0.50 M solution in water, 0.029 mL, 0.015 mmol) and copper(II) sulfate pentahydrate (1.00 M solution in water, 0.001 mL, 0.001 mmol) were dissolved in tert-butanol (0.5 mL)/water (0.5 mL) at room temperature, after which the resulting solution was stirred at the same temperature for 2 hours. N-ammonium chloride carbonate aqueous solution was poured into the resulting reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (3 mL) and hexane (50 mL) were added to the resulting concentrate and stirred to filter out a precipitated solid, washed with hexane, and dried to obtain 2-(difluoromethyl)-5-(5-fluoro-6-((4-phenyl-1H-1,2,3-triazol-1-yl)methyl)pyridin-3-yl)-1,3,4-oxadiazole (0.012 g, 21.9%) in a yellow oil form.

$^1H$ NMR (400 MHz, DMSO-$d_6$) δ 9.05 (s, 1H), 8.69 (s, 1H), 8.50 (dd, J=9.8, 1.6 Hz, 1H), 7.87 (d, J=7.3 Hz, 2H), 7.72-7.44 (m, 3H), 7.35 (t, J=7.4 Hz, 1H), 6.00 (d, J=1.4 Hz, 2H); LRMS (ES) m/z 373.2 ($M^+$+1).

The compounds of table 145 were synthesized according to substantially the same process as described in the synthesis of compounds 3657, 3658, 3736 and 17347 by using azide compound 1-2 and acetylene compound 2-3 in table 144 for reactants and using a click reaction thereof.

TABLE 144

| Example | Compound No. | Reactant (acetylene) | Reactant (azide) | Yield (%) |
|---|---|---|---|---|
| 3 | 3659 | 3-ethynylbenzoic acid | 2-(4-(azidomethyl)phenyl)-5-(difluoromethyl)-1,3,4-oxadiazole | 47 |
| 4 | 3660 | 3-ethynylbenzoic acid | 2-(4-(azidomethyl)-3-fluorophenyl)-5-(difluoromethyl)-1,3,4-oxadiazole | 56 |
| 5 | 3661 | 4-ethynyl-1,2-difluorobenzene | 2-(4-(azidomethyl)phenyl)-5-(difluoromethyl)-1,3,4-oxadiazole | 56 |
| 6 | 3662 | 4-ethynyl-1,2-difluorobenzene | 2-(4-(azidomethyl)-3-fluorophenyl)-5-(difluoromethyl)-1,3,4-oxadiazole | 62 |
| 7 | 3695 | 1-ethynyl-3,5-bis(trifluoromethyl)benzene | (difluoromethyl)-1,3,4-oxadiazole 2-(4-(azidomethyl)phenyl)-5- | 51 |
| 8 | 3696 | 1-ethynyl-3,5-bis(trifluoromethyl)benzene | 2-(4-(azidomethyl)-3-fluorophenyl)-5-(difluoromethyl)-1,3,4-oxadiazole | 53 |
| 9 | 3697 | Tert-butyl(3-ethynylphenyl)carbamate | 2-(4-(azidomethyl)phenyl)-5-(difluoromethyl)-1,3,4-oxadiazole | 38 |
| 10 | 3698 | Tert-butyl(3-ethynylphenyl)carbamate | 2-(4-(azidomethyl)-3-fluorophenyl)-5-(difluoromethyl)-1,3,4-oxadiazole | 50 |
| 11 | 3731 | 4-ethynylbenzoic acid | 2-(4-(azidomethyl)phenyl)-5-(difluoromethyl)-1,3,4-oxadiazole | 56 |
| 12 | 3732 | 4-ethynylbenzoic acid | 2-(4-(azidomethyl)-3-fluorophenyl)-5-(difluoromethyl)-1,3,4-oxadiazole | 68 |
| 13 | 3733 | 1-ethynyl-4-methylbenzene | 2-(4-(azidomethyl)-3-fluorophenyl)-5-(difluoromethyl)-1,3,4-oxadiazole | 58 |
| 14 | 3734 | Tert-butyl-3-ethy nylpyrrolidin-1-carboxylate | 2-(4-(azidomethyl)-3-fluorophenyl)-5-(difluoromethyl)-1,3,4-oxadiazole | 53 |
| 15 | 3735 | Tert-butyl-4-ethynylpiperidin-1-carboxylate | 2-(4-(azidomethyl)-3-fluorophenyl)-5-(difluoromethyl)-1,3,4-oxadiazole | 61 |
| 17 | 3737 | 4-ethynyl-1,2-difluorobenzene | 2-(6-(azidomethyl)pyridin-3-yl)-5-(difluoromethyl)-1,3,4-oxadiazole | 54 |
| 18 | 3738 | 1-ethynyl-4-methylbenzene | 2-(6-(azidomethyl)pyridin-3-yl)-5-(difluoromethyl)-1,3,4-oxadiazole | |
| 19 | 3739 | 3-ethynylbenzoic acid | 2-(6-(azidomethyl)pyridin-3-yl)-5-(difluoromethyl)-1,3,4-oxadiazole | 71 |
| 20 | 3741 | Tert-butyl (3-ethynylphenyl)carbamate | 2-(6-(azidomethyl)pyridin-3-yl)-5-(difluoromethyl)-1,3,4-oxadiazole | 80 |
| 34 | 3820 | Tert-butyl 3-ethynylpyrrolidin-1-carboxylate | 2-(6-(azidomethyl)pyridin-3-yl)-5-(difluoromethyl)-1,3,4-oxadiazole | 52 |
| 35 | 3822 | 2-(but-3-yne-1-yl)imidazo[1,2-a]pyridine | 2-(6-(azidomethyl)pyridin-3-yl)-5-(difluoromethyl)-1,3,4-oxadiazole | 66 |
| 43 | 3831 | Pent-1-yne | 2-(6-(azidomethyl)pyridin-3-yl)-5-(difluoromethyl)-1,3,4-oxadiazole | 56 |

TABLE 144-continued

| Example | Compound No. | Reactant (acetylene) | Reactant (azide) | Yield (%) |
|---|---|---|---|---|
| 44 | 3832 | Hex-1-yne | 2-(6-(azidomethyl)pyridin-3-yl)-5-(difluoromethyl)-1,3,4-oxadiazole | 62 |
| 45 | 3833 | Pent-1-yne-1-o1 | 2-(6-(azidomethyl)pyridin-3-yl)-5-(difluoromethyl)-1,3,4-oxadiazole | 73 |
| 46 | 3834 | Hex-5-yne-1-01 | 2-(6-(azidomethyl)pyridin-3-yl)-5-(difluoromethyl)-1,3,4-oxadiazole | 56 |
| 57 | 3846 | Ethynylcyclopentane | 2-(6-(azidomethyl)pyridin-3-yl)-5-(difluoromethyl)-1,3,4-oxadiazole | 47 |
| 58 | 3853 | 1-ethynyl-2-fluorobenzene | 2-(6-(azidomethyl)pyridin-3-yl)-5-(difluoromethyl)-1,3,4-oxadiazole | 27 |
| 59 | 3854 | 1-ethynyl-3-fluorobenzene | 2-(6-(azidomethyl)pyridin-3-yl)-5-(difluoromethyl)-1,3,4-oxadiazole | 50 |
| 60 | 3855 | 1-ethynyl-4-fluorobenzene | 2-(6-(azidomethyl)pyridin-3-yl)-5-(difluoromethyl)-1,3,4-oxadiazole | 73 |
| 61 | 3856 | 1-ethynyl-3-methylbenzene | 2-(6-(azidomethyl)pyridin-3-yl)-5-(difluoromethyl)-1,3,4-oxadiazole | 22 |
| 62 | 3860 | 1-ethynyl-2-methylbenzene | 2-(6-(azidomethyl)pyridin-3-yl)-5-(difluoromethyl)-1,3,4-oxadiazole | 69 |
| 63 | 3861 | 2-ethynylfuran | 2-(6-(azidomethyl)pyridin-3-yl)-5-(difluoromethyl)-1,3,4-oxadiazole | 70 |
| 66 | 3879 | 1-ethynylcyclohex-1-ene | 2-(6-(azidomethyl)pyridin-3-yl)-5-(difluoromethyl)-1,3,4-oxadiazole | 63 |
| 67 | 3880 | Ethynylcyclohexane | 2-(6-(azidomethyl)pyridin-3-yl)-5-(difluoromethyl)-1,3,4-oxadiazole | 68 |
| 83 | 3902 | 2-ethynylthiophene | 2-(6-(azidomethyl)pyridin-3-yl)-5-(difluoromethyl)-1,3,4-oxadiazole | 39 |
| 91 | 3926 | Tert-butyl 3-ethynylazetidin-1-carboxylate | 2-(6-(azidomethyl)pyridin-3-yl)-5-(difluoromethyl)-1,3,4-oxadiazole | 85 |
| 105 | 3960 | 5-ethynylpyrimidine | 2-(6-(azidomethyl)pyridin-3-yl)-5-(difluoromethyl)-1,3,4-oxadiazole | 84 |
| 106 | 3961 | Tert-butyl 3-ethynylpiperidin-1-carboxylate | 2-(6-(azidomethyl)pyridin-3-yl)-5-(difluoromethyl)-1,3,4-oxadiazole | 60 |
| 114 | 3985 | 4-ethynyl-1H-pyrazole | 2-(6-(azidomethyl)pyridin-3-yl)-5-(difluoromethyl)-1,3,4-oxadiazole | 8 |
| 121 | 3999 | Tert-butyl 4-ethynyl-4-fluoropiperidin-1-carboxylate | 2-(6-(azidomethyl)pyridin-3-yl)-5-(difluoromethyl)-1,3,4-oxadiazole | 85 |
| 122 | 4000 | Tert-butyl 4-(prop-2-yne-1-yl)piperidin-1-carboxylate | 2-(6-(azidomethyl)pyridin-3-yl)-5-(difluoromethyl)-1,3,4-oxadiazole | 92 |
| 197 | 4276 | 3-ethynyloxetan-3-o1 | 2-(6-(azidomethyl)pyridin-3-yl)-5-(difluoromethyl)-1,3,4-oxadiazole | 87 |
| 198 | 4277 | 3-ethynyltetrahydrofuran-3-ol | 2-(6-(azidomethyl)pyridin-3-yl)-5-(difluoromethyl)-1,3,4-oxadiazole | 81 |
| 199 | 4278 | 3-ethynyloxetan-3-ol | 2-(4-(azidomethyl)-3-fluorophenyl)-5-(difluoromethyl)-1,3,4-oxadiazole | 89 |
| 200 | 4279 | 3-ethynyltetrahydrofuran-3-ol | 2-(4-(azidomethyl)-3-fluorophenyl)-5-(difluoromethyl)-1,3,4-oxadiazole | 90 |
| 238 | 4336 | 1-(3-ethynylphenyl)-4-methylpiperazine | 2-(4-(azidomethyl)phenyl)-5-(difluoromethyl)-1,3,4-oxadiazole | 55 |
| 239 | 4337 | 1-(3-ethynylphenyl)-4-methylpiperazine | 2-(4-(azidomethyl)-3-fluorophenyl)-5-(difluoromethyl)-1,3,4-oxadiazole | 55 |
| 240 | 4338 | 4-(3-ethynylphenyl)morpholine | 2-(4-(azidomethyl)phenyl)-5-(difluoromethyl)-1,3,4-oxadiazole | 51 |
| 241 | 4339 | 4-(3-ethynylphenyl)morpholine | 2-(4-(azidomethyl)-3-fluorophenyl)-5-(difluoromethyl)-1,3,4-oxadiazole | 61 |
| 242 | 4340 | 6-ethynyl-1H-indazole | 2-(6-(azidomethyl)pyridin-3-yl)-5-(difluoromethyl)-1,3,4-oxadiazole | 58 |
| 243 | 4341 | 6-ethynyl-1H-indazole | 2-(6-(azidomethyl)phenyl)-5-(difluoromethyl)-1,3,4-oxadiazole | 60 |
| 244 | 4342 | 6-ethynyl-1H-indazole | 2-(4-(azidomethyl)-3-fluorophenyl)-5-(difluoromethyl)-1,3,4-oxadiazole | 55 |
| 245 | 4343 | 5-ethynyl-1H-indazole | 2-(6-(azidomethyl)pyridin-3-yl)-5-(difluoromethyl)-1,3,4-oxadiazole | 55 |
| 246 | 4344 | 5-ethynyl-1H-indazole | 2-(6-(azidomethyl)phenyl)-5-(difluoromethyl)-1,3,4-oxadiazole | 56 |
| 247 | 4345 | 5-ethynyl-1H-indazole | 2-(4-(azidomethyl)-3-fluorophenyl)-5-(difluoromethyl)-1,3,4-oxadiazole | 59 |
| 248 | 4346 | 4-ethynyl-1H-indazole | 2-(6-(azidomethyl)pyridin-3-yl)-5-(difluoromethyl)-1,3,4-oxadiazole | 60 |
| 249 | 4347 | 4-ethynyl-1H-indazole | 2-(6-(azidomethyl)phenyl)-5-(difluoromethyl)-1,3,4-oxadiazole | 54 |
| 250 | 4348 | 4-ethynyl-1H-indazole | 2-(4-(azidomethyl)-3-fluorophenyl)-5-(difluoromethyl)-1,3,4-oxadiazole | 59 |
| 395 | 4524 | 5-ethynyl-1H-pyrrolo[2,3-b]pyridine | 2-(4-(azidomethyl)-3-fluorophenyl)-5-(difluoromethyl)-1,3,4-oxadiazole | 49 |

TABLE 144-continued

| Example | Compound No. | Reactant (acetylene) | Reactant (azide) | Yield (%) |
|---|---|---|---|---|
| 396 | 4525 | 5-ethynyl-1H-pyrrolo[2,3-b]pyridine | 2-(4-(azidomethyl)phenyl)-5-(difluoromethyl)-1,3,4-oxadiazole | 43 |
| 397 | 4526 | 4-ethynyl-1H-pyrrolo[2,3-b]pyridine | 2-(4-(azidomethyl)-3-fluorophenyl)-5-(difluoromethyl)-1,3,4-oxadiazole | 51 |
| 398 | 4527 | 4-ethynyl-1H-pyrrolo[2,3-b]pyridine | 2-(4-(azidomethyl)phenyl)-5-(difluoromethyl)-1,3,4-oxadiazole | 54 |
| 479 | 16781 | 2-chloro-5-ethynylpyridine | 2-(4-(azidomethyl)-3-fluorophenyl)-5-(difluoromethyl)-1,3,4-oxadiazole | 79 |
| 482 | 16928 | 5-bromo-2-ethynylpyridine | 2-(4-(azidomethyl)-3-fluorophenyl)-5-(difluoromethyl)-1,3,4-oxadiazole | 56 |
| 483 | 16930 | 3-bromo-5-ethynylpyridine | 2-(4-(azidomethyl)-3-fluorophenyl)-5-(difluoromethyl)-1,3,4-oxadiazole | 89 |
| 488 | 17261 | 4-ethynyl-1H-pyrazole | 2-(4-(azidomethyl)-3-fluorophenyl)-5-(difluoromethyl)-1,3,4-oxadiazole | 3 |
| 521 | 17983 | 2-ethynylpyridine | 2-(6-(azidomethyl)-5-fluoropyridin-3-yl)-5-(difluoromethyl)-1,3,4-oxadiazole | 57 |
| 522 | 17984 | 2-ethynylthiophene | 2-(6-(azidomethyl)-5-fluoropyridin-3-yl)-5-(difluoromethyl)-1,3,4-oxadiazole | 50 |
| 534 | 18256 | 2-ethynylpyridine | 2-(4-(azidomethyl)-3-fluorophenyl)-5-(difluoromethyl)-1,3,4-oxadiazole | 71 |
| 535 | 18258 | 2-ethynylthiophene | 2-(4-(azidomethyl)-3-fluorophenyl)-5-(difluoromethyl)-1,3,4-oxadiazole | 41 |
| 547 | 18470 | 4-ethynyl-2,2-difluorobenzo[d][1,3]dioxol | 5-(difluoromethyl)-1,3,4-oxadiazole 2-(4-(azidomethyl)-3-fluorophenyl)- | 56 |
| 557 | 18868 | Tert-butyl 4-(3-ethynylphenyl)piperidin-1-carboxylate | 2-(6-(azidomethyl)-5-fluoropyridin-3-yl)-5-(difluoromethyl)-1,3,4-oxadiazole | 82 |
| 566 | 18918 | 6-ethynyl-1H-indole | 2-(6-(azidomethyl)-5-fluoropyridin-3-yl)-5-(difluoromethyl)-1,3,4-oxadiazole | 30 |
| 567 | 18919 | 6-ethynyl-1H-indazole | 2-(6-(azidomethyl)-5-fluoropyridin-3-yl)-5-(difluoromethyl)-1,3,4-oxadiazole | 31 |
| 568 | 18920 | 5-ethynyl-1H-indazole | 2-(6-(azidomethyl)-5-fluoropyridin-3-yl)-5-(difluoromethyl)-1,3,4-oxadiazole 2-(6-(azidomethyl)-5-fluoropyridin-3-yl)-5-(difluoromethyl)-1,3,4-oxadiazole | 32 |
| 569 | 18921 | 4-ethynyl-1H-indole | 2-(6-(azidomethyl)-5-fluoropyridin-3-yl)-5-(difluoromethyl)-1,3,4-oxadiazole | 33 |
| 579 | 19058 | 4-ethynyl-1H-indazole | 2-(6-(azidomethyl)-5-fluoropyridin-3-yl)-5-(difluoromethyl)-1,3,4-oxadiazole | 31 |

TABLE 145

| Example | Compound No. | Compound Name, $^1$H-NMR, MS (ESI) |
|---|---|---|
| 3 | 3659 | 3-(1-(4-(5-(difluoromethyl)-1,3,4-oxadiazol-2-yl)benzyl)-1H-1,2,3-triazol-4-yl)benzoic acid<br>$^1$H NMR (400 MHz, $CD_3OD$) δ 8.54 (s, 1H), 8.51 (t, J = 1.8 Hz, 1H), 8.20-8.14 (m, 2H), 8.12-8.06 (m, 1H), 8.03 (dt, J = 7.9, 1.3 Hz, 1H), 7.63 (d, J = 8.3 Hz, 2H), 7.58 (t, J = 7.7 Hz, 1H), 7.23 (t, J = 51.6 Hz, 1H), 5.82 (s, 2H); LRMS (ES) m/z 398.3 ($M^+$ + 1). |
| 4 | 3660 | 3-(1-(4-(5-(difluoromethyl)-1,3,4-oxadiazol-2-yl)-2-fluorobenzyl)-1H-1,2,3-triazol-4-yl)benzoic acid<br>$^1$H NMR (400 MHz, $CD_3OD$) δ 8.55 (s, 1H), 8.52 (t, J = 1.7 Hz, 1H), 8.09 (ddd, J = 7.8, 1.9, 1.2 Hz, 1H), 8.03 (dt, J = 7.8, 1.4 Hz, 1H), 8.00 (dd, J = 7.9, 1.7 Hz, 1H), 7.96 (dd, J = 10.1, 1.6 Hz, 1H), 7.60 (dt, J = 15.7, 7.6 Hz, 2H), 7.24 (t, J = 51.6 Hz, 1H), 5.87 (s, 2H); LRMS (ES) m/z 416.2 ($M^+$ + 1). |
| 5 | 3661 | 2-(difluoromethyl)-5-(4-((4-(3,4-difluorophenyl)-1H-1,2,3-triazol-1-yl)methyl)phenyl)-1,3,4-oxadiazole<br>$^1$H NMR (700 MHz, $CD_3OD$) δ 8.47 (s, 1H), 8.19-8.15 (m, 2H), 7.78 (ddd, J = 11.7, 7.6, 2.1 Hz, 1H), 7.66 (dddd, J = 8.6, 3.8, 2.2, 1.4 Hz, 1H), 7.64-7.59 (m, 2H), 7.36 (dt, J = 10.5, 8.5 Hz, 2H), 7.24 (t, J = 51.6 Hz, 1H), 5.80 (s, 2H); LRMS (ES) m/z 390.3 ($M^+$ + 1). |
| 6 | 3662 | 2-(difluoromethyl)-5-(4-((4-(3,4-difluorophenyl)-1H-1,2,3-triazol-1-yl)methyl)-3-fluorophenyl)-1,3,4-oxadiazole<br>$^1$H NMR (700 MHz, $CD_3OD$) δ 8.48 (s, 1H), 8.00 (dd, J = 8.0, 1.7 Hz, 1H), 7.96 (dd, J = 10.1, 1.6 Hz, 1H), 7.78 (ddd, J = 11.6, 7.6, 2.1 Hz, 1H), 7.67 (dddd, J = |

TABLE 145-continued

| Example | Compound No. | Compound Name, $^1$H-NMR, MS (ESI) |
| --- | --- | --- |
| | | 8.6, 4.2, 2.2, 1.4 Hz, 1H), 7.61 (t, J = 7.7 Hz, 1H), 7.36 (dt, J = 10.5, 8.5 Hz, 1H), 7.25 (t, J = 51.6 Hz, 1H), 5.85 (s, 2H); LRMS (ES) m/z 408.2 ($M^+$ + 1). |
| 7 | 3695 | 2-(4-((4-(3,5-bis(trifluoromethyl)phenyl)-1H-1,2,3-triazol-1-yl)methyl)phenyl)-5-(difluoromethyl)-1,3,4-oxadiazole<br>$^1$H NMR (400 MHz, $CDCl_3$) δ 8.30 (s, 2H), 8.20 (d, J = 8.2 Hz, 2H), 7.92 (s, 1H), 7.86 (s, 1H), 7.53 (d, J = 8.2 Hz, 2H), 6.94 (s, 1H), 5.75 (s, 2H); LRMS (ES) m/z 489.9 ($M^+$ + 1). |
| 8 | 3696 | 2-(4-((4-(3,5-bis(trifluoromethyl)phenyl)-1H-1,2,3-triazol-1-yl)methyl)-3-fluorophenyl)-5-(difluoromethyl)-1,3,4-oxadiazole<br>$^1$H NMR (400 MHz, $CDCl_3$) δ 8.33-8.28 (m, 2H), 8.03-7.93 (m, 4H), 7.86 (s, 1H), 7.55 (t, J = 7.7 Hz, 1H), 6.95 (t, J = 51.7 Hz, 1H), 5.79 (s, 2H); LRMS (ES) m/z 508.2 ($M^+$ + 1). |
| 9 | 3697 | Tert-butyl (3-(1-(4-(5-(difluoromethyl)-1,3,4-oxadiazol-2-yl)-2-fluorobenzyl)-1H-1,2,3-triazol-4-yl)phenyl)carbamate<br>$^1$H NMR (400 MHz, $CDCl_3$) δ 8.23 (s, 1H), 8.18 (d, J = 8.0 Hz, 2H), 8.06 (s, 1H), 7.50 (d, J = 8.1 Hz, 2H), 7.38 (d, J = 8.7 Hz, 1H), 6.94 (t, J = 51.7 Hz, 1H), 6.61 (s, 1H), 5.73 (s, 2H), 1.55 (s, 9H); LRMS (ES) m/z 487.0 ($M^+$ + 1). |
| 10 | 3698 | Tert-butyl (3-(1-(4-(5-(difluoromethyl)-1,3,4-oxadiazol-2-yl)benzyl)-1H-1,2,3-triazol-4-yl)phenyl)carbamate<br>$^1$H NMR (400 MHz, $CDCl_3$) δ 8.31 (s, 1H), 8.05 (d, J = 2.5 Hz, 1H), 7.98-7.90 (m, 5H), 7.51-7.43 (m, 2H), 7.39 (d, J = 8.7 Hz, 1H), 6.94 (t, J = 51.7 Hz, 1H), 6.60 (s, 1H), 5.77 (s, 2H), 1.55 (s, 9H); LRMS (ES) m/z 467.2 ($M^+$ + 1). |
| 11 | 3731 | 4-(1-(4-(5-(difluoromethyl)-1,3,4-oxadiazol-2-yl)benzyl)-1H-1,2,3-triazol-4-yl)benzoic acid<br>$^1$H NMR (400 MHz, $CDCl_3$) δ 8.15-8.04 (m, 4H), 7.90 (s, 1H), 7.85 (d, J = 8.4 Hz, 2H), 7.48 (d, J = 8.2 Hz, 2H), 6.92 (t, J = 51.7 Hz, 1H), 5.68 (s, 2H); LRMS (ES) m/z 398.3 ($M^+$ + 1). |
| 12 | 3732 | 4-(1-(4-(5-(difluoromethyl)-1,3,4-oxadiazol-2-yl)-2-fluorobenzyl)-1H-1,2,3-triazol-4-yl)benzoic acid<br>$^1$H NMR (400 MHz, $CD_3OD$) δ 8.57 (s, 1H), 8.14-8.07 (m, 2H), 7.98 (tt, J = 9.8, 2.2 Hz, 4H), 7.62 (t, J = 7.7 Hz, 1H), 7.24 (t, J = 51.6 Hz, 1H), 5.88 (s, 2H); LRMS (ES) m/z 416.0 ($M^+$ + 1). |
| 13 | 3733 | 2-(difluoromethyl)-5-(3-fluoro-4-((4-(p-tolyl)-1H-1,2,3-triazol-1-yl)methyl)phenyl)-1,3,4-oxadiazole<br>$^1$H NMR (400 MHz, $CDCl_3$) δ 7.93-7.85 (m, 2H), 7.83 (d, J = 1.8 Hz, 1H), 7.66 (dd, J = 8.0, 1.8 Hz, 2H), 7.45 (t, J = 7.7 Hz, 1H), 7.21 (d, J = 7.6 Hz, 2H), 6.92 (t, J = 51.9, 1.9 Hz, 1H), 5.70 (s, 2H), 2.96 (d, J = 1.9 Hz, 3H); LRMS (ES) m/z 386.3 ($M^+$ + 1). |
| 14 | 3734 | Tert-butyl 3-(1-(4-(5-(difluoromethyl)-1,3,4-oxadiazol-2-yl)-2-fluorobenzyl)-1H-1,2,3-triazol-4-yl)pyrrolidin-1-carboxylate<br>$^1$H NMR (400 MHz, $CDCl_3$) δ 7.90 (t, J = 9.1 Hz, 2H), 7.48-7.39 (m, 2H), 6.93 (t, J = 51.6, 1.0 Hz, 1H), 5.64 (s, 2H), 3.78 (dd, J = 10.4, 7.4 Hz, 1H), 3.56-3.48 (m, 2H), 3.42-3.33 (m, 3H), 2.30 (s, 1H), 1.44 (d, J = 1.0 Hz, 9H); LRMS (ES) m/z 465.3 ($M^+$ + 1). |
| 15 | 3735 | Tert-butyl 4-(1-(4-(5-(difluoromethyl)-1,3,4-oxadiazol-2-yl)-2-fluorobenzyl)-1H-1,2,3-triazol-4-yl)piperidin-1-carboxylate<br>$^1$H NMR (400 MHz, $CDCl_3$) δ 7.92-7.82 (m, 2H), 7.45-7.36 (m, 2H), 6.92 (t, J = 51.6 Hz, 1H), 5.62 (s, 2H), 4.10 (d, J = 13.4 Hz, 2H), 2.95-2.78 (m, 3H), 1.97 (d, J = 13.2 Hz, 2H), 1.60-1.54 (m, 1H), 1.51 (dd, J = 12.3, 4.3 Hz, 1H), 1.41 (d, J = 1.0 Hz, 9H); LRMS (ES) m/z 479.4 ($M^+$ + 1). |
| 17 | 3737 | 2-(difluoromethyl)-5-(6-((4-(3,4-difluorophenyl)-1H-1,2,3-triazol-1-yl)methyl)pyridin-3-yl)-1,3,4-oxadiazole<br>$^1$H NMR (400 MHz, $CDCl_3$) δ 9.33-9.28 (m, 1H), 8.42 (dd, J = 8.2, 2.2 Hz, 1H), 8.02 (s, 1H), 7.70-7.63 (m, 1H), 7.52 (s, 1H), 7.48 (d, J = 8.2 Hz, 1H), 7.26-7.16 (m, 2H), 6.95 (t, J = 51.6 Hz, 1H), 5.80 (s, 2H); LRMS (ES) m/z 391.1 ($M^+$ + 1). |
| 18 | 3738 | 2-(difluoromethyl)-5-(6-((4-(p-tolyl)-1H-1,2,3-triazol-1-yl)methyl)pyridin-3-yl)-1,3,4-oxadiazole<br>$^1$H NMR (400 MHz, $CDCl_3$) δ 9.30 (d, J = 2.2 Hz, 1H), 8.41 (dd, J = 8.2, 2.2 Hz, 1H), 7.99 (s, 1H), 7.69 (d, J = 7.9 Hz, 2H), 7.44 (d, J = 8.2 Hz, 1H), 7.23 (d, J = 7.9 Hz, 2H), 6.95 (t, J = 51.6 Hz, 1H), 5.80 (s, 2H), 2.65 (t, J = 2.5 Hz, 3H); LRMS (ES) m/z 369.2 ($M^+$ + 1). |
| 19 | 3739 | 3-(1-((5-(5-(difluoromethyl)-1,3,4-oxadiazol-2-yl)pyridin-2yl)methyl-1H-1,2,3-triazol-4-yl)benzoic acid<br>$^1$H NMR (400 MHz, $CD_3OD$) δ 9.29 (dd, J = 2.2, 0.9 Hz, 1H), 8.59 (s, 1H), 8.53 (dd, J = 8.2, 2.2 Hz, 2H), 8.13-8.06 (m, 1H), 8.06-8.00 (m, 1H), 7.64-7.55 (m, 2H), 7.26 (t, J = 51.6 Hz, 1H), 5.94 (s, 2H); LRMS (ES) m/z 399.2 ($M^+$ + 1). |
| 20 | 3741 | Tert-butyl (3-(1-((5-(5-(difluoromethyl)-1,3,4-oxadiazol-2-yl)pyridin-2-yl)methyl)-1H-1,2,3-triazol-4-yl)phenyl)carbamate<br>$^1$H NMR (400 MHz, $CDCl_3$) δ 9.30 (dd, J = 2.3, 0.9 Hz, 1H), 8.41 (dd, J = 8.2, 2.2 Hz, 1H), 8.10 (s, 1H), 7.75 (t, J = 2.0 Hz, 1H), 7.47 (d, J = 8.1 Hz, 1H), 7.45-7.41 (m, 2H), 7.32 (t, J = 7.9 Hz, 1H), 6.95 (t, J = 51.6 Hz, 1H), 5.80 (s, 2H), 1.51(s, 9H); LRMS (ES) m/z 470.1 ($M^+$ + 1). |
| 34 | 3820 | Tert-butyl 3-(1-((5-(5-(difluoromethyl)-1,3,4-oxadiazol-2-yl)pyridin-2-yl)methyl)-1H-1,2,3-triazol-4-yl)pyrrolidin-1-carboxylate<br>$^1$H NMR (400 MHz, DMSO-$d_6$) δ 9.19 (d, J = 2.2 Hz, 1H), 8.47 (dd, J = 8.2, 2.3 Hz, 1H), 8.12 (s, 1H), 7.58 (t, J = 51.3 Hz, 1H), 7.49 (d, J = 8.2 Hz, 1H), 5.83 (s, 2H), 4.10 (q, J = 5.3 Hz, 1H), 3.67 (q, J = 8.1 Hz, 1H), 3.54-3.45 (m, 1H), 3.41 |

TABLE 145-continued

| Example | Compound No. | Compound Name, $^1$H-NMR, MS (ESI) |
|---|---|---|
| | | (ddd, J = 10.8, 8.0, 4.2 Hz, 1H), 3.31 (s, 2H), 2.22 (d, J = 7.8 Hz, 1H), 2.01 (s, 1H), 1.41 (s, 9H); LRMS (ES) m/z 448.4 ($M^+$ + 1). |
| 35 | 3822 | 2-(difluoromethyl)-5-(6-((4-(2-(imidazo[1,2-a]pyridin-2-yl)ethyl)-1H-1,2,3-triazol-1-yl)methyl)pyridin-3-yl)-1,3,4-oxadiazole $^1$H NMR (400 MHz, DMSO-$d_6$) δ 9.19 (d, J = 2.2 Hz, 1H), 8.47 (dd, J = 8.2, 2.3 Hz, 1H), 8.12 (s, 1H), 7.58 (t, J = 51.3 Hz, 1H), 7.49 (d, J = 8.2 Hz, 1H), 5.83 (s, 2H), 4.10 (q, J = 5.3 Hz, 1H), 3.67 (q, J =8.1 Hz, 1H), 3.54-3.45 (m, 1H), 3.41 (ddd, J = 10.8, 8.0, 4.2 Hz, 1H), 3.31 (s, 2H), 2.22 (d, J = 7.8 Hz, 1H), 2.01 (s, 1H), 1.41 (s, 9H); LRMS (ES) m/z 423.2 ($M^+$ + 1). |
| 43 | 3831 | 2-(difluoromethyl)-5-(6-((4-propyl-1H-1,2,3-triazol-l-yl)methyl)pyridin-3-yl)-1,3,4-oxadiazole $^1$H NMR (400 MHz, $CDCl_3$) δ 9.33 (d, J = 1.6 Hz, 1H), 8.40 (dd, J = 8.2, 2.2 Hz, 1H), 7.49 (s, 1H), 7.33 (d, J = 8.2 Hz, 1H), 7.09 (s, 0.2H), 6.96 (s, 0.5H), 6.83 (s, 0.3H), 5.75 (s, 2H), 2.75 (t, J = 7.6 Hz, 2H), 1.83-1.63 (m, 2H), 1.00 (t, J = 7.4 Hz, 3H); LRMS (ES) m/z 321.0 ($M^+$ + 1). |
| 44 | 3832 | 2-(6-((4-butyl-1H-1,2,3-triazol-1-yl)methyl)pyridin-3-yl)-5-(difluoromethyl)-1,3,4-oxadiazole $^1$H NMR (400 MHz, $CDCl_3$) δ 9.33 (dd, J = 2.2, 0.7 Hz, 1H), 8.40 (dd, J = 8.2, 2.2 Hz, 1H), 7.48 (s, 1H), 7.33 (d, J = 8.2 Hz, 1H), 7.09 (s, 0.2H), 6.96 (s, 0.5H), 6.83 (s, 0.3H), 5.75 (s, 2H), 2.84-2.68 (m, 2H), 1.69 (ddd, J = 13.0, 8.5, 6.5 Hz, 2H), 1.41 (dq, J = 14.6, 7.4 Hz, 2H), 0.96 (t, J =7.4 Hz, 3H); LRMS (ES) m/z 335.3 ($M^+$ + 1). |
| 45 | 3833 | 3-(1-((5-(5-(difluoromethyl)-1,3,4-oxadiazol-2-yl)pyridin-2-yl)methyl)-1H-1,2,3-triazol-4-yl)propan-1-ol $^1$H NMR (400 MHz, $CDCl_3$) δ 9.41-9.25 (m, 1H), 8.41 (dd, J = 8.2, 2.2 Hz, 1H), 7.57 (s, 1H), 7.38 (d, J = 8.2 Hz, 1H), 7.09 (s, 0.2H), 6.96 (s, 0.5H), 6.83(s, 0.3H), 5.76 (s, 2H), 3.74 (t, J = 6.1 Hz, 2H), 2.90 (t, J = 7.3 Hz, 2H), 2.71 (s, 1H), 2.09-1.87 (m, 2H); LRMS (ES) m/z 337.2 ($M^+$ + 1). |
| 46 | 3834 | 4-(1-((5-(5-(difluoromethyl)-1,3,4-oxadiazol-2-yl)pyridin-2-yl)methyl)-1H-1,2,3-triazol-4-yl)butan-1-ol $^1$H NMR (400 MHz, $CDCl_3$) δ 9.32 (d, J = 1.5 Hz, 1H), 8.40 (dd, J = 8.2, 2.2 Hz, 1H), 7.54 (s, 1H), 7.36 (d, J = 8.2 Hz, 1H), 7.09 (s, 0.2H), 6.96 (s, 0.5H), 6.83 (s, 0.3H), 5.75 (s, 2H), 3.70 (t, J = 6.4 Hz, 2H), 2.81 (t, J =7.5 Hz, 2H), 2.31 (s, 1H), 1.89-1.73 (m, 2H), 1.73-1.60 (m, 2H); LRMS (ES) m/z 351.2 ($M^+$ + 1). |
| 57 | 3846 | 2-(6-((4-cyclopentyl-1H-1,2,3-triazol-1-yl)methyl)pyridin-3-yl)-5-(difluoromethyl)-1,3,4-oxadiazole $^1$H NMR (400 MHz, $CDCl_3$) δ 9.34 (d, J = 1.6 Hz, 1H), 8.40 (dd, J = 8.2, 2.2 Hz, 1H), 7.47 (s, 1H), 7.35 (d, J = 8.2 Hz, 1H), 7.09 (s, 0.2H), 6.96 (s, 0.5H), 6.83 (s, 0.3H), 5.75 (s, 2H), 3.24 (dd, J = 16.0, 8.2 Hz, 1H), 2.13 (dd, J=10.6, 6.4 Hz, 2H), 1.91-1.55 (m, 6H); LRMS (ES) m/z 347.3 ($M^+$ + 1). |
| 58 | 3853 | 2-(difluoromethyl)-5-(6-((4-(2-fluorophenyl)-1H-1,2,3-triazol-1-yl)methyl)pyridin-3-yl)-1,3,4-oxadiazole $^1$H NMR (400 MHz, DMSO-$d_6$) δ 9.19 (dd, J = 2.3, 0.9 Hz, 1H), 8.62 (d, J = 3.8 Hz, 1H), 8.48 (dd, J = 8.2, 2.3 Hz, 1H), 8.16 (td, J = 7.6, 1.7 Hz, 1H), 7.57 (t, J = 51.3 Hz, 1H), 7.55 (dd, J = 8.2, 0.8 Hz, 1H), 7.44-7.39 (m, 1H), 7.39-7.31 (m, 2H), 5.98 (s, 2H); LRMS (ESI) m/z 373.2 ($M^+$ + H). |
| 59 | 3854 | 2-(difluoromethyl)-5-(6-((4-(3-fluorophenyl)-1H-1,2,3-triazol-1-yl)methyl)pyridin-3-yl)-1,3,4-oxadiazole $^1$H NMR (400 MHz, DMSO-$d_6$) δ 9.19 (dd, J = 2.2, 0.8 Hz, 1H), 8.79 (s, 1H), 8.49 (dd, J = 8.2, 2.3 Hz, 1H), 7.77-7.65 (m, 2H), 7.62-7.42 (m, 3H), 7.18 (dddd, J = 9.2, 8.3, 2.7, 1.0 Hz, 1H), 5.94 (s, 2H); LRMS (ESI) m/z 373.2 ($M^+$ + H). |
| 60 | 3855 | 2-(difluoromethyl)-5-(6-((4-(4-fluoropheny])-1H-1,2,3-triazol-1-yl)methyl)pyridin-3-yl)-1,3,4-oxadiazole $^1$H NMR (400 MHz, DMSO-$d_6$) δ 9.19 (dd, J = 2.3, 0.8 Hz, 1H), 8.71 (s, 1H), 8.48 (dd, J = 8.2, 2.3 Hz, 1H), 7.96-7.87 (m, 2H), 7.71-7.44 (m, 2H), 7.35-7.24 (m, 2H), 5.93 (s, 2H); LRMS (ESI) m/z 373.2 ($M^+$ + H). |
| 61 | 3856 | 2-(difluoromethyl)-5-(6-((4-(m-tolyl)-1H-1,2,3-triazol-1-yl)methyl)pyridin-3-yl)-1,3,4-oxadiazole $^1$H NMR (400 MHz, DMSO-$d_6$) δ 9.19 (dd, J = 2.3, 0.9 Hz, 1H), 8.68 (s, 1H), 8.48 (dd, J = 8.2, 2.3 Hz, 1H), 7.73-7.68 (m, 1H), 7.66 (d, J = 7.7 Hz, 1H), 7.60-7.44 (m, 2H), 7.33 (t, J = 7.6 Hz, 1H), 7.16 (ddt, J =7.5, 1.9, 0.9 Hz, 1H), 5.92 (s, 2H), 2.36 (s, 3H); LRMS (ESI) m/z 369.2 ($M^+$ + H). |
| 62 | 3860 | 2-(difluoromethyl)-5-(6-((4-(o-tolyl)-1H-1,2,3-triazol-1-yl)methyl)pyridin-3-yl)-1,3,4-oxadiazole $^1$H NMR (400 MHz, DMSO-$d_6$) δ 9.21 (dd, J = 2.2, 0.8 Hz, 1H), 8.57 (s, 1H), 8.49 (dd, J = 8.2, 2.3 Hz, 1H), 7.81-7.77 (m, 1H), 7.58 (t, J = 51.3 Hz, 1H), 7.55 (dd, J = 8.3, 0.9 Hz, 1H), 7.34-7.25 (m, 3H), 5.95 (s, 2H), 2.46 (d, J = 0.6 Hz, 3H); LRMS (ESI) m/z 369.2 ($M^+$ + H). |
| 63 | 3861 | 2-(difluoromethyl)-5-(6-((4-(furan-2-yl)-1H-1,2,3-triazol-1-yl)methyl)pyridin-3-yl)-1,3,4-oxadiazole $^1$H NMR (400 MHz, DMSO-$d_6$) δ 9.19 (dd, J = 2.3, 0.8 Hz, 1H), 8.56 (s, 1H), 8.49 (dd, J = 8.2, 2.3 Hz, 1H), 7.77 (dd, J = 1.8, 0.8 Hz, 1H), 7.72-7.44 (m, 2H), 6.83 (dd, J = 3.3, 0.8 Hz, 1H), 6.62 (dd, J = 3.3, 1.8 Hz, 1H), 5.94 (s, 2H); LRMS (ESI) m/z 345.1 ($M^+$ + H). |
| 66 | 3879 | 2-(6-((4-(cyclohex-1-ene-1-yl)-1H-1,2,3-triazol-1-yl)methyl)pyridin-3-yl)-5-(difluoromethyl)-1,3,4-oxadiazole |

TABLE 145-continued

| Example | Compound No. | Compound Name, $^1$H-NMR, MS (ESI) |
|---|---|---|
| | | $^1$H NMR (400 MHz, $CDCl_3$) δ 9.32 (d, J = 1.6 Hz, 1H), 8.38 (dd, J = 8.2, 2.2 Hz, 1H), 7.59 (s, 1H), 7.33 (d, J = 8.2 Hz, 1H), 7.09 (s, 0.2H), 6.96 (s, 0.5H), 6.83 (s, 0.3H), 6.60-6.52 (m, 1H), 5.76 (s, 2H), 2.45-2.33 (m, 2H), 2.27-2.15 (m, 2H), 1.83-1.73 (m, 2H), 1.72-1.62 (m, 2H); LRMS (ES) m/z 359.26 ($M^+$ + 1). |
| 67 | 3880 | 2-(6-((4-cyclohexyl-1H-1,2,3-triazol-1-yl)methyl)pyridin-3-yl)-5-(difluoromethyl)-1,3,4-oxadiazole<br>$^1$H NMR (400 MHz, $CDCl_3$) δ 9.41-9.27 (m, 1H), 8.40 (dd, J = 8.2, 2.2 Hz, 1H), 7.45 (s, 1H), 7.34 (d, J = 8.2 Hz, 1H), 7.09 (s, 0.2H), 6.96 (s, 0.5H), 6.83 (s, 0.3H), 5.75 (s, 2H), 2.81 (dd, J = 9.1, 5.4 Hz, 1H), 2.09 (d, J = 8.1 Hz, 2H), 1.82 (dd, J= 8.4, 3.7 Hz, 2H), 1.75 (d, J = 12.6 Hz, 1H), 1.51-1.34 (m, 4H), 1.34-1.19 (m, 1H); LRMS (ES) m/z 361.33 ($M^+$ + 1). |
| 83 | 3902 | 2-(difluoromethyl)-5-(6-((4-(thiophen-2-yl)-1H-1,2,3-triazol-1-yl)methyl)pyridin-3-yl)-1,3,4-oxadiazole<br>$^1$H NMR (400 MHz, $CD_3OD$) δ 9.28 (dd, J = 2.2, 0.9 Hz, 1H), 8.53 (dd, J = 8.2, 2.2 Hz, 1H), 8.40 (s, 1H), 7.60 (d, J = 8.3 Hz, 1H), 7.48-7.42 (m, 2H), 7.39-7.09 (m, 2H), 5.90 (s, 2H); LRMS (ESI) m/z 361.2 ($M^+$ + H). |
| 91 | 3926 | Tert-butyl 3-(1-((5-(5-(difluoromethyl)-1,3,4-oxadiazol-2-yl)pyridin-2-yl)methyl)-1H-1,2,3-triazol-4-yl)azetidin-1-carboxylate<br>$^1$H NMR (400 MHz, DMSO-$d_6$) δ 9.19 (dd, J = 2.3, 0.8 Hz, 1H), 8.47 (dd, J = 8.2, 2.3 Hz, 1H), 8.23 (s, 1H), 7.58 (t, J = 51.3 Hz, 1H), 7.50 (dd, J = 8.2, 0.9 Hz, 1H), 5.85 (s, 2H), 4.22 (s, 2H), 3.91 (dq, J = 11.5, 5.8 Hz, 3H), 1.40 (s, 9H); LRMS (ESI) m/z 432.2 ($M^+$ + H). |
| 105 | 3960 | 2-(difluoromethyl)-5-(6-((4-(pyrimidin-5-yl)-1H-1,2,3-triazol-1-yl)methyl)pyridin-3-yl)-1,3,4-oxadiazole<br>$^1$H NMR (400 MHz, $CD_3OD$) δ 9.30-9.24 (m, 3H), 9.15 (s, 1H), 8.76 (s, 1H), 8.54 (dd, J = 8.2, 2.3 Hz, 1H), 7.65 (dd, J = 8.2, 0.8 Hz, 1H), 7.26 (t, J = 51.6 Hz, 1H), 5.97 (s, 2H); LRMS (ESI) m/z 357.2 ($M^+$ + H). |
| 106 | 3961 | Tert-butyl 3-(1-((5-(5-(difluoromethyl)-1,3,4-oxadiazol-2-yl)pyridin-2-yl)methyl)-1H-1,2,3-triazol-4-yl)piperidin-1-carboxylate<br>$^1$H NMR (400 MHz, $CD_3OD$) δ 9.26 (dd, J = 2.2, 0.9 Hz, 1H), 8.51 (dd, J = 8.2, 2.3 Hz, 1H), 7.99 (s, 1H), 7.53 (d, J = 8.2 Hz, 1H), 7.26 (t, J = 51.6 Hz, 1H), 5.84 (s, 2H), 4.22-4.13 (m, 1H), 3.96 (d, J = 13.2 Hz, 1H), 3.12-2.88 (m, 3H), 2.18-2.10 (m, 1H), 1.78 (q, J = 10.2, 9.4 Hz, 2H), 1.59 (t, J = 12.2 Hz, 1H), 1.47 (s, 9H); LRMS (ESI) m/z 462.3 ($M^+$ + H). |
| 114 | 3985 | 2-(6-((4-(1H-pyrazol-4-yl)-1H-1,2,3-triazol-1-yl)methyl)pyridin-3-yl)-5-(difluoromethyl)-1,3,4-oxadiazole<br>$^1$H NMR (400 MHz, $CD_3OD$) δ 9.28 (dd, J = 2.2, 0.9 Hz, 1H), 8.53 (dd, J = 8.2, 2.2 Hz, 1H), 8.29 (s, 1H), 7.96 (s, 2H), 7.58 (d, J = 8.2 Hz, 1H), 7.26 (t, J = 51.6 Hz, 1H), 5.90 (s, 2H); LRMS (ESI) m/z 345.2 ($M^+$ + H). |
| 121 | 3999 | Tert-butyl 4-(1-((5-(5-(difluoromethyl)-1,3,4-oxadiazol-2-yl)pyridin-2-yl)methyl)-1H-1,2,3-triazol-4-yl)-4-fluoropiperidin-1-carboxylate<br>$^1$H NMR (400 MHz, $CDCl_3$) δ 9.34 (dd, J = 2.2, 0.8 Hz, 1H), 8.43 (dd, J = 8.2, 2.2 Hz, 1H), 7.80 (d, J = 0.6 Hz, 1H), 7.43 (dd, J = 8.2, 0.8 Hz, 1H), 7.09 (s, 0.2H), 6.96 (s, 0.5H), 6.83 (s, 0.3H), 5.78 (s, 2H), 4.01 (d, J = 11.8 Hz, 2H), 3.27 (d, J = 10.7 Hz, 2H), 2.32-2.20 (m, 1H), 2.21-2.10 (m, 3H), 1.49 (s, 9H); LRMS (ES) m/z 478.2 ($M^+$ − 1). |
| 122 | 4000 | Tert-butyl 4-((1-((5-(5-(difluoromethyl)-1,3,4-oxadiazol-2-yl)pyridin-2-yl)methyl)-1H-1,2,3-triazol-4-yl)methyl)piperidin-1-carboxylate<br>$^1$H NMR (400 MHz, $CDCl_3$) δ 9.33 (dd, J = 2.2, 0.8 Hz, 1H), 8.41 (dd, J = 8.2, 2.2 Hz, 1H), 7.50 (s, 1H), 7.36 (d, J = 8.2 Hz, 1H), 7.09 (s, 0.2H), 6.96 (s, 0.5H), 6.83 (s, 0.3H), 5.75 (s, 2H), 4.09 (s, 2H), 2.76-2.60 (m, 4H), 1.87 (ddt, J = 15.3, 7.7, 3.8 Hz, 1H), 1.68 (d, J = 13.0 Hz, 2H), 1.46 (s, 9H), 1.18 (ddd, J = 25.0, 12.7, 4.4 Hz, 2H); LRMS (ES) m/z 476.4 ($M^+$ − 1). |
| 197 | 4276 | 3-(1-((5-(5-(difluoromethyl)-1,3,4-oxadiazol-2-yl)pyridin-2-yl)methyl)-1H-1,2,3-triazol-4-yl)oxetan-3-ol<br>$^1$H NMR (400 MHz, $CDCl_3$) δ 9.34 (d, J = 1.7 Hz, 1H), 8.44 (dd, J = 8.2, 2.2 Hz, 1H), 7.93 (s, 1H), 7.46 (d, J = 8.2 Hz, 1H), 7.10 (s, 0.2H), 6.97 (s, 0.5H), 6.84 (s, 0.3H), 5.81 (s, 2H), 5.02-4.84 (m, 4H); LRMS (ES) m/z 351.31 ($M^+$ + 1). |
| 198 | 4277 | 3-(1-((5-(5-(difluoromethyl)-1,3,4-oxadiazol-2-yl)pyridin-2-yl)methyl)-1H-1,2,3-triazol-4-yl)tetrahydrofuran-3-ol<br>$^1$H NMR (400 MHz, $CDCl_3$) δ 9.34 (d, J = 1.6 Hz, 1H), 8.43 (dd, J = 8.2, 2.2 Hz, 1H), 7.80 (s, 1H), 7.43 (d, J = 8.2 Hz, 1H), 7.09 (s, 0.2H), 6.97 (s, 0.5H), 6.84 (s, 0.3H), 5.77 (s, 2H), 4.21 (td, J = 8.5, 7.4 Hz, 1H), 4.12 (td, J = 8.9, 4.1 Hz, 1H), 3.96 (s, 2H), 2.61 (dt, J = 13.1, 8.8 Hz, 1H), 2.44-2.18 (m, 2H); LRMS (ES) m/z 365.22 ($M^+$ + 1). |
| 199 | 4278 | 3-(1-(4-(5-(difluoromethyl)-1,3,4-oxadiazol-2-yl)-2-fluorobenzyl)-1H-1,2,3-triazol-4-yl)oxetan-3-ol<br>$^1$H NMR (400 MHz, $CDCl_3$) δ 8.01-7.88 (m, 2H), 7.77 (s, 1H), 7.55-7.44 (m, 1H), 7.08 (s, 0.2H), 6.95 (s, 0.5H), 6.82 (s, 0.3H), 5.72 (s, 2H), 4.92 (q, J = 7.0 Hz, 4H); LRMS (ES) m/z 368.23 ($M^+$ + 1). |
| 200 | 4279 | 3-(1-(4-(5-(difluoromethyl)-1,3,4-oxadiazol-2-yl)-2-fluorobenzyl)-1H-1,2,3-triazol-4-yl)tetrahydrofuran-3-ol<br>$^1$H NMR (400 MHz, $CDCl_3$) δ 7.97-7.89 (m, 2H), 7.66 (s, 1H), 7.48 (t, J = 7.6 Hz, 1H), 7.06 (s, 0.2H), 6.94 (s, 0.5H), 6.78 (s, 0.3H), 5.68 (s, 2H), 4.25-4.16 (m, 1H), 4.12 (ddd, J = 17.7, 7.9, 4.5 Hz, 1H), 4.02-3.96 (m, 2H), 2.61 (dt, J = 13.2, 8.8 Hz, 1H), 2.36-2.25 (m, 1H); LRMS (ES) m/z 382.26 ($M^+$ + 1). |

TABLE 145-continued

| Example | Compound No. | Compound Name, $^1$H-NMR, MS (ESI) |
|---|---|---|
| 238 | 4336 | 2-(difluoromethyl)-5-(4-((4-(3-(4-methylpiperazin-1-yl)phenyl)-1H-1,2,3-triazol-1-yl)methyl)phenyl)-1,3,4-oxadiazole<br>$^1$H NMR (400 MHz, $CD_3OD$) δ 8.42 (s, 1H), 8.20-8.13 (m, 2H), 7.65-7.57 (m, 2H), 7.50-7.45 (m, 1H), 7.35-7.26 (m, 2H), 7.23 (t, J = 51.7 Hz, 1H), 6.99 (dt, J = 7.3, 2.3 Hz, 1H), 5.79 (s, 2H), 3.31-3.26 (m, 4H), 2.69-2.62 (m, 4H), 2.37 (s, 3H); LRMS (ES) m/z 452.6 ($M^+$ + 1). |
| 239 | 4337 | 2-(difluoromethyl)-5-(3-fluoro-4-((4-(3-(4-methylpiperazin-1-yl)phenyl)-1H-1,2,3-triazol-1-yl)methyl)phenyl)-1,3,4-oxadiazole<br>$^1$H NMR (400 MHz, $CD_3OD$) δ 8.43 (s, 1H), 8.03-7.93 (m, 2H), 7.60 (t, J = 7.7 Hz, 1H), 7.47 (s, 1H), 7.35-7.27 (m, 2H), 7.24 (t, J = 51.6 Hz, 1H), 6.99 (dt, J = 7.1, 2.4 Hz, 1H), 5.85 (s, 2H), 3.29 (t, J = 5.1 Hz, 4H), 2.69-2.62 (m, 4H), 2.38 (s, 3H); LRMS (ES) m/z 470.5 ($M^+$ + 1). |
| 240 | 4338 | 4-(3-(1-(4-(5-(difluoromethyl)-1,3,4-oxadiazol-2-yl)benzyl)-1H-1,2,3-triazol-4-yl)phenyl)morpholine<br>$^1$H NMR (400 MHz, $CD_3OD$) δ 8.42 (s, 1H), 8.20-8.13 (m, 2H), 7.61 (d, J = 8.4 Hz, 2H), 7.47 (t, J = 2.0 Hz, 1H), 7.36-7.27 (m, 2H), 7.23 (t, J = 51.7 Hz, 1H), 6.99 (dt, J = 7.4, 2.2 Hz, 1H), 5.79 (s, 2H), 3.90-3.83 (m, 4H), 3.25-3.18 (m, 4H); LRMS (ES) m/z 439.3 ($M^+$ + 1). |
| 241 | 4339 | 4-(3-(1-(4-(5-(difluoromethyl)-1,3,4-oxadiazol-2-yl)-2-fluorobenzyl)-1H-1,2,3-triazol-4-yl)phenyl)morpholine<br>$^1$H NMR (400 MHz, $CD_3OD$) δ 8.43 (s, 1H), 8.03-7.92 (m, 2H), 7.60 (t, J = 7.7 Hz, 1H), 7.50-7.44 (m, 1H), 7.36-7.28 (m, 2H), 7.24 (t, J = 51.6 Hz, 1H), 6.99 (dt, J = 7.2, 2.3 Hz, 1H), 5.85 (s, 2H), 3.90-3.83 (m, 4H), 3.25-3.19 (m, 4H); LRMS (ES) m/z 457.1 ($M^+$ + 1). |
| 242 | 4340 | 2-(6-((4-(1H-indazol-6-yl)-1H-1,2,3-triazol-1-yl)methyl)pyridin-3-yl)-5-(difluoromethyl)-1,3,4-oxadiazole<br>$^1$H NMR (400 MHz, $CD_3OD$) δ 9.29 (dd, J = 2.2, 0.9 Hz, 1H), 8.59 (s, 1H), 8.54 (dd, J = 8.2, 2.2 Hz, 1H), 8.08 (d, J = 1.7 Hz, 2H), 7.87 (dd, J = 8.4, 0.7 Hz, 1H), 7.63 (td, J = 8.5, 1.1 Hz, 2H), 7.26 (t, J = 51.6 Hz, 1H), 5.95 (s, 2H); LRMS (ES) m/z 395.2 ($M^+$ + 1). |
| 243 | 4341 | 2-(4-((4-(1H-indazol-6-yl)-1H-1,2,3-triazol-1-yl)methyl)phenyl)-5-(difluoromethyl)-1,3,4-oxadiazole<br>$^1$H NMR (400 MHz, $CDD_3OD$) δ 8.53 (s, 1H), 8.21-8.14 (m, 2H), 8.07 (s, 2H), 7.85 (dd, J = 8.5, 0.8 Hz, 1H), 7.67-7.59 (m, 2H), 7.23 (t, J = 51.6 Hz, 1H), 5.83 (s, 2H); LRMS (ES) m/z 394.2 ($M^+$ + 1). |
| 244 | 4342 | 2-(4-((4-(1H-indazol-6-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.53 (s, 1H), 8.07 (d, J = 2.0 Hz, 2H), 8.04-7.93 (m, 2H), 7.86 (dd, J = 8.5, 0.8 Hz, 1H), 7.67-7.59 (m, 2H), 7.24 (t, J = 51.6 Hz, 1H), 5.88 (s, 2H); LRMS (ES) m/z 412.2 ($M^+$ + 1). |
| 245 | 4343 | 2-(6-((4-(1H-indazol-5-yl)-1H-1,2,3-triazol-1-yl)methyl)pyridin-3-yl)-5-(difluoromethyl)-1,3,4-oxadiazole<br>$^1$H NMR (400 MHz, $CD_3OD$) δ 9.29 (d, J = 2.0 Hz, 1H), 8.54 (dd, J = 8.2, 2.2 Hz, 1H), 8.51 (s, 1H), 8.28 (t, J = 1.2 Hz, 1H), 8.12 (s, 1H), 7.92 (dd, J =8.8, 1.6 Hz, 1H), 7.63 (dd, J = 11.8, 8.4 Hz, 2H), 7.26 (t, J = 51.6 Hz, 1H), 5.94 (s, 2H); LRMS (ES) m/z 395.8 ($M^+$ + 1). |
| 246 | 4344 | 2-(4-((4-(1H-indazol-5-yl)-1H-1,2,3-triazol-1-yl)methyl)phenyl)-5-(difluoromethyl)-1,3,4-oxadiazole<br>$^1$H NMR (400 MHz, $CD_3OD$) δ 8.44 (s, 1H), 8.26 (s, 1H), 8.18 (d, J = 8.8 Hz, 2H), 8.11 (s, 1H), 7.90 (d, J = 8.9 Hz, 1H), 7.63 (d, J = 8.7 Hz, 3H), 7.23 (t, J = 51.4 Hz, 1H), 5.82 (s, 2H); LRMS (ES) m/z 394.2 ($M^+$ + 1). |
| 247 | 4345 | 2-(4-((4-(1H-indazol-5-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.45 (s, 1H), 8.26 (s, 1H), 8.12 (s, 1H), 7.99 (t, J = 10.9 Hz, 2H), 7.90 (d, J = 9.1 Hz, 1H), 7.62 (t, J = 8.1 Hz, 2H), 7.24 (t, J = 51.4 Hz, 1H), 5.87 (s, 2H), 1.25 (d, J = 7.8 Hz, 1H); LRMS (ES) m/z 412.2 ($M^+$ + 1). |
| 248 | 4346 | 2-(6-((4-(1H-indazol-4-yl)-1H-1,2,3-triazol-1-yl)methyl)pyridin-3-yl)-5-(difluoromethyl)-1,3,4-oxadiazole<br>$^1$H NMR (400 MHz, $CD_3OD$) δ 9.29 (dd, J = 2.3, 0.9 Hz, 1H), 8.73 (s, 1H), 8.59 (d, J = 1.1 Hz, 1H), 8.54 (dd, J = 8.2, 2.2 Hz, 1H), 7.69-7.62 (m, 2H), 7.58 (d, J = 8.4 Hz, 1H), 7.49 (dd, J = 8.4, 7.1 Hz, 1H), 7.26 (t, J = 51.6 Hz, 1H), 5.99 (s, 2H); LRMS (ES) m/z 395.2 ($M^+$ + 1). |
| 249 | 4347 | 2-(4-((4-(1H-indazol-4-yl)-1H-1,2,3-triazol-1-yl)methyl)phenyl)-5-(difluoromethyl)-1,3,4-oxadiazole<br>$^1$H NMR (400 MHz, $CD_3OD$) δ 8.67 (s, 1H), 8.58 (s, 1H), 8.21-8.14 (m, 2H), 7.69-7.61 (m, 3H), 7.57 (d, J = 8.4 Hz, 1H), 7.48 (dd, J = 8.4, 7.1 Hz, 1H), 7.23 (t, J = 51.6 Hz, 1H), 5.86 (s, 2H); LRMS (ES) m/z 394.2 ($M^+$ + 1). |
| 250 | 4348 | 2-(4-((4-(1H-indazol-4-yl)-1H-1,2,3-triazol-1-yl)methyl)-3-fluorophenyl)-5-(difluoromethyl)-1,3,4-oxadiazole (0.091 g, 59.6%) was obtained in a beige solid form.<br>$^1$H NMR (400 MHz, $CD_3OD$) δ 8.67 (s, 1H), 8.60-8.55 (m, 1H), 8.04-7.94 (m, 2H), 7.67-7.60 (m, 2H), 7.58 (d, J = 8.3 Hz, 1H), 7.48 (dd, J = 8.4, 7.1 Hz, 1H), 7.24 (t, J = 51.6 Hz, 1H), 5.92 (s, 2H); LRMS (ES) m/z 12.2 ($M^+$ + 1). |
| 395 | 4524 | 2-(4-((4-(1H-pyrrolo[2,3-b]pyridin-5-yl)-1H-1,2,3-triazol-1-yl)methyl)-3-fluorophenyl)-5-(difluoromethyl)-1,3,4-oxadiazole |

TABLE 145-continued

| Example | Compound No. | Compound Name, $^1$H-NMR, MS (ESI) |
|---|---|---|
| | | $^1$H NMR (400 MHz, $CD_3OD$) δ 8.69 (s, 1H), 8.50 (s, 1H), 8.44 (s, 1H), 8.04-7.94 (m, 2H), 7.63 (t, J = 7.6 Hz, 1H), 7.45 (d, J = 3.5 Hz, 1H), 7.24 (t, J = 51.6 Hz, 1H), 6.57 (d, J = 3.5 Hz, 1H), 5.88 (s, 2H); LRMS (ES) m/z 412.3 ($M^+$ + 1). |
| 396 | 4525 | 2-(4-((4-(1H-pyrrolo[2,3-b]pyridin-5-yl)-1H-1,2,3-triazol-1-yl)methyl)phenyl)-5-(difluoromethyl)-1,3,4-oxadiazole<br>$^1$H NMR (400 MHz, $CD_3OD$) δ 8.68 (s, 1H), 8.49 (s, 1H), 8.44 (d, J = 2.1 Hz, 1H), 8.18 (d, J = 8.2 Hz, 2H), 7.64 (d, J = 8.1 Hz, 2H), 7.45 (d, J = 3.5 Hz, 1H), 7.23 (t, J = 51.6 Hz, 1H), 6.57 (d, J = 3.4 Hz, 1H), 5.83 (s, 2H); LRMS (ES) m/z 394.4 ($M^+$ + 1). |
| 397 | 4526 | 2-(4-((4-(1H-pyrrolo[2,3-b]pyridin-4-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.78 (s, 1H), 8.27 (d, J = 5.2 Hz, 1H), 7.99 (t, J = 10.2 Hz, 2H), 7.68-7.60 (m, 2H), 7.51 (d, J = 3.5 Hz, 1H), 7.24 (t, J = 51.6 Hz, 3H), 7.01 (d, J = 3.6 Hz, 1H), 5.94 (s, 2H); LRMS (ES) m/z 412.3 ($M^+$ + 1). |
| 398 | 4527 | 2-(4-((4-(1H-pyrrolo[2,3-b]pyridin-4-yl)-1H-1,2,3-triazol-1-yl)methyl)phenyl)-5-(difluoromethyl)-1,3,4-oxadiazole<br>$^1$H NMR (400 MHz, $CD_3OD$) δ 8.78 (s, 1H), 8.27 (d, J = 5.2 Hz, 1H), 8.18 (d, J = 8.2 Hz, 2H), 7.64 (dd, J = 10.5, 6.7 Hz, 3H), 7.50 (d, J = 3.6 Hz, 1H), 7.23 (t, J = 51.6 Hz, 1H), 7.01 (d, J = 3.5 Hz, 1H), 5.88 (s, 2H); LRMS (ES) m/z 394.4 ($M^+$ + 1). |
| 479 | 16781 | 2-(4-((4-(6-chloropyridin-3-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.86-8.85 (m, 1H), 8.60 (s, 1H), 8.27 (dd, J = 8.4, 2.4 Hz, 1H), 8.00-7.94 (m, 2H), 7.63 (t, J = 7.7 Hz, 1H), 7.56 (dd, J = 8.4, 0.6 Hz, 1H), 7.24 (t, J = 51.6 Hz, 1H), 5.88 (s, 2H); LRMS (ESI) m/z 407.1 ($M^+$ + H). |
| 482 | 16928 | 2-(4-((4-(5-bromopyridin-2-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.78 (s, 1H), 8.74 (s, 1H), 8.16 (dd, J = 8.5, 2.2 Hz, 1H), 8.01 (d, J = 8.5 Hz, 1H), 7.94 (d, J = 9.2 Hz, 2H), 7.60 (t, J = 7.6 Hz, 1H), 7.55 (t, J = 51.3 Hz, 1H), 5.88 (s, 2H); LRMS (ESI) m/z 451.2 ($M^+$ + H). |
| 483 | 16930 | 2-(4-((4-(5-bromopyridin-3-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 9.01 (s, 1H), 8.65 (d, J = 4.3 Hz, 2H), 8.50 (t, J = 1.9 Hz, 1H), 8.00-7.95 (m, 2H), 7.63 (t, J =7.7 Hz, 1H), 7.24 (t, J = 51.6 Hz, 1H), 5.88 (s, 2H); LRMS (ESI) m/z 451.0 ($M^+$ + H). |
| 488 | 17261 | 2-(4-((4-(1H-pyrazol-4-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.23 (s, 1H), 8.00-7.97 (m, 3H), 7.95-7.95 (m, 1H), 7.75 (s, 1H), 7.60 (t, J = 7.6 Hz, 1H), 7.24 (t, J = 51.6 Hz, 1H), 5.83 (s, 2H); LRMS (ESI) m/z 451.2 ($M^+$ + H). |
| 521 | 17983 | 2-(difluoromethyl)-5-(5-fluoro-6-((4-(pyridin-2-yl)-1H-1,2,3-triazol-1-yl)methyl)pyridin-3-yl)-1,3,4-oxadiazole<br>$^1$H NMR (400 MHz, $CD_3OD$) δ 9.10 (s, 1H), 8.61-8.59 (m, 2H), 8.39 (dd, J = 9.6, 1.6 Hz, 1H), 8.11 (d, J = 8.0 Hz, 1H), 7.94 (td, J = 7.8, 1.6 Hz, 1H), 7.41-7.14 (m, 2H), 6.05 (d, J = 1.7 Hz, 1H); LRMS (ESI) m/z 374.2 ($M^+$ + H). |
| 522 | 17984 | 2-(difluoromethyl)-5-(5-fluoro-6-((4-(thiophen-2-yl)-1H-1,2,3-triazol-1-yl)methyl)pyridin-3-yl)-1,3,4-oxadiazole<br>$^1$H NMR (400 MHz, $CD_3OD$) δ 9.11 (s, 1H), 8.40-8.38 (m, 2H), 7.46-7.44 (m, 2H), 7.40-7.11 (m, 2H), 5.99 (d, J = 1.8 Hz, 2H); LRMS (ESI) m/z 379.2 ($M^+$ + H). |
| 534 | 18256 | 2-(difluoromethyl)-5-(3-fluoro-4-((4-(pyridin-2-yl)-1H-1,2,3-triazol-1-yl)methyl)phenyl)-1,3,4-oxadiazole<br>$^1$H NMR (400 MHz, DMSO-$d_6$) δ 8.74 (s, 1H), 8.61 (s, 1H), 8.05 (d, J = 7.6 Hz, 1H), 7.96-7.89 (m, 3H), 7.69-7.43 (m, 2H), 7.36 (s, 1H), 5.89 (s, 2H); LRMS (ESI) m/z 373.3 ($M^+$ + H). |
| 535 | 18258 | 2-(difluoromethyl)-5-(3-fluoro-4-((4-(thiophen-2-yl)-1H-1,2,3-triazol-1-yl)methyl)phenyl)-1,3,4-oxadiazole<br>$^1$H NMR (400 MHz, $CD_3OD$) δ 8.35 (s, 1H), 8.00-7.94 (m, 2H), 7.60 (t, J = 7.7 Hz, 1H), 7.44 (d, J = 4.3 Hz, 2H), 7.37-7.10 (m, 2H), 5.84 (s, 2H); LRMS (ESI) m/z 378.2 ($M^+$ + H). |
| 547 | 18470 | 2-(4-((4-(2,2-difluorobenzo[d][1,3]dioxol-4-yl)-1H-1,2,3-triazol-1-yl)methyl)-3-fluorophenyl)-5-(difluoromethyl)-1,3,4-oxadiazole<br>$^1$H NMR (400 MHz, $CDCl_3$) δ 8.07 (s, 1H), 7.99-7.93 (m, 3H), 7.47 (t, J = 7.7 Hz, 1H), 7.21 (t, J = 8.1 Hz, 1H), 7.05 (s, 1H), 7.05 (s, 0.2H), 6.94 (s, 0.5H), 6.81 (s, 0.2H), 5.79 (s, 2H); LRMS (ES) m/z 453.55 ($M^+$ + 1). |
| 557 | 18868 | Tert-butyl 4-(3-(1-((5-(5-(difluoromethyl)-1,3,4-oxadiazol-2-yl)-3-fluoropyridin-2-yl)methyl)-1H-1,2,3-triazol-4-yl)phenyl)piperidin-1-carboxylate<br>$^1$H NMR (400 MHz, $CDCl_3$) δ 9.08 (s, 1H), 8.18 (d, J = 7.5 Hz, 1H), 7.52 (s, 0.5H), 7.34-7.22 (m, 5H), 7.14 (s, 0.5H), 5.48 (s, 2H), 4.62-4.54 (m, 4H), 3.93 (s, 3H), 3.44 (s, 2H), 1.39-1.24 (m, 9H); LRMS (ES) m/z ($M^+$ + 1). |
| 566 | 18918 | 2-(6-((4-(1H-indol-6-yl)-1H-1,2,3-triazol-1-yl)methyl)-5-fluoropyridin-3-yl)-5-(difluoromethyl)-1,3,4-oxadiazole<br>$^1$H NMR (400 MHz, DMSO-$d_6$) δ 11.21 (s, 1H), 9.06 (d, J = 1.0 Hz, 1H), 8.62 (s, 1H), 8.51 (dd, J = 9.8, 1.7 Hz, 1H), 7.92 (s, 1H), 7.73-7.46 (m, 3H), 7.40-7.37 (m, 1H), 6.44 (dd, J = 2.5, 1.5 Hz, 1H), 5.98 (d, J = 1.5 Hz, 2H); LRMS (ES) m/z 412.53 ($M^+$ + 1). |

TABLE 145-continued

| Example | Compound No. | Compound Name, $^1$H-NMR, MS (ESI) |
|---|---|---|
| 567 | 18919 | 2-(6-((4-(1H-indazol-6-yl)-1H-1,2,3-triazol-1-yl)methyl)-5-fluoropyridin-3-yl)-5-(difluoromethyl)-1,3,4-oxadiazole $^1$H NMR (400 MHz, DMSO-$d_6$) δ 13.17 (s, 1H), 9.06 (d, J = 1.0 Hz, 1H), 8.79 (s, 1H), 8.51 (dd, J = 9.8, 1.7 Hz, 1H), 8.09 (s, 1H), 8.04 (d, J = 0.9 Hz, 1H), 7.83 (dd, J = 8.4, 0.7 Hz, 1H), 7.63 (dd, J = 8.4, 1.3 Hz, 1H), 7.59 (t, J = 51.2 Hz, 1H), 6.01 (d, J = 1.4 Hz, 2H); LRMS (ES) m/z 413.29 ($M^+$ + 1). |
| 568 | 18920 | 2-(6-((4-(1H-indazol-5-yl)-1H-1,2,3-triazol-1-yl)methyl)-5-fluoropyridin-3-yl)-5-(difluoromethyl)-1,3,4-oxadiazole $^1$H NMR (400 MHz, DMSO-$d_6$) δ 13.17 (s, 1H), 9.06 (d, J = 1.0 Hz, 1H), 8.67 (s, 1H), 8.51 (dd, J = 9.8, 1.7 Hz, 1H), 8.26 (s, 1H), 8.13 (s, 1H), 7.88 (dd, J = 8.7, 1.5 Hz, 1H), 7.62 (d, J = 8.7 Hz, 1H), 7.59 (t, J = 51.2 Hz, 1H), 6.00 (d, J =1.4 Hz, 2H); LRMS (ES) m/z 413.29 ($M^+$ + 1). |
| 569 | 18921 | 2-(6-((4-(1H-indol-4-yl)-1H-1,2,3-triazol-1-yl)methyl)-5-fluoropyridin-3-yl)-5-(difluoromethyl)-1,3,4-oxadiazole $^1$H NMR (400 MHz, DMSO-$d_6$) δ 11.29 (s, 1H), 9.05 (s, 1H), 8.77 (s, 1H), 8.51 (dd, J = 9.8, 1.7 Hz, 1H), 7.74-7.38 (m, 4H), 7.21-7.13 (m, 1H), 6.98-6.91 (m, 1H), 6.03 (d, J = 1.3 Hz, 2H); LRMS (ES) m/z 412.53 ($M^+$ + 1). |
| 579 | 19058 | 2-(6-((4-(1H-indazol-4-yl)-1H-1,2,3-triazol-1-yl)methyl)-5-fluoropyridin-3-yl)-5-(difluoromethyl)-1,3,4-oxadiazole $^1$H NMR (400 MHz, DMSO-$d_6$) δ 9.05 (s, 1H), 8.93 (s, 1H), 8.57 (s, 1H), 8.51 (dd, J = 9.8, 1.7 Hz, 1H), 7.74-7.37 (m, 4H), 6.05 (d, J =1.3 Hz, 2H); LRMS (ES) m/z 413.29 ($M^+$ + 1). |

Example 491: Synthesis of compound 17362, 2-(difluoromethyl)-5-(4-((4-(6-(4-ethylpiperazin-1-yl)pyridin-2-yl)-1H-1,2,3-triazol-1-yl)methyl)-3-fluorophenyl)-1,3,4-oxadiazole

[Step 1] Synthesis of tert-butyl 4-(6-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate

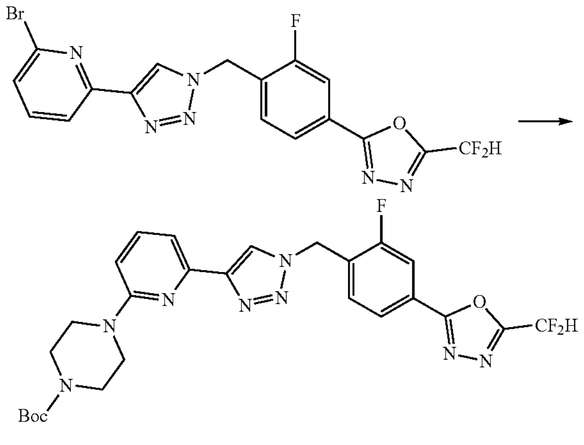

The 2-(4-((4-(6-bromopyridin-2-yl)-1H-1,2,3-triazol-1-yl)methyl)-3-fluorophenyl)-5-(difluoromethyl)-1,3,4-oxadiazole (0.800 g, 1.773 mmol) prepared in step 2 of example 489, tert-butyl piperazin-1-carboxylate (0.660 g, 3.546 mmol) and N,N-diisopropylethylamine (0.463 mL, 2.660 mmol) were dissolved in dimethyl sulfoxide (10 mL) at 130 °C, after which the resulting solution was stirred at the same temperature for 18 hours, and then a reaction was finished by lowering a temperature to room temperature. Water was poured into the reaction mixture and an extraction was performed with ethyl acetate. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(6-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate (0.407 g, 41.2%) in a yellow oil form.

[Step 2] Synthesis of 2-(difluoromethyl)-5-(3-fluoro-4-((4-(6-(piperazin-1-yl)pyridin-2-yl)-1H-1,2,3-triazol-1-yl)methyl)phenyl)-1,3,4-oxadiazole

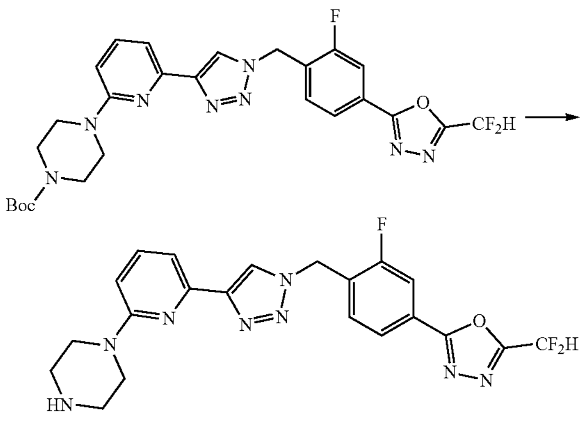

The tert-butyl 4-(6-(1-(4-(5-(difluoromethyl)-1,3,4-oxadiazol-2-yl)-2-fluorobenzyl)-1H-1,2,3-triazol-4-yl)pyridin-2-yl)piperazin-1-carboxylate (0.407 g, 0.731 mmol) prepared in step 1 and trifluoroacetic acid (0.560 mL, 7.313 mmol) were dissolved in dichloromethane (5 mL) at room temperature, after which the resulting solution was stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The obtained product was used without an additional purification process (2-(difluoromethyl)-5-(3-fluoro-4-((4-(6-(piperazin-1-yl)pyridin-2-yl)-1H-1,2,3-triazol-1-yl)methyl)phenyl)-1,3,4-oxadiazole, 0.325 g, 97.4%, brown oil).

[Step 3] Synthesis of Compound 17362

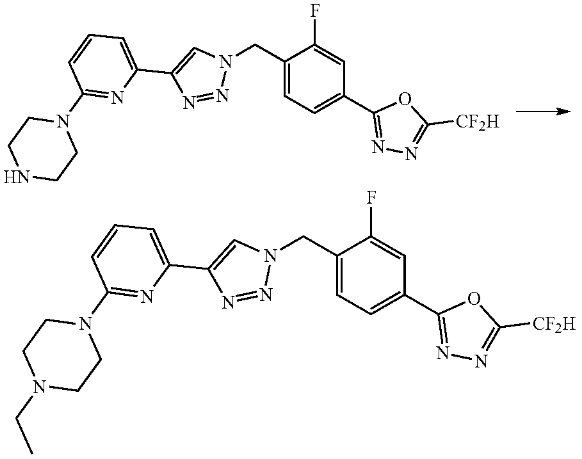

The 2-(difluoromethyl)-5-(3-fluoro-4-((4-(6-(piperazin-1-yl)pyridin-2-yl)-1H-1,2,3-triazol-1-yl)methyl)phenyl)-1,3,4-oxadiazole (0.065 g, 0.142 mmol) prepared in step 2 and acetaldehyde (0.016 mL, 0.285 mmol) were dissolved in dichloromethane (1 mL), after which the resulting solution was stirred at room temperature for 15 minutes, and then sodium triacetoxyborohydride (0.091 g, 0.427 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(4-((4-(6-(4-ethylpiperazin-1-yl)pyridin-2-yl)-1H-1,2,3-triazol-1-yl)methyl)-3-fluorophenyl)-1,3,4-oxadiazole (0.020 g, 29.0%) in a yellow solid form.

$^1$H NMR (400 MHz, $CD_3OD$) δ 8.50 (s, 1H), 7.98 (t, J=10.0 Hz, 2H), 7.67 (t, J=7.9 Hz, 1H), 7.60 (t, J=7.7 Hz, 1H), 7.39 (d, J=7.4 Hz, 1H), 7.24 (t, J=51.6 Hz, 1H), 6.83 (d, J=8.6 Hz, 1H), 5.87 (s, 2H), 3.76 (s, 4H), 2.90 (s, 4H), 2.82-2.76 (m, 2H), 1.26 (t, J=7.2 Hz, 3H); LRMS (ES) m/z 485.4 ($M^+$+1).

The compounds of table 147 were synthesized according to substantially the same process as described above in the synthesis of compound 17362 with an exception of using 2-(difluoromethyl)-5-(3-fluoro-4-((4-(6-(piperazin-1-yl)pyridin-2-yl)-1H-1,2,3-triazol-1-yl)methyl)phenyl)-1,3,4-oxadiazole and the reactant of table 146.

TABLE 146

| Example | Compound No. | Reactant | Yield (%) |
|---|---|---|---|
| 492 | 17363 | Acetone | 79 |
| 493 | 17364 | Cyclobutanone | 37 |
| 494 | 17365 | Oxetanone | 75 |

TABLE 147

| Example | Compound No. | Compound Name, 1H-NMR, MS (ESI) |
|---|---|---|
| 492 | 17363 | 2-(difluoromethyl)-5-(3-fluoro-4-((4-(6-(4-isopropylpiperazin-1-yl)pyridin-2-yl)-1H-1,2,3-triazol-1-yl)methyl)phenyl)-1,3,4-oxadiazole<br>$^1$H NMR (400 MHz, $CD_3OD$) δ 8.48 (s, 1H), 7.99-7.94 (m, 2H), 7.65-7.57 (m, 2H), 7.37-7.11 (m, 2H), 6.78 (d, J = 8.6 Hz, 1H), 5.86 (s, 2H), 3.64 (t, J = 5.0 Hz, 4H), 2.79-2.69 (m, 5H), 1.15 (d, J = 6.5 Hz, 6H); LRMS (ESI) m/z 499.2 ($M^+$ + H). |
| 493 | 17364 | 2-(4-((4-(6-(4-cyclobutylpiperazin-1-yl)pyridin-2-yl)-1H-1,2,3-triazol-1-yl)methyl)-3-fluorophenyl)-5-(difluoromethyl)-1,3,4-oxadiazole<br>$^1$H NMR (400 MHz, $CD_3OD$) δ 8.48 (s, 1H), 7.97 (t, J = 11.7 Hz, 2H), 7.65-7.56 (m, 2H), 7.36-7.11 (m, 2H), 6.78 (d, J = 8.5 Hz, 1H), 5.86 (s, 2H), 3.64 (t, J = 5.0 Hz, 4H), 2.89-2.81 (m, 1H), 2.50 (t, J = 5.0 Hz, 4H), 2.13-2.10 (m, 2H), 2.03-1.93 (m, 2H), 1.82-1.75 (m, 2H); LRMS (ESI) m/z 511.4 ($M^+$ + H). |
| 494 | 17365 | 2-(difluoromethyl)-5-(3-fluoro-4-((4-(6-(4-(oxetan-3-yl)piperazin-1-yl)pyridin-2-yl)-1H-1,2,3-triazol-1-yl)methyl)phenyl)-1,3,4-oxadiazole<br>$^1$H NMR (400 MHz, $CD_3OD$) δ 8.47 (s, 1H), 7.96 (t, J = 10.0 Hz, 2H), 7.65-7.55 (m, 2H), 7.34-7.11 (m, 2H), 6.77 (d, J = 8.5 Hz, 1H), 5.85 (s, 2H), 4.70 (dt, J = 28.9, 6.4 Hz, 4H), 3.66 (t, J = 4.9 Hz, 4H), 3.58-3.50 (m, 1H), 2.48 (t, J = 4.9 Hz, 4H); LRMS (ESI) m/z 513.2 ($M^+$ + H). |

Example 497: Synthesis of compound 17532, 2-(4-((4-(5-(azetidin-1-yl-methyl)pyridin-2-yl)-1H-1,2,3-triazol-1-yl)methyl)-3-fluorophenyl)$_5$-(difluoromethyl)-1,3,4-oxadiazole

[Step 1] Synthesis of 6-((trimethylsilyl)ethynyl)nicotinealdehyde

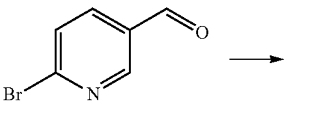

-continued

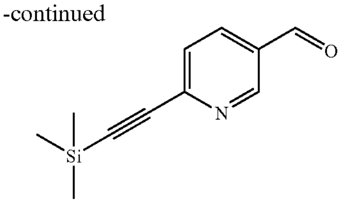

6-bromonicotinealdehyde (1.000 g, 5.376 mmol), bis(triphenylphosphine)palladium dichloride (0.151 g, 0.215 mmol), copper iodide (I/II, 0.102 g, 0.538 mmol) and 4,5-bis(diphenylphosphino)-9,9-diphenylxanthene (Xantphos, 0.124 g, 0.215 mmol) were dissolved in triethylamine (15 mL), after which trimethylsilyl acetylene (0.836 mL, 5.914 mmol) was added to the resulting solution at room temperature and stirred at the same temperature for 18 hours. The reaction mixture was filtered via a celite pad to remove a solid therefrom, after which solvent was removed from the resulting filtrate without the solid under reduced pressure. Then, the resulting concentrate was purified via column chromatography ($SiO_2$, 24 g cartridge; ethyl acetate/hexane=0 to 50%), and concentrated to obtain 6-((trimethylsilyl)ethynyl)nicotinealdehyde (0.400 g, 36.6%) in a light brown solid form.

[Step 2] Synthesis of 6-ethynylnicotinealdehyde

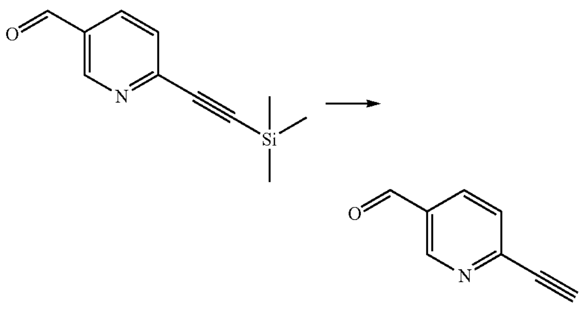

The 6-((trimethylsilyl)ethynyl)nicotinealdehyde (0.370 g, 1.820 mmol) prepared in step 1 and potassium carbonate (0.755 g, 5.459 mmol) were dissolved in methanol (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 40%) and concentrated to obtain 6-ethynylnicotinealdehyde (0.200 g, 83.8%) in beige solid form.

[Step 3] Synthesis of 6-(1-(4-(5-(difluoromethyl)-1,3,4-oxadiazol-2-yl)-2-fluorobenzyl)-1H-1,2,3-triazol-4-yl)nicotinealdehyde

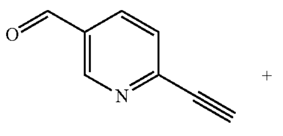

-continued

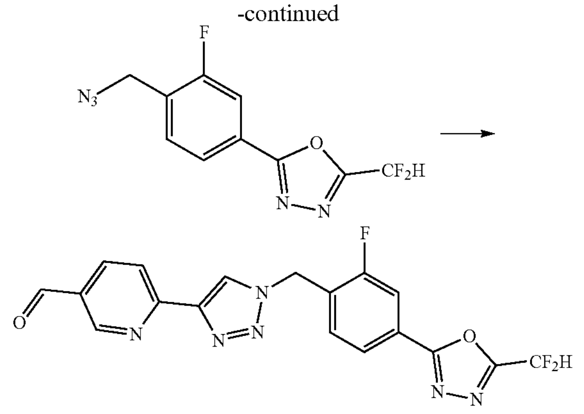

The 6-ethynylnicotinealdehyde (0.100 g, 0.763 mmol) prepared in step 2 and 2-(4-(azidomethyl)-3-fluorophenyl)-5-(difluoromethyl)-1,3,4-oxadiazole (0.205 g, 0.763 mmol) prepared in step 1 of example 2 were dissolved in tert-butanol (2 mL)/water (2 mL) at room temperature, after which sodium ascorbate (1.00 M solution, 0.076 mL, 0.076 mmol) and copper sulfate (I/II, 1.00 M solution, 0.038 mL, 0.038 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain 6-(1-(4-(5-(difluoromethyl)-1,3,4-oxadiazol-2-yl)-2-fluorobenzyl)-1H-1,2,3-triazol-4-yl)nicotinealdehyde (0.190 g, 62.2%) in a light yellow solid form.

[Step 4] Synthesis of Compound 17532

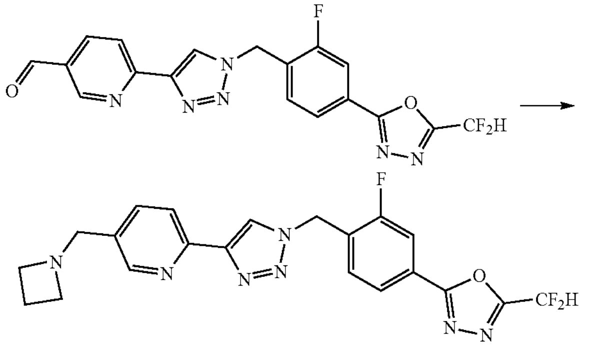

The 6-(1-(4-(5-(difluoromethyl)-1,3,4-oxadiazol-2-yl)-2-fluorobenzyl)-1H-1,2,3-triazol-4-yl)nicotinealdehyde (0.040 g, 0.104 mmol) prepared in step 3 and azetidine (0.020 g, 0.209 mmol) were dissolved in dichloromethane (1 mL) at room temperature, after which sodium triacetoxyborohydride (0.111 g, 0.522 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 80%) and concentrated to obtain 2-(4-((4-(5-(azetidin-1-yl-methyl)pyridin-2-yl)-1H-1,2,3-triazol-1-yl)methyl)-3-fluorophenyl)$_5$-(difluoromethyl)-1,3,4-oxadiazole (0.021 g, 47.4%) in a white solid form.

$^1$H NMR (400 MHz, $CD_3OD$) δ 8.53 (s, 1H), 8.07 (d, J=8.2 Hz, 1H), 7.98 (dd, J=11.6, 9.1 Hz, 1H), 7.87 (dd, J=8.0, 2.0 Hz, 1H), 7.63 (t, J=7.7 Hz, 1H), 7.24 (t, J=51.6 Hz, 1H), 5.89 (s, 2H), 4.60 (s, 2H), 3.75 (s, 2H), 3.41 (t, J=7.2 Hz, 4H), 2.19 (p, J=7.3 Hz, 2H); LRMS (ES) m/z 442.89 ($M^+$+1).

The compounds of table 149 were synthesized according to substantially the same process as described above in the synthesis of compound 17532 with an exception of using 6-(1-(4-(5-(difluoromethyl)-1,3,4-oxadiazol-2-yl)-2-fluorobenzyl)-1H-1,2,3-triazol-4-yl)nicotinealdehyde and the reactant of table 148.

TABLE 148

| Example | Compound No. | Reactant | Yield (%) |
|---|---|---|---|
| 498 | 17533 | Pyrrolidine | 58 |
| 499 | 17534 | Dimethylamine | 65 |
| 500 | 17535 | 4-methylpiperidine | 63 |
| 501 | 17545 | — | 12 |
| 531 | 18185 | (S)-(+)-3-fluoropyrrolidine | 44 |
| 536 | 18260 | (R)-(−)-3-fluoropyrrolidine | 46 |

TABLE 149

| Example | Compound No. | Compound Name, $^1$H-NMR, MS (ESI) |
|---|---|---|
| 498 | 17533 | 2-(difluoromethyl)-5-(3-fluoro-4-((4-(5-(pyrrolidin-1-ylmethyl)pyridin-2-yl)-1H-1,2,3-triazol-1-yl)methyl)phenyl)-1,3,4-oxadiazole $^1$H NMR (400 MHz, $CD_3OD$) δ 8.57 (s, 1H), 8.54 (s, 1H), 8.08 (d, J = 8.8 Hz, 1H), 7.98 (dd, J = 11.3, 9.1 Hz, 2H), 7.93 (d, J = 6.1 Hz, 1H), 7.63 (t, J = 7.6 Hz, 1H), 7.24 (t, J = 51.6 Hz, 1H), 5.89 (s, 2H), 3.75 (s, 2H), 2.69-2.54 (m, 4H), 1.90-1.78 (m, 4H); LRMS (ESI) m/z 455.92 ($M^+$ + 1). |
| 499 | 17534 | 1-(6-(1-(4-(5-(difluoromethyl)-1,3,4-oxadiazol-2-yl)-2-fluorobenzyl)-1H-1,2,3-triazol-4-yl)pyridin-3-yl)-N,N-dimethylmethanamine $^1$H NMR (400 MHz, $CDCl_3$) δ 8.50 (s, 1H), 8.21 (s, J = 49.6 Hz, 1H), 8.18 (d, J = 8.1 Hz, 1H), 7.98-7.87 (m, 1H), 7.80 (d, J = 8.0 Hz, 1H), 7.49 (t, J = 7.7 Hz, 1H), 6.94 (t, J = 51.7 Hz, 1H), 5.76 (s, 2H), 3.50 (s, 2H), 2.30 (s, 6H); LRMS (ESI) m/z 429.92 ($M^+$ + 1). |
| 500 | 17535 | 2-(difluoromethyl)-5-(3-fluoro-4-((4-(5-((4-methylpiperidin-1-yl)methyl)pyridin-2-yl)-1H-1,2,3-triazol-1-yl)methyl)phenyl)-1,3,4-oxadiazole $^1$H NMR (400 MHz, $CD_3OD$) δ 8.53 (d, J = 2.6 Hz, 1H), 8.07 (d, J = 7.8 Hz, 1H), 8.02-7.93 (m, 2H), 7.91 (dd, J = 8.1, 2.2 Hz, 1H), 7.63 (t, J = 7.7 Hz, 1H), 7.24 (t, J = 51.6 Hz, 1H), 5.89 (s, 2H), 3.60 (s, 2H), 2.90 (d, J = 11.6 Hz, 2H), 2.09 (t, J = 10.8 Hz, 2H), 1.67 (d, J = 12.8 Hz, 2H), 1.41 (s, 1H), 1.35-1.19 (m, 2H), 0.95 (d, J = 6.5 Hz, 3H); LRMS (ESI) m/z 484.99 ($M^+$ + 1). |
| 501 | 17545 | (6-(1-(4-(5-(difluoromethyl)-1,3,4-oxadiazol-2-yl)-2-fluorobenzyl)-1H-1,2,3-triazol-4-yl)pyridin-3-yl)methanol $^1$H NMR (400 MHz, $CD_3OD$) δ 8.60 (s, 1H), 8.04-7.88 (m, 4H), 7.64 (t, J = 7.7 Hz, 1H), 7.60-7.42 (m, 1H), 7.24 (t, J = 51.6 Hz, 1H), 5.89 (s, 2H), 4.72 (s, 2H); LRMS (ESI) m/z 403.30 ($M^+$ + 1). |
| 531 | 18185 | (S)-2-(difluoromethyl)-5-(3-fluoro-4-((4-(5-((3-fluoropyrrolidin-1-yl)methyl)pyridin-2-yl)-1H-1,2,3-triazol-1-yl)methyl)phenyl)-1,3,4-oxadiazole $^1$H NMR (400 MHz, $CD_3OD$) δ 8.57 (s, 1H), 8.53 (s, 1H), 8.08 (d, J = 8.2 Hz, 1H), 8.03-7.97 (m, 1H), 7.97-7.91 (m, 2H), 7.64 (t, J = 7.7 Hz, 1H), 7.24 (t, J = 51.6 Hz, 1H), 5.90 (s, 2H), 5.31-5.08 (m, J = 56.8 Hz, 1H), 3.83-3.68 (m, 2H), 3.44-3.34 (m, 1H), 3.01-2.85 (m, 2H), 2.74 (ddd, J = 16.8, 11.5, 4.9 Hz, 1H), 2.49 (dd, J = 15.3, 8.7 Hz, 1H), 2.24 (ddd, J = 22.0, 14.4, 8.2 Hz, 1H), 2.14-1.94 (m, 1H); LRMS (ESI) m/z 474.72 ($M^+$ + 1). |
| 536 | 18260 | (R)-2-(difluoromethyl)-5-(3-fluoro-4-((4-(5-((3-fluoropyrrolidin-1-yl)methyl)pyridin-2-yl)-1H-1,2,3-triazol-1-yl)methyl)phenyl)-1,3,4-oxadiazole $^1$H NMR (400 MHz, $CD_3OD$) δ 8.57 (s, 1H), 8.53 (s, 1H), 8.08 (d, J = 8.2 Hz, 1H), 8.02-7.91 (m, 3H), 7.64 (t, J = 7.6 Hz, 1H), 7.24 (t, J = 51.6 Hz, 1H), 5.90 (s, 2H), 5.29-5.09 (m, J = 53.8 Hz, 1H), 3.76 (q, J = 13.1 Hz, 2H), 3.49-3.36 (m, 1H), 3.00-2.86 (m, 2H), 2.81-2.65 (m, 1H), 2.49 (dd, J = 16.2, 8.5 Hz, 1H), 2.32-2.15 (m, 1H), 2.13-1.96 (m, 1H); LRMS (ESI) m/z 474.72 ($M^+$ + 1). |

Example 502: Synthesis of compound 17698, 2-(4-((4-(4-(1-cyclobutylazetidin-3-yl)phenyl)-1H-1,2,3-triazol-1-yl)methyl)-3-fluorophenyl)-5-(difluoromethyl)-1,3,4-oxadiazole

[Step 1] Synthesis of tert-butyl 3-(4-ethynylphenyl)azetidin-1-carboxylate

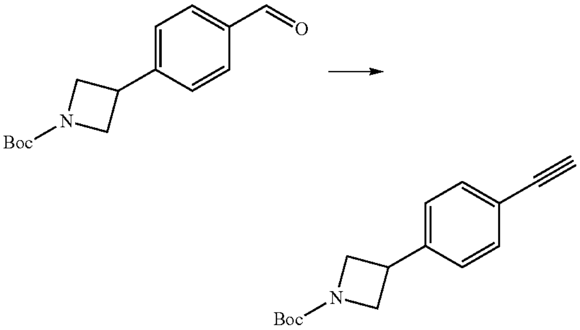

Dimethyl (1-diazo-2-oxopropyl)phosphonate (0.316 mL, 2.105 mmol) and potassium carbonate (0.529 g, 3.827 mmol) were dissolved in methanol (10 mL) at room temperature, after which tert-butyl 3-(4-formylphenyl)azetidin-1-carboxylate (0.500 g, 1.913 mmol) was added into the resulting solution and stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 30%) and concentrated to obtain tert-butyl 3-(4-ethynylphenyl) azetidin-1-carboxylate (0.287 g, 58.3%) in a yellow oil form.

[Step 2] Synthesis of tert-butyl 3-(4-(1-(4-(5-(difluoromethyl)-1,3,4-oxadiazol-2-yl)-2-fluorobenzyl)-1H-1,2,3-triazol-4-yl)phenyl)azetidin-1-carboxylate

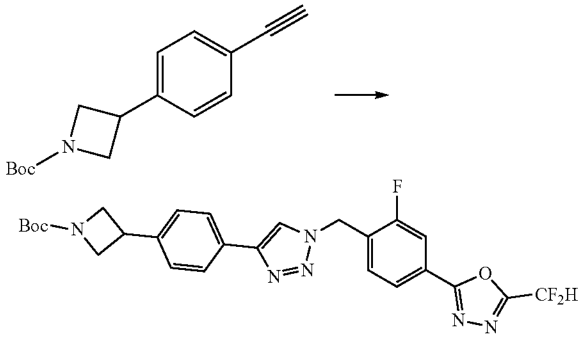

The tert-butyl 3-(4-ethynylphenyl)azetidin-1-carboxylate (0.095 g, 0.369 mmol) prepared in step 1, 2-(4-(azidomethyl)-3-fluorophenyl)-5-(difluoromethyl)-1,3,4-oxadiazole (0.099 g, 0.369 mmol) prepared in step 1 of example 2, sodium ascorbate (0.50 M solution in water, 0.074 mL, 0.037 mmol) and copper(II) sulfate pentahydrate (1.00 M solution in water, 0.007 mL, 0.007 mmol) were dissolved in tert-butanol (1 mL)/water (1 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 50%) and concentrated to obtain tert-butyl 3-(4-(1-(4-(5-(difluoromethyl)-1,3,4-oxadiazol-2-yl)-2-fluorobenzyl)-1H-1,2,3-triazol-4-yl)phenyl)azetidin-1-carboxylate (0.155 g, 79.7%) in a light yellow solid form.

[Step 3] Synthesis of 2-(4-((4-(4-(azetidin-3-yl)phenyl)-1H-1,2,3-triazol-1-yl)methyl)-3-fluorophenyl)-5-(difluoromethyl)-1,3,4-oxadiazole

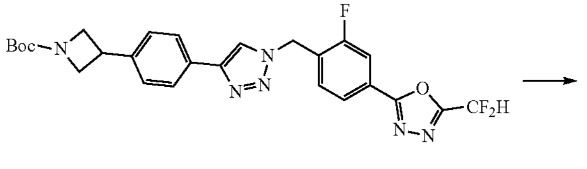

-continued

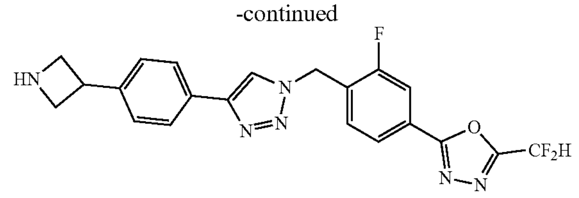

The tert-butyl 3-(4-(1-(4-(5-(difluoromethyl)-1,3,4-oxadiazol-2-yl)-2-fluorobenzyl)-1H-1,2,3-triazol-4-yl)phenyl) azetidin-1-carboxylate (0.155 g, 0.294 mmol) prepared in step 2 and trifluoroacetic acid (0.225 mL, 2.944 mmol) were dissolved in dichloromethane (2 mL) at room temperature, after which the resulting solution was stirred at the same temperature for 4 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Then, the obtained product was used without an additional purification process (2-(4-((4-(4-(azetidin-3-yl) phenyl)-1H-1,2,3-triazol-1-yl)methyl)-3-fluorophenyl)-5-(difluoromethyl)-1,3,4-oxadiazole, 0.120 g, 95.6%, yellow oil).

[Step 4] Synthesis of Compound 17698

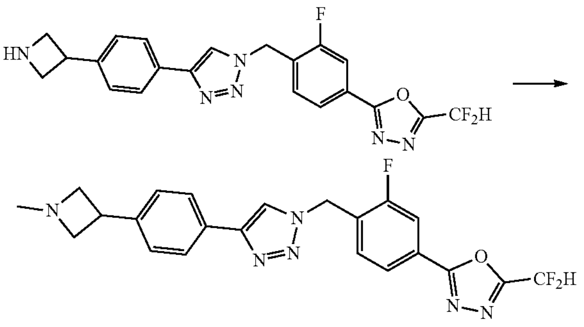

The 2-(4-((4-(4-(azetidin-3-yl)phenyl)-1H-1,2,3-triazol-1-yl)methyl)-3-fluorophenyl)-5-(difluoromethyl)-1,3,4-oxadiazole (0.040 g, 0.094 mmol) prepared in step 3 and formaldehyde (37.00% solution in water, 0.019 mL, 0.188 mmol) were dissolved in dichloromethane (1 mL), after which the resulting solution was stirred at room temperature for 15 minutes, and then sodium triacetoxyborohydride (0.060 g, 0.281 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(4-((4-(4-(1-cyclobutylazetidin-3-yl)phenyl)-1H-1,2,3-triazol-1-yl)methyl)-3-fluorophenyl)-5-(difluoromethyl)-1,3,4-oxadiazole (0.013 g, 31.5%) in a white solid form.

$^1H$ NMR (400 MHz, $CD_3OD$) δ 8.43 (s, 1H), 8.00-7.94 (m, 2H), 7.82 (d, J=8.2 Hz, 2H), 7.60 (t, J=7.7 Hz, 1H), 7.41 (d, J=8.3 Hz, 2H), 7.24 (t, J=51.6 Hz, 1H), 5.85 (s, 2H), 3.98-3.80 (m, 3H), 3.42 (t, J=7.5 Hz, 2H), 2.50 (s, 3H); LRMS (ES) m/z 441.3 ($M^+$+1).

The compounds of table 151 were synthesized according to substantially the same process as described above in the synthesis of compound 17698 with an exception of using 2-(4-((4-(4-(azetidin-3-yl)phenyl)-1H-1,2,3-triazol-1-yl)methyl)-3-fluorophenyl)-5-(difluoromethyl)-1,3,4-oxadiazole and the reactant of table 150.

TABLE 150

| Example | Compound No. | Reactant | Yield (%) |
|---|---|---|---|
| 503 | 17699 | Cyclobutanone | 58 |
| 504 | 17700 | Oxetan-3-one | 82 |

TABLE 151

| Example | Compound No. | Compound Name, $^1H$-NMR, MS (ESI) |
|---|---|---|
| 503 | 17699 | 2-(4-((4-(4-(1-cyclobutylazetidin-3-yl)phenyl)-1H-1,2,3-triazol-1-yl)methyl)-3-fluorophenyl)-5-(difluoromethyl)-1,3,4-oxadiazole<br>$^1H$ NMR (400 MHz, $CD_3OD$) δ 8.42 (s, 1H), 8.00-7.94 (m, 2H), 7.82 (d, J = 8.2 Hz, 2H), 7.60 (t, J = 7.7 Hz, 1H), 7.39 (d, J = 8.3 Hz, 2H), 7.24 (t, J = 51.6 Hz, 1H), 5.85 (s, 2H), 3.84-3.75 (m, 3H), 3.35-3.33 (m, 3H), 2.13-2.05 (m, 2H), 1.99-1.92 (m, 2H), 1.90-1.73 (m, 2H); MS (ESI) m/z 481.3 ($M^+$ + H). |
| 504 | 17700 | 2-(difluoromethyl)-5-(3-fluoro-4-((4-(4-(1-(oxetan-3-yl)azetidin-3-yl)phenyl)-1H-1,2,3-triazol-1-yl)methyl)phenyl)-1,3,4-oxadiazole<br>$^1H$ NMR (400 MHz, $CD_3OD$) δ 8.43 (s, 1H), 8.00-7.95 (m, 2H), 7.82 (d, J = 8.2 Hz, 2H), 7.60 (t, J = 7.7 Hz, 1H), 7.43 (d, J = 8.2 Hz, 2H), 7.24 (t, J = 51.6 Hz, 1H), 5.85 (s, 2H), 4.78 (t, J = 6.7 Hz, 2H), 4.57-4.54 (m, 2H), 3.92-3.81 (m, 4H), 3.38-3.35 (m, 2H); MS (ESI) m/z 483.3 ($M^+$ + H). |

Example 505: Synthesis of compound 17773, (S)-2-(difluoromethyl)-5-(3-fluoro-4-((4-(6-((3-fluoropyrrolidin-1-yl)methyl)pyridin-3-yl)-1H-1,2,3-triazol-1-yl)methyl)phenyl)-1,3,4-oxadiazole

[Step 1] Synthesis of 5-((trimethylsilyl)ethynyl)picolinealdehyde

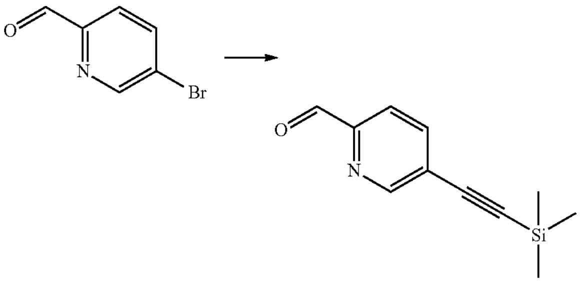

5-bromopicolinealdehyde (2.000 g, 10.752 mmol), trimethylsilyl acetylene (3.039 mL, 21.504 mmol), bis(triphenylphosphine)palladium dichloride (0.755 g, 1.075 mmol), copper iodide (I/II, 0.205 g, 1.075 mmol) and triphenylphosphine triphenylphosphine (0.282 g, 1.075 mmol) were mixed in tetrahydrofuran (20 mL)/triethylamine (8 mL), heated at 100 °C for 0.5 hours by irradiation with microwaves, and a reaction was finished by lowering a temperature to room temperature. The reaction mixture was filtered via a celite pad to remove a solid therefrom, after which solvent was removed from the resulting filtrate without the solid under reduced pressure. Then, the resulting concentrate was purified via column chromatography ($SiO_2$, 24 g cartridge; ethyl acetate/hexane=0 to 30%), and concentrated to obtain 5-((trimethylsilyl)ethynyl)picolinealdehyde (0.780 g, 35.7%) in a light brown solid form.

[Step 2]5-ethynylpicolinealdehyde

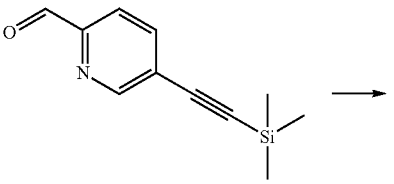

-continued

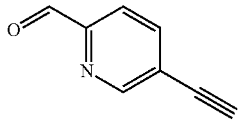

The 5-((trimethylsilyl)ethynyl)picolinealdehyde (0.247 g, 1.215 mmol) prepared in step 1 and potassium carbonate (0.504 g, 3.645 mmol) were dissolved in methanol (10 mL) at room temperature, after which the resulting solution was stirred at the same temperature for 18 hours. Solvent was removed from the reaction mixture under reduced pressure, after which saturated ammonium chloride aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain 5-ethynylpicolinealdehyde (0.120 g, 75.3%) in a yellow solid form.

[Step 3] Synthesis of 5-(1-(4-(5-(difluoromethyl)-1,3,4-oxadiazol-2-yl)-2-fluorobenzyl)-1H-1,2,3-triazol-4-yl)picolinealdehyde

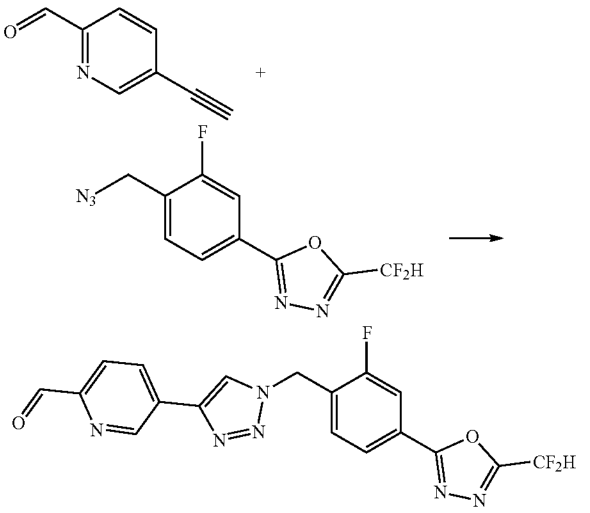

The 5-ethynylpicolinealdehyde (0.150 g, 1.144 mmol) prepared in step 2 and 2-(4-(azidomethyl)-3-fluorophenyl)-5-(difluoromethyl)-1,3,4-oxadiazole (0.308 g, 1.144 mmol) prepared in step 1 of example 2 were dissolved in tert-butanol (2 mL)/water (2 mL) at room temperature, after which sodium ascorbate (1.00 M solution, 0.114 mL, 0.114 mmol) and copper sulfate (I/II, 0.50 M solution, 0.114 mL, 0.057 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain 5-(1-(4-(5-(difluoromethyl)-1,3,4-oxadiazol-2-yl)-2-fluorobenzyl)-1H-1,2,3-triazol-4-yl)picolinealdehyde (0.350 g, 76.4%) in a light yellow solid form.

[Step 4] Synthesis of Compound 17773

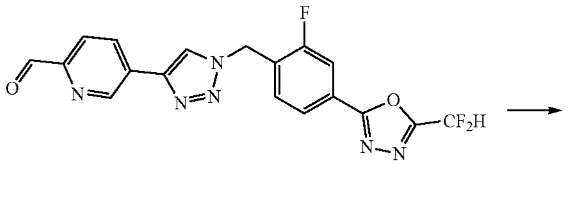

-continued

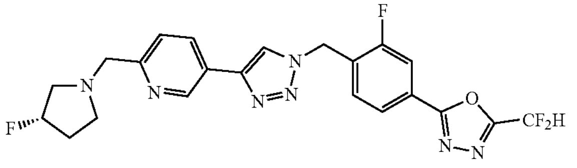

The 5-(1-(4-(5-(difluoromethyl)-1,3,4-oxadiazol-2-yl)-2-fluorobenzyl)-1H-1,2,3-triazol-4-yl)picolinealdehyde (0.040 g, 0.100 mmol) prepared in step 3, (S)-(+)-3-fluoropyrrolidine and hydrochloric acid (0.025 g, 0.200 mmol) were dissolved in dichloromethane (1 mL) at room temperature, after which sodium triacetoxyborohydride (0.106 g, 0.500 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 80%) and concentrated to obtain (S)-2-(difluoromethyl)-5-(3-fluoro-4-((4-(6-((3-fluoropyrrolidin-1-yl)methyl)pyridin-3-yl)-1H-1,2,3-triazol-1-yl)methyl)phenyl)-1,3,4-oxadiazole (0.029 g, 61.3%) in a white solid form.

$^1$H NMR (400 MHz, $CDCl_3$) δ 8.97 (s, 1H), 8.80 (s, 1H), 8.25-8.18 (m, 1H), 7.96 (d, J=9.1 Hz, 2H), 7.61 (t, J=7.7 Hz, 1H), 7.56 (t, J=51.3 Hz, 1H), 7.51 (d, J=8.1 Hz, 1H), 5.87 (s, 2H), 5.34-5.09 (m, J=55.8 Hz, 1H), 3.77 (s, 2H), 2.86 (dd, J=25.6, 11.1 Hz, 2H), 2.77-2.61 (m, 1H), 2.44-2.36 (m, J=7.2 Hz, 1H), 2.26-2.04 (m, 1H), 2.01-1.79 (m, 1H); LRMS (ES) m/z 474.28 ($M^+$+1).

The compounds of table 153 were synthesized according to substantially the same process as described above in the synthesis of compound 17773 with an exception of using 5-(1-(4-(5-(difluoromethyl)-1,3,4-oxadiazol-2-yl)-2-fluorobenzyl)-1H-1,2,3-triazol-4-yl)picolinealdehyde and the reactant of table 152.

TABLE 152

| Example | Compound No. | Reactant | Yield (%) |
|---|---|---|---|
| 506 | 17774 | (R)-(−)-3-fluoropyrrolidine | 67 |
| 507 | 17775 | 3,3-difluoropyrrolidine | 67 |
| 508 | 17777 | 4,4-dimethylpiperidine | 58 |
| 509 | 17778 | 4,4-difluoropiperidine | 53 |
| 525 | 18174 | Azetidine | 52 |
| 526 | 18175 | Pyrrolidine | 61 |
| 527 | 18176 | Dimethylamine | 51 |
| 528 | 18177 | 4-methylpiperidine | 55 |

TABLE 153

| Example | Compound No. | Compound Name, $^1$H-NMR, MS (ESI) |
|---|---|---|
| 506 | 17774 | (R)-2-(difluoromethyl)-5-(3-fluoro-4-((4-(6-((3-fluoropyrrolidin-1-yl)methyl)pyridin-3-yl)-1H-1,2,3-triazol-1-yl)methyl)phenyl)-1,3,4-oxadiazole $^1$H NMR (400 MHz, DMSO-$d_6$) δ 8.98 (s, 1H), 8.79 (s, 1H), 8.25-8.18 (m, 1H), 7.96 (d, J = 9.1 Hz, 2H), 7.61 (t, J = 7.7 Hz, 1H), 7.56 (t, J = 51.3 Hz, 1H), 7.51 (d, J = 8.1 Hz, 1H), 5.87 (s, 2H), 5.34-5.09 (m, J = 55.8 Hz, 1H), 3.77 (s, 2H), |

TABLE 153-continued

| Example | Compound No. | Compound Name, $^1$H-NMR, MS (ESI) |
|---|---|---|
| | | 2.86 (dd, J = 25.6, 11.1 Hz, 2H), 2.77-2.61 (m, 1H), 2.44-2.36 (m, J =7.2 Hz, 1H), 2.26-2.04 (m, 1H), 2.01-1.79 (m, 1H); LRMS (ESI) m/z 474.21 ($M^+$ + 1). |
| 507 | 17775 | 2-(difluoromethyl)-5-(4-((4-(6-((3,3-difluoropyrrolidin-1-yl)methyl)pyridin-3-yl)-1H-1,2,3-triazol-1-yl)methyl)-3-fluorophenyl)-1,3,4-oxadiazole $^1$H NMR (400 MHz, DMSO-$d_6$) δ 8.99 (d, J = 2.0 Hz, 1H), 8.80 (s, 1H), 8.23 (dd, J = 8.0, 2.2 Hz, 1H), 7.97 (s, 1H), 7.95 (s, 1H), 7.61 (t, J = 9.0 Hz, 1H), 7.56 (t, J = 51.3 Hz, 1H), 7.51 (d, J = 8.1 Hz, 1H), 5.88 (s, 2H), 3.78 (s, 2H), 2.96 (t, J = 13.4 Hz, 2H), 2.78 (t, J = 6.9 Hz, 2H), 2.26 (td, J = 15.4, 7.6 Hz, 2H); LRMS (ESI) m/z 492.32 ($M^+$ + 1). |
| 508 | 17777 | 2-(difluoromethyl)-5-(4-((4-(6-((4,4-dimethylpiperidin-1-yl)methyl)pyridin-3-yl)-1H-1,2,3-triazol-1-yl)methyl)-3-fluorophenyl)-1,3,4-oxadiazole $^1$H NMR (400 MHz, DMSO-$d_6$) δ 8.96 (d, J = 2.2 Hz, 1H), 8.78 (s, 1H), 8.19 (dd, J = 8.1, 2.2 Hz, 1H), 7.97 (s, 1H), 7.94 (s, 1H), 7.61 (t, J =7.6 Hz, 1H), 7.56 (t, J = 51.3 Hz, 1H), 7.51 (d, J = 8.1 Hz, 1H), 5.87 (s, 2H), 3.62 (s, 2H), 2.40 (s, 4H), 1.40-1.30 (m, 4H), 0.91 (s, 6H); LRMS (ESI) m/z 498.17 ($M^+$ + 1). |
| 509 | 17778 | 2-(difluoromethyl)-5-(4-((4-(6-((4,4-difluoropiperidin-1-yl)methyl)pyridin-3-yl)-1H-1,2,3-triazol-1-yl)methyl)-3-fluorophenyl)-1,3,4-oxadiazole $^1$H NMR (400 MHz, DMSO-$d_6$) δ 8.98 (d, J = 2.2 Hz, 1H), 8.80 (s, 1H), 8.22 (dd, J = 8.1, 2.2 Hz, 1H), 7.97 (s, 1H), 7.95 (s, 1H), 7.61 (t, J = 7.7 Hz, 1H), 7.56 (t, J = 51.2 Hz, 1H), 7.55 (d, J = 8.2 Hz, 1H), 5.87 (s, 2H), 3.71 (s, 2H), 2.61-2.53 (m, 4H), 2.07-1.88 (m, 4H); LRMS (ESI) m/z 506.29 ($M^+$ + 1). |
| 525 | 18174 | 2-(4-((4-(6-(azetidin-1-ylmethyl)pyridin-3-yl)-1H-1,2,3-triazol-1-yl)methyl)-3-fluorophenyl)-5-(difluoromethyl)-1,3,4-oxadiazole $^1$H NMR (400 MHz, $CD_3OD$) δ 8.99 (s, 1H), 8.59 (s, 1H), 8.26 (d, J = 7.9 Hz, 1H), 7.98 (dd, J = 12.0, 9.1 Hz, 2H), 7.63 (t, J = 7.7 Hz, 1H), 7.50 (d, J = 8.3 Hz, 1H), 7.24 (t, J = 51.6 Hz, 1H), 5.88 (s, 2H), 3.88 (s, 2H), 3.50 (s, 4H), 2.27-2.17 (m, 2H); LRMS (ESI) m/z 442.32 ($M^+$ + 1). |
| 526 | 18175 | 2-(difluoromethyl)-5-(3-fluoro-4-((4-(6-(pyrrolidin-1-ylmethyl)pyridin-3-yl)-1H-1,2,3-triazol-1-yl)methyl)phenyl)-1,3,4-oxadiazole $^1$H NMR (400 MHz, $CD_3OD$) δ 8.99 (s, 1H), 8.59 (s, 1H), 8.27 (d, J = 5.8 Hz, 1H), 7.98 (dd, J = 11.9, 9.1 Hz, 2H), 7.62 (dd, J = 14.0, 6.5 Hz, 2H), 7.24 (t, J = 51.6 Hz, 1H), 5.88 (s, 2H), 3.87 (s, 2H), 2.68 (s, 4H), 1.86 (s, 4H); LRMS (ESI) m/z 456.76 ($M^+$ + 1). |
| 527 | 18176 | 1-(5-(1-(4-(5-(difluoromethyl)-1,3,4-oxadiazol-2-yl)-2-fluorobenzyl)-1H-1,2,3-triazol-4-yl)pyridin-2-yl)-N,N-dimethylmethanamine $^1$H NMR (400 MHz, $CD_3OD$) δ 9.00 (s, 1H), 8.60 (s, 1H), 8.27 (s, 1H), 7.98 (dd, J = 11.9, 9.1 Hz, 2H), 7.70-7.51 (m, J = 7.7 Hz, 2H), 7.24 (t, J = 51.6 Hz, 1H), 5.88 (s, 2H), 3.67 (s, 2H), 2.33 (s, 6H); LRMS (ESI) m/z 430.77 ($M^+$ + 1). |
| 528 | 18177 | 2-(difluoromethyl)-5-(3-fluoro-4-((4-(6-((4-methylpiperidin-1-yl)methyl)pyridin-3-yl)-1H-1,2,3-triazol-1-yl)methyl)phenyl)-1,3,4-oxadiazole $^1$H NMR (400 MHz, $CD_3OD$) δ 8.98 (s, 1H), 8.59 (s, 1H), 8.26 (d, J = 8.1 Hz, 1H), 7.98 (dd, J = 11.7, 9.1 Hz, 2H), 7.63 (t, J = 7.5 Hz, 2H), 7.24 (t, J = 51.6 Hz, 1H), 5.88 (s, 2H), 3.69 (s, 2H), 2.92 (d, J = 12.3 Hz, 2H), 2.19-2.08 (m, 2H), 1.66 (d, J = 13.0 Hz, 2H), 1.49-1.36 (m, 1H), 1.31 (t, J = 10.2 Hz, 2H), 0.96 (d, J = 6.3 Hz, 3H); LRMS (ESI) m/z 484.74 ($M^+$ + 1). |

Example 514: Synthesis of compound 17912, 2-(4-((4-(5-(azetidin-1-ylmethyl)thiophen-2-yl)-1H-1,2,3-triazol-1-yl)methyl)-3-fluorophenyl)-5-(difluoromethyl)-1,3,4-oxadiazole

[Step 1]5-((trimethylsilyl)ethynyl)thiophen-2-carbaldehyde

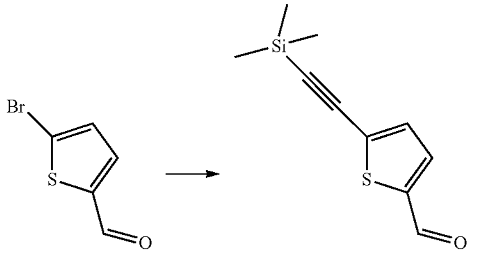

5-bromothiophen-2-carbaldehyde (0.622 mL, 5.210 mmol), bis(triphenylphosphine)palladium dichloride (0.073 g, 0.104 mmol), copper iodide (I/II, 0.010 g, 0.052 mmol) and diethylamine (10.778 mL, 104.199 mmol) were dissolved in tetrahydrofuran, after which trimethylsilyl acetylene (0.810 mL, 5.731 mmol) was added to the resulting solution at 0 °C, stirred at the same temperature for 0.5 hours, and further stirred at room temperature for 18 hours. Solvent was removed from the reaction mixture under reduced pressure, after which water was poured into the resulting concentrate, and then an extraction was performed with diethyl ether. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/hexane=0 to 50%) and concentrated to obtain 5-((trimethylsilyl)ethynyl)thiophen-2-carbaldehyde (0.600 g, 55.3%) in a brown solid form.

[Step 2] Synthesis of 5-ethynylthiophen-2-carbaldehyde

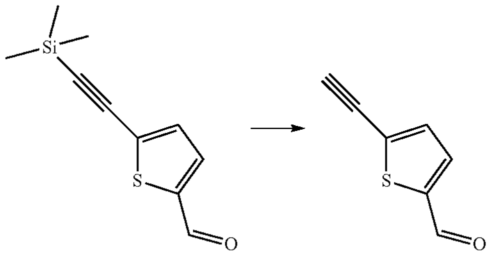

The 5-((trimethylsilyl)ethynyl)thiophen-2-carbaldehyde (0.550 g, 2.640 mmol) prepared in step 1 and potassium carbonate (1.094 g, 7.919 mmol) were dissolved in methanol (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%) and concentrated to obtain 5-ethynylthiophen-2-carbaldehyde (0.300 g, 83.5%) in a light yellow solid form.

[Step 3] Synthesis of 5-(1-(4-(5-(difluoromethyl)-1,3,4-oxadiazol-2-yl)-2-fluorobenzyl)-1H-1,2,3-triazol-4-yl)thiophen-2-carbaldehyde

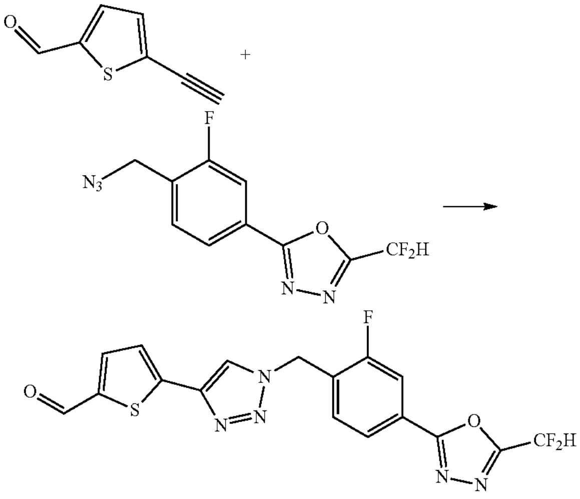

The 5-ethynylthiophen-2-carbaldehyde (0.250 g, 1.836 mmol) prepared in step 2 and 2-(4-(azidomethyl)-3-fluorophenyl)-5-(difluoromethyl)-1,3,4-oxadiazole (0.494 g, 1.836 mmol) prepared in step 1 of example 2 were dissolved in tert-butanol (1 mL)/water (1 mL) at room temperature, after which sodium ascorbate (1.00 M solution, 0.184 mL, 0.184 mmol) and copper sulfate (I/II, 0.50 M solution, 0.184 mL, 0.092 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 40%) and concentrated to obtain 5-(1-(4-(5-(difluoromethyl)-1,3,4-oxadiazol-2-yl)-2-fluorobenzyl)-1H-1,2,3-triazol-4-yl)thiophen-2-carbaldehyde (0.590 g, 79.3%) in a light yellow solid form.

[Step 4] Synthesis of Compound 17912

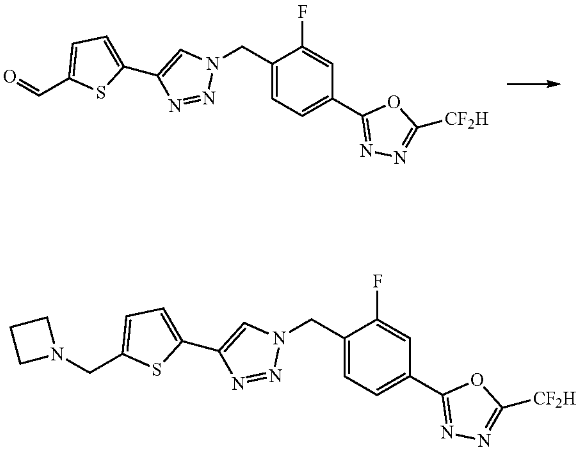 [SMILES: O=Cc1ccc(-c2cn(Cc3ccc(-c4nnc(C(F)F)o4)cc3F)nn2)s1 ; Fc1cc(-c2nnc(C(F)F)o2)ccc1Cn1cc(-c2ccc(CN3CCC3)s2)nn1]

The 5-(1-(4-(5-(difluoromethyl)-1,3,4-oxadiazol-2-yl)-2-fluorobenzyl)-1H-1,2,3-triazol-4-yl)thiophen-2-carbaldehyde (0.050 g, 0.123 mmol) prepared in step 3, azetidine and hydrochloric acid (0.023 g, 0.247 mmol) were dissolved in dichloromethane (1 mL) at room temperature, after which sodium triacetoxyborohydride (0.131 g, 0.617 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 80%) and concentrated to obtain 2-(4-((4-(5-(azetidin-1-ylmethyl)thiophen-2-yl)-1H-1,2,3-triazol-1-yl)methyl)-3-fluorophenyl)-5-(difluoromethyl)-1,3,4-oxadiazole (0.042 g, 76.3%) in a beige solid form.

$^1$H NMR (400 MHz, DMSO-$d_6$) δ 8.54 (s, 1H), 7.96 (s, 1H), 7.94 (s, 1H), 7.58 (d, J=7.6 Hz, 1H), 7.56 (t, J=51.3 Hz, 1H), 7.26 (d, J=3.5 Hz, 1H), 6.91 (d, J=3.6 Hz, 1H), 5.82 (s, 2H), 3.68 (s, 2H), 3.16 (t, J=7.0 Hz, 4H), 2.05-1.93 (m, 2H); LRMS (ES) m/z 447.31 ($M^+$+1).

The compounds of table 155 were synthesized according to substantially the same process as described above in the synthesis of compound 17912 with an exception of using 5-(1-(4-(5-(difluoromethyl)-1,3,4-oxadiazol-2-yl)-2-fluorobenzyl)-1H-1,2,3-triazol-4-yl)thiophen-2-carbaldehyde and the reactant of table 154.

TABLE 154

| Example | Compound No. | Reactant | Yield (%) |
|---|---|---|---|
| 515 | 17913 | Pyrrolidine | 72 |
| 516 | 17914 | Dimethylamine | 72 |
| 517 | 17915 | 4-methylpiperidine | 71 |
| 518 | 17916 | (S)-(+)-3-fluoropyrrolidine | 76 |
| 519 | 17917 | (R)-(−)-3-fluoropyrrolidine | 72 |
| 520 | 17922 | — | 11 |

TABLE 155

| Example | Compound No. | Compound Name, $^1$H-NMR, MS (ESI) |
|---|---|---|
| 515 | 17913 | 2-(difluoromethyl)-5-(3-fluoro-4-((4-(5-(pyrrolidin-1-ylmethyl)thiophen-2-yl)-1H-1,2,3-triazol-1-yl)methyl)phenyl)-1,3,4-oxadiazole $^1$H NMR (400 MHz, DMSO-$d_6$) δ 8.54 (s, 1H), 7.96 (s, 1H), 7.94 (s, 1H), 7.59 (d, J = 7.8 Hz, 1H), 7.56 (t, J = 51.3 Hz, 1H), 7.26 (d, J =3.6 Hz, 1H), 6.93 (d, J = 3.5 Hz, 1H), 5.82 (s, 2H), 3.77 (s, 2H), 2.51-2.43 (m, 4H), 1.71 (s, 4H); LRMS (ESI) m/z 461.34 ($M^+$ + 1). |
| 516 | 17914 | 1-(5-(1-(4-(5-(difluoromethyl)-1,3,4-oxadiazol-2-yl)-2-fluorobenzyl)-1H-1,2,3-triazol-4-yl)thiophen-2-yl)-N,N-dimethylmethanamine $^1$H NMR (400 MHz, DMSO-$d_6$) δ 8.55 (s, 1H), 7.96 (s, 1H), 7.94 (s, 1H), 7.59 (d, J = 7.6 Hz, 1H), 7.56 (t, J = 51.3 Hz, 1H), 7.28 (d, J = 3.5 Hz, 1H), 6.94 (d, J = 3.5 Hz, 1H), 5.83 (s, 2H), 3.60 (s, 2H), 2.19 (s, 6H); LRMS (ESI) m/z 435.26 ($M^+$ + 1). |
| 517 | 17915 | 2-(difluoromethyl)-5-(3-fluoro-4-((4-(5-((4-methylpiperidin-1-yl)methyl)thiophen-2-yl)-1H-1,2,3-triazol-1-yl)methyl)phenyl))-1,3,4-oxadiazole $^1$H NMR (400 MHz, DMSO-$d_6$) δ 8.54 (s, 3H), 7.96 (s, 1H), 7.94 (s, 1H), 7.58 (d, J = 7.9 Hz, 1H), 7.56 (t, J = 51.3 Hz, 1H), 7.27 (d, J = 3.5 Hz, 1H), 6.92 (d, J = 3.6 Hz, 1H), 5.82 (s, 2H), 3.64 (s, 2H), 2.84 (d, J = 11.2 Hz, 2H), 1.95 (t, J = 10.6 Hz, 2H), 1.58 (d, J = 10.7 Hz, 2H), 1.32 (s, 1H), 1.21-1.06 (m, 2H), 0.89 (d, J = 6.5 Hz, 3H); LRMS (ESI) m/z 489.34 ($M^+$ + 1). |
| 518 | 17916 | (S)-2-(difluoromethyl)-5-(3-fluoro-4-((4-(5-((3-fluoropyrrolidin-1-yl)methyl)thiophen-2-yl)-1H-1,2,3-triazol-1-yl)methyl)phenyl))-1,3,4-oxadiazole $^1$H NMR (400 MHz, DMSO) δ 8.56 (s, 2H), 7.96 (s, 1H), 7.94 (s, 1H), 7.59 (d, J = 7.7 Hz, 1H), 7.56 (t, J = 51.3 Hz, 1H), 7.28 (d, J = 3.6 Hz, 1H), 6.96 (d, J = 3.6 Hz, 1H), 5.83 (s, 2H), 5.31-5.10 (m, J = 54.7 Hz, 1H), 3.82 (s, 2H), 2.91-2.76 (m, 2H), 2.74-2.60 (m, 1H), 2.45-2.36 (m, 1H), 2.24-2.04 (m, 1H), 2.00-1.80 (m, 1H); LRMS (ESI) m/z 479.28 ($M^+$ + 1). |
| 519 | 17917 | (R)-2-(difluoromethyl)-5-(3-fluoro-4-((4-(5-((3-fluoropyrrolidin-1-yl)methyl)thiophen-2-yl)-1H-1,2,3-triazol-1-yl)methyl)phenyl))-1,3,4-oxadiazole $^1$H NMR (400 MHz, DMSO-$d_6$) δ 8.56 (s, 2H), 7.96 (s, 1H), 7.94 (s, 1H), 7.59 (d, J = 7.7 Hz, 1H), 7.56 (t, J = 51.3 Hz, 1H), 7.28 (d, J = 3.6 Hz, 1H), 6.96 (d, J = 3.6 Hz, 1H), 5.83 (s, 2H), 5.31-5.10 (m, J=54.7 Hz, 1H), 3.82 (s, 2H), 2.91-2.76 (m, 2H), 2.74-2.60 (m, 1H), 2.45-2.36 (m, 1H), 2.24-2.04 (m, 1H), 2.00-1.80 (m, 1H); LRMS (ESI) m/z 479.34 ($M^+$ + 1). |
| 520 | 17922 | $^1$H NMR (400 MHz, DMSO-$d_6$) δ 9.93 (s, 1H), 8.86 (s, 1H), 8.05 (d, J = 3.9 Hz, 1H), 7.96 (d, J = 8.8 Hz, 1H), 7.68 (d, J = 4.0 Hz, 1H), 7.64 (t, J = 7.6 Hz, 1H), 7.56 (t, J = 51.3 Hz, 1H), 5.88 (s, 2H), 3.29 (s, 2H); LRMS (ESI) m/z 406.67 ($M^+$ + 1). |

Example 523: Synthesis of compound 18058, 2-(difluoromethyl)-5-(5-fluoro-6-((4-(4-(pyrrolidin-1-ylmethyl)phenyl)-1H-1,2,3-triazol-1-yl)methyl)pyridin-3-yl)-1,3,4-oxadiazole

[Step 1] Synthesis of 4-(1-((5-(5-(difluoromethyl)-1,3,4-oxadiazol-2-yl)-3-fluoropyridin-2-yl)methyl)-1H-1,2,3-triazol-4-yl)benzaldehyde

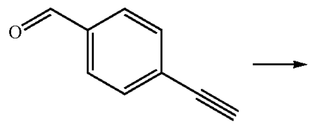

-continued

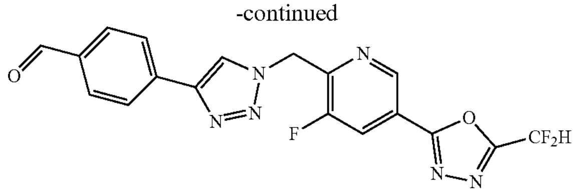

4-ethynylbenzaldehyde (0.050 mL, 0.423 mmol), 2-(6-(azidomethyl)-5-fluoropyridin-3-yl)-5-(difluoromethyl)-1,3,4-oxadiazole (0.114 g, 0.423 mmol) prepared in step 1 of example 490, sodium ascorbate (0.50 M solution in water, 0.085 mL, 0.042 mmol) and copper(II) sulfate pentahydrate (1.00 M solution in water, 0.004 mL, 0.004 mmol) were dissolved in tert-butanol (1 mL)/water (1 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added to the resulting solution and stirred to filter out a precipitated solid, washed with hexane, and dried to obtain 4-(1-((5-(5-(difluoromethyl)-1,3,4-oxadiazol-2-yl)-3-fluoropyridin-2-yl)methyl)-1H-1,2,3-triazol-4-yl)benzaldehyde (0.089 g, 52.6%) in a yellow solid form.

[Step 2] Synthesis of Compound 18058

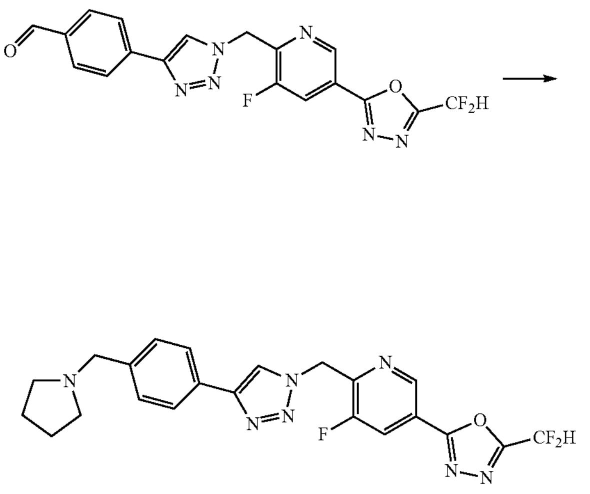

The 4-(1-((5-(5-(difluoromethyl)-1,3,4-oxadiazol-2-yl)-3-fluoropyridin-2-yl)methyl)-1H-1,2,3-triazol-4-yl)benzaldehyde (0.089 g, 0.222 mmol) prepared in step 1, pyrrolidine (0.036 mL, 0.444 mmol) and acetic acid (0.013 mL, 0.222 mmol) were dissolved in dichloromethane (0.5 mL)/methanol (0.5 mL), after which the resulting solution was stirred at room temperature for 1 hour, and then sodium triacetoxyborohydride (0.141 g, 0.666 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(5-fluoro-6-((4-(4-(pyrrolidin-1-ylmethyl)phenyl)-1H-1,2,3-triazol-1-yl)methyl)pyridin-3-yl)-1,3,4-oxadiazole (0.032 g, 31.6%) in a yellow solid form.

$^1H$ NMR (400 MHz, $CD_3OD$) δ 9.10 (s, 1H), 8.49 (s, 1H), 8.39 (dd, J=9.6, 1.7 Hz, 1H), 7.83 (d, J=8.2 Hz, 2H), 7.45 (d, J=8.2 Hz, 2H), 7.27 (t, J=51.5 Hz, 1H), 6.30 (d, J=238.5 Hz, 2H), 3.71 (s, 2H), 2.62 (s, 4H), 1.87-1.83 (m, 4H); LRMS (ES) m/z 456.4 ($M^+$+1).

Example 524: Synthesis of compound 18059, 2-(difluoromethyl)-5-(5-fluoro-6-((4-(5-(pyrrolidin-1-ylmethyl)thiophen-2-yl)-1H-1,2,3-triazol-1-yl)methyl)pyridin-3-yl)-1,3,4-oxadiazole

[Step 1] Synthesis of 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde

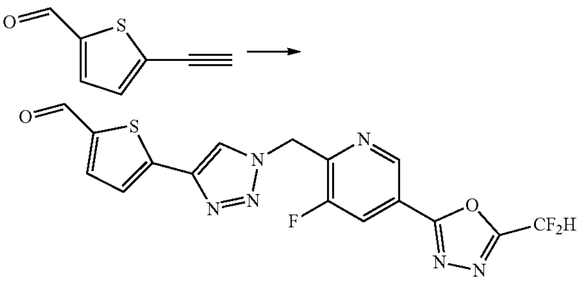

5-ethynylthiophen-2-carbaldehyde (0.060 g, 0.441 mmol), 2-(6-(azidomethyl)-5-fluoropyridin-3-yl)-5-(difluoromethyl)-1,3,4-oxadiazole (0.119 g, 0.441 mmol) prepared in step 1 of example 490, sodium ascorbate (0.50 M solution in water, 0.088 mL, 0.044 mmol) and copper(II) sulfate pentahydrate (1.00 M solution in water, 0.004 mL, 0.004 mmol) were dissolved in tert-butanol (1 mL)/water (1 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde (0.075 g, 41.9%) in a yellow solid form.

[Step 2] Synthesis of Compound 18059

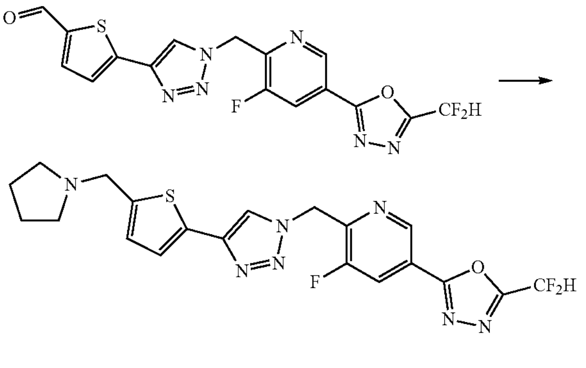

The 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde (0.075 g, 0.185 mmol) prepared in step 1, pyrrolidine (0.030 mL, 0.369 mmol) and acetic acid (0.011 mL, 0.185 mmol) were dissolved in dichloromethane (0.5 mL)/methanol (0.5 mL), after which the resulting solution was stirred at room temperature for 1 hour, and then sodium triacetoxyborohydride (0.117 g, 0.554 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(5-fluoro-6-((4-(5-(pyrrolidin-1-ylmethyl)thiophen-2-yl)-1H-1,2,3-triazol-1-yl)methyl)pyridin-3-yl)-1,3,4-oxadiazole (0.023 g, 27.0%) in a yellow solid form.

$^1H$ NMR (400 MHz, $CD_3OD$) δ 9.10 (s, 1H), 8.40-8.37 (m, 2H), 7.30 (d, J=3.6 Hz, 1H), 7.27 (t, J=51.5 Hz, 1H), 7.01 (d, J=3.6 Hz, 1H), 5.98 (d, J=1.8 Hz, 2H), 3.89 (s, 2H), 2.66-2.64 (m, 4H), 1.87-1.84 (m, 4H); LRMS (ES) m/z 462.4 ($M^+$+1).

Example 529: Synthesis of compound 18178, 2-(4-((4-(5-(azetidin-1-ylmethyl)thiophen-3-yl)-1H-1,2,3-triazol-1-yl)methyl)-3-fluorophenyl)-5-(difluoromethyl)-1,3,4-oxadiazole

[Step 1] Synthesis of 4-((trimethylsilyl)ethynyl)thiophen-2-carbaldehyde

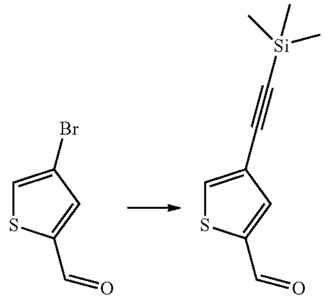

4-bromothiophen-2-carbaldehyde (2.000 g, 10.420 mmol), bis(triphenylphosphine)palladium dichloride (0.366 g, 0.521 mmol) and copper iodide (I/II, 0.198 g, 1.042 mmol) were dissolved in tetrahydrofuran (15 mL)/triethylamine (15 mL), after which trimethylsilyl acetylene (2.209 mL, 15.630 mmol) was added to the resulting solution at room temperature, and stirred at 60 °C for 2 hours, and then a reaction was finished by lowering a temperature to room temperature. The reaction mixture was filtered via a celite pad to remove a solid therefrom, after which solvent was removed from the resulting filtrate without the solid under reduced pressure. Then, the resulting concentrate was purified via column chromatography ($SiO_2$, 24 g cartridge; ethyl acetate/hexane=0 to 10%), and concentrated to obtain 4-((trimethylsilyl)ethynyl)thiophen-2-carbaldehyde (1.200 g, 55.3%) in a brown solid form.

[Step 2] Synthesis of 4-ethynylthiophen-2-carbaldehyde

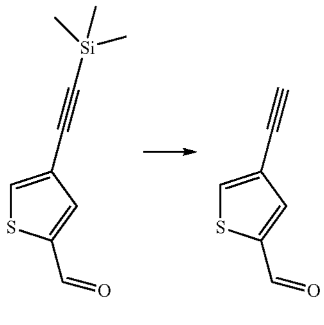

The 4-((trimethylsilyl)ethynyl)thiophen-2-carbaldehyde (1.500 g, 7.199 mmol) prepared in step 1 and potassium carbonate (2.985 g, 21.598 mmol) were dissolved in methanol (10 mL) at room temperature, after which the resulting solution was stirred at the same temperature for 18 hours. Solvent was removed from the reaction mixture under reduced pressure, after which saturated ammonium chloride aqueous solution was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 20%) and concentrated to obtain 4-ethynylthiophen-2-carbaldehyde (0.650 g, 66.3%) in a yellow solid form.

[Step 3] Synthesis of 4-(1-(4-(5-(difluoromethyl)-1,3,4-oxadiazol-2-yl)-2-fluorobenzyl)-1H-1,2,3-triazol-4-yl)thiophen-2-carbaldehyde

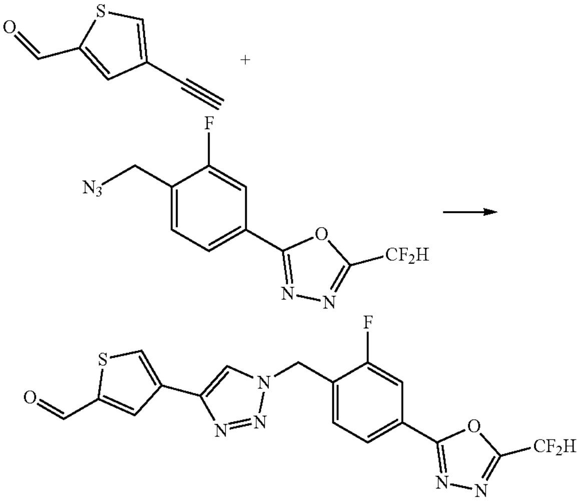

The 4-ethynylthiophen-2-carbaldehyde (0.150 g, 1.102 mmol) prepared in step 2 and 2-(4-(azidomethyl)-3-fluorophenyl)-5-(difluoromethyl)-1,3,4-oxadiazole (0.297 g, 1.102 mmol) prepared in step 1 of example 2 were dissolved in tert-butanol (2 mL)/water (2 mL) at room temperature, after which sodium ascorbate (1.00 M solution, 0.110 mL, 0.110 mmol) and copper sulfate (I/II, 0.50 M solution, 0.110 mL, 0.055 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain 4-(1-(4-(5-(difluoromethyl)-1,3,4-oxadiazol-2-yl)-2-fluorobenzyl)-1H-1,2,3-triazol-4-yl)thiophen-2-carbaldehyde (0.370 g, 82.9%) in a beige solid form.

[Step 4] Synthesis of Compound 18178

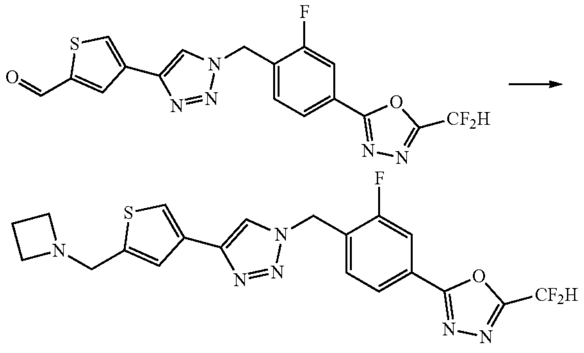

The 4-(1-(4-(5-(difluoromethyl)-1,3,4-oxadiazol-2-yl)-2-fluorobenzyl)-1H-1,2,3-triazol-4-yl)thiophen-2-carbaldehyde (0.040 g, 0.099 mmol) prepared in step 3 and azetidine (0.011 g, 0.197 mmol) were dissolved in dichloromethane (1 mL) at room temperature, after which sodium triacetoxyborohydride (0.105 g, 0.493 mmol) was added to the resulting solution and stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; dichloromethane/methanol=100 to 80%) and concentrated to obtain 2-(4-((4-(5-(azetidin-1-ylmethyl)thiophen-3-yl)-1H-1,2,3-triazol-1-yl)methyl)-3-fluorophenyl)-5-(difluoromethyl)-1,3,4-oxadiazole (0.020 g, 45.4%) in a light yellow solid form.

$^1H$ NMR (400 MHz, $CD_3OD$) δ 8.31 (s, 2H), 7.97 (dd, J=11.0, 9.2 Hz, 2H), 7.68 (d, J=1.2 Hz, 1H), 7.59 (t, J=7.6 Hz, 1H), 7.36 (s, 1H), 7.24 (t, J=51.6 Hz, 1H), 5.83 (s, 2H), 3.82 (s, 2H), 3.40-3.33 (m, 4H), 2.21-2.09 (m, 2H); LRMS (ES) m/z 447.69 ($M^+$+1).

The compounds of table 157 were synthesized according to substantially the same process as described above in the synthesis of compound 18178 with an exception of using 4-(1-(4-(5-(difluoromethyl)-1,3,4-oxadiazol-2-yl)-2-fluorobenzyl)-1H-1,2,3-triazol-4-yl)thiophen-2-carbaldehyde and the reactant of table 156.

TABLE 156

| Example | Compound No. | Reactant | Yield (%) |
|---|---|---|---|
| 530 | 18180 | (R)-(−)-3-fluoropyrrolidine | 46 |
| 532 | 18187 | Pyrrolidine | 48 |
| 533 | 18188 | Dimethylamine | 44 |

TABLE 157

| Example | Compound No. | Compound Name, $^1H$-NMR, MS (ESI) |
|---|---|---|
| 530 | 18180 | (R)-2-(difluoromethyl)-5-(3-fluoro-4-((4-(5-((3-fluoropyrrolidin-1-yl)methyl)thiophen-3-yl)-1H-1,2,3-triazol-1-yl)methyl)phenyl)-1,3,4-oxadiazole $^1H$ NMR (400 MHz, $CD_3OD$) δ 8.31 (s, 1H), 7.97 (dd, J = 11.0, 9.1 Hz, 2H), 7.69 (d, J = 1.2 Hz, 1H), 7.59 (t, J = 7.7 Hz, 1H), 7.39 (s, 1H), 7.24 (t, J = 51.6 Hz, 1H), 5.83 (s, 2H), 5.29-5.07 (m, 1H), 3.98-3.86 (m, 2H), 3.75 (dd, J = 25.3, 15.5 Hz, 1H), 3.02-2.88 (m, 2H), 2.78 (ddd, J = 30.6, 11.7, 5.1 Hz, 1H), 2.55 (dd, J = 14.9, 8.4 Hz, 1H), 2.34-2.13 (m, 1H), 2.08-1.93 (m, 1H); LRMS (ESI) m/z 479.73 ($M^+$ + 1). |
| 532 | 18187 | 2-(difluoromethyl)-5-(3-fluoro-4-((4-(5-(pyrrolidin-1-ylmethyl)thiophen-3-yl)-1H-1,2,3-triazol-1-yl)methyl)phenyl)-1,3,4-oxadiazole $^1H$ NMR (400 MHz, $CD_3OD$) δ 8.31 (s, 1H), 7.97 (dd, J = 11.0, 9.1 Hz, 2H), 7.69 (d, J = 1.3 Hz, 1H), 7.59 (t, J =7.6 Hz, 1H), 7.39 (s, 1H), 7.24 (t, J = 51.6 Hz, 2H), 5.84 (s, 2H), 3.89 (s, 2H), 2.64 (s, 4H), 1.85 (dd, J = 6.8, 3.3 Hz, 4H); LRMS (ESI) m/z 461.68 ($M^+$ + 1). |
| 533 | 18188 | 1-(4-(1-(4-(5-(difluoromethyl)-1,3,4-oxadiazol-2-yl)-2-fluorobenzyl)-1H-1,2,3-triazol-4-yl)thiophen-2-yl)-N,N-dimethylmethanamine $^1H$ NMR (400 MHz, $CD_3OD$) δ 8.31 (s, 1H), 7.98 (dd, J = 10.8, 9.1 Hz, 2H), 7.71 (d, J = 1.3 Hz, 1H), 7.59 (t, J = 7.7 Hz, 1H), 7.39 (s, 1H), 7.24 (t, J = 51.6 Hz, 1H), 5.84 (s, 2H), 3.74 (s, 2H), 2.31 (s, 6H); LRMS (ESI) m/z 435.69 ($M^+$ + 1). |

Example 537: Synthesis of compound 18305, 2-(difluoromethyl)-5-(5-fluoro-6-((4-(pyridin-3-yl)-1H-1,2,3-triazol-1-yl)methyl)pyridin-3-yl)-1,3,4-oxadiazole

[Step 1] Synthesis of 3-ethynylpyridine

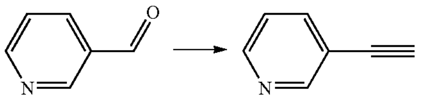

Dimethyl (1-diazo-2-oxopropyl)phosphonate (0.462 mL, 3.081 mmol) and potassium carbonate (0.774 g, 5.602 mmol) were dissolved in methanol (10 mL) at room temperature, after which nicotinealdehyde (0.263 mL, 2.801 mmol) was added into the resulting solution and stirred at the same temperature for 4 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 30%) and concentrated to obtain 3-ethynylpyridine (0.130 g, 45.0%) in a yellow oil form.

[Step 2] Synthesis of Compound 18305

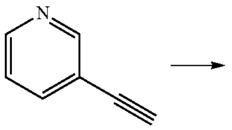

-continued

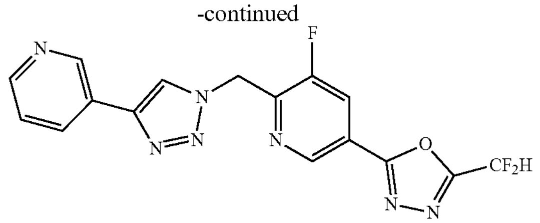

The 3-ethynylpyridine (0.130 g, 1.261 mmol) prepared in example 1, 2-(6-(azidomethyl)-5-fluoropyridin-3-yl)-5-(difluoromethyl)-1,3,4-oxadiazole (0.341 g, 1.261 mmol) prepared in step 1 of example 490, sodium ascorbate (0.50 M solution in water, 0.252 mL, 0.126 mmol) and copper(II) sulfate pentahydrate (1.00 M solution in water, 0.013 mL, 0.013 mmol) were dissolved in tert-butanol (3 mL)/water (3 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (5 mL) and hexane (50 mL) were added to the resulting concentrate and stirred to filter out a precipitated solid, washed with hexane, and dried to obtain 2-(difluoromethyl)-5-(5-fluoro-6-((4-(pyridin-3-yl)-1H-1,2,3-triazol-1-yl)methyl)pyridin-3-yl)-1,3,4-oxadiazole (0.121 g, 25.7%) in a white solid form.

$^1H$ NMR (400 MHz, $CD_3OD$) δ 9.10-9.06 (m, 2H), 8.66 (s, 1H), 8.55 (s, 1H), 8.40 (dd, J=9.6, 1.4 Hz, 1H), 8.32 (d, J=8.0 Hz, 1H), 7.27-7.54 (m, 1H), 7.27 (t, J=51.5 Hz, 1H), 6.04 (d, J=1.6 Hz, 2H); LRMS (ES) m/z 374.4 ($M^+$+1).

The compounds of table 159 were synthesized according to substantially the same process as described in the synthesis of(compounds 3835, 4487, 4488 and 18305 by using azide compound 1-2 and acetylene compound 2-3 in table 158 for reactants and using a click reaction thereof.

TABLE 158

| Example | Compound No. | Reactant (acetylene) | Reactant (azide) | Yield (%) |
|---|---|---|---|---|
| 48 | 3837 | 4-ethynylpyridine | 2-(6-(azidomethyl)pyridin-3-yl)-5-(difluoromethyl)-1,3,4-oxadiazole | 71 |
| 49 | 3838 | 6-ethynyl-1H-indole | 2-(6-(azidomethyl)pyridin-3-yl)-5-(difluoromethyl)-1,3,4-oxadiazole | 41 |
| 50 | 3839 | 4-ethynyl-1H-indole | 2-(6-(azidomethyl)pyridin-3-yl)-5-(difluoromethyl)-1,3,4-oxadiazole | 32 |
| 51 | 3840 | 4-ethynyl-1H-pyrrolo[2,3-b]pyridine | 2-(6-(azidomethyl)pyridin-3-yl)-5-(difluoromethyl)-1,3,4-oxadiazole | 28 |
| 52 | 3841 | 5-ethynyl-1H-pyrrolo[2,3-b]pyridine | 2-(6-(azidomethyl)pyridin-3-yl)-5-(difluoromethyl)-1,3,4-oxadiazole | 44 |
| 53 | 3842 | 4-ethynyl-1-methyl-1H-indazole | 2-(6-(azidomethyl)pyridin-3-yl)-5-(difluoromethyl)-1,3,4-oxadiazole | 27 |
| 54 | 3843 | 6-ethynyl-1H-benzo[d]imidazole | 2-(6-(azidomethyl)pyridin-3-yl)-5-(difluoromethyl)-1,3,4-oxadiazole | 35 |
| 55 | 3844 | 3-ethynylpyridin-2(1H)-one | 2-(6-(azidomethyl)pyridin-3-yl)-5-(difluoromethyl)-1,3,4-oxadiazole | 40 |
| 56 | 3845 | 5-ethynylpyridin-2(1H)-one | 2-(6-(azidomethyl)pyridin-3-yl)-5-(difluoromethyl)-1,3,4-oxadiazole | 40 |
| 64 | 3866 | 4-(3-ethynylphenyl)morpholine | 2-(6-(azidomethyl)pyridin-3-yl)-5-(difluoromethyl)-1,3,4-oxadiazole | 45 |
| 65 | 3867 | 1-(3-ethynylpheny])-4-methylpiperazine | 2-(6-(azidomethyl)pyridin-3-yl)-5-(difluoromethyl)-1,3,4-oxadiazole | 33 |
| 68 | 3881 | 2-ethynylpyridine | 2-(6-(azidomethyl)pyridin-3-yl)-5-(difluoromethyl)-1,3,4-oxadiazole | 81 |
| 69 | 3882 | 2-chloro-5-ethynylpyridine | 2-(6-(azidomethyl)pyridin-3-yl)-5-(difluoromethyl)-1,3,4-oxadiazole | 87 |
| 70 | 3883 | 3-chloro-5-ethynylpyridine | 2-(6-(azidomethyl)pyridin-3-yl)-5-(difluoromethyl)-1,3,4-oxadiazole | 92 |

TABLE 158-continued

| Example | Compound No. | Reactant (acetylene) | Reactant (azide) | Yield (%) |
|---|---|---|---|---|
| 71 | 3884 | 3-ethynyl-5-methylpyridine | 2-(6-(azidomethyl)pyridin-3-yl)-5-(difluoromethyl)-1,3,4-oxadiazole | 62 |
| 90 | 3925 | 5-ethynyl-2-methylpyridine | 2-(6-(azidomethyl)pyridin-3-yl)-5-(difluoromethyl)-1,3,4-oxadiazole | 76 |
| 149 | 4071 | 7-ethynyl-1H-indole | 2-(6-(azidomethyl)pyridin-3-yl)-5-(difluoromethyl)-1,3,4-oxadiazole | 67 |
| 150 | 4072 | 5-ethynyl-1H-indole | 2-(6-(azidomethyl)pyridin-3-yl)-5-(difluoromethyl)-1,3,4-oxadiazole | 56 |
| 151 | 4073 | 5-ethynylbenzofuran | 2-(6-(azidomethyl)pyridin-3-yl)-5-(difluoromethyl)-1,3,4-oxadiazole | 79 |
| 152 | 4074 | 5-ethynylbenzo[b]thiophene | 2-(6-(azidomethyl)pyridin-3-yl)-5-(difluoromethyl)-1,3,4-oxadiazole | 49 |
| 153 | 4075 | 1-(3-ethynylphenyl)-1H-imidazole | 2-(6-(azidomethyl)pyridin-3-yl)-5-(difluoromethyl)-1,3,4-oxadiazole | 67 |
| 154 | 4076 | 6-ethynyl-1H-indole | 2-(4-(azidomethyl)phenyl)-5-(difluoromethyl)-1,3,4-oxadiazole | 72 |
| 155 | 4077 | 6-ethynyl-1H-indole | 2-(4-(azidomethyl)-3-fluorophenyl)-5-(difluoromethyl)-1,3,4-oxadiazole | 64 |
| 156 | 4078 | 4-ethynyl-1H-indole | 2-(4-(azidomethyl)phenyl)-5-(difluoromethyl)-1,3,4-oxadiazole | 59 |
| 157 | 4079 | 4-ethynyl-1H-indole | 2-(4-(azidomethyl)-3-fluorophenyl)-5-(difluoromethyl)-1,3,4-oxadiazole | 70 |
| 158 | 4080 | 5-ethynyl-1H-indole | 2-(4-(azidomethyl)phenyl)-5-(difluoromethyl)-1,3,4-oxadiazole | 41 |
| 159 | 4081 | 7-ethynyl-1H-indole | 2-(4-(azidomethyl)phenyl)-5-(difluoromethyl)-1,3,4-oxadiazole | 48 |
| 160 | 4082 | 7-ethynyl-1H-indole | 2-(4-(azidomethyl)-3-fluorophenyl)-5-(difluoromethyl)-1,3,4-oxadiazole | 42 |
| 161 | 4104 | 4-(2-ethynylphenyl)morpholine | 2-(6-(azidomethyl)pyridin-3-yl)-5-(difluoromethyl)-1,3,4-oxadiazole | 52 |
| 162 | 4105 | 4-(4-ethynylphenyl)morpholine | 2-(6-(azidomethyl)pyridin-3-yl)-5-(difluoromethyl)-1,3,4-oxadiazole | 54 |
| 163 | 4106 | 1-(2-ethynylphenyl)-4-methylpiperazine | 2-(6-(azidomethyl)pyridin-3-yl)-5-(difluoromethyl)-1,3,4-oxadiazole | 47 |
| 164 | 4107 | 1-(4-ethynylphenyl)-4-methylpiperazine | 2-(6-(azidomethyl)pyridin-3-yl)-5-(difluoromethyl)-1,3,4-oxadiazole | 51 |
| 172 | 4135 | 5-ethynyl-1H-indole | 2-(4-(azidomethyl)-3-fluorophenyl)-5-(difluoromethyl)-1,3,4-oxadiazole | 79 |
| 174 | 4178 | 2-ethynyl-3-fluoropyridine | 2-(6-(azidomethyl)pyridin-3-yl)-5-(difluoromethyl)-1,3,4-oxadiazole | 72 |
| 175 | 4179 | 2-ethynyl-4-fluoropyridine | 2-(6-(azidomethyl)pyridin-3-yl)-5-(difluoromethyl)-1,3,4-oxadiazole | 52 |
| 176 | 4180 | 5-bromo-2-ethynylpyridine | 2-(6-(azidomethyl)pyridin-3-yl)-5-(difluoromethyl)-1,3,4-oxadiazole | 71 |
| 177 | 4181 | 3-ethynyl-4-methylpyridine | 2-(6-(azidomethyl)pyridin-3-yl)-5-(difluoromethyl)-1,3,4-oxadiazole | 56 |
| 178 | 4182 | 3-bromo-5-ethynylpyridine | 2-(6-(azidomethyl)pyridin-3-yl)-5-(difluoromethyl)-1,3,4-oxadiazole | 90 |
| 179 | 4183 | 2-bromo-5-ethynylpyridine | 2-(6-(azidomethyl)pyridin-3-yl)-5-(difluoromethyl)-1,3,4-oxadiazole | 56 |
| 180 | 4184 | 4-ethynyl-3-fluoropyridine | 2-(6-(azidomethyl)pyridin-3-yl)-5-(difluoromethyl)-1,3,4-oxadiazole | 73 |
| 181 | 4185 | 4-ethynyl-2-fluoropyridine | 2-(6-(azidomethyl)pyridin-3-yl)-5-(difluoromethyl)-1,3,4-oxadiazole | 81 |
| 205 | 4284 | 1-(4-ethynylphenyl)-1H-imidazole | 2-(4-(azidomethyl)phenyl)-5-(difluoromethyl)-1,3,4-oxadiazole | 66 |
| 206 | 4285 | 1-(4-ethynylphenyl)-1H-1,2,4-triazole | 2-(4-(azidomethyl)phenyl)-5-(difluoromethyl)-1,3,4-oxadiazole | 58 |
| 207 | 4286 | 1-(2-ethynylphenyl)-1H-1,2,4-triazole | 2-(4-(azidomethyl)phenyl)-5-(difluoromethyl)-1,3,4-oxadiazole | 74 |
| 210 | 4289 | 5-ethynyl-2-methyl-1H-indole | 2-(6-(azidomethyl)pyridin-3-yl)-5-(difluoromethyl)-1,3,4-oxadiazole | 62 |
| 363 | 4489 | 1-(difluoromethyl)-3-ethynylbenzene | 2-(6-(azidomethyl)pyridin-3-yl)-5-(difluoromethyl)-1,3,4-oxadiazole | 90 |
| 485 | 17198 | 7-ethynylimidazo[1,2-a]pyridine | 2-(4-(azidomethyl)-3-fluorophenyl)-5-(difluoromethyl)-1,3,4-oxadiazole | 68 |
| 486 | 17201 | 2-ethynylimidazo[1,2-a]pyridine | 2-(4-(azidomethyl)-3-fluorophenyl)-5-(difluoromethyl)-1,3,4-oxadiazole | 58 |
| 489 | 17263 | 2-bromo-6-ethynylpyridine | 2-(4-(azidomethyl)-3-fluorophenyl)-5-(difluoromethyl)-1,3,4-oxadiazole | 74 |
| 510 | 17848 | 2-ethynylthiazole | 2-(4-(azidomethyl)-3-fluorophenyl)-5-(difluoromethyl)-1,3,4-oxadiazole | 73 |
| 511 | 17851 | 5-ethynylthiazole | 2-(4-(azidomethyl)-3-fluorophenyl)-5-(difluoromethyl)-1,3,4-oxadiazole | 68 |
| 512 | 17854 | 2-ethynyl-4-methylthiazole | 2-(4-(azidomethyl)-3-fluorophenyl)-5-(difluoromethyl)-1,3,4-oxadiazole | 81 |

TABLE 158-continued

| Example | Compound No. | Reactant (acetylene) | Reactant (azide) | Yield (%) |
|---|---|---|---|---|
| 513 | 17857 | 2-ethynyl-5-methylthiazole | 2-(4-(azidomethyl)-3-fluorophenyl)-5-(difluoromethyl)-1,3,4-oxadiazole | 75 |

TABLE 159

| Example | Compound No. | Compound Name, $^1$H-NMR, MS (ESI) |
|---|---|---|
| 48 | 3837 | 2-(difluoromethyl)-5-(6-((4-(pyridin-4-yl)-1H-1,2,3-triazol-1-yl)methyl)pyridin-3-yl)-1,3,4-oxadiazole<br>$^1$H NMR (400 MHZ, $CD_3OD$) δ 9.27 (dd, J = 2.3, 0.8 Hz, 1H), 8.76 (s, 1H), 8.62 (d, J = 5.5 Hz, 2H), 8.54 (dd, J = 8.2, 2.2 Hz, 1H), 7.95-7.89 (m, 2H), 7.64 (dd, J = 8.2, 0.9 Hz, 1H), 7.26 (t, J = 51.6 Hz, 1H), 5.96 (s, 2H); LRMS (ES) m/z 356.1 ($M^+$ + 1). |
| 49 | 3838 | 2-(6-((4-(1H-indol-6-yl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 11.20 (s, 1H), 9.21 (dd, J = 2.3, 0.8 Hz, 1H), 8.65 (s, 1H), 8.50 (dd, J = 8.2, 2.3 Hz, 1H), 7.93 (dt, J = 1.6, 0.9 Hz, 1H), 7.60 (d, J = 8.3 Hz, 1H), 7.58 (t, J = 51.3 Hz, 1H), 7.56 (dd, J = 8.2, 0.9 Hz, 1H), 7.50 (dd, J = 8.2, 1.5 Hz, 1H), 7.42-7.36 (m, 1H), 6.45 (ddd, J = 3.0, 1.9, 0.9 Hz, 1H), 5.92 (s, 2H); LRMS (ES) m/z 394.3 ($M^+$ + 1). |
| 50 | 3839 | 2-(6-((4-(1H-indol-4-yl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 9.21 (dd, J = 2.3, 0.9 Hz, 1H), 8.78 (s, 1H), 8.49 (dd, J = 8.2, 2.3 Hz, 1H), 7.60 (dd, J = 7.4, 1.0 Hz, 1H), 7.55 (dd, J = 8.2, 0.9 Hz, 1H), 7.68-7.41 (m, 1H), 7.44 (d, J = 3.2 Hz, 1H), 7.40 (d, J = 1.3 Hz, 1H), 7.22-7.13 (m, 1H), 6.97 (dd, J = 3.2, 0.9 Hz, 1H), 5.96 (s, 2H); LRMS (ES) m/z 394.2 ($M^+$ + 1). |
| 51 | 3840 | 2-(6-((4-(1H-pyrrolo[2,3-b]pyridin-4-yl)-1H-1,2,3-triazol-1-yl)methyl)pyridin-3-yl)-5-(difluoromethyl)-1,3,4-oxadiazole<br>$^1$H NMR (400 MHZ, $CD_3OD$) δ 9.31 (s, 1H), 8.89 (s, 1H), 8.60-8.48 (m, 1H), 7.66 (d, J = 8.5 Hz, 2H), 7.55 (d, J = 3.5 Hz, 1H), 7.32 (t, J = 51.5 Hz, 1H), 7.07 (d, J = 3.6 Hz, 1H), 6.03 (s, 2H); LRMS (ES) m/z 395.1 ($M^+$ + 1). |
| 52 | 3841 | 2-(6-((4-(1H-pyrrolo[2,3-b]pyridin-5-yl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 11.74 (s, 1H), 9.22 (dd, J = 2.3, 0.9 Hz, 1H), 8.77-8.70 (m, 2H), 8.50 (dd, J = 8.2, 2.3 Hz, 1H), 8.41 (d, J = 2.1 Hz, 1H), 7.60 (d, J = 7.9 Hz, 1H), 7.58 (t, J = 51.3 Hz, 1H), 7.55-7.49 (m, 1H), 6.52 (dd, J = 3.4, 1.8 Hz, 1H), 5.95 (s, 2H); LRMS (ES) m/z 395.4 ($M^+$ + 1). |
| 53 | 3842 | 2-(difluoromethyl)-5-(6-((4-(1-methyl-1H-indazol-4-yl)-1H-1,2,3-triazol-1-yl)methyl)pyridin-3-yl)-1,3,4-oxadiazole<br>$^1$H NMR (400 MHZ, $CD_3OD$) δ 9.31 (s, 1H), 8.78 (s, 1H), 8.58 (d, J = 1.0 Hz, 1H), 8.56 (dd, J = 8.2, 2.2 Hz, 1H), 7.71 (dd, J = 7.1, 0.9 Hz, 1H), 7.67-7.61 (m, 2H), 7.54 (dd, J = 8.5, 7.1 Hz, 1H), 7.32 (t, J = 51.6 Hz, 1H), 6.01 (s, 2H); LRMS (ES) m/z 409.2 ($M^+$ + 1). |
| 54 | 3843 | 2-(6-((4-(1H-benzo[d]imidazol-5-yl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 9.24-9.19 (m, 1H), 8.71 (d, J = 6.6 Hz, 1H), 8.50 (dd, J = 8.2, 2.3 Hz, 1H), 8.28-8.12 (m, 1H), 7.78 (d, J = 7.6 Hz, 1H), 7.71 (s, 1H), 7.61-7.44 (m, 2H), 5.93 (s, 2H); LRMS (ES) m/z 395.2 ($M^+$ + 1). |
| 55 | 3844 | 3-(1-((5-(5-(difluoromethyl)-1,3,4-oxadiazol-2-yl)pyridin-2-yl)methyl)-1H-1,2,3-triazol-4-yl)pyridin-2(1H)-one<br>$^1$H NMR (400 MHZ, DMSO-$d_6$) δ 9.21-9.16 (m, 1H), 8.77 (s, 1H), 8.48 (dd, J = 8.2, 2.3 Hz, 1H), 8.32 (dd, J = 7.0, 2.1 Hz, 1H), 7.74-7.42 (m, 2H), 7.52 (d, J = 8.0 Hz, 1H), 6.39 (t, J = 6.7 Hz, 1H), 5.96 (s, 2H); LRMS (ES) m/z 372.2 ($M^+$ + 1). |
| 56 | 3845 | 5-(1-((5-(5-(difluoromethyl)-1,3,4-oxadiazol-2-yl)pyridin-2-yl)methyl)-1H-1,2,3-triazol-4-yl)pyridin-2(1H)-one<br>$^1$H NMR (400 MHZ, DMSO-$d_6$) δ 9.19 (d, J = 2.0 Hz, 1H), 8.77 (s, 1H), 8.48 (dd, J = 8.2, 2.3 Hz, 1H), 8.32 (dd, J = 7.1, 2.2 Hz, 1H), 7.72-7.41 (m, 2H), 7.52 (d, J = 8.5 Hz, 1H), 6.40 (d, J = 6.5 Hz, 1H), 5.96 (s, 2H); LRMS (ES) m/z 372.2 ($M^+$ + 1). |
| 64 | 3866 | 4-(3-(1-((5-(5-(difluoromethyl)-1,3,4-oxadiazol-2-yl)pyridin-2-yl)methyl)-1H-1,2,3-triazol-4-yl)phenyl)morpholin<br>$^1$H NMR (400 MHZ, $CD_3OD$) δ 9.28 (s, 1H), 8.53 (dd, J = 8.2, 2.3 Hz, 1H), 8.48 (s, 1H), 7.60 (d, J = 8.3 Hz, 1H), 7.49 (s, 1H), 7.34 (d, J = 6.6 Hz, 2H), 7.26 (t, J = 51.5 Hz, 1H), 7.02-6.97 (m, 1H), 5.92 (s, 2H), 3.91-3.84 (m, 4H), 3.26-3.19 (m, 4H); LRMS (ES) m/z 440.3 ($M^+$ + 1). |
| 65 | 3867 | 2-(difluoromethyl)-5-(6-((4-(3-(4-methylpiperazin-1-yl)phenyl)-1H-1,2,3-triazol-1-yl)methyl)pyridin-3-yl)-1,3,4-oxadiazole<br>$^1$H NMR (400 MHZ, $CD_3OD$) δ 9.28 (dd, J = 2.2, 0.9 Hz, 1H), 8.53 (dd, J = 8.2, 2.2 Hz, 1H), 8.48 (s, 1H), 7.59 (dd, J = 8.2, 0.8 Hz, 1H), 7.50 (q, J = 1.3 Hz, 1H), 7.36-7.30 (m, 2H), 7.26 (t, J = 51.6 Hz, 1H), 7.00 (dt, J = 6.6, 2.7 Hz, 1H), 5.92 (s, 2H), 3.33-3.27 (m, 4H), 2.71-2.64 (m, 4H), 2.39 (s, 3H); LRMS (ES) m/z 453.3 ($M^+$ + 1). |

TABLE 159-continued

| Example | Compound No. | Compound Name, $^1$H-NMR, MS (ESI) |
|---|---|---|
| 68 | 3881 | 2-(difluoromethyl)-5-(6-((4-(pyridin-2-yl)-1H-1,2,3-triazol-1-yl)methyl)pyridin-3-yl)-1,3,4-oxadiazole $^1$H NMR (400 MHZ, DMSO-$d_6$) δ 9.20 (dd, J = 2.2, 0.9 Hz, 1H), 8.76 (d, J = 1.0 Hz, 1H), 8.66-8.58 (m, 1H), 8.49 (dt, J = 8.3, 1.8 Hz, 1H), 8.07 (dt, J = 7.9, 1.1 Hz, 1H), 7.92 (tt, J = 7.8, 1.6 Hz, 1H), 7.72-7.45 (m, 2H), 7.40-7.34 (m, 1H), 5.98 (s, 2H); LRMS (ESI) m/z 356.2 ($M^+$ + H). |
| 69 | 3882 | 2-(6-((4-(6-chloropyridin-3-yl)-1H-1,2,3-triazol-1-yl)methyl)pyridin-3-yl)-5-(difluoromethyl)-1,3,4-oxadiazole $^1$H NMR (400 MHZ, DMSO-$d_6$) δ 9.20 (dd, J = 2.3, 0.8 Hz, 1H), 8.96-8.86 (m, 2H), 8.50 (dd, J = 8.2, 2.3 Hz, 1H), 8.32 (dd, J = 8.3, 2.5 Hz, 1H), 7.63 (ddd, J = 8.2, 2.7, 0.8 Hz, 2H), 7.58 (t, J = 51.2 Hz, 1H), 5.98 (s, 2H); LRMS (ESI) m/z 390.2 ($M^+$ + H). |
| 70 | 3883 | 2-(6-((4-(5-chloropyridin-3-yl)-1H-1,2,3-triazol-1-yl)methyl)pyridin-3-yl)-5-(difluoromethyl)-1,3,4-oxadiazole $^1$H NMR (400 MHZ, DMSO-$d_6$) δ 9.20 (dd, J = 2.2, 0.8 Hz, 1H), 9.07 (dd, J = 1.9, 0.4 Hz, 1H), 8.93 (s, 1H), 8.61 (dd, J = 2.3, 0.4 Hz, 1H), 8.51 (dd, J = 8.2, 2.3 Hz, 1H), 8.39 (dd, J = 2.3, 1.9 Hz, 1H), 7.73-7.44 (m, 2H), 5.98 (s, 2H); LRMS (ESI) m/z 390.1 ($M^+$ + H). |
| 71 | 3884 | 2-(difluoromethyl)-5-(6-((4-(5-methylpyridin-3-yl)-1H-1,2,3-triazol-1-yl)methyl)pyridin-3-yl)-1,3,4-oxadiazole $^1$H NMR (400 MHZ, DMSO-$d_6$) δ 9.20 (dd, J = 2.3, 0.9 Hz, 1H), 8.91-8.86 (m, 1H), 8.82 (s, 1H), 8.50 (dd, J = 8.2, 2.3 Hz, 1H), 8.40 (dd, J = 2.2, 0.9 Hz, 1H), 8.09 (td, J = 2.1, 0.8 Hz, 1H), 7.61 (dd, J = 8.2, 0.8 Hz, 1H), 7.58 (t, J = 51.2 Hz, 1H), 5.96 (s, 2H), 2.37 (q, J = 0.7 Hz, 3H); LRMS (ESI) m/z 370.2 ($M^+$ + H). |
| 90 | 3925 | 2-(difluoromethyl)-5-(6-((4-(6-methylpyridin-3-yl)-1H-1,2,3-triazol-1-yl)methyl)pyridin-3-yl)-1,3,4-oxadiazole $^1$H NMR (400 MHZ, $CD_3OD$) δ 9.34 (dd, J = 2.2, 0.8 Hz, 1H), 8.90 (d, J = 2.3 Hz, 1H), 8.42 (dd, J = 8.2, 2.2 Hz, 1H), 8.17 (dd, J = 8.1, 2.3 Hz, 1H), 8.06 (s, 1H), 7.46 (dd, J = 8.2, 0.8 Hz, 1H), 7.28 (d, J = 8.1 Hz, 2H), 6.94 (t, J = 51.6 Hz, 1H), 5.83 (s, 2H), 2.63 (s, 3H); LRMS (ESI) m/z 370.2 ($M^+$ + H). |
| 149 | 4071 | 2-(6-((4-(1H-indol-7-yl)-1H-1,2,3-triazol-1-yl)methyl)pyridin-3-yl)-5-(difluoromethyl)-1,3,4-oxadiazole $^1$H NMR (400 MHZ, $CD_3OD$) δ 8.55 (s, 1H), 8.03-7.93 (m, 2H), 7.64-7.57 (m, 2H), 7.50 (dd, J = 7.4, 1.0 Hz, 1H), 7.39 (d, J = 3.2 Hz, 1H), 7.37-7.12 (m, 1H), 7.12-7.08 (m, 1H), 6.54 (d, J =3.2 Hz, 1H), 5.90 (s, 2H); LRMS (ES) m/z 394.2 ($M^+$ + 1). |
| 150 | 4072 | 2-(6-((4-(1H-indol-5-yl)-1H-1,2,3-triazol-1-yl)methyl)pyridin-3-yl)-5-(difluoromethyl)-1,3,4-oxadiazole $^1$H NMR (400 MHZ, $CD_3OD$) δ 9.30 (dd, J = 2.3, 0.9 Hz, 1H), 8.52 (dd, J = 8.2, 2.3 Hz, 1H), 8.41 (s, 1H), 8.05 (dd, J = 1.7, 0.7 Hz, 1H), 7.82 (s, 1H), 7.59 (dt, J = 8.4, 1.4 Hz, 2H), 7.47 (dd, J = 8.5, 0.8 Hz, 1H), 7.28 (s, 1H), 7.40-7.06 (m, 1H), 5.92 (s, 2H); LRMS (ES) m/z 394.3 ($M^+$ + 1). |
| 151 | 4073 | 2-(6-((4-(benzofuran-5-yl)-1H-1,2,3-triazol-1-yl)methyl)pyridin-3-yl)-5-(difluoromethyl)-1,3,4-oxadiazole $^1$H NMR (400 MHZ, $CD_3OD$) δ 9.29 (dd, J = 2.2, 0.8 Hz, 1H), 8.52 (dd, J = 8.2, 2.3 Hz, 1H), 8.45 (s, 1H), 8.10 (dd, J = 1.9, 0.7 Hz, 1H), 7.82 (s, 1H), 7.79 (dd, J = 8.9, 2.0 Hz, 2H), 7.63-7.54 (m, 2H), 7.22 (t, J = 51.6 Hz, 1H), 6.89 (dd, J = 2.2, 1.0 Hz, 1H), 5.92 (s, 2H); LRMS (ES) m/z 395.3 ($M^+$ + 1). |
| 152 | 4074 | 2-(6-((4-(benzo[b]thiophen-5-yl)-1H-1,2,3-triazol-1-yl)methyl)pyridin-3-yl)-5-(difluoromethyl)-1,3,4-oxadiazole $^1$H NMR (400 MHZ, $CD_3OD$) δ 9.29 (d, J = 2.0 Hz, 1H), 8.56 (s, 1H), 8.54 (dd, J = 8.2, 2.3 Hz, 1H), 8.38-8.33 (m, 1H), 8.00 (d, J = 8.4 Hz, 1H), 7.85 (dd, J= 8.4, 1.7 Hz, 1H), 7.65 (d, J = 5.5 Hz, 1H), 7.62 (d, J = 8.1 Hz, 1H), 7.46 (dd, J = 5.5, 0.8 Hz, 1H), 7.26 (t, J = 51.6 Hz, 1H), 5.95 (s, 2H); LRMS (ES) m/z 411.3 ($M^+$ + 1). |
| 153 | 4075 | 2-(6-((4-(3-(1H-imidazol-1-yl)phenyl)-1H-1,2,3-triazol-1-yl)methyl)pyridin-3-yl)-5-(difluoromethyl)-1,3,4-oxadiazole $^1$H NMR (400 MHZ, $CD_3OD$) δ 9.29 (dd, J = 2.3, 0.9 Hz, 1H), 8.64 (s, 1H), 8.54 (dd, J = 8.2, 2.2 Hz, 1H), 8.40-8.20 (m, 2H), 8.10 (s, 1H), 7.96-7.89 (m, 1H), 7.80-7.57 (m, 4H), 7.26 (t, J = 51.6 Hz, 1H), 5.95 (s, 2H); LRMS (ES) m/z 421.4 ($M^+$ + 1). |
| 154 | 4076 | 2-(4-((4-(1H-indol-6-yl)-1H-1,2,3-triazol-1-yl)methyl)phenyl)-5-(difluoromethyl)-1,3,4-oxadiazole $^1$H NMR (400 MHZ, $CD_3OD$) δ 8.36 (s, 1H), 8.17 (d, J = 8.4 Hz, 2H), 7.90 (d, J = 1.0 Hz, 1H), 7.66-7.58 (m, 3H), 7.46 (dd, J = 8.2, 1.5 Hz, 1H), 7.29 (d, J = 3.1 Hz, 1H), 7.23 (t, J = 51.6 Hz, 1H), 6.47 (dd, J = 3.2, 0.9 Hz, 1H), 5.80 (s, 2H); LRMS (ES) m/z 393.2 ($M^+$ + 1). |
| 155 | 4077 | 2-(4-((4-(1H-indol-6-yl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.35 (s, 1H), 8.02-7.92 (m, 2H), 7.90 (s, 1H), 7.65-7.56 (m, 2H), 7.45 (dd, J = 8.2, 1.5 Hz, 1H), 7.31-7.26 (m, 1H), 7.20 (t, J = 51.6 Hz, 1H), 6.48 (dd, J = 3.2, 0.9 Hz, 1H), 5.85 (s, 2H); LRMS (ES) m/z 411.2 ($M^+$ + 1). |
| 156 | 4078 | 2-(4-((4-(1H-indol-4-yl)-1H-1,2,3-triazol-1-yl)methyl)phenyl)-5-(difluoromethyl)-1,3,4-oxadiazole |

TABLE 159-continued

| Example | Compound No. | Compound Name, $^1$H-NMR, MS (ESI) |
|---|---|---|
| | | $^1$H NMR (400 MHZ, $CD_3OD$) δ 8.46 (s, 1H), 8.20-8.13 (m, 2H), 7.82 (s, 1H), 7.67-7.60 (m, 2H), 7.55 (dd, J = 7.4, 0.9 Hz, 1H), 7.44 (dd, J = 8.1, 0.9 Hz, 1H), 7.34 (t, J = 1.6 Hz, 1H), 7.21 (d, J = 7.5 Hz, 1H), 7.32-7.04 (m, 1H), 5.84 (s, 2H); LRMS (ES) m/z 393.3 ($M^+$ + 1). |
| 157 | 4079 | 2-(4-((4-(1H-indol-4-yl)-1H-1,2,3-triazol-1-yl)methyl)-3-fluorophenyl)-5-(difluoromethyl)-1,3,4-oxadiazole (0.043 g, 70.5%) $^1$H NMR (400 MHZ, $CD_3OD$) δ 8.51 (s, 1H), 8.02-7.93 (m, 2H), 7.61 (t, J = 7.8 Hz, 1H), 7.55 (dd, J = 7.4, 0.9 Hz, 1H), 7.44 (dt, J = 8.1, 0.9 Hz, 1H), 7.35 (d, J = 3.2 Hz, 1H), 7.24 (t, J = 51.6 Hz, 1H), 7.20 (dd, J = 8.1, 7.3 Hz, 1H), 6.86 (dd, J = 3.2, 1.0 Hz, 1H), 5.91 (s, 2H); LRMS (ES) m/z 411.4 ($M^+$ + 1). |
| 158 | 4080 | 2-(4-((4-(1H-indol-5-yl)-1H-1,2,3-triazol-1-yl)methyl)phenyl)-5-(difluoromethyl)-1,3,4-oxadiazole $^1$H NMR (400 MHZ, $CD_3OD$) δ 8.32 (s, 1H), 8.20-8.13 (m, 2H), 8.03 (dd, J = 1.7, 0.7 Hz, 1H), 7.82 (s, 1H), 7.66-7.60 (m, 1H), 7.58 (dd, J = 8.5, 1.7 Hz, 1H), 7.46 (dd, J = 8.4, 0.7 Hz, 1H), 7.27 (t, J = 1.6 Hz, 1H), 7.19 (t, J = 51.6 Hz, 1H), 6.51 (dd, J = 3.2, 0.9 Hz, 1H), 5.79 (s, 2H); LRMS (ES) m/z 393.2 ($M^+$ + 1). |
| 159 | 4081 | 2-(4-((4-(1H-indol-7-yl)-1H-1,2,3-triazol-1-yl)methyl)phenyl)-5-(difluoromethyl)-1,3,4-oxadiazole $^1$H NMR (400 MHZ, $CD_3OD$) δ 8.49 (s, 1H), 8.16 (d, J = 8.4 Hz, 2H), 7.62 (d, J = 8.3 Hz, 2H), 7.59 (dd, J = 7.9, 1.0 Hz, 1H), 7.49 (d, J = 7.5 Hz, 1H), 7.38 (s, 1H), 7.18 (t, J = 51.7 Hz, 1H), 7.12-7.07 (m, 1H), 6.54 (d, J = 3.2 Hz, 1H), 5.83 (s, 2H); LRMS (ES) m/z 393.1 ($M^+$ + 1). |
| 160 | 4082 | 2-(4-((4-(1H-indol-7-yl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.49 (s, 1H), 8.01-7.91 (m, 2H), 7.82 (s, 1H), 7.64-7.55 (m, 2H), 7.49 (dd, J = 7.4, 1.0 Hz, 1H), 7.38 (s, 1H), 7.20 (t, J = 51.6 Hz, 1H), 7.10 (dd, J = 7.9, 7.4 Hz, 1H), 5.88 (s, 2H); LRMS (ES) m/z 411.3 ($M^+$ + 1). |
| 161 | 4104 | 4-(2-(1-((5-(5-(difluoromethyl)-1,3,4-oxadiazol-2-yl)pyridin-2-yl)methyl)-1H-1,2,3-triazol-4-yl)phenyl)morpholin $^1$H NMR (400 MHZ, $CDCl_3$) δ 9.35 (dd, J = 2.2, 0.7 Hz, 1H), 8.62 (s, 1H), 8.43 (dd, J = 8.2, 2.2 Hz, 1H), 8.15 (dd, J = 7.7, 1.6 Hz, 1H), 7.47 (d, J = 8.2 Hz, 1H), 7.36 (ddd, J = 7.9, 7.5, 1.7 Hz, 1H), 7.26-7.16 (m, 2H), 7.09 (s, 0.2H), 6.96 (s, 0.5H), 6.83 (s, 0.3H), 5.85 (s, 2H), 3.82-3.73 (m, 4H), 2.96-2.86 (m, 4H); LRMS (ES) m/z 440.4 ($M^+$ + 1). |
| 162 | 4105 | 4-(4-(1-((5-(5-(difluoromethyl)-1,3,4-oxadiazol-2-yl)pyridin-2-yl)methyl)-1H-1,2,3-triazol-4-yl)phenyl)morpholin $^1$H NMR (400 MHZ, $CDCl_3$) δ 9.35 (d, J = 1.5 Hz, 1H), 8.41 (dd, J = 8.2, 2.2 Hz, 1H), 7.89 (s, 1H), 7.83-7.72 (m, 2H), 7.41 (d, J = 7.9 Hz, 1H), 7.09 (s, 0.2H), 7.00 (d, J = 8.5 Hz, 2H), 6.96 (s, 0.5H), 6.83 (s, 0.2H), 5.82 (s, 2H), 3.96-3.85 (m, 4H), 3.30-3.17 (m, 4H); LRMS (ES) m/z 440.4 ($M^+$ + 1). |
| 163 | 4106 | 2-(difluoromethyl)-5-(6-((4-(2-(4-methylpiperazin-1-yl)phenyl)-1H-1,2,3-triazol-1-yl)methyl)pyridin-3-yl)-1,3,4-oxadiazole $^1$H NMR (400 MHZ, $CDCl_3$) δ 9.36 (dd, J = 2.1, 0.6 Hz, 1H), 8.57 (s, 1H), 8.41 (dd, J = 8.2, 2.2 Hz, 1H), 8.20-8.10 (m, 1H), 7.45 (d, J = 8.2 Hz, 1H), 7.37-7.29 (m, 1H), 7.25-7.15 (m, 2H), 7.06 (m, 0.3H), 6.96 (s, 0.5H), 6.83 (s, 0.2H), 5.84 (s, 2H), 2.92 (t, J = 4.8 Hz, 4H), 2.59-2.36 (m, 4H), 2.31 (s, 3H); LRMS (ES) m/z 453.2 ($M^+$ + 1). |
| 164 | 4107 | 2-(difluoromethyl)-5-(6-((4-(4-(4-methylpiperazin-1-yl)phenyl)-1H-1,2,3-triazol-1-yl)methyl)pyridin-3-yl)-1,3,4-oxadiazole $^1$H NMR (400 MHZ, $CDCl_3$) δ 9.34 (dd, J = 2.2, 0.7 Hz, 1H), 8.39 (dd, J = 8.2, 2.2 Hz, 1H), 7.87 (s, 1H), 7.79-7.69 (m, 2H), 7.39 (dd, J = 8.2, 0.6 Hz, 1H), 7.09 (s, 0.2H), 7.01-6.96 (m, 2H), 6.96 (s, 0.5H), 6.83 (s, 0.3H), 5.81 (s,2H),3.34-3.23 (m, 4H), 2.60 (dd, J = 16.1, 11.1 Hz, 4H), 2.39 (s, 3H); LRMS (ES) m/z 453.1 ($M^+$ + 1). |
| 172 | 4135 | 2-(4-((4-(1H-indol-5-yl)-1H-1,2,3-triazol-1-yl)methyl)-3-fluorophenyl)-5-(difluoromethyl)-1,3,4-oxadiazole $^1$H NMR (400 MHZ, $CDCl_3$) δ 8.04 (s, 1H), 7.94 (s, 1H), 7.84 (t, J = 10.4 Hz, 3H), 7.51 (d, J = 8.5 Hz, 2H), 7.39 (d, J = 8.5 Hz, 1H), 7.17 (s, 1H), 6.89 (t, J = 51.5 Hz, 1H), 5.71 (s, 2H); LRMS (ES) m/z 411.91 ($M^+$ + 1). |
| 174 | 4178 | 2-(difluoromethyl)-5-(6-((4-(3-fluoropyridin-2-yl)-1H-1,2,3-triazol-1-(yl)methyl)pyridin-3-yl)-1,3,4-oxadiazole $^1$H NMR (400 MHZ, $CD_3OD$) δ 9.27 (dd, J = 2.2, 0.9 Hz, 1H), 8.67 (d, J = 2.6 Hz, 1H), 8.56-8.49 (m, 2H), 7.76 (ddd, J = 10.8, 8.4, 1.3 Hz, 1H), 7.62 (dd, J = 8.2, 0.9 Hz, 1H), 7.48 (ddd, J = 8.6, 4.7, 4.1 Hz, 1H), 7.26 (t, J = 51.6 Hz, 1H), 5.99 (s, 2H); LRMS (ESI) m/z 374.3 ($M^+$ + H). |
| 175 | 4179 | 2-(difluoromethyl)-5-(6-((4-(4-fluoropyridin-2-yl)-1H-1,2,3-triazol-1-yl)methyl)pyridin-3-yl)-1,3,4-oxadiazole $^1$H NMR (400 MHZ, $CD_3OD$) δ 9.27 (dd, J = 2.3, 0.9 Hz, 1H), 8.66 (s, 1H), 8.61 (dd, J = 8.4, 5.7 Hz, 1H), 8.53 (dd, J = 8.2, 2.2 Hz, 1H), 7.87 (dd, J = 10.0, 2.5 Hz, 1H), 7.63 (dd, J = 8.2, 0.8 Hz, 1H), 7.26 (t, J = 51.6 Hz, 1H), 7.20 (ddd, J = 8.4, 5.7, 2.5 Hz, 1H), 5.97 (s, 2H); LRMS (ESI) m/z 374.0 ($M^+$ + H). |
| 176 | 4180 | 2-(6-((4-(5-bromopyridin-2-yl)-1H-1,2,3-triazol-1-yl)methyl)pyridin-3-yl)-5-(difluoromethyl)-1,3,4-oxadiazole |

TABLE 159-continued

| Example | Compound No. | Compound Name, $^1$H-NMR, MS (ESI) |
|---|---|---|
| | | $^1$H NMR (400 MHZ, $CD_3OD$) δ 9.27 (dd, J = 2.2, 0.8 Hz, 1H), 8.69 (dd, J = 2.3, 0.8 Hz, 1H), 8.64 (s, 1H), 8.53 (ddd, J = 8.2, 2.3, 1.2 Hz, 1H), 8.10 (dd, J = 8.5, 2.3 Hz, 1H), 8.03 (dd, J = 8.5, 0.8 Hz, 1H), 7.73-7.61 (m, 1H), 7.26 (td, J = 51.6, 5.1 Hz, 1H), 5.96 (s, 2H); LRMS (ESI) m/z 434.3 ($M^+$ + H). |
| 177 | 4181 | 2-(difluoromethyl)-5-(6-((4-(4-methylpyridin-3-yl)-1H-1,2,3-triazol-1-yl)methyl)pyridin-3-yl)-1,3,4-oxadiazole<br>$^1$H NMR (400 MHZ, $CD_3OD$) δ 9.28 (dd, J = 2.3, 0.9 Hz, 1H), 8.82 (s, 1H), 8.57-8.51 (m, 2H), 8.42 (d, J = 5.2 Hz, 1H), 7.63 (dd, J = 8.2, 0.8 Hz, 1H), 7.42 (d, J = 5.1 Hz, 1H), 7.26 (t, J = 51.6 Hz, 1H), 5.98 (s, 2H), 2.56 (d, J = 0.7 Hz, 3H); LRMS (ESI) m/z 370.3 ($M^+$ + H). |
| 178 | 4182 | 2-(6-((4-(5-bromopyridin-3-yl)-1H-1,2,3-triazol-1-yl)methyl)pyridin-3-yl)-5-(difluoromethyl)-1,3,4-oxadiazole<br>$^1$H NMR (400 MHZ, $CD_3OD$) δ 9.27 (dd, J = 2.2, 0.9 Hz, 1H), 9.03 (d, J = 1.8 Hz, 1H), 8.70 (s, 1H), 8.65 (d, J = 2.2 Hz, 1H), 8.57-8.49 (m, 2H), 7.64 (dd, J = 8.2, 0.8 Hz, 1H), 7.26 (t, J = 51.6 Hz, 1H), 5.95 (s, 2H)); LRMS (ESI) m/z 434.2 ($M^+$ + H). |
| 179 | 4183 | 2-(6-((4-(6-bromopyridin-3-yl)-1H-1,2,3-triazol-1-yl)methyl)pyridin-3-yl)-5-(difluoromethyl)-1,3,4-oxadiazole<br>$^1$H NMR (400 MHZ, $CD_3OD$) δ 9.27 (dd, J = 2.2, 0.9 Hz, 1H), 8.86 (dd, J = 2.5, 0.8 Hz, 1H), 8.66 (s, 1H), 8.53 (dd, J = 8.3, 2.2 Hz, 1H), 8.19 (dd, J = 8.3, 2.5 Hz, 1H), 7.72 (dd, J = 8.4, 0.8 Hz, 1H), 7.63 (d, J = 8.3 Hz, 1H), 7.26 (t, J = 51.6 Hz, 1H), 5.95 (s, 2H); LRMS (ESI) m/z 434.3 ($M^+$ + H). |
| 180 | 4184 | 2-(difluoromethyl)-5-(6-((4-(3-fluoropyridin-4-yl)-1H-1,2,3-triazol-1-yl)methyl)pyridin-3-yl)-1,3,4-oxadiazole<br>$^1$H NMR (400 MHZ, $CD_3OD$) δ 9.27 (dd, J = 2.3, 0.9 Hz, 1H), 8.72 (d, J = 3.4 Hz, 1H), 8.60 (d, J = 2.7 Hz, 1H), 8.57-8.47 (m, 2H), 8.22 (dd, J = 6.4, 5.1 Hz, 1H), 7.63 (dd, J = 8.2, 0.8 Hz, 1H), 7.26 (t, J = 51.6 Hz, 1H), 5.99 (s, 2H); LRMS (ESI) m/z 374.3 ($M^+$ + H). |
| 181 | 4185 | 2-(difluoromethyl)-5-(6-((4-(2-fluoropyridin-4-yl)-1H-1,2,3-triazol-1-yl)methyl)pyridin-3-yl)-1,3,4-oxadiazole<br>$^1$H NMR (400 MHZ, $CD_3OD$) δ 9.27 (dd, J = 2.3, 0.9 Hz, 1H), 8.79 (s, 1H), 8.54 (dd, J = 8.2, 2.3 Hz, 1H), 8.28 (dt, J = 5.2, 0.7 Hz, 1H), 7.80 (ddd, J = 5.3, 2.0, 1.3 Hz, 1H), 7.65 (dd, J = 8.3, 0.8 Hz, 1H), 7.56 (q, J = 1.2 Hz, 1H), 7.26 (t, J = 51.6 Hz, 1H), 5.96 (s, 2H); LRMS (ESI) m/z 374.4 ($M^+$ + H). |
| 205 | 4284 | 2-(6-((4-(4-(1H-imidazol-1-yl)phenyl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 9.21 (d, J = 2.0 Hz, 1H), 8.80 (s, 1H), 8.54-8.48 (m, 1H), 8.34 (s, 1H), 8.02 (d, J = 8.2 Hz, 2H), 7.83 (s, 1H), 7.77 (d, J = 8.2 Hz, 2H), 7.73-7.44 (m, 2H), 7.15 (s, 1H), 5.96 (s, 2H); LRMS (ES) m/z 421.2 ($M^+$ + 1). |
| 206 | 4285 | 2-(6-((4-(4-(1H-1,2,4-triazol-1-yl)phenyl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 9.36 (s, 1H), 9.21 (d, J = 2.2 Hz, 1H), 8.82 (s, 1H), 8.51 (dd, J = 8.3, 2.3 Hz, 1H), 8.27 (s, 1H), 8.11-8.04 (m, 2H), 7.98 (d, J = 8.5 Hz, 2H), 7.73-7.44 (m, 2H), 5.96 (s, 2H); LRMS (ES) m/z 422.9 ($M^+$ + 1). |
| 207 | 4286 | 2-(6-((4-(2-(1H-1,2,4-triazol-1-yl)phenyl)-1H-1,2,3-triazol-1-yl)methyl)pyridin-3-yl)-5-(difluoromethyl)-1,3,4-oxadiazole<br>$^1$H NMR (400 MHZ, DMSO-$d_6$) δ 9.18 (dd, J = 2.3, 0.8 Hz, 1H), 8.76 (s, 1H), 8.48 (dd, J = 8.2, 2.3 Hz, 1H), 8.21 (s, 1H), 8.09 (dd, J = 7.9, 1.5 Hz, 1H), 7.71 (td, J = 7.4, 1.6 Hz, 1H), 7.58 (pd, J = 7.9, 1.5 Hz, 3H), 7.48-7.40 (m, 1H), 7.35 (s, 1H), 5.85 (s, 2H); LRMS (ES) m/z 422.2 ($M^+$ + 1). |
| 210 | 4289 | 2-(difluoromethyl)-5-(6-((4-(2-methyl-1H-indol-5-yl)-1H-1,2,3-triazol-1-yl)methyl)pyridin-3-yl)-1,3,4-oxadiazole<br>$^1$H NMR (400 MHZ, $CD_3OD$) δ 9.28 (dd, J = 2.3, 0.9 Hz, 1H), 8.52 (dd, J = 8.2, 2.2 Hz, 1H), 8.36 (s, 1H), 7.89 (d, J = 1.6 Hz, 1H), 7.64-7.54 (m, 1H), 7.54-7.43 (m, 1H), 7.39-7.12 (m, 2H), 6.21-6.16 (m, 1H), 5.90 (s, 2H), 2.44 (d, J = 1.0 Hz, 3H); LRMS (ESI) m/z 408.3 ($M^+$ + H). |
| 363 | 4489 | 2-(difluoromethyl)-5-(6-((4-(3-(difluoromethyl)phenyl)-1H-1,2,3-triazol-1-yl)methyl)pyridin-3-yl)-1,3,4-oxadiazole<br>$^1$H NMR (400 MHZ, $CDCl_3$) δ 9.31 (d, J = 2.3 Hz, 1H), 8.39 (dd, J = 8.2, 2.3 Hz, 1H), 8.10 – 7.92 (m, 3H), 7.47 (ddd, J = 23.1, 15.2, 7.9 Hz, 3H), 7.10 – 6.47 (m, 2H), 5.81 (s, 2H); LRMS (ES) m/z ($M^+$ + 1). |
| 485 | 17198 | 2-(difluoromethyl)-5-(3-fluoro-4-((4-(imidazo[1,2-a]pyridin-7-yl)-1H-1,2,3-triazol-1-yl)methyl)phenyl)-1,3,4-oxadiazole<br>$^1$H NMR (400 MHZ, $CD_3OD$) δ 8.65 (s, 1H), 8.59 (s, 1H), 8.09-7.89 (m, 4H), 7.68 (dt, J = 27.7, 7.7 Hz, 2H), 7.48 (d, J = 7.1 Hz, 1H), 7.24 (t, J = 51.6 Hz, 1H), 5.89 (s, 2H); LRMS (ES) m/z 412.34 ($M^+$ + 1). |
| 486 | 17201 | 2-(difluoromethyl)-5-(3-fluoro-4-((4-(imidazo[1,2-a]pyridin-2-yl)-1H-1,2,3-triazol-1-yl)methyl)phenyl)-1,3,4-oxadiazole<br>$^1$H NMR (400 MHZ, $CD_3OD$) δ 8.71-8.24 (m, 2H), 7.99 (dd, J = 11.8, 8.9 Hz, 3H), 7.64 (t, J = 7.5 Hz, 1H), 7.56 (s, 1H), 7.45-7.34 (m, 1H), 7.24 (t, J = 51.6 Hz, 8H), 6.98 (t, J = 6.8 Hz, 1H), 5.91 (s, 2H), 4.87 (s, 119H), 3.33 (dt, J = 3.3, 1.6 Hz, 196H), 3.30-3.16 (m, 6H), 1.93 (s, 5H), 1.24 (s, 1H); LRMS (ES) m/z 412.34 ($M^+$ + 1). |

TABLE 159-continued

| Example | Compound No. | Compound Name, $^1$H-NMR, MS (ESI) |
|---|---|---|
| 489 | 17263 | 2-(4-((4-(6-bromopyridin-2-yl)-1H-1,2,3-triazol-1-yl)methyl)-3-fluorophenyl)-5-(difluoromethyl)-1,3,4-oxadiazole $^1$H NMR (400 MHZ, $CD_3OD$) δ 8.60 (s, 1H), 8.06 (d, J = 7.6 Hz, 1H), 8.00-7.95 (m, 2H), 7.79 (t, J = 7.8 Hz, 1H), 7.63 (t, J = 7.6 Hz, 1H), 7.55 (d, J = 7.8 Hz, 1H), 7.24 (t, J = 51.6 Hz, 1H), 5.88 (s, 2H); LRMS (ESI) m/z 451.1 ($M^+$ + H). |
| 510 | 17848 | 2-(difluoromethyl)-5-(3-fluoro-4-((4-(thiazol-2-yl)-1H-1,2,3-triazol-1-yl)methyl)phenyl)-1,3,4-oxadiazole $^1$H NMR (400 MHZ, DMSO-$d_6$) δ 8.84 (s, 1H), 7.96 (d, J = 2.7 Hz, 1H), 7.95-7.92 (m, 2H), 7.80 (d, J = 3.2 Hz, 1H), 7.60 (t, J = 7.8 Hz, 1H), 7.56 (t, J = 51.3 Hz, 1H), 5.89 (s, 2H); ; LRMS (ES) m/z 379.64 ($M^+$ + 1). |
| 511 | 17851 | 2-(difluoromethyl)-5-(3-fluoro-4-((4-(thiazol-5-yl)-1H-1,2,3-triazol-1-yl)methyl)phenyl)-1,3,4-oxadiazole $^1$H NMR (400 MHZ, DMSO-$d_6$) δ 9.13 (s, 1H), 8.72 (s, 1H), 8.30 (s, 1H), 7.96 (d, J = 8.8 Hz, 2H), 7.62 (t, J = 7.7 Hz, 1H), 7.56 (t, J = 51.3 Hz, 1H), 5.87 (s, 2H); LRMS (ES) m/z 379.63 ($M^+$ + 1). |
| 512 | 17854 | 2-(difluoromethyl)-5-(3-fluoro-4-((4-(4-methylthiazol-2-yl)-1H-1,2,3-triazol-1-yl)methyl)phenyl)-1,3,4-oxadiazole $^1$H NMR (400 MHZ, DMSO-d6) δ 8.80 (s, 1H), 7.96 (s, 1H), 7.94 (s, 1H), 7.60 (t, J = 7.8 Hz, 1H), 7.56 (t, J = 51.4 Hz, 1H), 7.33 (s, 1H), 5.88 (s, 2H), 2.41 (s, 3H); LRMS (ES) m/z 393.63 ($M^+$ + 1). |
| 513 | 17857 | 2-(difluoromethyl)-5-(3-fluoro-4-((4-(5-methylthiazol-2-yl)-1H-1,2,3-triazol-1-yl)methyl)phenyl)-1,3,4-oxadiazole $^1$H NMR (400 MHZ, DMSO-$d_6$) δ 8.76 (s, 1H), 7.96 (s, 1H), 7.93 (s, 1H), 7.64-7.57 (m, 2H), 7.56 (t, J = 51.3 Hz, 1H), 5.88 (s, 2H), 2.47 (s, 3H); LRMS (ES) m/z 393.63 ($M^+$ + 1). |

Example 538: Synthesis of compound 18306, 2-(6-((4-(4-(azetidin-1-ylmethyl)phenyl)-1H-1,2,3-triazol-1-yl)methyl)-5-fluoropyridin-3-yl)-5-(difluoromethyl)-1,3,4-oxadiazole

[Step 1] Synthesis of 4-(1-((5-(5-(difluoromethyl)-1,3,4-oxadiazol-2-yl)-3-fluoropyridin-2-yl)methyl)-1H-1,2,3-triazol-4-yl)benzaldehyde

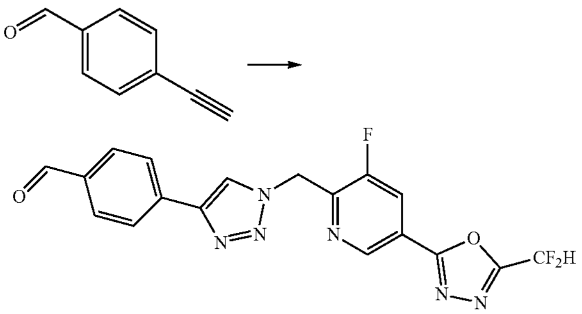

4-ethynylbenzaldehyde (0.200 g, 1.537 mmol), 2-(6-(azidomethyl)-5-fluoropyridin-3-yl)-5-(difluoromethyl)-1,3,4-oxadiazole (0.415 g, 1.537 mmol) prepared in step 1 of example 490, sodium ascorbate (0.50 M solution in water, 0.307 mL, 0.154 mmol) and copper(II) sulfate pentahydrate (1.00 M solution in water, 0.015 mL, 0.015 mmol) were dissolved in tert-butanol (3 mL)/water (3 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (5 mL) and hexane (50 mL) were added and stirred to the resulting concentrate to filter out a precipitated solid, washed with hexane, and dried to obtain 4-(1-((5-(5-(difluoromethyl)-1,3,4-oxadiazol-2-yl)-3-fluoropyridin-2-yl)methyl)-1H-1,2,3-triazol-4-yl)benzaldehyde (0.367 g, 59.7%) in a yellow solid form.

[Step 2] Synthesis of Compound 18306

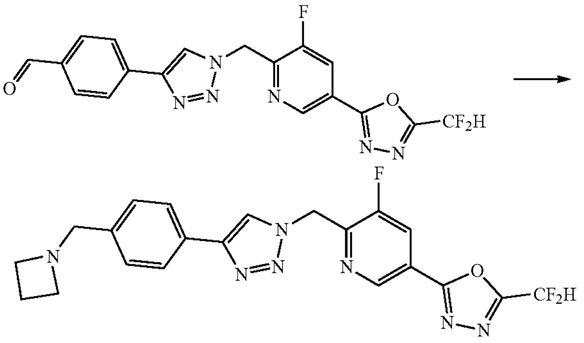

The 4-(1-((5-(5-(difluoromethyl)-1,3,4-oxadiazol-2-yl)-3-fluoropyridin-2-yl)methyl)-1H-1,2,3-triazol-4-yl)benzaldehyde (0.090 g, 0.225 mmol) prepared in step 1, azetidine (0.030 mL, 0.450 mmol) and acetic acid (0.013 mL, 0.225 mmol) were dissolved in dichloromethane (1 mL), after which the resulting solution was stirred at room temperature for 1 hour, and then sodium triacetoxyborohydride (0.143 g, 0.674 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(6-((4-(4-(azetidin-1-ylmethyl)phenyl)-1H-1,2,3-triazol-1-yl)methyl)pyridin-3-yl)-5-(difluoromethyl)-1,3,4-oxadiazole (0.050 g, 50.4%) in a yellow solid form.

$^1$H NMR (400 MHz, $CD_3OD$) δ 9.10 (s, 1H), 8.48 (s, 1H), 8.38 (dd, J=9.6, 1.7 Hz, 1H), 7.83 (d, J=8.2 Hz, 2H), 7.41-7.14 (m, 3H), 6.00 (d, J=1.8 Hz, 2H), 3.72 (s, 2H), 3.40 (t, J=7.3 Hz, 4H), 2.21-2.14 (m, 2H); LRMS (ES) m/z 442.4 ($M^+$+1).

The compounds of table 161 were synthesized according to substantially the same process as described above in the synthesis of compound 18306 with an exception of using 4-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 160.

TABLE 160

| Example | Compound No. | Reactant | Yield (%) |
|---|---|---|---|
| 539 | 18307 | 4-methylpiperidine | 60 |
| 540 | 18308 | Dimethylamine | 58 |

TABLE 161

| Example | Compound No. | Compound Name, $^1$H-NMR, MS (ESI) |
|---|---|---|
| 539 | 18307 | 2-(difluoromethyl)-5-(5-fluoro-6-((4-(4-((4-methylpiperidin-1-yl)methyl)phenyl)-1H-1,2,3-triazol-1-yl)methyl)pyridin-3-yl)-1,3,4-oxadiazole $^1$H NMR (400 MHZ, $CD_3OD$) δ 9.11 (s, 1H), 8.48 (s, 1H), 8.39 (dd, J = 9.6, 1.7 Hz, 1H), 7.82 (d, J = 8.2 Hz, 2H), 7.44 (d, J = 8.2 Hz, 2H), 5.27 (t, J = 1200.0 Hz, 1H), 6.00 (d, J = 1.8 Hz, 2H), 3.58 (s, 2H), 2.92 (d, J = 11.7 Hz, 2H), 2.07 (t, J = 10.7 Hz, 2H), 1.67 (d, J = 14.1 Hz, 2H), 1.44-1.38 (m, 1H), 1.32-1.22 (m, 2H), 0.95 (d, J = 6.4 Hz, 3H); LRMS (ESI) m/z 484.4 ($M^+$ + H). |
| 540 | 18308 | 1-(4-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine $^1$H NMR (400 MHZ, $CD_3OD$) δ 9.10 (s, 1H), 8.49 (s, 1H), 8.39 (dd, J = 9.6, 1.7 Hz, 1H), 7.84 (d, J = 8.2 Hz, 2H), 7.43 (d, J = 8.2 Hz, 2H), 7.27 (t, J = 51.5 Hz, 1H), 6.00 (d, J = 1.7 Hz, 2H), 3.53 (s, 2H), 2.29 (s, 6H); LRMS (ESI) m/z 430.3 ($M^+$ + H). |

Example 541: Synthesis of compound 18309, 2-(6-((4-(5-(azetidin-1-ylmethyl)thiophen-2-yl)-1H-1,2,3-triazol-1-yl)methyl)-5-fluoropyridin-3-yl)-5-(difluoromethyl)-1,3,4-oxadiazole

[Step 1] Synthesis of 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde

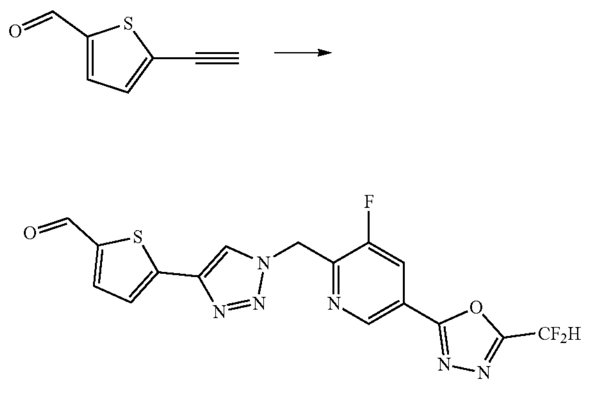

5-ethynylthiophen-2-carbaldehyde (0.171 mL, 1.469 mmol), 2-(6-(azidomethyl)-5-fluoropyridin-3-yl)-5-(difluoromethyl)-1,3,4-oxadiazole (0.397 g, 1.469 mmol) prepared in step 1 of example 490, sodium ascorbate (0.50 M solution in water, 0.294 mL, 0.147 mmol) and copper(II) sulfate pentahydrate (1.00 M solution in water, 0.015 mL, 0.015 mmol) were dissolved in tert-butanol (3 mL)/water (3 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (5 mL) and hexane (50 mL) were added and stirred to the resulting concentrate to filter out a precipitated solid, washed with hexane, and dried to obtain 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde (0.370 g, 62.0%) in a yellow solid form.

[Step 2] Synthesis of Compound 18309

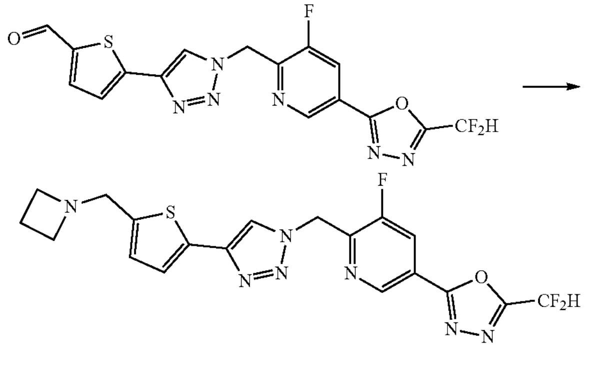

The 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde (0.090 g, 0.221 mmol) prepared in step 1, azetidine (0.030 mL, 0.443 mmol) and acetic acid (0.013 mL, 0.221 mmol) were dissolved in dichloromethane (1 mL), after which the resulting solution was stirred at room temperature for 1 hour, and then sodium triacetoxyborohydride (0.141 g, 0.664 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(6-((4-(5-(azetidin-1-ylmethyl)thiophen-2-yl)-1H-1,2,3-triazol-1-yl)methyl)-5-fluoropyridin-3-yl)-5-(difluoromethyl)-1,3,4-oxadiazole (0.042 g, 42.4%) in a light yellow solid form.

$^1$H NMR (400 MHz, $CD_3OD$) δ 9.10 (s, 1H), 8.40-8.36 (m, 2H), 7.30 (d, J=3.6 Hz, 1H), 7.27 (t, J=51.5 Hz, 1H), 6.97 (d, J=3.6 Hz, 1H), 5.98 (d, J=1.7 Hz, 2H), 3.82 (s, 2H), 3.37-3.32 (m, 4H), 2.18-2.11 (m, 2H); LRMS (ES) m/z 448.4 ($M^+$+1).

The compounds of table 163 were synthesized according to substantially the same process as described above in the synthesis of compound 18309 with an exception of using 5-(1-((5-(5-(difluoromethyl)-1,3,4-oxadiazol-2-yl)-3-fluoropyridin-2-yl)methyl)-1H-1,2,3-triazol-4-yl)thiophen-2-carbaldehyde and the reactant of table 162.

TABLE 162

| Example | Compound No. | Reactant | Yield (%) |
|---|---|---|---|
| 542 | 18310 | 4-methylpiperidine | 84 |
| 543 | 18311 | Dimethylamine | 24 |

TABLE 163

| Example | Compound No. | Compound Name, $^1$H-NMR, MS (ESI) |
|---|---|---|
| 542 | 18310 | 2-(difluoromethyl)-5-(5-fluoro-6-((4-(5-((4-methylpiperidin-1-yl)methyl)thiophen-2-yl)-1H-1,2,3-triazol-1-yl)methyl)pyridin-3-yl)-1,3,4-oxadiazole<br>$^1$H NMR (400 MHZ, $CD_3OD$) δ 9.10 (s, 1H), 8.40-8.36 (m, 2H), 7.30 (d, J = 3.6 Hz, 1H), 7.27 (t, J = 51.6 Hz, 1H), 6.98 (d, J = 3.6 Hz, 1H), 5.98 (d, J = 1.6 Hz, 2H), 3.76 (s, 2H), 2.96 (d, J = 11.6 Hz, 2H), 2.10 (t, J = 10.6 Hz, 2H), 1.67 (d, J = 11.2 Hz, 2H), 1.42-1.36 (m, 1H), 1.33-1.23 (m, 2H), 0.96 (d, J = 6.4 Hz, 3H); LRMS (ESI) m/z 490.5 ($M^+$ + H). |
| 543 | 18311 | 1-(5-(1-((5-(5-(difluoromethyl)-1,3,4-oxadiazol-2-yl)-3-fluoropyridin-2-yl)methyl)-1H-1,2,3-triazol-4-yl)thiophen-2-yl)-N,N-dimethylmethanamine<br>$^1$H NMR (400 MHZ, $CD_3OD$) δ 9.10 (s, 1H), 8.40-8.37 (m, 2H), 7.32 (d, J = 3.6 Hz, 1H), 7.27 (t, J = 51.6 Hz, 1H), 7.00 (d, J = 3.6 Hz, 1H), 5.98 (d, J = 1.7 Hz, 2H), 3.73 (s, 2H), 2.32 (s, 6H); LRMS (ESI) m/z 436.3 ($M^+$ + H). |

Example 544: Synthesis of Compound 18327

2-(difluoromethyl)-5-(3-fluoro-4-((4-(3-fluoro-4-(4-(tetrahydro-2H-pyran-4-yl)piperazin-1-yl)phenyl)-1H-1,2,3-triazol-1-yl)methyl)phenyl)-1,3,4-oxadiazole [Step 1] Synthesis of 2-(4-bromo-3-fluorophenyl)-1,3-dioxolane

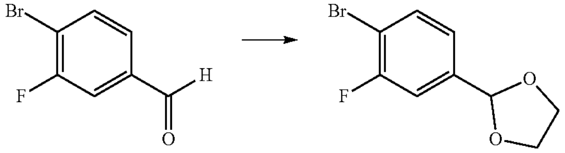 [SMILES: O=Cc1ccc(Br)c(F)c1 ; Fc1cc(C2OCCO2)ccc1Br]

4-bromo-3-fluorobenzaldehyde (10.000 g, 49.259 mmol), p-toluenesulfonic acid (0.094 g, 0.493 mmol) and ethylene glycol (13.157 mL, 59.110 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%) and concentrated to obtain 2-(4-bromo-3-fluorophenyl)-1,3-dioxolane (11.410 g, 93.8%) in a transparent liquid form.

[Step 2] Synthesis of tert-butyl 4-(4-(1,3-dioxolan-2-yl)-2-fluorophenyl)piperazin-1-carboxylate

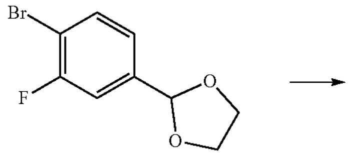

-continued

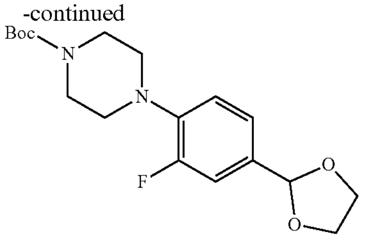

2-(4-bromo-3-fluorophenyl)-1,3-dioxolane (5.000 g, 20.238 mmol), tert-butyl piperazin-1-carboxylate (4.523 g, 24.286 mmol), tris(dibenzylidene acetone)dipalladium ($Pd_2(dba)_3$, 0.185 g, 0.202 mmol), rac-BINAP (0.252 g, 0.405 mmol) and NaOBut (3.890 g, 40.476 mmol) were dissolved in toluene (50 mL) at room temperature, after which the resulting solution was heated under reflux for 18 hours, and then a reaction was finished by lowering a temperature to room temperature. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 50%) and concentrated to obtain tert-butyl 4-(4-(1,3-dioxolan-2-yl)-2-fluorophenyl)piperazin-1-carboxylate (7.200 g, 101.0%) in a yellow solid form.

[Step 3] Synthesis of tert-butyl 4-(2-fluoro-4-formylphenyl)piperazin-1-carboxylate

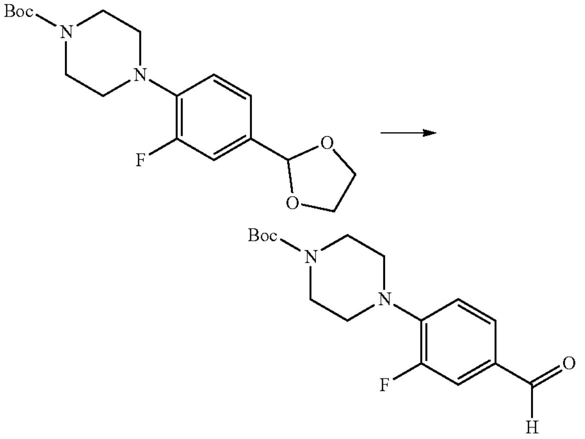

Tert-butyl 4-(4-(1,3-dioxolan-2-yl)-2-fluorophenyl)piperazin-1-carboxylate (7.200 g, 20.431 mmol) and hydrochloric acid (1.00 M solution, 61.292 mL, 61.292 mmol) were dissolved in methanol (20 mL) at room temperature, after which the resulting solution was stirred at the same temperature for 3 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. A precipitated solid was filtered, washed with hexane, and dried to obtain tert-butyl 4-(2-fluoro-4-formylphenyl)piperazin-1-carboxylate (6.550 g, 104.0%) in a yellow solid form.

[Step 4] Synthesis of tert-butyl 4-(4-(2,2-dibromovinyl)-2-fluorophenyl)piperazin-1-carboxylate

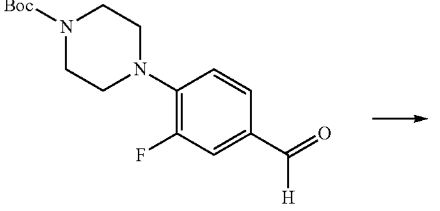

-continued

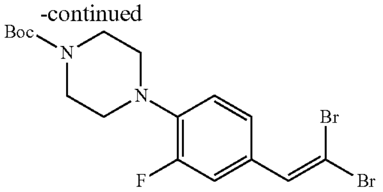

Tert-butyl 4-(2-fluoro-4-formylphenyl)piperazin-1-carboxylate (6.550 g, 21.242 mmol), carbon tetrabromide (14.089 g, 42.484 mmol) and triphenylphosphine triphenylphosphine (16.715 g, 63.726 mmol) were dissolved in dichloromethane (150 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 40 g cartridge; ethyl acetate/hexane=0 to 20%) and concentrated to obtain tert-butyl 4-(4-(2,2-dibromovinyl)-2-fluorophenyl)piperazin-1-carboxylate (5.670 g, 57.5%) in a white solid form.

[Step 5] Synthesis of tert-butyl 4-(4-ethynyl-2-fluorophenyl)piperazin-1-carboxylate

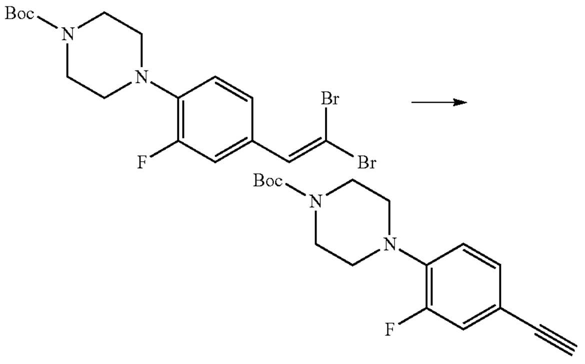

Tert-butyl 4-(4-(2,2-dibromovinyl)-2-fluorophenyl)piperazin-1-carboxylate (5.670 g, 12.215 mmol) and 2,3,4,6,7,8,9,10-octahydropyrimido[1,2-a]azepine (DBU, 7.307 mL, 48.861 mmol) were dissolved in acetonitrile (50 mL) at room temperature, after which the resulting solution was stirred at the same temperature for 12 hours. Solvent was removed from the reaction mixture under reduced pressure, after which water was poured into the resulting concentrate, and then an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(4-ethynyl-2-fluorophenyl)piperazin-1-carboxylate (1.100 g, 29.6%) in a white solid form.

[Step 6] Synthesis of tert-butyl 4-(4-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate

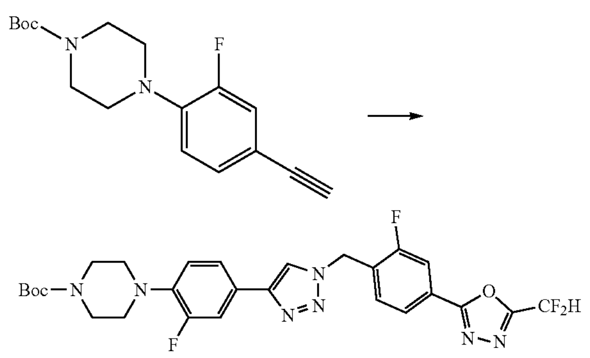

Tert-butyl 4-(4-ethynyl-2-fluorophenyl)piperazin-1-carboxylate (0.430 g, 1.413 mmol), 2-(4-(azidomethyl)-3-fluorophenyl)-5-(difluoromethyl)-1,3,4-oxadiazole (0.418 g, 1.554 mmol) prepared in step 1 of example 2, copper(II) sulfate pentahydrate (0.004 g, 0.014 mmol) and sodium ascorbate (0.028 g, 0.141 mmol) were dissolved in tert-butanol (20 mL)/water (10 mL) at room temperature, after which the resulting solution was stirred at the same temperature for 2 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(4-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.330 g, 40.7%) in a white solid form.

[Step 7] Synthesis of 2-(difluoromethyl)-5-(3-fluoro-4-((4-(3-fluoro-4-(piperazin-1-yl)phenyl)-1H-1,2,3-triazol-1-yl)methyl)phenyl)-1,3,4-oxadiazole

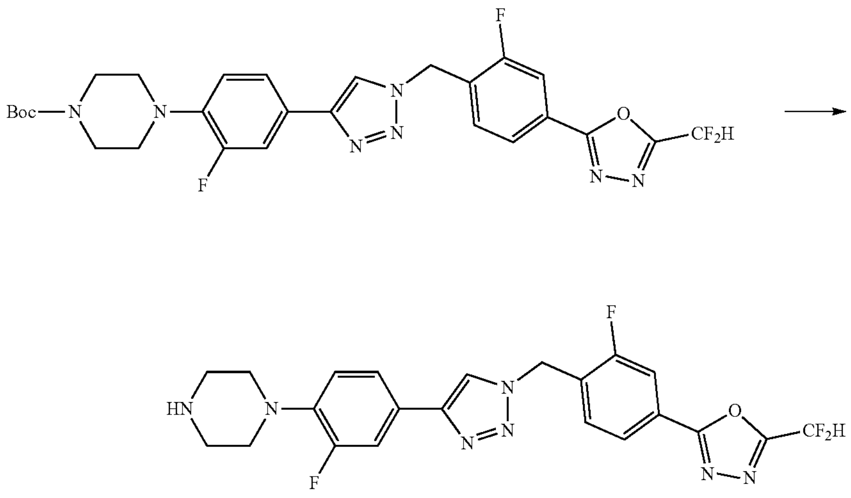

Tert-butyl 4-(4-(1-(4-(5-(difluoromethyl)-1,3,4-oxadiazol-2-yl)-2-fluorobenzyl)-1H-1,2,3-triazol-4-yl)-2-fluorophenyl)piperazin-1-carboxylate (0.380 g, 0.663 mmol) and trifluoroacetic acid (0.507 mL, 6.625 mmol) were dissolved in dichloromethane (25 mL) at room temperature, after which the resulting solution was stirred at the same temperature for 12 hours. Solvent was removed from the reaction mixture under reduced pressure, after which the obtained product was used without an additional purification process (2-(difluoromethyl)-5-(3-fluoro-4-((4-(3-fluoro-4-(piperazin-1-yl)phenyl)-1H-1,2,3-triazol-1-yl)methyl)phenyl)-1,3,4-oxadiazole, 0.300 g, 95.6%, yellow oil).

[Step 8] Synthesis of Compound 18327

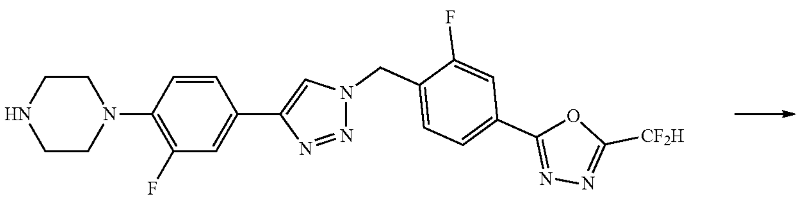

-continued

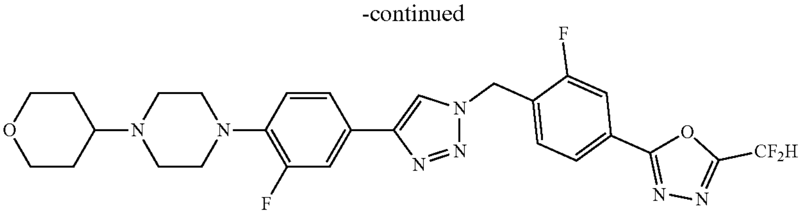

2-(difluoromethyl)-5-(3-fluoro-4-((4-(3-fluoro-4-(piperazin-1-yl)phenyl)-1H-1,2,3-triazol-1-yl)methyl)phenyl)-1,3,4-oxadiazole (0.080 g, 0.169 mmol), tetrahydro-4H-pyran-4-one (0.034 g, 0.338 mmol) and sodium triacetoxyborohydride (0.072 g, 0.338 mmol) were dissolved in dichloromethane (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(difluoromethyl)-5-(3-fluoro-4-((4-(3-fluoro-4-(4-(tetrahydro-2H-pyran-4-yl)piperazin-1-yl)phenyl)-1H-1,2,3-triazol-1-yl)methyl)phenyl)-1,3,4-oxadiazole (0.035 g, 37.2%) in a white solid form.

$^1$H NMR (400 MHz, $CDCl_3$) δ d 7.91~7.88 (m, 2H), 7.75 (s, 1H), 7.52~7.42 (m, 3H), 7.04~6.79 (m, 2H), 5.70 (s, 1H), 4.04 (dd, J=11.3, 3.4 Hz, 2H), 3.40 (t, J=11.3 Hz, 2H), 3.18 (t, J=0.0 Hz, 4H), 2.79 (t, J=2.0 Hz, 4H), 2.53 (t, J=11.3 Hz, 1H), 1.83 (d, J=12.2 Hz, 2H), 1.68~1.58 (m, 2H); LRMS (ES) m/z 558.4 ($M^+$+1).

Example 545: Synthesis of compound 18457, 1-(3-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine

[Step 1] Synthesis of 3-(1-((5-(5-(difluoromethyl)-1,3,4-oxadiazol-2-yl)-3-fluoropyridin-2-yl)methyl)-1H-1,2,3-triazol-4-yl)benzaldehyde

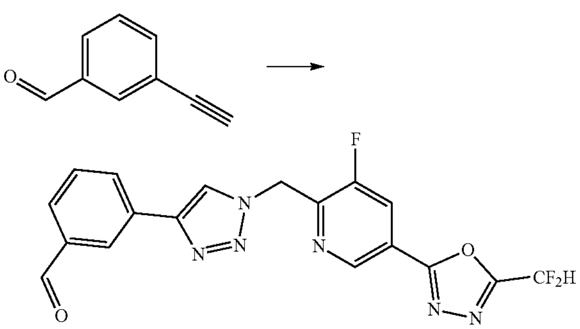

3-ethynylbenzaldehyde (0.200 g, 1.537 mmol), 2-(6-(azidomethyl)-5-fluoropyridin-3-yl)-5-(difluoromethyl)-1,3,4-oxadiazole (0.415 g, 1.537 mmol) prepared in step 1 of example 490, sodium ascorbate (0.50 M solution in water, 0.307 mL, 0.154 mmol) and copper(II) sulfate pentahydrate (1.00 M solution in water, 0.015 mL, 0.015 mmol) were dissolved in tert-butanol (3 mL)/water (3 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain 3-(1-((5-(5-(difluoromethyl)-1,3,4-oxadiazol-2-yl)-3-fluoropyridin-2-yl)methyl)-1H-1,2,3-triazol-4-yl)benzaldehyde (0.420 g, 68.3%) in a light yellow solid form.

[Step 2] Synthesis of Compound 18457

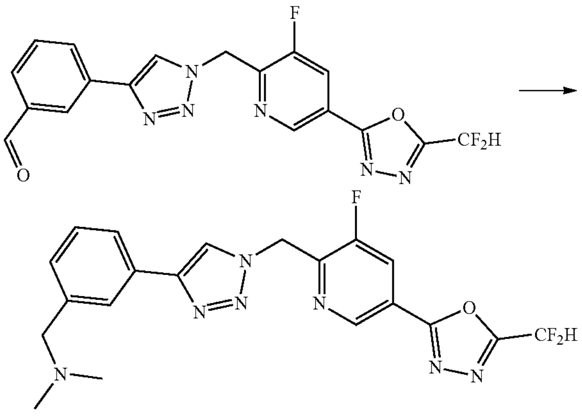

3-(1-((5-(5-(difluoromethyl)-1,3,4-oxadiazol-2-yl)-3-fluoropyridin-2-yl)methyl)-1H-1,2,3-triazol-4-yl)benzaldehyde (0.100 g, 0.250 mmol), dimethylamine (2.00 M solution in MeOH, 0.250 mL, 0.500 mmol) and acetic acid (0.014 mL, 0.250 mmol) were dissolved in dichloromethane (1 mL), after which the resulting solution was stirred at room temperature for 1 hour, and then sodium triacetoxyborohydride (0.159 g, 0.749 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 1-(3-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine (0.031 g, 28.9%) in a yellow solid form.

$^1$H NMR (400 MHz, $CD_3OD$) δ 9.11 (s, 1H), 8.49 (s, 1H), 8.39 (dd, J=9.6, 1.7 Hz, 1H), 7.82-7.79 (m, 2H), 7.45 (t, J=7.6 Hz, 1H), 7.35 (d, J=7.7 Hz, 1H), 7.27 (t, J=51.5 Hz, 1H), 6.01 (d, J=1.8 Hz, 2H), 3.57 (s, 2H), 2.30 (s, 6H); LRMS (ES) m/z 430.4 ($M^+$+1).

The compound of table 165 was synthesized according to substantially the same process as described above in the synthesis of compound 18457 by using 3-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 164.

TABLE 164

| Example | Compound No. | Reactant | Yield (%) |
|---|---|---|---|
| 546 | 18459 | 4-methylpiperidine | 55 |

TABLE 165

| Example | Compound No. | Compound Name, $^1$H-NMR, MS (ESI) |
|---|---|---|
| 546 | 18459 | 2-(difluoromethyl)-5-(5-fluoro-6-((4-(3-((4-methylpiperidin-1-yl)methyl)phenyl)-1H-1,2,3-triazol-1-yl)methyl)pyridin-3-yl)-1,3,4-oxadiazole $^1$H NMR (400 MHZ, $CD_3OD$) δ 9.11 (s, 1H), 8.48 (s, 1H), 8.39 (dd, J = 9.6, 1.6 Hz, 1H), 7.83 (s, 1H), 7.78 (d, J = 7.8 Hz, 1H), 7.45-7.14 (m, 3H), 6.01 (d, J = 1.6 Hz, 2H), 3.59 (s, 2H), 2.93 (d, J = 11.8 Hz, 2H), 2.07 (t, J = 10.7 Hz, 2H), 1.66 (d, J = 12.1 Hz, 2H), 1.43-1.37 (m, 1H), 1.32-1.22 (m, 2H), 0.95 (d, J = 6.4 Hz, 3H); LRMS (ESI) m/z 484.4 ($M^+$ + H). |

Example 548: Synthesis of compound 18483, 1-(3-chloro-5-(1-(4-(5-(difluoromethyl)-1,3,4-oxadiazol-2-yl)-2-fluorobenzyl)-1H-1,2,3-triazol-4-yl)phenyl)-N,N-dimethylmethanamine

[Step 1] Synthesis of 3-chloro-5-(1-(4-(5-(difluoromethyl)-1,3,4-oxadiazol-2-yl)-2-fluorobenzyl)-1H-1,2,3-triazol-4-yl)benzaldehyde

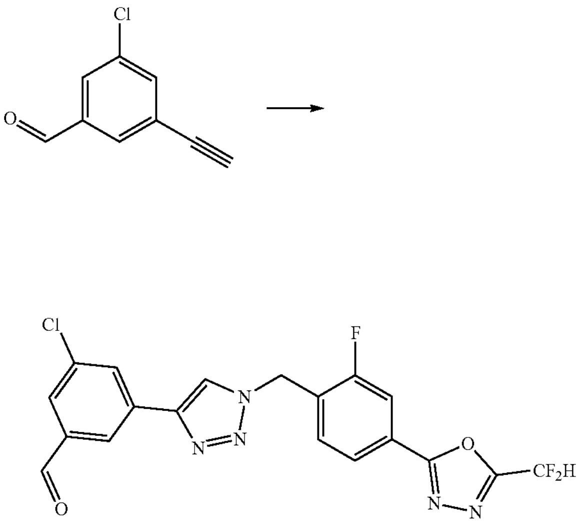

3-chloro-5-ethynylbenzaldehyde (0.112 g, 0.680 mmol), 2-(4-(azidomethyl)-3-fluorophenyl)-5-(difluoromethyl)-1,3,4-oxadiazole (0.183 g, 0.680 mmol) prepared in step 1 of example 2, sodium ascorbate (0.50 M solution in water, 0.136 mL, 0.068 mmol) and copper(II) sulfate pentahydrate (1.00 M solution in water, 0.007 mL, 0.007 mmol) were dissolved in tert-butanol (2 mL)/water (2 mL) at room temperature, after which the resulting solution was stirred at the same temperature for 2 hours. Tert ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated to obtain 3-chloro-5-(1-(4-(5-(difluoromethyl)-1,3,4-oxadiazol-2-yl)-2-fluorobenzyl)-1H-1,2,3-triazol-4-yl)benzaldehyde (0.110 g, 37.3%) in a yellow solid form.

[Step 2] Synthesis of Compound 18483

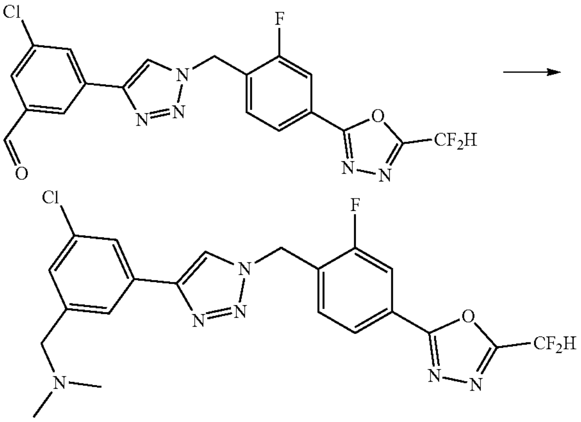

The 3-chloro-5-(1-(4-(5-(difluoromethyl)-1,3,4-oxadiazol-2-yl)-2-fluorobenzyl)-1H-1,2,3-triazol-4-yl)benzaldehyde (0.055 g, 0.127 mmol) in step 1, dimethylamine (2.00 M solution in MeOH, 0.127 mL, 0.254 mmol) and acetic acid (0.007 mL, 0.127 mmol) were dissolved in dichloromethane (1 mL), after which the resulting solution was stirred at room temperature for 1 hour, and then sodium triacetoxyborohydride (0.081 g, 0.380 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 1-(3-chloro-5-(1-(4-(5-(difluoromethyl)-1,3,4-oxadiazol-2-yl)-2-fluorobenzyl)-1H-1,2,3-triazol-4-yl)phenyl)-N,N-dimethylmethanamine (0.041 g, 69.9%) in a yellow solid form.

$^1$H NMR (400 MHz, $CD_3OD$) δ 8.51 (s, 1H), 8.00-7.95 (m, 2H), 7.83 (s, 1H), 7.74 (s, 1H), 7.61 (t, J=7.7 Hz, 1H), 7.24 (t, J=51.6 Hz, 1H), 5.86 (s, 2H), 3.53 (s, 2H), 2.28 (s, 6H); LRMS (ES) m/z 463.3 ($M^+$+1).

Example 549: Synthesis of compound 18554, 1-(2-chloro-3-(1-(4-(5-(difluoromethyl)-1,3,4-oxadiazol-2-yl)-2-fluorobenzyl)-1H-1,2,3-triazol-4-yl)phenyl)-N,N-dimethylmethanamine

[Step 1] Synthesis of 2-chloro-3-(1-(4-(5-(difluoromethyl)-1,3,4-oxadiazol-2-yl)-2-fluorobenzyl)-1H-1,2,3-triazol-4-yl)benzaldehyde

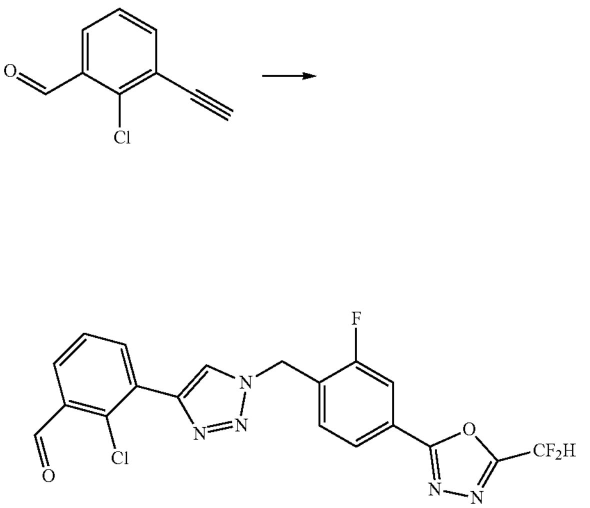

2-chloro-3-ethynylbenzaldehyde (0.095 g, 0.577 mmol), 2-(4-(azidomethyl)-3-fluorophenyl)-5-(difluoromethyl)-1,3,4-oxadiazole (0.156 g, 0.577 mmol) prepared in step 1 of example 2, sodium ascorbate (0.50 M solution in water, 0.115 mL, 0.058 mmol) and copper(II) sulfate pentahydrate (1.00 M solution in water, 0.006 mL, 0.006 mmol) were dissolved in tert-butanol (1 mL)/water (1 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (5 mL) and hexane (100 mL) were added and stirred to the resulting concentrate to filter out a precipitated solid, washed with hexane, and dried to obtain 2-chloro-3-(1-(4-(5-(difluoromethyl)-1,3,4-oxadiazol-2-yl)-2-fluorobenzyl)-1H-1,2,3-triazol-4-yl)benzaldehyde (0.046 g, 18.4%) in a light yellow solid form.

[Step 2] Synthesis of Compound 18554

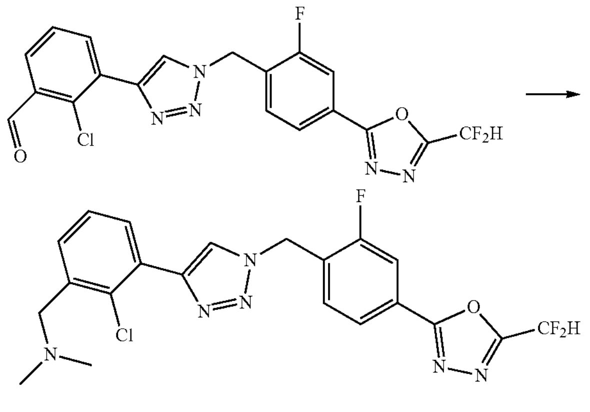

The 2-chloro-3-(1-(4-(5-(difluoromethyl)-1,3,4-oxadiazol-2-yl)-2-fluorobenzyl)-1H-1,2,3-triazol-4-yl)benzaldehyde (0.046 g, 0.106 mmol) in step 1, dimethylamine (2.00 M solution in MeOH, 0.106 mL, 0.212 mmol) and acetic acid (0.006 mL, 0.106 mmol) were dissolved in dichloromethane (1 mL), after which the resulting solution was stirred at room temperature for 1 hour, and then sodium triacetoxyborohydride (0.067 g, 0.318 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 15%) and concentrated, after which the obtained product was purified again via column chromatography ($SiO_2$, 4 g cartridge; methanol/dichloromethane=0 to 10%) and concentrated to obtain 1-(2-chloro-3-(1-(4-(5-(difluoromethyl)-1,3,4-oxadiazol-2-yl)-2-fluorobenzyl)-1H-1,2,3-triazol-4-yl)phenyl)-N,N-dimethylmethanamine (0.014 g, 28.5%) in a white solid form.

$^1$H NMR (400 MHz, $CD_3OD$) δ 8.60 (s, 1H), 8.00-7.91 (m, 3H), 7.60 (t, J=7.6 Hz, 1H), 7.52-7.51 (m, 1H), 7.43 (t, J=7.6 Hz, 1H), 7.24 (t, J=51.5 Hz, 1H), 5.90 (s, 2H), 3.70 (s, 2H), 2.33 (s, 6H); LRMS (ES) m/z 463.3 ($M^+$+1).

Example 550: Synthesis of compound 18622, 2-(6-((4-(5-(azetidin-1-ylmethyl)pyridin-2-yl)-1H-1,2,3-triazol-1-yl)methyl)-5-fluoropyridin-3-yl)-5-(difluoromethyl)-1,3,4-oxadiazole

[Step 1] Synthesis of 6-((trimethylsilyl)ethynyl)nicotinealdehyde

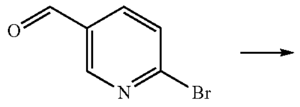

-continued

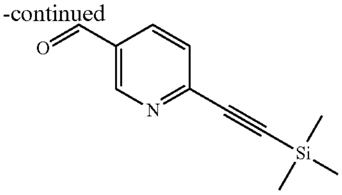

6-bromonicotinealdehyde (1.000 g, 5.376 mmol), bis(triphenylphosphine)palladium dichloride (0.189 g, 0.269 mmol), and copper iodide (I/II, 0.102 g, 0.538 mmol) were dissolved in tetrahydrofuran (20 mL)/triethylamine (4 mL), after which trimethylsilyl acetylene (1.081 mL, 8.064 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%), and concentrated to obtain 6-((trimethylsilyl)ethynyl)nicotinealdehyde (0.527 g, 48.3%) in a yellow solid form.

[Step 2] Synthesis of 6-ethynylnicotinealdehyde

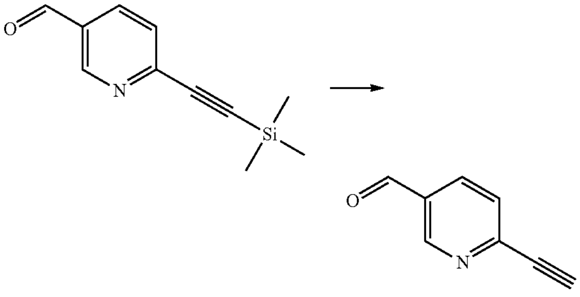

The 6-((trimethylsilyl)ethynyl)nicotinealdehyde (0.527 g, 2.595 mmol) prepared in step 1 and potassium carbonate (1.076 g, 7.785 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%) and concentrated to obtain 6-ethynylnicotinealdehyde (0.340 g, 99.9%) in a yellow solid form.

[Step 3] Synthesis of 6-(1-((5-(5-(difluoromethyl)-1,3,4-oxadiazol-2-yl)-3-fluoropyridin-2-yl)methyl)-1H-1,2,3-triazol-4-yl)nicotinealdehyde

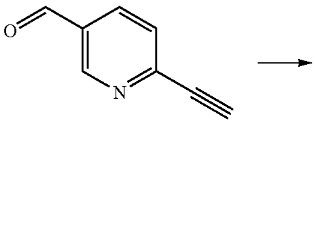

-continued

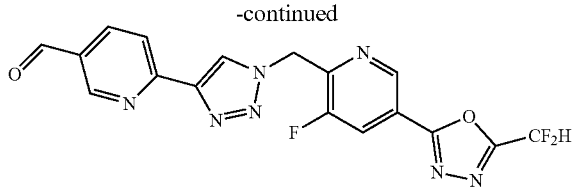

The 6-ethynylnicotinealdehyde (0.150 g, 1.144 mmol) prepared in example 2, 2-(6-(azidomethyl)-5-fluoropyridin-3-yl)-5-(difluoromethyl)-1,3,4-oxadiazole (0.309 g, 1.144 mmol) prepared in step 1 of example 490, sodium ascorbate (0.50 M solution in water, 0.229 mL, 0.114 mmol) and copper(II) sulfate pentahydrate (1.00 M solution in water, 0.011 mL, 0.011 mmol) were dissolved in tert-butanol (3 mL)/water (3 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (3 mL) and hexane (50 mL) were added and stirred to the resulting concentrate to filter out a precipitated solid, washed with hexane, and dried to obtain 6-(1-((5-(5-(difluoromethyl)-1,3,4-oxadiazol-2-yl)-3-fluoropyridin-2-yl)methyl)-1H-1,2,3-triazol-4-yl)nicotinealdehyde (0.138 g, 30.1%) in a yellow solid form.

[Step 4] Synthesis of Compound 18622

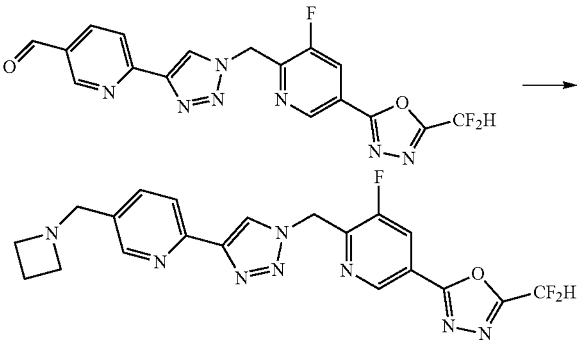

The 6-(1-((5-(5-(difluoromethyl)-1,3,4-oxadiazol-2-yl)-3-fluoropyridin-2-yl)methyl)-1H-1,2,3-triazol-4-yl)nicotinealdehyde (0.050 g, 0.125 mmol) prepared in step 3, azetidine (0.017 mL, 0.249 mmol) and acetic acid (0.007 mL, 0.125 mmol) were dissolved in dichloromethane (1 mL), after which the resulting solution was stirred at room temperature for 1 hour, and then sodium triacetoxyborohydride (0.079 g, 0.374 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 15%) and concentrated to obtain 2-(6-((4-(5-(azetidin-1-ylmethyl)pyridin-2-yl)-1H-1, 2,3-triazol-1-yl)methyl)-5-fluoropyridin-3-yl)-5-(difluoromethyl)-1,3,4-oxadiazole (0.016 g, 29.0%) in a light yellow solid form.

$^1$H NMR (400 MHz, $CD_3OD$) δ 9.10 (s, 1H), 8.60 (s, 1H), 8.53 (d, J=1.8 Hz, 1H), 8.39 (dd, J=9.5, 1.5 Hz, 1H), 8.07 (d, J=8.2 Hz, 1H), 7.87 (dd, J=8.1, 2.1 Hz, 1H), 7.26 (t, J=51.5 Hz, 1H), 6.04 (d, J=1.6 Hz, 2H), 3.70 (s, 2H), 3.37-3.33 (m, 4H), 2.20-2.13 (m, 2H); LRMS (ES) m/z 443.4 ($M^+$+1).

Example 551: Synthesis of compound 18711, 1-(2-chloro-4-(1-(4-(5-(difluoromethyl)-1,3,4-oxadiazol-2-yl)-2-fluorobenzyl)-1H-1,2,3-triazol-4-yl)phenyl)-N,N-dimethylmethanamine

[Step 1] Synthesis of 2-chloro-4-((trimethylsilyl)ethynyl)benzaldehyde

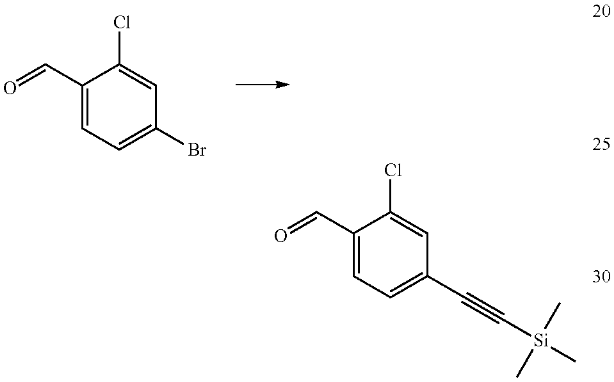

4-bromo-2-chlorobenzaldehyde (1.000 g, 4.557 mmol), bis(triphenylphosphine)palladium(II) dichloride (0.160 g, 0.228 mmol), and copper iodide (I/II, 0.087 g, 0.456 mmol) were dissolved in tetrahydrofuran (20 mL)/triethylamine (4 mL), after which trimethylsilyl acetylene (0.917 mL, 6.835 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%), and concentrated to obtain 2-chloro-4-((trimethylsilyl)ethynyl)benzaldehyde (1.000 g, 92.7%) in a brown liquid form.

[Step 2] Synthesis of 2-chloro-4-ethynylbenzaldehyde

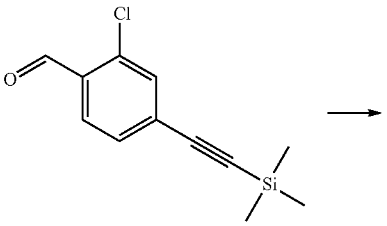

-continued

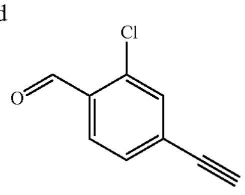

The 2-chloro-4-((trimethylsilyl)ethynyl)benzaldehyde (1.000 g, 4.224 mmol) prepared in step 1 and potassium carbonate (1.751 g, 12.671 mmol) were dissolved in methanol (20 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%) and concentrated to obtain 2-chloro-4-ethynylbenzaldehyde (0.528 g, 76.0%) in a yellow solid form.

[Step 3] Synthesis of 2-chloro-4-(1-(4-(5-(difluoromethyl)-1,3,4-oxadiazol-2-yl)-2-fluorobenzyl)-1H-1,2,3-triazol-4-yl)benzaldehyde

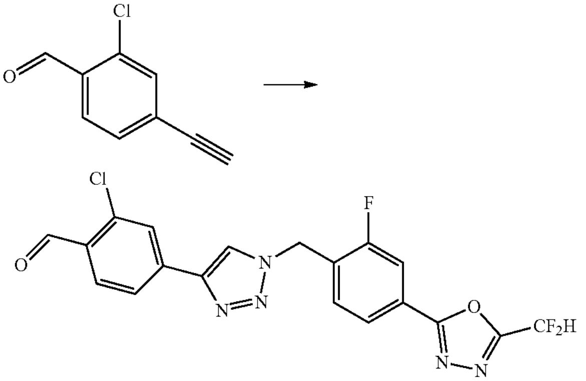

The 2-chloro-4-ethynylbenzaldehyde (0.170 g, 1.033 mmol) prepared in step 2, 2-(4-(azidomethyl)-3-fluorophenyl)-5-(difluoromethyl)-1,3,4-oxadiazole (0.278 g, 1.033 mmol) prepared in step 1 of example 2, sodium ascorbate (0.50 M solution in water, 0.207 mL, 0.103 mmol) and copper(II) sulfate pentahydrate (1.00 M solution in water, 0.010 mL, 0.010 mmol) were dissolved in tert-butanol (2 mL)/water (2 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. Dichloromethane (5 mL) and hexane (100 mL) were added and stirred to the resulting concentrate to filter out a precipitated solid, washed with hexane, and dried to obtain 2-chloro-4-(1-(4-(5-(difluoromethyl)-1,3,4-oxadiazol-2-yl)-2-fluorobenzyl)-1H-1,2,3-triazol-4-yl)benzaldehyde (0.332 g, 74.1%) in a yellow solid form.

[Step 4] Synthesis of Compound 18711

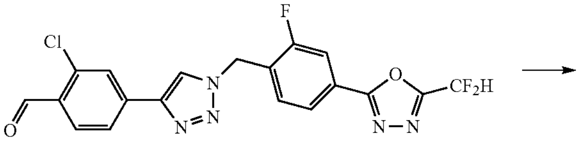

-continued

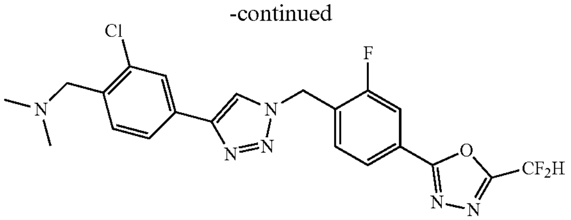

The 2-chloro-4-(1-(4-(5-(difluoromethyl)-1,3,4-oxadiazol-2-yl)-2-fluorobenzyl)-1H-1,2,3-triazol-4-yl)benzaldehyde (0.080 g, 0.184 mmol) in step 3, dimethylamine (2.00 M solution in MeOH, 0.184 mL, 0.369 mmol) and acetic acid (0.011 mL, 0.184 mmol) were dissolved in dichloromethane (1 mL), after which the resulting solution was stirred at room temperature for 1 hour, and then sodium triacetoxyborohydride (0.117 g, 0.553 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 15%) and concentrated to obtain 1-(2-chloro-4-(1-(4-(5-(difluoromethyl)-1,3,4-oxadiazol-2-yl)-2-fluorobenzyl)-1H-1,2,3-triazol-4-yl)phenyl)-N,N-dimethylmethanamine (0.024 g, 28.1%) in a light yellow solid form.

$^1$H NMR (400 MHz, $CD_3OD$) δ 8.51 (s, 1H), 8.00-7.93 (m, 3H), 7.78 (dd, J=8.0, 1.7 Hz, 1H), 7.61 (t, J=7.7 Hz, 1H), 7.54 (d, J=8.0 Hz, 1H), 7.24 (t, J=51.6 Hz, 1H), 5.86 (s, 2H), 3.65 (s, 2H), 2.32 (s, 6H); LRMS (ES) m/z 463.2 ($M^+$+1).

The compounds of table 167 were synthesized according to substantially the same process as described above in the synthesis of compound 18711 with an exception of using 2-chloro-4-(1-(4-(5-(difluoromethyl)-1,3,4-oxadiazol-2-yl)-2-fluorobenzyl)-1H-1,2,3-triazol-4-yl)benzaldehyde and the reactant of table 166.

TABLE 166

| Example | Compound No. | Reactant | Yield (%) |
|---|---|---|---|
| 552 | 18712 | Azetidine | 27 |
| 553 | 18713 | Pyrrolidine | 29 |

TABLE 167

| Example | Compound No. | Compound Name, $^1$H-NMR, MS (ESI) |
|---|---|---|
| 552 | 18712 | 2-(4-((4-(4-(azetidin-1-ylmethy])-3-chlorophenyl)-1H-1,2,3-triazol-1-yl)methyl)-3-fluorophenyl)-5-(difluoromethyl)-1,3,4-oxadiazole<br>$^1$H NMR (400 MHZ, $CD_3OD$) δ 8.50 (s, 1H), 8.00-7.92 (m, 3H), 7.77 (d, J = 7.3 Hz, 1H), 7.61 (t, J = 7.5 Hz, 1H), 7.47 (d, J = 8.0 Hz, 1H), 7.24 (t, J = 51.6 Hz, 1H), 5.85 (s, 2H), 3.79 (s, 2H), 3.40 (t, J = 7.1 Hz, 4H), 2.20-2.13 (m, 2H); LRMS (ESI) m/z 475.4 ($M^+$ + H). |
| 553 | 18713 | 2-(4-((4-(3-chloro-4-(pyrrolidin-1-ylmethyl)phenyl)-1H-1,2,3-triazol-1-yl)methyl)-3-fluorophenyl)-5-(difluoromethyl)-1,3,4-oxadiazole<br>$^1$H NMR (400 MHZ, $CD_3OD$) δ 8.51 (s, 1H), 8.00-7.93 (m, 3H), 7.78 (dd, J = 8.0, 1.6 Hz, 1H), 7.63-7.57 (m, 2H), 7.24 (t, J = 51.6 Hz, 1H), 5.86 (s, 2H), 3.86 (s, 2H), 2.69 (s, 4H), 1.87-1.84 (m, 4H); LRMS (ESI) m/z 489.3 ($M^+$ + H). |

Example 554: Synthesis of compound 18736, 2-(difluoromethyl)-5-(3-fluoro-4-((4-(6-methoxypyridin-2-yl)-1H-1,2,3-triazol-1-yl)methyl)phenyl)-1,3,4-oxadiazole

[Step 1] Synthesis of 2-(2,2-dibromovinyl)-6-methoxypyridine

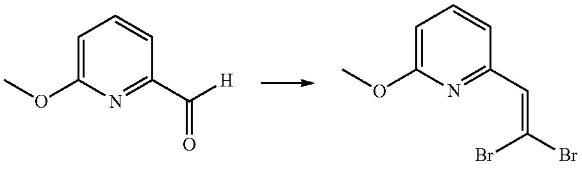

6-methoxypicolinealdehyde (0.200 g, 1.458 mmol), carbon tetrabromide (0.967 g, 2.917 mmol) and triphenylphosphine triphenylphosphine (1.148 g, 4.375 mmol) were dissolved in dichloromethane (10 mL) at room temperature, after which the resulting solution was stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; ethyl acetate/hexane=0 to 20%) and concentrated to obtain 2-(2,2-dibromovinyl)-6-methoxypyridine (0.180 g, 42.1%) in a yellow oil form.

[Step 2] Synthesis of 2-ethynyl-6-methoxypyridine

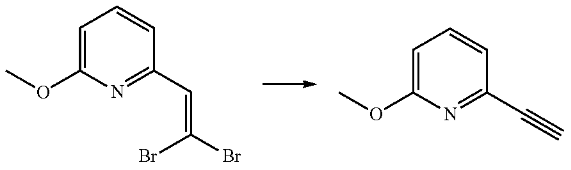

2-(2,2-dibromovinyl)-6-methoxypyridine (0.200 g, 0.683 mmol) and 2,3,4,6,7,8,9,10-octahydropyrimido[1,2-a]azepine (DBU, 0.306 mL, 2.048 mmol) were dissolved in acetonitrile (5 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-ethynyl-6-methoxypyridine (0.090 g, 99.0%) in a white solid form.

[Step 3] Synthesis of Compound 18736

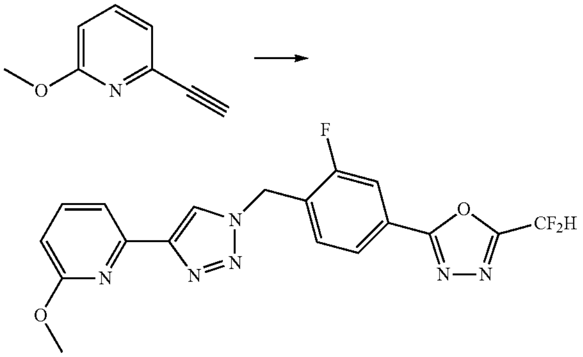

2-ethynyl-6-methoxypyridine (0.100 g, 0.751 mmol), 2-(4-(azidomethyl)-3-fluorophenyl)-5-(difluoromethyl)-1,3,4-oxadiazole (0.202 g, 0.751 mmol) prepared in step 1 of example 2, copper(II) sulfate pentahydrate (0.002 g, 0.008 mmol) and sodium ascorbate (0.015 g, 0.075 mmol) were dissolved in dichloromethane (5 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 30%) and concentrated to obtain 2-(difluoromethyl)-5-(3-fluoro-4-((4-(6-methoxypyridin-2-yl)-1H-1,2,3-triazol-1-yl)methyl)phenyl)-1,3,4-oxadiazole (0.035 g, 11.6%) in a white solid form.

$^1H$ NMR (400 MHz, $CDCl_3$) δ 7.99 (d, J=4.0 Hz, 1H), 7.92-7.83 (m, 3H), 7.42 (t, J=7.8 Hz, 1H), 7.15 (t, J=7.9 Hz, 1H), 7.03-6.78 (m, 2H), 5.72 (s, 2H), 3.10 (q, J=8.2, 6.4 Hz, 4H), 2.68-2.54 (m, 9H), 2.23 (ddd, J=21.2, 10.3, 4.7 Hz, 2H); LRMS (ES) m/z 578.4 ($M^++1$).

Example 555 Synthesis of compound 18822, 2-(6-((4-(2-(azetidin-1-ylmethyl)phenyl)-1H-1,2,3-triazol-1-yl)methyl)-5-fluoropyridin-3-yl)-5-(difluoromethyl)-1,3,4-oxadiazole

[Step 1] Synthesis of 2-(1-((5-(5-(difluoromethyl)-1,3,4-oxadiazol-2-yl)-3-fluoropyridin-2-yl)methyl)-1H-1,2,3-triazol-4-yl)benzaldehyde

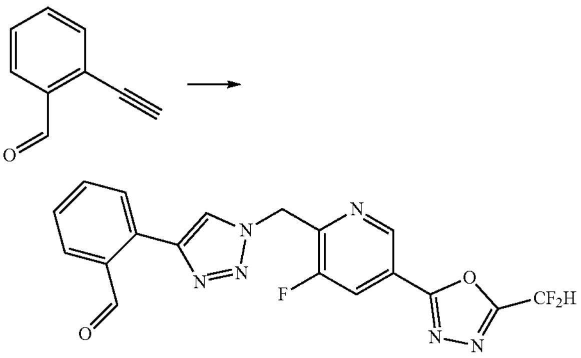

2-ethynylbenzaldehyde (0.100 g, 0.768 mmol), (6-(azidomethyl)-5-fluoropyridin-3-yl)-5-(difluoromethyl)-1,3,4-oxadiazole (0.208 g, 0.768 mmol) prepared in step 1 of example 490, sodium ascorbate (0.50 M solution in water, 0.154 mL, 0.077 mmol) and copper(II) sulfate pentahydrate (1.00 M solution in water, 0.008 mL, 0.008 mmol) were dissolved in tert-butanol (2 mL)/water (2 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 2-(1-((5-(5-(difluoromethyl)-1,3,4-oxadiazol-2-yl)-3-fluoropyridin-2-yl)methyl)-1H-1,2,3-triazol-4-yl)benzaldehyde (0.108 g, 35.1%) in a yellow solid form.

[Step 2] Synthesis of Compound 18822

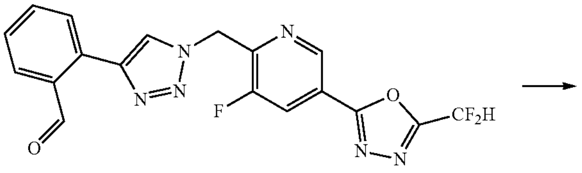

-continued

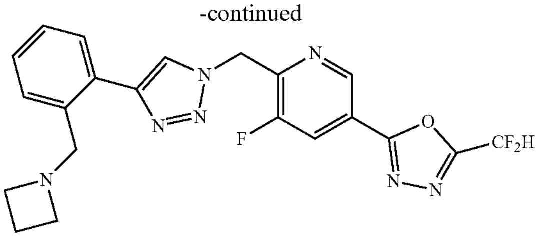

The 2-(1-((5-(5-(difluoromethyl)-1,3,4-oxadiazol-2-yl)-3-fluoropyridin-2-yl)methyl)-1H-1,2,3-triazol-4-yl)benzaldehyde (0.050 g, 0.125 mmol) prepared in step 1, azetidine (0.017 mL, 0.250 mmol) and acetic acid (0.007 mL, 0.125 mmol) were dissolved in dichloromethane (0.5 mL), after which the resulting solution was stirred at room temperature for 1 hour, and then sodium triacetoxyborohydride (0.079 g, 0.375 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(6-((4-(2-(azetidin-1-ylmethyl)phenyl)-1H-1,2,3-triazol-1-yl)methyl)pyridin-3-yl)-5-(difluoromethyl)-1,3,4-oxadiazole (0.010 g, 18.1%) in a red oil form.

$^1$H NMR (400 MHz, $CD_3OD$) δ 9.11 (s, 1H), 8.45 (s, 1H), 8.40 (d, J=9.9 Hz, 1H), 7.68-7.66 (m, 1H), 7.48-7.46 (m, 1H), 7.42-7.14 (m, 3H), 6.04 (s, 2H), 3.84 (s, 2H), 3.38-3.33 (m, 4H), 2.17-2.10 (m, 2H); LRMS (ES) m/z 442.4 ($M^+$+1).

The compound of table 169 was synthesized according to substantially the same process as described above in the synthesis of compound 18822 with an exception of using 2-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 168.

TABLE 168

| Example | Compound No. | Reactant | Yield (%) |
|---|---|---|---|
| 556 | 18823 | Pyrrolidine | 18 |

TABLE 169

| Example | Compound No. | Compound Name, $^1$H-NMR, MS (ESI) |
|---|---|---|
| 556 | 18823 | 2-(difluoromethyl)-5-(5-fluoro-6-((4-(2-(pyrrolidin-1-ylmethyl)phenyl)-1H-1,2,3-triazol-1-yl)methyl)pyridin-3-yl)-1,3,4-oxadiazole $^1$H NMR (400 MHZ, $CD_3OD$) δ 9.11 (s, 1H), 8.52 (s, 1H), 8.40 (dd, J = 9.6, 1.4 (Hz, 1H), 7.73-7.71 (m, 1H), 7.54-7.51 (m, 1H), 7.45-7.14 (m, 3H), 6.04 (d, J = 1.4 Hz, 2H), 3.87 (s, 2H), 2.68 (s, 4H), 1.84 (s, 4H); LRMS (ESI) m/z 456.4 ($M^+$ + H). |

Example 558: Synthesis of compound 18869, 2-(difluoromethyl)-5-(5-fluoro-6-((4-(3-(1-methylpiperidin-4-yl)phenyl)-1H-1,2,3-triazol-1-yl)methyl)pyridin-3-yl)-1,3,4-oxadiazole

[Step 1] Synthesis of 2-(difluoromethyl)-5-(5-fluoro-6-((4-(3-(piperidin-4-yl)phenyl)-1H-1,2,3-triazol-1-yl)methyl)pyridin-3-yl)-1,3,4-oxadiazole 2,2,2-trifluoroacetate

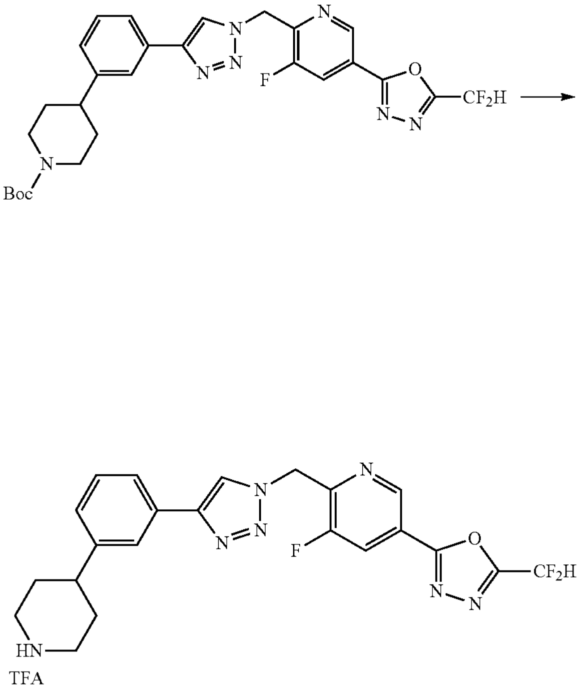

The tert-butyl 4-(3-(1-((5-(5-(difluoromethyl)-1,3,4-oxadiazol-2-yl)-3-fluoropyridin-2-yl)methyl)-1H-1,2,3-triazol-4-yl)phenyl)piperidin-1-carboxylate (0.320 g, 0.576 mmol) corresponding to compound 18868 according to example 557 and trifluoroacetic acid (0.132 mL, 1.728 mmol) were dissolved in dichloromethane (20 mL) at room temperature, after which the resulting solution was stirred at the same temperature for 3 hours. Solvent was removed from the reaction mixture under reduced pressure, after which a product obtained was used without an additional purification process (2-(difluoromethyl)-5-(5-fluoro-6-((4-(3-(piperidin-4-yl)phenyl)-1H-1,2,3-triazol-1-yl)methyl)pyridin-3-yl)-1,3,4-oxadiazole 2,2,2-trifluoroacetate, 0.300 g, 94.3%, yellow oil).

[Step 2] Synthesis of Compound 18869

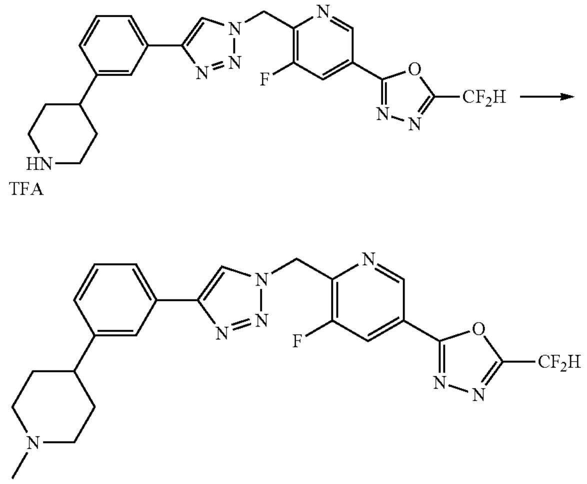 [SMILES: Fc1cc(-c2nnc(C(F)F)o2)cnc1Cn1cc(-c2cccc(C3CCNCC3)c2)nn1 ; CN1CCC(c2cccc(-c3cn(Cc4ncc(-c5nnc(C(F)F)o5)cc4F)nn3)c2)CC1]

$^1H$ NMR (400 MHz, $CDCl_3$) δ 7.99 (d, J=4.0 Hz, 1H), 7.92-7.83 (m, 3H), 7.42 (t, J=7.8 Hz, 1H), 7.15 (t, J=7.9 Hz, 1H), 7.03-6.78 (m, 2H), 5.72 (s, 2H), 3.10 (q, J=8.2, 6.4 Hz, 4H), 2.68-2.54 (m, 9H), 2.23 (ddd, J=21.2, 10.3, 4.7 Hz, 2H); LRMS (ES) m/z 578.4 ($M^+$+1).

The compounds of table 171 were synthesized according to substantially the same process as described above in the synthesis of compound 18869 with an exception of using 2-(difluoromethyl)-5-(5-fluoro-6-((4-(3-(piperidin-4-yl) phenyl)-1H-1,2,3-triazol-1-yl)methyl)pyridin-3-yl)-1,3,4-oxadiazole 2,2,2-trifluoroacetate and the reactant of table 170.

TABLE 170

| Example | Compound No. | Reactant | Yield (%) |
|---|---|---|---|
| 559 | 18870 | Cyclobutanone | 73 |
| 560 | 18871 | Oxetan-3-one | 54 |

TABLE 171

| Example | Compound No. | Compound Name, $^1H$-NMR, MS (ESI) |
|---|---|---|
| 559 | 18870 | 2-(6-((4-(3-(1-cyclobutylpiperidin-4-yl)phenyl)-1H-1,2,3-triazol-1-yl)methyl)-5-fluoropyridin-3-yl)-5-(difluoromethyl)-1,3,4-oxadiazole<br>$^1H$ NMR (400 MHZ, $CDCl_3$) δ 9.17 (s, 1H), 8.21 (d, J = 9.0 Hz, 1 H), 8.00 (s, 1H), 7.73-7.69 (m, 2H), 7.37 (t, J = 7.6 Hz, 1H), 7.24-7.22 (m, 2H), 7.09 (s, 0.2H), 6.96 (s, 0.5H), 6.83 (s, 0.2H), 5.89 (s, 2H), 3.11 (brs, 2H), 2.84 (brs, 1H), 2.59 (brs, 1H), 2.19-1.91 (m, 10H), 1.79-1.68 (m, 2 H); LRMS (ES) m/z 510.43 ($M^+$ + 1). |
| 560 | 18871 | 2-(difluoromethyl)-5-(5-fluoro-6-((4-(3-(1-(oxetan-3-yl)piperidin-4-yl)phenyl)-1H-1,2,3-triazol-1-yl)methyl)pyridin-3-yl)-1,3,4-oxadiazole<br>$^1H$ NMR (400 MHZ, $CDCl_3$) δ 9.16 (s, 1H), 8.21 (d, J = 9.0 Hz, 1 H), 8.01 (s, 1H), 7.76 (s, 1H), 7.68 (d, J = 7.6 Hz, 1H), 7.38 (t, J = 7.7 Hz, 1H), 7.23 (d, J = 7.7 Hz, 1H), 7.09 (s, 0.2 H), 6.96 (s, 0.5H), 6.83 (s, 0.2 H), 5.89 (s, 2H), 4.70 (d, J = 6.5 Hz, 4H), 3.57-3.53 (m, 1H), 2.92 (d, J = 9.8 Hz, 2H), 2.62-2.58 (m, 1H), 1.98-1.91 (m, 6H); LRMS (ES) m/z 512.13 ($M^+$ + 1). |

The 2-(difluoromethyl)-5-(5-fluoro-6-((4-(3-(piperidin-4-yl)phenyl)-1H-1,2,3-triazol-1-yl)methyl)pyridin-3-yl)-1,3,4-oxadiazole 2,2,2-trifluoroacetate (0.050 g, 0.091 mmol) prepared in step 1 and N,N-diisopropylethylamine (0.032 mL, 0.181 mmol) were dissolved in dichloromethane (5 mL), after which the resulting solution was stirred at room temperature for 30 minutes, and then formaldehyde (0.005 g, 0.181 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(difluoromethyl)-5-(5-fluoro-6-((4-(3-(1-methylpiperidin-4-yl)phenyl)-1H-1,2,3-triazol-1-yl) methyl)pyridin-3-yl)-1,3,4-oxadiazole (0.027 g, 63.5%) in a yellow solid form.

Example 561: Synthesis of compound 18872, tert-butyl 3-(4-(3-(1-((5-(5-(difluoromethyl)-1,3,4-oxadiazol-2-yl)-3-fluoropyridin-2-yl)methyl)-1H-1,2,3-triazol-4-yl)phenyl)piperidin-1-yl)azetidin-1-carboxylate

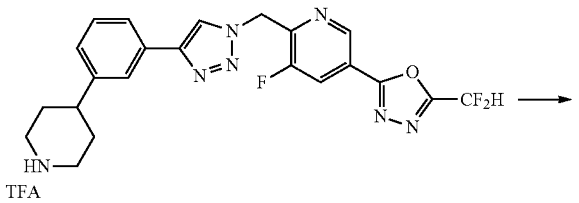

-continued

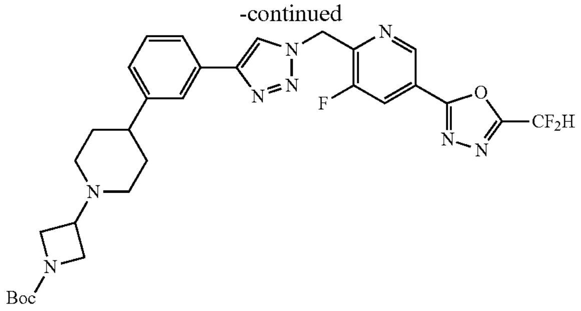

The 2-(difluoromethyl)-5-(5-fluoro-6-((4-(3-(piperidin-4-yl)phenyl)-1H-1,2,3-triazol-1-yl)methyl)pyridin-3-yl)-1,3,4-oxadiazole 2,2,2-trifluoroacetate (0.120 g, 0.217 mmol) prepared in step 1 of example 558, tert-butyl 3-oxoazetidin-1-carboxylate (0.045 g, 0.260 mmol) and N,N-diisopropylethylamine (0.076 mL, 0.434 mmol) were dissolved in dichloromethane (10 mL), after which the resulting solution was stirred at room temperature for 30 minutes, and then sodium triacetoxyborohydride (0.138 g, 0.650 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain tert-butyl 3-(4-(3-(1-((5-(5-(difluoromethyl)-1,3,4-oxadiazol-2-yl)-3-fluoropyridin-2-yl)methyl)-1H-1,2,3-triazol-4-yl)phenyl)piperidin-1-yl)azetidin-1-carboxylate (0.100 g, 75.5%) in a yellow solid form.

$^1$H NMR (400 MHz, $CDCl_3$) δ 7.99 (d, J=4.0 Hz, 1H), 7.92-7.83 (m, 3H), 7.42 (t, J=7.8 Hz, 1H), 7.15 (t, J=7.9 Hz, 1H), 7.03-6.78 (m, 2H), 5.72 (s, 2H), 3.10 (q, J=8.2, 6.4 Hz, 4H), 2.68-2.54 (m, 9H), 2.23 (ddd, J=21.2, 10.3, 4.7 Hz, 2H); LRMS (ES) m/z 578.4 ($M^+$+1).

Example 562: Synthesis of compound 18877, 2-(difluoromethyl)-5-(5-fluoro-6-((4-(3-(1-(1-methylazetidin-3-yl)piperidin-4-yl)phenyl)-1H-1,2,3-triazol-1-yl)methyl)pyridin-3-yl)-1,3,4-oxadiazole

[Step 1] Synthesis of 2-(6-((4-(3-(1-(azetidin-3-yl)piperidin-4-yl)phenyl)-1H-1,2,3-triazol-1-yl)methyl)-5-fluoropyridin-3-yl)-5-(difluoromethyl)-1,3,4-oxadiazole 2,2,2-trifluoroacetate

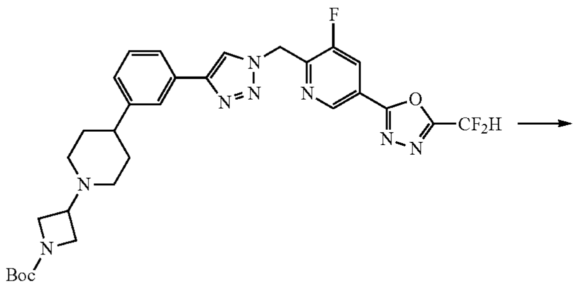

-continued

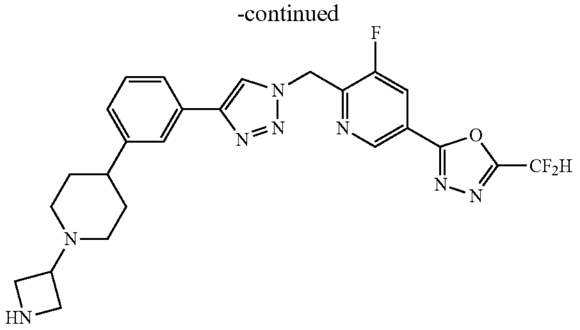

TFA

The tert-butyl 3-(4-(3-(1-((5-(5-(difluoromethyl)-1,3,4-oxadiazol-2-yl)-3-fluoropyridin-2-yl)methyl)-1H-1,2,3-triazol-4-yl)phenyl)piperidin-1-yl)azetidin-1-carboxylate (0.100 g, 0.164 mmol) prepared in example 561 and trifluoroacetic acid (0.050 mL, 0.655 mmol) were dissolved in dichloromethane (10 mL) at room temperature, after which the resulting solution was stirred at the same temperature for 3 hours. Solvent was removed from the reaction mixture under reduced pressure, after which a product obtained was used without an additional purification process (2-(6-((4-(3-(1-(azetidin-3-yl)piperidin-4-yl)phenyl)-1H-1,2,3-triazol-1-yl)methyl)-5-fluoropyridin-3-yl)-5-(difluoromethyl)-1,3,4-oxadiazole 2,2,2-trifluoroacetate, 0.090 g, 90.5%, yellow oil)

[Step 2] Synthesis of Compound 18877

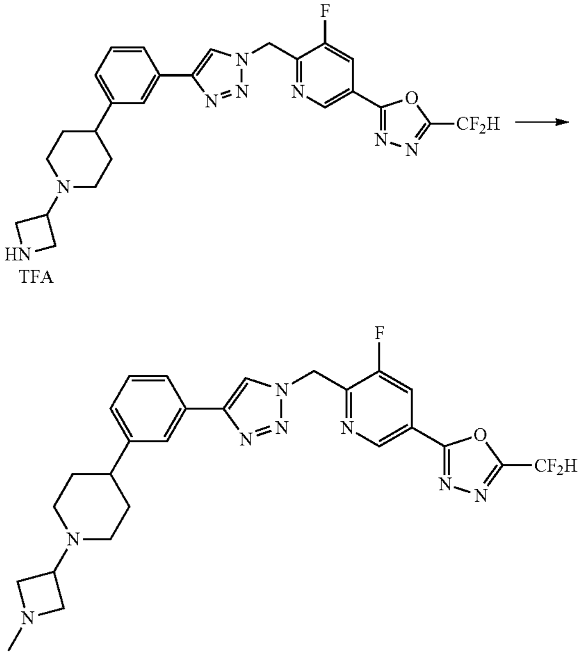 [SMILES: Fc1cc(-c2nnc(C(F)F)o2)cnc1Cn1cc(-c2cccc(C3CCN(C4CNC4)CC3)c2)nn1 ; CN1CC(N2CCC(c3cccc(-c4cn(Cc5ncc(-c6nnc(C(F)F)o6)cc5F)nn4)c3)CC2)C1]

The 2-(6-((4-(3-(1-(azetidin-3-yl)piperidin-4-yl)phenyl)-1H-1,2,3-triazol-1-yl)methyl)-5-fluoropyridin-3-yl)-5-(difluoromethyl)-1,3,4-oxadiazole 2,2,2-trifluoroacetate (0.045 g, 0.074 mmol) prepared in step 1 and formaldehyde (0.004 g, 0.148 mmol) were dissolved in dichloromethane (5 mL), after which the resulting solution was stirred at room temperature for 30 minutes, and then sodium triacetoxyborohydride (0.031 g, 0.148 mmol) was added thereto and further stirred at the same temperature for 12 hours. Water was poured into the reaction mixture and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(5-fluoro-6-((4-(3-(1-(1-methylazetidin-3-yl)piperidin-4-yl) phenyl)-1H-1,2,3-triazol-1-yl)methyl)pyridin-3-yl)-1,3,4-oxadiazole (0.019 g, 48.9%) in a yellow solid form.

$^1$H NMR (400 MHz, $CDCl_3$) δ 7.99 (d, J=4.0 Hz, 1H), 7.92-7.83 (m, 3H), 7.42 (t, J=7.8 Hz, 1H), 7.15 (t, J=7.9 Hz, 1H), 7.03-6.78 (m, 2H), 5.72 (s, 2H), 3.10 (q, J=8.2, 6.4 Hz, 4H), 2.68-2.54 (m, 9H), 2.23 (ddd, J=21.2, 10.3, 4.7 Hz, 2H); LRMS (ES) m/z 578.4 ($M^+$+1).

The compound of table 173 was synthesized according to substantially the same process as described above in the synthesis of compound 18877 with an exception of using 2-(6-((4-(3-(1-(azetidin-3-yl)piperidin-4-yl)phenyl)-1H-1,2,3-triazol-1-yl)methyl)-5-fluoropyridin-3-yl)-5-(difluoromethyl)-1,3,4-oxadiazole 2,2,2-trifluoroacetate and the reactant of table 172.

TABLE 172

| Example | Compound No. | Reactant | Yield (%) |
|---|---|---|---|
| 563 | 18878 | Cyclobutanone | 50 |

TABLE 173

| Example | Compound No. | Compound Name, $^1$H-NMR, MS (ESI) |
|---|---|---|
| 563 | 18878 | 2-(6-((4-(3-(1-(1-cyclobutylazetidin-3-yl)piperidin-4-yl)phenyl)-1H-1,2,3-triazol-1-yl)methyl)-5-fluoropyridin-3-yl)-5-(difluoromethyl)-1,3,4-oxadiazole $^1$H NMR (400 MHZ, $CDCl_3$) δ 9.15 (s, 1H), 8.21 (d, J = 9.0 Hz, 1 H), 8.01 (s, 1H), 7.77 (s, 1H), 7.66 (d, J = 7.7 Hz, 1H), 7.36 (t, J = 7.7 Hz, 1H), 7.20 (d, J = 7.6 Hz, 1H), 7.09 (s, 0.2 H), 6.96 (s, 0.5H), 6.83 (s, 0.2 H), 5.89 (s, 2H), 3.84 (brs, 1H), 3.75 (s, 2H), 3.47-3.43 (m, 1H), 3.22-3.19 (m, 3H), 2.87 (d, J = 11.0 Hz, 2H), 2.56-2.54 (m, 1H), 2.13-2.09 (m, 3H), 2.06-2.00 (m, 2H), 1.97-1.71 (m, 6H); LRMS (ES) m/z 565.46 ($M^+$ + 1). |

Example 564: Synthesis of compound 18882, 2-(6-((4-(5-(azetidin-1-ylmethyl)pyridin-3-yl)-1H-1,2,3-triazol-1-yl)methyl)-5-fluoropyridin-3-yl)-5-(difluoromethyl)-1,3,4-oxadiazole

[Step 1] Synthesis of 5-((trimethylsilyl)ethynyl)nicotinealdehyde

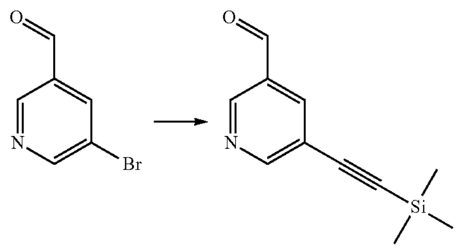

5-bromonicotinealdehyde (0.300 g, 1.613 mmol), bis(triphenylphosphine)palladium dichloride (0.057 g, 0.081 mmol), and copper iodide (I/II, 0.031 g, 0.161 mmol) were dissolved in tetrahydrofuran (5 mL)/triethylamine (1 mL), after which trimethylsilyl acetylene (0.324 mL, 2.419 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 24 g cartridge; ethyl acetate/hexane=0 to 10%), and concentrated to obtain 5-((trimethylsilyl)ethynyl)nicotinealdehyde (0.097 g, 29.6%) in a brown solid form.

[Step 2] Synthesis of 5-ethynylnicotinealdehyde

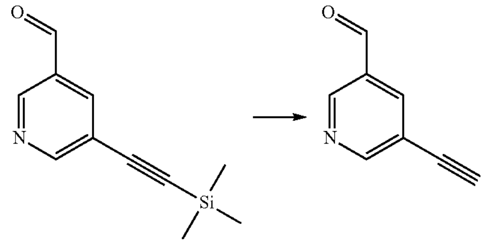

The 5-((trimethylsilyl)ethynyl)nicotinealdehyde (0.097 g, 0.477 mmol) prepared in step 1 and potassium carbonate (0.198 g, 1.431 mmol) were dissolved in methanol (2 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 30%) and concentrated to obtain 5-ethynylnicotinealdehyde (0.023 g, 36.8%) in a white solid form.

[Step 3] Synthesis of 5-(1-((5-(5-(difluoromethyl)-1,3,4-oxadiazol-2-yl)-3-fluoropyridin-2-yl)methyl)-1H-1,2,3-triazol-4-yl)nicotinealdehyde

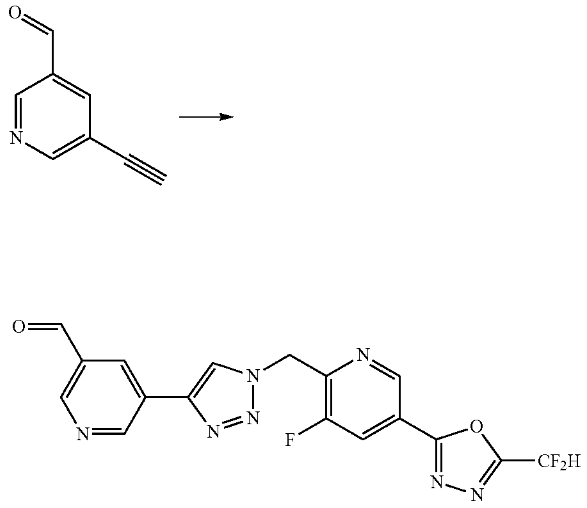

The 5-ethynylnicotinealdehyde (0.023 g, 0.175 mmol) prepared in step 2, 2-(6-(azidomethyl)-5-fluoropyridin-3-yl)-5-(difluoromethyl)-1,3,4-oxadiazole (0.047 g, 0.175 mmol) prepared in step 1 of example 490, sodium ascorbate (0.50 M solution in water, 0.035 mL, 0.018 mmol) and copper(II) sulfate pentahydrate (1.00 M solution in water, 0.002 mL, 0.002 mmol) were dissolved in tert-butanol (0.5 mL)/water (0.5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 5-(1-((5-(5-(difluoromethyl)-1,3,4-oxadiazol-2-yl)-3-fluoropyridin-2-yl)methyl)-1H-1,2,3-triazol-4-yl)nicotinealdehyde (0.035 g, 49.7%) in a white solid form.

[Step 4] Synthesis of Compound 18882

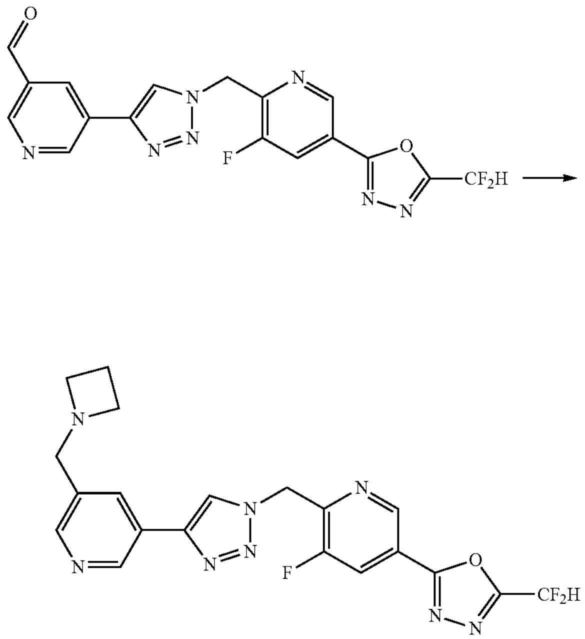

The 5-(1-((5-(5-(difluoromethyl)-1,3,4-oxadiazol-2-yl)-3-fluoropyridin-2-yl)methyl)-1H-1,2,3-triazol-4-yl)nicotinealdehyde (0.035 g, 0.087 mmol) prepared in step 3, azetidine (0.012 mL, 0.174 mmol) and acetic acid (0.005 mL, 0.087 mmol) were dissolved in dichloromethane (0.5 mL), after which the resulting solution was stirred at room temperature for 1 hour, and then sodium triacetoxyborohydride (0.055 g, 0.262 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 2-(6-((4-(5-(azetidin-1-ylmethyl)pyridin-3-yl)-1H-1,2,3-triazol-1-yl)methyl)-5-fluoropyridin-3-yl)-5-(difluoromethyl)-1,3,4-oxadiazole (0.014 g, 36.3%) in a pink solid form.

$^1H$ NMR (400 MHz, $CD_3OD$) δ 9.10 (s, 1H), 8.96 (d, J=1.6 Hz, 1H), 8.67 (s, 1H), 8.48 (s, 1H), 8.40 (d, J=9.6 Hz, 1H), 8.25 (s, 1H), 7.27 (t, J=51.6 Hz, 1H), 6.04 (s, 2H), 3.75 (s, 2H), 3.38 (t, J=7.1 Hz, 4H), 2.21-2.13 (m, 2H); LRMS (ES) m/z 443.6 ($M^+$+1).

Example 565: Synthesis of compound 18893, 2-(difluoromethyl)-5-(6-((4-(3-((3R,5S)-3,5-dimethylpiperazin-1-yl)phenyl)-1H-1,2,3-triazol-1-yl)methyl)-5-fluoropyridin-3-yl)-1,3,4-oxadiazole

[Step 1] Synthesis of tert-butyl (2R,6S)-4-(3-(1-((5-(5-(difluoromethyl)-1,3,4-oxadiazol-2-yl)-3-fluoropyridin-2-yl)methyl)-1H-1,2,3-triazol-4-yl)phenyl)-2,6-dimethylpiperazin-1-carboxylate

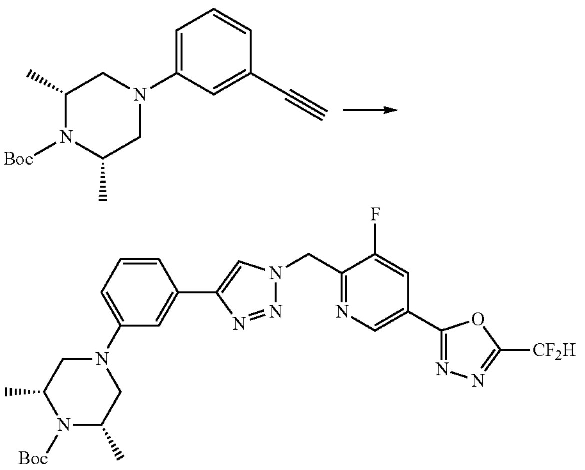

The tert-butyl (2R,6S)-4-(3-ethynylphenyl)-2,6-dimethylpiperazin-1-carboxylate (0.300 g, 0.954 mmol) prepared in step 5 of example 321, 2-(6-(azidomethyl)-5-fluoropyridin-3-yl)-5-(difluoromethyl)-1,3,4-oxadiazole (0.387 g, 1.431 mmol) prepared in step 1 of example 490, copper(II) sulfate pentahydrate (0.002 g, 0.010 mmol) and sodium ascorbate (0.019 g, 0.095 mmol) were dissolved in tert-butanol (4 mL)/water (2 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 100%) and concentrated to obtain tert-butyl (2R,6S)-4-(3-(1-((5-(5-(difluoromethyl)-1,3,4-oxadiazol-2-yl)-3-fluoropyridin-2-yl)methyl)-1H-1,2,3-triazol-4-yl)phenyl)-2,6-dimethylpiperazin-1-carboxylate (0.400 g, 71.7%) in a brown solid form.

[Step 2] Synthesis of Compound 18893

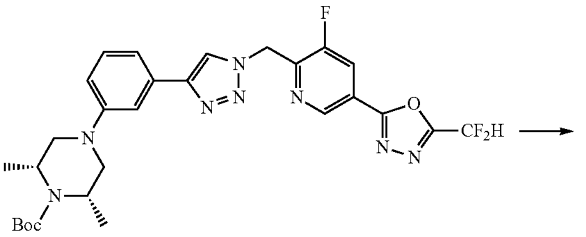

-continued

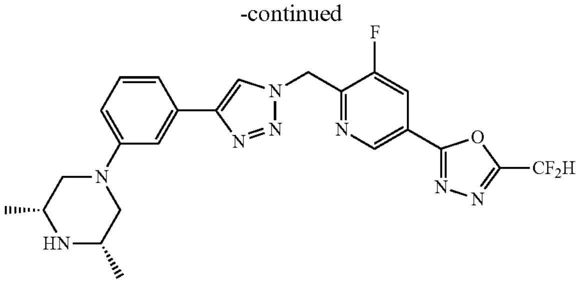

Tert-butyl (2R,6S)-4-(3-ethynylphenyl)-2,6-dimethylpiperazin-1-carboxylate (0.300 g, 0.954 mmol), 2-(6-(azidomethyl)-5-fluoropyridin-3-yl)-5-(difluoromethyl)-1,3,4-oxadiazole (0.387 g, 1.431 mmol), copper(II) sulfate pentahydrate (0.002 g, 0.010 mmol) and sodium ascorbate (0.019 g, 0.095 mmol) were dissolved in tert-butanol (4 mL)/water (2 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 100%) and concentrated to obtain 2-(difluoromethyl)-5-(6-((4-(3-((3R,5S)-3,5-dimethylpiperazin-1-yl)phenyl)-1H-1,2,3-triazol-1-yl)methyl)-5-fluoropyridin-3-yl)-1,3,4-oxadiazole (0.400 g, 71.7%) in a brown solid form.

$^1H$ NMR (400 MHz, $CDCl_3$) δ 9.09 (s, 1H), 8.15 (dd, J=9.0, 1.7 Hz, 1H), 8.00 (s, 1H), 7.47 (s, 1H), 7.28~7.24 (m, 1H), 7.18 (d, J=7.6 Hz, 1H), 7.07~6.82 (m, 2H), 5.85 (s, 2H), 3.54 (d, J=11.3 Hz, 2H), 2.74 (t, J=11.5 Hz, 2H), 2.59~2.54 (m, 2H), 1.23 (d, J=6.3 Hz, 6H); LRMS (ES) m/z 485.8 ($M^+$+1).

Example 570: Synthesis of compound 18924, 2-(difluoromethyl)-5-(5-fluoro-6-((4-(3-(4-methylpiperazin-1-yl)phenyl)-1H-1,2,3-triazol-1-yl)methyl)pyridin-3-yl)-1,3,4-oxadiazole

[Step 1] Synthesis of tert-butyl 4-(3-(1-((5-(5-(difluoromethyl)-1,3,4-oxadiazol-2-yl)-3-fluoropyridin-2-yl)methyl)-1H-1,2,3-triazol-4-yl)phenyl)piperazin-1-carboxylate

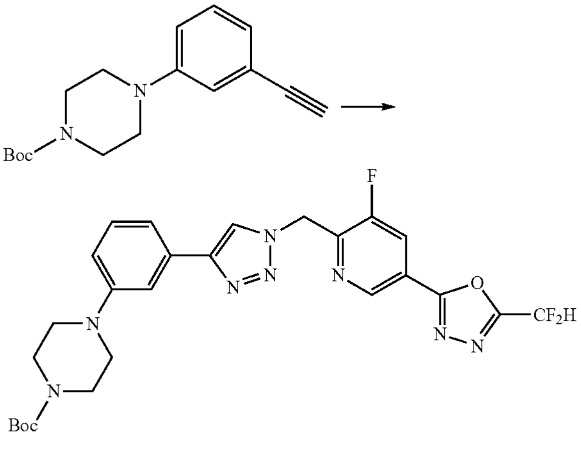

The tert-butyl 4-(3-ethynylphenyl)piperazin-1-carboxylate (0.300 g, 1.048 mmol) prepared in step 1 of example 117, 2-(6-(azidomethyl)-5-fluoropyridin-3-yl)-5-(difluoromethyl)-1,3,4-oxadiazole (0.425 g, 1.571 mmol) prepared in step 1 of example 490, copper(II) sulfate pentahydrate (0.003 g, 0.010 mmol) and sodium ascorbate (0.021 g, 0.105 mmol) were dissolved in tert-butanol (4 mL)/water (2 mL) at room temperature, after which the resulting solution was stirred at the same temperature for 12 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 100%) and concentrated to obtain tert-butyl 4-(3-(1-((5-(5-(difluoromethyl)-1,3,4-oxadiazol-2-yl)-3-fluoropyridin-2-yl)methyl)-1H-1,2,3-triazol-4-yl)phenyl)piperazin-1-carboxylate (0.400 g, 68.6%) in a brown solid form.

[Step 2] Synthesis of 2-(difluoromethyl)-5-(5-fluoro-6-((4-(3-(piperazin-1-yl)phenyl)-1H-1,2,3-triazol-1-yl)methyl)pyridin-3-yl)-1,3,4-oxadiazole

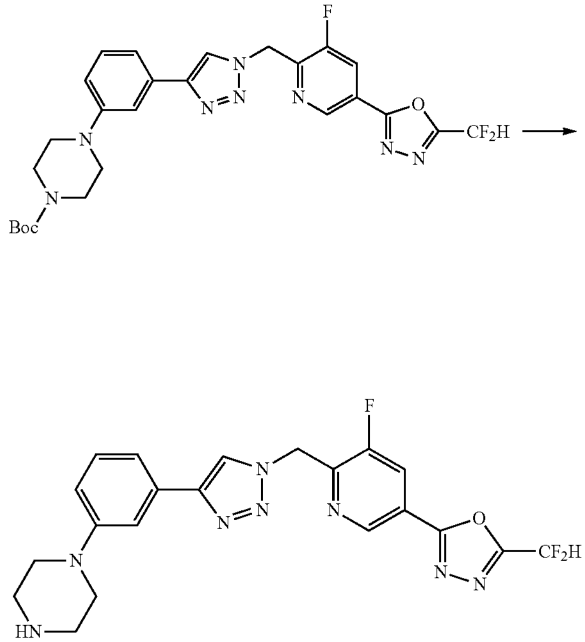

Tert-butyl 4-(3-(1-((5-(5-(difluoromethyl)-1,3,4-oxadiazol-2-yl)-3-fluoropyridin-2-yl)methyl)-1H-1,2,3-triazol-4-yl)phenyl)piperazin-1-carboxylate (0.500 g, 0.898 mmol) and trifluoroacetic acid (0.688 mL, 8.984 mmol) were dissolved in dichloromethane (10 mL) at room temperature, after which the resulting solution was stirred at the same temperature for 12 hours. Solvent was removed from the reaction mixture under reduced pressure, after which the obtained product was used without an additional purification process (2-(difluoromethyl)-5-(5-fluoro-6-((4-(3-(piperazin-1-yl)phenyl)-1H-1,2,3-triazol-1-yl)methyl)pyridin-3-yl)-1,3,4-oxadiazole, 0.400 g, 97.5%, brown solid).

[Step 3] Synthesis of Compound 18924

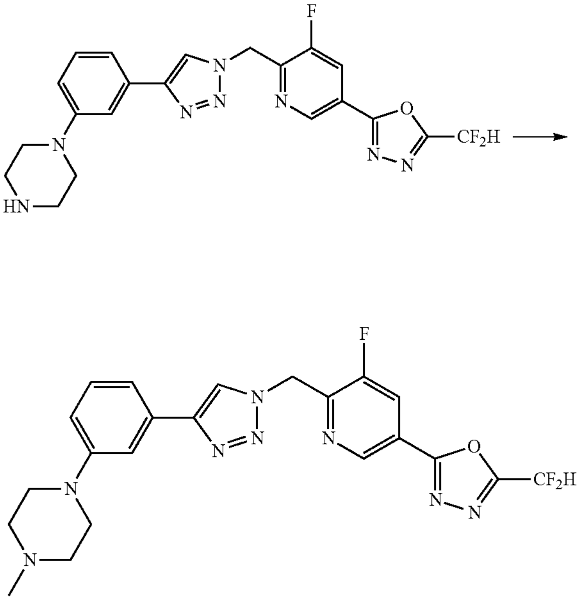

2-(difluoromethyl)-5-(5-fluoro-6-((4-(3-(piperazin-1-yl)phenyl)-1H-1,2,3-triazol-1-yl)methyl)pyridin-3-yl)-1,3,4-oxadiazole (0.100 g, 0.219 mmol), formaldehyde (0.013 g, 0.438 mmol) and sodium triacetoxyborohydride (0.093 g, 0.438 mmol) were dissolved in dichloromethane (5 mL) at room temperature, after which the resulting solution was stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(5-fluoro-6-((4-(3-(4-methylpiperazin-1-yl)phenyl)-1H-1,2,3-triazol-1-yl)methyl)pyridin-3-yl)-1,3,4-oxadiazole (0.035 g, 34.0%) in a yellow solid form.

$^1H$ NMR (400 MHz, $CDCl_3$) δ 9.10 (s, 1H), 8.16 (dd, J=9.0, 1.7 Hz, 1H), 7.99 (s, 1H), 7.47 (s, 1H), 7.30~7.21 (m, 2H), 7.07~6.81 (m, 2H), 5.85 (s, 2H), 3.32 (t, J=4.9 Hz, 4H), 2.74 (t, J=4.9 Hz, 4H), 2.43 (s, 3H); LRMS (ES) m/z 471.7 ($M^+$+1).

The compound of table 175 was synthesized according to substantially the same process as described above in the synthesis of compound 18924 with an exception of using 2-(difluoromethyl)-5-(5-fluoro-6-((4-(3-(piperazin-1-yl)phenyl)-1H-1,2,3-triazol-1-yl)methyl)pyridin-3-yl)-1,3,4-oxadiazole and the reactant of table 174.

TABLE 174

| Example | Compound No. | Reactant | Yield (%) |
|---|---|---|---|
| 571 | 18926 | Propan-2-one | 39 |

TABLE 175

| Example | Compound No. | Compound Name, 1H-NMR, MS (ESI) |
|---|---|---|
| 571 | 18926 | 2-(difluoromethyl)-5-(5-fluoro-6-((4-(3-(4-isopropylpiperazin-1-yl)phenyl)-1H-1,2,3-triazol-1-yl)methyl)pyridin-3-yl)-1,3,4-oxadiazole $^1$H NMR (400 MHZ, $CDCl_3$) δ 9.04 (s, 1H), 8.10 (dd, J = 9.0, 1.7 Hz, 1H), 8.01 (s, 1H), 7.40 (s, 1H), 7.26-7.22 (m, 2H), 7.07-6.80 (m, 2H), 5.82 (s, 2H), 3.40 (t, J = 4.8 Hz, 4H), 3.21-3.17 (m, 1H), 3.01 (t, J = 4.6 Hz, 4H), 1.23 (d, J = 6.6 Hz, 6H); LRMS (ES) m/z 499.8 ($M^+$ + 1). |

Example 572: Synthesis of compound 18947, 2-(6-((4-(4-(azetidin-1-ylmethyl)-3-fluorophenyl)-1H-1,2,3-triazol-1-yl)methyl)-5-fluoropyridin-3-yl)-5-(difluoromethyl)-1,3,4-oxadiazole

[Step 1] Synthesis of 4-(1-((5-(5-(difluoromethyl)-1,3,4-oxadiazol-2-yl)-3-fluoropyridin-2-yl)methyl)-1H-1,2,3-triazol-4-yl)-2-fluorobenzaldehyde

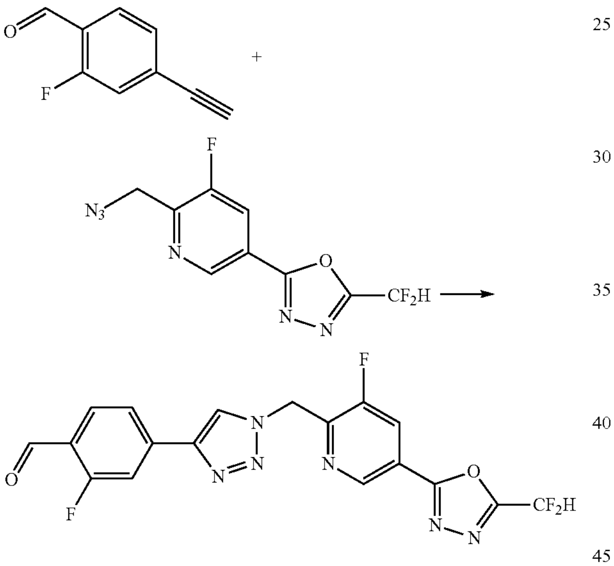

4-Ethynyl-2-fluorobenzaldehyde (0.200 g, 1.350 mmol) and 2-(6-(azidomethyl)pyridin-3-yl)-5-(difluoromethyl)-1,3,4-oxadiazole (0.365 g, 1.350 mmol) prepared in step 1 of example 490 were dissolved in tert-butanol (2 mL)/water (2 mL) at room temperature, after which sodium ascorbate (1.00 M solution, 0.135 mL, 0.135 mmol) and copper sulfate (I/II, 0.50 M solution, 0.135 mL, 0.068 mmol) were added to the resulting solution and stirred at the same temperature for 18 hours. Saturated ammonium chloride aqueous solution was poured into the reaction mixture, and an extraction was performed with ethyl acetate. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 70%) and concentrated to obtain 4-(1-((5-(5-(difluoromethyl)-1,3,4-oxadiazol-2-yl)-3-fluoropyridin-2-yl)methyl)-1H-1,2,3-triazol-4-yl)-2-fluorobenzaldehyde (0.420 g, 74.4%) in a light yellow solid form.

[Step 2] Synthesis of Compound 18947

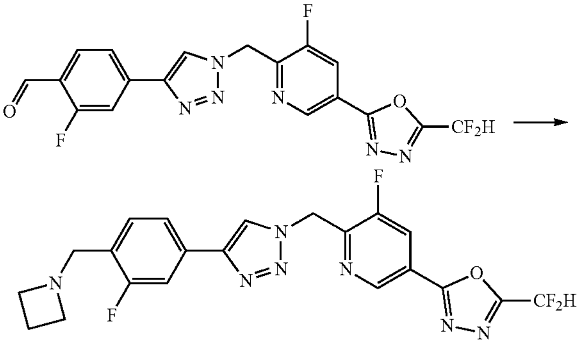

The 4-(1-((5-(5-(difluoromethyl)-1,3,4-oxadiazol-2-yl)-3-fluoropyridin-2-yl)methyl)-1H-1,2,3-triazol-4-yl)-2-fluorobenzaldehyde (0.050 g, 0.120 mmol) prepared in step 1, azetidine (0.014 g, 0.239 mmol) and sodium triacetoxyborohydride (0.127 g, 0.598 mmol) were dissolved in dichloromethane (3 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=100 to 80%) and concentrated to obtain 2-(6-((4-(4-(azetidin-1-ylmethyl)-3-fluorophenyl)-1H-1,2,3-triazol-1-yl)methyl)-5-fluoropyridin-3-yl)-5-(difluoromethyl)-1,3,4-oxadiazole (0.028 g, 51.0%) in a white solid form.

$^1$H NMR (400 MHz, $CD_3OD$) δ 9.10 (s, 1H), 8.54 (s, 1H), 8.39 (dd, J=9.6, 1.7 Hz, 1H), 7.69-7.58 (m, 2H), 7.44 (t, J=7.8 Hz, 1H), 7.27 (t, J=51.6 Hz, 2H), 6.01 (s, J=1.8 Hz, 2H), 3.71 (s, 2H), 3.41-3.34 (m, 4H), 2.20-2.06 (m, 2H); LRMS (ES) m/z 461.58 ($M^+$+1).

The compounds of table 177 were synthesized according to substantially the same process as described above in the synthesis of compound 18947 with an exception of using 4-(1-((5-(5-(difluoromethyl)-1,3,4-oxadiazol-2-yl)-3-fluoropyridin-2-yl)methyl)-1H-1,2,3-triazol-4-yl)-2-fluorobenzaldehyde and the reactant of table 176.

TABLE 176

| Example | Compound No. | Reactant | Yield (%) |
|---|---|---|---|
| 573 | 18948 | Pyrrolidine | 51 |
| 574 | 18949 | Dimethylamine | 33 |
| 575 | 18950 | Piperidine | 36 |

TABLE 177

| Example | Compound No. | Compound Name, ¹H-NMR, MS (ESI) |
|---|---|---|
| 573 | 18948 | 2-(difluoromethyl)-5-(5-fluoro-6-((4-(3-fluoro-4-(pyrrolidin-1-ylmethyl)phenyl)-1H-1,2,3-triazol-1-yl)methyl)pyridin-3-yl)-1,3,4-oxadiazole ¹H NMR (400 MHZ, $CD_3OD$) δ 9.10 (s, 1H), 8.55 (s, 1H), 8.39 (dd, J = 9.6, 1.7 Hz, 1H), 7.65 (ddd, J = 12.6, 9.5, 1.6 Hz, 3H), 7.51 (t, J = 7.8 Hz, 1H), 7.27 (t, J = 51.6 Hz, 2H), 6.01 (s, J = 5.5 Hz, 2H), 3.77 (s, 2H), 2.64 (s, 4H), 1.89-1.78 (m, 4H); LRMS (ES) m/z 475.76 ($M^+$ + 1). |
| 574 | 18949 | 1-(4-(1-((5-(5-(difluoromethyl)-1,3,4-oxadiazol-2-yl)-3-fluoropyridin-2-yl)methyl)-1H-1,2,3-triazol-4-yl)-2-fluorophenyl)-N,N-dimethylmethanamine ¹H NMR (400 MHZ, $CD_3OD$) δ 9.10 (s, 1H), 8.55 (s, 1H), 8.39 (dd, J = 9.6, 1.7 Hz, 1H), 7.65 (ddd, J = 12.6, 9.5, 1.6 Hz, 2H), 7.48 (t, J = 7.8 Hz, 1H), 7.27 (t, J = 51.6 Hz, 2H), 6.01 (s, J = 1.8 Hz, 2H), 3.60 (s, 2H), 2.30 (s, 6H); LRMS (ES) m/z 449.86 ($M^+$ + 1). |
| 575 | 18950 | 2-(difluoromethyl)-5-(5-fluoro-6-((4-(3-fluoro-4-(piperidin-1-ylmethyl)phenyl)-1H-1,2,3-triazol-1-yl)methyl)pyridin-3-yl)-1,3,4-oxadiazole ¹H NMR (400 MHZ, $CD_3OD$) δ 9.11 (s, 1H), 8.54 (s, 1H), 8.39 (dd, J = 9.6, 1.7 Hz, 1H), 7.64 (ddd, J = 12.5, 9.4, 1.6 Hz, 2H), 7.50 (t, J = 7.7 Hz, 1H), 7.27 (t, J = 51.6 Hz, 2H), 6.01 (d, J = 1.8 Hz, 2H), 3.63 (s, 2H), 2.52 (s, 4H), 1.69-1.56 (m, 4H), 1.48 (s, 2H); LRMS (ES) m/z 489.75 ($M^+$ + 1). |

Example 576: Synthesis of compound 18961, 2-(difluoromethyl)-5-(5-fluoro-6-((4-(3-((3R,5S)-3,4,5-trimethylpiperazin-1-yl)phenyl)-1H-1,2,3-triazol-1-yl)methyl)pyridin-3-yl)-1,3,4-oxadiazole

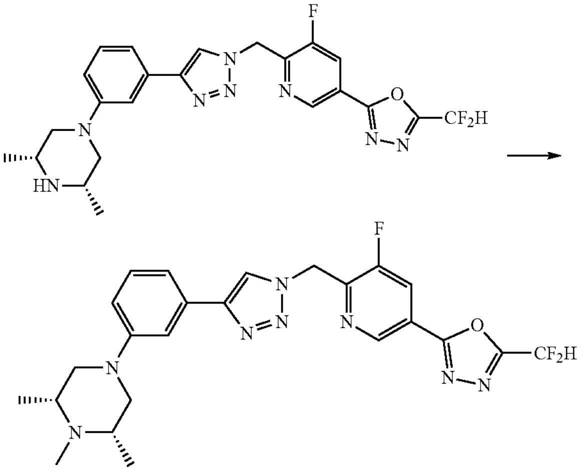

The 2-(difluoromethyl)-5-(6-((4-(3-((3R,5S)-3,5-dimethylpiperazin-1-yl)phenyl)-1H-1,2,3-triazol-1-yl)methyl)-5-fluoropyridin-3-yl)-1,3,4-oxadiazole (0.100 g, 0.206 mmol) prepared in step 2 of example 569, formaldehyde (0.012 g, 0.413 mmol) and sodium triacetoxyborohydride (0.087 g, 0.413 mmol) were dissolved in dichloromethane (5 mL) at room temperature, after which the resulting solution was stirred at the same temperature for 12 hours. Water was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(5-fluoro-6-((4-(3-((3R,5S)-3,4,5-trimethylpiperazin-1-yl)phenyl)-1H-1,2,3-triazol-1-yl)methyl)pyridin-3-yl)-1,3,4-oxadiazole (0.040 g, 38.9%) in a yellow solid form.

¹H NMR (400 MHz, $CDCl_3$) δ 9.09 (s, 1H), 8.15 (dd, J=9.0, 1.7 Hz, 1H), 8.00 (s, 1H), 7.47 (s, 1H), 7.28~7.24 (m, 1H), 7.18 (d, J=7.6 Hz, 1H), 7.07~6.82 (m, 2H), 5.85 (s, 2H), 3.54 (d, J=11.3 Hz, 2H), 2.74 (t, J=11.5 Hz, 2H), 2.59~2.54 (m, 2H), 2.39 (s, 3H), 1.23 (d, J=6.3 Hz, 6H); LRMS (ES) m/z 499.7 ($M^+$+1).

Example 577: Synthesis of compound 19002, 2-(difluoromethyl)-5-(5-fluoro-6-((4-(2-methyl-1,2,3,4-tetrahydroisoquinolin-7-yl)-1H-1,2,3-triazol-1-yl)methyl)pyridin-3-yl)-1,3,4-oxadiazole

[Step 1] Synthesis of tert-butyl 7-(1-((5-(5-(difluoromethyl)-1,3,4-oxadiazol-2-yl)-3-fluoropyridin-2-yl)methyl)-1H-1,2,3-triazol-4-yl)-3,4-dihydroisoquinolin-2(1H)-carboxylate

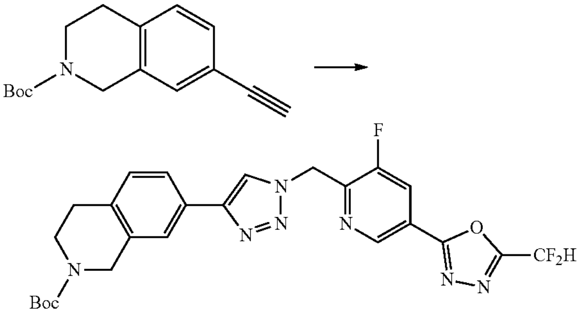

The tert-butyl 7-ethynyl-3,4-dihydroisoquinolin-2(1H)-carboxylate (0.350 g, 1.360 mmol) prepared in step 1 of example 261, 2-(6-(azidomethyl)-5-fluoropyridin-3-yl)-5-(difluoromethyl)-1,3,4-oxadiazole (0.441 g, 1.632 mmol) prepared in step 1 of example 490, copper(II) sulfate pentahydrate (0.003 g, 0.014 mmol) and sodium ascorbate (0.027 g, 0.136 mmol) were dissolved in tert-butanol (4 mL)/water (2 mL) at room temperature, after which the resulting solution was stirred at the same temperature for 2 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 12 g cartridge; ethyl acetate/hexane=0 to 100%) and concentrated to obtain tert-butyl 7-(1-((5-(5-(difluoromethyl)-1,3,4-oxadiazol-2-yl)-3-fluoropyridin-2-yl)methyl)-1H-1,2,3-triazol-4-yl)-3,4-dihydroisoquinolin-2(1H)-carboxylate (0.630 g, 87.8%) in a brown solid form.

[Step 2] Synthesis of 2-(difluoromethyl)-5-(5-fluoro-6-((4-(1,2,3,4-tetrahydroisoquinolin-7-yl)-1H-1,2,3-triazol-1-yl)methyl)pyridin-3-yl)-1,3,4-oxadiazole

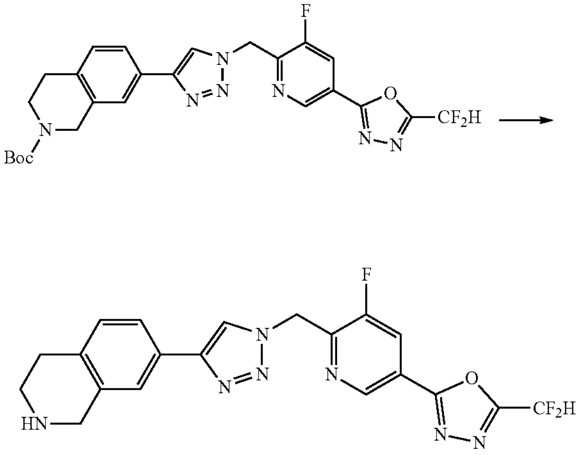

Tert-butyl 7-(1-((5-(5-(difluoromethyl)-1,3,4-oxadiazol-2-yl)-3-fluoropyridin-2-yl)methyl)-1H-1,2,3-triazol-4-yl)-3,4-dihydroisoquinolin-2(1H)-carboxylate (0.630 g, 1.194 mmol) and trifluoroacetic acid (0.915 mL, 11.943 mmol) were dissolved in dichloromethane (50 mL) at room temperature, after which the resulting solution was stirred at the same temperature for 12 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 12 g cartridge; dichloromethane/methanol=0 to 10%) and concentrated to obtain 2-(difluoromethyl)-5-(5-fluoro-6-((4-(1,2,3,4-tetrahydroisoquinolin-7-yl)-1H-1,2,3-triazol-1-yl)methyl)pyridin-3-yl)-1,3,4-oxadiazole (0.500 g, 98.0%) in a brown oil form.

[Step 3] Synthesis of Compound 19002

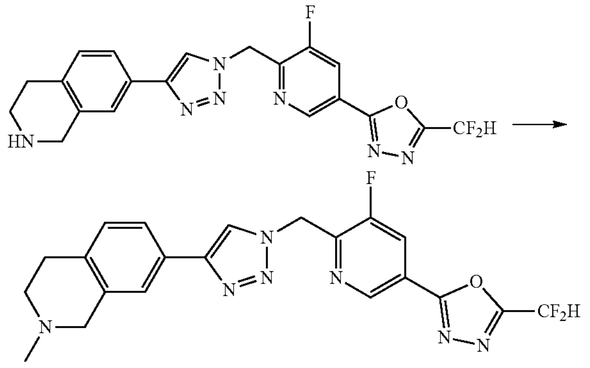

2-(difluoromethyl)-5-(5-fluoro-6-((4-(1,2,3,4-tetrahydroisoquinolin-7-yl)-1H-1,2,3-triazol-1-yl)methyl)pyridin-3-yl)-1,3,4-oxadiazole (0.070 g, 0.164 mmol), formaldehyde (0.010 g, 0.328 mmol) and sodium triacetoxyborohydride (0.069 g, 0.328 mmol) were dissolved in dichloromethane (5 mL) at room temperature, after which the resulting solution was stirred at the same temperature for 12 hours. Saturated sodium hydrogen carbonate aqueous solution was poured into the reaction mixture, after which an extraction was performed with dichloromethane, then filtered via a plastic filter to remove a solid residue and an aqueous solution layer therefrom, and then concentrated under reduced pressure. The resulting concentrate was purified via column chromatography ($SiO_2$, 4 g cartridge; dichloromethane/methanol=0 to 10%) and concentrated to obtain 2-(difluoromethyl)-5-(5-fluoro-6-((4-(2-methyl-1,2,3,4-tetrahydroisoquinolin-7-yl)-1H-1,2,3-triazol-1-yl)methyl)pyridin-3-yl)-1,3,4-oxadiazole (0.020 g, 27.7%) in a yellow solid form.

$^1$H NMR (400 MHz, $CDCl_3$) δ 9.09 (s, 1H), 8.14 (d, J=8.8 Hz, 1H), 7.96 (s, 1H), 7.56 7.50 (m, 2H), 7.14~6.81 (m, 2H), 5.83 (s, 2H), 3.66 (s, 2H), 2.96 (t, J=0.0 Hz, 2H), 2.85 (t, J=0.0 Hz, 2H), 2.52 (s, 3H); LRMS (ES) m/z 442.3 ($M^+$+1).

The compound of table 179 was synthesized according to substantially the same process as described above in the synthesis of compound 19002 with an exception of using 2-(difluoromethyl)-5-(5-fluoro-6-((4-(1,2,3,4-tetrahydroisoquinolin-7-yl)-1H-1,2,3-triazol-1-yl)methyl)pyridin-3-yl)-1,3,4-oxadiazole and the reactant of table 178.

TABLE 178

| Example | Compound No. | Reactant | Yield (%) |
|---|---|---|---|
| 578 | 19004 | Cyclobutanone | 28 |

TABLE 179

| Example | Compound No. | Compound Name, $^1$H-NMR, MS (ESI) |
|---|---|---|
| 578 | 19004 | 2-(6-((4-(2-cyclobutyl-1,2,3,4-tetrahydroisoquinolin-7-yl)-1H-1,2,3-triazol-1-yl)methyl)-5-fluoropyridin-3-yl)-5-(difluoromethyl)-1,3,4-oxadiazole<br>$^1$H NMR (400 MHZ, $CDCl_3$) δ 9.10 (s, 1H), 8.15 (d, J = 8.8 Hz, 1H), 7.95 (s, 1H), 7.56-7.52 (m, 2H), 7.13 (d, J = 7.8 Hz, 1H), 6.94 (t, J = 51.6 Hz, 1H), 5.84 (S, 2H), 3.65 (s, 2H), 3.04-3.01 (m, 1H), 2.92 (t, J = 2.9 Hz, 2H), 2.75 (t, J = 5.6 Hz, 2H), 2.15-2.10 (m, 4H), 1.79-1.69 (m, 2H); LRMS (ES) m/z 482.4 ($M^+$ + 1). |

Example 580: Synthesis of compound 19087, 2-(difluoromethyl)-5-(5-fluoro-6-((4-(4-(1-methylpiperidin-4-yl)phenyl)-1H-1,2,3-triazol-1-yl)methyl)pyridin-3-yl)-1,3,4-oxadiazole

[Step 1] Synthesis of 1-bromo-4-ethynylbenzene

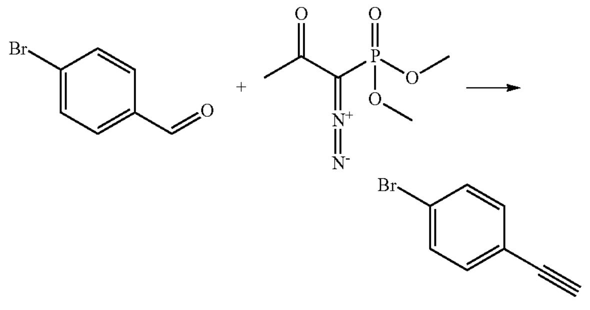

4-bromobenzaldehyde (1.000 g, 5.405 mmol), potassium carbonate (0.896 g, 6.486 mmol) and dimethyl (1-diazo-2-oxopropyl)phosphonate (1.142 g, 5.945 mmol) were dissolved in methanol (30 mL) at room temperature, after which the resulting solution was stirred at the same temperature for 12 hours. Water was poured into the reaction mixture and an extraction was performed with dichloromethane. An organic layer was washed with saturated ammonium chloride aqueous solution, dehydrated with anhydrous magnesium sulfate, filtered, and concentrated under reduced pressure. The obtained product was used without an additional purification process (1-bromo-4-ethynylbenzene, 0.800 g, 81.8%, yellow solid).

[Step 2] Synthesis of methyl 6-(azidomethyl)-5-fluoronicotinate

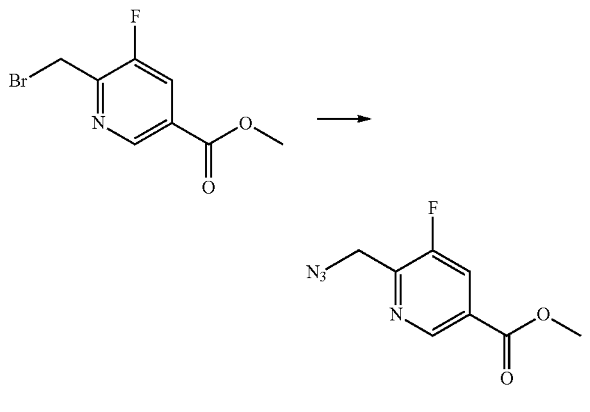

Methyl 6-(bromomethyl)-5-fluoronicotinate (1.000 g, 4.031 mmol) and sodium azide (0.315 g, 4.838 mmol) were dissolved in N,N-dimethylformamide (20 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 40%), and concentrated to obtain methyl 6-(azidomethyl)-5-fluoronicotinate (0.650 g, 76.7%) in yellow solid form.

[Step 3] Synthesis of methyl 6-((4-(4-bromophenyl)-1H-1,2,3-triazol-1-yl)methyl)-5-fluoronicotinate

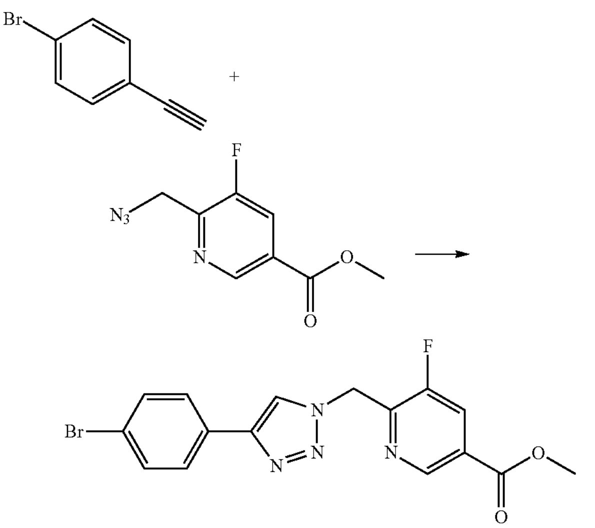

The 1-bromo-4-ethynylbenzene (0.400 g, 2.210 mmol) prepared in step 1, methyl 6-(azidomethyl)-5-fluoronicotinate (0.441 g, 2.099 mmol) prepared in step 2, sodium ascorbate (1.00 M solution in H2O, 0.221 mL, 0.221 mmol) and copper(II) sulfate pentahydrate (0.50 M solution in H2O, 0.044 mL, 0.022 mmol) were dissolved in tert-butanol (5 mL)/water (5 mL) at room temperature, after which the resulting solution was stirred at the same temperature for 12 hours. Water was poured into the reaction mixture and an extraction was performed with ethyl acetate. An organic layer was washed with saturated ammonium chloride aqueous solution, dehydrated with anhydrous sodium sulfate, filtered, and concentrated under reduced pressure. The resulting concentrate was purified via column chromatography ($SiO_2$, 12 g cartridge; ethyl acetate/hexane=0 to 50%), and concentrated to obtain methyl 6-((4-(4-bromophenyl)-1H-1,2,3-triazol-1-yl)methyl)-5-fluoronicotinate (0.300 g, 34.7%) in a yellow solid form.

[Step 4] Synthesis of methyl 6-((4-(4-(1-(tert-butoxycarbonyl)-1,2,3,6-tetrahydropyridin-4-yl)phenyl)-1H-1,2,3-triazol-1-yl)methyl)-5-fluoronicotinate

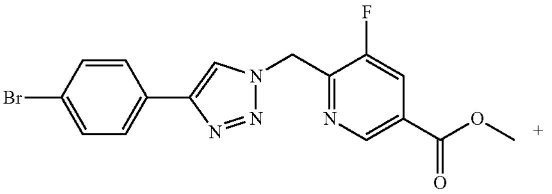

-continued

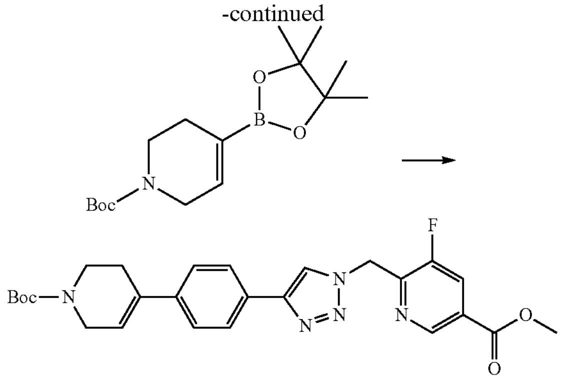

The methyl 6-((4-(4-bromophenyl)-1H-1,2,3-triazol-1-yl) methyl)-5-fluoronicotinate (0.500 g, 1.278 mmol) prepared in step 3, tert-butyl 4-(4,4,5,5-tetramethyl-1,3,2-dioxaborolan-2-yl)-3,6-dihydropyridin-1(2H)-carboxylate (0.474 g, 1.534 mmol), bis(triphenylphosphine)palladium(II) dichloride (0.090 g, 0.128 mmol) and sodium carbonate (0.271 g, 2.556 mmol) were mixed in N,N-dimethylformamide (10 mL)/water (5 mL) at 80 °C, after which the resulting mixture was stirred at the same temperature for 5 hours, and then a reaction was finished by lowering a temperature to room temperature. The reaction mixture was filtered via a celite pad to remove a solid therefrom, after which water was poured into the resulting concentrate and then an extraction was performed with ethyl acetate. An organic layer was washed with saturated ammonium chloride aqueous solution, dehydrated with anhydrous magnesium sulfate, filtered, and concentrated under reduced pressure. The resulting concentrate was purified via column chromatography ($SiO_2$, 24 g cartridge; ethyl acetate/hexane=0 to 50%) and concentrated to obtain methyl 6-((4-(4-(1-(tert-butoxycarbonyl)-1,2,3,6-tetrahydropyridin-4-yl)phenyl)-1H-1,2,3-triazol-1-yl) methyl)-5-fluoronicotinate (0.290 g, 46.0%) in a white solid form.

[Step 5] Synthesis of methyl 6-((4-(4-(1-(tert-butoxycarbonyl)piperidin-4-yl)phenyl)-1H-1,2,3-triazol-1-yl)methyl)-5-fluoronicotinate

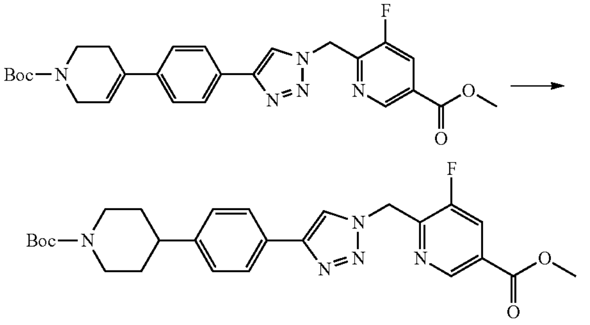

The methyl 6-((4-(4-(1-(tert-butoxycarbonyl)-1,2,3,6-tetrahydropyridin-4-yl)phenyl)-1H-1,2,3-triazol-1-yl)methyl)-5-fluoronicotinate (0.290 g, 0.588 mmol) prepared in step 4 was dissolved in methanol (20 mL) at room temperature, after which the resulting solution was stirred for 5 hours. The reaction mixture was filtered via a celite pad to remove a solid therefrom, after which solvent was removed from the resulting filtrate under reduced pressure, and then the resulting concentrate was purified via column chromatography ($SiO_2$, 12 g cartridge; ethyl acetate/hexane=0 to 30%) and concentrated to obtain methyl 6-((4-(4-(1-(tert-butoxycarbonyl)piperidin-4-yl)phenyl)-1H-1,2,3-triazol-1-yl)methyl)-5-fluoronicotinate (0.150 g, 51.5%) in a yellow solid form.

[Step 6] Synthesis of tert-butyl 4-(4-(1-((3-fluoro-5-(hydrazinecarbonyl)pyridin-2-yl)methyl)-1H-1,2,3-triazol-4-yl)phenyl)piperidin-1-carboxylate

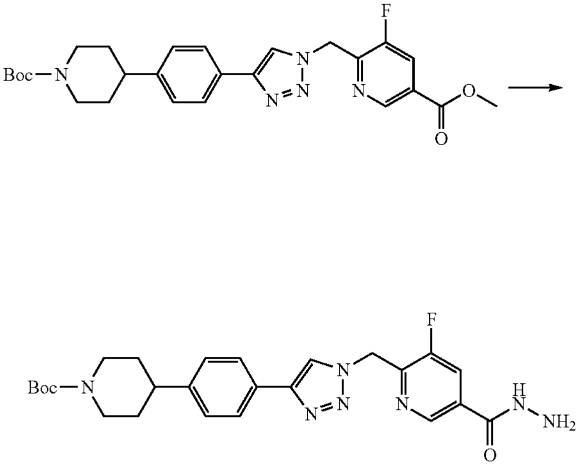

The methyl 6-((4-(4-(1-(tert-butoxycarbonyl)piperidin-4-yl)phenyl)-1H-1,2,3-triazol-1-yl)methyl)-5-fluoronicotinate (0.150 g, 0.303 mmol) prepared in step 5 and hydrazine monohydrate (0.147 mL, 3.027 mmol) were dissolved in ethanol (20 mL) at 90 °C, after which the resulting solution was stirred at the same temperature for 12 hours, and then a reaction was finished by lowering a temperature to room temperature. Solvent was removed from the reaction mixture under reduced pressure, after which the obtained product was used without an additional purification process (tert-butyl 4-(4-(1-((3-fluoro-5-(hydrazinecarbonyl)pyridin-2-yl)methyl)-1H-1,2,3-triazol-4-yl)phenyl)piperidin-1-carboxylate, 0.140 g, 93.3%, white solid).

[Step 7] Synthesis of tert-butyl 4-(4-(1-((5-(5-(difluoromethyl)-1,3,4-oxadiazol-2-yl)-3-fluoropyridin-2-yl)methyl)-1H-1,2,3-triazol-4-yl)phenyl)piperidin-1-carboxylate

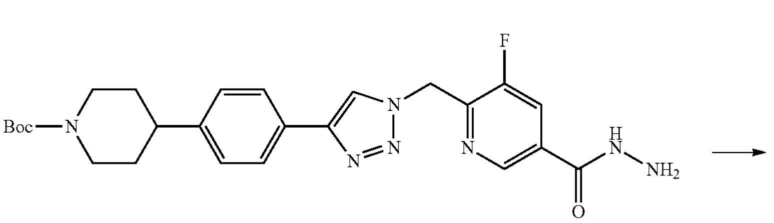

-continued

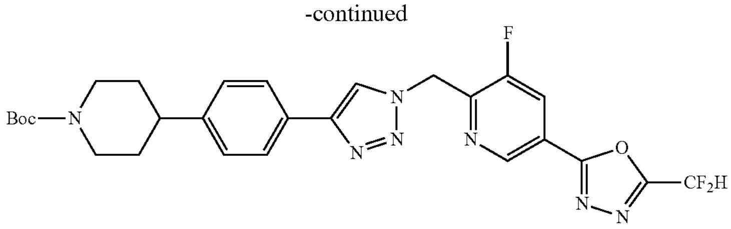

The tert-butyl 4-(4-(1-((3-fluoro-5-(hydrazinecarbonyl)pyridin-2-yl)methyl)-1H-1,2,3-triazol-4-yl)phenyl)piperidin-1-carboxylate (0.150 g, 0.303 mmol) prepared in step 6, imidazole (0.062 g, 0.908 mmol) and 2,2-difluoroacetic anhydride (0.113 mL, 0.908 mmol) were mixed in dichloromethane (30 mL) at room temperature, after which the resulting mixture was heated under reflux for 12 hours and cooled down to room temperature. Then, water was poured into the reaction mixture and an extraction was performed with dichloromethane. An organic layer was washed with saturated sodium hydrogen carbonate aqueous solution, dehydrated with anhydrous magnesium sulfate, filtered, and concentrated under reduced pressure. The resulting concentrate was purified via column chromatography ($SiO_2$, 12 g cartridge; ethyl acetate/hexane=0 to 50%) and concentrated to obtain tert-butyl 4-(4-(1-((5-(5-(difluoromethyl)-1,3,4-oxadiazol-2-yl)-3-fluoropyridin-2-yl)methyl)-1H-1,2,3-triazol-4-yl)phenyl)piperidin-1-carboxylate (0.100 g, 59.5%) in a white solid form.

[Step 8] Synthesis of 2-(difluoromethyl)-5-(5-fluoro-6-((4-(4-(piperidin-4-yl)phenyl)-1H-1,2,3-triazol-1-yl)methyl)pyridin-3-yl)-1,3,4-oxadiazole 2,2,2-trifluoroacetate

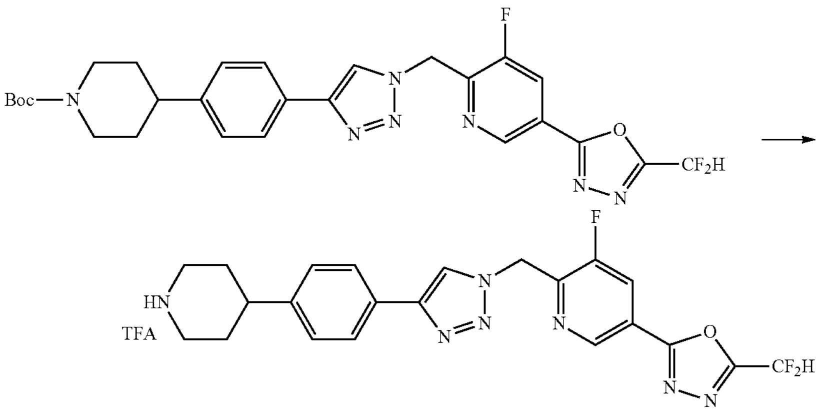

The tert-butyl 4-(4-(1-((5-(5-(difluoromethyl)-1,3,4-oxadiazol-2-yl)-3-fluoropyridin-2-yl)methyl)-1H-1,2,3-triazol-4-yl)phenyl)piperidin-1-carboxylate (0.100 g, 0.180 mmol) prepared in step 7 and trifluoroacetic acid (0.041 mL, 0.540 mmol) were dissolved in dichloromethane (10 mL) at room temperature, after which the resulting solution was stirred at the same temperature for 3 hours. Solvent was removed from the reaction mixture under reduced pressure, after which the obtained product was used without an additional purification process (2-(difluoromethyl)-5-(5-fluoro-6-((4-(4-(piperidin-4-yl)phenyl)-1H-1,2,3-triazol-1-yl)methyl)pyridin-3-yl)-1,3,4-oxadiazole 2,2,2-trifluoroacetate, 0.090 g, 87.8%, yellow oil).

[Step 9] Synthesis of Compound 19087

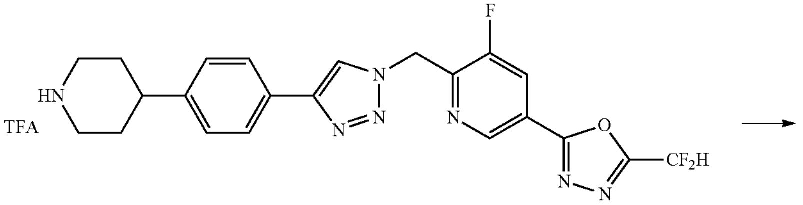

-continued

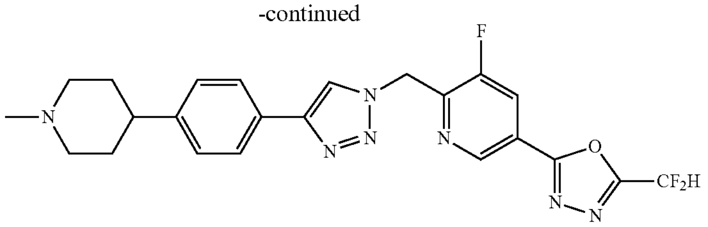

The 2-(difluoromethyl)-5-(5-fluoro-6-((4-(4-(piperidin-4-yl)phenyl)-1H-1,2,3-triazol-1-yl)methyl)pyridin-3-yl)-1,3,4-oxadiazole 2,2,2-trifluoroacetate (0.080 g, 0.140 mmol) prepared in step 8 was dissolved in dichloromethane (5 mL), after which the resulting solution was stirred at room temperature for 30 minutes and N,N-diisopropylethylamine (0.049 mL, 0.281 mmol), formaldehyde (0.008 g, 0.281 mmol) and sodium triacetoxyborohydride (0.089 g, 0.421 mmol) were added thereto and stirred at the same temperature for 12 hours. Water was poured into the reaction mixture and an extraction was performed with dichloromethane. An organic layer was washed with saturated sodium hydrogen carbonate aqueous solution, dehydrated with anhydrous sodium sulfate, filtered, and concentrated under reduced pressure. The resulting concentrate was purified via column chromatography ($SiO_2$, 4 g cartridge; methanol/dichloromethane=0 to 5%) and concentrated to obtain 2-(difluoromethyl)-5-(5-fluoro-6-((4-(4-(1-methylpiperidin-4-yl)phenyl)-1H-1,2,3-triazol-1-yl)methyl)pyridin-3-yl)-1,3,4-oxadiazole (0.029 g, 44.0%) in a white solid form.

$^1H$ NMR (400 MHz, $CDCl_3$) δ 7.99 (d, J=4.0 Hz, 1H), 7.92-7.83 (m, 3H), 7.42 (t, J=7.8 Hz, 1H), 7.15 (t, J=7.9 Hz, 1H), 7.03-6.78 (m, 2H), 5.72 (s, 2H), 3.10 (q, J=8.2, 6.4 Hz, 4H), 2.68-2.54 (m, 9H), 2.23 (ddd, J=21.2, 10.3, 4.7 Hz, 2H); LRMS (ES) m/z 578.4 ($M^+$+1).

Example 581: Synthesis of compound 19088, 1-(2-chloro-3-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine

[Step 1] Synthesis of 2-chloro-3-((trimethylsilyl)ethynyl)benzaldehyde

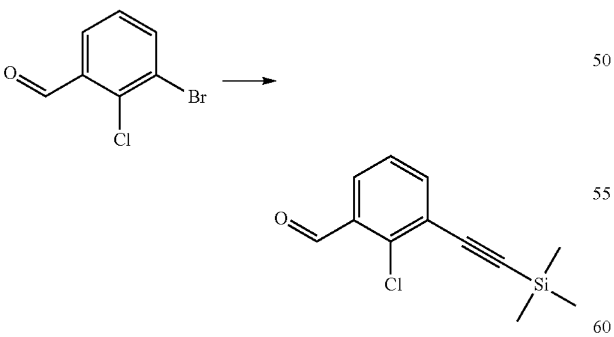

3-bromo-2-chlorobenzaldehyde (1.000 g, 4.557 mmol), bis(triphenylphosphine)palladium dichloride (0.160 g, 0.228 mmol), and copper iodide (I/II, 0.087 g, 0.456 mmol) were dissolved in tetrahydrofuran (20 mL)/triethylamine (4 mL), after which trimethylsilyl acetylene (0.917 mL, 6.835 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 10%), and concentrated to obtain 2-chloro-3-((trimethylsilyl)ethynyl)benzaldehyde (0.718 g, 66.6%) in an orange color liquid form.

[Step 2] Synthesis of 2-chloro-3-ethynylbenzaldehyde

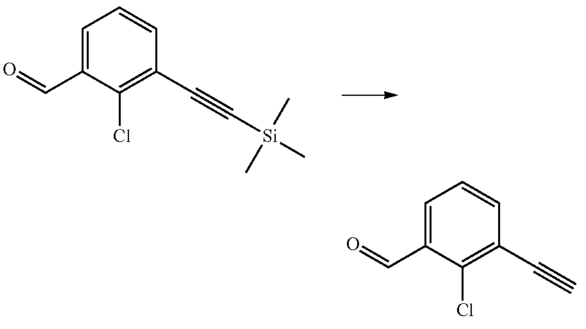

The 2-chloro-3-((trimethylsilyl)ethynyl)benzaldehyde (0.718 g, 3.032 mmol) prepared in step 1 and potassium carbonate (1.257 g, 9.097 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 10%) and concentrated to obtain 2-chloro-3-ethynylbenzaldehyde (0.480 g, 96.2%) in a light yellow solid form.

[Step 3] Synthesis of 2-chloro-3-(1-((5-(5-(difluoromethyl)-1,3,4-oxadiazol-2-yl)-3-fluoropyridin-2-yl)methyl)-1H-1,2,3-triazol-4-yl)benzaldehyde

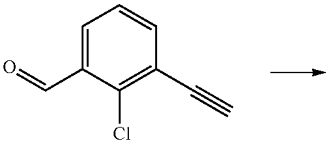

-continued

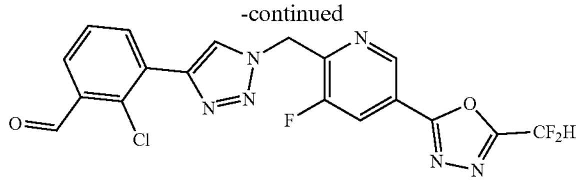

The 2-chloro-3-ethynylbenzaldehyde (0.480 g, 2.916 mmol) prepared in step 2, 2-(6-(azidomethyl)-5-fluoropyridin-3-yl)-5-(difluoromethyl)-1,3,4-oxadiazole (0.788 g, 2.916 mmol) prepared in step 1 of example 490, sodium ascorbate (0.50 M solution in water, 0.583 mL, 0.292 mmol) and copper(II) sulfate pentahydrate (1.00 M solution in water, 0.029 mL, 0.029 mmol) were dissolved in tert-butanol (5 mL)/water (5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 2-chloro-3-(1-((5-(5-(difluoromethyl)-1,3,4-oxadiazol-2-yl)-3-fluoropyridin-2-yl)methyl)-1H-1,2,3-triazol-4-yl)benzaldehyde (0.210 g, 16.6%) in a green solid form.

[Step 4] Synthesis of Compound 19088

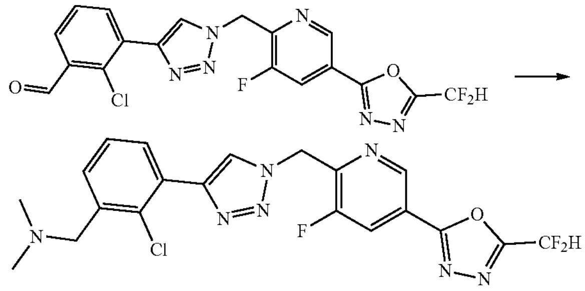

The 2-chloro-3-(1-((5-(5-(difluoromethyl)-1,3,4-oxadiazol-2-yl)-3-fluoropyridin-2-yl)methyl)-1H-1,2,3-triazol-4-yl)benzaldehyde (0.100 g, 0.230 mmol) prepared in step 3, dimethylamine (2.00 M solution in MeOH, 0.230 mL, 0.460 mmol) and acetic acid (0.013 mL, 0.230 mmol) were dissolved in dichloromethane (1 mL), after which the resulting solution was stirred at room temperature for 1 hour, and then sodium triacetoxyborohydride (0.146 g, 0.690 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 10%) and concentrated to obtain 1-(2-chloro-3-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine (0.076 g, 71.2%) in a brown solid form.

$^1H$ NMR (400 MHz, $CD_3OD$) δ 9.10 (s, 1H), 8.66 (s, 1H), 8.39 (dd, J=9.6, 1.6 Hz, 1H), 7.93 (dd, J=7.7, 1.6 Hz, 1H), 7.51 (dd, J=7.6, 1.5 Hz, 1H), 7.45-7.14 (m, 2H), 6.04 (d, J=1.5 Hz, 2H), 3.71 (s, 2H), 2.34 (s, 6H); LRMS (ES) m/z 464.3 ($M^+$+1).

The compound of table 181 was synthesized according to substantially the same process as described above in the synthesis of compound 19088 with an exception of using 2-chloro-3-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 180.

TABLE 180

| Example | Compound No. | Reactant | Yield (%) |
|---|---|---|---|
| 582 | 19089 | Pyrrolidine | 10 |

TABLE 181

| Example | Compound No. | Compound Name, $^1H$-NMR, MS (ESI) |
|---|---|---|
| 582 | 19089 | 2-(6-((4-(2-chloro-3-(pyrrolidin-1-ylmethyl)phenyl)-1H-1,2,3-triazol-1-yl)methyl)-5-fluoropyridin-3-yl)-5-(difluoromethyl)-1,3,4-oxadiazole $^1H$ NMR (400 MHZ, $CD_3OD$) δ 9.10 (d, J = 0.6 Hz, 1H), 8.65 (s, 1H), 8.38 (dd, J = 9.6, 1.7 Hz, 1H), 7.92 (dd, J = 7.8, 1.7 Hz, 1H), 7.55 (dd, J = 7.6, 1.7 Hz, 1H), 7.45-7.14 (m, 2H), 6.04 (d, J = 1.8 Hz, 2H), 3.91 (s, 2H), 2.71-2.68 (m, 4H), 1.87-1.84 (m, 4H); LRMS (ESI) m/z 490.3 ($M^+$ + H). |

Example 583: Synthesis of compound 19090, 1-(3-chloro-5-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine

[Step 1] Synthesis of 3-chloro-5-((trimethylsilyl)ethynyl)benzaldehyde

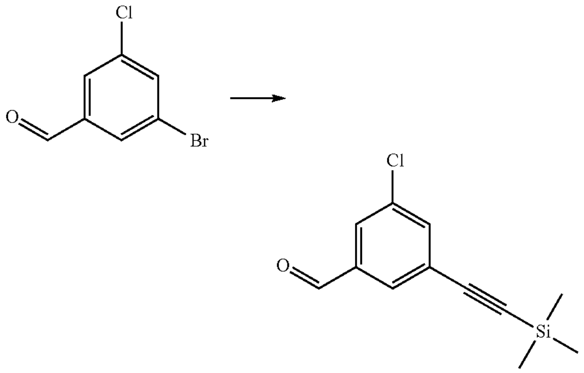

3-bromo-5-chlorobenzaldehyde (1.000 g, 4.557 mmol), bis(triphenylphosphine)palladium dichloride (0.160 g, 0.228 mmol), and copper iodide (I/II, 0.087 g, 0.456 mmol) were dissolved in tetrahydrofuran (20 mL)/triethylamine (4 mL), after which trimethylsilyl acetylene (0.917 mL, 6.835 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 10%), and concentrated to obtain 3-chloro-5-((trimethylsilyl)ethynyl)benzaldehyde (1.019 g, 94.5%) in a brown liquid form.

[Step 2] Synthesis of 3-chloro-5-ethynylbenzaldehyde

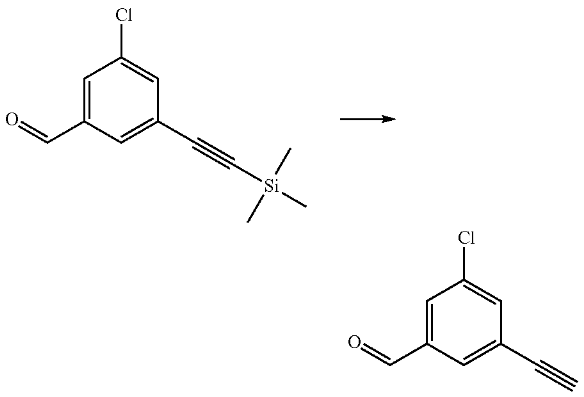

The 3-chloro-5-((trimethylsilyl)ethynyl)benzaldehyde (1.019 g, 4.304 mmol) prepared in step 1 and potassium carbonate (1.784 g, 12.911 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 10%) and concentrated to obtain 3-chloro-5-ethynylbenzaldehyde (0.530 g, 74.8%) in a light yellow solid form.

[Step 3] Synthesis of 3-chloro-5-(1-((5-(5-(difluoromethyl)-1,3,4-oxadiazol-2-yl)-3-fluoropyridin-2-yl)methyl)-1H-1,2,3-triazol-4-yl)benzaldehyde

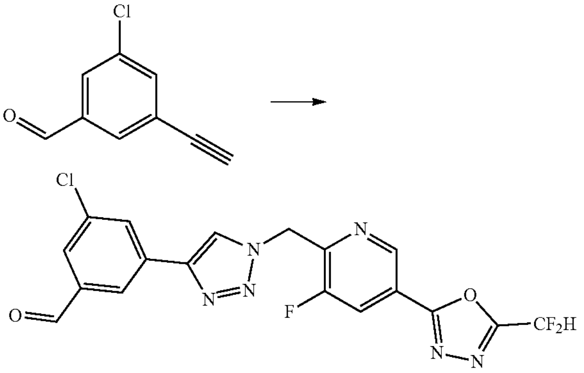

The 3-chloro-5-ethynylbenzaldehyde (0.530 g, 3.220 mmol) prepared in step 2, 2-(6-(azidomethyl)-5-fluoropyridin-3-yl)-5-(difluoromethyl)-1,3,4-oxadiazole (0.870 g, 3.220 mmol) prepared in step 1 of example 490, sodium ascorbate (0.50 M solution in water, 0.644 mL, 0.322 mmol) and copper(II) sulfate pentahydrate (1.00 M solution in water, 0.032 mL, 0.032 mmol) were dissolved in tert-butanol (5 mL)/water (5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 3-chloro-5-(1-((5-(5-(difluoromethyl)-1,3,4-oxadiazol-2-yl)-3-fluoropyridin-2-yl)methyl)-1H-1,2,3-triazol-4-yl)benzaldehyde (0.571 g, 40.8%) in a green solid form.

[Step 4] Synthesis of Compound 19090

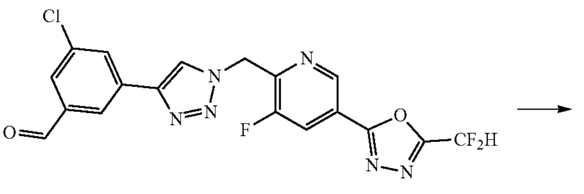

-continued

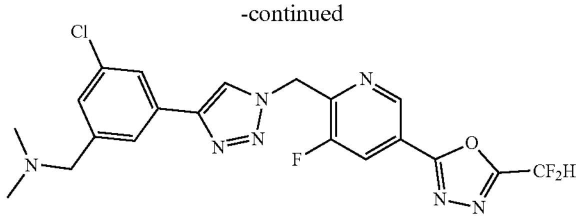

The 3-chloro-5-(1-((5-(5-(difluoromethyl)-1,3,4-oxadiazol-2-yl)-3-fluoropyridin-2-yl)methyl)-1H-1,2,3-triazol-4-yl)benzaldehyde (0.100 g, 0.230 mmol) prepared in step 3, dimethylamine (2.00 M solution in MeOH, 0.230 mL, 0.460 mmol) and acetic acid (0.013 mL, 0.230 mmol) were dissolved in dichloromethane (1 mL), after which the resulting solution was stirred at room temperature for 1 hour, and then sodium triacetoxyborohydride (0.146 g, 0.690 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 15%) and concentrated to obtain 1-(3-chloro-5-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine (0.067 g, 62.8%) in a light yellow solid form.

$^1$H NMR (400 MHz, $CD_3OD$) δ 9.09 (d, J=0.6 Hz, 1H), 8.55 (s, 1H), 8.38 (dd, J=9.6, 1.7 Hz, 1H), 7.83-7.82 (m, 1H), 7.75 (s, 1H), 7.37-7.37 (m, 1H), 7.27 (t, J=51.5 Hz, 1H), 6.01 (d, J=1.8 Hz, 2H), 3.53 (s, 2H), 2.29 (s, 6H); LRMS (ES) m/z 464.3 ($M^+$+1).

The compounds of table 183 were synthesized according to substantially the same process as described above in the synthesis of compound 19090 with an exception of using 2-chloro-3-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 182.

TABLE 182

| Example | Compound No. | Reactant | Yield (%) |
|---|---|---|---|
| 584 | 19091 | Azetidine | 14 |
| 585 | 19092 | Pyrrolidine | 42 |
| 586 | 19093 | 4-methylpiperidine | 76 |

TABLE 183

| Example | Compound No. | Compound Name, $^1$H-NMR, MS (ESI) |
|---|---|---|
| 584 | 19091 | 2-(6-((4-(3(-azetidin-1-ylmethyl)-5-chlorophenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.55 (s, 1H), 8.39 (dd, J = 9.6, 1.7 Hz, 1H), 7.81 (t, J = 1.7 Hz, 1H), 7.72 (s, 1H), 7.33 (s, 1H), 7.27 (t, J = 51.5 Hz, 1H), 6.01 (d, J = 1.8 Hz, 2H), 3.68 (s, 2H), 3.38-3.34 (m, 4H), 2.20-2.12 (m, 2H); LRMS (ESI) m/z 476.4 ($M^+$ + H). |
| 585 | 19092 | 2-(6-((4-(3-chloro-5-(pyrrolidin-1-ylmethyl)phenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.55 (s, 1H), 8.39 (dd, J = 9.6, 1.7 Hz, 1H), 7.83-7.78 (m, 2H), 7.41-7.14 (m, 2H), 6.01 (d, J = 1.8 Hz, 2H), 3.73 (s, 2H), 2.63-2.61 (m, 4H), 1.87-1.84 (m, 4H); LRMS (ESI) m/z 490.3 ($M^+$ + H). |
| 586 | 19093 | 2-(6-((4-(3-chloro-5-((4-methylpiperidin-1-yl)methyl)phenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.55 (s, 1H), 8.40-8.38 (m, 1H), 7.81 (s, 1H), 7.76 (s, 1H), 7.40-7.14 (m, 2H), 6.01 (d, J = 1.8 Hz, 2H), 3.57 (s, 2H), 2.92-2.86 (m, 2H), 2.18-2.05 (m, 2H), 1.67 (d, J = 12.5 Hz, 2H), 1.33-1.23 (m, 3H), 0.95 (d, J = 6.4 Hz, 3H); LRMS (ESI) m/z 518.4 ($M^+$ + H). |

Example 587: Synthesis of compound 19094, 1-(2-chloro-4-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine

[Step 1] Synthesis of 2-chloro-4-((trimethylsilyl)ethynyl)benzaldehyde

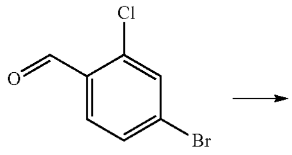

-continued

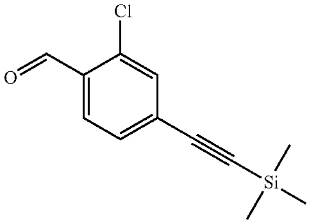

4-bromo-2-chlorobenzaldehyde (1.000 g, 4.557 mmol), bis(triphenylphosphine)palladium dichloride (0.160 g, 0.228 mmol), and copper iodide (I/II, 0.087 g, 0.456 mmol) were dissolved in tetrahydrofuran (20 mL)/triethylamine (4 mL), after which trimethylsilyl acetylene (0.917 mL, 6.835 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 10%), and concentrated to obtain 2-chloro-4-((trimethylsilyl)ethynyl)benzaldehyde (0.691 g, 64.0%) in a brown liquid form.

[Step 2] Synthesis of 2-chloro-4-ethynylbenzaldehyde

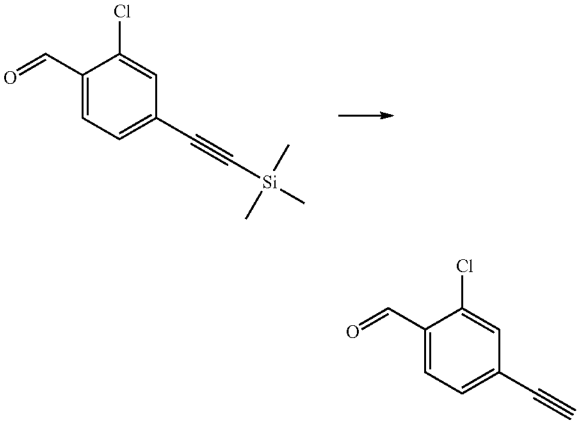

The 2-chloro-4-((trimethylsilyl)ethynyl)benzaldehyde (0.691 g, 2.918 mmol) prepared in step 1 and potassium carbonate (1.210 g, 8.755 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 10%) and concentrated to obtain 2-chloro-4-ethynylbenzaldehyde (0.380 g, 79.1%) in a light yellow solid form.

[Step 3] Synthesis of 2-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde

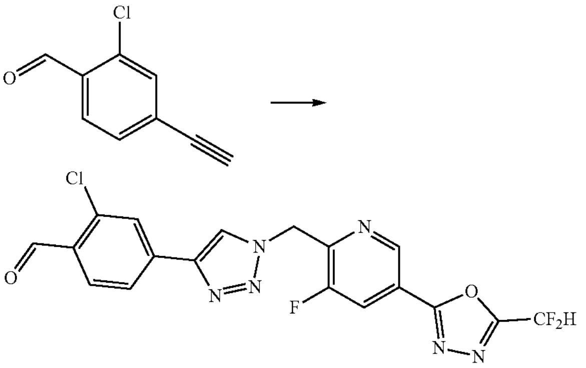

The 2-chloro-4-ethynylbenzaldehyde (0.380 g, 2.309 mmol) prepared in step 2, 2-(6-(azidomethyl)-5-fluoropyridin-3-yl)-5-(difluoromethyl)-1,3,4-oxadiazole (0.624 g, 2.309 mmol) prepared in step 1 of example 490, sodium ascorbate (0.50 M solution in water, 0.462 mL, 0.231 mmol) and copper(II) sulfate pentahydrate (1.00 M solution in water, 0.023 mL, 0.023 mmol) were dissolved in tert-butanol (5 mL)/water (5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 2-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde (0.537 g, 53.5%) in a green solid form.

[Step 4] Synthesis of Compound 19094

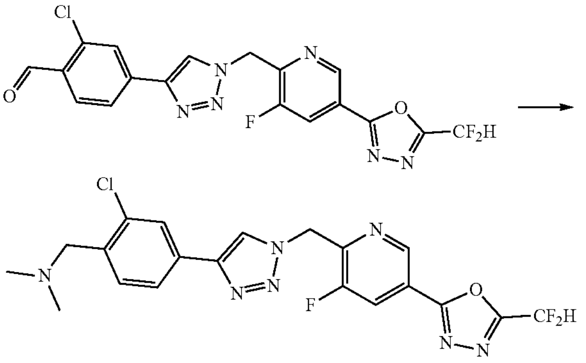

The 2-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde (0.100 g, 0.230 mmol) prepared in step 3, dimethylamine (2.00 M solution in MeOH, 0.230 mL, 0.460 mmol) and acetic acid (0.013 mL, 0.230 mmol) were dissolved in dichloromethane (1 mL), after which the resulting solution was stirred at room temperature for 1 hour, and then sodium triacetoxyborohydride (0.146 g, 0.690 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 15%) and concentrated to obtain 1-(2-chloro-4-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine (0.072 g, 67.5%) in a yellow solid form.

$^1$H NMR (400 MHz, $CD_3OD$) δ 9.10 (s, 1H), 8.56 (s, 1H), 8.39 (d, J=9.6 Hz, 1H), 7.94 (s, 1H), 7.79 (d, J=7.9 Hz, 1H), 7.55 (d, J=7.9 Hz, 1H), 7.27 (t, J=51.5 Hz, 1H), 6.01 (s, 2H), 3.66 (s, 2H), 2.33 (s, 6H); LRMS (ES) m/z 464.3 ($M^+$+1).

The compound of table 185 was synthesized according to substantially the same process as described above in the synthesis of compound 19094 with an exception of using 2-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 184.

TABLE 184

| Example | Compound No. | Reactant | Yield (%) |
|---|---|---|---|
| 588 | 19096 | Pyrrolidine | 36 |

TABLE 185

| Example | Compound No. | Compound Name, $^1$H-NMR, MS (ESI) |
|---|---|---|
| 588 | 19096 | 2-(6-((4-(3-chloro-4-(pyrrolidin-1-ylmethyl)phenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.68 (s, 1H), 8.39 (dd, J = 9.6, 1.7 Hz, 1H), 8.03 (d, J = 8.0 Hz, 1H), 7.54 (d, J = 1.6 Hz, 1H), 7.41-7.14 (m, 2H), 6.04 (d, J = 1.8 Hz, 2H), 3.53 (s, 2H), 2.29 (s, 6H); LRMS (ESI) m/z 490.3 ($M^+$ + H). |

Example 589: Synthesis of compound 19098, 1-(3-chloro-4-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine

[Step 1] Synthesis of 3-chloro-4-((trimethylsilyl)ethynyl)benzaldehyde

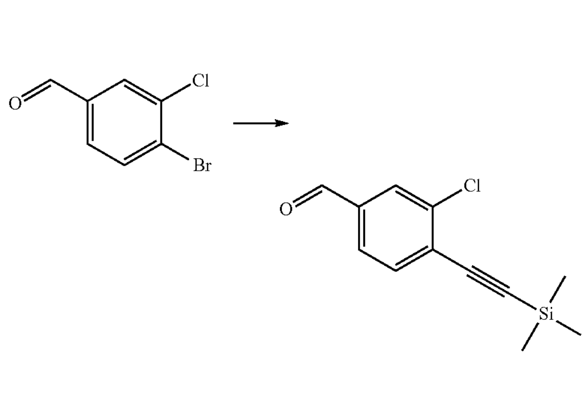

4-bromo-3-chlorobenzaldehyde (1.000 g, 4.557 mmol), bis(triphenylphosphine)palladium dichloride (0.160 g, 0.228 mmol), and copper iodide (I/II, 0.087 g, 0.456 mmol) were dissolved in tetrahydrofuran (20 mL)/triethylamine (4 mL), after which trimethylsilyl acetylene (0.917 mL, 6.835 mmol) was added to the resulting solution at room temperature and stirred at the same temperature for 5 hours. Water was poured into the reaction mixture and an extraction was performed with dichloromethane. An organic layer was washed with saturated sodium chloride aqueous solution, dehydrated with anhydrous sodium sulfate, filtered, and concentrated under reduced pressure. The resulting concentrate was purified via column chromatography ($SiO_2$, 4 g cartridge; ethyl acetate/hexane=0 to 10%), and concentrated to obtain 3-chloro-4-((trimethylsilyl)ethynyl)benzaldehyde (0.736 g, 68.2%) in an orange color liquid form.

[Step 2] Synthesis of 3-chloro-4-ethynylbenzaldehyde

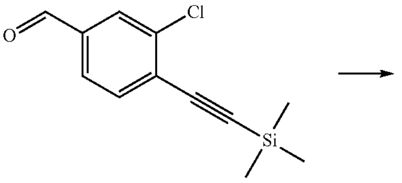

-continued

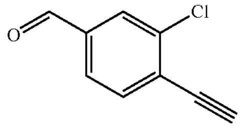

The 3-chloro-4-((trimethylsilyl)ethynyl)benzaldehyde (0.736 g, 3.109 mmol) prepared in step 1 and potassium carbonate (1.289 g, 9.326 mmol) were dissolved in methanol (10 mL) at room temperature, after which the resulting solution was stirred at the same temperature for 18 hours. Water was poured into the reaction mixture and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; ethyl acetate/hexane=0 to 10%) and concentrated to obtain 3-chloro-4-ethynylbenzaldehyde (0.398 g, 77.8%) in a light yellow solid form.

[Step 3] Synthesis of 3-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde

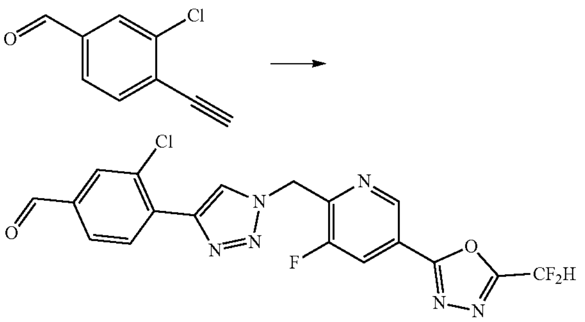

The 3-chloro-4-ethynylbenzaldehyde (0.230 g, 1.397 mmol) prepared in step 2, 2-(6-(azidomethyl)-5-fluoropyridin-3-yl)-5-(difluoromethyl)-1,3,4-oxadiazole (0.378 g, 1.397 mmol) prepared in step 1 of example 490, sodium ascorbate (0.50 M solution in water, 0.279 mL, 0.140 mmol) and copper(II) sulfate pentahydrate (1.00 M solution in water, 0.014 mL, 0.014 mmol) were dissolved in tert-butanol (5 mL)/water (5 mL) at room temperature, after which the resulting solution was stirred at the same temperature for 2 hours. Saturated ammonium chloride aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; dichloromethane/methanol=0 to 10%) and concentrated, after which dichloromethane (5 mL) and hexane (100 mL) were added and stirred to the resulting solution to filter out a precipitated solid, washed with hexane, and dried to obtain 3-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde (0.310 g, 51.0%) in a yellow solid form.

[Step 4] Synthesis of Compound 19098

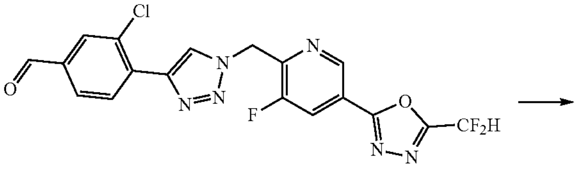

-continued

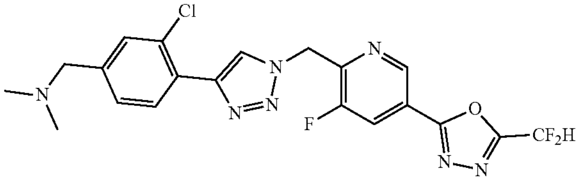

The 3-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde (0.100 g, 0.230 mmol) prepared in step 3, dimethylamine (2.00 M solution in MeOH, 0.230 mL, 0.460 mmol) and acetic acid (0.013 mL, 0.230 mmol) were dissolved in dichloromethane (1 mL), after which the resulting solution was stirred at room temperature for 1 hour, and then sodium triacetoxyborohydride (0.146 g, 0.690 mmol) was added thereto and further stirred at the same temperature for 18 hours. Saturated sodium hydrogen carbonate aqueous solution was poured into the reaction mixture, and an extraction was performed with dichloromethane. An organic layer was washed with saturated sodium chloride aqueous solution, dehydrated with anhydrous magnesium sulfate, filtered, and concentrated under reduced pressure. The resulting concentrate was purified via column chromatography ($SiO_2$, 4 g cartridge; methanol/dichloromethane=0 to 15%) and concentrated to obtain 1-(3-chloro-4-(1-((5-(5-(difluoromethyl)-1,3,4-oxadiazol-2-yl)-3-fluoropyridin-2-yl)methyl)-1H-1,2,3-triazol-4-yl)phenyl)-N,N-dimethylmethanamine (0.065 g, 60.9%) in a light yellow solid form.

$^1$H NMR (400 MHz, $CD_3OD$) δ 9.10 (s, 1H), 8.68 (s, 1H), 8.39 (dd, J=9.6, 1.7 Hz, 1H), 8.03 (d, J=8.0 Hz, 1H), 7.54 (d, J=1.6 Hz, 1H), 7.41-7.14 (m, 2H), 6.04 (d, J=1.8 Hz, 2H), 3.53 (s, 2H), 2.29 (s, 6H); LRMS (ES) m/z 464.4 ($M^+$+1).

The compounds of table 187 were synthesized according to substantially the same process as described above in the synthesis of compound 19098 with an exception of using 3-chloro-4-(1-((5-(5-(difluoromethyl)-1,3,4-oxadiazol-2-yl)-3-fluoropyridin-2-yl)methyl)-1H-1,2,3-triazol-4-yl)benzaldehyde and the reactant of table 186.

TABLE 186

| Example | Compound No. | Reactant | Yield (%) |
|---|---|---|---|
| 590 | 19099 | Azetidine | 25 |
| 591 | 19100 | Pyrrolidine | 23 |

TABLE 187

| Example | Compound No. | Compound Name, $^1$H-NMR, MS (ESI) |
|---|---|---|
| 590 | 19099 | 2-(6-((4-(4-(azetidin-1-ylmethyl)-2-chlorophenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.67 (s, 1H), 8.39 (dd, J = 9.6, 1.7 Hz, 1H), 8.02 (d, J = 8.0 Hz, 1H), 7.50 (d, J = 1.5 Hz, 1H), 7.37 (dd, J = 8.1, 1.6 Hz, 1H), 7.26 (t, J = 51.5 Hz, 1H), 6.04 (d, J = 1.8 Hz, 2H), 3.68 (s, 2H), 3.38-3.33 (m, 4H), 2.20-2.13 (m, 2H); LRMS (ESI) m/z 476.0 ($M^+$ + H). |
| 591 | 19100 | 2-(6-((4-(2-chloro-4-(pyrrolidin-1-ylmethyl)phenyl)-1H-1,2,3-triazol-1-yl)methyl)-5-fluoropyridin-3-yl)-5-(difluoromethyl)-1,3,4-oxadiazole $^1$H NMR (400 MHZ, $CD_3OD$) δ 9.10 (s, 1H), 8.68 (s, 1H), 8.39 (dd, J = 9.6, 1.7 Hz, 1H), 8.03 (d, J = 8.0 Hz, 1H), 7.57 (d, J = 1.5 Hz, 1H), 7.43 (dd, J = 8.1, 1.6 Hz,1H), 7.27 (t, J = 51.5 Hz, 1H), 6.04 (d, J = 1.7 Hz, 2H), 3.72 (s, 2H), 2.63 (s,4H), 1.88-1.85 (m, 4H); LRMS (ESI) m/z 490.4 ($M^+$ + H). |

Protocol for Measuring and Analyzing the Activity of the Compounds of the Present Invention Experimental Example 1. Search for HDAC Enzyme Activity Inhibition (In Vitro)

An experiment was conducted to identify the selectivity of the compound represented by formula I of the present invention to HDAC6 through an experiment on HDAC1 and HDAC6 enzyme activity inhibition.

The HDAC enzyme activity was measured with HDAC Fluorimetric Drug Discovery Kit (BML-AK511, 516) of Enzo Life Science, Inc. For the test on the HDAC1 enzyme activity, human recombinant HDAC1 (BML-SE456) was used as an enzyme source and Fluor de Lys® -"SIRT1 (BNL-K1177)" was used as a substrate. A 5-fold dilution of the compound was divided into a 96-well plate, after which 0.3 μg of the enzyme and 10 μM of the substrate were inserted into each well and subjected to reaction at 30 °C for 60 minutes, such that Fluor de Lys® Developer II (BML-K1176) was inserted thereinto and subjected to reaction for 30 minutes and finished. After that, a fluorescence value (Ex 360, Em 460) was measured with a multi-plate reader (Flexstation 3, Molecular Device). An experiment on HDAC6 enzyme was conducted in accordance with the same protocol as an HDAC1 enzyme activity test method by using human recombinant HDAC6 (382180) of Calbiochem Inc. For final result values, each $IC_{50}$ value was calculated with GraphPad Prism 4.0 program.

TABLE 188

| Example | Compound | HDAC1 (uM) | HDAC6 (uM) | HDAC6 selectivity (fold) |
|---|---|---|---|---|
| 1 | 3657 | >50 | 0.0948 | 527 |
| 2 | 3658 | >50 | 0.0579 | 863 |
| 3 | 3659 | >50 | 0.4089 | 122 |
| 4 | 3660 | >50 | 0.2854 | 175 |
| 5 | 3661 | >50 | 0.3987 | 125 |
| 6 | 3662 | >50 | 0.1730 | 289 |
| 7 | 3695 | >50 | 1.186 | 42 |
| 8 | 3696 | >50 | 0.9453 | 52 |
| 9 | 3697 | >50 | 0.0454 | 1101 |
| 10 | 3698 | >50 | 0.0456 | 1096 |
| 11 | 3731 | >50 | 1.723 | 29 |
| 12 | 3732 | >50 | 0.6722 | 74 |
| 13 | 3733 | >50 | 0.2325 | 215 |
| 14 | 3734 | >50 | 0.2438 | 500 |
| 15 | 3735 | >50 | 0.1562 | 320 |
| 16 | 3736 | >50 | 0.0222 | 2252 |
| 17 | 3737 | >50 | 0.0479 | 1043 |
| 18 | 3738 | >50 | 0.0440 | 1136 |
| 19 | 3739 | >50 | 0.0639 | 782 |
| 20 | 3741 | >50 | 0.0285 | 1754 |
| 21 | 3774 | >50 | 0.1211 | 412 |
| 22 | 3775 | >50 | 0.0292 | 1712 |
| 23 | 3776 | >50 | 0.0252 | 1984 |
| 24 | 3777 | >50 | 0.0225 | 2222 |
| 25 | 3805 | >50 | 0.0592 | 844 |
| 26 | 3806 | >50 | 0.3717 | 134 |
| 27 | 3807 | >50 | 0.3012 | 166 |
| 28 | 3808 | >50 | 0.3480 | 143 |
| 29 | 3809 | >50 | 0.1976 | 253 |
| 30 | 3810 | >50 | 0.2799 | 178 |
| 31 | 3811 | >50 | 0.2069 | 241 |
| 32 | 3812 | >50 | 0.1119 | 446 |
| 33 | 3813 | >50 | 0.2998 | 166 |
| 34 | 3820 | >50 | 0.1697 | 294 |
| 35 | 3822 | >50 | 0.2047 | 244 |
| 36 | 3824 | >50 | 0.0205 | 2439 |
| 37 | 3825 | >50 | 0.0112 | 4464 |
| 38 | 3826 | >50 | 0.0121 | 4132 |

TABLE 188-continued

| Example | Compound | HDAC1 (uM) | HDAC6 (uM) | HDAC6 selectivity (fold) |
|---|---|---|---|---|
| 39 | 3827 | >50 | 0.0201 | 2487 |
| 40 | 3828 | >50 | 0.0418 | 1196 |
| 41 | 3829 | >50 | 0.0302 | 1655 |
| 42 | 3830 | >50 | 0.0228 | 219 |
| 43 | 3831 | >50 | 0.1454 | 343 |
| 44 | 3832 | >50 | 0.1896 | 263 |
| 45 | 3833 | >50 | 0.4244 | 117 |
| 46 | 3834 | >50 | 0.2380 | 217 |
| 47 | 3835 | >50 | 0.0427 | 1170 |
| 48 | 3837 | >50 | 0.0518 | 965 |
| 49 | 3838 | >50 | 0.0070 | 7142 |
| 50 | 3839 | >50 | 0.0074 | 6756 |
| 51 | 3840 | >50 | 0.0088 | 5681 |
| 52 | 3841 | >50 | 0.0084 | 5952 |
| 53 | 3842 | >50 | 0.0246 | 2032 |
| 54 | 3843 | >50 | 0.0084 | 5952 |
| 55 | 3844 | >50 | 0.0207 | 2415 |
| 56 | 3845 | >50 | 0.0161 | 3105 |
| 57 | 3846 | >50 | 0.0793 | 630 |
| 58 | 3853 | >50 | 0.0310 | 1612 |
| 59 | 3854 | >50 | 0.0397 | 1259 |
| 60 | 3855 | >50 | 0.0275 | 1818 |
| 61 | 3856 | >50 | 0.0332 | 1506 |
| 62 | 3860 | >50 | 0.1278 | 391 |
| 63 | 3861 | >50 | 0.0542 | 922 |
| 64 | 3866 | >50 | 0.0186 | 2688 |
| 65 | 3867 | >50 | 0.0256 | 1953 |
| 66 | 3879 | >50 | 0.0646 | 773 |
| 67 | 3880 | >50 | 0.0797 | 627 |
| 68 | 3881 | >50 | 0.0340 | 1470 |
| 69 | 3882 | >50 | 0.0506 | 988 |
| 70 | 3883 | >50 | 0.0339 | 1474 |
| 71 | 3884 | >50 | 0.0376 | 1329 |
| 72 | 3885 | >50 | 0.0543 | 920 |
| 73 | 3886 | >50 | 0.0447 | 1118 |
| 74 | 3887 | >50 | 0.0571 | 875 |
| 75 | 3889 | >50 | 0.0413 | 1210 |
| 76 | 3890 | >50 | 0.0379 | 1319 |
| 77 | 3891 | >50 | 0.1741 | 287 |
| 78 | 3892 | >50 | 0.1398 | 357 |
| 79 | 3893 | >50 | 0.1532 | 326 |
| 80 | 3894 | >50 | 0.1004 | 498 |
| 81 | 3895 | >50 | 0.2927 | 171 |
| 82 | 3896 | >50 | 0.2671 | 187 |
| 83 | 3902 | >50 | 0.0207 | 2415 |
| 84 | 3914 | >50 | 0.0432 | 1190 |
| 85 | 3915 | >50 | 0.0382 | 1308 |
| 86 | 3916 | >50 | 0.0285 | 1754 |
| 87 | 3917 | >50 | 0.0328 | 1524 |
| 88 | 3918 | >50 | 0.0420 | 1190 |
| 89 | 3919 | >50 | 0.0368 | 1358 |
| 90 | 3925 | >50 | 0.0351 | 1424 |
| 91 | 3926 | >50 | 0.1621 | 308 |
| 92 | 3944 | >50 | 0.0067 | 7462 |
| 93 | 3945 | >50 | 0.1931 | 258 |
| 94 | 3949 | >50 | 0.1122 | 445 |
| 95 | 3950 | >50 | 0.0524 | 954 |
| 96 | 3951 | >50 | 0.6132 | 81 |
| 97 | 3952 | >50 | 0.6529 | 76 |
| 98 | 3953 | >50 | 0.4981 | 100 |
| 99 | 3954 | >50 | 0.4286 | 116 |
| 100 | 3955 | >50 | 0.5216 | 95 |
| 101 | 3956 | >50 | 0.5363 | 93 |
| 102 | 3957 | >50 | 0.4959 | 100 |
| 103 | 3958 | >50 | 0.4291 | 116 |
| 104 | 3959 | >50 | 0.2386 | 209 |
| 105 | 3960 | >50 | 0.1055 | 473 |
| 106 | 3961 | >50 | 0.1294 | 386 |
| 107 | 3962 | >50 | 0.0108 | 4629 |
| 108 | 3963 | >50 | 0.0594 | 841 |
| 109 | 3964 | >50 | 0.0262 | 1908 |
| 110 | 3965 | >50 | 0.0359 | 1392 |
| 111 | 3966 | >50 | 0.0295 | 1694 |
| 112 | 3980 | >50 | 0.1836 | 272 |
| 113 | 3981 | >50 | 1.200 | 41 |
| 114 | 3985 | >50 | 0.0342 | 1461 |

TABLE 188-continued

| Example | Compound | HDAC1 (uM) | HDAC6 (uM) | HDAC6 selectivity (fold) |
|---|---|---|---|---|
| 115 | 3986 | >50 | 0.0074 | 6756 |
| 116 | 3987 | >50 | 0.0091 | 5494 |
| 117 | 3988 | >50 | 0.0106 | 4716 |
| 118 | 3989 | >50 | 0.0313 | 1597 |
| 119 | 3990 | >50 | 0.0190 | 2631 |
| 120 | 3991 | >50 | 0.0282 | 1773 |
| 121 | 3999 | >50 | 0.0869 | 575 |
| 122 | 4000 | >50 | 0.3431 | 145 |
| 123 | 4001 | >50 | 0.1687 | 296 |
| 124 | 4002 | >50 | 0.5198 | 96 |
| 125 | 4003 | >50 | 0.4839 | 103 |
| 126 | 4004 | >50 | 0.3325 | 150 |
| 127 | 4005 | >50 | 0.1317 | 379 |
| 128 | 4006 | >50 | 0.1332 | 375 |
| 129 | 4007 | >50 | 0.0174 | 2873 |
| 130 | 4008 | >50 | 0.1224 | 408 |
| 131 | 4009 | >50 | 0.1234 | 405 |
| 132 | 4010 | >50 | 0.0211 | 2369 |
| 133 | 4011 | >50 | 0.0244 | 2049 |
| 134 | 4012 | >50 | 0.0212 | 2358 |
| 135 | 4013 | >50 | 0.0229 | 2183 |
| 136 | 4014 | >50 | 0.2029 | 246 |
| 137 | 4015 | >50 | 0.4711 | 106 |
| 138 | 4023 | >50 | 1.560 | 32 |
| 139 | 4026 | >50 | 0.2634 | 189 |
| 140 | 4027 | >50 | 5.000 | 10 |
| 141 | 4028 | >50 | 0.2098 | 238 |
| 142 | 4029 | >50 | 0.2084 | 239 |
| 143 | 4051 | >50 | 0.0308 | 1623 |
| 144 | 4052 | >50 | 0.0443 | 1128 |
| 145 | 4053 | >50 | 0.0568 | 880 |
| 146 | 4054 | >50 | 0.0457 | 1094 |
| 147 | 4055 | >50 | 0.0576 | 868 |
| 148 | 4070 | >50 | 0.0385 | 1298 |
| 149 | 4071 | >50 | 0.1438 | 347 |
| 150 | 4072 | >50 | 0.0103 | 4854 |
| 151 | 4073 | >50 | 0.0608 | 822 |
| 152 | 4074 | >50 | 0.0830 | 602 |
| 153 | 4075 | >50 | 0.0164 | 3048 |
| 154 | 4076 | >50 | 0.0676 | 739 |
| 155 | 4077 | >50 | 0.0845 | 591 |
| 156 | 4078 | >50 | 0.0351 | 1424 |
| 157 | 4079 | >50 | 0.0251 | 1992 |
| 158 | 4080 | >50 | 0.0233 | 2145 |
| 159 | 4081 | >50 | 0.1045 | 478 |
| 160 | 4082 | >50 | 0.1432 | 349 |
| 161 | 4104 | 33 | 0.0660 | 500 |
| 162 | 4105 | 34 | 0.0347 | 979 |
| 163 | 4106 | >50 | 0.0570 | 877 |
| 164 | 4107 | >50 | 0.0398 | 1256 |
| 165 | 4108 | >50 | 0.0085 | 5882 |
| 166 | 4109 | >50 | 0.0137 | 3649 |
| 167 | 4110 | >50 | 0.0165 | 3030 |
| 168 | 4111 | >50 | 0.0109 | 4587 |
| 169 | 4112 | >50 | 0.0160 | 3125 |
| 170 | 4133 | >50 | 0.1125 | 444 |
| 171 | 4134 | >50 | 0.0165 | 3030 |
| 172 | 4135 | >50 | 0.0167 | 2941 |
| 173 | 4136 | >50 | 0.0174 | 2873 |
| 174 | 4178 | >50 | 0.0558 | 896 |
| 175 | 4179 | >50 | 0.0744 | 672 |
| 176 | 4180 | >50 | 0.0332 | 1506 |
| 177 | 4181 | >50 | 0.0357 | 1400 |
| 178 | 4182 | >50 | 0.0222 | 2252 |
| 179 | 4183 | >50 | 0.0558 | 896 |
| 180 | 4184 | >50 | 0.0387 | 1291 |
| 181 | 4185 | >50 | 0.0685 | 729 |
| 182 | 4186 | >50 | 0.0112 | 4464 |
| 183 | 4187 | >50 | 0.0089 | 5617 |
| 184 | 4208 | >50 | 0.0338 | 1479 |
| 185 | 4209 | >50 | 0.0385 | 1298 |
| 186 | 4210 | >50 | 0.0519 | 963 |
| 187 | 4211 | >50 | 0.0481 | 1039 |
| 188 | 4212 | >50 | 0.0312 | 1602 |
| 189 | 4213 | >50 | 0.0289 | 1730 |
| 190 | 4229 | >50 | 0.0287 | 1742 |

TABLE 188-continued

| Example | Compound | HDAC1 (uM) | HDAC6 (uM) | HDAC6 selectivity (fold) |
|---|---|---|---|---|
| 191 | 4230 | >50 | 0.0230 | 2173 |
| 192 | 4231 | >50 | 0.0547 | 914 |
| 193 | 4232 | >50 | 0.0224 | 2232 |
| 194 | 4233 | >50 | 0.0130 | 3846 |
| 195 | 4234 | >50 | 0.0168 | 2976 |
| 196 | 4235 | >50 | 0.1719 | 290 |
| 197 | 4276 | >50 | 0.3485 | 143 |
| 198 | 4277 | >50 | 0.2349 | 212 |
| 199 | 4278 | >50 | 0.3113 | 160 |
| 200 | 4279 | >50 | 0.2741 | 182 |
| 201 | 4280 | >50 | 0.1712 | 292 |
| 202 | 4281 | >50 | 0.1213 | 412 |
| 203 | 4282 | >50 | 0.2383 | 209 |
| 204 | 4283 | >50 | 0.2456 | 203 |
| 205 | 4284 | >50 | 0.0261 | 1915 |
| 206 | 4285 | >50 | 0.0317 | 1577 |
| 207 | 4286 | >50 | 0.3242 | 154 |
| 208 | 4287 | >50 | 0.0239 | 2092 |
| 209 | 4288 | >50 | 0.1028 | 486 |
| 210 | 4289 | >50 | 0.0120 | 416 |
| 211 | 4290 | >50 | 0.0550 | 909 |
| 212 | 4291 | >50 | 0.0427 | 1170 |
| 213 | 4292 | >50 | 0.0517 | 967 |
| 214 | 4293 | >50 | 0.0809 | 618 |
| 215 | 4294 | >50 | 0.0632 | 791 |
| 216 | 4295 | >50 | 0.0452 | 1106 |
| 217 | 4296 | >50 | 0.0323 | 1547 |
| 218 | 4316 | >50 | 0.2423 | 206 |
| 219 | 4317 | >50 | 0.0836 | 598 |
| 220 | 4318 | >50 | 0.0364 | 1373 |
| 221 | 4319 | >50 | 0.0340 | 1470 |
| 222 | 4320 | >50 | 0.0695 | 719 |
| 223 | 4321 | >50 | 0.1115 | 434 |
| 224 | 4322 | >50 | 0.0940 | 531 |
| 225 | 4323 | >50 | 0.1611 | 310 |
| 226 | 4324 | >50 | 0.2939 | 170 |
| 227 | 4325 | >50 | 0.0602 | 830 |
| 228 | 4326 | >50 | 0.0562 | 889 |
| 229 | 4327 | >50 | 0.0358 | 1396 |
| 230 | 4328 | >50 | 0.0591 | 846 |
| 231 | 4329 | >50 | 0.0613 | 815 |
| 232 | 4330 | >50 | 0.1859 | 268 |
| 233 | 4331 | >50 | 0.0452 | 1106 |
| 234 | 4332 | >50 | 0.0416 | 1201 |
| 235 | 4333 | >50 | 0.0226 | 2212 |
| 236 | 4334 | >50 | 0.0263 | 1901 |
| 237 | 4335 | >50 | 0.0627 | 797 |
| 238 | 4336 | >50 | 0.0324 | 1543 |
| 239 | 4337 | >50 | 0.0239 | 2092 |
| 240 | 4338 | >50 | 0.0653 | 765 |
| 241 | 4339 | >50 | 0.0308 | 1623 |
| 242 | 4340 | >50 | 0.0066 | 7575 |
| 243 | 4341 | >50 | 0.0409 | 1222 |
| 244 | 4342 | >50 | 0.0344 | 1453 |
| 245 | 4343 | >50 | 0.0085 | 5882 |
| 246 | 4344 | >50 | 0.0116 | 4310 |
| 247 | 4345 | >50 | 0.0129 | 3875 |
| 248 | 4346 | >50 | 0.0055 | 9090 |
| 249 | 4347 | >50 | 0.0073 | 6849 |
| 250 | 4348 | >50 | 0.0068 | 7352 |
| 251 | 4349 | >50 | 0.3629 | 137 |
| 252 | 4350 | >50 | 0.6049 | 82 |
| 253 | 4351 | >50 | 0.0419 | 1193 |
| 254 | 4352 | >50 | 0.0332 | 1562 |
| 255 | 4353 | >50 | 0.0416 | 1201 |
| 256 | 4358 | >50 | 0.0330 | 1515 |
| 257 | 4359 | >50 | 0.0423 | 1182 |
| 258 | 4360 | >50 | 0.0567 | 881 |
| 259 | 4361 | >50 | 0.0748 | 668 |
| 260 | 4362 | >50 | 0.0656 | 762 |
| 261 | 4363 | >50 | 0.0361 | 1385 |
| 262 | 4364 | >50 | 0.0431 | 1160 |
| 263 | 4365 | >50 | 0.0459 | 1089 |
| 264 | 4366 | >50 | 0.0368 | 1358 |
| 265 | 4367 | >50 | 0.0413 | 1210 |
| 266 | 4368 | >50 | 0.0326 | 1533 |

TABLE 188-continued

| Example | Compound | HDAC1 (uM) | HDAC6 (uM) | HDAC6 selectivity (fold) |
|---|---|---|---|---|
| 267 | 4369 | >50 | 0.0548 | 912 |
| 268 | 4370 | >50 | 0.0699 | 715 |
| 269 | 4371 | >50 | 0.0545 | 917 |
| 270 | 4372 | >50 | 0.0690 | 724 |
| 271 | 4373 | >50 | 0.0149 | 335 |
| 272 | 4374 | >50 | 0.0219 | 228 |
| 273 | 4375 | >50 | 0.0350 | 1428 |
| 274 | 4376 | >50 | 0.0457 | 1094 |
| 275 | 4377 | >50 | 0.0481 | 1039 |
| 276 | 4392 | >50 | 0.0396 | 1262 |
| 277 | 4393 | >50 | 0.0362 | 1381 |
| 278 | 4394 | >50 | 0.0708 | 706 |
| 279 | 4395 | >50 | 0.0488 | 1024 |
| 280 | 4396 | >50 | 0.0807 | 619 |
| 281 | 4397 | >50 | 0.0652 | 766 |
| 282 | 4398 | >50 | 0.0506 | 988 |
| 283 | 4399 | >50 | 0.1085 | 460 |
| 284 | 4400 | >50 | 0.0307 | 1628 |
| 285 | 4401 | >50 | 0.0444 | 1126 |
| 286 | 4402 | >50 | 0.0738 | 677 |
| 287 | 4403 | >50 | 0.0412 | 1213 |
| 288 | 4404 | >50 | 0.0597 | 837 |
| 289 | 4405 | >50 | 0.0629 | 794 |
| 290 | 4406 | >50 | 0.0560 | 892 |
| 291 | 4407 | >50 | 0.0397 | 1259 |
| 292 | 4408 | >50 | 0.0515 | 970 |
| 293 | 4409 | >50 | 0.5189 | 96 |
| 294 | 4410 | >50 | 0.0640 | 781 |
| 295 | 4411 | >50 | 0.0755 | 662 |
| 296 | 4412 | >50 | 0.1156 | 432 |
| 297 | 4413 | >50 | 0.1435 | 348 |
| 298 | 4414 | >50 | 0.0797 | 627 |
| 299 | 4415 | >50 | 0.0917 | 545 |
| 300 | 4416 | >50 | 0.1117 | 427 |
| 301 | 4417 | >50 | 0.1025 | 487 |
| 302 | 4418 | >50 | 0.0597 | 837 |
| 303 | 4419 | >50 | 0.1586 | 315 |
| 304 | 4420 | >50 | 0.1739 | 287 |
| 305 | 4421 | >50 | 0.2465 | 202 |
| 306 | 4422 | >50 | 0.3920 | 127 |
| 307 | 4424 | >50 | 0.0894 | 559 |
| 308 | 4425 | >50 | 0.1160 | 431 |
| 309 | 4426 | >50 | 0.1497 | 334 |
| 310 | 4427 | >50 | 0.0912 | 548 |
| 311 | 4429 | >50 | 0.0669 | 747 |
| 312 | 4430 | >50 | 0.1424 | 351 |
| 313 | 4431 | >50 | 0.0190 | 2631 |
| 314 | 4432 | >50 | 0.0206 | 2427 |
| 315 | 4433 | >50 | 0.0331 | 1510 |
| 316 | 4434 | >50 | 0.0209 | 2392 |
| 317 | 4435 | >50 | 0.0298 | 1677 |
| 318 | 4436 | >50 | 0.0365 | 1369 |
| 319 | 4437 | >50 | 0.0833 | 600 |
| 320 | 4438 | >50 | 0.0535 | 934 |
| 321 | 4439 | >50 | 0.0273 | 1831 |
| 322 | 4440 | >50 | 0.0302 | 1655 |
| 323 | 4441 | >50 | 0.0380 | 1315 |
| 324 | 4442 | >50 | 0.0398 | 1256 |
| 325 | 4443 | >50 | 0.0229 | 2183 |
| 326 | 4444 | >50 | 0.0267 | 1872 |
| 327 | 4448 | >50 | 0.0174 | 2873 |
| 328 | 4449 | >50 | 0.0133 | 3759 |
| 329 | 4450 | >50 | 0.0192 | 2604 |
| 330 | 4451 | >50 | 0.0168 | 1976 |
| 331 | 4452 | >50 | 0.0203 | 2463 |
| 332 | 4453 | >50 | 0.0159 | 3144 |
| 333 | 4454 | >50 | 0.0791 | 632 |
| 334 | 4455 | >50 | 0.0961 | 520 |
| 335 | 4460 | >50 | 0.3374 | 148 |
| 336 | 4461 | >50 | 0.0658 | 759 |
| 337 | 4462 | >50 | 0.0925 | 540 |
| 338 | 4463 | >50 | 0.0478 | 1046 |
| 339 | 4464 | >50 | 0.0303 | 1650 |
| 340 | 4465 | >50 | 0.0225 | 2222 |
| 341 | 4466 | >50 | 0.0072 | 6944 |
| 342 | 4467 | >50 | 0.0219 | 2283 |
| 343 | 4468 | >50 | 0.0135 | 370 |
| 344 | 4469 | >50 | 0.0590 | 847 |
| 345 | 4470 | >50 | 0.0546 | 915 |
| 346 | 4471 | >50 | 0.0448 | 1116 |
| 347 | 4472 | >50 | 0.1228 | 407 |
| 348 | 4473 | >50 | 0.0399 | 1253 |
| 349 | 4474 | >50 | 0.0412 | 1213 |
| 350 | 4475 | >50 | 0.0394 | 1269 |
| 351 | 4476 | >50 | 0.0489 | 1022 |
| 352 | 4477 | >50 | 0.0249 | 2008 |
| 353 | 4478 | >50 | 0.1142 | 437 |
| 354 | 4479 | >50 | 0.4835 | 103 |
| 355 | 4480 | >50 | 0.0360 | 1388 |
| 356 | 4482 | >50 | 0.0530 | 943 |
| 357 | 4483 | >50 | 0.0341 | 1466 |
| 358 | 4484 | >50 | 0.0163 | 3067 |
| 359 | 4485 | >50 | 0.0227 | 2202 |
| 360 | 4486 | >50 | 0.0309 | 1618 |
| 361 | 4487 | >50 | 0.0797 | 627 |
| 362 | 4488 | >50 | 0.0472 | 1059 |
| 363 | 4489 | >50 | 0.0147 | 3401 |
| 364 | 4490 | >50 | 0.0875 | 571 |
| 365 | 4491 | >50 | 0.1154 | 433 |
| 366 | 4492 | >50 | 0.0150 | 3333 |
| 367 | 4493 | >50 | 0.0065 | 7692 |
| 368 | 4494 | >50 | 0.0341 | 1466 |
| 369 | 4495 | >50 | 0.0221 | 2262 |
| 370 | 4496 | >50 | 0.0149 | 3355 |
| 371 | 4497 | >50 | 0.0133 | 3759 |
| 372 | 4498 | >50 | 0.0307 | 1628 |
| 373 | 4499 | >50 | 0.0542 | 922 |
| 374 | 4500 | >50 | 0.1210 | 413 |
| 375 | 4501 | >50 | 0.1367 | 365 |
| 376 | 4502 | >50 | 0.0142 | 3571 |
| 377 | 4503 | >50 | 0.0107 | 4672 |
| 378 | 4504 | >50 | 0.0135 | 3703 |
| 379 | 4505 | >50 | 0.0246 | 2032 |
| 380 | 4506 | >50 | 0.0221 | 2262 |
| 381 | 4507 | >50 | 0.0281 | 1779 |
| 382 | 4508 | >50 | 0.0362 | 1381 |
| 383 | 4509 | >50 | 0.0209 | 2392 |
| 384 | 4510 | >50 | 0.0230 | 2173 |
| 385 | 4511 | >50 | 0.0642 | 325 |
| 386 | 4513 | >50 | 0.1010 | 495 |
| 387 | 4515 | >50 | 0.0555 | 900 |
| 388 | 4516 | >50 | 0.0735 | 680 |
| 389 | 4517 | >50 | 0.0406 | 1231 |
| 390 | 4518 | >50 | 0.0507 | 986 |
| 391 | 4519 | >50 | 0.0503 | 994 |
| 392 | 4521 | >50 | 0.0112 | 4464 |
| 393 | 4522 | >50 | 0.0207 | 2415 |
| 394 | 4523 | >50 | 0.0111 | 4504 |
| 395 | 4524 | >50 | 0.0083 | 6024 |
| 396 | 4525 | >50 | 0.0088 | 5681 |
| 397 | 4526 | >50 | 0.0130 | 3846 |
| 398 | 4527 | >50 | 0.0116 | 4310 |
| 399 | 4528 | >50 | 0.1346 | 371 |
| 400 | 4529 | >50 | 0.1596 | 313 |
| 401 | 4530 | >50 | 0.1113 | 449 |
| 402 | 4531 | >50 | 0.1211 | 412 |
| 403 | 4532 | >50 | 0.1526 | 327 |
| 404 | 4533 | >50 | 0.1569 | 318 |
| 405 | 4534 | >50 | 0.0944 | 529 |
| 406 | 4535 | >50 | 0.0975 | 512 |
| 407 | 4536 | >50 | 0.0874 | 572 |
| 408 | 4537 | >50 | 0.0760 | 657 |
| 409 | 4538 | >50 | 0.0927 | 539 |
| 410 | 4539 | >50 | 0.0644 | 776 |
| 411 | 4540 | >50 | 0.0857 | 583 |
| 412 | 4541 | >50 | 0.0340 | 1470 |
| 413 | 4542 | >50 | 0.0374 | 1336 |
| 414 | 4543 | >50 | 0.0377 | 1326 |
| 415 | 4548 | >50 | 0.0131 | 4545 |
| 416 | 4549 | >50 | 0.0412 | 1213 |
| 417 | 4550 | >50 | 0.0181 | 2762 |
| 418 | 4551 | >50 | 0.0105 | 4761 |

TABLE 188-continued

| Example | Compound | HDAC1 (uM) | HDAC6 (uM) | HDAC6 selectivity (fold) |
|---|---|---|---|---|
| 419 | 4552 | >50 | 0.0422 | 1184 |
| 420 | 4553 | >50 | 0.0507 | 986 |
| 421 | 4554 | >50 | 0.0646 | 773 |
| 422 | 4555 | >50 | 0.0238 | 2100 |
| 423 | 4556 | >50 | 0.0733 | 682 |
| 424 | 4557 | >50 | 0.0624 | 801 |
| 425 | 4558 | >50 | 0.0085 | 5882 |
| 426 | 4559 | >50 | 0.0213 | 2347 |
| 427 | 4560 | >50 | 0.0107 | 4672 |
| 428 | 4561 | >50 | 0.0140 | 3571 |
| 429 | 4562 | >50 | 0.0240 | 2083 |
| 430 | 4563 | >50 | 0.0225 | 2222 |
| 431 | 4564 | >50 | 0.0212 | 2358 |
| 432 | 4565 | >50 | 0.0083 | 6024 |
| 433 | 4566 | >50 | 0.0398 | 1256 |
| 434 | 4567 | >50 | 0.0375 | 1333 |
| 435 | 4569 | >50 | 0.0137 | 3649 |
| 436 | 4570 | >50 | 0.0202 | 2475 |
| 437 | 4571 | >50 | 0.0183 | 2732 |
| 438 | 4572 | >50 | 0.0195 | 2564 |
| 439 | 4573 | >50 | 0.0216 | 2314 |
| 440 | 4576 | >50 | 0.0175 | 2857 |
| 441 | 4577 | >50 | 0.0186 | 2688 |
| 442 | 4578 | >50 | 0.0260 | 1923 |
| 443 | 4579 | >50 | 0.0398 | 1256 |
| 444 | 4580 | >50 | 0.0262 | 1908 |
| 445 | 4582 | >50 | 0.0219 | 2283 |
| 446 | 4583 | >50 | 0.3602 | 138 |
| 447 | 4585 | >50 | 0.2104 | 237 |
| 448 | 4586 | >50 | 0.2220 | 225 |
| 449 | 4587 | >50 | 0.1820 | 274 |
| 450 | 4588 | >50 | 0.2178 | 229 |
| 451 | 4589 | >50 | 0.2904 | 172 |
| 452 | 4590 | >50 | 0.1620 | 308 |
| 453 | 4591 | >50 | 0.0141 | 3546 |
| 454 | 4592 | >50 | 0.0154 | 3246 |
| 455 | 4593 | >50 | 0.0235 | 2127 |
| 456 | 4594 | >50 | 0.0243 | 2057 |
| 457 | 4595 | >50 | 0.0478 | 1046 |
| 458 | 4596 | >50 | 0.0639 | 782 |
| 459 | 4597 | >50 | 0.0615 | 813 |
| 460 | 4598 | >50 | 0.0451 | 1108 |
| 461 | 4599 | >50 | 0.0755 | 662 |
| 462 | 4600 | >50 | 0.0326 | 1533 |
| 463 | 4601 | >50 | 0.0359 | 1392 |
| 464 | 4602 | >50 | 0.1597 | 313 |
| 465 | 4603 | >50 | 0.0672 | 744 |
| 466 | 4604 | >50 | 0.0213 | 2347 |
| 467 | 4605 | >50 | 0.0210 | 2380 |
| 468 | 4606 | >50 | 0.0207 | 2415 |
| 469 | 4607 | >50 | 0.0199 | 2512 |
| 470 | 4608 | >50 | 0.0264 | 1893 |
| 471 | 4609 | >50 | 0.0158 | 3164 |
| 472 | 4610 | >50 | 0.0143 | 3496 |
| 473 | 4611 | >50 | 0.0179 | 2793 |
| 474 | 4633 | >50 | 0.0168 | 2976 |
| 475 | 4634 | >50 | 0.0241 | 2074 |
| 476 | 4635 | >50 | 0.0198 | 2525 |
| 477 | 4636 | >50 | 0.0319 | 1567 |
| 478 | 4640 | >50 | 0.0619 | 807 |
| 479 | 16781 | >50 | 0.0915 | 546 |
| 480 | 16789 | >50 | 0.0795 | 628 |
| 481 | 16797 | >50 | 0.0677 | 738 |
| 482 | 16928 | >50 | 0.0853 | 586 |
| 483 | 16930 | >50 | 0.0479 | 1043 |
| 484 | 17058 | >50 | 0.0180 | 2777 |
| 485 | 17198 | >50 | 0.0964 | 518 |
| 486 | 17201 | >50 | 0.0782 | 639 |
| 487 | 17255 | >50 | 0.0097 | 5154 |
| 488 | 17261 | >50 | 0.0494 | 1012 |
| 489 | 17263 | >50 | 0.0444 | 1126 |
| 490 | 17347 | >50 | 0.0796 | 628 |
| 491 | 17362 | >50 | 0.0246 | 2032 |
| 492 | 17363 | >50 | 0.0226 | 2212 |
| 493 | 17364 | >50 | 0.0512 | 976 |
| 494 | 17365 | >50 | 0.0363 | 1377 |
| 495 | 17458 | >50 | 0.0807 | 619 |
| 496 | 17460 | >50 | 0.0874 | 572 |
| 497 | 17532 | >50 | 0.0238 | 2100 |
| 498 | 17533 | >50 | 0.0220 | 2272 |
| 499 | 17534 | >50 | 0.0379 | 1319 |
| 500 | 1535 | >50 | 0.0467 | 1070 |
| 501 | 17545 | >50 | 0.0568 | 880 |
| 502 | 17698 | >50 | 0.0406 | 1231 |
| 503 | 17699 | >50 | 0.0479 | 1043 |
| 504 | 17700 | >50 | 0.0798 | 626 |
| 505 | 17773 | >50 | 0.0650 | 769 |
| 506 | 17774 | >50 | 0.0557 | 897 |
| 507 | 17775 | >50 | 0.0941 | 531 |
| 508 | 17777 | >50 | 0.0525 | 952 |
| 509 | 17778 | >50 | 0.0829 | 603 |
| 510 | 17848 | >50 | 0.0773 | 646 |
| 511 | 17851 | >50 | 0.0849 | 588 |
| 512 | 17854 | >50 | 0.0834 | 599 |
| 513 | 17857 | >50 | 0.0618 | 809 |
| 514 | 17912 | >50 | 0.0404 | 1237 |
| 515 | 17913 | >50 | 0.0323 | 1547 |
| 516 | 17914 | >50 | 0.0440 | 1136 |
| 517 | 17915 | >50 | 0.0879 | 568 |
| 518 | 17916 | >50 | 0.0898 | 556 |
| 519 | 17917 | >50 | 0.0567 | 881 |
| 520 | 17922 | >50 | 0.0976 | 512 |
| 521 | 17983 | >50 | 0.0789 | 633 |
| 522 | 17984 | >50 | 0.0565 | 884 |
| 523 | 18058 | >50 | 0.0220 | 2272 |
| 524 | 18059 | >50 | 0.0386 | 1295 |
| 525 | 18174 | >50 | 0.0510 | 980 |
| 526 | 18175 | >50 | 0.0422 | 1184 |
| 527 | 18176 | >50 | 0.0709 | 705 |
| 528 | 18177 | >50 | 0.0637 | 784 |
| 529 | 18178 | >50 | 0.0761 | 657 |
| 530 | 18180 | >50 | 0.0743 | 672 |
| 531 | 18185 | >50 | 0.0620 | 806 |
| 532 | 18187 | >50 | 0.0826 | 605 |
| 533 | 18188 | >50 | 0.0748 | 668 |
| 534 | 18256 | >50 | 0.0437 | 1144 |
| 535 | 18258 | >50 | 0.0859 | 582 |
| 536 | 18260 | >50 | 0.0645 | 775 |
| 537 | 18305 | >50 | 0.0927 | 539 |
| 538 | 18306 | >50 | 0.0422 | 1184 |
| 539 | 18307 | >50 | 0.0486 | 1028 |
| 540 | 18308 | >50 | 0.0649 | 770 |
| 541 | 18309 | >50 | 0.0431 | 1160 |
| 542 | 18310 | >50 | 0.0507 | 986 |
| 543 | 18311 | >50 | 0.0535 | 934 |
| 544 | 18327 | >50 | 0.0995 | 502 |
| 545 | 18457 | >50 | 0.0901 | 554 |
| 546 | 18459 | >50 | 0.0642 | 778 |
| 547 | 18470 | >50 | 0.0987 | 506 |
| 548 | 18483 | >50 | 0.0515 | 970 |
| 549 | 18554 | >50 | 0.0494 | 1012 |
| 550 | 18622 | >50 | 0.0824 | 606 |
| 551 | 18711 | >50 | 0.0954 | 524 |
| 552 | 18712 | >50 | 0.0436 | 1146 |
| 553 | 18713 | >50 | 0.0729 | 685 |
| 554 | 18736 | >50 | 0.0803 | 622 |
| 555 | 18822 | >50 | 0.5052 | 98 |
| 556 | 18823 | >50 | 0.3795 | 131 |
| 557 | 18868 | >50 | 0.5509 | 90 |
| 558 | 18869 | >50 | 0.0465 | 1075 |
| 559 | 18870 | >50 | 0.0445 | 1123 |
| 560 | 18871 | >50 | 0.0740 | 675 |
| 561 | 18872 | >50 | 0.2988 | 167 |
| 562 | 18877 | >50 | 0.1359 | 367 |
| 563 | 18878 | >50 | 0.1165 | 429 |
| 564 | 18882 | >50 | 0.1629 | 306 |
| 565 | 18893 | >50 | 0.1288 | 388 |
| 566 | 18918 | >50 | 0.0459 | 1089 |
| 567 | 18919 | >50 | 0.0602 | 830 |
| 568 | 18920 | >50 | 0.0420 | 1190 |
| 569 | 18921 | >50 | 0.0314 | 1592 |
| 570 | 18924 | >50 | 0.0800 | 625 |

TABLE 188-continued

| Example | Compound | HDAC1 (uM) | HDAC6 (uM) | HDAC6 selectivity (fold) |
|---|---|---|---|---|
| 571 | 18926 | >50 | 0.0639 | 782 |
| 572 | 18947 | >50 | 0.0396 | 1262 |
| 573 | 18948 | >50 | 0.0584 | 856 |
| 574 | 18949 | >50 | 0.0658 | 759 |
| 575 | 18950 | >50 | 0.0876 | 570 |
| 576 | 18961 | >50 | 0.0639 | 782 |
| 577 | 19002 | >50 | 0.0851 | 587 |
| 578 | 19004 | >50 | 0.0781 | 640 |
| 579 | 19058 | >50 | 0.0217 | 2304 |
| 580 | 19087 | >50 | 0.0769 | 650 |
| 581 | 19088 | >50 | 0.0782 | 639 |
| 582 | 19089 | >50 | 0.0751 | 665 |
| 583 | 19090 | >50 | 0.0686 | 728 |
| 584 | 19091 | >50 | 0.1147 | 435 |
| 585 | 19092 | >50 | 0.0924 | 541 |
| 586 | 19093 | >50 | 0.2359 | 211 |
| 587 | 19094 | >50 | 0.0980 | 510 |
| 588 | 19096 | >50 | 0.0944 | 529 |
| 589 | 19098 | >50 | 0.0380 | 1315 |
| 590 | 19099 | >50 | 0.0471 | 1061 |
| 591 | 19100 | >50 | 0.0576 | 868 |

As described in above table 188, it was confirmed from the results of testing the activity inhibition to HDAC1 and HDAC6 that 1,3,4-oxadiazole triazol derivative compounds of the present invention, stereoisomers thereof or pharmaceutically acceptable salts thereof show an excellent selective HDAC6 inhibitory activity about 10 to about 9090 times.

Experimental Example 2. Analysis of Effect of HDAC6-Specific Inhibitor on Axonal Transport of Mitochondria (In Vitro)

By analyzing an effect of HDAC6-specific inhibitor on axonal transport of mitochondria, an experiment was performed to identify if a compound represented by formula I of the present invention selectively inhibits an HDAC6 activity and thus increases acetylation of tubulin, a key substrate of HDAC6 so as to show an effect of improving a transport velocity of mitochondria, which had been decreased by amyloid-beta treatment within a neuronal axon.

On the $17^{th}$ to $18^{th}$ days (E17-18) of insemination, the hippocampal neurons from a Sprague-Dawley (SD) rat fetus were cultured in a culture container for imaging, which had been coated with extracellular matrix, and were treated with amyloid-beta protein fragments at a concentration of 1M. In 24 hours later, the neurons were treated with the compound on the $8^{th}$ day of in vitro culture. In three hours later, the resulting neurons were treated with MitoTracker Red CMXRos (Life Technologies, NY, USA) for last five minutes to stain mitochondria. An image on the axonal transport of stained neuron mitochondria was taken with a confocal microscope (Leica SP8; Leica microsystems, UK) at an interval of one second for one minute to measure a transport velocity of each mitochondria per second with an IMARIS analysis program (BITPLANE, Zurich, Switzerland).

In result, after setting a section, in which the group treated with amyloid-beta had shown a significant decrease in the transport velocity of mitochondria compared to a vehicle, it was confirmed for 1,3,4-oxadiazole triazol derivative compounds of the present invention, stereoisomers thereof or pharmaceutically acceptable salts thereof that the vehicles is represented as 100%, the amyloid beta treatment group is represented as 0, a velocity distribution of the compound after normalization is represented as *, 0%~50%; , 50%~100%; *, >100%.

TABLE 189

| Example | Compound | Velocity distribution (%) |
|---|---|---|
| Vehicle | — | 100% |
| Amyloid beta | — | 0% |
| 2 | 3658 | * |
| 16 | 3736 | *** |
| 18 | 3738 | *** |
| 22 | 3775 | * |
| 23 | 3776 | *** |
| 24 | 3777 | * |
| 37 | 3825 | *** |
| 38 | 3826 | * |
| 39 | 3827 | *** |
| 40 | 3828 | * |
| 49 | 3838 | * |
| 50 | 3839 | * |
| 51 | 3840 | ** |
| 52 | 3841 | *** |
| 53 | 3842 | ** |
| 58 | 3853 | ** |
| 59 | 3854 | *** |
| 61 | 3856 | *** |
| 64 | 3866 | ** |
| 65 | 3867 | ** |
| 68 | 3881 | *** |
| 70 | 3883 | * |
| 73 | 3886 | * |
| 83 | 3902 | *** |
| 84 | 3914 | * |
| 86 | 3916 | *** |
| 90 | 3925 | *** |
| 92 | 3944 | * |
| 107 | 3962 | *** |
| 115 | 3986 | *** |
| 116 | 3987 | * |
| 119 | 3990 | ** |
| 120 | 3991 | ** |
| 132 | 4010 | *** |
| 134 | 4012 | *** |
| 135 | 4013 | ** |
| 144 | 4052 | ** |
| 147 | 4055 | * |
| 148 | 4070 | ** |
| 150 | 4072 | ** |
| 151 | 4073 | ** |
| 153 | 4075 | *** |
| 154 | 4076 | *** |
| 157 | 4079 | ** |
| 158 | 4080 | *** |
| 164 | 4107 | ** |
| 165 | 4108 | *** |
| 166 | 4109 | *** |
| 167 | 4110 | ** |
| 168 | 4111 | ** |
| 169 | 4112 | *** |
| 171 | 4134 | ** |
| 172 | 4135 | ** |
| 173 | 4136 | ** |
| 178 | 4182 | ** |
| 181 | 4185 | *** |
| 183 | 4187 | * |
| 184 | 4208 | ** |
| 186 | 4210 | * |
| 193 | 4232 | ** |
| 195 | 4234 | *** |
| 208 | 4287 | *** |
| 210 | 4289 | *** |
| 217 | 4296 | ** |
| 238 | 4336 | *** |
| 239 | 4337 | *** |
| 243 | 4341 | ** |
| 244 | 4342 | * |
| 247 | 4345 | * |

TABLE 189-continued
| Example | Compound | Velocity distribution (%) |
|---|---|---|
| 248 | 4346 | *** |
| 249 | 4347 | * |
| 250 | 4348 | ** |
| 259 | 4361 | ** |
| 264 | 4366 | *** |
| 268 | 4370 | *** |
| 269 | 4371 | ** |
| 271 | 4373 | *** |
| 273 | 4375 | * |
| 313 | 4431 | *** |
| 314 | 4432 | *** |
| 486 | 17201 | * |
| 492 | 17363 | ** |
| 497 | 17532 | *** |
| 498 | 17533 | * |
| 499 | 17534 | *** |
| 521 | 17983 | *** |
| 523 | 18058 | *** |
| 527 | 18176 | ** |
| 531 | 18185 | *** |
| 538 | 18306 | *** |
| 539 | 18307 | *** |
| 540 | 18308 | *** |
| 541 | 18309 | ** |
| 579 | 19058 | *** |
The invention claimed is:
1. A compound, stereoisomers thereof or pharmaceutically acceptable salts thereof, wherein the compound is any one selected from the group consisting of compounds below:
| Example | Compound | Structure |
|---|---|---|
| 2 | 3658 | 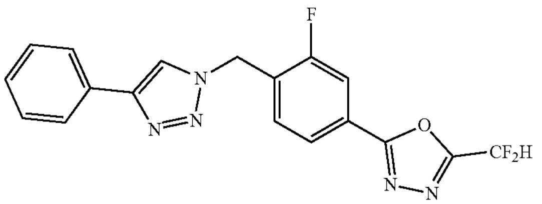 [SMILES: Fc1cc(-c2nnc(C(F)F)o2)ccc1Cn1cc(-c2ccccc2)nn1] |
| 3 | 3659 | 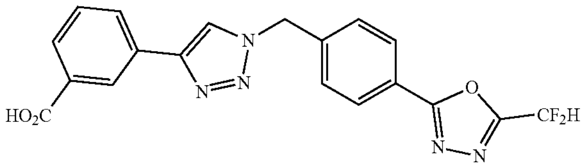 |
| 4 | 3660 | 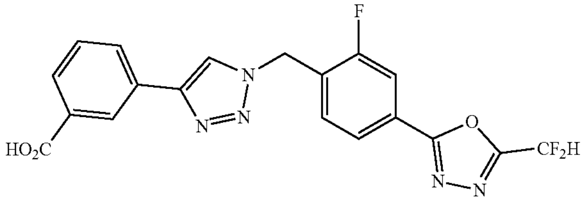 |
| 5 | 3661 | 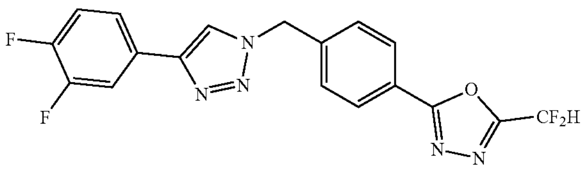 [SMILES: Fc1ccc(-c2cn(Cc3ccc(-c4nnc(C(F)F)o4)cc3)nn2)cc1F] |
| 6 | 3662 | 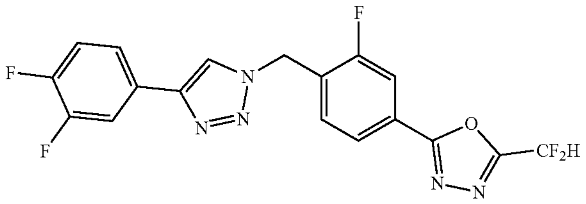 [SMILES: Fc1ccc(-c2cn(Cc3ccc(-c4nnc(C(F)F)o4)cc3F)nn2)cc1F] |

-continued
| Example | Compound | Structure |
| --- | --- | --- |
| 7 | 3695 | 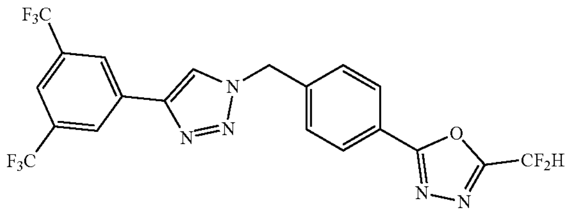 [SMILES: FC(F)c1nnc(-c2ccc(Cn3cc(-c4cc(C(F)(F)F)cc(C(F)(F)F)c4)nn3)cc2)o1] |
| 8 | 3696 | 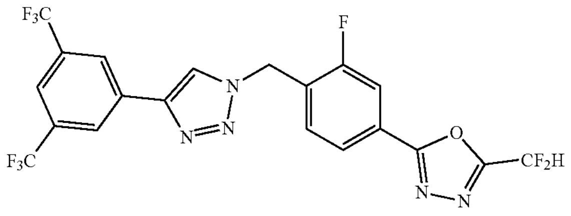 [SMILES: Fc1cc(-c2nnc(C(F)F)o2)ccc1Cn1cc(-c2cc(C(F)(F)F)cc(C(F)(F)F)c2)nn1] |
| 9 | 3697 | 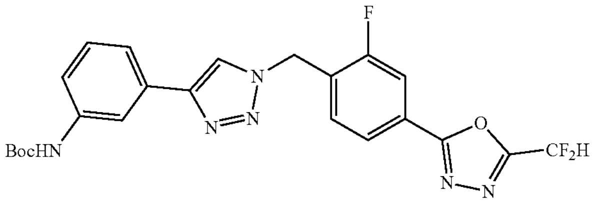 [SMILES: CC(C)(C)OC(=O)Nc1cccc(-c2cn(Cc3ccc(-c4nnc(C(F)F)o4)cc3F)nn2)c1] |
| 10 | 3698 | 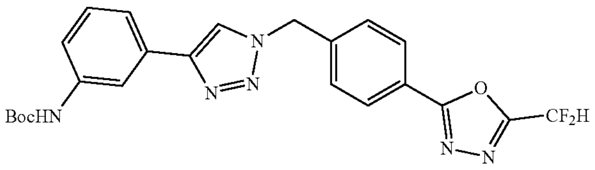 [SMILES: CC(C)(C)OC(=O)Nc1cccc(-c2cn(Cc3ccc(-c4nnc(C(F)F)o4)cc3)nn2)c1] |
| 11 | 3731 | 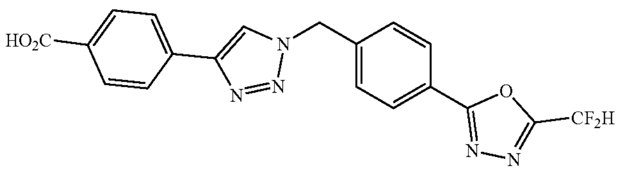 [SMILES: O=C(O)c1ccc(-c2cn(Cc3ccc(-c4nnc(C(F)F)o4)cc3)nn2)cc1] |
| 12 | 3732 | 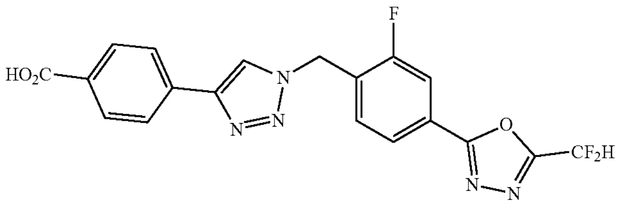 [SMILES: O=C(O)c1ccc(-c2cn(Cc3ccc(-c4nnc(C(F)F)o4)cc3F)nn2)cc1] |
| 13 | 3733 | 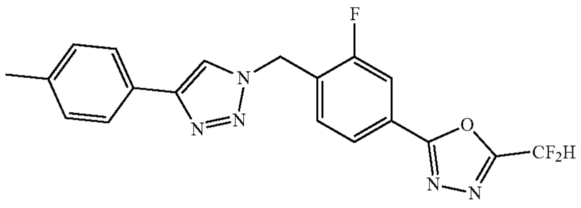 [SMILES: Cc1ccc(-c2cn(Cc3ccc(-c4nnc(C(F)F)o4)cc3F)nn2)cc1] |

-continued
| Example | Compound | Structure |
| --- | --- | --- |
| 14 | 3734 | 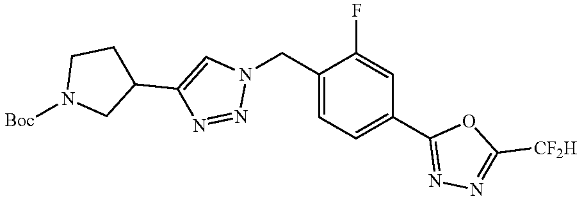 [SMILES: CC(C)(C)OC(=O)N1CCC(c2cn(Cc3ccc(-c4nnc(C(F)F)o4)cc3F)nn2)C1] |
| 15 | 3735 | 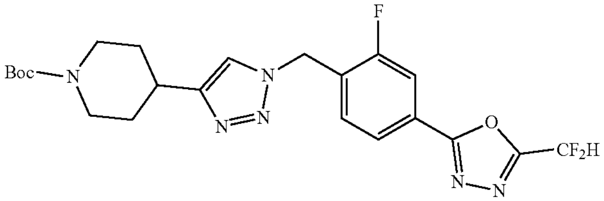 [SMILES: CC(C)(C)OC(=O)N1CCC(c2cn(Cc3ccc(-c4nnc(C(F)F)o4)cc3F)nn2)CC1] |
| 17 | 3737 | 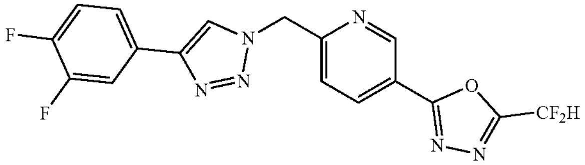 [SMILES: Fc1ccc(-c2cn(Cc3ccc(-c4nnc(C(F)F)o4)cn3)nn2)cc1F] |
| 18 | 3738 | 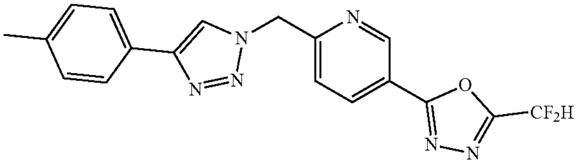 [SMILES: Cc1ccc(-c2cn(Cc3ccc(-c4nnc(C(F)F)o4)cn3)nn2)cc1] |
| 19 | 3739 | 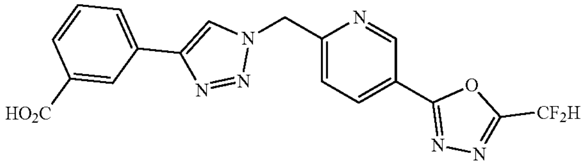 |
| 20 | 3741 | 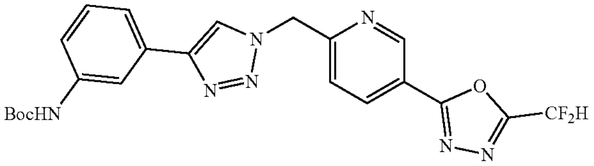 [SMILES: CC(C)(C)OC(=O)Nc1cccc(-c2cn(Cc3ccc(-c4nnc(C(F)F)o4)cn3)nn2)c1] |
| 21 | 3774 | 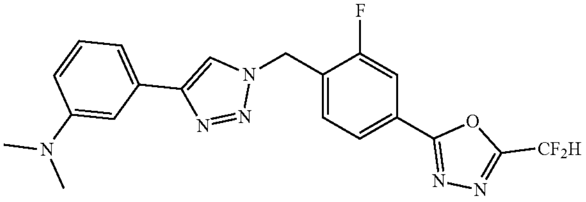 [SMILES: CN(C)c1cccc(-c2cn(Cc3ccc(-c4nnc(C(F)F)o4)cc3F)nn2)c1] |
| 22 | 3775 | 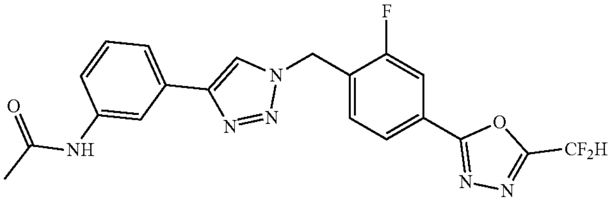 [SMILES: CC(=O)Nc1cccc(-c2cn(Cc3ccc(-c4nnc(C(F)F)o4)cc3F)nn2)c1] |

-continued
| Example | Compound | Structure |
| --- | --- | --- |
| 23 | 3776 | 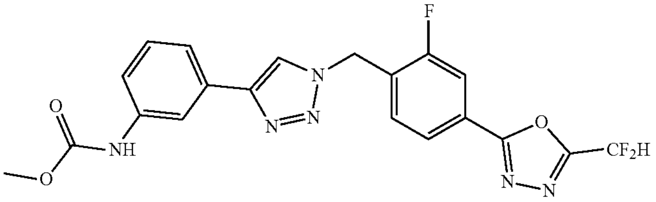 [SMILES: COC(=O)Nc1cccc(-c2cn(Cc3ccc(-c4nnc(C(F)F)o4)cc3F)nn2)c1] |
| 24 | 3777 | 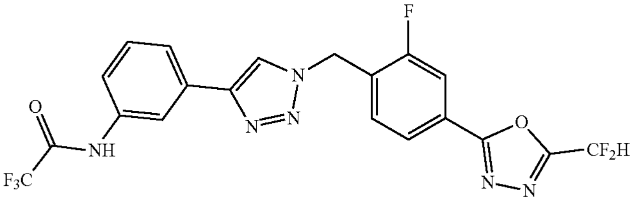 [SMILES: O=C(Nc1cccc(-c2cn(Cc3ccc(-c4nnc(C(F)F)o4)cc3F)nn2)c1)C(F)(F)F] |
| 25 | 3805 | 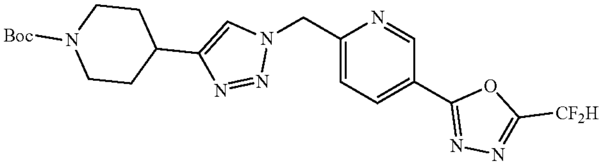 [SMILES: CC(C)(C)OC(=O)N1CCC(c2cn(Cc3ccc(-c4nnc(C(F)F)o4)cn3)nn2)CC1] |
| 26 | 3806 | 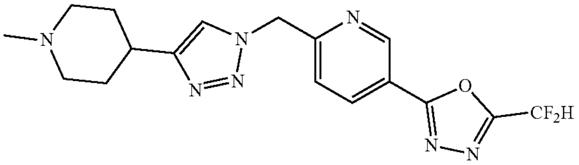 [SMILES: CN1CCC(c2cn(Cc3ccc(-c4nnc(C(F)F)o4)cn3)nn2)CC1] |
| 27 | 3807 | 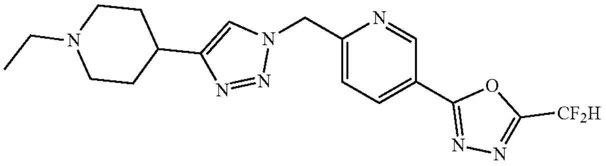 [SMILES: CCN1CCC(c2cn(Cc3ccc(-c4nnc(C(F)F)o4)cn3)nn2)CC1] |
| 28 | 3808 | 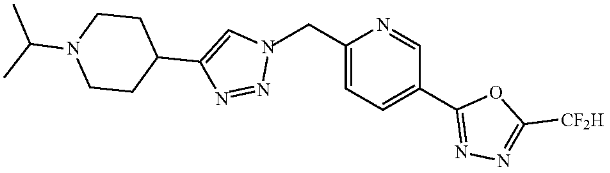 |
| 29 | 3809 | 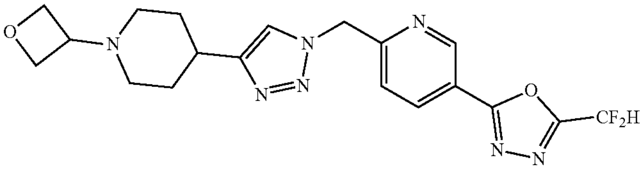 [SMILES: FC(F)c1nnc(-c2ccc(Cn3cc(C4CCN(C5COC5)CC4)nn3)nc2)o1] |
| 30 | 3810 | 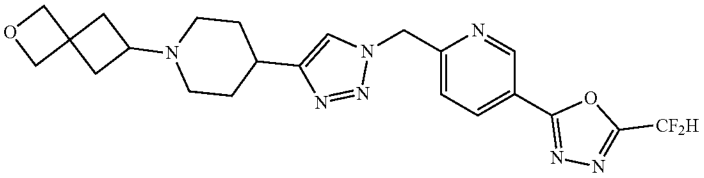 [SMILES: FC(F)c1nnc(-c2ccc(Cn3cc(C4CCN(C5CC6(COC6)C5)CC4)nn3)nc2)o1] |

-continued
| Example | Compound | Structure |
| --- | --- | --- |
| 31 | 3811 | 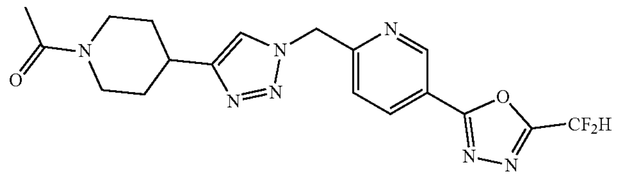 [SMILES: CC(=O)N1CCC(c2cn(Cc3ccc(-c4nnc(C(F)F)o4)cn3)nn2)CC1] |
| 32 | 3812 | 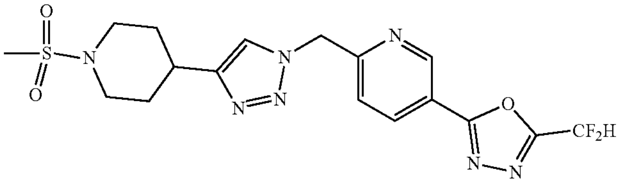 [SMILES: CS(=O)(=O)N1CCC(c2cn(Cc3ccc(-c4nnc(C(F)F)o4)cn3)nn2)CC1] |
| 33 | 3813 | 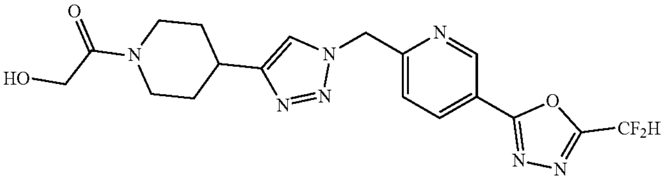 [SMILES: O=C(CO)N1CCC(c2cn(Cc3ccc(-c4nnc(C(F)F)o4)cn3)nn2)CC1] |
| 34 | 3820 | 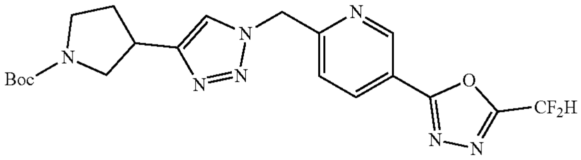 [SMILES: CC(C)(C)OC(=O)N1CCC(c2cn(Cc3ccc(-c4nnc(C(F)F)o4)cn3)nn2)C1] |
| 35 | 3822 | 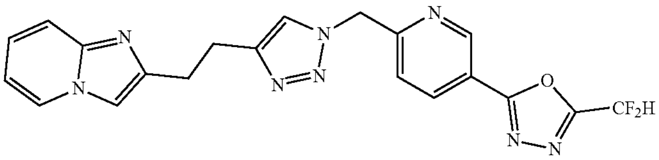 [SMILES: FC(F)c1nnc(-c2ccc(Cn3cc(CCc4cn5ccccc5n4)nn3)nc2)o1] |
| 36 | 3824 | 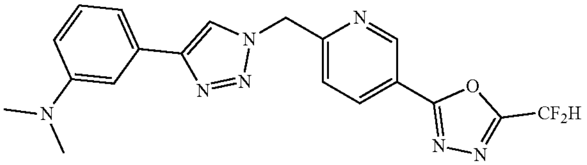 [SMILES: CN(C)c1cccc(-c2cn(Cc3ccc(-c4nnc(C(F)F)o4)cn3)nn2)c1] |
| 37 | 3825 | 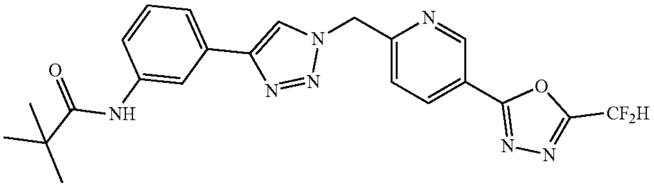 [SMILES: CC(C)(C)C(=O)Nc1cccc(-c2cn(Cc3ccc(-c4nnc(C(F)F)o4)cn3)nn2)c1] |
| 38 | 3826 | 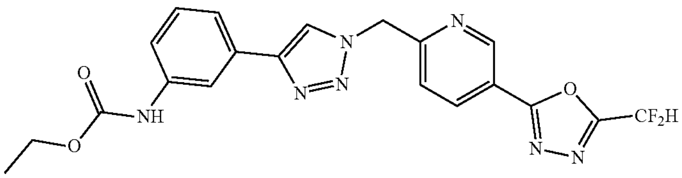 [SMILES: CCOC(=O)Nc1cccc(-c2cn(Cc3ccc(-c4nnc(C(F)F)o4)cn3)nn2)c1] |

-continued
| Example | Compound | Structure |
|---|---|---|
| 39 | 3827 | 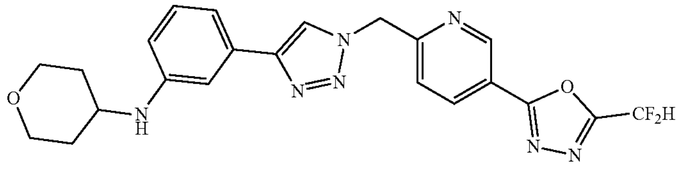 [SMILES: FC(F)c1nnc(-c2ccc(Cn3cc(-c4cccc(NC5CCOCC5)c4)nn3)nc2)o1] |
| 40 | 3828 | 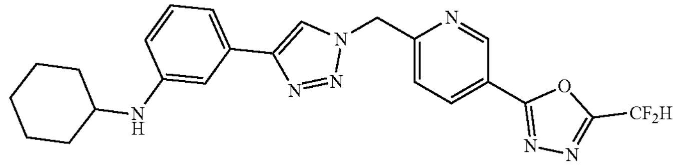 [SMILES: FC(F)c1nnc(-c2ccc(Cn3cc(-c4cccc(NC5CCCCC5)c4)nn3)nc2)o1] |
| 41 | 3829 | 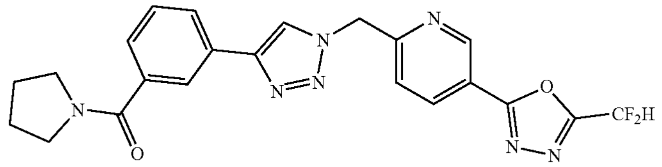 [SMILES: O=C(c1cccc(-c2cn(Cc3ccc(-c4nnc(C(F)F)o4)cn3)nn2)c1)N1CCCC1] |
| 42 | 3830 | 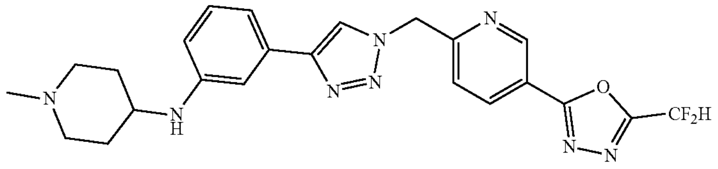 [SMILES: CN1CCC(Nc2cccc(-c3cn(Cc4ccc(-c5nnc(C(F)F)o5)cn4)nn3)c2)CC1] |
| 43 | 3831 | 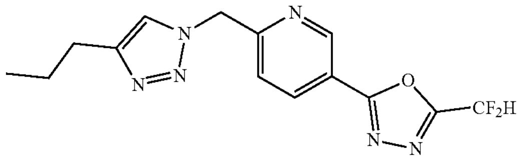 [SMILES: CCCc1cn(Cc2ccc(-c3nnc(C(F)F)o3)cn2)nn1] |
| 44 | 3832 | 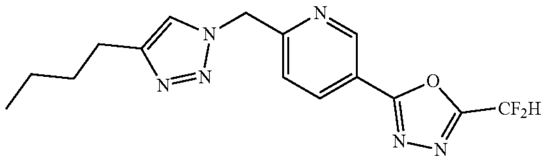 [SMILES: CCCCc1cn(Cc2ccc(-c3nnc(C(F)F)o3)cn2)nn1] |
| 45 | 3833 | 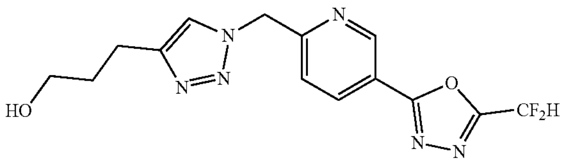 [SMILES: OCCCc1cn(Cc2ccc(-c3nnc(C(F)F)o3)cn2)nn1] |
| 46 | 3834 | 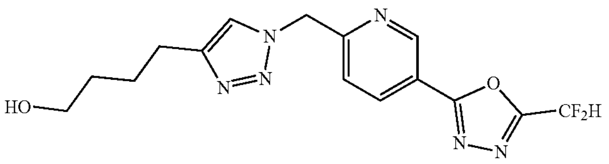 [SMILES: OCCCCc1cn(Cc2ccc(-c3nnc(C(F)F)o3)cn2)nn1] |
| 47 | 3835 | 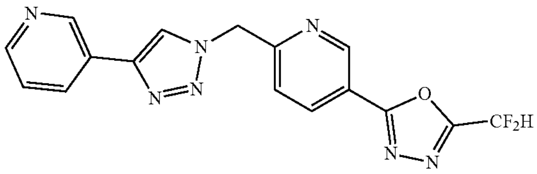 [SMILES: FC(F)c1nnc(-c2ccc(Cn3cc(-c4cccnc4)nn3)nc2)o1] |

-continued
| Example | Compound | Structure |
| --- | --- | --- |
| 48 | 3837 | 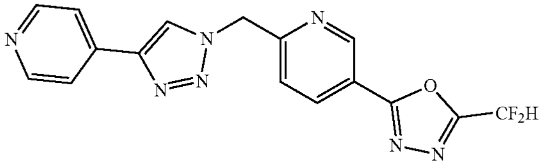 [SMILES: FC(F)c1nnc(-c2ccc(Cn3cc(-c4ccncc4)nn3)nc2)o1] |
| 49 | 3838 | 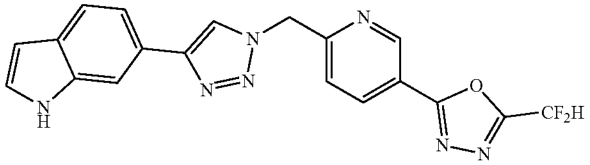 |
| 50 | 3839 | 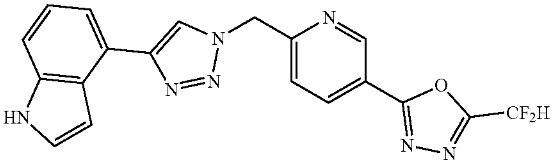 [SMILES: FC(F)c1nnc(-c2ccc(Cn3cc(-c4cccc5[nH]ccc45)nn3)nc2)o1] |
| 51 | 3840 | 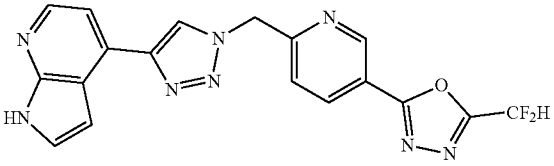 [SMILES: FC(F)c1nnc(-c2ccc(Cn3cc(-c4ccnc5[nH]ccc45)nn3)nc2)o1] |
| 52 | 3841 | 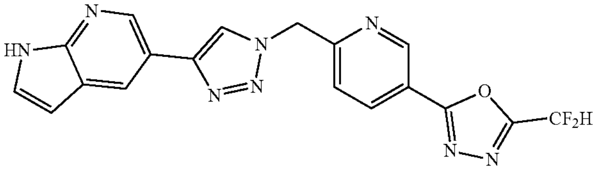 [SMILES: FC(F)c1nnc(-c2ccc(Cn3cc(-c4cnc5[nH]ccc5c4)nn3)nc2)o1] |
| 53 | 3842 | 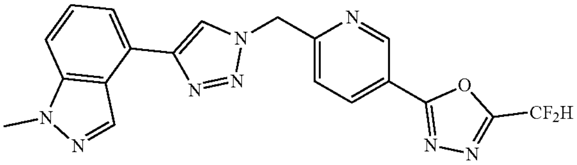 [SMILES: Cn1ncc2c(-c3cn(Cc4ccc(-c5nnc(C(F)F)o5)cn4)nn3)cccc21] |
| 54 | 3843 | 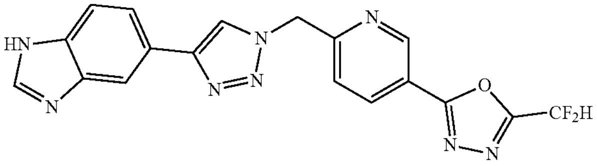 [SMILES: FC(F)c1nnc(-c2ccc(Cn3cc(-c4ccc5[nH]cnc5c4)nn3)nc2)o1] |
| 55 | 3844 | 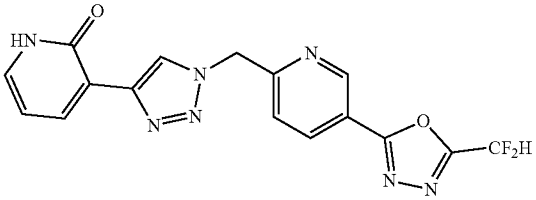 [SMILES: O=c1[nH]cccc1-c1cn(Cc2ccc(-c3nnc(C(F)F)o3)cn2)nn1] |

-continued
| Example | Compound | Structure |
|---|---|---|
| 56 | 3845 | 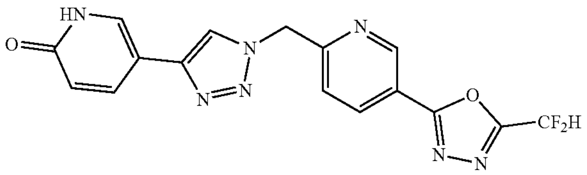 [SMILES: O=c1ccc(-c2cn(Cc3ccc(-c4nnc(C(F)F)o4)cn3)nn2)c[nH]1] |
| 57 | 3846 | 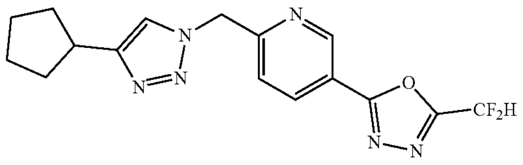 [SMILES: FC(F)c1nnc(-c2ccc(Cn3cc(C4CCCC4)nn3)nc2)o1] |
| 59 | 3854 | 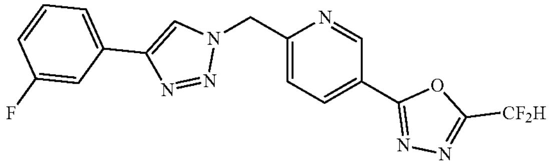 [SMILES: Fc1cccc(-c2cn(Cc3ccc(-c4nnc(C(F)F)o4)cn3)nn2)c1] |
| 60 | 3855 | 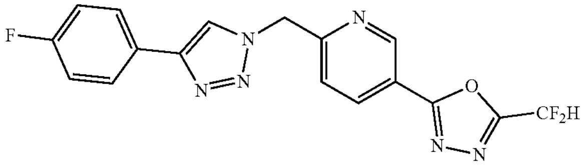 [SMILES: Fc1ccc(-c2cn(Cc3ccc(-c4nnc(C(F)F)o4)cn3)nn2)cc1] |
| 61 | 3856 | 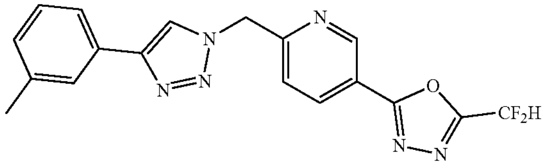 [SMILES: Cc1cccc(-c2cn(Cc3ccc(-c4nnc(C(F)F)o4)cn3)nn2)c1] |
| 62 | 3860 | 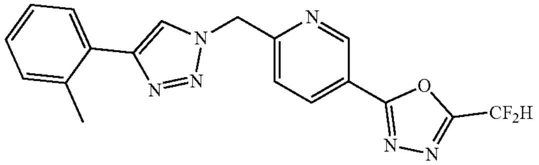 [SMILES: Cc1ccccc1-c1cn(Cc2ccc(-c3nnc(C(F)F)o3)cn2)nn1] |
| 63 | 3861 | 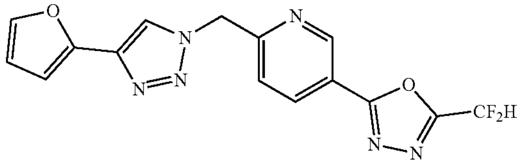 [SMILES: FC(F)c1nnc(-c2ccc(Cn3cc(-c4ccco4)nn3)nc2)o1] |
| 64 | 3866 | 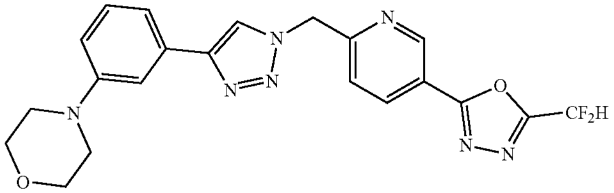 [SMILES: FC(F)c1nnc(-c2ccc(Cn3cc(-c4cccc(N5CCOCC5)c4)nn3)nc2)o1] |

-continued
| Example | Compound | Structure |
|---|---|---|
| 65 | 3867 | 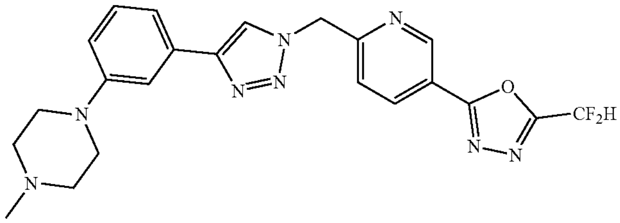 [SMILES: CN1CCN(c2cccc(-c3cn(Cc4ccc(-c5nnc(C(F)F)o5)cn4)nn3)c2)CC1] |
| 66 | 3879 | 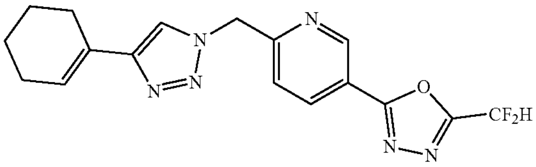 [SMILES: FC(F)c1nnc(-c2ccc(Cn3cc(C4=CCCCC4)nn3)nc2)o1] |
| 67 | 3880 | 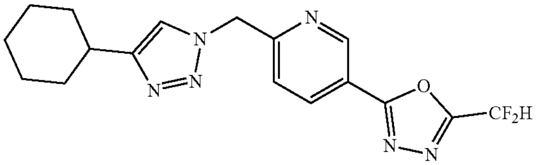 [SMILES: FC(F)c1nnc(-c2ccc(Cn3cc(C4CCCCC4)nn3)nc2)o1] |
| 68 | 3881 | 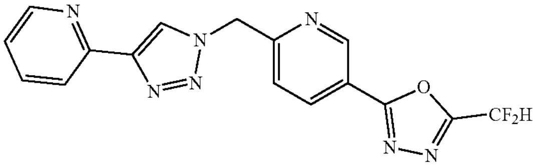 [SMILES: FC(F)c1nnc(-c2ccc(Cn3cc(-c4ccccn4)nn3)nc2)o1] |
| 69 | 3882 | 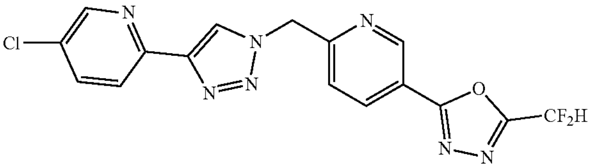 [SMILES: FC(F)c1nnc(-c2ccc(Cn3cc(-c4ccc(Cl)cn4)nn3)nc2)o1] |
| 70 | 3883 | 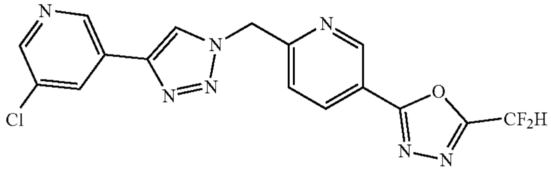 [SMILES: FC(F)c1nnc(-c2ccc(Cn3cc(-c4cncc(Cl)c4)nn3)nc2)o1] |
| 71 | 3884 | 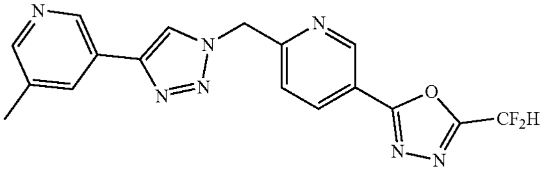 [SMILES: Cc1cncc(-c2cn(Cc3ccc(-c4nnc(C(F)F)o4)cn3)nn2)c1] |
| 72 | 3885 | 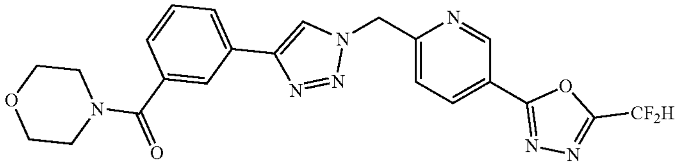 [SMILES: O=C(c1cccc(-c2cn(Cc3ccc(-c4nnc(C(F)F)o4)cn3)nn2)c1)N1CCOCC1] |

-continued
| Example | Compound | Structure |
|---|---|---|
| 73 | 3886 | 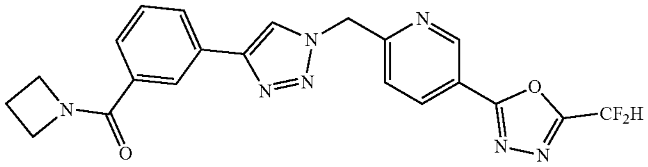 [SMILES: O=C(c1cccc(-c2cn(Cc3ccc(-c4nnc(C(F)F)o4)cn3)nn2)c1)N1CCC1] |
| 74 | 3887 | 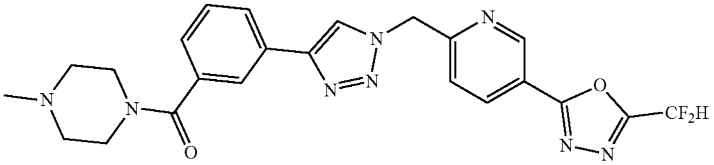 [SMILES: CN1CCN(C(=O)c2cccc(-c3cn(Cc4ccc(-c5nnc(C(F)F)o5)cn4)nn3)c2)CC1] |
| 75 | 3889 | 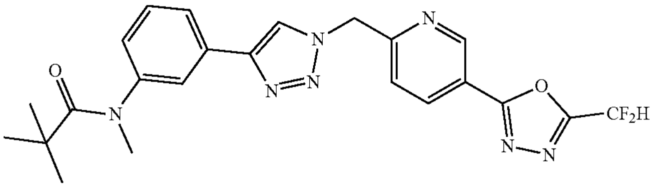 [SMILES: CN(C(=O)C(C)(C)C)c1cccc(-c2cn(Cc3ccc(-c4nnc(C(F)F)o4)cn3)nn2)c1] |
| 76 | 3890 | 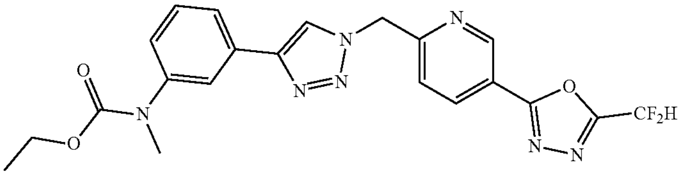 [SMILES: CCOC(=O)N(C)c1cccc(-c2cn(Cc3ccc(-c4nnc(C(F)F)o4)cn3)nn2)c1] |
| 77 | 3891 | 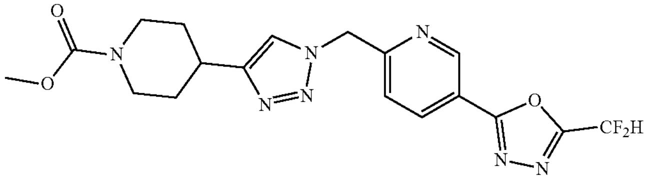 [SMILES: COC(=O)N1CCC(c2cn(Cc3ccc(-c4nnc(C(F)F)o4)cn3)nn2)CC1] |
| 78 | 3892 | 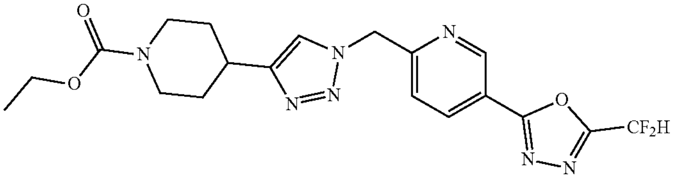 [SMILES: CCOC(=O)N1CCC(c2cn(Cc3ccc(-c4nnc(C(F)F)o4)cn3)nn2)CC1] |
| 79 | 3893 | 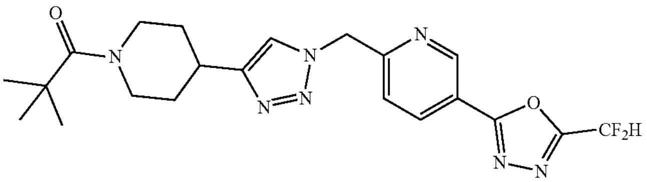 [SMILES: CC(C)(C)C(=O)N1CCC(c2cn(Cc3ccc(-c4nnc(C(F)F)o4)cn3)nn2)CC1] |
| 80 | 3894 | 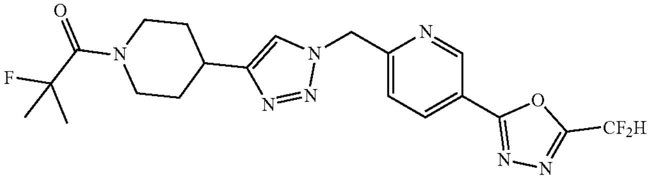 [SMILES: CC(C)(F)C(=O)N1CCC(c2cn(Cc3ccc(-c4nnc(C(F)F)o4)cn3)nn2)CC1] |

-continued
| Example | Compound | Structure |
|---|---|---|
| 81 | 3895 | 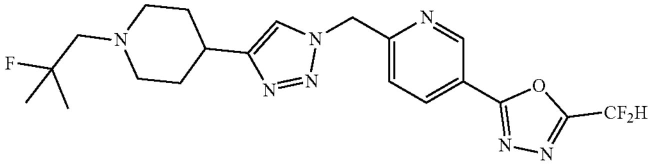 [SMILES: CC(C)(F)CN1CCC(c2cn(Cc3ccc(-c4nnc(C(F)F)o4)cn3)nn2)CC1] |
| 82 | 3896 | 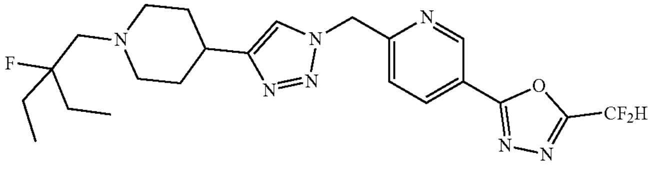 [SMILES: CCC(F)(CC)CN1CCC(c2cn(Cc3ccc(-c4nnc(C(F)F)o4)cn3)nn2)CC1] |
| 83 | 3902 | 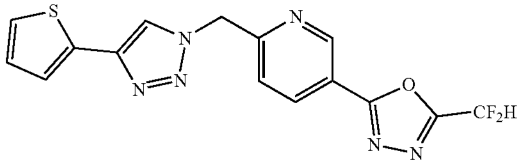 |
| 84 | 3914 | 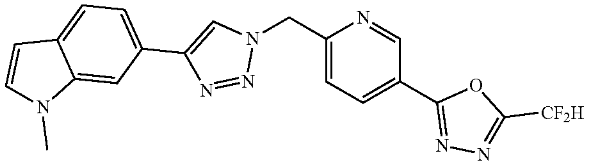 [SMILES: Cn1ccc2ccc(-c3cn(Cc4ccc(-c5nnc(C(F)F)o5)cn4)nn3)cc21] |
| 85 | 3915 | 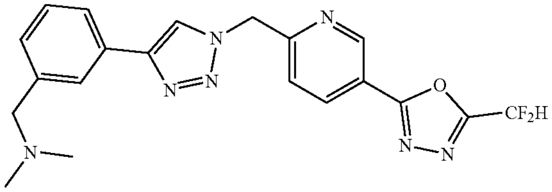 [SMILES: CN(C)Cc1cccc(-c2cn(Cc3ccc(-c4nnc(C(F)F)o4)cn3)nn2)c1] |
| 86 | 3916 | 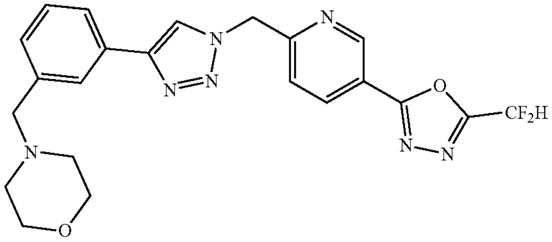 [SMILES: FC(F)c1nnc(-c2ccc(Cn3cc(-c4cccc(CN5CCOCC5)c4)nn3)nc2)o1] |
| 87 | 3917 | 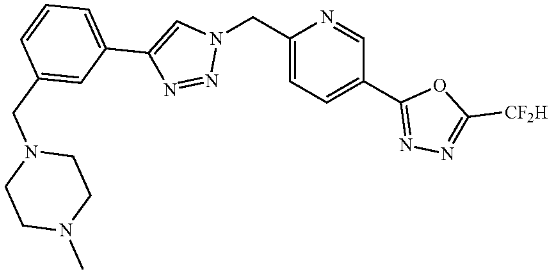 [SMILES: CN1CCN(Cc2cccc(-c3cn(Cc4ccc(-c5nnc(C(F)F)o5)cn4)nn3)c2)CC1] |

-continued
| Example | Compound | Structure |
|---|---|---|
| 88 | 3918 | 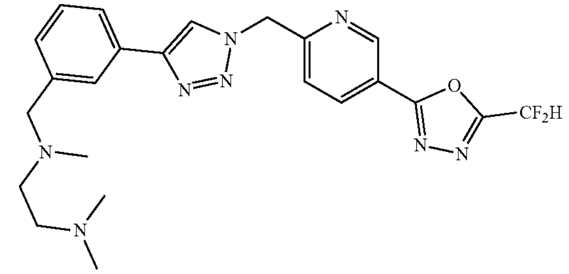 [SMILES: CN(C)CCN(C)Cc1cccc(-c2cn(Cc3ccc(-c4nnc(C(F)F)o4)cn3)nn2)c1] |
| 89 | 3919 | 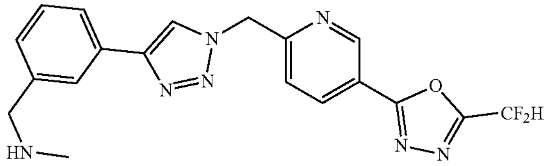 [SMILES: CNCc1cccc(-c2cn(Cc3ccc(-c4nnc(C(F)F)o4)cn3)nn2)c1] |
| 90 | 3925 | 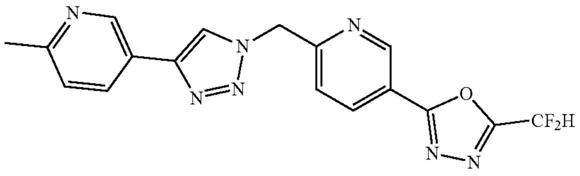 [SMILES: Cc1ccc(-c2cn(Cc3ccc(-c4nnc(C(F)F)o4)cn3)nn2)cn1] |
| 91 | 3926 | 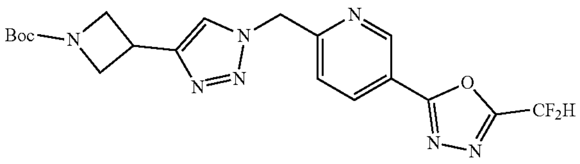 [SMILES: CC(C)(C)OC(=O)N1CC(c2cn(Cc3ccc(-c4nnc(C(F)F)o4)cn3)nn2)C1] |
| 92 | 3944 | 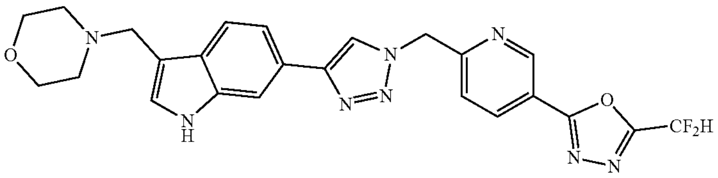 [SMILES: FC(F)c1nnc(-c2ccc(Cn3cc(-c4ccc5c(CN6CCOCC6)c[nH]c5c4)nn3)nc2)o1] |
| 93 | 3945 | 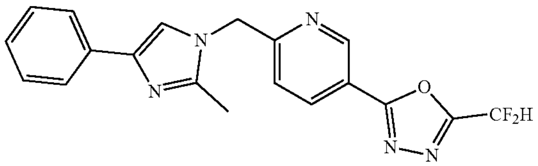 [SMILES: Cc1nc(-c2ccccc2)cn1Cc1ccc(-c2nnc(C(F)F)o2)cn1] |
| 94 | 3949 | 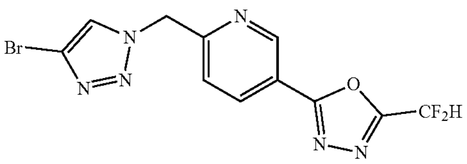 [SMILES: FC(F)c1nnc(-c2ccc(Cn3cc(Br)nn3)nc2)o1] |
| 96 | 3951 | 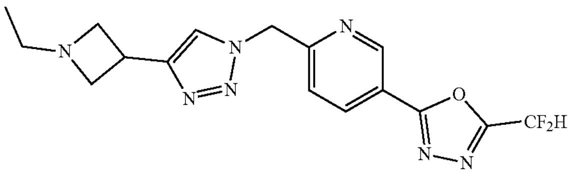 [SMILES: CCN1CC(c2cn(Cc3ccc(-c4nnc(C(F)F)o4)cn3)nn2)C1] |

-continued
| Example | Compound | Structure |
|---|---|---|
| 97 | 3952 | 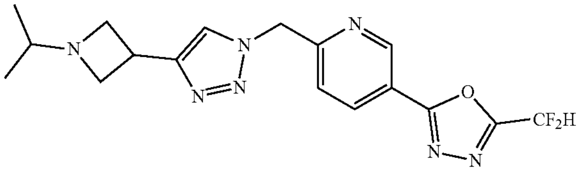 [SMILES: CC(C)N1CC(c2cn(Cc3ccc(-c4nnc(C(F)F)o4)cn3)nn2)C1] |
| 98 | 3953 | 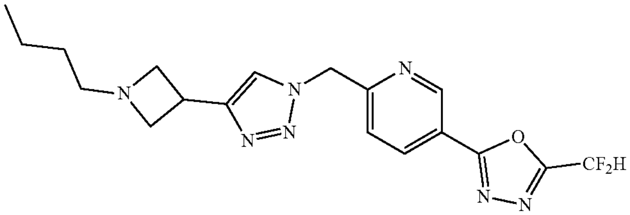 [SMILES: CCCCN1CC(c2cn(Cc3ccc(-c4nnc(C(F)F)o4)cn3)nn2)C1] |
| 99 | 3954 | 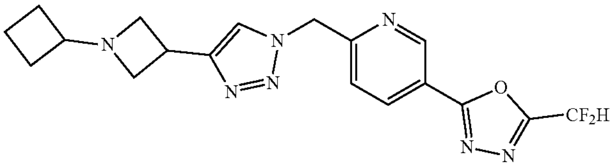 [SMILES: FC(F)c1nnc(-c2ccc(Cn3cc(C4CN(C5CCC5)C4)nn3)nc2)o1] |
| 100 | 3955 | 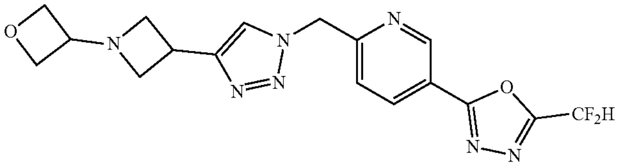 [SMILES: FC(F)c1nnc(-c2ccc(Cn3cc(C4CN(C5COC5)C4)nn3)nc2)o1] |
| 101 | 3956 | 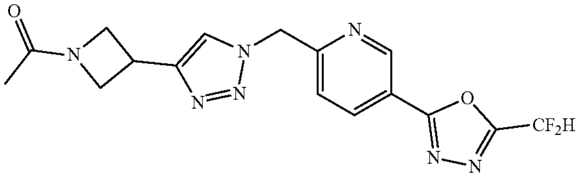 [SMILES: CC(=O)N1CC(c2cn(Cc3ccc(-c4nnc(C(F)F)o4)cn3)nn2)C1] |
| 102 | 3957 | 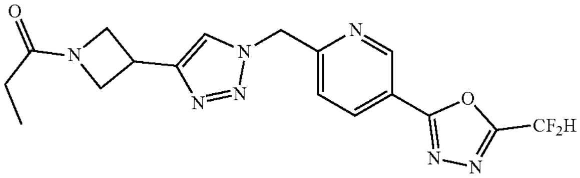 [SMILES: CCC(=O)N1CC(c2cn(Cc3ccc(-c4nnc(C(F)F)o4)cn3)nn2)C1] |
| 103 | 3958 | 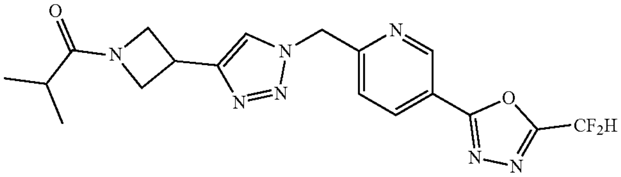 [SMILES: CC(C)C(=O)N1CC(c2cn(Cc3ccc(-c4nnc(C(F)F)o4)cn3)nn2)C1] |
| 104 | 3959 | 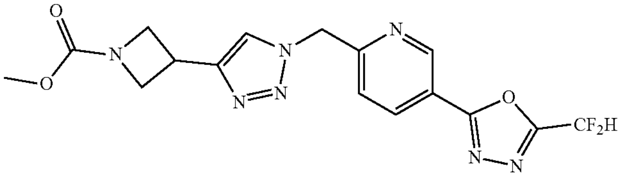 [SMILES: COC(=O)N1CC(c2cn(Cc3ccc(-c4nnc(C(F)F)o4)cn3)nn2)C1] |

-continued
| Example | Compound | Structure |
|---|---|---|
| 105 | 3960 | 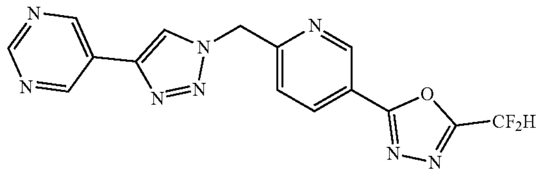 |
| 106 | 3961 | 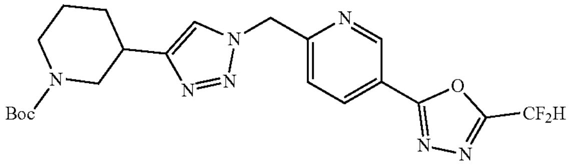 [SMILES: CC(C)(C)OC(=O)N1CCCC(c2cn(Cc3ccc(-c4nnc(C(F)F)o4)cn3)nn2)C1] |
| 107 | 3962 | 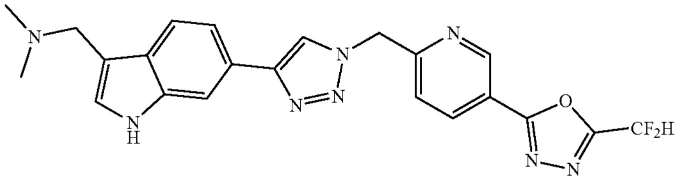 [SMILES: CN(C)Cc1c[nH]c2cc(-c3cn(Cc4ccc(-c5nnc(C(F)F)o5)cn4)nn3)ccc12] |
| 108 | 3963 | 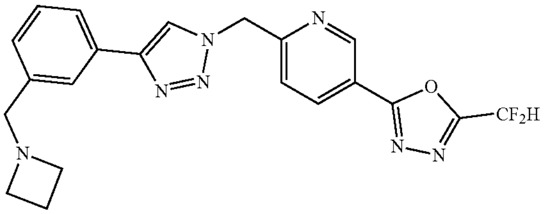 [SMILES: FC(F)c1nnc(-c2ccc(Cn3cc(-c4cccc(CN5CCC5)c4)nn3)nc2)o1] |
| 109 | 3964 | 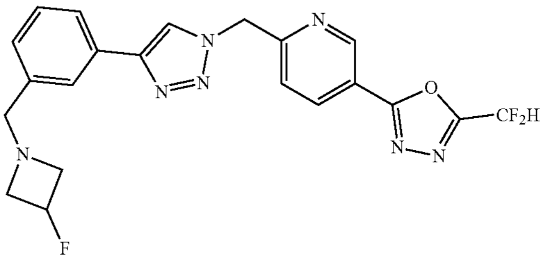 [SMILES: FC1CN(Cc2cccc(-c3cn(Cc4ccc(-c5nnc(C(F)F)o5)cn4)nn3)c2)C1] |
| 110 | 3965 | 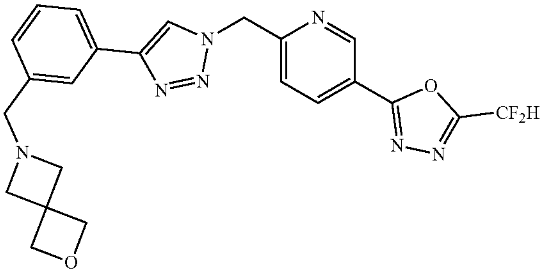 [SMILES: FC(F)c1nnc(-c2ccc(Cn3cc(-c4cccc(CN5CC6(COC6)C5)c4)nn3)nc2)o1] |
| 111 | 3966 | 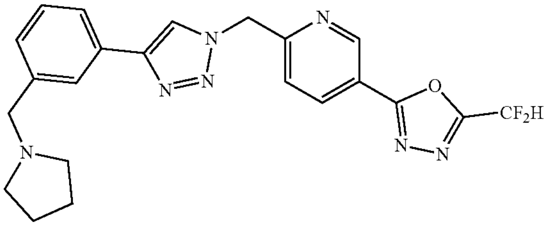 [SMILES: FC(F)c1nnc(-c2ccc(Cn3cc(-c4cccc(CN5CCCC5)c4)nn3)nc2)o1] |

-continued
| Example | Compound | Structure |
|---|---|---|
| 112 | 3980 | 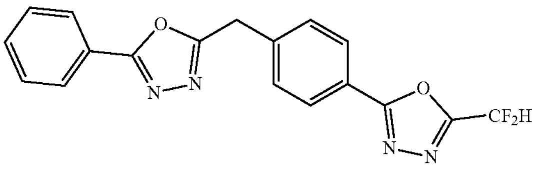 [SMILES: FC(F)c1nnc(-c2ccc(Cc3nnc(-c4ccccc4)o3)cc2)o1] |
| 113 | 3981 | 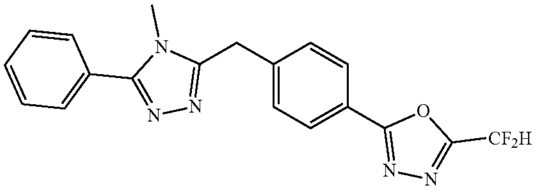 [SMILES: Cn1c(Cc2ccc(-c3nnc(C(F)F)o3)cc2)nnc1-c1ccccc1] |
| 114 | 3985 | 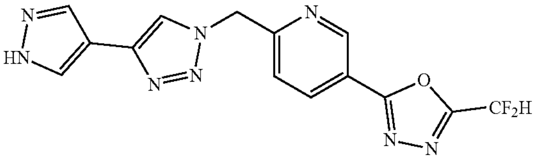 [SMILES: FC(F)c1nnc(-c2ccc(Cn3cc(-c4cn[nH]c4)nn3)nc2)o1] |
| 115 | 3986 | 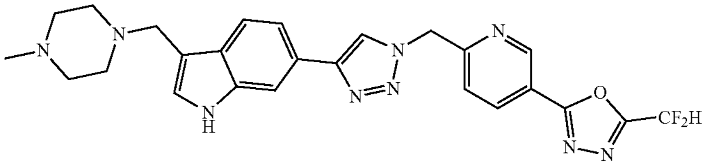 [SMILES: CN1CCN(Cc2c[nH]c3cc(-c4cn(Cc5ccc(-c6nnc(C(F)F)o6)cn5)nn4)ccc23)CC1] |
| 116 | 3987 | 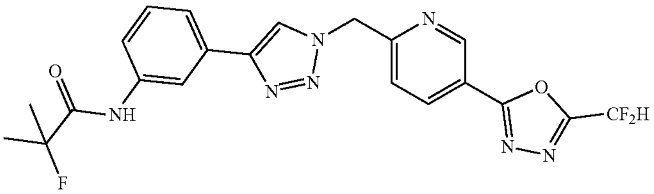 [SMILES: CC(C)(F)C(=O)Nc1cccc(-c2cn(Cc3ccc(-c4nnc(C(F)F)o4)cn3)nn2)c1] |
| 117 | 3988 | 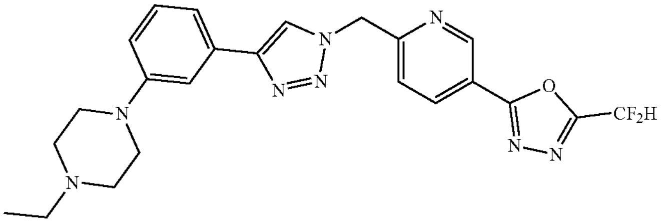 [SMILES: CCN1CCN(c2cccc(-c3cn(Cc4ccc(-c5nnc(C(F)F)o5)cn4)nn3)c2)CC1] |
| 118 | 3989 | 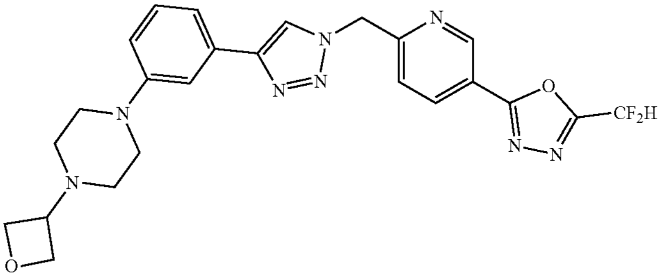 [SMILES: FC(F)c1nnc(-c2ccc(Cn3cc(-c4cccc(N5CCN(C6COC6)CC5)c4)nn3)nc2)o1] |

-continued
| Example | Compound | Structure |
| --- | --- | --- |
| 119 | 3990 | 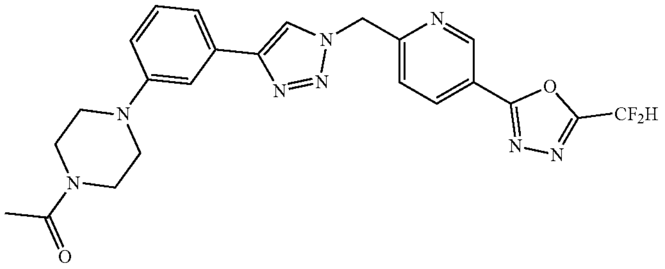 [SMILES: CC(=O)N1CCN(c2cccc(-c3cn(Cc4ccc(-c5nnc(C(F)F)o5)cn4)nn3)c2)CC1] |
| 120 | 3991 | 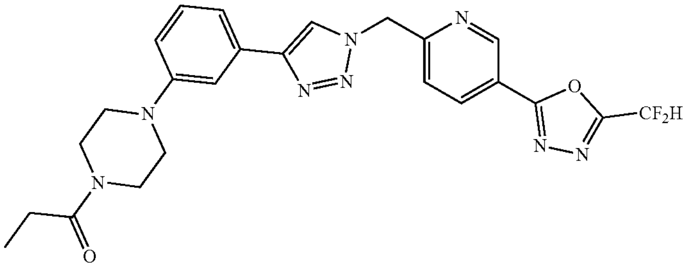 [SMILES: CCC(=O)N1CCN(c2cccc(-c3cn(Cc4ccc(-c5nnc(C(F)F)o5)cn4)nn3)c2)CC1] |
| 121 | 3999 | 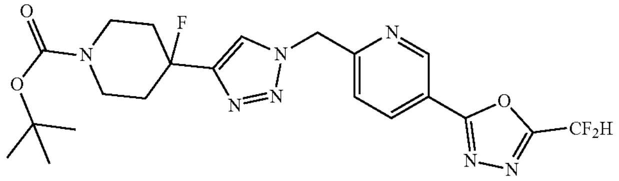 [SMILES: CC(C)(C)OC(=O)N1CCC(F)(c2cn(Cc3ccc(-c4nnc(C(F)F)o4)cn3)nn2)CC1] |
| 122 | 4000 | 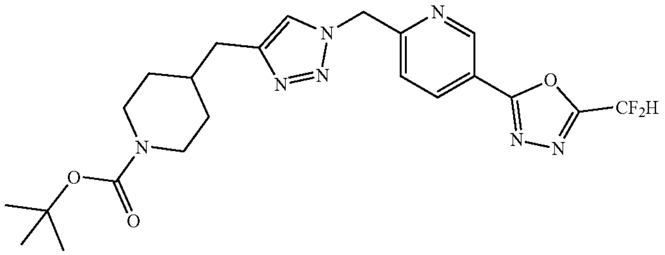 [SMILES: CC(C)(C)OC(=O)N1CCC(Cc2cn(Cc3ccc(-c4nnc(C(F)F)o4)cn3)nn2)CC1] |
| 123 | 4001 | 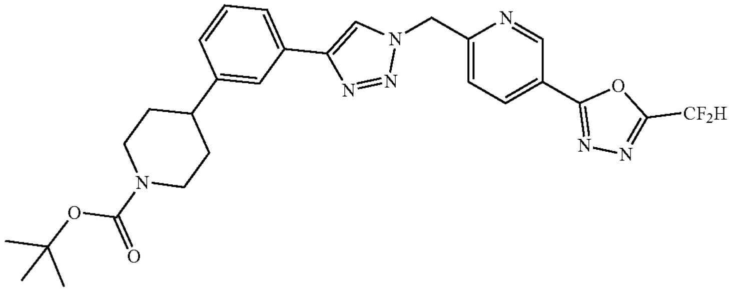 [SMILES: CC(C)(C)OC(=O)N1CCC(c2cccc(-c3cn(Cc4ccc(-c5nnc(C(F)F)o5)cn4)nn3)c2)CC1] |
| 124 | 4002 | 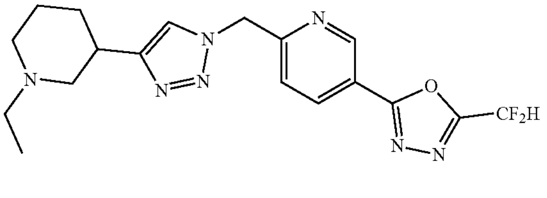 [SMILES: CCN1CCCC(c2cn(Cc3ccc(-c4nnc(C(F)F)o4)cn3)nn2)C1] |

-continued
| Example | Compound | Structure |
| --- | --- | --- |
| 125 | 4003 | 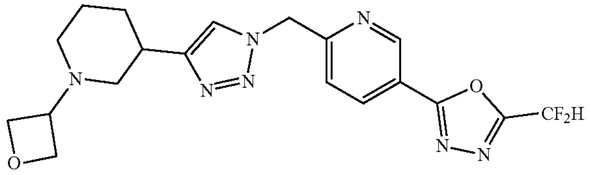 [SMILES: FC(F)c1nnc(-c2ccc(Cn3cc(C4CCCN(C5COC5)C4)nn3)nc2)o1] |
| 126 | 4004 | 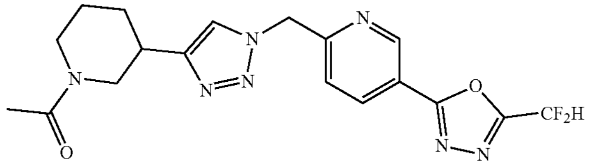 [SMILES: CC(=O)N1CCCC(c2cn(Cc3ccc(-c4nnc(C(F)F)o4)cn3)nn2)C1] |
| 127 | 4005 | 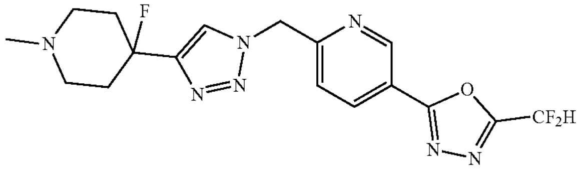 [SMILES: CN1CCC(F)(c2cn(Cc3ccc(-c4nnc(C(F)F)o4)cn3)nn2)CC1] |
| 128 | 4006 | 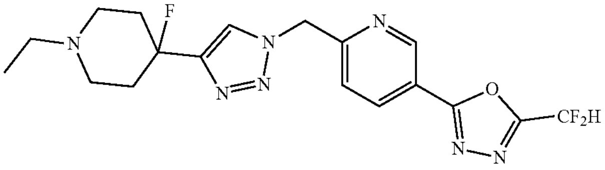 [SMILES: CCN1CCC(F)(c2cn(Cc3ccc(-c4nnc(C(F)F)o4)cn3)nn2)CC1] |
| 129 | 4007 | 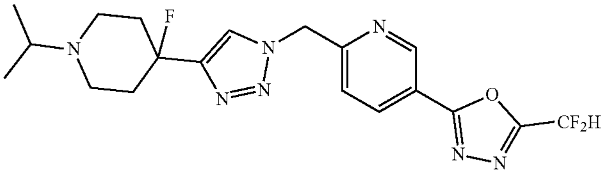 [SMILES: CC(C)N1CCC(F)(c2cn(Cc3ccc(-c4nnc(C(F)F)o4)cn3)nn2)CC1] |
| 130 | 4008 | 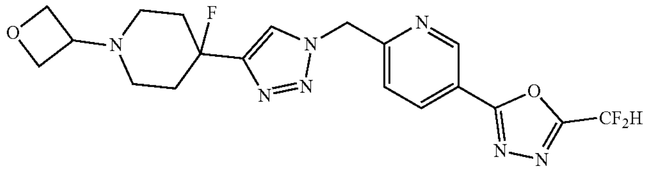 [SMILES: FC(F)c1nnc(-c2ccc(Cn3cc(C4(F)CCN(C5COC5)CC4)nn3)nc2)o1] |
| 131 | 4009 | 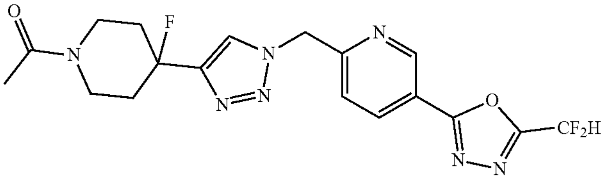 [SMILES: CC(=O)N1CCC(F)(c2cn(Cc3ccc(-c4nnc(C(F)F)o4)cn3)nn2)CC1] |
| 132 | 4010 | 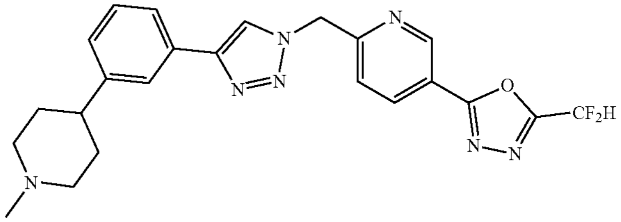 [SMILES: CN1CCC(c2cccc(-c3cn(Cc4ccc(-c5nnc(C(F)F)o5)cn4)nn3)c2)CC1] |

-continued
| Example | Compound | Structure |
| --- | --- | --- |
| 133 | 4011 | 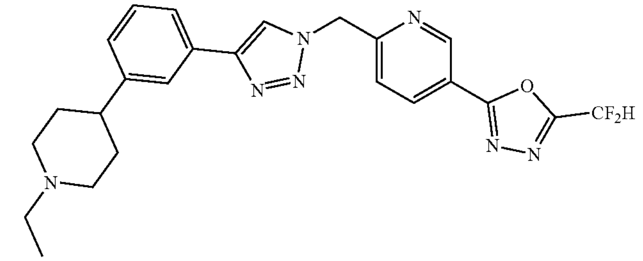 [SMILES: CCN1CCC(c2cccc(-c3cn(Cc4ccc(-c5nnc(C(F)F)o5)cn4)nn3)c2)CC1] |
| 134 | 4012 | 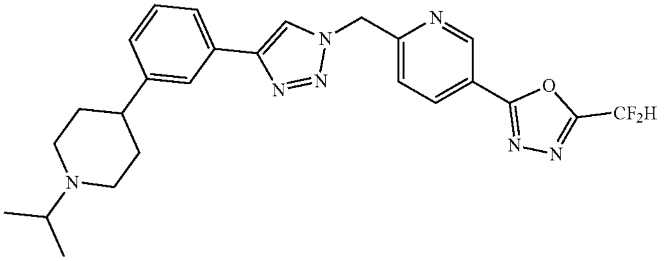 |
| 135 | 4013 | 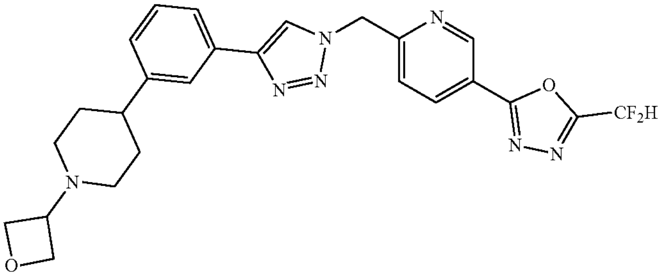 [SMILES: FC(F)c1nnc(-c2ccc(Cn3cc(-c4cccc(C5CCN(C6COC6)CC5)c4)nn3)nc2)o1] |
| 136 | 4014 | 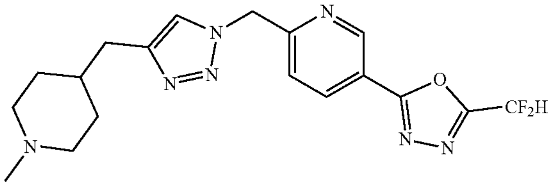 [SMILES: CN1CCC(Cc2cn(Cc3ccc(-c4nnc(C(F)F)o4)cn3)nn2)CC1] |
| 137 | 4015 | 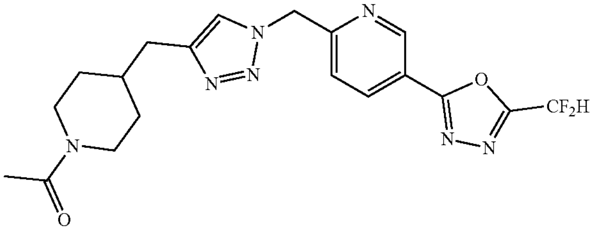 [SMILES: CC(=O)N1CCC(Cc2cn(Cc3ccc(-c4nnc(C(F)F)o4)cn3)nn2)CC1] |
| 138 | 4023 | 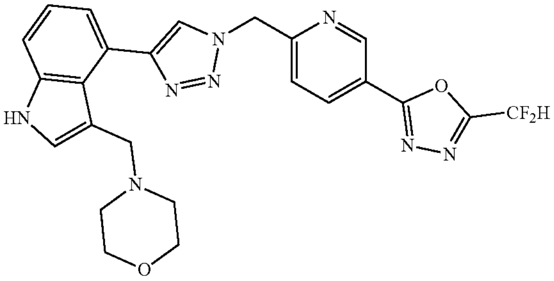 [SMILES: FC(F)c1nnc(-c2ccc(Cn3cc(-c4cccc5[nH]cc(CN6CCOCC6)c45)nn3)nc2)o1] |

-continued
| Example | Compound | Structure |
|---|---|---|
| 139 | 4026 | 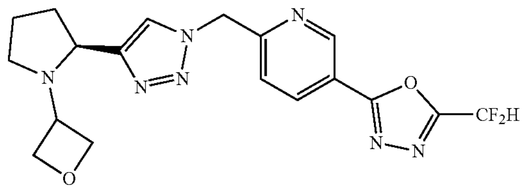 [SMILES: FC(F)c1nnc(-c2ccc(Cn3cc([C@@H]4CCCN4C4COC4)nn3)nc2)o1] |
| 140 | 4027 | 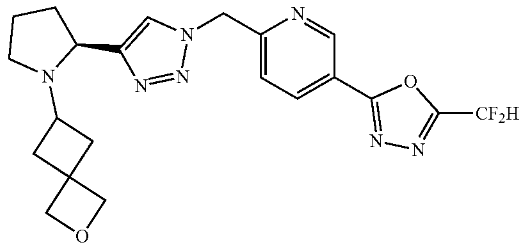 [SMILES: FC(F)c1nnc(-c2ccc(Cn3cc([C@@H]4CCCN4C4CC5(COC5)C4)nn3)nc2)o1] |
| 141 | 4028 | 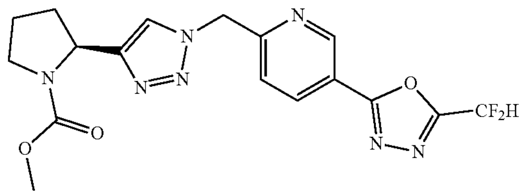 [SMILES: COC(=O)N1CCC[C@H]1c1cn(Cc2ccc(-c3nnc(C(F)F)o3)cn2)nn1] |
| 142 | 4029 | 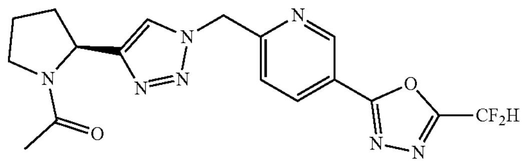 [SMILES: CC(=O)N1CCC[C@H]1c1cn(Cc2ccc(-c3nnc(C(F)F)o3)cn2)nn1] |
| 143 | 4051 | 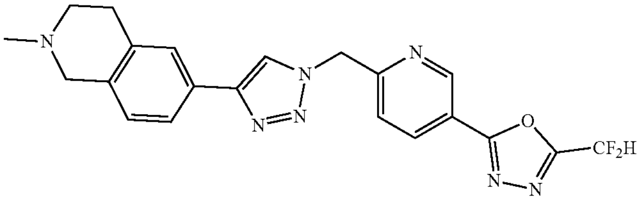 [SMILES: CN1CCc2cc(-c3cn(Cc4ccc(-c5nnc(C(F)F)o5)cn4)nn3)ccc2C1] |
| 144 | 4052 | 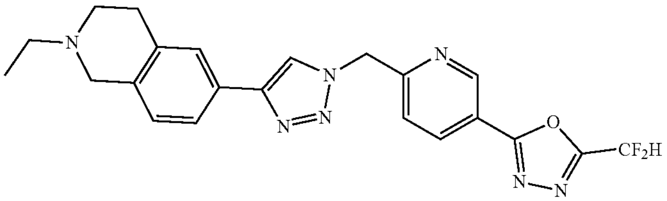 [SMILES: CCN1CCc2cc(-c3cn(Cc4ccc(-c5nnc(C(F)F)o5)cn4)nn3)ccc2C1] |
| 145 | 4053 | 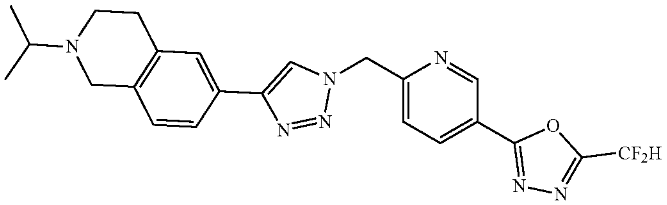 [SMILES: CC(C)N1CCc2cc(-c3cn(Cc4ccc(-c5nnc(C(F)F)o5)cn4)nn3)ccc2C1] |

-continued
| Example | Compound | Structure |
| --- | --- | --- |
| 146 | 4054 | 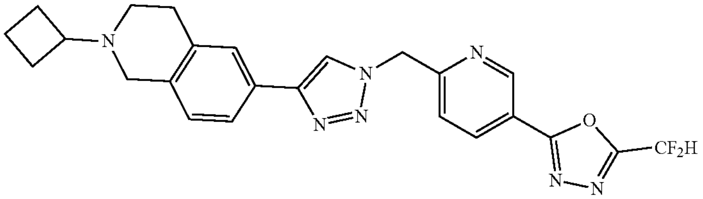 [SMILES: FC(F)c1nnc(-c2ccc(Cn3cc(-c4ccc5c(c4)CCN(C4CCC4)C5)nn3)nc2)o1] |
| 147 | 4055 | 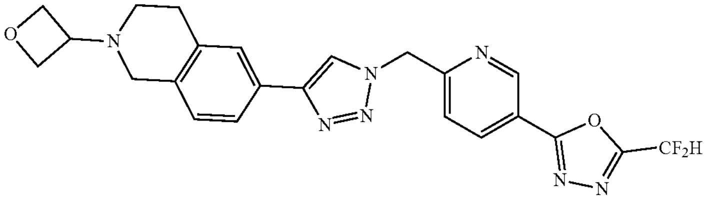 [SMILES: FC(F)c1nnc(-c2ccc(Cn3cc(-c4ccc5c(c4)CCN(C4COC4)C5)nn3)nc2)o1] |
| 148 | 4070 | 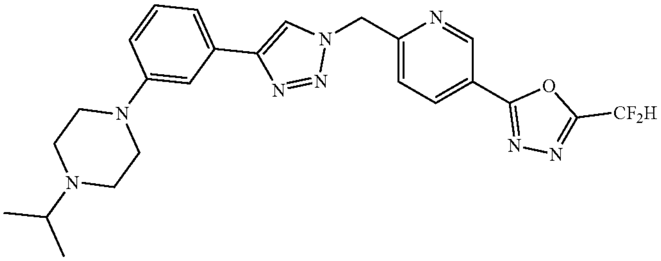 [SMILES: CC(C)N1CCN(c2cccc(-c3cn(Cc4ccc(-c5nnc(C(F)F)o5)cn4)nn3)c2)CC1] |
| 149 | 4071 | 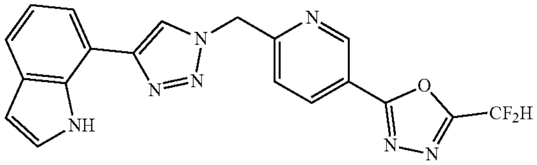 |
| 150 | 4072 | 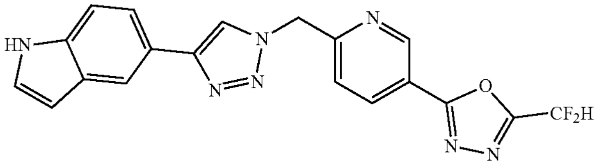 |
| 151 | 4073 | 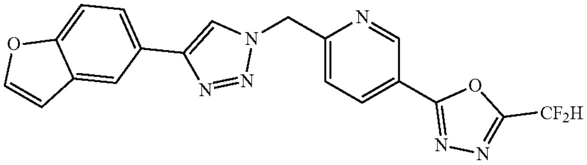 [SMILES: FC(F)c1nnc(-c2ccc(Cn3cc(-c4ccc5occc5c4)nn3)nc2)o1] |
| 152 | 4074 | 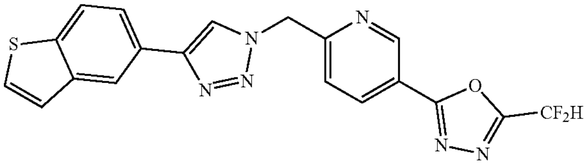 [SMILES: FC(F)c1nnc(-c2ccc(Cn3cc(-c4ccc5sccc5c4)nn3)nc2)o1] |
| 153 | 4075 | 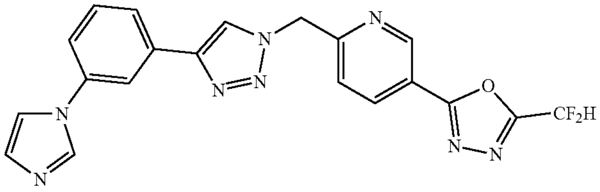 [SMILES: FC(F)c1nnc(-c2ccc(Cn3cc(-c4cccc(-n5ccnc5)c4)nn3)nc2)o1] |

-continued
| Example | Compound | Structure |
|---|---|---|
| 154 | 4076 | 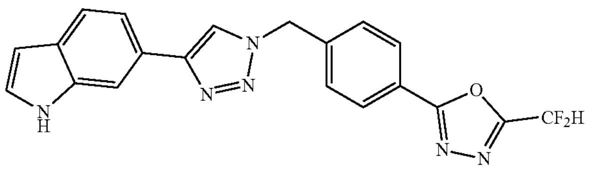 |
| 155 | 4077 | 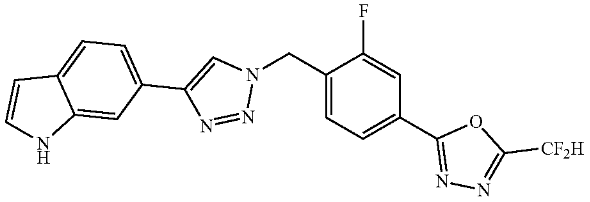 |
| 156 | 4078 | 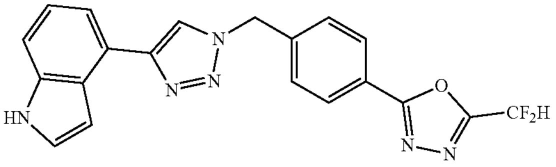 [SMILES: FC(F)c1nnc(-c2ccc(Cn3cc(-c4cccc5[nH]ccc45)nn3)cc2)o1] |
| 157 | 4079 | 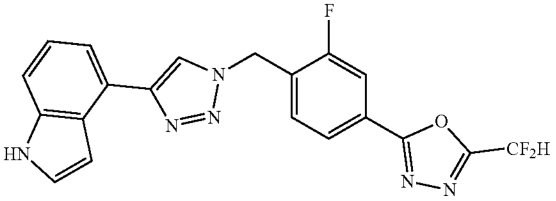 [SMILES: Fc1cc(-c2nnc(C(F)F)o2)ccc1Cn1cc(-c2cccc3[nH]ccc23)nn1] |
| 158 | 4080 | 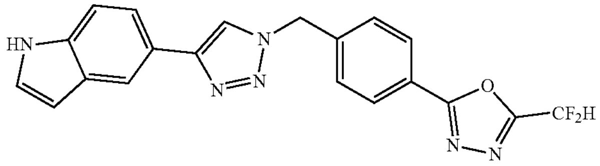 [SMILES: FC(F)c1nnc(-c2ccc(Cn3cc(-c4ccc5[nH]ccc5c4)nn3)cc2)o1] |
| 159 | 4081 | 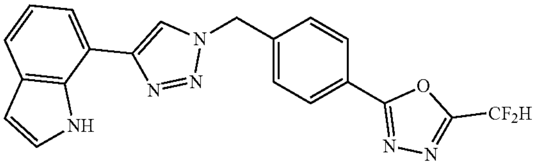 [SMILES: FC(F)c1nnc(-c2ccc(Cn3cc(-c4cccc5cc[nH]c45)nn3)cc2)o1] |
| 160 | 4082 | 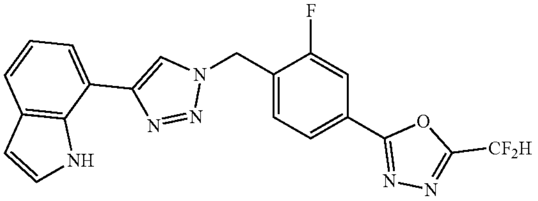 [SMILES: Fc1cc(-c2nnc(C(F)F)o2)ccc1Cn1cc(-c2cccc3cc[nH]c23)nn1] |
| 161 | 4104 | 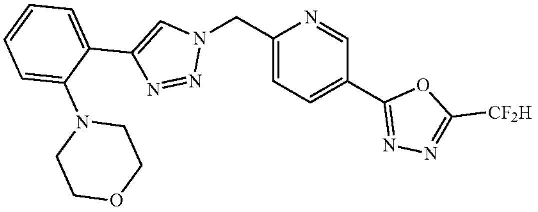 [SMILES: FC(F)c1nnc(-c2ccc(Cn3cc(-c4ccccc4N4CCOCC4)nn3)nc2)o1] |

-continued
| Example | Compound | Structure |
| --- | --- | --- |
| 162 | 4105 | 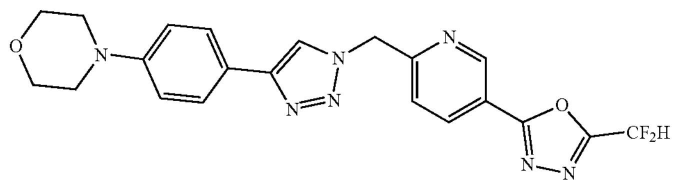 [SMILES: FC(F)c1nnc(-c2ccc(Cn3cc(-c4ccc(N5CCOCC5)cc4)nn3)nc2)o1] |
| 163 | 4106 | 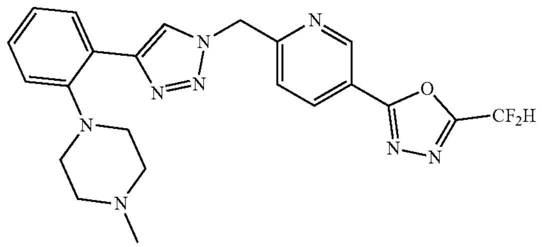 [SMILES: CN1CCN(c2ccccc2-c2cn(Cc3ccc(-c4nnc(C(F)F)o4)cn3)nn2)CC1] |
| 164 | 4107 | 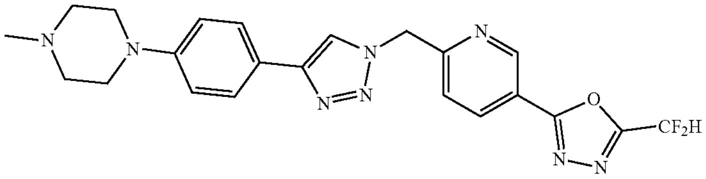 [SMILES: CN1CCN(c2ccc(-c3cn(Cc4ccc(-c5nnc(C(F)F)o5)cn4)nn3)cc2)CC1] |
| 165 | 4108 | 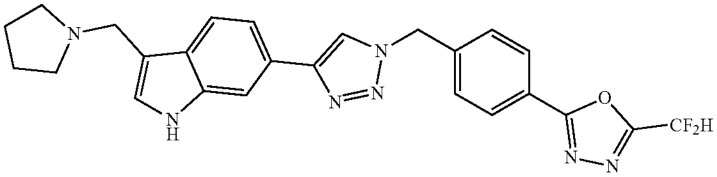 [SMILES: FC(F)c1nnc(-c2ccc(Cn3cc(-c4ccc5c(CN6CCCC6)c[nH]c5c4)nn3)cc2)o1] |
| 166 | 4109 | 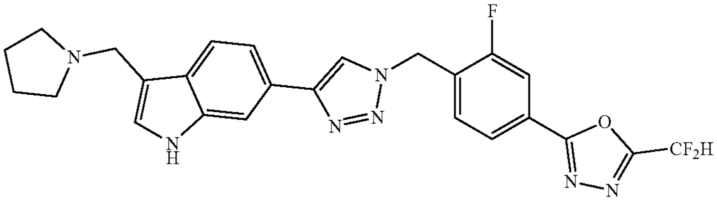 [SMILES: Fc1cc(-c2nnc(C(F)F)o2)ccc1Cn1cc(-c2ccc3c(CN4CCCC4)c[nH]c3c2)nn1] |
| 167 | 4110 | 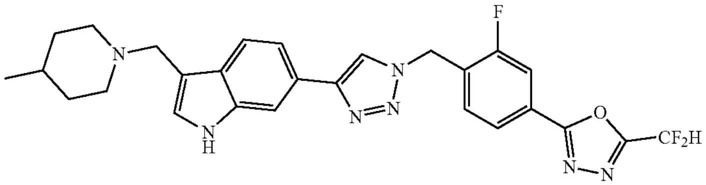 [SMILES: CC1CCN(Cc2c[nH]c3cc(-c4cn(Cc5ccc(-c6nnc(C(F)F)o6)cc5F)nn4)ccc23)CC1] |
| 168 | 4111 | 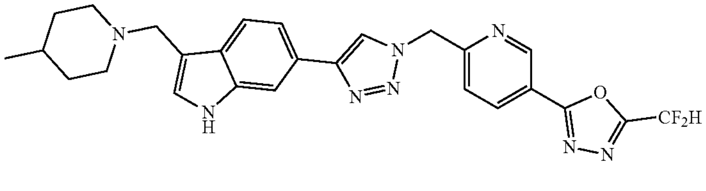 [SMILES: CC1CCN(Cc2c[nH]c3cc(-c4cn(Cc5ccc(-c6nnc(C(F)F)o6)cn5)nn4)ccc23)CC1] |

-continued
| Example | Compound | Structure |
| --- | --- | --- |
| 169 | 4112 | 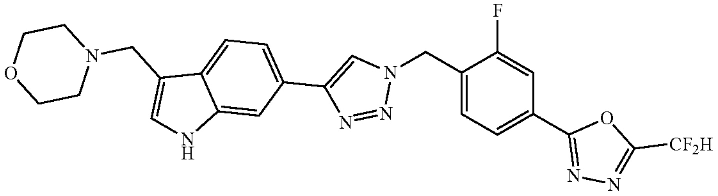 [SMILES: Fc1cc(-c2nnc(C(F)F)o2)ccc1Cn1cc(-c2ccc3c(CN4CCOCC4)c[nH]c3c2)nn1] |
| 170 | 4133 | 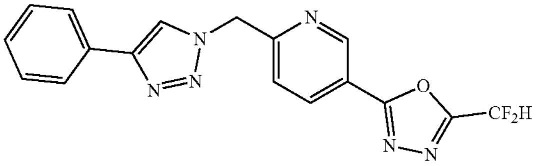 [SMILES: FC(F)c1nnc(-c2ccc(Cn3cc(-c4ccccc4)nn3)nc2)o1] |
| 171 | 4134 | 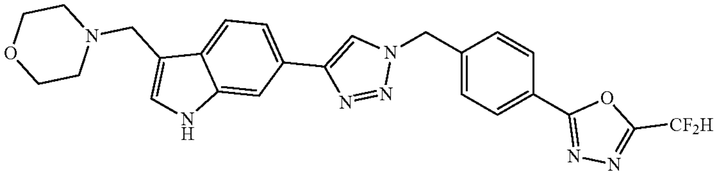 |
| 172 | 4135 | 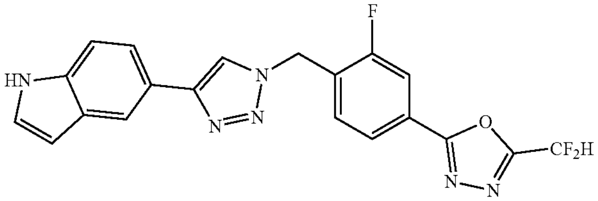 |
| 173 | 4136 | 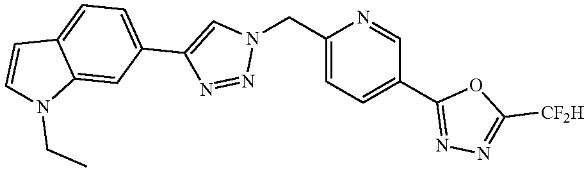 [SMILES: CCn1ccc2ccc(-c3cn(Cc4ccc(-c5nnc(C(F)F)o5)cn4)nn3)cc21] |
| 174 | 4178 | 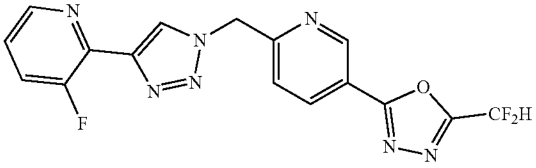 [SMILES: Fc1cccnc1-c1cn(Cc2ccc(-c3nnc(C(F)F)o3)cn2)nn1] |
| 175 | 4179 | 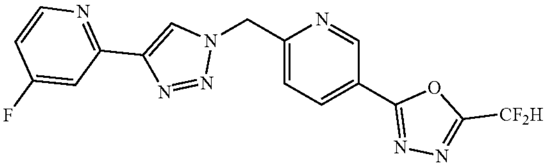 [SMILES: Fc1ccnc(-c2cn(Cc3ccc(-c4nnc(C(F)F)o4)cn3)nn2)c1] |
| 176 | 4180 | 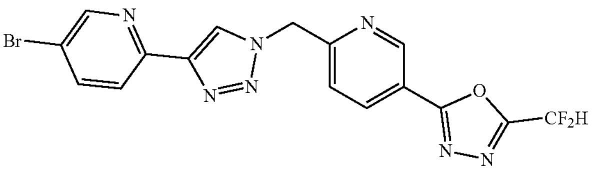 [SMILES: FC(F)c1nnc(-c2ccc(Cn3cc(-c4ccc(Br)cn4)nn3)nc2)o1] |

-continued
| Example | Compound | Structure |
|---|---|---|
| 177 | 4181 | 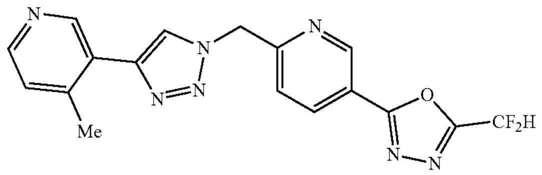 [SMILES: Cc1ccncc1-c1cn(Cc2ccc(-c3nnc(C(F)F)o3)cn2)nn1] |
| 178 | 4182 | 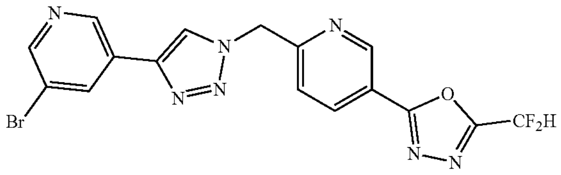 [SMILES: FC(F)c1nnc(-c2ccc(Cn3cc(-c4cncc(Br)c4)nn3)nc2)o1] |
| 179 | 4183 | 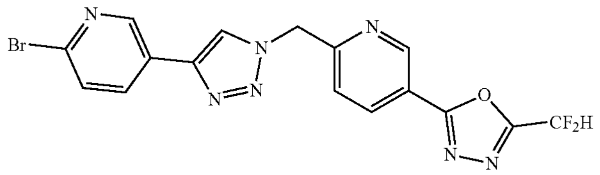 [SMILES: FC(F)c1nnc(-c2ccc(Cn3cc(-c4ccc(Br)nc4)nn3)nc2)o1] |
| 180 | 4184 | 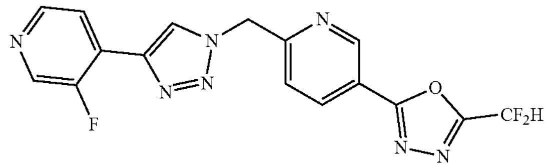 [SMILES: Fc1cnccc1-c1cn(Cc2ccc(-c3nnc(C(F)F)o3)cn2)nn1] |
| 181 | 4185 | 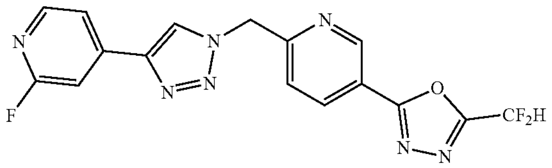 [SMILES: Fc1cc(-c2cn(Cc3ccc(-c4nnc(C(F)F)o4)cn3)nn2)ccn1] |
| 182 | 4186 | 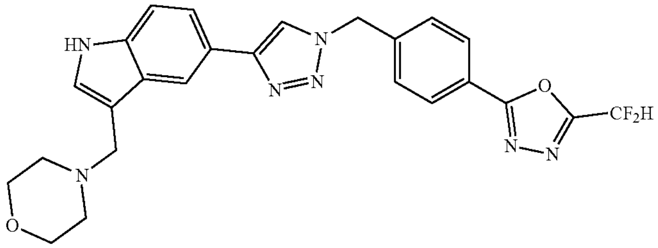 [SMILES: FC(F)c1nnc(-c2ccc(Cn3cc(-c4ccc5[nH]cc(CN6CCOCC6)c5c4)nn3)cc2)o1] |
| 183 | 4187 | 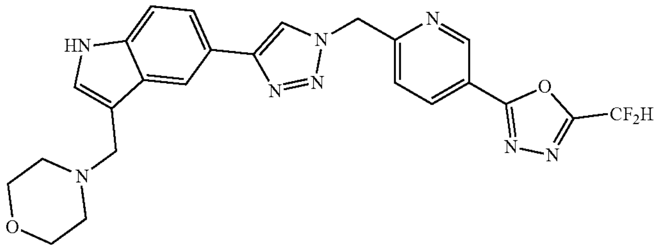 [SMILES: FC(F)c1nnc(-c2ccc(Cn3cc(-c4ccc5[nH]cc(CN6CCOCC6)c5c4)nn3)nc2)o1] |
| 184 | 4208 | 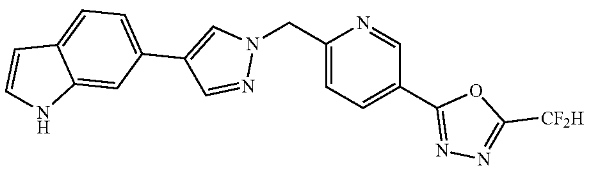 [SMILES: FC(F)c1nnc(-c2ccc(Cn3cc(-c4ccc5cc[nH]c5c4)cn3)nc2)o1] |

-continued
| Example | Compound | Structure |
|---|---|---|
| 185 | 4209 | 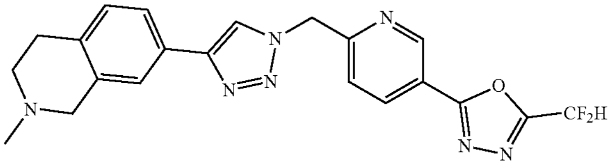 [SMILES: CN1CCc2ccc(-c3cn(Cc4ccc(-c5nnc(C(F)F)o5)cn4)nn3)cc2C1] |
| 186 | 4210 | 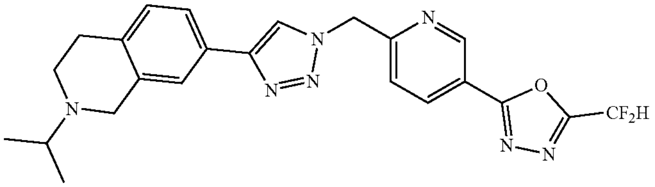 [SMILES: CC(C)N1CCc2ccc(-c3cn(Cc4ccc(-c5nnc(C(F)F)o5)cn4)nn3)cc2C1] |
| 187 | 4211 | 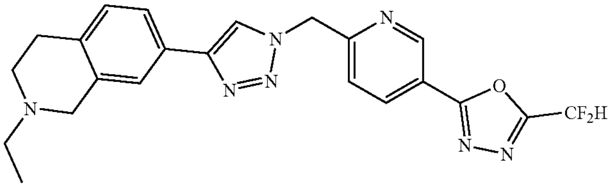 [SMILES: CCN1CCc2ccc(-c3cn(Cc4ccc(-c5nnc(C(F)F)o5)cn4)nn3)cc2C1] |
| 188 | 4212 | 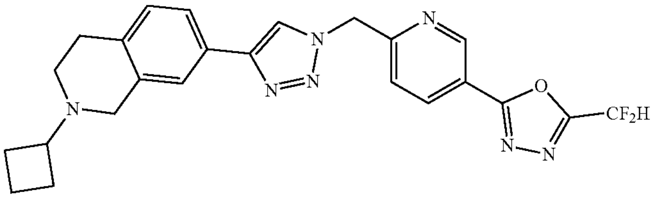 [SMILES: FC(F)c1nnc(-c2ccc(Cn3cc(-c4ccc5c(c4)CN(C4CCC4)CC5)nn3)nc2)o1] |
| 189 | 4213 | 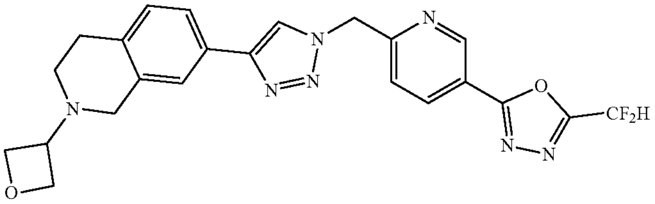 [SMILES: FC(F)c1nnc(-c2ccc(Cn3cc(-c4ccc5c(c4)CN(C4COC4)CC5)nn3)nc2)o1] |
| 190 | 4229 | 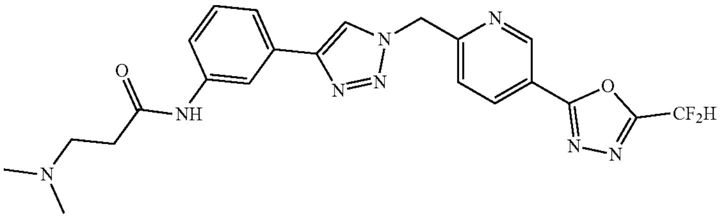 [SMILES: CN(C)CCC(=O)Nc1cccc(-c2cn(Cc3ccc(-c4nnc(C(F)F)o4)cn3)nn2)c1] |
| 191 | 4230 | 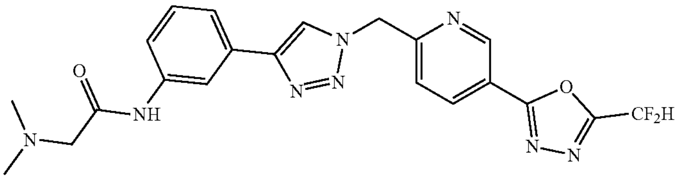 [SMILES: CN(C)CC(=O)Nc1cccc(-c2cn(Cc3ccc(-c4nnc(C(F)F)o4)cn3)nn2)c1] |

-continued
| Example | Compound | Structure |
| --- | --- | --- |
| 192 | 4231 | 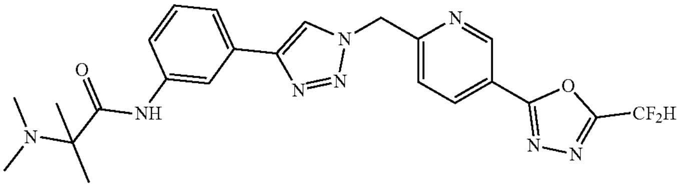 [SMILES: CN(C)C(C)(C)C(=O)Nc1cccc(-c2cn(Cc3ccc(-c4nnc(C(F)F)o4)cn3)nn2)c1] |
| 193 | 4232 | 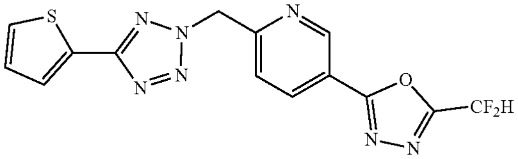 [SMILES: FC(F)c1nnc(-c2ccc(Cn3nnc(-c4cccs4)n3)nc2)o1] |
| 194 | 4233 | 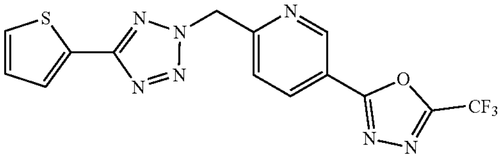 [SMILES: FC(F)(F)c1nnc(-c2ccc(Cn3nnc(-c4cccs4)n3)nc2)o1] |
| 195 | 4234 | 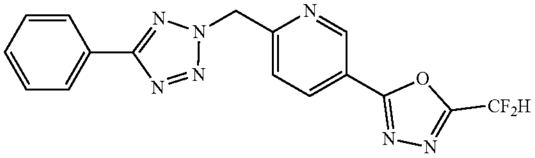 [SMILES: FC(F)c1nnc(-c2ccc(Cn3nnc(-c4ccccc4)n3)nc2)o1] |
| 196 | 4235 | 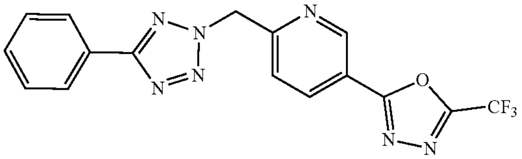 [SMILES: FC(F)(F)c1nnc(-c2ccc(Cn3nnc(-c4ccccc4)n3)nc2)o1] |
| 197 | 4276 | 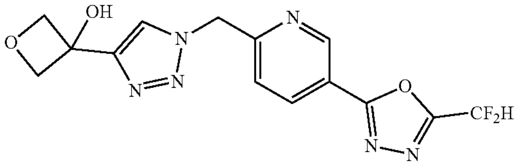 [SMILES: OC1(c2cn(Cc3ccc(-c4nnc(C(F)F)o4)cn3)nn2)COC1] |
| 198 | 4277 | 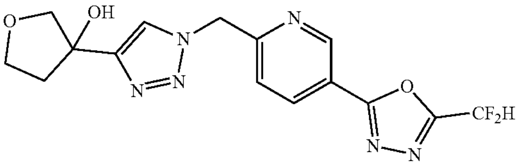 |
| 199 | 4278 | 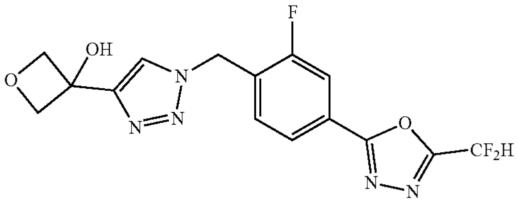 [SMILES: OC1(c2cn(Cc3ccc(-c4nnc(C(F)F)o4)cc3F)nn2)COC1] |

-continued
| Example | Compound | Structure |
|---|---|---|
| 200 | 4279 | 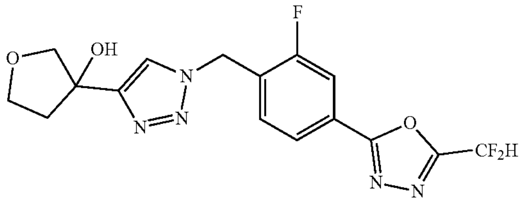 [SMILES: OC1(c2cn(Cc3ccc(-c4nnc(C(F)F)o4)cc3F)nn2)CCOC1] |
| 201 | 4280 | 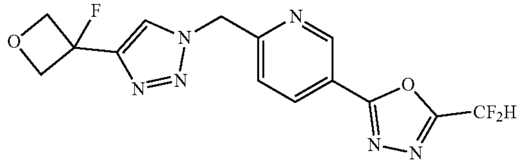 [SMILES: FC(F)c1nnc(-c2ccc(Cn3cc(C4(F)COC4)nn3)nc2)o1] |
| 202 | 4281 | 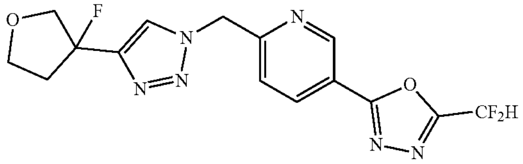 [SMILES: FC(F)c1nnc(-c2ccc(Cn3cc(C4(F)CCOC4)nn3)nc2)o1] |
| 203 | 4282 | 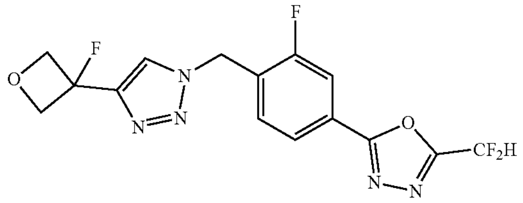 [SMILES: Fc1cc(-c2nnc(C(F)F)o2)ccc1Cn1cc(C2(F)COC2)nn1] |
| 204 | 4283 | 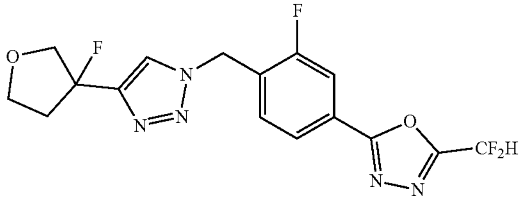 [SMILES: Fc1cc(-c2nnc(C(F)F)o2)ccc1Cn1cc(C2(F)CCOC2)nn1] |
| 205 | 4284 | 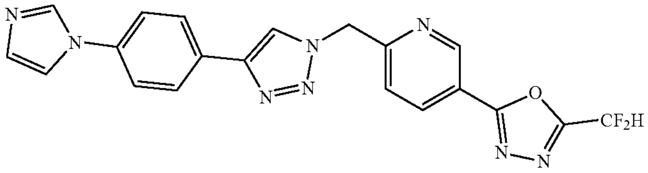 [SMILES: FC(F)c1nnc(-c2ccc(Cn3cc(-c4ccc(-n5ccnc5)cc4)nn3)nc2)o1] |
| 206 | 4285 | 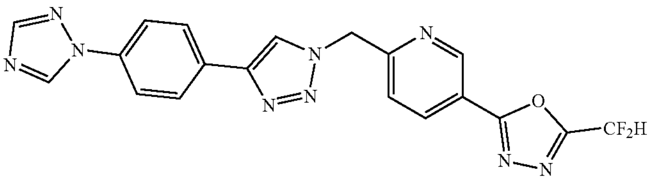 [SMILES: FC(F)c1nnc(-c2ccc(Cn3cc(-c4ccc(-n5cncn5)cc4)nn3)nc2)o1] |
| 207 | 4286 | 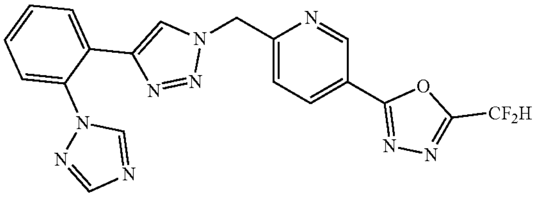 [SMILES: FC(F)c1nnc(-c2ccc(Cn3cc(-c4ccccc4-n4cncn4)nn3)nc2)o1] |

-continued
| Example | Compound | Structure |
|---|---|---|
| 208 | 4287 | 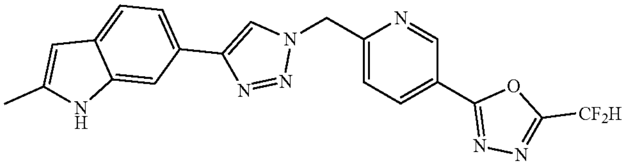 [SMILES: Cc1cc2ccc(-c3cn(Cc4ccc(-c5nnc(C(F)F)o5)cn4)nn3)cc2[nH]1] |
| 209 | 4288 | 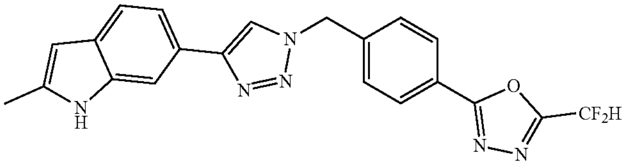 [SMILES: Cc1cc2ccc(-c3cn(Cc4ccc(-c5nnc(C(F)F)o5)cc4)nn3)cc2[nH]1] |
| 210 | 4289 | 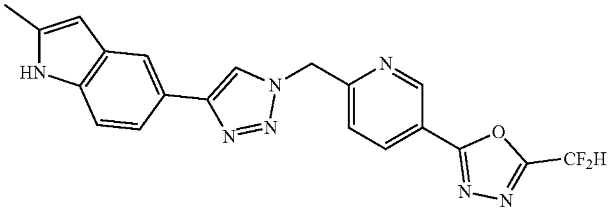 [SMILES: Cc1cc2cc(-c3cn(Cc4ccc(-c5nnc(C(F)F)o5)cn4)nn3)ccc2[nH]1] |
| 211 | 4290 | 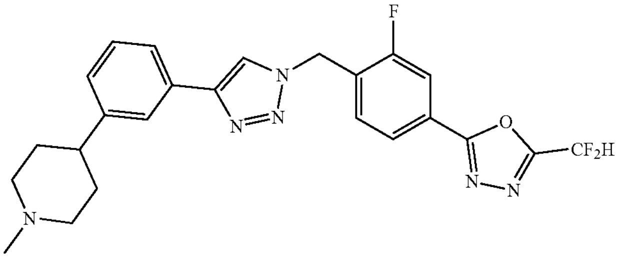 [SMILES: CN1CCC(c2cccc(-c3cn(Cc4ccc(-c5nnc(C(F)F)o5)cc4F)nn3)c2)CC1] |
| 212 | 4291 | 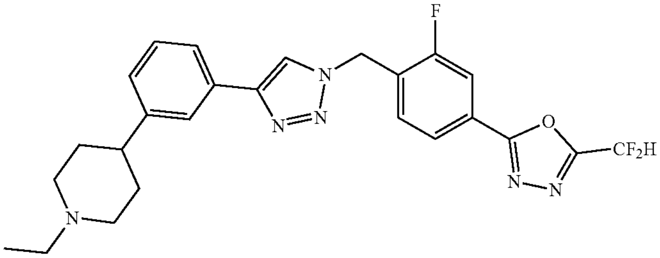 [SMILES: CCN1CCC(c2cccc(-c3cn(Cc4ccc(-c5nnc(C(F)F)o5)cc4F)nn3)c2)CC1] |
| 213 | 4292 | 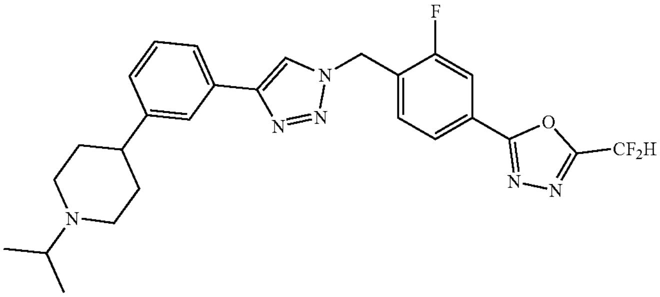 [SMILES: CC(C)N1CCC(c2cccc(-c3cn(Cc4ccc(-c5nnc(C(F)F)o5)cc4F)nn3)c2)CC1] |

-continued
| Example | Compound | Structure |
|---|---|---|
| 214 | 4293 | 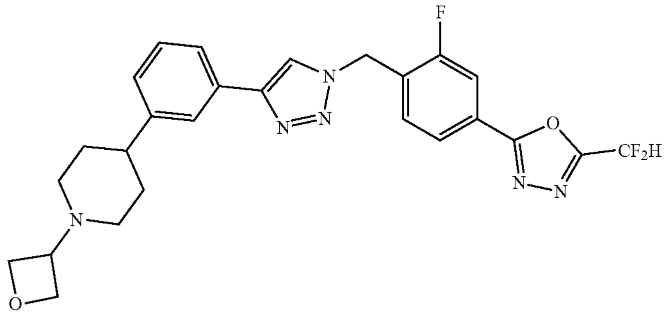 [SMILES: Fc1cc(-c2nnc(C(F)F)o2)ccc1Cn1cc(-c2cccc(C3CCN(C4COC4)CC3)c2)nn1] |
| 215 | 4294 | 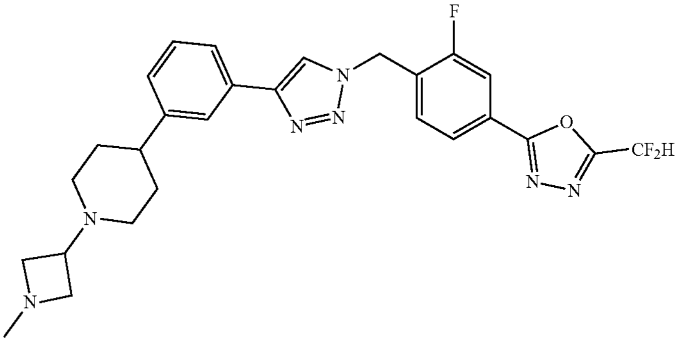 [SMILES: CN1CC(N2CCC(c3cccc(-c4cn(Cc5ccc(-c6nnc(C(F)F)o6)cc5F)nn4)c3)CC2)C1] |
| 216 | 4295 | 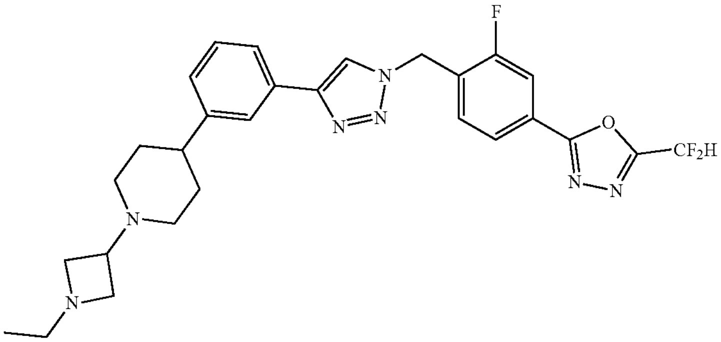 [SMILES: CCN1CC(N2CCC(c3cccc(-c4cn(Cc5ccc(-c6nnc(C(F)F)o6)cc5F)nn4)c3)CC2)C1] |
| 217 | 4296 | 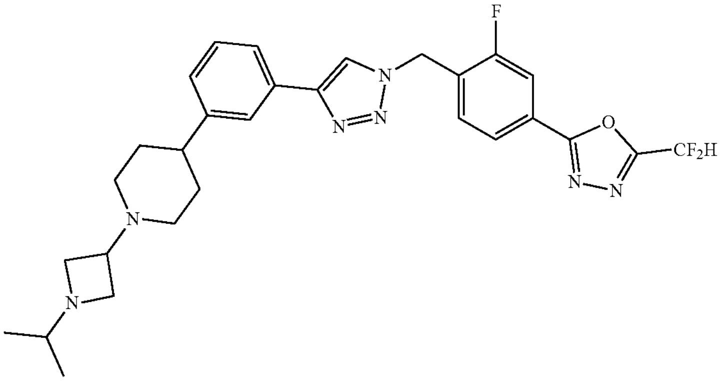 [SMILES: CC(C)N1CC(N2CCC(c3cccc(-c4cn(Cc5ccc(-c6nnc(C(F)F)o6)cc5F)nn4)c3)CC2)C1] |

-continued
| Example | Compound | Structure |
|---|---|---|
| 218 | 4316 | 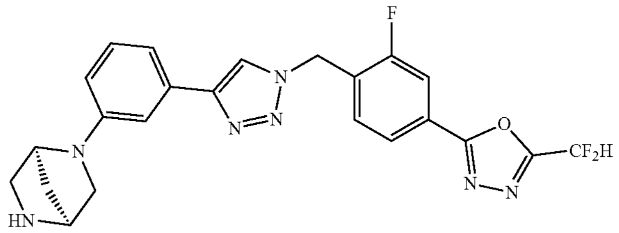 [SMILES: Fc1cc(-c2nnc(C(F)F)o2)ccc1Cn1cc(-c2cccc(N3C[C@@H]4C[C@H]3CN4)c2)nn1] |
| 219 | 4317 | 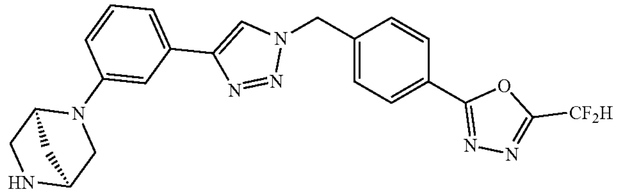 [SMILES: FC(F)c1nnc(-c2ccc(Cn3cc(-c4cccc(N5C[C@@H]6C[C@H]5CN6)c4)nn3)cc2)o1] |
| 220 | 4318 | 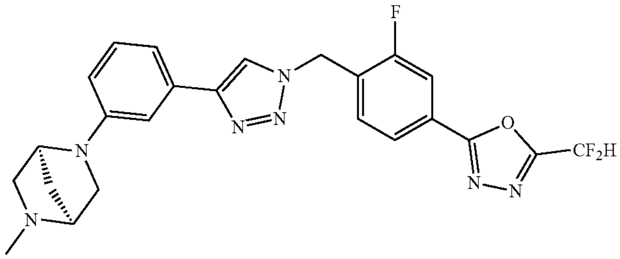 [SMILES: CN1C[C@@H]2C[C@H]1CN2c1cccc(-c2cn(Cc3ccc(-c4nnc(C(F)F)o4)cc3F)nn2)c1] |
| 221 | 4319 | 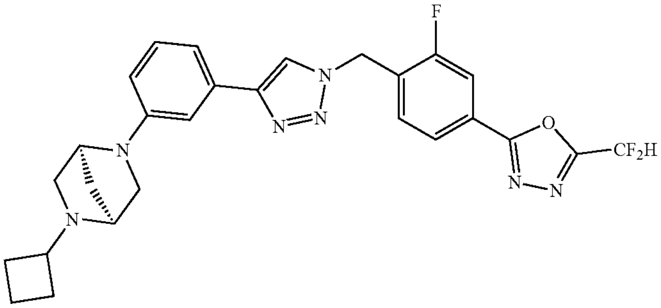 [SMILES: Fc1cc(-c2nnc(C(F)F)o2)ccc1Cn1cc(-c2cccc(N3C[C@@H]4C[C@H]3CN4C3CCC3)c2)nn1] |
| 222 | 4320 | 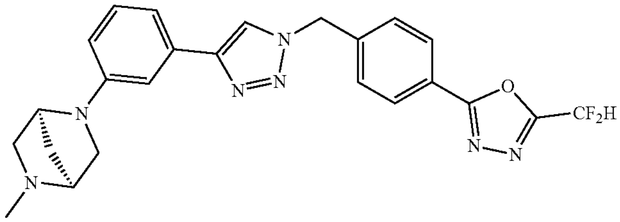 [SMILES: CN1C[C@@H]2C[C@H]1CN2c1cccc(-c2cn(Cc3ccc(-c4nnc(C(F)F)o4)cc3)nn2)c1] |
| 223 | 4321 | 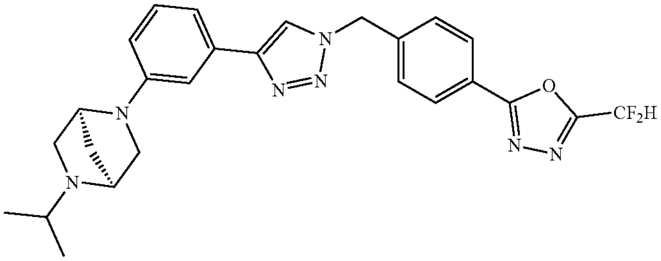 [SMILES: CC(C)N1C[C@@H]2C[C@H]1CN2c1cccc(-c2cn(Cc3ccc(-c4nnc(C(F)F)o4)cc3)nn2)c1] |

-continued
| Example | Compound | Structure |
| --- | --- | --- |
| 224 | 4322 | 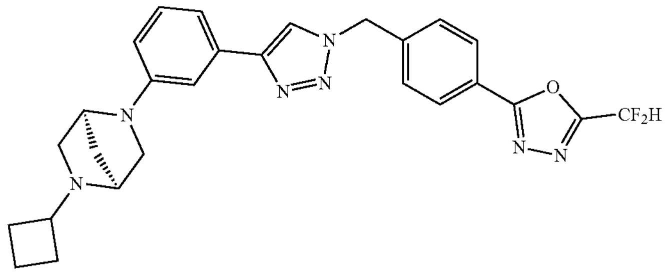 [SMILES: FC(F)c1nnc(-c2ccc(Cn3cc(-c4cccc(N5C[C@@H]6C[C@H]5CN6C5CCC5)c4)nn3)cc2)o1] |
| 225 | 4323 | 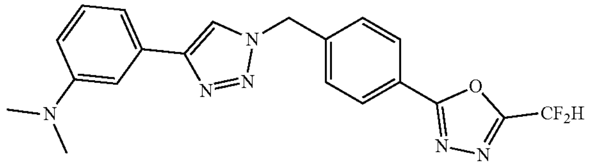 [SMILES: CN(C)c1cccc(-c2cn(Cc3ccc(-c4nnc(C(F)F)o4)cc3)nn2)c1] |
| 226 | 4324 | 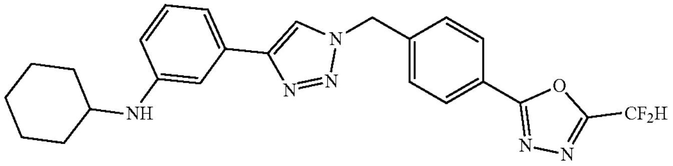 [SMILES: FC(F)c1nnc(-c2ccc(Cn3cc(-c4cccc(NC5CCCCC5)c4)nn3)cc2)o1] |
| 227 | 4325 | 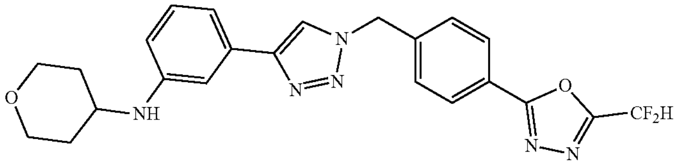 [SMILES: FC(F)c1nnc(-c2ccc(Cn3cc(-c4cccc(NC5CCOCC5)c4)nn3)cc2)o1] |
| 228 | 4326 | 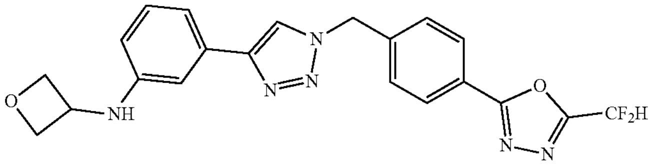 [SMILES: FC(F)c1nnc(-c2ccc(Cn3cc(-c4cccc(NC5COC5)c4)nn3)cc2)o1] |
| 229 | 4327 | 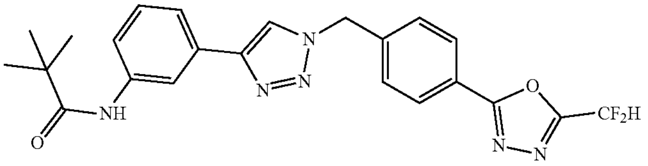 [SMILES: CC(C)(C)C(=O)Nc1cccc(-c2cn(Cc3ccc(-c4nnc(C(F)F)o4)cc3)nn2)c1] |
| 230 | 4328 | 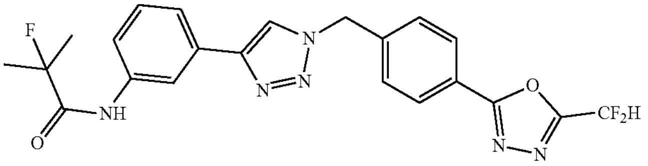 |
| 231 | 4329 | 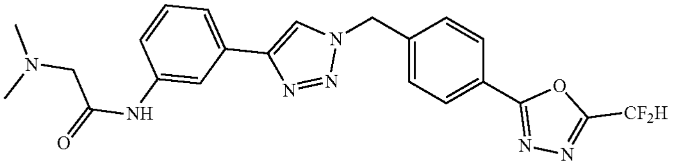 [SMILES: CN(C)CC(=O)Nc1cccc(-c2cn(Cc3ccc(-c4nnc(C(F)F)o4)cc3)nn2)c1] |

-continued
| Example | Compound | Structure |
|---|---|---|
| 232 | 4330 | 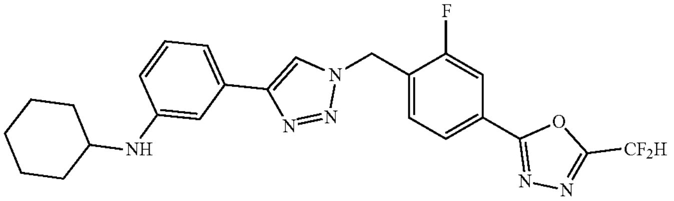 [SMILES: Fc1cc(-c2nnc(C(F)F)o2)ccc1Cn1cc(-c2cccc(NC3CCCCC3)c2)nn1] |
| 233 | 4331 | 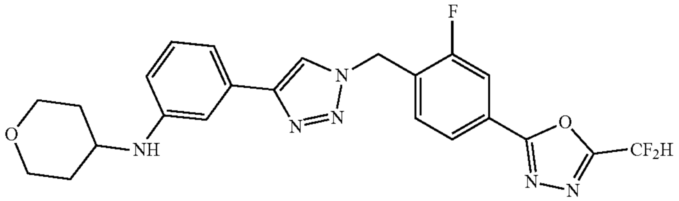 [SMILES: Fc1cc(-c2nnc(C(F)F)o2)ccc1Cn1cc(-c2cccc(NC3CCOCC3)c2)nn1] |
| 234 | 4332 | 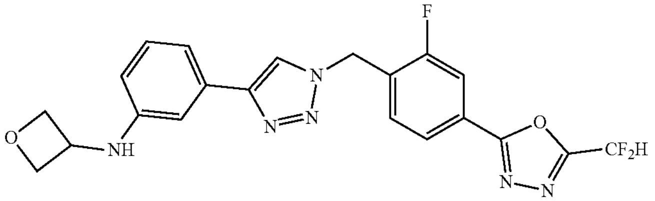 [SMILES: Fc1cc(-c2nnc(C(F)F)o2)ccc1Cn1cc(-c2cccc(NC3COC3)c2)nn1] |
| 235 | 4333 | 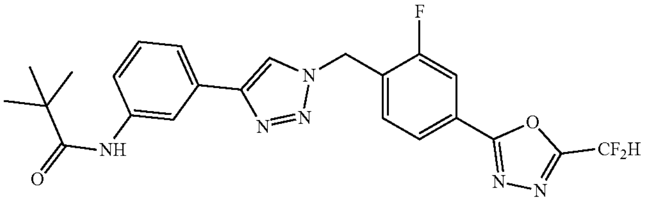 [SMILES: CC(C)(C)C(=O)Nc1cccc(-c2cn(Cc3ccc(-c4nnc(C(F)F)o4)cc3F)nn2)c1] |
| 236 | 4334 | 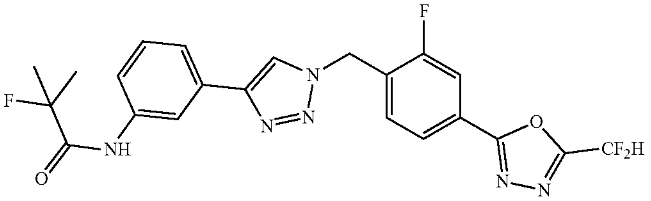 [SMILES: CC(C)(F)C(=O)Nc1cccc(-c2cn(Cc3ccc(-c4nnc(C(F)F)o4)cc3F)nn2)c1] |
| 237 | 4335 | 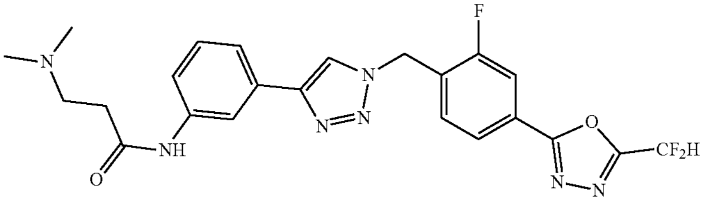 [SMILES: CN(C)CCC(=O)Nc1cccc(-c2cn(Cc3ccc(-c4nnc(C(F)F)o4)cc3F)nn2)c1] |
| 238 | 4336 | 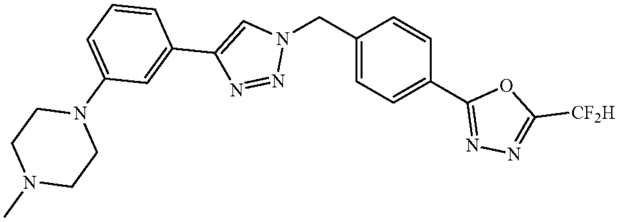 [SMILES: CN1CCN(c2cccc(-c3cn(Cc4ccc(-c5nnc(C(F)F)o5)cc4)nn3)c2)CC1] |

-continued
| Example | Compound | Structure |
|---|---|---|
| 239 | 4337 | 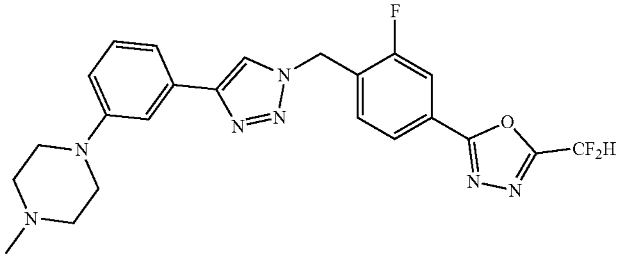 [SMILES: CN1CCN(c2cccc(-c3cn(Cc4ccc(-c5nnc(C(F)F)o5)cc4F)nn3)c2)CC1] |
| 240 | 4338 | 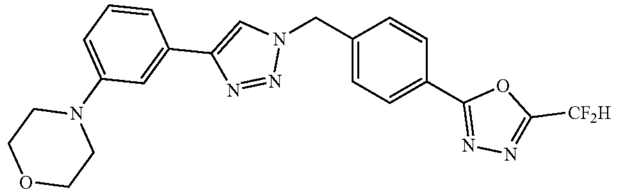 [SMILES: FC(F)c1nnc(-c2ccc(Cn3cc(-c4cccc(N5CCOCC5)c4)nn3)cc2)o1] |
| 241 | 4339 | 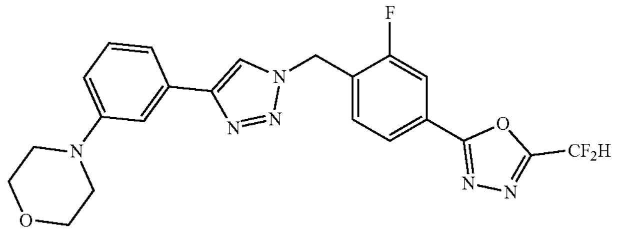 [SMILES: Fc1cc(-c2nnc(C(F)F)o2)ccc1Cn1cc(-c2cccc(N3CCOCC3)c2)nn1] |
| 242 | 4340 | 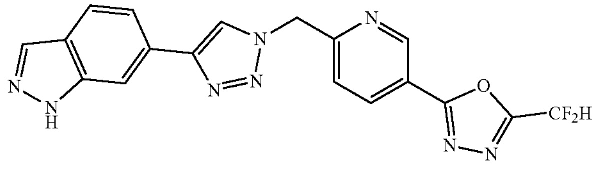 [SMILES: FC(F)c1nnc(-c2ccc(Cn3cc(-c4ccc5cn[nH]c5c4)nn3)nc2)o1] |
| 243 | 4341 | 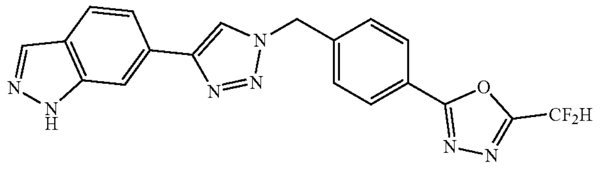 [SMILES: FC(F)c1nnc(-c2ccc(Cn3cc(-c4ccc5cn[nH]c5c4)nn3)cc2)o1] |
| 244 | 4342 | 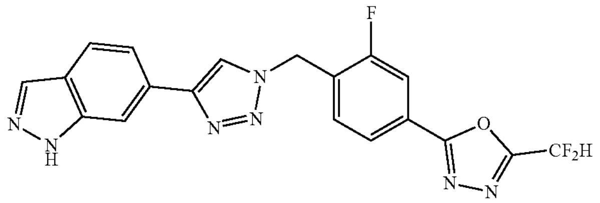 [SMILES: Fc1cc(-c2nnc(C(F)F)o2)ccc1Cn1cc(-c2ccc3cn[nH]c3c2)nn1] |
| 245 | 4343 | 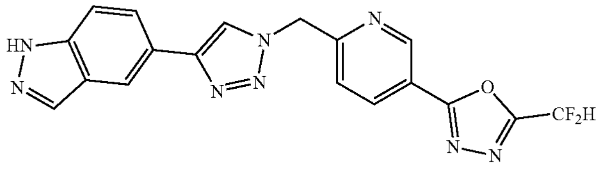 [SMILES: FC(F)c1nnc(-c2ccc(Cn3cc(-c4ccc5[nH]ncc5c4)nn3)nc2)o1] |

-continued
| Example | Compound | Structure |
| --- | --- | --- |
| 246 | 4344 | 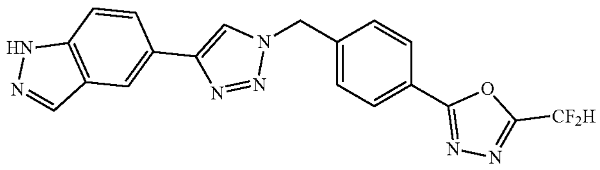 [SMILES: FC(F)c1nnc(-c2ccc(Cn3cc(-c4ccc5[nH]ncc5c4)nn3)cc2)o1] |
| 247 | 4345 | 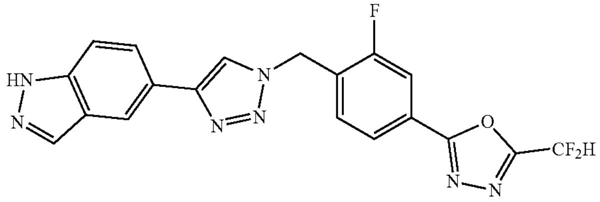 [SMILES: Fc1cc(-c2nnc(C(F)F)o2)ccc1Cn1cc(-c2ccc3[nH]ncc3c2)nn1] |
| 248 | 4346 | 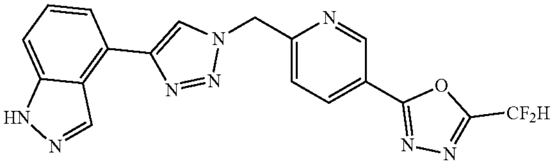 [SMILES: FC(F)c1nnc(-c2ccc(Cn3cc(-c4cccc5[nH]ncc45)nn3)nc2)o1] |
| 249 | 4347 | 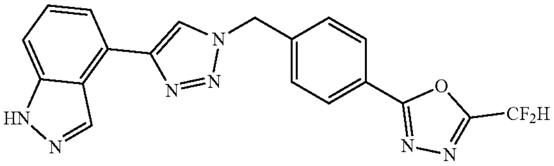 [SMILES: FC(F)c1nnc(-c2ccc(Cn3cc(-c4cccc5[nH]ncc45)nn3)cc2)o1] |
| 250 | 4348 | 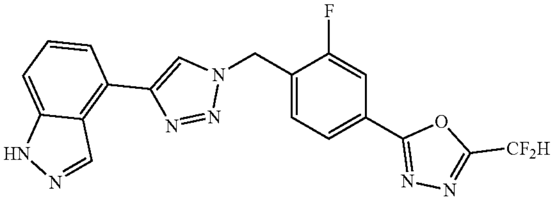 [SMILES: Fc1cc(-c2nnc(C(F)F)o2)ccc1Cn1cc(-c2cccc3[nH]ncc23)nn1] |
| 251 | 4349 | 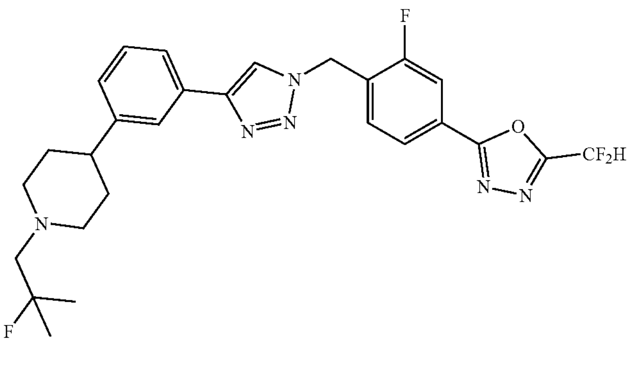 [SMILES: CC(C)(F)CN1CCC(c2cccc(-c3cn(Cc4ccc(-c5nnc(C(F)F)o5)cc4F)nn3)c2)CC1] |

-continued
| Example | Compound | Structure |
| --- | --- | --- |
| 252 | 4350 | 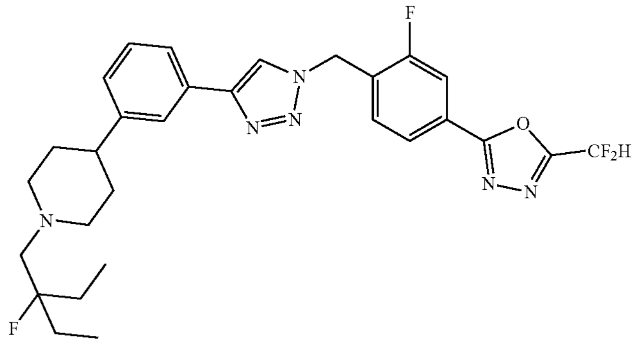 [SMILES: CCC(F)(CC)CN1CCC(c2cccc(-c3cn(Cc4ccc(-c5nnc(C(F)F)o5)cc4F)nn3)c2)CC1] |
| 253 | 4351 | 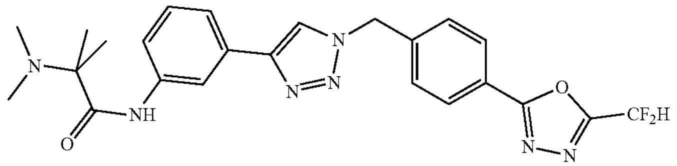 [SMILES: CN(C)C(C)(C)C(=O)Nc1cccc(-c2cn(Cc3ccc(-c4nnc(C(F)F)o4)cc3)nn2)c1] |
| 254 | 4352 | 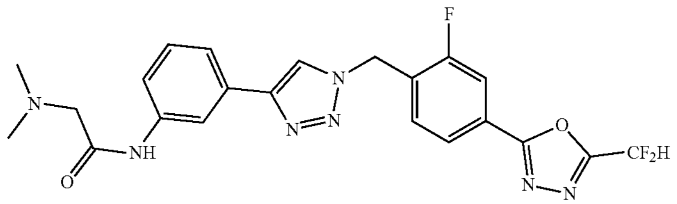 [SMILES: CN(C)CC(=O)Nc1cccc(-c2cn(Cc3ccc(-c4nnc(C(F)F)o4)cc3F)nn2)c1] |
| 255 | 4353 | 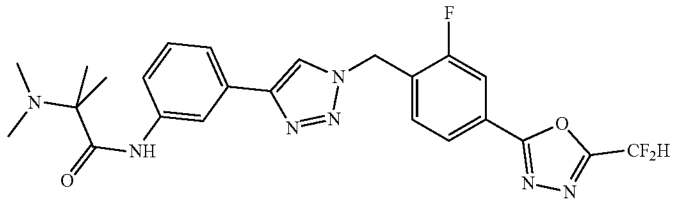 [SMILES: CN(C)C(C)(C)C(=O)Nc1cccc(-c2cn(Cc3ccc(-c4nnc(C(F)F)o4)cc3F)nn2)c1] |
| 256 | 4358 | 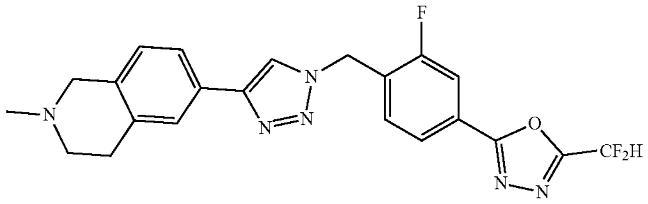 [SMILES: CN1CCc2cc(-c3cn(Cc4ccc(-c5nnc(C(F)F)o5)cc4F)nn3)ccc2C1] |
| 257 | 4359 | 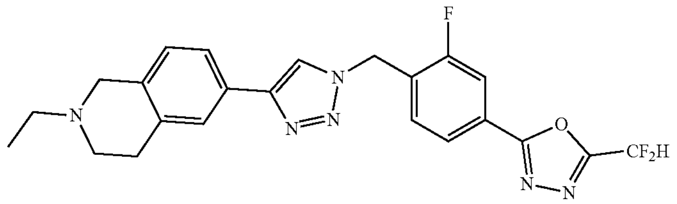 [SMILES: CCN1CCc2cc(-c3cn(Cc4ccc(-c5nnc(C(F)F)o5)cc4F)nn3)ccc2C1] |
| 258 | 4360 | 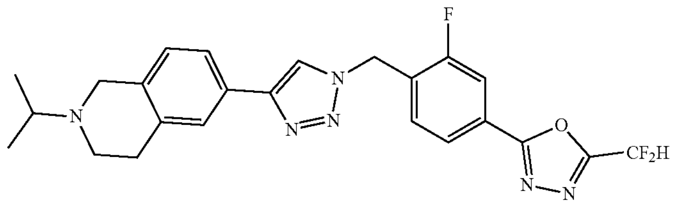 [SMILES: CC(C)N1CCc2cc(-c3cn(Cc4ccc(-c5nnc(C(F)F)o5)cc4F)nn3)ccc2C1] |

-continued
| Example | Compound | Structure |
|---|---|---|
| 259 | 4361 | 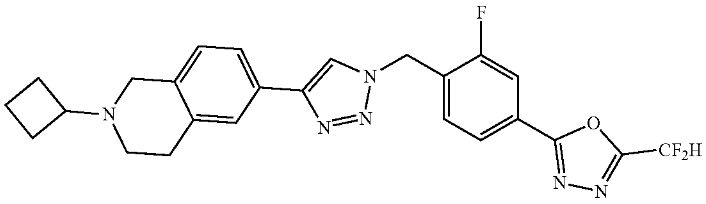 [SMILES: Fc1cc(-c2nnc(C(F)F)o2)ccc1Cn1cc(-c2ccc3c(c2)CCN(C2CCC2)C3)nn1] |
| 260 | 4362 | 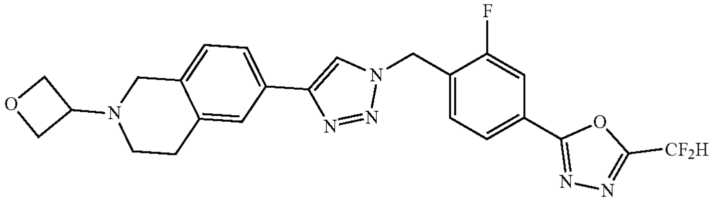 [SMILES: Fc1cc(-c2nnc(C(F)F)o2)ccc1Cn1cc(-c2ccc3c(c2)CCN(C2COC2)C3)nn1] |
| 261 | 4363 | 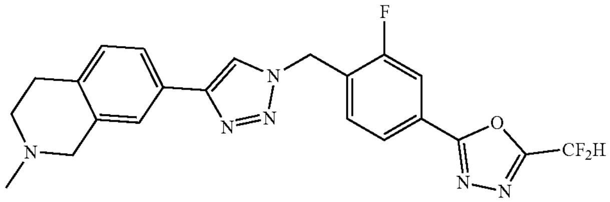 [SMILES: CN1CCc2ccc(-c3cn(Cc4ccc(-c5nnc(C(F)F)o5)cc4F)nn3)cc2C1] |
| 262 | 4364 | 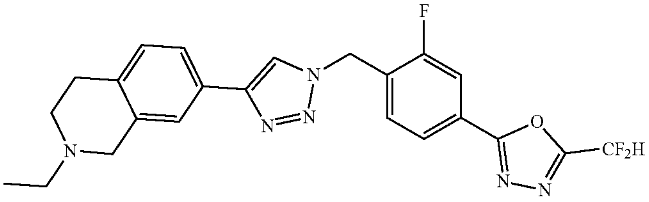 [SMILES: CCN1CCc2ccc(-c3cn(Cc4ccc(-c5nnc(C(F)F)o5)cc4F)nn3)cc2C1] |
| 263 | 4365 | 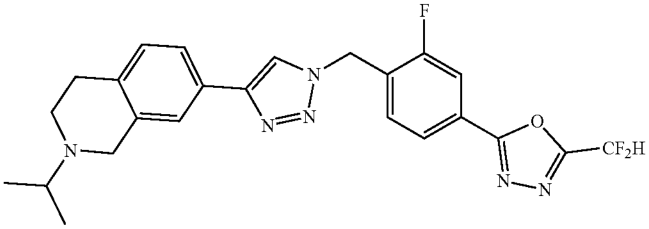 [SMILES: CC(C)N1CCc2ccc(-c3cn(Cc4ccc(-c5nnc(C(F)F)o5)cc4F)nn3)cc2C1] |
| 264 | 4366 | 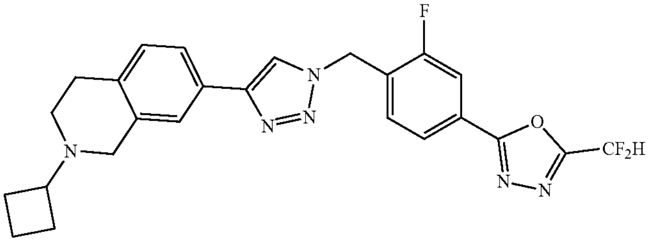 [SMILES: Fc1cc(-c2nnc(C(F)F)o2)ccc1Cn1cc(-c2ccc3c(c2)CN(C2CCC2)CC3)nn1] |
| 265 | 4367 | 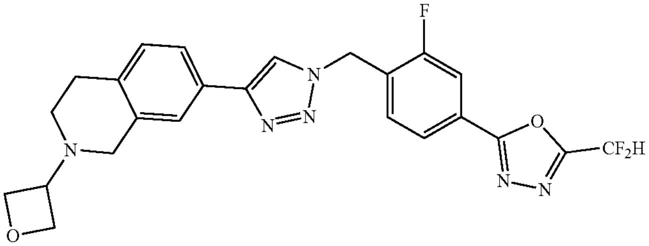 [SMILES: Fc1cc(-c2nnc(C(F)F)o2)ccc1Cn1cc(-c2ccc3c(c2)CN(C2COC2)CC3)nn1] |

-continued
| Example | Compound | Structure |
| --- | --- | --- |
| 266 | 4368 | 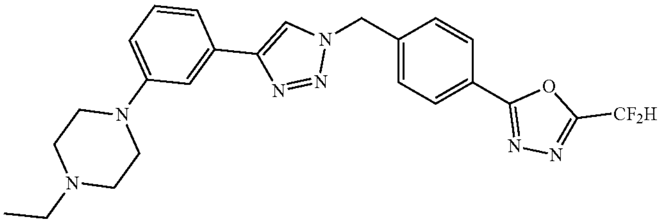 [SMILES: CCN1CCN(c2cccc(-c3cn(Cc4ccc(-c5nnc(C(F)F)o5)cc4)nn3)c2)CC1] |
| 267 | 4369 | 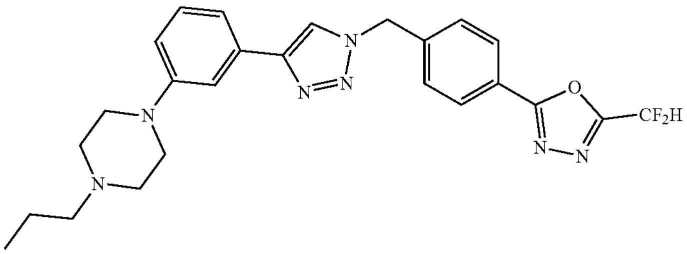 [SMILES: CCCN1CCN(c2cccc(-c3cn(Cc4ccc(-c5nnc(C(F)F)o5)cc4)nn3)c2)CC1] |
| 268 | 4370 | 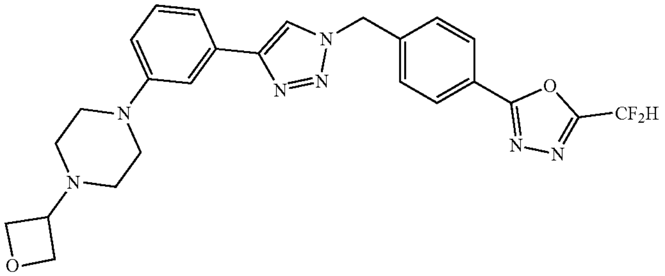 [SMILES: FC(F)c1nnc(-c2ccc(Cn3cc(-c4cccc(N5CCN(C6COC6)CC5)c4)nn3)cc2)o1] |
| 269 | 4371 | 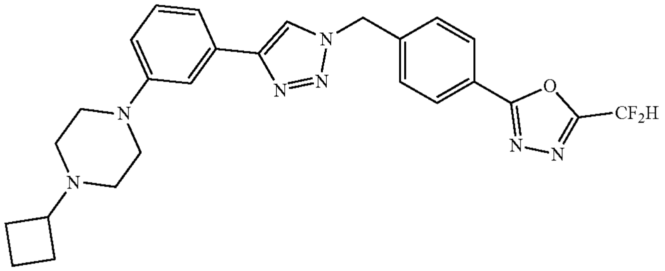 [SMILES: FC(F)c1nnc(-c2ccc(Cn3cc(-c4cccc(N5CCN(C6CCC6)CC5)c4)nn3)cc2)o1] |
| 270 | 4372 | 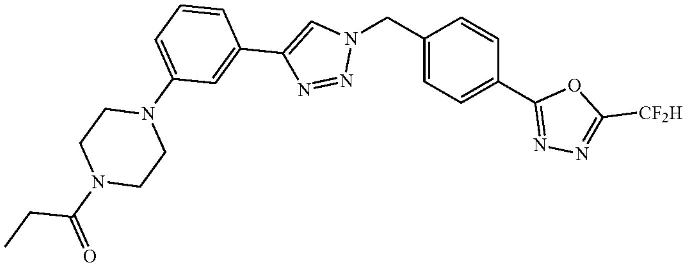 [SMILES: CCC(=O)N1CCN(c2cccc(-c3cn(Cc4ccc(-c5nnc(C(F)F)o5)cc4)nn3)c2)CC1] |

-continued
| Example | Compound | Structure |
| --- | --- | --- |
| 271 | 4373 | 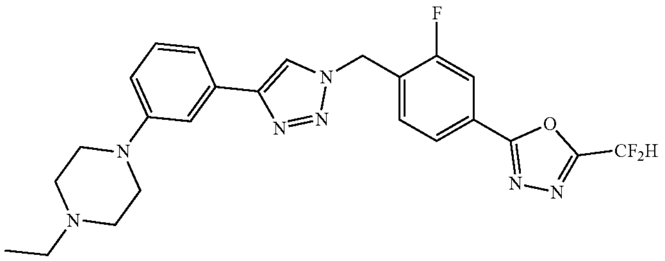 [SMILES: CCN1CCN(c2cccc(-c3cn(Cc4ccc(-c5nnc(C(F)F)o5)cc4F)nn3)c2)CC1] |
| 272 | 4374 | 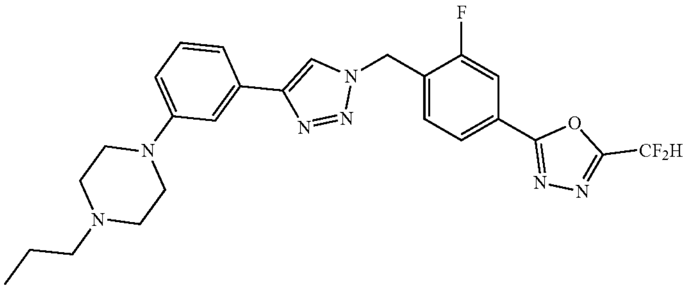 [SMILES: CCCN1CCN(c2cccc(-c3cn(Cc4ccc(-c5nnc(C(F)F)o5)cc4F)nn3)c2)CC1] |
| 273 | 4375 | 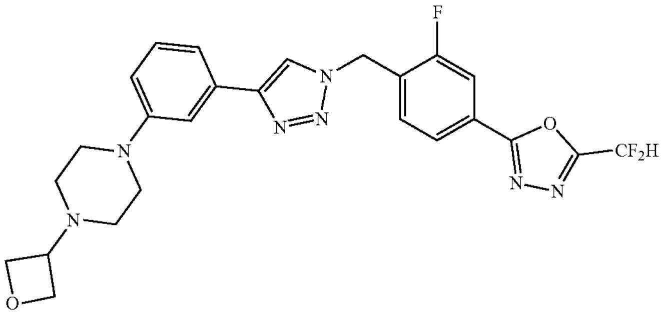 [SMILES: Fc1cc(-c2nnc(C(F)F)o2)ccc1Cn1cc(-c2cccc(N3CCN(C4COC4)CC3)c2)nn1] |
| 274 | 4376 | 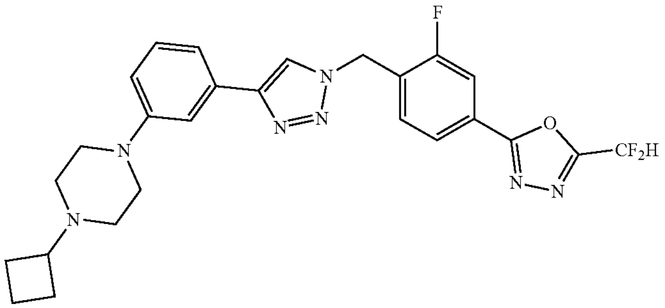 [SMILES: Fc1cc(-c2nnc(C(F)F)o2)ccc1Cn1cc(-c2cccc(N3CCN(C4CCC4)CC3)c2)nn1] |
| 275 | 4377 | 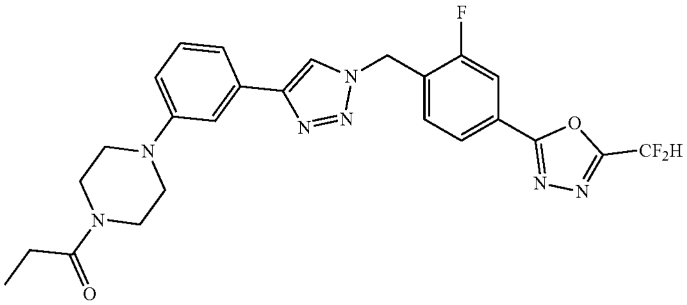 [SMILES: CCC(=O)N1CCN(c2cccc(-c3cn(Cc4ccc(-c5nnc(C(F)F)o5)cc4F)nn3)c2)CC1] |

-continued
| Example | Compound | Structure |
| --- | --- | --- |
| 276 | 4392 | 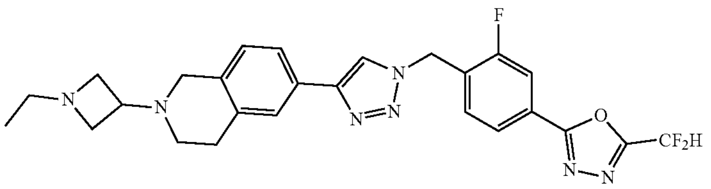 [SMILES: CCN1CC(N2CCc3cc(-c4cn(Cc5ccc(-c6nnc(C(F)F)o6)cc5F)nn4)ccc3C2)C1] |
| 277 | 4393 | 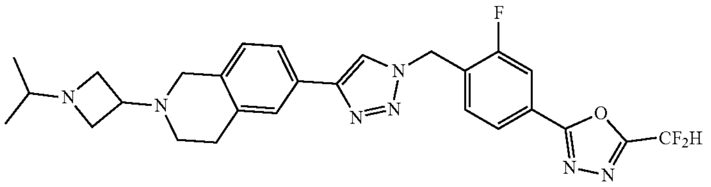 [SMILES: CC(C)N1CC(N2CCc3cc(-c4cn(Cc5ccc(-c6nnc(C(F)F)o6)cc5F)nn4)ccc3C2)C1] |
| 278 | 4394 | 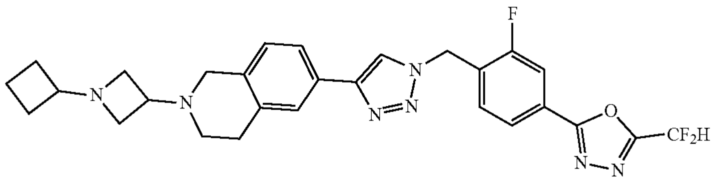 [SMILES: Fc1cc(-c2nnc(C(F)F)o2)ccc1Cn1cc(-c2ccc3c(c2)CCN(C2CN(C4CCC4)C2)C3)nn1] |
| 279 | 4395 | 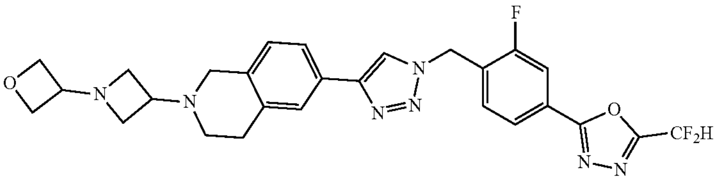 [SMILES: Fc1cc(-c2nnc(C(F)F)o2)ccc1Cn1cc(-c2ccc3c(c2)CCN(C2CN(C4COC4)C2)C3)nn1] |
| 280 | 4396 | 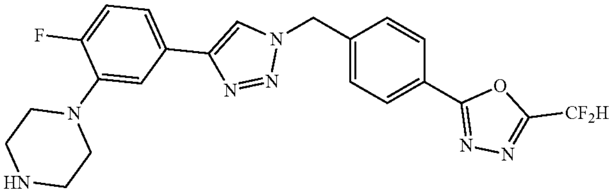 [SMILES: Fc1ccc(-c2cn(Cc3ccc(-c4nnc(C(F)F)o4)cc3)nn2)cc1N1CCNCC1] |
| 281 | 4397 | 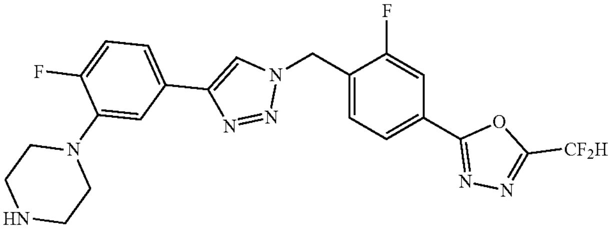 [SMILES: Fc1cc(-c2nnc(C(F)F)o2)ccc1Cn1cc(-c2ccc(F)c(N3CCNCC3)c2)nn1] |
| 282 | 4398 | 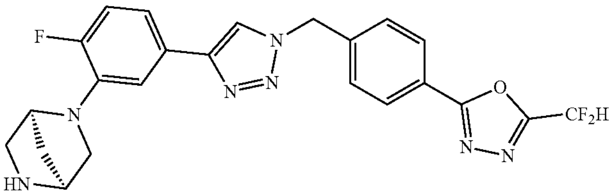 [SMILES: Fc1ccc(-c2cn(Cc3ccc(-c4nnc(C(F)F)o4)cc3)nn2)cc1N1C[C@@H]2C[C@H]1CN2] |

-continued
| Example | Compound | Structure |
| --- | --- | --- |
| 283 | 4399 | 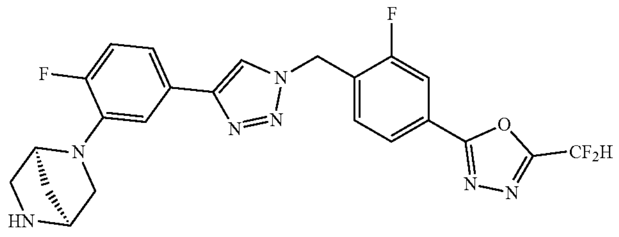 [SMILES: Fc1cc(-c2nnc(C(F)F)o2)ccc1Cn1cc(-c2ccc(F)c(N3C[C@@H]4C[C@H]3CN4)c2)nn1] |
| 284 | 4400 | 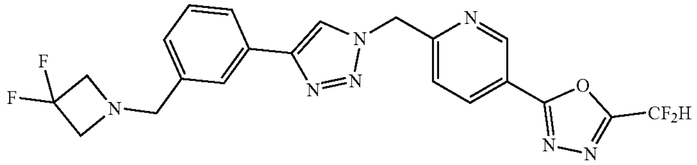 [SMILES: FC(F)c1nnc(-c2ccc(Cn3cc(-c4cccc(CN5CC(F)(F)C5)c4)nn3)nc2)o1] |
| 285 | 4401 | 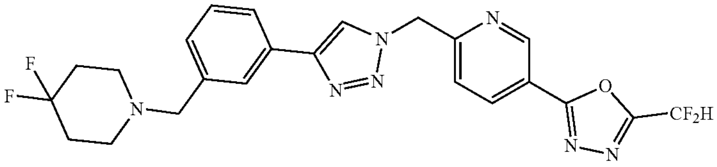 |
| 286 | 4402 | 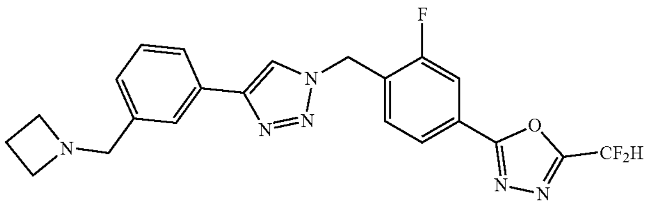 [SMILES: Fc1cc(-c2nnc(C(F)F)o2)ccc1Cn1cc(-c2cccc(CN3CCC3)c2)nn1] |
| 287 | 4403 | 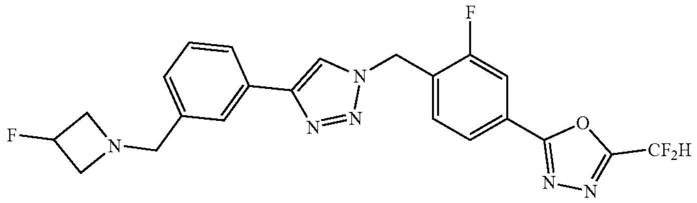 [SMILES: Fc1cc(-c2nnc(C(F)F)o2)ccc1Cn1cc(-c2cccc(CN3CC(F)C3)c2)nn1] |
| 288 | 4404 | 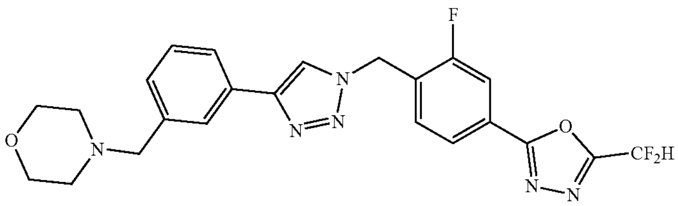 [SMILES: Fc1cc(-c2nnc(C(F)F)o2)ccc1Cn1cc(-c2cccc(CN3CCOCC3)c2)nn1] |
| 289 | 4405 | 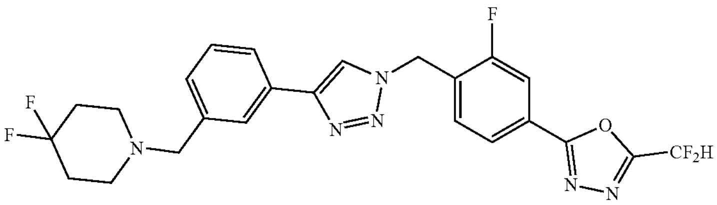 [SMILES: Fc1cc(-c2nnc(C(F)F)o2)ccc1Cn1cc(-c2cccc(CN3CCC(F)(F)CC3)c2)nn1] |

-continued
| Example | Compound | Structure |
|---|---|---|
| 290 | 4406 | 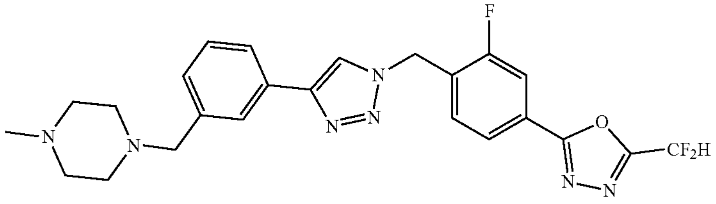 [SMILES: CN1CCN(Cc2cccc(-c3cn(Cc4ccc(-c5nnc(C(F)F)o5)cc4F)nn3)c2)CC1] |
| 291 | 4407 | 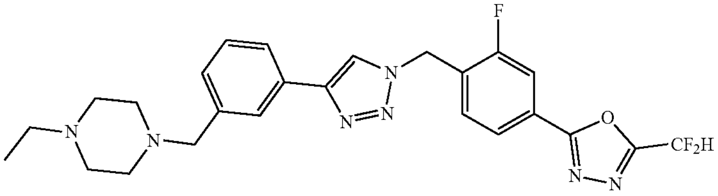 [SMILES: CCN1CCN(Cc2cccc(-c3cn(Cc4ccc(-c5nnc(C(F)F)o5)cc4F)nn3)c2)CC1] |
| 292 | 4408 | 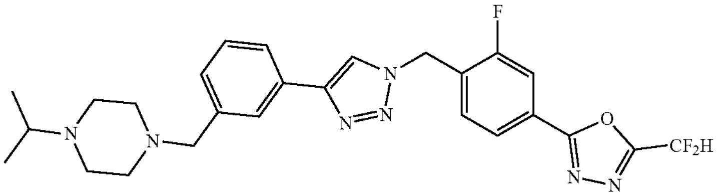 [SMILES: CC(C)N1CCN(Cc2cccc(-c3cn(Cc4ccc(-c5nnc(C(F)F)o5)cc4F)nn3)c2)CC1] |
| 293 | 4409 | 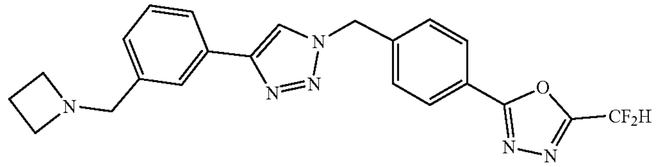 [SMILES: FC(F)c1nnc(-c2ccc(Cn3cc(-c4cccc(CN5CCC5)c4)nn3)cc2)o1] |
| 294 | 4410 | 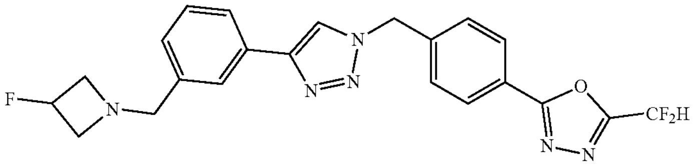 [SMILES: FC1CN(Cc2cccc(-c3cn(Cc4ccc(-c5nnc(C(F)F)o5)cc4)nn3)c2)C1] |
| 295 | 4411 | 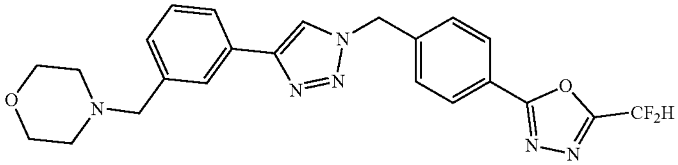 [SMILES: FC(F)c1nnc(-c2ccc(Cn3cc(-c4cccc(CN5CCOCC5)c4)nn3)cc2)o1] |
| 296 | 4412 | 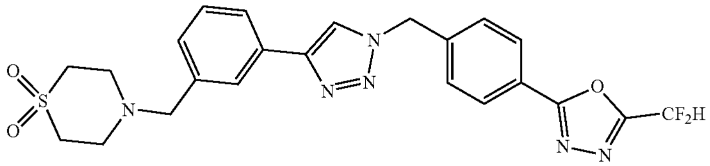 [SMILES: O=S1(=O)CCN(Cc2cccc(-c3cn(Cc4ccc(-c5nnc(C(F)F)o5)cc4)nn3)c2)CC1] |
| 297 | 4413 | 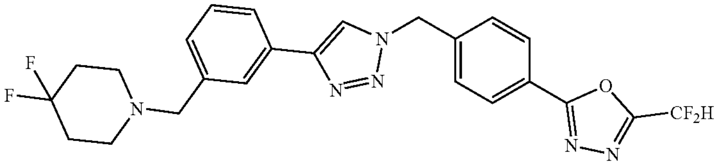 [SMILES: FC(F)c1nnc(-c2ccc(Cn3cc(-c4cccc(CN5CCC(F)(F)CC5)c4)nn3)cc2)o1] |

-continued
| Example | Compound | Structure |
|---|---|---|
| 298 | 4414 | 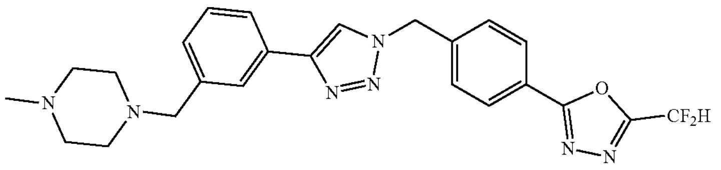 [SMILES: CN1CCN(Cc2cccc(-c3cn(Cc4ccc(-c5nnc(C(F)F)o5)cc4)nn3)c2)CC1] |
| 299 | 4415 | 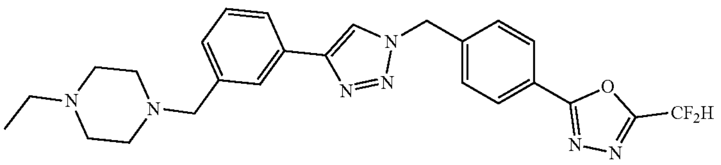 |
| 300 | 4416 | 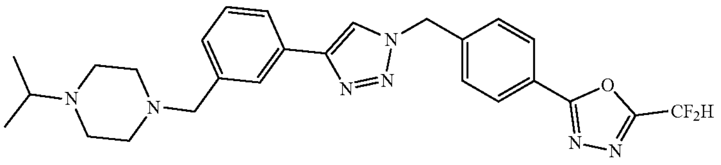 [SMILES: CC(C)N1CCN(Cc2cccc(-c3cn(Cc4ccc(-c5nnc(C(F)F)o5)cc4)nn3)c2)CC1] |
| 301 | 4417 | 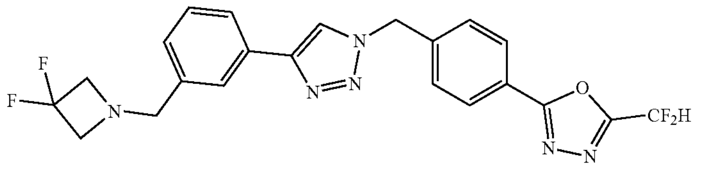 [SMILES: FC(F)c1nnc(-c2ccc(Cn3cc(-c4cccc(CN5CC(F)(F)C5)c4)nn3)cc2)o1] |
| 302 | 4418 | 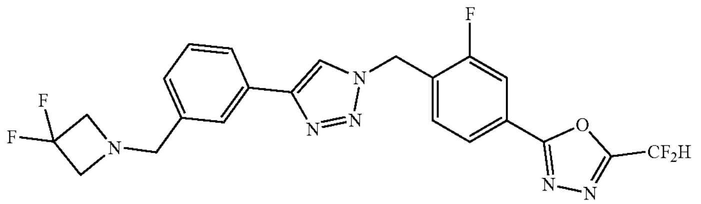 [SMILES: Fc1cc(-c2nnc(C(F)F)o2)ccc1Cn1cc(-c2cccc(CN3CC(F)(F)C3)c2)nn1] |
| 303 | 4419 | 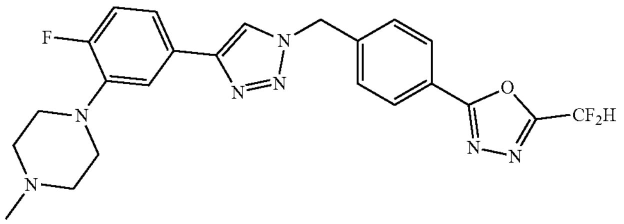 [SMILES: CN1CCN(c2cc(-c3cn(Cc4ccc(-c5nnc(C(F)F)o5)cc4)nn3)ccc2F)CC1] |
| 304 | 4420 | 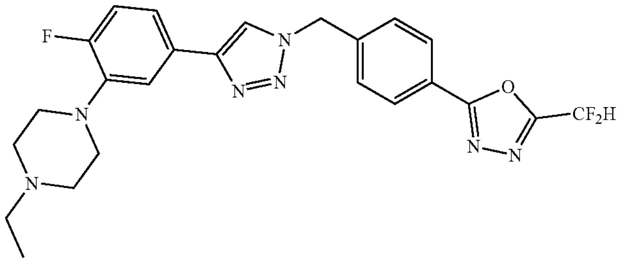 [SMILES: CCN1CCN(c2cc(-c3cn(Cc4ccc(-c5nnc(C(F)F)o5)cc4)nn3)ccc2F)CC1] |

-continued
| Example | Compound | Structure |
| --- | --- | --- |
| 305 | 4421 | 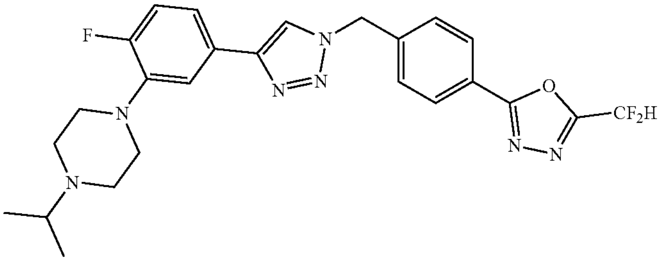 [SMILES: CC(C)N1CCN(c2cc(-c3cn(Cc4ccc(-c5nnc(C(F)F)o5)cc4)nn3)ccc2F)CC1] |
| 306 | 4422 | 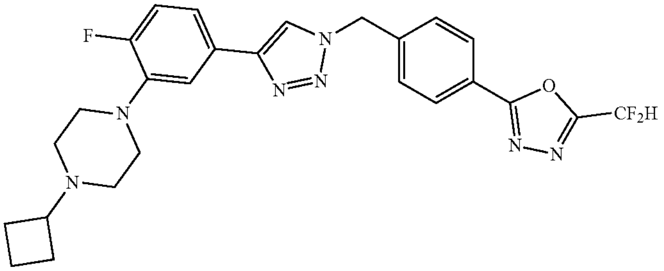 [SMILES: Fc1ccc(-c2cn(Cc3ccc(-c4nnc(C(F)F)o4)cc3)nn2)cc1N1CCN(C2CCC2)CC1] |
| 307 | 4424 | 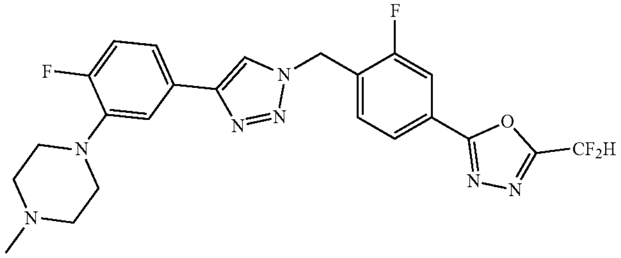 [SMILES: CN1CCN(c2cc(-c3cn(Cc4ccc(-c5nnc(C(F)F)o5)cc4F)nn3)ccc2F)CC1] |
| 308 | 4425 | 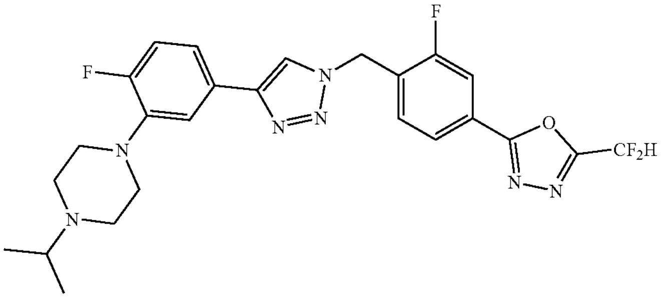 [SMILES: CC(C)N1CCN(c2cc(-c3cn(Cc4ccc(-c5nnc(C(F)F)o5)cc4F)nn3)ccc2F)CC1] |
| 309 | 4426 | 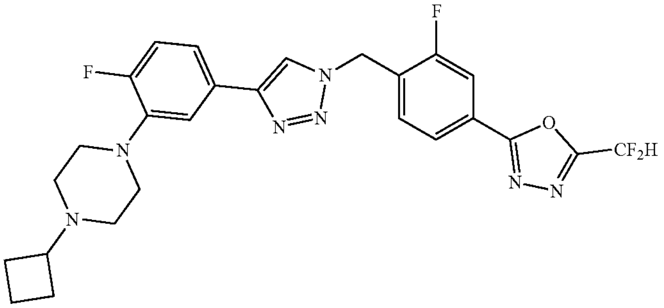 [SMILES: Fc1cc(-c2nnc(C(F)F)o2)ccc1Cn1cc(-c2ccc(F)c(N3CCN(C4CCC4)CC3)c2)nn1] |

-continued
| Example | Compound | Structure |
| --- | --- | --- |
| 310 | 4427 | 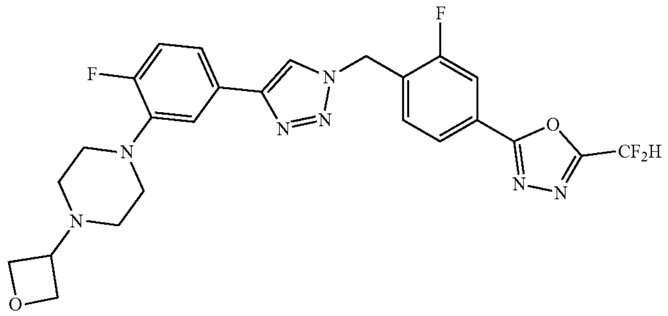 [SMILES: Fc1cc(-c2nnc(C(F)F)o2)ccc1Cn1cc(-c2ccc(F)c(N3CCN(C4COC4)CC3)c2)nn1] |
| 311 | 4429 | 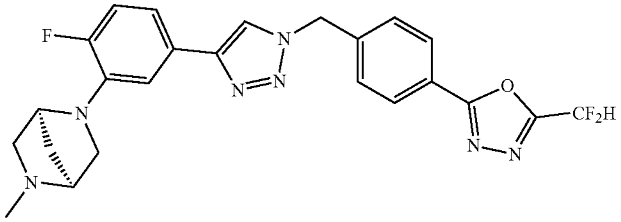 [SMILES: CN1C[C@@H]2C[C@H]1CN2c1cc(-c2cn(Cc3ccc(-c4nnc(C(F)F)o4)cc3)nn2)ccc1F] |
| 312 | 4430 | 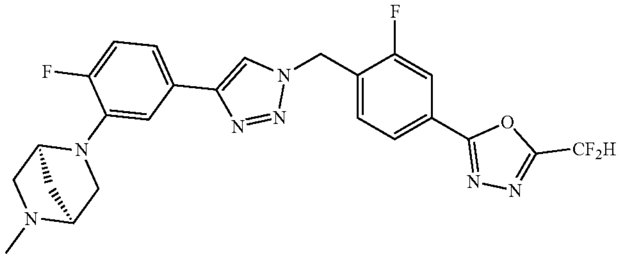 [SMILES: CN1C[C@@H]2C[C@H]1CN2c1cc(-c2cn(Cc3ccc(-c4nnc(C(F)F)o4)cc3F)nn2)ccc1F] |
| 313 | 4431 | 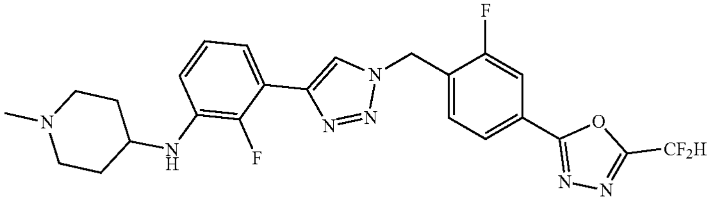 [SMILES: CN1CCC(Nc2cccc(-c3cn(Cc4ccc(-c5nnc(C(F)F)o5)cc4F)nn3)c2F)CC1] |
| 314 | 4432 | 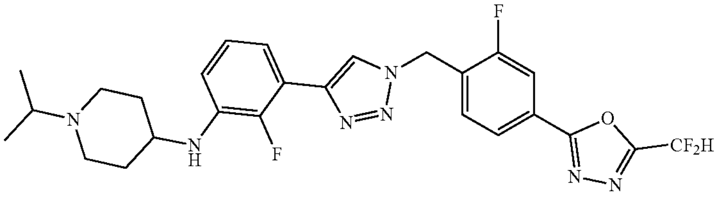 [SMILES: CC(C)N1CCC(Nc2cccc(-c3cn(Cc4ccc(-c5nnc(C(F)F)o5)cc4F)nn3)c2F)CC1] |
| 315 | 4433 | 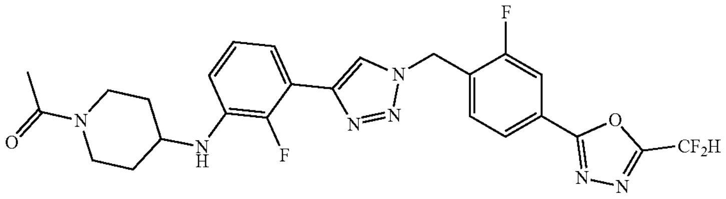 [SMILES: CC(=O)N1CCC(Nc2cccc(-c3cn(Cc4ccc(-c5nnc(C(F)F)o5)cc4F)nn3)c2F)CC1] |

-continued
| Example | Compound | Structure |
| --- | --- | --- |
| 316 | 4434 | 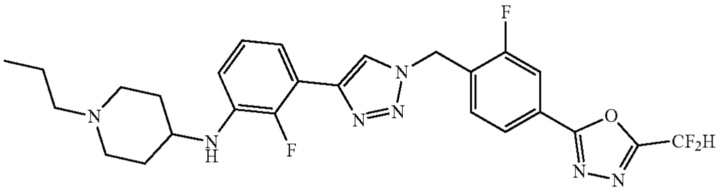 [SMILES: CCCN1CCC(Nc2cccc(-c3cn(Cc4ccc(-c5nnc(C(F)F)o5)cc4F)nn3)c2F)CC1] |
| 317 | 4435 | 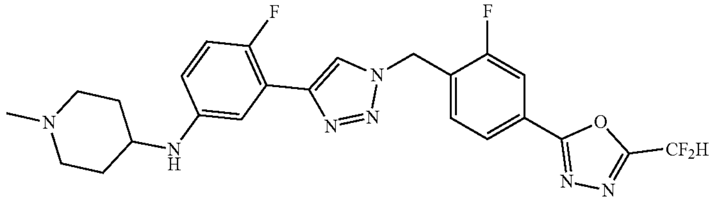 [SMILES: CN1CCC(Nc2ccc(F)c(-c3cn(Cc4ccc(-c5nnc(C(F)F)o5)cc4F)nn3)c2)CC1] |
| 318 | 4436 | 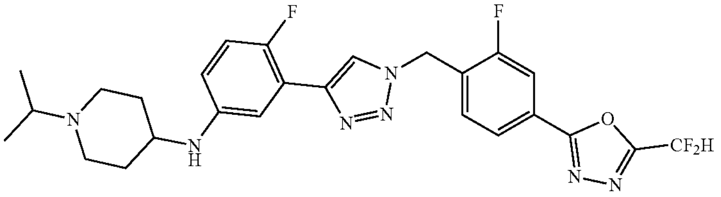 [SMILES: CC(C)N1CCC(Nc2ccc(F)c(-c3cn(Cc4ccc(-c5nnc(C(F)F)o5)cc4F)nn3)c2)CC1] |
| 319 | 4437 | 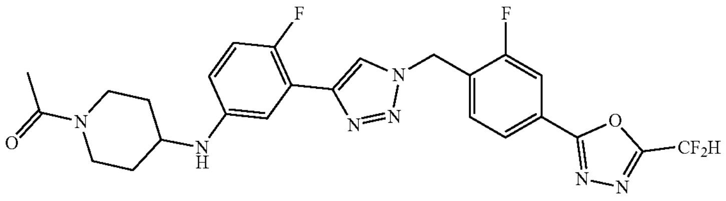 [SMILES: CC(=O)N1CCC(Nc2ccc(F)c(-c3cn(Cc4ccc(-c5nnc(C(F)F)o5)cc4F)nn3)c2)CC1] |
| 320 | 4438 | 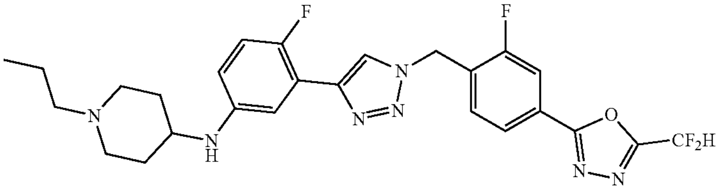 [SMILES: CCCN1CCC(Nc2ccc(F)c(-c3cn(Cc4ccc(-c5nnc(C(F)F)o5)cc4F)nn3)c2)CC1] |
| 321 | 4439 | 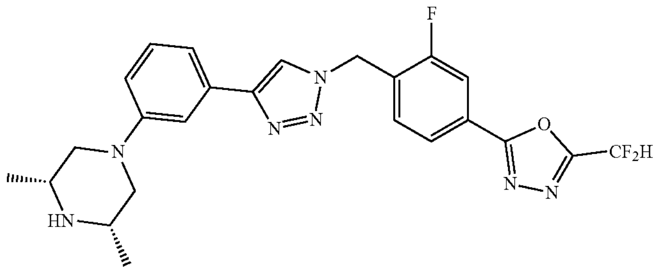 [SMILES: C[C@@H]1CN(c2cccc(-c3cn(Cc4ccc(-c5nnc(C(F)F)o5)cc4F)nn3)c2)C[C@H](C)N1] |
| 322 | 4440 | 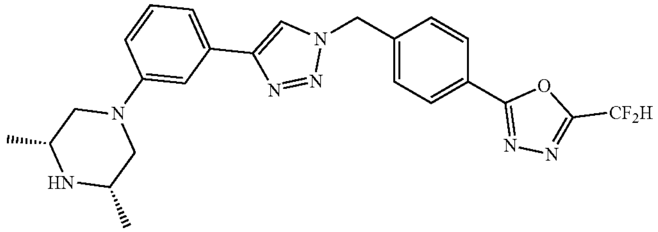 [SMILES: C[C@@H]1CN(c2cccc(-c3cn(Cc4ccc(-c5nnc(C(F)F)o5)cc4)nn3)c2)C[C@H](C)N1] |

-continued
| Example | Compound | Structure |
| --- | --- | --- |
| 323 | 4441 | 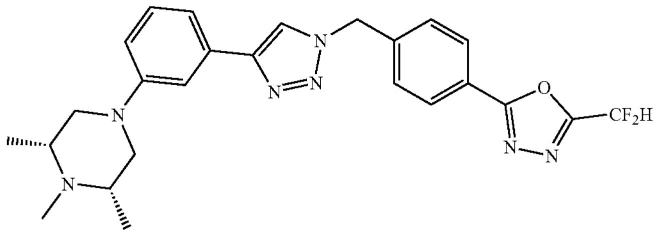 [SMILES: C[C@@H]1CN(c2cccc(-c3cn(Cc4ccc(-c5nnc(C(F)F)o5)cc4)nn3)c2)C[C@H](C)N1C] |
| 324 | 4442 | 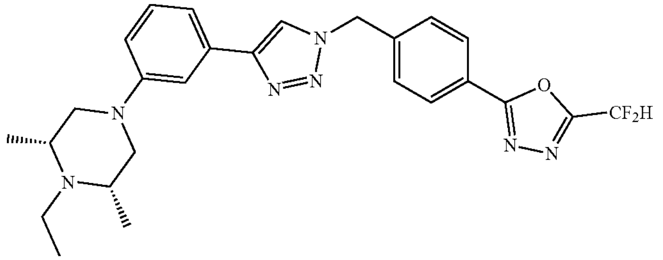 [SMILES: CCN1[C@H](C)CN(c2cccc(-c3cn(Cc4ccc(-c5nnc(C(F)F)o5)cc4)nn3)c2)C[C@@H]1C] |
| 325 | 4443 | 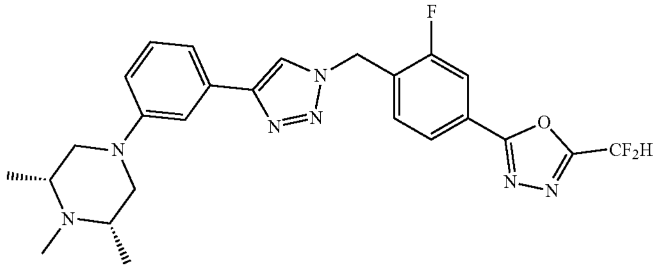 [SMILES: C[C@@H]1CN(c2cccc(-c3cn(Cc4ccc(-c5nnc(C(F)F)o5)cc4F)nn3)c2)C[C@H](C)N1C] |
| 326 | 4444 | 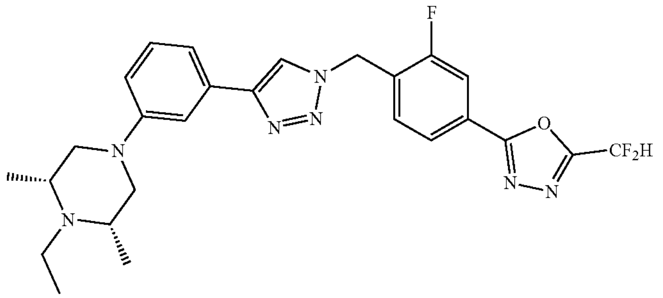 [SMILES: CCN1[C@H](C)CN(c2cccc(-c3cn(Cc4ccc(-c5nnc(C(F)F)o5)cc4F)nn3)c2)C[C@@H]1C] |
| 327 | 4448 | 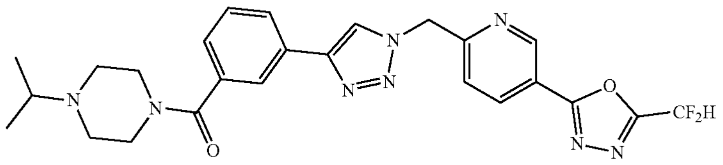 [SMILES: CC(C)N1CCN(C(=O)c2cccc(-c3cn(Cc4ccc(-c5nnc(C(F)F)o5)cn4)nn3)c2)CC1] |
| 328 | 4449 | 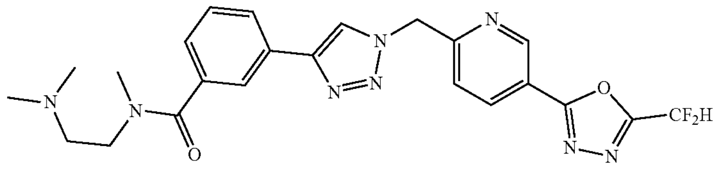 [SMILES: CN(C)CCN(C)C(=O)c1cccc(-c2cn(Cc3ccc(-c4nnc(C(F)F)o4)cn3)nn2)c1] |

-continued
| Example | Compound | Structure |
|---|---|---|
| 329 | 4450 | 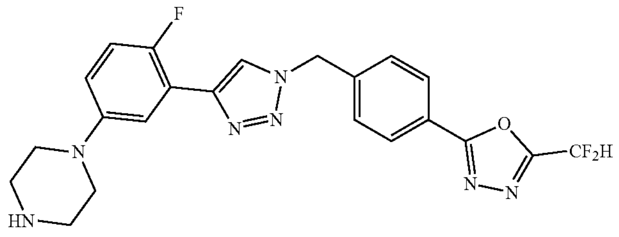 [SMILES: Fc1ccc(N2CCNCC2)cc1-c1cn(Cc2ccc(-c3nnc(C(F)F)o3)cc2)nn1] |
| 330 | 4451 | 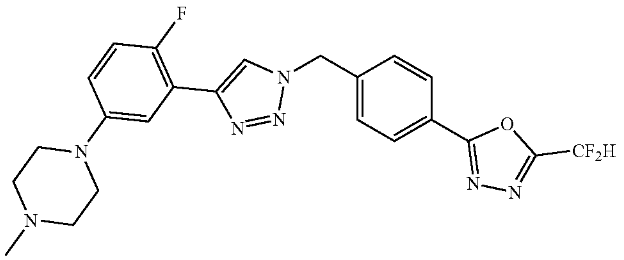 [SMILES: CN1CCN(c2ccc(F)c(-c3cn(Cc4ccc(-c5nnc(C(F)F)o5)cc4)nn3)c2)CC1] |
| 331 | 4452 | 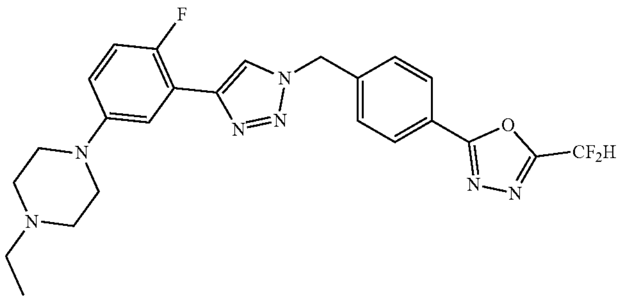 [SMILES: CCN1CCN(c2ccc(F)c(-c3cn(Cc4ccc(-c5nnc(C(F)F)o5)cc4)nn3)c2)CC1] |
| 332 | 4453 | 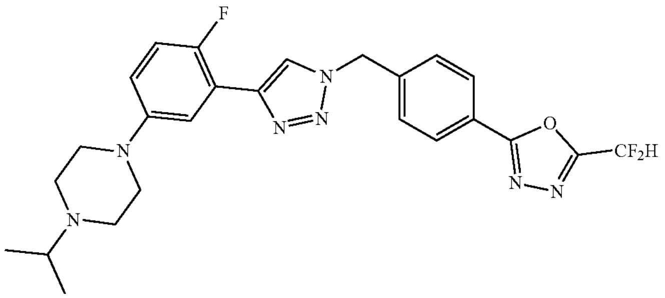 [SMILES: CC(C)N1CCN(c2ccc(F)c(-c3cn(Cc4ccc(-c5nnc(C(F)F)o5)cc4)nn3)c2)CC1] |
| 333 | 4454 | 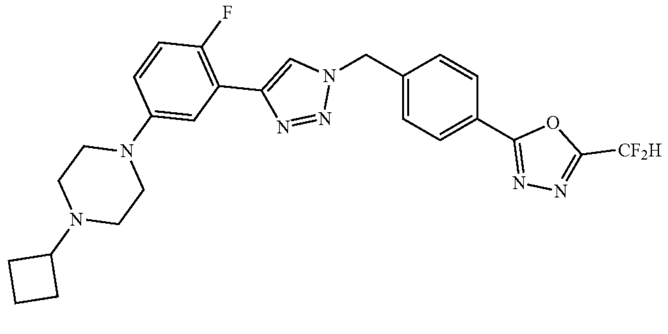 [SMILES: Fc1ccc(N2CCN(C3CCC3)CC2)cc1-c1cn(Cc2ccc(-c3nnc(C(F)F)o3)cc2)nn1] |

-continued
| Example | Compound | Structure |
|---|---|---|
| 334 | 4455 | 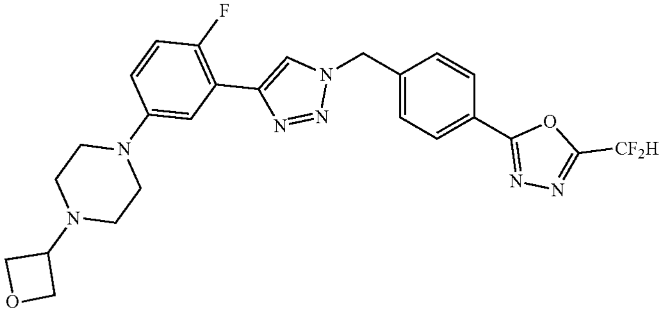 [SMILES: Fc1ccc(N2CCN(C3COC3)CC2)cc1-c1cn(Cc2ccc(-c3nnc(C(F)F)o3)cc2)nn1] |
| 335 | 4460 | 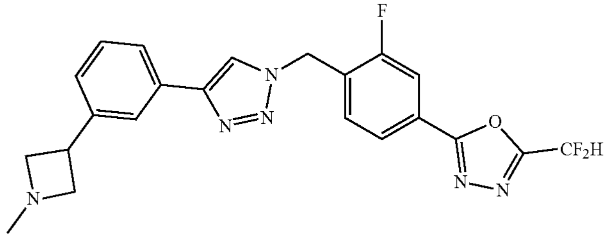 [SMILES: CN1CC(c2cccc(-c3cn(Cc4ccc(-c5nnc(C(F)F)o5)cc4F)nn3)c2)C1] |
| 336 | 4461 | 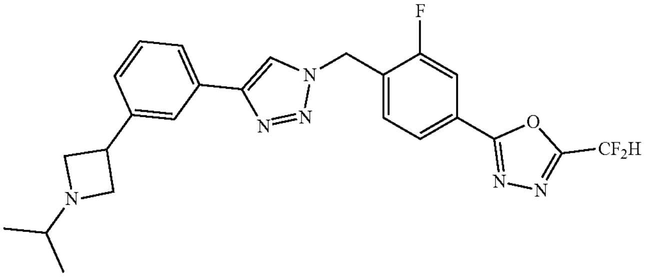 [SMILES: CC(C)N1CC(c2cccc(-c3cn(Cc4ccc(-c5nnc(C(F)F)o5)cc4F)nn3)c2)C1] |
| 337 | 4462 | 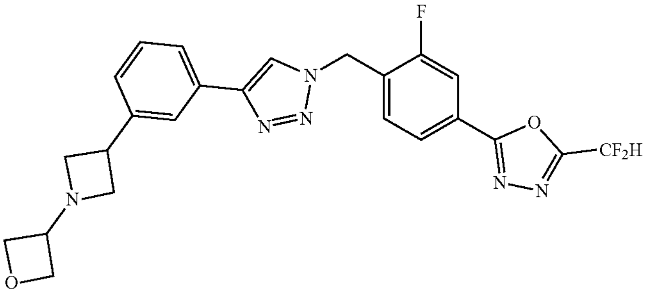 [SMILES: Fc1cc(-c2nnc(C(F)F)o2)ccc1Cn1cc(-c2cccc(C3CN(C4COC4)C3)c2)nn1] |
| 338 | 4463 | 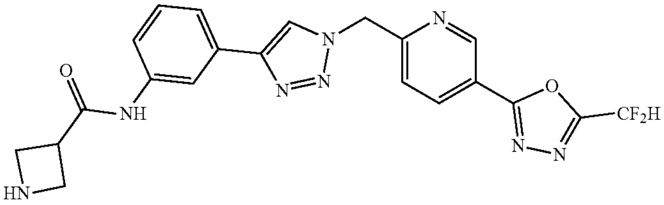 [SMILES: O=C(Nc1cccc(-c2cn(Cc3ccc(-c4nnc(C(F)F)o4)cn3)nn2)c1)C1CNC1] |
| 339 | 4464 | 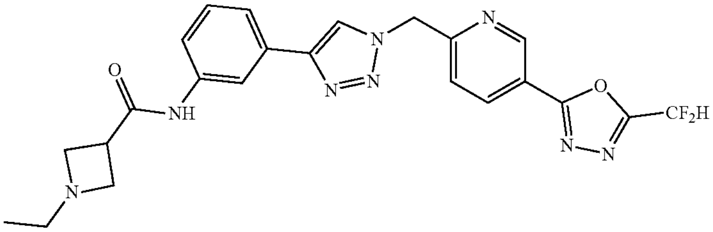 [SMILES: CCN1CC(C(=O)Nc2cccc(-c3cn(Cc4ccc(-c5nnc(C(F)F)o5)cn4)nn3)c2)C1] |

-continued
| Example | Compound | Structure |
|---|---|---|
| 340 | 4465 | 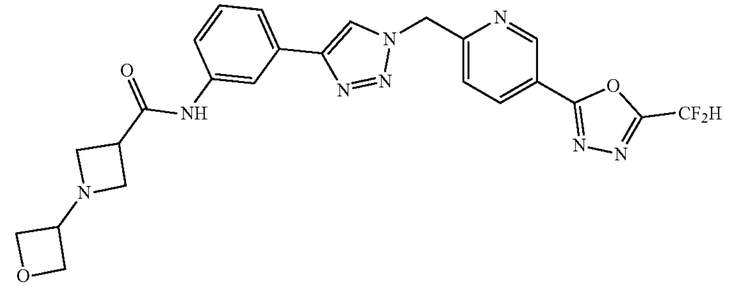 [SMILES: O=C(Nc1cccc(-c2cn(Cc3ccc(-c4nnc(C(F)F)o4)cn3)nn2)c1)C1CN(C2COC2)C1] |
| 341 | 4466 | 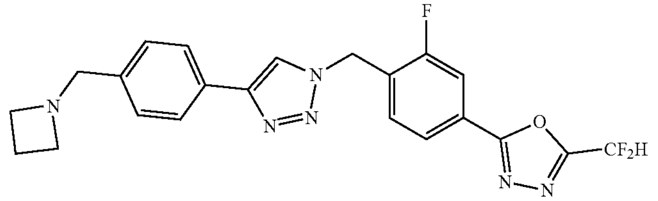 |
| 342 | 4467 | 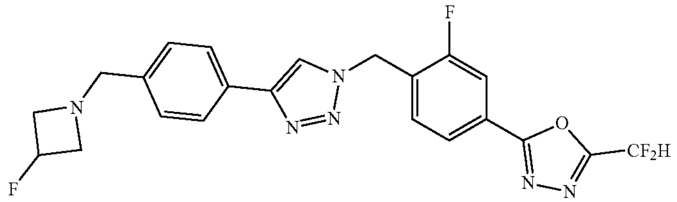 [SMILES: Fc1cc(-c2nnc(C(F)F)o2)ccc1Cn1cc(-c2ccc(CN3CC(F)C3)cc2)nn1] |
| 343 | 4468 | 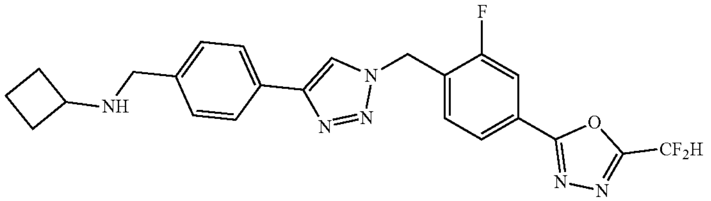 [SMILES: Fc1cc(-c2nnc(C(F)F)o2)ccc1Cn1cc(-c2ccc(CNC3CCC3)cc2)nn1] |
| 344 | 4469 | 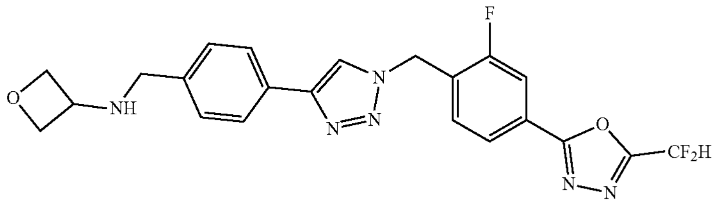 [SMILES: Fc1cc(-c2nnc(C(F)F)o2)ccc1Cn1cc(-c2ccc(CNC3COC3)cc2)nn1] |
| 345 | 4470 | 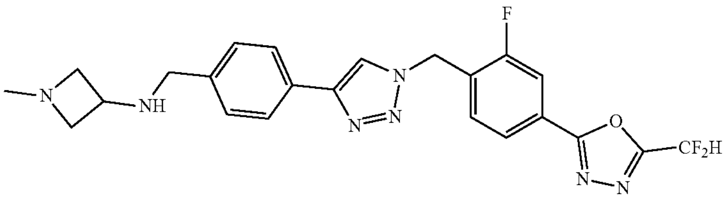 [SMILES: CN1CC(NCc2ccc(-c3cn(Cc4ccc(-c5nnc(C(F)F)o5)cc4F)nn3)cc2)C1] |
| 346 | 4471 | 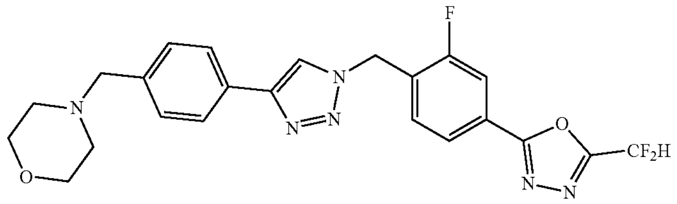 [SMILES: Fc1cc(-c2nnc(C(F)F)o2)ccc1Cn1cc(-c2ccc(CN3CCOCC3)cc2)nn1] |

-continued
| Example | Compound | Structure |
|---|---|---|
| 347 | 4472 | 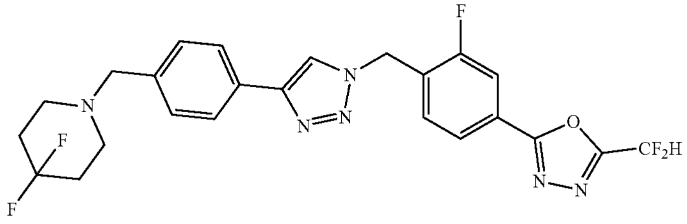 |
| 348 | 4473 | 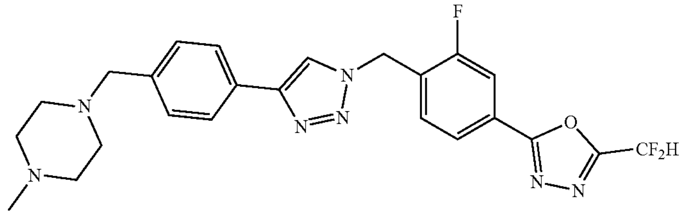 [SMILES: CN1CCN(Cc2ccc(-c3cn(Cc4ccc(-c5nnc(C(F)F)o5)cc4F)nn3)cc2)CC1] |
| 349 | 4474 | 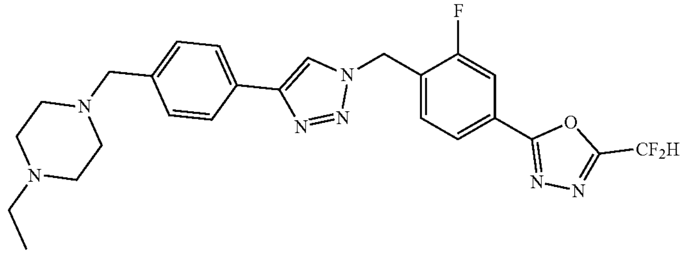 [SMILES: CCN1CCN(Cc2ccc(-c3cn(Cc4ccc(-c5nnc(C(F)F)o5)cc4F)nn3)cc2)CC1] |
| 350 | 4475 | 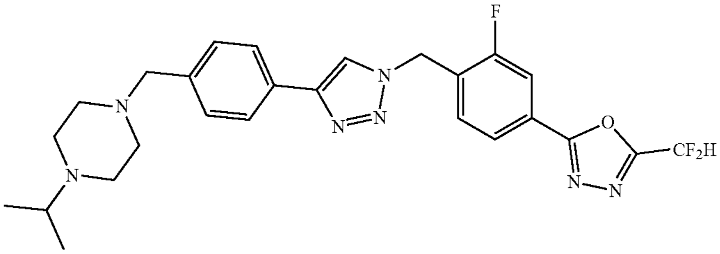 [SMILES: CC(C)N1CCN(Cc2ccc(-c3cn(Cc4ccc(-c5nnc(C(F)F)o5)cc4F)nn3)cc2)CC1] |
| 351 | 4476 | 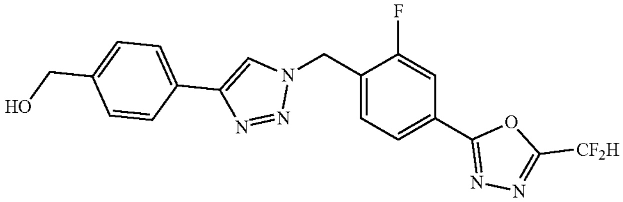 [SMILES: OCc1ccc(-c2cn(Cc3ccc(-c4nnc(C(F)F)o4)cc3F)nn2)cc1] |
| 352 | 4477 | 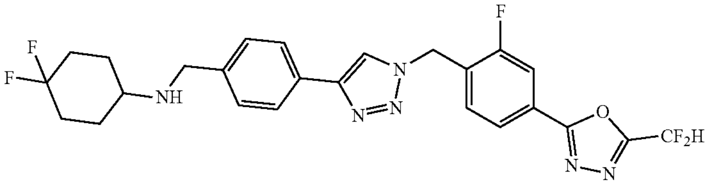 [SMILES: Fc1cc(-c2nnc(C(F)F)o2)ccc1Cn1cc(-c2ccc(CNC3CCC(F)(F)CC3)cc2)nn1] |
| 353 | 4478 | 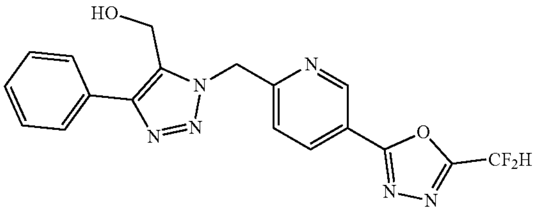 [SMILES: OCc1c(-c2ccccc2)nnn1Cc1ccc(-c2nnc(C(F)F)o2)cn1] |

-continued
| Example | Compound | Structure |
| --- | --- | --- |
| 354 | 4479 | 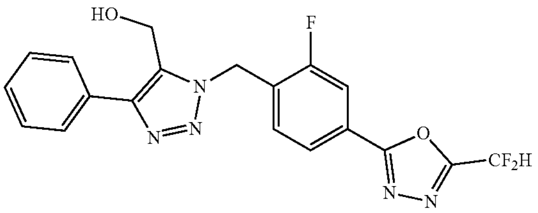 [SMILES: OCc1c(-c2ccccc2)nnn1Cc1ccc(-c2nnc(C(F)F)o2)cc1F] |
| 355 | 4480 | 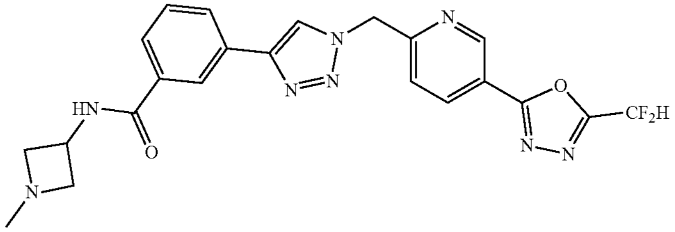 [SMILES: CN1CC(NC(=O)c2cccc(-c3cn(Cc4ccc(-c5nnc(C(F)F)o5)cn4)nn3)c2)C1] |
| 356 | 4482 | 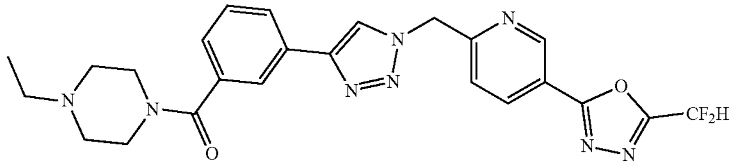 [SMILES: CCN1CCN(C(=O)c2cccc(-c3cn(Cc4ccc(-c5nnc(C(F)F)o5)cn4)nn3)c2)CC1] |
| 357 | 4483 | 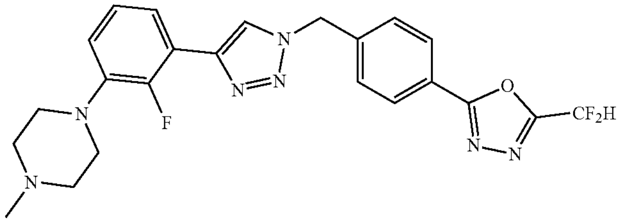 [SMILES: CN1CCN(c2cccc(-c3cn(Cc4ccc(-c5nnc(C(F)F)o5)cc4)nn3)c2F)CC1] |
| 358 | 4484 | 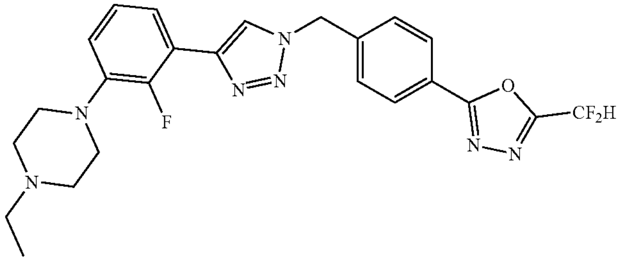 [SMILES: CCN1CCN(c2cccc(-c3cn(Cc4ccc(-c5nnc(C(F)F)o5)cc4)nn3)c2F)CC1] |
| 359 | 4485 | 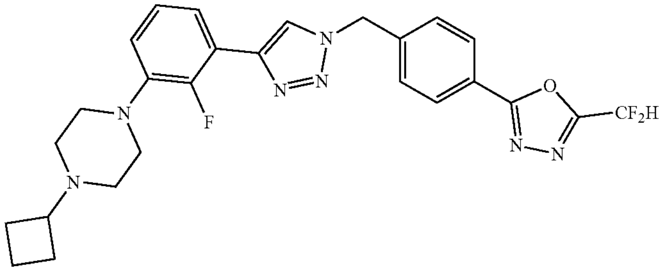 [SMILES: Fc1c(-c2cn(Cc3ccc(-c4nnc(C(F)F)o4)cc3)nn2)cccc1N1CCN(C2CCC2)CC1] |

-continued
| Example | Compound | Structure |
| --- | --- | --- |
| 360 | 4486 | 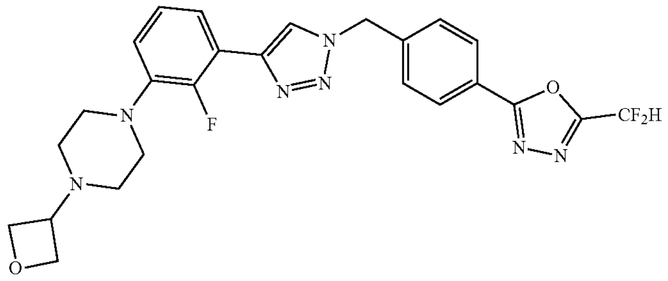 [SMILES: Fc1c(-c2cn(Cc3ccc(-c4nnc(C(F)F)o4)cc3)nn2)cccc1N1CCN(C2COC2)CC1] |
| 361 | 4487 | 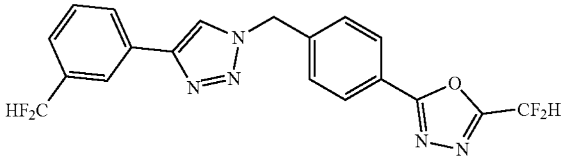 |
| 362 | 4488 | 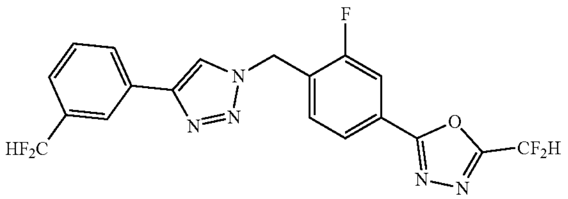 |
| 363 | 4489 | 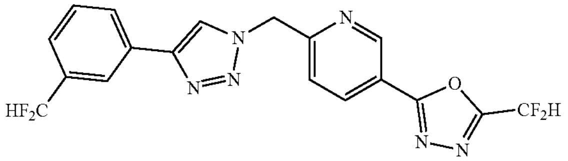 |
| 364 | 4490 | 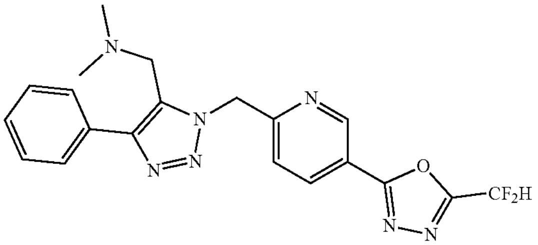 [SMILES: CN(C)Cc1c(-c2ccccc2)nnn1Cc1ccc(-c2nnc(C(F)F)o2)cn1] |
| 365 | 4491 | 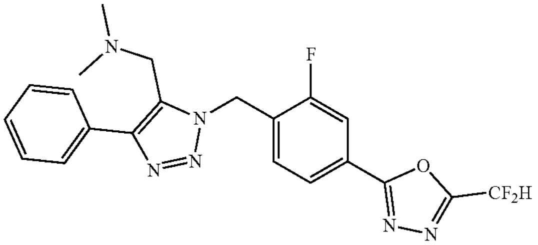 [SMILES: CN(C)Cc1c(-c2ccccc2)nnn1Cc1ccc(-c2nnc(C(F)F)o2)cc1F] |
| 366 | 4492 | 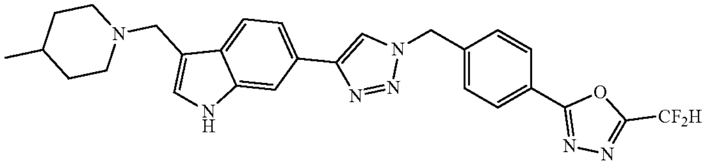 [SMILES: CC1CCN(Cc2c[nH]c3cc(-c4cn(Cc5ccc(-c6nnc(C(F)F)o6)cc5)nn4)ccc23)CC1] |

-continued
| Example | Compound | Structure |
| --- | --- | --- |
| 367 | 4493 | 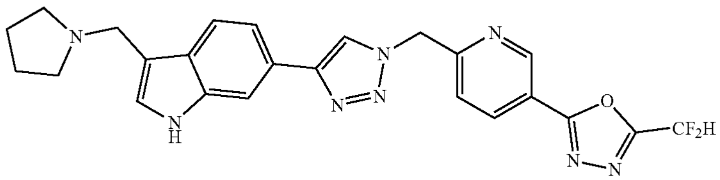 [SMILES: FC(F)c1nnc(-c2ccc(Cn3cc(-c4ccc5c(CN6CCCC6)c[nH]c5c4)nn3)nc2)o1] |
| 368 | 4494 | 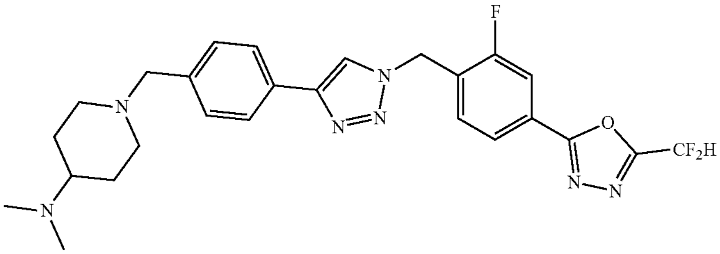 [SMILES: CN(C)C1CCN(Cc2ccc(-c3cn(Cc4ccc(-c5nnc(C(F)F)o5)cc4F)nn3)cc2)CC1] |
| 369 | 4495 | 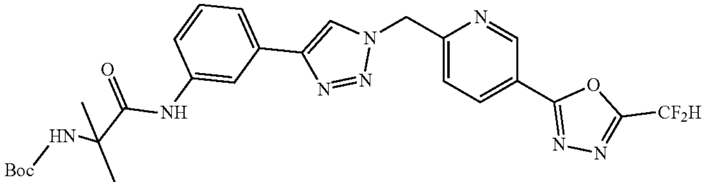 [SMILES: CC(C)(C)OC(=O)NC(C)(C)C(=O)Nc1cccc(-c2cn(Cc3ccc(-c4nnc(C(F)F)o4)cn3)nn2)c1] |
| 370 | 4496 | 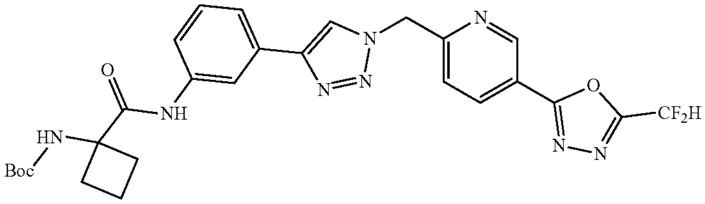 [SMILES: CC(C)(C)OC(=O)NC1(C(=O)Nc2cccc(-c3cn(Cc4ccc(-c5nnc(C(F)F)o5)cn4)nn3)c2)CCC1] |
| 371 | 4497 | 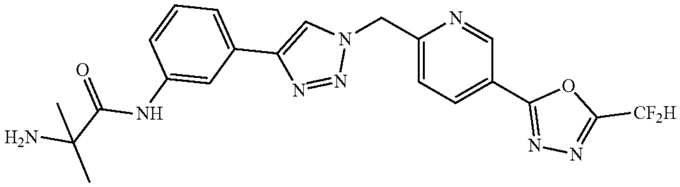 [SMILES: CC(C)(N)C(=O)Nc1cccc(-c2cn(Cc3ccc(-c4nnc(C(F)F)o4)cn3)nn2)c1] |
| 372 | 4498 | 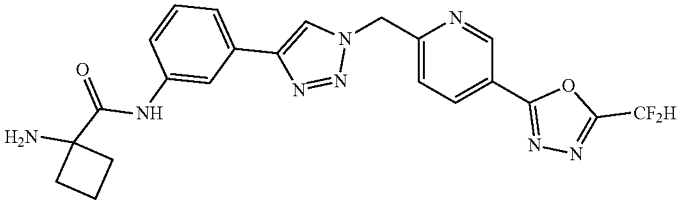 [SMILES: NC1(C(=O)Nc2cccc(-c3cn(Cc4ccc(-c5nnc(C(F)F)o5)cn4)nn3)c2)CCC1] |
| 373 | 4499 | 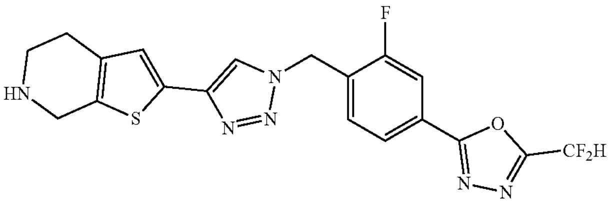 [SMILES: Fc1cc(-c2nnc(C(F)F)o2)ccc1Cn1cc(-c2cc3c(s2)CNCC3)nn1] |

-continued
| Example | Compound | Structure |
|---|---|---|
| 374 | 4500 | 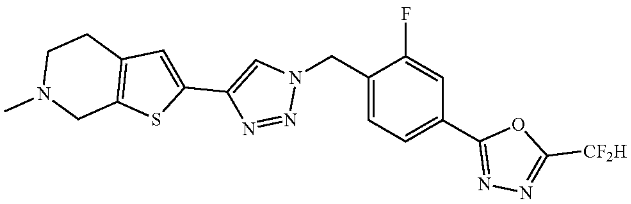 [SMILES: CN1CCc2cc(-c3cn(Cc4ccc(-c5nnc(C(F)F)o5)cc4F)nn3)sc2C1] |
| 375 | 4501 | 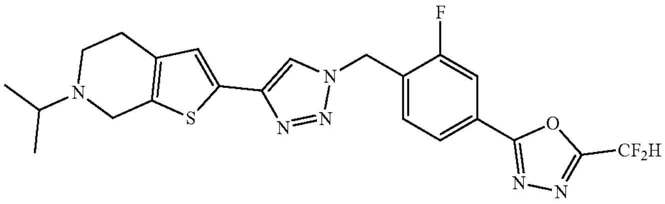 [SMILES: CC(C)N1CCc2cc(-c3cn(Cc4ccc(-c5nnc(C(F)F)o5)cc4F)nn3)sc2C1] |
| 376 | 4502 | 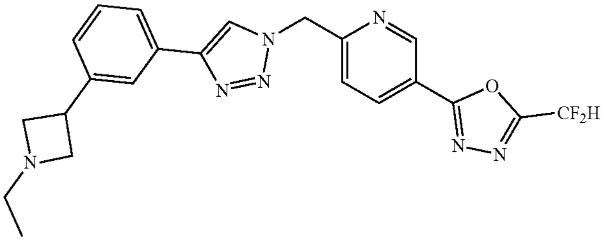 [SMILES: CCN1CC(c2cccc(-c3cn(Cc4ccc(-c5nnc(C(F)F)o5)cn4)nn3)c2)C1] |
| 377 | 4503 | 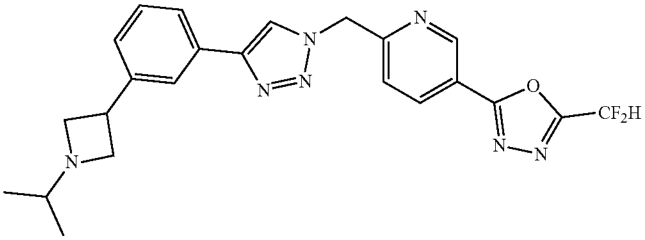 [SMILES: CC(C)N1CC(c2cccc(-c3cn(Cc4ccc(-c5nnc(C(F)F)o5)cn4)nn3)c2)C1] |
| 378 | 4504 | 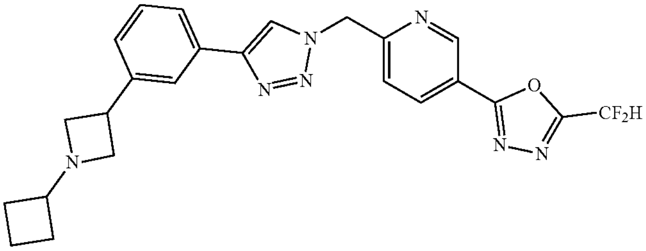 [SMILES: FC(F)c1nnc(-c2ccc(Cn3cc(-c4cccc(C5CN(C6CCC6)C5)c4)nn3)nc2)o1] |
| 379 | 4505 | 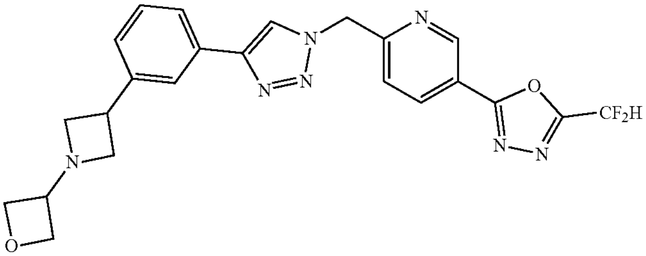 [SMILES: FC(F)c1nnc(-c2ccc(Cn3cc(-c4cccc(C5CN(C6COC6)C5)c4)nn3)nc2)o1] |

-continued
| Example | Compound | Structure |
|---|---|---|
| 380 | 4506 | 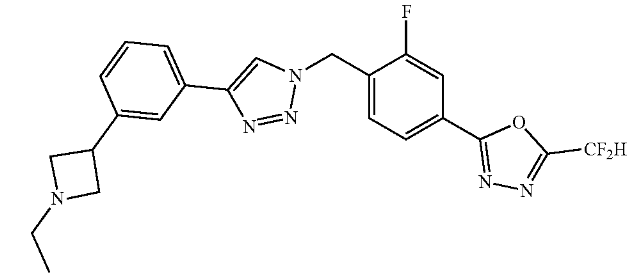 [SMILES: CCN1CC(c2cccc(-c3cn(Cc4ccc(-c5nnc(C(F)F)o5)cc4F)nn3)c2)C1] |
| 381 | 4507 | 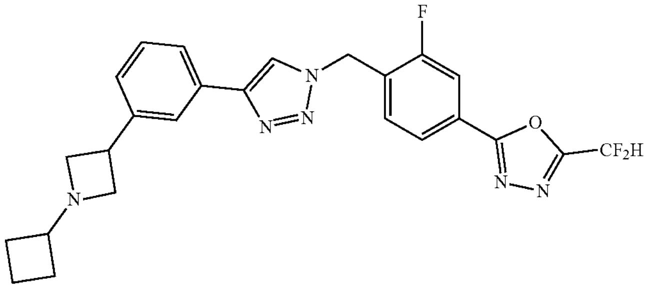 [SMILES: Fc1cc(-c2nnc(C(F)F)o2)ccc1Cn1cc(-c2cccc(C3CN(C4CCC4)C3)c2)nn1] |
| 382 | 4508 | 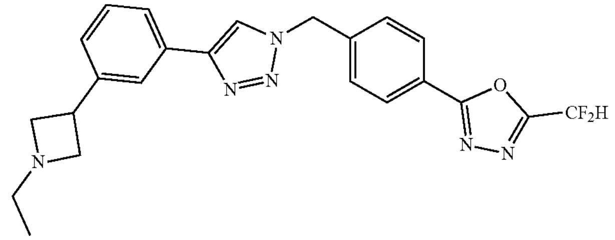 [SMILES: CCN1CC(c2cccc(-c3cn(Cc4ccc(-c5nnc(C(F)F)o5)cc4)nn3)c2)C1] |
| 383 | 4509 | 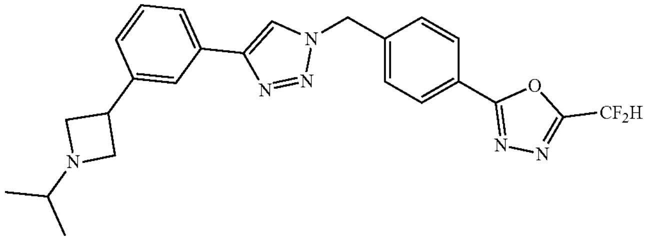 [SMILES: CC(C)N1CC(c2cccc(-c3cn(Cc4ccc(-c5nnc(C(F)F)o5)cc4)nn3)c2)C1] |
| 384 | 4510 | 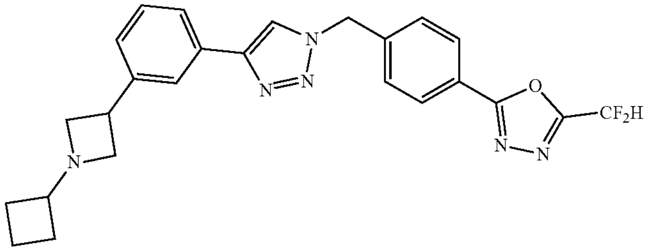 [SMILES: FC(F)c1nnc(-c2ccc(Cn3cc(-c4cccc(C5CN(C6CCC6)C5)c4)nn3)cc2)o1] |
| 385 | 4511 | 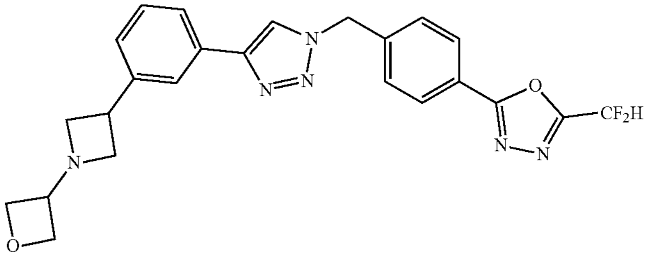 [SMILES: FC(F)c1nnc(-c2ccc(Cn3cc(-c4cccc(C5CN(C6COC6)C5)c4)nn3)cc2)o1] |

-continued
| Example | Compound | Structure |
| --- | --- | --- |
| 386 | 4513 | 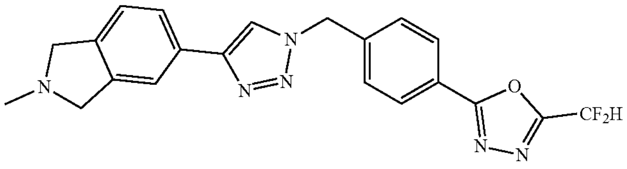 [SMILES: CN1Cc2ccc(-c3cn(Cc4ccc(-c5nnc(C(F)F)o5)cc4)nn3)cc2C1] |
| 387 | 4515 | 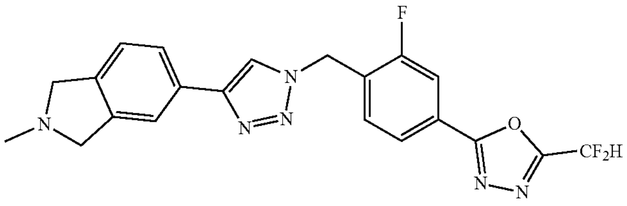 [SMILES: CN1Cc2ccc(-c3cn(Cc4ccc(-c5nnc(C(F)F)o5)cc4F)nn3)cc2C1] |
| 388 | 4516 | 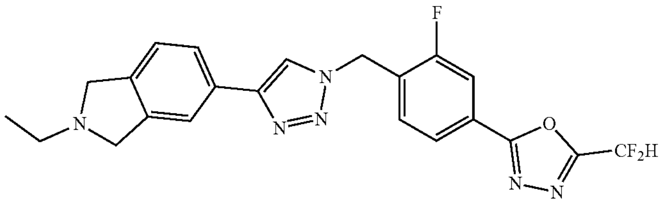 [SMILES: CCN1Cc2ccc(-c3cn(Cc4ccc(-c5nnc(C(F)F)o5)cc4F)nn3)cc2C1] |
| 389 | 4517 | 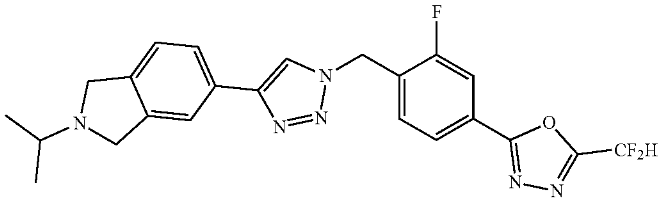 [SMILES: CC(C)N1Cc2ccc(-c3cn(Cc4ccc(-c5nnc(C(F)F)o5)cc4F)nn3)cc2C1] |
| 390 | 4518 | 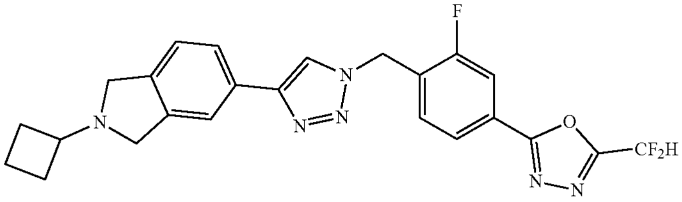 [SMILES: Fc1cc(-c2nnc(C(F)F)o2)ccc1Cn1cc(-c2ccc3c(c2)CN(C2CCC2)C3)nn1] |
| 391 | 4519 | 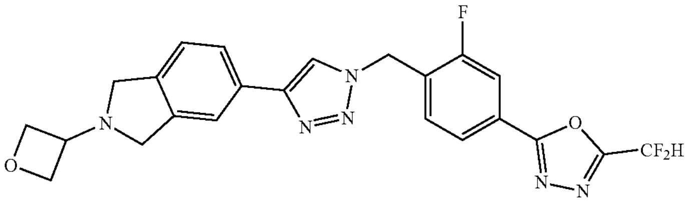 [SMILES: Fc1cc(-c2nnc(C(F)F)o2)ccc1Cn1cc(-c2ccc3c(c2)CN(C2COC2)C3)nn1] |
| 392 | 4521 | 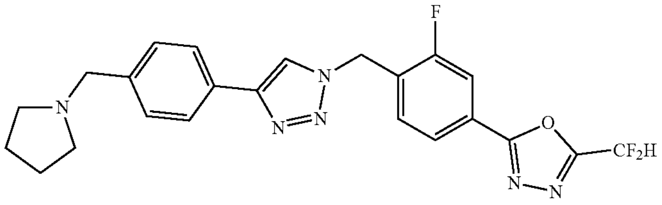 [SMILES: Fc1cc(-c2nnc(C(F)F)o2)ccc1Cn1cc(-c2ccc(CN3CCCC3)cc2)nn1] |

-continued
| Example | Compound | Structure |
|---|---|---|
| 393 | 4522 | 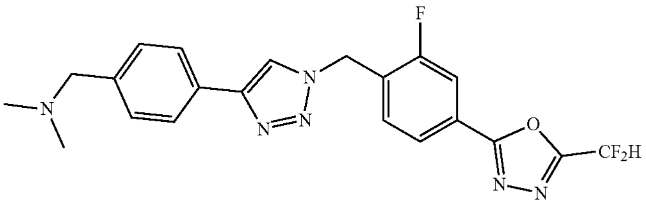 [SMILES: CN(C)Cc1ccc(-c2cn(Cc3ccc(-c4nnc(C(F)F)o4)cc3F)nn2)cc1] |
| 394 | 4523 | 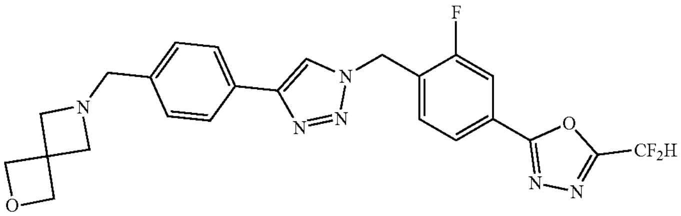 [SMILES: Fc1cc(-c2nnc(C(F)F)o2)ccc1Cn1cc(-c2ccc(CN3CC4(COC4)C3)cc2)nn1] |
| 395 | 4524 | 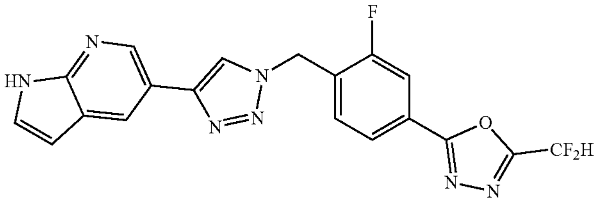 [SMILES: Fc1cc(-c2nnc(C(F)F)o2)ccc1Cn1cc(-c2cnc3[nH]ccc3c2)nn1] |
| 396 | 4525 | 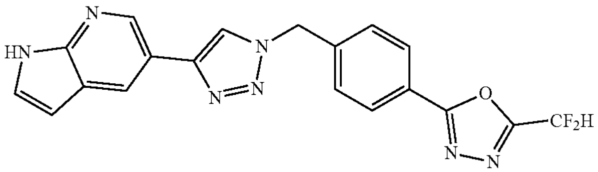 [SMILES: FC(F)c1nnc(-c2ccc(Cn3cc(-c4cnc5[nH]ccc5c4)nn3)cc2)o1] |
| 397 | 4526 | 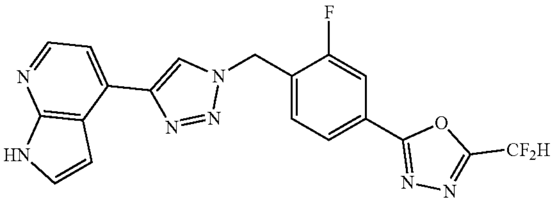 [SMILES: Fc1cc(-c2nnc(C(F)F)o2)ccc1Cn1cc(-c2ccnc3[nH]ccc23)nn1] |
| 398 | 4527 | 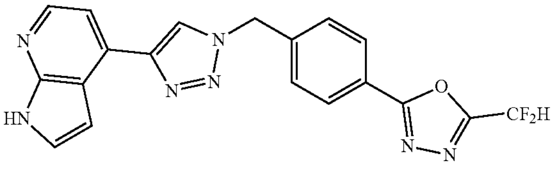 [SMILES: FC(F)c1nnc(-c2ccc(Cn3cc(-c4ccnc5[nH]ccc45)nn3)cc2)o1] |
| 399 | 4528 | 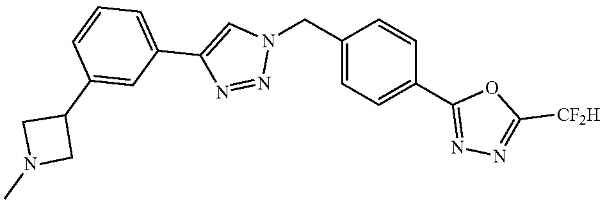 [SMILES: CN1CC(c2cccc(-c3cn(Cc4ccc(-c5nnc(C(F)F)o5)cc4)nn3)c2)C1] |

-continued
| Example | Compound | Structure |
| --- | --- | --- |
| 400 | 4529 | 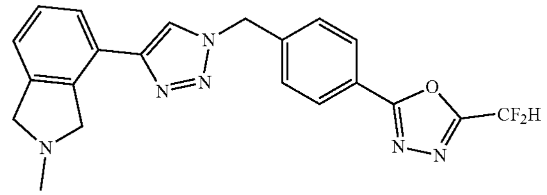 [SMILES: CN1Cc2cccc(-c3cn(Cc4ccc(-c5nnc(C(F)F)o5)cc4)nn3)c2C1] |
| 401 | 4530 | 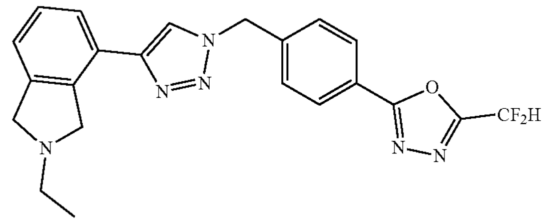 [SMILES: CCN1Cc2cccc(-c3cn(Cc4ccc(-c5nnc(C(F)F)o5)cc4)nn3)c2C1] |
| 402 | 4531 | 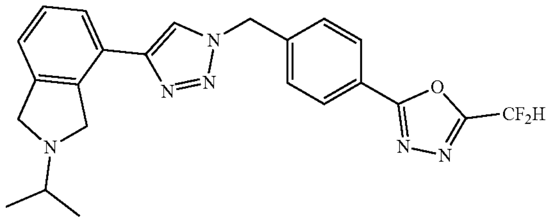 [SMILES: CC(C)N1Cc2cccc(-c3cn(Cc4ccc(-c5nnc(C(F)F)o5)cc4)nn3)c2C1] |
| 403 | 4532 | 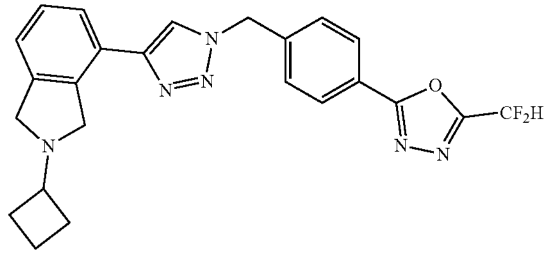 [SMILES: FC(F)c1nnc(-c2ccc(Cn3cc(-c4cccc5c4CN(C4CCC4)C5)nn3)cc2)o1] |
| 404 | 4533 | 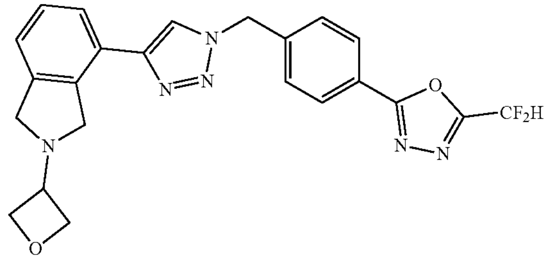 |
| 405 | 4534 | 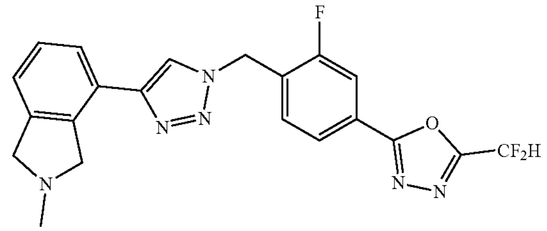 [SMILES: CN1Cc2cccc(-c3cn(Cc4ccc(-c5nnc(C(F)F)o5)cc4F)nn3)c2C1] |

-continued
| Example | Compound | Structure |
|---|---|---|
| 406 | 4535 | 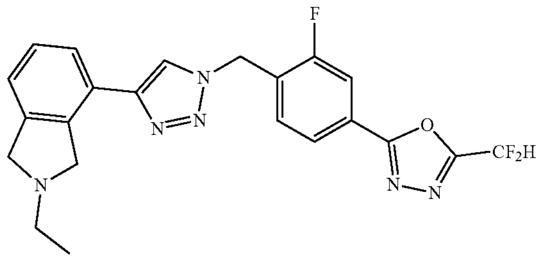 [SMILES: CCN1Cc2cccc(-c3cn(Cc4ccc(-c5nnc(C(F)F)o5)cc4F)nn3)c2C1] |
| 407 | 4536 | 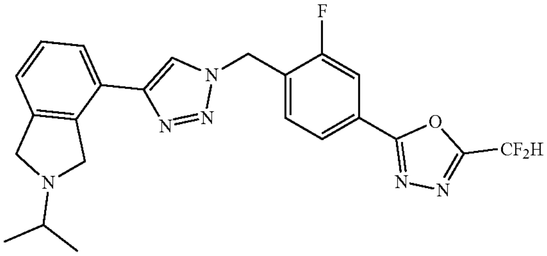 [SMILES: CC(C)N1Cc2cccc(-c3cn(Cc4ccc(-c5nnc(C(F)F)o5)cc4F)nn3)c2C1] |
| 408 | 4537 | 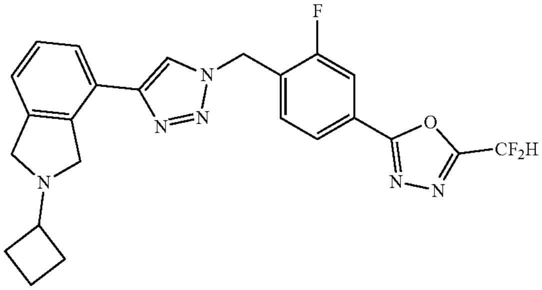 [SMILES: Fc1cc(-c2nnc(C(F)F)o2)ccc1Cn1cc(-c2cccc3c2CN(C2CCC2)C3)nn1] |
| 409 | 4538 | 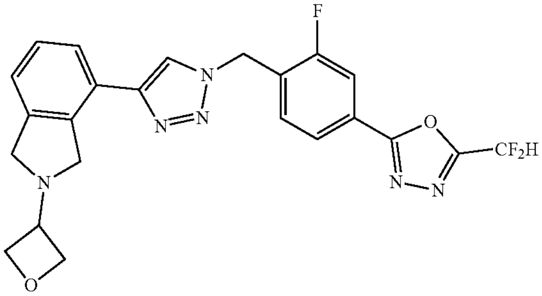 [SMILES: Fc1cc(-c2nnc(C(F)F)o2)ccc1Cn1cc(-c2cccc3c2CN(C2COC2)C3)nn1] |
| 410 | 4539 | 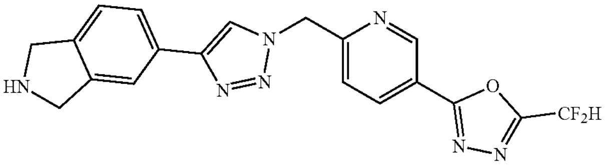 [SMILES: FC(F)c1nnc(-c2ccc(Cn3cc(-c4ccc5c(c4)CNC5)nn3)nc2)o1] |
| 411 | 4540 | 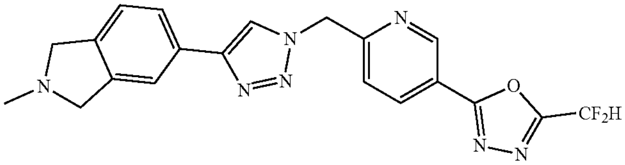 [SMILES: CN1Cc2ccc(-c3cn(Cc4ccc(-c5nnc(C(F)F)o5)cn4)nn3)cc2C1] |

-continued
| Example | Compound | Structure |
|---|---|---|
| 412 | 4541 | 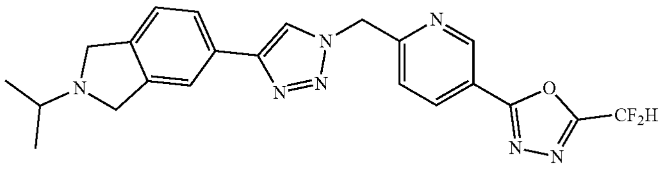 [SMILES: CC(C)N1Cc2ccc(-c3cn(Cc4ccc(-c5nnc(C(F)F)o5)cn4)nn3)cc2C1] |
| 413 | 4542 | 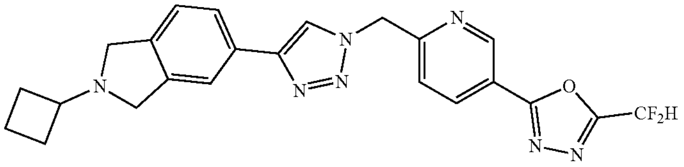 [SMILES: FC(F)c1nnc(-c2ccc(Cn3cc(-c4ccc5c(c4)CN(C4CCC4)C5)nn3)nc2)o1] |
| 414 | 4543 | 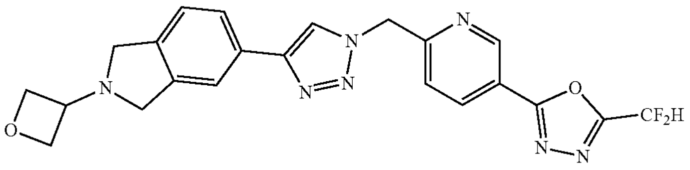 [SMILES: FC(F)c1nnc(-c2ccc(Cn3cc(-c4ccc5c(c4)CN(C4COC4)C5)nn3)nc2)o1] |
| 415 | 4548 | 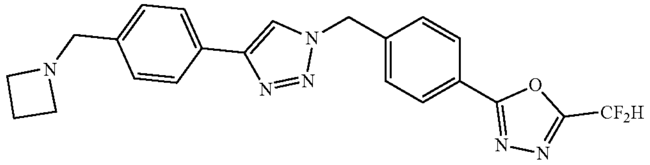 [SMILES: FC(F)c1nnc(-c2ccc(Cn3cc(-c4ccc(CN5CCC5)cc4)nn3)cc2)o1] |
| 416 | 4549 | 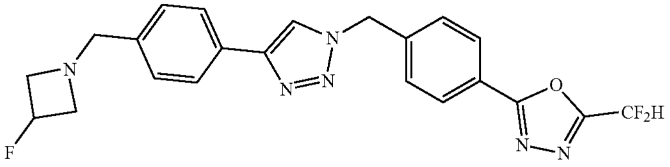 [SMILES: FC1CN(Cc2ccc(-c3cn(Cc4ccc(-c5nnc(C(F)F)o5)cc4)nn3)cc2)C1] |
| 417 | 4550 | 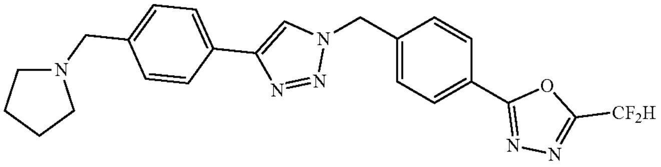 [SMILES: FC(F)c1nnc(-c2ccc(Cn3cc(-c4ccc(CN5CCCC5)cc4)nn3)cc2)o1] |
| 418 | 4551 | 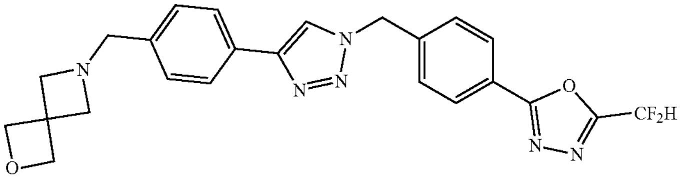 [SMILES: FC(F)c1nnc(-c2ccc(Cn3cc(-c4ccc(CN5CC6(COC6)C5)cc4)nn3)cc2)o1] |
| 419 | 4552 | 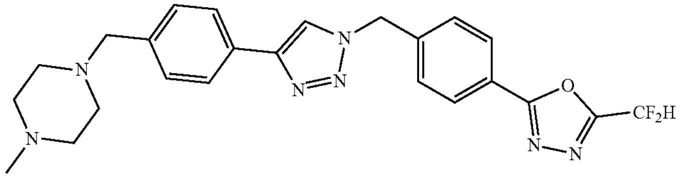 [SMILES: CN1CCN(Cc2ccc(-c3cn(Cc4ccc(-c5nnc(C(F)F)o5)cc4)nn3)cc2)CC1] |

-continued
| Example | Compound | Structure |
|---|---|---|
| 420 | 4553 | 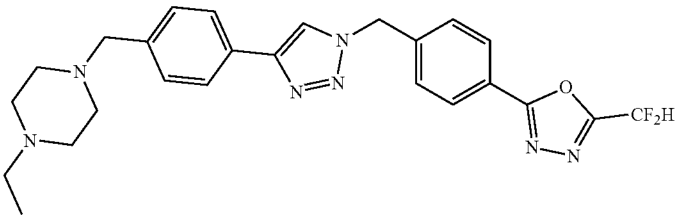 [SMILES: CCN1CCN(Cc2ccc(-c3cn(Cc4ccc(-c5nnc(C(F)F)o5)cc4)nn3)cc2)CC1] |
| 421 | 4554 | 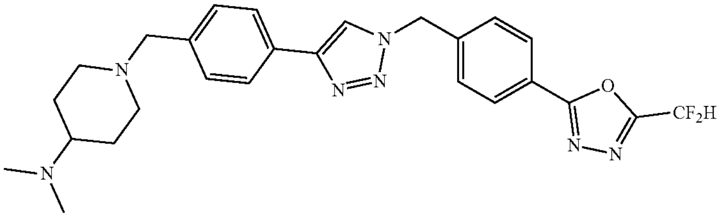 [SMILES: CN(C)C1CCN(Cc2ccc(-c3cn(Cc4ccc(-c5nnc(C(F)F)o5)cc4)nn3)cc2)CC1] |
| 422 | 4555 | 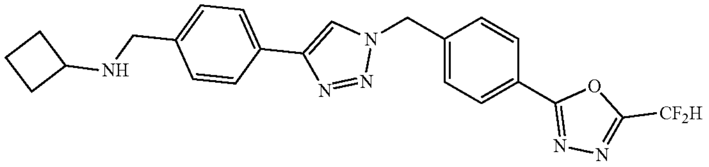 [SMILES: FC(F)c1nnc(-c2ccc(Cn3cc(-c4ccc(CNC5CCC5)cc4)nn3)cc2)o1] |
| 423 | 4556 | 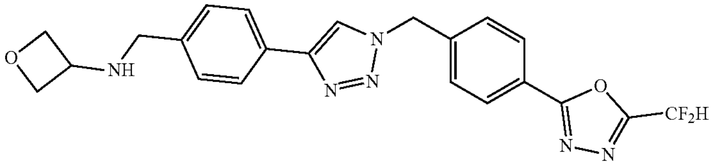 [SMILES: FC(F)c1nnc(-c2ccc(Cn3cc(-c4ccc(CNC5COC5)cc4)nn3)cc2)o1] |
| 424 | 4557 | 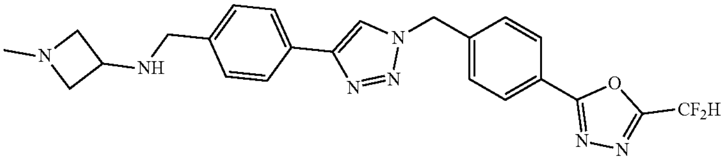 [SMILES: CN1CC(NCc2ccc(-c3cn(Cc4ccc(-c5nnc(C(F)F)o5)cc4)nn3)cc2)C1] |
| 425 | 4558 | 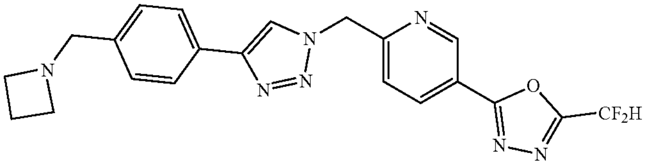 [SMILES: FC(F)c1nnc(-c2ccc(Cn3cc(-c4ccc(CN5CCC5)cc4)nn3)nc2)o1] |
| 426 | 4559 | 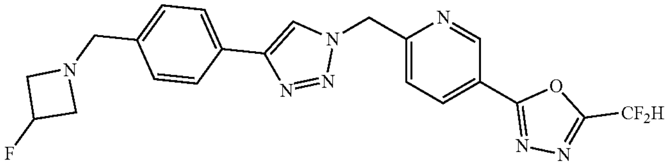 [SMILES: FC1CN(Cc2ccc(-c3cn(Cc4ccc(-c5nnc(C(F)F)o5)cn4)nn3)cc2)C1] |
| 427 | 4560 | 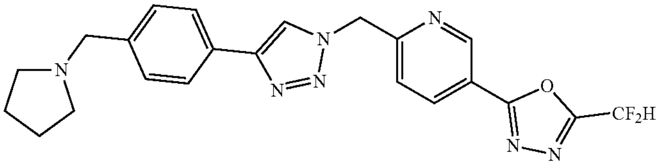 |

-continued
| Example | Compound | Structure |
| --- | --- | --- |
| 428 | 4561 | 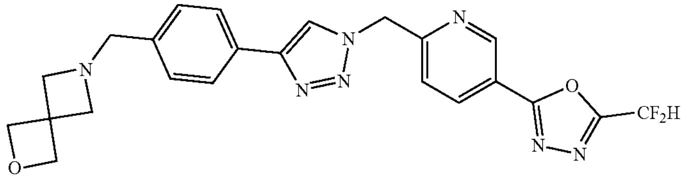 [SMILES: FC(F)c1nnc(-c2ccc(Cn3cc(-c4ccc(CN5CC6(COC6)C5)cc4)nn3)nc2)o1] |
| 429 | 4562 | 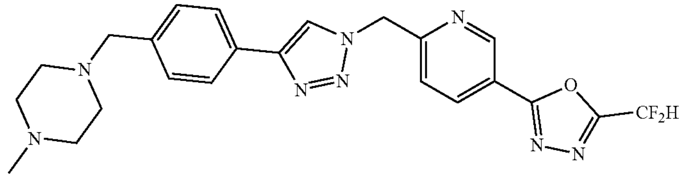 [SMILES: CN1CCN(Cc2ccc(-c3cn(Cc4ccc(-c5nnc(C(F)F)o5)cn4)nn3)cc2)CC1] |
| 430 | 4563 | 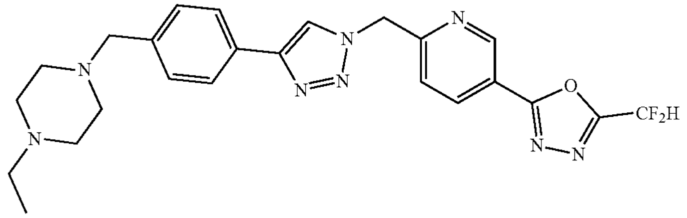 [SMILES: CCN1CCN(Cc2ccc(-c3cn(Cc4ccc(-c5nnc(C(F)F)o5)cn4)nn3)cc2)CC1] |
| 431 | 4564 | 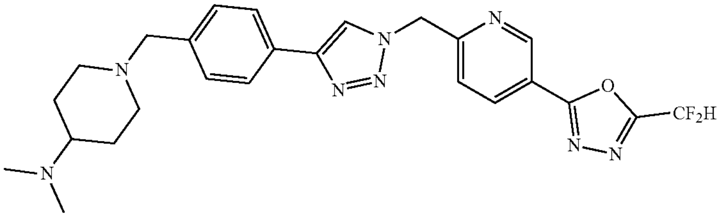 |
| 432 | 4565 | 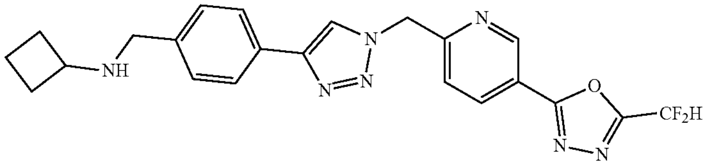 |
| 433 | 4566 | 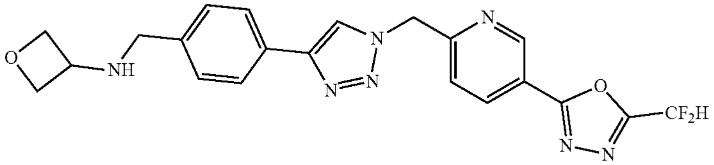 [SMILES: FC(F)c1nnc(-c2ccc(Cn3cc(-c4ccc(CNC5COC5)cc4)nn3)nc2)o1] |
| 434 | 4567 | 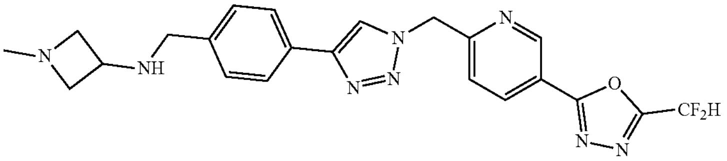 [SMILES: CN1CC(NCc2ccc(-c3cn(Cc4ccc(-c5nnc(C(F)F)o5)cn4)nn3)cc2)C1] |
| 435 | 4569 | 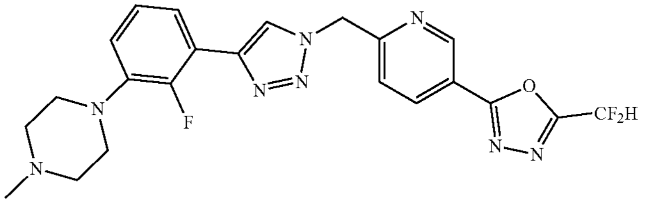 [SMILES: CN1CCN(c2cccc(-c3cn(Cc4ccc(-c5nnc(C(F)F)o5)cn4)nn3)c2F)CC1] |

-continued
| Example | Compound | Structure |
|---|---|---|
| 436 | 4570 | 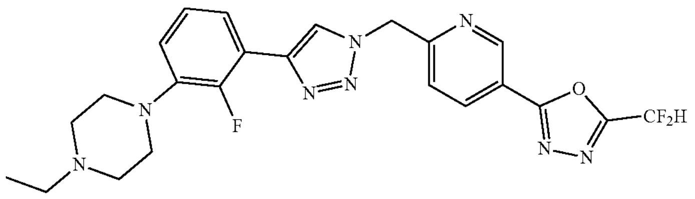 [SMILES: CCN1CCN(c2cccc(-c3cn(Cc4ccc(-c5nnc(C(F)F)o5)cn4)nn3)c2F)CC1] |
| 437 | 4571 | 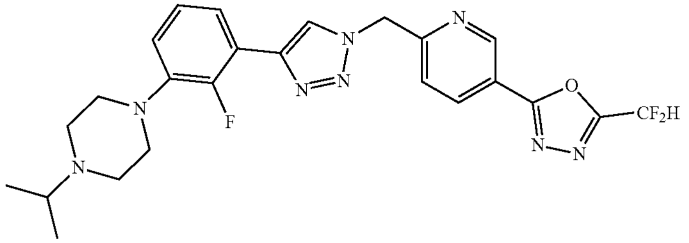 [SMILES: CC(C)N1CCN(c2cccc(-c3cn(Cc4ccc(-c5nnc(C(F)F)o5)cn4)nn3)c2F)CC1] |
| 438 | 4572 | 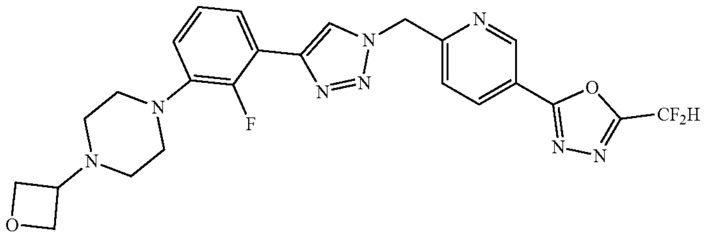 [SMILES: Fc1c(-c2cn(Cc3ccc(-c4nnc(C(F)F)o4)cn3)nn2)cccc1N1CCN(C2COC2)CC1] |
| 439 | 4573 | 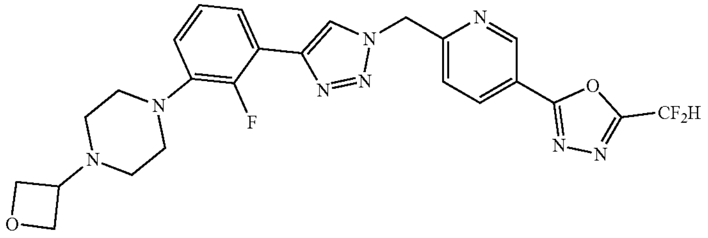 [SMILES: Fc1c(-c2cn(Cc3ccc(-c4nnc(C(F)F)o4)cn3)nn2)cccc1N1CCN(C2COC2)CC1] |
| 440 | 4576 | 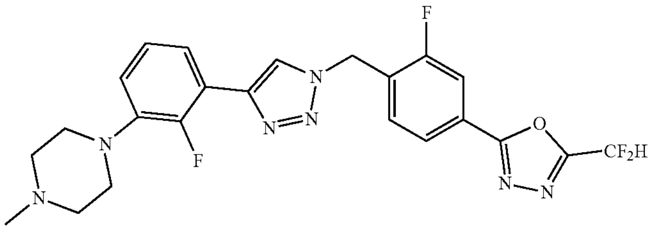 [SMILES: CN1CCN(c2cccc(-c3cn(Cc4ccc(-c5nnc(C(F)F)o5)cc4F)nn3)c2F)CC1] |
| 441 | 4577 | 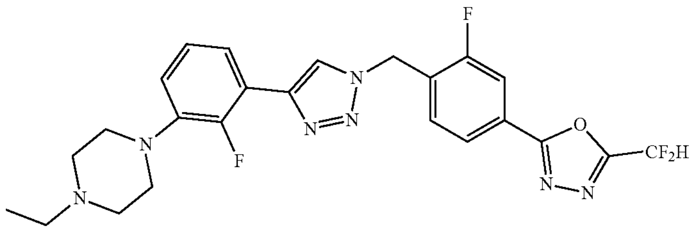 [SMILES: CCN1CCN(c2cccc(-c3cn(Cc4ccc(-c5nnc(C(F)F)o5)cc4F)nn3)c2F)CC1] |

-continued
| Example | Compound | Structure |
| --- | --- | --- |
| 442 | 4578 | 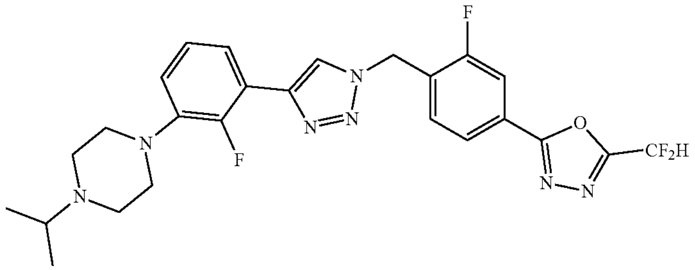 [SMILES: CC(C)N1CCN(c2cccc(-c3cn(Cc4ccc(-c5nnc(C(F)F)o5)cc4F)nn3)c2F)CC1] |
| 443 | 4579 | 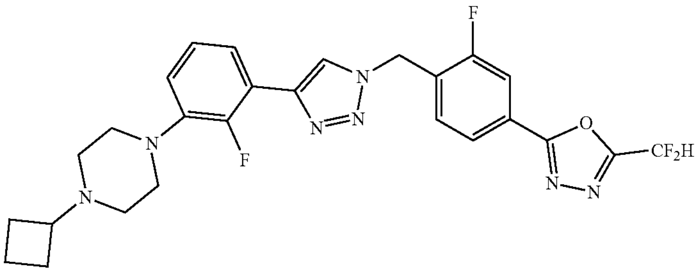 [SMILES: Fc1cc(-c2nnc(C(F)F)o2)ccc1Cn1cc(-c2cccc(N3CCN(C4CCC4)CC3)c2F)nn1] |
| 444 | 4580 | 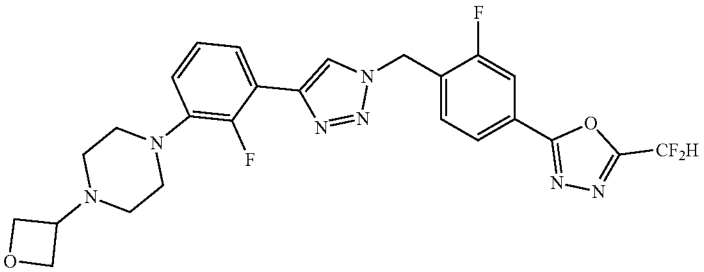 [SMILES: Fc1cc(-c2nnc(C(F)F)o2)ccc1Cn1cc(-c2cccc(N3CCN(C4COC4)CC3)c2F)nn1] |
| 445 | 4582 | 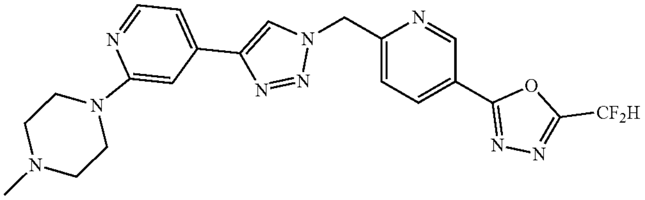 [SMILES: CN1CCN(c2cc(-c3cn(Cc4ccc(-c5nnc(C(F)F)o5)cn4)nn3)ccn2)CC1] |
| 446 | 4583 | 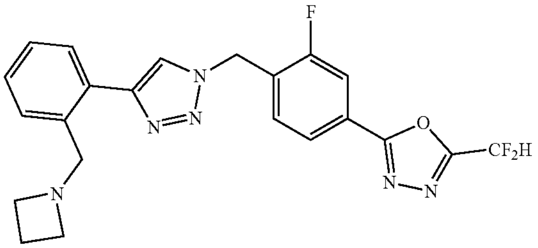 [SMILES: Fc1cc(-c2nnc(C(F)F)o2)ccc1Cn1cc(-c2ccccc2CN2CCC2)nn1] |
| 447 | 4585 | 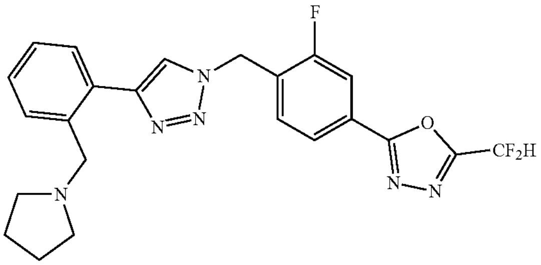 [SMILES: Fc1cc(-c2nnc(C(F)F)o2)ccc1Cn1cc(-c2ccccc2CN2CCCC2)nn1] |

-continued
| Example | Compound | Structure |
|---|---|---|
| 448 | 4586 | 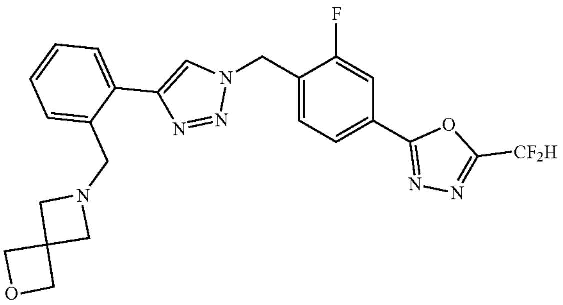 [SMILES: Fc1cc(-c2nnc(C(F)F)o2)ccc1Cn1cc(-c2ccccc2CN2CC3(COC3)C2)nn1] |
| 449 | 4587 | 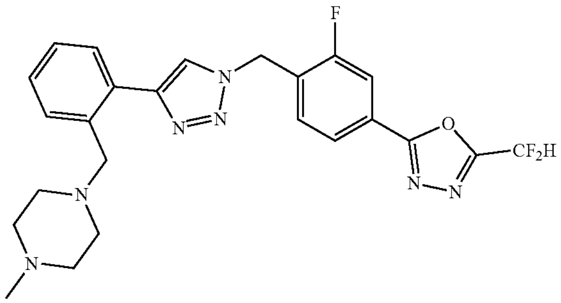 [SMILES: CN1CCN(Cc2ccccc2-c2cn(Cc3ccc(-c4nnc(C(F)F)o4)cc3F)nn2)CC1] |
| 450 | 4588 | 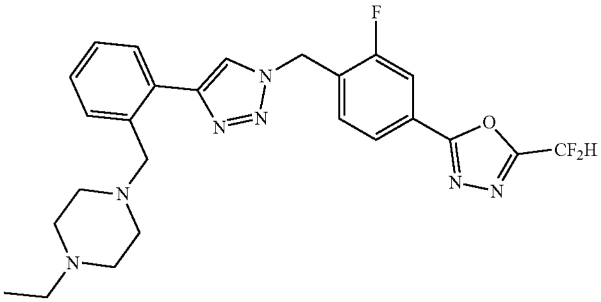 [SMILES: CCN1CCN(Cc2ccccc2-c2cn(Cc3ccc(-c4nnc(C(F)F)o4)cc3F)nn2)CC1] |
| 451 | 4589 | 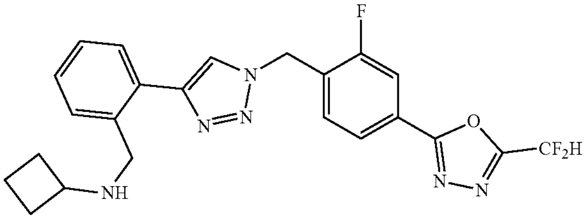 [SMILES: Fc1cc(-c2nnc(C(F)F)o2)ccc1Cn1cc(-c2ccccc2CNC2CCC2)nn1] |
| 452 | 4590 | 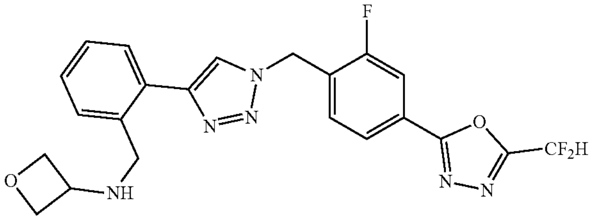 [SMILES: Fc1cc(-c2nnc(C(F)F)o2)ccc1Cn1cc(-c2ccccc2CNC2COC2)nn1] |

-continued
| Example | Compound | Structure |
| --- | --- | --- |
| 453 | 4591 | 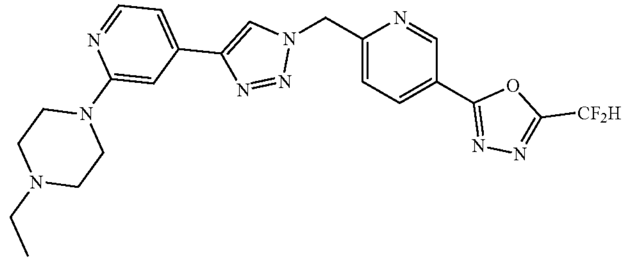 |
| 454 | 4592 | 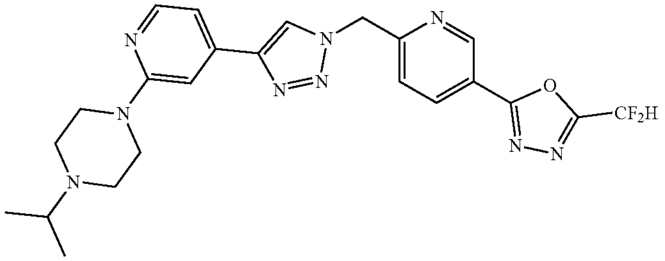 [SMILES: CC(C)N1CCN(c2cc(-c3cn(Cc4ccc(-c5nnc(C(F)F)o5)cn4)nn3)ccn2)CC1] |
| 455 | 4593 | 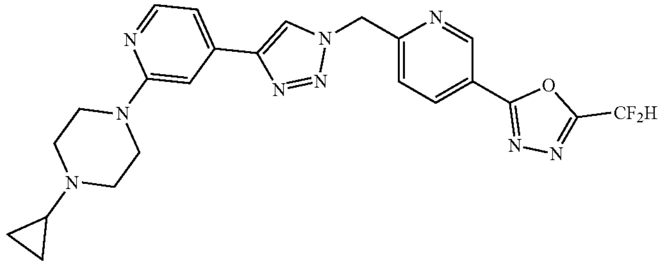 [SMILES: FC(F)c1nnc(-c2ccc(Cn3cc(-c4ccnc(N5CCN(C6CC6)CC5)c4)nn3)nc2)o1] |
| 456 | 4594 | 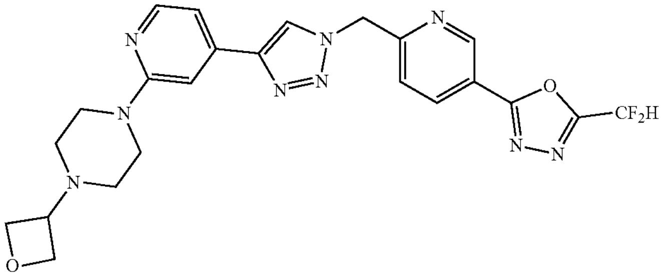 [SMILES: FC(F)c1nnc(-c2ccc(Cn3cc(-c4ccnc(N5CCN(C6COC6)CC5)c4)nn3)nc2)o1] |
| 457 | 4595 | 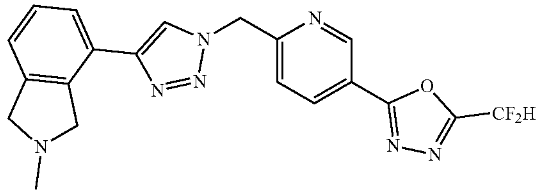 |
| 458 | 4596 | 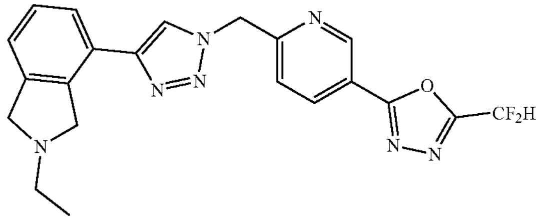 [SMILES: CCN1Cc2cccc(-c3cn(Cc4ccc(-c5nnc(C(F)F)o5)cn4)nn3)c2C1] |

-continued
| Example | Compound | Structure |
|---|---|---|
| 459 | 4597 | 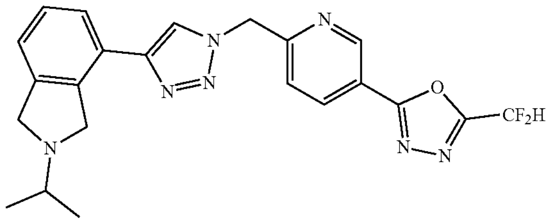 [SMILES: CC(C)N1Cc2cccc(-c3cn(Cc4ccc(-c5nnc(C(F)F)o5)cn4)nn3)c2C1] |
| 460 | 4598 | 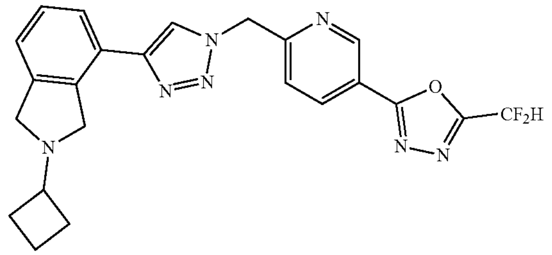 [SMILES: FC(F)c1nnc(-c2ccc(Cn3cc(-c4cccc5c4CN(C4CCC4)C5)nn3)nc2)o1] |
| 461 | 4599 | 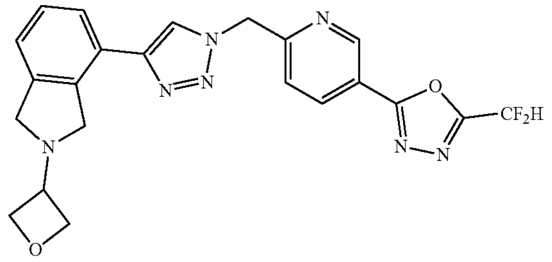 [SMILES: FC(F)c1nnc(-c2ccc(Cn3cc(-c4cccc5c4CN(C4COC4)C5)nn3)nc2)o1] |
| 462 | 4600 | 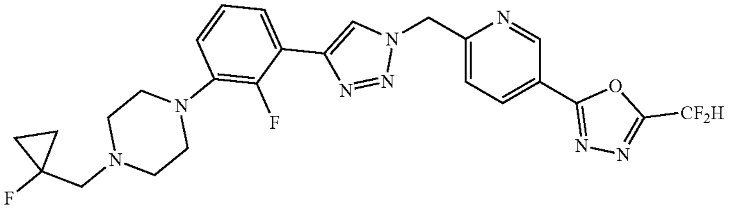 [SMILES: Fc1c(-c2cn(Cc3ccc(-c4nnc(C(F)F)o4)cn3)nn2)cccc1N1CCN(CC2(F)CC2)CC1] |
| 463 | 4601 | 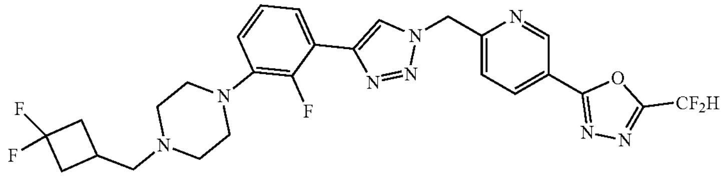 [SMILES: Fc1c(-c2cn(Cc3ccc(-c4nnc(C(F)F)o4)cn3)nn2)cccc1N1CCN(CC2CC(F)(F)C2)CC1] |
| 464 | 4602 | 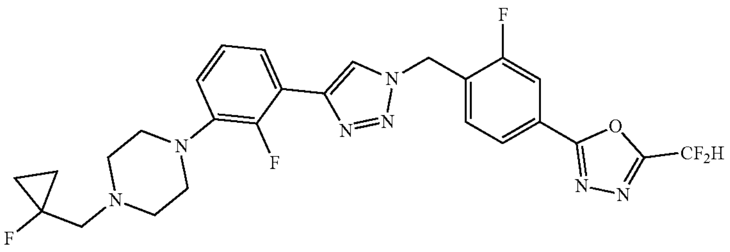 [SMILES: Fc1cc(-c2nnc(C(F)F)o2)ccc1Cn1cc(-c2cccc(N3CCN(CC4(F)CC4)CC3)c2F)nn1] |

-continued
| Example | Compound | Structure |
| --- | --- | --- |
| 465 | 4603 | 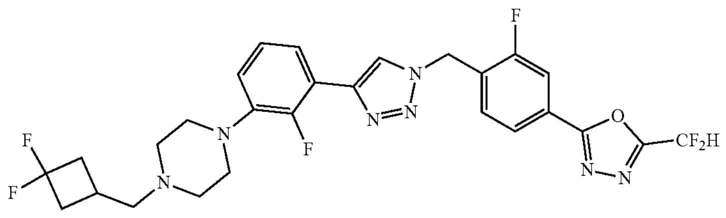 [SMILES: Fc1cc(-c2nnc(C(F)F)o2)ccc1Cn1cc(-c2cccc(N3CCN(CC4CC(F)(F)C4)CC3)c2F)nn1] |
| 466 | 4604 | 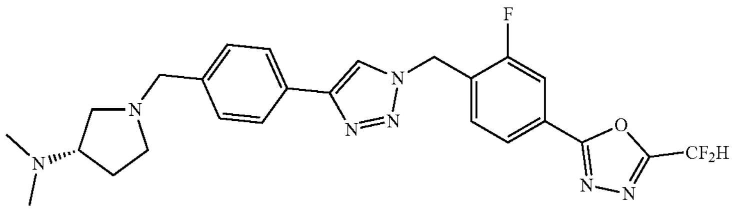 [SMILES: CN(C)[C@H]1CCN(Cc2ccc(-c3cn(Cc4ccc(-c5nnc(C(F)F)o5)cc4F)nn3)cc2)C1] |
| 467 | 4605 | 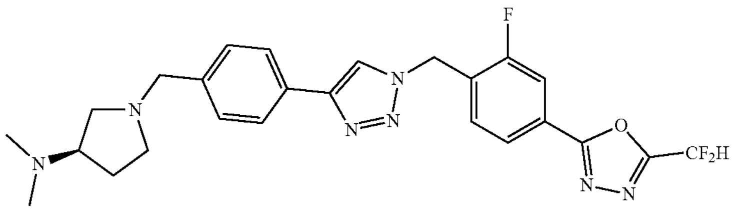 [SMILES: CN(C)[C@@H]1CCN(Cc2ccc(-c3cn(Cc4ccc(-c5nnc(C(F)F)o5)cc4F)nn3)cc2)C1] |
| 468 | 4606 | 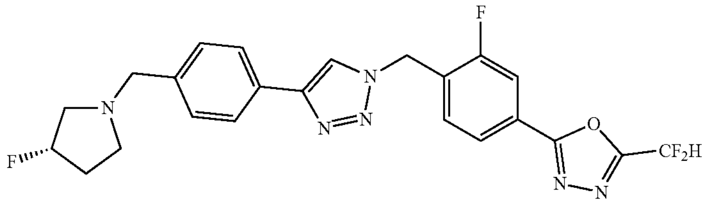 |
| 469 | 4607 | 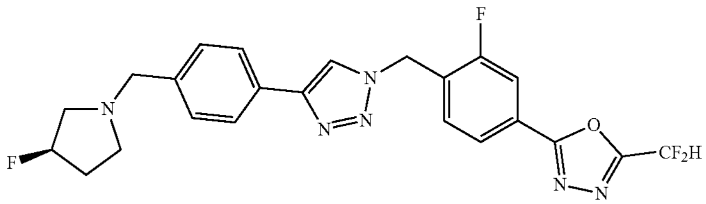 [SMILES: Fc1cc(-c2nnc(C(F)F)o2)ccc1Cn1cc(-c2ccc(CN3CC[C@@H](F)C3)cc2)nn1] |
| 470 | 4608 | 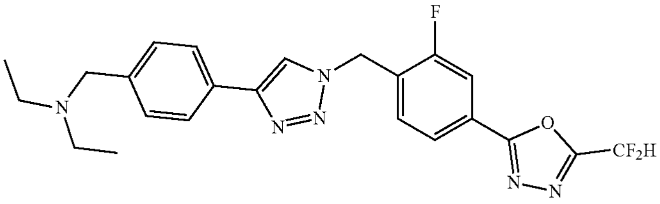 [SMILES: CCN(CC)Cc1ccc(-c2cn(Cc3ccc(-c4nnc(C(F)F)o4)cc3F)nn2)cc1] |
| 471 | 4609 | 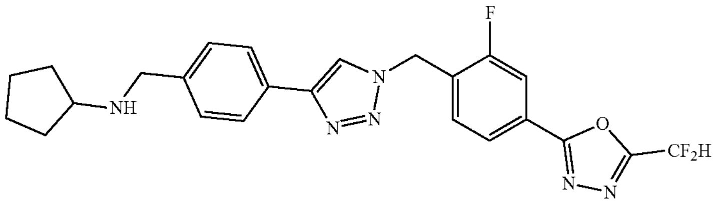 [SMILES: Fc1cc(-c2nnc(C(F)F)o2)ccc1Cn1cc(-c2ccc(CNC3CCCC3)cc2)nn1] |

-continued
| Example | Compound | Structure |
|---|---|---|
| 472 | 4610 | 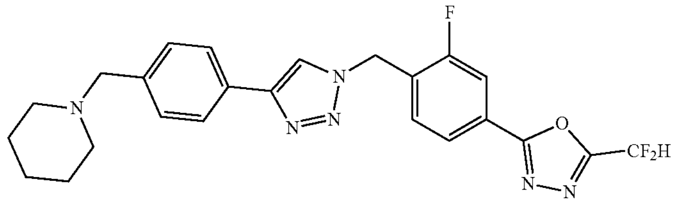 |
| 473 | 4611 | 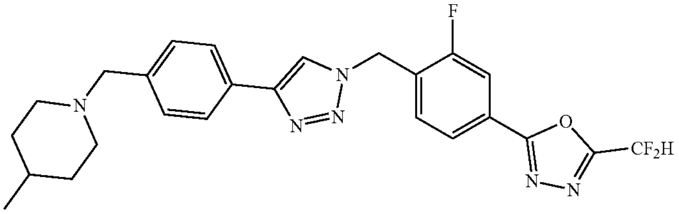 [SMILES: CC1CCN(Cc2ccc(-c3cn(Cc4ccc(-c5nnc(C(F)F)o5)cc4F)nn3)cc2)CC1] |
| 474 | 4633 | 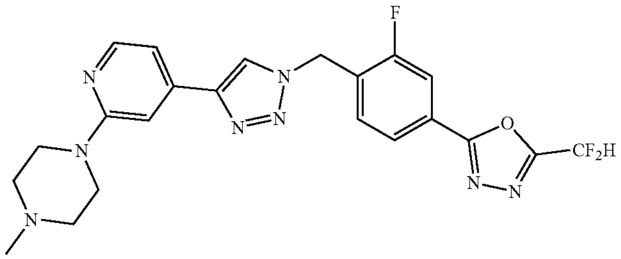 [SMILES: CN1CCN(c2cc(-c3cn(Cc4ccc(-c5nnc(C(F)F)o5)cc4F)nn3)ccn2)CC1] |
| 475 | 4634 | 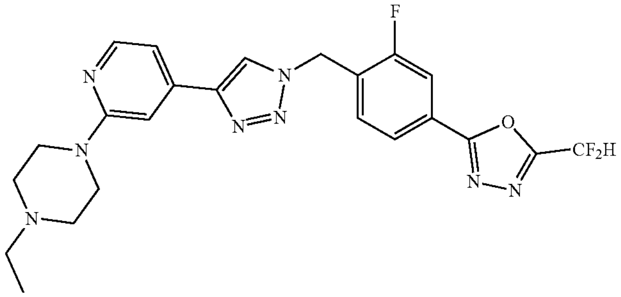 [SMILES: CCN1CCN(c2cc(-c3cn(Cc4ccc(-c5nnc(C(F)F)o5)cc4F)nn3)ccn2)CC1] |
| 476 | 4635 | 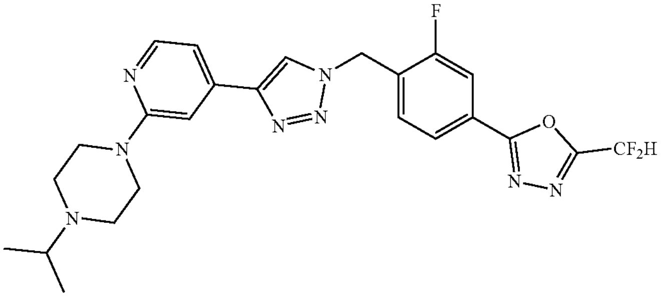 [SMILES: CC(C)N1CCN(c2cc(-c3cn(Cc4ccc(-c5nnc(C(F)F)o5)cc4F)nn3)ccn2)CC1] |

-continued
| Example | Compound | Structure |
| --- | --- | --- |
| 477 | 4636 | 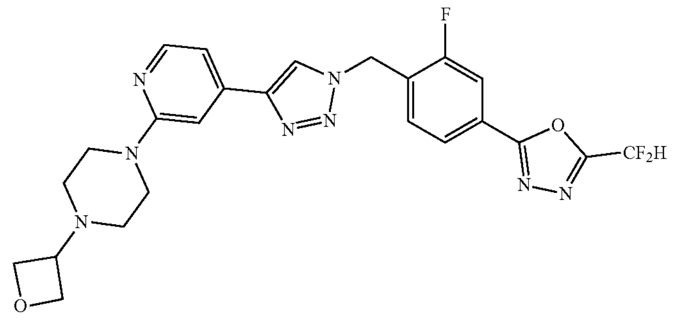 [SMILES: Fc1cc(-c2nnc(C(F)F)o2)ccc1Cn1cc(-c2ccnc(N3CCN(C4COC4)CC3)c2)nn1] |
| 478 | 4640 | 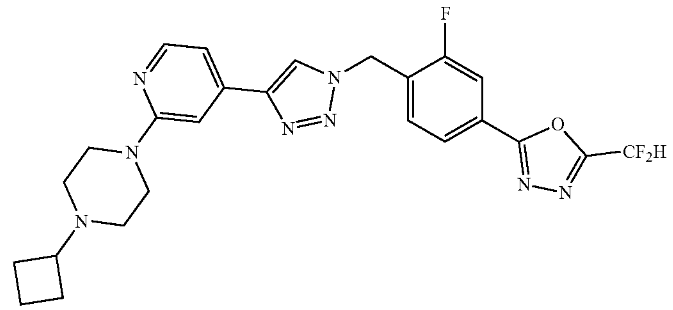 [SMILES: Fc1cc(-c2nnc(C(F)F)o2)ccc1Cn1cc(-c2ccnc(N3CCN(C4CCC4)CC3)c2)nn1] |
| 479 | 16781 | 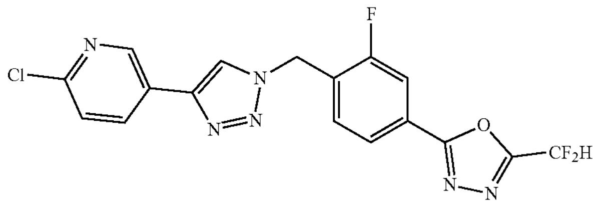 [SMILES: Fc1cc(-c2nnc(C(F)F)o2)ccc1Cn1cc(-c2ccc(Cl)nc2)nn1] |
| 480 | 16789 | 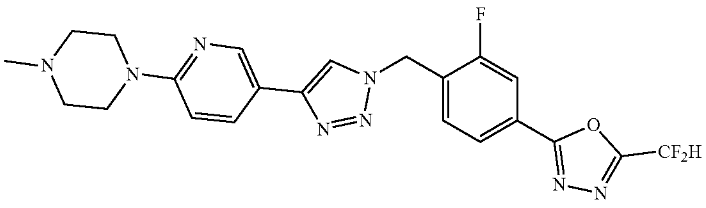 [SMILES: CN1CCN(c2ccc(-c3cn(Cc4ccc(-c5nnc(C(F)F)o5)cc4F)nn3)cn2)CC1] |
| 481 | 16797 | 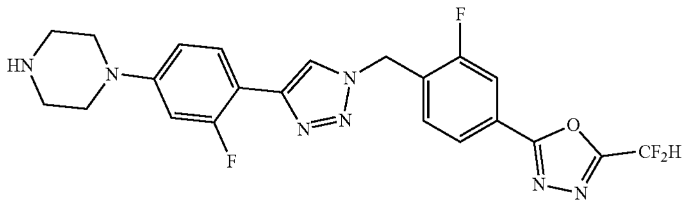 [SMILES: Fc1cc(-c2nnc(C(F)F)o2)ccc1Cn1cc(-c2ccc(N3CCNCC3)cc2F)nn1] |
| 482 | 16928 | 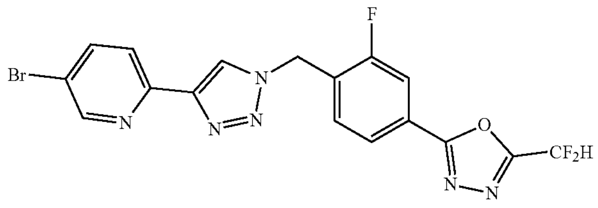 [SMILES: Fc1cc(-c2nnc(C(F)F)o2)ccc1Cn1cc(-c2ccc(Br)cn2)nn1] |

-continued
| Example | Compound | Structure |
| --- | --- | --- |
| 483 | 16930 | 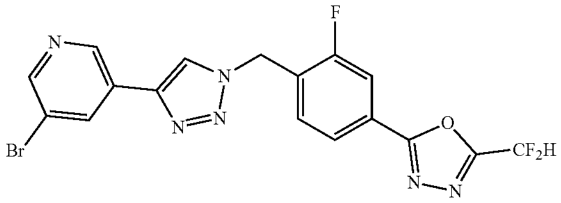 [SMILES: Fc1cc(-c2nnc(C(F)F)o2)ccc1Cn1cc(-c2cncc(Br)c2)nn1] |
| 484 | 17058 | 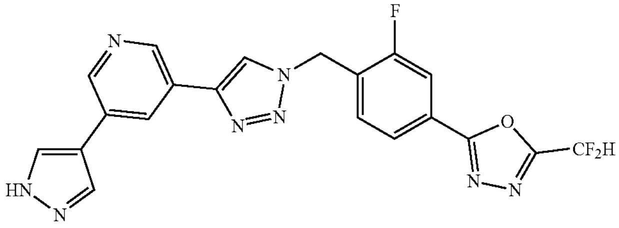 [SMILES: Fc1cc(-c2nnc(C(F)F)o2)ccc1Cn1cc(-c2cncc(-c3cn[nH]c3)c2)nn1] |
| 485 | 17198 | 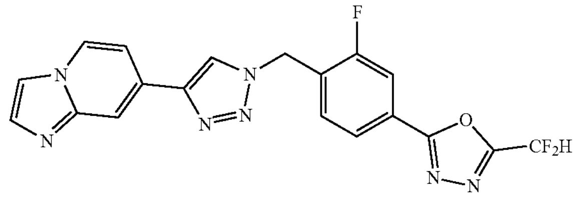 [SMILES: Fc1cc(-c2nnc(C(F)F)o2)ccc1Cn1cc(-c2ccn3ccnc3c2)nn1] |
| 486 | 17201 | 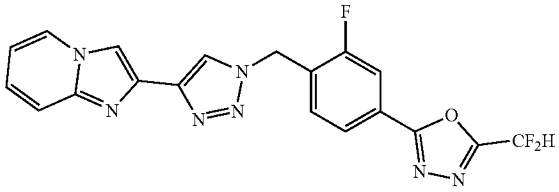 [SMILES: Fc1cc(-c2nnc(C(F)F)o2)ccc1Cn1cc(-c2cn3ccccc3n2)nn1] |
| 487 | 17255 | 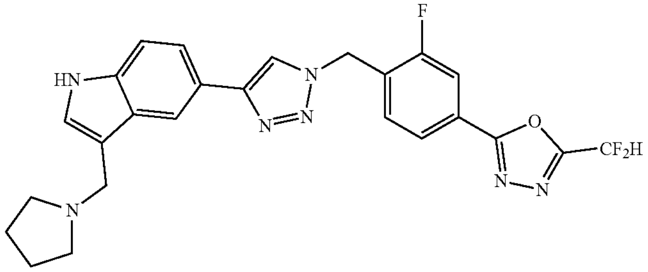 [SMILES: Fc1cc(-c2nnc(C(F)F)o2)ccc1Cn1cc(-c2ccc3[nH]cc(CN4CCCC4)c3c2)nn1] |
| 488 | 17261 | 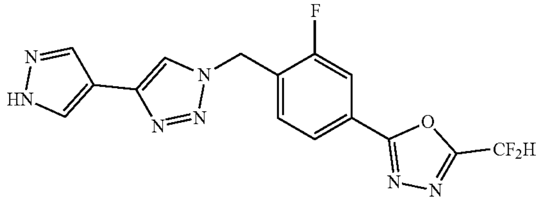 [SMILES: Fc1cc(-c2nnc(C(F)F)o2)ccc1Cn1cc(-c2cn[nH]c2)nn1] |
| 489 | 17263 | 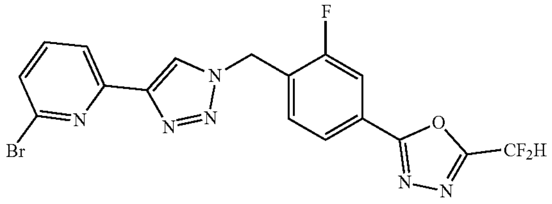 [SMILES: Fc1cc(-c2nnc(C(F)F)o2)ccc1Cn1cc(-c2cccc(Br)n2)nn1] |

-continued
| Example | Compound | Structure |
|---|---|---|
| 490 | 17347 | 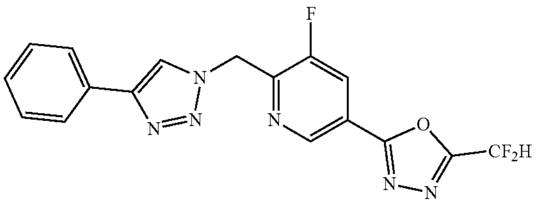 [SMILES: Fc1cc(-c2nnc(C(F)F)o2)cnc1Cn1cc(-c2ccccc2)nn1] |
| 491 | 17362 | 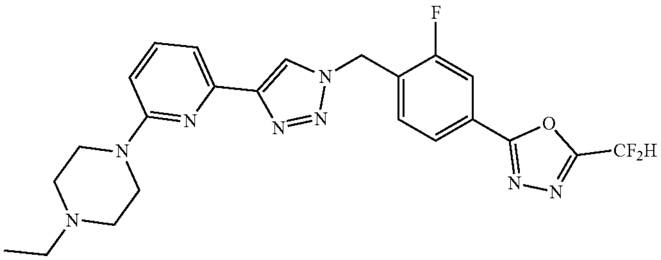 |
| 492 | 17363 | 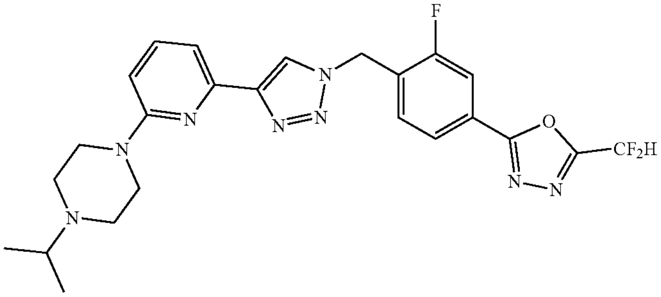 [SMILES: CC(C)N1CCN(c2cccc(-c3cn(Cc4ccc(-c5nnc(C(F)F)o5)cc4F)nn3)n2)CC1] |
| 493 | 17364 | 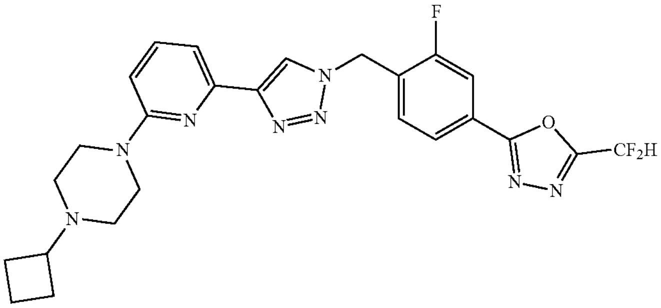 [SMILES: Fc1cc(-c2nnc(C(F)F)o2)ccc1Cn1cc(-c2cccc(N3CCN(C4CCC4)CC3)n2)nn1] |
| 494 | 17365 | 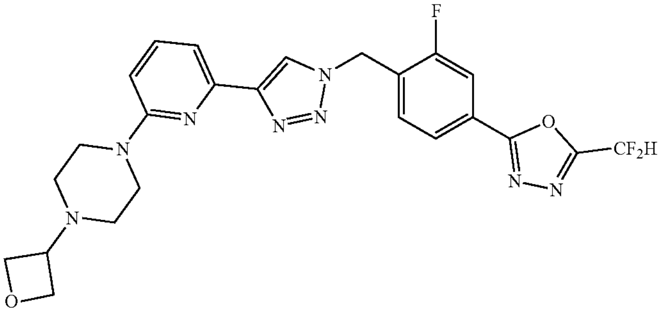 [SMILES: Fc1cc(-c2nnc(C(F)F)o2)ccc1Cn1cc(-c2cccc(N3CCN(C4COC4)CC3)n2)nn1] |

-continued
| Example | Compound | Structure |
|---|---|---|
| 495 | 17458 | 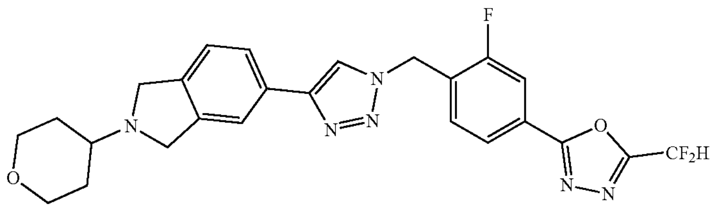 [SMILES: Fc1cc(-c2nnc(C(F)F)o2)ccc1Cn1cc(-c2ccc3c(c2)CN(C2CCOCC2)C3)nn1] |
| 496 | 17460 | 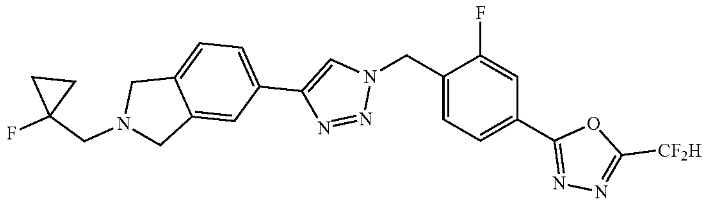 [SMILES: Fc1cc(-c2nnc(C(F)F)o2)ccc1Cn1cc(-c2ccc3c(c2)CN(CC2(F)CC2)C3)nn1] |
| 497 | 17532 | 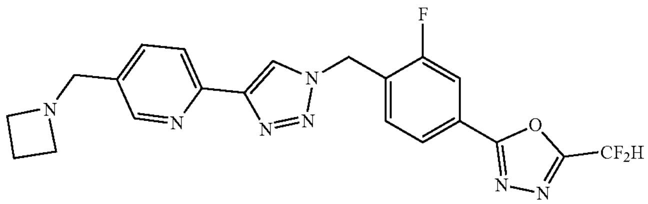 |
| 498 | 17533 | 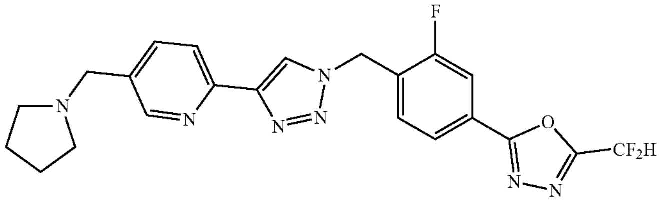 [SMILES: Fc1cc(-c2nnc(C(F)F)o2)ccc1Cn1cc(-c2ccc(CN3CCCC3)cn2)nn1] |
| 499 | 17534 | 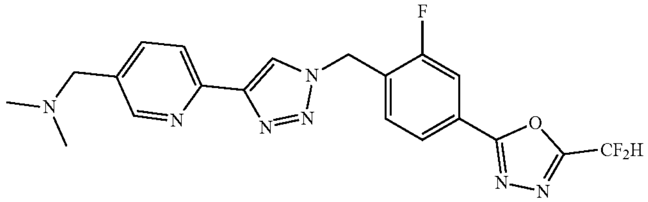 [SMILES: CN(C)Cc1ccc(-c2cn(Cc3ccc(-c4nnc(C(F)F)o4)cc3F)nn2)nc1] |
| 500 | 17535 | 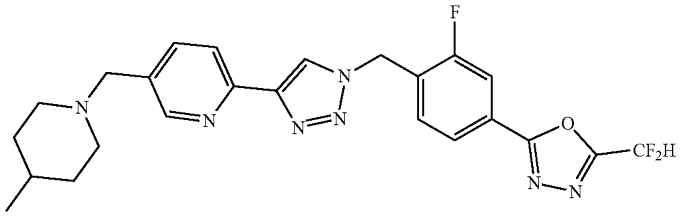 [SMILES: CC1CCN(Cc2ccc(-c3cn(Cc4ccc(-c5nnc(C(F)F)o5)cc4F)nn3)nc2)CC1] |
| 501 | 17545 | 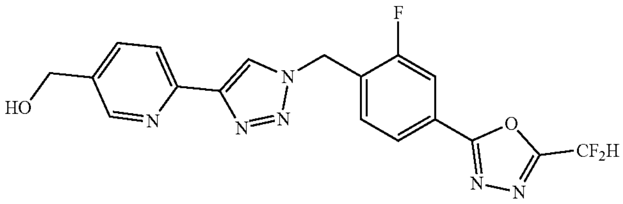 [SMILES: OCc1ccc(-c2cn(Cc3ccc(-c4nnc(C(F)F)o4)cc3F)nn2)nc1] |

-continued
| Example | Compound | Structure |
|---|---|---|
| 502 | 17698 | 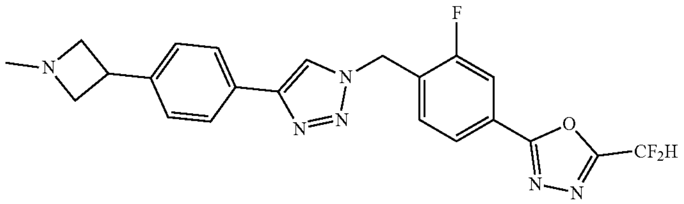 [SMILES: CN1CC(c2ccc(-c3cn(Cc4ccc(-c5nnc(C(F)F)o5)cc4F)nn3)cc2)C1] |
| 503 | 17699 | 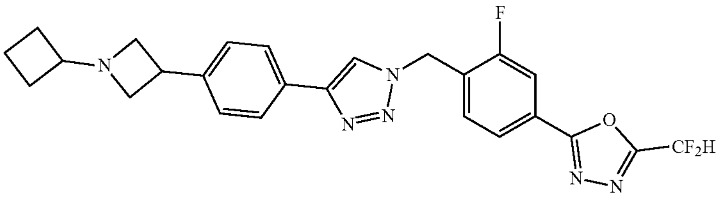 [SMILES: Fc1cc(-c2nnc(C(F)F)o2)ccc1Cn1cc(-c2ccc(C3CN(C4CCC4)C3)cc2)nn1] |
| 504 | 17700 | 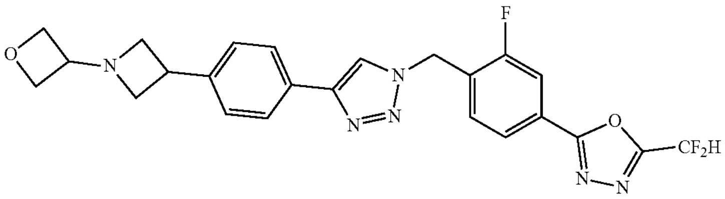 [SMILES: Fc1cc(-c2nnc(C(F)F)o2)ccc1Cn1cc(-c2ccc(C3CN(C4COC4)C3)cc2)nn1] |
| 505 | 17773 | 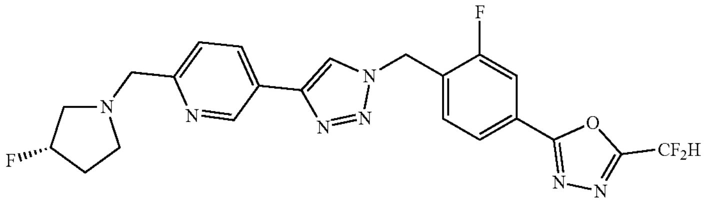 [SMILES: Fc1cc(-c2nnc(C(F)F)o2)ccc1Cn1cc(-c2ccc(CN3CC[C@H](F)C3)nc2)nn1] |
| 506 | 17774 | 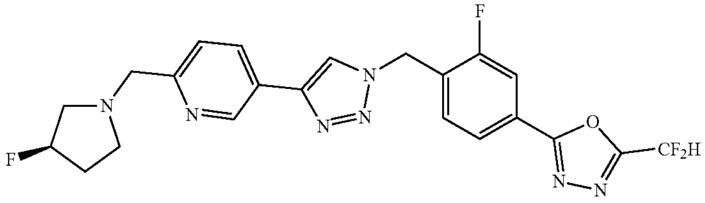 [SMILES: Fc1cc(-c2nnc(C(F)F)o2)ccc1Cn1cc(-c2ccc(CN3CC[C@@H](F)C3)nc2)nn1] |
| 507 | 17775 | 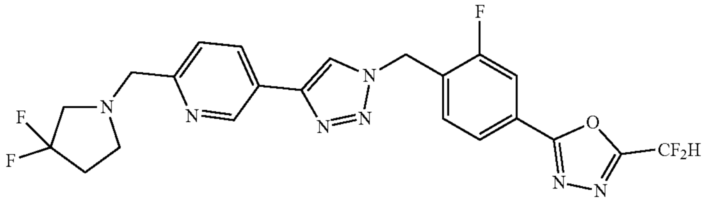 [SMILES: Fc1cc(-c2nnc(C(F)F)o2)ccc1Cn1cc(-c2ccc(CN3CCC(F)(F)C3)nc2)nn1] |
| 508 | 17777 | 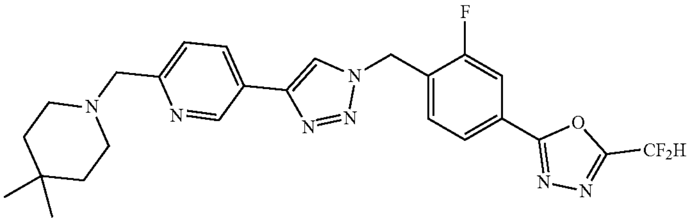 [SMILES: CC1(C)CCN(Cc2ccc(-c3cn(Cc4ccc(-c5nnc(C(F)F)o5)cc4F)nn3)cn2)CC1] |

-continued
| Example | Compound | Structure |
|---|---|---|
| 509 | 17778 | 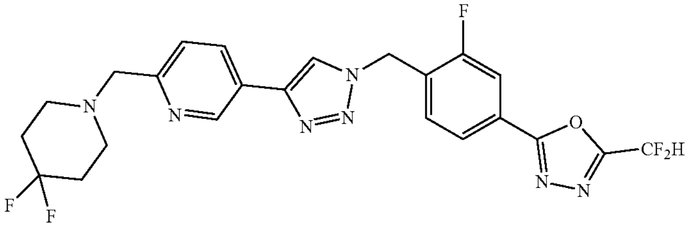 [SMILES: Fc1cc(-c2nnc(C(F)F)o2)ccc1Cn1cc(-c2ccc(CN3CCC(F)(F)CC3)nc2)nn1] |
| 510 | 17848 | 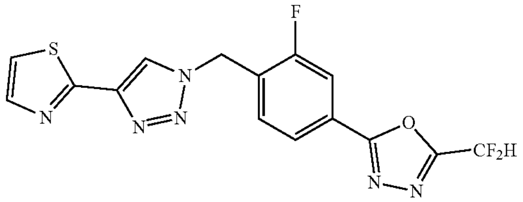 [SMILES: Fc1cc(-c2nnc(C(F)F)o2)ccc1Cn1cc(-c2nccs2)nn1] |
| 511 | 17851 | 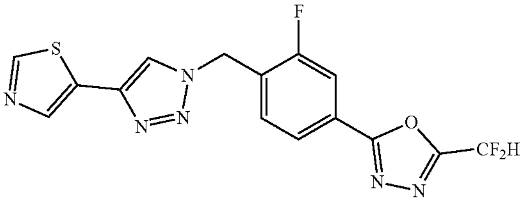 [SMILES: Fc1cc(-c2nnc(C(F)F)o2)ccc1Cn1cc(-c2cncs2)nn1] |
| 512 | 17854 | 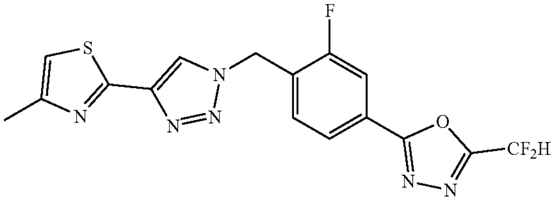 [SMILES: Cc1csc(-c2cn(Cc3ccc(-c4nnc(C(F)F)o4)cc3F)nn2)n1] |
| 513 | 17857 | 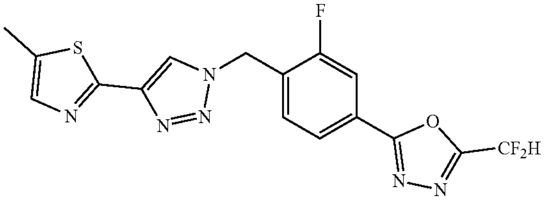 [SMILES: Cc1cnc(-c2cn(Cc3ccc(-c4nnc(C(F)F)o4)cc3F)nn2)s1] |
| 514 | 17912 | 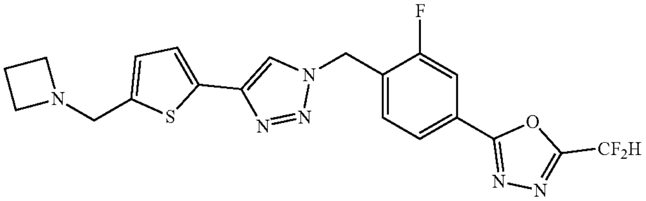 [SMILES: Fc1cc(-c2nnc(C(F)F)o2)ccc1Cn1cc(-c2ccc(CN3CCC3)s2)nn1] |
| 515 | 17913 | 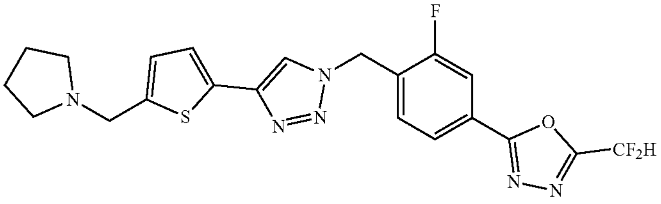 [SMILES: Fc1cc(-c2nnc(C(F)F)o2)ccc1Cn1cc(-c2ccc(CN3CCCC3)s2)nn1] |

-continued
| Example | Compound | Structure |
|---|---|---|
| 516 | 17914 | 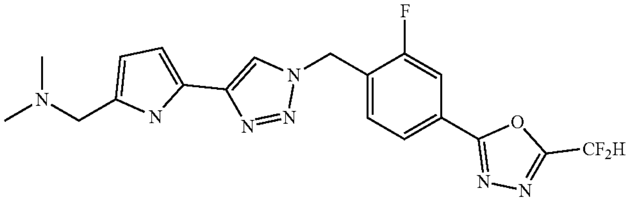 [SMILES: CN(C)Cc1ccc(-c2cn(Cc3ccc(-c4nnc(C(F)F)o4)cc3F)nn2)[nH]1] |
| 517 | 17915 | 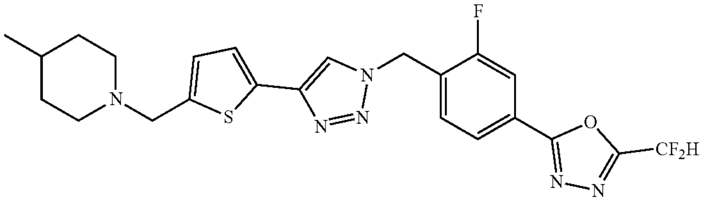 [SMILES: CC1CCN(Cc2ccc(-c3cn(Cc4ccc(-c5nnc(C(F)F)o5)cc4F)nn3)s2)CC1] |
| 518 | 17916 | 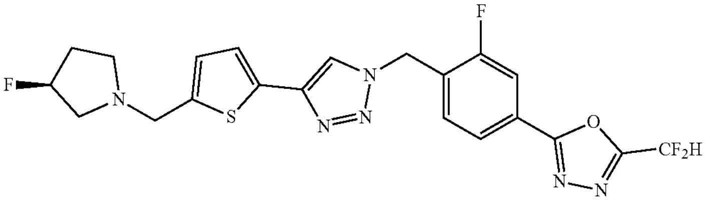 [SMILES: Fc1cc(-c2nnc(C(F)F)o2)ccc1Cn1cc(-c2ccc(CN3CC[C@H](F)C3)s2)nn1] |
| 519 | 17917 | 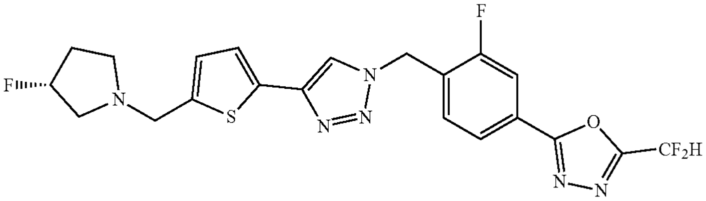 [SMILES: Fc1cc(-c2nnc(C(F)F)o2)ccc1Cn1cc(-c2ccc(CN3CC[C@@H](F)C3)s2)nn1] |
| 520 | 17922 | 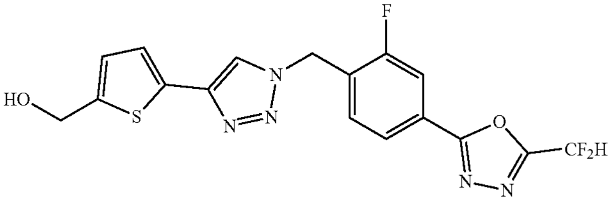 [SMILES: OCc1ccc(-c2cn(Cc3ccc(-c4nnc(C(F)F)o4)cc3F)nn2)s1] |
| 521 | 17983 | 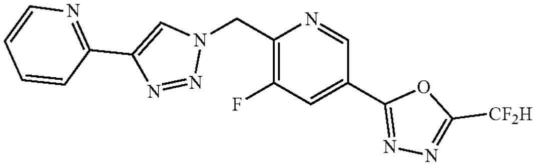 [SMILES: Fc1cc(-c2nnc(C(F)F)o2)cnc1Cn1cc(-c2ccccn2)nn1] |
| 522 | 17984 | 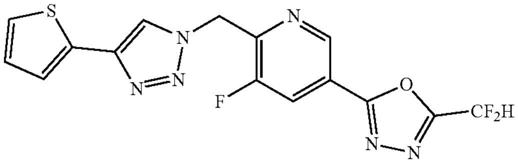 [SMILES: Fc1cc(-c2nnc(C(F)F)o2)cnc1Cn1cc(-c2cccs2)nn1] |
| 523 | 18058 | 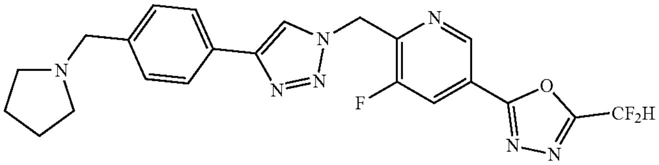 [SMILES: Fc1cc(-c2nnc(C(F)F)o2)cnc1Cn1cc(-c2ccc(CN3CCCC3)cc2)nn1] |

-continued
| Example | Compound | Structure |
| --- | --- | --- |
| 524 | 18059 | 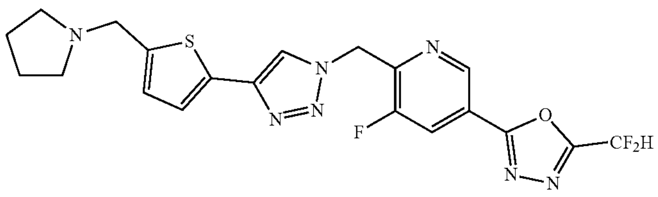 [SMILES: Fc1cc(-c2nnc(C(F)F)o2)cnc1Cn1cc(-c2ccc(CN3CCCC3)s2)nn1] |
| 525 | 18174 | 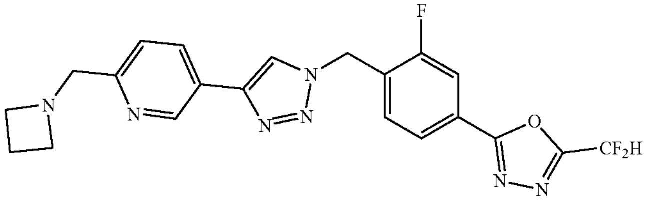 [SMILES: Fc1cc(-c2nnc(C(F)F)o2)ccc1Cn1cc(-c2ccc(CN3CCC3)nc2)nn1] |
| 526 | 18175 | 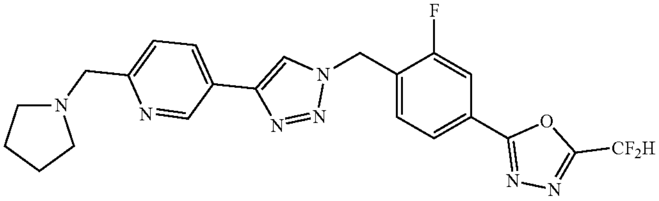 |
| 527 | 18176 | 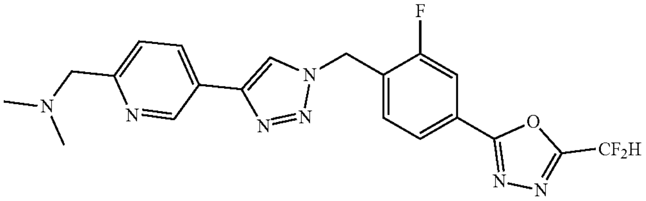 [SMILES: CN(C)Cc1ccc(-c2cn(Cc3ccc(-c4nnc(C(F)F)o4)cc3F)nn2)cn1] |
| 528 | 18177 | 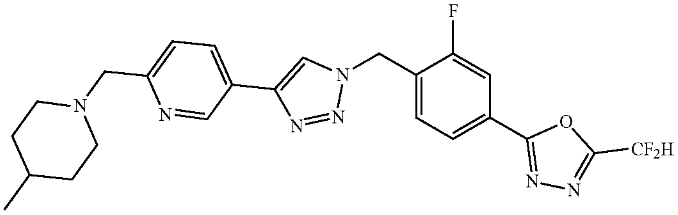 [SMILES: CC1CCN(Cc2ccc(-c3cn(Cc4ccc(-c5nnc(C(F)F)o5)cc4F)nn3)cn2)CC1] |
| 529 | 18178 | 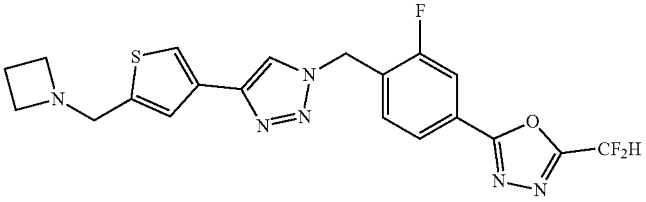 [SMILES: Fc1cc(-c2nnc(C(F)F)o2)ccc1Cn1cc(-c2csc(CN3CCC3)c2)nn1] |
| 530 | 18180 | 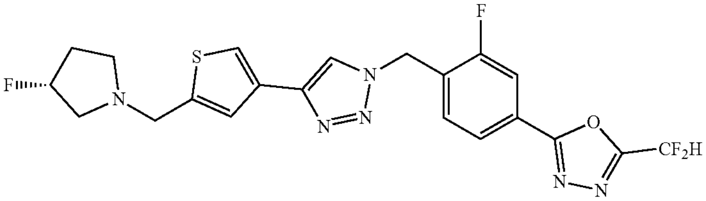 [SMILES: Fc1cc(-c2nnc(C(F)F)o2)ccc1Cn1cc(-c2csc(CN3CC[C@@H](F)C3)c2)nn1] |

-continued
| Example | Compound | Structure |
|---|---|---|
| 531 | 18185 | 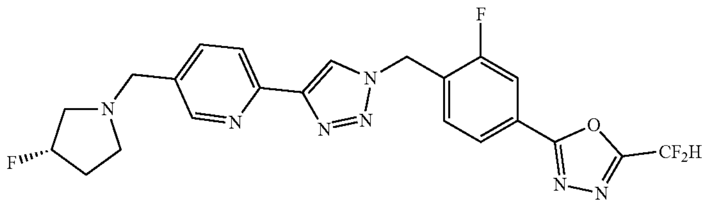 [SMILES: Fc1cc(-c2nnc(C(F)F)o2)ccc1Cn1cc(-c2ccc(CN3CC[C@H](F)C3)cn2)nn1] |
| 532 | 18187 | 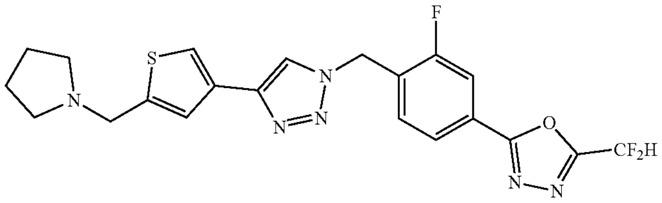 [SMILES: Fc1cc(-c2nnc(C(F)F)o2)ccc1Cn1cc(-c2csc(CN3CCCC3)c2)nn1] |
| 533 | 18188 | 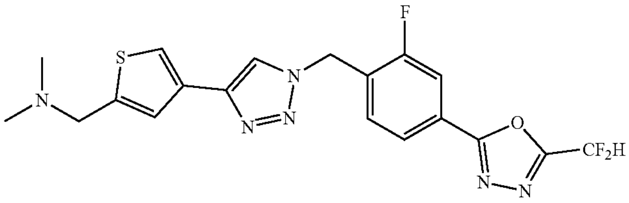 [SMILES: CN(C)Cc1cc(-c2cn(Cc3ccc(-c4nnc(C(F)F)o4)cc3F)nn2)cs1] |
| 534 | 18256 | 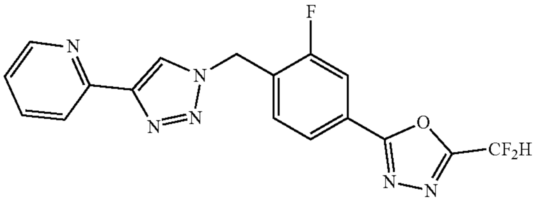 [SMILES: Fc1cc(-c2nnc(C(F)F)o2)ccc1Cn1cc(-c2ccccn2)nn1] |
| 535 | 18258 | 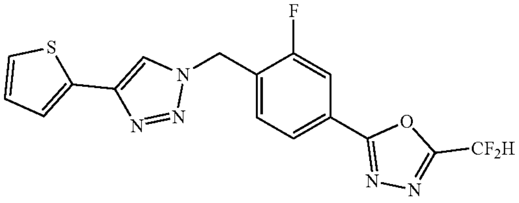 [SMILES: Fc1cc(-c2nnc(C(F)F)o2)ccc1Cn1cc(-c2cccs2)nn1] |
| 536 | 18260 | 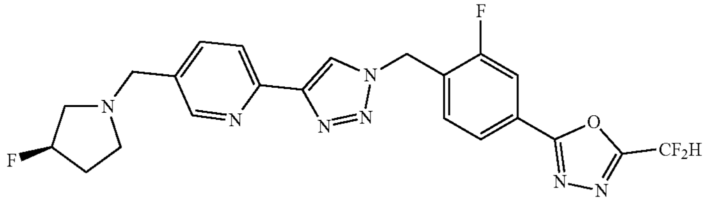 [SMILES: Fc1cc(-c2nnc(C(F)F)o2)ccc1Cn1cc(-c2ccc(CN3CC[C@@H](F)C3)cn2)nn1] |
| 537 | 18305 | 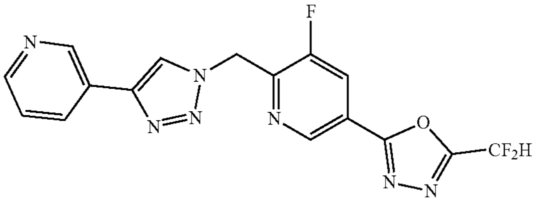 [SMILES: Fc1cc(-c2nnc(C(F)F)o2)cnc1Cn1cc(-c2cccnc2)nn1] |

-continued
| Example | Compound | Structure |
|---|---|---|
| 538 | 18306 | 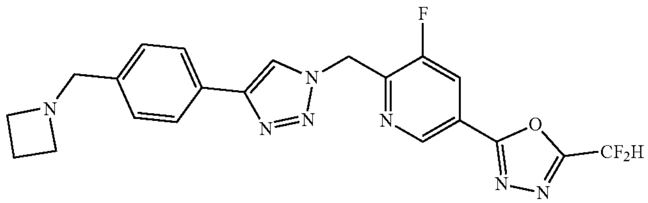 [SMILES: Fc1cc(-c2nnc(C(F)F)o2)cnc1Cn1cc(-c2ccc(CN3CCC3)cc2)nn1] |
| 539 | 18307 | 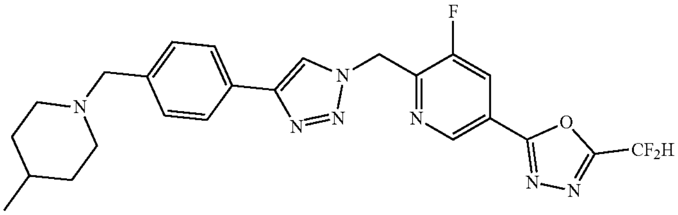 |
| 540 | 18308 | 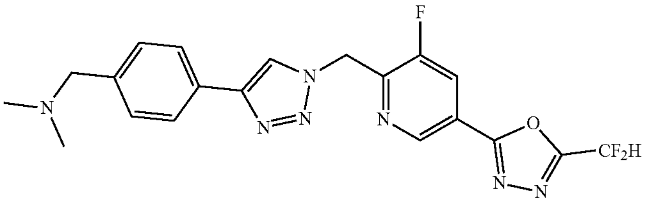 [SMILES: CN(C)Cc1ccc(-c2cn(Cc3ncc(-c4nnc(C(F)F)o4)cc3F)nn2)cc1] |
| 541 | 18309 | 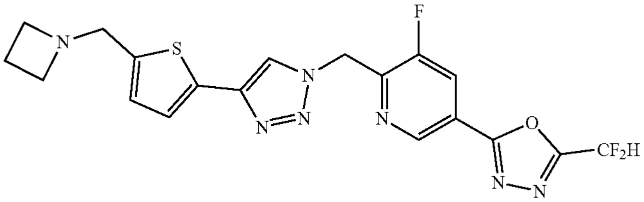 [SMILES: Fc1cc(-c2nnc(C(F)F)o2)cnc1Cn1cc(-c2ccc(CN3CCC3)s2)nn1] |
| 542 | 18310 | 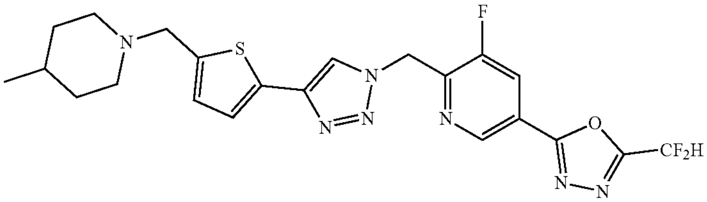 [SMILES: CC1CCN(Cc2ccc(-c3cn(Cc4ncc(-c5nnc(C(F)F)o5)cc4F)nn3)s2)CC1] |
| 543 | 18311 | 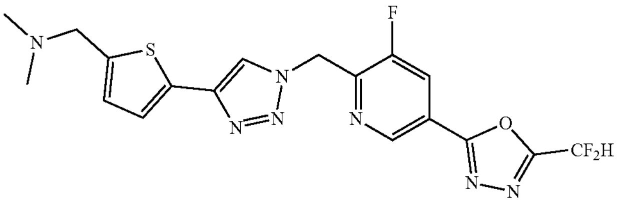 [SMILES: CN(C)Cc1ccc(-c2cn(Cc3ncc(-c4nnc(C(F)F)o4)cc3F)nn2)s1] |
| 544 | 18327 | 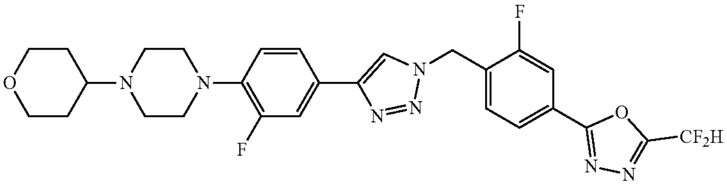 [SMILES: Fc1cc(-c2nnc(C(F)F)o2)ccc1Cn1cc(-c2ccc(N3CCN(C4CCOCC4)CC3)c(F)c2)nn1] |

-continued
| Example | Compound | Structure |
|---|---|---|
| 545 | 18457 | 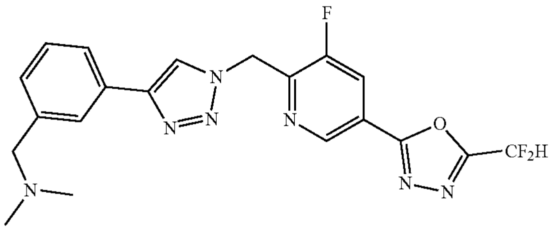 [SMILES: CN(C)Cc1cccc(-c2cn(Cc3ncc(-c4nnc(C(F)F)o4)cc3F)nn2)c1] |
| 546 | 18459 | 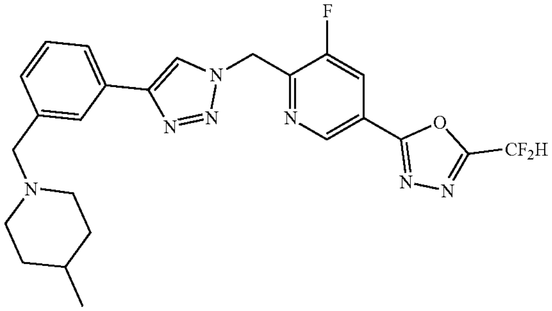 [SMILES: CC1CCN(Cc2cccc(-c3cn(Cc4ncc(-c5nnc(C(F)F)o5)cc4F)nn3)c2)CC1] |
| 547 | 18470 | 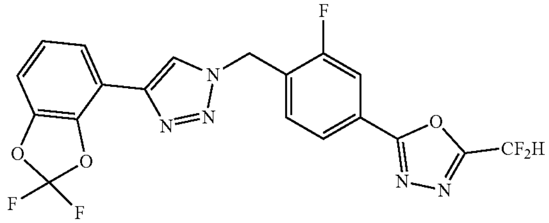 [SMILES: Fc1cc(-c2nnc(C(F)F)o2)ccc1Cn1cc(-c2cccc3c2OC(F)(F)O3)nn1] |
| 548 | 18483 | 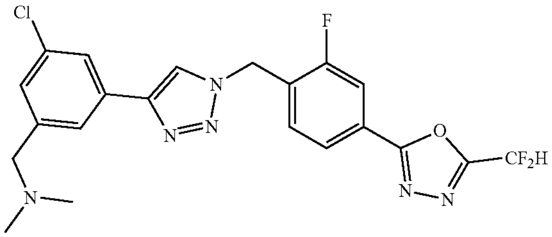 [SMILES: CN(C)Cc1cc(Cl)cc(-c2cn(Cc3ccc(-c4nnc(C(F)F)o4)cc3F)nn2)c1] |
| 549 | 18554 | 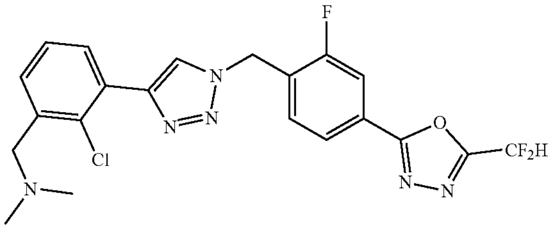 [SMILES: CN(C)Cc1cccc(-c2cn(Cc3ccc(-c4nnc(C(F)F)o4)cc3F)nn2)c1Cl] |
| 550 | 18622 | 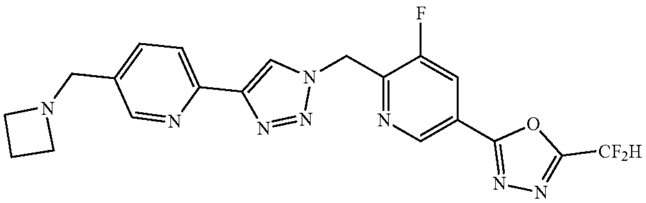 [SMILES: Fc1cc(-c2nnc(C(F)F)o2)cnc1Cn1cc(-c2ccc(CN3CCC3)cn2)nn1] |

-continued
| Example | Compound | Structure |
| --- | --- | --- |
| 551 | 18711 | 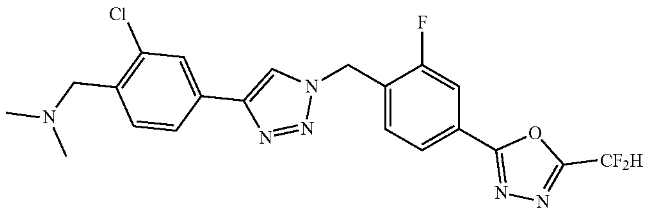 [SMILES: CN(C)Cc1ccc(-c2cn(Cc3ccc(-c4nnc(C(F)F)o4)cc3F)nn2)cc1Cl] |
| 552 | 18712 | 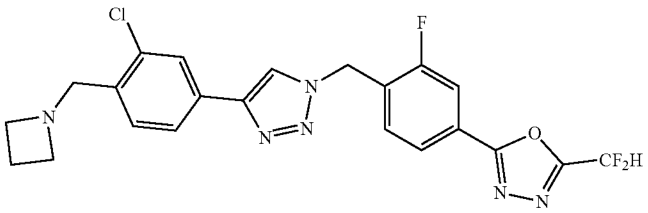 [SMILES: Fc1cc(-c2nnc(C(F)F)o2)ccc1Cn1cc(-c2ccc(CN3CCC3)c(Cl)c2)nn1] |
| 553 | 18713 | 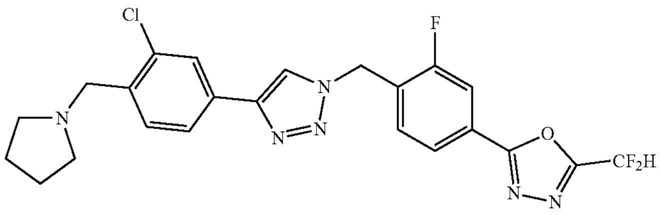 [SMILES: Fc1cc(-c2nnc(C(F)F)o2)ccc1Cn1cc(-c2ccc(CN3CCCC3)c(Cl)c2)nn1] |
| 554 | 18736 | 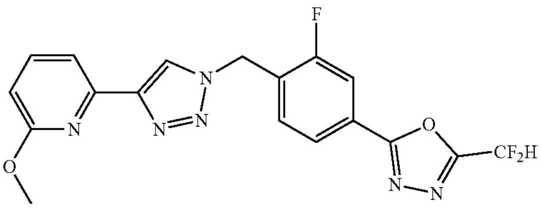 [SMILES: COc1cccc(-c2cn(Cc3ccc(-c4nnc(C(F)F)o4)cc3F)nn2)n1] |
| 555 | 18822 | 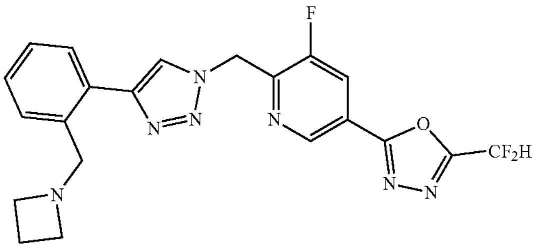 [SMILES: Fc1cc(-c2nnc(C(F)F)o2)cnc1Cn1cc(-c2ccccc2CN2CCC2)nn1] |
| 556 | 18823 | 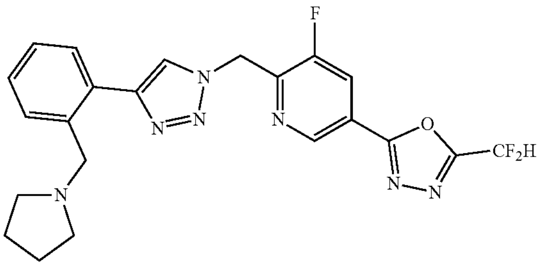 [SMILES: Fc1cc(-c2nnc(C(F)F)o2)cnc1Cn1cc(-c2ccccc2CN2CCCC2)nn1] |

-continued
| Example | Compound | Structure |
|---|---|---|
| 557 | 18868 | 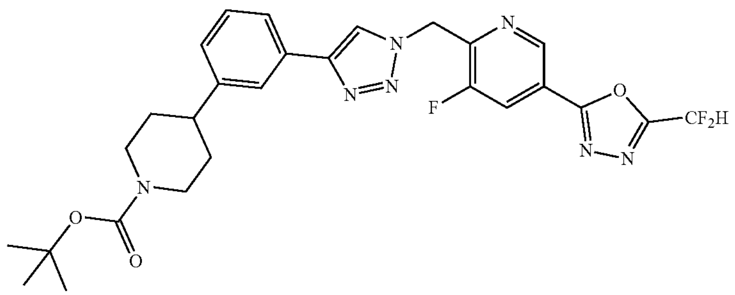 [SMILES: CC(C)(C)OC(=O)N1CCC(c2cccc(-c3cn(Cc4ncc(-c5nnc(C(F)F)o5)cc4F)nn3)c2)CC1] |
| 558 | 18869 | 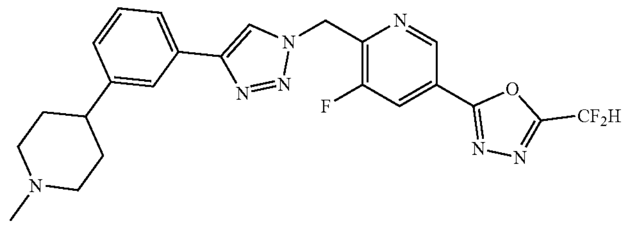 [SMILES: CN1CCC(c2cccc(-c3cn(Cc4ncc(-c5nnc(C(F)F)o5)cc4F)nn3)c2)CC1] |
| 559 | 18870 | 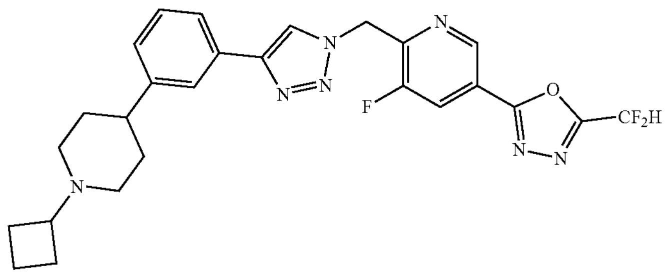 [SMILES: Fc1cc(-c2nnc(C(F)F)o2)cnc1Cn1cc(-c2cccc(C3CCN(C4CCC4)CC3)c2)nn1] |
| 560 | 18871 | 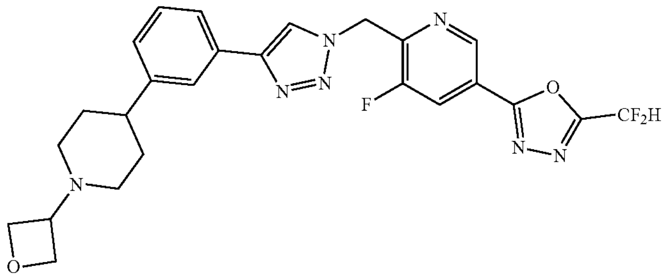 [SMILES: Fc1cc(-c2nnc(C(F)F)o2)cnc1Cn1cc(-c2cccc(C3CCN(C4COC4)CC3)c2)nn1] |
| 561 | 18872 | 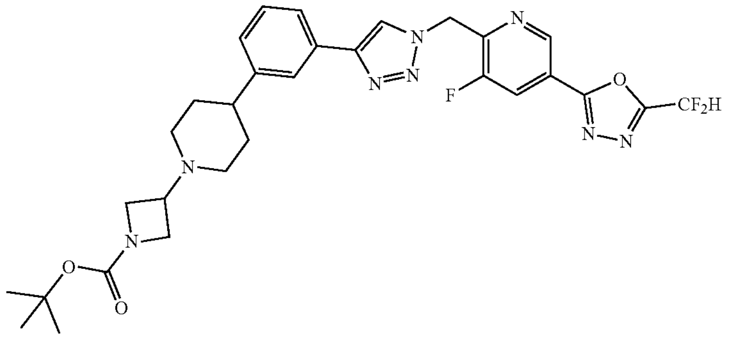 [SMILES: CC(C)(C)OC(=O)N1CC(N2CCC(c3cccc(-c4cn(Cc5ncc(-c6nnc(C(F)F)o6)cc5F)nn4)c3)CC2)C1] |

-continued
| Example | Compound | Structure |
| --- | --- | --- |
| 562 | 18877 | 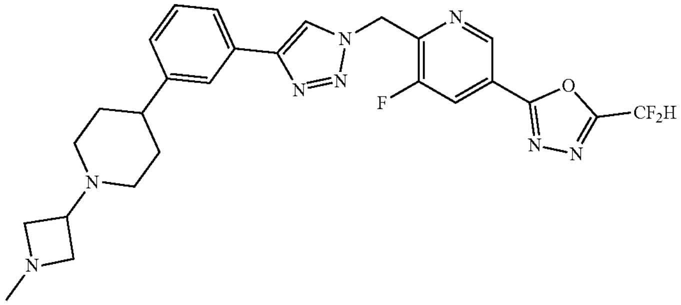 [SMILES: CN1CC(N2CCC(c3cccc(-c4cn(Cc5ncc(-c6nnc(C(F)F)o6)cc5F)nn4)c3)CC2)C1] |
| 563 | 18878 | 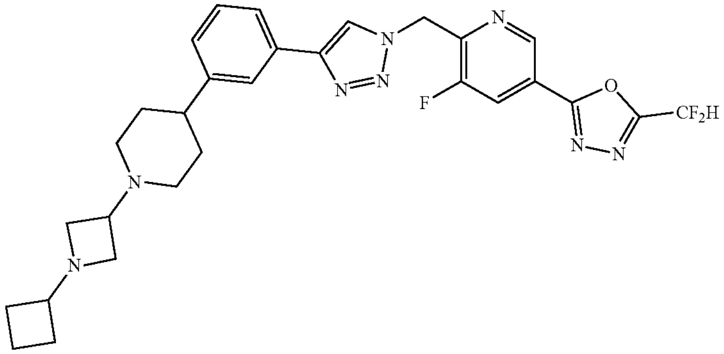 [SMILES: Fc1cc(-c2nnc(C(F)F)o2)cnc1Cn1cc(-c2cccc(C3CCN(C4CN(C5CCC5)C4)CC3)c2)nn1] |
| 564 | 18882 | 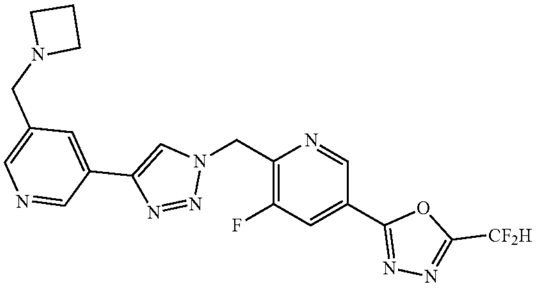 [SMILES: Fc1cc(-c2nnc(C(F)F)o2)cnc1Cn1cc(-c2cncc(CN3CCC3)c2)nn1] |
| 565 | 18893 | 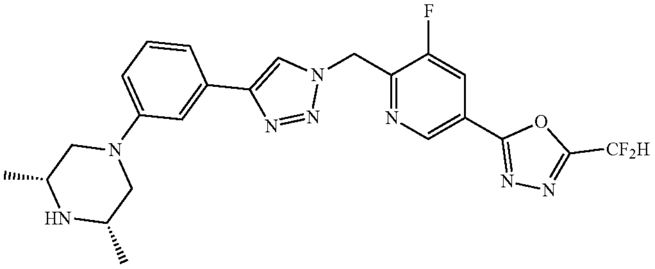 [SMILES: C[C@@H]1CN(c2cccc(-c3cn(Cc4ncc(-c5nnc(C(F)F)o5)cc4F)nn3)c2)C[C@H](C)N1] |
| 566 | 18918 | 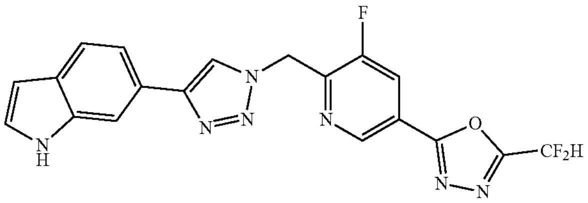 [SMILES: Fc1cc(-c2nnc(C(F)F)o2)cnc1Cn1cc(-c2ccc3cc[nH]c3c2)nn1] |

-continued
| Example | Compound | Structure |
|---|---|---|
| 567 | 18919 | 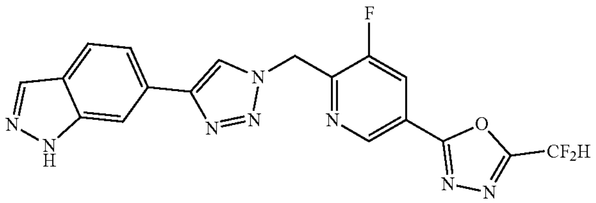 [SMILES: Fc1cc(-c2nnc(C(F)F)o2)cnc1Cn1cc(-c2ccc3cn[nH]c3c2)nn1] |
| 568 | 18920 | 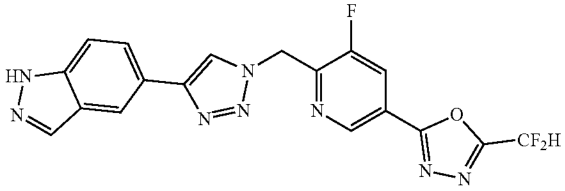 [SMILES: Fc1cc(-c2nnc(C(F)F)o2)cnc1Cn1cc(-c2ccc3[nH]ncc3c2)nn1] |
| 569 | 18921 | 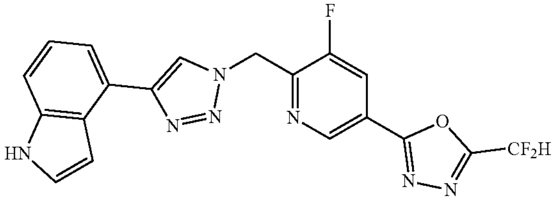 [SMILES: Fc1cc(-c2nnc(C(F)F)o2)cnc1Cn1cc(-c2cccc3[nH]ccc23)nn1] |
| 570 | 18924 | 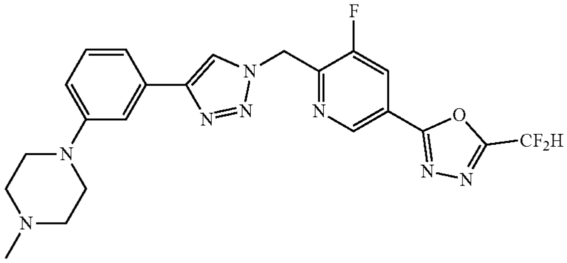 [SMILES: CN1CCN(c2cccc(-c3cn(Cc4ncc(-c5nnc(C(F)F)o5)cc4F)nn3)c2)CC1] |
| 571 | 18926 | 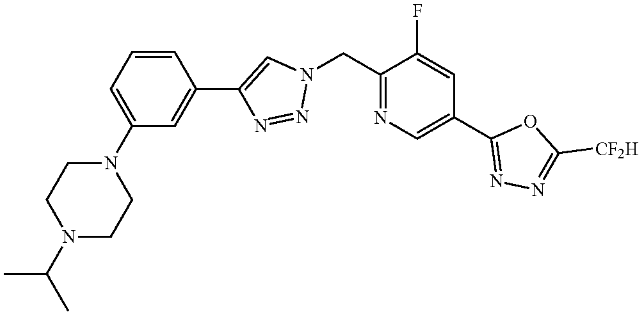 [SMILES: CC(C)N1CCN(c2cccc(-c3cn(Cc4ncc(-c5nnc(C(F)F)o5)cc4F)nn3)c2)CC1] |
| 572 | 18947 | 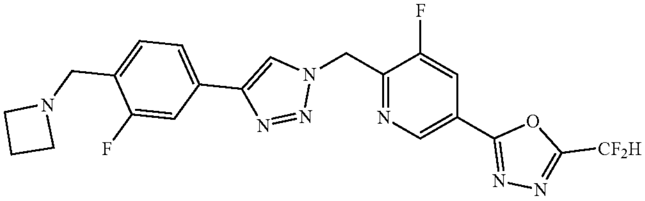 [SMILES: Fc1cc(-c2cn(Cc3ncc(-c4nnc(C(F)F)o4)cc3F)nn2)ccc1CN1CCC1] |

-continued
| Example | Compound | Structure |
| --- | --- | --- |
| 573 | 18948 | 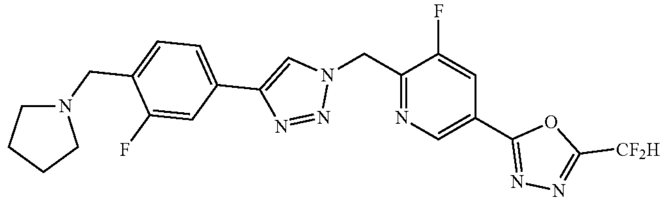 [SMILES: Fc1cc(-c2cn(Cc3ncc(-c4nnc(C(F)F)o4)cc3F)nn2)ccc1CN1CCCC1] |
| 574 | 18949 | 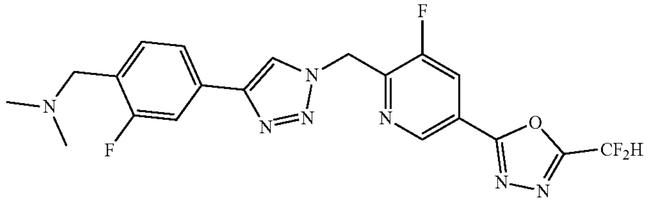 [SMILES: CN(C)Cc1ccc(-c2cn(Cc3ncc(-c4nnc(C(F)F)o4)cc3F)nn2)cc1F] |
| 575 | 18950 | 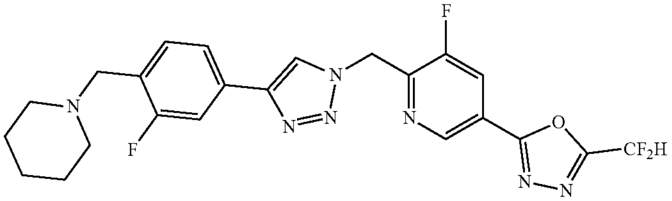 [SMILES: Fc1cc(-c2cn(Cc3ncc(-c4nnc(C(F)F)o4)cc3F)nn2)ccc1CN1CCCCC1] |
| 576 | 18961 | 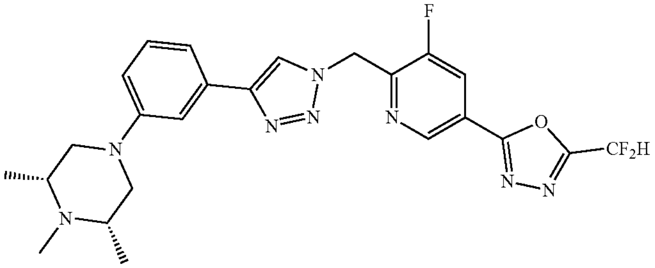 [SMILES: C[C@@H]1CN(c2cccc(-c3cn(Cc4ncc(-c5nnc(C(F)F)o5)cc4F)nn3)c2)C[C@H](C)N1C] |
| 577 | 19002 | 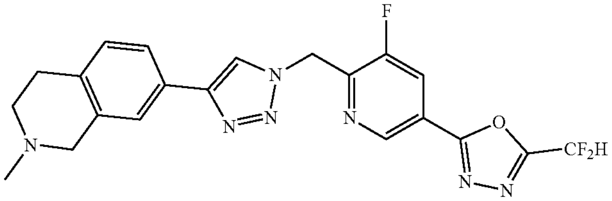 [SMILES: CN1CCc2ccc(-c3cn(Cc4ncc(-c5nnc(C(F)F)o5)cc4F)nn3)cc2C1] |
| 578 | 19004 | 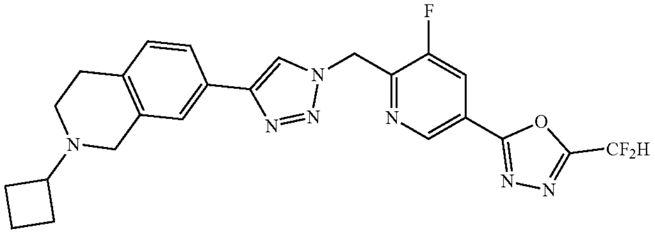 [SMILES: Fc1cc(-c2nnc(C(F)F)o2)cnc1Cn1cc(-c2ccc3c(c2)CN(C2CCC2)CC3)nn1] |
| 579 | 19058 | 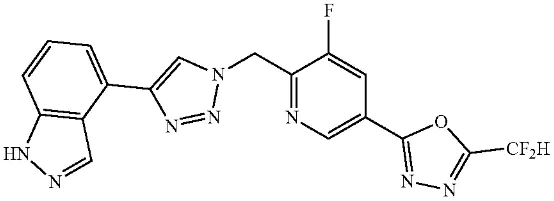 |

-continued
| Example | Compound | Structure |
| --- | --- | --- |
| 580 | 19087 | 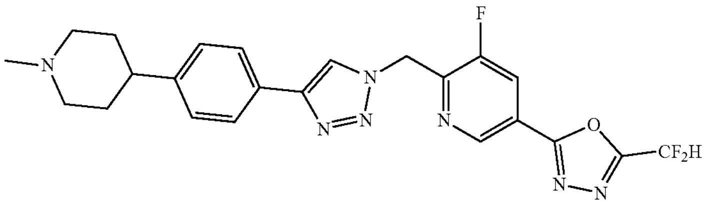 [SMILES: CN1CCC(c2ccc(-c3cn(Cc4ncc(-c5nnc(C(F)F)o5)cc4F)nn3)cc2)CC1] |
| 581 | 19088 | 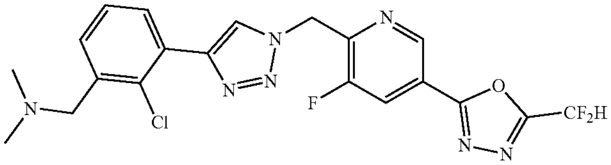 [SMILES: CN(C)Cc1cccc(-c2cn(Cc3ncc(-c4nnc(C(F)F)o4)cc3F)nn2)c1Cl] |
| 582 | 19089 | 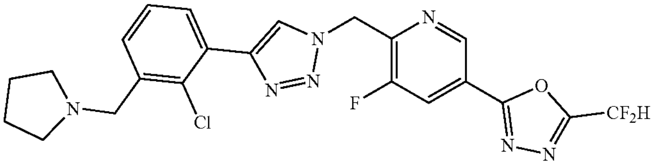 [SMILES: Fc1cc(-c2nnc(C(F)F)o2)cnc1Cn1cc(-c2cccc(CN3CCCC3)c2Cl)nn1] |
| 583 | 19090 | 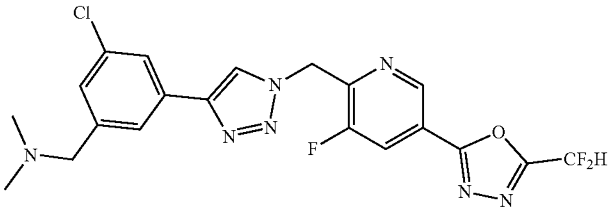 [SMILES: CN(C)Cc1cc(Cl)cc(-c2cn(Cc3ncc(-c4nnc(C(F)F)o4)cc3F)nn2)c1] |
| 584 | 19091 | 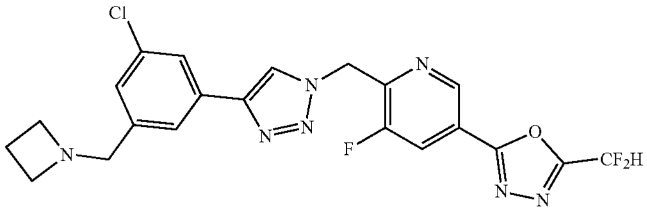 [SMILES: Fc1cc(-c2nnc(C(F)F)o2)cnc1Cn1cc(-c2cc(Cl)cc(CN3CCC3)c2)nn1] |
| 585 | 19092 | 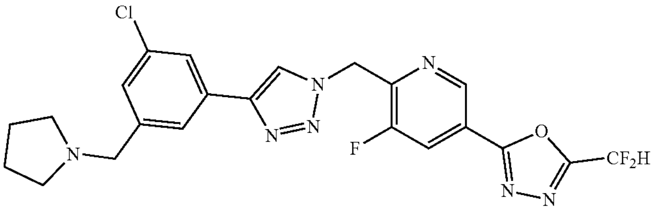 [SMILES: Fc1cc(-c2nnc(C(F)F)o2)cnc1Cn1cc(-c2cc(Cl)cc(CN3CCCC3)c2)nn1] |
| 586 | 19093 | 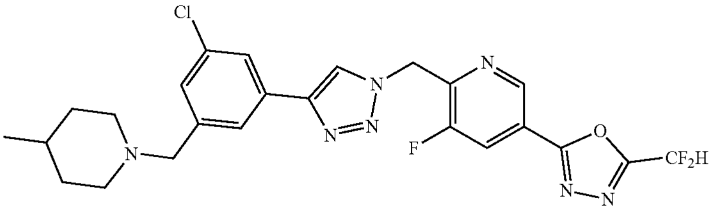 [SMILES: CC1CCN(Cc2cc(Cl)cc(-c3cn(Cc4ncc(-c5nnc(C(F)F)o5)cc4F)nn3)c2)CC1] |

-continued

| Example | Compound | Structure |
| --- | --- | --- |
| 587 | 19094 | 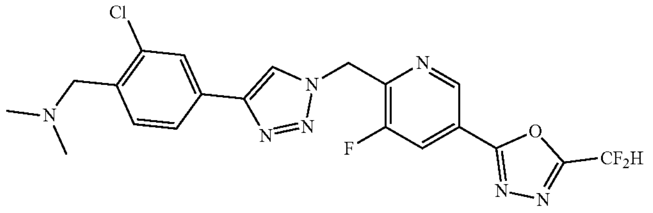 [SMILES: CN(C)Cc1ccc(-c2cn(Cc3ncc(-c4nnc(C(F)F)o4)cc3F)nn2)cc1Cl] |
| 588 | 19096 | 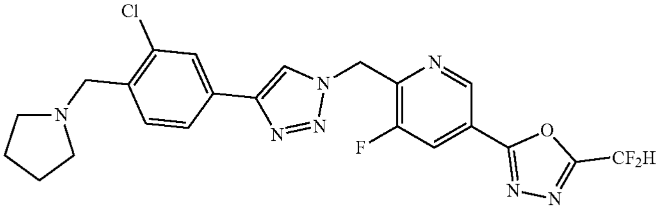 [SMILES: Fc1cc(-c2nnc(C(F)F)o2)cnc1Cn1cc(-c2ccc(CN3CCCC3)c(Cl)c2)nn1] |
| 589 | 19098 | 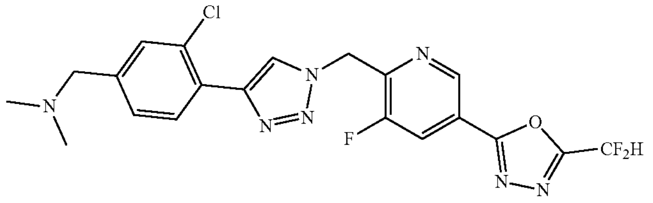 [SMILES: CN(C)Cc1ccc(-c2cn(Cc3ncc(-c4nnc(C(F)F)o4)cc3F)nn2)c(Cl)c1] |
| 590 | 19099 | 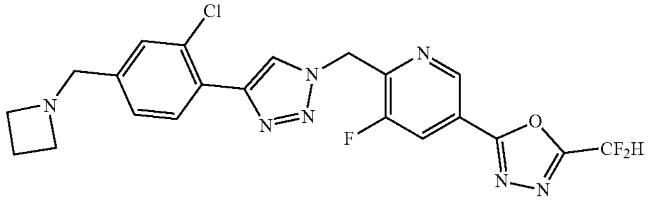 [SMILES: Fc1cc(-c2nnc(C(F)F)o2)cnc1Cn1cc(-c2ccc(CN3CCC3)cc2Cl)nn1] |
| 591 | 19100 | 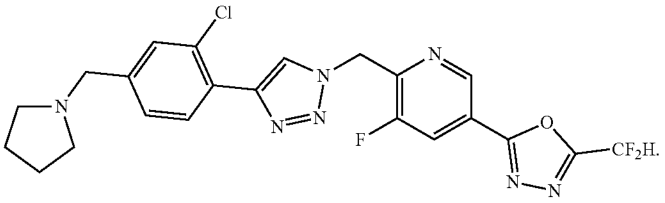 [SMILES: Fc1cc(-c2nnc(C(F)F)o2)cnc1Cn1cc(-c2ccc(CN3CCCC3)cc2Cl)nn1] |

2. A pharmaceutical composition comprising a compound according to claim 1, stereoisomers thereof or pharmaceutically acceptable salts thereof as an effective ingredient.

3. The pharmaceutical composition according to claim 2, wherein the pharmaceutical composition is for treating cancer, inflammatory disease, or neurodegenerative disease.

4. A method for treating cancer, inflammatory disease, or neurodegenerative disease, the method comprising administering a therapeutically effective amount of the compound according to claim 1, stereoisomers thereof or pharmaceutically acceptable salts thereof as an effective ingredient to a subject in need thereof.

5. The pharmaceutical composition according to claim 2, wherein the pharmaceutical composition further comprises a pharmaceutically acceptable carrier.

* * * * *